US012139512B2

(12) United States Patent
Swanson et al.

(10) Patent No.: US 12,139,512 B2
(45) **Date of Patent: *Nov. 12, 2024**

(54) PRE-FUSION RSV F ANTIGENS

(71) Applicant: GLAXOSMITHKLINE BIOLOGICALS SA, Rixensart (BE)

(72) Inventors: Kurt Swanson, Newton, MA (US); Andrea Carfi, Cambridge, MA (US)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 12 days.

This patent is subject to a terminal disclaimer.

(21) Appl. No.: 17/848,230

(22) Filed: Jun. 23, 2022

(65) Prior Publication Data

US 2022/0332766 A1 Oct. 20, 2022

Related U.S. Application Data

(63) Continuation of application No. 17/314,649, filed on May 7, 2021, now abandoned, which is a continuation of application No. 15/789,074, filed on Oct. 20, 2017, now abandoned, which is a continuation of application No. 14/117,588, filed as application No. PCT/US2012/037773 on May 14, 2012, now abandoned.

(60) Provisional application No. 61/486,005, filed on May 13, 2011.

(51) Int. Cl.

| | |
|---|---|
| ***C07K 14/005*** | (2006.01) |
| ***A61K 39/12*** | (2006.01) |
| ***A61K 39/155*** | (2006.01) |
| *A61K 39/00* | (2006.01) |

(52) U.S. Cl.

CPC ............ *C07K 14/005* (2013.01); *A61K 39/12* (2013.01); *A61K 39/155* (2013.01); *A61K 2039/53* (2013.01); *C07K 2319/735* (2013.01); *C12N 2760/18522* (2013.01); *C12N 2760/18534* (2013.01)

(58) Field of Classification Search

None

See application file for complete search history.

(56) References Cited

U.S. PATENT DOCUMENTS

| | | | |
|---|---|---|---|
| 4,235,877 | A | 11/1980 | Fullerton |
| 4,372,945 | A | 2/1983 | Likhite |
| 4,436,727 | A | 3/1984 | Ribi |
| 4,474,757 | A | 10/1984 | Arnon et al. |
| 4,707,543 | A | 11/1987 | Zollinger et al. |
| 4,866,034 | A | 9/1989 | Ribi |
| 4,877,611 | A | 10/1989 | Cantrell |
| 4,912,094 | A | 3/1990 | Myers et al. |
| 5,057,540 | A | 10/1991 | Kensil et al. |
| 5,149,650 | A | 9/1992 | Wertz et al. |
| 5,194,595 | A | 3/1993 | Wathen |
| 5,278,302 | A | 1/1994 | Caruthers et al. |
| 5,639,853 | A | 6/1997 | Paradiso et al. |
| 5,666,153 | A | 9/1997 | Copeland |
| 5,691,449 | A | 11/1997 | Paradiso et al. |
| 5,726,292 | A | 3/1998 | Lowell |
| 5,750,110 | A | 5/1998 | Prieels et al. |
| 5,776,468 | A | 7/1998 | Hauser et al. |
| 5,856,462 | A | 1/1999 | Agrawal |
| 5,958,765 | A | 9/1999 | Brams et al. |
| 5,985,284 | A | 11/1999 | Lowell |
| 6,005,099 | A | 12/1999 | Davies et al. |
| 6,060,308 | A | 5/2000 | Parrington |
| 6,113,911 | A | 9/2000 | Binz et al. |
| 6,303,347 | B1 | 10/2001 | Johnson et al. |
| 6,764,840 | B2 | 7/2004 | Johnson et al. |
| 7,357,936 | B1 | 4/2008 | Garcon |
| 7,368,537 | B2 | 5/2008 | Anderson et al. |
| 8,563,002 | B2 | 10/2013 | Baudoux et al. |
| 2003/0044425 | A1 | 3/2003 | Burt et al. |
| 2003/0232326 | A1 | 12/2003 | Fouchier et al. |
| 2004/0161846 | A1 | 8/2004 | Mason et al. |
| 2005/0042230 | A1 | 2/2005 | Anderson et al. |
| 2007/0178469 | A1 | 8/2007 | Mermod et al. |
| 2008/0233150 | A1 | 9/2008 | Smith et al. |
| 2008/0300382 | A1 | 12/2008 | Libon et al. |
| 2010/0261155 | A1 | 10/2010 | Peeples et al. |
| 2010/0291147 | A1 | 11/2010 | Baudoux et al. |
| 2011/0177117 | A1 | 7/2011 | Blais et al. |
| 2011/0206758 | A1 | 8/2011 | Vandepapeliere |
| 2012/0093847 | A1 | 4/2012 | Baudoux et al. |

(Continued)

FOREIGN PATENT DOCUMENTS

| | | |
|---|---|---|
| CA | 2710600 | 6/2017 |
| EP | 0109942 B1 | 3/1991 |

(Continued)

OTHER PUBLICATIONS

US 6,008,200 A, 12/1999, Krieg (withdrawn)
McLellan et al. Science vol. 340 (Year: 2013).*
McClellan et al Science vol. 342, p. 592, 2013, (Year: 2013).*
Day et al., "Contribution of cysteine residues in the extracellular domain of the F protein of human respiratory syncytial virus to its function", Virology Journal, vol. 3, No. 34, May 24, 2006, 11 pages.

(Continued)

*Primary Examiner* — Shanon A. Foley
*Assistant Examiner* — Myron G Hill
(74) *Attorney, Agent, or Firm* — Morgan, Lewis & Bockius LLP

(57) ABSTRACT

The invention relates to pre-fusion RSV F protein and polypeptides that contain one or more amino acid mutations that stabilize the pre-fusion conformation or destabilize the post-fusion conformation. The invention also relates to methods for inducing an immune response to pre-fusion RSV F.

9 Claims, 39 Drawing Sheets

Specification includes a Sequence Listing.

(56) References Cited

U.S. PATENT DOCUMENTS

| | | | |
|---|---|---|---|
| 2012/0135028 A1 | 5/2012 | Blais et al. | |
| 2012/0164176 A1 | 6/2012 | Swanson et al. | |

FOREIGN PATENT DOCUMENTS

| | | | | |
|---|---|---|---|---|
| EP | 0362279 B1 | 1/1995 | | |
| EP | 0689454 B1 | 9/1997 | | |
| EP | 3508505 A1 | 7/2019 | | |
| GB | 2220211 A | 1/1990 | | |
| JP | 2001-514857 | 9/2001 | | |
| WO | 1989/005823 A1 | 6/1989 | | |
| WO | 1994/015968 A1 | 7/1994 | | |
| WO | 1994/21292 A1 | 9/1994 | | |
| WO | 1995/14026 A1 | 5/1995 | | |
| WO | 1995/26204 A1 | 10/1995 | | |
| WO | 1996/02555 A1 | 2/1996 | | |
| WO | 1996/11711 A1 | 4/1996 | | |
| WO | 1996/33739 A1 | 10/1996 | | |
| WO | 1998/50399 A1 | 11/1998 | | |
| WO | 99/11808 A1 | 3/1999 | | |
| WO | 1999/14334 A1 | 3/1999 | | |
| WO | 1999/33488 A2 | 7/1999 | | |
| WO | 1999/64301 A1 | 12/1999 | | |
| WO | 2000/00462 A1 | 1/2000 | | |
| WO | 2001/46127 A1 | 6/2001 | | |
| WO | 2002/42326 A1 | 5/2002 | | |
| WO | 2002/074969 A2 | 9/2002 | | |
| WO | 2002/085905 A1 | 10/2002 | | |
| WO | 2003/011223 A2 | 2/2003 | | |
| WO | 2003/043572 A2 | 5/2003 | | |
| WO | 2003/083095 A1 | 10/2003 | | |
| WO | 2003/099195 A2 | 12/2003 | | |
| WO | 2004/071459 A2 | 8/2004 | | |
| WO | 2006/011060 A2 | 2/2006 | | |
| WO | 2006/038131 A2 | 4/2006 | | |
| WO | 2006/042156 A2 | 4/2006 | | |
| WO | 2008/061243 A2 | 5/2008 | | |
| WO | 2008/114149 A2 | 9/2008 | | |
| WO | 2008/154456 A2 | 12/2008 | | |
| WO | WO 2009/079796 A1 | 7/2009 | | |
| WO | 2009/128951 A2 | 10/2009 | | |
| WO | 2010/009277 A2 | 1/2010 | | |
| WO | 2010/077712 A1 | 7/2010 | | |
| WO | 2010/077717 A1 | 7/2010 | | |
| WO | WO 2010/149743 A2 | 12/2010 | | |
| WO | WO-2010149745 A1 * | 12/2010 | ............ | A61K 39/12 |
| WO | WO 2011/008974 A2 | 1/2011 | | |
| WO | 2012/128628 A1 | 9/2012 | | |
| WO | 2012/158613 A1 | 11/2012 | | |
| WO | 2013/017713 A1 | 2/2013 | | |
| WO | 2016/061240 A1 | 4/2016 | | |
| WO | 2018/176103 A1 | 10/2018 | | |

OTHER PUBLICATIONS

Lee et al., "Reversible Inhibition of the Fusion Activity of Measles Virus F Protein by an Engineered Intersubunit Disulfide Bridge", Journal of Virology, vol. 81, No. 16, Aug. 2007, pp. 8821-8826.

McClellan et al., "Structure of RSV Fusion Glycoprotein Trimer Bound to a Prefusion-Specific Neutralizing Antibody", Science, vol. 340, May 31, 2013, pp. 1113-1117.

McClellan et al., "Structure-Based Design of a Fusion Glycoprotein Vaccine for Respiratory Syncytial Virus", Science, vol. 342, Nov. 1, 2013, pp. 592-598.

Ruiz-Arguello et al., "Thermostability of the human respiratory syncytial virus fusion protein before and after activation: implications for the membrane-fusion mechanism", Journal of General Virology, vol. 85, 2004, pp. 3677-3687.

Swanson et al., "Structural basis or immunization with postfusion respiratory syncytial virus fusion F glycoprotein (RSV F) to elicit high neutralizing antibody titers", Proceedings of the National Academy of Sciences, vol. 108, No. 23, Jun. 7, 2011, pp. 9619-9624.

Yin et al., "Structure of the parainfluenza virus 5 F protein in its metastable, prefusion conformation", Nature, vol. 439, No. 7072, Jan. 5, 2006, pp. 38-44.

U.S. Appl. No. 17/314,649, filed May 7, 2021.

U.S. Appl. No. 15/789,074, filed Oct. 20, 2017.

Blais, N. et al., "Characterization of Pre-F-GCN4t, a Modified Human Respiratory Syncytial Virus Fusion Protein Stabilized in a Noncleaved Prefusion Conformation." Journal of virology vol. 91,13 (2017):e02437-16.

European Search Report for European Patent Application No. 22181398.3 mailed Nov. 24, 2022, 8 pages.

Sastre, P. et al., "Comparison of affinity chromatography and adsorption to vaccinia virus recombinant infected cells for depletion of antibodies directed against respiratory syncytial virus glycoproteins present in a human immunoglobulin preparation." Journal of medical virology vol. 76,2 (2005): 248-55.

Singh, S. et al., "Immunogenicity and efficacy of recombinant RSV-F vaccine in a mouse model." Vaccine vol. 25,33 (2007): 6211-23.

Van Drunen Littel-van den Hurk, S. et al., "Immunopathology of RSV infection: prospects for developing vaccines without this complication." Reviews in medical virology vol. 17,1 (2007): 5-34.

Russell, C. and Luque L., "The structural basis of paramyxovirus invasion." Trends in microbiology vol. 14,6 (2006): 243-6.

Schmidt, U. et al., "Mucosal immunization with live recombinant bovine respiratory syncytial virus (BRSV) and recombinant BRSV lacking the envelope glycoprotein G protects against challenge with wild-type BRSV." Journal of virology vol. 76,23 (2002): 12355-9.

Abstracts for oral presentations given at the "RSV 2007 Symposium" in Marco Island, FL, USA, 122 pages.

Bakkers, M. et al. "Addition of a trimerization domain (e.g. foldon) to a soluble RSV F protein," supplementary data dated Oct. 21, 2019.

Belshe, R. et al., "Immunogenicity of purified F glycoprotein of respiratory syncytial virus: clinical and immune responses to subsequent natural infection in children." The Journal of infectious diseases vol. 168,4 (1993): 1024-9.

Beran, J. et al., "Safety and Immunogenicity of 3 Formulations of an Investigational Respiratory Syncytial Virus Vaccine in Nonpregnant Women: Results From 2 Phase 2 Trials." The Journal of infectious diseases vol. 217,10 (2018): 1616-1625.

Chu, R., "CpG Oligodeoxynudeotides Act as Adjuvants that Switch on T Helper 1 (Thl) Immunity." J. Exp. Med vol. 186, 10 (1997): 1623-1631.

Connors, M. et al., "Respiratory syncytial virus (RSV) F, G, M2 (22K), and N proteins each induce resistance to RSV challenge, but resistance induced by M2 and N proteins is relatively short-lived." Journal of virology vol. 65,3 (1991): 1634-7.

Crank, M. et al., "A proof of concept for structure-based vaccine design targeting RSV in humans." Science vol. 365,6452 (2019): 505-509.

Decision from opposition division in opposition to European Patent No. 3109258 dated Jul. 8, 2021, 11 pages.

Declaration of Theodore Jardetzky, Ph.D. dated Dec. 8, 2020, 4 pages.

Doolittle, R., "The multiplicity of domains in proteins." Annual review of biochemistry vol. 64 (1995): 287-314.

Dudas, R., and Karron, R., "Respiratory syncytial virus vaccines." Clinical microbiology reviews vol. 11,3 (1998): 430-9.

Experimental data filed in opposition to European Patent No. 3109258 dated Apr. 8, 2021, 4 pages.

Gilman, M. et al., "Transient opening of trimeric prefusion RSV F proteins." Nature communications vol. 10,1 (2019):2105.

Graham, B. et al., "Novel antigens for RSV vaccines." Current opinion in immunology vol. 35 (2015): 30-8.

Jardetzky, T., "Structures of the pre- and post-entry paramyxovirus F protein: implications for RSV vaccine and therapeutic development." RSV 2007 Symposium, Oct. 26, 2007, Marco Island, FL, USA. Conference Presentation, 13 pages.

Langley, J. et al., "A Randomized, Controlled, Observer-Blinded Phase 1 Study of the Safety and Immunogenicity of a Respiratory Syncytial Virus Vaccine With or Without Alum Adjuvant." The Journal of infectious diseases vol. 215,1 (2017): 24-33.

(56) References Cited

OTHER PUBLICATIONS

Letter relating to appeal procedure in opposition to European Patent No. 3109258 dated Aug. 15, 2022, 8 pages.
Letter relating to oral proceedings during appeal procedure in opposition to European Patent No. 3109258 dated Nov. 29, 2022, 2 pages.
Ngwuta, J. et al., "Prefusion F-specific antibodies determine the magnitude of RSV neutralizing activity in human sera." Science translational medicine vol. 7,309 (2015): 309ra162.
Notice of opposition to European Patent No. 3109258 dated Oct. 23, 2019, 27 pages.
Notice of opposition to European Patent No. 3109258 dated Oct. 23, 2019, 51 pages.
Piedra, P., "Clinical experience with respiratory syncytial virus vaccines." The Pediatric infectious disease journal vol. 22,2 Suppl (2003): S94-9.
Preliminary opinion from opposition division in opposition to European Patent No. 3109258 dated Aug. 11, 2020, 9 pages.
Program for "RSV 2007 Symposium," in Marco Island, FL, USA, 2 pages.
Reply from opponent to submission of proprietor in opposition to European Patent No. 3109258 dated Jul. 2, 2020, 19 pages.
Reply to appeal in opposition to European Patent No. 3109258 dated Apr. 1, 2022, 31 pages.
Reply to appeal in opposition to European Patent No. 3109258 dated Apr. 4, 2022, 34 pages.
Reply to opposition to European Patent No. 3109258 dated Mar. 16, 2020, 36 pages.
Schwarz, T. et al., "Immunogenicity and Safety of 3 Formulations of a Respiratory Syncytial Virus Candidate Vaccine in Nonpregnant Women: A Phase 2, Randomized Trial." The Journal of infectious diseases vol. 220,11 (2019): 1816-1825.
Smith, B. et al., "Modelling the structure of the fusion protein from human respiratory syncytial virus." Protein engineering vol. 15,5 (2002): 365-71.
Statement of grounds of appeal in opposition to European Patent No. 3109258 dated Nov. 18, 2021, 36 pages.
Swanson, K. et al., "A monomeric uncleaved respiratory syncytial virus F antigen retains prefusion-specific neutralizing epitopes." Journal of virology vol. 88,20 (2014): 11802-10.
U.S. Appl. No. 60/942,456, filed Jun. 6, 2007.
U.S. Appl. No. 61/016,524, filed Dec. 24, 2007.
U.S. Appl. No. 61/056,206, filed May 27, 2008.
Wathen, M. et al., "Characterization of a novel human respiratory syncytial virus chimeric FG glycoprotein expressed using a baculovirus vector." The Journal of general virology vol. 70 (Pt 10) (1989): 2625-35.
Wertz, G. et al., "Expression of the fusion protein of human respiratory syncytial virus from recombinant vaccinia virus vectors and protection of vaccinated mice." Journal of virology vol. 61,2 (1987): 293-301.
Widjaja, I. et al., "Recombinant Soluble Respiratory Syncytial Virus F Protein That Lacks Heptad Repeat B, Contains a GCN4 Trimerization Motif and Is Not Cleaved Displays Prefusion-Like Characteristics." PloS one vol. 10,6 (2015): 1-19.
Written submission in preparation to oral proceedings in opposition to European Patent No. 3109258 dated Apr. 8, 2021, 3 pages.
Written submission in preparation to oral proceedings in opposition to European Patent No. 3109258 dated Apr. 8, 2021, 7 pages.
Written submission in preparation to oral proceedings in opposition to European Patent No. 3109258 dated Apr. 8, 2021, 8 pages.
Written submission in preparation to oral proceedings in opposition to European Patent No. 3109258 dated Dec. 9, 2020, 4 pages.
Written submission in preparation to oral proceedings in opposition to European Patent No. 3109258 dated May 21, 2021, 4 pages.
Yang, X. et al., "Modifications that stabilize human immunodeficiency virus envelope glycoprotein trimers in solution." Journal of virology vol. 74,10 (2000): 4746-54.
Zhao, X. et al., "Structural characterization of the human respiratory syncytial virus fusion protein core." Proceedings of the National Academy of Sciences of the United States of America vol. 97,26 (2000): 14172-7.
Bembridge, G. et al., "Priming with a secreted form of the fusion protein of respiratory syncytial virus (RSV) promotes interleukin-4 (IL-4) and IL-5 production but not pulmonary eosinophilia following RSV challenge." Journal of virology vol. 73,12 (1999): 10086-94.
Bolt, G. et al., "Cleavage of the respiratory syncytial virus fusion protein is required for its surface expression: role of furin." Virus research vol. 68,1 (2000): 25-33.
Brideau, R. and Wathen, M., "A chimeric glycoprotein of human respiratory syncytial virus termed FG induces T-cell mediated immunity in mice." Vaccine vol. 9,12 (1991): 863-4.
Connors, M. et al., "Cotton rats previously immunized with a chimeric RSV FG glycoprotein develop enhanced pulmonary pathology when infected with RSV, a phenomenon not encountered following immunization with vaccinia—RSV recombinants or RSV." Vaccine vol. 10,7 (1992): 475-84.
Dormitzer, P. et al., "Structure-based antigen design: a strategy for next generation vaccines." Trends in biotechnology vol. 26,12 (2008): 659-67.
Eckardt-Michel, J. et al., "The fusion protein of respiratory syncytial virus triggers p53-dependent apoptosis." Journal of virology vol. 82,7 (2008): 3236-49.
Elliott, S. et al., "Enhancement of therapeutic protein in vivo activities through glycoengineering." Nature biotechnology vol. 21,4 (2003): 414-21.
EP10724879: Oct. 17, 2014 Written Submission by Applicant.
EP10724879: Jun. 3, 2013 Response by Applicant.
EP10724879: Oct. 6, 2014 Written Submission by Applicant.
Ewasyshyn, M et al., "Comparative analysis of the immunostimulatory properties of different adjuvants on the immunogenicity of a prototype parainfluenza virus type 3 subunit vaccine." Vaccine vol. 10,6 (1992): 412-20.
Falsey, A.et al., "Comparison of the safety and immunogenicity of 2 respiratory syncytial virus (rsv) vaccines—nonadjuvanted vaccine or vaccine adjuvanted with alum—given concomitantly with influenza vaccine to high-risk elderly individuals." The Journal of infectious diseases vol. 198,9 (2008): 1317-26.
Hancock, G. et al., "Generation of atypical pulmonary inflammatory responses in BALB/c mice after immunization with the native attachment (G) glycoprotein of respiratory syncytial virus." Journal of virology vol. 70,11 (1996): 7783-91.
Hancock, G. et al., "Serum neutralizing antibody titers of seropositive chimpanzees immunized with vaccines coformulated with natural fusion and attachment proteins of respiratory syncytial virus." The Journal of infectious diseases vol. 181,5 (2000): 1768-71.
Harrison, R. and Jarvis, D., "Protein N-glycosylation in the baculovirus-insect cell expression system and engineering of insect cells to produce "mammalianized" recombinant glycoproteins." Advances in virus research vol. 68 (2006): 159-91.
Huang, Y. and Anderson, R., "Modulation of protective immunity, eosinophilia, and cytokine responses by selective mutagenesis of a recombinant G protein vaccine against respiratory syncytial virus." Journal of virology vol. 79,7 (2005): 4527-32.
Klink, H. A et al., "Influence of bovine respiratory syncytial virus F glycoprotein N-linked glycans on in vitro expression and on antibody responses in BALB/c mice." Vaccine vol. 24,16 (2006): 3388-95.
Ladunga, I. and Smith, R., "Amino acid substitutions preserve protein folding by conserving steric and hydrophobicity properties." Protein engineering vol. 10,3 (1997): 187-96.
Langley, J. et al., "A dose-ranging study of a subunit Respiratory Syncytial Virus subtype A vaccine with and without aluminum phosphate adjuvantation in adults greater than or equal to 65 years of age." Vaccine vol. 27,42 (2009): 5913-9.
Matthews, J. et al., "The core of the respiratory syncytial virus fusion protein is a trimeric coiled coil." Journal of virology vol. 74,13 (2000): 5911-20.

(56) References Cited

OTHER PUBLICATIONS

Mejias, A. et al., “New Approaches to reduce the burden of RSV infection,” Drug Discovery Today: Therapeutic Strategies vol. 3,2 (2006): 173-181.

Melero, J., “Molecular Biology of Human Respiratory Syncytial Virus.” Respiratory Syncytial Virus, Patricia Cane, Editor, Perspectives in Medical Virology, 14, (2007), p. 10-11.

Morton, C. et al., “Structural characterization of respiratory syncytial virus fusion inhibitor escape mutants: homology model of the F protein and a syncytium formation assay.” Virology vol. 311,2 (2003): 275-88.

NCBI BLAST Accession No. EF566942.1.

Olmsted, R. et al., “Expression of the F glycoprotein of respiratory syncytial virus by a recombinant vaccinia virus: comparison of the individual contributions of the F and G glycoproteins to host immunity.” Proceedings of the National Academy of Sciences of the United States of America vol. 83,19 (1986): 7462-6.

Olson, M. and Varga, S., “Pulmonary immunity and immunopathology: lessons from respiratory syncytial virus.” Expert review of vaccines vol. 7,8 (2008): 1239-55.

Piedra, P. et al. “Immunogenicity of a new purified fusion protein vaccine to respiratory syncytial virus: a multi-center trial in children with cystic fibrosis.” Vaccine vol. 21,19-20 (2003): 2448-60.

Prince, G. et al. “Efficacy and safety studies of a recombinant chimeric respiratory syncytial virus FG glycoprotein vaccine in cotton rats.” Journal of virology vol. 74,22 (2000): 10287-92.

Sakurai, H. et al., “Human antibody responses to mature and immature forms of viral envelope in respiratory syncytial virus infection: significance for subunit vaccines.” Journal of virology vol. 73,4 (1999): 2956-62.

Schmidt, A. et al., “Mucosal immunization of rhesus monkeys against respiratory syncytial virus subgroups A and B and human parainfluenza virus type 3 by using a live cDNA-derived vaccine based on a host range-attenuated bovine parainfluenza virus type 3 vector backbone.” Journal of virology vol. 76,3 (2002): 1089-99.

Simoes, E. et al., “Respiratory syncytial virus vaccine: a systematic overview with emphasis on respiratory syncytial virus subunit vaccines.” Vaccine vol. 20,5-6 (2001): 954-60.

Sinclair, A., and Elliott, S., “Glycoengineering: the effect of glycosylation on the properties of therapeutic proteins.” Journal of pharmaceutical sciences vol. 94,8 (2005): 1626-35.

Tang, R. et al., “Parainfluenza virus type 3 expressing the native or soluble fusion (F) Protein of Respiratory Syncytial Virus (RSV) confers protection from RSV infection in African green monkeys.” Journal of virology vol. 78,20 (2004): 11198-207.

Ternette, N. et al., “Expression of RNA virus proteins by RNA polymerase II dependent expression plasmids is hindered at multiple steps.” Virology journal vol. 4 (2007): 51.

Ternette, N. et al., “Immunogenicity and efficacy of codon optimized DNA vaccines encoding the F-protein of respiratory syncytial virus.” Vaccine vol. 25,41 (2007): 7271-9.

Tian, S. et al., “A 20 Residues Motif Delineates the Furin Cleavage Site and its Physical Properties May Influence Viral Fusion.” Biochemistry insights vol. 2 (2009):9-20.

Ulbrandt, N. et al., “Identification of antibody neutralization epitopes on the fusion protein of human metapneumovirus.” The Journal of general virology vol. 89,Pt 12 (2008): 3113-3118.

Walsh, E. et al., “Immunization with glycoprotein subunits of respiratory syncytial virus to protect cotton rats against viral infection.” The Journal of infectious diseases vol. 155,6 (1987): 1198-204.

Zhang, Z. and Henzel, W., “Signal peptide prediction based on analysis of experimentally verified cleavage sites.” Protein science : a publication of the Protein Society vol. 13,10 (2004): 2819-24.

Zimmer, G. et al., “N-glycans of F protein differentially affect fusion activity of human respiratory syncytial virus.” Journal of virology vol. 75,10 (2001): 4744-51.

Arndt, K M et al., “Comparison of in vivo selection and rational design of heterodimeric coiled coils.” Structure vol. 10,9 (2002): 1235-48.

Blanco, J. et al., “New insights for development of a safe and protective RSV vaccine.” Human vaccines vol. 6,6 (2010): 482-92.

Calder, L J et al., “Electron microscopy of the human respiratory syncytial virus fusion protein and complexes that it forms with monoclonal antibodies.” Virology vol. 271,1 (2000): 122-31.

Chao, H. et al., “Use of a heterodimeric coiled-coil system for biosensor application and affinity purification.” Journal of chromatography. B, Biomedical sciences and applications vol. 715,1 (1998): 307-29.

Chen, B. et al., “A chimeric protein of simian immunodeficiency virus envelope glycoprotein gp140 and *Escherichia coli* aspartate transcarbamoylase.” Journal of virology vol. 78,9 (2004): 4508-16.

Connolly, S. et al., “Refolding of a paramyxovirus F protein from prefusion to postfusion conformations observed by liposome binding and electron microscopy.” Proceedings of the National Academy of Sciences of the United States of America vol. 103,47 (2006): 17903-8.

Durbin, A. and Karron, R., “Progress in the development of respiratory syncytial virus and parainfluenza virus vaccines.” Clinical infectious diseases: an official publication of the Infectious Diseases Society of America vol. 37,12 (2003): 1668-77.

Extended European Search Report for European Application No. 21199223.5, dated Jul. 18, 2022, 16 pages.

Fretzayas, A. and Moustaki, M., “The challenges of RSV vaccines. Where do we stand?” Recent patents on anti-infective drug discovery vol. 5,2 (2010): 99-108.

Gardner, A. and Dutch, R., “A conserved region in the F(2) subunit of paramyxovirus fusion proteins is involved in fusion regulation.” Journal of virology vol. 81,15 (2007): 8303-14.

GI: 138250; UniProtKB: locus FUS_HRSV1, accession P13843.

GI: 138251; UniProtKB: locus FUS_HRSVA, accession P03420.

González-Reyes, L. et al., “Cleavage of the human respiratory syncytial virus fusion protein at two distinct sites is required for activation of membrane fusion.” Proceedings of the National Academy of Sciences of the United States of America vol. 98,17 (2001): 9859-64.

Harbury, P. et al., “A switch between two-, three-, and four-stranded coiled coils in GCN4 leucine zipper mutants.” Science vol. 262,5138 (1993): 1401-7.

International Search Report and Written Opinion of International Application No. PCT/US2010/042161, dated Mar. 10, 2011, 30 pages.

Kammerer, R., “Alpha-helical coiled-coil oligomerization domains in extracellular proteins.” Matrix biology: journal of the International Society for Matrix Biology vol. 15,8-9 (1997): 555-65.

Lamb, R. and Jardetzky, T., “Structural basis of viral invasion: lessons from paramyxovirus F.” Current opinion in structural biology vol. 17,4 (2007): 427-36.

Liu, J. and Lu, M., “An alanine-zipper structure determined by long range intermolecular interactions.” The Journal of biological chemistry vol. 277,50 (2002): 48708-13.

Magro, M. et al., “Neutralizing antibodies against the preactive form of respiratory syncytial virus fusion protein offer unique possibilities for clinical intervention.” Proceedings of the National Academy of Sciences of the United States of America vol. 109,8 (2012): 3089-94.

Martín, D. et al., “Sequence elements of the fusion peptide of human respiratory syncytial virus fusion protein required for activity.” The Journal of general virology vol. 87,Pt 6 (2006): 1649-1658.

McLellan, J. et al., “Structural basis of respiratory syncytial virus neutralization by motavizumab.” Nature structural & molecular biology vol. 17,2 (2010): 248-50.

McLellan, J. et al., “Structure of a major antigenic site on the respiratory syncytial virus fusion glycoprotein in complex with neutralizing antibody 101F.” Journal of virology vol. 84,23 (2010): 12236-44.

McLellan, J. et al., “Structure of respiratory syncytial virus fusion glycoprotein in the postfusion conformation reveals preservation of neutralizing epitopes.” Journal of virology vol. 85,15 (2011): 7788-96.

Müller, K. et al., “Protein fusions to coiled-coil domains.” Methods in enzymology vol. 328 (2000): 261-82.

(56) References Cited

OTHER PUBLICATIONS

Pancera, M. et al., "Soluble mimetics of human immunodeficiency virus type 1 viral spikes produced by replacement of the native trimerization domain with a heterologous trimerization motif: characterization and ligand binding analysis." Journal of virology vol. 79,15 (2005): 9954-69.
Partial European Search Report for European Application No. 21199223.5, dated Mar. 14, 2022, 14 pages.
Rigter, A. et al., "A protective and safe intranasal RSV vaccine based on a recombinant prefusion-like form of the F protein bound to bacterium-like particles." PloS one vol. 8,8 (2013): e71072.
Ruiz-Argüello, M. et al., "Effect of proteolytic processing at two distinct sites on shape and aggregation of an anchorless fusion protein of human respiratory syncytial virus and fate of the intervening segment." Virology vol. 298,2 (2002): 317-26.
Sarmiento, R. et al., "Characterization of a persistent respiratory syncytial virus showing a low-fusogenic activity associated to an impaired F protein." Virus research vol. 139,1 (2009): 39-47.
Schmidt, Alexander C., "Progress in respiratory virus vaccine development." Seminars in respiratory and critical care medicine vol. 32,4 (2011): 527-40.
Sissoëff, L. et al., "Stable trimerization of recombinant rabies virus glycoprotein ectodomain is required for interaction with the p75NTR receptor." The Journal of general virology vol. 86,Pt 9 (2005): 2543-2552.
Stevens, J. et al., "Structure of the uncleaved human H1 hemagglutinin from the extinct 1918 influenza virus." Science vol. 303,5665 (2004): 1866-70.
Sugrue, R. et al., "Furin cleavage of the respiratory syncytial virus fusion protein is not a requirement for its transport to the surface of virus-infected cells." The Journal of general virology vol. 82,Pt 6 (2001): 1375-1386.
Valarcher, J. et al., "Bovine respiratory syncytial virus lacking the virokinin or with a mutation in furin cleavage site RA (R/K)R109 induces less pulmonary inflammation without impeding the induction of protective immunity in calves." The Journal of general virology vol. 87,Pt 6 (2006): 1659-1667.
Van Braeckel-Budimir, N. et al., "Bacterium-like particles for efficient immune stimulation of existing vaccines and new subunit vaccines in mucosal applications." Frontiers in immunology vol. 4 (2013): 282.
Yang, X. et al., "Highly stable trimers formed by human immunodeficiency virus type 1 envelope glycoproteins fused with the trimeric motif of T4 bacteriophage fibritin." Journal of virology vol. 76,9 (2002): 4634-42.
Yin, H.S. et al., "Structure of the uncleaved ectodomain of the paramyxovirus (hPIV3) fusion protein." Proceedings of the National Academy of Sciences of the United States of America vol. 102,26 (2005): 9288-93.
Zhang, Y. and Chen, Q., "The noncollagenous domain 1 of type X collagen. A novel motif for trimer and higher order multimer formation without a triple helix." The Journal of biological chemistry vol. 274,32 (1999): 22409-13.
Zimmer, G. et al., "Cleavage at the furin consensus sequence RAR/KR(109) and presence of the intervening peptide of the respiratory syncytial virus fusion protein are dispensable for virus replication in cell culture." Journal of virology vol. 76,18 (2002): 9218-24.
Zimmer, G. et al., "Proteolytic activation of respiratory syncytial virus fusion protein. Cleavage at two furin consensus sequences." The Journal of biological chemistry vol. 276,34 (2001): 31642-50.
International Preliminary Report on Patentability of International Patent Application No. PCT/US2010/042161, dated Jan. 17, 2012, 20 pages.
Cseke, G. (2006). Cloning, Expression and Structural Characterization of Human Metapneumovirus Fusion Glycoprotein [Doctoral dissertation, Vanderbilt University], 140 pages.
Grounds of Invalidity in respect of EP3109258, EP2222710, and EP3178490 dated Jun. 8, 2022, 12 pages.
McLellan, J. et al., "Structural basis of respiratory syncytial virus neutralization by motavizumab with supplementary information." Nature Structural & Molecular Biology, vol. 17,2, (2010), 17 pages.
Yang, X. et al., "Improved elicitation of neutralizing antibodies against primary human immunodeficiency viruses by soluble stabilized envelope glycoprotein trimers." Journal of virology vol. 75,3 (2001): 1165-71.
Bakkers, M. et al. "Characterization of EP3178490 designs," dated Jan. 17, 2023, 12 pages.
Harrison, Stephen C., "Viral membrane fusion." Nature Structural & Molecular Biology, vol. 15,7 (2008): 690-698.
McLellan, J. et al., "Structure-based design of a fusion glycoprotein vaccine for respiratory syncytial virus with supplementary information." Science vol. 342,6158 (2013): 592-8, 33 pages.
McLellan, J. et al., "Structure of RSV fusion glycoprotein trimer bound to a prefusion-specific neutralizing antibody with supplementary information." Science vol. 340,6136 (2013): 1113-7, 18 pages.
Gilman, M. et al., "Characterization of a prefusion-specific antibody that recognizes a quaternary, cleavage-dependent epitope on the RSV fusion glycoprotein." PLoS pathogens vol. 11,7 (2015): 1-17.
Stevens, J. et al., "Structure of the uncleaved human H1 hemagglutinin from the extinct 1918 influenza virus with supplementary information." Science, vol. 303 (2004):1866-1870, 20 pages.
Sequence Alignment of SEQ ID No. 611 of WO2009/128951 and SEQ ID No. 1 and 2 of EP3178490, 4 pages.
Meier, S. et al., "Foldon, the natural trimerization domain of T4 fibritin, dissociates into a monomeric A-state form containing a stable beta-hairpin: atomic details of trimer dissociation and local beta-hairpin stability from residual dipolar couplings." Journal of molecular biology vol. 344,4 (2004): 1051-69.
Sequence Alignment of SEQ ID No. 1 of EP3178490 and SEQ ID No. 2 and 6 of WO2009/079796, 5 pages.
Yang, X. et al., "Characterization of stable, soluble trimers containing complete ectodomains of human immunodeficiency virus type 1 envelope glycoproteins." Journal of virology vol. 74,12 (2000): 5716-25.
Frank, S. et al., "Stabilization of short collagen-like triple helices by protein engineering." Journal of molecular biology vol. 308,5 (2001): 1081-9.
Tao, Y. et al., "Structure of bacteriophage T4 fibritin: a segmented coiled coil and the role of the C-terminal domain." Structure vol. 5,6 (1997): 789-98.
McLellan, J. et al., "Structure of RSV fusion glycoprotein trimer bound to a prefusion-specific neutralizing antibody with supplementary information." Science vol. 340,6136 (2013): 1113-7, 24 pages.
Notice of Opposition and Opposition Statement against EP3178490B1 dated Jan. 20, 2023, 57 pages.
Notice of Opposition and Opposition Statement against EP3178490B1 dated Jan. 19, 2023, 49 pages.

* cited by examiner

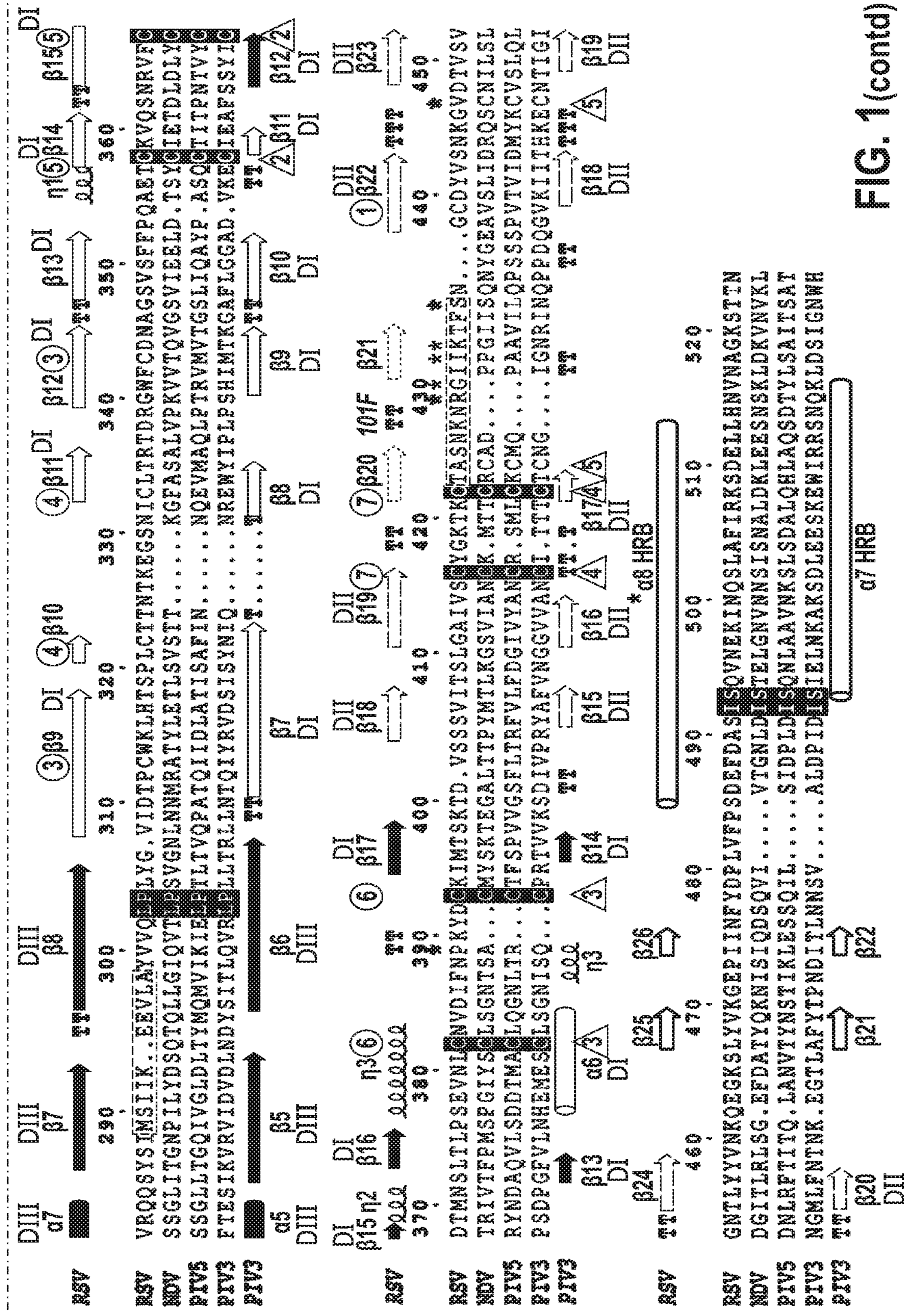
FIG. 1(contd)

RSV F post fusion structure
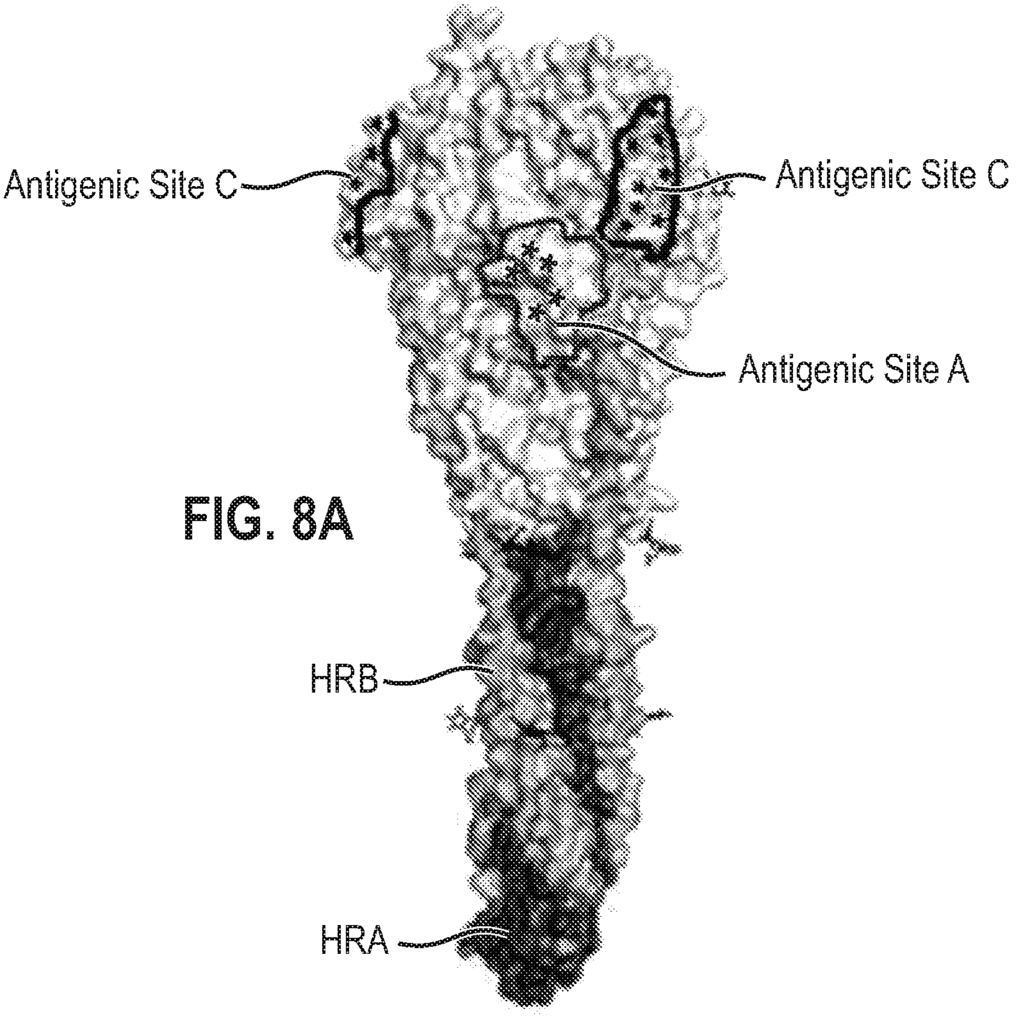
FIG. 8A
FIG. 8C
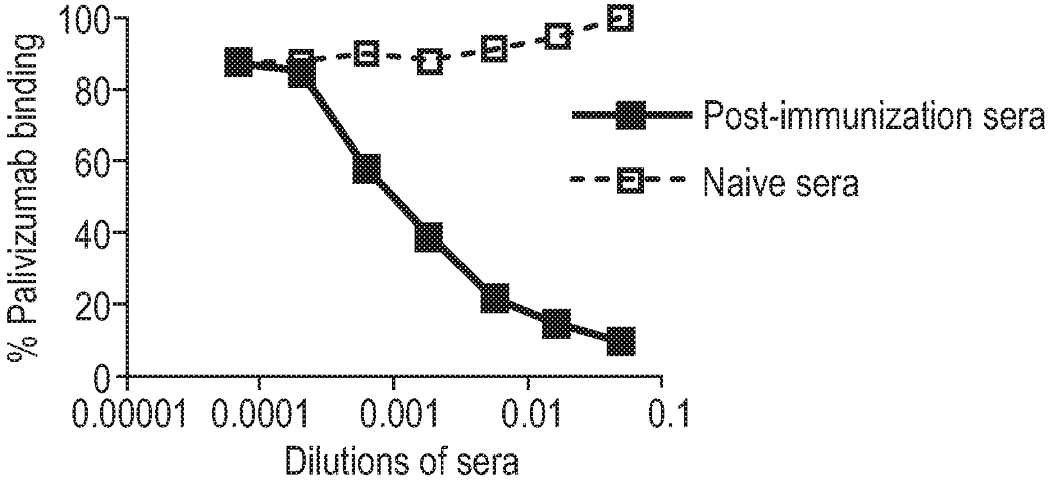

Pre-fusion model 165-296 and 56-164 proposed to account for potential model bias HRB Stalk SEC-HPLC analysis of HRA disulfide T58C V164C pre fusion attempt
RSV F disulfide retention time ~5 min (rosette) and 6.3 (trimer)

EM: NDV F
Pre-fusion

NDV F rods
10%PEG 3350, 2%
Tascimate, Tris pH 7.5

NDV F rods
15%PEG 1000, 6%
Tascimate, Tris pH 8.5

EM: RSV F
Del-HRB Containing FP

SEC: RSV F
Del-FB Del-HRB

Void/rosette peak

Trimer peak

SEC: RSV F Del-FB Del-HRB

20nm
HV=80.0KV
Direct Mag: 100000x
AMT Camera System

EM: RSV F Del-HRB Containing FP

EM: NDV F
Pre-fusion

EM: RSV F
Del-FB Del-HRB

1 RSV-F NDV HRB del fus trunc
2 RSV-F NDV HRB trunc
3 RSV-F NDV HRB2 del fus trunc
4 RSV-F NDV HRB2 trunc
5 RSV-F PIV5 HRB2 del fus trunc
6 RSV-F PIV5 HRB2 trunc

PRE-FUSION RSV F ANTIGENS

RELATED APPLICATION

This application is a Continuation of copending application Ser. No. 17/314,649, filed on May 7, 2021, which is Continuation of copending application Ser. No. 15/789,074, filed on Oct. 20, 2017, which is a Continuation of application Ser. No. 14/117,588, filed on May 16, 2014, which is the National Phase under 35 U.S.C. § 371 of International Application No. PCT/US2012/37773, filed on May 14, 2012, which claims the benefit under 35 U.S.C. § 119(e) to U.S. Provisional Application No. 61/486,005, filed on May 13, 2011, all of which are hereby expressly incorporated by reference into the present application.

SEQUENCE LISTING

The instant application contains a Sequence Listing which was previously submitted in ASCII format via EFS-Web on Oct. 20, 2017, and transferred to the present application upon filing, and is hereby incorporated by reference in its entirety. Said ASCII copy, created on May 11, 2012, is named Pat05457.txt and is 98,385 bytes in size.

BACKGROUND OF THE INVENTION

Respiratory syncytial virus (RSV) is an enveloped non-segmented negative-strand RNA virus in the family Paramyxoviridae, genus Pneumovirus. It is the most common cause of bronchiolitis and pneumonia among children in their first year of life. RSV also causes repeated infections including severe lower respiratory tract disease, which may occur at any age, especially among the elderly or those with compromised cardiac, pulmonary, or immune systems.

To infect a host cell, paramyxoviruses such as RSV, like other enveloped viruses such as influenza virus and HIV, require fusion of the viral membrane with a host cell's membrane. For RSV the conserved fusion protein (RSV F) fuses the viral and cellular membranes by coupling irreversible protein refolding with juxtaposition of the membranes. In current models, based on paramyxovirus studies, the RSV F protein initially folds into a "pre-fusion" conformation. During cell entry, the pre-fusion conformation undergoes refolding and conformational changes to its "post-fusion" conformation.

The RSV F protein is translated from mRNA into an approximately 574 amino acid protein designated $F_0$. Post-translational processing of $F_0$ includes removal of an N-terminal signal peptide by a signal peptidase in the endoplasmic reticulum. $F_0$ is also cleaved at two sites (109/110 and 136/137) by cellular proteases (in particular furin) in the trans-Golgi. This cleavage results in the removal of a short intervening sequence and generates two subunits designated $F_1$ (~50 kDa; C-terminal; approximately residues 137-574) and $F_2$ (~20 kDa; N-terminal; approximately residues 1-109) that remain associated with each other. $F_1$ contains a hydrophobic fusion peptide at its N-terminus and also two amphipathic heptad-repeat regions (HRA and HRB). HRA is near the fusion peptide and HRB is near the transmembrane domain. Three $F_1$-$F_2$ heterodimers are assembled as homotrimers of $F_1$-$F_2$ on the surface of the virion.

A vaccine against RSV infection is not currently available, but is desired. Vaccine candidates based on the chief RSV neutralization antigen, the F glycoprotein, have foundered due to problems with stability, purity, reproducibility, and potency. Crystal structures of related parainfluenza F glycoproteins have revealed a large conformational change between the pre-fusion and post-fusion states. The magnitude of the rearrangement suggested that post-fusion F antigens would not efficiently elicit neutralizing antibodies, which presumably must bind epitopes exposed on the pre-fusion conformation. Accordingly, efforts to produce a vaccine against RSV have focused on developing subunit vaccines that contain pre-fusion forms of RSV F. (See, e.g., WO 2010/149745, WO 2010/149743, WO 2009/079796) This focus on pre-fusion forms of RSV F has been corroborated by available models of RSV F.

Pre-fusion F is a "metastable" structure that readily rearranges into the lower energy post-fusion state, which then aggregates due to exposure of a hydrophobic fusion peptide (Begona Ruiz-Arguello, M. et al. *Virology* 298, 317-326 (2002) (142)). Large structural differences between the lollipop-shaped pre-fusion F trimer and the crutch-shaped post-fusion F trimer are apparent even at the resolution of electron microscopy of negatively stained specimens, suggesting that pre-fusion and post-fusion F may be antigenically distinct (Calder, L. J. et al. *Virology* 271, 122-131 (2000) (143)). To prevent viral entry, F-specific neutralizing antibodies presumably must bind the pre-fusion conformation of F on the virion, before the viral envelope fuses with a cellular membrane. However, efforts to generate a soluble, stabilized pre-fusion F subunit antigen have not yet yielded candidates suitable for testing in humans. Furthermore, analysis of a Motavizumab-peptide complex and homology modeling suggested that the dominant neutralizing epitope recognized by Palivizumab and Motavizumab might be buried in trimeric F, requiring at least a local dissociation for surface exposure to allow antibody binding (McLellan, J. S. et al. *Nat Struct Mol Biol* 17, 248-250 (2010)). There is a need for improved RSV F protein compositions and methods for making RSV F protein compositions.

SUMMARY OF THE INVENTION

The invention relates to pre-fusion respiratory syncytial virus (RSV) F polypeptides and pre-fusion chimeric F polypeptides.

In some aspects, the pre-fusion respiratory syncytial virus (RSV) F polypeptide comprises at least two introduced cysteine residues that are in close proximity to one another, and form a disulfide bond that stabilizes the pre-fusion RSV F polypeptide. In particular embodiments, the HRB region contains an introduced cysteine residue and the DI and/or DII region contain an introduced cysteine residue, and a disulfide bond is formed between the introduced cysteine residue in the HRB region and the introduced cysteine residue in the D1 or DII region. In other embodiments, the HRA region contains an introduced cysteine residue and the DIII region contains an introduced cysteine residue, and a disulfide bond is formed between the introduced cysteine residue in the HRA region and the introduced cysteine residue in the III region. In other embodiments, the HRA region contains at least 2 introduced cysteine residues, and a disulfide bond is formed between the introduced cysteine residues in the HRA region.

In other aspects, the pre-fusion respiratory syncytial virus (RSV) F polypeptide comprises a post-fusion modification selected from the group consisting of deletion of the HRA helix, deletion of the HRB helix, introduction of point mutations, addition of glycosylation sites and combinations thereof, wherein said post-fusion modification destabilizes the post-fusion conformation. In some embodiments, the destabilizing post-fusion modification is deletion of the HRB helix, in whole or in part. If desired, the destabilizing post-fusion modification can further comprise deletion of the fusion peptide, in whole or in part. In other embodiments, the destabilizing post-fusion modification includes addition of a glycosylation site, such as glycosylation on a residue selected from the group consisting of position 173, position 175 and position 184.

In another aspect, the invention is a pre-fusion respiratory syncytial virus (RSV) F protein comprising three RSV F monomers, wherein at least two of the monomers contain an introduced cysteine residue, the introduced cysteine residues are in close proximity to one another and form a disulfide bond that stabilizes the pre-fusion RSV F protein.

In another aspect, the invention is a chimeric pre-fusion F protein comprising a stabilized F protein from a virus other than RSV, such as parainfluenza virus F polypeptide or a metapneumovirus virus F polypeptide, that contains one or more neutralizing epitope of RSV F. Suitable neutralizing epitopes can be selected from the group consisting of the epitopes that are recognized by motavizumab, palivizumab, mAb 11, mAb 151, mAb 1129, mAb 1153, mAb 1200, mAb 1214, mAb 1237, mAb 47F, mAb 7C2, mAb B4, Fab 19, mAb AK13A2, mAb 7.936, mAb 9.936, mAb 19, mAb 20, mAb 101F and combinations thereof.

The invention relates to methods for inducing an anti-respiratory syncytial virus (RSV) immune response in a subject, comprising administering to the subject an effective amount of an immunogenic composition comprising a pre-fusion RSV F protein or a pre-fusion chimeric F protein. Preferably, the induced immune response is characterized by neutralizing antibodies to RSV and/or protective immunity against RSV.

In particular aspects, the invention relates to a method for inducing or raising neutralizing anti-respiratory syncytial virus (RSV) F protein antibodies in a subject, comprising administering to the subject an effective amount of an immunogenic composition comprising a pre-fusion RSV F protein or a pre-fusion chimeric F protein.

In particular aspects, the invention relates to a method for inducing or raising protective immunity against respiratory syncytial virus (RSV) in a subject, comprising administering to the subject an effective amount of an immunogenic composition comprising a pre-fusion RSV F protein or a pre-fusion chimeric F protein.

In particular aspects, the invention relates to immunogenic compositions comprising a pre-fusion respiratory syncytial virus (RSV) F protein or a pre-fusion chimeric F protein.

The pre-fusion RSV F protein that is used in the invention can be full length or truncated, such as a soluble ectodomain that lacks the cytoplasmic and transmembrane domains. The pre-fusion RSV F protein, e.g., full length or soluble ectodomain, may comprise functional furin cleavage sites at positions 109/110 and 136/137. In some preferred embodiments, that pre-fusion RSV F protein (e.g., full length or soluble ecto-domain) contains the amino acid sequence of the corresponding portion (e.g., ecto-domain) of a naturally occurring RSV F protein. In any of the aspects of the invention, the pre-fusion RSV F protein can be administered with or without an adjuvant as desired, and the immunogenic composition can comprise an adjuvant if desired.

BRIEF DESCRIPTION OF THE DRAWINGS

FIG. 2 A-C shows electron microscopy and circular dichroism analysis of the RSV F post-fusion trimer.

FIG. 3 A-F shows representative electron densities of the crystallized RSV F protein.

FIGS. 5 A and B shows superposition of domains I and II of RSV F and PIV3 F.

FIG. 6 A-D illustrates a comparison between RSV and PIV3.

FIGS. 7 A and B illustrates the Motavizumab epitope.

FIG. 8 A-C illustrates RSV F conformational changes, antigenic structure and Palivizumab binding. FIG. 8A is a surface representation of the post-fusion structure. Antigenic sites A and C are outlined and labeled. Asterisks indicate residues selected in neutralization escape variants or forming contacts with an antibody in the determined structures of neutralizing antibody-peptide complexes. The HRA and HRB surfaces are shaded. FIG. 8C is a graph showing inhibition of Palivizumab binding to post-fusion RSV F by pooled sera from un-immunized mice or mice immunized with the RSV F antigen. Palivizumab binding (percentage of ELISA signal without competing sera) is plotted as a function of the dilution of competing pooled sera.

FIGS. 9 A and B shows the exposure of the Motavizumab epitope in the post-fusion RSV F structure (A) and pre-fusion RSV F model (B).

FIGS. 10 A and B shows a model of neutralizing antibody 101F bound to the post-fusion RSV F trimer. FIG. 10B discloses "IIKTF" as SEQ ID NO: 37.

FIG. 11A (Center), The pre-fusion RSV F model is shaded/colored to show structural features which are labeled (THRB, HRA, DIII). FIG. 11B (Left) is a zoom-in view of the packing of HRA on domain III in the pre-fusion model. The paired numbers indicate residues in close proximity which, if mutated to cysteines could form a disulfide bond. FIG. 11C (Right) is a zoom-in view of the packing of the HRB-stalk on domains I and III (white). The paired numbers indicate residues which, if mutated to cysteines could form a disulfide bond. Amino acid residues 165 and 296, and 56 and 164 are not at ideal distances to one another, in the pre-fusion model, to form disulfide bonds, but are in correct orientation and can form disulfides if the model is biased by the PIV5 structure, on which the model was built.

(FIG. 15 A) Fusion peptide-stabilized RSV F rosettes migrated with the void volume by SEC (retention time of 5 minutes on Bio-Sil 250 SEC column). Anti-HIS-tag western blotting confirmed that the protein was in the void volume peak. (FIG. 15 B) Fusion peptide-deletion RSV F trimers migrated with an SEC retention time of approximately 6.5 minutes. Anti-HIS-tag western blot similarly confirmed that the protein was in the included volume trimer peak. Although the void peak is larger than the included volume peak, the anti-HIS western shows approximately equal amounts of RSV F are in the two peaks. (FIG. 15 C) These data show that the RSV F T58C V164C construct had a population of cleaved RSV F that was in the form of monodispersed trimers rather than rosettes, suggesting that population of the protein construct was in the prefusion form.

FIG. 16 A shows purification of the RSV F N165C/V296C construct. Columns are labeled for flow-through (FT), wash (W), elution (E) and resin (R) from a chelating purification. Unlike other protein constructs that contained introduced disulfide mutations and were expressed in insect cells, N165C/V296C secreted as a cleaved species, similar to its profile when expressed in mammalian cells. FIG. 16 B shows a gel-shift analysis of the K168C/V296C and M396C/F483C RSV F protein constructs. On the left side of the standards are the two constructs run with boiling and reducing agent present. On the right side of the standards, the two constructs are run after boiling with no reducing agent (b/nr) or no boiling and no reducing agent (nb/nr). The western blot shows the protein is largely uncleaved, but that unexpectedly no inter-chain disulfide bonds were formed. K168C/V296C without boiling shifted to the trimer band, while non-boiled M396C/F483C ran as a monomer band. FIG. 16 C shows a coomasie-stained gel of the K168C/V296C and M396C/F483C RSV F protein constructs with reducing and boiling. Approximately 50% of the material was cleaved.

FIGS. 18 A-E show analysis of several RSV F protein constructs.

DETAILED DESCRIPTION OF THE INVENTION

Definitions

Figure 1:
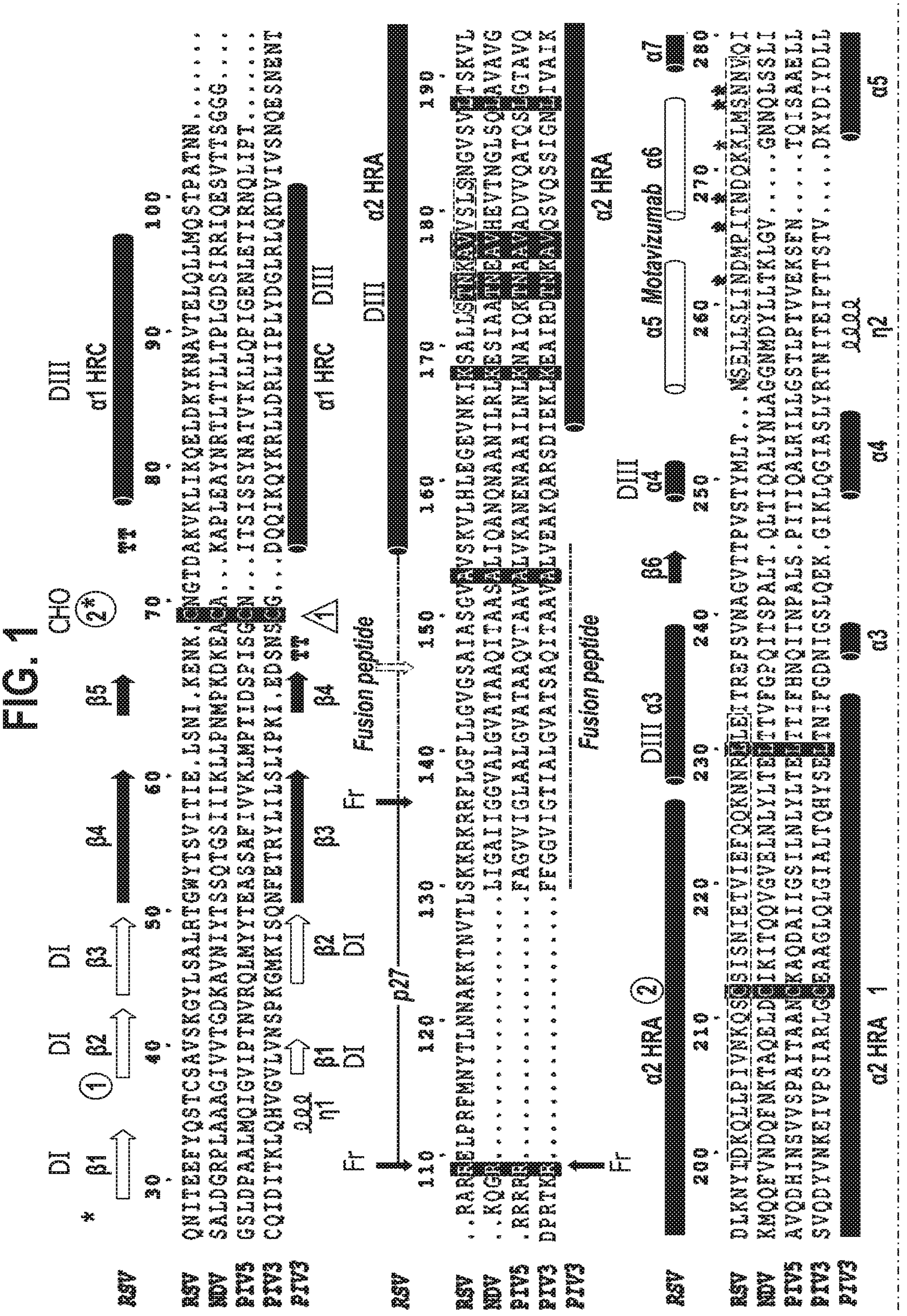
FIG. 1 shows a structure-based sequence alignment of four F proteins, secondary assignment, and key features. The alignment of RSV (SEQ ID NO:33), Newcastle disease virus (NDV) (SEQ ID NO:34), PIV3 (SEQ ID NO:36) and PIV5 (SEQ ID NO:35) Fs was generated with ClustalW2 (http://www.ebi.ac.uk/Tools/msa/clustalw2/), adjusted manually based on structural superposition using Lsqkab from the CCP4 suite of programs and displayed using ESPript version 2.2 (http://espript.ibcp.fr/ESPript/ESPript/). Features of RSV F are indicated above the sequences; features of PIV3 F are indicated below the sequences. *CHO indicates RSV F glycosylation sites. Secondary structure elements are indicated, with arrows parallel to the sequences designating β-sheets, cylinders designating α-helices, "TT" designating turns, and coils designating $3_{10}$ helices. The domain location of secondary structure symbols are indicated (DI, DII, DIII), except for RSV helices α5 and α6, which are labeled to indicate that they form the Motavizumab binding site and β20 and β21, which are labeled to indicate that they form the 101F binding site. Circled numbers (RSV) or triangled numbers (PIV3) designate residues that form disulfide bonds, with the same number for each partner in a disulfide-linked pair. The furin cleavage sites for RSV F and PIV3 F are indicated by vertical arrows labeled Fr. The RSV F p27 region released from the protein after furin cleavage is indicated by a black bar. The fusion peptides of RSV F and PIV3 F are labeled. The arrow in the fusion peptide indicates the first residue of the F1 fragment in the fusion peptide deletion construct used in this study. Residues that are identical in all four proteins are indicated by shaded boxes. Peptides used to investigate neutralizing binding sites are in open boxes and resistance mutations are indicated by asterisks.

As used herein, "pre-fusion" RSV F proteins are RSV F proteins that share general structural architecture more similar to the PIV5 pre-fusion structure rather than the RSV F post-fusion structure. Pre-fusion RSV F proteins include the following characteristics: the HRA region is packed against domain III in the RSV F head region and/or the HRB region forms a trimer coil-coil stalk in proximity to domains I and II rather than associating with the HRA region in the context of the 6-helix bundle.

As used herein, "post-fusion conformation" of RSV F protein are RSV F proteins that share more general structural architecture with the RSV F post-fusion structure rather than the PIV5 pre-fusion structure. Post-fusion RSV F proteins include an HRA-HRB 6-helix bundle.

As used herein, HRA region in prefusion RSV F is approximately residues 137-239 of RSV F protein (SEQ ID NOS: 1 and 2) and comprises the fusion peptide, helix α1, helix α2, helix α3, helix α4, strand β31 and strand P2. See, FIG. 9B.

As used herein, the HRA helix in post fusion RSV F is formed by approximately residues 155-226 of RSV F protein (SEQ ID NOS: 1 and 2).

As used herein, the fusion peptide is defined by residues 137-154 of RSV F protein (SEQ ID NOS: 1 and 2).

As used herein, helix α1 in the prefusion RSV F HRA region is formed by approximately residues 145-157 of RSV F protein (SEQ ID NOS: 1 and 2).

As used herein, helix α2 in the prefusion RSV F HRA region is formed by approximately residues 158-167 of RSV F protein (SEQ ID NOS: 1 and 2).

As used herein, helix α3 in the prefusion RSV F HRA region is formed by approximately residues 168-176 of RSV F protein (SEQ ID NOS: 1 and 2).

As used herein, helix α4 in the prefusion RSV F HRA region is formed by approximately residues 194-212 of RSV F protein (SEQ ID NOS: 1 and 2).

As used herein, strand β31 in the prefusion RSV F HRA region is formed by approximately residues 177-184 of RSV F protein (SEQ ID NOS: 1 and 2).

As used herein, strand β2 in the prefusion RSV F HRA region is formed by approximately residues 185-193 of RSV F protein (SEQ ID NOS: 1 and 2).

As used herein, HRB region in RSV F is approximately residues 461-515 of RSV F protein (SEQ ID NOS: 1 and 2) and includes the HRB helix and the HRB linker As used herein, the HRB helix in RSV F is formed by approximately residues 485-515 of RSV F protein (SEQ ID NOS: 1 and 2).

As used herein, the HRB linker in RSV F is formed by approximately residues 461-484 of RSV F protein (SEQ ID NOS: 1 and 2).

As used herein, domain I (DI) is formed by approximately residues 26-50 and 309-401 of RSV F protein (SEQ ID NOS: 1 and 2).

As used herein, domain II (DII) is formed by approximately residues 400-460 of RSV F protein (SEQ ID NOS: 1 and 2).

As used herein, domain III (DIII) is formed by approximately residues 51-98 and 206-308, or residues 51-308 of RSV F protein (SEQ ID NOS: 1 and 2).

As used herein, a "purified" protein or polypeptide is a protein or polypeptide which is recombinantly or synthetically produced, or produced by its natural host, and has been isolated from other components of the recombinant or synthetic production system or natural host such that the amount of the protein relative to other macromolecular components present in a composition is substantially higher than that present in a crude preparation. In general, a purified protein will be at least about 50% homogeneous and more preferably at least about 75%, at least about 80%, at least about 85%, at least about 90%, at least about 95% or substantially homogeneous.

As used herein, "substantially free of lipids and lipoproteins" refers to compositions, proteins and polypeptides that are at least about 95% free of lipids and lipoproteins on a mass basis when protein and/or polypeptide (e.g., RSV F polypeptide) purity is observed on an SDS PAGE gel and total protein content is measured using either UV280 absorption or BCA analysis, and lipid and lipoprotein content is determined using the Phospholipase C assay (Wako, code no. 433-36201).

As used herein, "close proximity" refers to a distance of not more than about 10 Å, not more than about 8 Å, not more than about 6 Å, not more than about 4 Å, or not more than about 2 Å. When two or more amino acid residues are in close proximity, the distance between the alpha carbons of the amino acid residues are is more than about 10 Å, not more than about 8 Å, not more than about 6 Å, not more than about 4 Å, or not more than about 2 Å.

Features of RSV F protein suitable for use in this invention are described herein with reference to particular amino acids that are identified by the position of the amino acid in the sequence of RSV F protein from the A2 strain (SEQ ID NO:1). RSV F proteins can have the amino acid sequence of the F protein from the A2 strain or any other desired strain. When the F protein from a strain other than the A2 strain is used, the amino acids of the F protein are to be numbered with reference to the numbering of the F protein from the A2 strain, with the insertion of gaps as needed. This can be achieved by aligning the sequence of any desired RSV F protein with the F protein of the strain A2. Sequence alignments are preferably produced using the algorithm disclosed by Corpet, Nucleic Acids Research, 1998, 16(22): 10881-10890, using default parameters (Blossum 62 symbol comparison table, gap open penalty: 12, gap extension penalty: 2).

As described and exemplified herein, the 3.2 Å x-ray crystal structure of a post-fusion form of RSV F protein has been determined. A model of the pre-fusion form of RSV F protein was made by comparing the RSV F post-fusion x-ray crystal structure to the known structures of the pre- and post-fusion parainfluenza virus F proteins. This model of the pre-fusion form of RSV F reveals structural features that differ from those of prior models of pre-fusion RSV F and allows for rational structure-based design of stabilized pre-fusion forms of RSV F.

Accordingly, the invention relates to pre-fusion respiratory syncytial virus F (RSV F) polypeptides and/or proteins, and immunogenic compositions comprising pre-fusion RSV F polypeptides and/or proteins. The invention also relates to methods and use of pre-fusion RSV F polypeptides and/or proteins for inducing an immune response, and or by protective immunity against RSV. The invention also relates to nucleic acids that encode pre-fusion RSV F polypeptides and/or proteins.

Generally, the immunogenic compositions comprise pre-fusion RSV F polypeptides and/or proteins that elicit neutralizing antibodies. For example, antibodies that bind to the same epitopes as Palivizumab, Motavizumab and 101F.

Figure 9A:
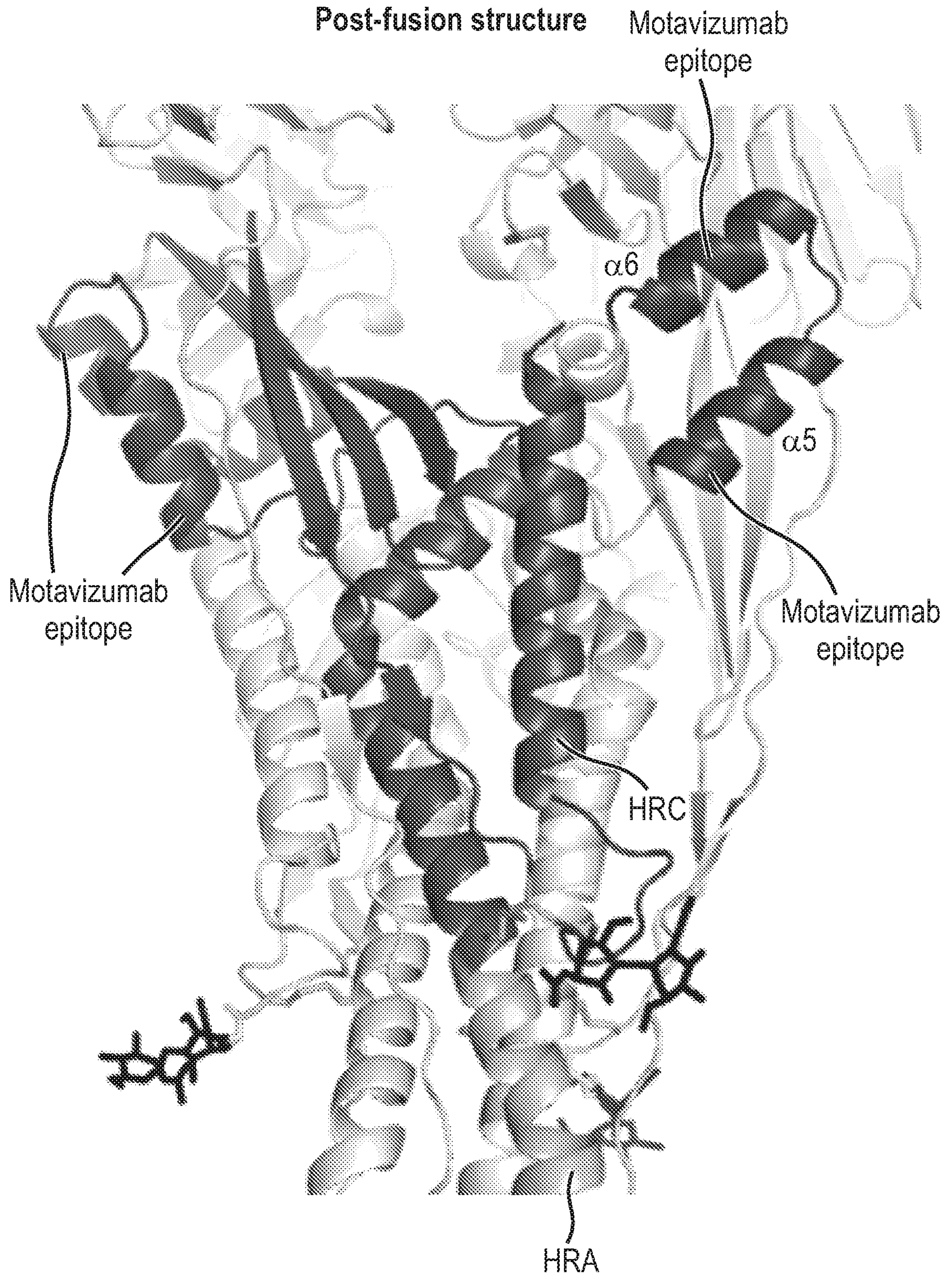
FIG. 9A shows Domain III of one subunit from the post-fusion structure shaded black and grey while the remaining parts of RSV F are in white. Structural elements that do not significantly change between pre- and post-fusion are in black while HRA (labeled with arrow), which refolds in the transition from the pre- to post-fusion conformation, is lighter grey. Motavizumab epitopes on two subunits are also labeled. A third Motavizumab epitope is present on the trimer surface, but is not easily visible in this orientation. The Motavizumab epitope α5 and α6 helices are labeled on one example.
Figure 9B:
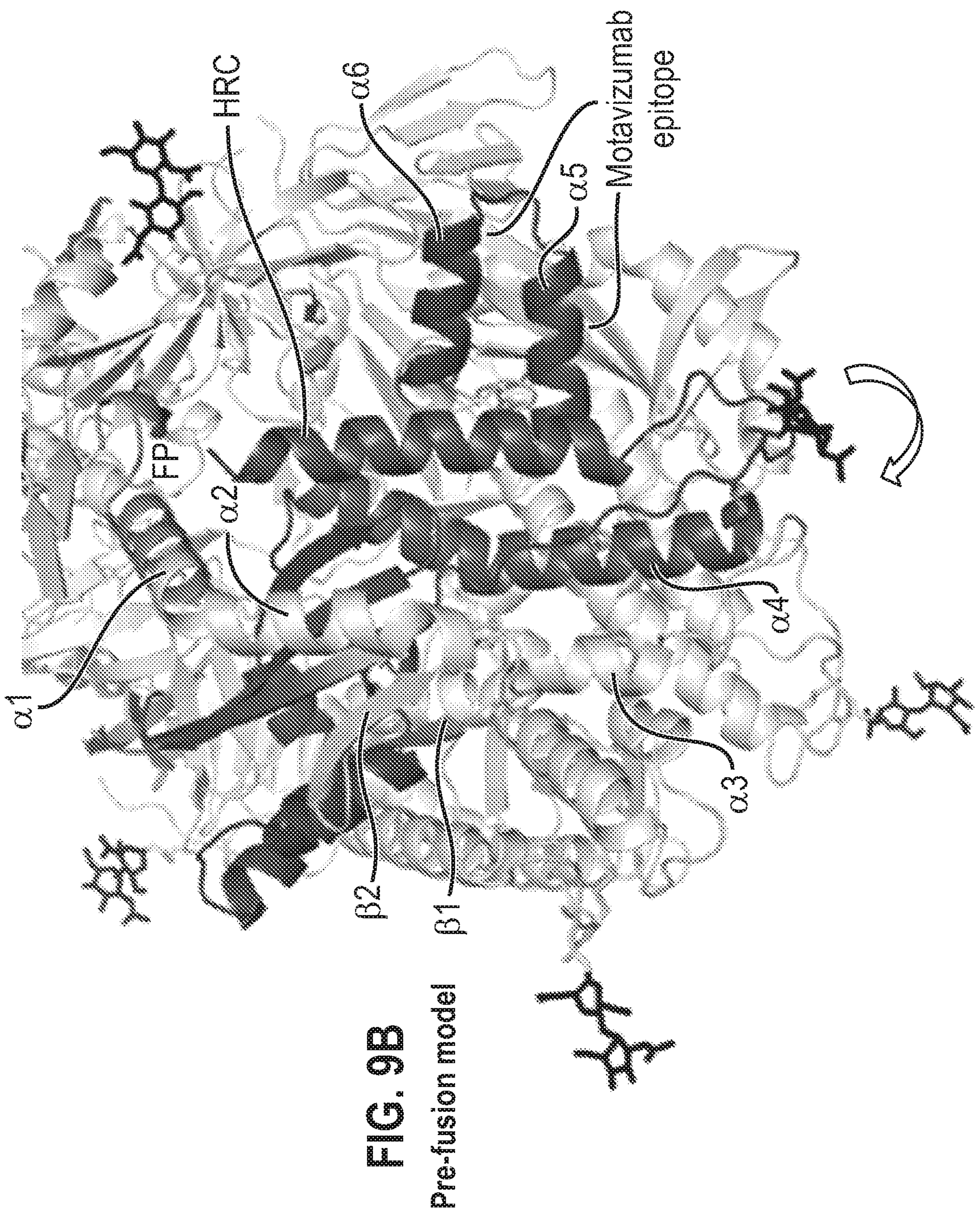
FIG. 9B shows Domain III of the pre-fusion model shaded as in A. The fusion peptide region is shaded and labeled FP. The HRA region is broken into structural elements α1, α2, α3, β1 and β2; labeled and shaded grey for one subunit. In both the pre-fusion and post-fusion structures, the α5 and α6 helices of the Motavizumab epitope are surface exposed. However, in the pre-fusion model, the HRC loop may need to shift to accommodate antibody binding (as indicated by the arrow).

Pre-fusion and post-fusion PIV F structures reveal en bloc shifts of domains and large rearrangements of HRA and HRB. In domain III of the pre-fusion PIV5 structure, HRA folds into three α-helices and two β-strands rather than the long post-fusion HRA helix (Yin et al, 2006). However, when pre-fusion and post-fusion conformations of individual PIV F domains are compared, the non-rearranging parts superimpose well. Superimposing post-fusion RSV F domains on their pre-fusion PIV5 F counterparts did not result in major clashes and positioned all the pairs of cysteines that form interdomain disulfide bonds in proximity to each other. The pre-fusion RSV F model obtained by thus combining information from the post-fusion RSV F x-ray crystal structure and the pre-fusion PIV5 F structure revealed a feature not apparent from prior homology models of pre-fusion RSV F based solely on the PIV5 pre-fusion structure (McLellan et al *NSMB* 2010 (141)). The helices of the Palivizumab/Motivizumab epitope are exposed on the surface of the pre-fusion RSV F trimer model, as they are on post-fusion RSV F trimer x-ray crystal structure (FIG. 9). In our pre-fusion RSV F model, the loop connecting β4 and HRC (part of domain III) could hinder access of Palivizumab or Motavizumab to their epitope. However, it is likely that the loop has sufficient flexibility to adopt an alternative conformation that permits antibody binding (FIG. 9B).

The pre-fusion model disclosed herein, which is based on the RSV F post-fusion x-ray crystal structure and the PIV5 prefusion structure (Yin et al, 2006 (145)), shows that the elongated HRA helix of the post-fusion RSV F (residues 137-212) folds into strands and helices similar to the PIV5 pre-fusion crystal structure. The fusion peptide of RSV F, residues 137-154, forms a coil and helix that is packed into the RSV F pre-fusion head. Four helices are formed; helix a1 is approximately residues 145-157, helix a2 is approximately residues 158-167, helix a3 is approximately residues 168-176 and helix a4 is approximately residues 194-212. Two strands are formed; strand b1 is approximately residues 177-184, strand b2 is approximately residues 185-193 (FIG. 9).

Pre-Fusion Conformation

The invention includes pre-fusion RSV F polypeptides and proteins and immunogenic compositions that contain pre-fusion RSV F polypeptides and proteins. The RSV F protein and polypeptides can contain 1 or more amino acid replacements, deletions and/or additions that stabilize the pre-fusion conformation or destabilize the post-fusion conformation, for example, a pre-fusion RSV F stabilized with disulfide bonds, or a pre-fusion RSV F formed by destabilizing the post-fusion conformation.

Stabilization Through Disulfide Bonds

The RSV F pre-fusion model may be used as a guide to select amino acid residues that are in close proximity to each other in the pre-fusion conformation and that are no longer in close proximity in the post-fusion conformation. Such amino acids may be mutated to cysteine residues to allow disulfide formation that stabilizes the prefusion conformation, for example by preventing the HRB helix from associating with the HRA helix, thus preventing refolding to the post-fusion conformation.

A stabilized pre-fusion RSV F protein of the invention may comprise a disulfide bond between any two structural elements, or between one structural element and the remainder of the RSV F protein, or between a structural element of one subunit of a trimer and a structural element of another subunit of the same trimer. Generally, a first amino acid in one structural element and a second amino acid that is in a different structural element, or the same structural element on a separate monomer, and that is also in close proximity to the first amino acid in the prefusion model are selected for replacement with cysteine. The distance between the residues (e.g., the alpha carbons) can be less than about 10 Å, less than about 8 Å, less than about 6 Å, less than about 5 Å, less than about 4 Å, or less than about 3 Å. The cysteine replacements of the first amino acid and the second amino acid, and a disulfide bond between them can be modeled. The length of the modeled disulfide bond, in some embodiments, does not exactly match the ~2 Å length considered to be optimal for disulfide bonds. Preferably, the modeled disulfide bond length (distance between sulfur nuclei) is about 0.5 Å-3.5 Å, about 1.0 Å-3.0 Å, or about 1.5 Å-2.5 Å, which, due to structural flexibility, are expected to form disulfide bonds in the protein.

In one embodiment, pre-fusion RSV F protein may be stabilized in the pre-fusion conformation through the introduction of at least one cysteine mutation in a first structural element in close proximity to at least one other cysteine (natural or introduced) in a second structural element or the remaining RSV F head region. Disulfide bonds form between the introduced cysteine that prevent the post-fusion HRA-HRB six-helix bundle from forming. For example, pre-fusion RSV F protein may be stabilized in the pre-fusion conformation through the introduction of at least one cysteine mutation in the HRA helix region, HRB helix region, the fusion peptide, helix α1, helix α2, helix α3, helix α4, strand β1, strand 02, DI, DII, or DIII in close proximity to at least one other cysteine (natural or introduced) in a different structural region (e.g., selected from the HRA helix region, HRB helix region, the fusion peptide, helix α1, helix α2, helix α3, helix α4, strand β1, strand β2, DI, DII, or DIII), thereby forming one or more disulfide bridges that would prevent the post-fusion HRA-HRB six-helix bundle from forming.

The cysteines may be introduced to the HRB or the HRB linker to create disulfide bonds between the cysteines. In one embodiment, one or more cysteines may be introduced to the HRB linker and helix region (approximately residues 452 to 515) to form disulfides with portions of the RSV F head region. In another embodiment, a disulfide bond between the HRB linker or helix and the remainder of the RSV F protein may be used to stabilize the protein in the pre-fusion conformation. In a preferred embodiment, a disulfide bridge is formed between the HRB pre-fusion stalk and the DI or DII region at the "top" of the head (e.g., M396C+F483C).

In a preferred embodiment, the pre-fusion RSV F protein comprises two cysteine mutations, M396C and F483C, thereby comprising a disulfide bond between the HRB pre-fusion stalk and the DI region.

In other preferred embodiments, a disulfide bridge is formed between the HRA region and DIII region. For example, the RSV F protein can contain amino acid replacements selected from the group consisting of V56C+V164C, I57C+S190C, T58C+V164C, N165C+V296C, K168C+V296C, and combinations thereof.

In one embodiment, the pre-fusion RSV F protein comprises a first cysteine mutation in the HRA region, and a second cysteine (natural or introduced) in the fusion peptide, helix α1, helix α2, helix α3, helix α4, strand β1, strand β2 of the pre-fusion HRA region, or DIII. In this embodiment, the protein comprises a disulfide bond between the first and second cysteine that prevents the post fusion HRA-HRB six-helix bundle from forming.

In one embodiment, the pre-fusion RSV F protein comprises a first cysteine mutation in the HRB helix region, and a second cysteine (natural or introduced) in DI or DII. In this embodiment, the protein comprises a disulfide bond between the first and second cysteine that prevents the post-fusion HRA-HRB six-helix bundle from forming.

In one embodiment, the pre-fusion RSV F protein comprises a first cysteine mutation in the fusion peptide, and a second cysteine (natural or introduced) in the HRA region, helix α1, helix α2, helix α3, helix α4, strand β1, strand β2 or DIII. In this embodiment, the protein comprises a disulfide bond between the first and second cysteine that prevents the post-fusion HRA elongated helix from forming.

In one embodiment, the pre-fusion RSV F protein comprises a first cysteine mutation in the helix α1, and a second cysteine (natural or introduced) in the HRA region, the fusion peptide, helix α2, helix α3, helix α4, strand β1, strand β2, or DIII. In this embodiment, the protein comprises a disulfide bond between the first and second cysteine that prevents the post-fusion HRA-HRB six-helix bundle from forming.

In one embodiment, the pre-fusion RSV F protein comprises a first cysteine mutation in the helix α2, and a second cysteine (natural or introduced) in the HRA region, the fusion peptide, helix α1, helix α3, helix α4, strand β1, strand β2, or DIII. In this embodiment, the protein comprises a disulfide bond between the first and second cysteine that prevents the post-fusion HRA-HRB six-helix bundle from forming.

In one embodiment, the pre-fusion RSV F protein comprises a first cysteine mutation in the helix 3, and a second cysteine (natural or introduced) in the HRA region, the fusion peptide, helix α1, helix α2, helix α4, strand β1, strand β2, or DIII. In this embodiment, the protein comprises a disulfide bond between the first and second cysteine that prevents the post-fusion HRA-HRB six-helix bundle from forming.

In one embodiment, the pre-fusion RSV F protein comprises a first cysteine mutation in the helix α4, and a second cysteine (natural or introduced) in the HRA region, the fusion peptide, helix α1, helix α2, helix 3, strand β1, strand β2, or DIII. In this embodiment, the protein comprises a disulfide bond between the first and second cysteine that prevents the post-fusion HRA-HRB six-helix bundle from forming.

In one embodiment, the pre-fusion RSV F protein comprises a first cysteine mutation in the strand β1, and a second cysteine (natural or introduced) in the HRA region, the fusion peptide, helix α1, helix α2, helix 3, helix α4, strand β2, or DIII. In this embodiment, the protein comprises a disulfide bond between the first and second cysteine that prevents the post-fusion HRA-HRB six-helix bundle from forming.

In one embodiment, the pre-fusion RSV F protein comprises a first cysteine mutation in the strand β2, and a cysteine (natural or introduced) in the HRA helix region, the fusion peptide, helix α1, helix α2, helix 3, helix α4, strand β1, DI, DII, or DIII. In this embodiment, the protein comprises a disulfide bond between the first and second cysteine that prevents the post-fusion HRA-HRB six-helix bundle from forming.

In one embodiment, the pre-fusion RSV F protein comprises a first cysteine mutation in the DI region, and a second cysteine (natural or introduced) in the HRB helix region. In this embodiment, the protein comprises a disulfide bond between the first and second cysteine that prevents the post-fusion HRA-HRB six-helix bundle from forming.

In one embodiment, the pre-fusion RSV F protein comprises a first cysteine mutation in the DII region, and a second cysteine (natural or introduced) in the HRB helix region. In this embodiment, the protein comprises a disulfide bond between the first and second cysteine that prevents the post-fusion HRA-HRB six-helix bundle from forming.

In one embodiment, the pre-fusion RSV F protein comprises a first cysteine mutation in the DIII region, and a second cysteine (natural or introduced) in the HRA helix region. In this embodiment, the protein comprises a disulfide bond between the first and second cysteine that prevents the post-fusion HRA-HRB six-helix bundle from forming.

In another embodiment, the pre-fusion RSV F protein comprises a first introduced cysteine in the HRA helix region, HRB helix region, the fusion peptide, helix α1, helix α2, helix α3, helix α4, strand β1, strand β2, DI, DII, or DIII region and a second cysteine (natural or introduced) in any other region of the RSV F protein that is in close proximity to the introduced cysteine. In this embodiment, the protein comprises a disulfide bond between the first and second cysteine that prevents the post-fusion HRA-HRB six-helix bundle from forming.

In a specific embodiment, the pre-fusion RSV F protein comprises two cysteine mutations selected from the group consisting of V56C+V164C, I57C+S190C, T58C+V164C, N165C+V296C, and K168C+V296C, and combinations thereof, thereby comprising a disulfide bridge between the HRA region and the DIII region.

In one embodiment, the pre-fusion RSV F protein comprises two cysteine mutations, V56C and V164C, thereby comprising a disulfide bridge between the HRA region and the DIII region.

In one embodiment, the pre-fusion RSV F protein comprises two cysteine mutations, I57C and S190C, thereby comprising a disulfide bridge between the HRA region and the DIII region.

In one embodiment, the pre-fusion RSV F protein comprises two cysteine mutations, T58C and V164C, thereby comprising a disulfide bridge between the HRA region and the DIII region.

In one embodiment, the pre-fusion RSV F protein comprises two cysteine mutations, N165C and T296C, thereby comprising a disulfide bridge between the HRA region and the DIII region.

In one embodiment, the pre-fusion RSV F protein comprises two cysteine mutations, K168C and T296C, thereby comprising a disulfide bridge between the HRA region and the DIII region.

In one embodiment, the pre-fusion RSV F protein comprises two cysteine mutations, M396C+F483C, thereby comprising a disulfide bridge between the HRB region and the DII region.

The RSV F pre-fusion protein of the present invention is stabilized in the pre-fusion conformation by mutations that stabilize the pre-fusion subunit, which forms trimers.

In some embodiments, the RSV F pre-fusion protein of the present invention is a trimer of RSV F monomers, and pre-fusion conformation is stabilized by one or more disulfide bonds between cysteine residues that are introduced into different monomers.

Exemplary amino acid sequences of RSV F monomers that contain introduced cysteine residues that stabilize the pre-fusion conformation are presented below (SEQ ID NOS: 4-9). The presented sequences contain a signal peptide and a HIS tag (GGSAGSGHIIHH; SEQ ID NO:3). The pre-fusion RSV F protein of the invention can contain any of the amino acid sequences shown below, with or without the signal peptide and/or HIS tag.

>RSV F HRA disulfide1 (V56C + V164C)

(SEQ ID NO: 4)

MELLILKANAITTILTAVTFCFASGQNITEEFYQSTCSAVSKGYLSALRTGWYTSCITIELSNIKEN

KCNGTDAKVKLIKQELDKYKNAVTELQLLMQSTPATNNRARRELPRFMNYTLNNAKKTNVTLSKKRK

RRFLGFLLGVGSAIASGVAVSKVLHLEGECNKIKSALLSTNKAVVSLSNGVSVLTSKVLDLKNYIDK

QLLPIVNKQSCSISNIETVIEFQQKNNRLLEITREFSVNAGVTTPVSTYMLTNSELLSLINDMPITN

DQKKLMSNNVQIVRQQSYSIMSIIKEEVLAYVVQLPLYGVIDTPCWKLHTSPLCTTNTKEGSNICLT

RTDRGWYCDNAGSVSFFPQAETCKVQSNRVFCDTMNSLTLPSEVNLCNVDIFNPKYDCKIMTSKTDV

-continued

SSSVITSLGAIVSCYGKTKCTASNKNRGIIKTFSNGCDYVSNKGVDTVSVGNTLYYVNKQEGKSLYV

KGEPIINFYDPLVFPSDEFDASISQVNEKINQSLAFIRKSDELLHNVNAGKSTTNGGSAGSGHHHHH

H

>RSV F HRA disulfide2 (I57C + S190C)

(SEQ ID NO: 5)

MELLILKANAITTILTAVTFCFASGQNITEEFYQSTCSAVSKGYLSALRTGWYTSVCTIELSNIKEN

KCNGTDAKVKLIKQELDKYKNAVTELQLLMQSTPATNNRARRELPRFMNYTLNNAKKTNVTLSKKRK

RRFLGFLLGVGSAIASGVAVSKVLHLEGEVNKIKSALLSTNKAVVSLSNGVSVLTCKVLDLKNYIDK

QLLPIVNKQSCSISNIETVIEFQQKNNRLLEITREFSVNAGVTTPVSTYMLTNSELLSLINDMPITN

DQKKLMSNNVQIVRQQSYSIMSIIKEEVLAYVVQLPLYGVIDTPCWKLHTSPLCTTNTKEGSNICLT

RTDRGWYCDNAGSVSFFPQAETCKVQSNRVFCDTMNSLTLPSEVNLCNVDIFNPKYDCKIMTSKTDV

SSSVITSLGAIVSCYGKTKCTASNKNRGIIKTFSNGCDYVSNKGVDTVSVGNTLYYVNKQEGKSLYV

KGEPIINFYDPLVFPSDEFDASISQVNEKINQSLAFIRKSDELLHNVNAGKSTTNGGSAGSGHHHHH

H

>RSV F HRA disulfide3 (T58C + V164C)

(SEQ ID NO: 6)

MELLILKANAITTILTAVTFCFASGQNITEEFYQSTCSAVSKGYLSALRTGWYTSVICIELSNIKEN

KCNGTDAKVKLIKQELDKYKNAVTELQLLMQSTPATNNRARRELPRFMNYTLNNAKKTNVTLSKKRK

RRFLGFLLGVGSAIASGVAVSKVLHLEGECNKIKSALLSTNKAVVSLSNGVSVLTSKVLDLKNYIDK

QLLPIVNKQSCSISNIETVIEFQQKNNRLLEITREFSVNAGVTTPVSTYMLTNSELLSLINDMPITN

DQKKLMSNNVQIVRQQSYSIMSIIKEEVLAYVVQLPLYGVIDTPCWKLHTSPLCTTNTKEGSNICLT

RTDRGWYCDNAGSVSFFPQAETCKVQSNRVFCDTMNSLTLPSEVNLCNVDIFNPKYDCKIMTSKTDV

SSSVITSLGAIVSCYGKTKCTASNKNRGIIKTFSNGCDYVSNKGVDTVSVGNTLYYVNKQEGKSLYV

KGEPIINFYDPLVFPSDEFDASISQVNEKINQSLAFIRKSDELLHNVNAGKSTTNGGSAGSGHHHHH

H

>RSV F HRA disulfide4 (N165C + V296C)

(SEQ ID NO: 7)

MELLILKANAITTILTAVTFCFASGQNITEEFYQSTCSAVSKGYLSALRTGWYTSVITIELSNIKEN

KCNGTDAKVKLIKQELDKYKNAVTELQLLMQSTPATNNRARRELPRFMNYTLNNAKKTNVTLSKKRK

RRFLGFLLGVGSAIASGVAVSKVLHLEGEVCKIKSALLSTNKAVVSLSNGVSVLTSKVLDLKNYIDK

QLLPIVNKQSCSISNIETVIEFQQKNNRLLEITREFSVNAGVTTPVSTYMLTNSELLSLINDMPITN

DQKKLMSNNVQIVRQQSYSIMSIIKEECLAYVVQLPLYGVIDTPCWKLHTSPLCTTNTKEGSNICLT

RTDRGWYCDNAGSVSFFPQAETCKVQSNRVFCDTMNSLTLPSEVNLCNVDIFNPKYDCKIMTSKTDV

SSSVITSLGAIVSCYGKTKCTASNKNRGIIKTFSNGCDYVSNKGVDTVSVGNTLYYVNKQEGKSLYV

KGEPIINFYDPLVFPSDEFDASISQVNEKINQSLAFIRKSDELLHNVNAGKSTTNGGSAGSGHHHHH

H

>RSV F HRA disulfide5 (K168C + V296C)

(SEQ ID NO: 8)

MELLILKANAITTILTAVTFCFASGQNITEEFYQSTCSAVSKGYLSALRTGWYTSVITIELSNIKEN

KCNGTDAKVKLIKQELDKYKNAVTELQLLMQSTPATNNRARRELPRFMNYTLNNAKKTNVTLSKKRK

RRFLGFLLGVGSAIASGVAVSKVLHLEGEVNKICSALLSTNKAVVSLSNGVSVLTSKVLDLKNYIDK

QLLPIVNKQSCSISNIETVIEFQQKNNRLLEITREFSVNAGVTTPVSTYMLTNSELLSLINDMPITN

DQKKLMSNNVQIVRQQSYSIMSIIKEECLAYVVQLPLYGVIDTPCWKLHTSPLCTTNTKEGSNICLT

RTDRGWYCDNAGSVSFFPQAETCKVQSNRVFCDTMNSLTLPSEVNLCNVDIFNPKYDCKIMTSKTDV

-continued

```
SSSVITSLGAIVSCYGKTKCTASNKNRGIIKTFSNGCDYVSNKGVDTVSVGNTLYYVNKQEGKSLYV

KGEPIINFYDPLVFPSDEFDASISQVNEKINQSLAFIRKSDELLHNVNAGKSTTNGGSAGSGHHHHH

H

>RSV F HRB disulfide (M396C + F483C)
                                                    (SEQ ID NO: 9)
MELLILKANAITTILTAVTFCFASGQNITEEFYQSTCSAVSKGYLSALRTGWYTSVITIELSNIKEN

KCNGTDAKVKLIKQELDKYKNAVTELQLLMQSTPATNNRARRELPRFMNYTLNNAKKTNVTLSKKRK

RRFLGFLLGVGSAIASGVAVSKVLHLEGEVNKIKSALLSTNKAVVSLSNGVSVLTSKVLDLKNYIDK

QLLPIVNKQSCSISNIETVIEFQQKNNRLLEITREFSVNAGVTTPVSTYMLTNSELLSLINDMPITN

DQKKLMSNNVQIVRQQSYSIMSIIKEEVLAYVVQLPLYGVIDTPCWKLHTSPLCTTNTKEGSNICLT

RTDRGWYCDNAGSVSFFPQAETCKVQSNRVFCDTMNSLTLPSEVNLCNVDIFNPKYDCKICTSKTDV

SSSVITSLGAIVSCYGKTKCTASNKNRGIIKTFSNGCDYVSNKGVDTVSVGNTLYYVNKQEGKSLYV

KGEPIINFYDPLVCPSDEFDASISQVNEKINQSLAFIRKSDELLHNVNAGKSTTNGGSAGSGHHHHH

H
```

Destabilization of Post-Fusion RSV F

A major feature of the RSV F post-fusion structure is the 6-helix bundle in the stalk region. In the post-fusion conformation, the three HRA helices and the three HRB helices form a very stable 6-helix bundle. An alternative strategy for producing a stabilized pre-fusion RSV F protein of the invention, is by destabilizing the post-fusion 6-helix bundle, and/or preventing the 6-helix bundle formation (e.g., through deletion of the HRB helix, introduction of point mutations, addition of glycosylation or other modification sites).

The 6-helix bundle formation may be prevented by deleting the HRA helix or the HRB helix.

Preferably, the HRB helical region is deleted or mutated to prevent formation of the post-fusion conformation. The HRB region forms the stalk of the RSV F pre-fusion conformation, is in close proximity to the viral membrane and likely does not contain important neutralizing epitopes. Deletion of the HRB helix (residues 484 and C-terminal) may prevent the refolding of the RSV F protein from the pre-fusion state to the post-fusion state.

A stabilized pre-fusion RSV F protein of the invention may comprise the RSV ectodomain sequence with the HRB region deleted or mutated, and preferably further comprises an additional mutation or deletion to the remaining ectodomain sequence. For example, the RSV ectodomain may comprise one or more introduced cysteines to create disulfide bridges that stabilize the prefusion structure as described herein, mutated or deleted furin cleavage sites, mutated or deleted fusion peptide sequence, or other mutations previously described in WO 2011/008974, incorporated herein in its entirety. The RSV ectodomain may be the ectodomain of a naturally occurring RSV F protein, or it may contain mutations in addition to the deletions and/or mutations of the HRA or HRB region.

In one embodiment, the stabilized pre-fusion RSV F protein comprises an ectodomain of a naturally occurring RSV F protein in which the HRB region is deleted and one or more mutations that prevent cleavage at one or both of the furin cleavage sites (i.e, amino acids 109 and 136 of SEQ ID NOS:1 and 2) are present.

In one embodiment, the stabilized pre-fusion RSV F protein comprises an ectodomain of a naturally occurring RSV F protein in which the HRB region is deleted and the fusion peptide is mutated (amino acids 137 and 153 of SEQ ID NOS: 1 or 2). For example, this region can be deleted in whole or in part.

In another embodiment, the stabilized pre-fusion RSV F protein comprises a wild-type RSV ectodomain in which the HRB region and the fusion peptide is deleted, in whole or in part.

In another embodiment, the stabilized pre-fusion RSV F protein comprises a wild-type RSV ectodomain in which the HRB region is deleted and an oligomerization sequence has been added. When an oligomerization sequence is present, it is preferably a trimerization sequence. Suitable oligomerization sequences are well known in the art and include, for example, the coiled coil of the yeast GCN4 leucine zipper protein, trimerizing sequence from bacteriophage T4 fibritin ("foldon"), and the trimer domain of influenza HA.

In another embodiment, the stabilized pre-fusion RSV F protein comprises a wild-type RSV ectodomain in which the HRB region is deleted and the p27 region is mutated (amino acids 110-136 of SEQ ID NOS: 1 or 2), including deletion of the p27 region in whole or in part. For example, lysine and/or arginine residues in the p27 region (about amino acids 110-136 of SEQ ID NOS: 1 or 2) can be substituted or deleted.

In another embodiment, the stabilized pre-fusion RSV F protein comprises a wild-type RSV ectodomain in which the HRB region is deleted and an amino acid sequence that provides a protease cleavage site is added. Generally, the amino acid sequence that provides a protease cleavage site will be located within about 60 amino acids, about 50 amino acids, about 40 amino acids, about 30 amino acids, about 20 amino acids, about 10 amino acids, or substantially adjacent to the amino terminus of the transmembrane domain (amino acid 525 of SEQ ID NO:1 or 2).

An exemplary amino acid sequence of an RSV F monomer in which the fusion peptide and HRB are deleted to stabilize the pre-fusion conformation is presented below (SEQ ID NO: 10). The presented sequence contains a signal peptide and a HIS tag (GGSAGSGHIIHH; SEQ ID NO:3). The pre-fusion RSV F protein of the invention can contain the amino acid sequences shown below, with or without the signal peptide and/or HIS tag.

```
>RSV F delHRB fusion peptide deletion HIS
                                        (SEQ ID NO: 10)
MELLILKANAITTILTAVTFCFASGQNITEEFYQSTCSAVSKGYLSAL

RTGWYTSVITIELSNIKENKCNGTDAKVKLIKQELDKYKNAVTELQLL

MQSTPATNNRARRELPRFMNYTLNNAKKTNVTLSKKRKRRSAIASGVA

VSKVLHLEGEVNKIKSALLSTNKAVVSLSNGVSVLTSKVLDLKNYIDK

QLLPIVNKQSCSISNIETVIEFQQKNNRLLEITREFSVNAGVTTPVST

YMLTNSELLSLINDMPITNDQKKLMSNNVQIVRQQSYSIMSIIKEEVL

AYVVQLPLYGVIDTPCWKLHTSPLCTTNTKEGSNICLTRTDRGWYCDN

AGSVSFFPQAETCKVQSNRVFCDTMNSLTLPSEVNLCNVDIFNPKYDC

KIMTSKTDVSSSVITSLGAIVSCYGKTKCTASNKNRGIIKTFSNGCDY

VSNKGVDTVSVGNTLYYVNKQEGKSLYVKGEPIINFYDPLVFPSGGSA

GSGHHHHHH
```

The stabilized pre-fusion RSV F protein of the invention may also be formed by hindering 6-helix bundle formation in the HRA or HRB regions (approximately residues 154-212 and 484 to 513, respectively) through engineered point mutations or introduction of glycosylation sites (e.g., AsnXaaSer/Thr; SEQ ID NO:11) or other modification sites (e.g., lipidation, phosphorylation). Glycosylation sites, or other post-translational modification sites or point mutations which interfere with 6-helix bundle formation through electrostatic or steric hindrance, can be introduced through the HRA or HRB helical regions. Glycosylation can interfere with 6-helix bundle formation and prevent flipping of the RSV F construct to the post-fusion conformation.

A stabilized pre-fusion RSV F protein of the invention may comprise one or more mutations that form one or more glycosylation sites in the HRA or HRB helical regions. The RSV F protein may contain mutations or deletions in addition to those that introduce the glycosylation sites in the HRA or HRB helical regions.

In one embodiment, the RSV F protein comprises S173N and N175T mutations and the pre-fusion RSV F protein has a glycosylation site on current serine residue 173.

In another embodiment, the RSV F protein comprises a mutation A177T, so that the pre-fusion RSV F protein has a glycosylation site on current residue N175.

In another embodiment, the RSV F protein comprises G184N and S186T mutations and the pre-fusion RSV F protein has a glycosylation site on current residue G184.

Chimeric Pre-Fusion F Structures with Relevant RSV F Epitopes

The invention also relates to chimeric pre-fusion F proteins that contain neutralizing epitopes from RSV F protein. Generally, the chimeric pre-fusion F proteins comprise a stabilized F protein from a different virus, such as the Parainfluenza Virus (PIV1, PIV2, PIV3, PIV4, PIV5), Newcastle Disease Virus (NDV), Sendai virus (SeV), Hendra Virus, Nipah Virus (NiV), human metapneumovirus or avian metapneumovirus, in which portions that are exposed on the surface of the protein are replaced with corresponding portions of RSV F. Preferably, the portions contain neutralizing epitopes of RSV F.

For example, any non-RSV (e.g., parainfluenza virus or metapneumovirus) F protein that is stabilized in the pre-fusion conformation (e.g., by virtue of a GCN trimer domain fused C-terminally to the HRB region), may be used as a template for the protein (i.e., an uncleaved NDV F-GCN fusion protein). For example, the SV5 of PIV5 pre-fusion F protein, described by Yin et al., 2006 (145) or the NDV pre-fusion F described by Swanson et al, 2010 (146) may be used in the chimeric F protein construct. The template may then be mutated to introduce known or suspected neutralizing epitopes of RSV F. Thus, the protein may have a pre-fusion F structure exhibiting the neutralizing epitopes, but not non-neutralizing epitopes, of RSV F. A clear benefit to this construct is that it would not raise non-neutralizing RSV F antibodies.

A pre-fusion chimera protein of the invention may comprise a parainfluenza virus F protein, stabilized in the pre-fusion conformation that is mutated to introduce neutralizing epitopes of RSV F. The parainfluenza virus F protein may be any parainfluenza virus F protein, preferably the SV5 of PIV5 pre-fusion F protein, described by Yin et al., 2006 (147) or the NDV pre-fusion F described by Swanson et al, 2010 (146). Exemplary neutralizing epitopes that may be introduced by mutation include the epitopes disclosed in Table 1. For example, the amino acids that form the epitopes recognized by the antibodies listed in Table 1 can be introduced into the corresponding positions (e.g., identified by structural comparison, such as structure based alignment) of a non RSV-F protein (e.g., parainfluenza virus F protein or metapneumovirus F protein) that is stabilized in the pre-fusion conformation. For example, the chimeric F protein can contain the RSV F site A epitope or site C epitope. In particular example, the chimeric F protein contains one or more RSV F residues selected from the amino acid residues at positions 262-276 of RSV F. In another particular example, the chimeric F protein contains one or more RSV F residues selected from the amino acid residues at positions 429-447 of RSV F.

TABLE 1

Neutralizing epitopes of RSV F[a]

| Site[b] | mAb | Residues | Method | Reference |
|---|---|---|---|---|
| A | 11 | N268I | Escape[c] | (149) |
| A | 151 | K272N | Escape | (150) |
| A | 1129 | S275F | Escape | (150) |
| A | 1153 | N262S | Escape | (150) |
| A | 1200 | K272N | Escape | (150) |
| A | 1214 | N276Y | Escape | (150) |
| A | 1237 | N276Y | Escape | (150) |
| A | 47F | N262Y, N268I | Escape | (151) |
| A | 7C2 | K272E, K272T | Escape | (149) |
| A | B4 | K272T | Escape | (149) |
| A | Fab 19[d] | I266M | Escape | (149) |
| A | AK13A2 | N262Y | Escape | (149) |
| A | PVZ[e] | K272M, K272Q, N268I | Escape | (152) |
| A | PVZ[e] | K272M, K272T, S275F | Engineered[f] | (153) |
| A | MVZ[g] | N262, N268, D269, K272, S275 | Structure[h] | (141) |
| C | 7.936 | I432T, K433T, V447A | Escape | (154) |
| C | 9.432 | S436F | Escape | (154) |
| C | 19[d] | R429S | Escape | (149) |
| C | 19[d] | R429K, R429S, G430A | Engineered | (153) |
| C | 20 | R429S | Escape | (149) |

TABLE 1-continued

| Neutralizing epitopes of RSV F[a] | | | | |
|---|---|---|---|---|
| Site[b] | mAb | Residues | Method | Reference |
| C | 101F | K433T | Escape | (155) |
| C | 101F | K433D, K433L, K433N, K433Q, K433R | Engineered | (153) |
| C | 101F | R429, 1431, 1432, K433, T434, F435, S436, N437 | Structure | (148) |

[a]Results of studies using peptide binding or peptide inhibition are not included in this table.
[b]Sites are based on the competition and cross-neutralization analysis of Beeler et al., 1989 (156).
[c]An escape mutation is included if it is the sole mutation in an antibody-resistant strain.
[d]Fabl9 and 19 are unrelated antibodies. The similar names are coincidental.
[e]Palivizumab
[f]Engineered mutations in intact recombinant RSV F that allowed intact processing, full fusion activity and reduced monoclonal antibody binding to less than 15% of wild type are included.
[g]Motavizumab
[h]Residues from peptides in peptide-Fab complex structures are included if either their side chain or backbone atoms make significant contact with the antibody. The biological significance of the peptide-antibody interactions observed in these structural studies has been confirmed by other techniques.

In one embodiment, the chimeric F protein of the invention comprises the HRA region of RSV F (residues 137-212) in place of the equivalent HRA residues of NDV-GCN pre-fusion F. Thus, prefusion F protein (NDV-GCN) is expressed with potential neutralizing epitope sites (HRA region of RSV F) on the top of the pre-fusion F head, permitting neutralizing RSV F antibodies to be elicited. Additional neutralizing epitopes may be added if desired, for example the motavizumab epitope or the 101F epitope.

An exemplary amino acid sequence of a chimeric protein containing prefusion NDV F mutated to include RSV F HRA amino acid sequences is presented below (SEQ ID NO: 13). The presented sequences contain a signal peptide, a GCN-trimerization domain and a HIS tag. The chimeric pre-fusion F protein of the invention can contain the amino acid sequence shown below, with or without the signal peptide and/or GCN-trimerization domain and/or HIS tag. NDV RSV HRA prefusion (underlined portion is RSV HRA, italicized portion is C-terminal GCN trimeric domain and HIS6 (SEQ ID NO: 12) affinity purification tag) (SEQ ID NO: 13).

```
MGSRSSTRIPVPLMLTVRVMLALSCVCPTSALDGRPLAAAGIVVTGDK

AVNIYTSSQTGSIIIKLLPNMPKDKEACAKAPLEAYNRTLTTLLTPLG

DSIRRIQESVTTSGGGKQGRLIGAIIGFLGFLLGVGSAIASGVAVSKV

LHLEGEVNKIKSALLSTNKAVVSLSNGVSVLTSKVLDLKNYIDKQLLP

IVNKQSCIKITQVGVELNLYLTELTTVFGPQITSPALTQLTIQALYN

LAGGNMDYLLTKLGVGNNQLSSLISSGLITGNPILYDSQTQLLGIQVT

LPSVGNLNNMRATYLETLSVSTTKGFASALVPKVVTQVGSVIEELDTS
```

-continued

```
YCIETDLDLYCTRIVTFPMSPGIYSCLSGNTSACMYSKTEGALTTPYM

TLKGSVIANCKMTTCRCADPPGIISQNYGEAVSLIDRQSCNILSLDGI

TLRLSGEFDATYQKNISIQDSQVIVTGNLDISTELGNVNNSISNALDK

LEESNSKLDKVEDKIEEILSKIYHIENEIARIKKLIGEAGGPLVPRGS

HHHHHH
```

The RSV F Glycoprotein

The F glycoprotein of RSV directs viral penetration by fusion between the virion envelope and the host cell plasma membrane. It is a type I single-pass integral membrane protein having four general domains: N-terminal ER-translocating signal sequence (SS), ectodomain (ED), transmembrane domain (TM), and a cytoplasmic tail (CT). CT contains a single palmitoylated cysteine residue. The sequence of F protein is highly conserved among RSV isolates, but is constantly evolving (7). Unlike most paramyxoviruses, the F protein in RSV can mediate entry and syncytium formation independent of the other viral proteins (HN is usually necessary in addition to F in other paramyxoviruses).

The hRSV F mRNA is translated into a 574 amino acid precursor protein designated $F_0$, which contains a signal peptide sequence at the N-terminus that is removed by a signal peptidase in the endoplasmic reticulum. $F_0$ is cleaved at two sites (a.a. 109/110 and 136/137) by cellular proteases (in particular furin) in the trans-Golgi, removing a short glycosylated intervening sequence and generating two subunits designated $F_1$ (~50 kDa; C-terminus; residues 137-574) and $F_2$ (~20 kDa; N-terminus; residues 1-109) (See, e.g., FIG. 4A). $F_1$ contains a hydrophobic fusion peptide at its N-terminus and also two hydrophobic heptad-repeat regions (HRA and HRB). HRA is near the fusion peptide and HRB is near to the transmembrane domain (See, e.g., FIG. 4A). The $F_1$-$F_2$ heterodimers are assembled as homotrimers in the virion.

RSV exists as a single serotype but has two antigenic subgroups: A and B. The F glycoproteins of the two groups are about 90% identical. The A subgroup, the B subgroup, or a combination or hybrid of both can be used in the invention. An example sequence for the A subgroup is SEQ ID NO: 1 (A2 strain; GenBank GI: 138251; Swiss Prot P03420), and for the B subgroup is SEQ ID NO: 2 (18537 strain; GI: 138250; Swiss Prot P13843). SEQ ID NO:1 and SEQ ID NO:2 are both 574 amino acid sequences. The signal peptide in A2 strain is a.a. 1-21, but in 18537 strain it is 1-22. In both sequences the TM domain is from about a.a. 530-550, but has alternatively been reported as 525-548.

SEQ ID NO: 1

```
  1 MELLILKANAITTILTAVTFCFASGQNITEEFYQSTCSAVSKGYLSALRTGWYTSVITIE  60

 61 LSNIKENKCNGTDAKVKLIKQELDKYKNAVTELQLLMQSTPPTNNRARRELPRFMNYTLN 120

121 NAKKTNVTLSKKRKRRFLGFLLGVGSAIASGVAVSKVLHLEGEVNKIKSALLSTNKAVVS 180

181 LSNGVSVLTSKVLDLKNYIDKQLLPIVNKQSCSISNIETVIEFQQKNNRLLEITREFSVN 240

241 AGVTTPVSTYMLTNSELLSLINDMPITNDQKKLMSNNVQIVRQQSYSIMSIIKEEVLAYV 300
```

-continued

```
301 VQLPLYGVIDTPCWKLHTSPLCTTNTKEGSNICLTRTDRGWYCDNAGSVSFFPQAETCKV 360

361 QSNRVFCDTMNSLTLPSEINLCNVDIFNPKYDCKIMTSKTDVSSSVITSLGAIVSCYGKT 420

421 KCTASNKNRGIIKTFSNGCDYVSNKGMDTVSVGNTLYYVNKQEGKSLYVKGEPIINFYDP 480

481 LVFPSDEFDASISQVNEKINQSLAFIRKSDELLHNVNAGKSTTNIMITTIIIVIIVILLS 540

541 LIAVGLLLYCKARSTPVTLSKDQLSGINNIAFSN                           574

                                                      SEQ ID NO: 2
  1 MELLIHRSSAIFLTLAVNALYLTSSQNITEEFYQSTCSAVSRGYFSALRTGWYTSVITIE  60

 61 LSNIKETKCNGTDTKVKLIKQELDKYKNAVTELQLLMQNTPAANNRARREAPQYMNYTIN 120

121 TTKNLNVSISKKRKRRFLGFLLGVGSAIASGIAVSKVLHLEGEVNKIKNALLSTNKAVVS 180

181 LSNGVSVLTSKVLDLKNYINNRLLPIVNQQSCRISNIETVIEFQQMNSRLLEITREFSVN 240

241 AGVTTPLSTYMLTNSELLSLINDMPITNDQKKLMSSNVQIVRQQSYSIMSIIKEEVLAYV 300

301 VQLPIYGVIDTPCWKLHTSPLCTTNIKEGSNICLTRTDRGWYCDNAGSVSFFPQADTCKV 360

361 QSNRVFCDTMNSLTLPSEVSLCNTDIFNSKYDCKIMTSKTDISSSVITSLGAIVSCYGKT 420

421 KCTASNKNRGIIKTFSNGCDYVSNKGVDTVSVGNTLYYVNKLEGKNLYVKGEPIINYYDP 480

481 LVFPSDEFDASISQVNEKINQSLAFIRRSDELLHNVNTGKSTTNIMITTIIIVIIVVLLS 540

541 LIAIGLLLYCKAKNTPVTLSKDQLSGINNIAFSK                           574
```

The invention may use any desired RSV F amino acid sequence, such as the amino acid sequence of SEQ ID NO: 1 or 2, or a sequence having identity to SEQ ID NO: 1 or 2. Typically it will have at least 75% identity to SEQ ID NO: 1 or 2 e.g., at least 80%, at least 85%, at least 90%, at least 95%, at least 97%, at least 98%, at least 99%, identity to SEQ ID NO:1 or 2. The sequence may be found naturally in RSV.

Where the invention uses an ectodomain of F protein, in whole or in part, it may comprise:

(i) a polypeptide comprising about amino acid 22-525 of SEQ ID NO: 1.

(ii) a polypeptide comprising about amino acids 23-525 of SEQ ID NO: 2.

(iii) a polypeptide comprising an amino acid sequence having at least 75% identity (e.g., at least 80%, at least 85%, at least 90%, at least 95%, at least 97%, at least 98%, at least 99% identity) to (i) or (ii).

(iv) a polypeptide comprising a fragment of (i), (ii) or (iii), wherein the fragment comprises at least one F protein epitope. The fragment will usually be at least about 100 amino acids long, e.g., at least about 150, at least about 200, at least about 250, at least about 300, at least about 350, at least about 400, at least about 450 amino acids long.

The ectodomain can be an $F_0$ form with or without the signal peptide, or can comprise two separate peptide chains (e.g., an $F_1$ subunit and a $F_2$ subunit) that are associated with each other, for example, the subunits may be linked by a disulfide bridge. Accordingly, all or a portion of about amino acid 101 to about 161, such as amino acids 110-136, may be absent from the ectodomain. Thus the ectodomain, in whole or in part, can comprise:

(v) a first peptide chain and a second peptide chain that is associated with the first polypeptide chain, where the first peptide chain comprises an amino acid sequence having at least 75% identity (e.g., at least 80%, at least 85%, at least 90%, at least 95%, at least 97%, at least 98%, at least 99%, or even 100% identity) to about amino acid 22 to about amino acid 101 of SEQ ID NO: 1 or to about amino acid 23 to about amino acid 101 of SEQ ID NO: 2, and the second peptide chain comprises an amino acid sequence having at least 75% identity (e.g., at least 80%, at least 85%, at least 90%, at least 95%, at least 97%, at least 98%, at least 99%, or even 100% identity) to about amino acid 162 to about 525 of SEQ ID NO: 1 or to about amino acid 162 to 525 of SEQ ID NO: 2.

(vi) a first peptide chain and a second peptide chain that is associated with the first polypeptide chain, where the first peptide chain comprises an amino acid sequence comprising a fragment of about amino acid 22 to about amino acid 101 of SEQ ID NO: 1 or of about amino acid 23 to about amino acid 109 of SEQ ID NO: 2, and the second peptide chain comprises a fragment of about amino acid 162 to about amino acid 525 of SEQ ID NO: 1 or of about amino acid 161 to about amino acid 525 of SEQ ID NO: 2. One or both of the fragments will comprise at least one F protein epitope. The fragment in the first peptide chain will usually be at least 20 amino acids long, e.g., at least 30, at least 40, at least 50, at least 60, at least 70, at least 80 amino acids long. The fragment in the second peptide chain will usually be at least 100 amino acids long, e.g., at least 150, at least 200, at least 250, at least 300, at least 350, at least 400, at least 450 amino acids long.

(vii) a molecule obtainable by furin digestion of (i), (ii), (iii) or (iv).

Thus an amino acid sequence used with the invention may be found naturally within RSV F protein (e.g., a soluble RSV F protein lacking TM and CT, about amino acids 522-574 of SEQ ID NOS: 1 or 2), and/or it may have one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30) single amino acid mutations (insertions, deletions or substitutions) relative to a natural RSV sequence. For instance, it is known to mutate F proteins to eliminate their furin cleavage sequences, thereby preventing intracellular processing. In certain embodiments, the RSV F protein lacks TM and CT (about amino acids 522-574 of SEQ ID NOS: 1 or 2) and contains one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30) single amino acid mutations (insertions, deletions or substitutions) relative to a natural RSV sequence.

Furin-Cleavage, Trypsin-Cleavage and Fusion Peptide Mutations

If desired, post-fusion RSV F polypeptides or proteins may contain one or more mutations, for example, mutations that prevent cleavage at one or both of the furin cleavage sites (i.e., amino acids 109 and 136 of SEQ ID NOS: 1 and 2), that prevent cleavage of or introduce trypsin cleavage sites, mutations in the p27 region, and/or mutation in the fusion peptide. Such mutations can prevent aggregation of the soluble polypeptides or proteins and thereby facilitate purifications, can prevent cell-cell fusion if the RSV F protein is expressed on the surface of a cell, such as by expression from a viral replicon (e.g., alphavirus replicon particles), or if the RSV F protein is a component of a virus-like particle.

Examples of suitable furin cleavage mutations include replacement of amino acid residues 106-109 of SEQ ID NO: 1 or 2 with RARK (SEQ ID NO:14), RARQ (SEQ ID NO:15), QAQN (SEQ ID NO:16), or IEGR (SEQ ID NO:17). Alternatively, or in addition, amino acid residues 133-136 of SEQ ID NO: 1 or 2 can be replaced with RKKK (SEQ ID NO:18), AAAR, QNQN (SEQ ID NO:19), QQQR (SEQ ID NO:20) or IEGR (SEQ ID NO:17). (A indicates that the amino acid residue has been deleted.) These furin cleavage mutations can be combined, if desired, with other mutations described herein, such as trypsin cleavage mutations and fusion peptide mutations.

Examples of suitable trypsin cleavage mutations include deletion of any lysine or arginine residue between about position 101 and position 161 of SEQ ID NO:1 or 2, or replacement of any such lysine or arginine residue with an amino acid other than lysine or arginine. For example, lysine and/or arginine residues in the p27 region (about amino acids 110-136 of SEQ ID NOS: 1 or 2) can be substituted or deleted, including deletion of the p27 region in whole or in part.

The mutations described herein can be combined, if desired, in any combination. For example, furin mutations can be combined with partial or complete deletion of the fusion peptide region and/or deletion of the HRA or HRB helical region.

In addition to the mutations described above, e.g., furin-cleavage and fusion peptide mutations, or alternatively, soluble RSV F polypeptides or proteins, such as those that lack the transmembrane region and cytoplasmic tail, or HRA and HRB deletions, or cysteine mutations, may contain one or more oligomerization sequences. When an oligomerization sequence is present, it is preferably a trimerization sequence. Suitable oligomerization sequences are well known in the art and include, for example, the coiled coil of the yeast GCN4 leucine zipper protein, trimerizing sequence from bacteriophage T4 fibritin ("foldon"), and the trimer domain of influenza HA. These and other suitable oligomerization sequences are described in greater detail herein.

In particular embodiments, the sequence of the carboxy terminus of the RSV F polypeptide or protein, starting from position 480, is

```
(GCN)
                                        (SEQ ID NO: 21)
PLVFPSDEFDASISQVNEKINQSLAFIRKSDELLHNVNDKIEEILSKIYHI

ENEIARIKKLIGE

(HA)
                                        (SEQ ID NO: 22)
PLVFPSDEFDASISQVNEKINQSLAFIRKSDELLHNVNEKFHQIEKEFSEV

EGRIQDLEK

(Idealized helix)
                                        (SEQ ID NO: 23)
PLVFPSDEFDASISQINEKINQILAFIRKIDELLHNIN

(foldon short)
                                        (SEQ ID NO: 24)
PLVFPSDEFDASISQVNEKINQSLAFIRKSDELLHNVNGSGYIPEAPRDGQ

AYVRKDGEWVLLSTFL;
or

(foldon long)
                                        (SEQ ID NO: 25)
PLVFPSDEFDASISQVNEKINQSLAFIRKSDELLHNVNNKNDDKGSGYIPE

APRDGQAYVRKDGEWVLLSTFL
```

If desired, RSV F polypeptides or proteins that contain a transmembrane region may contain an added amino acid sequence that provides a protease cleavage site. This type of RSV F polypeptide or protein can be produced by expression on the surface of a cell, and recovered in soluble form after cleavage from the cell surface using an appropriate protease. Generally, the amino acid sequence that provides a protease cleavage site will be located within about 60 amino acids, about 50 amino acids, about 40 amino acids, about 30 amino acids, about 20 amino acids, about 10 amino acids, or substantially adjacent to the amino terminus of the transmembrane domain (amino acid 525 of SEQ ID NO:1 or 2). Many suitable amino acid sequences that are cleaved by commercially available proteases are well-known in the art. For example, thrombin cleaves the sequence LVPR (SEQ ID NO:26), factor Xa cleaves the sequence IEGR (SEQ ID NO:17) and enterokinase cleaves the sequence DDDDK (SEQ ID NO:27). These amino acid sequences can be introduced into an RSV F polypeptide.

Immunogenic polypeptides used according to the invention will usually be isolated or purified. Thus, they will not be associated with molecules with which they are normally, if applicable, found in nature. For example, an F protein used with the invention will not be in the form of a RSV virion (although it may be in the form of an artificial virion, such as a virosome or VLP).

Polypeptides will usually be prepared by expression in a recombinant host system. Generally, they (e.g., RSV ecto-domains) are produced by expression of recombinant constructs that encode the ecto-domains in suitable recombinant host cells, although any suitable methods can be used. Suitable recombinant host cells include, for example, insect cells (e.g., *Aedes aegypti, Autographa californica, Bombyx mori, Drosophila melanogaster, Spodoptera frugiperda*, and *Trichoplusia ni*), mammalian cells (e.g., human, non-human primate, horse, cow, sheep, dog, cat, and rodent (e.g., hamster), avian cells (e.g., chicken, duck, and geese), bacteria (e.g., *E. coli, Bacillus subtilis*, and *Streptococcus* spp.), yeast cells (e.g., *Saccharomyces cerevisiae, Candida albi-*

*cans, Candida maltosa, Hansenual polymorpha, Kluyveromyces fragilis, Kluyveromyces lactis, Pichia guillerimondii, Pichia pastoris, Schizosaccharomyces pombe* and *Yarrowia lipolytica*), Tetrahymena cells (e.g., Tetrahymena *thermophila*) or combinations thereof. Many suitable insect cells and mammalian cells are well-known in the art. Suitable insect cells include, for example, Sf9 cells, Sf21 cells, Tn5 cells, Schneider S2 cells, and High Five cells (a clonal isolate derived from the parental *Trichoplusia ni* BTI-TN-5B1-4 cell line (Invitrogen)). Suitable mammalian cells include, for example, Chinese hamster ovary (CHO) cells, human embryonic kidney cells (HEK293 cells, typically transformed by sheared adenovirus type 5 DNA), NIH-3T3 cells, 293-T cells, Vero cells, HeLa cells, PERC.6 cells (ECACC deposit number 96022940), Hep G2 cells, MRC-5 (ATCC CCL-171), WI-38 (ATCC CCL-75), fetal rhesus lung cells (ATCC CL-160), Madin-Darby bovine kidney ("MDBK") cells, Madin-Darby canine kidney ("MDCK") cells (e.g., MDCK (NBL2), ATCC CCL34; or MDCK 33016, DSM ACC 2219), baby hamster kidney (BHK) cells, such as BHK21-F, HKCC cells, and the like. Suitable avian cells include, for example, chicken embryonic stem cells (e.g., EBx® cells), chicken embryonic fibroblasts, chicken embryonic germ cells, duck cells (e.g., AGE1.CR and AGE1.CR.pIX cell lines (ProBioGen) which are described, for example, in Vaccine 27:4975-4982 (2009) and WO2005/042728), EB66 cells, and the like.

Suitable insect cell expression systems, such as baculovirus systems, are known to those of skill in the art and described in, e.g., Summers and Smith, *Texas Agricultural Experiment Station Bulletin* No. 1555 (1987). Materials and methods for baculovirus/insert cell expression systems are commercially available in kit form from, inter alia, Invitrogen, San Diego CA. Avian cell expression systems are also known to those of skill in the art and described in, e.g., U.S. Pat. Nos. 5,340,740; 5,656,479; 5,830,510; 6,114,168; and 6,500,668; European Patent No. EP 0787180B; European Patent Application No. EP03291813.8; WO 03/043415; and WO 03/076601. Similarly, bacterial and mammalian cell expression systems are also known in the art and described in, e.g., *Yeast Genetic Engineering* (Barr et al., eds., 1989) Butterworths, London.

Recombinant constructs encoding pre-fusion RSV F protein can be prepared in suitable vectors using conventional methods. A number of suitable vectors for expression of recombinant proteins in insect or mammalian cells are well-known and conventional in the art. Suitable vectors can contain a number of components, including, but not limited to one or more of the following: an origin of replication; a selectable marker gene; one or more expression control elements, such as a transcriptional control element (e.g., a promoter, an enhancer, a terminator), and/or one or more translation signals; and a signal sequence or leader sequence for targeting to the secretory pathway in a selected host cell (e.g., of mammalian origin or from a heterologous mammalian or non-mammalian species). For example, for expression in insect cells a suitable baculovirus expression vector, such as pFastBac (Invitrogen), is used to produce recombinant baculovirus particles. The baculovirus particles are amplified and used to infect insect cells to express recombinant protein. For expression in mammalian cells, a vector that will drive expression of the construct in the desired mammalian host cell (e.g., Chinese hamster ovary cells) is used.

Pre-fusion RSV F protein polypeptides can be purified using any suitable methods. For example, methods for purifying pre-fusion RSV F polypeptides by immunoaffinity chromatography are known in the art. Ruiz-Arguello et al., *J. Gen. Virol.*, 85:3677-3687 (2004). Suitable methods for purifying desired proteins including precipitation and various types of chromatography, such as hydrophobic interaction, ion exchange, affinity, chelating and size exclusion are well-known in the art. Suitable purification schemes can be created using two or more of these or other suitable methods. If desired, the pre-fusion RSV F protein polypeptides can include a "tag" that facilitates purification, such as an epitope tag or a HIS tag. Such tagged polypeptides can conveniently be purified, for example from conditioned media, by chelating chromatography or affinity chromatography.

The pre-fusion RSV F polypeptides may also be produced in situ by expression of nucleic acids that encode them in the cells of a subject. For example, by expression of a self-replicating RNA described herein.

Polypeptides may include additional sequences in addition to the pre-fusion RSV sequences. For example, a polypeptide may include a sequence to facilitate purification (e.g., a poly-His sequence). Similarly, for expression purposes, the natural leader peptide of F protein may be substituted for a different one. For example, reference 6 used a honeybee melittin leader peptide in place of the natural one.

Self-Replicating RNA

The pre-fusion RSV-F polypeptides described herein can be produced by expression of recombinant nucleic acids that encode the polypeptides in the cells of a subject. Preferred nucleic acids that can be administered to a subject to cause the production of pre-fusion RSV-F polypeptides are self-replicating RNA molecules. The self-replicating RNA molecules of the invention are based on the genomic RNA of RNA viruses, but lack the genes encoding one or more structural proteins. The self-replicating RNA molecules are capable of being translated to produce non-structural proteins of the RNA virus and heterologous proteins encoded by the self-replicating RNA.

The self-replicating RNA generally contains at least one or more genes selected from the group consisting of viral replicase, viral proteases, viral helicases and other nonstructural viral proteins, and also comprise 5'- and 3'-end cis-active replication sequences, and if desired, a heterologous sequences that encode a desired amino acid sequences (e.g., a protein, an antigen). A subgenomic promoter that directs expression of the heterologous sequence can be included in the self-replicating RNA. If desired, the heterologous sequence may be fused in frame to other coding regions in the self-replicating RNA and/or may be under the control of an internal ribosome entry site (IRES).

Self-replicating RNA molecules of the invention can be designed so that the self-replicating RNA molecule cannot induce production of infectious viral particles. This can be achieved, for example, by omitting one or more viral genes encoding structural proteins that are necessary for the production of viral particles in the self-replicating RNA. For example, when the self-replicating RNA molecule is based on an alpha virus, such as Sinebis virus (SIN), Semliki forest virus and Venezuelan equine encephalitis virus (VEE), one or more genes encoding viral structural proteins, such as capsid and/or envelope glycoproteins, can be omitted. If desired, self-replicating RNA molecules of the invention can be designed to induce production of infectious viral particles that are attenuated or virulent, or to produce viral particles that are capable of a single round of subsequent infection.

A self-replicating RNA molecule can, when delivered to a vertebrate cell even without any proteins, lead to the production of multiple daughter RNAs by transcription from itself (or from an antisense copy of itself). The self-replicating RNA can be directly translated after delivery to a cell, and this translation provides a RNA-dependent RNA polymerase which then produces transcripts from the delivered RNA. Thus the delivered RNA leads to the production of multiple daughter RNAs. These transcripts are antisense relative to the delivered RNA and may be translated themselves to provide in situ expression of a gene product, or may be transcribed to provide further transcripts with the same sense as the delivered RNA which are translated to provide in situ expression of the encoded RSV-F polypeptide.

One suitable system for achieving self-replication is to use an alphavirus-based RNA replicon. These + stranded replicons are translated after delivery to a cell to give of a replicase (or replicase-transcriptase). The replicase is translated as a polyprotein which auto cleaves to provide a replication complex which creates genomic − strand copies of the + strand delivered RNA. These − strand transcripts can themselves be transcribed to give further copies of the + stranded parent RNA and also to give a subgenomic transcript which encodes the RSV-F polypeptide. Translation of the subgenomic transcript thus leads to in situ expression of the RSV-F polypeptide by the infected cell. Suitable alphavirus replicons can use a replicase from a sindbis virus, a semliki forest virus, an eastern equine encephalitis virus, a venezuelan equine encephalitis virus, etc.

A preferred self-replicating RNA molecule thus encodes (i) a RNA-dependent RNA polymerase which can transcribe RNA from the self-replicating RNA molecule and (ii) an RSV-F polypeptide. The polymerase can be an alphavirus replicase e.g. comprising alphavirus protein nsP4.

Whereas natural alphavirus genomes encode structural virion proteins in addition to the non structural replicase polyprotein, it is preferred that an alphavirus based self-replicating RNA molecule of the invention does not encode alphavirus structural proteins. Thus the self replicating RNA can lead to the production of genomic RNA copies of itself in a cell, but not to the production of RNA-containing alphavirus virions. The inability to produce these virions means that, unlike a wild-type alphavirus, the self-replicating RNA molecule cannot perpetuate itself in infectious form. The alphavirus structural proteins which are necessary for perpetuation in wild-type viruses are absent from self replicating RNAs of the invention and their place is taken by gene(s) encoding the desired gene product, such that the subgenomic transcript encodes the desired gene product rather than the structural alphavirus virion proteins.

Thus a self-replicating RNA molecule useful with the invention may have two open reading frames. The first (5') open reading frame encodes a replicase; the second (3') open reading frame encodes an RSV-F polypeptide. In some embodiments the RNA may have additional (downstream) open reading frames e.g. that encode further desired gene products. A self-replicating RNA molecule can have a 5' sequence which is compatible with the encoded replicase.

In one aspect, the self-replicating RNA molecule is derived from or based on an alphavirus. In other aspects, the self-replicating RNA molecule is derived from or based on a virus other than an alphavirus, preferably, a positive-stranded RNA viruses, and more preferably a picornavirus, flavivirus, rubivirus, pestivirus, hepacivirus, calicivirus, or coronavirus. Suitable wild-type alphavirus sequences are well-known and are available from sequence depositories, such as the American Type Culture Collection, Rockville, Md. Representative examples of suitable alphaviruses include Aura (ATCC VR-368), Bebaru virus (ATCC VR-600, ATCC VR-1240), Cabassou (ATCC VR-922), Chikungunya virus (ATCC VR-64, ATCC VR-1241), Eastern equine encephalomyelitis virus (ATCC VR-65, ATCC VR-1242), Fort Morgan (ATCC VR-924), Getah virus (ATCC VR-369, ATCC VR-1243), Kyzylagach (ATCC VR-927), Mayaro (ATCC VR-66), Mayaro virus (ATCC VR-1277), Middleburg (ATCC VR-370), Mucambo virus (ATCC VR-580, ATCC VR-1244), Ndumu (ATCC VR-371), Pixuna virus (ATCC VR-372, ATCC VR-1245), Ross River virus (ATCC VR-373, ATCC VR-1246), Semliki Forest (ATCC VR-67, ATCC VR-1247), Sindbis virus (ATCC VR-68, ATCC VR-1248), Tonate (ATCC VR-925), Triniti (ATCC VR-469), Una (ATCC VR-374), Venezuelan equine encephalomyelitis (ATCC VR-69, ATCC VR-923, ATCC VR-1250 ATCC VR-1249, ATCC VR-532), Western equine encephalomyelitis (ATCC VR-70, ATCC VR-1251, ATCC VR-622, ATCC VR-1252), Whataroa (ATCC VR-926), and Y-62-33 (ATCC VR-375).

The self-replicating RNA may be associated with a delivery system. The self-replicating RNA may be administered with or without an adjuvant.

RNA Delivery Systems

The self-replicating RNA of the invention are suitable for delivery in a variety of modalities, such as naked RNA delivery or in combination with lipids, polymers or other compounds that facilitate entry into the cells. Self-replicating RNA molecules of the present invention can be introduced into target cells or subjects using any suitable technique, e.g., by direct injection, microinjection, electroporation, lipofection, biolystics, and the like. The self-replicating RNA molecule may also be introduced into cells by way of receptor-mediated endocytosis. See e.g., U.S. Pat. No. 6,090,619; Wu and Wu, J. Biol. Chem., 263:14621 (1988); and Curiel et al., Proc. Natl. Acad. Sci. USA, 88:8850 (1991). For example, U.S. Pat. No. 6,083,741 discloses introducing an exogenous nucleic acid into mammalian cells by associating the nucleic acid to a polycation moiety (e.g., poly-L-lysine having 3-100 lysine residues), which is itself coupled to an integrin receptor-binding moiety (e.g., a cyclic peptide having the sequence Arg-Gly-Asp).

The self-replicating RNA molecule of the present invention can be delivered into cells via amphiphiles. See e.g., U.S. Pat. No. 6,071,890. Typically, a nucleic acid molecule may form a complex with the cationic amphiphile. Mammalian cells contacted with the complex can readily take it up.

The self-replicating RNA can be delivered as naked RNA (e.g. merely as an aqueous solution of RNA) but, to enhance entry into cells and also subsequent intercellular effects, the self-replicating RNA is preferably administered in combination with a delivery system, such as a particulate or emulsion delivery system. A large number of delivery systems are well known to those of skill in the art. Such delivery systems include, for example liposome-based delivery (Debs and Zhu (1993) WO 93/24640; Mannino and Gould-Fogerite (1988) BioTechniques 6(7): 682-691; Rose U.S. Pat. No. 5,279,833; Brigham (1991) WO 91/06309; and Felgner et al. (1987) Proc. Natl. Acad. Sci. USA 84: 7413-7414), as well as use of viral vectors (e.g., adenoviral (see, e.g., Berns et al. (1995) Ann. NY Acad. Sci. 772: 95-104; Ali et al. (1994) Gene Ther. 1: 367-384; and Haddada et al. (1995) Curr. Top. Microbiol. Immunol. 199 (Pt 3): 297-306 for review), papillomaviral, retroviral (see, e.g., Buchscher et al. (1992) J. Virol. 66(5) 2731-2739; Johann et al. (1992) J. Virol. 66 (5): 1635-1640 (1992); Sommerfelt et al., (1990)

Virol. 176:58-59; Wilson et al. (1989) J. Virol. 63:2374-2378; Miller et al., J. Virol. 65:2220-2224 (1991); Wong-Staal et al., PCT/US94/05700, and Rosenburg and Fauci (1993) in Fundamental Immunology, Third Edition Paul (ed) Raven Press, Ltd., New York and the references therein, and Yu et al., Gene Therapy (1994) supra.), and adeno-associated viral vectors (see, West et al. (1987) Virology 160:38-47; Carter et al. (1989) U.S. Pat. No. 4,797,368; Carter et al. WO 93/24641 (1993); Kotin (1994) Human Gene Therapy 5:793-801; Muzyczka (1994) J. Clin. Invst. 94:1351 and Samulski (supra) for an overview of AAV vectors; see also, Lebkowski, U.S. Pat. No. 5,173,414; Tratschin et al. (1985) Mol. Cell. Biol. 5(11):3251-3260; Tratschin, et al. (1984) Mol. Cell. Biol., 4:2072-2081; Hermonat and Muzyczka (1984) Proc. Natl. Acad. Sci. USA, 81:6466-6470; McLaughlin et al. (1988) and Samulski et al. (1989) J. Virol., 63:03822-3828), and the like.

Three particularly useful delivery systems are (i) liposomes (ii) non-toxic and biodegradable polymer microparticles (iii) cationic submicron oil-in-water emulsions.

Liposomes

Various amphiphilic lipids can form bilayers in an aqueous environment to encapsulate a RNA-containing aqueous core as a liposome. These lipids can have an anionic, cationic or zwitterionic hydrophilic head group. Formation of liposomes from anionic phospholipids dates back to the 1960s, and cationic liposome-forming lipids have been studied since the 1990s. Some phospholipids are anionic whereas other are zwitterionic. Suitable classes of phospholipid include, but are not limited to, phosphatidylethanolamines, phosphatidylcholines, phosphatidylserines, and phosphatidylglycerols, and some useful phospholipids are listed in Table 2. Useful cationic lipids include, but are not limited to, dioleoyl trimethylammonium propane (DOTAP), 1,2-distearyloxy-N,N-dimethyl-3-aminopropane (DSDMA), 1,2-dioleyloxy-N,Ndimethyl-3-aminopropane (DODMA), 1,2-dilinoleyloxy-N,N-dimethyl-3-aminopropane (DLinDMA), 1,2-dilinolenyloxy-N,N-dimethyl-3-aminopropane (DLenDMA). Zwitterionic lipids include, but are not limited to, acyl zwitterionic lipids and ether zwitterionic lipids. Examples of useful zwitterionic lipids are DPPC, DOPC and dodecylphosphocholine. The lipids can be saturated or unsaturated.

Liposomes can be formed from a single lipid or from a mixture of lipids. A mixture may comprise (i) a mixture of anionic lipids (ii) a mixture of cationic lipids (iii) a mixture of zwitterionic lipids (iv) a mixture of anionic lipids and cationic lipids (v) a mixture of anionic lipids and zwitterionic lipids (vi) a mixture of zwitterionic lipids and cationic lipids or (vii) a mixture of anionic lipids, cationic lipids and zwitterionic lipids. Similarly, a mixture may comprise both saturated and unsaturated lipids. For example, a mixture may comprise DSPC (zwitterionic, saturated), DlinDMA (cationic, unsaturated), and/or DMPG (anionic, saturated). Where a mixture of lipids is used, not all of the component lipids in the mixture need to be amphiphilic e.g. one or more amphiphilic lipids can be mixed with cholesterol.

The hydrophilic portion of a lipid can be PEGylated (i.e. modified by covalent attachment of a polyethylene glycol). This modification can increase stability and prevent non-specific adsorption of the liposomes. For instance, lipids can be conjugated to PEG using techniques such as those disclosed in Heyes et al. (2005) *J Controlled Release* 107: 276-287.

A mixture of DSPC, DlinDMA, PEG-DMPG and cholesterol is used in the examples. A separate aspect of the invention is a liposome comprising DSPC, DlinDMA, PEG-DMG and cholesterol. This liposome preferably encapsulates RNA, such as a self-replicating RNA e.g. encoding an immunogen.

Liposomes are usually divided into three groups: multilamellar vesicles (MLV); small unilamellar vesicles (SUV); and large unilamellar vesicles (LUV). MHLVs have multiple bilayers in each vesicle, forming several separate aqueous compartments. SUVs and LUVs have a single bilayer encapsulating an aqueous core; SUVs typically have a diameter<50 nm, and LUVs have a diameter>50 nm. Liposomes useful with of the invention are ideally LUVs with a diameter in the range of 50-220 nm. For a composition comprising a population of LUVs with different diameters: (i) at least 80% by number should have diameters in the range of 20-220 nm, (ii) the average diameter (Zav, by intensity) of the population is ideally in the range of 40-200 nm, and/or (iii) the diameters should have a polydispersity index<0.2.

Techniques for preparing suitable liposomes are well known in the art e.g. see Liposomes: Methods and Protocols, Volume 1: Pharmaceutical Nanocarriers: Methods and Protocols. (ed. Weissig). Humana Press, 2009. ISBN 160327359X; Liposome Technology, volumes I, II & III. (ed. Gregoriadis). Informa Healthcare, 2006; and Functional Polymer Colloids and Microparticles volume 4 (Microspheres, microcapsules & liposomes). (eds. Arshady & Guyot). Citus Books, 2002. One useful method involves mixing (i) an ethanolic solution of the lipids (ii) an aqueous solution of the nucleic acid and (iii) buffer, followed by mixing, equilibration, dilution and purification (Heyes et al. (2005) *J Controlled Release* 107:276-87.).

RNA is preferably encapsulated within the liposomes, and so the liposome forms a outer layer around an aqueous RNA-containing core. This encapsulation has been found to protect RNA from RNase digestion. The liposomes can include some external RNA (e.g. on the surface of the liposomes), but at least half of the RNA (and ideally all of it) is encapsulated.

Polymeric Microparticles

Various polymers can form microparticles to encapsulate or adsorb RNA. The use of a substantially non-toxic polymer means that a recipient can safely receive the particles, and the use of a biodegradable polymer means that the particles can be metabolised after delivery to avoid long-term persistence. Useful polymers are also sterilisable, to assist in preparing pharmaceutical grade formulations.

Suitable non-toxic and biodegradable polymers include, but are not limited to, poly(α-hydroxy acids), polyhydroxy butyric acids, polylactones (including polycaprolactones), polydioxanones, polyvalerolactone, polyorthoesters, polyanhydrides, polycyanoacrylates, tyrosine-derived polycarbonates, polyvinyl-pyrrolidinones or polyester-amides, and combinations thereof.

In some embodiments, the microparticles are formed from poly(α-hydroxy acids), such as a poly(lactides) ("PLA"), copolymers of lactide and glycolide such as a poly(D,L-lactide-co-glycolide) ("PLG"), and copolymers of D,L-lactide and caprolactone. Useful PLG polymers include those having a lactide/glycolide molar ratio ranging, for example, from 20:80 to 80:20 e.g. 25:75, 40:60, 45:55, 55:45, 60:40, 75:25. Useful PLG polymers include those having a molecular weight between, for example, 5,000-200,000 Da e.g. between 10,000-100,000, 20,000-70,000, 40,000-50,000 Da.

The microparticles ideally have a diameter in the range of 0.02 μm to 8 μm. For a composition comprising a population of microparticles with different diameters at least 80% by number should have diameters in the range of 0.03-7 μm.

Techniques for preparing suitable microparticles are well known in the art e.g. see Functional Polymer Colloids and Microparticles volume 4 (Microspheres, microcapsules & liposomes). (eds. Arshady & Guyot). Citus Books, 2002; *Polymers in Drug Delivery*. (eds. Uchegbu & Schatzlein). CRC Press, 2006. (in particular chapter 7) and *Microparticulate Systems for the Delivery of Proteins and Vaccines*. (eds. Cohen & Bernstein). CRC Press, 1996. To facilitate adsorption of RNA, a microparticle may include a cationic surfactant and/or lipid e.g. as disclosed in O'Hagan et al. (2001) *J Virology* 75:9037-9043; and Singh et al. (2003) *Pharmaceutical Research* 20: 247-251. An alternative way of making polymeric microparticles is by molding and curing e.g. as disclosed in WO2009/132206.

Microparticles of the invention can have a zeta potential of between 40-100 mV.

RNA can be adsorbed to the microparticles, and adsorption is facilitated by including cationic materials (e.g. cationic lipids) in the microparticle.

Oil-In-Water Cationic Emulsions

Oil-in-water emulsions are known for adjuvanting influenza vaccines e.g. the MF59™ adjuvant in the FLUAD™ product, and the AS03 adjuvant in the PREPANDRIX™ product. RNA delivery according to the present invention can utilise an oil-in-water emulsion, provided that the emulsion includes one or more cationic molecules. For instance, a cationic lipid can be included in the emulsion to provide a positive droplet surface to which negatively-charged RNA can attach.

The emulsion comprises one or more oils. Suitable oil(s) include those from, for example, an animal (such as fish) or a vegetable source. The oil is ideally biodegradable (metabolisable) and biocompatible. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and so may be used. The procedures for separation, purification, saponification and other means necessary for obtaining pure oils from animal sources are well known in the art.

Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Squalane, the saturated analog to squalene, can also be used. Fish oils, including squalene and squalane, are readily available from commercial sources or may be obtained by methods known in the art.

Other useful oils are the tocopherols, particularly in combination with squalene. Where the oil phase of an emulsion includes a tocopherol, any of the α, β, γ, δ, ε or ξ tocopherols can be used, but α-tocopherols are preferred. D-α-tocopherol and DL-α-tocopherol can both be used. A preferred α-tocopherol is DL-α-tocopherol. An oil combination comprising squalene and a tocopherol (e.g. DL-α-tocopherol) can be used.

Preferred emulsions comprise squalene, a shark liver oil which is a branched, unsaturated terpenoid ($C_{30}H_{50}$; $[(CH_3)_2C[{=}CHCH_2CH_2C(CH_3)]_2{=}CHCH_2\text{-}]_2$; 2,6,10,15,19,23-hexamethyl-2,6,10,14,18,22-tetracosahexaene; CAS RN 7683-64-9).

The oil in the emulsion may comprise a combination of oils e.g. squalene and at least one further oil.

The aqueous component of the emulsion can be plain water (e.g. w.f.i.) or can include further components e.g. solutes. For instance, it may include salts to form a buffer e.g. citrate or phosphate salts, such as sodium salts. Typical buffers include: a phosphate buffer; a Tris buffer; a borate buffer; a succinate buffer; a histidine buffer; or a citrate buffer. A buffered aqueous phase is preferred, and buffers will typically be included in the 5-20 mM range.

The emulsion also includes a cationic lipid. Preferably this lipid is a surfactant so that it can facilitate formation and stabilisation of the emulsion. Useful cationic lipids generally contains a nitrogen atom that is positively charged under physiological conditions e.g. as a tertiary or quaternary amine. This nitrogen can be in the hydrophilic head group of an amphiphilic surfactant. Useful cationic lipids include, but are not limited to: 1,2-dioleoyloxy-3-(trimethylammonio) propane (DOTAP), 3'-[N—(N',N'-Dimethylaminoethane)-carbamoyl]Cholesterol (DC Cholesterol), dimethyldioctadecyl-ammonium (DDA e.g. the bromide), 1,2-Dimyristoyl-3-Trimethyl-AmmoniumPropane (DMTAP), dipalmitoyl (C16:0)trimethyl ammonium propane (DPTAP), distearoyltrimethylammonium propane (DSTAP). Other useful cationic lipids are: benzalkonium chloride (BAK), benzethonium chloride, cetramide (which contains tetradecyltrimethylammonium bromide and possibly small amounts of dedecyltrimethylammonium bromide and hexadecyltrimethyl ammonium bromide), cetylpyridinium chloride (CPC), cetyl trimethylammonium chloride (CTAC), N,N',N'-polyoxyethylene (10)-N-tallow-1,3-diaminopropane, dodecyltrimethylammonium bromide, hexadecyltrimethyl-ammonium bromide, mixed alkyl-trimethyl-ammonium bromide, benzyldimethyldodecylammonium chloride, benzyldimethylhexadecyl-ammonium chloride, benzyltrimethylammonium methoxide, cetyldimethylethylammonium bromide, dimethyldioctadecyl ammonium bromide (DDAB), methylbenzethonium chloride, decamethonium chloride, methyl mixed trialkyl ammonium chloride, methyl trioctylammonium chloride), N,N-dimethyl-N-[2 (2-methyl-4-(1,1,3,3tetramethylbutyl)-phenoxy]-ethoxy)ethyl]-benzenemetha-naminium chloride (DEBDA), dialkyldimetylammonium salts, [1-(2,3-dioleyloxy)-propyl]-N,N,N, trimethylammonium chloride, 1,2-diacyl-3-(trimethylammonio) propane (acyl group=dimyristoyl, dipalmitoyl, distearoyl, dioleoyl), 1,2-diacyl-3 (dimethylammonio)propane (acyl group=dimyristoyl, dipalmitoyl, distearoyl, dioleoyl), 1,2-dioleoyl-3-(4'-trimethyl-ammonio) butanoyl-sn-glycerol, 1,2-dioleoyl 3-succinyl-sn-glycerol choline ester, cholesteryl (4'-trimethylammonio) butanoate), N-alkyl pyridinium salts (e.g. cetylpyridinium bromide and cetylpyridinium chloride), N-alkylpiperidinium salts, dicationic bolaform electrolytes (C12Me6; C12BU6), dialkylglycetylphosphorylcholine, lysolecithin, L-α dioleoylphosphatidylethanolamine, cholesterol hemisuccinate choline ester, lipopolyamines, including but not limited to dioctadecylamidoglycylspermine (DOGS), dipalmitoyl phosphatidylethanol-amidospermine (DPPES), lipopoly-L (or D)-lysine (LPLL, LPDL), poly (L (or D)-lysine conjugated to N-glutarylphosphatidylethanolamine, didodecyl glutamate ester with pendant amino group (C^GluPhCnN), ditetradecyl glutamate ester with pendant amino group (C14GIuCnN+), cationic derivatives of cholesterol, including but not limited to cholesteryl-3 β-oxysuccinamidoethylenetrimethylammonium salt, cholesteryl-3 β-oxysuccinamidoethylene-dimethylamine, cholesteryl-3 β-carboxyamidoethylenetrimethylammonium salt, and cholesteryl-3 β-carboxyamidoethylenedimethylamine. Other useful cationic lipids are described in US 2008/0085870 and US 2008/0057080, which are incorporated herein by reference.

The cationic lipid is preferably biodegradable (metabolisable) and biocompatible.

In addition to the oil and cationic lipid, an emulsion can include a non-ionic surfactant and/or a zwitterionic surfactant. Such surfactants include, but are not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); polyoxyethylene fatty ethers derived from lauryl, cetyl, stearyl and oleyl alcohols (known as Brij surfactants), such as triethyleneglycol monolauryl ether (Brij 30); polyoxyethylene-9-lauryl ether; and sorbitan esters (commonly known as the Spans), such as sorbitan trioleate (Span 85) and sorbitan monolaurate. Preferred surfactants for including in the emulsion are polysorbate 80 (Tween 80; polyoxyethylene sorbitan monooleate), Span 85 (sorbitan trioleate), lecithin and Triton X-100.

Mixtures of these surfactants can be included in the emulsion e.g. Tween 80/Span 85 mixtures, or Tween 80/Triton-X100 mixtures. A combination of a polyoxyethylene sorbitan ester such as polyoxyethylene sorbitan monooleate (Tween 80) and an octoxynol such as t-octylphenoxy-polyethoxyethanol (Triton X-100) is also suitable. Another useful combination comprises laureth 9 plus a polyoxyethylene sorbitan ester and/or an octoxynol. Useful mixtures can comprise a surfactant with a HLB value in the range of 10-20 (e.g. polysorbate 80, with a HLB of 15.0) and a surfactant with a HLB value in the range of 1-10 (e.g. sorbitan trioleate, with a HLB of 1.8).

Preferred amounts of oil (% by volume) in the final emulsion are between 2-20% e.g. 5-15%, 6-14%, 7-13%, 8-12%. A squalene content of about 4-6% or about 9-11% is particularly useful.

Preferred amounts of surfactants (% by weight) in the final emulsion are between 0.001% and 8%. For example: polyoxyethylene sorbitan esters (such as polysorbate 80) 0.2 to 4%, in particular between 0.4-0.6%, between 0.45-0.55%, about 0.5% or between 1.5-2%, between 1.8-2.2%, between 1.9-2.1%, about 2%, or 0.85-0.95%, or about 1%; sorbitan esters (such as sorbitan trioleate) 0.02 to 2%, in particular about 0.5% or about 1%; octyl- or nonylphenoxy polyoxyethanols (such as Triton X-100) 0.001 to 0.1%, in particular 0.005 to 0.02%; polyoxyethylene ethers (such as laureth 9) 0.1 to 8%, preferably 0.1 to 10% and in particular 0.1 to 1% or about 0.5%.

The absolute amounts of oil and surfactant, and their ratio, can be varied within wide limits while still forming an emulsion. A skilled person can easily vary the relative proportions of the components to obtain a desired emulsion, but a weight ratio of between 4:1 and 5:1 for oil and surfactant is typical (excess oil).

An important parameter for ensuring immunostimulatory activity of an emulsion, particularly in large animals, is the oil droplet size (diameter). The most effective emulsions have a droplet size in the submicron range. Suitably the droplet sizes will be in the range 50-750 nm. Most usefully the average droplet size is less than 250 nm e.g. less than 200 nm, less than 150 nm. The average droplet size is usefully in the range of 80-180 nm. Ideally, at least 80% (by number) of the emulsion's oil droplets are less than 250 nm in diameter, and preferably at least 90%. Apparatuses for determining the average droplet size in an emulsion, and the size distribution, are commercially available. These typically use the techniques of dynamic light scattering and/or single-particle optical sensing e.g. the Accusizer™ and Nicomp™ series of instruments available from Particle Sizing Systems (Santa Barbara, USA), or the Zetasizer™ instruments from Malvern Instruments (UK), or the Particle Size Distribution Analyzer instruments from Horiba (Kyoto, Japan).

Ideally, the distribution of droplet sizes (by number) has only one maximum i.e. there is a single population of droplets distributed around an average (mode), rather than having two maxima. Preferred emulsions have a polydispersity of <0.4 e.g. 0.3, 0.2, or less.

Suitable emulsions with submicron droplets and a narrow size distribution can be obtained by the use of microfluidisation. This technique reduces average oil droplet size by propelling streams of input components through geometrically fixed channels at high pressure and high velocity. These streams contact channel walls, chamber walls and each other. The results shear, impact and cavitation forces cause a reduction in droplet size. Repeated steps of microfluidisation can be performed until an emulsion with a desired droplet size average and distribution are achieved.

As an alternative to microfluidisation, thermal methods can be used to cause phase inversion. These methods can also provide a submicron emulsion with a tight particle size distribution.

Preferred emulsions can be filter sterilized i.e. their droplets can pass through a 220 nm filter. As well as providing a sterilization, this procedure also removes any large droplets in the emulsion.

In certain embodiments, the cationic lipid in the emulsion is DOTAP. The cationic oil-in-water emulsion may comprise from about 0.5 mg/ml to about 25 mg/ml DOTAP. For example, the cationic oil-in-water emulsion may comprise DOTAP at from about 0.5 mg/ml to about 25 mg/ml, from about 0.6 mg/ml to about 25 mg/ml, from about 0.7 mg/ml to about 25 mg/ml, from about 0.8 mg/ml to about 25 mg/ml, from about 0.9 mg/ml to about 25 mg/ml, from about 1.0 mg/ml to about 25 mg/ml, from about 1.1 mg/ml to about 25 mg/ml, from about 1.2 mg/ml to about 25 mg/ml, from about 1.3 mg/ml to about 25 mg/ml, from about 1.4 mg/ml to about 25 mg/ml, from about 1.5 mg/ml to about 25 mg/ml, from about 1.6 mg/ml to about 25 mg/ml, from about 1.7 mg/ml to about 25 mg/ml, from about 0.5 mg/ml to about 24 mg/ml, from about 0.5 mg/ml to about 22 mg/ml, from about 0.5 mg/ml to about 20 mg/ml, from about 0.5 mg/ml to about 18 mg/ml, from about 0.5 mg/ml to about 15 mg/ml, from about 0.5 mg/ml to about 12 mg/ml, from about 0.5 mg/ml to about 10 mg/ml, from about 0.5 mg/ml to about 5 mg/ml, from about 0.5 mg/ml to about 2 mg/ml, from about 0.5 mg/ml to about 1.9 mg/ml, from about 0.5 mg/ml to about 1.8 mg/ml, from about 0.5 mg/ml to about 1.7 mg/ml, from about 0.5 mg/ml to about 1.6 mg/ml, from about 0.6 mg/ml to about 1.6 mg/ml, from about 0.7 mg/ml to about 1.6 mg/ml, from about 0.8 mg/ml to about 1.6 mg/ml, about 0.5 mg/ml, about 0.6 mg/ml, about 0.7 mg/ml, about 0.8 mg/ml, about 0.9 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 12 mg/ml, about 18 mg/ml, about 20 mg/ml, about 21.8 mg/ml, about 24 mg/ml, etc. In an exemplary embodiment, the cationic oil-in-water emulsion comprises from about 0.8 mg/ml to about 1.6 mg/ml DOTAP, such as 0.8 mg/ml, 1.2 mg/ml, 1.4 mg/ml or 1.6 mg/ml.

In certain embodiments, the cationic lipid is DC Cholesterol. The cationic oil-in-water emulsion may comprise DC Cholesterol at from about 0.1 mg/ml to about 5 mg/ml DC Cholesterol. For example, the cationic oil-in-water emulsion may comprise DC Cholesterol from about 0.1 mg/ml to about 5 mg/ml, from about 0.2 mg/ml to about 5 mg/ml, from about 0.3 mg/ml to about 5 mg/ml, from about 0.4 mg/ml to about 5 mg/ml, from about 0.5 mg/ml to about 5 mg/ml, from about 0.62 mg/ml to about 5 mg/ml, from about 1 mg/ml to about 5 mg/ml, from about 1.5 mg/ml to about 5 mg/ml, from about 2 mg/ml to about 5 mg/ml, from about 2.46 mg/ml to about 5 mg/ml, from about 3 mg/ml to about 5 mg/ml, from about 3.5 mg/ml to about 5 mg/ml, from about 4 mg/ml to about 5 mg/ml, from about 4.5 mg/ml to about 5 mg/ml, from about 0.1 mg/ml to about 4.92 mg/ml, from about 0.1 mg/ml to about 4.5 mg/ml, from about 0.1 mg/ml to about 4 mg/ml, from about 0.1 mg/ml to about 3.5 mg/ml, from about 0.1 mg/ml to about 3 mg/ml, from about 0.1 mg/ml to about 2.46 mg/ml, from about 0.1 mg/ml to about 2 mg/ml, from about 0.1 mg/ml to about 1.5 mg/ml, from about 0.1 mg/ml to about 1 mg/ml, from about 0.1 mg/ml to about 0.62 mg/ml, about 0.15 mg/ml, about 0.3 mg/ml, about 0.6 mg/ml, about 0.62 mg/ml, about 0.9 mg/ml, about 1.2 mg/ml, about 2.46 mg/ml, about 4.92 mg/ml, etc. In an exemplary embodiment, the cationic oil-in-water emulsion comprises from about 0.62 mg/ml to about 4.92 mg/ml DC Cholesterol, such as 2.46 mg/ml.

In certain embodiments, the cationic lipid is DDA. The cationic oil-in-water emulsion may comprise from about 0.1 mg/ml to about 5 mg/ml DDA. For example, the cationic oil-in-water emulsion may comprise DDA at from about 0.1 mg/ml to about 5 mg/ml, from about 0.1 mg/ml to about 4.5 mg/ml, from about 0.1 mg/ml to about 4 mg/ml, from about 0.1 mg/ml to about 3.5 mg/ml, from about 0.1 mg/ml to about 3 mg/ml, from about 0.1 mg/ml to about 2.5 mg/ml, from about 0.1 mg/ml to about 2 mg/ml, from about 0.1 mg/ml to about 1.5 mg/ml, from about 0.1 mg/ml to about 1.45 mg/ml, from about 0.2 mg/ml to about 5 mg/ml, from about 0.3 mg/ml to about 5 mg/ml, from about 0.4 mg/ml to about 5 mg/ml, from about 0.5 mg/ml to about 5 mg/ml, from about 0.6 mg/ml to about 5 mg/ml, from about 0.73 mg/ml to about 5 mg/ml, from about 0.8 mg/ml to about 5 mg/ml, from about 0.9 mg/ml to about 5 mg/ml, from about 1.0 mg/ml to about 5 mg/ml, from about 1.2 mg/ml to about 5 mg/ml, from about 1.45 mg/ml to about 5 mg/ml, from about 2 mg/ml to about 5 mg/ml, from about 2.5 mg/ml to about 5 mg/ml, from about 3 mg/ml to about 5 mg/ml, from about 3.5 mg/ml to about 5 mg/ml, from about 4 mg/ml to about 5 mg/ml, from about 4.5 mg/ml to about 5 mg/ml, about 1.2 mg/ml, about 1.45 mg/ml, etc. Alternatively, the cationic oil-in-water emulsion may comprise DDA at about 20 mg/ml, about 21 mg/ml, about 21.5 mg/ml, about 21.6 mg/ml, about 25 mg/ml. In an exemplary embodiment, the cationic oil-in-water emulsion comprises from about 0.73 mg/ml to about 1.45 mg/ml DDA, such as 1.45 mg/ml.

Catheters or like devices may be used to deliver the self-replicating RNA molecules of the invention, as naked RNA or in combination with a delivery system, into a target organ or tissue. Suitable catheters are disclosed in, e.g., U.S. Pat. Nos. 4,186,745; 5,397,307; 5,547,472; 5,674,192; and 6,129,705, all of which are incorporated herein by reference.

The present invention includes the use of suitable delivery systems, such as liposomes, polymer microparticles or sub-micron emulsion microparticles with encapsulated or adsorbed self-replicating RNA, to deliver a self-replicating RNA molecule that encodes an RSV-F polypeptide, for example, to elicit an immune response alone, or in combination with another macromolecule. The invention includes liposomes, microparticles and submicron emulsions with adsorbed and/or encapsulated self-replicating RNA molecules, and combinations thereof.

As demonstrated further in the Examples, the self-replicating RNA molecules associated with liposomes and sub-micron emulsion microparticles can be effectively delivered to the host cell, and can induce an immune response to the protein encoded by the self-replicating RNA.

Immunogenic Compositions

The invention provides immunogenic compositions. The immunogenic compositions may include a single active immunogenic agent, or several immunogenic agents. For example, the immunogenic composition can comprise pre-fusion RSV F polypeptides or a combination of pre-fusion chimeric RSV F polypeptides. The immunogenic composition can comprise a self-replicating RNA encoding a pre-fusion RSV-F polypeptide, and preferably also comprises a suitable delivery system, such as liposomes, polymeric microparticles, an oil-in-water emulsion and combinations thereof.

Immunogenic compositions of the invention may also comprise one or more immunoregulatory agents. Preferably, one or more of the immunoregulatory agents include one or more adjuvants, for example two, three, four or more adjuvants. The adjuvants may include a TH1 adjuvant and/or a TH2 adjuvant, further discussed below.

In another embodiment, an immunogenic composition of the invention comprises a polypeptide that displays an epitope present in a pre-fusion conformation of RSV-F glycoprotein.

In another embodiment, an immunogenic composition of the invention comprises one or more pre-fusion chimera proteins based on two different pre-fusion non-RSV (F proteins (e.g, metapneumovirus, parainfluenza, such asPIV5, NDV), in which both have the same RSV F neutralizing epitopes mutated on the protein surface.

The compositions of the invention are preferably suitable for administration to a mammalian subject, such as a human, and include one or more pharmaceutically acceptable carrier(s) and/or excipient(s), including adjuvants. A thorough discussion of such components is available in reference 29. Compositions will generally be in aqueous form. When the composition is an immunogenic composition, it will elicit an immune response when administered to a mammal, such as a human. The immunogenic composition can be used to prepare a vaccine formulation for immunizing a mammal.

The immunogenic compositions may include a single active immunogenic agent, or several immunogenic agents. For example, the pre-fusion RSV F protein can be full length or a ecto-domain polypeptide and can be in a single form (e.g., uncleaved monomer, cleaved monomer, uncleaved trimer, cleaved trimer) or in two or more forms (e.g., a mixture of uncleaved monomer and uncleaved trimer or a dynamic equilibrium between uncleaved monomer and uncleaved trimer). In addition, the compositions can contain a pre-fusion RSV F protein and one or more other RSV proteins (e.g., a G protein and/or an M protein) and/or it may be combined with immunogens from other pathogens.

The composition may include preservatives such as thiomersal or 2-phenoxyethanol. It is preferred, however, that the vaccine should be substantially free from (i.e., less than 5 μg/ml) mercurial material, e.g., thiomersal-free. Immunogenic compositions containing no mercury are more preferred. Preservative-free immunogenic compositions are particularly preferred.

To control tonicity, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, and the like.

Compositions will generally have an osmolality of between 200 mOsm/kg and 400 mOsm/kg, preferably between 240-360 mOsm/kg, and will more preferably fall within the range of 290-310 mOsm/kg.

Compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range. The pH of a composition will generally be between 5.0 and 8.1, and more typically between 6.0 and 8.0, e.g., between 6.5 and 7.5, or between 7.0 and 7.8. A process of the invention may therefore include a step of adjusting the pH of the bulk vaccine prior to packaging.

The composition is preferably sterile. The composition is preferably non-pyrogenic, e.g., containing<1 EU (endotoxin unit, a standard measure) per dose, and preferably <0.1 EU per dose. The composition is preferably gluten free. Human vaccines are typically administered in a dosage volume of about 0.5 ml, although a half dose (i.e., about 0.25 ml) may be administered to children.

Adjuvants

Compositions of the invention, that contain RSV-F polypeptides, or nucleic acids that encode RSV-F polypeptides, may also include one or more adjuvants, for example two, three, four or more adjuvants, which can function to enhance the immune responses (humoral and/or cellular) elicited in a patient who receives the composition. The adjuvants may include a TH1 adjuvant and/or a TH2 adjuvant. Adjuvants which may be used in compositions of the invention include, but are not limited to:

- Mineral-containing compositions. Mineral-containing compositions suitable for use as adjuvants in the invention include mineral salts, such as calcium salts and aluminum salts (or mixtures thereof). The invention includes mineral salts such as hydroxides (e.g. oxyhydroxides), phosphates (e.g. hydroxyphosphates, orthophosphates), sulphates, etc., or mixtures of different mineral compounds, with the compounds taking any suitable form (e.g. gel, crystalline, amorphous, etc.), and with adsorption being preferred. Calcium salts include calcium phosphate (e.g., the "CAP" particles disclosed in ref 38). Aluminum salts include hydroxides, phosphates, sulfates, and the like. The mineral containing compositions may also be formulated as a particle of metal salt (39). Aluminum salt adjuvants are described in more detail below.
- Oil emulsion compositions (see in more detail below). Oil emulsion compositions suitable for use as adjuvants in the invention include squalene-water emulsions, such as MF59 (5% Squalene, 0.5% Tween 80 and 0.5% Span, formulated into submicron particles using a microfluidizer).
- Cytokine-inducing agents (see in more detail below). Cytokine-inducing agents suitable for use in the invention include toll-like receptor 7 (TLR7) agonists (e.g. benzonaphthyridine compounds disclosed in WO 2009/111337.
- Saponins (chapter 22 of ref 74), which are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as STIMULON™. Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 40. Saponin formulations may also comprise a sterol, such as cholesterol (41). Combinations of saponins and cholesterols can be used to form unique particles called immunostimulating complexes (ISCOMs) (chapter 23 of ref. 74). ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in refs. 41-43. Optionally, the ISCOMS may be devoid of additional detergent (44). A review of the development of saponin based adjuvants can be found in refs. 45 & 46.
- Fatty adjuvants (see in more detail below), including oil-in-water emulsions, modified natural lipid As derived from enterobacterial lipopolysaccharides, phospholipid compounds (such as the synthetic phospholipid dimer, E6020) and the like.
- Bacterial ADP-ribosylating toxins (e.g., the *E. coli* heat labile enterotoxin "LT", cholera toxin "CT", or pertussis toxin "PT") and detoxified derivatives thereof, such as the mutant toxins known as LT-K63 and LT-R72 (47). The use of detoxified ADP-ribosylating toxins as mucosal adjuvants is described in ref. 48 and as parenteral adjuvants in ref 49.
- Bioadhesives and mucoadhesives, such as esterified hyaluronic acid microspheres (50) or chitosan and its derivatives (51).
- Microparticles (i.e., a particle of ~100 nm to ~150 m in diameter, more preferably ~200 nm to ~30 m in diameter, or ~500 nm to ~10 m in diameter) formed from materials that are biodegradable and non-toxic (e.g., a poly(α-hydroxy acid), a polyhydroxybutyric acid, a polyorthoester, a polyanhydride, a polycaprolactone, and the like), with poly(lactide-co-glycolide) being preferred, optionally treated to have a negatively-charged surface (e.g., with SDS) or a positively-charged surface (e.g., with a cationic detergent, such as CTAB).
- Liposomes (Chapters 13 & 14 of ref 74). Examples of liposome formulations suitable for use as adjuvants are described in refs. 52-54.

Polyoxyethylene ethers and polyoxyethylene esters (55). Such formulations further include polyoxyethylene sorbitan ester surfactants in combination with an octoxynol (56) as well as polyoxyethylene alkyl ethers or ester surfactants in combination with at least one additional non-ionic surfactant such as an octoxynol (57). Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

Muramyl peptides, such as N-acetylmuramyl-L-threonyl-D-isoglutamine ("thr-MDP"), N-acetyl-normuramyl-L-alanyl-D-isoglutamine (nor-MDP), N-acetylglucsaminyl-N-acetylmuramyl-L-Al-D-isoglu-L-Ala-dipalmitoxy propylamide ("DTP-DPP", or "Theramide™), N-acetylmuramyl-L-alanyl-D-isoglutaminyl-L-alanine-2-(1'-2'dipalmitoyl-sn-glycero-3-hydroxyphosphoryloxy)-ethylamine ("MTP-PE").

An outer membrane protein proteosome preparation prepared from a first Gram-negative bacterium in combination with a liposaccharide preparation derived from a second Gram-negative bacterium, wherein the outer membrane protein proteosome and liposaccharide preparations form a stable non-covalent adjuvant complex. Such complexes include "IVX-908", a complex comprised of *Neisseria meningitidis* outer membrane and lipopolysaccharides.

A polyoxidonium polymer (58, 59) or other N-oxidized polyethylene-piperazine derivative.

Methyl inosine 5'-monophosphate ("MIMP") (60).

A polyhydroxlated pyrrolizidine compound (61), such as one having formula:

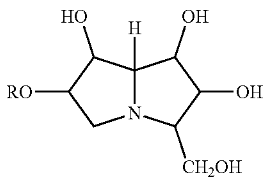

where R is selected from the group comprising hydrogen, straight or branched, unsubstituted or substituted, saturated or unsaturated acyl, alkyl (e.g., cycloalkyl), alkenyl, alkynyl and aryl groups, or a pharmaceutically acceptable salt or derivative thereof. Examples include, but are not limited to: casuarine, casuarine-6-α-D-glucopyranose, 3-epi-casuarine, 7-epi-casuarine, 3,7-diepi-casuarine, and the like A CD1d ligand, such as an α-glycosylceramide (62-69) (e.g., α-galactosylceramide), phytosphingosine-containing α-glycosylceramides, OCH, KRN7000 [(2S,3S,4R)-1-O-(α-D-galactopyranosyl)-2-(N-hexacosanoylamino)-1,3,4-octadecanetriol], CRONY-101, 3"-O-sulfo-galactosylceramide, etc.

A gamma inulin (70) or derivative thereof, such as algammulin.

Virosomes and virus-like particles (VLPs). These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Q13-phage (such as coat proteins), GA-phage, fr-phage, AP205 phage, and Ty (such as retrotransposon Ty protein p1).

These and other adjuvant-active substances are discussed in more detail in references 74 & 75.

Compositions may include two, three, four or more adjuvants. For example, compositions of the invention may advantageously include both an oil-in-water emulsion and a cytokine-inducing agent, or both a mineral-containing composition and a cytokine-inducing agent, or two oil-in-water emulsion adjuvants, or two benzonaphthyridine compounds, etc.

Antigens and adjuvants in a composition will typically be in admixture.

Oil Emulsion Adjuvants

Oil emulsion compositions suitable for use as adjuvants in the invention include squalene-water emulsions, such as MF59 (5% Squalene, 0.5% Tween 80, and 0.5% Span 85, formulated into submicron particles using a microfluidizer). Complete Freund's adjuvant (CFA) and incomplete Freund's adjuvant (IFA) may also be used.

Various oil-in-water emulsions are known, and they typically include at least one oil and at least one surfactant, with the oil(s) and surfactant(s) being biodegradable (metabolizable) and biocompatible. The oil droplets in the emulsion are generally less than 5 μm in diameter, and may even have a sub-micron diameter, with these small sizes being achieved with a microfluidizer to provide stable emulsions. Droplets with a size less than 220 nm are preferred as they can be subjected to filter sterilization.

The invention can be used with oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used, e.g., obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoid known as squalene, 2,6,10,15,19,23-hexamethyl-2,6,10,14,18,22-tetracosahexaene, which is particularly preferred herein. Squalane, the saturated analog to squalene, is also preferred oil. Fish oils, including squalene and squalane, are readily available from commercial sources or may be obtained by methods known in the art. Other preferred oils are the tocopherols (see below). Mixtures of oils can be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); nonylphenol ethoxylates, such as the TERGITOL™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Non-ionic surfactants are preferred. Preferred surfactants for including in the emulsion are TWEEN 80 ™ (polyoxyethylene sorbitan monooleate), Span 85 (sorbitan trioleate), lecithin and Triton X-100.

Mixtures of surfactants can be used e.g., TWEEN 80 ™/Span 85 mixtures. A combination of a polyoxyethylene sorbitan ester such as polyoxyethylene sorbitan monooleate (TWEEN 80 ™) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as TWEEN 80 ™) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Specific oil-in-water emulsion adjuvants useful with the invention include, but are not limited to:

- A submicron emulsion of squalene, TWEEN 80 ™, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59' (71-73), as described in more detail in Chapter 10 of ref. 74 and chapter 12 of ref 75. The MF59 emulsion advantageously includes citrate ions, e.g., 10 mM sodium citrate buffer.
- An emulsion of squalene, a tocopherol, and TWEEN 80 ™. The emulsion may include phosphate buffered saline. It may also include Span 85 (e.g., at 1%) and/or lecithin. These emulsions may have from 2 to 10% squalene, from 2 to 10% tocopherol and from 0.3 to 3% TWEEN 80 ™, and the weight ratio of squalene: tocopherol is preferably <1 as this provides a more stable emulsion. Squalene and TWEEN 80 ™ may be present volume ratio of about 5:2. One such emulsion can be made by dissolving TWEEN 80 ™ in PBS to give a 2% solution, then mixing 90 ml of this solution with a mixture of (5 g of DL-α-tocopherol and 5 ml squalene), then microfluidizing the mixture. The resulting emulsion may have submicron oil droplets, e.g., with an average diameter of between 100 and 250 nm, preferably about 180 nm.
- An emulsion of squalene, a tocopherol, and a Triton detergent (e.g., Triton X-100). The emulsion may also include a 3d-MPL (see below). The emulsion may contain a phosphate buffer.
- An emulsion comprising a polysorbate (e.g., polysorbate 80), a Triton detergent (e.g., Triton X-100) and a tocopherol (e.g., an α-tocopherol succinate). The emulsion may include these three components at a mass ratio of about 75:11:10 (e.g., 750 μg/ml polysorbate 80, 110 μg/ml Triton X-100 and 100 μg/ml α-tocopherol succinate), and these concentrations should include any contribution of these components from antigens. The emulsion may also include squalene. The emulsion may also include a 3d-MPL (see below). The aqueous phase may contain a phosphate buffer.
- An emulsion of squalane, polysorbate 80 and poloxamer 401 ("PLURONIC™ L121"). The emulsion can be formulated in phosphate buffered saline, pH 7.4. This emulsion is a useful delivery vehicle for muramyl dipeptides, and has been used with threonyl-MDP in the "SAF-1" adjuvant (76) (0.05-1% Thr-MDP, 5% squalane, 2.5% Pluronic L121 and 0.2% polysorbate 80). It can also be used without the Thr-MDP, as in the "AF" adjuvant (77) (5% squalane, 1.25% Pluronic L121 and 0.2% polysorbate 80). Microfluidization is preferred.
- An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm. The emulsion may also include one or more of: alditol; a cryoprotective agent (e.g. a sugar, such as dodecylmaltoside and/or sucrose); and/or an alkylpolyglycoside. Such emulsions may be lyophilized.
- An emulsion having from 0.5-50% of an oil, 0.1-10% of a phospholipid, and 0.05-5% of a non-ionic surfactant. As described in reference 78, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.
- A submicron oil-in-water emulsion of a non-metabolizable oil (such as light mineral oil) and at least one surfactant (such as lecithin, TWEEN 80 ™ or Span 80). Additives may be included, such as QuilA saponin, cholesterol, a saponin-lipophile conjugate (such as GPI-0100, described in reference 79, produced by addition of aliphatic amine to desacylsaponin via the carboxyl group of glucuronic acid), dimethyidioctadecylammonium bromide and/or N,N-dioctadecyl-N, N-bis (2-hydroxyethyl)propanediamine.

An emulsion comprising a mineral oil, a non-ionic lipophilic ethoxylated fatty alcohol, and a non-ionic hydrophilic surfactant (e.g. an ethoxylated fatty alcohol and/or polyoxyethylene-polyoxypropylene block copolymer).

An emulsion comprising a mineral oil, a non-ionic hydrophilic ethoxylated fatty alcohol, and a non-ionic lipophilic surfactant (e.g. an ethoxylated fatty alcohol and/or polyoxyethylene-polyoxypropylene block copolymer).

An emulsion in which a saponin (e.g., QuilA or QS21) and a sterol (e.g., a cholesterol) are associated as helical micelles (80).

The emulsions may be mixed with antigen extemporaneously, at the time of delivery. Thus the adjuvant and antigen may be kept separately in a packaged or distributed vaccine, ready for final formulation at the time of use. The antigen will generally be in an aqueous form, such that the vaccine is finally prepared by mixing two liquids. The volume ratio of the two liquids for mixing can vary (e.g., between 5:1 and 1:5) but is generally about 1:1.

Cytokine-Inducing Agents

Cytokine-inducing agents for inclusion in compositions of the invention are able, when administered to a patient, to elicit the immune system to release cytokines, including interferons and interleukins. Preferred agents can elicit the release of one or more of: interferon-γ; interleukin-1; interleukin-2; interleukin-12; TNF-α; TNF-β; and GM-CSF. Preferred agents elicit the release of cytokines associated with a Th1-type immune response, e.g., interferon-γ, TNF-α, interleukin-2. Stimulation of both interferon-γ and interleukin-2 is preferred.

As a result of receiving a composition of the invention, therefore, a patient will have T cells that, when stimulated with a RSV F protein, will release the desired cytokine(s) in an antigen-specific manner. For example, T cells purified from their blood will release 7-interferon when exposed in vitro to F protein. Methods for measuring such responses in peripheral blood mononuclear cells (PBMC) are known in the art, and include ELISA, ELISPOT, flow-cytometry and real-time PCR. For example, reference 81 reports a study in which antigen-specific T cell-mediated immune responses against tetanus toxoid, specifically 7-interferon responses, were monitored, and found that ELISPOT was the most sensitive method to discriminate antigen-specific TT-induced responses from spontaneous responses, but that intracytoplasmic cytokine detection by flow cytometry was the most efficient method to detect re-stimulating effects.

Suitable cytokine-inducing agents include, but are not limited to:

An immunostimulatory oligonucleotide, such as one containing a CpG motif (a dinucleotide sequence containing an unmethylated cytosine linked by a phosphate bond to a guanosine), or a double-stranded RNA, or an oligonucleotide containing a palindromic sequence, or an oligonucleotide containing a poly(dG) sequence.

3-O-deacylated monophosphoryl lipid A ('3dMPL', also known as 'MPL™') (82-85).

An imidazoquinoline compound, such as IMIQUIMOD™ ("R-837") (86, 87), RESIQUIMOD™ ("R-848") (88), and their analogs; and salts thereof (e.g., the hydrochloride salts). Further details about immunostimulatory imidazoquinolines can be found in references 89 to 93.

A benzonaphthyridine compound, such as: (a) a compound having the formula:

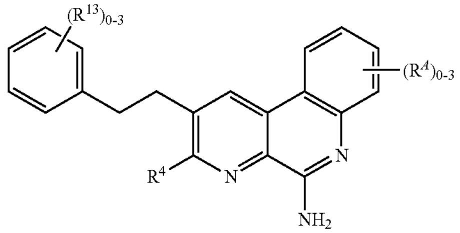

wherein:

$R^4$ is selected from H, halogen, —C(O)OR$^7$, —C(O)R$^7$, —C(O)N(R$^{11}$R$^{12}$), —N(R$^{11}$R$^{12}$), —N(R$^9$)$_2$, —NHN(R$^9$)$_2$, —SR$^7$, —(CH$_2$)$_n$OR$^7$, —(CH$_2$)$_n$R$^7$, -LR$^8$, -LR$^{10}$, —OLR$^8$, —OLR$^{10}$, $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl groups of $R^4$ are each optionally substituted with 1 to 3 substituents independently selected from halogen, —CN, —NO$_2$, —R$^7$, —OR$^8$, —C(O)R$^8$, —OC(O)R$^8$, —C(O)OR$^8$, —N(R$^9$)$_2$, —P(O)(OR$^8$)$_2$, —OP(O)(OR$^8$)$_2$, —P(O)(OR$^{10}$)$_2$, —OP(O)(OR$^{10}$)$_2$, —C(O)N(R$^9$)$_2$, —S(O)$_2$R$^8$, —S(O)R$^8$, —S(O)$_2$N(R$^9$)$_2$, and —NR$^9$S(O)$_2$R$^8$;

each L is independently selected from a bond, —(O(CH$_2$)$_m$)$_t$—, $C_1$-$C_6$alkyl, $C_2$-$C_6$alkenylene and $C_2$-$C_6$alkynylene, wherein the $C_1$-$C_6$alkyl, $C_2$-$C_6$alkenylene and $C_2$-$C_6$alkynylene of L are each optionally substituted with 1 to 4 substituents independently selected from halogen, —R$^8$, —OR$^8$, —N(R$^9$)$_2$, —P(O)(OR$^8$)$_2$, —OP(O)(OR$^8$)$_2$, —P(O)(OR$^{10}$)$_2$, and —OP(O)(OR$^{10}$)$_2$;

$R^7$ is selected from H, $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl, wherein the $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl groups of $R^7$ are each optionally substituted with 1 to 3 $R^{13}$ groups;

each $R^8$ is independently selected from H, —CH(R$^{10}$)$_2$, $C_1$-$C_8$alkyl, $C_2$-$C_8$alkene, $C_2$-$C_8$alkyne, $C_1$-$C_6$haloalkyl, $C_1$-$C_6$alkoxy, $C_1$-$C_6$heteroalkyl, $C_3$-$C_8$cycloalkyl, $C_2$-$C_8$heterocycloalkyl, $C_1$-$C_6$hydroxyalkyl and $C_1$-$C_6$haloalkoxy, wherein the $C_1$-$C_8$alkyl, $C_2$-$C_8$alkene, $C_2$-$C_8$alkyne, $C_1$-$C_6$heteroalkyl, $C_1$-$C_6$haloalkyl, $C_1$-$C_6$alkoxy, $C_3$-$C_8$cycloalkyl, $C_2$-$C_8$heterocycloalkyl, $C_1$-$C_6$hydroxyalkyl and $C_1$-$C_6$haloalkoxy groups of $R^8$are each optionally substituted with 1 to 3 substituents independently selected from —CN, R$^{11}$, —$OR^{11}$, —$SR^{11}$, —$C(O)R^{11}$, —$OC(O)R^{11}$, —$C(O)N(R^9)_2$, —$C(O)OR^{11}$, —$NR^9C(O)R^{11}$, —$NR^9R^{10}$, —$NR^{11}R^{11}$, —$N(R^9)_2$, —$OR^9$, —$OR^{10}$, —$C(O)NR^{11}R^{12}$, —$C(O)NR^{11}OH$, —$S(O)_2R^{11}$, —$S(O)R^{11}$, —$S(O)_2NR^{11}R^{12}$, —$NR^{11}S(O)_2R^{11}$, —$P(O)(OR^{11})_2$, and —$OP(O)(OR^{11})_2$;

each $R^9$ is independently selected from H, —$C(O)R^8$, —$C(O)OR^8$, —$C(O)R^{10}$, —$C(O)OR^{10}$, —$S(O)_2R^{10}$, —$C_1$-$C_6$ alkyl, $C_1$-$C_6$ heteroalkyl and $C_3$-$C_6$ cycloalkyl, or each $R^9$ is independently a $C_1$-$C_6$alkyl that together with N they are attached to form a $C_3$-$C_8$heterocycloalkyl, wherein the $C_3$-$C_8$heterocycloalkyl ring optionally contains an additional heteroatom selected from N, O and S, and wherein the $C_1$-$C_6$ alkyl, $C_1$-$C_6$ heteroalkyl, $C_3$-$C_6$ cycloalkyl, or $C_3$-$C_8$heterocycloalkyl groups of $R^9$ are each optionally substituted with 1 to 3 substituents independently selected from —CN, $R^{11}$, —$OR^{11}$, —$SR^{11}$, —$C(O)R^{11}$, —$OC(O)R^{11}$, —$C(O)OR^{11}$, —$NR^{11}R^{12}$, —$C(O)NR^{11}R^{12}$, —$C(O)NR^{11}OH$, —$S(O)_2R^{11}$, —$S(O)R^{11}$, —$S(O)_2NR^{11}R^{12}$, —$NR^{11}S(O)_2R^{11}$, —$P(O)(OR^{11})_2$, and —$OP(O)(OR^{11})_2$;

each $R^{10}$ is independently selected from aryl, $C_3$-$C_8$cycloalkyl, $C_3$-$C_8$heterocycloalkyl and heteroaryl, wherein the aryl, $C_3$-$C_8$cycloalkyl, $C_3$-$C_8$heterocycloalkyl and heteroaryl groups are optionally substituted with 1 to 3 substituents selected from halogen, —$R^8$, —$OR^8$, -$LR^9$, -$LOR^9$, —$N(R^9)_2$, —$NR^9C(O)R^8$, —$NR^9CO_2R^8$, —$CO_2R^8$, —$C(O)R^8$and —$C(O)N(R^9)_2$;

$R^{11}$ and $R^{12}$ are independently selected from H, $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl groups of $R^{11}$ and $R^{12}$ are each optionally substituted with 1 to 3 substituents independently selected from halogen, —CN, $R^8$, —$OR^8$, —$C(O)R^8$, —$OC(O)R^8$, —$C(O)OR^8$, —$N(R^9)_2$, —$NR^8C(O)R^8$, —$NR^8C(O)OR^8$, —$C(O)N(R^9)_2$, $C_3$-$C_8$heterocycloalkyl, —$S(O)_2R^8$, —$S(O)_2N(R^9)_2$, —$NR^9S(O)_2R^8$, $C_1$-$C_6$haloalkyl and $C_1$-$C_6$haloalkoxy;

or $R^{11}$ and $R^{12}$ are each independently $C_1$-$C_6$alkyl and taken together with the N atom to which they are attached form an optionally substituted $C_3$-$C_8$heterocycloalkyl ring optionally containing an additional heteroatom selected from N, O and S;

each $R^{13}$ is independently selected from halogen, —CN, -$LR^9$, -$LOR^9$, —$OLR^9$, -$LR^{10}$, -$LOR^{10}$, —$OLR^{10}$, -$LR^8$, -$LOR^8$, —$OLR^8$, -$LSR^8$, -$LSR^{10}$, -$LC(O)R^8$, —$OLC(O)R^8$, -$LC(O)OR^8$, -$LC(O)R^{10}$, -$LOC(O)OR^8$, -$LC(O)NR^9R^{11}$, -$LC(O)NR^9R^8$, -$LN(R^9)_2$, -$LNR^9R^8$, -$LNR^9R^{10}$, -$LC(O)N(R^9)_2$, -$LS(O)_2R^8$, -$LS(O)R^8$, -$LC(O)NR^8OH$, -$LNR^9C(O)R^8$, -$LNR^9C(O)OR^8$, -$LS(O)_2N(R^9)_2$, —$OLS(O)_2N(R^9)_2$, -$LNR^9S(O)_2R^8$, -$LC(O)NR^9LN(R^9)_2$, -$LP(O)(OR^8)_2$, -$LOP(O)(OR^8)_2$, -$LP(O)(OR^{10})_2$ and —$OLP(O)(OR^{10})_2$;

each $R^A$ is independently selected from —$R^8$, —$R^7$, —$OR^7$, —$OR^8$, —$R^{10}$, —$OR^{10}$, —$SR^8$, —$NO_2$, —CN, —$N(R^9)_2$, —$NR^9C(O)R^8$, —$NR^9C(S)R^8$, —$NR^9C(O)N(R^9)_2$, —$NR^9C(S)N(R^9)_2$, —$NR^9CO_2R^8$, —$NR^9NR^9C(O)R^8$, —$NR^9NR^9C(O)N(R^9)_2$, —$NR^9NR^9CO_2R^8$, —$C(O)C(O)R^8$, —$C(O)CH_2C(O)R^8$, —$CO_2R^8$, —$(CH_2)_nCO_2R^8$, —$C(O)R^8$, —$C(S)R^8$, —$C(O)N(R^9)_2$, —$C(S)N(R^9)_2$, —$OC(O)N(R^9)_2$, —$OC(O)R^8$, —$C(O)N(OR^8)R^8$, —$C(NOR^8)R^8$, —$S(O)_2R^8$, —$S(O)_3R^8$, —$SO_2N(R^9)_2$, —$S(O)R^8$, —$NR^9SO_2N(R^9)_2$, —$NR^9SO_2R^8$, —$P(O)(OR^8)_2$, —$OP(O)(OR^8)_2$, —$P(O)(OR^{10})_2$, —$OP(O)(OR^{10})_2$, —$N(OR^8)R^8$, —$CH{=}CHCO_2R^8$, —$C(=NH)$—$N(R^9)_2$, and —$(CH_2)_nNHC(O)R^8$; or two adjacent $R^A$ substituents on Ring A form a 5-6 membered ring that contains up to two heteroatoms as ring members;

n is, independently at each occurrence, 0, 1, 2, 3, 4, 5, 6, 7 or 8;

each m is independently selected from 1, 2, 3, 4, 5 and 6, and t is 1, 2, 3, 4, 5, 6, 7 or 8; (b) a compound having the formula:

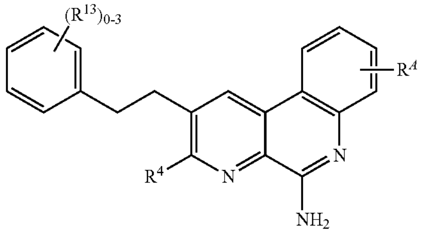

wherein:

$R^4$ is selected from H, halogen, —$C(O)OR^7$, —$C(O)R^7$, —$C(O)N(R^{11}R^{12})$, —$N(R^{11}R^{12})$, —$N(R^9)_2$, —$NHN(R^9)_2$, —$SR^7$, —$(CH_2)_nOR^7$, —$(CH_2)_nR^7$, -$LR^8$, -$LR^{10}$, —$OLR^8$, —$OLR^{10}$, $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl groups of $R^4$ are each optionally substituted with 1 to 3 substituents independently selected from halogen, —CN, —$NO_2$, —$R^7$, —$OR^8$, —$C(O)R^8$, —$OC(O)R^8$, —$C(O)OR^8$, —$N(R^9)_2$, —$P(O)(OR^8)_2$, —$OP(O)(OR^8)_2$, —$P(O)(OR^{10})_2$, —$OP(O)(OR^{10})_2$, —$C(O)N(R^9)_2$, —$S(O)_2R^8$, —$S(O)R^8$, —$S(O)_2N(R^9)_2$, and —$NR^9S(O)_2R^8$;

each L is independently selected from a bond, —$(O(CH_2)_m)_t$—, $C_1$-$C_6$alkyl, $C_2$-$C_6$alkenylene and $C_2$-$C_6$alkynylene, wherein the $C_1$-$C_6$alkyl, $C_2$-$C_6$alkenylene and $C_2$-$C_6$alkynylene of L are each optionally substituted with 1 to 4 substituents independently selected from halogen, —$R^8$, —$OR^8$, —$N(R^9)_2$, —$P(O)(OR^8)_2$, —$OP(O)(OR^8)_2$, —$P(O)(OR^{10})_2$, and —$OP(O)(OR^{10})_2$;

$R^7$ is selected from H, $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl, wherein the $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl groups of $R^7$ are each optionally substituted with 1 to 3 $R^{13}$ groups;

each $R^8$ is independently selected from H, —$CH(R^{10})_2$, $C_1$-$C_8$alkyl, $C_2$-$C_8$alkene, $C_2$-$C_8$alkyne, $C_1$-$C_6$haloalkyl, $C_1$-$C_6$alkoxy, $C_1$-$C_6$heteroalkyl, $C_3$-$C_8$cycloalkyl, $C_2$-$C_8$heterocycloalkyl, $C_1$-$C_6$hydroxyalkyl and $C_1$-$C_6$haloalkoxy, wherein the $C_1$-$C_8$alkyl, $C_2$-$C_8$alkene, $C_2$-$C_8$alkyne, $C_1$-$C_6$heteroalkyl, $C_1$-$C_6$haloalkyl, $C_1$-$C_6$alkoxy, $C_3$-$C_8$cycloalkyl, $C_2$-$C_8$heterocycloalkyl, $C_1$-$C_6$hydroxyalkyl and $C_1$-$C_6$haloalkoxy groups of $R^8$ are each optionally substituted with 1 to 3 substituents independently selected from —CN, $R^{11}$, —$OR^{11}$, —$SR^{11}$, —$C(O)R^{11}$, —$OC(O)R^{11}$, —$C(O)N(R^9)_2$, —$C(O)OR^{11}$, —$NR^9C(O)R^{11}$, —$NR^9R^{10}$, —$NR^{11}R^{12}$, —$N(R^9)_2$, —$OR^9$, —$OR^{10}$, —$C(O)NR^{11}R^{12}$, —$C(O)NR^{11}OH$, —$S(O)_2R^{11}$, —$S(O)R^{11}$, —$S(O)_2NR^{11}R^{12}$, —$NR^{11}S(O)_2R^{11}$, —$P(O)(OR^{11})_2$, and —$OP(O)(OR^{11})_2$;

each $R^9$ is independently selected from H, —$C(O)R^8$, —$C(O)OR^8$, —$C(O)R^{10}$, —$C(O)OR^{10}$, —$S(O)_2R^{10}$, —$C_1$-$C_6$ alkyl, $C_1$-$C_6$ heteroalkyl and $C_3$-$C_6$ cycloalkyl, or each $R^9$ is independently a $C_1$-$C_6$alkyl that together with N they are attached to form a $C_3$-$C_8$heterocycloalkyl, wherein the $C_3$-$C_8$heterocycloalkyl ring optionally contains an additional heteroatom selected from N, O and S, and wherein the $C_1$-$C_6$ alkyl, $C_1$-$C_6$ heteroalkyl, $C_3$-$C_6$ cycloalkyl, or $C_3$-$C_8$heterocycloalkyl groups of $R^9$ are each optionally substituted with 1 to 3 substituents independently selected from —CN, $R^{11}$, —$OR^{11}$, —$SR^{11}$, —$C(O)R^{11}$, —$OC(O)R^{11}$, —$C(O)OR^{11}$, —$NR^{11}R^{12}$, —$C(O)NR^{11}R^{12}$, —$C(O)NR^{11}OH$, —$S(O)_2R^{11}$, —$S(O)R^{11}$, —$S(O)_2NR^{11}R^{12}$, —$NR^{11}S(O)_2R^{11}$, —$P(O)(OR^{11})_2$, and —$OP(O)(OR^{11})_2$;

each $R^{10}$ is independently selected from aryl, $C_3$-$C_8$cycloalkyl, $C_3$-$C_8$heterocycloalkyl and heteroaryl, wherein the aryl, $C_3$-$C_8$cycloalkyl, $C_3$-$C_8$heterocycloalkyl and heteroaryl groups are optionally substituted with 1 to 3 substituents selected from halogen, —$R^8$, —$OR^8$, -$LR^9$, -$LOR^9$, —$N(R^9)_2$, —$NR^9C(O)R^8$, —$NR^8CO_2R^8$, —$CO_2R^8$, —$C(O)R^8$ and —$C(O)N(R^9)_2$;

$R^{11}$ and $R^{12}$ are independently selected from H, $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl groups of $R^{11}$ and $R^{12}$ are each optionally substituted with 1 to 3 substituents independently selected from halogen, —CN, $R^8$, —$OR^8$, —$C(O)R^8$, —$OC(O)R^8$, —$C(O)OR^8$, —$N(R^9)_2$, —$NR^8C(O)R^8$, —$NR^8C(O)OR^8$, —$C(O)N(R^9)_2$, $C_3$-$C_8$heterocycloalkyl, —$S(O)_2R^8$, —$S(O)_2N(R^9)_2$, —$NR^9S(O)_2R^8$, $C_1$-$C_6$haloalkyl and $C_1$-$C_6$haloalkoxy;

or $R^{11}$ and $R^{12}$ are each independently $C_1$-$C_6$alkyl and taken together with the N atom to which they are attached form an optionally substituted $C_3$-$C_8$heterocycloalkyl ring optionally containing an additional heteroatom selected from N, O and S;

each $R^{13}$ is independently selected from halogen, —CN, -$LR^9$, -$LOR^9$, —$OLR^9$, -$LR^{10}$, -$LOR^{10}$, —$OLR^{10}$, -$LR^8$, -$LOR^8$, —$OLR^8$, -$LSR^8$, -$LSR^{10}$, -$LC(O)R^8$, —$OLC(O)R^8$, -$LC(O)OR^8$, -$LC(O)R^{10}$, -$LOC(O)OR^8$, -$LC(O)NR^9R^{11}$, -$LC(O)NR^9R^8$, -$LN(R^9)_2$, -$LNR^9R^8$, -$LNR^9R^{10}$, -$LC(O)N(R^9)_2$, -$LS(O)_2R^8$, -$LS(O)R^8$, -$LC(O)NR^8OH$, -$LNR^9C(O)R^8$, -$LNR^9C(O)OR^8$, -$LS(O)_2N(R^9)_2$, —$OLS(O)_2N(R^9)_2$, -$LNR^9S(O)_2R^8$, -$LC(O)NR^9LN(R^9)_2$, -$LP(O)(OR^8)_2$, -$LOP(O)(OR^8)_2$, -$LP(O)(OR^{10})_2$ and —$OLP(O)(OR^{10})_2$;

each $R^A$ is independently selected from —$R^8$, —$R^7$, —$OR^7$, —$OR^8$, —$R^{10}$, —$OR^{10}$, —$SR^8$, —$NO_2$, —CN, —$N(R^9)_2$, —$NR^9C(O)R^8$, —$NR^9C(S)R^8$, —$NR^9C(O)N(R^9)_2$, —$NR^9C(S)N(R^9)_2$, —$NR^9CO_2R^8$, —$NR^9NR^9C(O)R^8$, —$NR^9NR^9C(O)N(R^9)_2$, —$NR^9NR^9CO_2R^8$, —$C(O)C(O)R^8$, —$C(O)CH_2C(O)R^8$, —$CO_2R^8$, —$(CH_2)_nCO_2R^8$, —$C(O)R^8$, —$C(S)R^8$, —$C(O)N(R^9)_2$, —$C(S)N(R^9)_2$, —$OC(O)N(R^9)_2$, —$OC(O)R^8$, —$C(O)N(OR^8)R^8$, —$C(NOR^8)R^8$, —$S(O)_2R^8$, —$S(O)_3R^8$, —$SO_2N(R^9)_2$, —$S(O)R^8$, —$NR^9SO_2N(R^9)_2$, —$NR^9SO_2R^8$, —$P(O)(OR^8)_2$, —$OP(O)(OR^8)_2$, —$P(O)(OR^{10})_2$, —$OP(O)(OR^{10})_2$, —$N(OR^8)R^8$, —$CH{=}CHCO_2R^8$, —$C({=}NH)$—$N(R^9)_2$, and —$(CH_2)_nNHC(O)R^8$;

n is, independently at each occurrence, 0, 1, 2, 3, 4, 5, 6, 7 or 8; each m is independently selected from 1, 2, 3, 4, 5 and 6, and t is 1, 2, 3, 4, 5, 6, 7 or 8; or (c) a pharmaceutically acceptable salt of any of (a) or (b).

Other benzonaphthyridine compounds, and methods of making benzonaphthyridine compounds, are described in WO 2009/111337. A benzonaphthyridine compound, or a salt thereof, can be used on its own, or in combination with one or more further compounds. For example, a benzonaphthyridine compound can be used in combination with an oil-in-water emulsion or a mineral-containing composition. In a particular embodiment, a benzonaphthyridine compound is used in combination with an oil-in-water emulsion (e.g. a squalene-water emulsion, such as MF59) or a mineral-containing composition (e.g., a mineral sald such as an aluminum salt or a calcium salt).

A thiosemicarbazone compound, such as those disclosed in reference 94. Methods of formulating, manufacturing, and screening for active compounds are also described in reference 94. The thiosemicarbazones are particularly effective in the stimulation of human peripheral blood mononuclear cells for the production of cytokines, such as TNF-α.

A tryptanthrin compound, such as those disclosed in reference 95. Methods of formulating, manufacturing, and screening for active compounds are also described in reference 95. The thiosemicarbazones are particularly effective in the stimulation of human peripheral blood mononuclear cells for the production of cytokines, such as TNF-α.

A nucleoside analog, such as: (a) Isatorabine (ANA-245; 7-thia-8-oxoguanosine):

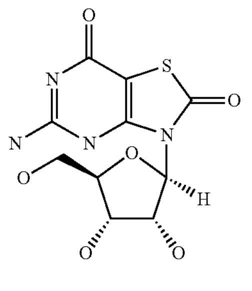 [SMILES: Nc1nc(=O)c2sc(=O)n([C@@H]3O[C@H](CO)[C@@H](O)[C@H]3O)c2[nH]1]

and prodrugs thereof; (b) ANA975; (c) ANA-025-1; (d) ANA380; (e) the compounds disclosed in references 96 to 98; (f) a compound having the formula:

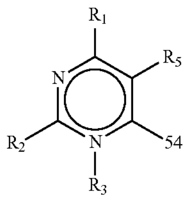

wherein:

$R_1$ and $R_2$ are each independently H, halo, —$NR_aR_b$, —OH, $C_{1-6}$ alkoxy, substituted $C_{1-6}$ alkoxy, heterocyclyl, substituted heterocyclyl, $C_{6-10}$ aryl, substituted $C_{6-10}$ aryl, $C_{1-6}$ alkyl, or substituted $C_{1-6}$ alkyl;

$R_3$ is absent, H, $C_{1-6}$ alkyl, substituted $C_{1-6}$ alkyl, $C_{6-10}$ aryl, substituted $C_{6-10}$ aryl, heterocyclyl, or substituted heterocyclyl;

$R_4$ and $R_5$ are each independently H, halo, heterocyclyl, substituted heterocyclyl, —C(O)—$R_d$, $C_{1-6}$ alkyl, substituted $C_{1-6}$ alkyl, or bound together to form a 5 membered ring as in $R_{4-5}$:

$R_{4-5}$

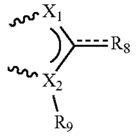

the binding being achieved at the bonds indicated by ∿ $X_1$ and $X_2$ are each independently N, C, O, or S;

$R_8$ is H, halo, —OH, $C_{1-6}$ alkyl, $C_{2-6}$ alkenyl, $C_{2-6}$ alkynyl, —OH, —$NR_aR_b$, —$(CH_2)_n$—O—$R_c$, —O—($C_{1-6}$ alkyl), —$S(O)_pR_e$, or —C(O)—$R_d$;

$R_9$ is H, $C_{1-6}$ alkyl, substituted $C_{1-6}$ alkyl, heterocyclyl, substituted heterocyclyl or $R_{9a}$, wherein $R_{9a}$ is:

$R_{9a}$

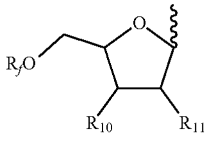

the binding being achieved at the bond indicated by a ∿ $R_{10}$ and $R_{11}$ are each independently H, halo, $C_{1-6}$ alkoxy, substituted $C_{1-6}$ alkoxy, —$NR_aR_b$, or —OH;

each $R_a$ and $R_b$ is independently H, $C_{1-6}$ alkyl, substituted $C_{1-6}$ alkyl, —C(O)$R_d$, $C_{6-10}$ aryl;

each $R_c$ is independently H, phosphate, diphosphate, triphosphate, $C_{1-6}$ alkyl, or substituted $C_{1-6}$ alkyl;

each $R_d$ is independently H, halo, $C_{1-6}$ alkyl, substituted $C_{1-6}$ alkyl, $C_{1-6}$ alkoxy, substituted $C_{1-6}$ alkoxy, —$NH_2$, —NH($C_{1-6}$ alkyl), —NH(substituted $C_{1-6}$ alkyl), —N($C_{1-6}$ alkyl)$_2$, —N(substituted $C_{1-6}$ alkyl)$_2$, $C_{6-10}$ aryl, or heterocyclyl;

each $R_e$ is independently H, $C_{1-6}$ alkyl, substituted $C_{1-6}$ alkyl, $C_{6-10}$ aryl, substituted $C_{6-10}$ aryl, heterocyclyl, or substituted heterocyclyl;

each $R_f$ is independently H, $C_{1-6}$ alkyl, substituted $C_{1-6}$ alkyl, —C(O)$R_d$, phosphate, diphosphate, or triphosphate;

each n is independently 0, 1, 2, or 3;

each p is independently 0, 1, or 2; or or (g) a pharmaceutically acceptable salt of any of (a) to (f), a tautomer of any of (a) to (f), or a pharmaceutically acceptable salt of the tautomer.

Loxoribine (7-allyl-8-oxoguanosine) (99).

Compounds disclosed in reference 100, including: Acylpiperazine compounds, Indoledione compounds, Tetrahydraisoquinoline (THIQ) compounds, Benzocyclodione compounds, Aminoazavinyl compounds, Aminobenzimidazole quinolinone (ABIQ) compounds (101, 102), Hydrapthalamide compounds, Benzophenone compounds, Isoxazole compounds, Sterol compounds, Quinazilinone compounds, Pyrrole compounds (103), Anthraquinone compounds, Quinoxaline compounds, Triazine compounds, Pyrazalopyrimidine compounds, and Benzazole compounds (104).

Compounds disclosed in reference 105.

An aminoalkyl glucosaminide phosphate derivative, such as RC-529 (106, 107).

A phosphazene, such as poly[di(carboxylatophenoxy) phosphazene] ("PCPP") as described, for example, in references 108 and 109.

Small molecule immunopotentiators (SMIPs) such as:

N2-methyl-1-(2-methylpropyl)-1H-imidazo[4,5-c]quinoline-2,4-diamine

N2,N2-dimethyl-1-(2-methylpropyl)-1H-imidazo[4,5-c]quinoline-2,4-diamine

N2-ethyl-N2-methyl-1-(2-methylpropyl)-1H-imidazo[4,5-c]quinoline-2,4-diamine

N2-methyl-1-(2-methylpropyl)-N2-propyl-1H-imidazo[4,5-c]quinoline-2,4-diamine 1-(2-methylpropyl)-N2-propyl-1H-imidazo[4,5-c]quinoline-2,4-diamine N2-butyl-1-(2-methylpropyl)-1H-imidazo[4,5-c]quinoline-2,4-diamine N2-butyl-N2-methyl-1-(2-methylpropyl)-1H-imidazo[4,5-c]quinoline-2,4-diamine N2-methyl-1-(2-methylpropyl)-N2-pentyl-1H-imidazo[4,5-c]quinoline-2,4-diamine N2-methyl-1-(2-methylpropyl)-N2-prop-2-enyl-1H-imidazo[4,5-c]quinoline-2,4-diamine 1-(2-methylpropyl)-2-[(phenylmethyl)thio]-1H-imidazo[4,5-c]quinolin-4-amine 1-(2-methylpropyl)-2-(propylthio)-1H-imidazo[4,5-c]quinolin-4-amine 2-[[4-amino-1-(2-methylpropyl)-1H-imidazo[4,5-c]quinolin-2-yl](methyl)amino]ethanol 2-[[4-amino-1-(2-methylpropyl)-1H-imidazo[4,5-c]quinolin-2-yl](methyl)amino]ethyl acetate 4-amino-i-(2-methylpropyl)-1,3-dihydro-2H-imidazo[4,5-c]quinolin-2-one N2-butyl-1-(2-methylpropyl)-N4,N4-bis(phenylmethyl)-1H-imidazo[4,5-c]quinoline-2,4-diamine N2-butyl-N2-methyl-1-(2-methylpropyl)-N4,N4-bis(phenylmethyl)-1H-imidazo[4,5-c]quinoline-2,4-diamine N2-methyl-1-(2-methylpropyl)-N4,N4-bis(phenylmethyl)-1H-imidazo[4,5-c]quinoline-2,4-diamine N2,N2-dimethyl-1-(2-methylpropyl)-N4,N4-bis(phenylmethyl)-1H-imidazo[4,5-c]quinoline-2,4-diamine 1-[4-amino-2-[methyl(propyl)amino]-1H-imidazo[4,5-c]quinolin-1-yl]-2-methylpropan-2-ol 1-[4-amino-2-(propylamino)-1H-imidazo[4,5-c]quinolin-1-yl]-2-methylpropan-2-ol N4,N4-dibenzyl-1-(2-methoxy-2-methylpropyl)-N2-propyl-1H-imidazo[4,5-c]quinoline-2,4-diamine.

The cytokine-inducing agents for use in the present invention may be modulators and/or agonists of Toll-Like Receptors (TLR). For example, they may be agonists of one or more of the human TLR1, TLR2, TLR3, TLR4, TLR7, TLR8, and/or TLR9 proteins. Preferred agents are agonists of TLR4 (e.g., modified natural lipid As derived from enterobacterial lipopolysaccharides, phospholipid compounds, such as the synthetic phospholipid dimer, E6020), TLR7 (e.g., benzonaphthyridines, imidazoquinolines) and/or TLR9 (e.g., CpG oligonucleotides). These agents are useful for activating innate immunity pathways.

The cytokine-inducing agent can be added to the composition at various stages during its production. For example, it may be within an antigen composition, and this mixture can then be added to an oil-in-water emulsion. As an alternative, it may be within an oil-in-water emulsion, in which case the agent can either be added to the emulsion components before emulsification, or it can be added to the emulsion after emulsification. Similarly, the agent may be coacervated within the emulsion droplets. The location and distribution of the cytokine-inducing agent within the final composition will depend on its hydrophilic/lipophilic properties, e.g., the agent can be located in the aqueous phase, in the oil phase, and/or at the oil-water interface.

The cytokine-inducing agent can be conjugated to a separate agent, such as an antigen (e.g., CRM197). A general review of conjugation techniques for small molecules is provided in ref 110. As an alternative, the adjuvants may be non-covalently associated with additional agents, such as by way of hydrophobic or ionic interactions.

Preferred cytokine-inducing agents are (a) benzonapthridine compounds; (b) immunostimulatory oligonucleotides and (c) 3dMPL.

Immunostimulatory oligonucleotides can include nucleotide modifications/analogs such as phosphorothioate modifications and can be double-stranded or (except for RNA) single-stranded. References 111, 112, and 113disclose possible analog substitutions, e.g., replacement of guanosine with 2'-deoxy-7-deazaguanosine. The adjuvant effect of CpG oligonucleotides is further discussed in refs. 114 to 119. A CpG sequence may be directed to TLR9, such as the motif GTCGTT or TTCGTT (120). The CpG sequence may be specific for inducing a Th1 immune response, such as a CpG-A ODN (oligodeoxynucleotide), or it may be more specific for inducing a B cell response, such a CpG-B ODN. CpG-A and CpG-B ODNs are discussed in refs. 121-123. Preferably, the CpG is a CpG-A ODN. Preferably, the CpG oligonucleotide is constructed so that the 5' end is accessible for receptor recognition. Optionally, two CpG oligonucleotide sequences may be attached at their 3' ends to form "immunomers". See, for example, references 120 & 124-126. A useful CpG adjuvant is CpG7909, also known as PROMUNE™ (Coley Pharmaceutical Group, Inc.).

As an alternative, or in addition, to using CpG sequences, TpG sequences can be used (127). These oligonucleotides may be free from unmethylated CpG motifs.

The immunostimulatory oligonucleotide may be pyrimidine-rich. For example, it may comprise more than one consecutive thymidine nucleotide (e.g., TTTT, as disclosed in ref. 127), and/or it may have a nucleotide composition with >25% thymidine (e.g., >35%, >40%, >50%, >60%, >80%, etc.). For example, it may comprise more than one consecutive cytosine nucleotide (e.g., CCCC, as disclosed in ref. 127), and/or it may have a nucleotide composition with >25% cytosine (e.g., >35%, >40%, >50%, >60%, >80%, etc.). These oligonucleotides may be free from unmethylated CpG motifs.

Immunostimulatory oligonucleotides will typically comprise at least 20 nucleotides. They may comprise fewer than 100 nucleotides.

3dMPL (also known as 3 de-O-acylated monophosphoryl lipid A or 3-O-desacyl-4'-monophosphoryl lipid A) is an adjuvant in which position 3 of the reducing end glucosamine in monophosphoryl lipid A has been de-acylated. 3dMPL has been prepared from a heptoseless mutant of *Salmonella minnesota*, and is chemically similar to lipid A but lacks an acid-labile phosphoryl group and a base-labile acyl group. It activates cells of the monocyte/macrophage lineage and stimulates release of several cytokines, including IL-1, IL-12, TNF-α and GM-CSF (see also ref. 128). Preparation of 3dMPL was originally described in reference 129.

3dMPL can take the form of a mixture of related molecules, varying by their acylation (e.g., having 3, 4, 5 or 6 acyl chains, which may be of different lengths). The two glucosamine (also known as 2-deoxy-2-amino-glucose) monosaccharides are N-acylated at their 2-position carbons (i.e., at positions 2 and 2'), and there is also O-acylation at the 3' position. The group attached to carbon 2 has formula $-NH-CO-CH_2-CR^1R^{1'}$. The group attached to carbon 2' has formula $-NH-CO-CH_2-CR^2R^{2'}$. The group attached to carbon 3' has formula $-O-CO-CH_2-CR^3R^{3'}$. A representative structure is:

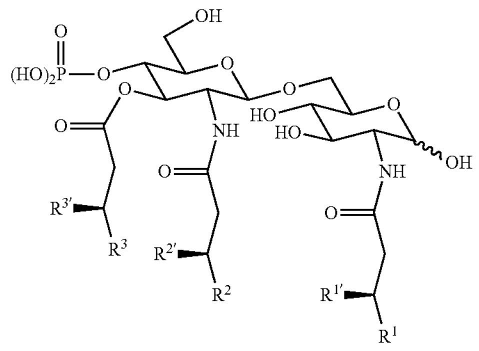

Groups $R^1$, $R^2$ and $R^3$ are each independently $-(CH_2)_n-CH_3$. The value of n is preferably between 8 and 16, more preferably between 9 and 12, and is most preferably 10.

Groups $R^{1'}$, $R^{2'}$ and $R^{3'}$ can each independently be: (a) —H; (b) —OH; or (c) $-O-CO-R^4$, where $R^4$ is either —H or —$(CH_2)_m$—$CH_3$, wherein the value of m is preferably between 8 and 16, and is more preferably 10, 12 or 14. At the 2 position, m is preferably 14. At the 2' position, m is preferably 10. At the 3' position, m is preferably 12. Groups $R^{1'}$, $R^{2'}$ and $R^{3'}$ are thus preferably —O-acyl groups from dodecanoic acid, tetradecanoic acid or hexadecanoic acid.

When all of $R^{1'}$, $R^{2'}$ and $R^{3'}$ are —H then the 3dMPL has only 3 acyl chains (one on each of positions 2, 2' and 3'). When only two of $R^{1'}$, $R^{2'}$ and $R^{3'}$ are —H then the 3dMPL can have 4 acyl chains. When only one of $R^{1'}$, $R^{2'}$ and $R^{3'}$ is —H then the 3dMPL can have 5 acyl chains. When none of $R^{1'}$, $R^{2'}$ and $R^{3'}$ is —H then the 3dMPL can have 6 acyl chains. The 3dMPL adjuvant used according to the invention can be a mixture of these forms, with from 3 to 6 acyl chains, but it is preferred to include 3dMPL with 6 acyl chains in the mixture, and in particular to ensure that the hexaacyl chain form makes up at least 10% by weight of the total 3dMPL e.g., >20%, >30%, >40%, >50% or more. 3dMPL with 6 acyl chains has been found to be the most adjuvant-active form.

Thus the most preferred form of 3dMPL for inclusion in compositions of the invention has formula (IV), shown below.

Where 3dMPL is used in the form of a mixture then references to amounts or concentrations of 3dMPL in compositions of the invention refer to the combined 3dMPL species in the mixture.

In aqueous conditions, 3dMPL can form micellar aggregates or particles with different sizes e.g., with a diameter<150 nm or >500 nm. Either or both of these can be used with the invention, and the better particles can be selected by routine assay. Smaller particles (e.g., small enough to give a clear aqueous suspension of 3dMPL) are preferred for use according to the invention because of their superior activity (130). Preferred particles have a mean diameter less than 220 nm, more preferably less than 200 nm or less than 150 nm or less than 120 nm, and can even have a mean diameter less than 100 nm. In most cases, however, the mean diameter will not be lower than 50 nm. These particles are small enough to be suitable for filter sterilization. Particle diameter can be assessed by the routine technique of dynamic light scattering, which reveals a mean particle diameter. Where a particle is said to have a diameter of x nm, there will generally be a distribution of particles about this mean, but at least 50% by number (e.g., >60%, >70%, >80%, >90%, or more) of the particles will have a diameter within the range x+25%.

3dMPL can advantageously be used in combination with an oil-in-water emulsion. Substantially all of the 3dMPL may be located in the aqueous phase of the emulsion.

The 3dMPL can be used on its own, or in combination with one or more further compounds. For example, it is known to use 3dMPL in combination with the QS21 saponin (131) (including in an oil-in-water emulsion (132)), with an immunostimulatory oligonucleotide, with both QS21 and an immunostimulatory oligonucleotide, with aluminum phosphate (133), with aluminum hydroxide (134), or with both aluminum phosphate and aluminum hydroxide.

Formula (IV)

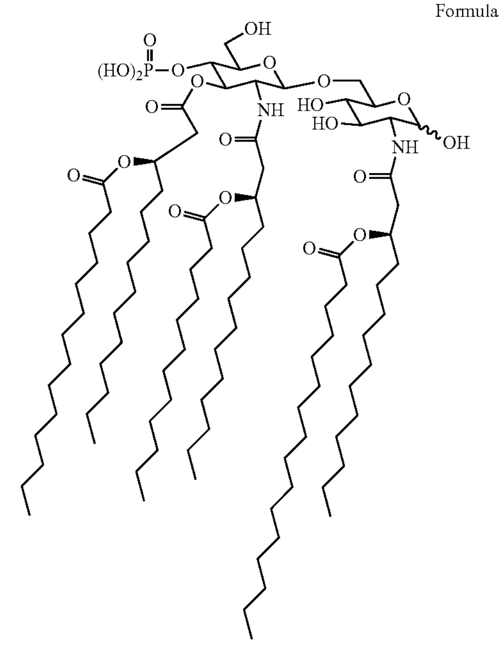

Fatty Adjuvants

Fatty adjuvants that can be used with the invention include the oil-in-water emulsions described above, and also include, for example:

A phospholipid compound of formula I, II or III, or a salt thereof:

I

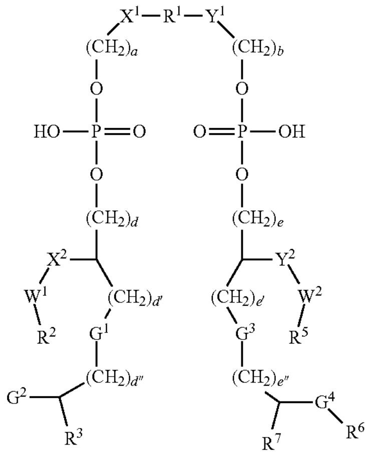

-continued
II
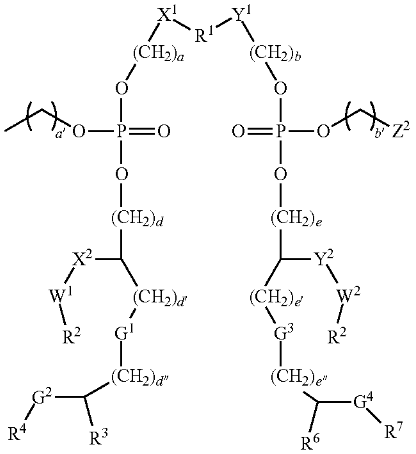
III
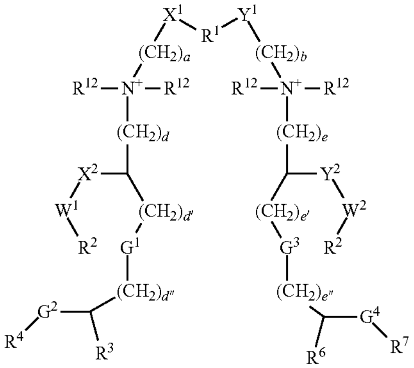
as defined in reference 135, such as 'ER 803058', 'ER 803732', 'ER 804053', ER 804058', 'ER 804059', 'ER 804442', 'ER 804680', 'ER 804764', ER 803022 or 'ER 804057' e.g.:
ER804057
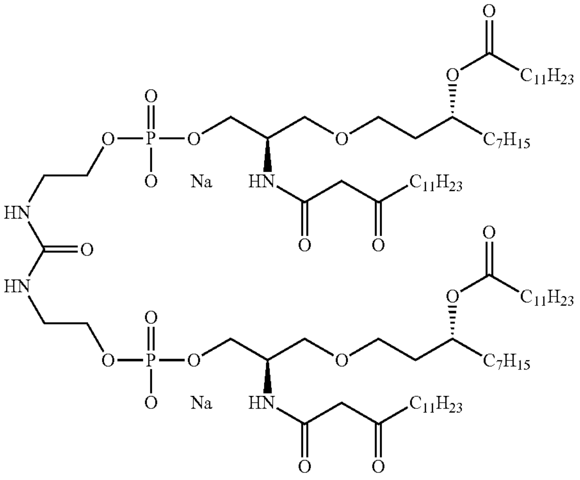

-continued

ER-803022

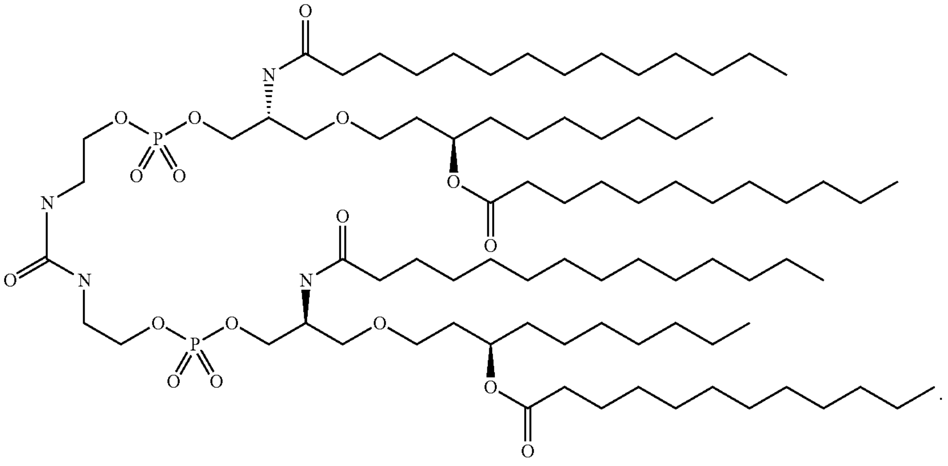

ER804057 is also called E6020. A phospholipid compound of formula I, II or III, or a salt thereof, can be used on its own, or in combination with one or more further compounds. For example, a compound of formula I, II or III, can be used in combination with an oil-in-water emulsion or a mineral-containing composition. In a particular embodiment, E6020 is used in combination with an oil-in-water emulsion (e.g. a squalene-water emulsion, such as MF59) or a mineral-containing composition (e.g., a mineral sald such as an aluminum salt or a calcium salt).

Derivatives of lipid A from *Escherichia coli* such as OM-174 (described in refs. 136 & 137).

A formulation of a cationic lipid and a (usually neutral) co-lipid, such as aminopropyl-dimethyl-myristoleyloxy-propanaminium bromide-diphytanoylphosphatidyl-ethanolamine ("VAXFECTIN™") or aminopropyl-dimethyl-bis-dodecyloxy-propanaminium bromide-dioleoylphosphatidyl-ethanolamine ("GAP-DLRIE DOPE"). Formulations containing (+)—N-(3-aminopropyl)-N,N-dimethyl-2,3-bis(syn-9-tetradeceneyloxy)-1-propanaminium salts are preferred (138).

3-O-deacylated monophosphoryl lipid A (see above).

Compounds containing lipids linked to a phosphate-containing acyclic backbone, such as the TLR4 antagonist E5564 (139, 140):

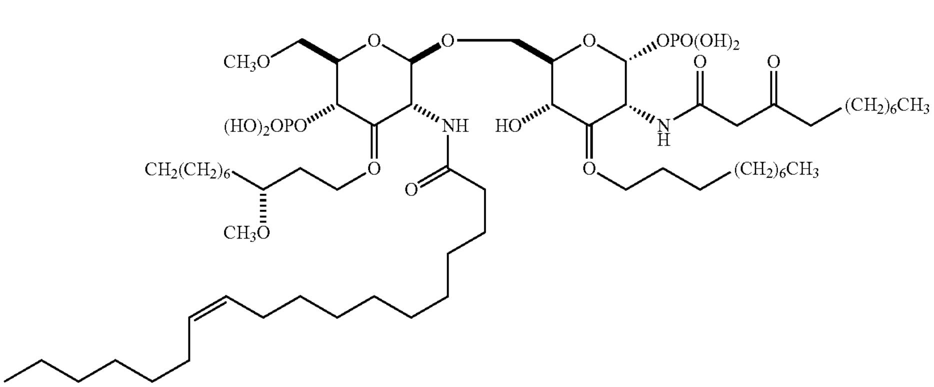

Lipopeptides (i.e., compounds comprising one or more fatty acid residues and two or more amino acid residues), such as lipopeptides based on glycerylcysteine. Specific examples of such peptides include compounds of the following formula

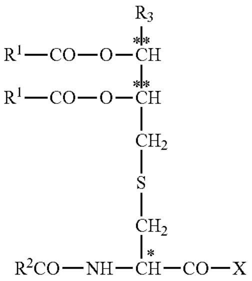

* = R
** = R or S in which each of $R^1$ and $R^2$ represents a saturated or unsaturated, aliphatic or mixed aliphatic-cycloaliphatic hydrocarbon radical having from 8 to 30, preferably 11 to 21, carbon atoms that is optionally also substituted by oxygen functions, $R^3$ represents hydrogen or the radical $R_1$—CO—O—$CH_2$— in which $R^1$ has the same meaning as above, and X represents an amino acid bonded by a peptide linkage and having a free, esterified or amidated carboxy group, or an amino acid sequence of from 2 to 10 amino acids of which the terminal carboxy group is in free, esterified or amidated form. In certain embodiments, the amino acid sequence comprises a D-amino acid, for example, D-glutamic acid (D-Glu) or D-gamma-carboxy-glutamic acid (D-Gla).

Bacterial lipopeptides generally recognize TLR2, without requiring TLR6 to participate. (TLRs operate cooperatively to provide specific recognition of various triggers, and TLR2 plus TLR6 together recognize peptidoglycans, while TLR2 recognizes lipopeptides without TLR6.) These are sometimes classified as natural lipopeptides and synthetic lipopeptides. Synthetic lipopeptides tend to behave similarly, and are primarily recognized by TLR2.

Lipopeptides suitable for use as adjuvants include compounds have the formula:

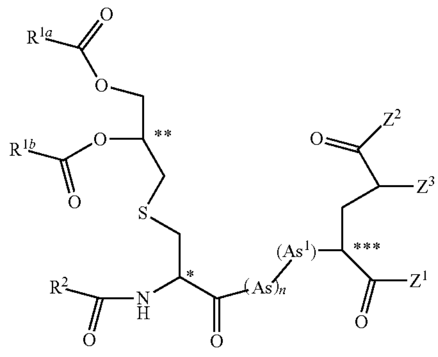

where the chiral center labeled * and the one labeled * are both in the R configuration; the chiral center labeled  is either in the R or S configuration;

each $R^{1a}$ and $R^{1b}$ is independently an aliphatic or cycloaliphatic-aliphatic hydrocarbon group having 7-21 carbon atoms, optionally substituted by oxygen functions, or one of $R^{1a}$ and $R^{1b}$, but not both, is H;

$R^2$ is an aliphatic or cycloaliphatic hydrocarbon group having 1-21 carbon atoms and optionally substituted by oxygen functions;

n is 0 or 1;

As represents either —O-Kw-CO— or —NH-Kw-CO—, where Kw is an aliphatic hydrocarbon group having 1-12 carbon atoms;

$As^1$ is a D- or L-alpha-amino acid;

$Z^1$ and $Z^2$ each independently represent —OH or the N-terminal radical of a D- or L-alpha amino acid of an amino-(lower alkane)-sulfonic acid or of a peptide having up to 6 amino acids selected from the D- and L-alpha aminocarboxylic acids and amino-lower alkyl-sulfonic acids; and $Z^3$ is H or —CO—$Z^4$, wher $Z^4$ is —OH or the N-terminal radical of a D- or L-alpha amino acid of an amino-(lower alkane)-sulfonic acid or of a peptide having up to 6 amino acids selected from the D and L-alpha aminocarboxylic acids and amino-lower alkyl-sulfonic acids; or an ester or amide formed from the carboxylic acid of such compounds. Suitable amides include —$NH_2$ and NH(lower alkyl), and suitable esters include C1-C4 alkyl esters. (lower alkyl or lower alkane, as used herein, refers to $C_1$-$C_6$ straight chain or branched alkyls).

Such compounds are described in more detail in U.S. Pat. No. 4,666,886. In one particular embodiment, the lipopeptide has the formula:

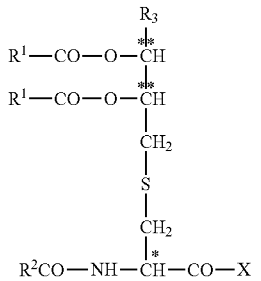

* = R
** = R or S

Another example of a lipopeptide species is called LP40, and is an agonist of TLR2. Akdis, et al., *Eur. J. Immunology,* 33: 2717-26 (2003).

These are related to a known class of lipopeptides from *E. coli,* referred to as murein lipoproteins. Certain partial degradation products of those proteins called murein lipopetides are described in Hantke, et al., *Eur. J. Biochem.,* 34: 284-296 (1973). These comprise a peptide linked to N-acetyl muramic acid and are thus related to Muramyl peptides, which are described in Baschang, et al., *Tetrahedron,* 45(20): 6331-6360 (1989).

Aluminum Salt Adjuvants

The adjuvants known as "aluminum hydroxide" and "aluminum phosphate" may be used. These names are conventional, but are used for convenience only, as neither is a precise description of the actual chemical compound which is present (e.g., see chapter 9 of reference 74). The invention can use any of the "hydroxide" or "phosphate" adjuvants that are in general use as adjuvants.

The adjuvants known as "aluminum hydroxide" are typically aluminum oxyhydroxide salts, which are usually at least partially crystalline. Aluminum oxyhydroxide, which can be represented by the formula AlO(OH), can be distinguished from other aluminum compounds, such as aluminum hydroxide $Al(OH)_3$, by infrared (IR) spectroscopy, in particular by the presence of an adsorption band at 1070 $cm^{-1}$ and a strong shoulder at 3090-3100 $cm^{-1}$ (chapter 9 of ref. 74). The degree of crystallinity of an aluminum hydroxide adjuvant is reflected by the width of the diffraction band at half height (WHH), with poorly-crystalline particles showing greater line broadening due to smaller crystallite sizes. The surface area increases as WHH increases, and adjuvants with higher WHH values have been seen to have greater capacity for antigen adsorption. A fibrous morphology (e.g., as seen in transmission electron micrographs) is typical for aluminum hydroxide adjuvants. The pI of aluminum hydroxide adjuvants is typically about 11, i.e., the adjuvant itself has a positive surface charge at physiological pH. Adsorptive capacities of between 1.8-2.6 mg protein per mg $Al^{+++}$ at pH 7.4 have been reported for aluminum hydroxide adjuvants.

The adjuvants known as "aluminum phosphate" are typically aluminum hydroxyphosphates, often also containing a small amount of sulfate (i.e., aluminum hydroxyphosphate sulfate). They may be obtained by precipitation, and the reaction conditions and concentrations during precipitation influence the degree of substitution of phosphate for hydroxyl in the salt. Hydroxyphosphates generally have a $PO_4$/Al molar ratio between 0.3 and 1.2. Hydroxyphosphates can be distinguished from strict $AlPO_4$ by the presence of hydroxyl groups. For example, an IR spectrum band at 3164 $cm^{-1}$ (e.g., when heated to 200° C.) indicates the presence of structural hydroxyls (ch.9 of ref 74)

The $PO_4/Al^{3+}$ molar ratio of an aluminum phosphate adjuvant will generally be between 0.3 and 1.2, preferably between 0.8 and 1.2, and more preferably 0.95+0.1. The aluminum phosphate will generally be amorphous, particularly for hydroxyphosphate salts. A typical adjuvant is amorphous aluminum hydroxyphosphate with $PO_4/Al$ molar ratio between 0.84 and 0.92, included at 0.6 mg $Al^{3+}$/ml. The aluminum phosphate will generally be particulate (e.g., plate-like morphology as seen in transmission electron micrographs). Typical diameters of the particles are in the range 0.5-20 μm (e.g., about 5-10 μm) after any antigen adsorption. Adsorptive capacities of between 0.7-1.5 mg protein per mg $Al^{+++}$ at pH 7.4 have been reported for aluminum phosphate adjuvants.

The point of zero charge (PZC) of aluminum phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminum phosphates used according to the invention will generally have a PZC of between 4.0 and 7.0, more preferably between 5.0 and 6.5, e.g., about 5.7.

Suspensions of aluminum salts used to prepare compositions of the invention may contain a buffer (e.g., a phosphate or a histidine or a Tris buffer), but this is not always necessary. The suspensions are preferably sterile and pyrogen-free. A suspension may include free aqueous phosphate ions e.g., present at a concentration between 1.0 and 20 mM, preferably between 5 and 15 mM, and more preferably about 10 mM. The suspensions may also comprise sodium chloride.

The invention can use a mixture of both an aluminum hydroxide and an aluminum phosphate. In this case there may be more aluminum phosphate than hydroxide e.g., a weight ratio of at least 2:1 e.g., >5:1, >6:1, >7:1, >8:1, >9:1, etc.

The concentration of $Al^{+++}$ in a composition for administration to a patient is preferably less than 10 mg/ml e.g., <5 mg/ml, <4 mg/ml, <3 mg/ml, <2 mg/ml, <1 mg/ml, etc. A preferred range is between 0.3 and 1 mg/ml. A maximum of 0.85 mg/dose is preferred.

As well as including one or more aluminum salt adjuvants, the adjuvant component may include one or more further adjuvant or immunostimulating agents. Such additional components include, but are not limited to: a benzonaphthyridine compound, a 3-O-deacylated monophosphoryl lipid A adjuvant ('3d-MPL'); and/or an oil-in-water emulsion. 3d-MPL has also been referred to as 3 de-O-acylated monophosphoryl lipid A or as 3-O-desacyl-4'-monophosphoryl lipid A. The name indicates that position 3 of the reducing end glucosamine in monophosphoryl lipid A is de-acylated. It has been prepared from a heptoseless mutant of *S. minnesota*, and is chemically similar to lipid A but lacks an acid-labile phosphoryl group and a base-labile acyl group. It activates cells of the monocyte/macrophage lineage and stimulates release of several cytokines, including IL-1, IL-12, TNF-α and GM-CSF. Preparation of 3d-MPL was originally described in reference 129, and the product has been manufactured and sold by Corixa Corporation under the name MPL™. Further details can be found in refs 82 to 85.

The use of an aluminum hydroxide and/or aluminum phosphate adjuvant is useful, particularly in children, and antigens are generally adsorbed to these salts. Squalene-in-water emulsions are also preferred, particularly in the elderly. Useful adjuvant combinations include combinations of Th1 and Th2 adjuvants such as CpG and alum, or resiquimod and alum. A combination of aluminum phosphate and 3dMPL may be used. Other combinations that may be used include: alum and a benzonapthridine compound or a SMIP, a squalene-in-water emulsion (such as MF59) and a benzonapthridine compound or a SMIP, and E6020 and a squalene-in-water emulsion, such as MF59) or alum.

The compositions of the invention may elicit both a cell mediated immune response as well as a humoral immune response.

Two types of T cells, CD4 and CD8 cells, are generally thought necessary to initiate and/or enhance cell mediated immunity and humoral immunity. CD8 T cells can express a CD8 co-receptor and are commonly referred to as Cytotoxic T lymphocytes (CTLs). CD8 T cells are able to recognized or interact with antigens displayed on MHC Class I molecules.

CD4 T cells can express a CD4 co-receptor and are commonly referred to as T helper cells. CD4 T cells are able to recognize antigenic peptides bound to MHC class II molecules. Upon interaction with a MHC class II molecule, the CD4 cells can secrete factors such as cytokines. These secreted cytokines can activate B cells, cytotoxic T cells, macrophages, and other cells that participate in an immune response. Helper T cells or CD4+ cells can be further divided into two functionally distinct subsets: TH1 phenotype and TH2 phenotypes which differ in their cytokine and effector function.

Activated TH1 cells enhance cellular immunity (including an increase in antigen-specific CTL production) and are therefore of particular value in responding to intracellular infections. Activated TH1 cells may secrete one or more of IL-2, IFN-7, and TNF-β. A TH1 immune response may result in local inflammatory reactions by activating macrophages, NK (natural killer) cells, and CD8 cytotoxic T cells (CTLs). A TH1 immune response may also act to expand the immune response by stimulating growth of B and T cells with IL-12. TH1 stimulated B cells may secrete IgG2a.

Activated TH2 cells enhance antibody production and are therefore of value in responding to extracellular infections. Activated TH2 cells may secrete one or more of IL-4, IL-5, IL-6, and IL-10. A TH2 immune response may result in the production of IgG1, IgE, IgA and memory B cells for future protection.

An enhanced immune response may include one or more of an enhanced TH1 immune response and a TH2 immune response.

A THI immune response may include one or more of an increase in CTLs, an increase in one or more of the cytokines associated with a TH1 immune response (such as IL-2, IFN-7, and TNF-0), an increase in activated macrophages, an increase in NK activity, or an increase in the production of IgG2a. Preferably, the enhanced TH1 immune response will include an increase in IgG2a production.

A TH1 immune response may be elicited using a TH1 adjuvant. A TH1 adjuvant will generally elicit increased levels of IgG2a production relative to immunization of the antigen without adjuvant. TH1 adjuvants suitable for use in the invention may include for example saponin formulations, virosomes and virus like particles, non-toxic derivatives of enterobacterial lipopolysaccharide (LPS), immunostimulatory oligonucleotides. Immunostimulatory oligonucleotides, such as oligonucleotides containing a CpG motif, are preferred TH1 adjuvants for use in the invention.

A TH2 immune response may include one or more of an increase in one or more of the cytokines associated with a TH2 immune response (such as IL-4, IL-5, IL-6 and IL-10), or an increase in the production of IgG1, IgE, IgA and memory B cells. Preferably, the enhanced TH2 immune response will include an increase in IgG1 production.

A TH2 immune response may be elicited using a TH2 adjuvant. A TH2 adjuvant will generally elicit increased levels of IgG1 production relative to immunization of the antigen without adjuvant. TH2 adjuvants suitable for use in the invention include, for example, mineral containing compositions, oil-emulsions, and ADP-ribosylating toxins and detoxified derivatives thereof. Mineral containing compositions, such as aluminium salts are preferred TH2 adjuvants for use in the invention.

A composition may include a combination of a TH1 adjuvant and a TH2 adjuvant. Preferably, such a composition elicits an enhanced TH1 and an enhanced TH2 response, i.e., an increase in the production of both IgG1 and IgG2a production relative to immunization without an adjuvant. Still more preferably, the composition comprising a combination of a TH1 and a TH2 adjuvant elicits an increased TH1 and/or an increased TH2 immune response relative to immunization with a single adjuvant (i.e., relative to immunization with a TH1 adjuvant alone or immunization with a TH2 adjuvant alone).

The immune response may be one or both of a TH1 immune response and a TH2 response. Preferably, immune response provides for one or both of an enhanced TH1 response and an enhanced TH2 response.

The enhanced immune response may be one or both of a systemic and a mucosal immune response. Preferably, the immune response provides for one or both of an enhanced systemic and an enhanced mucosal immune response. Preferably the mucosal immune response is a TH2 immune response. Preferably, the mucosal immune response includes an increase in the production of IgA.

Methods of Treatment, and Administration

Compositions of the invention are suitable for administration to mammals, and the invention provides a method of inducing an immune response in a mammal, comprising the step of administering a composition (e.g., an immunogenic composition) of the invention to the mammal. The compositions (e.g., an immunogenic composition) can be used to produce a vaccine formulation for immunizing a mammal. The mammal is typically a human, and the RSV F protein is typically a human RSV F protein. However, the mammal can be any other mammal that is susceptible to infection with RSV, such as a cow that can be infected with bovine RSV. For example, the immune response may be raised following administration of a purified RSV F protein, an alphavirus particle, or self-replicating RNA.

The invention also provides the use of two or more pre-fusion chimerid proteins based on two or more different non-RSV (e.g., parainfluenza virus, metapneumovirus) F pre-fusion proteins (i.e., PIV5 and NDV) that each have the same RSV F neutralizing epitopes mutated on the protein surface. Thus, inoculation with one chimeric pre-fusion F, and a second inoculation with the second pre-fusion F may prime several antibodies, some to RSV and some to the template protein backbone. The second inoculation may bias boosting of only the shared RSV F neutralizing epitopes.

The invention also provides a composition of the invention for use as a medicament, e.g., for use in immunizing a patient against RSV infection.

The invention also provides the use of a polypeptide as described above in the manufacture of a medicament for raising an immune response in a patient.

The immune response raised by these methods and uses will generally include an antibody response, preferably a protective antibody response. Methods for assessing antibody responses after RSV vaccination are well known in the art.

Compositions of the invention can be administered in a number of suitable ways, such as intramuscular injection (e.g., into the arm or leg), subcutaneous injection, intranasal administration, oral administration, intradermal administration, transcutaneous administration, transdermal administration, and the like. The appropriate route of administration will be dependent upon the age, health and other characteristics of the mammal. A clinician will be able to determine an appropriate route of administration based on these and other factors.

Immunogenic compositions, and vaccine formulations, may be used to treat both children and adults, including pregnant women. Thus a subject may be less than 1 year old, 1-5 years old, 5-15 years old, 15-55 years old, or at least 55 years old. Preferred subjects for receiving the vaccines are the elderly (e.g., >50 years old, >60 years old, and preferably >65 years), the young (e.g., <6 years old, such as 4-6 years old, <5 years old), and pregnant women. The vaccines are not suitable solely for these groups, however, and may be used more generally in a population.

Treatment can be by a single dose schedule or a multiple dose schedule. Multiple doses may be used in a primary immunization schedule and/or in a booster immunization schedule. In a multiple dose schedule the various doses may be given by the same or different routes, e.g., a parenteral prime and mucosal boost, a mucosal prime and parenteral boost, etc. Administration of more than one dose (typically two doses) is particularly useful in immunologically naive patients. Multiple doses will typically be administered at least 1 week apart (e.g., about 2 weeks, about 3 weeks, about 4 weeks, about 6 weeks, about 8 weeks, about 10 weeks, about 12 weeks, about 16 weeks, and the like.).

Vaccine formulations produced using a composition of the invention may be administered to patients at substantially the same time as (e.g., during the same medical consultation or visit to a healthcare professional or vaccination centre) other vaccines.

General

The term “comprising” encompasses “including” as well as “consisting” and “consisting essentially of” e.g., a composition “comprising” X may consist exclusively of X or may include something additional e.g., X+Y.

The word “substantially” does not exclude “completely” e.g., a composition which is “substantially free” from Y may be completely free from Y. Where necessary, the word “substantially” may be omitted from the definition of the invention.

The term “about” in relation to a numerical value x means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encaphalopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

Where a cell substrate is used for reassortment or reverse genetics procedures, it is preferably one that has been approved for use in human vaccine production e.g., as in Ph Eur general chapter 5.2.3.

Identity between polypeptide sequences is preferably determined by the Smith-Waterman homology search algorithm as implemented in the MPSRCH program (Oxford Molecular), using an affine gap search with parameters gap open penalty=12 and gap extension penalty=1.

TABLE 2

| Phospholipids | |
|---|---|
| DDPC | 1,2-Didecanoyl-sn-Glycero-3-phosphatidylcholine |
| DEPA | 1,2-Dierucoyl-sn-Glycero-3-Phosphate |
| DEPC | 1,2-Erucoyl-sn-Glycero-3-phosphatidylcholine |
| DEPE | 1,2-Dierucoyl-sn-Glycero-3-phosphatidylethanolamine |
| DEPG | 1,2-Dierucoyl-sn-Glycero-3[Phosphatidyl-rac-(l-glyceroL . . . ) |
| DLOPC | 1,2-Linoleoyl-sn-Glycero-3-phosphatidylcholine |
| DLPA | 1,2-Dilauroyl-sn-Glycero-3-Phosphate |
| DLPC | 1,2-Dilauroyl-sn-Glycero-3-phosphatidylcholine |
| DLPE | 1,2-Dilauroyl-sn-Glycero-3-phosphatidylethanolamine |
| DLPG | 1,2-Dilauroyl-sn-Glycero-3[Phosphatidyl-rac-(l -glycerol . . . ) |
| DLPS | 1,2-Dilauroyl-sn-Glycero-3-phosphatidylserine |
| DMG | 1,2-Dimyristoyl-sn-glycero-3-phosphoethanolamine |
| DMPA | 1,2-Dimyristoyl-sn-Glycero-3-Phosphate |
| DMPC | 1,2-Dimyristoyl-sn-Glycero-3-phosphatidylcholine |
| DMPE | 1,2-Dimyristoyl-sn-Glycero-3-phosphatidylethanolamine |
| DMPG | 1,2-Myristoyl-sn-Glycero-3[Phosphatidyl-rac-(l -glycerol . . . ) |
| DMPS | 1,2-Dimyristoyl-sn-Glycero-3-phosphatidylserine |
| DOPA | 1,2-Dioleoyl-sn-Glycero-3-Phosphate |
| DOPC | 1,2-Dioleoyl-sn-Glycero-3-phosphatidylcholine |
| DOPE | 1,2-Dioleoyl-sn-Glycero-3-phosphatidylethanolamine |
| DOPG | 1,2-Dioleoyl-sn-Glycero-3[Phosphatidyl-rac-(l-glycerol . . . ) |
| DOPS | 1,2-Dioleoyl-sn-Glycero-3-phosphatidylserine |
| DPPA | 1,2-Dipalmitoyl-sn-Glycero-3-Phosphate |
| DPPC | 1,2-Dipalmitoyl-sn-Glycero-3-phosphatidylcholine |
| DPPE | 1,2-Dipalmitoyl-sn-Glycero-3-phosphatidylethanolamine |
| DPPG | 1,2-Dipalmitoyl-sn-Glycero-3[Phosphatidyl-rac-(l-glycerol . . . ) |
| DPPS | 1,2-Dipalmitoyl-sn-Glycero-3-phosphatidylserine |
| DPyPE | 1,2-diphytanoyl-sn-glycero-3-phosphoethanolamine |
| DSPA | 1,2-Distearoyl-sn-Glycero-3-Phosphate |
| DSPC | 1,2-Distearoyl-sn-Glycero-3-phosphatidylcholine |
| DSPE | 1,2-Diostearpyl-sn-Glycero-3-phosphatidylethanolamine |
| DSPG | 1,2-Distearoyl-sn-Glycero-3 [Phosphatidyl-rac-(l-glycerol . . . ) |
| DSPS | 1,2-Distearoyl-sn-Glycero-3-phosphatidylserine |
| EPC | Egg-PC |
| HEPC | Hydrogenated Egg PC |
| HSPC | High purity Hydrogenated Soy PC |
| HSPC | Hydrogenated Soy PC |
| LYSOPC MYRISTIC | 1-Myristoyl-sn-Glycero-3-phosphatidylcholine |
| LYSOPC PALMITIC | 1-Palmitoyl-sn-Glycero-3-phosphatidylcholine |
| LYSOPC STEARIC | l-Stearoyl-sn-Glycero-3-phosphatidylcholine |
| Milk Sphingomyelin MPPC | 1-Myristoyl,2-palmitoyl-sn-Glycero 3-phosphatidylcholine |
| MSPC | 1-Myristoyl,2-stearoyl-sn-Glycero-3-phosphatidylcholine |
| PMPC | 1-Palmitoyl,2-myristoyl-sn-Glycero-3-phosphatidylcholine |
| POPC | 1-Palmitoyl,2-oleoyl-sn-Glycero-3-phosphatidylcholine |
| POPE | 1-Palmitoyl-2-oleoyl-sn-Glycero-3-phosphatidylethanolamine |
| POPG | 1,2-Dioleoyl-sn-Glycero-3[Phosphatidyl-rac-(l -glycerol) . . . ] |
| PSPC | 1-Palmitoyl,2-stearoyl-sn-Glycero-3-phosphatidylcholine |
| SMPC | 1-Stearoyl,2-myristoyl-sn-Glycero-3-phosphatidylcholine |
| SOPC | 1-Stearoyl,2-oleoyl-sn-Glycero-3-phosphatidylcholine |
| SPPC | 1-Stearoyl,2-palmitoyl-sn-Glycero-3-phosphatidylcholine |

Exemplification

1. Post-Fusion Structure and Pre-Fusion Model

Post-Fusion RSV F Structure

Figure 2A:
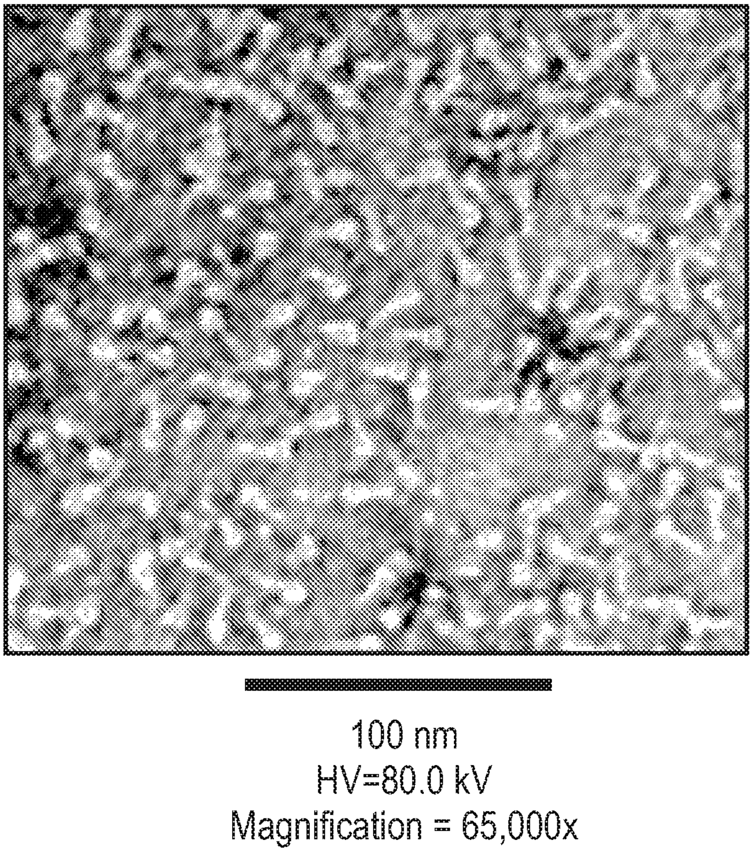
In FIG. 2A an electron micrograph of the RSV F protein shows a field of uniform crutch phenotypes consistent with the structure of post-fusion F proteins.
Figure 2B:
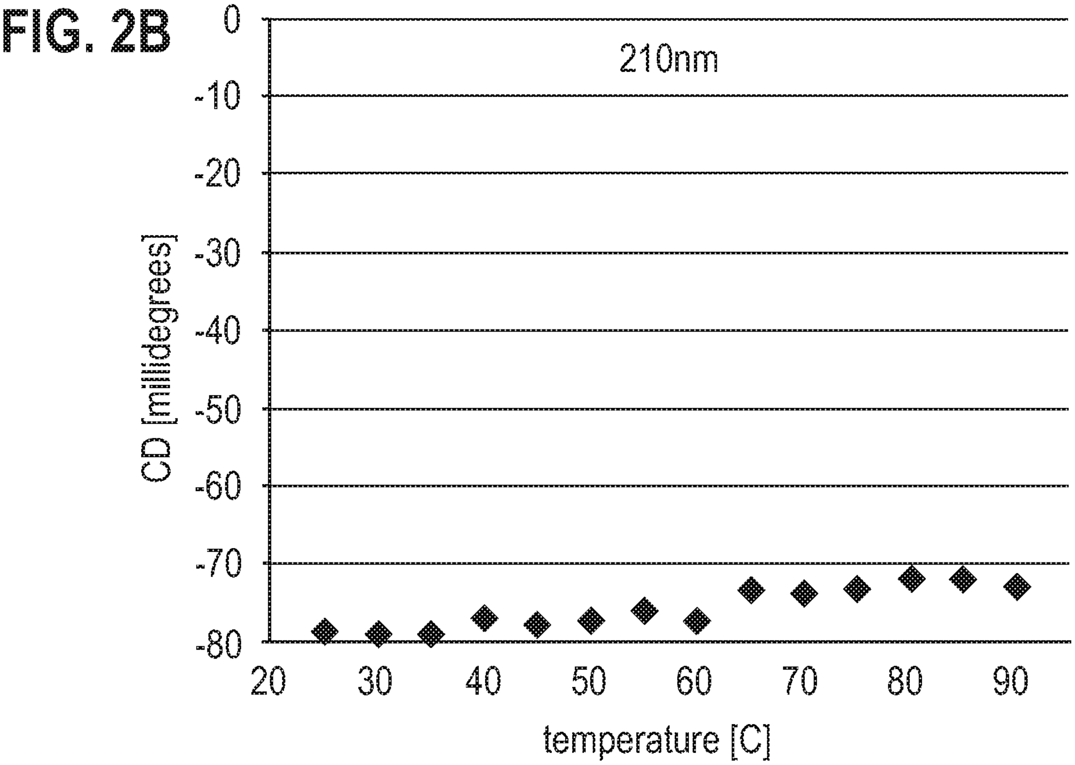
FIG. 2B shows a CD melting curve of the post-fusion RSV F trimer observed at 210 nm, the observed spectral minimum of the folded RSV F protein. The CD absorption, y-axis, is plotted against temperature, x-axis.
Figure 2C:
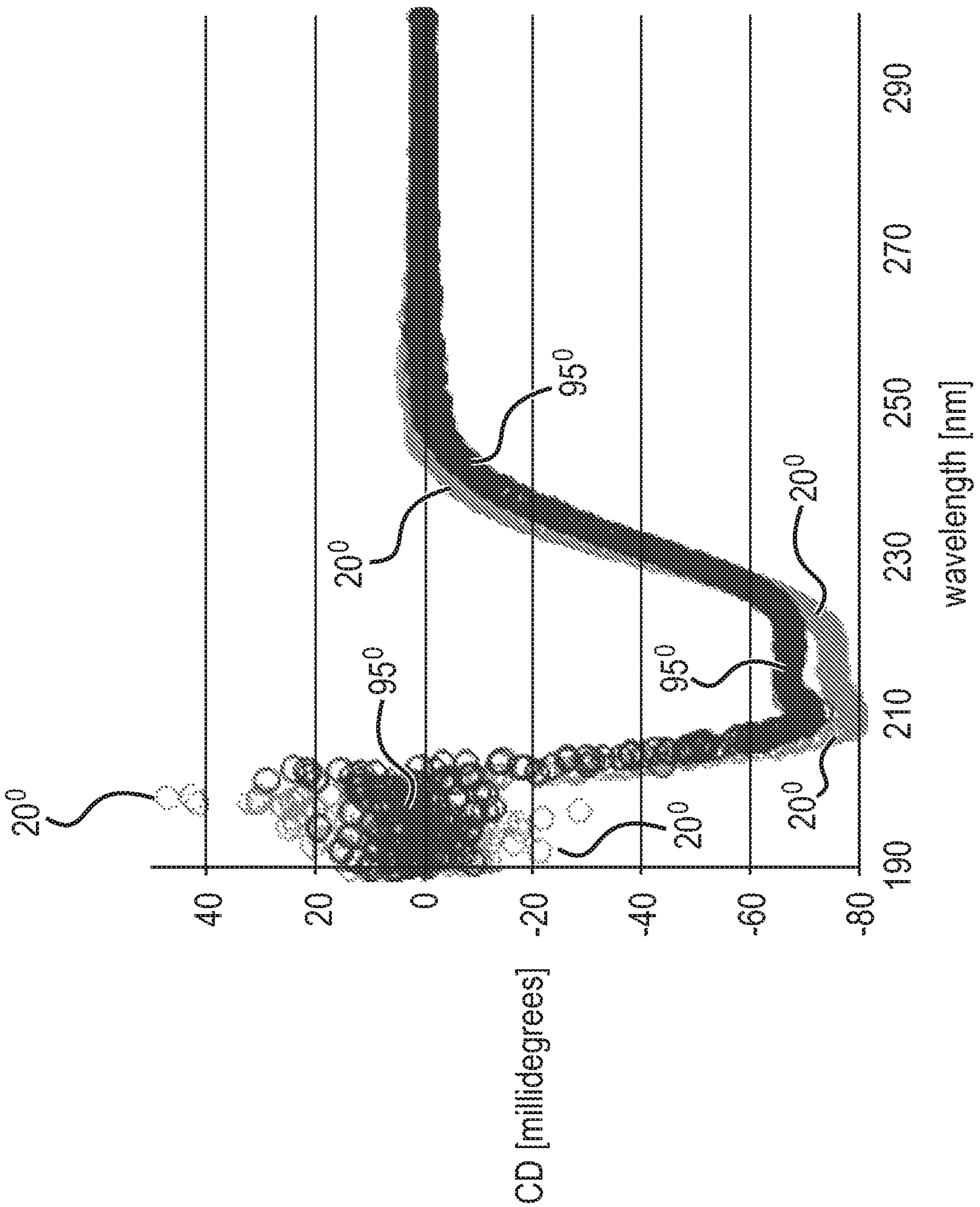
FIG. 2C shows a CD spectra of the post-fusion RSV F trimer at 200 and 95° C. The spectra were recorded from 320 to 190 nm and show at both temperatures characteristic helical minima for a folded protein.
Figure 3B:
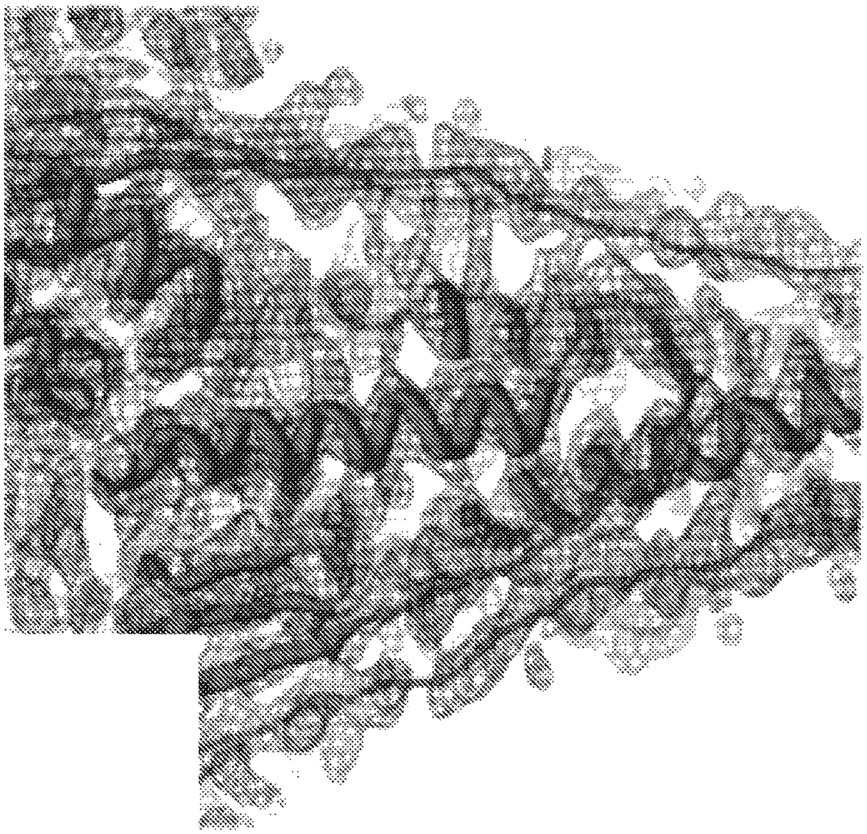
FIG. 3B Side view. The final model of RSV F shown in the averaged electron density map as described in FIG. 4A.
Figure 3A:
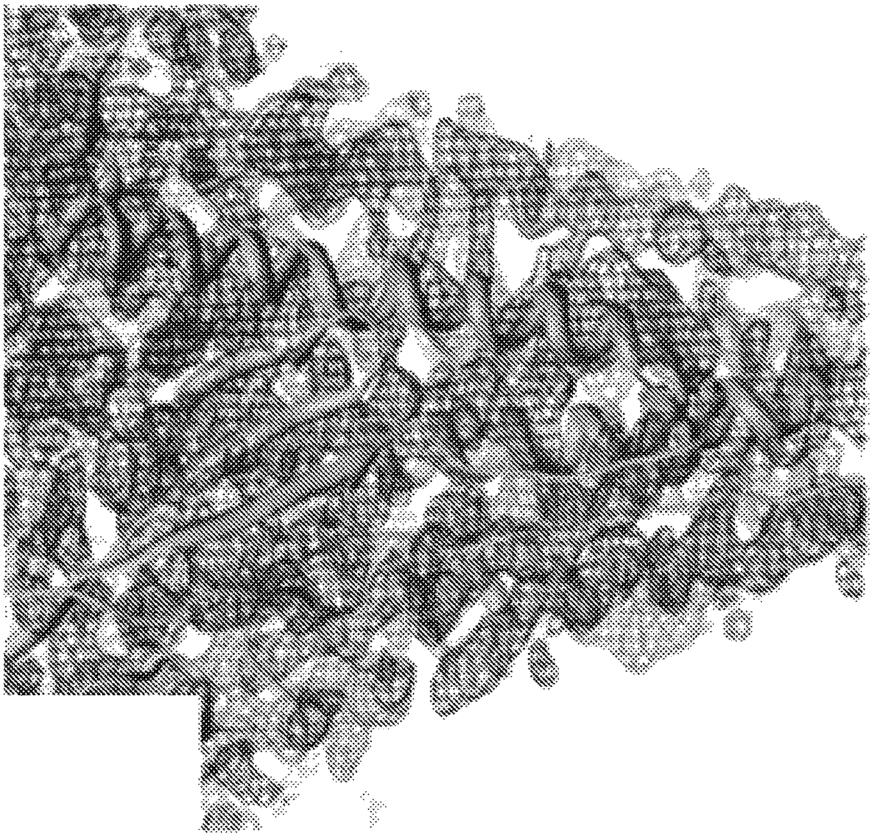
FIG. 3A is a side view of the original molecular replacement solution model, which contains the PIV3 post-fusion head in-frame with the 6-helix bundle of RSV F, shown in the initial electron density map (1σ) calculated after iterative real-space NCS three-fold averaging, histogram matching, and solvent flattening with phase extension from 7.0 to 3.2 Å and no phase recombination. The head region fits poorly in the electron density.
Figure 3C:
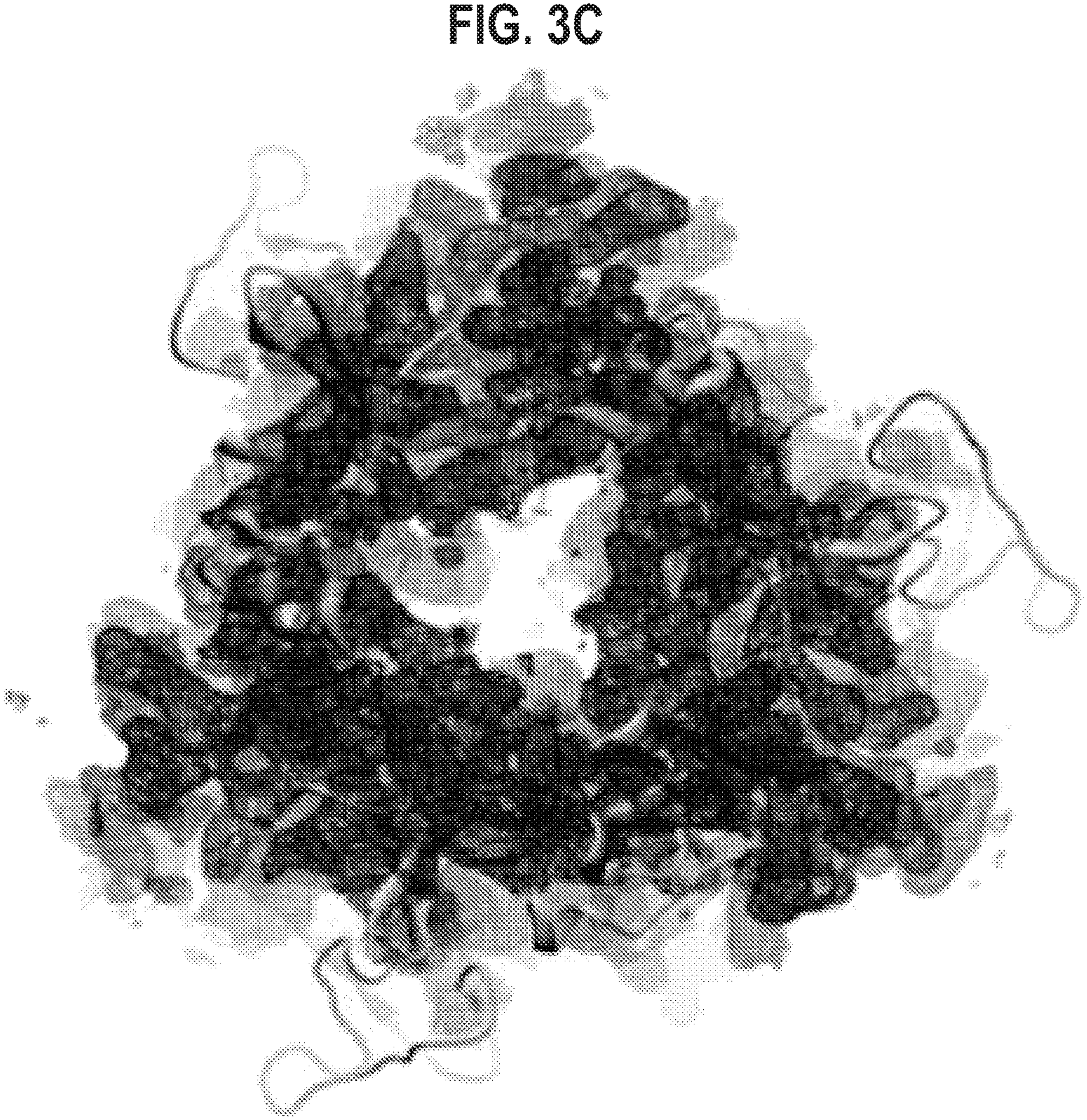
FIG. 3C shows a top view of the RSV F protein structure shown in FIG. 4A.
Figure 3D:
FIG. 3D shows a top view of B. Model and electron density depicted as in FIG. 4B.
Figure 3F:
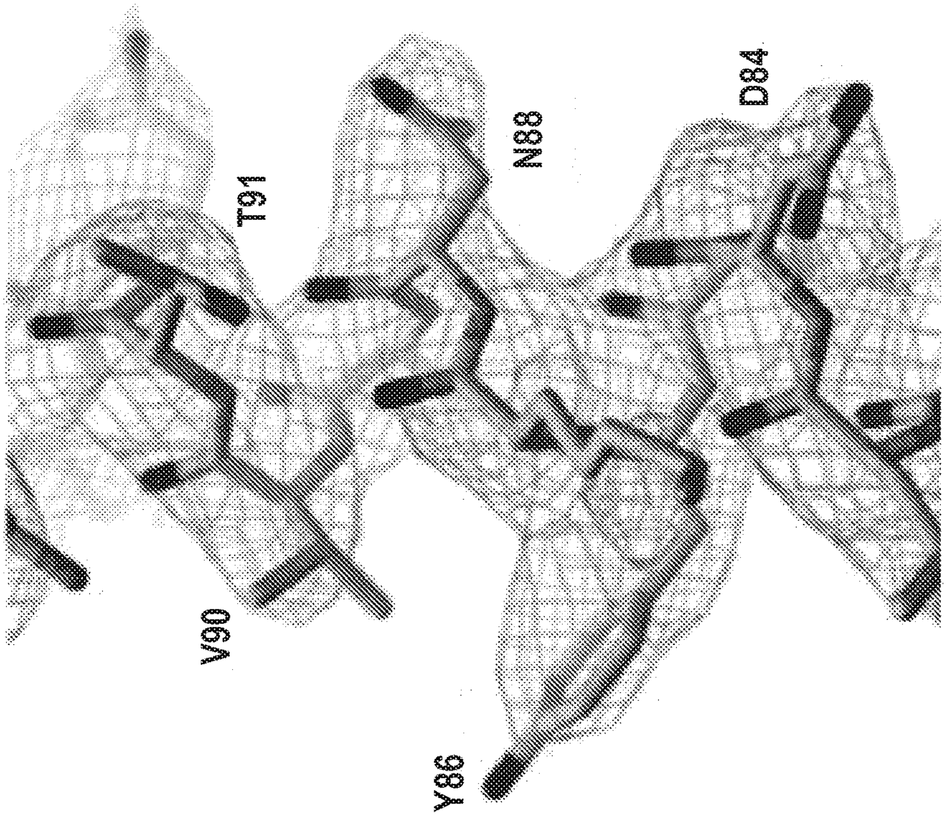
FIG. 3F shows the same view as in FIG. 4E but with final 2mFo-dFc electron density map contoured at 1.56.
Figure 3E:
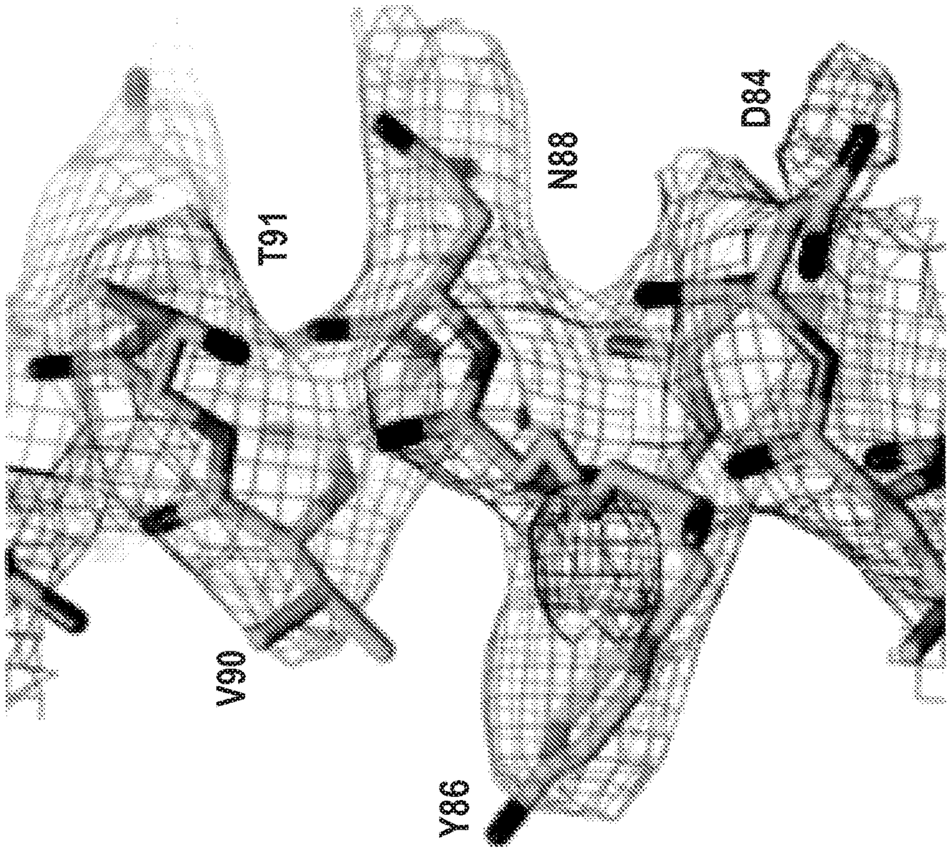
FIG. 3E is a close up of a representative averaged electron density (gray) with the final model in stick representation.

A stable, non-aggregating soluble RSV F subunit antigen was prepared by deletion of the fusion peptide, transmembrane region, and cytoplasmic domain (FIG. 1). This engineered F was expressed efficiently and was readily purified. Electron microscopy of negatively stained specimens showed that it formed non-aggregated, homogeneous crutch-shaped molecules, consistent with post-fusion F trimers (FIG. 2A). This engineered F trimer was stable, and circular dichroism spectroscopy revealed no significant melting at temperatures up to 95° C. (FIGS. 2B and 2C).

This RSV F protein was crystallized and its structure was determined by molecular replacement and three-fold non-crystallographic symmetry (NCS) averaging (Table 3 and FIG. 3). The structure does not include the p27 fragment (the peptide between the two furin sites that is lost upon cleavage), the fusion peptide, the transmembrane region, or the cytoplasmic domain (FIG. 4).

TABLE 3

| Crystallographic data | |
|---|---|
| Data collection statistics | |
| Space Group | P $2_1$ $2_1$ $2_1$ |
| Cell dimensions (Å) | a = 87.930 |
| | b = 113.160 |
| | c = 311.370 |
| | α = β = γ = 90.00° |
| Resolution limit (Å) | 50-3.2 |
| Unique reflections | 51,911 |
| Unique reflections† | 40,398 |
| Redundancy | 3.9 (3.7)[¥] |
| Overall completeness (%) | 99.4 (99.4) |
| Overall completeness (%)[†] | 77.0 (26.7) |
| <I/σ> | 12.2 (2.2) |
| $R_{sym}$ (%) | 7.7 (71.0) |
| Refinement Statistics[††] | |
| Polypeptide chains | 3 |
| Protein atoms | 10,398 |
| Residues in allowed regions of the Ramachandran plot (%) | 98.5 |
| Residues in most favored regions of Ramachandran plot (%) | 83.5 |
| RMSD bond lengths (Å) | 0.021 |
| RMSD bond angles (deg) | 2.053 |
| Mean B values ($Å^2$) | 15.71 |
| Resolution range (Å) | 30-3.2 |
| $R_{work}$ (%) | 23.1 (34.9) |
| $R_{free}$ (%) | 26.6 (40.2) |

[¥]Values in parentheses refer to data in the highest resolution shell

[†]Statistics for the data after anisotropic correction.

[††]Refinement values for the data after anisotropic correction.

Figure 4A:
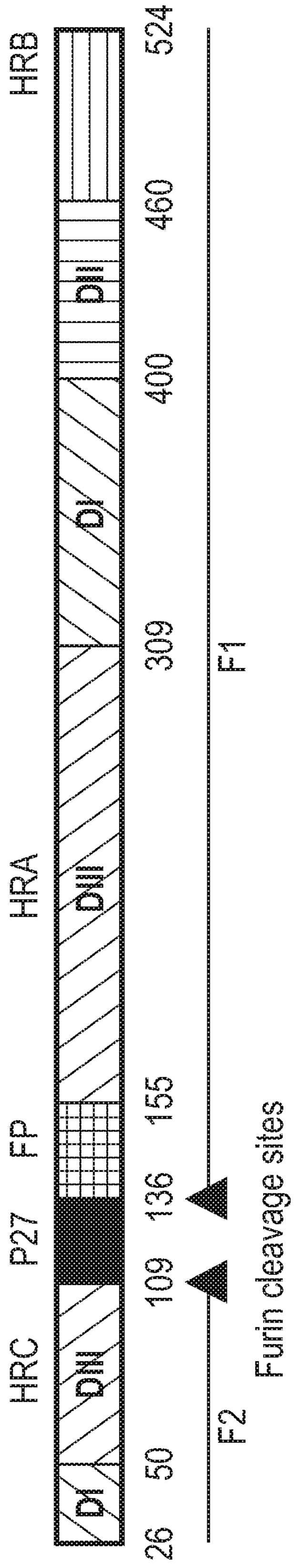
FIG. 4 A-C shows the RSV F ectodomain structure. 4A is a linear diagram. Listed residue numbers correspond to the N-terminus of each segment, the furin cleavage sites (arrow heads), and the C-terminus. DI-III, domains I-III; p27, excised peptide; FP, fusion peptide; HRA, B, and C, heptad repeats A, B, and C. 4B shows a ribbon representation of one subunit of the RSV F ectodomain trimer. Domains are labeled and shaded as in 4A, glycans are shown in black. 4C shows surface representation of the RSV F ectodomain trimer. The domains of one subunit are labeled and shaded as in 4A, the other two subunits are white and gray.
Figure 4B:
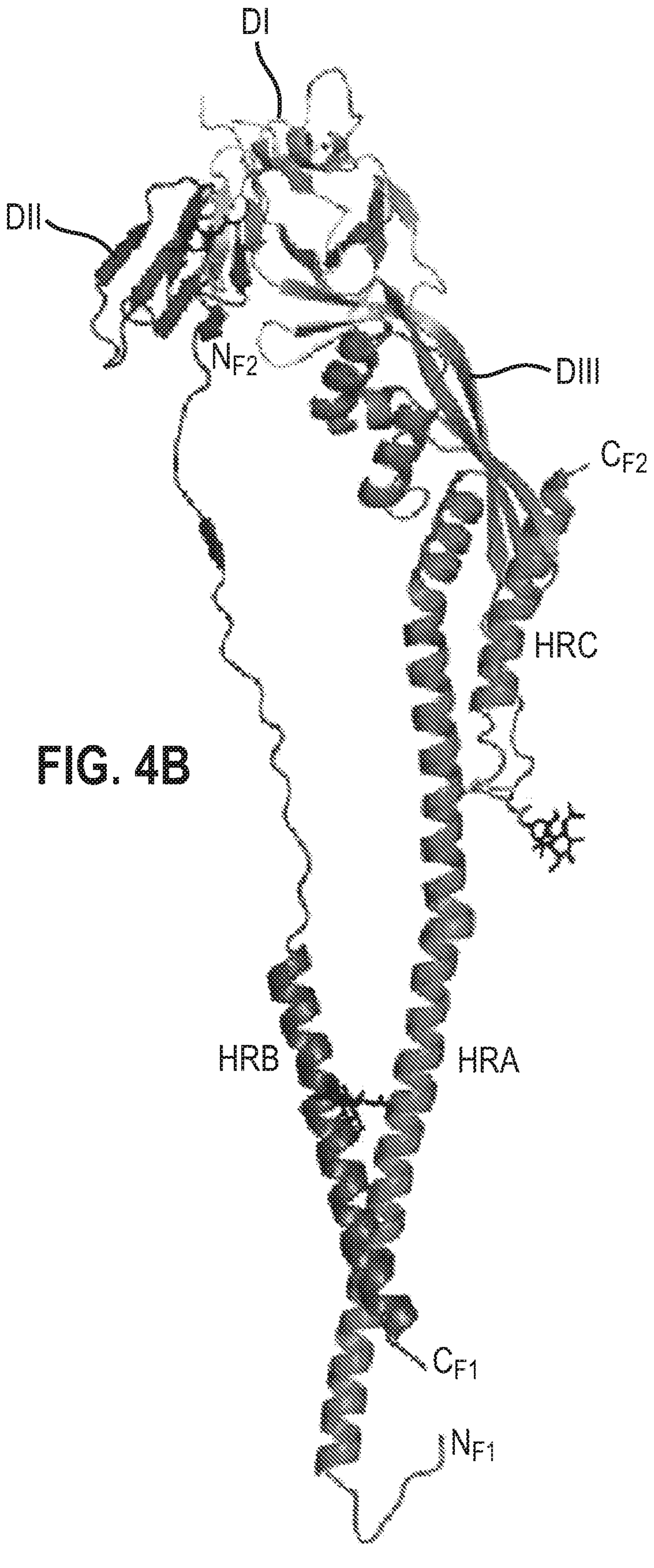
Figure 4C:
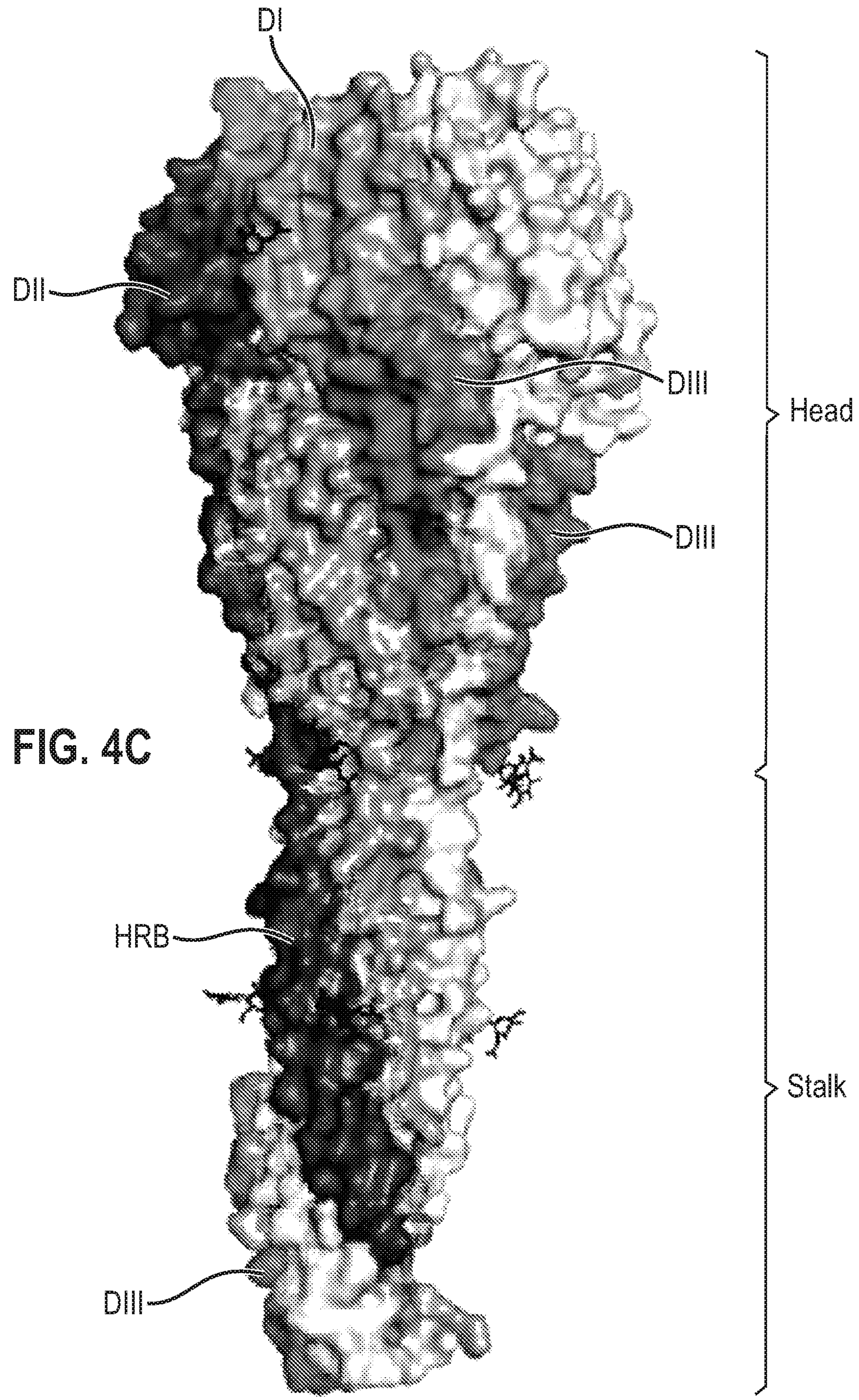

The overall architecture of post-fusion RSV F is shared with other post-fusion parainfluenza fusion proteins. The protein is composed of three tightly intertwined subunits, forming a globular head and an elongated stalk. Each subunit contains three domains, designated I, II, and III (FIGS. 4A-C). Domains I and II are at the top of the trimeric head and form a triangular crown. Domain III forms the base of the head. A long helix, HRA, extends from domain III and forms the trimeric coiled-coil in the center of the stalk. The HRB helix is tethered to domain II and reaches down to the head-distal end of the stalk, where it forms the outer coils of a six-helix bundle with the HRA interior coiled-coil. In full-length F, the hydrophobic fusion peptide (N-terminal to HRA) and the transmembrane region (C-terminal to HRB), would be juxtaposed at the bottom of the stalk and inserted into the target cell membrane.

Figure 5A:
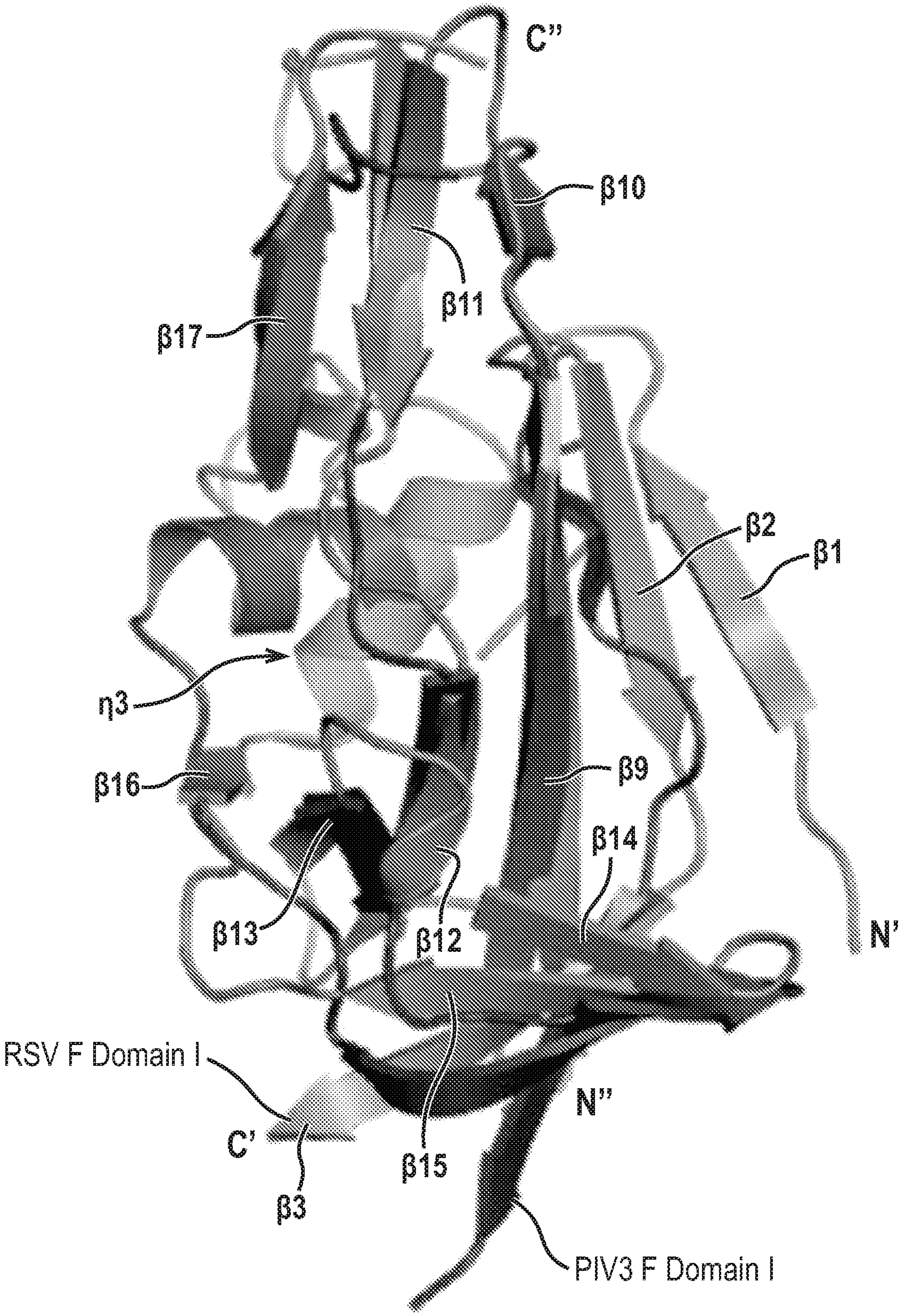
FIG. 5A shows a ribbon diagram of domain I from RSV and PIV3 superimposed by matching the common β-sheets.
Figure 5B:
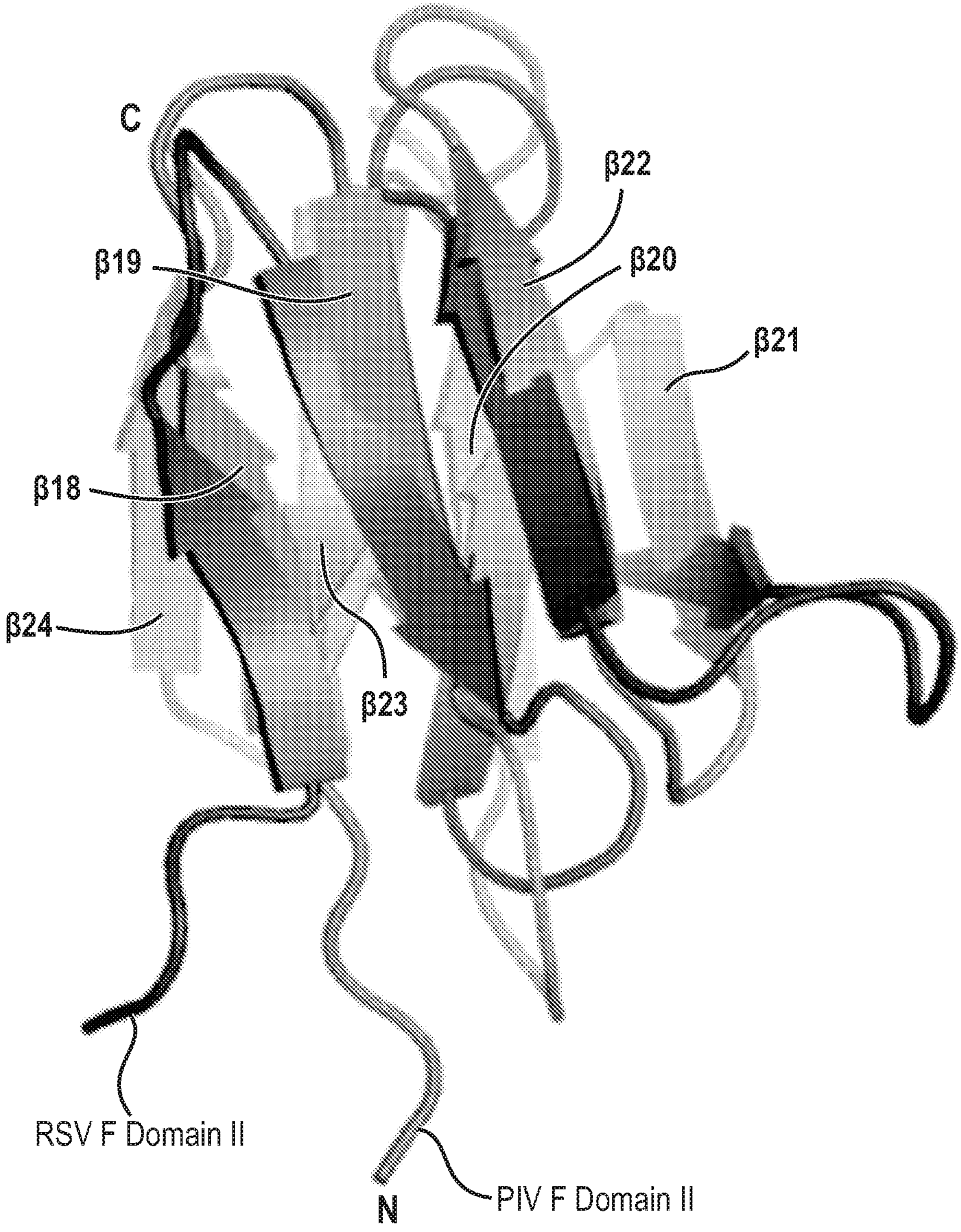
FIG. 5B shows a ribbon diagram of domain II from RSV F and PIV3 F superimposed based on common β-strands. The secondary structure elements of RSV F are labeled.
Figure 6A:
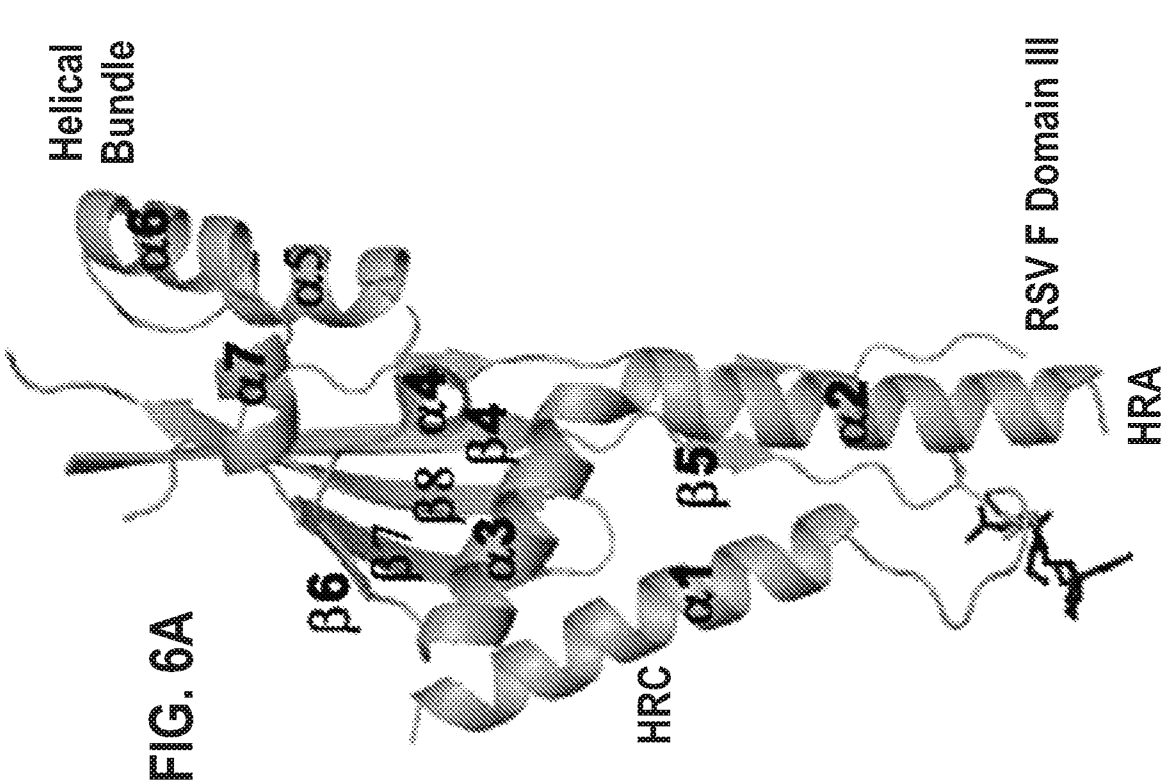
FIG. 6A is a ribbon diagram of RSV F domain III.
Figure 6B:
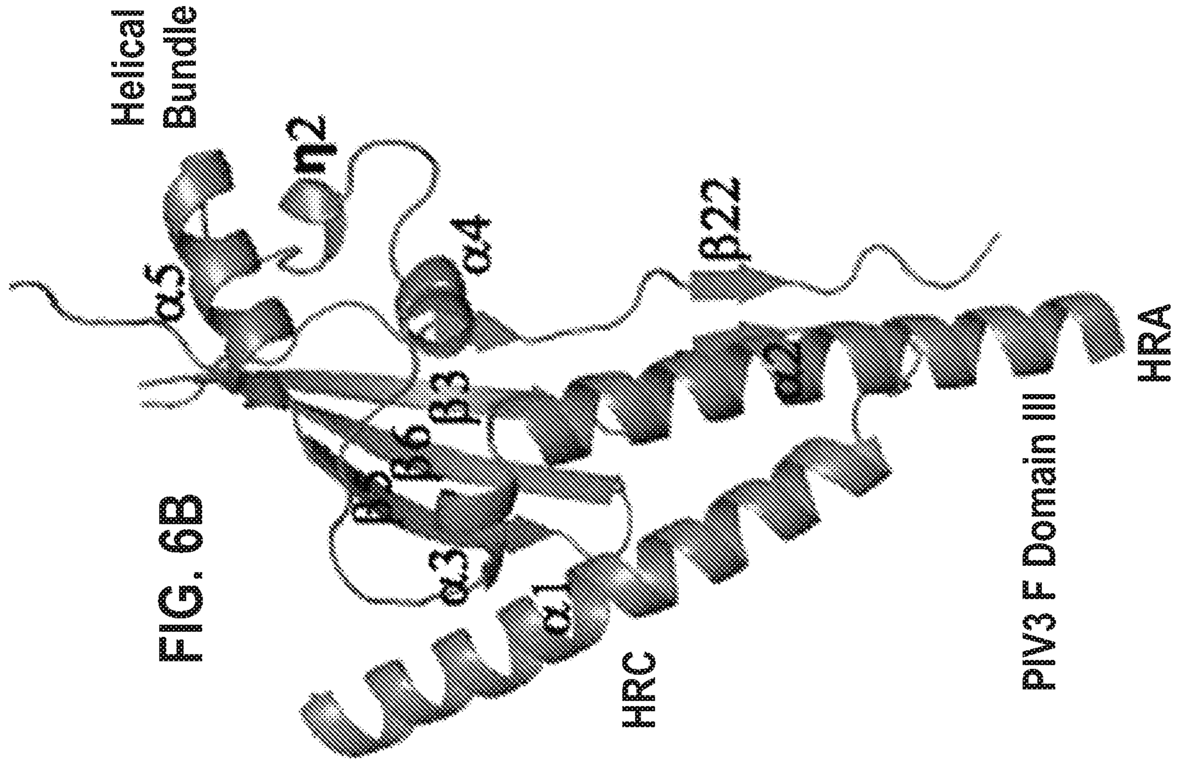
FIG. 6B shows a ribbon diagram of the PIV3 domain III oriented to match orientation shown in FIG. 6A.
Figure 6C:
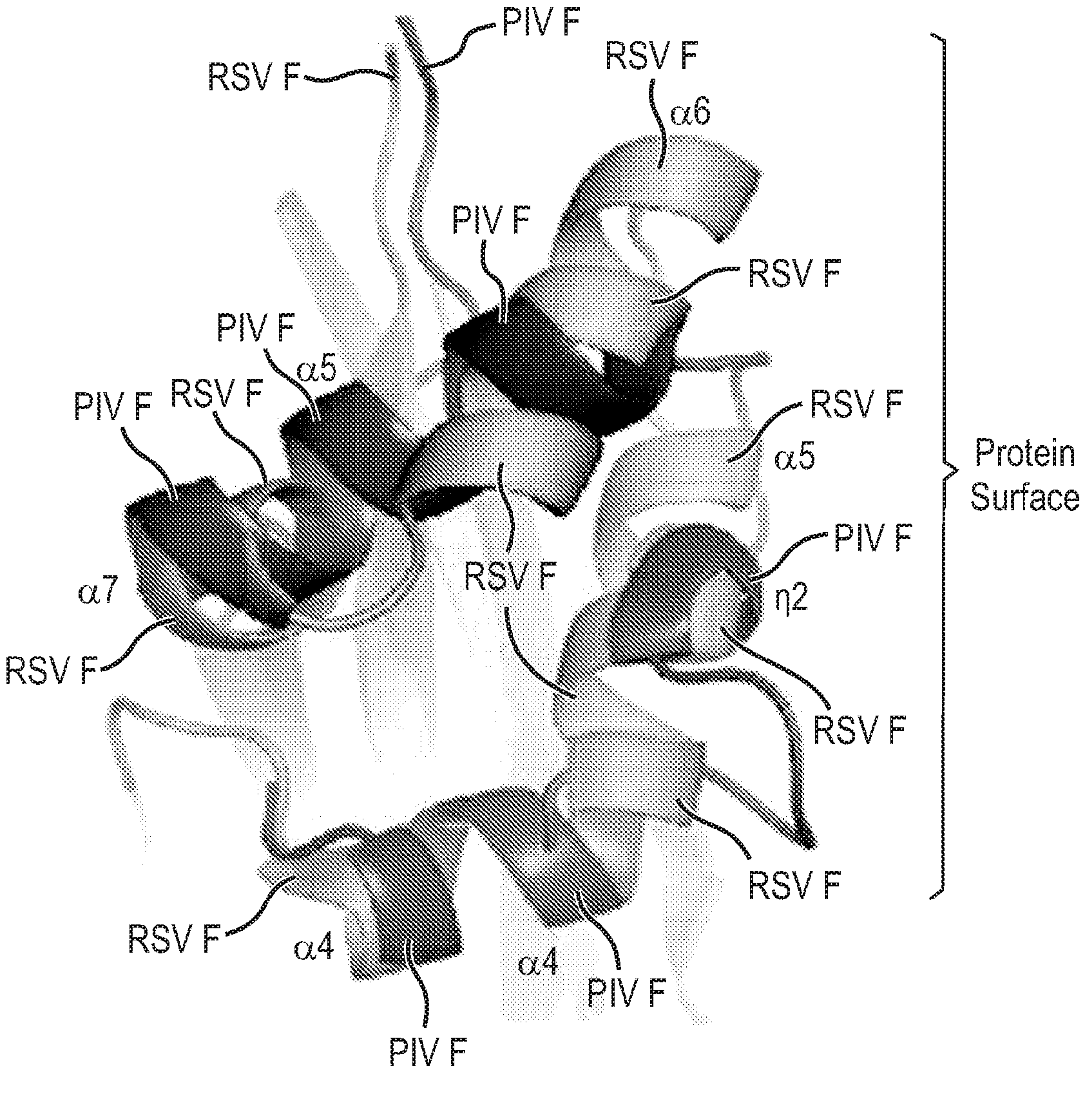
FIG. 6C shows the detail of the RSV and PIV3 (which are shaded differently) domain III helical bundles superimposed based on domain III β-sheets.
Figure 6D:
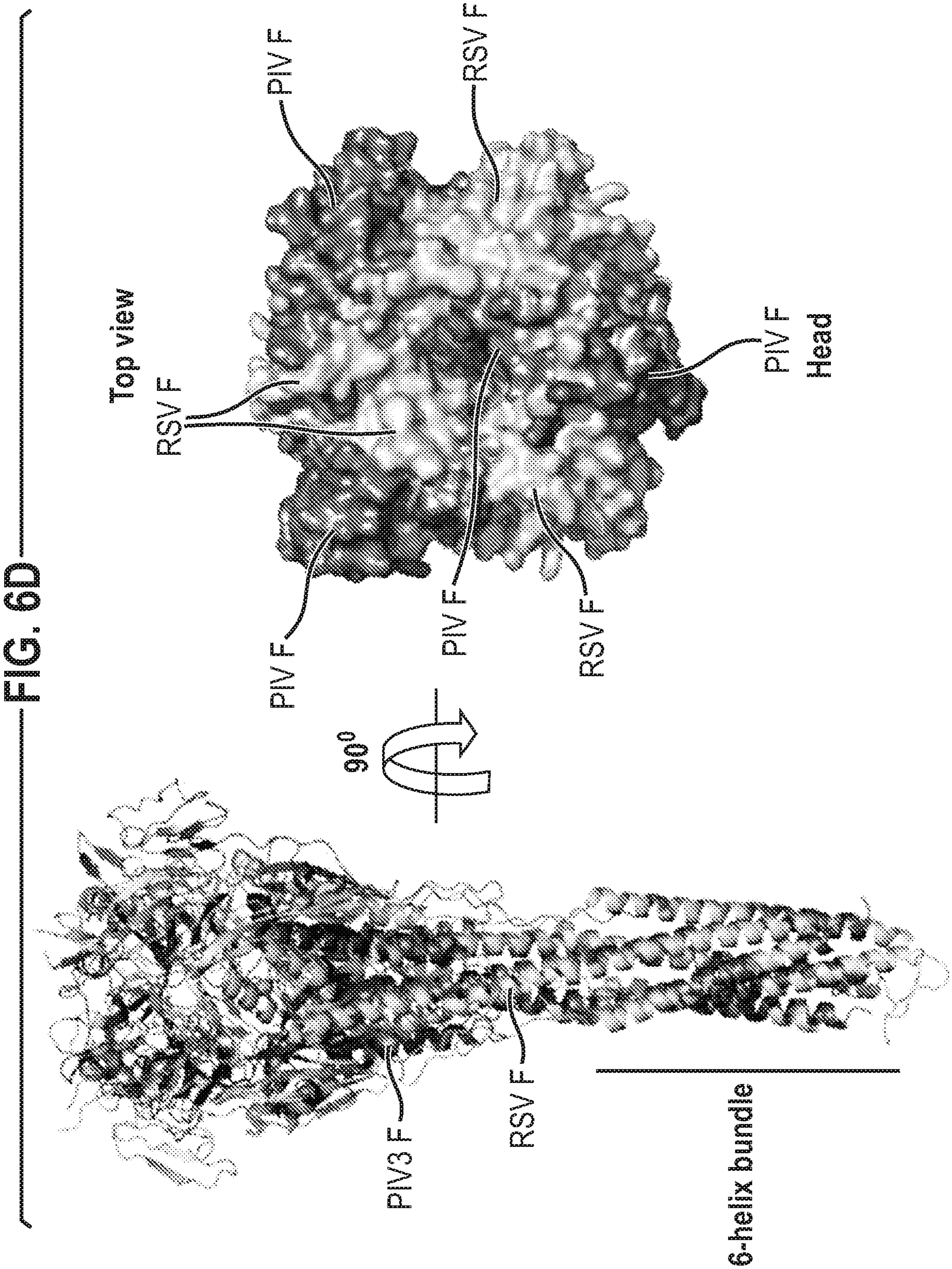
FIG. 6D shows RSV and PIV3 F ectodomain trimers (shaded as in A and B) superimposed based on their six-helix bundles. The image on the left shows a ribbon diagram viewed perpendicular to the three-fold axis; the image on the right is a surface representation viewed along the three-fold axis from the top of the head.

Domains I and II of RSV, parainfluenza virus 3 (PIV3), and parainfluenza virus 5 (PIV5) F proteins are structurally conserved (FIGS. 5A and 5B). The only significant difference is in the orientation of the sole helix of domain I (η3 of RSV F and α6 of PIV3 and PIV5 Fs) relative to their common β-sheets. In contrast, RSV F domain III has features that were not predicted from parainfluenza-based modeling (FIG. 6). When the four-stranded Q-sheets of RSV F domain III and PIV3 F domain III are superimposed, key differences in the domains' helical regions are apparent. Helix HRA kinks at a more N-terminal position in RSV F than in PIV3 F, causing an approximately 600 difference in the rotation of the heads relative to the stalks (FIGS. 6A, 6B, 6D). Influenza hemagglutinins also vary in the orientations of their heads relative to their stalks, with 30°-50° differences in rotation between subtypes. (Ha, Y. et al., *Embo Journal* 21, 865-875 (2002)).

Figure 7A:
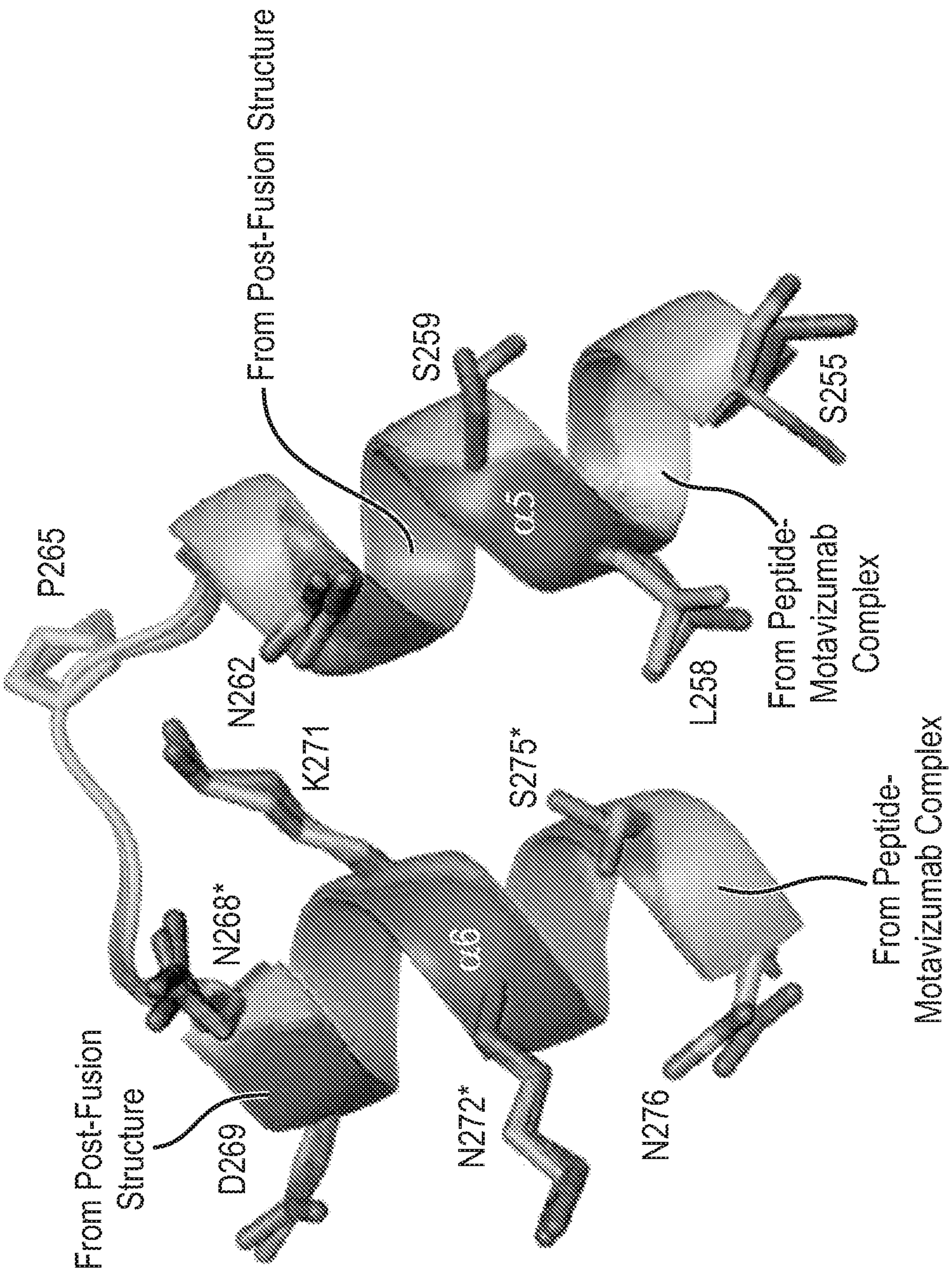
FIG. 7A is a superposition of the Motavizumab-binding helices, α5 and α6, from the RSV F post-fusion trimer and the peptide-Motavizumab complex (PDB code 3IXT). The post fusion trimer structure and the peptide-motavizumab complex structure are shaded differently. RSV residues bound by Motavizumab are shown in stick representation. Asterisks denote Palivizumab escape mutations.
Figure 7B:
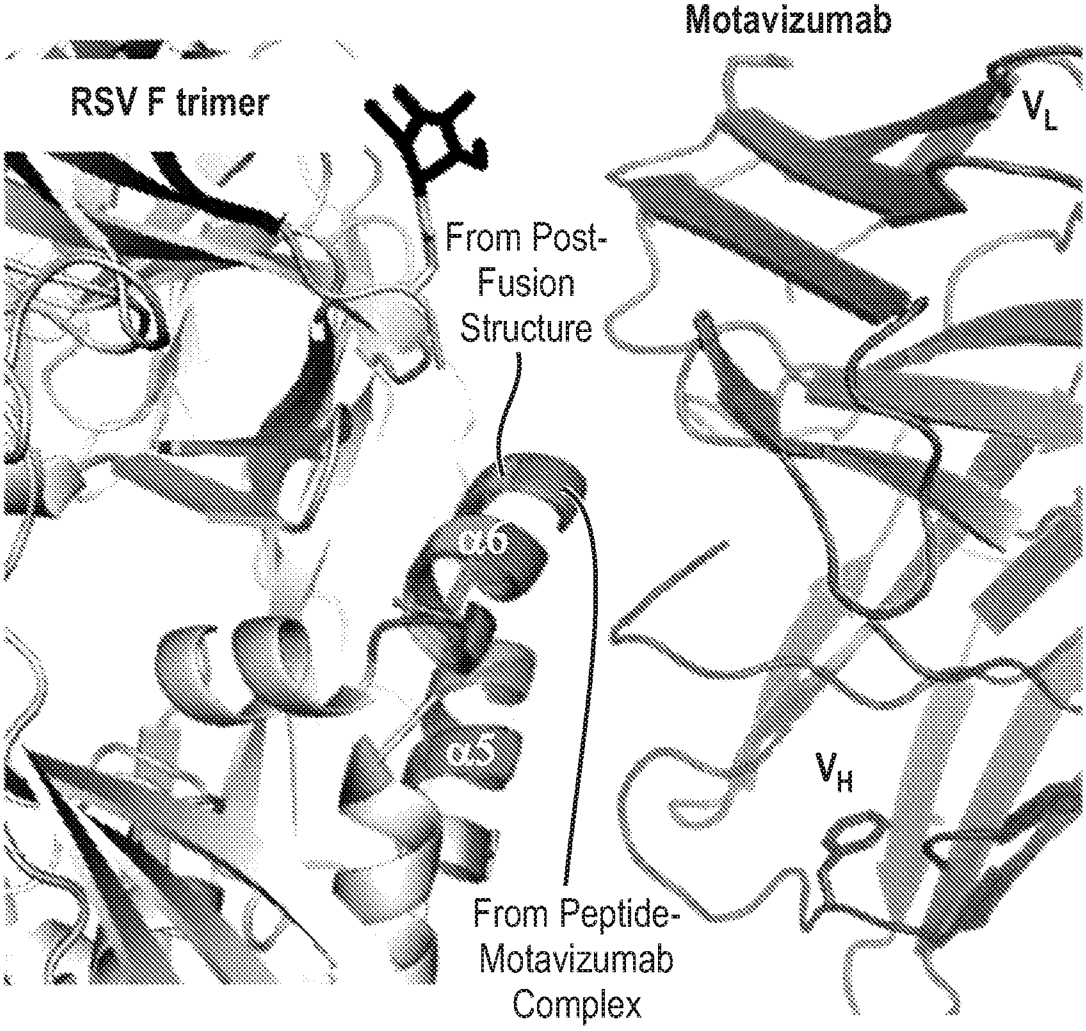
FIG. 7B shows a ribbon representation modeling a Motavizumab-RSV F post-fusion trimer complex. The $V_H$ and $V_L$ domains of the Fab are labeled; helices α5 and α6 from the RSV F structure and the peptide-Motavizumab structure are shaded differently; a glycan on RSV F is black; and the remainder of RSV F is white.

The RSV F domain III helical bundle region contains an extra helix (α6), changing the orientation of the bundled helices relative to those in parainfluenza Fs (FIGS. 6A-C and FIG. 1). RSV F helices α5 and α6 are almost parallel and are exposed on the trimer surface; the equivalent to RSV F α6 helix in the PIV3 helical bundle (α5, FIG. 6C) is buried in the inter-subunit interface of the trimer. RSV F helices α5 and α6 form the epitope bound by the related neutralizing antibodies Palivizumab and Motavizumab. The structure of a complex between the Motavizumab Fab and a 24-residue RSV F peptide that includes α5 and α6 has been reported (McLellan, J. S. et al. *Nat Struct Mol Biol* 17, 248-250 (2010)). Comparison between this structure and the post-fusion RSV F structure revealed a close match between the α5-α6 helices (r.m.s.d.=0.52 Å; FIG. 7A). Superposition of the two structures based on these helices models a complex between Motavizumab and post-fusion RSV F (FIG. 7B). This model reveals no steric hindrance that would prevent Motavizumab (or, presumably, Palivizumab) from binding to post-fusion RSV F. Binding of Palivizumab to the post-fusion F ectodomain in solution using surface plasmon resonance ($K_D$ of $4.2\times10^{-10}$ M) was confirmed.

Figure 8B:
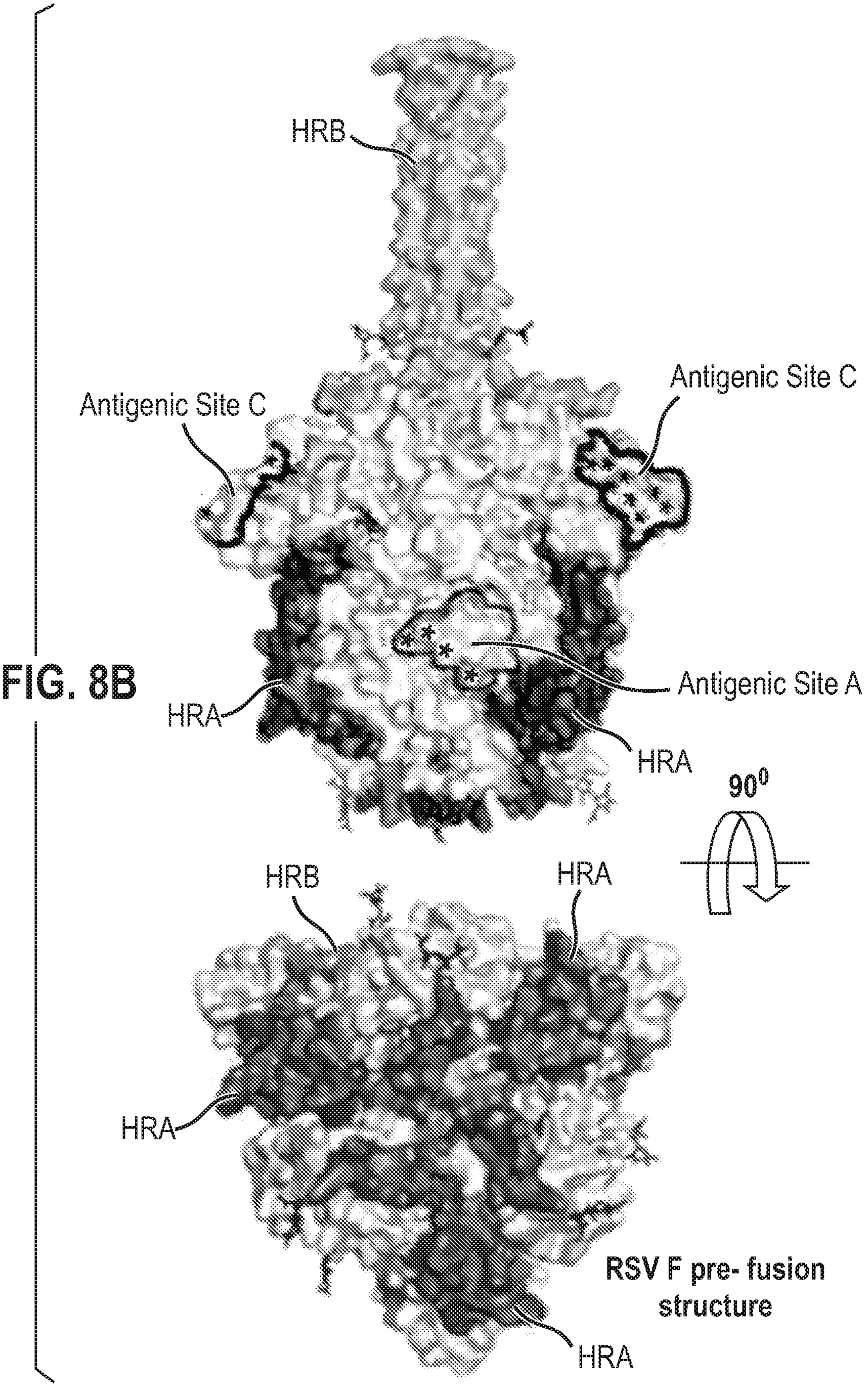
FIG. 8B is a surface representation of a pre-fusion model, annotated as in A.

Pre-fusion and post-fusion parainfluenza F structures reveal en bloc shifts of domains and large rearrangements of HRA and HRB. In domain III of the pre-fusion PIV5 F structure (the only reported pre-fusion parainfluenza F structure), HRA folds into three α-helices and two β-strands rather than the long post-fusion HRA helix (Yin, H. S., et al. Nature 439, 38-44 (2006)). However, when pre-fusion and post-fusion conformations of individual parainfluenza F protein domains are compared, the non-rearranging parts superimpose well. Superimposing post-fusion RSV F domains on their pre-fusion PIV5 F counterparts did not result in major clashes and positions all the pairs of cysteines that form interdomain disulfide bonds in proximity (FIG. 8B).

The resulting pre-fusion RSV F model reveals a feature not apparent from modeling pre-fusion RSV F domains based on the PIV5 pre-fusion domain structures (McLellan, J. S. et al. *Nat Struct Mol Biol* 17, 248-250 (2010)). The helices of the Motavizumab epitope are exposed on the surface of the pre-fusion RSV F trimer, as they are on post-fusion RSV F trimer (FIG. 9). In the current pre-fusion RSV F model, the loop connecting β4 and HRC (part of domain III) would hinder access of Palivizumab or Motavizumab to the epitope. However, the loop may have sufficient flexibility to adopt an alternative conformation that permits antibody binding (FIG. 9B).

Figure 10A:
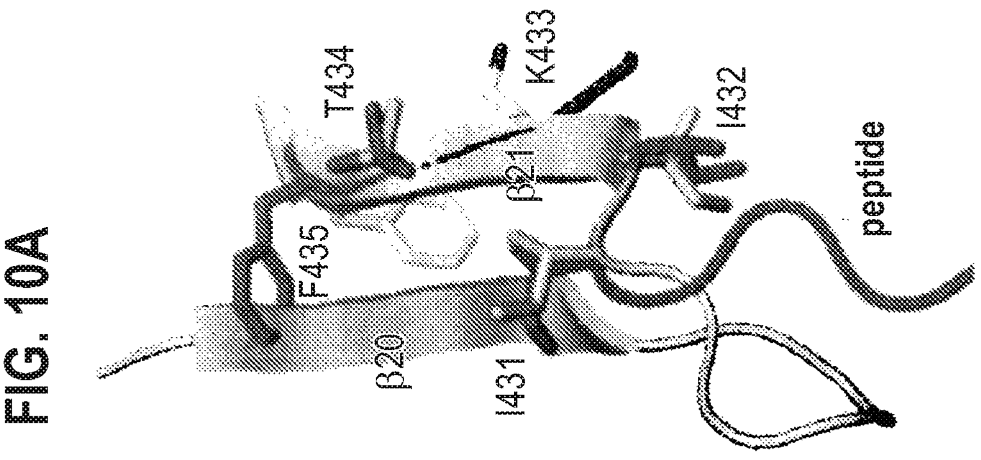
FIG. 10A shows the peptide (residues 431-435) (SEQ ID NO:37) from the 101F Fab-peptide complex structure (PDB code 3O4I[21]) superposed on equivalent residues of the RSV F structure (β-strand 20 to β-strand 21).
Figure 10B:
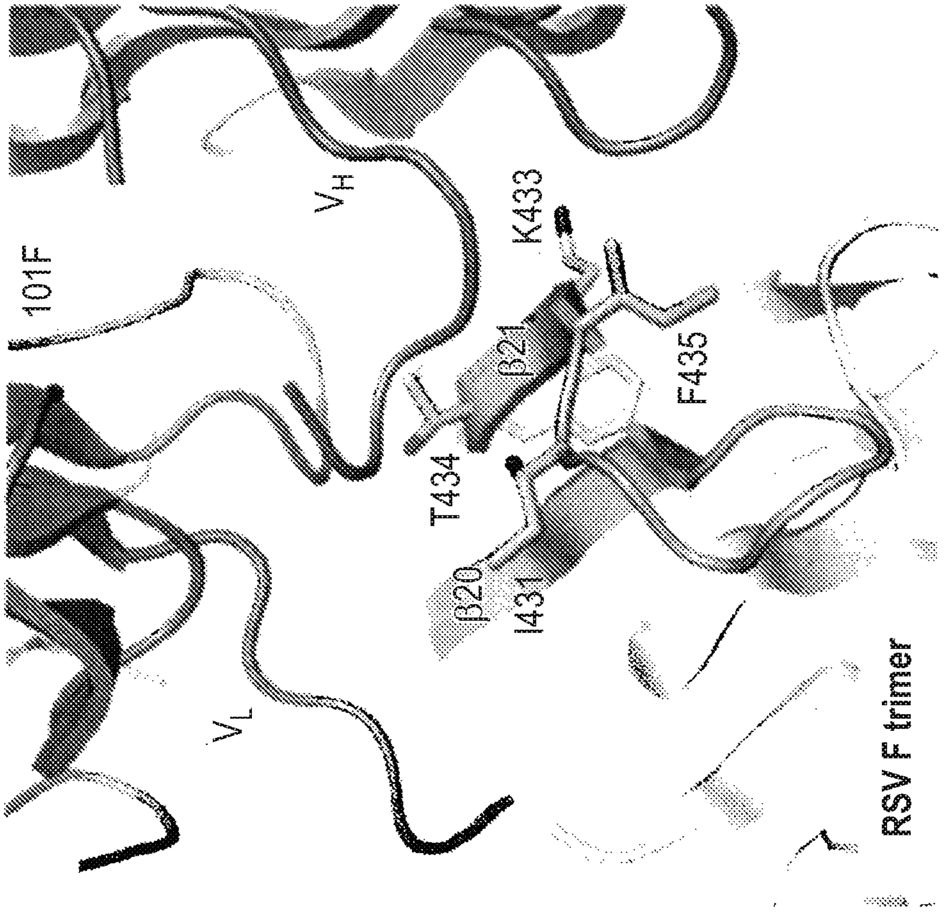
FIG. 10B is a ribbon representation of a model of the 101F Fab bound to the RSV F post-fusion trimer. 101F Fab $V_H$ and $V_L$ domains are labeled; RSV F β-strand 20 and β-strand 21 and labeled as in A. The remaining parts of RSV F are in white.

The antigenic structure of RSV F has been mapped by a variety of techniques (FIG. 1). The best documented epitope clusters are designated A and C (Beeler, J. A. & van Wyke Coelingh, K. *J Virol* 63, 2941-2950 (1989)), and others have been proposed. The Motavizumab-peptide structure corroborated the location of site A, although it called into question the site's exposure on the RSF F trimer (McLellan, J. S. et al. Structural basis of respiratory syncytial virus neutralization by motavizumab. *Nat Struct Mol Biol* 17, 248-250 (2010)); a crystal structure of an RSV F peptide (residues 422-436) bound to the 101F neutralizing antibody corroborated the location of site C (McLellan, J. S. et al. *J Virol* 84, 12236-12244 (2010)). The post-fusion structure of RSV F and the pre-fusion RSV F model indicate that sites A and C remain exposed and structurally similar in both conformations (FIGS. 8A and 8B). Superposition of the 101F-peptide complex on the RSV F pre-fusion model and post-fusion structure confirmed that 101F would not clash with F in either conformation (FIG. 10).

Provided in the Appendix is the PDB file of the RSV F pre-fusion model based on the RSV F post-fusion structure and sequence/domain alignments to the PIV5 pre-fusion structure. The PDB file contains the atomic coordinates for the pre-fusion model, and can be used with suitable software for molecular visualization and analysis (e.g., Roger Sayle and E. James Milner-White. "RasMol: Biomolecular graphics for all", *Trends in Biochemical Sciences* (*TIBS*), September 1995, Vol. 20, No. 9, p. 374.) to display the model. Included in the model are the three subunit chains with the fusion peptide and HRA region folded as in PIV5, making significant contacts with DIII. HRB regions of the three subunits trimerize into the pre-fusion stalk and are associated with D1 and DII.

2. Destablizing the Post-Fusion 6-Helix Bundle Through Deletion of the HRB Helix An HRB deletion construct was designed to prevent formation of the post-fusion conformation. Two constructs have been designed to address this strategy. The first is a wild-type ectodomain lacking the HRB region (RSV F residues 1-483) call Del HRB:

The sequence presented below contain a signal peptide and a HIS tag (GGSAGSGHHIHHHH; SEQ ID NO:3). The pre-fusion RSV F protein of the invention can contain the amino acid sequences shown below, with or without the signal peptide and/or HIS tag.

>RSV F delHRB HIS
(SEQ ID NO: 28)
MELLILKANAITTILTAVTFCFASGQNITEEFYQSTCSAVSKGYLSALRT

GWYTSVITIELSNIKENKCNGTDAKVKLIKQELDKYKNAVTELQLLMQST

PATNNRARRELPRFMNYTLNNAKKTNVTLSKKRKRRFLGFLLGVGSAIAS

GVAVSKVLHLEGEVNKIKSALLSTNKAVVSLSNGVSVLTSKVLDLKNYID

KQLLPIVNKQSCSISNIETVIEFQQKNNRLLEITREFSVNAGVTTPVSTY

MLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVS

FFPQAETCKVQSNRVFCDTMNSLTLPSEVNLCNVDIFNPKYDCKIMTSKT

DVSSSVITSLGAIVSCYGKTKCTASNKNRGIIKTFSNGCDYVSNKGVDTV

SVGNTLYYVNKQEGKSLYVKGEPIINFYDPLVFPSGGSAGSGHHHHHH

Figure 12:
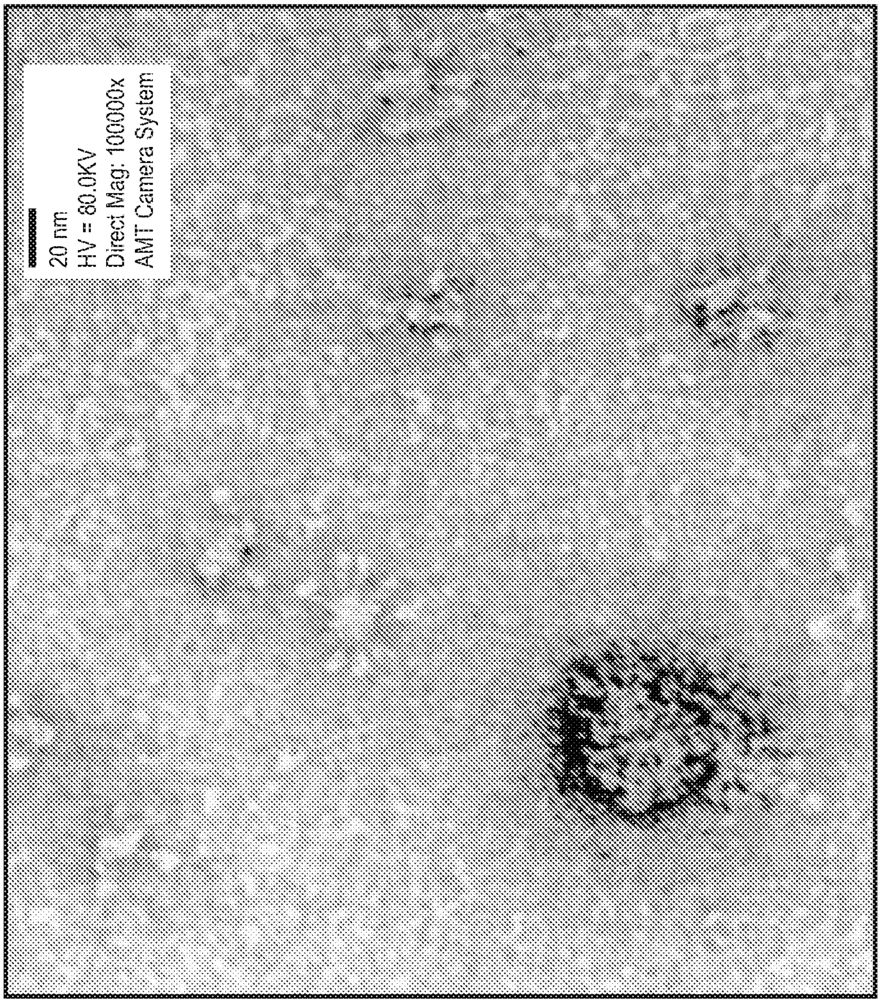
FIG. 12 shows a negative stained electron micrograph of the HRB-deleted RSV F construct (RSV F delHRB HIS, SEQ ID NO:28). Electron microscopy of the HRB-deleted RSV F construct demonstrated the RSV F protein formed rosettes, likely through the fusion peptide. The formation of rosettes through the fusion peptide is a feature of post-fusion RSV F rather than a predicted behavior of pre-fusion F proteins (Ruiz-Arguello et al. 2004 (142) and Connolly et al, 2006 (144)). This result shows the HRB-deleted RSV F construct does not appreciably stabilize the protein in the desired pre-fusion conformation.
Figure 13:
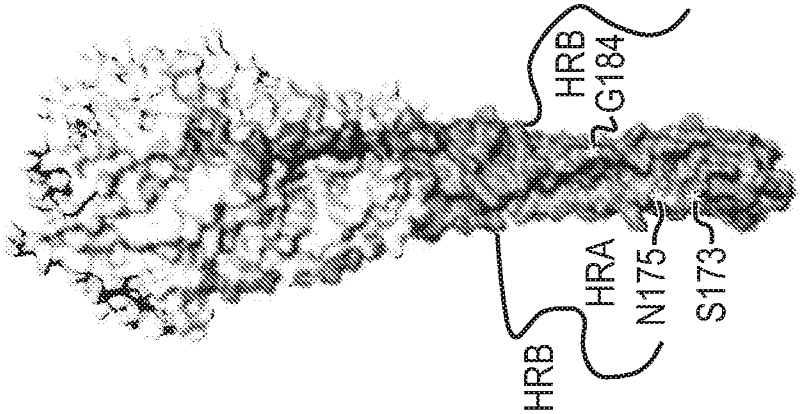
FIG. 13 shows the structure of RSV F protein in which certain mutations are introduced to inhibit 6-helix bundle formation. Shown is the RSV F post-fusion structure in which the HRB helix has been removed and replaced with a hypothetical random coil (represented by the lines). The elongated HRA helix of the post-fusion RSV F is labeled. The numbers represent potential sites for introduced glycosylation sites or other mutations which interfere with formation of the 6-helix bundle characteristic of the post-fusion structure. A mutation on the HRA helix which interferes with HRB interaction would destabilize the post-fusion conformation, which in turn would cause the protein to remain in the favored pre-fusion conformation.

The above sequence has both furin cleavage sites unaltered, and was expected to be processed by the cell. In addition, the above sequence has the wild-type fusion peptide sequence. In previous experiments, when the RSV F ectodomain-based proteins were cleaved by the cell and contained fusion peptides, they formed soluble aggregates with cellular debris in the form of RSV F rosettes. If this construct remained in the pre-fusion conformation (due to the lack of the HRB helix thought to be required for post-fusion conformation) than the fusion peptide should be burried in the RSV F head domain and should not form rosette aggreagates. This construct was expressed, purified by affinity purification and evaluated by EM analysis (FIG. 12).

It is clear both by its migration on an SEC column in the void volume, as well as from the EM micrograph that the construct formed rosettes similar to the rosettes formed by post-fusion RSV F proteins. This result was a surprise as it was hypothesized that the HRB is required to stabilize the HRA in its elongated helix formation (as it is observed that HRA peptides do not form trimers). Thus, we hypothesized that the fusion peptides, binding with one another or with cellular debris, are stabilizing the HRA helixes in their elongated, post-fusion formation.

We have hypothesized that the post-fusion like phenotype of the DelHRB construct was due to stabilization of the HRA into elongated helices by binding of the fusion peptides to one another or cellular debris. To test this hypothesis we are generating the following construct (DelHRB fusion peptide deletion:below) which is similar to the DelHRB but has the fusion peptide deletion consistent with our post-fusion trimer. We will test by EM microscopy the phenotype of the contruct to see if it forms crutch-like structures similar to that of the post-fusion like phenotype observed in the DelHRB rosettes of if the construct forms pre-fusion head shapes, which are similar to the spherical shape of the lollipop phenotype published in the literature.

The sequence presented below contain a signal peptide and a HIS tag (GGSAGSGHHHHHHH; SEQ ID NO:3). The pre-fusion RSV F protein of the invention can contain the amino acid sequences shown below, with or without the signal peptide and/or HIS tag.

>RSV F delHRB fusion peptide deletion HIS
(SEQ ID NO: 10)
MELLILKANAITTILTAVTFCFASGQNITEEFYQSTCSAVSKGYLSALRT

GWYTSVITIELSNIKENKCNGTDAKVKLIKQELDKYKNAVTELQLLMQST

PATNNRARRELPRFMNYTLNNAKKTNVTLSKKRKRRSAIASGVAVSKVLH

LEGEVNKIKSALLSTNKAVVSLSNGVSVLTSKVLDLKNYIDKQLLPIVNK

QSCSISNIETVIEFQQKNNRLLEITREFSVNAGVTTPVSTYMLTNSELLS

LINDMPITNDQKKLMSNNVQIVRQQSYSIMSIIKEEVLAYVVQLPLYGVI

DTPCWKLHTSPLCTTNTKEGSNICLTRTDRGWYCDNAGSVSFFPQAETCK

VQSNRVFCDTMNSLTLPSEVNLCNVDIFNPKYDCKIMTSKTDVSSSVITS

LGAIVSCYGKTKCTASNKNRGIIKTFSNGCDYVSNKGVDTVSVGNTLYYV

NKQEGKSLYVKGEPIINFYDPLVFPSGGSAGSGHHHHHH

3. Prefusion Stabilization with Intrachain Disulfide Bond Formation

Figure 11A:
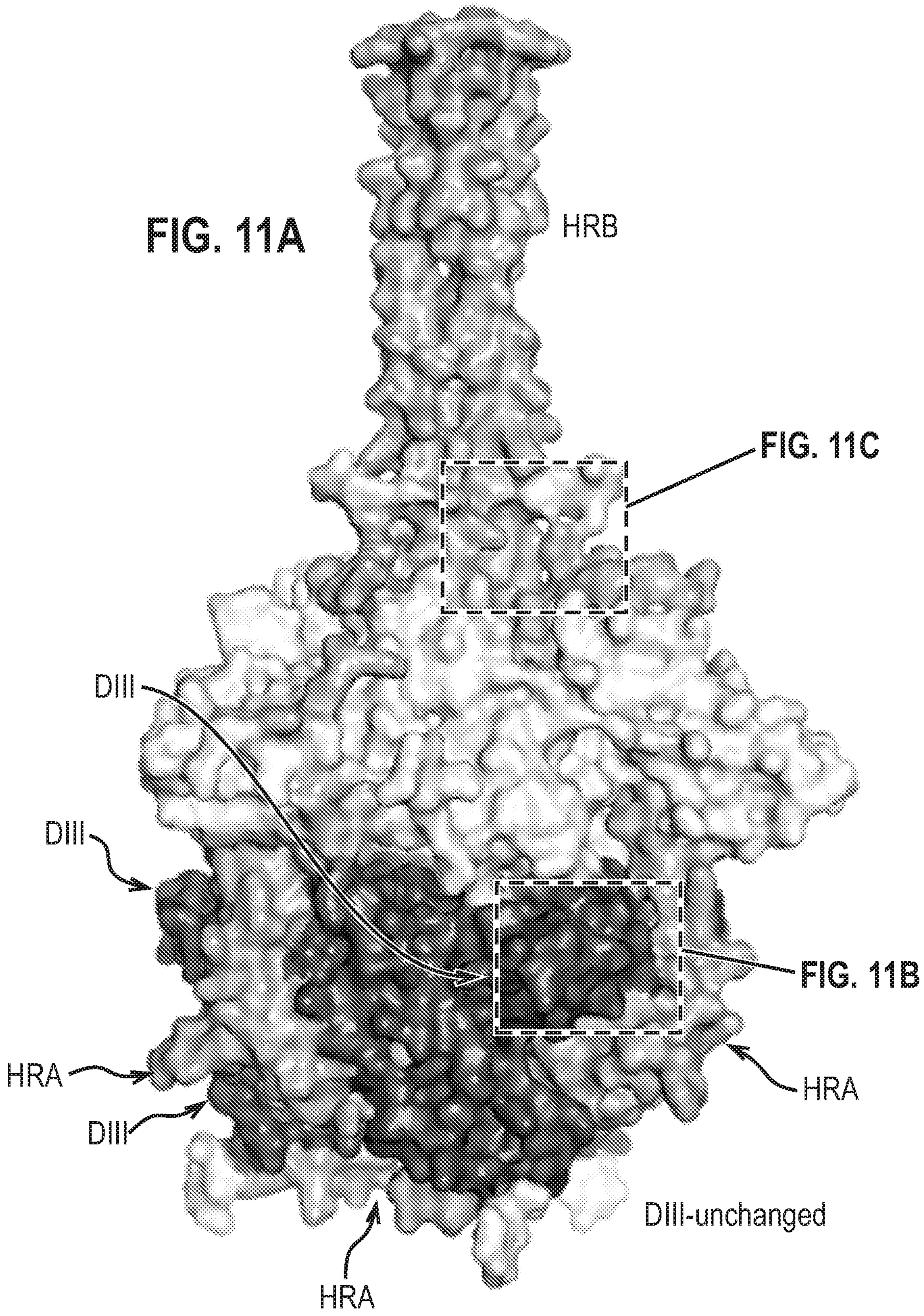
FIGS. 11A-C show that residues within appropriate distances to form disulfides can be identified, based on the current model of RSV F pre-fusion, can be identified.
Figure 11B:
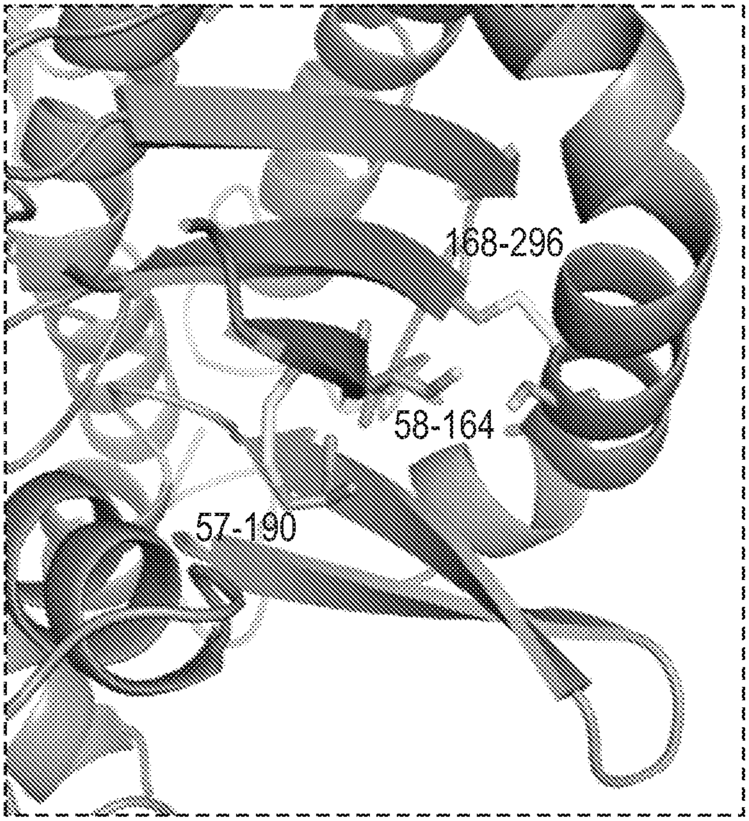
Figure 11C:
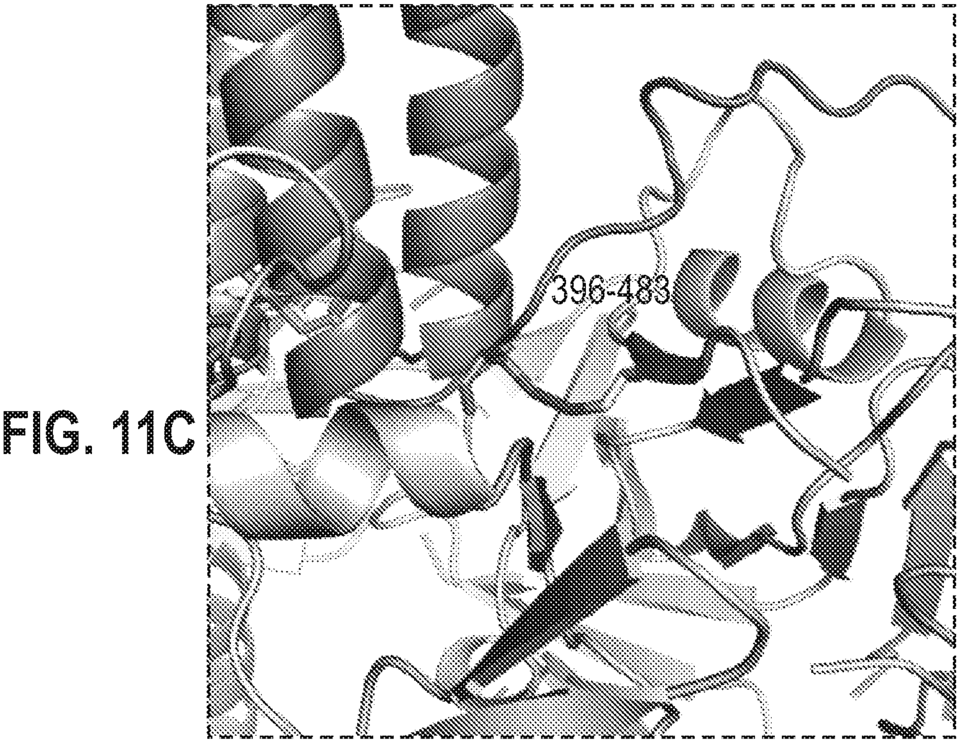
Figure 14A:
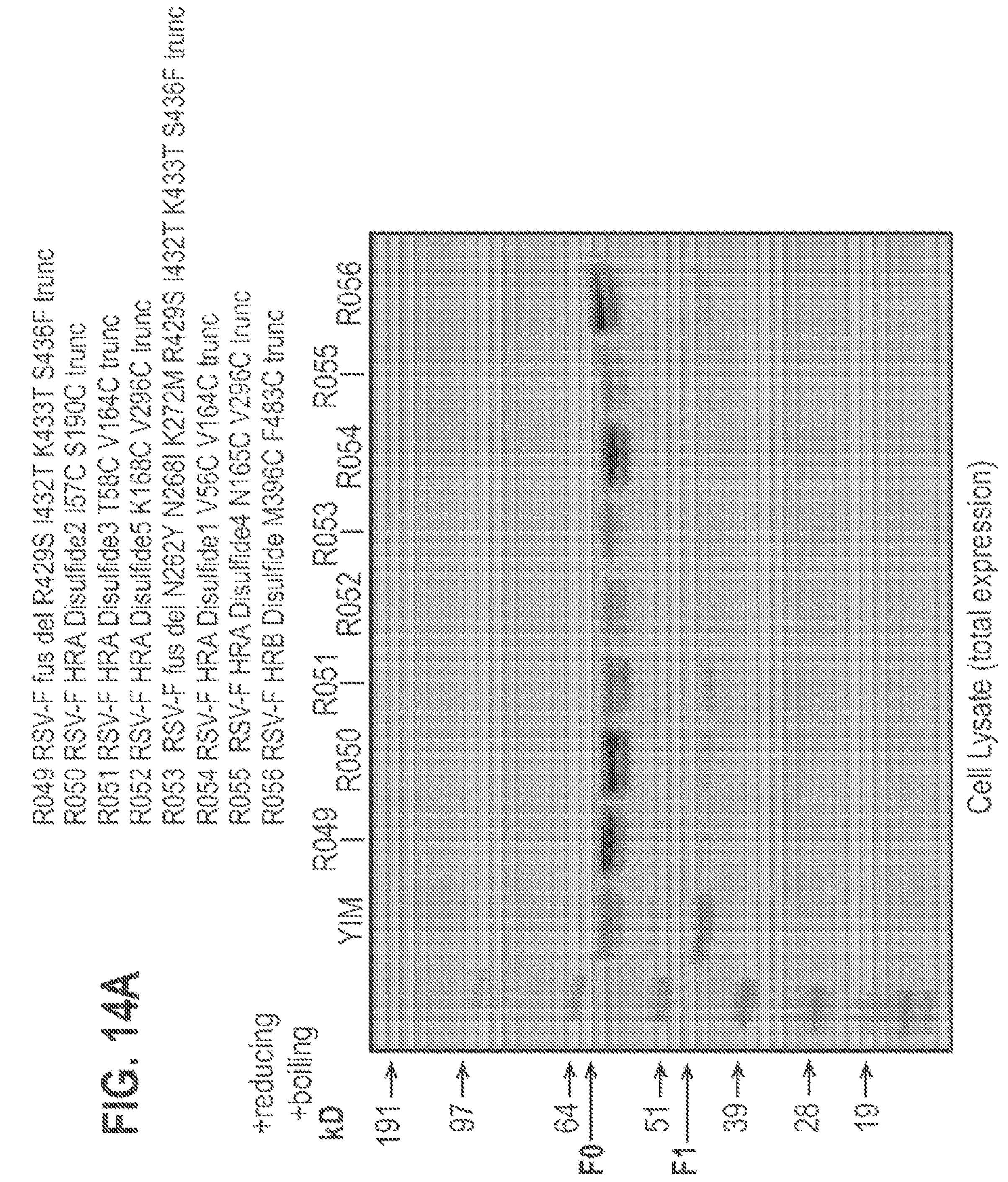
FIGS. 14 A and B are western blots of cell lysates (14A, showing total expression) or media (14B, showing secreted protein) under boiled and reducing conditions using an anti-His tag antibody. The westerns show the expression of RSV-F proteins, and that proteins with engineered cysteine residues were expressed and contained intra-chain disulfide bonds. Cleavage of RSV F protein from F0 to F1/F2 and secretion from the cell is evidence of proper protein folding of the RSV F proteins. Migrations for uncleaved F0 and cleaved F1 are indicated. The key for gel lane labeling is shown above the blots. (A) Western blot of cell lysate indicating total protein expression. Each protein construct was well expressed by the cell. (B) Western blot of RSV F secreted into the media. The secreted protein was predominantly cleaved (F1) and the amount of secretion varied among proteins. The results of this analysis indicate that the T58C & V164C, K168C & V296C and M396C & F483C protein constructs were the best expressed/secreted protein constructs. R049: RSV-F fus del R429S I432T K433T S436F trunc (SEQ ID NO:39); R050: RSV-F HRA Disulfide2 I57C S190C trun (SEQ ID NO:40); R051: RSV-F HRA Disulfide3 T58C V164C trunc (SEQ ID NO:6); R052: RSV-F HRA Disulfide5 K168C V296C trunc (SEQ ID NO:8); R053: RSV-F fus del N262Y N268I K272M R429S I432T K433T S436F trunc (SEQ ID NO:41); R054 RSV-F HRA Disulfidel V56C V164C trunc (SEQ ID NO:4); R055 RSV-F HRA Disulfide4 N165C V296C trunc (SEQ ID NO: 7); R056 RSV-F HRB Disulfide M396C F483C trunc (SEQ ID NO:9).
Figure 14B:
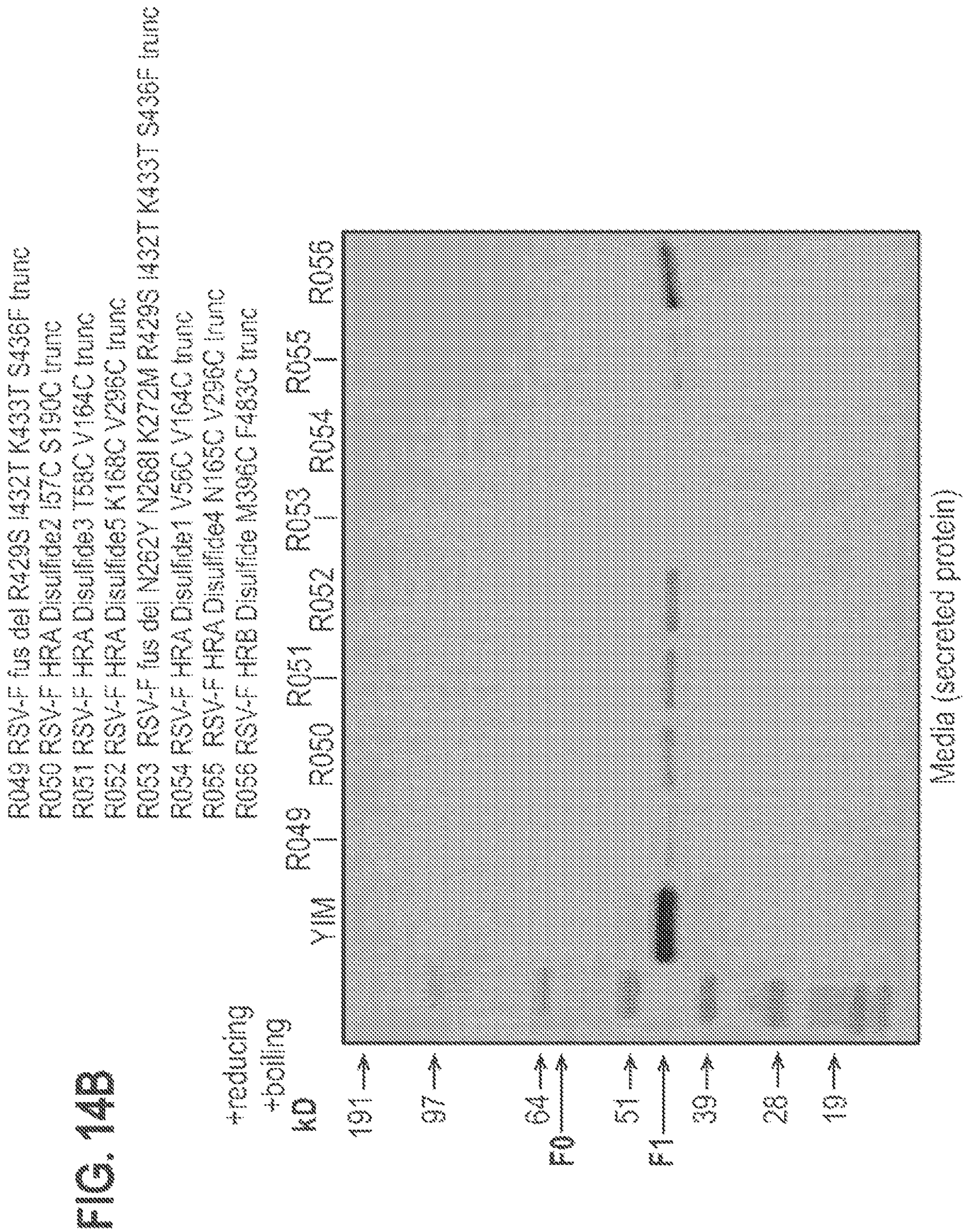
Figure 15A:
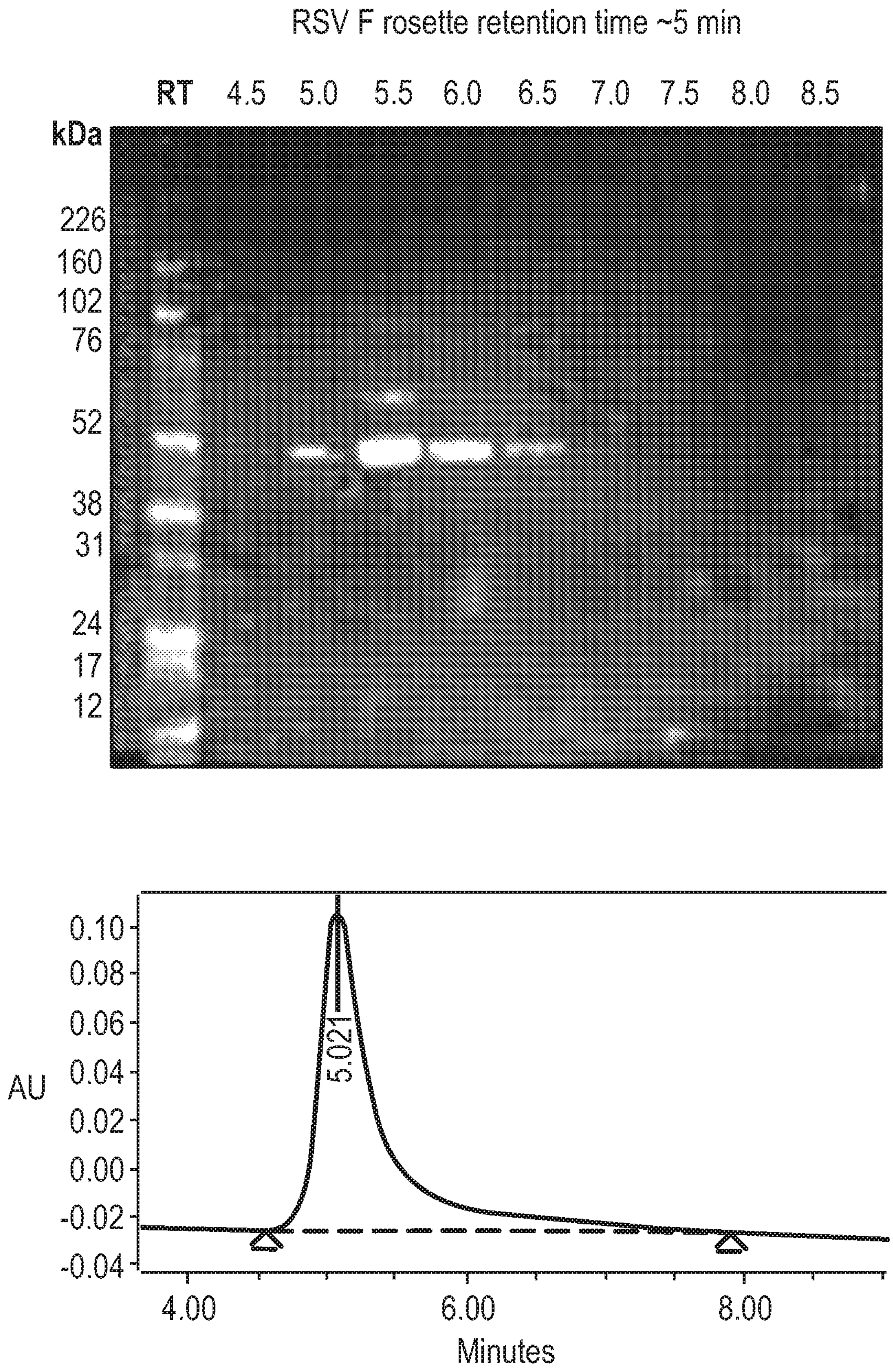
FIGS. 15 A-C show SEC analysis of RSV F intra-chain disulfide. Postfusion F rosettes and fusion peptide deleted RSV F trimers were used to develop an HPLC-SEC assay to differentiate between rosettes and trimers.
Figure 15B:
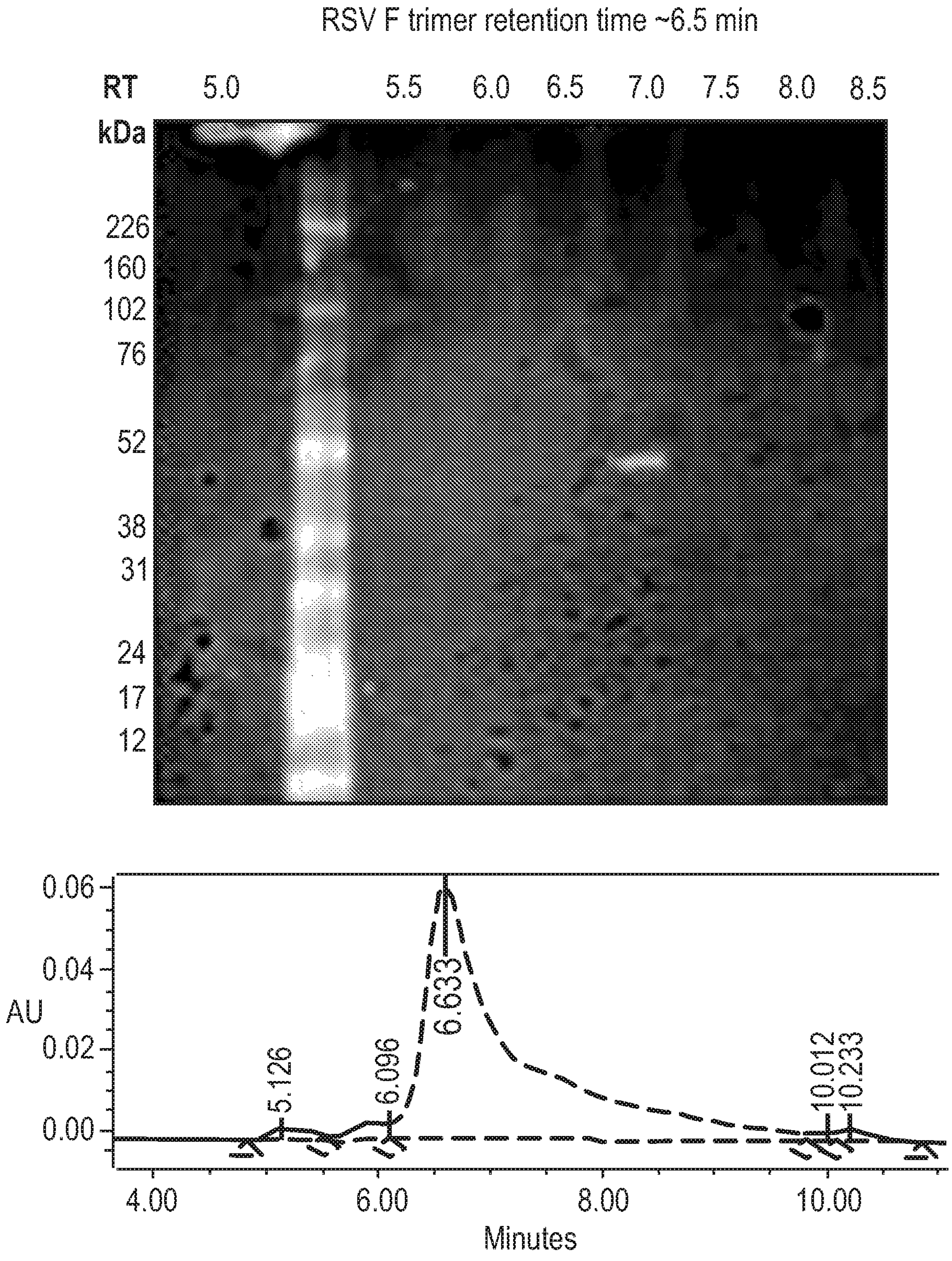
Figure 15C:
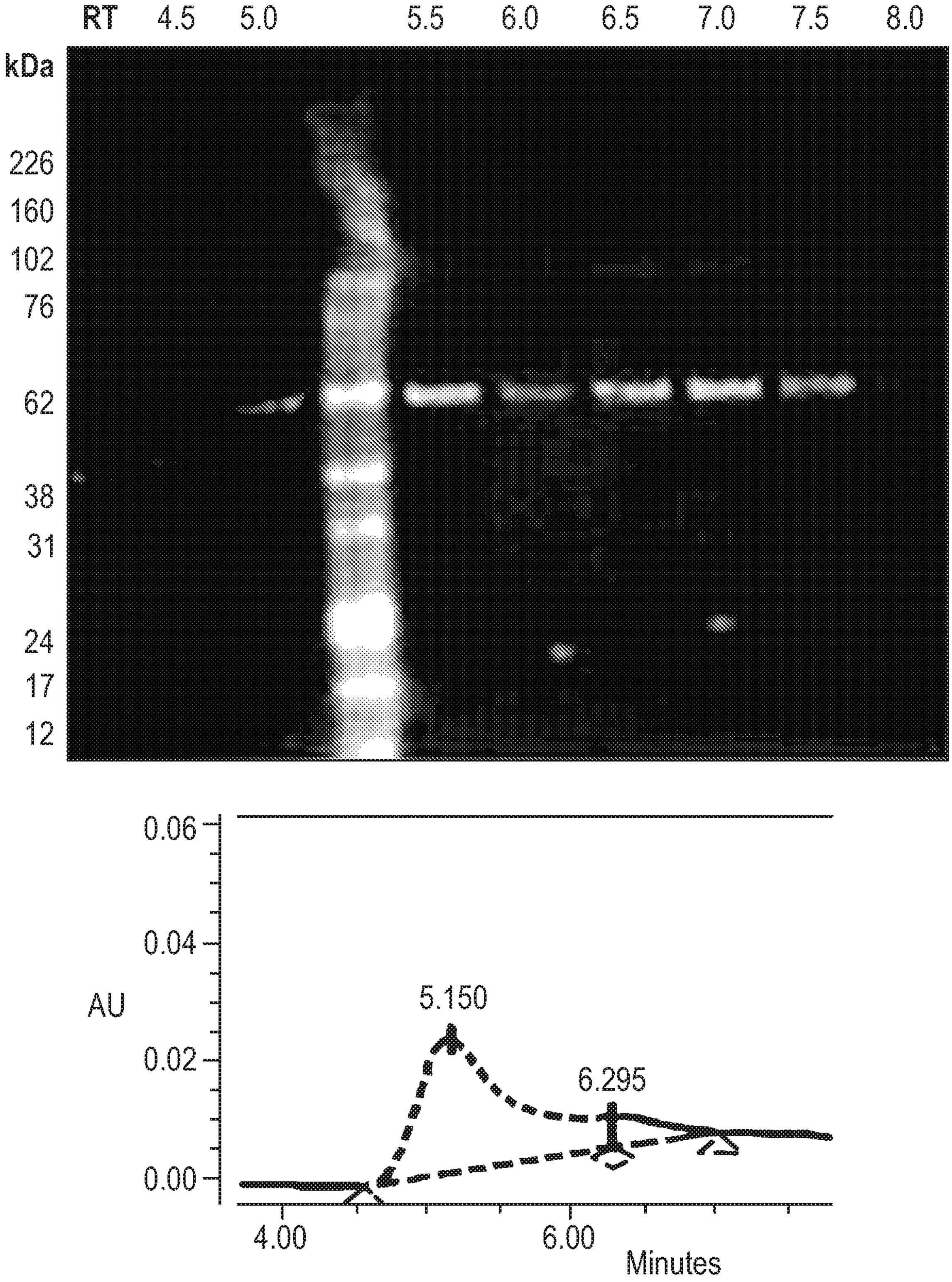

The RSV F model, based on the RSV F post-fusion structure and PIV5 pre-fusion structure, was used to engineer cysteine mutations intended to form disulfide bonds that stabilize RSV F in the pre-fusion conformation (FIG. 11). The intrachain disulfide bond constructs were expressed, and were secreted from the cell into the media and then cleaved from F0 to F1/F2 to various degrees (FIG. 14). RSV F T58C/V164C (expressed in mammalian cells) was found to express as a cleaved species which is secreted into the media. The material was purified by chelating purification and evaluated by the rosette/trimer HPLC-SEC assay using the Bio-Sil 250 SEC column with 2×PBS as mobile phase (FIG. 15). As this is a cleaved F containing a fusion peptide, it was expected that would be in the post-fusion form and would form rosettes and migrate in the void volume similar to postfusion RSV F rosettes (FIG. 15A). If the cleaved F protein harboring a fusion peptide was folded in the prefusion form, one would expect the fusion peptide to be buried in the prefusion head region preventing rosette formation. Prefusion trimers should migrate in the included volume with a retention time similar to the RSV F postfusion trimer lacking the fusion peptide (FIG. 15B). RSV F HRA Disulfide T58C V164C was run on HPLC-SEC, and the majority of material migrated in the column void volume, indicating the material was aggregating or forming rosettes of postfusion F. A smaller portion of the protein migrated in the included volume with a retention time consistent with an F trimer, suggesting some material formed the desired stabilized prefusion F.

Figure 16A:
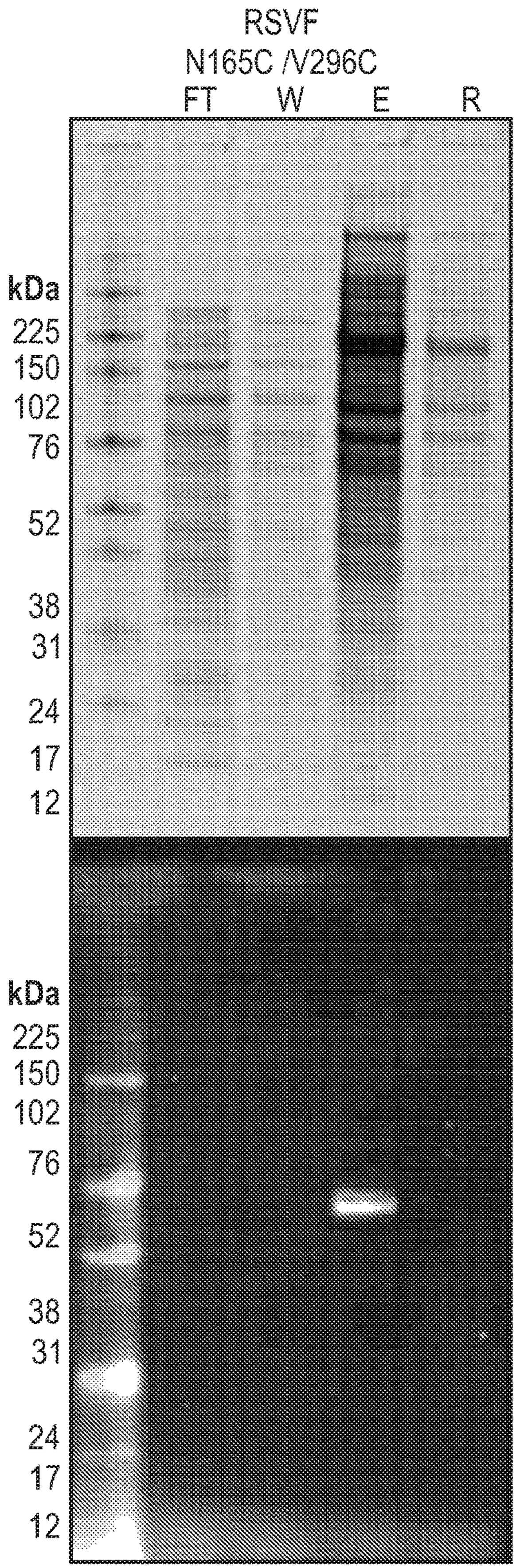
FIGS. 16 A-C show purification and analysis of RSV F protein constructs that contain engineered cysteins.
Figure 16B:
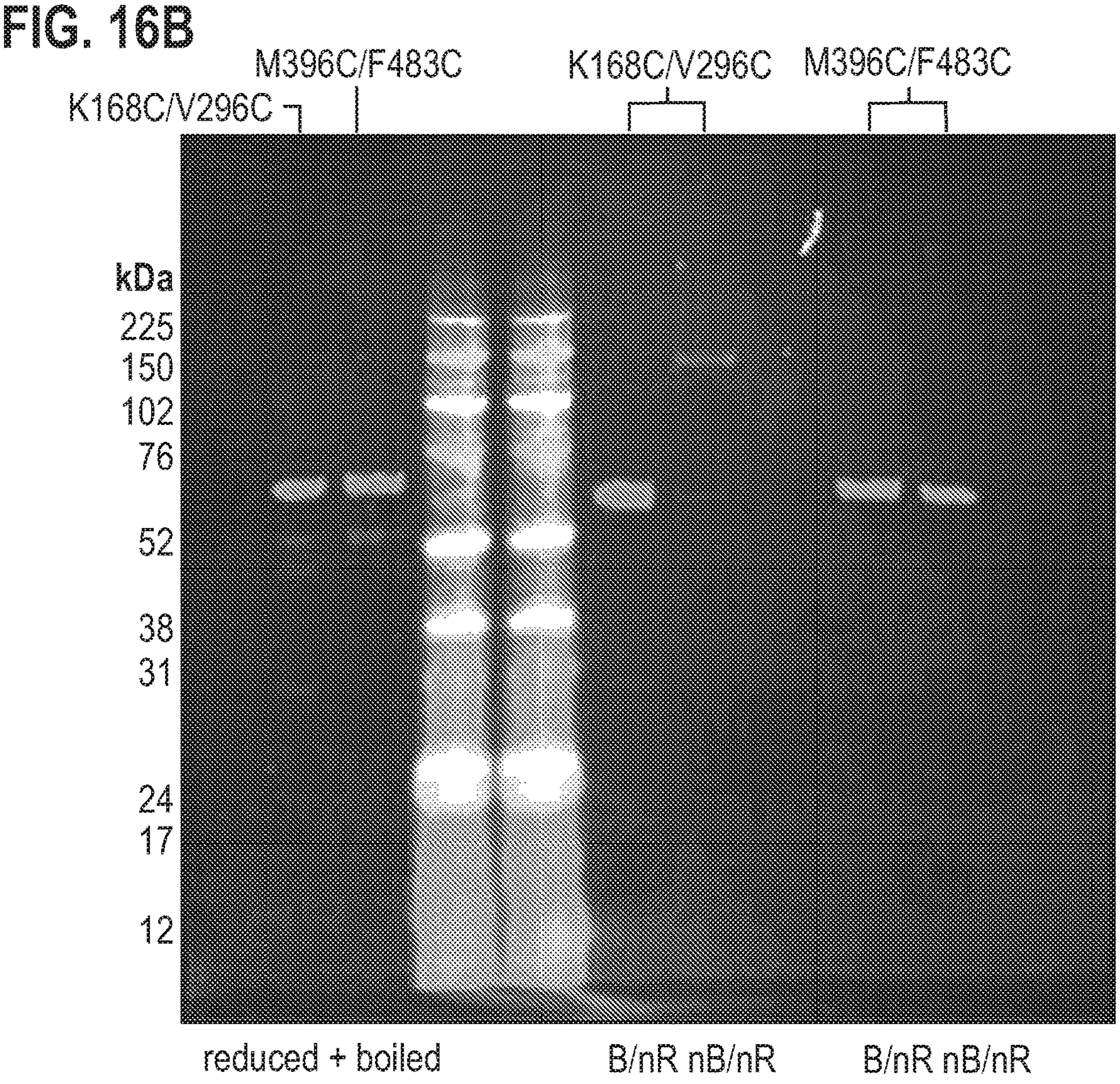
Figure 16C:
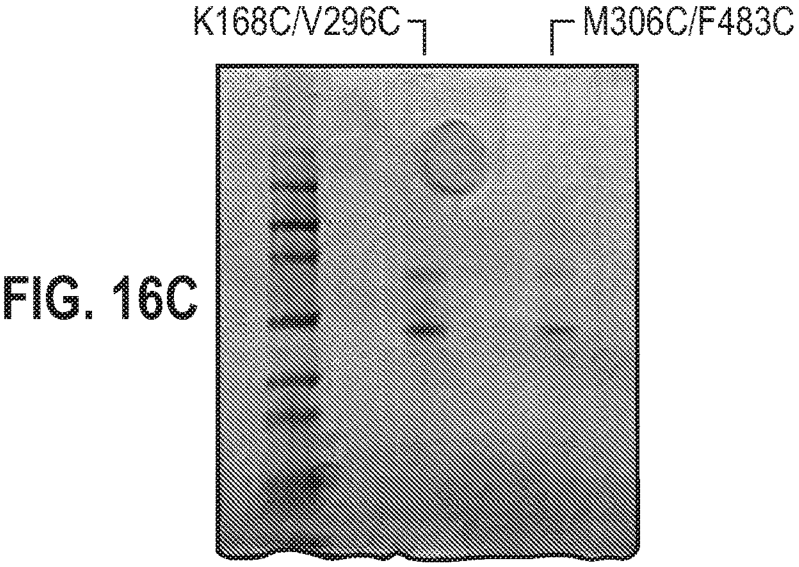
Figure 17A:
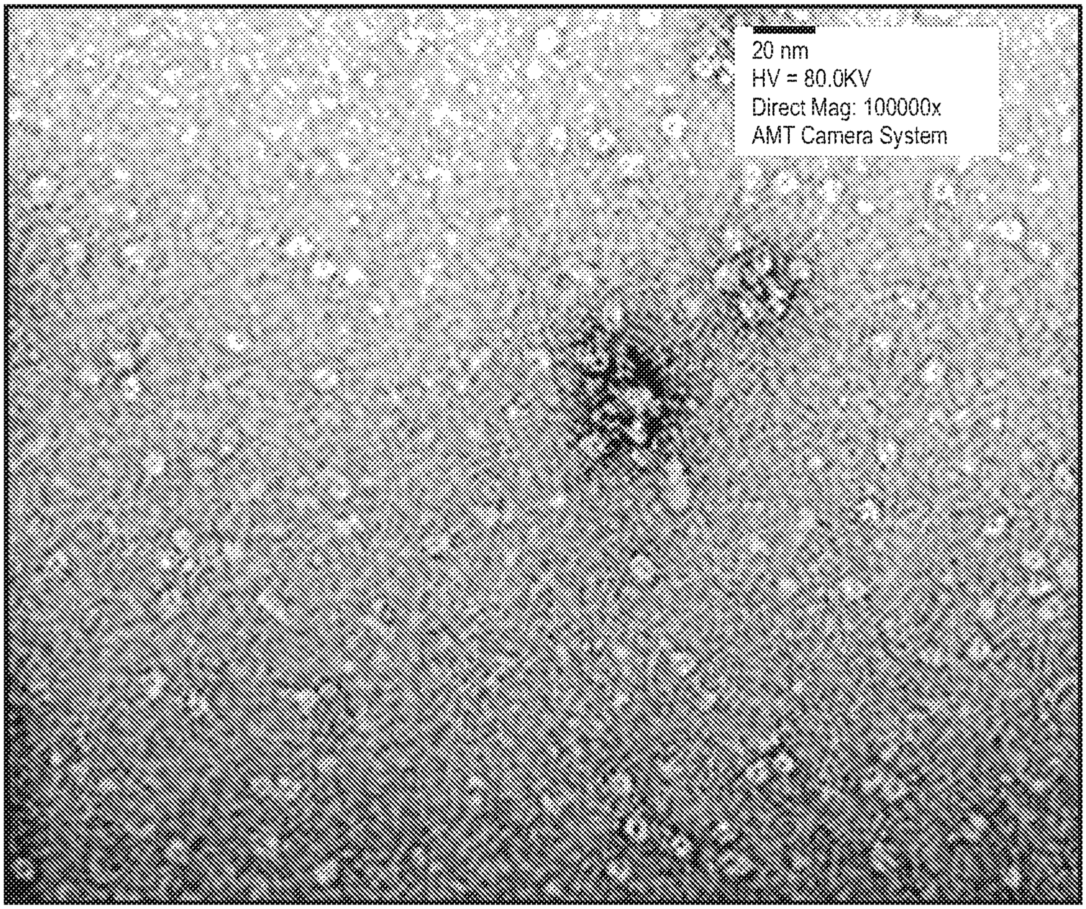
FIG. 17(A) shows electron microscopy analysis of NDV F (prefusion) with the expected spherical heads for prefusion F, with a few rosette-like aggregates.
Figure 17B:
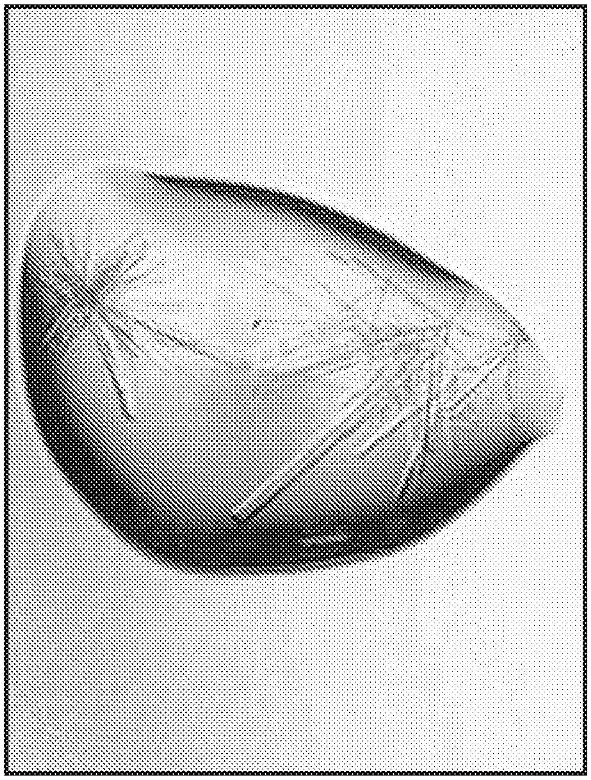
FIG. 17(B) shows NDV prefusion F forms rod-like crystals. An isolated rod was analyzed and a dataset with ~95% completion to ~3.7 angstroms was recorded.
Figure 17C:
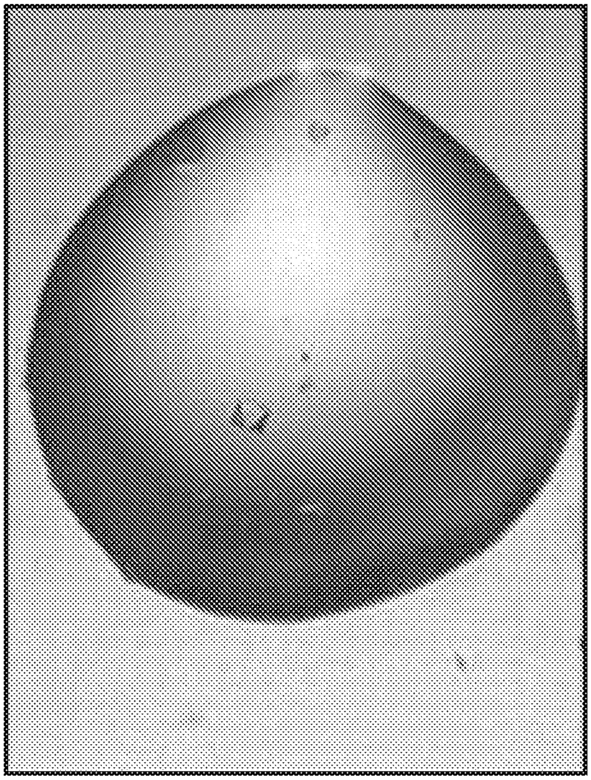
FIG. 17(C) shows NDV prefusion F forms bipiramidal crystals (50×50×50 μm size).

The disulfide constructs were subsequently cloned into baculovirus expression vectors and three constructs (HRA disulfides N165C/V296C and K168C/V296C and HRB M396C/F483C) were expressed. K168C/V296C and M396C/F483C, which were cleaved when expressed in mammalian cells, were secreted by insect cells predominantly as an uncleaved species (as shown by anti-HIS western blot). Both constructs migrated in the void fraction, which was inconsistent with previous observations that uncleaved species run as monomers. The proteins may have aggregated by virtue of incorrect disulfide formation. Gel shift analysis using anti-HIS western (FIG. 16) suggested that intra-chain disulfide bonds were not formed. The pure material taken from the void fraction of the SEC was analyzed with SDS-PAGE and coomassie staining, and each protein was found to be approximately 50% cleaved (FIG. 16). A third disulfide construct was expressed and N165C/V296C was secreted predominantly as the desired cleaved product as judged by western blot (FIG. 16A).

4. NDV F Prefusion Structure for Further Development of the RSV-NDV Chimera Subunit A strategy for rescuing the RSV HRA prefusion epitopes was developed to generate an NDV F prefusion construct and mutate select residues of the HRA to those of RSV F. Initial attempts to replace the HRA of NDV with the HRA of RSV generated a construct which was not expressed/secreted from the cell. This indicated that the protein was misfolded. Further refinement of the residues of NDV F available for mutagenisis (i.e. those located on the protein surface) was required. A new construct, NDV F stabilized with a GCN trimerization domain (uncleaved) migrated as a trimer by SEC analysis. This was expected as this construct was shown to be a pre-fusion trimer by electron microscopy (Swanson et al, 2010).

Figure 18A:
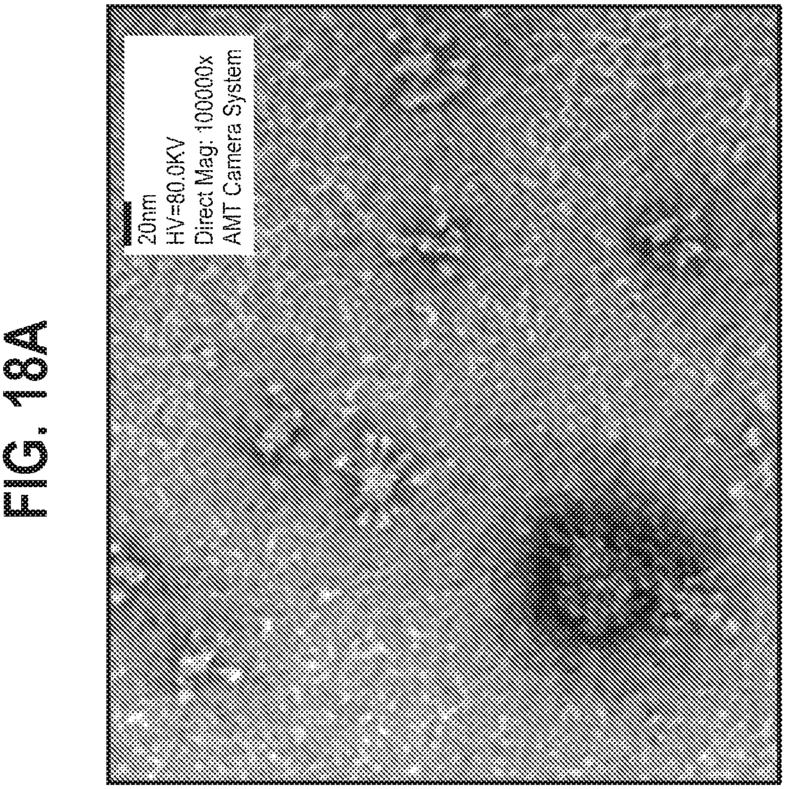
FIG. 18A shows EM analysis of RSV F Del-HRB showing that 100% formed rosettes. The protein eluted from the SEC column in the void/rosette retention peak.
Figure 18B:
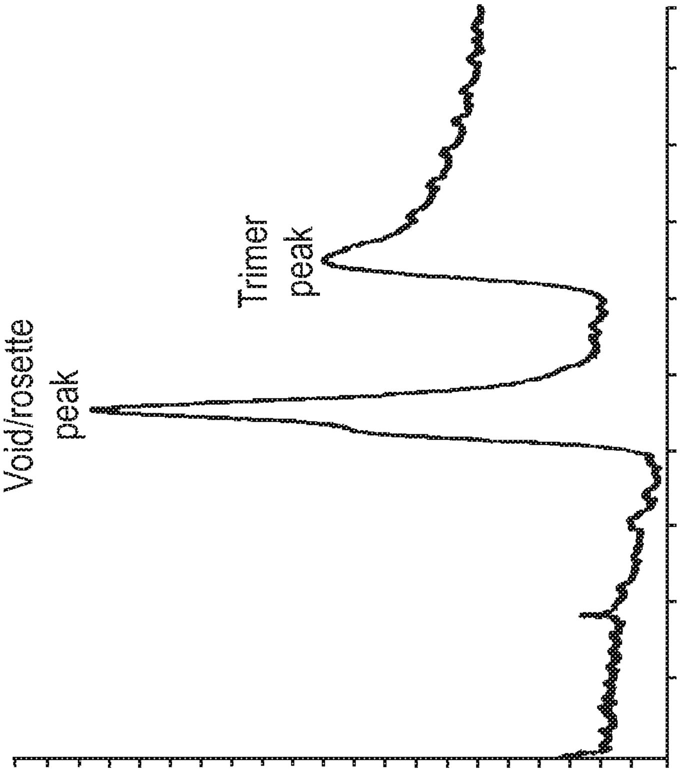
FIG. 18(B) shows analysis/purification of the Del-HRB Del-FP RSV F construct. The protein was found in both the void and trimer retention peaks.
Figure 18C:
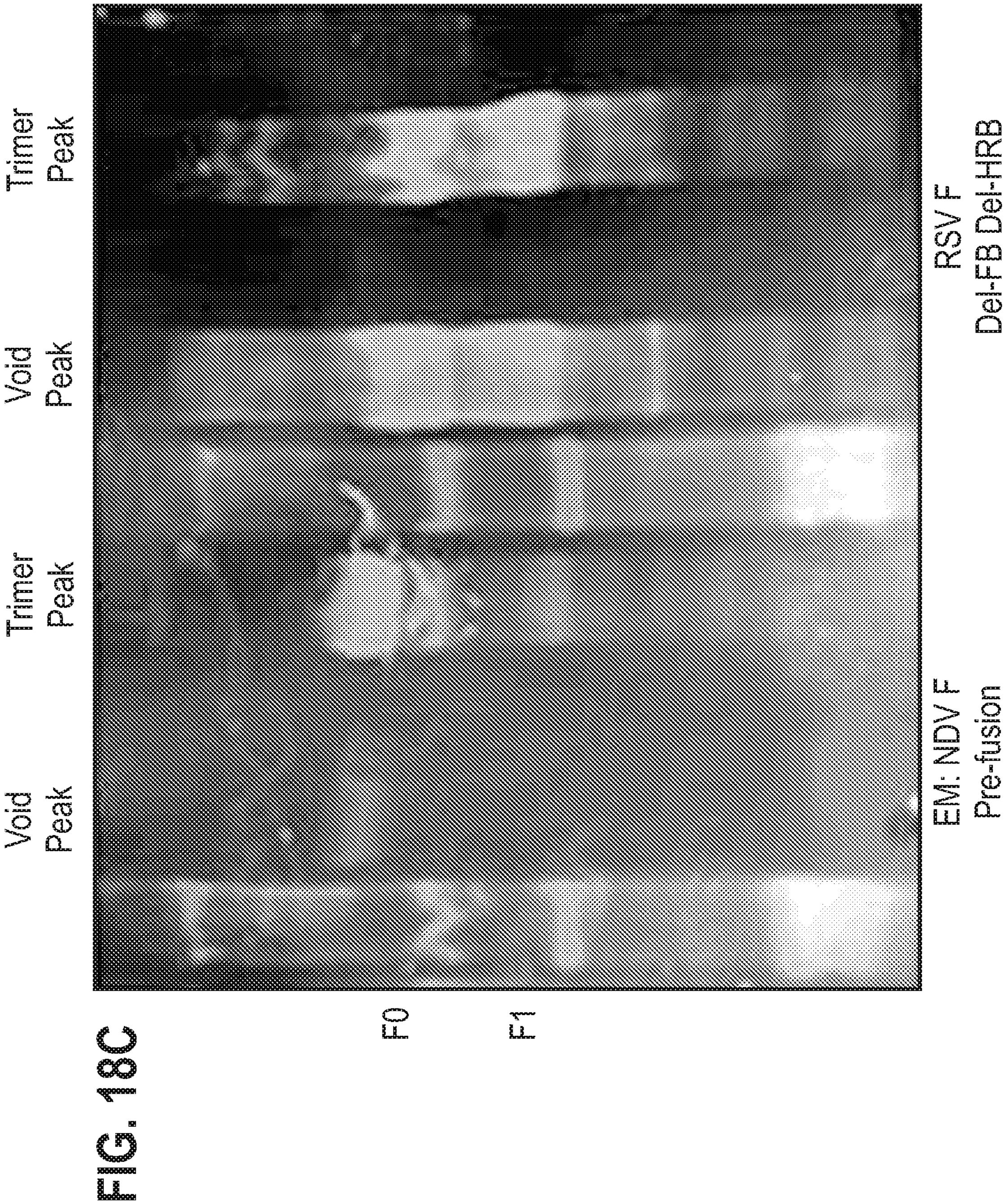
FIG. 18C shows gel-analysis, which suggests that there was partially cleaved RSV F Del-HRB Del-FP present in both the void and trimer peaks.

5. EM Analysis of RSV F with HRB and Fusion Peptide Deletion Related to NDV Pre-Fusion Construct The HRB-deleted RSV F harboring the fusion-peptide was generated, and the protein was purified. The construct migrated in the void volume of the SEC column consistent with RSV F rosettes. The construct was evaluated by EM and shown to form rosettes similar to the postfusion RSV F (FIG. 18A). An RSV F protein with both the HRB and fusion peptide deleted (Del-HRB Del-FP) was generated, expressed and purified. RSV F with the HRB and fusion peptide deleted ran partially as a trimer on SEC (FIG. 18B). Gel analysis showed that RSV F del-HRB and Del-FP migrated both in the aggregation/rosette peak and trimer peak (FIG. 18C). For comparison, the uncleaved NDV pre-fusion construct had very little material in the void fraction (FIG. 18C). The RSV F Del-HRB Del-FP was collected from the trimer volume and evaluated by EM.

Figure 18D:
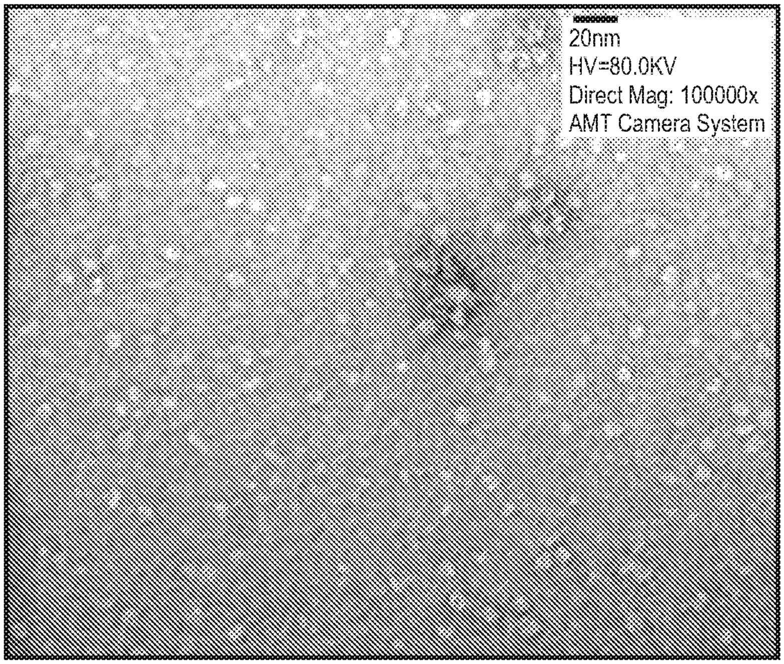
FIG. 18D shows EM of NDV F (prefusion), which shows the expected spherical heads for pre-fusion F with a few rosette-like aggregates.
Figure 18E:
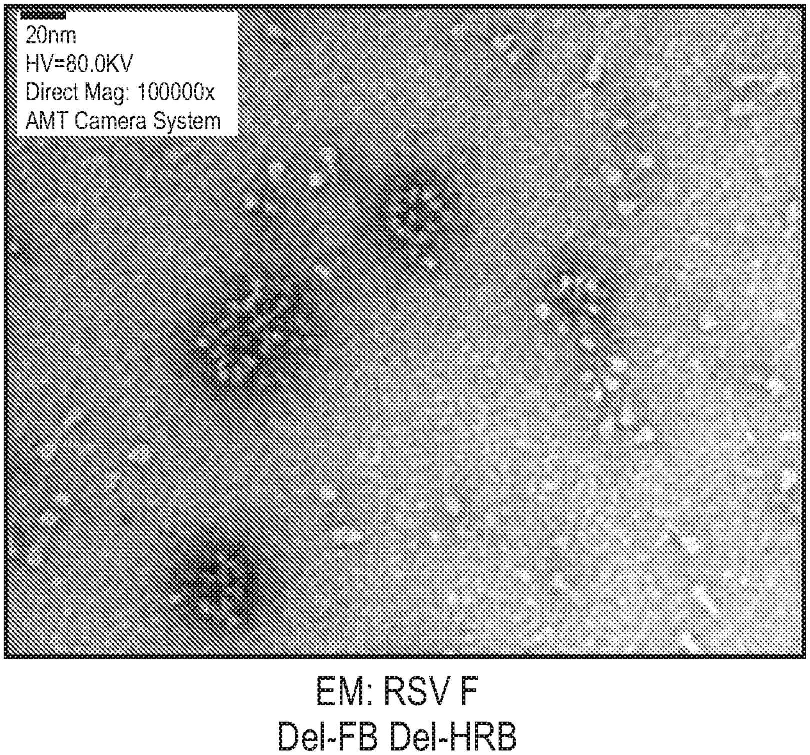
FIG. 18E shows that RSV F Del-HRB from the SEC trimer peak contains a heterogeneous mix of rosette-like structures, post-fusion crutches and pre-fusion head-like spherical species.

Electron micrographs of the NDV pre-fusion construct showed predominately the spherical heads expected for pre-fusion F (FIG. 18D). A portion of the material seemed to be associated in rosette-like aggregates, which should not be permitted as the construct is uncleaved and pre-fusion. This amount of association may be due to aggregation by the HIS-tag, and may explain why the RSV Del-HRB Del-FP contained some aggregate/rosette even when the fusion peptide was not present. EM analysis of RSV F Del-HRB Del-FP showed that the material was heterogeneous (FIG. 18E). RSV F Del-HRB Del-FP formed rosette-like structures similar to NDV F, as well as post-fusion like "crutches" and pre-fusion like "spheres".

```
R057 delHRB delFP trunc 6H (fusion peptide
deleted)
                                     (SEQ ID NO: 10)
MELLILKANAITTILTAVTFCFASGQNITEEFYQSTCSAVSKGYLSALRT

GWYTSVITIELSNIKENKCNGTDAKVKLIKQELDKYKNAVTELQLLMQ

STPATNNRARRELPRFMNYTLNNAKKTNVTLSKKRKRRSAIASGVAV

SKVLHLEGEVNKIKSALLSTNKAVVSLSNGVSVLTSKVLDLKNYIDKQ

LLPIVNKQSCSISNIETVIEFQQKNNRLLEITREFSVNAGVTTPVSTYML

TNSELLSLINDMPITNDQKKLMSNNVQIVRQQSYSIMSIIKEEVLAYVV

QLPLYGVIDTPCWKLHTSPLCTTNTKEGSNICLTRTDRGWYCDNAGSV

SFFPQAETCKVQSNRVFCDTMNSLTLPSEVNLCNVDIFNPKYDCKIMT

SKTDVSSSVITSLGAIVSCYGKTKCTASNKNRGIIKTFSNGCDYVSNKG

VDTVSVGNTLYYVNKQEGKSLYVKGEPIINFYDPLVFPSGGSAGSGHH

HHHH**

R105 delHRB delFP + linker trunk 6H (fusion
peptide and linker deleted)
                                     (SEQ ID NO: 38)
MELLILKANAITTILTAVTFCFASGQNITEEFYQSTCSAVSKGYLSALRT

GWYTSVITIELSNIKENKCNGTDAKVKLIKQELDKYKNAVTELQLLMQ

STPATNNRARRELPRFMNYTLNNAKKTNVTLSKKRKRRSAIASGVAV

SKVLHLEGEVNKIKSALLSTNKAVVSLSNGVSVLTSKVLDLKNYIDKQ

LLPIVNKQSCSISNIETVIEFQQKNNRLLEITREFSVNAGVTTPVSTYML

TNSELLSLINDMPITNDQKKLMSNNVQIVRQQSYSIMSIIKEEVLAYVV

QLPLYGVIDTPCWKLHTSPLCTTNTKEGSNICLTRTDRGWYCDNAGSV

SFFPQAETCKVQSNRVFCDTMNSLTLPSEVNLCNVDIFNPKYDCKIMT

SKTDVSSSVITSLGAIVSCYGKTKCTASNKNRGIIKTFSNGCDYVSNKG

VDTVSVGNTLYYVNKQEGGGSAGSGHHHHHH**
```

6. Design of RSV F Non-Native HRB Constructs

Figure 19:
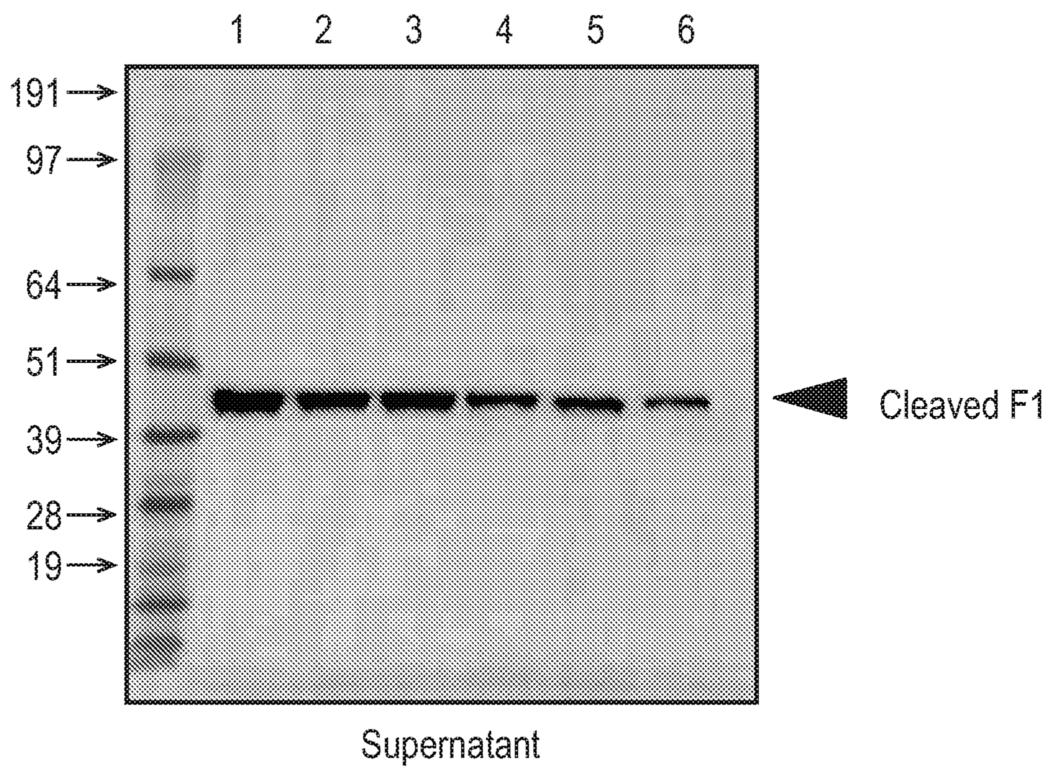
FIG. 19 shows SDS-PAGE analysis of chimeric RSV F/NDV and RSV F/PIV5 F protein constructs. The supernatant from cells transfected with one of the six constructs (1: RSV-F NDV HRB del fus trunc; 2: RSV-F NDV HRB trunc; 3: RSV-F NDV HRB2 del fus trunc; 4: RSV-F NDV HRB2 trunc; 5: RSV-F PIV5 HRB del fus trunc; 6: RSV-F PIV5 HRB trunc) was analyzed by SDS-PAGE. The constructs were engineered with or without (del fus) fusion peptide. The proteins either had an NDV HRB, an NDV HRB with an additional glycine residue as a linker (HRB2) or PIV5 HRB as indicated. For each construct, a cleaved F1 protein was observed consistent with a processed F protein. One liter expressions of each protein was performed.

A stable RSV prefusion F was generated by replacing the HRB region with either the HRB region of NDV (with or without an additional glycine linker: HRB2) or PIV5. Mammalian expression of the non-native HRB constructs showed that each of the constructs were expressed and secreted well (FIG. 19). Additionally, the band observed migrated consistent with the cleaved F1 species, suggesting that the proteins were properly processed. The constructs existed with or without fusion peptide (as indicated in FIG. 19).

ADDITIONAL REFERENCES

The following references are hereby incorporated by reference for all that they teach.

1. *Fields Virology*. 4th edition, 2001.
2. Snell et al. (1997) *Virus Genes* 14:63-72.
3. Bembridge et al. (1999) *J Virol* 73: 10086-10094.
4. Li et al. (1998) *J Exp Med* 188:681-688
5. U.S. Pat. No. 6,060,308.
6. Yin et al. (2006) *Nature* 439:38-45.
7. Kim et al. (2007) *J Med Virol* 79: 820-828.
8. Yin et al. (2005) *Proc Nat Acad Sci USA*. 102(26):9288-93.
9. Chen et al. (2004) *J Virol* 78:4508-16.
10. Yang et al. (2002) *J Virol* 76:4634-42.
11. Harbury et al. (1993) *Science* 262:1401-1407.
12. Stevens et al. (2004) *Science* 303:1866-70.
13. Burkhard et al. (2001) *Trends Cell Biol* 11:82-88.
14. Section 5.5.2 of Proteins by Creighton (ISBN 0-7167-2317-4).
15. Yu (2002) *Adv Drug Deliv Rev* 54:1113-1129.
16. Muller et al. (2000)*Methods Enzymol* 328:261-282.
17. Beck & Brodsky (1998) *J Struct Biol* 122:17-29.
18. Lupas (1996) *Trends Biochem Sci* 21:375-382.
19. Adamson et al. (1993) *Curr Opin Biotechnol* 4:428-347.
20. Kammerer (1997) *Matrix Biol* 15:555-568.
21. Chao et al. (1998) *J Chromatog B Biomed Sci Appl* 715:307-329.
22. Arndt et al. (2002) *Structure* 10:1235-1248.
23. Liu & Lu (2002) *J Biol Chem* 277:48708-48713.
24. WO2006/011060.
25. Section 5.5.3 of Proteins by Creighton (ISBN 0-7167-2317-4).
26. Zhang & Chen (1999) *J Biol Chem* 274:22409-22413.
27. Slovic et al. (2003) *Protein Sci* 12:337-348
28. Gardner & Dutch (2007) *J Virol* 8 1:8303-14.
29. Gennaro (2000) *Remington: The Science and Practice of Pharmacy*. 20th edition, ISBN: 0683306472.
30. Nony et al. (2001) *Vaccine* 27:3645-51.
31. Greenbaum et al. (2004) *Vaccine* 22:2566-77.
32. Zurbriggen et al. (2003) *Expert Rev Vaccines* 2:295-304.
33. Piascik (2003) *J Am Pharm Assoc* (*Wash DC*). 43:728-30.
34. Mann et al. (2004) *Vaccine* 22:2425-9.
35. Halperin et al. (1979) *Am J Public Health* 69:1247-50.
36. Herbert et al. (1979) *J Infect Dis* 140:234-8.
37. Chen et al. (2003) *Vaccine* 21:2830-6.
38. U.S. Pat. No. 6,355,271.
39. WO00/23105.
40. U.S. Pat. No. 5,057,540.
41. WO96/33739.
42. EP-A-0109942.
43. WO96/11711.
44. WO00/07621.
45. Barr et al. (1998) *Advanced Drug Delivery Reviews* 32:247-271.
46. Sjolanderet et al. (1998) *Advanced Drug Delivery Reviews* 32:321-338.
47. Pizza et al. (2000) *Int J Med Microbiol* 290:455-461.
48. WO95/17211.
49. WO98/42375.
50. Singh et al (2001) *J Cont Release* 70:267-276.
51. WO99/27960.
52. U.S. Pat. No. 6,090,406.
53. U.S. Pat. No. 5,916,588.
54. EP-A-0626169.
55. WO99/52549.
56. WO01/21207.
57. WO01/21152.
58. Dyakonova et al. (2004) *Int Immunopharmacol* 4(13): 1615-23.
59. FR-2859633.
60. Signorelli & Hadden (2003) *Int Immunopharmacol* 3(8):1177-86.
61. WO2004/064715.
62. De Libero et al, (2005) *Nature Reviews Immunology* 5:485-496
63. U.S. Pat. No. 5,936,076.
64. Old et al., *J Clin Investig*, 113:1631-1640
65. US2005/0192248
66. Yang et al. (2004) *Angew Chem Int Ed* 43:3 818-3 822
67. WO2005/102049.
68. Goffet et al (2004) *Am Chem Soc* 126:13602-13603
69. WO03/105769.
70. Cooper (1995) *Pharm Biotechnol* 6:559-80.
71. WO90/14837.
72. Podda & Del Giudice (2003) *Expert Rev Vaccines* 2:197-203.
73. Podda (2001) *Vaccine* 19: 2673-2680.
74. *Vaccine Design: The Subunit and Adjuvant Approach* (eds. Powell & Newman) Plenum Press 1995 (ISBN 0-306-44867-X).
75. *Vaccine Adjuvants: Preparation Methods and Research Protocols* (Volume 42 of *Methods in Molecular Medicine series*). ISBN: 1-59259-083-7. Ed. O'Hagan.
76. Allison & Byars (1992) *Res Immunol* 143:519-25.
77. Hariharan et al. (1995) *Cancer Res* 55:3486-9.
78. WO95/1 1700.
79. U.S. Pat. No. 6,080,725.
80. WO2005/0971 81.
81. Tassignon et al. (2005) *J Immunol Meth* 305:188-98.
82. Myers et al. (1990) pages 145-156 of *Cellular and molecular aspects of endotoxin reactions*.
83. Ulrich (2000) Chapter 16 (pages 273-282) of reference 75.
84. Johnson et al. (1999) *J Med Chem* 42:4640-9.
85. Baldrick et al. (2002) *Regulatory Toxicol Pharmacol* 35:398-413.
86. U.S. Pat. No. 4,680,338.
87. U.S. Pat. No. 4,988,815.
88. WO92/15582.
89. Stanley (2002) *Clin Exp Dermatol* 27:57 1-577.
90. Wu et al. (2004) *Antiviral Res*. 64(2):79-83.
91. Vasilakos et al. (2000) *Cell Immunol*. 204(1):64-74.
92. U.S. Pat. Nos. 4,689,338, 4,929,624, 5,238,944, 5,266,575, 5,268,376, 5,346,905, 5,352,784, 5,389,640, 5,395,937, 5,482,936, 5,494,916, 5,525,612, 6,083,505, 6,440,992, 6,627,640, 6,664,264, 6,664,265, 6,667,312, 6,677,347, 6,677,348, 6,677,349, 6,683,088, 6,703,402, 6,743,920, 6,800,624, 6,809,203, 6,888,000, and 6,924,293.
93. Jones (2003) *Curr Opin Investig Drugs* 4:214-218.
94. WO2004/060308.
95. WO2004/064759.
96. U.S. Pat. No. 6,924,271.
97. US2005/0070556.
98. U.S. Pat. No. 5,658,731.
99. U.S. Pat. No. 5,011,828.
100. WO2004/87 153.

101. U.S. Pat. No. 6,605,617.
102. WO02/18383.
103. WO2004/018455.
104. WO03/082272.
105. WO2006/002422.
106. Johnson et al. (1999) *Bioorg Med Chem Lett* 9:2273-2278.
107. Evans et al. (2003) *Expert Rev Vaccines* 2:219-229.
108. Andrianov et al. (1998) *Biomaterials* 19:109-115.
109. Payne et al. (1998) *Adv Drug Delivery Review* 31:185-196.
110. Thompson et al. (2003) *Methods in Molecular Medicine* 94:255-266.
111. Kandimalla et al. (2003) *Nucleic Acids Research* 31:2393-2400.
112. WO02/26757.
113. WO99/62923.
114. Krieg (2003) *Nature Medicine* 9:831-835.
115. McCluskie et al. (2002) *FEMS Immunology and Medical Microbiology* 32:179-185.
116. WO98/40100.
117. U.S. Pat. No. 6,207,646.
118. U.S. Pat. No. 6,239,116.
119. U.S. Pat. No. 6,429,199.
120. Kandimalla et al. (2003) *Biochemical Society Transactions* 31 (part 3): 654-658.
121. Blackwell et al. (2003) *J Immunol* 170:4061-4068.
122. Krieg (2002) *Trends Immunol* 23:64-65.
123. WO01/95935.
124. Kandimalla et al. (2003) *BBRC* 306:948-953.
125. Bhagat et al. (2003) *BBRC* 300:853-861.
126. WO03/035836.
127. WO01/22972.
128. Thompson et al. (2005) *J Leukoc Biol* 78: 'The low-toxicity versions of LPS, MPL® adjuvant and RC529, are efficient adjuvants for CD4+ T cells'.
129. UK patent application GB-A-22202 11.
130. WO94/21292.
131. WO94/00153.
132. WO95/17210.
133. WO96/26741.
134. WO93/19780.
135. WO03/011223.
136. Meraldi et al. (2003) *Vaccine* 21:2485-249 1.
137. Pajak et al. (2003) *Vaccine* 21:836-842.
138. U.S. Pat. No. 6,586,409.
139. Wong et al. (2003) *J Clin Pharmacol* 43(7):735-42.
140. US2005/0215517.
141. McLellan J S, et al. (2010) Structural basis of respiratory syncytial virus neutralization by motavizumab. *Nat Struct Mol Biol* 17(2):248-250.
142. Ruiz-Arguello M B, et al. (2004) Thermostability of the human respiratory syncytial virus fusion protein before and after activation: implications for the membrane-fusion mechanism. *J Gen Virol* 85(Pt 12):3677-3687.
143. Calder L J, et al. (2000) Electron microscopy of the human respiratory syncytial virus fusion protein and complexes that it forms with monoclonal antibodies. *Virology* 271(1):122-131.
144. Connolly S A, Leser G P, Yin H S, Jardetzky T S, & Lamb R A (2006) Refolding of a paramyxovirus F protein from prefusion to postfusion conformations observed by liposome binding and electron microscopy, *Proc Natl Acad Sci USA* 103(47):17903-17908.
145. Yin H S, Wen X L, Paterson R G, Lamb R A, & Jardetzky T S (2006) Structure of the parainfluenza virus 5 F protein in its metastable, prefusion conformation, *Nature* 439(7072):38-44.
146. Swanson K, et al. (2010) Structure of the Newcastle disease virus F protein in the post-fusion conformation, *Virology* 402(2):372-379.
147. Yin H S, Wen X, Paterson R G, Lamb R A, & Jardetzky T S (2006) Structure of the parainfluenza virus 5 F protein in its metastable, prefusion conformation, *Nature* 439 (7072):38-44.
148. McLellan J S, et al. (2010) Structure of a Major Antigenic Site on the Respiratory Syncytial Virus Fusion Glycoprotein in Complex with Neutralizing Antibody 101F. *J Virol* 84:12236-12244.
149. Arbiza J, et al. (1992) Characterization of two antigenic sites recognized by neutralizing monoclonal antibodies directed against the fusion glycoprotein of human respiratory syncytial virus. *J Gen Virol* 73:2225-2234.
150. Crowe J E, et al. (1998) Monoclonal antibody-resistant mutants selected with a respiratory syncytial virus-neutralizing human antibody fab fragment (Fab 19) define a unique epitope on the fusion (F) glycoprotein. *Virology* 252:373-375.
151. Lopez J A, Penas C, Garcia-Barreno B, Melero J A, & Portela A (1990) Location of a highly conserved neutralizing epitope in the F glycoprotein of human respiratory syncytial virus. *J Virol* 64:927-930.
152. Zhao X, Chen F P, & Sullender W M (2004) Respiratory syncytial virus escape mutant derived in vitro resists palivizumab prophylaxis in cotton rats. *Virology* 318:608-612.
153. Liu C, et al. (2007) Relationship between the loss of neutralizing antibody binding and fusion activity of the F protein of human respiratory syncytial virus. *Virol J* 4:71.
154. Lopez J A, et al. (1998) Antigenic structure of human respiratory syncytial virus fusion glycoprotein. *J Virol* 72:6922-6928.
155. Wu S J, et al. (2007) Characterization of the epitope for anti-human respiratory syncytial virus F protein monoclonal antibody 101F using synthetic peptides and genetic approaches. *J Gen Virol* 88:2719-2723.
156. Beeler J A & van Wyke Coelingh K (1989) Neutralization epitopes of the F glycoprotein of respiratory syncytial virus: effect of mutation upon fusion function. *J Virol* 63:2941-2950.

The entire teachings of all documents cited herein are hereby incorporated herein by reference.

Appendix (APPENDIX discloses SEQ ID NOS 29-32, 29-32 and 29-32, respectively, in order of appearance)

APPENDIX (APPENDIX discloses SEQ ID NOS 29-32, 29-32 and 29-32, respectively, in order of appearance)

```
HEADER   —                    XX-XXX-9- xxxx
COMPND   —
SSBOND   1 CYS G 69 CYS G 212
```

APPENDIX-continued (APPENDIX discloses SEQ ID NOS 29-32, 29-32 and 29-32, respectively, in order of appearance)

| | | | |
|---|---|---|---|
| SSBOND | 2 CYS G 313 CYS G 343 | | |
| SSBOND | 3 CYS G 322 CYS G 333 | | |
| SSBOND | 4 CYS G 358 CYS G 367 | | |
| SSBOND | 5 CYS G 382 CYS G 393 | | |
| SSBOND | 6 CYS G 416 CYS G 422 | | |
| LINKR | C1 NAG J1535 | ND2 ASN G 70 | NAG-ASN |
| LINKR | C1 NAG J1545 | ND2 ASN G 500 | NAG-ASN |
| LINKR | C1 NAG J1525 | ND2 ASN G 27 | NAG-ASN |
| SSBOND | 7 CYS H 69 CYS H 212 | | |
| SSBOND | 8 CYS H 313 CYS H 343 | | |
| SSBOND | 9 CYS H 322 CYS H 333 | | |
| SSBOND | 10 CYS H 358 CYS H 367 | | |
| SSBOND | 11 CYS H 382 CYS H 393 | | |
| SSBOND | 12 CYS H 416 CYS H 422 | | |
| LINKR | C1 NAG K1535 | ND2 ASN H 70 | NAG-ASN |
| LINKR | OD1 ASN H 500 | C7 NAG K1545 | ASN-NAG |
| LINKR | C1 NAG K1545 | ND2 ASN H 500 | NAG-ASN |
| LINKR | OD1 ASN H 27 | O7 NAG K1525 | ASN-NAG1 |
| LINKR | C1 NAG K1525 | ND2 ASN H 27 | NAG-ASN |
| SSBOND | 13 CYS I 69 CYS I 212 | | |
| SSBOND | 14 CYS I 313 CYS I 343 | | |
| SSBOND | 15 CYS I 322 CYS I 333 | | |
| SSBOND | 16 CYS I 358 CYS I 367 | | |
| SSBOND | 17 CYS I 382 CYS I 393 | | |
| SSBOND | 18 CYS I 416 CYS I 422 | | |
| LINKR | C1 NAG L1535 | ND2 ASN I 70 | NAG-ASN |
| LINKR | C1 NAG L1545 | ND2 ASN I 500 | NAG-ASN |
| LINKR | C1 NAG L1525 | ND2 ASN I 27 | NAG-ASN |
| LINKR | GLN G 98 | PHE G 137 | gap |
| LINKR | ASN G 325 | SER G 330 | gap |
| LINKR | LYS G 465 | GLU G 472 | gap |
| LINKR | NAG J1535 | NAG J1536 | BETA1-4 |
| LINKR | NAG J1545 | NAG J1546 | BETA1-4 |
| LINKR | NAG J1525 | NAG J1526 | BETA1-4 |
| LINKR | PRO G 304 | TYR G 306 | gap |
| LINKR | THR G 50 | ILE G 309 | gap |
| LINKR | GLN H 98 | PHE H 137 | gap |
| LINKR | ASN H 325 | SER H 330 | gap |
| LINKR | LYS H 465 | GLU H 472 | gap |
| LINKR | PRO H 304 | TYR H 306 | gap |
| LINKR | THR H 50 | ILE H 309 | gap |
| LINKR | GLN I 98 | PHE I 137 | gap |
| LINKR | ASN I 325 | SER I 330 | gap |
| LINKR | LYS I 465 | GLU I 472 | gap |
| LINKR | PRO I 304 | TYR I 306 | gap |
| LINKR | THR I 50 | ILE I 309 | gap |
| LINKR | NAG K1535 | NAG K1536 | BETA1-4 |
| LINKR | NAG L1535 | NAG L1536 | BETA1-4 |
| LINKR | NAG K1545 | NAG K1546 | BETA1-4 |
| LINKR | NAG L1545 | NAG L1546 | BETA1-4 |
| LINKR | NAG K1525 | NAG K1526 | BETA1-4 |
| LINKR | NAG L1525 | NAG L1526 | BETA1-4 |
| MODRES | NAG J 1535 NAG-b-D | | RENAME |
| MODRES | NAG J 1536 NAG-b-D | | RENAME |
| MODRES | NAG J 1545 NAG-b-D | | RENAME |
| MODRES | NAG J 1546 NAG-b-D | | RENAME |
| MODRES | NAG J 1525 NAG-b-D | | RENAME |
| MODRES | NAG J 1526 NAG-b-D | | RENAME |
| MODRES | NAG K 1535 NAG-b-D | | RENAME |
| MODRES | NAG K 1536 NAG-b-D | | RENAME |
| MODRES | NAG K 1545 NAG-b-D | | RENAME |
| MODRES | NAG K 1546 NAG-b-D | | RENAME |
| MODRES | NAG K 1525 NAG-b-D | | RENAME |
| MODRES | NAG K 1526 NAG-b-D | | RENAME |
| MODRES | NAG L 1535 NAG-b-D | | RENAME |
| MODRES | NAG L 1536 NAG-b-D | | RENAME |
| MODRES | NAG L 1545 NAG-b-D | | RENAME |
| MODRES | NAG L 1546 NAG-b-D | | RENAME |
| MODRES | NAG L 1525 NAG-b-D | | RENAME |
| MODRES | NAG L 1526 NAG-b-D | | RENAME |
| CRYST1 | 160.206 259.864 154.012 90.00 90.00 90.00 C 2 2 21 | | |
| SCALE1 | 0.006242 0.000000 0.000000 0.00000 | | |
| SCALE2 | 0.000000 0.003848 0.000000 0.00000 | | |
| SCALE3 | 0.000000 0.000000 0.006493 0.00000 | | |
| ATOM | 1 N GLN G 26 | 24.299 30.940 −8.771 1.00 23.62 | N |
| ATOM | 2 CA GLN G 26 | 22.913 30.470 −9.055 1.00 23.82 | C |
| ATOM | 3 CB GLN G 26 | 22.260 29.923 −7.783 1.00 23.94 | C |

APPENDIX-continued (APPENDIX discloses SEQ ID NOS 29-32, 29-32 and 29-32, respectively, in order of appearance)

| | | | |
|---|---|---|---|
| ATOM | 4 CG GLN G 26 | 23.103 28.894 −7.043 1.00 28.83 | C |
| ATOM | 5 CD GLN G 26 | 24.309 29.508 −6.355 1.00 36.36 | C |
| ATOM | 6 OE1 GLN G 26 | 25.367 29.671 −6.963 1.00 39.09 | O |
| ATOM | 7 NE2 GLN G 26 | 24.176 29.785 −5.063 1.00 37.86 | N |
| ATOM | 8 C GLN G 26 | 22.064 31.593 −9.645 1.00 23.09 | C |
| ATOM | 9 O GLN G 26 | 22.368 32.772 −9.466 1.00 24.21 | O |
| ATOM | 10 N ASN G 27 | 21.079 31.214 −10.452 1.00 20.98 | N |
| ATOM | 11 CA ASN G 27 | 20.182 32.172 −11.089 1.00 19.70 | C |
| ATOM | 12 CB ASN G 27 | 20.879 32.850 −12.269 1.00 20.41 | C |
| ATOM | 13 CG ASN G 27 | 19.973 33.815 −13.014 1.00 23.56 | C |
| ATOM | 14 OD1 ASN G 27 | 19.456 34.775 −12.440 1.00 24.42 | O |
| ATOM | 15 ND2 ASN G 27 | 19.784 33.561 −14.310 1.00 27.70 | N |
| ATOM | 16 C ASN G 27 | 18.931 31.465 −11.578 1.00 18.42 | C |
| ATOM | 17 O ASN G 27 | 18.705 31.356 −12.783 1.00 18.47 | O |
| ATOM | 18 N ILE G 28 | 18.240 30.807 −10.655 1.00 16.54 | N |
| ATOM | 19 CA ILE G 28 | 17.060 30.044 −11.018 1.00 14.59 | C |
| ATOM | 20 CB ILE G 28 | 16.771 28.910 −10.025 1.00 14.01 | C |
| ATOM | 21 CG1 ILE G 28 | 17.176 29.324 −8.610 1.00 15.60 | C |
| ATOM | 22 CD1 ILE G 28 | 16.159 30.199 −7.917 1.00 16.26 | C |
| ATOM | 23 CG2 ILE G 28 | 17.501 27.642 −10.441 1.00 12.57 | C |
| ATOM | 24 C ILE G 28 | 15.843 30.942 −11.157 1.00 13.86 | C |
| ATOM | 25 O ILE G 28 | 15.699 31.935 −10.443 1.00 13.70 | O |
| ATOM | 26 N THR G 29 | 15.098 30.702 −12.227 1.00 13.23 | N |
| ATOM | 27 CA THR G 29 | 13.968 31.532 −12.592 1.00 12.65 | C |
| ATOM | 28 CB THR G 29 | 14.306 32.435 −13.790 1.00 12.69 | C |
| ATOM | 29 OG1 THR G 29 | 15.728 32.530 −13.936 1.00 12.62 | O |
| ATOM | 30 CG2 THR G 29 | 13.723 33.825 −13.594 1.00 12.92 | C |
| ATOM | 31 C THR G 29 | 12.854 30.597 −13.010 1.00 12.47 | C |
| ATOM | 32 O THR G 29 | 13.106 29.526 −13.560 1.00 12.53 | O |
| ATOM | 33 N GLU G 30 | 11.622 31.050 −12.847 1.00 11.98 | N |
| ATOM | 34 CA GLU G 30 | 10.500 30.392 −13.480 1.00 11.68 | C |
| ATOM | 35 CB GLU G 30 | 9.587 29.781 −12.416 1.00 11.98 | C |
| ATOM | 36 CG GLU G 30 | 8.848 28.524 −12.856 1.00 13.38 | C |
| ATOM | 37 CD GLU G 30 | 8.295 27.732 −11.682 1.00 16.03 | C |
| ATOM | 38 OE1 GLU G 30 | 7.552 28.313 −10.863 1.00 16.65 | O |
| ATOM | 39 OE2 GLU G 30 | 8.577 26.519 −11.596 1.00 17.06 | O |
| ATOM | 40 C GLU G 30 | 9.743 31.433 −14.281 1.00 11.39 | C |
| ATOM | 41 O GLU G 30 | 9.521 32.547 −13.806 1.00 11.50 | O |
| ATOM | 42 N GLU G 31 | 9.449 31.119 −15.535 1.00 11.11 | N |
| ATOM | 43 CA GLU G 31 | 8.573 31.975 −16.305 1.00 11.06 | C |
| ATOM | 44 CB GLU G 31 | 9.345 32.716 −17.394 1.00 11.48 | C |
| ATOM | 45 CG GLU G 31 | 9.026 32.268 −18.803 1.00 13.90 | C |
| ATOM | 46 CD GLU G 31 | 9.622 33.190 −19.843 1.00 17.27 | C |
| ATOM | 47 OE1 GLU G 31 | 8.852 33.749 −20.653 1.00 17.55 | O |
| ATOM | 48 OE2 GLU G 31 | 10.849 33.418 −19.804 1.00 18.73 | O |
| ATOM | 49 C GLU G 31 | 7.370 31.240 −16.871 1.00 10.47 | C |
| ATOM | 50 O GLU G 31 | 7.459 30.080 −17.274 1.00 10.12 | O |
| ATOM | 51 N PHE G 32 | 6.220 31.890 −16.753 1.00 10.15 | N |
| ATOM | 52 CA PHE G 32 | 4.932 31.235 −16.887 1.00 9.62 | C |
| ATOM | 53 CB PHE G 32 | 3.967 31.777 −15.832 1.00 9.42 | C |
| ATOM | 54 CG PHE G 32 | 2.524 31.512 −16.141 1.00 9.27 | C |
| ATOM | 55 CD1 PHE G 32 | 2.021 30.222 −16.085 1.00 9.37 | C |
| ATOM | 56 CE1 PHE G 32 | 0.701 29.960 −16.407 1.00 9.52 | C |
| ATOM | 57 CZ PHE G 32 | −0.132 30.993 −16.800 1.00 9.82 | C |
| ATOM | 58 CE2 PHE G 32 | 0.362 32.285 −16.877 1.00 10.13 | C |
| ATOM | 59 CD2 PHE G 32 | 1.681 32.541 −16.536 1.00 10.06 | C |
| ATOM | 60 C PHE G 32 | 4.386 31.524 −18.276 1.00 9.64 | C |
| ATOM | 61 O PHE G 32 | 4.479 32.650 −18.763 1.00 9.84 | O |
| ATOM | 62 N TYR G 33 | 3.846 30.501 −18.926 1.00 9.59 | N |
| ATOM | 63 CA TYR G 33 | 3.342 30.662 −20.281 1.00 9.67 | C |
| ATOM | 64 CB TYR G 33 | 3.951 29.617 −21.212 1.00 9.52 | C |
| ATOM | 65 CG TYR G 33 | 5.422 29.834 −21.467 1.00 10.94 | C |
| ATOM | 66 CD1 TYR G 33 | 6.379 29.220 −20.670 1.00 12.23 | C |
| ATOM | 67 CE1 TYR G 33 | 7.726 29.448 −20.870 1.00 12.93 | C |
| ATOM | 68 CZ TYR G 33 | 8.128 30.348 −21.833 1.00 13.47 | C |
| ATOM | 69 OH TYR G 33 | 9.469 30.588 −22.028 1.00 14.54 | O |
| ATOM | 70 CE2 TYR G 33 | 7.195 31.019 −22.594 1.00 13.56 | C |
| ATOM | 71 CD2 TYR G 33 | 5.850 30.781 −22.388 1.00 12.96 | C |
| ATOM | 72 C TYR G 33 | 1.824 30.604 −20.327 1.00 9.94 | C |
| ATOM | 73 O TYR G 33 | 1.234 29.530 −20.446 1.00 10.16 | O |
| ATOM | 74 N GLN G 34 | 1.199 31.769 −20.211 1.00 10.06 | N |
| ATOM | 75 CA GLN G 34 | −0.225 31.846 −19.927 1.00 10.01 | C |
| ATOM | 76 CB GLN G 34 | −0.649 33.302 −19.751 1.00 10.22 | C |
| ATOM | 77 CG GLN G 34 | −2.138 33.486 −19.551 1.00 11.12 | C |
| ATOM | 78 CD GLN G 34 | −2.485 34.867 −19.039 1.00 13.13 | C |
| ATOM | 79 OE1 GLN G 34 | −2.668 35.804 −19.819 1.00 14.24 | O |
| ATOM | 80 NE2 GLN G 34 | −2.553 35.007 −17.719 1.00 13.79 | N |

APPENDIX-continued (APPENDIX discloses SEQ ID NOS 29-32, 29-32 and 29-32, respectively, in order of appearance)

| | | | |
|---|---|---|---|
| ATOM | 81 C GLN G 34 | −1.039 31.198 −21.039 1.00 9.94 | C |
| ATOM | 82 O GLN G 34 | −2.165 30.752 −20.819 1.00 10.08 | O |
| ATOM | 83 N SER G 35 | −0.468 31.167 −22.238 1.00 9.87 | N |
| ATOM | 84 CA SER G 35 | −1.185 30.690 −23.415 1.00 9.91 | C |
| ATOM | 85 CB SER G 35 | −0.619 31.337 −24.684 1.00 10.03 | C |
| ATOM | 86 OG SER G 35 | 0.776 31.572 −24.564 1.00 10.81 | O |
| ATOM | 87 C SER G 35 | −1.119 29.167 −23.518 1.00 9.56 | C |
| ATOM | 88 O SER G 35 | −1.688 28.566 −24.431 1.00 9.59 | O |
| ATOM | 89 N THR G 36 | −0.417 28.553 −22.572 1.00 9.21 | N |
| ATOM | 90 CA THR G 36 | −0.209 27.113 −22.573 1.00 9.06 | C |
| ATOM | 91 CB THR G 36 | 1.230 26.755 −23.010 1.00 9.49 | C |
| ATOM | 92 OG1 THR G 36 | 1.493 27.310 −24.305 1.00 10.82 | O |
| ATOM | 93 CG2 THR G 36 | 1.410 25.245 −23.074 1.00 9.45 | C |
| ATOM | 94 C THR G 36 | −0.455 26.599 −21.162 1.00 8.77 | C |
| ATOM | 95 O THR G 36 | −0.171 25.445 −20.845 1.00 8.60 | O |
| ATOM | 96 N CYS G 37 | −0.982 27.478 −20.315 1.00 8.69 | N |
| ATOM | 97 CA CYS G 37 | −1.097 27.201 −18.890 1.00 8.69 | C |
| ATOM | 98 CB CYS G 37 | −2.468 26.605 −18.571 1.00 8.81 | C |
| ATOM | 99 SG CYS G 37 | −3.003 26.848 −16.864 1.00 10.80 | S |
| ATOM | 100 C CYS G 37 | 0.005 26.263 −18.414 1.00 8.27 | C |
| ATOM | 101 O CYS G 37 | −0.268 25.166 −17.926 1.00 8.27 | O |
| ATOM | 102 N SER G 38 | 1.251 26.687 −18.586 1.00 7.92 | N |
| ATOM | 103 CA SER G 38 | 2.386 25.886 −18.157 1.00 7.51 | C |
| ATOM | 104 CB SER G 38 | 2.817 24.924 −19.264 1.00 7.63 | C |
| ATOM | 105 OG SER G 38 | 3.392 25.627 −20.351 1.00 8.54 | O |
| ATOM | 106 C SER G 38 | 3.558 26.757 −17.735 1.00 7.02 | C |
| ATOM | 107 O SER G 38 | 3.663 27.917 −18.132 1.00 6.83 | O |
| ATOM | 108 N ALA G 39 | 4.407 26.198 −16.882 1.00 6.64 | N |
| ATOM | 109 CA ALA G 39 | 5.466 26.961 −16.245 1.00 6.58 | C |
| ATOM | 110 CB ALA G 39 | 5.136 27.195 −14.782 1.00 6.67 | C |
| ATOM | 111 C ALA G 39 | 6.789 26.222 −16.382 1.00 6.93 | C |
| ATOM | 112 O ALA G 39 | 6.842 24.998 −16.261 1.00 7.38 | O |
| ATOM | 113 N VAL G 40 | 7.843 26.966 −16.698 1.00 6.87 | N |
| ATOM | 114 CA VAL G 40 | 9.175 26.388 −16.797 1.00 6.55 | C |
| ATOM | 115 CB VAL G 40 | 9.741 26.507 −18.222 1.00 6.22 | C |
| ATOM | 116 CG1 VAL G 40 | 11.237 26.233 −18.223 1.00 6.52 | C |
| ATOM | 117 CG2 VAL G 40 | 9.018 25.553 −19.160 1.00 6.62 | C |
| ATOM | 118 C VAL G 40 | 10.140 27.033 −15.813 1.00 6.73 | C |
| ATOM | 119 O VAL G 40 | 10.302 28.253 −15.789 1.00 6.83 | O |
| ATOM | 120 N SER G 41 | 10.772 26.198 −14.997 1.00 6.86 | N |
| ATOM | 121 CA SER G 41 | 11.897 26.625 −14.181 1.00 6.75 | C |
| ATOM | 122 CB SER G 41 | 11.974 25.785 −12.905 1.00 7.06 | C |
| ATOM | 123 OG SER G 41 | 10.751 25.110 −12.666 1.00 7.50 | O |
| ATOM | 124 C SER G 41 | 13.206 26.525 −14.958 1.00 6.56 | C |
| ATOM | 125 O SER G 41 | 13.526 25.482 −15.529 1.00 6.08 | O |
| ATOM | 126 N LYS G 42 | 13.972 27.612 −14.946 1.00 7.02 | N |
| ATOM | 127 CA LYS G 42 | 15.140 27.757 −15.809 1.00 7.83 | C |
| ATOM | 128 CB LYS G 42 | 14.949 28.933 −16.769 1.00 8.15 | C |
| ATOM | 129 CG LYS G 42 | 13.666 28.888 −17.578 1.00 9.75 | C |
| ATOM | 130 CD LYS G 42 | 13.510 30.148 −18.414 1.00 12.62 | C |
| ATOM | 131 CE LYS G 42 | 12.360 30.022 −19.398 1.00 14.04 | C |
| ATOM | 132 NZ LYS G 42 | 12.643 30.734 −20.675 1.00 14.96 | N |
| ATOM | 133 C LYS G 42 | 16.394 27.988 −14.971 1.00 7.80 | C |
| ATOM | 134 O LYS G 42 | 16.323 28.557 −13.882 1.00 8.15 | O |
| ATOM | 135 N GLY G 43 | 17.550 27.717 −15.566 1.00 7.59 | N |
| ATOM | 136 CA GLY G 43 | 18.820 28.160 −15.002 1.00 7.35 | C |
| ATOM | 137 C GLY G 43 | 19.529 27.058 −14.240 1.00 7.10 | C |
| ATOM | 138 O GLY G 43 | 20.294 27.323 −13.313 1.00 7.13 | O |
| ATOM | 139 N TYR G 44 | 19.309 25.819 −14.668 1.00 7.01 | N |
| ATOM | 140 CA TYR G 44 | 19.922 24.656 −14.033 1.00 6.89 | C |
| ATOM | 141 CB TYR G 44 | 18.878 23.561 −13.815 1.00 6.88 | C |
| ATOM | 142 CG TYR G 44 | 17.809 23.928 −12.816 1.00 6.41 | C |
| ATOM | 143 CD1 TYR G 44 | 16.553 24.343 −13.236 1.00 6.62 | C |
| ATOM | 144 CE1 TYR G 44 | 15.580 24.703 −12.325 1.00 6.48 | C |
| ATOM | 145 CZ TYR G 44 | 15.862 24.662 −10.976 1.00 6.88 | C |
| ATOM | 146 OH TYR G 44 | 14.897 25.025 −10.065 1.00 7.50 | O |
| ATOM | 147 CE2 TYR G 44 | 17.110 24.279 −10.536 1.00 6.68 | C |
| ATOM | 148 CD2 TYR G 44 | 18.077 23.922 −11.454 1.00 5.91 | C |
| ATOM | 149 C TYR G 44 | 21.060 24.106 −14.886 1.00 6.86 | C |
| ATOM | 150 O TYR G 44 | 21.012 24.190 −16.113 1.00 7.14 | O |
| ATOM | 151 N LEU G 45 | 21.979 23.385 −14.249 1.00 6.44 | N |
| ATOM | 152 CA LEU G 45 | 23.146 22.842 −14.946 1.00 6.12 | C |
| ATOM | 153 CB LEU G 45 | 24.425 23.552 −14.482 1.00 6.31 | C |
| ATOM | 154 CG LEU G 45 | 24.534 25.052 −14.775 1.00 6.38 | C |
| ATOM | 155 CD1 LEU G 45 | 25.624 25.690 −13.928 1.00 7.05 | C |
| ATOM | 156 CD2 LEU G 45 | 24.787 25.299 −16.255 1.00 7.05 | C |
| ATOM | 157 C LEU G 45 | 23.279 21.312 −14.800 1.00 5.84 | C |

APPENDIX-continued (APPENDIX discloses SEQ ID NOS 29-32, 29-32 and 29-32, respectively, in order of appearance)

| | | | |
|---|---|---|---|
| ATOM | 158 O LEU G 45 | 23.333 20.797 −13.683 1.00 5.94 | O |
| ATOM | 159 N SER G 46 | 23.470 20.620 −15.929 1.00 5.43 | N |
| ATOM | 160 CA SER G 46 | 23.249 19.157 −16.047 1.00 5.26 | C |
| ATOM | 161 CB SER G 46 | 22.913 18.795 −17.498 1.00 5.21 | C |
| ATOM | 162 OG SER G 46 | 24.090 18.532 −18.243 1.00 4.95 | O |
| ATOM | 163 C SER G 46 | 24.481 18.355 −15.585 1.00 5.51 | C |
| ATOM | 164 O SER G 46 | 25.480 18.961 −15.200 1.00 6.03 | O |
| ATOM | 165 N ALA G 47 | 24.453 17.015 −15.656 1.00 5.24 | N |
| ATOM | 166 CA ALA G 47 | 25.584 16.224 −15.104 1.00 4.83 | C |
| ATOM | 167 CB ALA G 47 | 25.690 16.412 −13.599 1.00 5.01 | C |
| ATOM | 168 C ALA G 47 | 25.854 14.751 −15.494 1.00 4.35 | C |
| ATOM | 169 O ALA G 47 | 24.926 13.972 −15.719 1.00 4.45 | O |
| ATOM | 170 N LEU G 48 | 27.119 14.348 −15.323 1.00 3.67 | N |
| ATOM | 171 CA LEU G 48 | 27.564 12.948 −15.451 1.00 3.15 | C |
| ATOM | 172 CB LEU G 48 | 28.365 12.755 −16.750 1.00 2.78 | C |
| ATOM | 173 CG LEU G 48 | 27.659 12.681 −18.108 1.00 2.18 | C |
| ATOM | 174 CD1 LEU G 48 | 28.223 11.532 −18.935 1.00 2.00 | C |
| ATOM | 175 CD2 LEU G 48 | 26.156 12.531 −17.934 1.00 3.94 | C |
| ATOM | 176 C LEU G 48 | 28.443 12.517 −14.259 1.00 3.06 | C |
| ATOM | 177 O LEU G 48 | 29.670 12.486 −14.373 1.00 3.27 | O |
| ATOM | 178 N ARG G 49 | 27.810 12.061 −13.177 1.00 2.91 | N |
| ATOM | 179 CA ARG G 49 | 28.509 11.788 −11.915 1.00 2.88 | C |
| ATOM | 180 CB ARG G 49 | 27.538 11.277 −10.847 1.00 2.69 | C |
| ATOM | 181 CG ARG G 49 | 28.117 11.273 −9.440 1.00 2.15 | C |
| ATOM | 182 CD ARG G 49 | 28.015 9.897 −8.806 1.00 2.00 | C |
| ATOM | 183 NE ARG G 49 | 29.322 9.271 −8.623 1.00 5.18 | N |
| ATOM | 184 CZ ARG G 49 | 29.526 7.956 −8.629 1.00 7.68 | C |
| ATOM | 185 NH1 ARG G 49 | 28.518 7.129 −8.866 1.00 8.32 | N |
| ATOM | 186 NH2 ARG G 49 | 30.748 7.469 −8.455 1.00 8.12 | N |
| ATOM | 187 C ARG G 49 | 29.678 10.816 −12.065 1.00 3.09 | C |
| ATOM | 188 O ARG G 49 | 29.570 9.796 −12.747 1.00 3.08 | O |
| ATOM | 189 N THR G 50 | 30.820 11.189 −11.489 1.00 3.37 | N |
| ATOM | 190 CA THR G 50 | 32.099 10.564 −11.823 1.00 3.55 | C |
| ATOM | 191 CB THR G 50 | 32.487 10.773 −13.299 1.00 3.25 | C |
| ATOM | 192 OG1 THR G 50 | 32.842 12.144 −13.519 1.00 2.66 | O |
| ATOM | 193 CG2 THR G 50 | 31.328 10.401 −14.212 1.00 3.46 | C |
| ATOM | 194 C THR G 50 | 33.259 10.968 −10.908 1.00 4.07 | C |
| ATOM | 195 O THR G 50 | 33.768 10.130 −10.165 1.00 4.35 | O |
| ATOM | 196 N GLY G 51 | 33.818 12.158 −11.108 1.00 4.24 | N |
| ATOM | 197 CA GLY G 51 | 34.942 12.544 −10.272 1.00 4.78 | C |
| ATOM | 198 C GLY G 51 | 34.692 11.849 −8.951 1.00 4.98 | C |
| ATOM | 199 O GLY G 51 | 33.618 12.018 −8.375 1.00 5.00 | O |
| ATOM | 200 N TRP G 52 | 35.476 10.816 −8.667 1.00 5.34 | N |
| ATOM | 201 CA TRP G 52 | 35.123 9.926 −7.569 1.00 5.42 | C |
| ATOM | 202 CB TRP G 52 | 34.864 8.497 −8.049 1.00 5.75 | C |
| ATOM | 203 CG TRP G 52 | 33.714 8.373 −9.001 1.00 6.38 | C |
| ATOM | 204 CD1 TRP G 52 | 33.776 7.964 −10.300 1.00 7.27 | C |
| ATOM | 205 NE1 TRP G 52 | 32.533 8.031 −10.878 1.00 7.46 | N |
| ATOM | 206 CE2 TRP G 52 | 31.627 8.449 −9.938 1.00 7.15 | C |
| ATOM | 207 CD2 TRP G 52 | 32.331 8.658 −8.735 1.00 7.02 | C |
| ATOM | 208 CE3 TRP G 52 | 31.627 9.102 −7.608 1.00 6.83 | C |
| ATOM | 209 CZ3 TRP G 52 | 30.261 9.289 −7.711 1.00 6.73 | C |
| ATOM | 210 CH2 TRP G 52 | 29.589 9.062 −8.922 1.00 7.13 | C |
| ATOM | 211 CZ2 TRP G 52 | 30.252 8.637 −10.041 1.00 6.82 | C |
| ATOM | 212 C TRP G 52 | 36.148 9.926 −6.456 1.00 5.34 | C |
| ATOM | 213 O TRP G 52 | 37.349 10.027 −6.698 1.00 5.47 | O |
| ATOM | 214 N TYR G 53 | 35.670 9.629 −5.256 1.00 5.29 | N |
| ATOM | 215 CA TYR G 53 | 36.528 9.560 −4.093 1.00 5.58 | C |
| ATOM | 216 CB TYR G 53 | 36.260 10.754 −3.176 1.00 5.51 | C |
| ATOM | 217 CG TYR G 53 | 37.079 10.756 −1.910 1.00 6.59 | C |
| ATOM | 218 CD1 TYR G 53 | 38.312 11.391 −1.858 1.00 8.25 | C |
| ATOM | 219 CE1 TYR G 53 | 39.043 11.436 −0.685 1.00 9.40 | C |
| ATOM | 220 CZ TYR G 53 | 38.524 10.875 0.462 1.00 9.24 | C |
| ATOM | 221 OH TYR G 53 | 39.246 10.915 1.633 1.00 9.61 | O |
| ATOM | 222 CE2 TYR G 53 | 37.287 10.272 0.443 1.00 8.78 | C |
| ATOM | 223 CD2 TYR G 53 | 36.559 10.247 −0.730 1.00 7.93 | C |
| ATOM | 224 C TYR G 53 | 36.286 8.245 −3.364 1.00 5.74 | C |
| ATOM | 225 O TYR G 53 | 35.186 7.996 −2.870 1.00 6.19 | O |
| ATOM | 226 N THR G 54 | 37.221 7.317 −3.532 1.00 6.04 | N |
| ATOM | 227 CA THR G 54 | 37.132 6.013 −2.888 1.00 6.67 | C |
| ATOM | 228 CB THR G 54 | 38.232 5.060 −3.396 1.00 6.97 | C |
| ATOM | 229 OG1 THR G 54 | 37.876 4.562 −4.691 1.00 7.51 | O |
| ATOM | 230 CG2 THR G 54 | 38.409 3.889 −2.442 1.00 7.98 | C |
| ATOM | 231 C THR G 54 | 37.254 6.158 −1.376 1.00 6.97 | C |
| ATOM | 232 O THR G 54 | 37.900 7.083 −0.884 1.00 7.32 | O |
| ATOM | 233 N SER G 55 | 36.616 5.254 −0.639 1.00 7.24 | N |
| ATOM | 234 CA SER G 55 | 37.025 4.966 0.732 1.00 7.65 | C |

APPENDIX-continued (APPENDIX discloses SEQ ID NOS 29-32, 29-32 and 29-32, respectively, in order of appearance)

| | | | |
|---|---|---|---|
| ATOM | 235 CB SER G 55 | 36.459 6.009 1.705 1.00 7.69 | C |
| ATOM | 236 OG SER G 55 | 36.690 5.632 3.053 1.00 7.51 | O |
| ATOM | 237 C SER G 55 | 36.629 3.561 1.171 1.00 8.03 | C |
| ATOM | 238 O SER G 55 | 35.510 3.109 0.924 1.00 8.43 | O |
| ATOM | 239 N VAL G 56 | 37.522 2.919 1.915 1.00 8.14 | N |
| ATOM | 240 CA VAL G 56 | 37.401 1.500 2.215 1.00 8.41 | C |
| ATOM | 241 CB VAL G 56 | 38.732 0.763 1.967 1.00 8.72 | C |
| ATOM | 242 CG1 VAL G 56 | 38.479 −0.703 1.654 1.00 9.29 | C |
| ATOM | 243 CG2 VAL G 56 | 39.509 1.433 0.843 1.00 9.51 | C |
| ATOM | 244 C VAL G 56 | 37.005 1.312 3.673 1.00 8.19 | C |
| ATOM | 245 O VAL G 56 | 37.760 1.658 4.578 1.00 8.54 | O |
| ATOM | 246 N ILE G 57 | 35.784 0.845 3.898 1.00 7.91 | N |
| ATOM | 247 CA ILE G 57 | 35.255 0.779 5.249 1.00 7.64 | C |
| ATOM | 248 CB ILE G 57 | 33.912 1.510 5.372 1.00 7.35 | C |
| ATOM | 249 CG1 ILE G 57 | 34.063 2.964 4.918 1.00 7.25 | C |
| ATOM | 250 CD1 ILE G 57 | 32.922 3.860 5.343 1.00 8.42 | C |
| ATOM | 251 CG2 ILE G 57 | 33.404 1.449 6.804 1.00 7.52 | C |
| ATOM | 252 C ILE G 57 | 35.125 −0.655 5.739 1.00 7.69 | C |
| ATOM | 253 O ILE G 57 | 34.629 −1.527 5.025 1.00 7.79 | O |
| ATOM | 254 N THR G 58 | 35.726 −0.917 6.894 1.00 7.85 | N |
| ATOM | 255 CA THR G 58 | 35.912 −2.275 7.379 1.00 8.15 | C |
| ATOM | 256 CB THR G 58 | 37.405 −2.631 7.469 1.00 8.14 | C |
| ATOM | 257 OG1 THR G 58 | 38.159 −1.761 6.615 1.00 8.62 | O |
| ATOM | 258 CG2 THR G 58 | 37.634 −4.075 7.053 1.00 7.94 | C |
| ATOM | 259 C THR G 58 | 35.291 −2.414 8.763 1.00 8.20 | C |
| ATOM | 260 O THR G 58 | 35.589 −1.633 9.664 1.00 8.18 | O |
| ATOM | 261 N ILE G 59 | 34.396 −3.384 8.915 1.00 8.54 | N |
| ATOM | 262 CA ILE G 59 | 33.617 −3.525 10.143 1.00 9.23 | C |
| ATOM | 263 CB ILE G 59 | 32.144 −3.139 9.912 1.00 8.92 | C |
| ATOM | 264 CG1 ILE G 59 | 32.031 −1.688 9.443 1.00 9.27 | C |
| ATOM | 265 CD1 ILE G 59 | 30.626 −1.285 9.045 1.00 10.89 | C |
| ATOM | 266 CG2 ILE G 59 | 31.326 −3.377 11.170 1.00 8.74 | C |
| ATOM | 267 C ILE G 59 | 33.648 −4.973 10.621 1.00 10.02 | C |
| ATOM | 268 O ILE G 59 | 33.170 −5.865 9.921 1.00 10.20 | O |
| ATOM | 269 N GLU G 60 | 34.251 −5.221 11.779 1.00 10.95 | N |
| ATOM | 270 CA GLU G 60 | 34.630 −6.586 12.133 1.00 12.13 | C |
| ATOM | 271 CB GLU G 60 | 35.311 −6.605 13.510 1.00 12.44 | C |
| ATOM | 272 CG GLU G 60 | 36.583 −5.750 13.558 1.00 15.04 | C |
| ATOM | 273 CD GLU G 60 | 37.500 −6.089 14.724 1.00 19.34 | C |
| ATOM | 274 OE1 GLU G 60 | 37.163 −5.716 15.869 1.00 20.63 | O |
| ATOM | 275 OE2 GLU G 60 | 38.625 −6.578 14.476 1.00 21.19 | O |
| ATOM | 276 C GLU G 60 | 33.397 −7.503 12.086 1.00 12.46 | C |
| ATOM | 277 O GLU G 60 | 32.369 −7.164 12.677 1.00 12.68 | O |
| ATOM | 278 N LEU G 61 | 33.448 −8.627 11.361 1.00 12.80 | N |
| ATOM | 279 CA LEU G 61 | 32.635 −9.731 11.843 1.00 12.71 | C |
| ATOM | 280 CB LEU G 61 | 32.816 −11.079 11.148 1.00 12.55 | C |
| ATOM | 281 CG LEU G 61 | 31.902 −12.059 11.912 1.00 12.39 | C |
| ATOM | 282 CD1 LEU G 61 | 30.438 −11.897 11.514 1.00 13.14 | C |
| ATOM | 283 CD2 LEU G 61 | 32.335 −13.513 11.814 1.00 12.50 | C |
| ATOM | 284 C LEU G 61 | 33.223 −9.800 13.207 1.00 12.94 | C |
| ATOM | 285 O LEU G 61 | 34.388 −10.187 13.351 1.00 12.78 | O |
| ATOM | 286 N SER G 62 | 32.676 −8.895 13.997 1.00 13.61 | N |
| ATOM | 287 CA SER G 62 | 32.941 −8.871 15.409 1.00 14.70 | C |
| ATOM | 288 CB SER G 62 | 32.339 −7.611 16.023 1.00 14.52 | C |
| ATOM | 289 OG SER G 62 | 32.798 −6.455 15.345 1.00 14.80 | O |
| ATOM | 290 C SER G 62 | 32.342 −10.111 16.051 1.00 15.48 | C |
| ATOM | 291 O SER G 62 | 31.132 −10.187 16.263 1.00 15.50 | O |
| ATOM | 292 N ASN G 63 | 33.164 −11.141 16.199 1.00 16.61 | N |
| ATOM | 293 CA ASN G 63 | 32.650 −12.422 16.635 1.00 17.77 | C |
| ATOM | 294 CB ASN G 63 | 33.597 −13.559 16.266 1.00 17.73 | C |
| ATOM | 295 CG ASN G 63 | 32.857 −14.834 15.934 1.00 18.52 | C |
| ATOM | 296 OD1 ASN G 63 | 31.848 −15.156 16.561 1.00 18.29 | O |
| ATOM | 297 ND2 ASN G 63 | 33.295 −15.516 14.883 1.00 19.40 | N |
| ATOM | 298 C ASN G 63 | 32.325 −12.448 18.119 1.00 18.53 | C |
| ATOM | 299 O ASN G 63 | 32.967 −11.768 18.919 1.00 18.82 | O |
| ATOM | 300 N ILE G 64 | 31.240 −13.135 18.457 1.00 19.60 | N |
| ATOM | 301 CA ILE G 64 | 30.912 −13.413 19.848 1.00 21.04 | C |
| ATOM | 302 CB ILE G 64 | 29.403 −13.648 20.038 1.00 20.60 | C |
| ATOM | 303 CG1 ILE G 64 | 28.593 −12.612 19.259 1.00 20.13 | C |
| ATOM | 304 CD1 ILE G 64 | 27.150 −12.497 19.722 1.00 20.19 | C |
| ATOM | 305 CG2 ILE G 64 | 29.040 −13.615 21.514 1.00 20.74 | C |
| ATOM | 306 C ILE G 64 | 31.660 −14.643 20.347 1.00 22.58 | C |
| ATOM | 307 O ILE G 64 | 31.672 −15.682 19.687 1.00 23.07 | O |
| ATOM | 308 N LYS G 65 | 32.173 −14.559 21.570 1.00 24.21 | N |
| ATOM | 309 CA LYS G 65 | 32.425 −15.751 22.374 1.00 25.86 | C |
| ATOM | 310 CB LYS G 65 | 33.801 −15.682 23.043 1.00 25.90 | C |
| ATOM | 311 CG LYS G 65 | 34.437 −14.301 23.031 1.00 26.69 | C |

APPENDIX-continued (APPENDIX discloses SEQ ID NOS 29-32, 29-32 and 29-32, respectively, in order of appearance)

| | | | |
|---|---|---|---|
| ATOM | 312 CD LYS G 65 | 33.621 −13.312 23.847 1.00 28.26 | C |
| ATOM | 313 CE LYS G 65 | 34.477 −12.614 24.890 1.00 28.67 | C |
| ATOM | 314 NZ LYS G 65 | 33.661 −12.120 26.034 1.00 28.95 | N |
| ATOM | 315 C LYS G 65 | 31.329 −15.991 23.413 1.00 26.81 | C |
| ATOM | 316 O LYS G 65 | 31.299 −15.345 24.461 1.00 26.72 | O |
| ATOM | 317 N GLU G 66 | 30.491 −16.990 23.149 1.00 27.90 | N |
| ATOM | 318 CA GLU G 66 | 29.237 −17.188 23.879 1.00 28.82 | C |
| ATOM | 319 CB GLU G 66 | 28.305 −18.104 23.076 1.00 28.88 | C |
| ATOM | 320 CG GLU G 66 | 27.621 −19.192 23.895 1.00 30.33 | C |
| ATOM | 321 CD GLU G 66 | 27.188 −20.381 23.052 1.00 33.17 | C |
| ATOM | 322 OE1 GLU G 66 | 26.253 −21.098 23.468 1.00 35.05 | O |
| ATOM | 323 OE2 GLU G 66 | 27.824 −20.634 22.007 1.00 33.14 | O |
| ATOM | 324 C GLU G 66 | 29.494 −17.783 25.263 1.00 29.12 | C |
| ATOM | 325 O GLU G 66 | 30.348 −18.655 25.418 1.00 29.28 | O |
| ATOM | 326 N ASN G 67 | 28.773 −17.301 26.272 1.00 29.32 | N |
| ATOM | 327 CA ASN G 67 | 29.094 −17.661 27.650 1.00 29.39 | C |
| ATOM | 328 CB ASN G 67 | 29.462 −16.429 28.477 1.00 29.62 | C |
| ATOM | 329 CG ASN G 67 | 30.963 −16.231 28.580 1.00 29.84 | C |
| ATOM | 330 OD1 ASN G 67 | 31.651 −17.000 29.252 1.00 29.93 | O |
| ATOM | 331 ND2 ASN G 67 | 31.494 −15.324 27.768 1.00 29.22 | N |
| ATOM | 332 C ASN G 67 | 28.069 −18.540 28.367 1.00 29.15 | C |
| ATOM | 333 O ASN G 67 | 27.324 −18.070 29.227 1.00 29.06 | O |
| ATOM | 334 N LYS G 68 | 27.964 −19.788 27.921 1.00 28.87 | N |
| ATOM | 335 CA LYS G 68 | 27.848 −20.936 28.819 1.00 28.78 | C |
| ATOM | 336 CB LYS G 68 | 29.127 −21.783 28.771 1.00 28.89 | C |
| ATOM | 337 CG LYS G 68 | 29.681 −22.003 27.364 1.00 29.26 | C |
| ATOM | 338 CD LYS G 68 | 31.070 −22.631 27.392 1.00 29.68 | C |
| ATOM | 339 CE LYS G 68 | 31.200 −23.648 28.514 1.00 29.46 | C |
| ATOM | 340 NZ LYS G 68 | 32.473 −24.417 28.425 1.00 29.58 | N |
| ATOM | 341 C LYS G 68 | 27.492 −20.555 30.268 1.00 28.60 | C |
| ATOM | 342 O LYS G 68 | 28.346 −20.603 31.154 1.00 28.64 | O |
| ATOM | 343 N CYS G 69 | 26.261 −20.069 30.468 1.00 28.09 | N |
| ATOM | 344 CA CYS G 69 | 25.535 −20.153 31.759 1.00 27.63 | C |
| ATOM | 345 CB CYS G 69 | 25.056 −18.753 32.214 1.00 27.07 | C |
| ATOM | 346 SG CYS G 69 | 23.368 −18.230 31.662 1.00 28.01 | S |
| ATOM | 347 C CYS G 69 | 24.339 −21.120 31.667 1.00 27.69 | C |
| ATOM | 348 O CYS G 69 | 23.967 −21.533 30.570 1.00 27.41 | O |
| ATOM | 349 N ASN G 70 | 23.718 −21.458 32.800 1.00 28.06 | N |
| ATOM | 350 CA ASN G 70 | 22.359 −22.029 32.778 1.00 28.87 | C |
| ATOM | 351 CB ASN G 70 | 22.332 −23.517 33.167 1.00 30.52 | C |
| ATOM | 352 CG ASN G 70 | 23.711 −24.156 33.213 1.00 39.60 | C |
| ATOM | 353 OD1 ASN G 70 | 24.336 −24.404 32.180 1.00 44.97 | O |
| ATOM | 354 ND2 ASN G 70 | 24.204 −24.392 34.429 1.00 51.04 | N |
| ATOM | 355 C ASN G 70 | 21.297 −21.261 33.577 1.00 26.97 | C |
| ATOM | 356 O ASN G 70 | 21.275 −21.320 34.807 1.00 26.50 | O |
| ATOM | 357 N GLY G 71 | 20.320 −20.703 32.866 1.00 25.46 | N |
| ATOM | 358 CA GLY G 71 | 19.231 −19.956 33.496 1.00 23.67 | C |
| ATOM | 359 C GLY G 71 | 17.990 −20.807 33.709 1.00 22.81 | C |
| ATOM | 360 O GLY G 71 | 18.004 −22.008 33.436 1.00 22.79 | O |
| ATOM | 361 N THR G 72 | 16.924 −20.195 34.225 1.00 21.93 | N |
| ATOM | 362 CA THR G 72 | 15.666 −20.910 34.453 1.00 21.30 | C |
| ATOM | 363 CB THR G 72 | 14.737 −20.162 35.441 1.00 21.12 | C |
| ATOM | 364 OG1 THR G 72 | 14.073 −19.090 34.761 1.00 19.87 | O |
| ATOM | 365 CG2 THR G 72 | 15.532 −19.609 36.619 1.00 20.76 | C |
| ATOM | 366 C THR G 72 | 14.923 −21.169 33.139 1.00 21.50 | C |
| ATOM | 367 O THR G 72 | 14.471 −20.236 32.474 1.00 21.85 | O |
| ATOM | 368 N ASP G 73 | 14.797 −22.445 32.781 1.00 21.43 | N |
| ATOM | 369 CA ASP G 73 | 14.514 −22.861 31.404 1.00 21.46 | C |
| ATOM | 370 CB ASP G 73 | 13.109 −22.427 30.971 1.00 21.69 | C |
| ATOM | 371 CG ASP G 73 | 12.794 −22.806 29.529 1.00 22.46 | C |
| ATOM | 372 OD1 ASP G 73 | 13.730 −22.837 28.701 1.00 23.01 | O |
| ATOM | 373 OD2 ASP G 73 | 11.611 −23.068 29.224 1.00 23.09 | O |
| ATOM | 374 C ASP G 73 | 15.561 −22.365 30.406 1.00 20.96 | C |
| ATOM | 375 O ASP G 73 | 15.703 −21.161 30.188 1.00 20.61 | O |
| ATOM | 376 N ALA G 74 | 16.237 −23.305 29.748 1.00 20.42 | N |
| ATOM | 377 CA ALA G 74 | 17.299 −22.967 28.802 1.00 20.38 | C |
| ATOM | 378 CB ALA G 74 | 18.658 −23.365 29.363 1.00 20.11 | C |
| ATOM | 379 C ALA G 74 | 17.092 −23.586 27.421 1.00 20.45 | C |
| ATOM | 380 O ALA G 74 | 18.059 −23.849 26.707 1.00 20.46 | O |
| ATOM | 381 N LYS G 75 | 15.839 −23.747 27.010 1.00 20.67 | N |
| ATOM | 382 CA LYS G 75 | 15.550 −24.031 25.610 1.00 20.99 | C |
| ATOM | 383 CB LYS G 75 | 14.110 −24.512 25.445 1.00 21.20 | C |
| ATOM | 384 CG LYS G 75 | 13.808 −25.810 26.181 1.00 22.02 | C |
| ATOM | 385 CD LYS G 75 | 12.692 −25.624 27.198 1.00 23.66 | C |
| ATOM | 386 CE LYS G 75 | 13.000 −26.348 28.498 1.00 24.93 | C |
| ATOM | 387 NZ LYS G 75 | 12.517 −25.588 29.683 1.00 25.55 | N |
| ATOM | 388 C LYS G 75 | 15.798 −22.788 24.765 1.00 20.92 | C |

APPENDIX-continued (APPENDIX discloses SEQ ID NOS 29-32, 29-32 and 29-32, respectively, in order of appearance)

| | | | | | | | | | |
|---|---|---|---|---|---|---|---|---|---|
| ATOM | 389 O LYS G 75 | 16.187 | −22.880 | 23.600 | 1.00 | 20.92 | O |
| ATOM | 390 N VAL G 76 | 15.659 | −21.629 | 25.399 | 1.00 | 20.63 | N |
| ATOM | 391 CA VAL G 76 | 16.187 | −20.379 | 24.872 | 1.00 | 20.36 | C |
| ATOM | 392 CB VAL G 76 | 15.654 | −19.174 | 25.673 | 1.00 | 20.25 | C |
| ATOM | 393 CG1 VAL G 76 | 16.330 | −17.891 | 25.215 | 1.00 | 20.82 | C |
| ATOM | 394 CG2 VAL G 76 | 14.139 | −19.068 | 25.530 | 1.00 | 20.09 | C |
| ATOM | 395 C VAL G 76 | 17.717 | −20.356 | 24.872 | 1.00 | 20.29 | C |
| ATOM | 396 O VAL G 76 | 18.353 | −20.568 | 25.905 | 1.00 | 20.21 | O |
| ATOM | 397 N LYS G 77 | 18.294 | −20.039 | 23.716 | 1.00 | 20.17 | N |
| ATOM | 398 CA LYS G 77 | 19.745 | −20.018 | 23.547 | 1.00 | 20.17 | C |
| ATOM | 399 CB LYS G 77 | 20.267 | −21.419 | 23.194 | 1.00 | 20.62 | C |
| ATOM | 400 CG LYS G 77 | 20.894 | −22.180 | 24.367 | 1.00 | 23.31 | C |
| ATOM | 401 CD LYS G 77 | 20.940 | −23.684 | 24.105 | 1.00 | 26.74 | C |
| ATOM | 402 CE LYS G 77 | 21.242 | −24.468 | 25.376 | 1.00 | 28.32 | C |
| ATOM | 403 NZ LYS G 77 | 21.041 | −25.932 | 25.189 | 1.00 | 29.66 | N |
| ATOM | 404 C LYS G 77 | 20.159 | −19.010 | 22.468 | 1.00 | 19.45 | C |
| ATOM | 405 O LYS G 77 | 20.754 | −19.378 | 21.453 | 1.00 | 19.36 | O |
| ATOM | 406 N LEU G 78 | 19.862 | −17.736 | 22.710 | 1.00 | 18.70 | N |
| ATOM | 407 CA LEU G 78 | 19.857 | −16.728 | 21.656 | 1.00 | 17.98 | C |
| ATOM | 408 CB LEU G 78 | 19.534 | −15.357 | 22.246 | 1.00 | 17.72 | C |
| ATOM | 409 CG LEU G 78 | 18.293 | −15.357 | 23.142 | 1.00 | 17.51 | C |
| ATOM | 410 CD1 LEU G 78 | 18.117 | −14.023 | 23.860 | 1.00 | 17.41 | C |
| ATOM | 411 CD2 LEU G 78 | 17.045 | −15.734 | 22.349 | 1.00 | 17.62 | C |
| ATOM | 412 C LEU G 78 | 21.181 | −16.680 | 20.908 | 1.00 | 17.77 | C |
| ATOM | 413 O LEU G 78 | 21.209 | −16.672 | 19.678 | 1.00 | 17.89 | O |
| ATOM | 414 N ILE G 79 | 22.273 | −16.585 | 21.657 | 1.00 | 17.29 | N |
| ATOM | 415 CA ILE G 79 | 23.592 | −16.438 | 21.058 | 1.00 | 17.00 | C |
| ATOM | 416 CB ILE G 79 | 24.691 | −16.295 | 22.126 | 1.00 | 16.96 | C |
| ATOM | 417 CG1 ILE G 79 | 24.486 | −15.011 | 22.932 | 1.00 | 17.21 | C |
| ATOM | 418 CD1 ILE G 79 | 25.529 | −14.794 | 24.009 | 1.00 | 17.51 | C |
| ATOM | 419 CG2 ILE G 79 | 26.066 | −16.303 | 21.477 | 1.00 | 17.30 | C |
| ATOM | 420 C ILE G 79 | 23.923 | −17.616 | 20.147 | 1.00 | 16.83 | C |
| ATOM | 421 O ILE G 79 | 24.307 | −17.428 | 18.992 | 1.00 | 17.02 | O |
| ATOM | 422 N LYS G 80 | 23.678 | −18.870 | 20.478 | 1.00 | 16.55 | N |
| ATOM | 423 CA LYS G 80 | 24.058 | −19.851 | 19.437 | 1.00 | 16.38 | C |
| ATOM | 424 CB LYS G 80 | 23.872 | −21.278 | 19.959 | 1.00 | 16.73 | C |
| ATOM | 425 CG LYS G 80 | 24.274 | −22.360 | 18.971 | 1.00 | 17.99 | C |
| ATOM | 426 CD LYS G 80 | 25.741 | −22.245 | 18.590 | 1.00 | 20.71 | C |
| ATOM | 427 CE LYS G 80 | 26.170 | −23.396 | 17.697 | 1.00 | 22.92 | C |
| ATOM | 428 NZ LYS G 80 | 25.352 | −23.472 | 16.454 | 1.00 | 24.75 | N |
| ATOM | 429 C LYS G 80 | 23.334 | −19.690 | 18.060 | 1.00 | 15.79 | C |
| ATOM | 430 O LYS G 80 | 23.970 | −19.700 | 16.969 | 1.00 | 15.32 | O |
| ATOM | 431 N GLN G 81 | 22.019 | −19.489 | 18.112 | 1.00 | 15.48 | N |
| ATOM | 432 CA GLN G 81 | 21.192 | −19.385 | 16.905 | 1.00 | 15.33 | C |
| ATOM | 433 CB GLN G 81 | 19.711 | −19.320 | 17.287 | 1.00 | 15.70 | C |
| ATOM | 434 CG GLN G 81 | 19.269 | −20.415 | 18.242 | 1.00 | 17.88 | C |
| ATOM | 435 CD GLN G 81 | 17.848 | −20.225 | 18.734 | 1.00 | 20.46 | C |
| ATOM | 436 OE1 GLN G 81 | 17.116 | −19.367 | 18.241 | 1.00 | 21.59 | O |
| ATOM | 437 NE2 GLN G 81 | 17.451 | −21.028 | 19.716 | 1.00 | 20.26 | N |
| ATOM | 438 C GLN G 81 | 21.546 | −18.192 | 16.019 | 1.00 | 14.63 | C |
| ATOM | 439 O GLN G 81 | 21.582 | −18.295 | 14.780 | 1.00 | 14.60 | O |
| ATOM | 440 N GLU G 82 | 21.808 | −17.057 | 16.658 | 1.00 | 13.81 | N |
| ATOM | 441 CA GLU G 82 | 22.159 | −15.854 | 15.925 | 1.00 | 13.37 | C |
| ATOM | 442 CB GLU G 82 | 22.317 | −14.664 | 16.873 | 1.00 | 13.20 | C |
| ATOM | 443 CG GLU G 82 | 21.010 | −13.984 | 17.235 | 1.00 | 15.04 | C |
| ATOM | 444 CD GLU G 82 | 20.314 | −13.388 | 16.026 | 1.00 | 17.51 | C |
| ATOM | 445 OE1 GLU G 82 | 19.726 | −12.293 | 16.154 | 1.00 | 18.22 | O |
| ATOM | 446 OE2 GLU G 82 | 20.355 | −14.015 | 14.946 | 1.00 | 17.87 | O |
| ATOM | 447 C GLU G 82 | 23.450 | −16.101 | 15.169 | 1.00 | 12.99 | C |
| ATOM | 448 O GLU G 82 | 23.584 | −15.705 | 14.014 | 1.00 | 12.89 | O |
| ATOM | 449 N LEU G 83 | 24.393 | −16.778 | 15.815 | 1.00 | 12.89 | N |
| ATOM | 450 CA LEU G 83 | 25.665 | −17.066 | 15.174 | 1.00 | 13.08 | C |
| ATOM | 451 CB LEU G 83 | 26.613 | −17.761 | 16.151 | 1.00 | 13.26 | C |
| ATOM | 452 CG LEU G 83 | 26.970 | −16.978 | 17.415 | 1.00 | 14.18 | C |
| ATOM | 453 CD1 LEU G 83 | 27.933 | −17.774 | 18.282 | 1.00 | 15.11 | C |
| ATOM | 454 CD2 LEU G 83 | 27.557 | −15.620 | 17.059 | 1.00 | 14.79 | C |
| ATOM | 455 C LEU G 83 | 25.444 | −17.940 | 13.949 | 1.00 | 13.18 | C |
| ATOM | 456 O LEU G 83 | 26.007 | −17.673 | 12.876 | 1.00 | 13.05 | O |
| ATOM | 457 N ASP G 84 | 24.588 | −18.953 | 14.074 | 1.00 | 13.56 | N |
| ATOM | 458 CA ASP G 84 | 24.346 | −19.788 | 12.891 | 1.00 | 14.15 | C |
| ATOM | 459 CB ASP G 84 | 23.439 | −20.973 | 13.232 | 1.00 | 14.80 | C |
| ATOM | 460 CG ASP G 84 | 24.004 | −21.841 | 14.338 | 1.00 | 18.26 | C |
| ATOM | 461 OD1 ASP G 84 | 24.605 | −22.891 | 14.026 | 1.00 | 21.11 | O |
| ATOM | 462 OD2 ASP G 84 | 23.837 | −21.480 | 15.520 | 1.00 | 22.12 | O |
| ATOM | 463 C ASP G 84 | 23.737 | −18.979 | 11.731 | 1.00 | 13.56 | C |
| ATOM | 464 O ASP G 84 | 24.147 | −19.111 | 10.549 | 1.00 | 13.70 | O |
| ATOM | 465 N LYS G 85 | 22.780 | −18.115 | 12.068 | 1.00 | 12.87 | N |

APPENDIX-continued (APPENDIX discloses SEQ ID NOS 29-32, 29-32 and 29-32, respectively, in order of appearance)

| | | | |
|---|---|---|---|
| ATOM | 466 CA LYS G 85 | 22.128 −17.318 11.033 1.00 12.31 | C |
| ATOM | 467 CB LYS G 85 | 20.987 −16.487 11.619 1.00 12.41 | C |
| ATOM | 468 CG LYS G 85 | 20.087 −15.857 10.568 1.00 12.26 | C |
| ATOM | 469 CD LYS G 85 | 19.083 −14.900 11.189 1.00 12.72 | C |
| ATOM | 470 CE LYS G 85 | 19.772 −13.667 11.750 1.00 14.40 | C |
| ATOM | 471 NZ LYS G 85 | 18.789 −12.676 12.268 1.00 16.45 | N |
| ATOM | 472 C LYS G 85 | 23.147 −16.409 10.353 1.00 11.85 | C |
| ATOM | 473 O LYS G 85 | 23.143 −16.238 9.125 1.00 11.66 | O |
| ATOM | 474 N TYR G 86 | 24.031 −15.839 11.165 1.00 11.32 | N |
| ATOM | 475 CA TYR G 86 | 25.051 −14.936 10.665 1.00 11.07 | C |
| ATOM | 476 CB TYR G 86 | 25.863 −14.349 11.820 1.00 11.12 | C |
| ATOM | 477 CG TYR G 86 | 27.216 −13.824 11.399 1.00 11.30 | C |
| ATOM | 478 CD1 TYR G 86 | 27.349 −12.561 10.838 1.00 12.16 | C |
| ATOM | 479 CE1 TYR G 86 | 28.584 −12.080 10.449 1.00 12.39 | C |
| ATOM | 480 CZ TYR G 86 | 29.705 −12.864 10.619 1.00 12.62 | C |
| ATOM | 481 OH TYR G 86 | 30.938 −12.388 10.233 1.00 12.72 | O |
| ATOM | 482 CE2 TYR G 86 | 29.599 −14.121 11.172 1.00 11.38 | C |
| ATOM | 483 CD2 TYR G 86 | 28.360 −14.595 11.558 1.00 11.05 | C |
| ATOM | 484 C TYR G 86 | 25.971 −15.667 9.708 1.00 10.75 | C |
| ATOM | 485 O TYR G 86 | 26.320 −15.140 8.656 1.00 10.45 | O |
| ATOM | 486 N LYS G 87 | 26.343 −16.894 10.053 1.00 10.66 | N |
| ATOM | 487 CA LYS G 87 | 27.220 −17.656 9.174 1.00 11.03 | C |
| ATOM | 488 CB LYS G 87 | 27.588 −18.996 9.813 1.00 11.36 | C |
| ATOM | 489 CG LYS G 87 | 28.300 −18.874 11.149 1.00 12.79 | C |
| ATOM | 490 CD LYS G 87 | 28.627 −20.242 11.722 1.00 14.76 | C |
| ATOM | 491 CE LYS G 87 | 29.336 −20.123 13.060 1.00 15.29 | C |
| ATOM | 492 NZ LYS G 87 | 29.664 −21.460 13.626 1.00 16.27 | N |
| ATOM | 493 C LYS G 87 | 26.541 −17.891 7.826 1.00 10.83 | C |
| ATOM | 494 O LYS G 87 | 27.163 −17.715 6.758 1.00 11.11 | O |
| ATOM | 495 N ASN G 88 | 25.256 −18.243 7.858 1.00 10.52 | N |
| ATOM | 496 CA ASN G 88 | 24.567 −18.464 6.584 1.00 10.21 | C |
| ATOM | 497 CB ASN G 88 | 23.149 −18.989 6.821 1.00 10.61 | C |
| ATOM | 498 CG ASN G 88 | 22.406 −19.271 5.529 1.00 11.81 | C |
| ATOM | 499 OD1 ASN G 88 | 22.998 −19.285 4.450 1.00 12.97 | O |
| ATOM | 500 ND2 ASN G 88 | 21.101 −19.496 5.633 1.00 13.82 | N |
| ATOM | 501 C ASN G 88 | 24.528 −17.187 5.730 1.00 9.42 | C |
| ATOM | 502 O ASN G 88 | 24.780 −17.206 4.500 1.00 8.94 | O |
| ATOM | 503 N ALA G 89 | 24.251 −16.068 6.395 1.00 8.77 | N |
| ATOM | 504 CA ALA G 89 | 24.164 −14.796 5.693 1.00 8.21 | C |
| ATOM | 505 CB ALA G 89 | 23.734 −13.693 6.647 1.00 7.99 | C |
| ATOM | 506 C ALA G 89 | 25.510 −14.465 5.063 1.00 7.78 | C |
| ATOM | 507 O ALA G 89 | 25.586 −13.988 3.927 1.00 7.88 | O |
| ATOM | 508 N VAL G 90 | 26.574 −14.738 5.809 1.00 7.01 | N |
| ATOM | 509 CA VAL G 90 | 27.921 −14.464 5.344 1.00 6.26 | C |
| ATOM | 510 CB VAL G 90 | 28.965 −14.771 6.433 1.00 5.91 | C |
| ATOM | 511 CG1 VAL G 90 | 30.361 −14.414 5.945 1.00 5.92 | C |
| ATOM | 512 CG2 VAL G 90 | 28.631 −14.020 7.714 1.00 5.26 | C |
| ATOM | 513 C VAL G 90 | 28.240 −15.284 4.104 1.00 6.25 | C |
| ATOM | 514 O VAL G 90 | 28.798 −14.758 3.144 1.00 6.32 | O |
| ATOM | 515 N THR G 91 | 27.858 −16.558 4.098 1.00 6.24 | N |
| ATOM | 516 CA THR G 91 | 28.129 −17.376 2.915 1.00 6.68 | C |
| ATOM | 517 CB THR G 91 | 27.705 −18.840 3.129 1.00 6.62 | C |
| ATOM | 518 OG1 THR G 91 | 28.438 −19.397 4.227 1.00 7.19 | O |
| ATOM | 519 CG2 THR G 91 | 27.971 −19.661 1.876 1.00 7.27 | C |
| ATOM | 520 C THR G 91 | 27.392 −16.808 1.698 1.00 7.02 | C |
| ATOM | 521 O THR G 91 | 27.953 −16.709 0.569 1.00 7.16 | O |
| ATOM | 522 N GLU G 92 | 26.143 −16.402 1.925 1.00 7.31 | N |
| ATOM | 523 CA GLU G 92 | 25.382 −15.849 0.812 1.00 7.81 | C |
| ATOM | 524 CB GLU G 92 | 23.942 −15.547 1.231 1.00 8.23 | C |
| ATOM | 525 CG GLU G 92 | 23.030 −16.761 1.222 1.00 10.91 | C |
| ATOM | 526 CD GLU G 92 | 22.895 −17.372 −0.161 1.00 14.95 | C |
| ATOM | 527 OE1 GLU G 92 | 21.801 −17.878 −0.489 1.00 16.14 | O |
| ATOM | 528 OE2 GLU G 92 | 23.884 −17.346 −0.923 1.00 16.53 | O |
| ATOM | 529 C GLU G 92 | 26.053 −14.587 0.267 1.00 7.47 | C |
| ATOM | 530 O GLU G 92 | 26.210 −14.432 −0.947 1.00 7.32 | O |
| ATOM | 531 N LEU G 93 | 26.501 −13.717 1.167 1.00 7.30 | N |
| ATOM | 532 CA LEU G 93 | 27.140 −12.467 0.759 1.00 7.47 | C |
| ATOM | 533 CB LEU G 93 | 27.442 −11.589 1.973 1.00 7.15 | C |
| ATOM | 534 CG LEU G 93 | 26.217 −11.021 2.692 1.00 7.20 | C |
| ATOM | 535 CD1 LEU G 93 | 26.638 −10.123 3.845 1.00 7.93 | C |
| ATOM | 536 CD2 LEU G 93 | 25.325 −10.266 1.716 1.00 6.91 | C |
| ATOM | 537 C LEU G 93 | 28.414 −12.761 −0.020 1.00 7.89 | C |
| ATOM | 538 O LEU G 93 | 28.746 −12.083 −0.991 1.00 7.94 | O |
| ATOM | 539 N GLN G 94 | 29.116 −13.789 0.434 1.00 8.31 | N |
| ATOM | 540 CA GLN G 94 | 30.361 −14.248 −0.160 1.00 9.05 | C |
| ATOM | 541 CB GLN G 94 | 30.985 −15.349 0.701 1.00 9.18 | C |
| ATOM | 542 CG GLN G 94 | 31.324 −14.908 2.114 1.00 10.79 | C |

APPENDIX-continued (APPENDIX discloses SEQ ID NOS 29-32, 29-32 and 29-32, respectively, in order of appearance)

| | | | |
|---|---|---|---|
| ATOM | 543 CD GLN G 94 | 31.993 −16.003 2.920 1.00 13.82 | C |
| ATOM | 544 OE1 GLN G 94 | 32.210 −17.109 2.427 1.00 14.98 | O |
| ATOM | 545 NE2 GLN G 94 | 32.324 −15.698 4.170 1.00 15.25 | N |
| ATOM | 546 C GLN G 94 | 30.220 −14.731 −1.603 1.00 9.25 | C |
| ATOM | 547 O GLN G 94 | 31.124 −14.514 −2.410 1.00 9.43 | O |
| ATOM | 548 N LEU G 95 | 29.114 −15.393 −1.941 1.00 9.55 | N |
| ATOM | 549 CA LEU G 95 | 29.003 −15.935 −3.318 1.00 10.17 | C |
| ATOM | 550 CB LEU G 95 | 27.752 −16.811 −3.437 1.00 9.79 | C |
| ATOM | 551 CG LEU G 95 | 27.700 −18.053 −2.545 1.00 8.86 | C |
| ATOM | 552 CD1 LEU G 95 | 26.403 −18.817 −2.764 1.00 8.31 | C |
| ATOM | 553 CD2 LEU G 95 | 28.904 −18.947 −2.798 1.00 7.62 | C |
| ATOM | 554 C LEU G 95 | 29.057 −14.945 −4.528 1.00 11.22 | C |
| ATOM | 555 O LEU G 95 | 29.643 −15.248 −5.567 1.00 11.55 | O |
| ATOM | 556 N LEU G 96 | 28.430 −13.786 −4.361 1.00 12.40 | N |
| ATOM | 557 CA LEU G 96 | 28.142 −12.747 −5.335 1.00 13.66 | C |
| ATOM | 558 CB LEU G 96 | 27.471 −11.548 −4.668 1.00 13.38 | C |
| ATOM | 559 CG LEU G 96 | 26.008 −11.779 −4.288 1.00 13.32 | C |
| ATOM | 560 CD1 LEU G 96 | 25.321 −10.462 −3.975 1.00 12.84 | C |
| ATOM | 561 CD2 LEU G 96 | 25.278 −12.519 −5.397 1.00 13.38 | C |
| ATOM | 562 C LEU G 96 | 29.392 −12.314 −6.094 1.00 14.97 | C |
| ATOM | 563 O LEU G 96 | 29.293 −11.741 −7.178 1.00 15.21 | O |
| ATOM | 564 N MET G 97 | 30.564 −12.678 −5.576 1.00 16.74 | N |
| ATOM | 565 CA MET G 97 | 31.799 −11.956 −5.894 1.00 18.96 | C |
| ATOM | 566 CB MET G 97 | 32.828 −12.102 −4.766 1.00 19.12 | C |
| ATOM | 567 CG MET G 97 | 32.353 −11.577 −3.413 1.00 21.87 | C |
| ATOM | 568 SD MET G 97 | 32.586 −9.794 −3.210 1.00 27.46 | S |
| ATOM | 569 CE MET G 97 | 32.408 −9.214 −4.899 1.00 24.25 | C |
| ATOM | 570 C MET G 97 | 32.408 −12.377 −7.233 1.00 20.09 | C |
| ATOM | 571 O MET G 97 | 33.064 −11.581 −7.905 1.00 20.58 | O |
| ATOM | 572 N GLN G 98 | 32.151 −13.618 −7.634 1.00 21.33 | N |
| ATOM | 573 CA GLN G 98 | 32.735 −14.171 −8.853 1.00 22.21 | C |
| ATOM | 574 CB GLN G 98 | 33.777 −15.243 −8.513 1.00 22.53 | C |
| ATOM | 575 CG GLN G 98 | 34.695 −14.883 −7.347 1.00 23.85 | C |
| ATOM | 576 CD GLN G 98 | 34.172 −15.376 −6.008 1.00 25.21 | C |
| ATOM | 577 OE1 GLN G 98 | 33.109 −14.957 −5.549 1.00 24.47 | O |
| ATOM | 578 NE2 GLN G 98 | 34.939 −16.243 −5.358 1.00 24.85 | N |
| ATOM | 579 C GLN G 98 | 31.660 −14.756 −9.766 1.00 22.15 | C |
| ATOM | 580 O GLN G 98 | 30.475 −14.451 −9.624 1.00 21.77 | O |
| ATOM | 581 N PHE G 137 | 36.645 −13.585 −16.969 1.00 33.25 | N |
| ATOM | 582 CA PHE G 137 | 35.365 −12.919 −16.764 1.00 36.79 | C |
| ATOM | 583 CB PHE G 137 | 35.255 −11.672 −17.642 1.00 20.00 | C |
| ATOM | 584 CG PHE G 137 | 36.265 −10.611 −17.319 1.00 20.00 | C |
| ATOM | 585 CD1 PHE G 137 | 36.015 −9.677 −16.331 1.00 20.00 | C |
| ATOM | 586 CE1 PHE G 137 | 36.932 −8.682 −16.050 1.00 20.00 | C |
| ATOM | 587 CZ PHE G 137 | 38.108 −8.607 −16.766 1.00 20.00 | C |
| ATOM | 588 CE2 PHE G 137 | 38.362 −9.523 −17.764 1.00 20.00 | C |
| ATOM | 589 CD2 PHE G 137 | 37.439 −10.510 −18.045 1.00 20.00 | C |
| ATOM | 590 C PHE G 137 | 34.195 −13.850 −17.063 1.00 48.73 | C |
| ATOM | 591 O PHE G 137 | 33.039 −13.434 −16.993 1.00 49.28 | O |
| ATOM | 592 N LEU G 138 | 34.498 −15.040 −17.571 1.00 42.04 | N |
| ATOM | 593 CA LEU G 138 | 33.471 −16.059 −17.783 1.00 44.26 | C |
| ATOM | 594 CB LEU G 138 | 34.037 −17.258 −18.553 1.00 20.00 | C |
| ATOM | 595 CG LEU G 138 | 34.341 −17.114 −20.050 1.00 20.00 | C |
| ATOM | 596 CD1 LEU G 138 | 34.975 −18.387 −20.605 1.00 20.00 | C |
| ATOM | 597 CD2 LEU G 138 | 33.095 −16.756 −20.843 1.00 20.00 | C |
| ATOM | 598 C LEU G 138 | 32.896 −16.527 −16.451 1.00 43.68 | C |
| ATOM | 599 O LEU G 138 | 31.839 −17.157 −16.406 1.00 50.27 | O |
| ATOM | 600 N GLY G 139 | 33.614 −16.234 −15.370 1.00 38.56 | N |
| ATOM | 601 CA GLY G 139 | 33.145 −16.544 −14.022 1.00 47.99 | C |
| ATOM | 602 C GLY G 139 | 31.826 −15.881 −13.662 1.00 44.53 | C |
| ATOM | 603 O GLY G 139 | 31.082 −16.383 −12.819 1.00 32.21 | O |
| ATOM | 604 N PHE G 140 | 31.510 −14.778 −14.337 1.00 46.33 | N |
| ATOM | 605 CA PHE G 140 | 30.319 −13.992 −14.021 1.00 42.95 | C |
| ATOM | 606 CB PHE G 140 | 30.530 −12.516 −14.386 1.00 20.00 | C |
| ATOM | 607 CG PHE G 140 | 31.590 −11.827 −13.564 1.00 20.00 | C |
| ATOM | 608 CD1 PHE G 140 | 31.295 −11.318 −12.310 1.00 20.00 | C |
| ATOM | 609 CE1 PHE G 140 | 32.272 −10.683 −11.553 1.00 20.00 | C |
| ATOM | 610 CZ PHE G 140 | 33.540 −10.511 −12.066 1.00 20.00 | C |
| ATOM | 611 CE2 PHE G 140 | 33.832 −10.970 −13.334 1.00 20.00 | C |
| ATOM | 612 CD2 PHE G 140 | 32.851 −11.591 −14.090 1.00 20.00 | C |
| ATOM | 613 C PHE G 140 | 29.077 −14.525 −14.731 1.00 38.13 | C |
| ATOM | 614 O PHE G 140 | 27.970 −14.040 −14.504 1.00 57.33 | O |
| ATOM | 615 N LEU G 141 | 29.271 −15.480 −15.634 1.00 35.20 | N |
| ATOM | 616 CA LEU G 141 | 28.173 −15.996 −16.446 1.00 27.01 | C |
| ATOM | 617 CB LEU G 141 | 26.983 −16.392 −15.560 1.00 20.00 | C |
| ATOM | 618 CG LEU G 141 | 27.185 −17.555 −14.580 1.00 20.00 | C |
| ATOM | 619 CD1 LEU G 141 | 25.930 −17.779 −13.747 1.00 20.00 | C |

APPENDIX-continued (APPENDIX discloses SEQ ID NOS 29-32, 29-32 and 29-32, respectively, in order of appearance)

| | | | |
|---|---|---|---|
| ATOM | 620 CD2 LEU G 141 | 27.588 −18.835 −15.306 1.00 20.00 | C |
| ATOM | 621 C LEU G 141 | 27.750 −14.978 −17.504 1.00 35.79 | C |
| ATOM | 622 O LEU G 141 | 28.543 −14.613 −18.370 1.00 46.92 | O |
| ATOM | 623 N LEU G 142 | 26.509 −14.508 −17.424 1.00 38.67 | N |
| ATOM | 624 CA LEU G 142 | 26.075 −13.372 −18.231 1.00 33.84 | C |
| ATOM | 625 CB LEU G 142 | 24.737 −13.667 −18.914 1.00 20.00 | C |
| ATOM | 626 CG LEU G 142 | 24.720 −14.676 −20.063 1.00 20.00 | C |
| ATOM | 627 CD1 LEU G 142 | 23.339 −14.707 −20.705 1.00 20.00 | C |
| ATOM | 628 CD2 LEU G 142 | 25.773 −14.324 −21.101 1.00 20.00 | C |
| ATOM | 629 C LEU G 142 | 25.959 −12.123 −17.368 1.00 36.89 | C |
| ATOM | 630 O LEU G 142 | 25.257 −12.119 −16.358 1.00 45.42 | O |
| ATOM | 631 N GLY G 143 | 26.763 −11.115 −17.688 1.00 26.84 | N |
| ATOM | 632 CA GLY G 143 | 26.817 −9.895 −16.892 1.00 27.41 | C |
| ATOM | 633 C GLY G 143 | 26.590 −8.645 −17.722 1.00 29.08 | C |
| ATOM | 634 O GLY G 143 | 26.918 −8.603 −18.908 1.00 40.24 | O |
| ATOM | 635 N VAL G 144 | 26.026 −7.622 −17.092 1.00 30.17 | N |
| ATOM | 636 CA VAL G 144 | 25.849 −6.331 −17.739 1.00 34.15 | C |
| ATOM | 637 CB VAL G 144 | 24.768 −5.496 −17.035 1.00 20.00 | C |
| ATOM | 638 CG1 VAL G 144 | 24.730 −4.081 −17.599 1.00 20.00 | C |
| ATOM | 639 CG2 VAL G 144 | 23.414 −6.166 −17.170 1.00 20.00 | C |
| ATOM | 640 C VAL G 144 | 27.152 −5.543 −17.760 1.00 36.67 | C |
| ATOM | 641 O VAL G 144 | 28.104 −5.880 −17.054 1.00 42.49 | O |
| ATOM | 642 N GLY G 145 | 27.185 −4.487 −18.567 1.00 47.09 | N |
| ATOM | 643 CA GLY G 145 | 28.309 −3.563 −18.568 1.00 44.51 | C |
| ATOM | 644 C GLY G 145 | 28.683 −3.184 −17.151 1.00 44.94 | C |
| ATOM | 645 O GLY G 145 | 29.809 −3.424 −16.714 1.00 40.58 | O |
| ATOM | 646 N SER G 146 | 27.732 −2.662 −16.387 1.00 42.06 | N |
| ATOM | 647 CA SER G 146 | 28.033 −2.190 −15.035 1.00 47.39 | C |
| ATOM | 648 CB SER G 146 | 26.797 −1.534 −14.414 1.00 20.00 | C |
| ATOM | 649 OG SER G 146 | 25.719 −2.450 −14.333 1.00 20.00 | O |
| ATOM | 650 C SER G 146 | 28.570 −3.280 −14.101 1.00 51.48 | C |
| ATOM | 651 O SER G 146 | 29.491 −3.034 −13.317 1.00 47.45 | O |
| ATOM | 652 N ALA G 147 | 28.004 −4.480 −14.183 1.00 39.51 | N |
| ATOM | 653 CA ALA G 147 | 28.430 −5.576 −13.316 1.00 43.38 | C |
| ATOM | 654 CB ALA G 147 | 27.531 −6.788 −13.513 1.00 20.00 | C |
| ATOM | 655 C ALA G 147 | 29.894 −5.954 −13.541 1.00 47.39 | C |
| ATOM | 656 O ALA G 147 | 30.635 −6.211 −12.587 1.00 50.18 | O |
| ATOM | 657 N ILE G 148 | 30.309 −5.983 −14.804 1.00 44.67 | N |
| ATOM | 658 CA ILE G 148 | 31.690 −6.311 −15.140 1.00 43.56 | C |
| ATOM | 659 CB ILE G 148 | 31.898 −6.390 −16.663 1.00 20.00 | C |
| ATOM | 660 CG1 ILE G 148 | 30.998 −7.469 −17.269 1.00 20.00 | C |
| ATOM | 661 CD1 ILE G 148 | 31.142 −7.612 −18.768 1.00 20.00 | C |
| ATOM | 662 CG2 ILE G 148 | 33.358 −6.663 −16.987 1.00 20.00 | C |
| ATOM | 663 C ILE G 148 | 32.633 −5.265 −14.558 1.00 51.18 | C |
| ATOM | 664 O ILE G 148 | 33.699 −5.592 −14.031 1.00 39.17 | O |
| ATOM | 665 N ALA G 149 | 32.226 −4.003 −14.651 1.00 42.17 | N |
| ATOM | 666 CA ALA G 149 | 33.020 −2.906 −14.116 1.00 36.76 | C |
| ATOM | 667 CB ALA G 149 | 32.386 −1.571 −14.466 1.00 20.00 | C |
| ATOM | 668 C ALA G 149 | 33.150 −3.058 −12.607 1.00 45.19 | C |
| ATOM | 669 O ALA G 149 | 34.222 −2.843 −12.041 1.00 47.83 | O |
| ATOM | 670 N SER G 150 | 32.054 −3.443 −11.961 1.00 43.64 | N |
| ATOM | 671 CA SER G 150 | 32.062 −3.643 −10.518 1.00 43.46 | C |
| ATOM | 672 CB SER G 150 | 30.657 −3.968 −10.010 1.00 20.00 | C |
| ATOM | 673 OG SER G 150 | 30.165 −5.160 −10.596 1.00 20.00 | O |
| ATOM | 674 C SER G 150 | 33.030 −4.762 −10.146 1.00 44.80 | C |
| ATOM | 675 O SER G 150 | 33.774 −4.653 −9.170 1.00 41.55 | O |
| ATOM | 676 N GLY G 151 | 33.025 −5.833 −10.935 1.00 27.01 | N |
| ATOM | 677 CA GLY G 151 | 33.927 −6.946 −10.697 1.00 35.21 | C |
| ATOM | 678 C GLY G 151 | 35.376 −6.519 −10.839 1.00 42.40 | C |
| ATOM | 679 O GLY G 151 | 36.246 −6.924 −10.055 1.00 45.11 | O |
| ATOM | 680 N VAL G 152 | 35.638 −5.691 −11.846 1.00 40.20 | N |
| ATOM | 681 CA VAL G 152 | 36.983 −5.185 −12.076 1.00 46.73 | C |
| ATOM | 682 CB VAL G 152 | 37.056 −4.330 −13.354 1.00 20.00 | C |
| ATOM | 683 CG1 VAL G 152 | 38.472 −3.816 −13.568 1.00 20.00 | C |
| ATOM | 684 CG2 VAL G 152 | 36.587 −5.134 −14.557 1.00 20.00 | C |
| ATOM | 685 C VAL G 152 | 37.424 −4.345 −10.885 1.00 48.62 | C |
| ATOM | 686 O VAL G 152 | 38.565 −4.438 −10.432 1.00 49.32 | O |
| ATOM | 687 N ALA G 153 | 36.502 −3.537 −10.370 1.00 35.09 | N |
| ATOM | 688 CA ALA G 153 | 36.788 −2.690 −9.220 1.00 42.37 | C |
| ATOM | 689 CB ALA G 153 | 35.604 −1.787 −8.918 1.00 20.00 | C |
| ATOM | 690 C ALA G 153 | 37.120 −3.557 −8.014 1.00 37.79 | C |
| ATOM | 691 O ALA G 153 | 38.029 −3.247 −7.243 1.00 39.25 | O |
| ATOM | 692 N VAL G 154 | 36.378 −4.648 −7.859 1.00 38.88 | N |
| ATOM | 693 CA VAL G 154 | 36.610 −5.579 −6.763 1.00 35.53 | C |
| ATOM | 694 CB VAL G 154 | 35.549 −6.695 −6.737 1.00 20.00 | C |
| ATOM | 695 CG1 VAL G 154 | 35.814 −7.651 −5.584 1.00 20.00 | C |
| ATOM | 696 CG2 VAL G 154 | 34.154 −6.098 −6.634 1.00 20.00 | C |

APPENDIX-continued (APPENDIX discloses SEQ ID NOS 29-32, 29-32 and 29-32, respectively, in order of appearance)

| | | | |
|---|---|---|---|
| ATOM | 697 C VAL G 154 | 37.996 −6.209 −6.863 1.00 41.00 | C |
| ATOM | 698 O VAL G 154 | 38.690 −6.353 −5.856 1.00 50.08 | O |
| ATOM | 699 N SER G 155 | 38.403 −6.579 −8.075 1.00 37.82 | N |
| ATOM | 700 CA SER G 155 | 39.733 −7.158 −8.271 1.00 44.68 | C |
| ATOM | 701 CB SER G 155 | 39.906 −7.630 −9.715 1.00 20.00 | C |
| ATOM | 702 OG SER G 155 | 39.757 −6.554 −10.625 1.00 20.00 | O |
| ATOM | 703 C SER G 155 | 40.817 −6.140 −7.914 1.00 41.82 | C |
| ATOM | 704 O SER G 155 | 41.834 −6.468 −7.304 1.00 49.37 | O |
| ATOM | 705 N LYS G 156 | 40.566 −4.900 −8.314 1.00 36.99 | N |
| ATOM | 706 CA LYS G 156 | 41.440 −3.756 −8.097 1.00 35.11 | C |
| ATOM | 707 CB LYS G 156 | 40.989 −2.562 −8.943 1.00 20.00 | C |
| ATOM | 708 CG LYS G 156 | 41.146 −2.767 −10.443 1.00 20.00 | C |
| ATOM | 709 CD LYS G 156 | 40.541 −1.606 −11.227 1.00 20.00 | C |
| ATOM | 710 CE LYS G 156 | 40.906 −1.679 −12.708 1.00 20.00 | C |
| ATOM | 711 NZ LYS G 156 | 40.298 −0.569 −13.497 1.00 20.00 | N |
| ATOM | 712 C LYS G 156 | 41.489 −3.378 −6.620 1.00 35.98 | C |
| ATOM | 713 O LYS G 156 | 42.501 −2.874 −6.136 1.00 42.31 | O |
| ATOM | 714 N VAL G 157 | 40.433 −3.719 −5.886 1.00 37.88 | N |
| ATOM | 715 CA VAL G 157 | 40.341 −3.361 −4.475 1.00 50.94 | C |
| ATOM | 716 CB VAL G 157 | 38.894 −3.057 −4.061 1.00 20.00 | C |
| ATOM | 717 CG1 VAL G 157 | 38.799 −2.928 −2.551 1.00 20.00 | C |
| ATOM | 718 CG2 VAL G 157 | 38.403 −1.790 −4.745 1.00 20.00 | C |
| ATOM | 719 C VAL G 157 | 40.882 −4.474 −3.591 1.00 47.82 | C |
| ATOM | 720 O VAL G 157 | 41.021 −4.309 −2.379 1.00 56.87 | O |
| ATOM | 721 N LEU G 158 | 41.279 −5.588 −4.192 1.00 39.52 | N |
| ATOM | 722 CA LEU G 158 | 41.557 −6.817 −3.448 1.00 50.27 | C |
| ATOM | 723 CB LEU G 158 | 41.899 −7.952 −4.419 1.00 20.00 | C |
| ATOM | 724 CG LEU G 158 | 40.817 −8.321 −5.435 1.00 20.00 | C |
| ATOM | 725 CD1 LEU G 158 | 41.287 −9.458 −6.330 1.00 20.00 | C |
| ATOM | 726 CD2 LEU G 158 | 39.521 −8.689 −4.729 1.00 20.00 | C |
| ATOM | 727 C LEU G 158 | 42.627 −6.743 −2.351 1.00 54.47 | C |
| ATOM | 728 O LEU G 158 | 42.456 −7.343 −1.285 1.00 49.26 | O |
| ATOM | 729 N HIS G 159 | 43.716 −6.021 −2.585 1.00 59.45 | N |
| ATOM | 730 CA HIS G 159 | 44.772 −5.947 −1.579 1.00 49.11 | C |
| ATOM | 731 CB HIS G 159 | 45.963 −5.146 −2.108 1.00 20.00 | C |
| ATOM | 732 CG HIS G 159 | 46.583 −5.728 −3.340 1.00 20.00 | C |
| ATOM | 733 ND1 HIS G 159 | 47.606 −6.651 −3.293 1.00 20.00 | N |
| ATOM | 734 CE1 HIS G 159 | 47.951 −6.984 −4.524 1.00 20.00 | C |
| ATOM | 735 NE2 HIS G 159 | 47.189 −6.311 −5.368 1.00 20.00 | N |
| ATOM | 736 CD2 HIS G 159 | 46.325 −5.518 −4.652 1.00 20.00 | C |
| ATOM | 737 C HIS G 159 | 44.256 −5.325 −0.280 1.00 44.09 | C |
| ATOM | 738 O HIS G 159 | 44.572 −5.797 0.819 1.00 42.13 | O |
| ATOM | 739 N LEU G 160 | 43.449 −4.277 −0.410 1.00 37.55 | N |
| ATOM | 740 CA LEU G 160 | 42.876 −3.609 0.751 1.00 43.52 | C |
| ATOM | 741 CB LEU G 160 | 42.095 −2.365 0.323 1.00 20.00 | C |
| ATOM | 742 CG LEU G 160 | 42.891 −1.283 −0.409 1.00 20.00 | C |
| ATOM | 743 CD1 LEU G 160 | 41.996 −0.107 −0.769 1.00 20.00 | C |
| ATOM | 744 CD2 LEU G 160 | 44.073 −0.825 0.432 1.00 20.00 | C |
| ATOM | 745 C LEU G 160 | 41.966 −4.559 1.523 1.00 47.22 | C |
| ATOM | 746 O LEU G 160 | 41.969 −4.578 2.756 1.00 43.25 | O |
| ATOM | 747 N GLU G 161 | 41.190 −5.350 0.788 1.00 40.88 | N |
| ATOM | 748 CA GLU G 161 | 40.292 −6.318 1.402 1.00 40.61 | C |
| ATOM | 749 CB GLU G 161 | 39.434 −7.005 0.338 1.00 20.00 | C |
| ATOM | 750 CG GLU G 161 | 38.558 −6.055 −0.462 1.00 20.00 | C |
| ATOM | 751 CD GLU G 161 | 37.719 −6.773 −1.501 1.00 20.00 | C |
| ATOM | 752 OE1 GLU G 161 | 36.959 −6.094 −2.224 1.00 20.00 | O |
| ATOM | 753 OE2 GLU G 161 | 37.819 −8.014 −1.596 1.00 20.00 | O |
| ATOM | 754 C GLU G 161 | 41.097 −7.352 2.179 1.00 39.76 | C |
| ATOM | 755 O GLU G 161 | 40.720 −7.747 3.284 1.00 44.02 | O |
| ATOM | 756 N GLY G 162 | 42.213 −7.781 1.599 1.00 34.18 | N |
| ATOM | 757 CA GLY G 162 | 43.079 −8.742 2.256 1.00 35.01 | C |
| ATOM | 758 C GLY G 162 | 43.637 −8.163 3.542 1.00 34.86 | C |
| ATOM | 759 O GLY G 162 | 43.706 −8.844 4.570 1.00 47.81 | O |
| ATOM | 760 N GLU G 163 | 44.019 −6.890 3.489 1.00 40.78 | N |
| ATOM | 761 CA GLU G 163 | 44.546 −6.213 4.669 1.00 37.20 | C |
| ATOM | 762 CB GLU G 163 | 45.016 −4.801 4.315 1.00 20.00 | C |
| ATOM | 763 CG GLU G 163 | 46.112 −4.758 3.264 1.00 20.00 | C |
| ATOM | 764 CD GLU G 163 | 46.555 −3.345 2.942 1.00 20.00 | C |
| ATOM | 765 OE1 GLU G 163 | 47.454 −3.181 2.090 1.00 20.00 | O |
| ATOM | 766 OE2 GLU G 163 | 46.003 −2.399 3.540 1.00 20.00 | O |
| ATOM | 767 C GLU G 163 | 43.480 −6.158 5.758 1.00 46.12 | C |
| ATOM | 768 O GLU G 163 | 43.770 −6.363 6.939 1.00 58.66 | O |
| ATOM | 769 N VAL G 164 | 42.243 −5.885 5.354 1.00 42.23 | N |
| ATOM | 770 CA VAL G 164 | 41.129 −5.833 6.292 1.00 35.45 | C |
| ATOM | 771 CB VAL G 164 | 39.827 −5.387 5.602 1.00 20.00 | C |
| ATOM | 772 CG1 VAL G 164 | 38.684 −5.343 6.604 1.00 20.00 | C |
| ATOM | 773 CG2 VAL G 164 | 40.015 −4.032 4.937 1.00 20.00 | C |

APPENDIX-continued (APPENDIX discloses SEQ ID NOS 29-32, 29-32 and 29-32, respectively, in order of appearance)

| | | | |
|---|---|---|---|
| ATOM | 774 C VAL G 164 | 40.908 −7.195 6.947 1.00 46.32 | C |
| ATOM | 775 O VAL G 164 | 40.656 −7.284 8.153 1.00 45.08 | O |
| ATOM | 776 N ASN G 165 | 41.011 −8.257 6.151 1.00 40.82 | N |
| ATOM | 777 CA ASN G 165 | 40.854 −9.603 6.687 1.00 46.48 | C |
| ATOM | 778 CB ASN G 165 | 40.897 −10.652 5.573 1.00 20.00 | C |
| ATOM | 779 CG ASN G 165 | 39.710 −10.560 4.634 1.00 20.00 | C |
| ATOM | 780 OD1 ASN G 165 | 38.643 −11.108 4.909 1.00 20.00 | O |
| ATOM | 781 ND2 ASN G 165 | 39.896 −9.881 3.509 1.00 20.00 | N |
| ATOM | 782 C ASN G 165 | 41.947 −9.884 7.708 1.00 50.90 | C |
| ATOM | 783 O ASN G 165 | 41.694 −10.455 8.769 1.00 47.11 | O |
| ATOM | 784 N LYS G 166 | 43.161 −9.451 7.385 1.00 48.36 | N |
| ATOM | 785 CA LYS G 166 | 44.305 −9.640 8.269 1.00 38.71 | C |
| ATOM | 786 CB LYS G 166 | 45.591 −9.154 7.595 1.00 20.00 | C |
| ATOM | 787 CG LYS G 166 | 45.907 −9.850 6.277 1.00 20.00 | C |
| ATOM | 788 CD LYS G 166 | 47.180 −9.298 5.649 1.00 20.00 | C |
| ATOM | 789 CE LYS G 166 | 47.495 −9.990 4.331 1.00 20.00 | C |
| ATOM | 790 NZ LYS G 166 | 48.735 −9.455 3.701 1.00 20.00 | N |
| ATOM | 791 C LYS G 166 | 44.090 −8.907 9.591 1.00 45.07 | C |
| ATOM | 792 O LYS G 166 | 44.459 −9.402 10.657 1.00 56.09 | O |
| ATOM | 793 N ILE G 167 | 43.491 −7.725 9.508 1.00 42.02 | N |
| ATOM | 794 CA ILE G 167 | 43.256 −6.876 10.673 1.00 43.86 | C |
| ATOM | 795 CB ILE G 167 | 43.338 −5.380 10.304 1.00 20.00 | C |
| ATOM | 796 CG1 ILE G 167 | 44.721 −5.042 9.743 1.00 20.00 | C |
| ATOM | 797 CD1 ILE G 167 | 44.884 −3.589 9.349 1.00 20.00 | C |
| ATOM | 798 CG2 ILE G 167 | 43.025 −4.514 11.516 1.00 20.00 | C |
| ATOM | 799 C ILE G 167 | 41.921 −7.143 11.377 1.00 49.02 | C |
| ATOM | 800 O ILE G 167 | 41.570 −6.443 12.327 1.00 37.71 | O |
| ATOM | 801 N LYS G 168 | 41.175 −8.142 10.911 1.00 33.87 | N |
| ATOM | 802 CA LYS G 168 | 39.851 −8.426 11.471 1.00 35.11 | C |
| ATOM | 803 CB LYS G 168 | 39.163 −9.533 10.667 1.00 20.00 | C |
| ATOM | 804 CG LYS G 168 | 38.874 −9.175 9.219 1.00 20.00 | C |
| ATOM | 805 CD LYS G 168 | 38.101 −10.286 8.524 1.00 20.00 | C |
| ATOM | 806 CE LYS G 168 | 37.755 −9.909 7.092 1.00 20.00 | C |
| ATOM | 807 NZ LYS G 168 | 36.921 −10.950 6.427 1.00 20.00 | N |
| ATOM | 808 C LYS G 168 | 39.820 −8.790 12.966 1.00 39.27 | C |
| ATOM | 809 O LYS G 168 | 38.932 −8.339 13.690 1.00 32.39 | O |
| ATOM | 810 N SER G 169 | 40.770 −9.599 13.428 1.00 41.30 | N |
| ATOM | 811 CA SER G 169 | 40.805 −10.008 14.827 1.00 43.23 | C |
| ATOM | 812 CB SER G 169 | 42.030 −10.884 15.100 1.00 20.00 | C |
| ATOM | 813 OG SER G 169 | 43.231 −10.175 14.847 1.00 20.00 | O |
| ATOM | 814 C SER G 169 | 40.796 −8.806 15.767 1.00 41.44 | C |
| ATOM | 815 O SER G 169 | 40.016 −8.759 16.718 1.00 44.82 | O |
| ATOM | 816 N ALA G 170 | 41.695 −7.857 15.522 1.00 39.78 | N |
| ATOM | 817 CA ALA G 170 | 41.753 −6.638 16.319 1.00 41.01 | C |
| ATOM | 818 CB ALA G 170 | 42.928 −5.775 15.887 1.00 20.00 | C |
| ATOM | 819 C ALA G 170 | 40.448 −5.857 16.211 1.00 46.04 | C |
| ATOM | 820 O ALA G 170 | 39.912 −5.381 17.211 1.00 46.67 | O |
| ATOM | 821 N LEU G 171 | 39.921 −5.766 14.995 1.00 34.26 | N |
| ATOM | 822 CA LEU G 171 | 38.642 −5.108 14.762 1.00 37.69 | C |
| ATOM | 823 CB LEU G 171 | 38.269 −5.179 13.280 1.00 20.00 | C |
| ATOM | 824 CG LEU G 171 | 39.239 −4.485 12.323 1.00 20.00 | C |
| ATOM | 825 CD1 LEU G 171 | 38.764 −4.625 10.881 1.00 20.00 | C |
| ATOM | 826 CD2 LEU G 171 | 39.417 −3.022 12.711 1.00 20.00 | C |
| ATOM | 827 C LEU G 171 | 37.534 −5.723 15.616 1.00 44.67 | C |
| ATOM | 828 O LEU G 171 | 36.683 −5.010 16.151 1.00 34.27 | O |
| ATOM | 829 N LEU G 172 | 37.577 −7.043 15.776 1.00 34.80 | N |
| ATOM | 830 CA LEU G 172 | 36.536 −7.765 16.498 1.00 28.87 | C |
| ATOM | 831 CB LEU G 172 | 36.606 −9.258 16.179 1.00 20.00 | C |
| ATOM | 832 CG LEU G 172 | 36.254 −9.646 14.744 1.00 20.00 | C |
| ATOM | 833 CD1 LEU G 172 | 36.412 −11.143 14.539 1.00 20.00 | C |
| ATOM | 834 CD2 LEU G 172 | 34.842 −9.201 14.414 1.00 20.00 | C |
| ATOM | 835 C LEU G 172 | 36.655 −7.547 18.001 1.00 29.90 | C |
| ATOM | 836 O LEU G 172 | 35.650 −7.435 18.704 1.00 41.09 | O |
| ATOM | 837 N SER G 173 | 37.889 −7.498 18.490 1.00 35.08 | N |
| ATOM | 838 CA SER G 173 | 38.139 −7.406 19.923 1.00 35.53 | C |
| ATOM | 839 CB SER G 173 | 39.578 −7.823 20.245 1.00 20.00 | C |
| ATOM | 840 OG SER G 173 | 40.515 −7.012 19.556 1.00 20.00 | O |
| ATOM | 841 C SER G 173 | 37.860 −5.999 20.450 1.00 35.07 | C |
| ATOM | 842 O SER G 173 | 37.581 −5.815 21.636 1.00 51.28 | O |
| ATOM | 843 N THR G 174 | 37.893 −5.021 19.550 1.00 46.35 | N |
| ATOM | 844 CA THR G 174 | 37.721 −3.621 19.922 1.00 43.83 | C |
| ATOM | 845 CB THR G 174 | 38.341 −2.681 18.860 1.00 20.00 | C |
| ATOM | 846 OG1 THR G 174 | 37.702 −2.897 17.595 1.00 20.00 | O |
| ATOM | 847 CG2 THR G 174 | 39.839 −2.940 18.719 1.00 20.00 | C |
| ATOM | 848 C THR G 174 | 36.236 −3.300 20.083 1.00 52.54 | C |
| ATOM | 849 O THR G 174 | 35.448 −3.528 19.165 1.00 64.10 | O |
| ATOM | 850 N ASN G 175 | 35.839 −2.919 21.295 1.00 55.57 | N |

APPENDIX-continued (APPENDIX discloses SEQ ID NOS 29-32, 29-32 and 29-32, respectively, in order of appearance)

| | | | | | | | | |
|---|---|---|---|---|---|---|---|---|
| ATOM | 851 CA ASN G 175 | 34.501 | −2.371 | 21.528 | 1.00 | 40.58 | | C |
| ATOM | 852 CB ASN G 175 | 34.109 | −2.499 | 23.005 | 1.00 | 20.00 | | C |
| ATOM | 853 CG ASN G 175 | 33.819 | −3.933 | 23.416 | 1.00 | 20.00 | | C |
| ATOM | 854 OD1 ASN G 175 | 33.530 | −4.786 | 22.578 | 1.00 | 20.00 | | O |
| ATOM | 855 ND2 ASN G 175 | 33.845 | −4.190 | 24.720 | 1.00 | 20.00 | | N |
| ATOM | 856 C ASN G 175 | 34.404 | −0.909 | 21.089 | 1.00 | 43.65 | | C |
| ATOM | 857 O ASN G 175 | 35.035 | −0.032 | 21.682 | 1.00 | 53.11 | | O |
| ATOM | 858 N LYS G 176 | 33.694 | −0.671 | 19.990 | 1.00 | 44.89 | | N |
| ATOM | 859 CA LYS G 176 | 33.519 | 0.680 | 19.463 | 1.00 | 46.42 | | C |
| ATOM | 860 CB LYS G 176 | 34.847 | 1.244 | 18.945 | 1.00 | 20.00 | | C |
| ATOM | 861 CG LYS G 176 | 35.789 | 1.756 | 20.031 | 1.00 | 20.00 | | C |
| ATOM | 862 CD LYS G 176 | 37.220 | 1.872 | 19.511 | 1.00 | 20.00 | | C |
| ATOM | 863 CE LYS G 176 | 38.243 | 1.433 | 20.560 | 1.00 | 20.00 | | C |
| ATOM | 864 NZ LYS G 176 | 39.542 | 1.012 | 19.953 | 1.00 | 20.00 | | N |
| ATOM | 865 C LYS G 176 | 32.478 | 0.701 | 18.352 | 1.00 | 45.00 | | C |
| ATOM | 866 O LYS G 176 | 32.405 | −0.217 | 17.534 | 1.00 | 60.64 | | O |
| ATOM | 867 N ALA G 177 | 31.674 | 1.756 | 18.330 | 1.00 | 46.01 | | N |
| ATOM | 868 CA ALA G 177 | 30.717 | 1.962 | 17.257 | 1.00 | 43.65 | | C |
| ATOM | 869 CB ALA G 177 | 29.708 | 3.027 | 17.652 | 1.00 | 20.00 | | C |
| ATOM | 870 C ALA G 177 | 31.437 | 2.359 | 15.977 | 1.00 | 41.42 | | C |
| ATOM | 871 O ALA G 177 | 31.168 | 1.813 | 14.907 | 1.00 | 45.37 | | O |
| ATOM | 872 N VAL G 178 | 32.360 | 3.308 | 16.097 | 1.00 | 35.70 | | N |
| ATOM | 873 CA VAL G 178 | 33.228 | 3.683 | 14.987 | 1.00 | 43.93 | | C |
| ATOM | 874 CB VAL G 178 | 32.876 | 5.083 | 14.432 | 1.00 | 20.00 | | C |
| ATOM | 875 CG1 VAL G 178 | 33.896 | 5.516 | 13.379 | 1.00 | 20.00 | | C |
| ATOM | 876 CG2 VAL G 178 | 31.463 | 5.090 | 13.860 | 1.00 | 20.00 | | C |
| ATOM | 877 C VAL G 178 | 34.685 | 3.676 | 15.427 | 1.00 | 34.16 | | C |
| ATOM | 878 O VAL G 178 | 35.005 | 4.063 | 16.550 | 1.00 | 44.45 | | O |
| ATOM | 879 N VAL G 179 | 35.560 | 3.200 | 14.550 | 1.00 | 44.87 | | N |
| ATOM | 880 CA VAL G 179 | 36.972 | 3.080 | 14.884 | 1.00 | 38.47 | | C |
| ATOM | 881 CB VAL G 179 | 37.255 | 1.806 | 15.696 | 1.00 | 20.00 | | C |
| ATOM | 882 CG1 VAL G 179 | 38.742 | 1.679 | 15.986 | 1.00 | 20.00 | | C |
| ATOM | 883 CG2 VAL G 179 | 36.457 | 1.817 | 16.984 | 1.00 | 20.00 | | C |
| ATOM | 884 C VAL G 179 | 37.855 | 3.091 | 13.643 | 1.00 | 44.79 | | C |
| ATOM | 885 O VAL G 179 | 37.560 | 2.423 | 12.650 | 1.00 | 51.88 | | O |
| ATOM | 886 N SER G 180 | 38.955 | 3.835 | 13.719 | 1.00 | 45.23 | | N |
| ATOM | 887 CA SER G 180 | 39.937 | 3.871 | 12.643 | 1.00 | 48.99 | | C |
| ATOM | 888 CB SER G 180 | 40.875 | 5.069 | 12.812 | 1.00 | 20.00 | | C |
| ATOM | 889 OG SER G 180 | 41.649 | 4.948 | 13.993 | 1.00 | 20.00 | | O |
| ATOM | 890 C SER G 180 | 40.740 | 2.577 | 12.610 | 1.00 | 48.15 | | C |
| ATOM | 891 O SER G 180 | 41.386 | 2.212 | 13.594 | 1.00 | 60.42 | | O |
| ATOM | 892 N LEU G 181 | 40.594 | 1.827 | 11.521 | 1.00 | 42.42 | | N |
| ATOM | 893 CA LEU G 181 | 41.389 | 0.622 | 11.302 | 1.00 | 43.22 | | C |
| ATOM | 894 CB LEU G 181 | 40.818 | −0.190 | 10.139 | 1.00 | 20.00 | | C |
| ATOM | 895 CG LEU G 181 | 39.415 | −0.753 | 10.350 | 1.00 | 20.00 | | C |
| ATOM | 896 CD1 LEU G 181 | 38.958 | −1.514 | 9.118 | 1.00 | 20.00 | | C |
| ATOM | 897 CD2 LEU G 181 | 39.394 | −1.643 | 11.577 | 1.00 | 20.00 | | C |
| ATOM | 898 C LEU G 181 | 42.838 | 0.984 | 11.011 | 1.00 | 29.14 | | C |
| ATOM | 899 O LEU G 181 | 43.144 | 1.559 | 9.967 | 1.00 | 43.42 | | O |
| ATOM | 900 N SER G 182 | 43.721 | 0.695 | 11.960 | 1.00 | 41.83 | | N |
| ATOM | 901 CA SER G 182 | 45.089 | 1.186 | 11.883 | 1.00 | 53.52 | | C |
| ATOM | 902 CB SER G 182 | 45.421 | 2.069 | 13.086 | 1.00 | 20.00 | | C |
| ATOM | 903 OG SER G 182 | 45.500 | 1.303 | 14.275 | 1.00 | 20.00 | | O |
| ATOM | 904 C SER G 182 | 46.110 | 0.063 | 11.741 | 1.00 | 44.76 | | C |
| ATOM | 905 O SER G 182 | 45.995 | −0.984 | 12.379 | 1.00 | 37.73 | | O |
| ATOM | 906 N ASN G 183 | 47.028 | 0.245 | 10.799 | 1.00 | 47.84 | | N |
| ATOM | 907 CA ASN G 183 | 48.262 | −0.525 | 10.744 | 1.00 | 59.45 | | C |
| ATOM | 908 CB ASN G 183 | 48.350 | −1.276 | 9.412 | 1.00 | 20.00 | | C |
| ATOM | 909 CG ASN G 183 | 47.312 | −2.375 | 9.290 | 1.00 | 20.00 | | C |
| ATOM | 910 OD1 ASN G 183 | 46.897 | −2.964 | 10.287 | 1.00 | 20.00 | | O |
| ATOM | 911 ND2 ASN G 183 | 46.954 | −2.715 | 8.057 | 1.00 | 20.00 | | N |
| ATOM | 912 C ASN G 183 | 49.445 | 0.428 | 10.872 | 1.00 | 75.41 | | C |
| ATOM | 913 O ASN G 183 | 49.386 | 1.559 | 10.391 | 1.00102.31 | | | O |
| ATOM | 914 N GLY G 184 | 50.463 | 0.021 | 11.624 | 1.00 | 79.30 | | N |
| ATOM | 915 CA GLY G 184 | 51.584 | 0.906 | 11.931 | 1.00 | 88.92 | | C |
| ATOM | 916 C GLY G 184 | 51.464 | 2.278 | 11.287 | 1.00101.85 | | | C |
| ATOM | 917 O GLY G 184 | 51.911 | 2.485 | 10.158 | 1.00113.48 | | | O |
| ATOM | 918 N VAL G 185 | 50.833 | 3.209 | 11.999 | 1.00 | 86.84 | | N |
| ATOM | 919 CA VAL G 185 | 50.888 | 4.635 | 11.665 | 1.00 | 81.80 | | C |
| ATOM | 920 CB VAL G 185 | 52.336 | 5.149 | 11.526 | 1.00 | 20.00 | | C |
| ATOM | 921 CG1 VAL G 185 | 52.340 | 6.607 | 11.085 | 1.00 | 20.00 | | C |
| ATOM | 922 CG2 VAL G 185 | 53.086 | 4.984 | 12.838 | 1.00 | 20.00 | | C |
| ATOM | 923 C VAL G 185 | 50.097 | 5.027 | 10.417 | 1.00 | 81.69 | | C |
| ATOM | 924 O VAL G 185 | 50.205 | 6.157 | 9.942 | 1.00 | 99.84 | | O |
| ATOM | 925 N SER G 186 | 49.286 | 4.109 | 9.902 | 1.00 | 70.63 | | N |
| ATOM | 926 CA SER G 186 | 48.501 | 4.392 | 8.705 | 1.00 | 72.29 | | C |
| ATOM | 927 CB SER G 186 | 49.173 | 3.803 | 7.463 | 1.00 | 20.00 | | C |

APPENDIX-continued (APPENDIX discloses SEQ ID NOS 29-32, 29-32 and 29-32, respectively, in order of appearance)

| | | | |
|---|---|---|---|
| ATOM | 928 OG SER G 186 | 49.228 2.389 7.534 1.00 20.00 | O |
| ATOM | 929 C SER G 186 | 47.066 3.893 8.820 1.00 62.99 | C |
| ATOM | 930 O SER G 186 | 46.820 2.769 9.258 1.00 58.35 | O |
| ATOM | 931 N VAL G 187 | 46.122 4.736 8.415 1.00 66.49 | N |
| ATOM | 932 CA VAL G 187 | 44.709 4.389 8.471 1.00 57.36 | C |
| ATOM | 933 CB VAL G 187 | 43.834 5.635 8.704 1.00 20.00 | C |
| ATOM | 934 CG1 VAL G 187 | 42.371 5.248 8.769 1.00 20.00 | C |
| ATOM | 935 CG2 VAL G 187 | 44.254 6.346 9.982 1.00 20.00 | C |
| ATOM | 936 C VAL G 187 | 44.266 3.684 7.191 1.00 53.67 | C |
| ATOM | 937 O VAL G 187 | 44.408 4.222 6.093 1.00 50.10 | O |
| ATOM | 938 N LEU G 188 | 43.768 2.460 7.338 1.00 43.20 | N |
| ATOM | 939 CA LEU G 188 | 43.289 1.678 6.201 1.00 41.76 | C |
| ATOM | 940 CB LEU G 188 | 43.404 0.183 6.495 1.00 20.00 | C |
| ATOM | 941 CG LEU G 188 | 44.821 −0.375 6.633 1.00 20.00 | C |
| ATOM | 942 CD1 LEU G 188 | 44.777 −1.845 7.014 1.00 20.00 | C |
| ATOM | 943 CD2 LEU G 188 | 45.605 −0.174 5.345 1.00 20.00 | C |
| ATOM | 944 C LEU G 188 | 41.843 2.021 5.862 1.00 44.75 | C |
| ATOM | 945 O LEU G 188 | 41.384 1.777 4.746 1.00 45.28 | O |
| ATOM | 946 N THR G 189 | 41.111 2.500 6.863 1.00 39.28 | N |
| ATOM | 947 CA THR G 189 | 39.710 2.863 6.694 1.00 36.51 | C |
| ATOM | 948 CB THR G 189 | 38.985 1.880 5.760 1.00 20.00 | C |
| ATOM | 949 OG1 THR G 189 | 38.871 0.604 6.400 1.00 20.00 | O |
| ATOM | 950 CG2 THR G 189 | 39.759 1.715 4.458 1.00 20.00 | C |
| ATOM | 951 C THR G 189 | 39.006 2.891 8.046 1.00 45.83 | C |
| ATOM | 952 O THR G 189 | 39.637 3.112 9.079 1.00 42.57 | O |
| ATOM | 953 N SER G 190 | 37.692 2.695 8.033 1.00 40.44 | N |
| ATOM | 954 CA SER G 190 | 36.902 2.779 9.255 1.00 41.82 | C |
| ATOM | 955 CB SER G 190 | 35.919 3.953 9.188 1.00 20.00 | C |
| ATOM | 956 OG SER G 190 | 34.930 3.737 8.196 1.00 20.00 | O |
| ATOM | 957 C SER G 190 | 36.153 1.479 9.527 1.00 33.81 | C |
| ATOM | 958 O SER G 190 | 35.609 0.860 8.611 1.00 49.61 | O |
| ATOM | 959 N LYS G 191 | 36.134 1.069 10.791 1.00 37.37 | N |
| ATOM | 960 CA LYS G 191 | 35.365 −0.097 11.208 1.00 41.23 | C |
| ATOM | 961 CB LYS G 191 | 36.239 −1.047 12.027 1.00 20.00 | C |
| ATOM | 962 CG LYS G 191 | 37.323 −1.731 11.216 1.00 20.00 | C |
| ATOM | 963 CD LYS G 191 | 38.193 −2.623 12.085 1.00 20.00 | C |
| ATOM | 964 CE LYS G 191 | 39.313 −3.257 11.267 1.00 20.00 | C |
| ATOM | 965 NZ LYS G 191 | 40.316 −3.959 12.119 1.00 20.00 | N |
| ATOM | 966 C LYS G 191 | 34.143 0.315 12.018 1.00 35.03 | C |
| ATOM | 967 O LYS G 191 | 34.267 0.958 13.059 1.00 40.06 | O |
| ATOM | 968 N VAL G 192 | 32.966 −0.093 11.555 1.00 33.70 | N |
| ATOM | 969 CA VAL G 192 | 31.712 0.327 12.171 1.00 27.61 | C |
| ATOM | 970 CB VAL G 192 | 30.816 1.081 11.173 1.00 20.00 | C |
| ATOM | 971 CG1 VAL G 192 | 29.505 1.481 11.832 1.00 20.00 | C |
| ATOM | 972 CG2 VAL G 192 | 31.540 2.293 10.617 1.00 20.00 | C |
| ATOM | 973 C VAL G 192 | 30.929 −0.857 12.723 1.00 31.74 | C |
| ATOM | 974 O VAL G 192 | 30.965 −1.954 12.167 1.00 25.58 | O |
| ATOM | 975 N LEU G 193 | 30.177 −0.610 13.790 1.00 28.88 | N |
| ATOM | 976 CA LEU G 193 | 29.272 −1.609 14.342 1.00 34.36 | C |
| ATOM | 977 CB LEU G 193 | 29.940 −2.349 15.504 1.00 20.00 | C |
| ATOM | 978 CG LEU G 193 | 31.127 −3.249 15.156 1.00 20.00 | C |
| ATOM | 979 CD1 LEU G 193 | 31.818 −3.743 16.418 1.00 20.00 | C |
| ATOM | 980 CD2 LEU G 193 | 30.677 −4.419 14.295 1.00 20.00 | C |
| ATOM | 981 C LEU G 193 | 27.982 −0.950 14.818 1.00 33.03 | C |
| ATOM | 982 O LEU G 193 | 27.963 −0.290 15.856 1.00 44.93 | O |
| ATOM | 983 N ASP G 194 | 26.896 −1.170 14.081 1.00 35.09 | N |
| ATOM | 984 CA ASP G 194 | 25.724 −0.298 14.150 1.00 41.39 | C |
| ATOM | 985 CB ASP G 194 | 24.766 −0.589 12.995 1.00 20.00 | C |
| ATOM | 986 CG ASP G 194 | 25.292 −0.090 11.667 1.00 20.00 | C |
| ATOM | 987 OD1 ASP G 194 | 26.173 0.795 11.668 1.00 20.00 | O |
| ATOM | 988 OD2 ASP G 194 | 24.863 −0.620 10.621 1.00 20.00 | O |
| ATOM | 989 C ASP G 194 | 24.976 −0.377 15.479 1.00 38.04 | C |
| ATOM | 990 O ASP G 194 | 24.097 0.442 15.752 1.00 48.03 | O |
| ATOM | 991 N LEU G 195 | 25.259 −1.410 16.263 1.00 43.64 | N |
| ATOM | 992 CA LEU G 195 | 24.463 −1.682 17.449 1.00 35.97 | C |
| ATOM | 993 CB LEU G 195 | 23.832 −3.071 17.366 1.00 20.00 | C |
| ATOM | 994 CG LEU G 195 | 22.988 −3.340 16.117 1.00 20.00 | C |
| ATOM | 995 CD1 LEU G 195 | 22.479 −4.773 16.112 1.00 20.00 | C |
| ATOM | 996 CD2 LEU G 195 | 21.847 −2.340 15.969 1.00 20.00 | C |
| ATOM | 997 C LEU G 195 | 25.254 −1.525 18.744 1.00 43.63 | C |
| ATOM | 998 O LEU G 195 | 24.675 −1.495 19.830 1.00 34.71 | O |
| ATOM | 999 N ASN G 196 | 26.558 −1.299 18.617 1.00 44.30 | N |
| ATOM | 1000 CA ASN G 196 | 27.458 −1.365 19.765 1.00 42.38 | C |
| ATOM | 1000 CA ASN G 196 | 27.458 −1.365 19.765 1.00 42.38 | C |
| ATOM | 1001 CB ASNG 196 | 28.900 −1.082 19.342 1.00 20.00 | C |
| ATOM | 1002 CG ASN G 196 | 29.508 −2.223 18.551 1.00 20.00 | C |
| ATOM | 1003 OD1 ASN G 196 | 29.101 −3.377 18.688 1.00 20.00 | O |

APPENDIX-continued (APPENDIX discloses SEQ ID NOS 29-32, 29-32 and 29-32, respectively, in order of appearance)

| | | | | |
|---|---|---|---|---|
| ATOM | 1004 ND2 ASN G 196 | 30.503 −1.908 17.731 1.00 20.00 | N |
| ATOM | 1005 C ASN G 196 | 27.041 −0.434 20.900 1.00 43.66 | C |
| ATOM | 1006 O ASN G 196 | 26.944 −0.855 22.053 1.00 33.62 | O |
| ATOM | 1007 N ASN G 197 | 26.706 0.806 20.560 1.00 34.31 | N |
| ATOM | 1008 CA ASN G 197 | 26.346 1.793 21.570 1.00 38.83 | C |
| ATOM | 1009 CB ASN G 197 | 26.089 3.153 20.926 1.00 20.00 | C |
| ATOM | 1010 CG ASN G 197 | 27.362 3.819 20.456 1.00 20.00 | C |
| ATOM | 1011 OD1 ASN G 197 | 28.459 3.458 20.880 1.00 20.00 | O |
| ATOM | 1012 ND2 ASN G 197 | 27.228 4.768 19.541 1.00 20.00 | N |
| ATOM | 1013 C ASN G 197 | 25.139 1.365 22.392 1.00 39.90 | C |
| ATOM | 1014 O ASN G 197 | 25.185 1.357 23.621 1.00 39.04 | O |
| ATOM | 1015 N TYR G 198 | 24.065 0.992 21.705 1.00 35.09 | N |
| ATOM | 1016 CA TYR G 198 | 22.875 0.482 22.373 1.00 41.03 | C |
| ATOM | 1017 CB TYR G 198 | 21.804 0.093 21.352 1.00 20.00 | C |
| ATOM | 1018 CG TYR G 198 | 21.274 1.257 20.549 1.00 20.00 | C |
| ATOM | 1019 CD1 TYR G 198 | 20.238 2.041 21.031 1.00 20.00 | C |
| ATOM | 1020 CE1 TYR G 198 | 19.753 3.105 20.299 1.00 20.00 | C |
| ATOM | 1021 CZ TYR G 198 | 20.310 3.398 19.069 1.00 20.00 | C |
| ATOM | 1022 OH TYR G 198 | 19.829 4.450 18.325 1.00 20.00 | O |
| ATOM | 1023 CE2 TYR G 198 | 21.321 2.616 18.559 1.00 20.00 | C |
| ATOM | 1024 CD2 TYR G 198 | 21.799 1.557 19.299 1.00 20.00 | C |
| ATOM | 1025 C TYR G 198 | 23.219 −0.712 23.252 1.00 43.65 | C |
| ATOM | 1026 O TYR G 198 | 22.800 −0.783 24.406 1.00 52.37 | O |
| ATOM | 1027 N ILE G 199 | 24.079 −1.587 22.744 1.00 35.86 | N |
| ATOM | 1028 CA ILE G 199 | 24.490 −2.772 23.486 1.00 45.39 | C |
| ATOM | 1029 CB ILE G 199 | 25.380 −3.704 22.627 1.00 20.00 | C |
| ATOM | 1030 CG1 ILE G 199 | 24.556 −4.357 21.512 1.00 20.00 | C |
| ATOM | 1031 CD1 ILE G 199 | 25.365 −5.260 20.598 1.00 20.00 | C |
| ATOM | 1032 CG2 ILE G 199 | 26.037 −4.775 23.487 1.00 20.00 | C |
| ATOM | 1033 C ILE G 199 | 25.210 −2.392 24.779 1.00 37.89 | C |
| ATOM | 1034 O ILE G 199 | 24.808 −2.808 25.865 1.00 45.28 | O |
| ATOM | 1035 N ASP G 200 | 26.185 −1.495 24.669 1.00 37.36 | N |
| ATOM | 1036 CA ASP G 200 | 26.988 −1.098 25.821 1.00 46.66 | C |
| ATOM | 1037 CB ASP G 200 | 28.069 −0.096 25.405 1.00 20.00 | C |
| ATOM | 1038 CG ASP G 200 | 29.216 −0.751 24.660 1.00 20.00 | C |
| ATOM | 1039 OD1 ASP G 200 | 29.360 −1.989 24.751 1.00 20.00 | O |
| ATOM | 1040 OD2 ASP G 200 | 29.996 −0.025 24.009 1.00 20.00 | O |
| ATOM | 1041 C ASP G 200 | 26.109 −0.506 26.916 1.00 51.05 | C |
| ATOM | 1042 O ASP G 200 | 26.370 −0.693 28.105 1.00 57.39 | O |
| ATOM | 1043 N LYS G 201 | 25.004 0.108 26.507 1.00 57.68 | N |
| ATOM | 1044 CA LYS G 201 | 24.104 0.766 27.443 1.00 44.02 | C |
| ATOM | 1045 CB LYS G 201 | 23.138 1.687 26.698 1.00 20.00 | C |
| ATOM | 1046 CG LYS G 201 | 23.815 2.816 25.941 1.00 20.00 | C |
| ATOM | 1047 CD LYS G 201 | 22.797 3.680 25.223 1.00 20.00 | C |
| ATOM | 1048 CE LYS G 201 | 23.464 4.802 24.446 1.00 20.00 | C |
| ATOM | 1049 NZ LYS G 201 | 22.489 5.542 23.596 1.00 20.00 | N |
| ATOM | 1050 C LYS G 201 | 23.325 −0.250 28.274 1.00 43.56 | C |
| ATOM | 1051 O LYS G 201 | 22.868 0.060 29.374 1.00 51.34 | O |
| ATOM | 1052 N GLN G 202 | 23.218 −1.475 27.764 1.00 46.06 | N |
| ATOM | 1053 CA GLN G 202 | 22.308 −2.472 28.333 1.00 44.95 | C |
| ATOM | 1054 CB GLN G 202 | 21.324 −2.975 27.277 1.00 20.00 | C |
| ATOM | 1055 CG GLN G 202 | 20.207 −1.997 26.966 1.00 20.00 | C |
| ATOM | 1056 CD GLN G 202 | 19.339 −2.450 25.809 1.00 20.00 | C |
| ATOM | 1057 OE1 GLN G 202 | 19.694 −3.372 25.074 1.00 20.00 | O |
| ATOM | 1058 NE2 GLN G 202 | 18.171 −1.835 25.672 1.00 20.00 | N |
| ATOM | 1059 C GLN G 202 | 23.029 −3.657 28.974 1.00 42.35 | C |
| ATOM | 1060 O GLN G 202 | 22.446 −4.374 29.787 1.00 47.00 | O |
| ATOM | 1061 N LEU G 203 | 24.253 −3.922 28.530 1.00 49.55 | N |
| ATOM | 1062 CA LEU G 203 | 25.003 −5.081 29.008 1.00 50.77 | C |
| ATOM | 1063 CB LEU G 203 | 26.244 −5.322 28.140 1.00 20.00 | C |
| ATOM | 1064 CG LEU G 203 | 26.031 −5.802 26.698 1.00 20.00 | C |
| ATOM | 1065 CD1 LEU G 203 | 27.361 −5.942 25.970 1.00 20.00 | C |
| ATOM | 1066 CD2 LEU G 203 | 25.263 −7.115 26.661 1.00 20.00 | C |
| ATOM | 1067 C LEU G 203 | 25.397 −4.938 30.479 1.00 52.51 | C |
| ATOM | 1068 O LEU G 203 | 25.830 −3.873 30.918 1.00 46.02 | O |
| ATOM | 1069 N LEU G 204 | 25.226 −6.017 31.238 1.00 51.45 | N |
| ATOM | 1070 CA LEU G 204 | 25.644 −6.053 32.635 1.00 58.44 | C |
| ATOM | 1071 CB LEU G 204 | 24.863 −7.127 33.399 1.00 20.00 | C |
| ATOM | 1072 CG LEU G 204 | 23.352 −6.918 33.522 1.00 20.00 | C |
| ATOM | 1073 CD1 LEU G 204 | 22.691 −8.136 34.147 1.00 20.00 | C |
| ATOM | 1074 CD2 LEU G 204 | 23.044 −5.665 34.328 1.00 20.00 | C |
| ATOM | 1075 C LEU G 204 | 27.146 −6.307 32.759 1.00 54.99 | C |
| ATOM | 1076 O LEU G 204 | 27.710 −7.096 31.998 1.00 55.13 | O |
| ATOM | 1077 N PRO G 205 | 27.783 −5.693 33.770 1.00 58.64 | N |
| ATOM | 1078 CA PRO G 205 | 29.236 −5.775 33.842 1.00 52.19 | C |
| ATOM | 1079 CB PRO G 205 | 29.551 −5.040 35.142 1.00 20.00 | C |
| ATOM | 1080 CG PRO G 205 | 28.379 −5.337 36.014 1.00 20.00 | C |

APPENDIX-continued (APPENDIX discloses SEQ ID NOS 29-32, 29-32 and 29-32, respectively, in order of appearance)

| | | | |
|---|---|---|---|
| ATOM | 1081 CD PRO G 205 | 27.182 −5.464 35.099 1.00 20.00 | C |
| ATOM | 1082 C PRO G 205 | 29.647 −7.230 33.970 1.00 54.30 | C |
| ATOM | 1083 O PRO G 205 | 30.783 −7.593 33.663 1.00 70.22 | O |
| ATOM | 1084 N ILE G 206 | 28.709 −8.050 34.430 1.00 62.70 | N |
| ATOM | 1085 CA ILE G 206 | 28.925 −9.480 34.557 1.00 68.19 | C |
| ATOM | 1086 CB ILE G 206 | 29.450 −9.843 35.957 1.00 20.00 | C |
| ATOM | 1087 CG1 ILE G 206 | 30.853 −9.269 36.164 1.00 20.00 | C |
| ATOM | 1088 CD1 ILE G 206 | 31.328 −9.317 37.600 1.00 20.00 | C |
| ATOM | 1089 CG2 ILE G 206 | 29.454 −11.352 36.151 1.00 20.00 | C |
| ATOM | 1090 C ILE G 206 | 27.618 −10.223 34.304 1.00 62.35 | C |
| ATOM | 1091 O ILE G 206 | 26.548 −9.772 34.715 1.00 67.16 | O |
| ATOM | 1092 N VAL G 207 | 27.702 −11.314 33.552 1.00 52.22 | N |
| ATOM | 1093 CA VAL G 207 | 26.527 −12.112 33.234 1.00 51.31 | C |
| ATOM | 1094 CB VAL G 207 | 26.414 −12.378 31.722 1.00 20.00 | C |
| ATOM | 1095 CG1 VAL G 207 | 25.235 −13.293 31.430 1.00 20.00 | C |
| ATOM | 1096 CG2 VAL G 207 | 26.279 −11.066 30.963 1.00 20.00 | C |
| ATOM | 1097 C VAL G 207 | 26.546 −13.438 33.985 1.00 62.09 | C |
| ATOM | 1098 O VAL G 207 | 27.257 −14.369 33.605 1.00 58.88 | O |
| ATOM | 1099 N ASN G 208 | 25.828 −13.484 35.102 1.00 71.72 | N |
| ATOM | 1100 CA ASN G 208 | 25.723 −14.698 35.900 1.00 70.92 | C |
| ATOM | 1101 CB ASN G 208 | 25.837 −14.370 37.390 1.00 20.00 | C |
| ATOM | 1102 CG ASN G 208 | 27.235 −13.938 37.787 1.00 20.00 | C |
| ATOM | 1103 OD1 ASN G 208 | 28.216 −14.286 37.129 1.00 20.00 | O |
| ATOM | 1104 ND2 ASN G 208 | 27.335 −13.190 38.880 1.00 20.00 | N |
| ATOM | 1105 C ASN G 208 | 24.423 −15.446 35.628 1.00 63.05 | C |
| ATOM | 1106 O ASN G 208 | 23.637 −15.050 34.767 1.00 61.34 | O |
| ATOM | 1107 N LYS G 209 | 24.168 −16.485 36.418 1.00 68.91 | N |
| ATOM | 1108 CA LYS G 209 | 23.006 −17.341 36.212 1.00 59.11 | C |
| ATOM | 1109 CB LYS G 209 | 23.129 −18.620 37.043 1.00 20.00 | C |
| ATOM | 1110 CG LYS G 209 | 24.239 −19.552 36.588 1.00 20.00 | C |
| ATOM | 1111 CD LYS G 209 | 24.335 −20.774 37.486 1.00 20.00 | C |
| ATOM | 1112 CE LYS G 209 | 25.423 −21.724 37.012 1.00 20.00 | C |
| ATOM | 1113 NZ LYS G 209 | 25.548 −22.912 37.901 1.00 20.00 | N |
| ATOM | 1114 C LYS G 209 | 21.696 −16.628 36.539 1.00 50.69 | C |
| ATOM | 1115 O LYS G 209 | 20.616 −17.121 36.212 1.00 51.01 | O |
| ATOM | 1116 N GLN G 210 | 21.792 −15.499 37.235 1.00 44.68 | N |
| ATOM | 1117 CA GLN G 210 | 20.621 −14.676 37.518 1.00 49.52 | C |
| ATOM | 1118 CB GLN G 210 | 20.828 −13.874 38.806 1.00 20.00 | C |
| ATOM | 1119 CG GLN G 210 | 20.877 −14.719 40.070 1.00 20.00 | C |
| ATOM | 1120 CD GLN G 210 | 21.149 −13.893 41.313 1.00 20.00 | C |
| ATOM | 1121 OE1 GLN G 210 | 21.709 −12.800 41.237 1.00 20.00 | O |
| ATOM | 1122 NE2 GLN G 210 | 20.755 −14.417 42.469 1.00 20.00 | N |
| ATOM | 1123 C GLN G 210 | 20.336 −13.730 36.356 1.00 62.08 | C |
| ATOM | 1124 O GLN G 210 | 19.271 −13.785 35.741 1.00 80.43 | O |
| ATOM | 1125 N SER G 211 | 21.324 −12.905 36.028 1.00 58.92 | N |
| ATOM | 1126 CA SER G 211 | 21.231 −11.987 34.898 1.00 47.88 | C |
| ATOM | 1127 CB SER G 211 | 22.594 −11.350 34.621 1.00 20.00 | C |
| ATOM | 1128 OG SER G 211 | 23.553 −12.334 34.274 1.00 20.00 | O |
| ATOM | 1129 C SER G 211 | 20.722 −12.689 33.642 1.00 57.32 | C |
| ATOM | 1130 O SER G 211 | 19.919 −12.133 32.893 1.00 50.74 | O |
| ATOM | 1131 N CYS G 212 | 21.149 −13.934 33.451 1.00 44.34 | N |
| ATOM | 1132 CA CYS G 212 | 20.890 −14.659 32.210 1.00 57.52 | C |
| ATOM | 1133 CB CYS G 212 | 21.127 −16.180 32.363 1.00 20.00 | C |
| ATOM | 1134 SG CYS G 212 | 22.836 −16.682 32.889 1.00 20.00 | S |
| ATOM | 1135 C CYS G 212 | 19.541 −14.314 31.540 1.00 60.91 | C |
| ATOM | 1136 O CYS G 212 | 19.536 −13.729 30.460 1.00 52.17 | O |
| ATOM | 1137 N SER G 213 | 18.465 −14.813 32.151 1.00 21.55 | N |
| ATOM | 1138 CA SER G 213 | 17.107 −14.631 31.656 1.00 21.67 | C |
| ATOM | 1139 CB SER G 213 | 16.133 −15.512 32.444 1.00 21.81 | C |
| ATOM | 1140 OG SER G 213 | 16.471 −16.882 32.323 1.00 23.00 | O |
| ATOM | 1141 C SER G 213 | 16.633 −13.188 31.682 1.00 21.45 | C |
| ATOM | 1142 O SER G 213 | 16.026 −12.728 30.722 1.00 21.98 | O |
| ATOM | 1143 N ILE G 214 | 16.856 −12.475 32.783 1.00 20.90 | N |
| ATOM | 1144 CA ILE G 214 | 16.585 −11.050 32.758 1.00 20.45 | C |
| ATOM | 1145 CB ILE G 214 | 16.587 −10.444 34.170 1.00 20.53 | C |
| ATOM | 1146 CG1 ILE G 214 | 15.498 −11.091 35.029 1.00 20.46 | C |
| ATOM | 1147 CD1 ILE G 214 | 15.418 −10.535 36.434 1.00 21.75 | C |
| ATOM | 1148 CG2 ILE G 214 | 16.393 −8.937 34.103 1.00 20.34 | C |
| ATOM | 1149 C ILE G 214 | 17.686 −10.409 31.926 1.00 20.15 | C |
| ATOM | 1150 O ILE G 214 | 17.435 −9.671 30.968 1.00 19.91 | O |
| ATOM | 1151 N SER G 215 | 18.918 −10.770 32.280 1.00 19.84 | N |
| ATOM | 1152 CA SER G 215 | 20.109 −10.297 31.594 1.00 19.58 | C |
| ATOM | 1153 CB SER G 215 | 21.369 −10.722 32.349 1.00 19.76 | C |
| ATOM | 1154 OG SER G 215 | 22.538 −10.269 31.688 1.00 19.97 | O |
| ATOM | 1155 C SER G 215 | 20.132 −10.852 30.189 1.00 19.34 | C |
| ATOM | 1156 O SER G 215 | 20.448 −10.152 29.230 1.00 19.54 | O |
| ATOM | 1157 N ASN G 216 | 19.774 −12.125 30.082 1.00 18.80 | N |

APPENDIX-continued (APPENDIX discloses SEQ ID NOS 29-32, 29-32 and 29-32, respectively, in order of appearance)

| | | | |
|---|---|---|---|
| ATOM | 1158 CA ASN G 216 | 19.738 −12.791 28.798 1.00 18.36 | C |
| ATOM | 1159 CB ASN G 216 | 19.394 −14.271 28.966 1.00 18.41 | C |
| ATOM | 1160 CG ASN G 216 | 20.426 −15.020 29.786 1.00 19.55 | C |
| ATOM | 1161 OD1 ASN G 216 | 20.308 −16.227 30.000 1.00 20.52 | O |
| ATOM | 1162 ND2 ASN G 216 | 21.445 −14.306 30.250 1.00 20.43 | N |
| ATOM | 1163 C ASN G 216 | 18.708 −12.107 27.927 1.00 17.78 | C |
| ATOM | 1164 O ASN G 216 | 18.930 −11.905 26.744 1.00 17.91 | O |
| ATOM | 1165 N ILE G 217 | 17.578 −11.750 28.527 1.00 17.02 | N |
| ATOM | 1166 CA ILE G 217 | 16.502 −11.089 27.804 1.00 16.60 | C |
| ATOM | 1167 CB ILE G 217 | 15.247 −10.916 28.680 1.00 16.46 | C |
| ATOM | 1168 CG1 ILE G 217 | 14.608 −12.275 28.969 1.00 16.26 | C |
| ATOM | 1169 CD1 ILE G 217 | 13.360 −12.195 29.822 1.00 16.44 | C |
| ATOM | 1170 CG2 ILE G 217 | 14.251 −9.987 28.005 1.00 16.70 | C |
| ATOM | 1171 C ILE G 217 | 16.953 −9.731 27.297 1.00 16.73 | C |
| ATOM | 1172 O ILE G 217 | 16.658 −9.355 26.166 1.00 16.80 | O |
| ATOM | 1173 N GLU G 218 | 17.679 −9.000 28.137 1.00 17.02 | N |
| ATOM | 1174 CA GLU G 218 | 18.177 −7.692 27.741 1.00 17.70 | C |
| ATOM | 1175 CB GLU G 218 | 18.867 −6.998 28.916 1.00 18.20 | C |
| ATOM | 1176 CG GLU G 218 | 17.955 −6.748 30.106 1.00 21.31 | C |
| ATOM | 1177 CD GLU G 218 | 18.652 −6.004 31.228 1.00 25.72 | C |
| ATOM | 1178 OE1 GLU G 218 | 18.016 −5.781 32.279 1.00 26.96 | O |
| ATOM | 1179 OE2 GLU G 218 | 19.834 −5.640 31.058 1.00 27.07 | O |
| ATOM | 1180 C GLU G 218 | 19.144 −7.855 26.578 1.00 17.29 | C |
| ATOM | 1181 O GLU G 218 | 19.123 −7.081 25.617 1.00 17.62 | O |
| ATOM | 1182 N THR G 219 | 19.983 −8.882 26.667 1.00 16.62 | N |
| ATOM | 1183 CA THR G 219 | 20.964 −9.150 25.630 1.00 15.95 | C |
| ATOM | 1184 CB THR G 219 | 21.879 −10.328 26.007 1.00 15.95 | C |
| ATOM | 1185 OG1 THR G 219 | 22.582 −10.021 27.218 1.00 15.63 | O |
| ATOM | 1186 CG2 THR G 219 | 22.884 −10.597 24.897 1.00 15.97 | C |
| ATOM | 1187 C THR G 219 | 20.250 −9.470 24.330 1.00 15.64 | C |
| ATOM | 1188 O THR G 219 | 20.656 −9.022 23.267 1.00 15.93 | O |
| ATOM | 1189 N VAL G 220 | 19.179 −10.248 24.431 1.00 14.98 | N |
| ATOM | 1190 CA VAL G 220 | 18.390 −10.644 23.278 1.00 14.51 | C |
| ATOM | 1191 CB VAL G 220 | 17.285 −11.644 23.665 1.00 14.29 | C |
| ATOM | 1192 CG1 VAL G 220 | 16.474 −12.037 22.440 1.00 14.24 | C |
| ATOM | 1193 CG2 VAL G 220 | 17.890 −12.871 24.329 1.00 14.10 | C |
| ATOM | 1194 C VAL G 220 | 17.759 −9.424 22.636 1.00 14.64 | C |
| ATOM | 1195 O VAL G 220 | 17.718 −9.315 21.420 1.00 14.79 | O |
| ATOM | 1196 N ILE G 221 | 17.264 −8.510 23.463 1.00 14.43 | N |
| ATOM | 1197 CA ILE G 221 | 16.658 −7.287 22.959 1.00 14.36 | C |
| ATOM | 1198 CB ILE G 221 | 16.046 −6.448 24.095 1.00 14.03 | C |
| ATOM | 1199 CG1 ILE G 221 | 14.955 −7.243 24.816 1.00 13.72 | C |
| ATOM | 1200 CD1 ILE G 221 | 13.820 −7.679 23.914 1.00 14.17 | C |
| ATOM | 1201 CG2 ILE G 221 | 15.487 −5.142 23.550 1.00 13.91 | C |
| ATOM | 1202 C ILE G 221 | 17.700 −6.459 22.222 1.00 14.82 | C |
| ATOM | 1203 O ILE G 221 | 17.427 −5.902 21.158 1.00 14.82 | O |
| ATOM | 1204 N GLU G 222 | 18.901 −6.390 22.788 1.00 15.51 | N |
| ATOM | 1205 CA GLU G 222 | 19.983 −5.640 22.165 1.00 16.52 | C |
| ATOM | 1206 CB GLU G 222 | 21.211 −5.601 23.076 1.00 16.80 | C |
| ATOM | 1207 CG GLU G 222 | 20.971 −4.899 24.403 1.00 19.14 | C |
| ATOM | 1208 CD GLU G 222 | 22.231 −4.780 25.236 1.00 22.62 | C |
| ATOM | 1209 OE1 GLU G 222 | 22.152 −4.246 26.362 1.00 24.35 | O |
| ATOM | 1210 OE2 GLU G 222 | 23.301 −5.219 24.765 1.00 23.98 | O |
| ATOM | 1211 C GLU G 222 | 20.335 −6.269 20.825 1.00 16.65 | C |
| ATOM | 1212 O GLU G 222 | 20.599 −5.574 19.842 1.00 16.95 | O |
| ATOM | 1213 N PHE G 223 | 20.339 −7.597 20.802 1.00 16.70 | N |
| ATOM | 1214 CA PHE G 223 | 20.652 −8.350 19.603 1.00 16.95 | C |
| ATOM | 1215 CB PHE G 223 | 20.705 −9.848 19.904 1.00 16.85 | C |
| ATOM | 1216 CG PHE G 223 | 21.104 −10.689 18.724 1.00 17.23 | C |
| ATOM | 1217 CD1 PHE G 223 | 22.438 −10.954 18.465 1.00 17.98 | C |
| ATOM | 1218 CE1 PHE G 223 | 22.808 −11.727 17.381 1.00 18.28 | C |
| ATOM | 1219 CZ PHE G 223 | 21.842 −12.243 16.541 1.00 18.19 | C |
| ATOM | 1220 CE2 PHE G 223 | 20.508 −11.986 16.788 1.00 18.14 | C |
| ATOM | 1221 CD2 PHE G 223 | 20.144 −11.213 17.874 1.00 17.75 | C |
| ATOM | 1222 C PHE G 223 | 19.610 −8.066 18.540 1.00 17.28 | C |
| ATOM | 1223 O PHE G 223 | 19.945 −7.907 17.382 1.00 17.17 | O |
| ATOM | 1224 N GLN G 224 | 18.348 −8.003 18.948 1.00 17.62 | N |
| ATOM | 1225 CA GLN G 224 | 17.243 −7.712 18.044 1.00 18.16 | C |
| ATOM | 1226 CB GLN G 224 | 15.898 −7.868 18.757 1.00 18.51 | C |
| ATOM | 1227 CG GLN G 224 | 15.586 −9.296 19.178 1.00 20.06 | C |
| ATOM | 1228 CD GLN G 224 | 14.158 −9.465 19.658 1.00 22.03 | C |
| ATOM | 1229 OE1 GLN G 224 | 13.769 −10.539 20.117 1.00 22.15 | O |
| ATOM | 1230 NE2 GLN G 224 | 13.368 −8.403 19.552 1.00 22.11 | N |
| ATOM | 1231 C GLN G 224 | 17.387 −6.309 17.475 1.00 18.04 | C |
| ATOM | 1232 O GLN G 224 | 17.090 −6.068 16.306 1.00 18.17 | O |
| ATOM | 1233 N GLN G 225 | 17.819 −5.382 18.323 1.00 17.90 | N |
| ATOM | 1234 CA GLN G 225 | 18.051 −4.012 17.894 1.00 17.95 | C |

APPENDIX-continued (APPENDIX discloses SEQ ID NOS 29-32, 29-32 and 29-32, respectively, in order of appearance)

| | | | |
|---|---|---|---|
| ATOM | 1235 CB GLN G 225 | 18.389 −3.120 19.090 1.00 18.13 | C |
| ATOM | 1236 CG GLN G 225 | 17.267 −3.006 20.109 1.00 19.04 | C |
| ATOM | 1237 CD GLN G 225 | 17.588 −2.034 21.227 1.00 21.22 | C |
| ATOM | 1238 OE1 GLN G 225 | 18.661 −1.431 21.252 1.00 22.55 | O |
| ATOM | 1239 NE2 GLN G 225 | 16.656 −1.876 22.159 1.00 22.48 | N |
| ATOM | 1240 C GLN G 225 | 19.168 −3.958 16.855 1.00 17.84 | C |
| ATOM | 1241 O GLN G 225 | 19.061 −3.239 15.861 1.00 17.71 | O |
| ATOM | 1242 N LYS G 226 | 20.235 −4.724 17.077 1.00 17.95 | N |
| ATOM | 1243 CA LYS G 226 | 21.328 −4.762 16.112 1.00 18.00 | C |
| ATOM | 1244 CB LYS G 226 | 22.486 −5.613 16.634 1.00 18.21 | C |
| ATOM | 1245 CG LYS G 226 | 23.157 −5.048 17.875 1.00 18.50 | C |
| ATOM | 1246 CD LYS G 226 | 24.365 −5.878 18.279 1.00 19.87 | C |
| ATOM | 1247 CE LYS G 226 | 25.066 −5.278 19.487 1.00 21.36 | C |
| ATOM | 1248 NZ LYS G 226 | 26.270 −6.061 19.878 1.00 21.83 | N |
| ATOM | 1249 C LYS G 226 | 20.772 −5.345 14.826 1.00 17.84 | C |
| ATOM | 1250 O LYS G 226 | 21.062 −4.880 13.723 1.00 17.94 | O |
| ATOM | 1251 N ASN G 227 | 19.954 −6.374 15.002 1.00 17.70 | N |
| ATOM | 1252 CA ASN G 227 | 19.238 −7.032 13.932 1.00 17.66 | C |
| ATOM | 1253 CB ASN G 227 | 18.471 −8.244 14.459 1.00 17.36 | C |
| ATOM | 1254 CG ASN G 227 | 19.384 −9.296 15.057 1.00 17.40 | C |
| ATOM | 1255 OD1 ASN G 227 | 18.929 −10.350 15.502 1.00 17.84 | O |
| ATOM | 1256 ND2 ASN G 227 | 20.682 −9.015 15.070 1.00 17.22 | N |
| ATOM | 1257 C ASN G 227 | 18.287 −6.028 13.328 1.00 17.76 | C |
| ATOM | 1258 O ASN G 227 | 18.159 −5.956 12.106 1.00 17.92 | O |
| ATOM | 1259 N ASN G 228 | 17.627 −5.226 14.164 1.00 17.78 | N |
| ATOM | 1260 CA ASN G 228 | 16.800 −4.172 13.548 1.00 17.59 | C |
| ATOM | 1261 CB ASN G 228 | 15.958 −3.344 14.528 1.00 17.89 | C |
| ATOM | 1262 CG ASN G 228 | 15.101 −2.277 13.809 1.00 18.43 | C |
| ATOM | 1263 OD1 ASN G 228 | 15.506 −1.119 13.688 1.00 18.74 | O |
| ATOM | 1264 ND2 ASN G 228 | 13.998 −2.715 13.205 1.00 18.61 | N |
| ATOM | 1265 C ASN G 228 | 17.603 −3.255 12.662 1.00 17.09 | C |
| ATOM | 1266 O ASN G 228 | 17.657 −3.466 11.456 1.00 17.17 | O |
| ATOM | 1267 N ARG G 229 | 18.197 −2.211 13.224 1.00 16.33 | N |
| ATOM | 1268 CA ARG G 229 | 19.046 −1.400 12.381 1.00 15.76 | C |
| ATOM | 1269 CB ARG G 229 | 19.957 −0.486 13.184 1.00 15.70 | C |
| ATOM | 1270 CG ARG G 229 | 20.207 0.822 12.468 1.00 14.99 | C |
| ATOM | 1271 CD ARG G 229 | 21.391 1.555 13.041 1.00 15.33 | C |
| ATOM | 1272 NE ARG G 229 | 22.116 2.303 12.021 1.00 15.59 | N |
| ATOM | 1273 CZ ARG G 229 | 23.182 3.053 12.276 1.00 15.85 | C |
| ATOM | 1274 NH1 ARG G 229 | 23.593 3.214 13.525 1.00 16.20 | N |
| ATOM | 1275 NH2 ARG G 229 | 23.859 3.614 11.285 1.00 16.63 | N |
| ATOM | 1276 C ARG G 229 | 19.863 −2.343 11.516 1.00 15.62 | C |
| ATOM | 1277 O ARG G 229 | 19.671 −2.402 10.304 1.00 15.73 | O |
| ATOM | 1278 N LEU G 230 | 20.612 −3.225 12.168 1.00 15.46 | N |
| ATOM | 1279 CA LEU G 230 | 21.409 −4.212 11.454 1.00 15.22 | C |
| ATOM | 1280 CB LEU G 230 | 22.161 −5.113 12.432 1.00 15.08 | C |
| ATOM | 1281 CG LEU G 230 | 23.055 −6.187 11.808 1.00 14.70 | C |
| ATOM | 1282 CD1 LEU G 230 | 24.375 −5.579 11.364 1.00 15.19 | C |
| ATOM | 1283 CD2 LEU G 230 | 23.300 −7.324 12.791 1.00 15.46 | C |
| ATOM | 1284 C LEU G 230 | 20.565 −5.055 10.501 1.00 15.31 | C |
| ATOM | 1285 O LEU G 230 | 20.963 −5.294 9.362 1.00 15.46 | O |
| ATOM | 1286 N LEU G 231 | 19.444 −5.573 10.997 1.00 15.48 | N |
| ATOM | 1287 CA LEU G 231 | 18.581 −6.442 10.197 1.00 15.75 | C |
| ATOM | 1288 CB LEU G 231 | 17.308 −6.793 10.967 1.00 15.90 | C |
| ATOM | 1289 CG LEU G 231 | 17.482 −7.640 12.226 1.00 16.63 | C |
| ATOM | 1290 CD1 LEU G 231 | 16.128 −8.049 12.772 1.00 18.45 | C |
| ATOM | 1291 CD2 LEU G 231 | 18.348 −8.858 11.954 1.00 16.67 | C |
| ATOM | 1292 C LEU G 231 | 18.210 −5.785 8.872 1.00 15.76 | C |
| ATOM | 1293 O LEU G 231 | 18.203 −6.432 7.824 1.00 15.84 | O |
| ATOM | 1294 N GLU G 232 | 17.824 −4.516 8.943 1.00 15.71 | N |
| ATOM | 1295 CA GLU G 232 | 17.298 −3.811 7.786 1.00 15.93 | C |
| ATOM | 1296 CB GLU G 232 | 16.537 −2.565 8.229 1.00 16.15 | C |
| ATOM | 1297 CG GLU G 232 | 15.461 −2.846 9.254 1.00 18.59 | C |
| ATOM | 1298 CD GLU G 232 | 14.077 −2.874 8.644 1.00 21.47 | C |
| ATOM | 1299 OE1 GLU G 232 | 13.964 −3.077 7.415 1.00 22.14 | O |
| ATOM | 1300 OE2 GLU G 232 | 13.100 −2.664 9.393 1.00 23.34 | O |
| ATOM | 1301 C GLU G 232 | 18.399 −3.431 6.806 1.00 15.45 | C |
| ATOM | 1302 O GLU G 232 | 18.169 −3.373 5.601 1.00 15.95 | O |
| ATOM | 1303 N ILE G 233 | 19.594 −3.169 7.323 1.00 14.54 | N |
| ATOM | 1304 CA ILE G 233 | 20.774 −3.128 6.476 1.00 13.69 | C |
| ATOM | 1305 CB ILE G 233 | 22.049 −2.830 7.281 1.00 13.63 | C |
| ATOM | 1306 CG1 ILE G 233 | 21.823 −1.640 8.211 1.00 13.58 | C |
| ATOM | 1307 CD1 ILE G 233 | 23.101 −0.917 8.578 1.00 13.55 | C |
| ATOM | 1308 CG2 ILE G 233 | 23.215 −2.543 6.348 1.00 13.88 | C |
| ATOM | 1309 C ILE G 233 | 20.927 −4.450 5.736 1.00 13.28 | C |
| ATOM | 1310 O ILE G 233 | 20.979 −4.473 4.508 1.00 13.04 | O |
| ATOM | 1311 N THR G 234 | 20.758 −5.546 6.469 1.00 13.18 | N |

APPENDIX-continued (APPENDIX discloses SEQ ID NOS 29-32, 29-32 and 29-32, respectively, in order of appearance)

| | | | |
|---|---|---|---|
| ATOM | 1312 CA THR G 234 | 21.038 −6.878 5.940 1.00 13.39 | C |
| ATOM | 1313 CB THR G 234 | 20.839 −7.965 7.015 1.00 13.21 | C |
| ATOM | 1314 OG1 THR G 234 | 21.845 −7.836 8.028 1.00 13.15 | O |
| ATOM | 1315 CG2 THR G 234 | 20.916 −9.351 6.394 1.00 13.22 | C |
| ATOM | 1316 C THR G 234 | 20.146 −7.204 4.748 1.00 13.76 | C |
| ATOM | 1317 O THR G 234 | 20.606 −7.766 3.753 1.00 13.95 | O |
| ATOM | 1318 N ARG G 235 | 18.849 −6.966 4.911 1.00 14.26 | N |
| ATOM | 1319 CA ARG G 235 | 17.891 −7.151 3.826 1.00 14.92 | C |
| ATOM | 1320 CB ARG G 235 | 16.463 −6.925 4.328 1.00 15.30 | C |
| ATOM | 1321 CG ARG G 235 | 15.771 −5.712 3.722 1.00 16.27 | C |
| ATOM | 1322 CD ARG G 235 | 14.867 −5.020 4.735 1.00 18.52 | C |
| ATOM | 1323 NE ARG G 235 | 14.345 −5.948 5.734 1.00 17.86 | N |
| ATOM | 1324 CZ ARG G 235 | 13.438 −6.884 5.478 1.00 16.91 | C |
| ATOM | 1325 NH1 ARG G 235 | 12.970 −7.035 4.248 1.00 16.59 | N |
| ATOM | 1326 NH2 ARG G 235 | 13.018 −7.687 6.444 1.00 16.86 | N |
| ATOM | 1327 C ARG G 235 | 18.192 −6.211 2.665 1.00 15.05 | C |
| ATOM | 1328 O ARG G 235 | 18.292 −6.640 1.517 1.00 15.15 | O |
| ATOM | 1329 N GLU G 236 | 18.386 −4.935 2.984 1.00 15.18 | N |
| ATOM | 1330 CA GLU G 236 | 18.751 −3.930 1.992 1.00 15.24 | C |
| ATOM | 1331 CB GLU G 236 | 19.179 −2.636 2.687 1.00 15.69 | C |
| ATOM | 1332 CG GLU G 236 | 18.875 −1.369 1.904 1.00 18.22 | C |
| ATOM | 1333 CD GLU G 236 | 19.004 −0.115 2.750 1.00 21.59 | C |
| ATOM | 1334 OE1 GLU G 236 | 19.395 0.937 2.199 1.00 24.41 | O |
| ATOM | 1335 OE2 GLU G 236 | 18.660 −0.168 3.953 1.00 21.59 | O |
| ATOM | 1336 C GLU G 236 | 19.870 −4.421 1.077 1.00 14.61 | C |
| ATOM | 1337 O GLU G 236 | 19.746 −4.377 −0.147 1.00 14.82 | O |
| ATOM | 1338 N PHE G 237 | 20.963 −4.883 1.675 1.00 14.05 | N |
| ATOM | 1339 CA PHE G 237 | 22.110 −5.358 0.907 1.00 13.84 | C |
| ATOM | 1340 CB PHE G 237 | 23.285 −5.682 1.836 1.00 14.04 | C |
| ATOM | 1341 CG PHE G 237 | 24.161 −4.500 2.143 1.00 14.84 | C |
| ATOM | 1342 CD1 PHE G 237 | 24.412 −4.131 3.454 1.00 15.30 | C |
| ATOM | 1343 CE1 PHE G 237 | 25.268 −3.087 3.743 1.00 15.15 | C |
| ATOM | 1344 CZ PHE G 237 | 25.871 −2.389 2.717 1.00 15.19 | C |
| ATOM | 1345 CE2 PHE G 237 | 25.645 −2.760 1.407 1.00 15.02 | C |
| ATOM | 1346 CD2 PHE G 237 | 24.796 −3.809 1.125 1.00 15.03 | C |
| ATOM | 1347 C PHE G 237 | 21.741 −6.586 0.078 1.00 13.51 | C |
| ATOM | 1348 O PHE G 237 | 22.027 −6.652 −1.117 1.00 13.43 | O |
| ATOM | 1349 N SER G 238 | 21.092 −7.551 0.721 1.00 13.11 | N |
| ATOM | 1350 CA SER G 238 | 20.669 −8.772 0.049 1.00 12.82 | C |
| ATOM | 1351 CB SER G 238 | 19.929 −9.688 1.021 1.00 12.86 | C |
| ATOM | 1352 OG SER G 238 | 20.730 −9.975 2.151 1.00 12.76 | O |
| ATOM | 1353 C SER G 238 | 19.770 −8.444 −1.131 1.00 12.69 | C |
| ATOM | 1354 O SER G 238 | 19.749 −9.165 −2.128 1.00 12.63 | O |
| ATOM | 1355 N VAL G 239 | 19.024 −7.352 −1.010 1.00 12.59 | N |
| ATOM | 1356 CA VAL G 239 | 18.143 −6.916 −2.082 1.00 12.80 | C |
| ATOM | 1357 CB VAL G 239 | 17.045 −5.961 −1.578 1.00 12.71 | C |
| ATOM | 1358 CG1 VAL G 239 | 16.215 −5.451 −2.747 1.00 13.63 | C |
| ATOM | 1359 CG2 VAL G 239 | 16.157 −6.658 −0.562 1.00 13.57 | C |
| ATOM | 1360 C VAL G 239 | 18.906 −6.242 −3.214 1.00 12.94 | C |
| ATOM | 1361 O VAL G 239 | 18.337 −5.980 −4.273 1.00 13.10 | O |
| ATOM | 1362 N ASN G 240 | 20.173 −5.913 −2.981 1.00 4.15 | N |
| ATOM | 1363 CA ASN G 240 | 20.892 −5.047 −3.909 1.00 4.33 | C |
| ATOM | 1364 CB ASN G 240 | 21.377 −3.779 −3.214 1.00 4.59 | C |
| ATOM | 1365 CG ASN G 240 | 20.260 −2.790 −2.978 1.00 5.36 | C |
| ATOM | 1366 OD1 ASN G 240 | 19.681 −2.263 −3.926 1.00 6.27 | O |
| ATOM | 1367 ND2 ASN G 240 | 19.828 −2.683 −1.727 1.00 7.15 | N |
| ATOM | 1368 C ASN G 240 | 22.025 −5.707 −4.689 1.00 4.19 | C |
| ATOM | 1369 O ASN G 240 | 22.565 −5.115 −5.625 1.00 4.19 | O |
| ATOM | 1370 N ALA G 241 | 22.299 −6.970 −4.382 1.00 3.93 | N |
| ATOM | 1371 CA ALA G 241 | 23.459 −7.657 −4.941 1.00 3.90 | C |
| ATOM | 1372 CB ALA G 241 | 23.179 −8.102 −6.368 1.00 3.86 | C |
| ATOM | 1373 C ALA G 241 | 24.702 −6.772 −4.887 1.00 4.22 | C |
| ATOM | 1374 O ALA G 241 | 25.347 −6.532 −5.907 1.00 4.47 | O |
| ATOM | 1375 N GLY G 242 | 24.955 −6.190 −3.719 1.00 4.53 | N |
| ATOM | 1376 CA GLY G 242 | 26.289 −5.717 −3.368 1.00 4.65 | C |
| ATOM | 1377 C GLY G 242 | 26.609 −4.323 −3.872 1.00 4.67 | C |
| ATOM | 1378 O GLY G 242 | 27.770 −3.913 −3.869 1.00 5.27 | O |
| ATOM | 1379 N VAL G 243 | 25.577 −3.570 −4.246 1.00 4.37 | N |
| ATOM | 1380 CA VAL G 243 | 25.750 −2.172 −4.646 1.00 4.32 | C |
| ATOM | 1381 CB VAL G 243 | 26.048 −2.039 −6.153 1.00 3.99 | C |
| ATOM | 1382 CG1 VAL G 243 | 26.962 −0.845 −6.414 1.00 4.22 | C |
| ATOM | 1383 CG2 VAL G 243 | 26.649 −3.327 −6.699 1.00 3.85 | C |
| ATOM | 1384 C VAL G 243 | 24.510 −1.342 −4.335 1.00 4.61 | C |
| ATOM | 1385 O VAL G 243 | 23.394 −1.734 −4.673 1.00 4.89 | O |
| ATOM | 1386 N THR G 244 | 24.722 −0.145 −3.801 1.00 4.95 | N |
| ATOM | 1387 CA THR G 244 | 23.615 0.714 −3.408 1.00 5.71 | C |
| ATOM | 1388 CB THR G 244 | 23.475 0.801 −1.879 1.00 6.11 | C |

APPENDIX-continued (APPENDIX discloses SEQ ID NOS 29-32, 29-32 and 29-32, respectively, in order of appearance)

| | | | |
|---|---|---|---|
| ATOM | 1389 OG1 THR G 244 | 24.257 −0.228 −1.260 1.00 7.17 | O |
| ATOM | 1390 CG2 THR G 244 | 22.028 0.651 −1.475 1.00 7.55 | C |
| ATOM | 1391 C THR G 244 | 23.802 2.114 −3.967 1.00 5.61 | C |
| ATOM | 1392 O THR G 244 | 24.927 2.590 −4.117 1.00 5.85 | O |
| ATOM | 1393 N THR G 245 | 22.695 2.794 −4.223 1.00 5.53 | N |
| ATOM | 1394 CA THR G 245 | 22.677 4.241 −4.120 1.00 5.81 | C |
| ATOM | 1395 CB THR G 245 | 22.461 4.903 −5.490 1.00 6.13 | C |
| ATOM | 1396 OG1 THR G 245 | 23.555 4.575 −6.355 1.00 8.11 | O |
| ATOM | 1397 CG2 THR G 245 | 22.394 6.408 −5.336 1.00 6.63 | C |
| ATOM | 1398 C THR G 245 | 21.609 4.679 −3.126 1.00 5.73 | C |
| ATOM | 1399 O THR G 245 | 20.778 3.869 −2.718 1.00 5.86 | O |
| ATOM | 1400 N PRO G 246 | 21.521 5.993 −2.867 1.00 5.68 | N |
| ATOM | 1401 CA PRO G 246 | 21.893 6.537 −1.574 1.00 5.11 | C |
| ATOM | 1402 CB PRO G 246 | 20.537 6.719 −0.893 1.00 5.19 | C |
| ATOM | 1403 CG PRO G 246 | 19.582 7.023 −2.060 1.00 5.90 | C |
| ATOM | 1404 CD PRO G 246 | 20.305 6.660 −3.353 1.00 6.36 | C |
| ATOM | 1405 C PRO G 246 | 22.831 5.666 −0.743 1.00 4.85 | C |
| ATOM | 1406 O PRO G 246 | 22.663 4.447 −0.677 1.00 5.25 | O |
| ATOM | 1407 N VAL G 247 | 23.900 6.281 −0.249 1.00 4.35 | N |
| ATOM | 1408 CA VAL G 247 | 24.742 5.647 0.749 1.00 3.82 | C |
| ATOM | 1409 CB VAL G 247 | 26.177 6.196 0.717 1.00 3.52 | C |
| ATOM | 1410 CG1 VAL G 247 | 27.082 5.352 1.597 1.00 3.62 | C |
| ATOM | 1411 CG2 VAL G 247 | 26.697 6.207 −0.707 1.00 3.60 | C |
| ATOM | 1412 C VAL G 247 | 24.134 5.824 2.131 1.00 3.69 | C |
| ATOM | 1413 O VAL G 247 | 24.038 6.942 2.637 1.00 3.36 | O |
| ATOM | 1414 N SER G 248 | 23.471 4.769 2.588 1.00 3.72 | N |
| ATOM | 1415 CA SER G 248 | 22.676 4.824 3.803 1.00 3.96 | C |
| ATOM | 1416 CB SER G 248 | 22.187 3.427 4.172 1.00 4.07 | C |
| ATOM | 1417 OG SER G 248 | 23.188 2.722 4.884 1.00 4.13 | O |
| ATOM | 1418 C SER G 248 | 23.484 5.392 4.959 1.00 4.35 | C |
| ATOM | 1419 O SER G 248 | 24.697 5.201 5.026 1.00 4.36 | O |
| ATOM | 1420 N THR G 249 | 22.776 5.880 5.972 1.00 4.53 | N |
| ATOM | 1421 CA THR G 249 | 23.405 6.259 7.226 1.00 4.61 | C |
| ATOM | 1422 CB THR G 249 | 22.408 6.945 8.175 1.00 4.70 | C |
| ATOM | 1423 OG1 THR G 249 | 21.562 5.959 8.778 1.00 5.42 | O |
| ATOM | 1424 CG2 THR G 249 | 21.553 7.945 7.412 1.00 4.88 | C |
| ATOM | 1425 C THR G 249 | 24.026 5.054 7.925 1.00 4.47 | C |
| ATOM | 1426 O THR G 249 | 24.830 5.210 8.844 1.00 4.74 | O |
| ATOM | 1427 N TYR G 250 | 23.694 3.855 7.454 1.00 4.32 | N |
| ATOM | 1428 CA TYR G 250 | 24.325 2.641 7.968 1.00 4.42 | C |
| ATOM | 1429 CB TYR G 250 | 23.393 1.435 7.845 1.00 4.91 | C |
| ATOM | 1430 CG TYR G 250 | 22.028 1.638 8.462 1.00 6.81 | C |
| ATOM | 1431 CD1 TYR G 250 | 20.881 1.242 7.790 1.00 8.89 | C |
| ATOM | 1432 CE1 TYR G 250 | 19.631 1.390 8.359 1.00 10.73 | C |
| ATOM | 1433 CZ TYR G 250 | 19.513 1.941 9.622 1.00 12.28 | C |
| ATOM | 1434 OH TYR G 250 | 18.265 2.135 10.172 1.00 12.24 | O |
| ATOM | 1435 CE2 TYR G 250 | 20.640 2.325 10.320 1.00 12.15 | C |
| ATOM | 1436 CD2 TYR G 250 | 21.890 2.148 9.749 1.00 9.81 | C |
| ATOM | 1437 C TYR G 250 | 25.656 2.342 7.285 1.00 4.21 | C |
| ATOM | 1438 O TYR G 250 | 26.539 1.730 7.886 1.00 4.20 | O |
| ATOM | 1439 N MET G 251 | 25.766 2.697 6.007 1.00 4.14 | N |
| ATOM | 1440 CA MET G 251 | 27.045 2.616 5.300 1.00 4.15 | C |
| ATOM | 1441 CB MET G 251 | 26.852 2.798 3.790 1.00 4.14 | C |
| ATOM | 1442 CG MET G 251 | 26.019 1.722 3.123 1.00 4.51 | C |
| ATOM | 1443 SD MET G 251 | 26.772 0.087 3.219 1.00 3.81 | S |
| ATOM | 1444 CE MET G 251 | 25.773 −0.814 2.036 1.00 4.55 | C |
| ATOM | 1445 C MET G 251 | 27.996 3.686 5.816 1.00 4.13 | C |
| ATOM | 1446 O MET G 251 | 29.178 3.427 6.043 1.00 4.24 | O |
| ATOM | 1447 N LEU G 252 | 27.495 4.913 5.886 1.00 4.23 | N |
| ATOM | 1448 CA LEU G 252 | 28.283 6.032 6.369 1.00 4.22 | C |
| ATOM | 1449 CB LEU G 252 | 28.645 6.965 5.215 1.00 4.14 | C |
| ATOM | 1450 CG LEU G 252 | 30.017 6.731 4.581 1.00 4.05 | C |
| ATOM | 1451 CD1 LEU G 252 | 30.513 7.997 3.891 1.00 5.22 | C |
| ATOM | 1452 CD2 LEU G 252 | 31.023 6.242 5.617 1.00 6.20 | C |
| ATOM | 1453 C LEU G 252 | 27.515 6.799 7.432 1.00 4.62 | C |
| ATOM | 1454 O LEU G 252 | 26.389 7.238 7.203 1.00 4.97 | O |
| ATOM | 1455 N THR G 253 | 28.127 6.949 8.600 1.00 4.90 | N |
| ATOM | 1456 CA THR G 253 | 27.659 7.913 9.583 1.00 5.57 | C |
| ATOM | 1457 CB THR G 253 | 28.420 7.769 10.903 1.00 5.55 | C |
| ATOM | 1458 OG1 THR G 253 | 28.440 6.390 11.293 1.00 6.43 | O |
| ATOM | 1459 CG2 THR G 253 | 27.757 8.598 11.988 1.00 6.28 | C |
| ATOM | 1460 C THR G 253 | 27.865 9.329 9.069 1.00 6.03 | C |
| ATOM | 1461 O THR G 253 | 28.888 9.629 8.453 1.00 6.68 | O |
| ATOM | 1462 N ASN G 254 | 26.974 10.230 9.460 1.00 6.39 | N |
| ATOM | 1463 CA ASN G 254 | 27.257 11.649 9.342 1.00 6.79 | C |
| ATOM | 1464 CB ASN G 254 | 26.292 12.459 10.198 1.00 6.85 | C |
| ATOM | 1465 CG ASN G 254 | 26.317 13.927 9.853 1.00 6.81 | C |

APPENDIX-continued (APPENDIX discloses SEQ ID NOS 29-32, 29-32 and 29-32, respectively, in order of appearance)

| | | | |
|---|---|---|---|
| ATOM | 1466 OD1 ASN G 254 | 25.991 14.303 8.728 1.00 7.67 | O |
| ATOM | 1467 ND2 ASN G 254 | 26.919 14.726 10.726 1.00 6.19 | N |
| ATOM | 1468 C ASN G 254 | 28.685 11.958 9.760 1.00 7.08 | C |
| ATOM | 1469 O ASN G 254 | 29.495 12.426 8.961 1.00 6.90 | O |
| ATOM | 1470 N SER G 255 | 28.974 11.718 11.034 1.00 7.21 | N |
| ATOM | 1471 CA SER G 255 | 30.320 11.869 11.561 1.00 7.37 | C |
| ATOM | 1472 CB SER G 255 | 30.477 11.067 12.859 1.00 8.09 | C |
| ATOM | 1473 OG SER G 255 | 29.239 10.928 13.536 1.00 10.47 | O |
| ATOM | 1474 C SER G 255 | 31.365 11.429 10.538 1.00 6.82 | C |
| ATOM | 1475 O SER G 255 | 32.237 12.207 10.150 1.00 6.99 | O |
| ATOM | 1476 N GLU G 256 | 31.240 10.192 10.068 1.00 6.17 | N |
| ATOM | 1477 CA GLU G 256 | 32.218 9.629 9.152 1.00 6.13 | C |
| ATOM | 1478 CB GLU G 256 | 31.913 8.158 8.883 1.00 6.22 | C |
| ATOM | 1479 CG GLU G 256 | 32.296 7.240 10.026 1.00 8.41 | C |
| ATOM | 1480 CD GLU G 256 | 31.422 6.006 10.099 1.00 10.26 | C |
| ATOM | 1481 OE1 GLU G 256 | 30.637 5.776 9.156 1.00 11.90 | O |
| ATOM | 1482 OE2 GLU G 256 | 31.532 5.255 11.090 1.00 9.55 | O |
| ATOM | 1483 C GLU G 256 | 32.231 10.401 7.845 1.00 5.76 | C |
| ATOM | 1484 O GLU G 256 | 33.275 10.892 7.418 1.00 5.93 | O |
| ATOM | 1485 N LEU G 257 | 31.075 10.476 7.194 1.00 5.67 | N |
| ATOM | 1486 CA LEU G 257 | 30.972 11.191 5.930 1.00 5.37 | C |
| ATOM | 1487 CB LEU G 257 | 29.512 11.334 5.486 1.00 5.03 | C |
| ATOM | 1488 CG LEU G 257 | 29.282 12.309 4.325 1.00 3.65 | C |
| ATOM | 1489 CD1 LEU G 257 | 29.846 11.755 3.024 1.00 2.00 | C |
| ATOM | 1490 CD2 LEU G 257 | 27.810 12.657 4.172 1.00 2.14 | C |
| ATOM | 1491 C LEU G 257 | 31.623 12.563 6.048 1.00 5.64 | C |
| ATOM | 1492 O LEU G 257 | 32.401 12.970 5.185 1.00 5.81 | O |
| ATOM | 1493 N LEU G 258 | 31.353 13.249 7.153 1.00 5.75 | N |
| ATOM | 1494 CA LEU G 258 | 31.792 14.629 7.301 1.00 5.91 | C |
| ATOM | 1495 CB LEU G 258 | 31.162 15.276 8.535 1.00 6.10 | C |
| ATOM | 1496 CG LEU G 258 | 29.897 16.091 8.256 1.00 5.75 | C |
| ATOM | 1497 CD1 LEU G 258 | 29.230 16.525 9.552 1.00 6.33 | C |
| ATOM | 1498 CD2 LEU G 258 | 30.219 17.294 7.385 1.00 7.33 | C |
| ATOM | 1499 C LEU G 258 | 33.315 14.758 7.331 1.00 6.03 | C |
| ATOM | 1500 O LEU G 258 | 33.874 15.664 6.713 1.00 5.73 | O |
| ATOM | 1501 N SER G 259 | 33.983 13.867 8.061 1.00 6.47 | N |
| ATOM | 1502 CA SER G 259 | 35.442 13.887 8.139 1.00 6.95 | C |
| ATOM | 1503 CB SER G 259 | 35.929 13.137 9.381 1.00 7.05 | C |
| ATOM | 1504 OG SER G 259 | 36.284 11.802 9.064 1.00 6.86 | O |
| ATOM | 1505 C SER G 259 | 36.060 13.284 6.883 1.00 6.74 | C |
| ATOM | 1506 O SER G 259 | 37.173 13.638 6.493 1.00 6.86 | O |
| ATOM | 1507 N LEU G 260 | 35.311 12.400 6.234 1.00 6.31 | N |
| ATOM | 1508 CA LEU G 260 | 35.715 11.854 4.946 1.00 6.09 | C |
| ATOM | 1509 CB LEU G 260 | 34.747 10.756 4.507 1.00 6.09 | C |
| ATOM | 1510 CG LEU G 260 | 35.306 9.334 4.473 1.00 6.24 | C |
| ATOM | 1511 CD1 LEU G 260 | 34.338 8.388 3.779 1.00 6.53 | C |
| ATOM | 1512 CD2 LEU G 260 | 36.663 9.309 3.790 1.00 5.98 | C |
| ATOM | 1513 C LEU G 260 | 35.775 12.947 3.887 1.00 6.25 | C |
| ATOM | 1514 O LEU G 260 | 36.696 12.982 3.072 1.00 6.37 | O |
| ATOM | 1515 N ILE G 261 | 34.724 13.760 3.826 1.00 6.63 | N |
| ATOM | 1516 CA ILE G 261 | 34.729 14.952 2.987 1.00 7.19 | C |
| ATOM | 1517 CB ILE G 261 | 33.504 15.840 3.262 1.00 7.09 | C |
| ATOM | 1518 CG1 ILE G 261 | 32.292 15.350 2.474 1.00 7.46 | C |
| ATOM | 1519 CD1 ILE G 261 | 30.991 15.952 2.951 1.00 8.38 | C |
| ATOM | 1520 CG2 ILE G 261 | 33.809 17.290 2.916 1.00 6.61 | C |
| ATOM | 1521 C ILE G 261 | 35.966 15.768 3.307 1.00 8.01 | C |
| ATOM | 1522 O ILE G 261 | 36.716 16.162 2.414 1.00 8.26 | O |
| ATOM | 1523 N ASN G 262 | 36.157 16.040 4.592 1.00 9.05 | N |
| ATOM | 1524 CA ASN G 262 | 37.337 16.748 5.049 1.00 9.88 | C |
| ATOM | 1525 CB ASN G 262 | 37.517 16.575 6.555 1.00 9.99 | C |
| ATOM | 1526 CG ASN G 262 | 38.185 17.770 7.197 1.00 11.16 | C |
| ATOM | 1527 OD1 ASN G 262 | 38.493 18.756 6.526 1.00 12.70 | O |
| ATOM | 1528 ND2 ASN G 262 | 38.391 17.701 8.506 1.00 13.20 | N |
| ATOM | 1529 C ASN G 262 | 38.585 16.282 4.316 1.00 10.17 | C |
| ATOM | 1530 O ASN G 262 | 39.426 17.093 3.928 1.00 10.52 | O |
| ATOM | 1531 N ASP G 263 | 38.684 14.976 4.094 1.00 10.62 | N |
| ATOM | 1532 CA ASP G 263 | 39.925 14.380 3.621 1.00 11.02 | C |
| ATOM | 1533 CB ASP G 263 | 40.022 12.917 4.055 1.00 11.49 | C |
| ATOM | 1534 CG ASP G 263 | 41.297 12.251 3.577 1.00 12.80 | C |
| ATOM | 1535 OD1 ASP G 263 | 42.377 12.863 3.715 1.00 14.72 | O |
| ATOM | 1536 OD2 ASP G 263 | 41.220 11.113 3.068 1.00 13.88 | O |
| ATOM | 1537 C ASP G 263 | 40.067 14.491 2.107 1.00 10.92 | C |
| ATOM | 1538 O ASP G 263 | 41.135 14.224 1.556 1.00 10.96 | O |
| ATOM | 1539 N MET G 264 | 39.003 14.931 1.442 1.00 10.91 | N |
| ATOM | 1540 CA MET G 264 | 38.989 14.992 −0.015 1.00 10.78 | C |
| ATOM | 1541 CB MET G 264 | 37.557 15.121 −0.534 1.00 10.51 | C |
| ATOM | 1542 CG MET G 264 | 36.669 13.937 −0.194 1.00 11.26 | C |

APPENDIX-continued (APPENDIX discloses SEQ ID NOS 29-32, 29-32 and 29-32, respectively, in order of appearance)

| | | | |
|---|---|---|---|
| ATOM | 1543 SD MET G 264 | 35.025 14.078 −0.916 1.00 12.70 | S |
| ATOM | 1544 CE MET G 264 | 34.634 15.778 −0.513 1.00 13.92 | C |
| ATOM | 1545 C MET G 264 | 39.851 16.135 −0.543 1.00 10.85 | C |
| ATOM | 1546 O MET G 264 | 39.830 17.238 0.002 1.00 11.03 | O |
| ATOM | 1547 N PRO G 265 | 40.626 15.863 −1.604 1.00 10.88 | N |
| ATOM | 1548 CA PRO G 265 | 41.558 16.827 −2.184 1.00 11.09 | C |
| ATOM | 1549 CB PRO G 265 | 42.357 15.986 −3.188 1.00 11.28 | C |
| ATOM | 1550 CG PRO G 265 | 41.513 14.787 −3.453 1.00 11.24 | C |
| ATOM | 1551 CD PRO G 265 | 40.807 14.515 −2.167 1.00 11.03 | C |
| ATOM | 1552 C PRO G 265 | 40.845 17.965 −2.908 1.00 11.19 | C |
| ATOM | 1553 O PRO G 265 | 41.070 18.175 −4.100 1.00 11.47 | O |
| ATOM | 1554 N ILE G 266 | 40.053 18.739 −2.173 1.00 11.54 | N |
| ATOM | 1555 CA ILE G 266 | 39.282 19.820 −2.777 1.00 12.15 | C |
| ATOM | 1556 CB ILE G 266 | 37.792 19.454 −2.914 1.00 12.22 | C |
| ATOM | 1557 CG1 ILE G 266 | 37.245 18.928 −1.585 1.00 12.53 | C |
| ATOM | 1558 CD1 ILE G 266 | 35.733 18.918 −1.510 1.00 12.40 | C |
| ATOM | 1559 CG2 ILE G 266 | 37.594 18.431 −4.023 1.00 12.74 | C |
| ATOM | 1560 C ILE G 266 | 39.413 21.132 −2.013 1.00 12.29 | C |
| ATOM | 1561 O ILE G 266 | 39.853 21.156 −0.863 1.00 12.36 | O |
| ATOM | 1562 N THR G 267 | 39.034 22.223 −2.670 1.00 12.29 | N |
| ATOM | 1563 CA THR G 267 | 39.039 23.541 −2.050 1.00 12.43 | C |
| ATOM | 1564 CB THR G 267 | 38.564 24.627 −3.034 1.00 12.40 | C |
| ATOM | 1565 OG1 THR G 267 | 37.340 25.204 −2.562 1.00 13.21 | O |
| ATOM | 1566 CG2 THR G 267 | 38.341 24.033 −4.417 1.00 12.21 | C |
| ATOM | 1567 C THR G 267 | 38.141 23.560 −0.819 1.00 12.37 | C |
| ATOM | 1568 O THR G 267 | 37.440 22.589 −0.537 1.00 12.29 | O |
| ATOM | 1569 N ASN G 268 | 38.174 24.664 −0.081 1.00 12.47 | N |
| ATOM | 1570 CA ASN G 268 | 37.523 24.720 1.219 1.00 12.57 | C |
| ATOM | 1571 CB ASN G 268 | 38.199 25.751 2.121 1.00 12.69 | C |
| ATOM | 1572 CG ASN G 268 | 39.221 25.127 3.048 1.00 13.65 | C |
| ATOM | 1573 OD1 ASN G 268 | 39.463 23.921 3.000 1.00 14.37 | O |
| ATOM | 1574 ND2 ASN G 268 | 39.843 25.949 3.884 1.00 15.74 | N |
| ATOM | 1575 C ASN G 268 | 36.028 24.995 1.123 1.00 12.43 | C |
| ATOM | 1576 O ASN G 268 | 35.232 24.403 1.853 1.00 12.51 | O |
| ATOM | 1577 N ASP G 269 | 35.655 25.926 0.252 1.00 12.34 | N |
| ATOM | 1578 CA ASP G 269 | 34.248 26.218 0.008 1.00 12.33 | C |
| ATOM | 1579 CB ASP G 269 | 34.106 27.359 −0.999 1.00 12.89 | C |
| ATOM | 1580 CG ASP G 269 | 34.761 28.639 −0.525 1.00 14.84 | C |
| ATOM | 1581 OD1 ASP G 269 | 34.594 28.989 0.663 1.00 16.90 | O |
| ATOM | 1582 OD2 ASP G 269 | 35.473 29.277 −1.328 1.00 17.65 | O |
| ATOM | 1583 C ASP G 269 | 33.532 24.978 −0.506 1.00 11.60 | C |
| ATOM | 1584 O ASP G 269 | 32.411 24.679 −0.095 1.00 11.65 | O |
| ATOM | 1585 N GLN G 270 | 34.189 24.260 −1.410 1.00 10.62 | N |
| ATOM | 1586 CA GLN G 270 | 33.728 22.943 −1.816 1.00 10.01 | C |
| ATOM | 1587 CB GLN G 270 | 34.795 22.236 −2.647 1.00 10.18 | C |
| ATOM | 1588 CG GLN G 270 | 34.248 21.533 −3.870 1.00 11.49 | C |
| ATOM | 1589 CD GLN G 270 | 35.200 21.598 −5.043 1.00 14.38 | C |
| ATOM | 1590 OE1 GLN G 270 | 35.516 20.579 −5.655 1.00 16.38 | O |
| ATOM | 1591 NE2 GLN G 270 | 35.718 22.789 −5.318 1.00 15.41 | N |
| ATOM | 1592 C GLN G 270 | 33.366 22.094 −0.606 1.00 9.48 | C |
| ATOM | 1593 O GLN G 270 | 32.213 21.698 −0.437 1.00 9.12 | O |
| ATOM | 1594 N LYS G 271 | 34.358 21.809 0.231 1.00 9.19 | N |
| ATOM | 1595 CA LYS G 271 | 34.126 21.040 1.445 1.00 8.89 | C |
| ATOM | 1596 CB LYS G 271 | 35.362 21.070 2.345 1.00 8.52 | C |
| ATOM | 1597 CG LYS G 271 | 36.541 20.285 1.797 1.00 9.14 | C |
| ATOM | 1598 CD LYS G 271 | 37.643 20.147 2.832 1.00 10.72 | C |
| ATOM | 1599 CE LYS G 271 | 39.013 20.137 2.176 1.00 10.79 | C |
| ATOM | 1600 NZ LYS G 271 | 40.035 19.472 3.030 1.00 9.77 | N |
| ATOM | 1601 C LYS G 271 | 32.907 21.563 2.199 1.00 8.83 | C |
| ATOM | 1602 O LYS G 271 | 31.959 20.820 2.452 1.00 9.05 | O |
| ATOM | 1603 N LYS G 272 | 32.899 22.863 2.474 1.00 8.65 | N |
| ATOM | 1604 CA LYS G 272 | 31.789 23.482 3.187 1.00 8.50 | C |
| ATOM | 1605 CB LYS G 272 | 31.997 24.992 3.304 1.00 9.14 | C |
| ATOM | 1606 CG LYS G 272 | 30.762 25.748 3.766 1.00 11.58 | C |
| ATOM | 1607 CD LYS G 272 | 30.925 27.246 3.575 1.00 15.78 | C |
| ATOM | 1608 CE LYS G 272 | 29.995 28.021 4.492 1.00 17.65 | C |
| ATOM | 1609 NZ LYS G 272 | 30.462 29.418 4.703 1.00 19.68 | N |
| ATOM | 1610 C LYS G 272 | 30.458 23.191 2.503 1.00 7.88 | C |
| ATOM | 1611 O LYS G 272 | 29.486 22.808 3.154 1.00 8.12 | O |
| ATOM | 1612 N LEU G 273 | 30.408 23.416 1.194 1.00 6.95 | N |
| ATOM | 1613 CA LEU G 273 | 29.217 23.104 0.413 1.00 5.70 | C |
| ATOM | 1614 CB LEU G 273 | 29.469 23.344 −1.077 1.00 5.85 | C |
| ATOM | 1615 CG LEU G 273 | 28.313 23.000 −2.020 1.00 4.65 | C |
| ATOM | 1616 CD1 LEU G 273 | 27.277 24.114 −2.032 1.00 4.57 | C |
| ATOM | 1617 CD2 LEU G 273 | 28.829 22.729 −3.425 1.00 3.69 | C |
| ATOM | 1618 C LEU G 273 | 28.781 21.663 0.644 1.00 5.14 | C |
| ATOM | 1619 O LEU G 273 | 27.678 21.409 1.128 1.00 5.25 | O |

APPENDIX-continued (APPENDIX discloses SEQ ID NOS 29-32, 29-32 and 29-32, respectively, in order of appearance)

| | | | |
|---|---|---|---|
| ATOM | 1620 N MET G 274 | 29.665 20.724 0.327 1.00 4.52 | N |
| ATOM | 1621 CA MET G 274 | 29.354 19.312 0.482 1.00 4.59 | C |
| ATOM | 1622 CB MET G 274 | 30.573 18.454 0.152 1.00 4.35 | C |
| ATOM | 1623 CG MET G 274 | 30.938 18.457 −1.319 1.00 4.50 | C |
| ATOM | 1624 SD MET G 274 | 32.305 17.344 −1.679 1.00 5.51 | S |
| ATOM | 1625 CE MET G 274 | 31.469 15.758 −1.633 1.00 5.26 | C |
| ATOM | 1626 C MET G 274 | 28.864 19.014 1.893 1.00 5.18 | C |
| ATOM | 1627 O MET G 274 | 27.893 18.280 2.075 1.00 5.61 | O |
| ATOM | 1628 N SER G 275 | 29.457 19.689 2.875 1.00 5.89 | N |
| ATOM | 1629 CA SER G 275 | 29.118 19.465 4.278 1.00 6.18 | C |
| ATOM | 1630 CB SER G 275 | 30.161 20.108 5.194 1.00 6.33 | C |
| ATOM | 1631 OG SER G 275 | 31.457 19.601 4.925 1.00 5.91 | O |
| ATOM | 1632 C SER G 275 | 27.726 19.989 4.619 1.00 6.58 | C |
| ATOM | 1633 O SER G 275 | 27.031 19.425 5.464 1.00 7.03 | O |
| ATOM | 1634 N ASN G 276 | 27.313 21.054 3.940 1.00 7.07 | N |
| ATOM | 1635 CA ASN G 276 | 25.979 21.606 4.140 1.00 7.86 | C |
| ATOM | 1636 CB ASN G 276 | 25.987 23.126 3.942 1.00 8.34 | C |
| ATOM | 1637 CG ASN G 276 | 26.343 23.881 5.214 1.00 9.77 | C |
| ATOM | 1638 OD1 ASN G 276 | 26.033 23.439 6.320 1.00 11.84 | O |
| ATOM | 1639 ND2 ASN G 276 | 26.964 25.044 5.057 1.00 11.15 | N |
| ATOM | 1640 C ASN G 276 | 24.908 20.954 3.262 1.00 7.71 | C |
| ATOM | 1641 O ASN G 276 | 23.780 21.442 3.191 1.00 7.84 | O |
| ATOM | 1642 N ASN G 277 | 25.239 19.819 2.649 1.00 7.77 | N |
| ATOM | 1643 CA ASN G 277 | 24.372 19.220 1.631 1.00 7.85 | C |
| ATOM | 1644 CB ASN G 277 | 24.704 19.777 0.246 1.00 7.58 | C |
| ATOM | 1645 CG ASN G 277 | 24.023 21.099 −0.027 1.00 8.29 | C |
| ATOM | 1646 OD1 ASN G 277 | 22.818 21.152 −0.272 1.00 9.04 | O |
| ATOM | 1647 ND2 ASN G 277 | 24.798 22.176 −0.008 1.00 9.57 | N |
| ATOM | 1648 C ASN G 277 | 24.410 17.693 1.590 1.00 7.86 | C |
| ATOM | 1649 O ASN G 277 | 24.154 17.089 0.549 1.00 7.85 | O |
| ATOM | 1650 N VAL G 278 | 24.886 17.093 2.674 1.00 7.67 | N |
| ATOM | 1651 CA VAL G 278 | 24.839 15.645 2.879 1.00 7.77 | C |
| ATOM | 1652 CB VAL G 278 | 24.594 15.309 4.352 1.00 7.98 | C |
| ATOM | 1653 CG1 VAL G 278 | 25.915 15.261 5.100 1.00 7.21 | C |
| ATOM | 1654 CG2 VAL G 278 | 23.655 16.332 4.977 1.00 8.99 | C |
| ATOM | 1655 C VAL G 278 | 23.843 14.865 2.019 1.00 7.76 | C |
| ATOM | 1656 O VAL G 278 | 24.183 13.811 1.483 1.00 7.84 | O |
| ATOM | 1657 N GLN G 279 | 22.569 15.228 2.118 1.00 7.47 | N |
| ATOM | 1658 CA GLN G 279 | 21.510 14.444 1.492 1.00 7.07 | C |
| ATOM | 1659 CB GLN G 279 | 20.187 15.204 1.550 1.00 7.62 | C |
| ATOM | 1660 CG GLN G 279 | 19.021 14.376 2.044 1.00 10.35 | C |
| ATOM | 1661 CD GLN G 279 | 17.682 14.997 1.702 1.00 13.70 | C |
| ATOM | 1662 OE1 GLN G 279 | 17.612 16.002 0.996 1.00 15.06 | O |
| ATOM | 1663 NE2 GLN G 279 | 16.607 14.383 2.179 1.00 13.97 | N |
| ATOM | 1664 C GLN G 279 | 21.852 14.121 0.042 1.00 6.02 | C |
| ATOM | 1665 O GLN G 279 | 22.032 12.958 −0.323 1.00 5.45 | O |
| ATOM | 1666 N ILE G 280 | 21.863 15.154 −0.792 1.00 5.25 | N |
| ATOM | 1667 CA ILE G 280 | 22.325 15.034 −2.169 1.00 4.74 | C |
| ATOM | 1668 CB ILE G 280 | 22.650 16.408 −2.771 1.00 4.58 | C |
| ATOM | 1669 CG1 ILE G 280 | 21.527 17.396 −2.461 1.00 4.16 | C |
| ATOM | 1670 CD1 ILE G 280 | 20.235 17.078 −3.177 1.00 3.88 | C |
| ATOM | 1671 CG2 ILE G 280 | 22.835 16.293 −4.271 1.00 3.92 | C |
| ATOM | 1672 C ILE G 280 | 23.550 14.135 −2.286 1.00 4.43 | C |
| ATOM | 1673 O ILE G 280 | 23.493 13.081 −2.917 1.00 4.39 | O |
| ATOM | 1674 N VAL G 281 | 24.676 14.596 −1.749 1.00 4.05 | N |
| ATOM | 1675 CA VAL G 281 | 25.906 13.816 −1.795 1.00 3.58 | C |
| ATOM | 1676 CB VAL G 281 | 26.918 14.251 −0.714 1.00 3.13 | C |
| ATOM | 1677 CG1 VAL G 281 | 28.296 13.684 −1.026 1.00 2.34 | C |
| ATOM | 1678 CG2 VAL G 281 | 26.978 15.768 −0.616 1.00 2.21 | C |
| ATOM | 1679 C VAL G 281 | 25.593 12.335 −1.626 1.00 3.96 | C |
| ATOM | 1680 O VAL G 281 | 25.875 11.534 −2.515 1.00 4.15 | O |
| ATOM | 1681 N ARG G 282 | 24.908 11.994 −0.539 1.00 4.23 | N |
| ATOM | 1682 CA ARG G 282 | 24.500 10.615 −0.296 1.00 4.45 | C |
| ATOM | 1683 CB ARG G 282 | 23.570 10.540 0.911 1.00 3.96 | C |
| ATOM | 1684 CG ARG G 282 | 24.225 10.953 2.203 1.00 2.99 | C |
| ATOM | 1685 CD ARG G 282 | 23.924 9.962 3.303 1.00 2.28 | C |
| ATOM | 1686 NE ARG G 282 | 24.332 10.474 4.605 1.00 2.00 | N |
| ATOM | 1687 CZ ARG G 282 | 25.026 9.777 5.498 1.00 2.44 | C |
| ATOM | 1688 NH1 ARG G 282 | 25.359 8.517 5.251 1.00 2.04 | N |
| ATOM | 1689 NH2 ARG G 282 | 25.369 10.333 6.650 1.00 3.44 | N |
| ATOM | 1690 C ARG G 282 | 23.798 10.039 −1.516 1.00 5.32 | C |
| ATOM | 1691 O ARG G 282 | 24.143 8.958 −1.997 1.00 5.95 | O |
| ATOM | 1692 N GLN G 283 | 22.800 10.765 −2.006 1.00 5.50 | N |
| ATOM | 1693 CA GLN G 283 | 22.045 10.327 −3.169 1.00 5.80 | C |
| ATOM | 1694 CB GLN G 283 | 20.910 11.303 −3.471 1.00 6.19 | C |
| ATOM | 1695 CG GLN G 283 | 19.768 11.219 −2.480 1.00 9.68 | C |
| ATOM | 1696 CD GLN G 283 | 18.840 12.406 −2.561 1.00 13.92 | C |

APPENDIX-continued (APPENDIX discloses SEQ ID NOS 29-32, 29-32 and 29-32, respectively, in order of appearance)

| | | | |
|---|---|---|---|
| ATOM | 1697 OE1 GLN G 283 | 18.991 13.269 −3.426 1.00 16.20 | O |
| ATOM | 1698 NE2 GLN G 283 | 17.833 12.428 −1.696 1.00 14.17 | N |
| ATOM | 1699 C GLN G 283 | 22.953 10.175 −4.379 1.00 5.44 | C |
| ATOM | 1700 O GLN G 283 | 22.687 9.364 −5.264 1.00 5.43 | O |
| ATOM | 1701 N GLN G 284 | 24.067 10.896 −4.371 1.00 5.26 | N |
| ATOM | 1702 CA GLN G 284 | 24.957 10.920 −5.521 1.00 5.18 | C |
| ATOM | 1703 CB GLN G 284 | 25.568 12.307 −5.702 1.00 5.32 | C |
| ATOM | 1704 CG GLN G 284 | 24.813 13.189 −6.673 1.00 6.85 | C |
| ATOM | 1705 CD GLN G 284 | 25.434 14.560 −6.804 1.00 9.21 | C |
| ATOM | 1706 OE1 GLN G 284 | 25.863 15.160 −5.819 1.00 9.74 | O |
| ATOM | 1707 NE2 GLN G 284 | 25.492 15.064 −8.027 1.00 9.79 | N |
| ATOM | 1708 C GLN G 284 | 26.060 9.882 −5.400 1.00 4.67 | C |
| ATOM | 1709 O GLN G 284 | 26.884 9.736 −6.302 1.00 4.19 | O |
| ATOM | 1710 N SER G 285 | 26.109 9.199 −4.262 1.00 4.51 | N |
| ATOM | 1711 CA SER G 285 | 27.204 8.281 −3.990 1.00 4.39 | C |
| ATOM | 1712 CB SER G 285 | 27.767 8.510 −2.587 1.00 4.13 | C |
| ATOM | 1713 OG SER G 285 | 28.180 9.856 −2.421 1.00 4.40 | O |
| ATOM | 1714 C SER G 285 | 26.767 6.834 −4.166 1.00 4.44 | C |
| ATOM | 1715 O SER G 285 | 25.587 6.555 −4.382 1.00 4.82 | O |
| ATOM | 1716 N TYR G 286 | 27.751 5.949 −4.271 1.00 4.53 | N |
| ATOM | 1717 CA TYR G 286 | 27.500 4.517 −4.291 1.00 4.80 | C |
| ATOM | 1718 CB TYR G 286 | 27.978 3.915 −5.612 1.00 4.88 | C |
| ATOM | 1719 CG TYR G 286 | 27.168 4.354 −6.809 1.00 5.68 | C |
| ATOM | 1720 CD1 TYR G 286 | 27.156 5.681 −7.218 1.00 7.34 | C |
| ATOM | 1721 CE1 TYR G 286 | 26.429 6.081 −8.322 1.00 9.02 | C |
| ATOM | 1722 CZ TYR G 286 | 25.720 5.145 −9.044 1.00 9.40 | C |
| ATOM | 1723 OH TYR G 286 | 24.998 5.538 −10.146 1.00 10.44 | O |
| ATOM | 1724 CE2 TYR G 286 | 25.730 3.820 −8.668 1.00 9.38 | C |
| ATOM | 1725 CD2 TYR G 286 | 26.444 3.433 −7.553 1.00 7.39 | C |
| ATOM | 1726 C TYR G 286 | 28.208 3.845 −3.124 1.00 4.76 | C |
| ATOM | 1727 O TYR G 286 | 29.130 4.411 −2.541 1.00 5.25 | O |
| ATOM | 1728 N SER G 287 | 27.765 2.642 −2.779 1.00 4.52 | N |
| ATOM | 1729 CA SER G 287 | 28.528 1.786 −1.884 1.00 4.45 | C |
| ATOM | 1730 CB SER G 287 | 27.888 1.743 −0.496 1.00 4.57 | C |
| ATOM | 1731 OG SER G 287 | 28.421 0.681 0.275 1.00 4.38 | O |
| ATOM | 1732 C SER G 287 | 28.670 0.381 −2.454 1.00 4.61 | C |
| ATOM | 1733 O SER G 287 | 27.683 −0.253 −2.820 1.00 4.40 | O |
| ATOM | 1734 N ILE G 288 | 29.914 −0.002 −2.717 1.00 5.11 | N |
| ATOM | 1735 CA ILE G 288 | 30.227 −1.318 −3.258 1.00 5.81 | C |
| ATOM | 1736 CB ILE G 288 | 31.376 −1.250 −4.288 1.00 5.52 | C |
| ATOM | 1737 CG1 ILE G 288 | 31.377 0.095 −5.021 1.00 5.47 | C |
| ATOM | 1738 CD1 ILE G 288 | 31.007 0.002 −6.487 1.00 6.23 | C |
| ATOM | 1739 CG2 ILE G 288 | 31.298 −2.421 −5.256 1.00 6.22 | C |
| ATOM | 1740 C ILE G 288 | 30.664 −2.245 −2.138 1.00 6.71 | C |
| ATOM | 1741 O ILE G 288 | 31.615 −1.948 −1.414 1.00 7.30 | O |
| ATOM | 1742 N MET G 289 | 30.085 −3.438 −2.118 1.00 7.71 | N |
| ATOM | 1743 CA MET G 289 | 30.585 −4.515 −1.277 1.00 8.57 | C |
| ATOM | 1744 CB MET G 289 | 29.605 −5.692 −1.306 1.00 8.71 | C |
| ATOM | 1745 CG MET G 289 | 29.648 −6.584 −0.077 1.00 9.70 | C |
| ATOM | 1746 SD MET G 289 | 28.615 −8.046 −0.280 1.00 12.59 | S |
| ATOM | 1747 CE MET G 289 | 29.227 −8.678 −1.839 1.00 12.41 | C |
| ATOM | 1748 C MET G 289 | 31.975 −4.963 −1.736 1.00 9.12 | C |
| ATOM | 1749 O MET G 289 | 32.231 −5.086 −2.935 1.00 9.31 | O |
| ATOM | 1750 N SER G 290 | 32.891 −5.122 −0.784 1.00 9.80 | N |
| ATOM | 1751 CA SER G 290 | 34.272 −5.469 −1.098 1.00 10.49 | C |
| ATOM | 1752 CB SER G 290 | 35.242 −4.513 −0.401 1.00 10.64 | C |
| ATOM | 1753 OG SER G 290 | 36.498 −4.486 −1.058 1.00 11.99 | O |
| ATOM | 1754 C SER G 290 | 34.592 −6.918 −0.742 1.00 10.75 | C |
| ATOM | 1755 O SER G 290 | 34.631 −7.778 −1.621 1.00 10.89 | O |
| ATOM | 1756 N ILE G 291 | 34.760 −7.206 0.544 1.00 11.04 | N |
| ATOM | 1757 CA ILE G 291 | 34.884 −8.596 0.965 1.00 11.41 | C |
| ATOM | 1758 CB ILE G 291 | 36.329 −9.120 0.900 1.00 11.80 | C |
| ATOM | 1759 CG1 ILE G 291 | 37.332 −7.977 1.061 1.00 11.81 | C |
| ATOM | 1760 CD1 ILE G 291 | 38.227 −8.113 2.277 1.00 11.76 | C |
| ATOM | 1761 CG2 ILE G 291 | 36.561 −9.846 −0.416 1.00 12.39 | C |
| ATOM | 1762 C ILE G 291 | 34.214 −8.982 2.277 1.00 11.13 | C |
| ATOM | 1763 O ILE G 291 | 34.299 −8.268 3.277 1.00 10.55 | O |
| ATOM | 1764 N ILE G 292 | 33.536 −10.124 2.246 1.00 11.36 | N |
| ATOM | 1765 CA ILE G 292 | 32.802 −10.620 3.398 1.00 11.82 | C |
| ATOM | 1766 CB ILE G 292 | 31.359 −11.016 3.029 1.00 11.86 | C |
| ATOM | 1767 CG1 ILE G 292 | 31.087 −10.734 1.550 1.00 13.42 | C |
| ATOM | 1768 CD1 ILE G 292 | 31.289 −9.282 1.158 1.00 15.86 | C |
| ATOM | 1769 CG2 ILE G 292 | 30.358 −10.287 3.923 1.00 10.85 | C |
| ATOM | 1770 C ILE G 292 | 33.505 −11.826 3.992 1.00 11.72 | C |
| ATOM | 1771 O ILE G 292 | 33.683 −12.849 3.330 1.00 11.28 | O |
| ATOM | 1772 N LYS G 293 | 33.946 −11.679 5.234 1.00 12.11 | N |
| ATOM | 1773 CA LYS G 293 | 34.275 −12.823 6.058 1.00 12.92 | C |

APPENDIX-continued (APPENDIX discloses SEQ ID NOS 29-32, 29-32 and 29-32, respectively, in order of appearance)

| | | | |
|---|---|---|---|
| ATOM | 1774 CB LYS G 293 | 35.715 −12.720 6.553 1.00 13.15 | C |
| ATOM | 1775 CG LYS G 293 | 36.674 −12.179 5.512 1.00 14.17 | C |
| ATOM | 1776 CD LYS G 293 | 38.000 −12.910 5.561 1.00 15.37 | C |
| ATOM | 1777 CE LYS G 293 | 38.720 −12.826 4.229 1.00 16.68 | C |
| ATOM | 1778 NZ LYS G 293 | 39.984 −13.607 4.242 1.00 18.18 | N |
| ATOM | 1779 C LYS G 293 | 33.310 −12.923 7.232 1.00 13.32 | C |
| ATOM | 1780 O LYS G 293 | 32.633 −11.952 7.578 1.00 13.17 | O |
| ATOM | 1781 N GLU G 294 | 33.140 −14.141 7.735 1.00 14.07 | N |
| ATOM | 1782 CA GLU G 294 | 32.217 −14.398 8.831 1.00 15.07 | C |
| ATOM | 1783 CB GLU G 294 | 32.474 −15.786 9.425 1.00 15.94 | C |
| ATOM | 1784 CG GLU G 294 | 32.183 −16.935 8.471 1.00 19.87 | C |
| ATOM | 1785 CD GLU G 294 | 32.165 −18.282 9.169 1.00 23.88 | C |
| ATOM | 1786 OE1 GLU G 294 | 31.348 −18.465 10.097 1.00 23.75 | O |
| ATOM | 1787 OE2 GLU G 294 | 32.950 −19.168 8.766 1.00 25.81 | O |
| ATOM | 1788 C GLU G 294 | 32.301 −13.320 9.917 1.00 14.40 | C |
| ATOM | 1789 O GLU G 294 | 31.281 −12.936 10.491 1.00 14.33 | O |
| ATOM | 1790 N GLU G 295 | 33.502 −12.779 10.132 1.00 13.97 | N |
| ATOM | 1791 CA GLU G 295 | 33.765 −11.861 11.251 1.00 13.84 | C |
| ATOM | 1792 CB GLU G 295 | 34.681 −12.508 12.299 1.00 14.67 | C |
| ATOM | 1793 CG GLU G 295 | 35.496 −13.688 11.794 1.00 17.56 | C |
| ATOM | 1794 CD GLU G 295 | 36.393 −13.328 10.626 1.00 21.41 | C |
| ATOM | 1795 OE1 GLU G 295 | 36.085 −13.752 9.493 1.00 22.35 | O |
| ATOM | 1796 OE2 GLU G 295 | 37.472 −12.745 10.861 1.00 23.20 | O |
| ATOM | 1797 C GLU G 295 | 34.340 −10.502 10.827 1.00 12.77 | C |
| ATOM | 1798 O GLU G 295 | 34.771 −9.712 11.670 1.00 12.58 | O |
| ATOM | 1799 N VAL G 296 | 34.389 −10.256 9.522 1.00 11.72 | N |
| ATOM | 1800 CA VAL G 296 | 34.634 −8.911 9.011 1.00 10.65 | C |
| ATOM | 1801 CB VAL G 296 | 36.143 −8.604 8.894 1.00 10.47 | C |
| ATOM | 1802 CG1 VAL G 296 | 36.369 −7.112 8.687 1.00 9.77 | C |
| ATOM | 1803 CG2 VAL G 296 | 36.879 −9.090 10.133 1.00 11.31 | C |
| ATOM | 1804 C VAL G 296 | 33.949 −8.664 7.669 1.00 10.26 | C |
| ATOM | 1805 O VAL G 296 | 33.931 −9.530 6.793 1.00 10.09 | O |
| ATOM | 1806 N LEU G 297 | 33.379 −7.473 7.525 1.00 9.77 | N |
| ATOM | 1807 CA LEU G 297 | 32.842 −7.027 6.250 1.00 8.97 | C |
| ATOM | 1808 CB LEU G 297 | 31.332 −6.796 6.367 1.00 8.64 | C |
| ATOM | 1809 CG LEU G 297 | 30.643 −6.020 5.243 1.00 9.01 | C |
| ATOM | 1810 CD1 LEU G 297 | 30.733 −6.773 3.927 1.00 9.79 | C |
| ATOM | 1811 CD2 LEU G 297 | 29.194 −5.752 5.606 1.00 9.43 | C |
| ATOM | 1812 C LEU G 297 | 33.544 −5.745 5.821 1.00 8.34 | C |
| ATOM | 1813 O LEU G 297 | 33.645 −4.793 6.595 1.00 8.64 | O |
| ATOM | 1814 N ALA G 298 | 34.131 −5.767 4.631 1.00 7.21 | N |
| ATOM | 1815 CA ALA G 298 | 34.751 −4.573 4.079 1.00 6.33 | C |
| ATOM | 1816 CB ALA G 298 | 36.231 −4.800 3.860 1.00 6.68 | C |
| ATOM | 1817 C ALA G 298 | 34.074 −4.177 2.778 1.00 5.85 | C |
| ATOM | 1818 O ALA G 298 | 33.727 −5.033 1.965 1.00 5.96 | O |
| ATOM | 1819 N TYR G 299 | 33.820 −2.883 2.620 1.00 5.28 | N |
| ATOM | 1820 CA TYR G 299 | 33.178 −2.376 1.417 1.00 4.63 | C |
| ATOM | 1821 CB TYR G 299 | 31.660 −2.340 1.595 1.00 4.36 | C |
| ATOM | 1822 CG TYR G 299 | 31.204 −1.517 2.776 1.00 4.34 | C |
| ATOM | 1823 CD1 TYR G 299 | 30.967 −0.156 2.648 1.00 4.48 | C |
| ATOM | 1824 CE1 TYR G 299 | 30.505 0.592 3.717 1.00 4.55 | C |
| ATOM | 1825 CZ TYR G 299 | 30.292 −0.019 4.937 1.00 3.72 | C |
| ATOM | 1826 OH TYR G 299 | 29.847 0.720 6.009 1.00 2.38 | O |
| ATOM | 1827 CE2 TYR G 299 | 30.540 −1.366 5.092 1.00 4.13 | C |
| ATOM | 1828 CD2 TYR G 299 | 31.007 −2.102 4.020 1.00 4.38 | C |
| ATOM | 1829 C TYR G 299 | 33.692 −0.988 1.063 1.00 4.32 | C |
| ATOM | 1830 O TYR G 299 | 34.067 −0.214 1.944 1.00 4.67 | O |
| ATOM | 1831 N VAL G 300 | 33.609 −0.641 −0.217 1.00 3.87 | N |
| ATOM | 1832 CA VAL G 300 | 34.121 0.636 −0.696 1.00 3.57 | C |
| ATOM | 1833 CB VAL G 300 | 34.892 0.481 −2.020 1.00 3.52 | C |
| ATOM | 1834 CG1 VAL G 300 | 35.278 1.843 −2.576 1.00 3.44 | C |
| ATOM | 1835 CG2 VAL G 300 | 36.127 −0.374 −1.808 1.00 3.90 | C |
| ATOM | 1836 C VAL G 300 | 32.999 1.654 −0.861 1.00 3.53 | C |
| ATOM | 1837 O VAL G 300 | 31.959 1.360 −1.451 1.00 3.68 | O |
| ATOM | 1838 N VAL G 301 | 33.163 2.795 −0.205 1.00 3.41 | N |
| ATOM | 1839 CA VAL G 301 | 32.321 3.950 −0.451 1.00 3.36 | C |
| ATOM | 1840 CB VAL G 301 | 32.264 4.847 0.789 1.00 3.24 | C |
| ATOM | 1841 CG1 VAL G 301 | 31.738 6.229 0.428 1.00 3.76 | C |
| ATOM | 1842 CG2 VAL G 301 | 31.431 4.190 1.884 1.00 3.10 | C |
| ATOM | 1843 C VAL G 301 | 32.854 4.766 −1.619 1.00 3.48 | C |
| ATOM | 1844 O VAL G 301 | 34.065 4.911 −1.786 1.00 3.92 | O |
| ATOM | 1845 N GLN G 302 | 31.943 5.410 −2.339 1.00 3.21 | N |
| ATOM | 1846 CA GLN G 302 | 32.285 6.084 −3.578 1.00 3.01 | C |
| ATOM | 1847 CB GLN G 302 | 31.901 5.213 −4.775 1.00 3.24 | C |
| ATOM | 1848 CG GLN G 302 | 31.990 5.924 −6.113 1.00 5.21 | C |
| ATOM | 1849 CD GLN G 302 | 32.153 4.963 −7.271 1.00 7.54 | C |
| ATOM | 1850 OE1 GLN G 302 | 32.555 3.814 −7.086 1.00 7.28 | O |

APPENDIX-continued (APPENDIX discloses SEQ ID NOS 29-32, 29-32 and 29-32, respectively, in order of appearance)

| | | | |
|---|---|---|---|
| ATOM | 1851 NE2 GLN G 302 | 31.793 5.412 −8.467 1.00 9.27 | N |
| ATOM | 1852 C GLN G 302 | 31.571 7.424 −3.652 1.00 2.42 | C |
| ATOM | 1853 O GLN G 302 | 30.344 7.479 −3.737 1.00 2.40 | O |
| ATOM | 1854 N LEU G 303 | 32.323 8.492 −3.426 1.00 2.00 | N |
| ATOM | 1855 CA LEU G 303 | 31.729 9.802 −3.232 1.00 2.00 | C |
| ATOM | 1856 CB LEU G 303 | 32.303 10.471 −1.979 1.00 2.00 | C |
| ATOM | 1857 CG LEU G 303 | 32.332 9.619 −0.706 1.00 2.00 | C |
| ATOM | 1858 CD1 LEU G 303 | 32.849 10.428 0.474 1.00 2.00 | C |
| ATOM | 1859 CD2 LEU G 303 | 30.960 9.033 −0.400 1.00 2.00 | C |
| ATOM | 1860 C LEU G 303 | 31.955 10.674 −4.460 1.00 2.00 | C |
| ATOM | 1861 O LEU G 303 | 32.835 10.391 −5.273 1.00 2.45 | O |
| ATOM | 1862 N PRO G 304 | 31.136 11.723 −4.614 1.00 2.00 | N |
| ATOM | 1863 CA PRO G 304 | 31.230 12.520 −5.827 1.00 2.07 | C |
| ATOM | 1864 CB PRO G 304 | 29.999 13.432 −5.754 1.00 2.00 | C |
| ATOM | 1865 CG PRO G 304 | 29.497 13.323 −4.348 1.00 2.00 | C |
| ATOM | 1866 CD PRO G 304 | 29.880 11.966 −3.888 1.00 2.06 | C |
| ATOM | 1867 C PRO G 304 | 32.513 13.340 −5.854 1.00 2.11 | C |
| ATOM | 1868 O PRO G 304 | 32.814 14.030 −4.878 1.00 2.13 | O |
| ATOM | 1869 N ALA G 305 | 33.407 12.935 −6.752 1.00 30.00 | N |
| ATOM | 1870 CA ALA G 305 | 33.971 13.839 −7.760 1.00 30.00 | C |
| ATOM | 1871 CB ALA G 305 | 35.427 13.480 −8.043 1.00 30.00 | C |
| ATOM | 1872 C ALA G 305 | 33.151 13.838 −9.059 1.00 30.00 | C |
| ATOM | 1873 O ALA G 305 | 32.743 12.775 −9.530 1.00 30.00 | O |
| ATOM | 1874 N TYR G 306 | 32.752 15.032 −9.522 1.00 13.49 | N |
| ATOM | 1875 CA TYR G 306 | 31.656 15.131 −10.505 1.00 13.70 | C |
| ATOM | 1876 CB TYR G 306 | 30.892 16.462 −10.539 1.00 13.93 | C |
| ATOM | 1877 CG TYR G 306 | 31.430 17.687 −9.879 1.00 14.08 | C |
| ATOM | 1878 CD1 TYR G 306 | 32.339 18.519 −10.551 1.00 14.59 | C |
| ATOM | 1879 CE1 TYR G 306 | 32.383 19.885 −10.286 1.00 14.82 | C |
| ATOM | 1880 CZ TYR G 306 | 31.470 20.425 −9.404 1.00 14.52 | C |
| ATOM | 1881 OH TYR G 306 | 31.626 21.709 −8.943 1.00 13.02 | O |
| ATOM | 1882 CE2 TYR G 306 | 30.465 19.645 −8.899 1.00 15.22 | C |
| ATOM | 1883 CD2 TYR G 306 | 30.596 18.296 −8.957 1.00 14.61 | C |
| ATOM | 1884 C TYR G 306 | 32.048 14.998 −11.938 1.00 13.68 | C |
| ATOM | 1885 O TYR G 306 | 33.051 14.374 −12.273 1.00 13.95 | O |
| ATOM | 1886 N GLY G 307 | 31.521 16.002 −12.645 1.00 13.54 | N |
| ATOM | 1887 CA GLY G 307 | 31.871 16.332 −14.033 1.00 13.37 | C |
| ATOM | 1888 C GLY G 307 | 30.772 16.073 −15.065 1.00 13.47 | C |
| ATOM | 1889 O GLY G 307 | 30.263 14.955 −15.138 1.00 13.90 | O |
| ATOM | 1890 N VAL G 308 | 30.591 16.991 −16.021 1.00 13.31 | N |
| ATOM | 1891 CA VAL G 308 | 29.883 16.654 −17.276 1.00 13.30 | C |
| ATOM | 1892 CB VAL G 308 | 28.555 15.924 −16.985 1.00 13.03 | C |
| ATOM | 1893 CG1 VAL G 308 | 28.183 15.008 −18.138 1.00 13.62 | C |
| ATOM | 1894 CG2 VAL G 308 | 28.619 15.178 −15.665 1.00 12.86 | C |
| ATOM | 1895 C VAL G 308 | 29.425 17.870 −18.046 1.00 13.58 | C |
| ATOM | 1896 O VAL G 308 | 30.236 18.677 −18.508 1.00 13.71 | O |
| ATOM | 1897 N ILE G 309 | 28.221 18.219 −17.643 1.00 4.08 | N |
| ATOM | 1898 CA ILE G 309 | 28.140 19.052 −16.487 1.00 4.84 | C |
| ATOM | 1899 CB ILE G 309 | 29.493 19.031 −15.728 1.00 4.89 | C |
| ATOM | 1900 CG1 ILE G 309 | 29.924 17.598 −15.412 1.00 5.85 | C |
| ATOM | 1901 CD1 ILE G 309 | 29.235 17.007 −14.197 1.00 8.12 | C |
| ATOM | 1902 CG2 ILE G 309 | 29.423 19.879 −14.473 1.00 4.44 | C |
| ATOM | 1903 C ILE G 309 | 28.075 20.346 −17.222 1.00 5.23 | C |
| ATOM | 1904 O ILE G 309 | 28.803 20.526 −18.199 1.00 5.92 | O |
| ATOM | 1905 N ASP G 310 | 26.984 21.057 −17.020 1.00 5.33 | N |
| ATOM | 1906 CA ASP G 310 | 26.985 22.446 −17.403 1.00 5.83 | C |
| ATOM | 1907 CB ASP G 310 | 28.432 22.938 −17.554 1.00 6.21 | C |
| ATOM | 1908 CG ASP G 310 | 29.280 22.660 −16.321 1.00 7.19 | C |
| ATOM | 1909 OD1 ASP G 310 | 30.432 22.200 −16.480 1.00 7.74 | O |
| ATOM | 1910 OD2 ASP G 310 | 28.844 23.021 −15.209 1.00 7.58 | O |
| ATOM | 1911 C ASP G 310 | 26.233 22.676 −18.712 1.00 6.02 | C |
| ATOM | 1912 O ASP G 310 | 26.323 23.760 −19.287 1.00 6.05 | O |
| ATOM | 1913 N THR G 311 | 25.448 21.696 −19.157 1.00 6.24 | N |
| ATOM | 1914 CA THR G 311 | 24.352 21.982 −20.088 1.00 6.14 | C |
| ATOM | 1915 CB THR G 311 | 23.883 20.720 −20.852 1.00 5.69 | C |
| ATOM | 1916 OG1 THR G 311 | 24.925 19.737 −20.850 1.00 5.34 | O |
| ATOM | 1917 CG2 THR G 311 | 23.526 21.069 −22.291 1.00 7.10 | C |
| ATOM | 1918 C THR G 311 | 23.160 22.578 −19.339 1.00 6.78 | C |
| ATOM | 1919 O THR G 311 | 22.863 22.163 −18.218 1.00 7.33 | O |
| ATOM | 1920 N PRO G 312 | 22.414 23.483 −19.992 1.00 7.00 | N |
| ATOM | 1921 CA PRO G 312 | 21.205 23.982 −19.341 1.00 7.23 | C |
| ATOM | 1922 CB PRO G 312 | 20.748 25.113 −20.267 1.00 7.00 | C |
| ATOM | 1923 CG PRO G 312 | 21.341 24.786 −21.593 1.00 6.59 | C |
| ATOM | 1924 CD PRO G 312 | 22.649 24.119 −21.300 1.00 6.99 | C |
| ATOM | 1925 C PRO G 312 | 20.138 22.895 −19.263 1.00 7.69 | C |
| ATOM | 1926 O PRO G 312 | 19.973 22.130 −20.213 1.00 7.55 | O |
| ATOM | 1927 N CYS G 313 | 19.469 22.781 −18.120 1.00 8.10 | N |

APPENDIX-continued (APPENDIX discloses SEQ ID NOS 29-32, 29-32 and 29-32, respectively, in order of appearance)

| | | | |
|---|---|---|---|
| ATOM | 1928 CA CYS G 313 | 18.164 22.128 −18.088 1.00 8.54 | C |
| ATOM | 1929 CB CYS G 313 | 18.165 20.883 −17.192 1.00 8.77 | C |
| ATOM | 1930 SG CYS G 313 | 19.762 20.065 −16.969 1.00 10.74 | S |
| ATOM | 1931 C CYS G 313 | 17.029 23.057 −17.686 1.00 8.19 | C |
| ATOM | 1932 O CYS G 313 | 17.246 24.212 −17.319 1.00 8.07 | O |
| ATOM | 1933 N TRP G 314 | 15.832 22.485 −17.634 1.00 7.93 | N |
| ATOM | 1934 CA TRP G 314 | 14.663 23.177 −17.125 1.00 7.80 | C |
| ATOM | 1935 CB TRP G 314 | 14.110 24.131 −18.184 1.00 8.13 | C |
| ATOM | 1936 CG TRP G 314 | 13.856 23.474 −19.505 1.00 9.09 | C |
| ATOM | 1937 CD1 TRP G 314 | 12.657 23.036 −19.985 1.00 10.26 | C |
| ATOM | 1938 NE1 TRP G 314 | 12.807 22.540 −21.257 1.00 10.86 | N |
| ATOM | 1939 CE2 TRP G 314 | 14.121 22.661 −21.628 1.00 10.68 | C |
| ATOM | 1940 CD2 TRP G 314 | 14.813 23.243 −20.547 1.00 10.49 | C |
| ATOM | 1941 CE3 TRP G 314 | 16.185 23.483 −20.675 1.00 11.67 | C |
| ATOM | 1942 CZ3 TRP G 314 | 16.814 23.119 −21.850 1.00 12.98 | C |
| ATOM | 1943 CH2 TRP G 314 | 16.104 22.513 −22.894 1.00 12.74 | C |
| ATOM | 1944 CZ2 TRP G 314 | 14.758 22.286 −22.807 1.00 11.73 | C |
| ATOM | 1945 C TRP G 314 | 13.603 22.153 −16.742 1.00 7.34 | C |
| ATOM | 1946 O TRP G 314 | 13.578 21.044 −17.275 1.00 7.47 | O |
| ATOM | 1947 N LYS G 315 | 12.783 22.500 −15.757 1.00 6.75 | N |
| ATOM | 1948 CA LYS G 315 | 11.667 21.654 −15.363 1.00 6.37 | C |
| ATOM | 1949 CB LYS G 315 | 11.631 21.475 −13.844 1.00 6.38 | C |
| ATOM | 1950 CG LYS G 315 | 10.746 20.331 −13.374 1.00 6.55 | C |
| ATOM | 1951 CD LYS G 315 | 10.695 20.252 −11.854 1.00 8.01 | C |
| ATOM | 1952 CE LYS G 315 | 9.848 19.077 −11.383 1.00 8.78 | C |
| ATOM | 1953 NZ LYS G 315 | 9.177 19.368 −10.085 1.00 10.21 | N |
| ATOM | 1954 C LYS G 315 | 10.348 22.231 −15.855 1.00 6.32 | C |
| ATOM | 1955 O LYS G 315 | 10.123 23.441 −15.798 1.00 6.21 | O |
| ATOM | 1956 N LEU G 316 | 9.529 21.370 −16.443 1.00 6.58 | N |
| ATOM | 1957 CA LEU G 316 | 8.273 21.796 −17.027 1.00 7.02 | C |
| ATOM | 1958 CB LEU G 316 | 8.140 21.253 −18.448 1.00 6.64 | C |
| ATOM | 1959 CG LEU G 316 | 6.756 21.379 −19.086 1.00 6.21 | C |
| ATOM | 1960 CD1 LEU G 316 | 6.358 22.841 −19.221 1.00 5.94 | C |
| ATOM | 1961 CD2 LEU G 316 | 6.730 20.687 −20.439 1.00 6.57 | C |
| ATOM | 1962 C LEU G 316 | 7.116 21.308 −16.172 1.00 7.77 | C |
| ATOM | 1963 O LEU G 316 | 6.942 20.105 −15.976 1.00 8.47 | O |
| ATOM | 1964 N HIS G 317 | 6.363 22.247 −15.613 1.00 8.05 | N |
| ATOM | 1965 CA HIS G 317 | 5.073 21.923 −15.031 1.00 8.21 | C |
| ATOM | 1966 CB HIS G 317 | 4.956 22.485 −13.614 1.00 9.04 | C |
| ATOM | 1967 CG HIS G 317 | 6.260 22.565 −12.886 1.00 11.41 | C |
| ATOM | 1968 ND1 HIS G 317 | 6.606 21.691 −11.877 1.00 13.62 | N |
| ATOM | 1969 CE1 HIS G 317 | 7.781 22.035 −11.383 1.00 14.91 | C |
| ATOM | 1970 NE2 HIS G 317 | 8.208 23.105 −12.029 1.00 14.25 | N |
| ATOM | 1971 CD2 HIS G 317 | 7.271 23.462 −12.969 1.00 12.67 | C |
| ATOM | 1972 C HIS G 317 | 3.943 22.453 −15.894 1.00 7.39 | C |
| ATOM | 1973 O HIS G 317 | 4.132 23.381 −16.680 1.00 7.23 | O |
| ATOM | 1974 N THR G 318 | 2.736 22.006 −15.580 1.00 7.11 | N |
| ATOM | 1975 CA THR G 318 | 1.704 21.826 −16.583 1.00 6.56 | C |
| ATOM | 1976 CB THR G 318 | 1.869 20.474 −17.309 1.00 6.28 | C |
| ATOM | 1977 OG1 THR G 318 | 2.413 20.694 −18.616 1.00 6.33 | O |
| ATOM | 1978 CG2 THR G 318 | 0.534 19.761 −17.435 1.00 6.52 | C |
| ATOM | 1979 C THR G 318 | 0.349 21.865 −15.893 1.00 6.58 | C |
| ATOM | 1980 O THR G 318 | 0.104 21.105 −14.958 1.00 6.67 | O |
| ATOM | 1981 N SER G 319 | −0.501 22.802 −16.301 1.00 6.81 | N |
| ATOM | 1982 CA SER G 319 | −1.840 22.911 −15.730 1.00 7.31 | C |
| ATOM | 1983 CB SER G 319 | −1.929 24.106 −14.779 1.00 7.14 | C |
| ATOM | 1984 OG SER G 319 | −3.255 24.292 −14.314 1.00 6.84 | O |
| ATOM | 1985 C SER G 319 | −2.922 23.006 −16.800 1.00 7.93 | C |
| ATOM | 1986 O SER G 319 | −2.717 23.624 −17.845 1.00 8.65 | O |
| ATOM | 1987 N PRO G 320 | −4.104 22.440 −16.514 1.00 8.08 | N |
| ATOM | 1988 CA PRO G 320 | −5.172 22.399 −17.500 1.00 8.34 | C |
| ATOM | 1989 CB PRO G 320 | −6.336 21.738 −16.743 1.00 7.99 | C |
| ATOM | 1990 CG PRO G 320 | −5.908 21.662 −15.304 1.00 8.01 | C |
| ATOM | 1991 CD PRO G 320 | −4.422 21.635 −15.324 1.00 8.10 | C |
| ATOM | 1992 C PRO G 320 | −5.564 23.793 −17.984 1.00 9.03 | C |
| ATOM | 1993 O PRO G 320 | −5.261 24.788 −17.325 1.00 8.74 | O |
| ATOM | 1994 N LEU G 321 | −6.134 23.854 −19.184 1.00 10.31 | N |
| ATOM | 1995 CA LEU G 321 | −6.366 25.113 −19.885 1.00 11.63 | C |
| ATOM | 1996 CB LEU G 321 | −5.207 25.402 −20.848 1.00 11.31 | C |
| ATOM | 1997 CG LEU G 321 | −4.949 26.848 −21.291 1.00 10.97 | C |
| ATOM | 1998 CD1 LEU G 321 | −4.174 26.884 −22.600 1.00 10.04 | C |
| ATOM | 1999 CD2 LEU G 321 | −6.241 27.639 −21.416 1.00 10.69 | C |
| ATOM | 2000 C LEU G 321 | −7.683 25.027 −20.662 1.00 12.92 | C |
| ATOM | 2001 O LEU G 321 | −7.890 24.095 −21.439 1.00 13.29 | O |
| ATOM | 2002 N CYS G 322 | −8.593 25.964 −20.400 1.00 13.39 | N |
| ATOM | 2003 CA CYS G 322 | −9.923 25.955 −21.017 1.00 14.16 | C |
| ATOM | 2004 CB CYS G 322 | −10.994 25.588 −19.990 1.00 13.72 | C |

APPENDIX-continued (APPENDIX discloses SEQ ID NOS 29-32, 29-32 and 29-32, respectively, in order of appearance)

| | | | |
|---|---|---|---|
| ATOM | 2005 SG CYS G 322 | −10.587 24.180 −18.943 1.00 13.42 | S |
| ATOM | 2006 C CYS G 322 | −10.274 27.299 −21.650 1.00 15.46 | C |
| ATOM | 2007 O CYS G 322 | −10.048 28.352 −21.054 1.00 15.94 | O |
| ATOM | 2008 N THR G 323 | −10.985 27.241 −22.773 1.00 16.70 | N |
| ATOM | 2009 CA THR G 323 | −11.694 28.395 −23.326 1.00 17.84 | C |
| ATOM | 2010 CB THR G 323 | −12.389 28.017 −24.647 1.00 17.50 | C |
| ATOM | 2011 OG1 THR G 323 | −12.703 26.618 −24.638 1.00 15.70 | O |
| ATOM | 2012 CG2 THR G 323 | −11.486 28.322 −25.831 1.00 18.05 | C |
| ATOM | 2013 C THR G 323 | −12.756 28.915 −22.359 1.00 19.54 | C |
| ATOM | 2014 O THR G 323 | −13.178 28.188 −21.461 1.00 19.84 | O |
| ATOM | 2015 N THR G 324 | −13.354 30.061 −22.684 1.00 21.17 | N |
| ATOM | 2016 CA THR G 324 | −14.592 30.460 −22.017 1.00 22.89 | C |
| ATOM | 2017 CB THR G 324 | −14.343 31.388 −20.821 1.00 22.69 | C |
| ATOM | 2018 OG1 THR G 324 | −12.937 31.469 −20.560 1.00 22.10 | O |
| ATOM | 2019 CG2 THR G 324 | −15.061 30.857 −19.587 1.00 22.03 | C |
| ATOM | 2020 C THR G 324 | −15.712 31.033 −22.885 1.00 24.39 | C |
| ATOM | 2021 O THR G 324 | −16.838 31.194 −22.414 1.00 24.53 | O |
| ATOM | 2022 N ASN G 325 | −15.427 31.299 −24.155 1.00 25.72 | N |
| ATOM | 2023 CA ASN G 325 | −16.490 31.473 −25.144 1.00 27.01 | C |
| ATOM | 2024 CB ASN G 325 | −16.986 32.922 −25.170 1.00 27.37 | C |
| ATOM | 2025 CG ASN G 325 | −18.079 33.184 −24.148 1.00 28.46 | C |
| ATOM | 2026 OD1 ASN G 325 | −19.267 33.164 −24.471 1.00 30.37 | O |
| ATOM | 2027 ND2 ASN G 325 | −17.678 33.444 −22.909 1.00 28.78 | N |
| ATOM | 2028 C ASN G 325 | −16.075 31.032 −26.543 1.00 27.36 | C |
| ATOM | 2029 O ASN G 325 | −14.887 30.902 −26.837 1.00 27.94 | O |
| ATOM | 2030 N SER G 330 | −15.165 27.730 −23.322 1.00 35.76 | N |
| ATOM | 2031 CA SER G 330 | −16.301 26.817 −23.281 1.00 35.01 | C |
| ATOM | 2032 CB SER G 330 | −17.459 27.366 −24.117 1.00 35.47 | C |
| ATOM | 2033 OG SER G 330 | −17.137 27.368 −25.497 1.00 33.31 | O |
| ATOM | 2034 C SER G 330 | −15.906 25.431 −23.779 1.00 34.35 | C |
| ATOM | 2035 O SER G 330 | −15.111 25.299 −24.709 1.00 34.33 | O |
| ATOM | 2036 N ASN G 331 | −16.430 24.399 −23.128 1.00 32.48 | N |
| ATOM | 2037 CA ASN G 331 | −16.609 23.102 −23.770 1.00 30.72 | C |
| ATOM | 2038 CB ASN G 331 | −17.432 23.247 −25.060 1.00 31.31 | C |
| ATOM | 2039 CG ASN G 331 | −18.924 23.445 −24.801 1.00 32.11 | C |
| ATOM | 2040 OD1 ASN G 331 | −19.426 23.149 −23.716 1.00 32.54 | O |
| ATOM | 2041 ND2 ASN G 331 | −19.651 23.849 −25.838 1.00 31.30 | N |
| ATOM | 2042 C ASN G 331 | −15.298 22.357 −24.074 1.00 28.71 | C |
| ATOM | 2043 O ASN G 331 | −15.322 21.324 −24.741 1.00 29.07 | O |
| ATOM | 2044 N ILE G 332 | −14.155 22.896 −23.649 1.00 25.44 | N |
| ATOM | 2045 CA ILE G 332 | −12.868 22.313 −24.053 1.00 21.83 | C |
| ATOM | 2046 CB ILE G 332 | −12.546 22.613 −25.536 1.00 21.42 | C |
| ATOM | 2047 CG1 ILE G 332 | −11.286 21.867 −25.981 1.00 19.89 | C |
| ATOM | 2048 CD1 ILE G 332 | −11.573 20.576 −26.724 1.00 17.67 | C |
| ATOM | 2049 CG2 ILE G 332 | −12.428 24.111 −25.776 1.00 20.61 | C |
| ATOM | 2050 C ILE G 332 | −11.667 22.657 −23.162 1.00 20.37 | C |
| ATOM | 2051 O ILE G 332 | −11.388 23.829 −22.903 1.00 19.95 | O |
| ATOM | 2052 N CYS G 333 | −10.896 21.634 −22.794 1.00 18.27 | N |
| ATOM | 2053 CA CYS G 333 | −9.666 21.842 −22.031 1.00 16.47 | C |
| ATOM | 2054 CB CYS G 333 | −9.923 21.703 −20.529 1.00 16.14 | C |
| ATOM | 2055 SG CYS G 333 | −11.374 22.595 −19.936 1.00 17.09 | S |
| ATOM | 2056 C CYS G 333 | −8.480 20.967 −22.450 1.00 15.73 | C |
| ATOM | 2057 O CYS G 333 | −8.652 19.820 −22.871 1.00 15.43 | O |
| ATOM | 2058 N LEU G 334 | −7.298 21.425 −22.047 1.00 15.06 | N |
| ATOM | 2059 CA LEU G 334 | −6.022 20.883 −22.498 1.00 13.79 | C |
| ATOM | 2060 CB LEU G 334 | −5.346 21.857 −23.472 1.00 13.39 | C |
| ATOM | 2061 CG LEU G 334 | −5.891 21.998 −24.895 1.00 13.93 | C |
| ATOM | 2062 CD1 LEU G 334 | −4.764 22.327 −25.858 1.00 14.20 | C |
| ATOM | 2063 CD2 LEU G 334 | −6.617 20.739 −25.331 1.00 14.52 | C |
| ATOM | 2064 C LEU G 334 | −5.142 20.748 −21.263 1.00 13.22 | C |
| ATOM | 2065 O LEU G 334 | −5.033 21.685 −20.472 1.00 13.31 | O |
| ATOM | 2066 N THR G 335 | −4.417 19.640 −21.169 1.00 12.58 | N |
| ATOM | 2067 CA THR G 335 | −3.277 19.561 −20.268 1.00 12.17 | C |
| ATOM | 2068 CB THR G 335 | −3.612 18.748 −19.001 1.00 12.02 | C |
| ATOM | 2069 OG1 THR G 335 | −5.021 18.815 −18.744 1.00 12.64 | O |
| ATOM | 2070 CG2 THR G 335 | −2.858 19.295 −17.803 1.00 11.47 | C |
| ATOM | 2071 C THR G 335 | −2.093 18.930 −20.986 1.00 11.97 | C |
| ATOM | 2072 O THR G 335 | −2.258 17.980 −21.751 1.00 11.93 | O |
| ATOM | 2073 N ARG G 336 | −0.942 19.586 −20.892 1.00 11.60 | N |
| ATOM | 2074 CA ARG G 336 | 0.254 19.122 −21.578 1.00 12.15 | C |
| ATOM | 2075 CB ARG G 336 | 1.293 20.239 −21.640 1.00 12.16 | C |
| ATOM | 2076 CG ARG G 336 | 2.162 20.208 −22.879 1.00 12.67 | C |
| ATOM | 2077 CD ARG G 336 | 2.261 21.590 −23.500 1.00 12.52 | C |
| ATOM | 2078 NE ARG G 336 | 3.341 22.374 −22.912 1.00 12.35 | N |
| ATOM | 2079 CZ ARG G 336 | 4.632 22.136 −23.117 1.00 12.54 | C |
| ATOM | 2080 NH1 ARG G 336 | 5.006 21.109 −23.867 1.00 12.38 | N |
| ATOM | 2081 NH2 ARG G 336 | 5.549 22.904 −22.545 1.00 12.48 | N |

APPENDIX-continued (APPENDIX discloses SEQ ID NOS 29-32, 29-32 and 29-32, respectively, in order of appearance)

| | | | |
|---|---|---|---|
| ATOM | 2082 C ARG G 336 | 0.841 17.907 −20.872 1.00 12.71 | C |
| ATOM | 2083 O ARG G 336 | 1.185 17.974 −19.693 1.00 12.62 | O |
| ATOM | 2084 N THR G 337 | 0.885 16.779 −21.574 1.00 13.70 | N |
| ATOM | 2085 CA THR G 337 | 1.284 15.514 −20.964 1.00 14.91 | C |
| ATOM | 2086 CB THR G 337 | 1.084 14.331 −21.931 1.00 15.27 | C |
| ATOM | 2087 OG1 THR G 337 | −0.264 14.329 −22.421 1.00 16.65 | O |
| ATOM | 2088 CG2 THR G 337 | 1.370 13.015 −21.226 1.00 15.94 | C |
| ATOM | 2089 C THR G 337 | 2.744 15.546 −20.519 1.00 15.16 | C |
| ATOM | 2090 O THR G 337 | 3.069 15.159 −19.396 1.00 15.60 | O |
| ATOM | 2091 N ASP G 338 | 3.623 15.968 −21.424 1.00 15.15 | N |
| ATOM | 2092 CA ASP G 338 | 5.055 15.721 −21.283 1.00 15.52 | C |
| ATOM | 2093 CB ASP G 338 | 5.781 15.935 −22.613 1.00 16.81 | C |
| ATOM | 2094 CG ASP G 338 | 5.051 16.899 −23.529 1.00 20.57 | C |
| ATOM | 2095 OD1 ASP G 338 | 5.160 16.744 −24.763 1.00 23.00 | O |
| ATOM | 2096 OD2 ASP G 338 | 4.290 17.747 −23.017 1.00 22.92 | O |
| ATOM | 2097 C ASP G 338 | 5.674 16.595 −20.201 1.00 14.21 | C |
| ATOM | 2098 O ASP G 338 | 6.235 17.654 −20.486 1.00 14.00 | O |
| ATOM | 2099 N ARG G 339 | 5.617 16.113 −18.965 1.00 12.79 | N |
| ATOM | 2100 CA ARG G 339 | 6.087 16.877 −17.822 1.00 11.71 | C |
| ATOM | 2101 CB ARG G 339 | 5.108 16.747 −16.665 1.00 11.73 | C |
| ATOM | 2102 CG ARG G 339 | 3.773 17.383 −16.931 1.00 12.49 | C |
| ATOM | 2103 CD ARG G 339 | 3.116 17.761 −15.633 1.00 13.24 | C |
| ATOM | 2104 NE ARG G 339 | 1.712 17.370 −15.607 1.00 12.04 | N |
| ATOM | 2105 CZ ARG G 339 | 0.844 17.804 −14.703 1.00 11.74 | C |
| ATOM | 2106 NH1 ARG G 339 | 1.259 18.579 −13.710 1.00 13.43 | N |
| ATOM | 2107 NH2 ARG G 339 | −0.427 17.428 −14.759 1.00 9.80 | N |
| ATOM | 2108 C ARG G 339 | 7.443 16.388 −17.365 1.00 11.16 | C |
| ATOM | 2109 O ARG G 339 | 7.703 15.185 −17.376 1.00 11.37 | O |
| ATOM | 2110 N GLY G 340 | 8.141 17.269 −16.660 1.00 10.43 | N |
| ATOM | 2111 CA GLY G 340 | 9.340 16.886 −15.933 1.00 9.52 | C |
| ATOM | 2112 C GLY G 340 | 10.559 17.608 −16.465 1.00 8.80 | C |
| ATOM | 2113 O GLY G 340 | 10.475 18.759 −16.903 1.00 8.56 | O |
| ATOM | 2114 N TRP G 341 | 11.700 16.935 −16.411 1.00 8.25 | N |
| ATOM | 2115 CA TRP G 341 | 12.965 17.581 −16.704 1.00 7.98 | C |
| ATOM | 2116 CB TRP G 341 | 14.089 16.966 −15.879 1.00 7.79 | C |
| ATOM | 2117 CG TRP G 341 | 14.110 17.460 −14.478 1.00 7.67 | C |
| ATOM | 2118 CD1 TRP G 341 | 13.519 16.869 −13.399 1.00 8.12 | C |
| ATOM | 2119 NE1 TRP G 341 | 13.686 17.648 −12.283 1.00 8.60 | N |
| ATOM | 2120 CE2 TRP G 341 | 14.304 18.815 −12.649 1.00 7.57 | C |
| ATOM | 2121 CD2 TRP G 341 | 14.536 18.754 −14.037 1.00 7.52 | C |
| ATOM | 2122 CE3 TRP G 341 | 15.176 19.830 −14.663 1.00 7.86 | C |
| ATOM | 2123 CZ3 TRP G 341 | 15.535 20.925 −13.898 1.00 7.14 | C |
| ATOM | 2124 CH2 TRP G 341 | 15.279 20.962 −12.521 1.00 6.39 | C |
| ATOM | 2125 CZ2 TRP G 341 | 14.663 19.919 −11.880 1.00 7.30 | C |
| ATOM | 2126 C TRP G 341 | 13.286 17.490 −18.180 1.00 8.26 | C |
| ATOM | 2127 O TRP G 341 | 13.320 16.402 −18.755 1.00 8.35 | O |
| ATOM | 2128 N TYR G 342 | 13.400 18.649 −18.811 1.00 8.44 | N |
| ATOM | 2129 CA TYR G 342 | 14.197 18.777 −20.012 1.00 8.53 | C |
| ATOM | 2130 CB TYR G 342 | 13.486 19.670 −21.015 1.00 8.43 | C |
| ATOM | 2131 CG TYR G 342 | 12.099 19.192 −21.318 1.00 9.17 | C |
| ATOM | 2132 CD1 TYR G 342 | 11.097 19.299 −20.363 1.00 10.32 | C |
| ATOM | 2133 CE1 TYR G 342 | 9.849 18.765 −20.582 1.00 10.99 | C |
| ATOM | 2134 CZ TYR G 342 | 9.618 18.033 −21.724 1.00 11.00 | C |
| ATOM | 2135 OH TYR G 342 | 8.365 17.521 −21.964 1.00 12.82 | O |
| ATOM | 2136 CE2 TYR G 342 | 10.626 17.838 −22.643 1.00 10.67 | C |
| ATOM | 2137 CD2 TYR G 342 | 11.871 18.365 −22.403 1.00 10.41 | C |
| ATOM | 2138 C TYR G 342 | 15.550 19.359 −19.680 1.00 8.64 | C |
| ATOM | 2139 O TYR G 342 | 15.754 19.906 −18.596 1.00 8.40 | O |
| ATOM | 2140 N CYS G 343 | 16.460 19.284 −20.641 1.00 8.87 | N |
| ATOM | 2141 CA CYS G 343 | 17.875 19.346 −20.332 1.00 9.35 | C |
| ATOM | 2142 CB CYS G 343 | 18.190 18.501 −19.092 1.00 9.17 | C |
| ATOM | 2143 SG CYS G 343 | 19.879 18.684 −18.466 1.00 11.88 | S |
| ATOM | 2144 C CYS G 343 | 18.722 18.920 −21.524 1.00 9.42 | C |
| ATOM | 2145 O CYS G 343 | 18.505 17.856 −22.103 1.00 9.96 | O |
| ATOM | 2146 N ASP G 344 | 19.534 19.857 −22.005 1.00 9.36 | N |
| ATOM | 2147 CA ASP G 344 | 20.127 19.778 −23.338 1.00 9.24 | C |
| ATOM | 2148 CB ASP G 344 | 20.797 21.108 −23.703 1.00 9.34 | C |
| ATOM | 2149 CG ASP G 344 | 19.874 22.037 −24.474 1.00 10.72 | C |
| ATOM | 2150 OD1 ASP G 344 | 19.475 21.677 −25.602 1.00 13.93 | O |
| ATOM | 2151 OD2 ASP G 344 | 19.548 23.127 −23.954 1.00 11.87 | O |
| ATOM | 2152 C ASP G 344 | 21.148 18.651 −23.425 1.00 9.09 | C |
| ATOM | 2153 O ASP G 344 | 22.100 18.605 −22.646 1.00 9.39 | O |
| ATOM | 2154 N ASN G 345 | 21.038 17.843 −24.474 1.00 9.13 | N |
| ATOM | 2155 CA ASN G 345 | 22.114 16.939 −24.849 1.00 9.52 | C |
| ATOM | 2156 CB ASN G 345 | 21.589 15.509 −24.978 1.00 9.61 | C |
| ATOM | 2157 CG ASN G 345 | 22.640 14.472 −24.643 1.00 9.21 | C |
| ATOM | 2158 OD1 ASN G 345 | 23.121 14.400 −23.512 1.00 6.21 | O |

APPENDIX-continued (APPENDIX discloses SEQ ID NOS 29-32, 29-32 and 29-32, respectively, in order of appearance)

| | | | |
|---|---|---|---|
| ATOM | 2159 ND2 ASN G 345 | 23.032 13.685 −25.638 1.00 11.05 | N |
| ATOM | 2160 C ASN G 345 | 22.772 17.381 −26.149 1.00 10.06 | C |
| ATOM | 2161 O ASN G 345 | 22.506 18.476 −26.644 1.00 11.10 | O |
| ATOM | 2162 N ALA G 346 | 23.644 16.539 −26.692 1.00 9.74 | N |
| ATOM | 2163 CA ALA G 346 | 24.410 16.904 −27.877 1.00 9.58 | C |
| ATOM | 2164 CB ALA G 346 | 25.241 15.723 −28.356 1.00 9.60 | C |
| ATOM | 2165 C ALA G 346 | 23.498 17.406 −28.994 1.00 9.66 | C |
| ATOM | 2166 O ALA G 346 | 22.977 16.618 −29.782 1.00 9.39 | O |
| ATOM | 2167 N GLY G 347 | 23.290 18.720 −29.038 1.00 10.04 | N |
| ATOM | 2168 CA GLY G 347 | 22.598 19.358 −30.157 1.00 10.68 | C |
| ATOM | 2169 C GLY G 347 | 21.105 19.098 −30.137 1.00 10.90 | C |
| ATOM | 2170 O GLY G 347 | 20.366 19.569 −31.002 1.00 11.46 | O |
| ATOM | 2171 N SER G 348 | 20.691 18.235 −29.219 1.00 10.30 | N |
| ATOM | 2172 CA SER G 348 | 19.301 17.838 −29.098 1.00 9.94 | C |
| ATOM | 2173 CB SER G 348 | 19.103 16.421 −29.639 1.00 9.88 | C |
| ATOM | 2174 OG SER G 348 | 19.440 16.352 −31.013 1.00 10.09 | O |
| ATOM | 2175 C SER G 348 | 18.950 17.883 −27.624 1.00 9.60 | C |
| ATOM | 2176 O SER G 348 | 19.775 18.267 −26.796 1.00 9.59 | O |
| ATOM | 2177 N VAL G 349 | 17.723 17.505 −27.292 1.00 9.54 | N |
| ATOM | 2178 CA VAL G 349 | 17.254 17.643 −25.925 1.00 9.56 | C |
| ATOM | 2179 CB VAL G 349 | 16.091 18.639 −25.823 1.00 9.28 | C |
| ATOM | 2180 CG1 VAL G 349 | 15.814 18.985 −24.360 1.00 9.24 | C |
| ATOM | 2181 CG2 VAL G 349 | 16.391 19.892 −26.641 1.00 9.94 | C |
| ATOM | 2182 C VAL G 349 | 16.824 16.309 −25.341 1.00 9.59 | C |
| ATOM | 2183 O VAL G 349 | 16.029 15.585 −25.939 1.00 9.69 | O |
| ATOM | 2184 N SER G 350 | 17.288 16.029 −24.130 1.00 9.93 | N |
| ATOM | 2185 CA SER G 350 | 16.915 14.800 −23.451 1.00 10.44 | C |
| ATOM | 2186 CB SER G 350 | 18.146 14.108 −22.858 1.00 10.04 | C |
| ATOM | 2187 OG SER G 350 | 18.768 13.261 −23.812 1.00 8.41 | O |
| ATOM | 2188 C SER G 350 | 15.854 15.039 −22.381 1.00 11.45 | C |
| ATOM | 2189 O SER G 350 | 15.882 16.041 −21.665 1.00 11.58 | O |
| ATOM | 2190 N PHE G 351 | 14.893 14.126 −22.318 1.00 12.28 | N |
| ATOM | 2191 CA PHE G 351 | 13.722 14.291 −21.469 1.00 13.04 | C |
| ATOM | 2192 CB PHE G 351 | 12.468 14.485 −22.321 1.00 12.87 | C |
| ATOM | 2193 CG PHE G 351 | 11.192 14.388 −21.539 1.00 13.52 | C |
| ATOM | 2194 CD1 PHE G 351 | 11.026 15.127 −20.378 1.00 13.76 | C |
| ATOM | 2195 CE1 PHE G 351 | 9.857 15.044 −19.648 1.00 14.10 | C |
| ATOM | 2196 CZ PHE G 351 | 8.855 14.175 −20.045 1.00 14.07 | C |
| ATOM | 2197 CE2 PHE G 351 | 9.028 13.395 −21.172 1.00 14.14 | C |
| ATOM | 2198 CD2 PHE G 351 | 10.202 13.489 −21.903 1.00 13.92 | C |
| ATOM | 2199 C PHE G 351 | 13.526 13.082 −20.563 1.00 13.84 | C |
| ATOM | 2200 O PHE G 351 | 13.246 11.979 −21.038 1.00 13.96 | O |
| ATOM | 2201 N PHE G 352 | 13.463 13.340 −19.263 1.00 14.72 | N |
| ATOM | 2202 CA PHE G 352 | 13.315 12.275 −18.286 1.00 15.98 | C |
| ATOM | 2203 CB PHE G 352 | 14.429 12.360 −17.243 1.00 15.75 | C |
| ATOM | 2204 CG PHE G 352 | 15.720 12.912 −17.780 1.00 15.51 | C |
| ATOM | 2205 CD1 PHE G 352 | 15.899 14.279 −17.924 1.00 15.05 | C |
| ATOM | 2206 CE1 PHE G 352 | 17.098 14.793 −18.375 1.00 14.05 | C |
| ATOM | 2207 CZ PHE G 352 | 18.126 13.938 −18.719 1.00 13.28 | C |
| ATOM | 2208 CE2 PHE G 352 | 17.948 12.570 −18.615 1.00 13.71 | C |
| ATOM | 2209 CD2 PHE G 352 | 16.745 12.064 −18.163 1.00 14.94 | C |
| ATOM | 2210 C PHE G 352 | 11.952 12.360 −17.612 1.00 17.56 | C |
| ATOM | 2211 O PHE G 352 | 11.591 13.401 −17.066 1.00 17.74 | O |
| ATOM | 2212 N PRO G 353 | 11.165 11.280 −17.705 1.00 19.05 | N |
| ATOM | 2213 CA PRO G 353 | 9.719 11.355 −17.537 1.00 20.40 | C |
| ATOM | 2214 CB PRO G 353 | 9.220 10.060 −18.189 1.00 20.26 | C |
| ATOM | 2215 CG PRO G 353 | 10.352 9.587 −19.046 1.00 19.71 | C |
| ATOM | 2216 CD PRO G 353 | 11.580 10.012 −18.325 1.00 18.97 | C |
| ATOM | 2217 C PRO G 353 | 9.291 11.404 −16.072 1.00 21.94 | C |
| ATOM | 2218 O PRO G 353 | 8.222 11.935 −15.768 1.00 22.29 | O |
| ATOM | 2219 N GLN G 354 | 10.105 10.851 −15.175 1.00 23.38 | N |
| ATOM | 2220 CA GLN G 354 | 9.731 10.792 −13.761 1.00 24.64 | C |
| ATOM | 2221 CB GLN G 354 | 9.107 9.440 −13.400 1.00 24.93 | C |
| ATOM | 2222 CG GLN G 354 | 9.407 8.322 −14.376 1.00 26.00 | C |
| ATOM | 2223 CD GLN G 354 | 10.859 7.909 −14.354 1.00 25.92 | C |
| ATOM | 2224 OE1 GLN G 354 | 11.380 7.473 −13.327 1.00 25.67 | O |
| ATOM | 2225 NE2 GLN G 354 | 11.521 8.030 −15.498 1.00 24.27 | N |
| ATOM | 2226 C GLN G 354 | 10.823 11.177 −12.759 1.00 24.85 | C |
| ATOM | 2227 O GLN G 354 | 12.009 10.943 −12.989 1.00 24.51 | O |
| ATOM | 2228 N ALA G 355 | 10.392 11.709 −11.618 1.00 25.22 | N |
| ATOM | 2229 CA ALA G 355 | 11.296 12.264 −10.619 1.00 25.34 | C |
| ATOM | 2230 CB ALA G 355 | 10.565 12.449 −9.296 1.00 25.09 | C |
| ATOM | 2231 C ALA G 355 | 12.531 11.390 −10.427 1.00 24.92 | C |
| ATOM | 2232 O ALA G 355 | 13.646 11.791 −10.766 1.00 25.23 | O |
| ATOM | 2233 N GLU G 356 | 12.339 10.258 −9.755 1.00 23.93 | N |
| ATOM | 2234 CA GLU G 356 | 13.282 9.141 −9.803 1.00 22.77 | C |
| ATOM | 2235 CB GLU G 356 | 12.642 7.925 −10.474 1.00 23.22 | C |

APPENDIX-continued (APPENDIX discloses SEQ ID NOS 29-32, 29-32 and 29-32, respectively, in order of appearance)

| | | | |
|---|---|---|---|
| ATOM | 2236 CG GLU G 356 | 11.489 7.338 −9.681 1.00 26.33 | C |
| ATOM | 2237 CD GLU G 356 | 11.607 7.632 −8.199 1.00 30.93 | C |
| ATOM | 2238 OE1 GLU G 356 | 11.148 8.711 −7.764 1.00 31.97 | O |
| ATOM | 2239 OE2 GLU G 356 | 12.276 6.846 −7.494 1.00 32.21 | O |
| ATOM | 2240 C GLU G 356 | 14.591 9.493 −10.492 1.00 21.31 | C |
| ATOM | 2241 O GLU G 356 | 15.656 9.462 −9.876 1.00 21.01 | O |
| ATOM | 2242 N THR G 357 | 14.511 9.752 −11.791 1.00 19.51 | N |
| ATOM | 2243 CA THR G 357 | 15.690 9.787 −12.639 1.00 17.55 | C |
| ATOM | 2244 CB THR G 357 | 15.305 9.928 −14.114 1.00 17.30 | C |
| ATOM | 2245 OG1 THR G 357 | 13.908 9.660 −14.273 1.00 17.32 | O |
| ATOM | 2246 CG2 THR G 357 | 16.099 8.958 −14.957 1.00 17.72 | C |
| ATOM | 2247 C THR G 357 | 16.596 10.949 −12.262 1.00 16.62 | C |
| ATOM | 2248 O THR G 357 | 17.761 10.991 −12.655 1.00 17.29 | O |
| ATOM | 2249 N CYS G 358 | 16.028 11.935 −11.579 1.00 14.88 | N |
| ATOM | 2250 CA CYS G 358 | 16.684 13.225 −11.440 1.00 13.15 | C |
| ATOM | 2251 CB CYS G 358 | 16.025 14.262 −12.349 1.00 13.04 | C |
| ATOM | 2252 SG CYS G 358 | 16.175 13.900 −14.114 1.00 14.02 | S |
| ATOM | 2253 C CYS G 358 | 16.711 13.714 −9.997 1.00 12.08 | C |
| ATOM | 2254 O CYS G 358 | 15.705 13.661 −9.289 1.00 12.15 | O |
| ATOM | 2255 N LYS G 359 | 17.890 14.140 −9.554 1.00 11.35 | N |
| ATOM | 2256 CA LYS G 359 | 18.024 14.888 −8.311 1.00 11.01 | C |
| ATOM | 2257 CB LYS G 359 | 18.968 14.165 −7.353 1.00 11.16 | C |
| ATOM | 2258 CG LYS G 359 | 19.450 12.824 −7.857 1.00 13.28 | C |
| ATOM | 2259 CD LYS G 359 | 19.029 11.720 −6.912 1.00 16.11 | C |
| ATOM | 2260 CE LYS G 359 | 19.561 10.378 −7.366 1.00 17.91 | C |
| ATOM | 2261 NZ LYS G 359 | 18.972 9.264 −6.575 1.00 20.99 | N |
| ATOM | 2262 C LYS G 359 | 18.561 16.282 −8.584 1.00 10.46 | C |
| ATOM | 2263 O LYS G 359 | 19.145 16.533 −9.637 1.00 10.70 | O |
| ATOM | 2264 N VAL G 360 | 18.526 17.128 −7.564 1.00 9.99 | N |
| ATOM | 2265 CA VAL G 360 | 18.797 18.538 −7.763 1.00 9.84 | C |
| ATOM | 2266 CB VAL G 360 | 17.573 19.270 −8.346 1.00 9.42 | C |
| ATOM | 2267 CG1 VAL G 360 | 16.360 19.095 −7.442 1.00 10.07 | C |
| ATOM | 2268 CG2 VAL G 360 | 17.886 20.740 −8.572 1.00 9.56 | C |
| ATOM | 2269 C VAL G 360 | 19.259 19.211 −6.478 1.00 9.98 | C |
| ATOM | 2270 O VAL G 360 | 18.707 18.970 −5.405 1.00 9.96 | O |
| ATOM | 2271 N GLN G 361 | 20.372 19.931 −6.578 1.00 10.39 | N |
| ATOM | 2272 CA GLN G 361 | 20.979 20.583 −5.427 1.00 11.53 | C |
| ATOM | 2273 CB GLN G 361 | 22.220 19.809 −4.971 1.00 12.03 | C |
| ATOM | 2274 CG GLN G 361 | 22.907 20.381 −3.737 1.00 16.44 | C |
| ATOM | 2275 CD GLN G 361 | 23.241 19.314 −2.714 1.00 25.16 | C |
| ATOM | 2276 OE1 GLN G 361 | 24.398 18.921 −2.564 1.00 29.01 | O |
| ATOM | 2277 NE2 GLN G 361 | 22.220 18.812 −2.029 1.00 27.20 | N |
| ATOM | 2278 C GLN G 361 | 21.373 22.005 −5.794 1.00 11.15 | C |
| ATOM | 2279 O GLN G 361 | 22.354 22.221 −6.506 1.00 11.80 | O |
| ATOM | 2280 N SER G 362 | 20.611 22.976 −5.308 1.00 10.90 | N |
| ATOM | 2281 CA SER G 362 | 20.759 24.332 −5.798 1.00 10.30 | C |
| ATOM | 2282 CB SER G 362 | 22.208 24.792 −5.625 1.00 10.47 | C |
| ATOM | 2283 OG SER G 362 | 22.406 26.082 −6.179 1.00 11.17 | O |
| ATOM | 2284 C SER G 362 | 20.385 24.348 −7.272 1.00 9.58 | C |
| ATOM | 2285 O SER G 362 | 19.409 23.717 −7.677 1.00 9.48 | O |
| ATOM | 2286 N ASN G 363 | 21.256 24.926 −8.089 1.00 9.12 | N |
| ATOM | 2287 CA ASN G 363 | 21.023 24.985 −9.525 1.00 8.73 | C |
| ATOM | 2288 CB ASN G 363 | 21.537 26.308 −10.085 1.00 9.01 | C |
| ATOM | 2289 CG ASN G 363 | 23.018 26.497 −9.849 1.00 9.29 | C |
| ATOM | 2290 OD1 ASN G 363 | 23.681 25.636 −9.270 1.00 9.82 | O |
| ATOM | 2291 ND2 ASN G 363 | 23.555 27.615 −10.323 1.00 10.08 | N |
| ATOM | 2292 C ASN G 363 | 21.701 23.822 −10.237 1.00 8.12 | C |
| ATOM | 2293 O ASN G 363 | 21.961 23.881 −11.439 1.00 8.10 | O |
| ATOM | 2294 N ARG G 364 | 22.103 22.828 −9.453 1.00 7.20 | N |
| ATOM | 2295 CA ARG G 364 | 22.733 21.628 −9.984 1.00 6.82 | C |
| ATOM | 2296 CB ARG G 364 | 23.843 21.154 −9.044 1.00 6.91 | C |
| ATOM | 2297 CG ARG G 364 | 25.110 20.721 −9.754 1.00 7.92 | C |
| ATOM | 2298 CD ARG G 364 | 25.588 21.797 −10.709 1.00 8.20 | C |
| ATOM | 2299 NE ARG G 364 | 25.809 21.275 −12.053 1.00 8.70 | N |
| ATOM | 2300 CZ ARG G 364 | 26.690 21.777 −12.910 1.00 8.88 | C |
| ATOM | 2301 NH1 ARG G 364 | 27.407 22.843 −12.578 1.00 8.57 | N |
| ATOM | 2302 NH2 ARG G 364 | 26.840 21.228 −14.107 1.00 10.59 | N |
| ATOM | 2303 C ARG G 364 | 21.703 20.519 −10.166 1.00 6.58 | C |
| ATOM | 2304 O ARG G 364 | 20.980 20.173 −9.233 1.00 6.65 | O |
| ATOM | 2305 N VAL G 365 | 21.719 19.897 −11.341 1.00 6.64 | N |
| ATOM | 2306 CA VAL G 365 | 20.802 18.805 −11.658 1.00 6.54 | C |
| ATOM | 2307 CB VAL G 365 | 19.823 19.208 −12.782 1.00 5.95 | C |
| ATOM | 2308 CG1 VAL G 365 | 19.069 17.993 −13.302 1.00 5.48 | C |
| ATOM | 2309 CG2 VAL G 365 | 18.861 20.277 −12.291 1.00 6.22 | C |
| ATOM | 2310 C VAL G 365 | 21.569 17.549 −12.089 1.00 7.35 | C |
| ATOM | 2311 O VAL G 365 | 22.611 17.641 −12.740 1.00 8.33 | O |
| ATOM | 2312 N PHE G 366 | 21.009 16.380 −11.781 1.00 7.37 | N |

APPENDIX-continued (APPENDIX discloses SEQ ID NOS 29-32, 29-32 and 29-32, respectively, in order of appearance)

| | | | |
|---|---|---|---|
| ATOM | 2313 CA PHE G 366 | 21.654 15.097 −12.072 1.00 7.44 | C |
| ATOM | 2314 CB PHE G 366 | 22.371 14.567 −10.822 1.00 7.30 | C |
| ATOM | 2315 CG PHE G 366 | 23.464 15.468 −10.314 1.00 6.70 | C |
| ATOM | 2316 CD1 PHE G 366 | 23.160 16.576 −9.538 1.00 6.70 | C |
| ATOM | 2317 CE1 PHE G 366 | 24.162 17.406 −9.068 1.00 5.94 | C |
| ATOM | 2318 CZ PHE G 366 | 25.487 17.053 −9.244 1.00 5.71 | C |
| ATOM | 2319 CE2 PHE G 366 | 25.804 15.897 −9.935 1.00 5.96 | C |
| ATOM | 2320 CD2 PHE G 366 | 24.793 15.094 −10.437 1.00 6.52 | C |
| ATOM | 2321 C PHE G 366 | 20.626 14.059 −12.546 1.00 7.45 | C |
| ATOM | 2322 O PHE G 366 | 19.770 13.635 −11.769 1.00 7.45 | O |
| ATOM | 2323 N CYS G 367 | 20.783 13.569 −13.777 1.00 8.00 | N |
| ATOM | 2324 CA CYS G 367 | 19.838 12.602 −14.369 1.00 8.90 | C |
| ATOM | 2325 CB CYS G 367 | 18.879 13.313 −15.335 1.00 9.46 | C |
| ATOM | 2326 SG CYS G 367 | 17.966 14.707 −14.624 1.00 10.79 | S |
| ATOM | 2327 C CYS G 367 | 20.563 11.445 −15.089 1.00 9.09 | C |
| ATOM | 2328 O CYS G 367 | 21.751 11.556 −15.396 1.00 9.24 | O |
| ATOM | 2329 N ASP G 368 | 19.864 10.330 −15.323 1.00 9.54 | N |
| ATOM | 2330 CA ASP G 368 | 20.480 9.110 −15.890 1.00 10.55 | C |
| ATOM | 2331 CB ASP G 368 | 20.253 7.906 −14.962 1.00 10.53 | C |
| ATOM | 2332 CG ASP G 368 | 21.043 6.674 −15.386 1.00 11.11 | C |
| ATOM | 2333 OD1 ASP G 368 | 21.241 6.475 −16.603 1.00 11.42 | O |
| ATOM | 2334 OD2 ASP G 368 | 21.441 5.892 −14.497 1.00 11.35 | O |
| ATOM | 2335 C ASP G 368 | 19.947 8.774 −17.285 1.00 11.45 | C |
| ATOM | 2336 O ASP G 368 | 19.035 7.958 −17.422 1.00 12.05 | O |
| ATOM | 2337 N THR G 369 | 20.606 9.281 −18.321 1.00 12.41 | N |
| ATOM | 2338 CA THR G 369 | 20.367 8.772 −19.666 1.00 13.00 | C |
| ATOM | 2339 CB THR G 369 | 21.685 8.338 −20.361 1.00 12.69 | C |
| ATOM | 2340 OG1 THR G 369 | 22.580 9.456 −20.444 1.00 11.72 | O |
| ATOM | 2341 CG2 THR G 369 | 21.409 7.813 −21.765 1.00 13.33 | C |
| ATOM | 2342 C THR G 369 | 19.406 7.585 −19.574 1.00 14.13 | C |
| ATOM | 2343 O THR G 369 | 18.260 7.681 −20.008 1.00 14.72 | O |
| ATOM | 2344 N MET G 370 | 19.790 6.577 −18.795 1.00 15.25 | N |
| ATOM | 2345 CA MET G 370 | 19.286 5.221 −18.993 1.00 16.60 | C |
| ATOM | 2346 CB MET G 370 | 19.132 4.486 −17.664 1.00 17.42 | C |
| ATOM | 2347 CG MET G 370 | 19.948 3.204 −17.580 1.00 20.31 | C |
| ATOM | 2348 SD MET G 370 | 19.542 1.991 −18.855 1.00 26.43 | S |
| ATOM | 2349 CE MET G 370 | 20.369 2.694 −20.281 1.00 24.07 | C |
| ATOM | 2350 C MET G 370 | 17.997 5.144 −19.811 1.00 16.54 | C |
| ATOM | 2351 O MET G 370 | 17.975 4.516 −20.870 1.00 16.74 | O |
| ATOM | 2352 N ASN G 371 | 16.923 5.762 −19.327 1.00 16.35 | N |
| ATOM | 2353 CA ASN G 371 | 15.648 5.694 −20.042 1.00 16.07 | C |
| ATOM | 2354 CB ASN G 371 | 14.554 5.050 −19.184 1.00 16.41 | C |
| ATOM | 2355 CG ASN G 371 | 14.652 3.531 −19.153 1.00 16.71 | C |
| ATOM | 2356 OD1 ASN G 371 | 14.117 2.843 −20.025 1.00 15.75 | O |
| ATOM | 2357 ND2 ASN G 371 | 15.228 3.003 −18.080 1.00 17.76 | N |
| ATOM | 2358 C ASN G 371 | 15.160 7.004 −20.661 1.00 15.55 | C |
| ATOM | 2359 O ASN G 371 | 14.132 7.023 −21.334 1.00 15.84 | O |
| ATOM | 2360 N SER G 372 | 16.006 8.030 −20.612 1.00 14.76 | N |
| ATOM | 2361 CA SER G 372 | 15.784 9.270 −21.364 1.00 13.91 | C |
| ATOM | 2362 CB SER G 372 | 17.101 10.025 −21.561 1.00 14.04 | C |
| ATOM | 2363 OG SER G 372 | 17.984 9.303 −22.405 1.00 15.09 | O |
| ATOM | 2364 C SER G 372 | 15.111 9.064 −22.717 1.00 13.07 | C |
| ATOM | 2365 O SER G 372 | 15.417 8.111 −23.437 1.00 13.02 | O |
| ATOM | 2366 N LEU G 373 | 14.347 10.072 −23.130 1.00 12.23 | N |
| ATOM | 2367 CA LEU G 373 | 13.882 10.192 −24.508 1.00 11.45 | C |
| ATOM | 2368 CB LEU G 373 | 12.358 10.365 −24.534 1.00 11.43 | C |
| ATOM | 2369 CG LEU G 373 | 11.464 9.123 −24.683 1.00 11.04 | C |
| ATOM | 2370 CD1 LEU G 373 | 11.965 7.948 −23.852 1.00 11.76 | C |
| ATOM | 2371 CD2 LEU G 373 | 10.020 9.434 −24.330 1.00 10.49 | C |
| ATOM | 2372 C LEU G 373 | 14.550 11.392 −25.176 1.00 11.17 | C |
| ATOM | 2373 O LEU G 373 | 14.658 12.460 −24.574 1.00 11.27 | O |
| ATOM | 2374 N THR G 374 | 15.011 11.208 −26.411 1.00 10.70 | N |
| ATOM | 2375 CA THR G 374 | 15.791 12.235 −27.102 1.00 10.23 | C |
| ATOM | 2376 CB THR G 374 | 16.998 11.634 −27.863 1.00 10.24 | C |
| ATOM | 2377 OG1 THR G 374 | 17.406 10.410 −27.239 1.00 11.25 | O |
| ATOM | 2378 CG2 THR G 374 | 18.168 12.612 −27.872 1.00 10.52 | C |
| ATOM | 2379 C THR G 374 | 14.934 13.032 −28.079 1.00 9.54 | C |
| ATOM | 2380 O THR G 374 | 14.316 12.468 −28.983 1.00 9.70 | O |
| ATOM | 2381 N LEU G 375 | 14.965 14.352 −27.935 1.00 8.83 | N |
| ATOM | 2382 CA LEU G 375 | 14.013 15.221 −28.611 1.00 7.83 | C |
| ATOM | 2383 CB LEU G 375 | 12.949 15.719 −27.631 1.00 7.38 | C |
| ATOM | 2384 CG LEU G 375 | 12.160 14.689 −26.824 1.00 5.06 | C |
| ATOM | 2385 CD1 LEU G 375 | 11.352 15.385 −25.741 1.00 2.41 | C |
| ATOM | 2386 CD2 LEU G 375 | 11.246 13.885 −27.734 1.00 4.31 | C |
| ATOM | 2387 C LEU G 375 | 14.728 16.416 −29.222 1.00 7.79 | C |
| ATOM | 2388 O LEU G 375 | 15.743 16.872 −28.696 1.00 7.92 | O |
| ATOM | 2389 N PRO G 376 | 14.102 17.026 −30.234 1.00 7.51 | N |

APPENDIX-continued (APPENDIX discloses SEQ ID NOS 29-32, 29-32 and 29-32, respectively, in order of appearance)

| | | | |
|---|---|---|---|
| ATOM | 2390 CA PRO G 376 | 14.606 18.224 −30.892 1.00 7.90 | C |
| ATOM | 2391 CB PRO G 376 | 13.837 18.238 −32.211 1.00 7.90 | C |
| ATOM | 2392 CG PRO G 376 | 12.558 17.556 −31.891 1.00 7.97 | C |
| ATOM | 2393 CD PRO G 376 | 12.913 16.481 −30.912 1.00 7.40 | C |
| ATOM | 2394 C PRO G 376 | 14.294 19.486 −30.095 1.00 8.35 | C |
| ATOM | 2395 O PRO G 376 | 13.205 19.611 −29.533 1.00 8.71 | O |
| ATOM | 2396 N SER G 377 | 15.206 20.451 −30.137 1.00 9.11 | N |
| ATOM | 2397 CA SER G 377 | 14.990 21.743 −29.494 1.00 9.91 | C |
| ATOM | 2398 CB SER G 377 | 16.155 22.691 −29.792 1.00 10.23 | C |
| ATOM | 2399 OG SER G 377 | 17.300 21.973 −30.222 1.00 10.90 | O |
| ATOM | 2400 C SER G 377 | 13.673 22.377 −29.937 1.00 10.14 | C |
| ATOM | 2401 O SER G 377 | 13.295 23.444 −29.450 1.00 10.08 | O |
| ATOM | 2402 N GLU G 378 | 13.011 21.749 −30.906 1.00 10.71 | N |
| ATOM | 2403 CA GLU G 378 | 11.714 22.222 −31.382 1.00 11.40 | C |
| ATOM | 2404 CB GLU G 378 | 11.357 21.569 −32.721 1.00 11.65 | C |
| ATOM | 2405 CG GLU G 378 | 11.978 22.250 −33.933 1.00 13.46 | C |
| ATOM | 2406 CD GLU G 378 | 13.490 22.160 −33.938 1.00 16.20 | C |
| ATOM | 2407 OE1 GLU G 378 | 14.046 21.522 −33.021 1.00 15.73 | O |
| ATOM | 2408 OE2 GLU G 378 | 14.121 22.732 −34.852 1.00 18.38 | O |
| ATOM | 2409 C GLU G 378 | 10.623 21.944 −30.353 1.00 11.27 | C |
| ATOM | 2410 O GLU G 378 | 9.561 22.565 −30.377 1.00 11.28 | O |
| ATOM | 2411 N VAL G 379 | 10.909 21.031 −29.430 1.00 11.31 | N |
| ATOM | 2412 CA VAL G 379 | 10.053 20.819 −28.269 1.00 11.59 | C |
| ATOM | 2413 CB VAL G 379 | 10.737 19.926 −27.216 1.00 11.27 | C |
| ATOM | 2414 CG1 VAL G 379 | 10.100 20.131 −25.850 1.00 11.60 | C |
| ATOM | 2415 CG2 VAL G 379 | 10.667 18.465 −27.631 1.00 11.54 | C |
| ATOM | 2416 C VAL G 379 | 9.665 22.144 −27.620 1.00 12.16 | C |
| ATOM | 2417 O VAL G 379 | 8.541 22.307 −27.146 1.00 12.51 | O |
| ATOM | 2418 N ASN G 380 | 10.587 23.100 −27.634 1.00 12.98 | N |
| ATOM | 2419 CA ASN G 380 | 10.415 24.335 −26.878 1.00 14.00 | C |
| ATOM | 2420 CB ASN G 380 | 11.703 25.156 −26.884 1.00 14.59 | C |
| ATOM | 2421 CG ASN G 380 | 12.829 24.474 −26.138 1.00 17.09 | C |
| ATOM | 2422 OD1 ASN G 380 | 13.073 24.764 −24.966 1.00 20.41 | O |
| ATOM | 2423 ND2 ASN G 380 | 13.432 23.471 −26.767 1.00 18.86 | N |
| ATOM | 2424 C ASN G 380 | 9.242 25.192 −27.349 1.00 13.96 | C |
| ATOM | 2425 O ASN G 380 | 8.640 25.915 −26.555 1.00 14.38 | O |
| ATOM | 2426 N LEU G 381 | 8.994 25.197 −28.655 1.00 13.61 | N |
| ATOM | 2427 CA LEU G 381 | 7.918 26.006 −29.220 1.00 13.72 | C |
| ATOM | 2428 CB LEU G 381 | 7.854 25.829 −30.737 1.00 13.79 | C |
| ATOM | 2429 CG LEU G 381 | 9.183 25.514 −31.424 1.00 14.92 | C |
| ATOM | 2430 CD1 LEU G 381 | 8.969 25.231 −32.902 1.00 15.56 | C |
| ATOM | 2431 CD2 LEU G 381 | 10.171 26.655 −31.230 1.00 15.78 | C |
| ATOM | 2432 C LEU G 381 | 6.590 25.603 −28.600 1.00 13.62 | C |
| ATOM | 2433 O LEU G 381 | 5.600 26.331 −28.682 1.00 13.57 | O |
| ATOM | 2434 N CYS G 382 | 6.590 24.440 −27.963 1.00 13.47 | N |
| ATOM | 2435 CA CYS G 382 | 5.383 23.876 −27.392 1.00 13.57 | C |
| ATOM | 2436 CB CYS G 382 | 5.572 22.380 −27.161 1.00 13.62 | C |
| ATOM | 2437 SG CYS G 382 | 4.877 21.350 −28.457 1.00 15.64 | S |
| ATOM | 2438 C CYS G 382 | 5.019 24.572 −26.085 1.00 13.33 | C |
| ATOM | 2439 O CYS G 382 | 3.861 24.561 −25.669 1.00 13.57 | O |
| ATOM | 2440 N ASN G 383 | 5.999 25.236 −25.480 1.00 13.21 | N |
| ATOM | 2441 CA ASN G 383 | 5.736 26.114 −24.345 1.00 13.22 | C |
| ATOM | 2442 CB ASN G 383 | 7.046 26.621 −23.742 1.00 13.18 | C |
| ATOM | 2443 CG ASN G 383 | 7.979 25.498 −23.349 1.00 13.42 | C |
| ATOM | 2444 OD1 ASN G 383 | 7.560 24.505 −22.755 1.00 13.68 | O |
| ATOM | 2445 ND2 ASN G 383 | 9.255 25.648 −23.682 1.00 14.32 | N |
| ATOM | 2446 C ASN G 383 | 4.872 27.298 −24.747 1.00 13.28 | C |
| ATOM | 2447 O ASN G 383 | 4.229 27.925 −23.906 1.00 13.50 | O |
| ATOM | 2448 N VAL G 384 | 5.000 27.699 −26.005 1.00 13.24 | N |
| ATOM | 2449 CA VAL G 384 | 4.313 28.878 −26.496 1.00 13.29 | C |
| ATOM | 2450 CB VAL G 384 | 5.234 29.751 −27.370 1.00 13.28 | C |
| ATOM | 2451 CG1 VAL G 384 | 4.414 30.627 −28.302 1.00 13.73 | C |
| ATOM | 2452 CG2 VAL G 384 | 6.145 30.599 −26.495 1.00 12.76 | C |
| ATOM | 2453 C VAL G 384 | 3.045 28.514 −27.261 1.00 13.57 | C |
| ATOM | 2454 O VAL G 384 | 2.050 29.233 −27.188 1.00 13.31 | O |
| ATOM | 2455 N ASP G 385 | 3.056 27.383 −27.960 1.00 14.07 | N |
| ATOM | 2456 CA ASP G 385 | 1.999 27.121 −28.932 1.00 14.61 | C |
| ATOM | 2457 CB ASP G 385 | 2.452 27.379 −30.366 1.00 14.71 | C |
| ATOM | 2458 CG ASP G 385 | 1.436 28.182 −31.154 1.00 16.69 | C |
| ATOM | 2459 OD1 ASP G 385 | 0.270 28.259 −30.713 1.00 18.63 | O |
| ATOM | 2460 OD2 ASP G 385 | 1.807 28.759 −32.197 1.00 19.10 | O |
| ATOM | 2461 C ASP G 385 | 1.170 25.841 −28.816 1.00 14.63 | C |
| ATOM | 2462 O ASP G 385 | −0.043 25.880 −29.017 1.00 14.34 | O |
| ATOM | 2463 N ILE G 386 | 1.820 24.697 −28.624 1.00 14.54 | N |
| ATOM | 2464 CA ILE G 386 | 1.116 23.413 −28.688 1.00 14.46 | C |
| ATOM | 2465 CB ILE G 386 | −0.230 23.466 −27.928 1.00 13.83 | C |
| ATOM | 2466 CG1 ILE G 386 | −0.004 23.458 −26.415 1.00 13.44 | C |

APPENDIX-continued (APPENDIX discloses SEQ ID NOS 29-32, 29-32 and 29-32, respectively, in order of appearance)

| | | | | | | | | | | |
|---|---|---|---|---|---|---|---|---|---|---|
| ATOM | 2467 | CD1 | ILE | G | 386 | −1.184 | 23.970 | −25.612 | 1.00 12.39 | C |
| ATOM | 2468 | CG2 | ILE | G | 386 | −1.119 | 22.301 | −28.341 | 1.00 13.51 | C |
| ATOM | 2469 | C | ILE | G | 386 | 0.791 | 23.079 | −30.134 | 1.00 14.73 | C |
| ATOM | 2470 | O | ILE | G | 386 | 1.282 | 22.092 | −30.683 | 1.00 14.68 | O |
| ATOM | 2471 | N | PHE | G | 387 | −0.191 | 23.797 | −30.667 | 1.00 14.71 | N |
| ATOM | 2472 | CA | PHE | G | 387 | −0.462 | 23.794 | −32.092 | 1.00 14.78 | C |
| ATOM | 2473 | CB | PHE | G | 387 | −1.889 | 24.254 | −32.366 | 1.00 14.77 | C |
| ATOM | 2474 | CG | PHE | G | 387 | −2.906 | 23.607 | −31.479 | 1.00 14.75 | C |
| ATOM | 2475 | CD1 | PHE | G | 387 | −3.418 | 24.287 | −30.390 | 1.00 15.03 | C |
| ATOM | 2476 | CE1 | PHE | G | 387 | −4.333 | 23.684 | −29.549 | 1.00 14.62 | C |
| ATOM | 2477 | CZ | PHE | G | 387 | −4.683 | 22.364 | −29.747 | 1.00 14.55 | C |
| ATOM | 2478 | CE2 | PHE | G | 387 | −4.113 | 21.651 | −30.780 | 1.00 14.68 | C |
| ATOM | 2479 | CD2 | PHE | G | 387 | −3.206 | 22.265 | −31.621 | 1.00 14.61 | C |
| ATOM | 2480 | C | PHE | G | 387 | 0.526 | 24.670 | −32.837 | 1.00 14.91 | C |
| ATOM | 2481 | O | PHE | G | 387 | 0.658 | 25.862 | −32.559 | 1.00 14.86 | O |
| ATOM | 2482 | N | ASN | G | 388 | 1.361 | 24.007 | −33.621 | 1.00 15.11 | N |
| ATOM | 2483 | CA | ASN | G | 388 | 2.352 | 24.663 | −34.443 | 1.00 15.38 | C |
| ATOM | 2484 | CB | ASN | G | 388 | 3.362 | 25.405 | −33.570 | 1.00 14.86 | C |
| ATOM | 2485 | CG | ASN | G | 388 | 4.097 | 24.480 | −32.625 | 1.00 14.86 | C |
| ATOM | 2486 | OD1 | ASN | G | 388 | 5.078 | 23.840 | −33.004 | 1.00 12.80 | O |
| ATOM | 2487 | ND2 | ASN | G | 388 | 3.575 | 24.338 | −31.413 | 1.00 15.97 | N |
| ATOM | 2488 | C | ASN | G | 388 | 3.057 | 23.576 | −35.229 | 1.00 16.11 | C |
| ATOM | 2489 | O | ASN | G | 388 | 3.416 | 22.537 | −34.670 | 1.00 15.92 | O |
| ATOM | 2490 | N | PRO | G | 389 | 3.071 | 23.722 | −36.557 | 1.00 16.99 | N |
| ATOM | 2491 | CA | PRO | G | 389 | 4.005 | 22.905 | −37.315 | 1.00 17.40 | C |
| ATOM | 2492 | CB | PRO | G | 389 | 4.169 | 23.689 | −38.618 | 1.00 17.72 | C |
| ATOM | 2493 | CG | PRO | G | 389 | 3.905 | 25.099 | −38.236 | 1.00 17.47 | C |
| ATOM | 2494 | CD | PRO | G | 389 | 2.825 | 25.023 | −37.203 | 1.00 17.05 | C |
| ATOM | 2495 | C | PRO | G | 389 | 5.338 | 22.827 | −36.583 | 1.00 17.86 | C |
| ATOM | 2496 | O | PRO | G | 389 | 5.638 | 23.687 | −35.755 | 1.00 18.45 | O |
| ATOM | 2497 | N | LYS | G | 390 | 6.139 | 21.817 | −36.902 | 1.00 17.97 | N |
| ATOM | 2498 | CA | LYS | G | 390 | 7.443 | 21.658 | −36.273 | 1.00 18.06 | C |
| ATOM | 2499 | CB | LYS | G | 390 | 7.947 | 22.997 | −35.730 | 1.00 17.92 | C |
| ATOM | 2500 | CG | LYS | G | 390 | 8.466 | 23.945 | −36.798 | 1.00 18.58 | C |
| ATOM | 2501 | CD | LYS | G | 390 | 9.962 | 23.777 | −37.006 | 1.00 20.61 | C |
| ATOM | 2502 | CE | LYS | G | 390 | 10.562 | 24.985 | −37.707 | 1.00 21.48 | C |
| ATOM | 2503 | NZ | LYS | G | 390 | 10.191 | 25.032 | −39.148 | 1.00 23.16 | N |
| ATOM | 2504 | C | LYS | G | 390 | 7.398 | 20.623 | −35.156 | 1.00 18.01 | C |
| ATOM | 2505 | O | LYS | G | 390 | 8.177 | 19.670 | −35.152 | 1.00 18.43 | O |
| ATOM | 2506 | N | TYR | G | 391 | 6.481 | 20.805 | −34.213 | 1.00 17.68 | N |
| ATOM | 2507 | CA | TYR | G | 391 | 6.234 | 19.780 | −33.211 | 1.00 17.33 | C |
| ATOM | 2508 | CB | TYR | G | 391 | 6.862 | 20.158 | −31.872 | 1.00 17.42 | C |
| ATOM | 2509 | CG | TYR | G | 391 | 7.485 | 18.979 | −31.173 | 1.00 17.27 | C |
| ATOM | 2510 | CD1 | TYR | G | 391 | 8.188 | 18.028 | −31.898 | 1.00 17.29 | C |
| ATOM | 2511 | CE1 | TYR | G | 391 | 8.672 | 16.885 | −31.297 | 1.00 17.32 | C |
| ATOM | 2512 | CZ | TYR | G | 391 | 8.408 | 16.653 | −29.965 | 1.00 16.51 | C |
| ATOM | 2513 | OH | TYR | G | 391 | 8.940 | 15.541 | −29.354 | 1.00 16.65 | O |
| ATOM | 2514 | CE2 | TYR | G | 391 | 7.656 | 17.552 | −29.237 | 1.00 16.52 | C |
| ATOM | 2515 | CD2 | TYR | G | 391 | 7.167 | 18.687 | −29.853 | 1.00 17.24 | C |
| ATOM | 2516 | C | TYR | G | 391 | 4.757 | 19.471 | −33.034 | 1.00 17.43 | C |
| ATOM | 2517 | O | TYR | G | 391 | 3.984 | 20.332 | −32.614 | 1.00 17.70 | O |
| ATOM | 2518 | N | ASP | G | 392 | 4.398 | 18.202 | −33.196 | 1.00 17.56 | N |
| ATOM | 2519 | CA | ASP | G | 392 | 3.191 | 17.693 | −32.565 | 1.00 17.69 | C |
| ATOM | 2520 | CB | ASP | G | 392 | 2.610 | 16.498 | −33.322 | 1.00 17.89 | C |
| ATOM | 2521 | CG | ASP | G | 392 | 3.494 | 16.038 | −34.456 | 1.00 18.86 | C |
| ATOM | 2522 | OD1 | ASP | G | 392 | 4.636 | 15.613 | −34.185 | 1.00 20.34 | O |
| ATOM | 2523 | OD2 | ASP | G | 392 | 3.008 | 15.998 | −35.604 | 1.00 18.51 | O |
| ATOM | 2524 | C | ASP | G | 392 | 3.428 | 17.344 | −31.107 | 1.00 17.11 | C |
| ATOM | 2525 | O | ASP | G | 392 | 4.495 | 16.860 | −30.731 | 1.00 17.04 | O |
| ATOM | 2526 | N | CYS | G | 393 | 2.452 | 17.684 | −30.280 | 1.00 16.33 | N |
| ATOM | 2527 | CA | CYS | G | 393 | 2.723 | 18.199 | −28.957 | 1.00 16.17 | C |
| ATOM | 2528 | CB | CYS | G | 393 | 2.419 | 19.693 | −28.910 | 1.00 16.11 | C |
| ATOM | 2529 | SG | CYS | G | 393 | 3.237 | 20.556 | −27.570 | 1.00 20.23 | S |
| ATOM | 2530 | C | CYS | G | 393 | 1.812 | 17.471 | −27.995 | 1.00 15.37 | C |
| ATOM | 2531 | O | CYS | G | 393 | 0.592 | 17.525 | −28.139 | 1.00 15.15 | O |
| ATOM | 2532 | N | LYS | G | 394 | 2.399 | 16.618 | −27.168 | 1.00 14.91 | N |
| ATOM | 2533 | CA | LYS | G | 394 | 1.608 | 15.678 | −26.398 | 1.00 14.50 | C |
| ATOM | 2534 | CB | LYS | G | 394 | 2.495 | 14.607 | −25.771 | 1.00 14.60 | C |
| ATOM | 2535 | CG | LYS | G | 394 | 3.531 | 14.052 | −26.730 | 1.00 16.44 | C |
| ATOM | 2536 | CD | LYS | G | 394 | 4.034 | 12.699 | −26.272 | 1.00 20.45 | C |
| ATOM | 2537 | CE | LYS | G | 394 | 4.868 | 12.823 | −25.009 | 1.00 23.05 | C |
| ATOM | 2538 | NZ | LYS | G | 394 | 4.057 | 13.264 | −23.841 | 1.00 24.13 | N |
| ATOM | 2539 | C | LYS | G | 394 | 0.767 | 16.388 | −25.344 | 1.00 14.00 | C |
| ATOM | 2540 | O | LYS | G | 394 | 1.249 | 17.268 | −24.630 | 1.00 14.14 | O |
| ATOM | 2541 | N | ILE | G | 395 | −0.486 | 15.955 | −25.236 | 1.00 13.28 | N |
| ATOM | 2542 | CA | ILE | G | 395 | −1.587 | 16.768 | −24.725 | 1.00 12.89 | C |
| ATOM | 2543 | CB | ILE | G | 395 | −2.234 | 17.626 | −25.843 | 1.00 12.75 | C |

APPENDIX-continued (APPENDIX discloses SEQ ID NOS 29-32, 29-32 and 29-32, respectively, in order of appearance)

| | | | | | | | | | | | |
|---|---|---|---|---|---|---|---|---|---|---|---|
| ATOM | 2544 | CG1 | ILE | G | 395 | −1.418 | 18.897 | −26.097 | 1.00 | 13.58 | C |
| ATOM | 2545 | CD1 | ILE | G | 395 | −1.635 | 19.507 | −27.466 | 1.00 | 15.33 | C |
| ATOM | 2546 | CG2 | ILE | G | 395 | −3.669 | 17.980 | −25.477 | 1.00 | 12.16 | C |
| ATOM | 2547 | C | ILE | G | 395 | −2.631 | 15.761 | −24.284 | 1.00 | 13.15 | C |
| ATOM | 2548 | O | ILE | G | 395 | −2.826 | 14.746 | −24.951 | 1.00 | 13.45 | O |
| ATOM | 2549 | N | MET | G | 396 | −3.440 | 16.127 | −23.303 | 1.00 | 13.06 | N |
| ATOM | 2550 | CA | MET | G | 396 | −4.668 | 15.392 | −23.085 | 1.00 | 13.00 | C |
| ATOM | 2551 | CB | MET | G | 396 | −4.579 | 14.539 | −21.824 | 1.00 | 13.34 | C |
| ATOM | 2552 | CG | MET | G | 396 | −5.208 | 15.167 | −20.600 | 1.00 | 14.30 | C |
| ATOM | 2553 | SD | MET | G | 396 | −5.006 | 14.087 | −19.179 | 1.00 | 18.50 | S |
| ATOM | 2554 | CE | MET | G | 396 | −3.465 | 13.282 | −19.611 | 1.00 | 17.80 | C |
| ATOM | 2555 | C | MET | G | 396 | −5.889 | 16.288 | −23.050 | 1.00 | 12.96 | C |
| ATOM | 2556 | O | MET | G | 396 | −5.811 | 17.453 | −22.663 | 1.00 | 13.04 | O |
| ATOM | 2557 | N | THR | G | 397 | −7.037 | 15.686 | −23.336 | 1.00 | 12.78 | N |
| ATOM | 2558 | CA | THR | G | 397 | −8.200 | 16.415 | −23.815 | 1.00 | 12.51 | C |
| ATOM | 2559 | CB | THR | G | 397 | −8.653 | 15.898 | −25.193 | 1.00 | 12.39 | C |
| ATOM | 2560 | OG1 | THR | G | 397 | −7.837 | 16.481 | −26.216 | 1.00 | 12.50 | O |
| ATOM | 2561 | CG2 | THR | G | 397 | −10.114 | 16.250 | −25.447 | 1.00 | 12.55 | C |
| ATOM | 2562 | C | THR | G | 397 | −9.343 | 16.223 | −22.834 | 1.00 | 12.58 | C |
| ATOM | 2563 | O | THR | G | 397 | −9.563 | 15.117 | −22.340 | 1.00 | 12.88 | O |
| ATOM | 2564 | N | SER | G | 398 | −10.157 | 17.255 | −22.663 | 1.00 | 12.55 | N |
| ATOM | 2565 | CA | SER | G | 398 | −11.452 | 17.049 | −22.049 | 1.00 | 12.76 | C |
| ATOM | 2566 | CB | SER | G | 398 | −11.323 | 16.949 | −20.527 | 1.00 | 12.52 | C |
| ATOM | 2567 | OG | SER | G | 398 | −12.592 | 16.781 | −19.919 | 1.00 | 12.72 | O |
| ATOM | 2568 | C | SER | G | 398 | −12.478 | 18.103 | −22.410 | 1.00 | 12.99 | C |
| ATOM | 2569 | O | SER | G | 398 | −12.269 | 18.917 | −23.311 | 1.00 | 13.13 | O |
| ATOM | 2570 | N | LYS | G | 399 | −13.435 | 18.245 | −21.504 | 1.00 | 13.01 | N |
| ATOM | 2571 | CA | LYS | G | 399 | −14.399 | 19.325 | −21.544 | 1.00 | 13.29 | C |
| ATOM | 2572 | CB | LYS | G | 399 | −15.777 | 18.777 | −21.908 | 1.00 | 13.79 | C |
| ATOM | 2573 | CG | LYS | G | 399 | −16.044 | 18.714 | −23.399 | 1.00 | 14.34 | C |
| ATOM | 2574 | CD | LYS | G | 399 | −16.965 | 19.840 | −23.833 | 1.00 | 16.43 | C |
| ATOM | 2575 | CE | LYS | G | 399 | −17.285 | 19.750 | −25.315 | 1.00 | 17.37 | C |
| ATOM | 2576 | NZ | LYS | G | 399 | −17.904 | 21.003 | −25.828 | 1.00 | 16.62 | N |
| ATOM | 2577 | C | LYS | G | 399 | −14.460 | 19.996 | −20.179 | 1.00 | 13.09 | C |
| ATOM | 2578 | O | LYS | G | 399 | −14.619 | 21.213 | −20.084 | 1.00 | 12.87 | O |
| ATOM | 2579 | N | THR | G | 400 | −14.348 | 19.198 | −19.123 | 1.00 | 13.04 | N |
| ATOM | 2580 | CA | THR | G | 400 | −14.535 | 19.715 | −17.776 | 1.00 | 13.38 | C |
| ATOM | 2581 | CB | THR | G | 400 | −15.257 | 18.709 | −16.861 | 1.00 | 13.74 | C |
| ATOM | 2582 | OG1 | THR | G | 400 | −15.856 | 17.678 | −17.655 | 1.00 | 14.38 | O |
| ATOM | 2583 | CG2 | THR | G | 400 | −16.337 | 19.409 | −16.051 | 1.00 | 14.32 | C |
| ATOM | 2584 | C | THR | G | 400 | −13.226 | 20.134 | −17.120 | 1.00 | 13.20 | C |
| ATOM | 2585 | O | THR | G | 400 | −12.169 | 19.594 | −17.445 | 1.00 | 13.12 | O |
| ATOM | 2586 | N | ASP | G | 401 | −13.378 | 20.770 | −15.963 | 1.00 | 12.97 | N |
| ATOM | 2587 | CA | ASP | G | 401 | −12.358 | 21.654 | −15.396 | 1.00 | 12.50 | C |
| ATOM | 2588 | CB | ASP | G | 401 | −13.014 | 22.766 | −14.590 | 1.00 | 12.73 | C |
| ATOM | 2589 | CG | ASP | G | 401 | −12.765 | 24.122 | −15.183 | 1.00 | 13.98 | C |
| ATOM | 2590 | OD1 | ASP | G | 401 | −13.073 | 24.301 | −16.380 | 1.00 | 16.55 | O |
| ATOM | 2591 | OD2 | ASP | G | 401 | −12.168 | 24.973 | −14.492 | 1.00 | 14.80 | O |
| ATOM | 2592 | C | ASP | G | 401 | −11.269 | 21.029 | −14.529 | 1.00 | 12.13 | C |
| ATOM | 2593 | O | ASP | G | 401 | −11.547 | 20.130 | −13.729 | 1.00 | 12.31 | O |
| ATOM | 2594 | N | VAL | G | 402 | −10.200 | 21.822 | −14.390 | 1.00 | 11.49 | N |
| ATOM | 2595 | CA | VAL | G | 402 | −9.667 | 22.261 | −13.080 | 1.00 | 10.74 | C |
| ATOM | 2596 | CB | VAL | G | 402 | −8.369 | 21.519 | −12.744 | 1.00 | 10.60 | C |
| ATOM | 2597 | CG1 | VAL | G | 402 | −7.449 | 22.413 | −11.914 | 1.00 | 11.26 | C |
| ATOM | 2598 | CG2 | VAL | G | 402 | −8.672 | 20.211 | −12.019 | 1.00 | 10.99 | C |
| ATOM | 2599 | C | VAL | G | 402 | −9.360 | 23.769 | −12.883 | 1.00 | 10.24 | C |
| ATOM | 2600 | O | VAL | G | 402 | −9.387 | 24.539 | −13.845 | 1.00 | 10.30 | O |
| ATOM | 2601 | N | SER | G | 403 | −8.762 | 24.081 | −11.719 | 1.00 | 9.76 | N |
| ATOM | 2602 | CA | SER | G | 403 | −8.493 | 25.474 | −11.271 | 1.00 | 9.18 | C |
| ATOM | 2603 | CB | SER | G | 403 | −9.790 | 26.197 | −10.893 | 1.00 | 9.41 | C |
| ATOM | 2604 | OG | SER | G | 403 | −10.714 | 25.319 | −10.274 | 1.00 | 10.82 | O |
| ATOM | 2605 | C | SER | G | 403 | −7.394 | 25.745 | −10.199 | 1.00 | 8.51 | C |
| ATOM | 2606 | O | SER | G | 403 | −7.465 | 25.236 | −9.076 | 1.00 | 8.30 | O |
| ATOM | 2607 | N | SER | G | 404 | −6.524 | 26.720 | −10.502 | 1.00 | 8.35 | N |
| ATOM | 2608 | CA | SER | G | 404 | −5.785 | 27.535 | −9.507 | 1.00 | 8.18 | C |
| ATOM | 2609 | CB | SER | G | 404 | −4.851 | 26.657 | −8.669 | 1.00 | 8.18 | C |
| ATOM | 2610 | OG | SER | G | 404 | −3.507 | 26.782 | −9.100 | 1.00 | 8.83 | O |
| ATOM | 2611 | C | SER | G | 404 | −4.979 | 28.665 | −10.187 | 1.00 | 7.62 | C |
| ATOM | 2612 | O | SER | G | 404 | −5.183 | 28.942 | −11.369 | 1.00 | 7.57 | O |
| ATOM | 2613 | N | SER | G | 405 | −4.041 | 29.282 | −9.462 | 1.00 | 7.08 | N |
| ATOM | 2614 | CA | SER | G | 405 | −3.258 | 30.409 | −10.003 | 1.00 | 6.53 | C |
| ATOM | 2615 | CB | SER | G | 405 | −3.844 | 31.752 | −9.555 | 1.00 | 6.42 | C |
| ATOM | 2616 | OG | SER | G | 405 | −2.883 | 32.790 | −9.662 | 1.00 | 5.66 | O |
| ATOM | 2617 | C | SER | G | 405 | −1.756 | 30.364 | −9.693 | 1.00 | 6.28 | C |
| ATOM | 2618 | O | SER | G | 405 | −1.338 | 29.830 | −8.666 | 1.00 | 5.98 | O |
| ATOM | 2619 | N | VAL | G | 406 | −0.980 | 31.079 | −10.506 | 1.00 | 6.22 | N |
| ATOM | 2620 | CA | VAL | G | 406 | 0.479 | 31.053 | −10.436 | 1.00 | 6.50 | C |

APPENDIX-continued (APPENDIX discloses SEQ ID NOS 29-32, 29-32 and 29-32, respectively, in order of appearance)

| | | | |
|---|---|---|---|
| ATOM | 2621 CB VAL G 406 | 1.068 30.055 −11.453 1.00 6.45 | C |
| ATOM | 2622 CG1 VAL G 406 | 2.518 29.743 −11.116 1.00 7.66 | C |
| ATOM | 2623 CG2 VAL G 406 | 0.236 28.783 −11.495 1.00 7.38 | C |
| ATOM | 2624 C VAL G 406 | 1.029 32.438 −10.760 1.00 6.24 | C |
| ATOM | 2625 O VAL G 406 | 0.763 32.981 −11.832 1.00 6.14 | O |
| ATOM | 2626 N ILE G 407 | 1.803 33.001 −9.840 1.00 6.32 | N |
| ATOM | 2627 CA ILE G 407 | 2.315 34.354 −10.014 1.00 6.60 | C |
| ATOM | 2628 CB ILE G 407 | 2.445 35.097 −8.674 1.00 6.27 | C |
| ATOM | 2629 CG1 ILE G 407 | 1.070 35.564 −8.194 1.00 6.19 | C |
| ATOM | 2630 CD1 ILE G 407 | 1.086 36.200 −6.824 1.00 8.34 | C |
| ATOM | 2631 CG2 ILE G 407 | 3.391 36.282 −8.813 1.00 6.42 | C |
| ATOM | 2632 C ILE G 407 | 3.657 34.361 −10.728 1.00 7.20 | C |
| ATOM | 2633 O ILE G 407 | 4.576 33.631 −10.356 1.00 7.42 | O |
| ATOM | 2634 N THR G 408 | 3.797 35.273 −11.682 1.00 7.57 | N |
| ATOM | 2635 CA THR G 408 | 4.983 35.324 −12.517 1.00 8.19 | C |
| ATOM | 2636 CB THR G 408 | 4.622 35.305 −14.011 1.00 8.15 | C |
| ATOM | 2637 OG1 THR G 408 | 3.785 36.426 −14.318 1.00 8.88 | O |
| ATOM | 2638 CG2 THR G 408 | 3.891 34.020 −14.364 1.00 7.93 | C |
| ATOM | 2639 C THR G 408 | 5.804 36.569 −12.225 1.00 8.55 | C |
| ATOM | 2640 O THR G 408 | 5.418 37.408 −11.410 1.00 9.07 | O |
| ATOM | 2641 N SER G 409 | 6.918 36.698 −12.935 1.00 8.70 | N |
| ATOM | 2642 CA SER G 409 | 7.843 37.799 −12.723 1.00 9.20 | C |
| ATOM | 2643 CB SER G 409 | 9.067 37.643 −13.628 1.00 9.72 | C |
| ATOM | 2644 OG SER G 409 | 9.571 36.320 −13.581 1.00 10.75 | O |
| ATOM | 2645 C SER G 409 | 7.153 39.125 −13.007 1.00 9.01 | C |
| ATOM | 2646 O SER G 409 | 7.433 40.135 −12.359 1.00 9.02 | O |
| ATOM | 2647 N LEU G 410 | 6.259 39.118 −13.990 1.00 8.91 | N |
| ATOM | 2648 CA LEU G 410 | 5.790 40.352 −14.604 1.00 9.29 | C |
| ATOM | 2649 CB LEU G 410 | 6.438 40.546 −15.976 1.00 9.61 | C |
| ATOM | 2650 CG LEU G 410 | 7.245 41.834 −16.150 1.00 9.70 | C |
| ATOM | 2651 CD1 LEU G 410 | 8.433 41.858 −15.200 1.00 11.11 | C |
| ATOM | 2652 CD2 LEU G 410 | 7.705 41.994 −17.591 1.00 9.16 | C |
| ATOM | 2653 C LEU G 410 | 4.272 40.351 −14.729 1.00 9.12 | C |
| ATOM | 2654 O LEU G 410 | 3.683 41.248 −15.332 1.00 9.08 | O |
| ATOM | 2655 N GLY G 411 | 3.646 39.332 −14.154 1.00 9.03 | N |
| ATOM | 2656 CA GLY G 411 | 2.203 39.315 −13.982 1.00 8.44 | C |
| ATOM | 2657 C GLY G 411 | 1.765 38.048 −13.284 1.00 7.91 | C |
| ATOM | 2658 O GLY G 411 | 2.435 37.568 −12.369 1.00 7.85 | O |
| ATOM | 2659 N ALA G 412 | 0.674 37.465 −13.763 1.00 7.30 | N |
| ATOM | 2660 CA ALA G 412 | 0.129 36.264 −13.153 1.00 6.92 | C |
| ATOM | 2661 CB ALA G 412 | −0.742 36.623 −11.960 1.00 6.90 | C |
| ATOM | 2662 C ALA G 412 | −0.661 35.453 −14.166 1.00 6.99 | C |
| ATOM | 2663 O ALA G 412 | −1.257 36.002 −15.093 1.00 6.94 | O |
| ATOM | 2664 N ILE G 413 | −0.621 34.137 −14.006 1.00 7.29 | N |
| ATOM | 2665 CA ILE G 413 | −1.478 33.244 −14.766 1.00 7.49 | C |
| ATOM | 2666 CB ILE G 413 | −0.711 31.990 −15.201 1.00 7.24 | C |
| ATOM | 2667 CG1 ILE G 413 | 0.314 32.350 −16.278 1.00 7.18 | C |
| ATOM | 2668 CD1 ILE G 413 | 0.927 31.150 −16.973 1.00 7.70 | C |
| ATOM | 2669 CG2 ILE G 413 | −1.674 30.916 −15.688 1.00 7.70 | C |
| ATOM | 2670 C ILE G 413 | −2.657 32.822 −13.908 1.00 7.94 | C |
| ATOM | 2671 O ILE G 413 | −2.544 32.749 −12.685 1.00 8.39 | O |
| ATOM | 2672 N VAL G 414 | −3.782 32.521 −14.544 1.00 8.22 | N |
| ATOM | 2673 CA VAL G 414 | −4.909 31.961 −13.816 1.00 8.77 | C |
| ATOM | 2674 CB VAL G 414 | −5.865 33.050 −13.296 1.00 8.57 | C |
| ATOM | 2675 CG1 VAL G 414 | −6.133 34.085 −14.376 1.00 9.12 | C |
| ATOM | 2676 CG2 VAL G 414 | −7.162 32.427 −12.803 1.00 8.90 | C |
| ATOM | 2677 C VAL G 414 | −5.674 30.901 −14.594 1.00 8.92 | C |
| ATOM | 2678 O VAL G 414 | −6.114 31.129 −15.722 1.00 9.00 | O |
| ATOM | 2679 N SER G 415 | −5.750 29.714 −14.004 1.00 8.97 | N |
| ATOM | 2680 CA SER G 415 | −6.472 28.598 −14.592 1.00 9.02 | C |
| ATOM | 2681 CB SER G 415 | −5.625 27.328 −14.520 1.00 8.98 | C |
| ATOM | 2682 OG SER G 415 | −4.353 27.532 −15.108 1.00 9.54 | O |
| ATOM | 2683 C SER G 415 | −7.791 28.390 −13.864 1.00 9.36 | C |
| ATOM | 2684 O SER G 415 | −7.818 27.884 −12.742 1.00 9.61 | O |
| ATOM | 2685 N CYS G 416 | −8.854 28.950 −14.430 1.00 9.57 | N |
| ATOM | 2686 CA CYS G 416 | −10.175 28.857 −13.831 1.00 9.61 | C |
| ATOM | 2687 CB CYS G 416 | −10.895 30.201 −13.912 1.00 9.62 | C |
| ATOM | 2688 SG CYS G 416 | −12.025 30.497 −12.543 1.00 11.33 | S |
| ATOM | 2689 C CYS G 416 | −11.000 27.796 −14.534 1.00 9.61 | C |
| ATOM | 2690 O CYS G 416 | −11.361 27.950 −15.700 1.00 9.80 | O |
| ATOM | 2691 N TYR G 417 | −11.298 26.717 −13.821 1.00 9.48 | N |
| ATOM | 2692 CA TYR G 417 | −11.930 25.566 −14.438 1.00 9.28 | C |
| ATOM | 2693 CB TYR G 417 | −10.888 24.501 −14.782 1.00 9.17 | C |
| ATOM | 2694 CG TYR G 417 | −10.011 24.860 −15.962 1.00 8.71 | C |
| ATOM | 2695 CD1 TYR G 417 | −8.661 24.543 −15.968 1.00 8.54 | C |
| ATOM | 2696 CE1 TYR G 417 | −7.857 24.869 −17.043 1.00 9.56 | C |
| ATOM | 2697 CZ TYR G 417 | −8.407 25.480 −18.149 1.00 9.83 | C |

APPENDIX-continued (APPENDIX discloses SEQ ID NOS 29-32, 29-32 and 29-32, respectively, in order of appearance)

| | | | |
|---|---|---|---|
| ATOM | 2698 OH TYR G 417 | −7.602 25.828 −19.207 1.00 10.51 | O |
| ATOM | 2699 CE2 TYR G 417 | −9.738 25.830 −18.159 1.00 9.36 | C |
| ATOM | 2700 CD2 TYR G 417 | −10.532 25.522 −17.068 1.00 8.95 | C |
| ATOM | 2701 C TYR G 417 | −13.034 24.978 −13.566 1.00 9.35 | C |
| ATOM | 2702 O TYR G 417 | −13.171 25.332 −12.395 1.00 9.11 | O |
| ATOM | 2703 N GLY G 418 | −13.848 24.115 −14.165 1.00 9.71 | N |
| ATOM | 2704 CA GLY G 418 | −14.993 23.534 −13.481 1.00 9.95 | C |
| ATOM | 2705 C GLY G 418 | −15.925 24.594 −12.936 1.00 10.09 | C |
| ATOM | 2706 O GLY G 418 | −16.170 25.611 −13.585 1.00 10.17 | O |
| ATOM | 2707 N LYS G 419 | −16.323 24.426 −11.681 1.00 10.17 | N |
| ATOM | 2708 CA LYS G 419 | −17.328 25.289 −11.075 1.00 10.50 | C |
| ATOM | 2709 CB LYS G 419 | −18.123 24.523 −10.015 1.00 11.09 | C |
| ATOM | 2710 CG LYS G 419 | −19.389 23.867 −10.538 1.00 12.94 | C |
| ATOM | 2711 CD LYS G 419 | −20.304 23.450 −9.397 1.00 15.52 | C |
| ATOM | 2712 CE LYS G 419 | −21.702 23.127 −9.899 1.00 17.07 | C |
| ATOM | 2713 NZ LYS G 419 | −21.688 22.058 −10.936 1.00 19.30 | N |
| ATOM | 2714 C LYS G 419 | −16.737 26.560 −10.464 1.00 10.23 | C |
| ATOM | 2715 O LYS G 419 | −17.451 27.325 −9.817 1.00 10.58 | O |
| ATOM | 2716 N THR G 420 | −15.429 26.755 −10.607 1.00 10.10 | N |
| ATOM | 2717 CA THR G 420 | −14.730 27.754 −9.801 1.00 9.74 | C |
| ATOM | 2718 CB THR G 420 | −13.232 27.432 −9.651 1.00 9.28 | C |
| ATOM | 2719 OG1 THR G 420 | −12.992 26.073 −10.034 1.00 9.21 | O |
| ATOM | 2720 CG2 THR G 420 | −12.788 27.635 −8.209 1.00 9.03 | C |
| ATOM | 2721 C THR G 420 | −14.900 29.178 −10.329 1.00 9.95 | C |
| ATOM | 2722 O THR G 420 | −15.143 29.387 −11.518 1.00 10.35 | O |
| ATOM | 2723 N LYS G 421 | −14.816 30.149 −9.424 1.00 10.07 | N |
| ATOM | 2724 CA LYS G 421 | −14.950 31.559 −9.780 1.00 10.21 | C |
| ATOM | 2725 CB LYS G 421 | −15.973 32.239 −8.867 1.00 10.30 | C |
| ATOM | 2726 CG LYS G 421 | −17.368 32.341 −9.457 1.00 12.43 | C |
| ATOM | 2727 CD LYS G 421 | −18.345 32.931 −8.452 1.00 15.12 | C |
| ATOM | 2728 CE LYS G 421 | −19.766 32.470 −8.727 1.00 15.21 | C |
| ATOM | 2729 NZ LYS G 421 | −20.617 32.544 −7.508 1.00 15.98 | N |
| ATOM | 2730 C LYS G 421 | −13.608 32.271 −9.658 1.00 10.09 | C |
| ATOM | 2731 O LYS G 421 | −12.911 32.125 −8.653 1.00 10.36 | O |
| ATOM | 2732 N CYS G 422 | −13.271 33.085 −10.653 1.00 9.81 | N |
| ATOM | 2733 CA CYS G 422 | −12.006 33.808 −10.631 1.00 9.56 | C |
| ATOM | 2734 CB CYS G 422 | −10.953 33.092 −11.475 1.00 9.72 | C |
| ATOM | 2735 SG CYS G 422 | −10.831 31.329 −11.131 1.00 11.42 | S |
| ATOM | 2736 C CYS G 422 | −12.126 35.268 −11.044 1.00 9.18 | C |
| ATOM | 2737 O CYS G 422 | −12.927 35.624 −11.909 1.00 9.27 | O |
| ATOM | 2738 N THR G 423 | −11.232 36.084 −10.497 1.00 8.93 | N |
| ATOM | 2739 CA THR G 423 | −11.422 37.525 −10.427 1.00 8.64 | C |
| ATOM | 2740 CB THR G 423 | −12.062 37.938 −9.088 1.00 8.32 | C |
| ATOM | 2741 OG1 THR G 423 | −13.201 37.111 −8.821 1.00 7.97 | O |
| ATOM | 2742 CG2 THR G 423 | −12.494 39.396 −9.130 1.00 8.36 | C |
| ATOM | 2743 C THR G 423 | −10.059 38.190 −10.513 1.00 8.86 | C |
| ATOM | 2744 O THR G 423 | −9.183 37.928 −9.688 1.00 9.26 | O |
| ATOM | 2745 N ALA G 424 | −9.913 39.124 −11.444 1.00 8.74 | N |
| ATOM | 2746 CA ALA G 424 | −8.792 40.052 −11.408 1.00 8.79 | C |
| ATOM | 2747 CB ALA G 424 | −8.164 40.180 −12.786 1.00 8.94 | C |
| ATOM | 2748 C ALA G 424 | −9.240 41.414 −10.894 1.00 8.84 | C |
| ATOM | 2749 O ALA G 424 | −10.084 42.070 −11.504 1.00 9.24 | O |
| ATOM | 2750 N SER G 425 | −8.669 41.836 −9.771 1.00 8.81 | N |
| ATOM | 2751 CA SER G 425 | −9.007 43.124 −9.180 1.00 8.85 | C |
| ATOM | 2752 CB SER G 425 | −9.483 42.942 −7.737 1.00 8.94 | C |
| ATOM | 2753 OG SER G 425 | −9.918 41.613 −7.507 1.00 7.69 | O |
| ATOM | 2754 C SER G 425 | −7.815 44.072 −9.222 1.00 9.01 | C |
| ATOM | 2755 O SER G 425 | −6.669 43.651 −9.059 1.00 8.63 | O |
| ATOM | 2756 N ASN G 426 | −8.089 45.354 −9.441 1.00 9.54 | N |
| ATOM | 2757 CA ASN G 426 | −7.033 46.328 −9.686 1.00 10.19 | C |
| ATOM | 2758 CB ASN G 426 | −7.537 47.462 −10.583 1.00 9.77 | C |
| ATOM | 2759 CG ASN G 426 | −8.273 48.540 −9.808 1.00 9.43 | C |
| ATOM | 2760 OD1 ASN G 426 | −8.253 48.561 −8.578 1.00 9.01 | O |
| ATOM | 2761 ND2 ASN G 426 | −8.938 49.436 −10.528 1.00 9.01 | N |
| ATOM | 2762 C ASN G 426 | −6.434 46.891 −8.400 1.00 11.16 | C |
| ATOM | 2763 O ASN G 426 | −6.629 46.340 −7.316 1.00 11.06 | O |
| ATOM | 2764 N LYS G 427 | −5.658 47.961 −8.543 1.00 12.38 | N |
| ATOM | 2765 CA LYS G 427 | −5.016 48.627 −7.413 1.00 13.52 | C |
| ATOM | 2766 CB LYS G 427 | −4.455 49.981 −7.851 1.00 14.00 | C |
| ATOM | 2767 CG LYS G 427 | −2.987 49.956 −8.233 1.00 16.18 | C |
| ATOM | 2768 CD LYS G 427 | −2.434 51.366 −8.365 1.00 18.24 | C |
| ATOM | 2769 CE LYS G 427 | −0.955 51.413 −8.022 1.00 19.72 | C |
| ATOM | 2770 NZ LYS G 427 | −0.707 51.116 −6.584 1.00 21.43 | N |
| ATOM | 2771 C LYS G 427 | −5.976 48.829 −6.245 1.00 13.71 | C |
| ATOM | 2772 O LYS G 427 | −5.630 48.562 −5.093 1.00 13.63 | O |
| ATOM | 2773 N ASN G 428 | −7.119 49.443 −6.535 1.00 14.28 | N |
| ATOM | 2774 CA ASN G 428 | −8.080 49.830 −5.505 1.00 14.60 | C |

APPENDIX-continued (APPENDIX discloses SEQ ID NOS 29-32, 29-32 and 29-32, respectively, in order of appearance)

| | | | |
|---|---|---|---|
| ATOM | 2775 CB ASN G 428 | −9.009 50.934 −6.020 1.00 14.57 | C |
| ATOM | 2776 CG ASN G 428 | −8.353 51.808 −7.071 1.00 13.24 | C |
| ATOM | 2777 OD1 ASN G 428 | −7.314 52.420 −6.823 1.00 9.74 | O |
| ATOM | 2778 ND2 ASN G 428 | −9.009 51.946 −8.217 1.00 12.83 | N |
| ATOM | 2779 C ASN G 428 | −8.914 48.658 −4.994 1.00 14.83 | C |
| ATOM | 2780 O ASN G 428 | −9.645 48.793 −4.013 1.00 15.25 | O |
| ATOM | 2781 N ARG G 429 | −8.920 47.564 −5.750 1.00 14.78 | N |
| ATOM | 2782 CA ARG G 429 | −9.725 46.395 −5.407 1.00 14.74 | C |
| ATOM | 2783 CB ARG G 429 | −10.088 46.405 −3.920 1.00 14.93 | C |
| ATOM | 2784 CG ARG G 429 | −8.949 45.999 −2.999 1.00 16.26 | C |
| ATOM | 2785 CD ARG G 429 | −8.954 44.502 −2.732 1.00 19.79 | C |
| ATOM | 2786 NE ARG G 429 | −7.694 44.046 −2.152 1.00 22.68 | N |
| ATOM | 2787 CZ ARG G 429 | −7.270 44.369 −0.935 1.00 23.54 | C |
| ATOM | 2788 NH1 ARG G 429 | −7.998 45.170 −0.168 1.00 22.87 | N |
| ATOM | 2789 NH2 ARG G 429 | −6.107 43.912 −0.492 1.00 23.53 | N |
| ATOM | 2790 C ARG G 429 | −10.989 46.304 −6.256 1.00 14.35 | C |
| ATOM | 2791 O ARG G 429 | −11.653 45.268 −6.287 1.00 14.62 | O |
| ATOM | 2792 N GLY G 430 | −11.306 47.386 −6.961 1.00 13.67 | N |
| ATOM | 2793 CA GLY G 430 | −12.201 47.311 −8.110 1.00 12.80 | C |
| ATOM | 2794 C GLY G 430 | −11.870 46.136 −9.009 1.00 12.11 | C |
| ATOM | 2795 O GLY G 430 | −10.707 45.903 −9.338 1.00 12.18 | O |
| ATOM | 2796 N ILE G 431 | −12.892 45.374 −9.380 1.00 11.58 | N |
| ATOM | 2797 CA ILE G 431 | −12.700 44.155 −10.157 1.00 10.76 | C |
| ATOM | 2798 CB ILE G 431 | −13.777 43.106 −9.812 1.00 10.43 | C |
| ATOM | 2799 CG1 ILE G 431 | −13.615 42.625 −8.368 1.00 10.95 | C |
| ATOM | 2800 CD1 ILE G 431 | −14.920 42.259 −7.695 1.00 12.08 | C |
| ATOM | 2801 CG2 ILE G 431 | −13.720 41.940 −10.785 1.00 10.07 | C |
| ATOM | 2802 C ILE G 431 | −12.770 44.465 −11.651 1.00 10.68 | C |
| ATOM | 2803 O ILE G 431 | −13.790 44.954 −12.136 1.00 10.40 | O |
| ATOM | 2804 N ILE G 432 | −11.677 44.225 −12.373 1.00 10.90 | N |
| ATOM | 2805 CA ILE G 432 | −11.658 44.482 −13.815 1.00 11.42 | C |
| ATOM | 2806 CB ILE G 432 | −10.276 44.936 −14.327 1.00 11.63 | C |
| ATOM | 2807 CG1 ILE G 432 | −9.411 45.460 −13.180 1.00 12.68 | C |
| ATOM | 2808 CD1 ILE G 432 | −7.977 45.738 −13.579 1.00 13.89 | C |
| ATOM | 2809 CG2 ILE G 432 | −10.432 45.992 −15.412 1.00 12.24 | C |
| ATOM | 2810 C ILE G 432 | −12.118 43.290 −14.648 1.00 11.41 | C |
| ATOM | 2811 O ILE G 432 | −12.834 43.463 −15.635 1.00 11.63 | O |
| ATOM | 2812 N LYS G 433 | −11.505 42.136 −14.405 1.00 11.52 | N |
| ATOM | 2813 CA LYS G 433 | −11.792 40.950 −15.203 1.00 11.96 | C |
| ATOM | 2814 CB LYS G 433 | −10.516 40.392 −15.837 1.00 12.31 | C |
| ATOM | 2815 CG LYS G 433 | −10.770 39.317 −16.885 1.00 14.42 | C |
| ATOM | 2816 CD LYS G 433 | −9.723 39.348 −17.987 1.00 16.74 | C |
| ATOM | 2817 CE LYS G 433 | −9.997 38.283 −19.038 1.00 17.08 | C |
| ATOM | 2818 NZ LYS G 433 | −9.612 38.735 −20.404 1.00 17.30 | N |
| ATOM | 2819 C LYS G 433 | −12.496 39.873 −14.387 1.00 11.65 | C |
| ATOM | 2820 O LYS G 433 | −12.479 39.899 −13.156 1.00 11.48 | O |
| ATOM | 2821 N THR G 434 | −13.143 38.946 −15.086 1.00 11.28 | N |
| ATOM | 2822 CA THR G 434 | −13.816 37.821 −14.445 1.00 11.21 | C |
| ATOM | 2823 CB THR G 434 | −15.222 38.216 −13.955 1.00 11.30 | C |
| ATOM | 2824 OG1 THR G 434 | −15.963 37.037 −13.619 1.00 11.83 | O |
| ATOM | 2825 CG2 THR G 434 | −15.966 38.988 −15.035 1.00 11.84 | C |
| ATOM | 2826 C THR G 434 | −13.939 36.646 −15.415 1.00 10.94 | C |
| ATOM | 2827 O THR G 434 | −14.257 36.836 −16.589 1.00 10.93 | O |
| ATOM | 2828 N PHE G 435 | −13.628 35.442 −14.939 1.00 11.10 | N |
| ATOM | 2829 CA PHE G 435 | −12.871 34.486 −15.744 1.00 11.96 | C |
| ATOM | 2830 CB PHE G 435 | −11.673 33.929 −14.977 1.00 11.51 | C |
| ATOM | 2831 CG PHE G 435 | −10.437 34.772 −15.100 1.00 11.19 | C |
| ATOM | 2832 CD1 PHE G 435 | −9.910 35.409 −13.989 1.00 10.86 | C |
| ATOM | 2833 CE1 PHE G 435 | −8.824 36.254 −14.107 1.00 10.24 | C |
| ATOM | 2834 CZ PHE G 435 | −8.286 36.516 −15.352 1.00 9.89 | C |
| ATOM | 2835 CE2 PHE G 435 | −8.834 35.927 −16.474 1.00 10.78 | C |
| ATOM | 2836 CD2 PHE G 435 | −9.920 35.082 −16.348 1.00 11.14 | C |
| ATOM | 2837 C PHE G 435 | −13.678 33.371 −16.403 1.00 13.00 | C |
| ATOM | 2838 O PHE G 435 | −14.218 32.494 −15.726 1.00 13.03 | O |
| ATOM | 2839 N SER G 436 | −13.506 33.272 −17.717 1.00 13.89 | N |
| ATOM | 2840 CA SER G 436 | −14.276 32.356 −18.546 1.00 14.67 | C |
| ATOM | 2841 CB SER G 436 | −14.391 32.910 −19.969 1.00 15.04 | C |
| ATOM | 2842 OG SER G 436 | −15.702 33.377 −20.235 1.00 16.58 | O |
| ATOM | 2843 C SER G 436 | −13.627 30.975 −18.578 1.00 14.75 | C |
| ATOM | 2844 O SER G 436 | −13.081 30.559 −19.601 1.00 14.75 | O |
| ATOM | 2845 N ASN G 437 | −13.713 30.256 −17.465 1.00 14.44 | N |
| ATOM | 2846 CA ASN G 437 | −13.595 28.805 −17.496 1.00 14.35 | C |
| ATOM | 2847 CB ASN G 437 | −14.935 28.179 −17.896 1.00 14.75 | C |
| ATOM | 2848 CG ASN G 437 | −14.999 26.690 −17.610 1.00 15.51 | C |
| ATOM | 2849 OD1 ASN G 437 | −15.013 26.275 −16.450 1.00 16.85 | O |
| ATOM | 2850 ND2 ASN G 437 | −15.246 25.906 −18.652 1.00 16.10 | N |
| ATOM | 2851 C ASN G 437 | −12.497 28.371 −18.464 1.00 13.69 | C |

APPENDIX-continued (APPENDIX discloses SEQ ID NOS 29-32, 29-32 and 29-32, respectively, in order of appearance)

| | | | |
|---|---|---|---|
| ATOM | 2852 O ASN G 437 | −12.754 27.652 −19.430 1.00 13.40 | O |
| ATOM | 2853 N GLY G 438 | −11.290 28.880 −18.237 1.00 13.39 | N |
| ATOM | 2854 CA GLY G 438 | −10.183 28.701 −19.170 1.00 12.92 | C |
| ATOM | 2855 C GLY G 438 | −8.839 28.941 −18.510 1.00 12.72 | C |
| ATOM | 2856 O GLY G 438 | −8.620 28.538 −17.367 1.00 12.83 | O |
| ATOM | 2857 N CYS G 439 | −7.971 29.677 −19.195 1.00 12.17 | N |
| ATOM | 2858 CA CYS G 439 | −6.654 29.999 −18.658 1.00 11.52 | C |
| ATOM | 2859 CB CYS G 439 | −5.696 28.822 −18.844 1.00 11.68 | C |
| ATOM | 2860 SG CYS G 439 | −3.974 29.301 −19.104 1.00 12.89 | S |
| ATOM | 2861 C CYS G 439 | −6.077 31.258 −19.297 1.00 10.95 | C |
| ATOM | 2862 O CYS G 439 | −5.762 31.275 −20.488 1.00 10.77 | O |
| ATOM | 2863 N ASP G 440 | −5.921 32.303 −18.490 1.00 10.41 | N |
| ATOM | 2864 CA ASP G 440 | −5.546 33.619 −18.993 1.00 10.06 | C |
| ATOM | 2865 CB ASP G 440 | −6.685 34.620 −18.778 1.00 10.85 | C |
| ATOM | 2866 CG ASP G 440 | −7.418 34.956 −20.062 1.00 13.11 | C |
| ATOM | 2867 OD1 ASP G 440 | −6.891 35.765 −20.854 1.00 14.97 | O |
| ATOM | 2868 OD2 ASP G 440 | −8.559 34.479 −20.237 1.00 15.27 | O |
| ATOM | 2869 C ASP G 440 | −4.276 34.131 −18.318 1.00 9.01 | C |
| ATOM | 2870 O ASP G 440 | −3.793 33.542 −17.350 1.00 9.09 | O |
| ATOM | 2871 N TYR G 441 | −3.806 35.287 −18.778 1.00 7.92 | N |
| ATOM | 2872 CA TYR G 441 | −2.645 35.959 −18.199 1.00 7.24 | C |
| ATOM | 2873 CB TYR G 441 | −1.457 35.871 −19.165 1.00 7.04 | C |
| ATOM | 2874 CG TYR G 441 | −0.227 36.631 −18.724 1.00 6.77 | C |
| ATOM | 2875 CD1 TYR G 441 | 0.762 36.008 −17.974 1.00 7.41 | C |
| ATOM | 2876 CE1 TYR G 441 | 1.902 36.688 −17.593 1.00 6.79 | C |
| ATOM | 2877 CZ TYR G 441 | 2.106 37.980 −18.034 1.00 6.49 | C |
| ATOM | 2878 OH TYR G 441 | 3.230 38.670 −17.635 1.00 5.09 | O |
| ATOM | 2879 CE2 TYR G 441 | 1.157 38.606 −18.817 1.00 7.52 | C |
| ATOM | 2880 CD2 TYR G 441 | 0.017 37.918 −19.186 1.00 7.12 | C |
| ATOM | 2881 C TYR G 441 | −3.005 37.421 −17.946 1.00 6.89 | C |
| ATOM | 2882 O TYR G 441 | −3.809 38.000 −18.677 1.00 7.12 | O |
| ATOM | 2883 N VAL G 442 | −2.452 37.999 −16.886 1.00 6.73 | N |
| ATOM | 2884 CA VAL G 442 | −2.612 39.427 −16.615 1.00 6.78 | C |
| ATOM | 2885 CB VAL G 442 | −3.614 39.671 −15.472 1.00 6.51 | C |
| ATOM | 2886 CG1 VAL G 442 | −5.041 39.483 −15.967 1.00 7.38 | C |
| ATOM | 2887 CG2 VAL G 442 | −3.322 38.742 −14.303 1.00 6.00 | C |
| ATOM | 2888 C VAL G 442 | −1.262 40.025 −16.234 1.00 7.13 | C |
| ATOM | 2889 O VAL G 442 | −0.272 39.301 −16.134 1.00 7.77 | O |
| ATOM | 2890 N SER G 443 | −1.210 41.335 −16.022 1.00 7.12 | N |
| ATOM | 2891 CA SER G 443 | 0.062 41.970 −15.700 1.00 7.64 | C |
| ATOM | 2892 CB SER G 443 | 0.770 42.447 −16.969 1.00 7.83 | C |
| ATOM | 2893 OG SER G 443 | 0.637 43.847 −17.131 1.00 7.99 | O |
| ATOM | 2894 C SER G 443 | −0.051 43.104 −14.690 1.00 8.16 | C |
| ATOM | 2895 O SER G 443 | −1.142 43.607 −14.420 1.00 8.69 | O |
| ATOM | 2896 N ASN G 444 | 1.086 43.484 −14.117 1.00 8.73 | N |
| ATOM | 2897 CA ASN G 444 | 1.139 44.600 −13.184 1.00 9.50 | C |
| ATOM | 2898 CB ASN G 444 | 2.521 44.684 −12.538 1.00 9.65 | C |
| ATOM | 2899 CG ASN G 444 | 3.256 43.357 −12.565 1.00 10.64 | C |
| ATOM | 2900 OD1 ASN G 444 | 2.641 42.291 −12.498 1.00 12.28 | O |
| ATOM | 2901 ND2 ASN G 444 | 4.578 43.416 −12.685 1.00 11.75 | N |
| ATOM | 2902 C ASN G 444 | 0.791 45.922 −13.857 1.00 10.24 | C |
| ATOM | 2903 O ASN G 444 | 1.086 46.126 −15.034 1.00 9.89 | O |
| ATOM | 2904 N LYS G 445 | 0.266 46.855 −13.069 1.00 11.63 | N |
| ATOM | 2905 CA LYS G 445 | −0.752 47.787 −13.545 1.00 13.07 | C |
| ATOM | 2906 CB LYS G 445 | −0.107 49.048 −14.123 1.00 13.70 | C |
| ATOM | 2907 CG LYS G 445 | −1.068 50.216 −14.307 1.00 15.80 | C |
| ATOM | 2908 CD LYS G 445 | −2.384 49.986 −13.575 1.00 18.31 | C |
| ATOM | 2909 CE LYS G 445 | −2.166 49.766 −12.086 1.00 19.03 | C |
| ATOM | 2910 NZ LYS G 445 | −1.048 50.592 −11.554 1.00 20.02 | N |
| ATOM | 2911 C LYS G 445 | −1.681 47.147 −14.572 1.00 12.96 | C |
| ATOM | 2912 O LYS G 445 | −1.258 46.313 −15.372 1.00 13.24 | O |
| ATOM | 2913 N GLY G 446 | −2.943 47.559 −14.558 1.00 13.08 | N |
| ATOM | 2914 CA GLY G 446 | −4.051 46.616 −14.597 1.00 12.42 | C |
| ATOM | 2915 C GLY G 446 | −4.212 45.900 −13.272 1.00 11.83 | C |
| ATOM | 2916 O GLY G 446 | −4.832 46.426 −12.347 1.00 12.44 | O |
| ATOM | 2917 N VAL G 447 | −3.517 44.777 −13.126 1.00 10.63 | N |
| ATOM | 2918 CA VAL G 447 | −3.875 43.795 −12.114 1.00 10.01 | C |
| ATOM | 2919 CB VAL G 447 | −3.898 42.365 −12.681 1.00 9.97 | C |
| ATOM | 2920 CG1 VAL G 447 | −4.591 41.422 −11.708 1.00 10.51 | C |
| ATOM | 2921 CG2 VAL G 447 | −4.594 42.345 −14.033 1.00 10.50 | C |
| ATOM | 2922 C VAL G 447 | −2.978 43.851 −10.882 1.00 9.53 | C |
| ATOM | 2923 O VAL G 447 | −1.761 44.008 −10.985 1.00 9.61 | O |
| ATOM | 2924 N ASP G 448 | −3.586 43.575 −9.735 1.00 9.16 | N |
| ATOM | 2925 CA ASP G 448 | −2.956 43.763 −8.437 1.00 8.75 | C |
| ATOM | 2926 CB ASP G 448 | −3.515 45.022 −7.771 1.00 9.22 | C |
| ATOM | 2927 CG ASP G 448 | −2.579 45.599 −6.729 1.00 11.44 | C |
| ATOM | 2928 OD1 ASP G 448 | −1.725 44.849 −6.212 1.00 13.83 | O |

APPENDIX-continued (APPENDIX discloses SEQ ID NOS 29-32, 29-32 and 29-32, respectively, in order of appearance)

| | | | | | | | | |
|---|---|---|---|---|---|---|---|---|
| ATOM | 2929 OD2 ASP G 448 | −2.713 | 46.799 | −6.409 | 1.00 | 14.13 | O |
| ATOM | 2930 C ASP G 448 | −3.313 | 42.546 | −7.598 | 1.00 | 8.18 | C |
| ATOM | 2931 O ASP G 448 | −2.555 | 42.122 | −6.725 | 1.00 | 8.06 | O |
| ATOM | 2932 N THR G 449 | −4.451 | 41.949 | −7.933 | 1.00 | 7.63 | N |
| ATOM | 2933 CA THR G 449 | −4.991 | 40.823 | −7.192 | 1.00 | 6.80 | C |
| ATOM | 2934 CB THR G 449 | −5.988 | 41.293 | −6.116 | 1.00 | 6.89 | C |
| ATOM | 2935 OG1 THR G 449 | −5.284 | 41.584 | −4.902 | 1.00 | 6.16 | O |
| ATOM | 2936 CG2 THR G 449 | −7.032 | 40.219 | −5.848 | 1.00 | 7.55 | C |
| ATOM | 2937 C THR G 449 | −5.717 | 39.906 | −8.164 | 1.00 | 6.53 | C |
| ATOM | 2938 O THR G 449 | −6.385 | 40.370 | −9.087 | 1.00 | 6.59 | O |
| ATOM | 2939 N VAL G 450 | −5.536 | 38.603 | −7.989 | 1.00 | 6.07 | N |
| ATOM | 2940 CA VAL G 450 | −6.531 | 37.646 | −8.434 | 1.00 | 6.02 | C |
| ATOM | 2941 CB VAL G 450 | −5.981 | 36.723 | −9.535 | 1.00 | 5.61 | C |
| ATOM | 2942 CG1 VAL G 450 | −5.377 | 37.545 | −10.663 | 1.00 | 5.32 | C |
| ATOM | 2943 CG2 VAL G 450 | −4.954 | 35.761 | −8.958 | 1.00 | 5.55 | C |
| ATOM | 2944 C VAL G 450 | −7.021 | 36.811 | −7.263 | 1.00 | 6.37 | C |
| ATOM | 2945 O VAL G 450 | −6.299 | 36.609 | −6.287 | 1.00 | 6.54 | O |
| ATOM | 2946 N SER G 451 | −8.307 | 36.486 | −7.288 | 1.00 | 6.41 | N |
| ATOM | 2947 CA SER G 451 | −8.857 | 35.507 | −6.370 | 1.00 | 6.70 | C |
| ATOM | 2948 CB SER G 451 | −9.995 | 36.120 | −5.553 | 1.00 | 7.13 | C |
| ATOM | 2949 OG SER G 451 | −10.537 | 37.254 | −6.207 | 1.00 | 9.26 | O |
| ATOM | 2950 C SER G 451 | −9.354 | 34.292 | −7.139 | 1.00 | 6.47 | C |
| ATOM | 2951 O SER G 451 | −9.896 | 34.423 | −8.238 | 1.00 | 6.54 | O |
| ATOM | 2952 N VAL G 452 | −8.962 | 33.116 | −6.664 | 1.00 | 6.56 | N |
| ATOM | 2953 CA VAL G 452 | −9.578 | 31.868 | −7.091 | 1.00 | 6.31 | C |
| ATOM | 2954 CB VAL G 452 | −8.516 | 30.849 | −7.542 | 1.00 | 5.74 | C |
| ATOM | 2955 CG1 VAL G 452 | −9.170 | 29.688 | −8.275 | 1.00 | 5.06 | C |
| ATOM | 2956 CG2 VAL G 452 | −7.471 | 31.523 | −8.419 | 1.00 | 5.56 | C |
| ATOM | 2957 C VAL G 452 | −10.381 | 31.264 | −5.944 | 1.00 | 6.60 | C |
| ATOM | 2958 O VAL G 452 | −9.861 | 31.079 | −4.844 | 1.00 | 7.04 | O |
| ATOM | 2959 N GLY G 453 | −11.652 | 30.975 | −6.198 | 1.00 | 6.54 | N |
| ATOM | 2960 CA GLY G 453 | −12.581 | 30.650 | −5.124 | 1.00 | 6.43 | C |
| ATOM | 2961 C GLY G 453 | −12.375 | 31.548 | −3.920 | 1.00 | 6.09 | C |
| ATOM | 2962 O GLY G 453 | −12.581 | 32.759 | −3.999 | 1.00 | 5.90 | O |
| ATOM | 2963 N ASN G 454 | −11.872 | 30.971 | −2.833 | 1.00 | 6.02 | N |
| ATOM | 2964 CA ASN G 454 | −11.672 | 31.727 | −1.603 | 1.00 | 6.39 | C |
| ATOM | 2965 CB ASN G 454 | −12.335 | 31.027 | −0.420 | 1.00 | 6.81 | C |
| ATOM | 2966 CG ASN G 454 | −13.717 | 31.567 | −0.135 | 1.00 | 8.99 | C |
| ATOM | 2967 OD1 ASN G 454 | −13.867 | 32.523 | 0.625 | 1.00 | 11.67 | O |
| ATOM | 2968 ND2 ASN G 454 | −14.693 | 31.112 | −0.911 | 1.00 | 10.25 | N |
| ATOM | 2969 C ASN G 454 | −10.211 | 32.020 | −1.296 | 1.00 | 6.15 | C |
| ATOM | 2970 O ASN G 454 | −9.900 | 32.765 | −0.367 | 1.00 | 6.47 | O |
| ATOM | 2971 N THR G 455 | −9.322 | 31.491 | −2.128 | 1.00 | 5.40 | N |
| ATOM | 2972 CA THR G 455 | −7.912 | 31.841 | −2.053 | 1.00 | 4.53 | C |
| ATOM | 2973 CB THR G 455 | −7.033 | 30.774 | −2.724 | 1.00 | 4.70 | C |
| ATOM | 2974 OG1 THR G 455 | −7.344 | 29.486 | −2.180 | 1.00 | 5.28 | O |
| ATOM | 2975 CG2 THR G 455 | −5.560 | 31.074 | −2.491 | 1.00 | 5.57 | C |
| ATOM | 2976 C THR G 455 | −7.659 | 33.187 | −2.717 | 1.00 | 4.01 | C |
| ATOM | 2977 O THR G 455 | −8.312 | 33.540 | −3.698 | 1.00 | 3.78 | O |
| ATOM | 2978 N LEU G 456 | −6.716 | 33.943 | −2.165 | 1.00 | 3.87 | N |
| ATOM | 2979 CA LEU G 456 | −6.355 | 35.237 | −2.726 | 1.00 | 4.05 | C |
| ATOM | 2980 CB LEU G 456 | −6.684 | 36.360 | −1.742 | 1.00 | 3.95 | C |
| ATOM | 2981 CG LEU G 456 | −6.595 | 37.779 | −2.306 | 1.00 | 3.76 | C |
| ATOM | 2982 CD1 LEU G 456 | −7.572 | 37.962 | −3.457 | 1.00 | 5.35 | C |
| ATOM | 2983 CD2 LEU G 456 | −6.845 | 38.809 | −1.216 | 1.00 | 4.10 | C |
| ATOM | 2984 C LEU G 456 | −4.879 | 35.288 | −3.105 | 1.00 | 4.47 | C |
| ATOM | 2985 O LEU G 456 | −4.006 | 35.028 | −2.276 | 1.00 | 4.94 | O |
| ATOM | 2986 N TYR G 457 | −4.609 | 35.652 | −4.355 | 1.00 | 4.59 | N |
| ATOM | 2987 CA TYR G 457 | −3.242 | 35.786 | −4.849 | 1.00 | 4.60 | C |
| ATOM | 2988 CB TYR G 457 | −3.056 | 34.938 | −6.113 | 1.00 | 4.71 | C |
| ATOM | 2989 CG TYR G 457 | −3.201 | 33.447 | −5.888 | 1.00 | 5.62 | C |
| ATOM | 2990 CD1 TYR G 457 | −4.451 | 32.838 | −5.896 | 1.00 | 7.09 | C |
| ATOM | 2991 CE1 TYR G 457 | −4.582 | 31.473 | −5.712 | 1.00 | 8.22 | C |
| ATOM | 2992 CZ TYR G 457 | −3.456 | 30.699 | −5.533 | 1.00 | 8.06 | C |
| ATOM | 2993 OH TYR G 457 | −3.580 | 29.341 | −5.349 | 1.00 | 8.80 | O |
| ATOM | 2994 CE2 TYR G 457 | −2.204 | 31.276 | −5.547 | 1.00 | 7.18 | C |
| ATOM | 2995 CD2 TYR G 457 | −2.083 | 32.639 | −5.735 | 1.00 | 6.66 | C |
| ATOM | 2996 C TYR G 457 | −2.924 | 37.256 | −5.152 | 1.00 | 4.46 | C |
| ATOM | 2997 O TYR G 457 | −3.742 | 37.959 | −5.745 | 1.00 | 4.92 | O |
| ATOM | 2998 N TYR G 458 | −1.727 | 37.706 | −4.772 | 1.00 | 3.90 | N |
| ATOM | 2999 CA TYR G 458 | −1.312 | 39.118 | −4.919 | 1.00 | 3.26 | C |
| ATOM | 3000 CB TYR G 458 | −0.740 | 39.635 | −3.582 | 1.00 | 3.16 | C |
| ATOM | 3001 CG TYR G 458 | −1.716 | 39.659 | −2.411 | 1.00 | 3.29 | C |
| ATOM | 3002 CD1 TYR G 458 | −1.782 | 38.602 | −1.509 | 1.00 | 3.93 | C |
| ATOM | 3003 CE1 TYR G 458 | −2.632 | 38.646 | −0.412 | 1.00 | 4.90 | C |
| ATOM | 3004 CZ TYR G 458 | −3.395 | 39.773 | −0.185 | 1.00 | 5.12 | C |
| ATOM | 3005 OH TYR G 458 | −4.250 | 39.817 | 0.893 | 1.00 | 5.42 | O |

APPENDIX-continued (APPENDIX discloses SEQ ID NOS 29-32, 29-32 and 29-32, respectively, in order of appearance)

| | | | |
|---|---|---|---|
| ATOM | 3006 CE2 TYR G 458 | −3.311 40.852 −1.039 1.00 4.72 | C |
| ATOM | 3007 CD2 TYR G 458 | −2.457 40.801 −2.128 1.00 3.89 | C |
| ATOM | 3008 C TYR G 458 | −0.248 39.290 −6.043 1.00 3.04 | C |
| ATOM | 3009 O TYR G 458 | 0.749 38.569 −6.041 1.00 3.37 | O |
| ATOM | 3010 N VAL G 459 | −0.351 40.348 −6.866 1.00 2.71 | N |
| ATOM | 3011 CA VAL G 459 | 0.376 40.435 −8.177 1.00 2.61 | C |
| ATOM | 3012 CB VAL G 459 | −0.589 40.554 −9.380 1.00 2.22 | C |
| ATOM | 3013 CG1 VAL G 459 | 0.154 40.287 −10.682 1.00 2.62 | C |
| ATOM | 3014 CG2 VAL G 459 | −1.756 39.589 −9.224 1.00 2.61 | C |
| ATOM | 3015 C VAL G 459 | 1.609 41.392 −8.360 1.00 3.03 | C |
| ATOM | 3016 O VAL G 459 | 2.575 41.281 −7.604 1.00 3.21 | O |
| ATOM | 3017 N ASN G 460 | 1.708 42.037 −9.537 1.00 106.93 | N |
| ATOM | 3018 CA ASN G 460 | 2.714 43.111 −9.870 1.00 95.54 | C |
| ATOM | 3019 CB ASN G 460 | 3.598 43.589 −8.700 1.00 20.00 | C |
| ATOM | 3020 CG ASN G 460 | 4.310 44.931 −9.000 1.00 20.00 | C |
| ATOM | 3021 OD1 ASN G 460 | 3.713 45.851 −9.563 1.00 20.00 | O |
| ATOM | 3022 ND2 ASN G 460 | 5.548 45.065 −8.532 1.00 20.00 | N |
| ATOM | 3023 C ASN G 460 | 3.403 43.322 −11.247 1.00 99.41 | C |
| ATOM | 3024 O ASN G 460 | 3.869 44.430 −11.523 1.00108.91 | O |
| ATOM | 3025 N LYS G 461 | 3.568 42.271 −12.055 1.00 97.04 | N |
| ATOM | 3026 CA LYS G 461 | 4.464 42.327 −13.236 1.00105.93 | C |
| ATOM | 3027 CB LYS G 461 | 5.335 41.068 −13.312 1.00 20.00 | C |
| ATOM | 3028 CG LYS G 461 | 6.382 40.951 −12.209 1.00 20.00 | C |
| ATOM | 3029 CD LYS G 461 | 7.131 39.623 −12.296 1.00 20.00 | C |
| ATOM | 3030 CE LYS G 461 | 8.255 39.536 −11.268 1.00 20.00 | C |
| ATOM | 3031 NZ LYS G 461 | 8.886 38.184 −11.223 1.00 20.00 | N |
| ATOM | 3032 C LYS G 461 | 3.727 42.546 −14.573 1.00102.28 | C |
| ATOM | 3033 O LYS G 461 | 2.507 42.702 −14.590 1.00105.02 | O |
| ATOM | 3034 N GLN G 462 | 4.464 42.556 −15.685 1.00 96.68 | N |
| ATOM | 3035 CA GLN G 462 | 3.854 42.633 −17.020 1.00105.71 | C |
| ATOM | 3036 CB GLN G 462 | 3.988 44.047 −17.593 1.00 20.00 | C |
| ATOM | 3037 CG GLN G 462 | 3.237 45.115 −16.814 1.00 20.00 | C |
| ATOM | 3038 CD GLN G 462 | 3.484 46.512 −17.353 1.00 20.00 | C |
| ATOM | 3039 OE1 GLN G 462 | 4.527 46.786 −17.947 1.00 20.00 | O |
| ATOM | 3040 NE2 GLN G 462 | 2.529 47.408 −17.135 1.00 20.00 | N |
| ATOM | 3041 C GLN G 462 | 4.479 41.626 −17.986 1.00101.50 | C |
| ATOM | 3042 O GLN G 462 | 5.701 41.501 −18.051 1.00105.94 | O |
| ATOM | 3043 N GLU G 463 | 3.646 40.946 −18.769 1.00 98.92 | N |
| ATOM | 3044 CA GLU G 463 | 4.140 39.928 −19.693 1.00108.59 | C |
| ATOM | 3045 CB GLU G 463 | 3.380 38.612 −19.512 1.00 20.00 | C |
| ATOM | 3046 CG GLU G 463 | 3.682 37.900 −18.201 1.00 20.00 | C |
| ATOM | 3047 CD GLU G 463 | 2.842 36.650 −18.005 1.00 20.00 | C |
| ATOM | 3048 OE1 GLU G 463 | 2.003 36.350 −18.881 1.00 20.00 | O |
| ATOM | 3049 OE2 GLU G 463 | 3.075 35.929 −17.011 1.00 20.00 | O |
| ATOM | 3050 C GLU G 463 | 4.074 40.384 −21.146 1.00116.39 | C |
| ATOM | 3051 O GLU G 463 | 3.025 40.814 −21.627 1.00118.70 | O |
| ATOM | 3052 N GLY G 464 | 5.200 40.272 −21.845 1.00127.70 | N |
| ATOM | 3053 CA GLY G 464 | 5.261 40.610 −23.261 1.00143.17 | C |
| ATOM | 3054 C GLY G 464 | 4.710 39.509 −24.146 1.00149.77 | C |
| ATOM | 3055 O GLY G 464 | 4.443 38.400 −23.681 1.00155.06 | O |
| ATOM | 3056 N LYS G 465 | 4.544 39.816 −25.428 1.00153.73 | N |
| ATOM | 3057 CA LYS G 465 | 3.994 38.862 −26.384 1.00153.69 | C |
| ATOM | 3058 CB LYS G 465 | 4.816 37.571 −26.389 1.00 20.00 | C |
| ATOM | 3059 CG LYS G 465 | 6.228 37.735 −26.927 1.00 20.00 | C |
| ATOM | 3060 CD LYS G 465 | 6.996 36.424 −26.873 1.00 20.00 | C |
| ATOM | 3061 CE LYS G 465 | 8.402 36.585 −27.426 1.00 20.00 | C |
| ATOM | 3062 NZ LYS G 465 | 9.172 35.312 −27.363 1.00 20.00 | N |
| ATOM | 3063 C LYS G 465 | 2.532 38.552 −26.080 1.00155.37 | C |
| ATOM | 3064 O LYS G 465 | 1.710 38.437 −26.988 1.00155.20 | O |
| ATOM | 3065 N GLU G 472 | −0.074 35.733 −32.259 1.00145.47 | N |
| ATOM | 3066 CA GLU G 472 | −0.706 34.866 −33.247 1.00151.12 | C |
| ATOM | 3067 CB GLU G 472 | 0.178 34.736 −34.490 1.00 20.00 | C |
| ATOM | 3068 CG GLU G 472 | 0.339 36.028 −35.276 1.00 20.00 | C |
| ATOM | 3069 CD GLU G 472 | 1.271 35.876 −36.463 1.00 20.00 | C |
| ATOM | 3070 OE1 GLU G 472 | 1.954 34.835 −36.556 1.00 20.00 | O |
| ATOM | 3071 OE2 GLU G 472 | 1.325 36.803 −37.299 1.00 20.00 | O |
| ATOM | 3072 C GLU G 472 | −0.993 33.486 −32.663 1.00153.35 | C |
| ATOM | 3073 O GLU G 472 | −0.069 32.755 −32.306 1.00159.41 | O |
| ATOM | 3074 N PRO G 473 | −2.282 33.131 −32.557 1.00150.51 | N |
| ATOM | 3075 CA PRO G 473 | −2.668 31.819 −32.081 1.00141.97 | C |
| ATOM | 3076 CB PRO G 473 | −3.684 32.152 −30.990 1.00 20.00 | C |
| ATOM | 3077 CG PRO G 473 | −4.311 33.467 −31.446 1.00 20.00 | C |
| ATOM | 3078 CD PRO G 473 | −3.423 34.059 −32.523 1.00 20.00 | C |
| ATOM | 3079 C PRO G 473 | −3.357 31.051 −33.200 1.00135.14 | C |
| ATOM | 3080 O PRO G 473 | −3.883 31.662 −34.131 1.00144.93 | O |
| ATOM | 3081 N ILE G 474 | −3.379 29.727 −33.098 1.00118.07 | N |
| ATOM | 3082 CA ILE G 474 | −3.969 28.899 −34.142 1.00105.14 | C |

APPENDIX-continued (APPENDIX discloses SEQ ID NOS 29-32, 29-32 and 29-32, respectively, in order of appearance)

| | | | |
|---|---|---|---|
| ATOM | 3083 CB ILE G 474 | −3.193 29.027 −35.469 1.00 20.00 | C |
| ATOM | 3084 CG1 ILE G 474 | −3.315 30.446 −36.028 1.00 20.00 | C |
| ATOM | 3085 CD1 ILE G 474 | −2.352 30.745 −37.156 1.00 20.00 | C |
| ATOM | 3086 CG2 ILE G 474 | −3.696 28.008 −36.481 1.00 20.00 | C |
| ATOM | 3087 C ILE G 474 | −4.007 27.432 −33.730 1.00104.75 | C |
| ATOM | 3088 O ILE G 474 | −3.033 26.702 −33.915 1.00111.83 | O |
| ATOM | 3089 N ILE G 475 | −5.149 26.992 −33.213 1.00 94.65 | N |
| ATOM | 3090 CA ILE G 475 | −5.249 25.667 −32.611 1.00 79.88 | C |
| ATOM | 3091 CB ILE G 475 | −5.443 25.753 −31.087 1.00 20.00 | C |
| ATOM | 3092 CG1 ILE G 475 | −4.165 26.260 −30.413 1.00 20.00 | C |
| ATOM | 3093 CD1 ILE G 475 | −4.414 27.012 −29.122 1.00 20.00 | C |
| ATOM | 3094 CG2 ILE G 475 | −5.873 24.406 −30.525 1.00 20.00 | C |
| ATOM | 3095 C ILE G 475 | −6.374 24.834 −33.223 1.00 79.52 | C |
| ATOM | 3096 O ILE G 475 | −7.554 25.117 −33.016 1.00 82.70 | O |
| ATOM | 3097 N ASN G 476 | −5.996 23.761 −33.912 1.00 69.64 | N |
| ATOM | 3098 CA ASN G 476 | −6.962 22.821 −34.472 1.00 68.88 | C |
| ATOM | 3099 CB ASN G 476 | −6.365 22.100 −35.683 1.00 20.00 | C |
| ATOM | 3100 CG ASN G 476 | −6.170 23.019 −36.872 1.00 20.00 | C |
| ATOM | 3101 OD1 ASN G 476 | −6.855 24.032 −37.009 1.00 20.00 | O |
| ATOM | 3102 ND2 ASN G 476 | −5.251 22.651 −37.756 1.00 20.00 | N |
| ATOM | 3103 C ASN G 476 | −7.434 21.799 −33.443 1.00 67.13 | C |
| ATOM | 3104 O ASN G 476 | −6.628 21.229 −32.707 1.00 73.10 | O |
| ATOM | 3105 N PHE G 477 | −8.735 21.527 −33.438 1.00 64.95 | N |
| ATOM | 3106 CA PHE G 477 | −9.327 20.624 −32.455 1.00 68.13 | C |
| ATOM | 3107 CB PHE G 477 | −10.854 20.711 −32.493 1.00 20.00 | C |
| ATOM | 3108 CG PHE G 477 | −11.397 22.047 −32.079 1.00 20.00 | C |
| ATOM | 3109 CD1 PHE G 477 | −11.580 22.352 −30.740 1.00 20.00 | C |
| ATOM | 3110 CE1 PHE G 477 | −12.086 23.580 −30.357 1.00 20.00 | C |
| ATOM | 3111 CZ PHE G 477 | −12.426 24.514 −31.316 1.00 20.00 | C |
| ATOM | 3112 CE2 PHE G 477 | −12.257 24.219 −32.654 1.00 20.00 | C |
| ATOM | 3113 CD2 PHE G 477 | −11.750 22.989 −33.030 1.00 20.00 | C |
| ATOM | 3114 C PHE G 477 | −8.890 19.180 −32.672 1.00 65.57 | C |
| ATOM | 3115 O PHE G 477 | −9.270 18.290 −31.911 1.00 49.83 | O |
| ATOM | 3116 N TYR G 478 | −8.204 18.931 −33.782 1.00 51.97 | N |
| ATOM | 3117 CA TYR G 478 | −7.618 17.619 −34.036 1.00 52.01 | C |
| ATOM | 3118 CB TYR G 478 | −7.356 17.428 −35.530 1.00 20.00 | C |
| ATOM | 3119 CG TYR G 478 | −8.609 17.426 −36.372 1.00 20.00 | C |
| ATOM | 3120 CD1 TYR G 478 | −9.337 16.259 −36.567 1.00 20.00 | C |
| ATOM | 3121 CE1 TYR G 478 | −10.489 16.255 −37.329 1.00 20.00 | C |
| ATOM | 3122 CZ TYR G 478 | −10.930 17.429 −37.902 1.00 20.00 | C |
| ATOM | 3123 OH TYR G 478 | −12.078 17.432 −38.658 1.00 20.00 | O |
| ATOM | 3124 CE2 TYR G 478 | −10.230 18.602 −37.717 1.00 20.00 | C |
| ATOM | 3125 CD2 TYR G 478 | −9.079 18.596 −36.954 1.00 20.00 | C |
| ATOM | 3126 C TYR G 478 | −6.325 17.459 −33.251 1.00 66.63 | C |
| ATOM | 3127 O TYR G 478 | −5.548 16.535 −33.492 1.00 63.45 | O |
| ATOM | 3128 N ASP G 479 | −6.062 18.423 −32.375 1.00 65.34 | N |
| ATOM | 3129 CA ASP G 479 | −4.928 18.351 −31.469 1.00 65.32 | C |
| ATOM | 3130 CB ASP G 479 | −4.205 19.698 −31.413 1.00 20.00 | C |
| ATOM | 3131 CG ASP G 479 | −3.509 20.038 −32.717 1.00 20.00 | C |
| ATOM | 3132 OD1 ASP G 479 | −3.293 19.119 −33.534 1.00 20.00 | O |
| ATOM | 3133 OD2 ASP G 479 | −3.184 21.225 −32.930 1.00 20.00 | O |
| ATOM | 3134 C ASP G 479 | −5.383 17.937 −30.076 1.00 64.83 | C |
| ATOM | 3135 O ASP G 479 | −4.561 17.574 −29.236 1.00 60.42 | O |
| ATOM | 3136 N PRO G 480 | −6.707 17.893 −29.861 1.00 47.60 | N |
| ATOM | 3137 CA PRO G 480 | −7.262 17.523 −28.572 1.00 46.52 | C |
| ATOM | 3138 CB PRO G 480 | −8.509 18.400 −28.480 1.00 20.00 | C |
| ATOM | 3139 CG PRO G 480 | −8.954 18.565 −29.904 1.00 20.00 | C |
| ATOM | 3140 CD PRO G 480 | −7.755 18.332 −30.799 1.00 20.00 | C |
| ATOM | 3141 C PRO G 480 | −7.662 16.056 −28.548 1.00 52.36 | C |
| ATOM | 3142 O PRO G 480 | −8.804 15.721 −28.860 1.00 64.15 | O |
| ATOM | 3143 N LEU G 481 | −6.698 15.183 −28.281 1.00 62.90 | N |
| ATOM | 3144 CA LEU G 481 | −6.977 13.759 −28.138 1.00 54.24 | C |
| ATOM | 3145 CB LEU G 481 | −6.143 12.944 −29.128 1.00 20.00 | C |
| ATOM | 3146 CG LEU G 481 | −6.449 13.142 −30.613 1.00 20.00 | C |
| ATOM | 3147 CD1 LEU G 481 | −5.475 12.348 −31.471 1.00 20.00 | C |
| ATOM | 3148 CD2 LEU G 481 | −7.884 12.747 −30.922 1.00 20.00 | C |
| ATOM | 3149 C LEU G 481 | −6.700 13.285 −26.717 1.00 59.81 | C |
| ATOM | 3150 O LEU G 481 | −6.199 14.041 −25.884 1.00 64.98 | O |
| ATOM | 3151 N VAL G 482 | −6.956 12.008 −26.470 1.00 59.66 | N |
| ATOM | 3152 CA VAL G 482 | −6.588 11.404 −25.203 1.00 49.67 | C |
| ATOM | 3153 CB VAL G 482 | −7.741 10.579 −24.619 1.00 20.00 | C |
| ATOM | 3154 CG1 VAL G 482 | −7.390 10.116 −23.220 1.00 20.00 | C |
| ATOM | 3155 CG2 VAL G 482 | −9.021 11.398 −24.607 1.00 20.00 | C |
| ATOM | 3156 C VAL G 482 | −5.357 10.525 −25.372 1.00 53.03 | C |
| ATOM | 3157 O VAL G 482 | −5.147 9.945 −26.437 1.00 46.27 | O |
| ATOM | 3158 N PHE G 483 | −4.464 10.579 −24.387 1.00 61.61 | N |
| ATOM | 3159 CA PHE G 483 | −3.282 9.723 −24.370 1.00 65.03 | C |

APPENDIX-continued (APPENDIX discloses SEQ ID NOS 29-32, 29-32 and 29-32, respectively, in order of appearance)

| | | | |
|---|---|---|---|
| ATOM | 3160 CB PHE G 483 | −2.011 10.562 −24.235 1.00 20.00 | C |
| ATOM | 3161 CG PHE G 483 | −1.788 11.500 −25.385 1.00 20.00 | C |
| ATOM | 3162 CD1 PHE G 483 | −1.173 11.059 −26.546 1.00 20.00 | C |
| ATOM | 3163 CE1 PHE G 483 | −1.039 11.897 −27.632 1.00 20.00 | C |
| ATOM | 3164 CZ PHE G 483 | −1.577 13.170 −27.589 1.00 20.00 | C |
| ATOM | 3165 CE2 PHE G 483 | −2.199 13.618 −26.442 1.00 20.00 | C |
| ATOM | 3166 CD2 PHE G 483 | −2.315 12.781 −25.355 1.00 20.00 | C |
| ATOM | 3167 C PHE G 483 | −3.358 8.663 −23.275 1.00 71.00 | C |
| ATOM | 3168 O PHE G 483 | −2.688 8.776 −22.248 1.00 100.44 | O |
| ATOM | 3169 N PRO G 484 | −4.338 7.759 −23.403 1.00 54.44 | N |
| ATOM | 3170 CA PRO G 484 | −4.502 6.677 −22.459 1.00 47.46 | C |
| ATOM | 3171 CB PRO G 484 | −5.761 7.096 −21.701 1.00 20.00 | C |
| ATOM | 3172 CG PRO G 484 | −6.554 7.922 −22.714 1.00 20.00 | C |
| ATOM | 3173 CD PRO G 484 | −5.649 8.206 −23.894 1.00 20.00 | C |
| ATOM | 3174 C PRO G 484 | −4.778 5.378 −23.204 1.00 41.56 | C |
| ATOM | 3175 O PRO G 484 | −5.689 5.321 −24.029 1.00 46.53 | O |
| ATOM | 3176 N SER G 485 | −3.961 4.363 −22.958 1.00 46.30 | N |
| ATOM | 3177 CA SER G 485 | −4.081 3.108 −23.686 1.00 49.30 | C |
| ATOM | 3178 CB SER G 485 | −3.559 1.943 −22.841 1.00 20.00 | C |
| ATOM | 3179 OG SER G 485 | −4.215 1.884 −21.588 1.00 20.00 | O |
| ATOM | 3180 C SER G 485 | −5.521 2.856 −24.147 1.00 41.24 | C |
| ATOM | 3181 O SER G 485 | −5.809 2.890 −25.345 1.00 46.93 | O |
| ATOM | 3182 N ASP G 486 | −6.437 2.720 −23.190 1.00 49.48 | N |
| ATOM | 3183 CA ASP G 486 | −7.816 2.321 −23.485 1.00 37.44 | C |
| ATOM | 3184 CB ASP G 486 | −8.659 2.287 −22.205 1.00 20.00 | C |
| ATOM | 3185 CG ASP G 486 | −8.296 1.125 −21.289 1.00 20.00 | C |
| ATOM | 3186 OD1 ASP G 486 | −7.611 0.188 −21.746 1.00 20.00 | O |
| ATOM | 3187 OD2 ASP G 486 | −8.637 1.184 −20.089 1.00 20.00 | O |
| ATOM | 3188 C ASP G 486 | −8.447 3.271 −24.491 1.00 45.66 | C |
| ATOM | 3189 O ASP G 486 | −9.005 2.844 −25.501 1.00 39.86 | O |
| ATOM | 3190 N GLU G 487 | −8.317 4.566 −24.225 1.00 49.20 | N |
| ATOM | 3191 CA GLU G 487 | −8.853 5.585 −25.116 1.00 45.70 | C |
| ATOM | 3192 CB GLU G 487 | −8.656 6.982 −24.525 1.00 20.00 | C |
| ATOM | 3193 CG GLU G 487 | −9.449 7.237 −23.251 1.00 20.00 | C |
| ATOM | 3194 CD GLU G 487 | −9.144 8.590 −22.635 1.00 20.00 | C |
| ATOM | 3195 OE1 GLU G 487 | −8.175 9.245 −23.078 1.00 20.00 | O |
| ATOM | 3196 OE2 GLU G 487 | −9.865 8.988 −21.695 1.00 20.00 | O |
| ATOM | 3197 C GLU G 487 | −8.222 5.504 −26.501 1.00 41.48 | C |
| ATOM | 3198 O GLU G 487 | −8.914 5.623 −27.512 1.00 48.92 | O |
| ATOM | 3199 N PHE G 488 | −6.910 5.306 −26.545 1.00 42.16 | N |
| ATOM | 3200 CA PHE G 488 | −6.206 5.215 −27.815 1.00 39.33 | C |
| ATOM | 3201 CB PHE G 488 | −4.701 5.086 −27.590 1.00 20.00 | C |
| ATOM | 3202 CG PHE G 488 | −4.074 6.308 −26.992 1.00 20.00 | C |
| ATOM | 3203 CD1 PHE G 488 | −3.910 7.454 −27.747 1.00 20.00 | C |
| ATOM | 3204 CE1 PHE G 488 | −3.320 8.574 −27.202 1.00 20.00 | C |
| ATOM | 3205 CZ PHE G 488 | −2.847 8.542 −25.898 1.00 20.00 | C |
| ATOM | 3206 CE2 PHE G 488 | −3.006 7.404 −25.136 1.00 20.00 | C |
| ATOM | 3207 CD2 PHE G 488 | −3.630 6.302 −25.678 1.00 20.00 | C |
| ATOM | 3208 C PHE G 488 | −6.724 4.040 −28.634 1.00 43.06 | C |
| ATOM | 3209 O PHE G 488 | −7.101 4.203 −29.794 1.00 61.71 | O |
| ATOM | 3210 N ASP G 489 | −6.910 2.906 −27.972 1.00 41.95 | N |
| ATOM | 3211 CA ASP G 489 | −7.330 1.695 −28.658 1.00 42.75 | C |
| ATOM | 3212 CB ASP G 489 | −7.257 0.499 −27.717 1.00 20.00 | C |
| ATOM | 3213 CG ASP G 489 | −5.838 0.116 −27.389 1.00 20.00 | C |
| ATOM | 3214 OD1 ASP G 489 | −4.920 0.637 −28.056 1.00 20.00 | O |
| ATOM | 3215 OD2 ASP G 489 | −5.636 −0.633 −26.411 1.00 20.00 | O |
| ATOM | 3216 C ASP G 489 | −8.733 1.825 −29.233 1.00 45.61 | C |
| ATOM | 3217 O ASP G 489 | −9.066 1.181 −30.226 1.00 54.39 | O |
| ATOM | 3218 N ALA G 490 | −9.568 2.622 −28.575 1.00 42.89 | N |
| ATOM | 3219 CA ALA G 490 | −10.929 2.848 −29.044 1.00 38.40 | C |
| ATOM | 3220 CB ALA G 490 | −11.760 3.516 −27.963 1.00 20.00 | C |
| ATOM | 3221 C ALA G 490 | −10.932 3.687 −30.315 1.00 39.67 | C |
| ATOM | 3222 O ALA G 490 | −11.651 3.386 −31.267 1.00 56.80 | O |
| ATOM | 3223 N SER G 491 | −10.138 4.752 −30.315 1.00 40.38 | N |
| ATOM | 3224 CA SER G 491 | −9.984 5.586 −31.499 1.00 41.77 | C |
| ATOM | 3225 CB SER G 491 | −9.155 6.831 −31.176 1.00 20.00 | C |
| ATOM | 3226 OG SER G 491 | −7.806 6.490 −30.912 1.00 20.00 | O |
| ATOM | 3227 C SER G 491 | −9.333 4.801 −32.631 1.00 39.01 | C |
| ATOM | 3228 O SER G 491 | −9.688 4.967 −33.798 1.00 36.91 | O |
| ATOM | 3229 N ILE G 492 | −8.387 3.938 −32.278 1.00 38.11 | N |
| ATOM | 3230 CA ILE G 492 | −7.741 3.077 −33.259 1.00 41.21 | C |
| ATOM | 3231 CB ILE G 492 | −6.630 2.211 −32.620 1.00 20.00 | C |
| ATOM | 3232 CG1 ILE G 492 | −5.507 3.092 −32.061 1.00 20.00 | C |
| ATOM | 3233 CD1 ILE G 492 | −4.533 2.346 −31.163 1.00 20.00 | C |
| ATOM | 3234 CG2 ILE G 492 | −6.067 1.219 −33.634 1.00 20.00 | C |
| ATOM | 3235 C ILE G 492 | −8.773 2.170 −33.916 1.00 39.22 | C |
| ATOM | 3236 O ILE G 492 | −8.778 2.008 −35.135 1.00 47.54 | O |

APPENDIX-continued (APPENDIX discloses SEQ ID NOS 29-32, 29-32 and 29-32, respectively, in order of appearance)

| | | | |
|---|---|---|---|
| ATOM | 3237 N SER G 493 | −9.703 1.662 −33.111 1.00 41.64 | N |
| ATOM | 3238 CA SER G 493 | −10.786 0.819 −33.612 1.00 35.15 | C |
| ATOM | 3239 CB SER G 493 | −11.579 0.202 −32.454 1.00 20.00 | C |
| ATOM | 3240 OG SER G 493 | −12.267 1.196 −31.716 1.00 20.00 | O |
| ATOM | 3241 C SER G 493 | −11.716 1.614 −34.523 1.00 47.90 | C |
| ATOM | 3242 O SER G 493 | −12.169 1.115 −35.555 1.00 50.94 | O |
| ATOM | 3243 N GLN G 494 | −11.936 2.877 −34.169 1.00 42.51 | N |
| ATOM | 3244 CA GLN G 494 | −12.789 3.766 −34.955 1.00 41.96 | C |
| ATOM | 3245 CB GLN G 494 | −13.107 5.036 −34.167 1.00 20.00 | C |
| ATOM | 3246 CG GLN G 494 | −13.991 4.813 −32.955 1.00 20.00 | C |
| ATOM | 3247 CD GLN G 494 | −14.211 6.084 −32.163 1.00 20.00 | C |
| ATOM | 3248 OE1 GLN G 494 | −13.406 7.013 −32.223 1.00 20.00 | O |
| ATOM | 3249 NE2 GLN G 494 | −15.317 6.140 −31.430 1.00 20.00 | N |
| ATOM | 3250 C GLN G 494 | −12.151 4.137 −36.291 1.00 33.86 | C |
| ATOM | 3251 O GLN G 494 | −12.829 4.195 −37.318 1.00 54.89 | O |
| ATOM | 3252 N VAL G 495 | −10.881 4.523 −36.241 1.00 34.99 | N |
| ATOM | 3253 CA VAL G 495 | −10.108 4.772 −37.451 1.00 38.42 | C |
| ATOM | 3254 CB VAL G 495 | −8.642 5.097 −37.120 1.00 20.00 | C |
| ATOM | 3255 CG1 VAL G 495 | −7.840 5.297 −38.394 1.00 20.00 | C |
| ATOM | 3256 CG2 VAL G 495 | −8.562 6.327 −36.231 1.00 20.00 | C |
| ATOM | 3257 C VAL G 495 | −10.152 3.573 −38.393 1.00 42.74 | C |
| ATOM | 3258 O VAL G 495 | −10.424 3.720 −39.584 1.00 44.00 | O |
| ATOM | 3259 N ASN G 496 | −9.947 2.383 −37.838 1.00 42.45 | N |
| ATOM | 3260 CA ASN G 496 | −9.967 1.147 −38.617 1.00 43.01 | C |
| ATOM | 3261 CB ASN G 496 | −9.572 −0.046 −37.743 1.00 20.00 | C |
| ATOM | 3262 CG ASN G 496 | −8.118 0.000 −37.319 1.00 20.00 | C |
| ATOM | 3263 OD1 ASN G 496 | −7.293 0.648 −37.965 1.00 20.00 | O |
| ATOM | 3264 ND2 ASN G 496 | −7.796 −0.684 −36.226 1.00 20.00 | N |
| ATOM | 3265 C ASN G 496 | −11.305 0.875 −39.310 1.00 43.13 | C |
| ATOM | 3266 O ASN G 496 | −11.334 0.405 −40.448 1.00 54.76 | O |
| ATOM | 3267 N GLU G 497 | −12.407 1.099 −38.598 1.00 42.08 | N |
| ATOM | 3268 CA GLU G 497 | −13.738 0.938 −39.183 1.00 43.13 | C |
| ATOM | 3269 CB GLU G 497 | −14.827 1.144 −38.127 1.00 20.00 | C |
| ATOM | 3270 CG GLU G 497 | −14.937 0.018 −37.110 1.00 20.00 | C |
| ATOM | 3271 CD GLU G 497 | −15.946 0.316 −36.017 1.00 20.00 | C |
| ATOM | 3272 OE1 GLU G 497 | −16.552 1.408 −36.049 1.00 20.00 | O |
| ATOM | 3273 OE2 GLU G 497 | −16.177 −0.566 −35.164 1.00 20.00 | O |
| ATOM | 3274 C GLU G 497 | −13.937 1.915 −40.337 1.00 49.77 | C |
| ATOM | 3275 O GLU G 497 | −14.552 1.580 −41.349 1.00 42.88 | O |
| ATOM | 3276 N LYS G 498 | −13.367 3.108 −40.195 1.00 41.82 | N |
| ATOM | 3277 CA LYS G 498 | −13.435 4.123 −41.240 1.00 53.60 | C |
| ATOM | 3278 CB LYS G 498 | −12.968 5.479 −40.705 1.00 20.00 | C |
| ATOM | 3279 CG LYS G 498 | −13.937 6.125 −39.728 1.00 20.00 | C |
| ATOM | 3280 CD LYS G 498 | −13.439 7.484 −39.269 1.00 20.00 | C |
| ATOM | 3281 CE LYS G 498 | −14.393 8.108 −38.265 1.00 20.00 | C |
| ATOM | 3282 NZ LYS G 498 | −13.896 9.421 −37.768 1.00 20.00 | N |
| ATOM | 3283 C LYS G 498 | −12.611 3.724 −42.458 1.00 55.29 | C |
| ATOM | 3284 O LYS G 498 | −13.033 3.926 −43.594 1.00 61.06 | O |
| ATOM | 3285 N ILE G 499 | −11.430 3.165 −42.214 1.00 52.22 | N |
| ATOM | 3286 CA ILE G 499 | −10.609 2.604 −43.284 1.00 48.26 | C |
| ATOM | 3287 CB ILE G 499 | −9.296 2.009 −42.729 1.00 20.00 | C |
| ATOM | 3288 CG1 ILE G 499 | −8.446 3.101 −42.072 1.00 20.00 | C |
| ATOM | 3289 CD1 ILE G 499 | −7.506 2.582 −41.002 1.00 20.00 | C |
| ATOM | 3290 CG2 ILE G 499 | −8.516 1.288 −43.825 1.00 20.00 | C |
| ATOM | 3291 C ILE G 499 | −11.376 1.515 −44.031 1.00 49.07 | C |
| ATOM | 3292 O ILE G 499 | −11.282 1.398 −45.253 1.00 58.45 | O |
| ATOM | 3293 N ASN G 500 | −12.183 0.764 −43.288 1.00 51.02 | N |
| ATOM | 3294 CA ASN G 500 | −12.992 −0.307 −43.857 1.00 52.06 | C |
| ATOM | 3295 CB ASN G 500 | −13.500 −1.238 −42.748 1.00 20.00 | C |
| ATOM | 3296 CG ASN G 500 | −14.173 −2.487 −43.292 1.00 20.00 | C |
| ATOM | 3297 OD1 ASN G 500 | −13.795 −3.005 −44.342 1.00 20.00 | O |
| ATOM | 3298 ND2 ASN G 500 | −15.127 −3.019 −42.536 1.00 20.00 | N |
| ATOM | 3299 C ASN G 500 | −14.161 0.250 −44.659 1.00 48.31 | C |
| ATOM | 3300 O ASN G 500 | −14.645 −0.386 −45.596 1.00 56.89 | O |
| ATOM | 3301 N GLN G 501 | −14.582 1.461 −44.312 1.00 55.87 | N |
| ATOM | 3302 CA GLN G 501 | −15.607 2.160 −45.074 1.00 53.55 | C |
| ATOM | 3303 CB GLN G 501 | −16.243 3.258 −44.222 1.00 20.00 | C |
| ATOM | 3304 CG GLN G 501 | −17.012 2.741 −43.015 1.00 20.00 | C |
| ATOM | 3305 CD GLN G 501 | −17.674 3.857 −42.226 1.00 20.00 | C |
| ATOM | 3306 OE1 GLN G 501 | −17.178 4.985 −42.189 1.00 20.00 | O |
| ATOM | 3307 NE2 GLN G 501 | −18.772 3.536 −41.553 1.00 20.00 | N |
| ATOM | 3308 C GLN G 501 | −15.030 2.751 −46.357 1.00 45.67 | C |
| ATOM | 3309 O GLN G 501 | −15.627 2.633 −47.429 1.00 58.31 | O |
| ATOM | 3310 N SER G 502 | −13.824 3.303 −46.258 1.00 43.44 | N |
| ATOM | 3311 CA SER G 502 | −13.117 3.801 −47.432 1.00 45.40 | C |
| ATOM | 3312 CB SER G 502 | −11.789 4.468 −47.045 1.00 20.00 | C |
| ATOM | 3313 OG SER G 502 | −10.928 3.572 −46.361 1.00 20.00 | O |

APPENDIX-continued (APPENDIX discloses SEQ ID NOS 29-32, 29-32 and 29-32, respectively, in order of appearance)

| | | | |
|---|---|---|---|
| ATOM | 3314 C SER G 502 | −12.891 2.677 −48.436 1.00 55.15 | C |
| ATOM | 3315 O SER G 502 | −13.234 2.819 −49.610 1.00 52.57 | O |
| ATOM | 3316 N LEU G 503 | −12.552 1.495 −47.922 1.00 55.35 | N |
| ATOM | 3317 CA LEU G 503 | −12.227 0.349 −48.768 1.00 52.12 | C |
| ATOM | 3318 CB LEU G 503 | −11.591 −0.778 −47.943 1.00 20.00 | C |
| ATOM | 3319 CG LEU G 503 | −10.187 −0.535 −47.373 1.00 20.00 | C |
| ATOM | 3320 CD1 LEU G 503 | −9.810 −1.609 −46.357 1.00 20.00 | C |
| ATOM | 3321 CD2 LEU G 503 | −9.144 −0.458 −48.481 1.00 20.00 | C |
| ATOM | 3322 C LEU G 503 | −13.471 −0.159 −49.489 1.00 55.74 | C |
| ATOM | 3323 O LEU G 503 | −13.402 −0.586 −50.642 1.00 57.75 | O |
| ATOM | 3324 N ALA G 504 | −14.618 −0.046 −48.826 1.00 57.22 | N |
| ATOM | 3325 CA ALA G 504 | −15.893 −0.410 −49.436 1.00 59.12 | C |
| ATOM | 3326 CB ALA G 504 | −16.981 −0.532 −48.377 1.00 20.00 | C |
| ATOM | 3327 C ALA G 504 | −16.293 0.605 −50.499 1.00 58.10 | C |
| ATOM | 3328 O ALA G 504 | −16.773 0.241 −51.573 1.00 63.64 | O |
| ATOM | 3329 N PHE G 505 | −16.075 1.881 −50.198 1.00 58.17 | N |
| ATOM | 3330 CA PHE G 505 | −16.303 2.940 −51.171 1.00 56.56 | C |
| ATOM | 3331 CB PHE G 505 | −15.991 4.309 −50.564 1.00 20.00 | C |
| ATOM | 3332 CG PHE G 505 | −16.870 4.665 −49.405 1.00 20.00 | C |
| ATOM | 3333 CD1 PHE G 505 | −18.185 5.035 −49.615 1.00 20.00 | C |
| ATOM | 3334 CE1 PHE G 505 | −19.045 5.205 −48.555 1.00 20.00 | C |
| ATOM | 3335 CZ PHE G 505 | −18.617 4.934 −47.269 1.00 20.00 | C |
| ATOM | 3336 CE2 PHE G 505 | −17.314 4.545 −47.047 1.00 20.00 | C |
| ATOM | 3337 CD2 PHE G 505 | −16.446 4.423 −48.109 1.00 20.00 | C |
| ATOM | 3338 C PHE G 505 | −15.462 2.715 −52.416 1.00 60.12 | C |
| ATOM | 3339 O PHE G 505 | −15.922 2.939 −53.535 1.00 65.46 | O |
| ATOM | 3340 N ILE G 506 | −14.235 2.242 −52.213 1.00 56.10 | N |
| ATOM | 3341 CA ILE G 506 | −13.325 1.960 −53.320 1.00 57.32 | C |
| ATOM | 3342 CB ILE G 506 | −11.911 1.590 −52.825 1.00 20.00 | C |
| ATOM | 3343 CG1 ILE G 506 | −11.167 2.839 −52.352 1.00 20.00 | C |
| ATOM | 3344 CD1 ILE G 506 | −10.010 2.533 −51.425 1.00 20.00 | C |
| ATOM | 3345 CG2 ILE G 506 | −11.126 0.882 −53.925 1.00 20.00 | C |
| ATOM | 3346 C ILE G 506 | −13.845 0.812 −54.170 1.00 67.33 | C |
| ATOM | 3347 O ILE G 506 | −13.674 0.803 −55.390 1.00 76.99 | O |
| ATOM | 3348 N ARG G 507 | −14.325 −0.230 −53.503 1.00 67.87 | N |
| ATOM | 3349 CA ARG G 507 | −14.920 −1.360 −54.195 1.00 62.11 | C |
| ATOM | 3350 CB ARG G 507 | −15.328 −2.440 −53.196 1.00 20.00 | C |
| ATOM | 3351 CG ARG G 507 | −14.151 −3.082 −52.491 1.00 20.00 | C |
| ATOM | 3352 CD ARG G 507 | −14.592 −4.218 −51.585 1.00 20.00 | C |
| ATOM | 3353 NE ARG G 507 | −13.453 −4.836 −50.911 1.00 20.00 | N |
| ATOM | 3354 CZ ARG G 507 | −13.555 −5.749 −49.950 1.00 20.00 | C |
| ATOM | 3355 NH1 ARG G 507 | −14.748 −6.221 −49.609 1.00 20.00 | N |
| ATOM | 3356 NH2 ARG G 507 | −12.459 −6.278 −49.422 1.00 20.00 | N |
| ATOM | 3357 C ARG G 507 | −16.119 −0.920 −55.026 1.00 67.30 | C |
| ATOM | 3358 O ARG G 507 | −16.131 −1.079 −56.247 1.00 67.02 | O |
| ATOM | 3359 N LYS G 508 | −17.080 −0.274 −54.375 1.00 66.83 | N |
| ATOM | 3360 CA LYS G 508 | −18.220 0.295 −55.078 1.00 68.12 | C |
| ATOM | 3361 CB LYS G 508 | −19.052 1.156 −54.133 1.00 20.00 | C |
| ATOM | 3362 CG LYS G 508 | −19.813 0.362 −53.096 1.00 20.00 | C |
| ATOM | 3363 CD LYS G 508 | −20.707 1.269 −52.270 1.00 20.00 | C |
| ATOM | 3364 CE LYS G 508 | −21.508 0.479 −51.248 1.00 20.00 | C |
| ATOM | 3365 NZ LYS G 508 | −22.370 1.366 −50.421 1.00 20.00 | N |
| ATOM | 3366 C LYS G 508 | −17.758 1.131 −56.261 1.00 65.22 | C |
| ATOM | 3367 O LYS G 508 | −18.149 0.880 −57.402 1.00 72.34 | O |
| ATOM | 3368 N SER G 509 | −16.859 2.071 −55.990 1.00 64.87 | N |
| ATOM | 3369 CA SER G 509 | −16.316 2.939 −57.028 1.00 56.47 | C |
| ATOM | 3370 CB SER G 509 | −15.268 3.896 −56.442 1.00 20.00 | C |
| ATOM | 3371 OG SER G 509 | −14.170 3.190 −55.888 1.00 20.00 | O |
| ATOM | 3372 C SER G 509 | −15.736 2.147 −58.205 1.00 56.96 | C |
| ATOM | 3373 O SER G 509 | −16.064 2.412 −59.363 1.00 65.57 | O |
| ATOM | 3374 N ASP G 510 | −14.906 1.154 −57.902 1.00 64.34 | N |
| ATOM | 3375 CA ASP G 510 | −14.282 0.340 −58.939 1.00 64.83 | C |
| ATOM | 3376 CB ASP G 510 | −13.338 −0.690 −58.316 1.00 20.00 | C |
| ATOM | 3377 CG ASP G 510 | −12.073 −0.063 −57.768 1.00 20.00 | C |
| ATOM | 3378 OD1 ASP G 510 | −11.789 1.104 −58.112 1.00 20.00 | O |
| ATOM | 3379 OD2 ASP G 510 | −11.361 −0.735 −56.993 1.00 20.00 | O |
| ATOM | 3380 C ASP G 510 | −15.339 −0.362 −59.782 1.00 62.11 | C |
| ATOM | 3381 O ASP G 510 | −15.346 −0.251 −61.008 1.00 67.61 | O |
| ATOM | 3382 N GLU G 511 | −16.244 −1.067 −59.112 1.00 64.95 | N |
| ATOM | 3383 CA GLU G 511 | −17.319 −1.774 −59.791 1.00 60.64 | C |
| ATOM | 3384 CB GLU G 511 | −18.359 −2.259 −58.780 1.00 20.00 | C |
| ATOM | 3385 CG GLU G 511 | −17.818 −3.293 −57.801 1.00 20.00 | C |
| ATOM | 3386 CD GLU G 511 | −18.840 −3.723 −56.760 1.00 20.00 | C |
| ATOM | 3387 OE1 GLU G 511 | −19.857 −3.017 −56.585 1.00 20.00 | O |
| ATOM | 3388 OE2 GLU G 511 | −18.603 −4.746 −56.083 1.00 20.00 | O |
| ATOM | 3389 C GLU G 511 | −17.970 −0.888 −60.842 1.00 59.91 | C |
| ATOM | 3390 O GLU G 511 | −18.090 −1.278 −62.003 1.00 55.45 | O |

APPENDIX-continued (APPENDIX discloses SEQ ID NOS 29-32, 29-32 and 29-32, respectively, in order of appearance)

| | | | |
|---|---|---|---|
| ATOM | 3391 N LEU G 512 | −18.270 0.349 −60.460 1.00 44.35 | N |
| ATOM | 3392 CA LEU G 512 | −18.978 1.259 −61.346 1.00 49.60 | C |
| ATOM | 3393 CB LEU G 512 | −19.424 2.511 −60.590 1.00 20.00 | C |
| ATOM | 3394 CG LEU G 512 | −20.377 2.256 −59.416 1.00 20.00 | C |
| ATOM | 3395 CD1 LEU G 512 | −20.747 3.550 −58.696 1.00 20.00 | C |
| ATOM | 3396 CD2 LEU G 512 | −21.624 1.499 −59.858 1.00 20.00 | C |
| ATOM | 3397 C LEU G 512 | −18.128 1.626 −62.557 1.00 58.00 | C |
| ATOM | 3398 O LEU G 512 | −18.542 1.415 −63.696 1.00 55.11 | O |
| ATOM | 3399 N LEU G 513 | −16.883 2.015 −62.305 1.00 57.91 | N |
| ATOM | 3400 CA LEU G 513 | −15.963 2.384 −63.378 1.00 57.49 | C |
| ATOM | 3401 CB LEU G 513 | −14.609 2.810 −62.801 1.00 20.00 | C |
| ATOM | 3402 CG LEU G 513 | −14.558 4.136 −62.038 1.00 20.00 | C |
| ATOM | 3403 CD1 LEU G 513 | −13.242 4.263 −61.282 1.00 20.00 | C |
| ATOM | 3404 CD2 LEU G 513 | −14.743 5.302 −62.996 1.00 20.00 | C |
| ATOM | 3405 C LEU G 513 | −15.775 1.231 −64.362 1.00 58.78 | C |
| ATOM | 3406 O LEU G 513 | −15.707 1.437 −65.574 1.00 59.88 | O |
| ATOM | 3407 N HIS G 514 | −15.708 0.015 −63.829 1.00 60.07 | N |
| ATOM | 3408 CA HIS G 514 | −15.540 −1.175 −64.652 1.00 62.82 | C |
| ATOM | 3409 CB HIS G 514 | −15.189 −2.383 −63.782 1.00 20.00 | C |
| ATOM | 3410 CG HIS G 514 | −13.924 −2.217 −63.001 1.00 20.00 | C |
| ATOM | 3411 ND1 HIS G 514 | −12.683 −2.154 −63.598 1.00 20.00 | N |
| ATOM | 3412 CE1 HIS G 514 | −11.757 −2.005 −62.668 1.00 20.00 | C |
| ATOM | 3413 NE2 HIS G 514 | −12.351 −1.975 −61.489 1.00 20.00 | N |
| ATOM | 3414 CD2 HIS G 514 | −13.706 −2.113 −61.669 1.00 20.00 | C |
| ATOM | 3415 C HIS G 514 | −16.796 −1.465 −65.463 1.00 65.10 | C |
| ATOM | 3416 O HIS G 514 | −16.745 −2.170 −66.470 1.00 66.73 | O |
| ATOM | 3417 N ASN G 515 | −17.926 −0.941 −65.000 1.00 63.45 | N |
| ATOM | 3418 CA ASN G 515 | −19.179 −1.062 −65.732 1.00 56.53 | C |
| ATOM | 3419 CB ASN G 515 | −20.370 −0.925 −64.783 1.00 20.00 | C |
| ATOM | 3420 CG ASN G 515 | −20.503 −2.107 −63.845 1.00 20.00 | C |
| ATOM | 3421 OD1 ASN G 515 | −19.979 −3.190 −64.113 1.00 20.00 | O |
| ATOM | 3422 ND2 ASN G 515 | −21.206 −1.906 −62.734 1.00 20.00 | N |
| ATOM | 3423 C ASN G 515 | −19.289 −0.043 −66.860 1.00 60.06 | C |
| ATOM | 3424 O ASN G 515 | −19.825 −0.335 −67.928 1.00 66.48 | O |
| ATOM | 3425 N VAL G 516 | −18.818 1.168 −66.598 1.00 54.29 | N |
| ATOM | 3426 CA VAL G 516 | −18.783 2.200 −67.620 1.00 52.70 | C |
| ATOM | 3427 CB VAL G 516 | −18.233 3.518 −67.056 1.00 20.00 | C |
| ATOM | 3428 CG1 VAL G 516 | −18.151 4.566 −68.153 1.00 20.00 | C |
| ATOM | 3429 CG2 VAL G 516 | −19.098 4.003 −65.904 1.00 20.00 | C |
| ATOM | 3430 C VAL G 516 | −17.910 1.753 −68.784 1.00 60.10 | C |
| ATOM | 3431 O VAL G 516 | −18.340 1.765 −69.937 1.00 61.55 | O |
| ATOM | 3432 N ASN G 517 | −16.733 1.232 −68.455 1.00 69.10 | N |
| ATOM | 3433 CA ASN G 517 | −15.793 0.770 −69.466 1.00 67.75 | C |
| ATOM | 3434 CB ASN G 517 | −14.564 0.137 −68.807 1.00 20.00 | C |
| ATOM | 3435 CG ASN G 517 | −13.665 1.163 −68.146 1.00 20.00 | C |
| ATOM | 3436 OD1 ASN G 517 | −13.646 2.330 −68.534 1.00 20.00 | O |
| ATOM | 3437 ND2 ASN G 517 | −12.873 0.718 −67.177 1.00 20.00 | N |
| ATOM | 3438 C ASN G 517 | −16.439 −0.209 −70.444 1.00 71.17 | C |
| ATOM | 3439 O ASN G 517 | −16.188 −0.154 −71.649 1.00 66.42 | O |
| ATOM | 3440 N ALA G 518 | −17.351 −1.033 −69.935 1.00 72.11 | N |
| ATOM | 3441 CA ALA G 518 | −18.026 −2.024 −70.764 1.00 74.82 | C |
| ATOM | 3442 CB ALA G 518 | −18.558 −3.164 −69.912 1.00 20.00 | C |
| ATOM | 3443 C ALA G 518 | −19.145 −1.399 −71.593 1.00 70.11 | C |
| ATOM | 3444 O ALA G 518 | −19.363 −1.789 −72.739 1.00 65.18 | O |
| ATOM | 3445 N GLY G 519 | −19.865 −0.448 −71.006 1.00 56.07 | N |
| ATOM | 3446 CA GLY G 519 | −20.825 0.357 −71.760 1.00 53.01 | C |
| ATOM | 3447 C GLY G 519 | −20.156 1.166 −72.856 1.00 63.58 | C |
| ATOM | 3448 O GLY G 519 | −20.684 1.295 −73.962 1.00 69.35 | O |
| ATOM | 3449 N LYS G 520 | −18.950 1.647 −72.561 1.00 58.33 | N |
| ATOM | 3450 CA LYS G 520 | −18.122 2.361 −73.533 1.00 53.44 | C |
| ATOM | 3451 CB LYS G 520 | −16.848 2.877 −72.865 1.00 20.00 | C |
| ATOM | 3452 CG LYS G 520 | −17.081 3.958 −71.831 1.00 20.00 | C |
| ATOM | 3453 CD LYS G 520 | −15.781 4.341 −71.152 1.00 20.00 | C |
| ATOM | 3454 CE LYS G 520 | −15.984 5.482 −70.173 1.00 20.00 | C |
| ATOM | 3455 NZ LYS G 520 | −14.753 5.730 −69.376 1.00 20.00 | N |
| ATOM | 3456 C LYS G 520 | −17.746 1.492 −74.731 1.00 58.24 | C |
| ATOM | 3457 O LYS G 520 | −17.445 2.006 −75.810 1.00 48.60 | O |
| ATOM | 3458 N SER G 521 | −17.583 0.198 −74.478 1.00 67.19 | N |
| ATOM | 3459 CA SER G 521 | −17.366 −0.776 −75.542 1.00 60.42 | C |
| ATOM | 3460 CB SER G 521 | −16.953 −2.131 −74.959 1.00 20.00 | C |
| ATOM | 3461 OG SER G 521 | −18.028 −2.751 −74.272 1.00 20.00 | O |
| ATOM | 3462 C SER G 521 | −18.588 −0.942 −76.444 1.00 54.19 | C |
| ATOM | 3463 O SER G 521 | −18.456 −1.004 −77.664 1.00 65.36 | O |
| ATOM | 3464 N THR G 522 | −19.761 −1.120 −75.840 1.00 50.09 | N |
| ATOM | 3465 CA THR G 522 | −21.001 −1.210 −76.608 1.00 57.59 | C |
| ATOM | 3466 CB THR G 522 | −22.235 −1.431 −75.705 1.00 20.00 | C |
| ATOM | 3467 OG1 THR G 522 | −22.276 −0.422 −74.689 1.00 20.00 | O |

APPENDIX-continued (APPENDIX discloses SEQ ID NOS 29-32, 29-32 and 29-32, respectively, in order of appearance)

| | | | |
|---|---|---|---|
| ATOM | 3468 CG2 THR G 522 | −22.196 −2.805 −75.058 1.00 20.00 | C |
| ATOM | 3469 C THR G 522 | −21.206 0.063 −77.423 1.00 59.16 | C |
| ATOM | 3470 O THR G 522 | −21.384 0.010 −78.640 1.00 65.90 | O |
| ATOM | 3471 N THR G 523 | −21.024 1.205 −76.768 1.00 52.59 | N |
| ATOM | 3472 CA THR G 523 | −21.234 2.498 −77.404 1.00 42.19 | C |
| ATOM | 3473 CB THR G 523 | −20.961 3.638 −76.423 1.00 20.00 | C |
| ATOM | 3474 OG1 THR G 523 | −19.578 3.622 −76.049 1.00 20.00 | O |
| ATOM | 3475 CG2 THR G 523 | −21.819 3.467 −75.180 1.00 20.00 | C |
| ATOM | 3476 C THR G 523 | −20.352 2.676 −78.636 1.00 48.90 | C |
| ATOM | 3477 O THR G 523 | −20.786 3.238 −79.641 1.00 63.19 | O |
| ATOM | 3478 N ASN G 524 | −19.113 2.197 −78.553 1.00 52.51 | N |
| ATOM | 3479 CA ASN G 524 | −18.206 2.200 −79.701 1.00 57.54 | C |
| ATOM | 3480 CB ASN G 524 | −16.783 1.822 −79.276 1.00 20.00 | C |
| ATOM | 3481 CG ASN G 524 | −16.110 2.908 −78.457 1.00 20.00 | C |
| ATOM | 3482 OD1 ASN G 524 | −16.515 4.069 −78.492 1.00 20.00 | O |
| ATOM | 3483 ND2 ASN G 524 | −15.087 2.529 −77.699 1.00 20.00 | N |
| ATOM | 3484 C ASN G 524 | −18.669 1.296 −80.843 1.00 54.12 | C |
| ATOM | 3485 O ASN G 524 | −18.530 1.652 −82.013 1.00 61.31 | O |
| ATOM | 3486 N SER G 525 | −19.149 0.102 −80.502 1.00 48.97 | N |
| ATOM | 3487 CA SER G 525 | −19.658 −0.841 −81.499 1.00 64.81 | C |
| ATOM | 3488 CB SER G 525 | −20.077 −2.157 −80.838 1.00 61.22 | C |
| ATOM | 3489 OG SER G 525 | −18.947 −2.929 −80.475 1.00 85.90 | O |
| ATOM | 3490 C SER G 525 | −20.840 −0.249 −82.254 1.00 69.67 | C |
| ATOM | 3491 O SER G 525 | −21.093 −0.600 −83.406 1.00 72.60 | O |
| ATOM | 3492 N LYS G 526 | −21.592 0.610 −81.577 1.00 66.06 | N |
| ATOM | 3493 CA LYS G 526 | −22.723 1.280 −82.197 1.00 63.67 | C |
| ATOM | 3494 CB LYS G 526 | −23.675 1.815 −81.127 1.00 70.55 | C |
| ATOM | 3495 CG LYS G 526 | −24.473 0.741 −80.407 1.00 75.29 | C |
| ATOM | 3496 CD LYS G 526 | −25.171 1.313 −79.183 1.00 85.03 | C |
| ATOM | 3497 CE LYS G 526 | −25.776 0.219 −78.325 1.00 82.65 | C |
| ATOM | 3498 NZ LYS G 526 | −26.303 0.770 −77.048 1.00 73.89 | N |
| ATOM | 3499 C LYS G 526 | −22.259 2.417 −83.103 1.00 55.36 | C |
| ATOM | 3500 O LYS G 526 | −22.797 2.611 −84.191 1.00 70.69 | O |
| ATOM | 3501 N ILE G 527 | −21.275 3.181 −82.638 1.00 57.52 | N |
| ATOM | 3502 CA ILE G 527 | −20.718 4.273 −83.431 1.00 58.48 | C |
| ATOM | 3503 CB ILE G 527 | −19.545 4.966 −82.712 1.00 57.00 | C |
| ATOM | 3504 CG1 ILE G 527 | −20.021 5.620 −81.415 1.00 49.07 | C |
| ATOM | 3505 CD1 ILE G 527 | −20.228 7.116 −81.534 1.00 46.18 | C |
| ATOM | 3506 CG2 ILE G 527 | −18.902 6.004 −83.621 1.00 52.63 | C |
| ATOM | 3507 C ILE G 527 | −20.224 3.758 −84.774 1.00 65.20 | C |
| ATOM | 3508 O ILE G 527 | −20.455 4.380 −85.810 1.00 66.48 | O |
| ATOM | 3509 N TYR G 528 | −19.487 2.652 −84.740 1.00 69.78 | N |
| ATOM | 3510 CA TYR G 528 | −18.985 2.034 −85.961 1.00 72.52 | C |
| ATOM | 3511 CB TYR G 528 | −18.268 0.712 −85.657 1.00 73.16 | C |
| ATOM | 3512 CG TYR G 528 | −17.130 0.810 −84.658 1.00 76.94 | C |
| ATOM | 3513 CD1 TYR G 528 | −16.667 −0.323 −83.994 1.00 70.95 | C |
| ATOM | 3514 CE1 TYR G 528 | −15.628 −0.245 −83.077 1.00 67.73 | C |
| ATOM | 3515 CZ TYR G 528 | −15.064 0.981 −82.789 1.00 71.89 | C |
| ATOM | 3516 OH TYR G 528 | −14.046 1.065 −81.866 1.00 75.44 | O |
| ATOM | 3517 CE2 TYR G 528 | −15.505 2.121 −83.433 1.00 77.03 | C |
| ATOM | 3518 CD2 TYR G 528 | −16.523 2.029 −84.373 1.00 77.84 | C |
| ATOM | 3519 C TYR G 528 | −20.130 1.796 −86.949 1.00 71.63 | C |
| ATOM | 3520 O TYR G 528 | −20.150 2.377 −88.036 1.00 84.20 | O |
| ATOM | 3521 N HIS G 529 | −21.116 1.002 −86.534 1.00 67.69 | N |
| ATOM | 3522 CA HIS G 529 | −22.239 0.633 −87.398 1.00 60.28 | C |
| ATOM | 3523 CB HIS G 529 | −23.215 −0.283 −86.659 1.00 67.84 | C |
| ATOM | 3524 CG HIS G 529 | −22.668 −1.645 −86.376 1.00 88.54 | C |
| ATOM | 3525 ND1 HIS G 529 | −23.472 −2.756 −86.236 1.00 93.34 | N |
| ATOM | 3526 CE1 HIS G 529 | −22.725 −3.802 −85.933 1.00 86.23 | C |
| ATOM | 3527 NE2 HIS G 529 | −21.465 −3.410 −85.871 1.00 91.95 | N |
| ATOM | 3528 CD2 HIS G 529 | −21.401 −2.067 −86.151 1.00 93.77 | C |
| ATOM | 3529 C HIS G 529 | −22.987 1.845 −87.944 1.00 63.30 | C |
| ATOM | 3530 O HIS G 529 | −23.453 1.828 −89.083 1.00 61.02 | O |
| ATOM | 3531 N ILE G 530 | −23.209 2.842 −87.091 1.00 59.79 | N |
| ATOM | 3532 CA ILE G 530 | −23.752 4.121 −87.543 1.00 45.70 | C |
| ATOM | 3533 CB ILE G 530 | −23.965 5.095 −86.374 1.00 40.57 | C |
| ATOM | 3534 CG1 ILE G 530 | −25.130 4.627 −85.499 1.00 42.86 | C |
| ATOM | 3535 CD1 ILE G 530 | −25.537 5.624 −84.437 1.00 51.01 | C |
| ATOM | 3536 CG2 ILE G 530 | −24.224 6.501 −86.901 1.00 35.31 | C |
| ATOM | 3537 C ILE G 530 | −22.822 4.775 −88.557 1.00 57.52 | C |
| ATOM | 3538 O ILE G 530 | −23.260 5.253 −89.604 1.00 71.18 | O |
| ATOM | 3539 N GLU G 531 | −21.534 4.787 −88.234 1.00 67.55 | N |
| ATOM | 3540 CA GLU G 531 | −20.508 5.305 −89.129 1.00 69.79 | C |
| ATOM | 3541 CB GLU G 531 | −19.126 5.105 −88.505 1.00 84.02 | C |
| ATOM | 3542 CG GLU G 531 | −18.143 6.228 −88.780 1.00104.22 | C |
| ATOM | 3543 CD GLU G 531 | −16.823 6.033 −88.058 1.00116.08 | C |
| ATOM | 3544 OE1 GLU G 531 | −16.849 5.706 −86.853 1.00118.71 | O |

APPENDIX-continued (APPENDIX discloses SEQ ID NOS 29-32, 29-32 and 29-32, respectively, in order of appearance)

| | | | | | | | | | | | | |
|---|---|---|---|---|---|---|---|---|---|---|---|---|
| ATOM | 3545 | OE2 | GLU | G | 531 | −15.762 | 6.211 | −88.693 | 1.00119.69 | | O |
| ATOM | 3546 | C | GLU | G | 531 | −20.567 | 4.624 | −90.495 | 1.00 | 64.87 | C |
| ATOM | 3547 | O | GLU | G | 531 | −20.720 | 5.285 | −91.522 | 1.00 | 55.58 | O |
| ATOM | 3548 | N | ASN | G | 532 | −20.409 | 3.304 | −90.499 | 1.00 | 65.70 | N |
| ATOM | 3549 | CA | ASN | G | 532 | −20.502 | 2.516 | −91.724 | 1.00 | 64.16 | C |
| ATOM | 3550 | CB | ASN | G | 532 | −20.351 | 1.026 | −91.402 | 1.00 | 60.58 | C |
| ATOM | 3551 | CG | ASN | G | 532 | −20.304 | 0.165 | −92.642 | 1.00 | 67.75 | C |
| ATOM | 3552 | OD1 | ASN | G | 532 | −19.416 | 0.312 | −93.481 | 1.00 | 53.59 | O |
| ATOM | 3553 | ND2 | ASN | G | 532 | −21.285 | −0.716 | −92.786 | 1.00 | 61.81 | N |
| ATOM | 3554 | C | ASN | G | 532 | −21.809 | 2.759 | −92.472 | 1.00 | 72.17 | C |
| ATOM | 3555 | O | ASN | G | 532 | −21.823 | 2.885 | −93.696 | 1.00 | 85.75 | O |
| ATOM | 3556 | N | GLU | G | 533 | −22.907 | 2.812 | −91.726 | 1.00 | 79.68 | N |
| ATOM | 3557 | CA | GLU | G | 533 | −24.220 | 3.041 | −92.307 | 1.00 | 71.96 | C |
| ATOM | 3558 | CB | GLU | G | 533 | −25.300 | 2.936 | −91.234 | 1.00 | 67.87 | C |
| ATOM | 3559 | CG | GLU | G | 533 | −26.680 | 2.653 | −91.788 | 1.00 | 81.94 | C |
| ATOM | 3560 | CD | GLU | G | 533 | −26.710 | 1.397 | −92.632 | 1.00 | 92.79 | C |
| ATOM | 3561 | OE1 | GLU | G | 533 | −26.313 | 0.331 | −92.119 | 1.00 | 95.90 | O |
| ATOM | 3562 | OE2 | GLU | G | 533 | −26.989 | 1.501 | −93.843 | 1.00 | 93.14 | O |
| ATOM | 3563 | C | GLU | G | 533 | −24.296 | 4.406 | −92.974 | 1.00 | 68.54 | C |
| ATOM | 3564 | O | GLU | G | 533 | −25.101 | 4.616 | −93.879 | 1.00 | 79.29 | O |
| ATOM | 3565 | N | ILE | G | 534 | −23.542 | 5.359 | −92.440 | 1.00 | 69.50 | N |
| ATOM | 3566 | CA | ILE | G | 534 | −23.498 | 6.702 | −93.003 | 1.00 | 72.55 | C |
| ATOM | 3567 | CB | ILE | G | 534 | −23.070 | 7.737 | −91.956 | 1.00 | 79.55 | C |
| ATOM | 3568 | CG1 | ILE | G | 534 | −24.053 | 7.740 | −90.784 | 1.00 | 80.41 | C |
| ATOM | 3569 | CD1 | ILE | G | 534 | −25.321 | 6.951 | −91.049 | 1.00 | 89.38 | C |
| ATOM | 3570 | CG2 | ILE | G | 534 | −22.981 | 9.118 | −92.588 | 1.00 | 78.63 | C |
| ATOM | 3571 | C | ILE | G | 534 | −22.538 | 6.766 | −94.180 | 1.00 | 74.92 | C |
| ATOM | 3572 | O | ILE | G | 534 | −22.589 | 7.693 | −94.987 | 1.00 | 81.01 | O |
| ATOM | 3573 | N | ALA | G | 535 | −21.648 | 5.786 | −94.255 | 1.00 | 79.52 | N |
| ATOM | 3574 | CA | ALA | G | 535 | −20.721 | 5.683 | −95.368 | 1.00 | 82.64 | C |
| ATOM | 3575 | CB | ALA | G | 535 | −19.529 | 4.824 | −94.974 | 1.00 | 75.39 | C |
| ATOM | 3576 | C | ALA | G | 535 | −21.416 | 5.115 | −96.604 | 1.00 | 81.39 | C |
| ATOM | 3577 | O | ALA | G | 535 | −21.170 | 5.557 | −97.727 | 1.00 | 85.54 | O |
| ATOM | 3578 | N | ARG | G | 536 | −22.325 | 4.171 | −96.380 | 1.00 | 78.41 | N |
| ATOM | 3579 | CA | ARG | G | 536 | −23.115 | 3.581 | −97.457 | 1.00 | 83.27 | C |
| ATOM | 3580 | CB | ARG | G | 536 | −23.781 | 2.287 | −96.984 | 1.00 | 84.58 | C |
| ATOM | 3581 | CG | ARG | G | 536 | −22.808 | 1.180 | −96.618 | 1.00 | 103.24 | C |
| ATOM | 3582 | CD | ARG | G | 536 | −23.316 | −0.171 | −97.085 | 1.00 | 114.72 | C |
| ATOM | 3583 | NE | ARG | G | 536 | −24.587 | −0.515 | −96.457 | 1.00 | 117.80 | N |
| ATOM | 3584 | CZ | ARG | G | 536 | −25.297 | −1.600 | −96.750 | 1.00 | 116.66 | C |
| ATOM | 3585 | NH1 | ARG | G | 536 | −24.875 | −2.439 | −97.685 | 1.00 | 114.57 | N |
| ATOM | 3586 | NH2 | ARG | G | 536 | −26.417 | −1.862 | −96.089 | 1.00 | 116.38 | N |
| ATOM | 3587 | C | ARG | G | 536 | −24.172 | 4.552 | −97.973 | 1.00 | 82.20 | C |
| ATOM | 3588 | O | ARG | G | 536 | −24.315 | 4.737 | −99.182 | 1.00 | 86.28 | O |
| ATOM | 3589 | N | ILE | G | 537 | −24.941 | 5.135 | −97.058 | 1.00 | 77.08 | N |
| ATOM | 3590 | CA | ILE | G | 537 | −25.917 | 6.156 | −97.430 | 1.00 | 66.79 | C |
| ATOM | 3591 | CB | ILE | G | 537 | −26.719 | 6.680 | −96.216 | 1.00 | 64.76 | C |
| ATOM | 3592 | CG1 | ILE | G | 537 | −27.614 | 5.583 | −95.640 | 1.00 | 66.92 | C |
| ATOM | 3593 | CD1 | ILE | G | 537 | −28.487 | 6.055 | −94.493 | 1.00 | 70.83 | C |
| ATOM | 3594 | CG2 | ILE | G | 537 | −27.593 | 7.848 | −96.631 | 1.00 | 51.02 | C |
| ATOM | 3595 | C | ILE | G | 537 | −25.221 | 7.330 | −98.108 | 1.00 | 74.94 | C |
| ATOM | 3596 | O | ILE | G | 537 | −25.824 | 8.043 | −98.907 | 1.00 | 97.16 | O |
| ATOM | 3597 | N | LYS | G | 538 | −23.941 | 7.514 | −97.804 | 1.00 | 75.09 | N |
| ATOM | 3598 | CA | LYS | G | 538 | −23.162 | 8.575 | −98.427 | 1.00 | 90.28 | C |
| ATOM | 3599 | CB | LYS | G | 538 | −22.051 | 9.054 | −97.491 | 1.00 | 93.73 | C |
| ATOM | 3600 | CG | LYS | G | 538 | −21.584 | 10.479 | −97.760 | 1.00 | 96.60 | C |
| ATOM | 3601 | CD | LYS | G | 538 | −20.446 | 10.876 | −96.830 | 1.00 | 95.37 | C |
| ATOM | 3602 | CE | LYS | G | 538 | −20.008 | 12.313 | −97.067 | 1.00 | 100.63 | C |
| ATOM | 3603 | NZ | LYS | G | 538 | −18.989 | 12.750 | −96.074 | 1.00 | 99.58 | N |
| ATOM | 3604 | C | LYS | G | 538 | −22.574 | 8.114 | −99.754 | 1.00 | 102.20 | C |
| ATOM | 3605 | O | LYS | G | 538 | −21.940 | 8.891 | −100.466 | 1.00 | 112.11 | O |
| ATOM | 3606 | N | LYS | G | 539 | −22.870 | 6.874 | −100.126 | 1.00 | 105.15 | N |
| ATOM | 3607 | CA | LYS | G | 539 | −22.411 | 6.328 | −101.396 | 1.00 | 105.65 | C |
| ATOM | 3608 | CB | LYS | G | 539 | −21.904 | 4.897 | −101.211 | 1.00 | 110.12 | C |
| ATOM | 3609 | CG | LYS | G | 539 | −21.426 | 4.246 | −102.498 | 1.00 | 113.31 | C |
| ATOM | 3610 | CD | LYS | G | 539 | −21.023 | 2.794 | −102.284 | 1.00 | 114.26 | C |
| ATOM | 3611 | CE | LYS | G | 539 | −20.414 | 2.201 | −103.550 | 1.00 | 118.39 | C |
| ATOM | 3612 | NZ | LYS | G | 539 | −19.511 | 1.047 | −103.263 | 1.00 | 121.77 | N |
| ATOM | 3613 | C | LYS | G | 539 | −23.517 | 6.364 | −102.444 | 1.00 | 108.88 | C |
| ATOM | 3614 | O | LYS | G | 539 | −23.375 | 5.808 | −103.532 | 1.00 | 110.77 | O |
| ATOM | 3615 | N | LEU | G | 540 | −24.625 | 7.011 | −102.102 | 1.00 | 111.50 | N |
| ATOM | 3616 | CA | LEU | G | 540 | −25.722 | 7.201 | −103.038 | 1.00 | 110.31 | C |
| ATOM | 3617 | CB | LEU | G | 540 | −27.025 | 6.656 | −102.451 | 1.00 | 101.19 | C |
| ATOM | 3618 | CG | LEU | G | 540 | −26.983 | 5.200 | −101.978 | 1.00 | 94.26 | C |
| ATOM | 3619 | CD1 | LEU | G | 540 | −28.376 | 4.691 | −101.683 | 1.00 | 86.40 | C |
| ATOM | 3620 | CD2 | LEU | G | 540 | −26.307 | 4.311 | −103.004 | 1.00 | 84.54 | C |
| ATOM | 3621 | C | LEU | G | 540 | −25.865 | 8.679 | −103.374 | 1.00 | 118.37 | C |

APPENDIX-continued (APPENDIX discloses SEQ ID NOS 29-32, 29-32 and 29-32, respectively, in order of appearance)

| | | | | |
|---|---|---|---|---|
| ATOM | 3622 O LEU G 540 | −26.802 9.081 −104.064 1.00 116.71 | O | |
| ATOM | 3623 N ILE G 541 | −24.894 9.474 −102.934 1.00 130.80 | N | |
| ATOM | 3624 CA ILE G 541 | −24.844 10.896 −103.267 1.00 140.48 | C | |
| ATOM | 3625 CB ILE G 541 | −25.701 11.746 −102.294 1.00 138.99 | C | |
| ATOM | 3626 CG1 ILE G 541 | −27.145 11.234 −102.257 1.00 133.30 | C | |
| ATOM | 3627 CD1 ILE G 541 | −28.050 11.879 −103.291 1.00 136.26 | C | |
| ATOM | 3628 CG2 ILE G 541 | −25.680 13.218 −102.707 1.00 136.12 | C | |
| ATOM | 3629 C ILE G 541 | −23.407 11.410 −103.250 1.00 144.97 | C | |
| ATOM | 3630 O ILE G 541 | −23.116 12.480 −103.783 1.00 145.83 | O | |
| ATOM | 3631 N GLY G 542 | −22.519 10.663 −102.602 1.00 148.77 | N | |
| ATOM | 3632 CA GLY G 542 | −21.119 11.060 −102.505 1.00 153.58 | C | |
| ATOM | 3633 C GLY G 542 | −20.209 10.194 −103.357 1.00 160.45 | C | |
| ATOM | 3634 O GLY G 542 | −20.636 9.643 −104.372 1.00 163.41 | O | |
| ATOM | 3635 N GLU G 543 | −18.962 10.042 −102.921 1.00 163.83 | N | |
| ATOM | 3636 CA GLU G 543 | −17.983 9.236 −103.649 1.00 165.52 | C | |
| ATOM | 3637 CB GLU G 543 | −16.557 9.674 −103.305 1.00 158.94 | C | |
| ATOM | 3642 C GLU G 543 | −18.156 7.742 −103.381 1.00 168.27 | C | |
| ATOM | 3643 O GLU G 543 | −19.116 7.322 −102.736 1.00 167.37 | O | |
| ATOM | 3644 N GLN H 26 | −24.590 4.282 7.491 1.00 23.62 | B | N |
| ATOM | 3645 CA GLN H 26 | −23.869 3.499 6.449 1.00 23.82 | B | C |
| ATOM | 3646 CB GLN H 26 | −22.633 2.827 7.055 1.00 23.94 | B | C |
| ATOM | 3647 CG GLN H 26 | −21.724 3.775 7.833 1.00 28.83 | B | C |
| ATOM | 3648 CD GLN H 26 | −22.314 4.205 9.165 1.00 36.36 | B | C |
| ATOM | 3649 OE1 GLN H 26 | −23.057 5.183 9.238 1.00 39.09 | B O | |
| ATOM | 3650 NE2 GLN H 26 | −21.891 3.545 10.238 1.00 37.86 | B N | |
| ATOM | 3651 C GLN H 26 | −24.797 2.460 5.813 1.00 23.09 | B C | |
| ATOM | 3652 O GLN H 26 | −25.818 2.096 6.397 1.00 24.21 | B O | |
| ATOM | 3653 N ASN H 27 | −24.543 2.146 4.544 1.00 20.98 | B N | |
| ATOM | 3654 CA ASN H 27 | −25.343 1.173 3.786 1.00 19.70 | B C | |
| ATOM | 3655 CB ASN H 27 | −26.642 1.832 3.269 1.00 20.41 | B C | |
| ATOM | 3656 CG ASN H 27 | −27.524 0.887 2.423 1.00 23.56 | B C | |
| ATOM | 3657 OD1 ASN H 27 | −27.835 −0.233 2.837 1.00 24.42 | B O | |
| ATOM | 3658 ND2 ASN H 27 | −27.836 1.322 1.182 1.00 27.70 | B N | |
| ATOM | 3659 C ASN H 27 | −24.507 0.652 2.619 1.00 18.42 | B C | |
| ATOM | 3660 O ASN H 27 | −24.904 0.783 1.462 1.00 18.47 | B O | |
| ATOM | 3661 N ILE H 28 | −23.291 0.196 2.907 1.00 16.54 | B N | |
| ATOM | 3662 CA ILE H 28 | −22.439 −0.335 1.849 1.00 14.59 | B C | |
| ATOM | 3663 CB ILE H 28 | −20.939 −0.378 2.223 1.00 14.01 | B C | |
| ATOM | 3664 CG1 ILE H 28 | −20.746 −0.823 3.674 1.00 15.60 | B C | |
| ATOM | 3665 CD1 ILE H 28 | −20.221 −2.240 3.815 1.00 16.26 | B C | |
| ATOM | 3666 CG2 ILE H 28 | −20.276 0.964 1.942 1.00 12.57 | B C | |
| ATOM | 3667 C ILE H 28 | −22.898 −1.700 1.360 1.00 13.86 | B C | |
| ATOM | 3668 O ILE H 28 | −23.458 −2.494 2.119 1.00 13.70 | B O | |
| ATOM | 3669 N THR H 29 | −22.868 −1.850 0.044 1.00 13.23 | B N | |
| ATOM | 3670 CA THR H 29 | −23.353 −3.045 −0.612 1.00 12.65 | B C | |
| ATOM | 3671 CB THR H 29 | −24.751 −2.816 −1.206 1.00 12.69 | B C | |
| ATOM | 3672 OG1 THR H 29 | −25.331 −1.643 −0.623 1.00 12.62 | B O | |
| ATOM | 3673 CG2 THR H 29 | −25.650 −4.012 −0.934 1.00 12.92 | B C | |
| ATOM | 3674 C THR H 29 | −22.392 −3.355 −1.741 1.00 12.47 | B C | |
| ATOM | 3675 O THR H 29 | −21.760 −2.457 −2.297 1.00 12.53 | B O | |
| ATOM | 3676 N GLU H 30 | −22.300 −4.626 −2.095 1.00 11.98 | B N | |
| ATOM | 3677 CA GLU H 30 | −21.668 −5.007 −3.338 1.00 11.68 | B C | |
| ATOM | 3678 CB GLU H 30 | −20.393 −5.803 −3.049 1.00 11.98 | B C | |
| ATOM | 3679 CG GLU H 30 | −19.274 −5.593 −4.058 1.00 13.38 | B C | |
| ATOM | 3680 CD GLU H 30 | −17.927 −6.054 −3.533 1.00 16.03 | B C | |
| ATOM | 3681 OE1 GLU H 30 | −17.846 −7.190 −3.019 1.00 16.65 | B O | |
| ATOM | 3682 OE2 GLU H 30 | −16.968 −5.253 −3.563 1.00 17.06 | B O | |
| ATOM | 3683 C GLU H 30 | −22.655 −5.860 −4.114 1.00 11.39 | B C | |
| ATOM | 3684 O GLU H 30 | −23.316 −6.727 −3.542 1.00 11.50 | B O | |
| ATOM | 3685 N GLU H 31 | −22.850 −5.534 −5.384 1.00 11.11 | B N | |
| ATOM | 3686 CA GLU H 31 | −23.602 −6.419 −6.248 1.00 11.06 | B C | |
| ATOM | 3687 CB GLU H 31 | −24.955 −5.813 −6.611 1.00 11.48 | B C | |
| ATOM | 3688 CG GLU H 31 | −25.093 −5.417 −8.063 1.00 13.90 | B C | |
| ATOM | 3689 CD GLU H 31 | −26.500 −4.981 −8.404 1.00 17.27 | B C | |
| ATOM | 3690 OE1 GLU H 31 | −27.092 −5.567 −9.335 1.00 17.55 | B O | |
| ATOM | 3691 OE2 GLU H 31 | −27.053 −4.130 −7.676 1.00 18.73 | B O | |
| ATOM | 3692 C GLU H 31 | −22.828 −6.839 −7.485 1.00 10.47 | B C | |
| ATOM | 3693 O GLU H 31 | −22.042 −6.071 −8.040 1.00 10.12 | B O | |
| ATOM | 3694 N PHE H 32 | −22.962 −8.116 −7.818 1.00 10.15 | B N | |
| ATOM | 3695 CA PHE H 32 | −22.042 −8.788 −8.716 1.00 9.62 | B C | |
| ATOM | 3696 CB PHE H 32 | −21.692 −10.167 −8.158 1.00 9.42 | B C | |
| ATOM | 3697 CG PHE H 32 | −21.130 −11.106 −9.179 1.00 9.27 | B C | |
| ATOM | 3698 CD1 PHE H 32 | −19.865 −10.896 −9.702 1.00 9.37 | B C | |
| ATOM | 3699 CE1 PHE H 32 | −19.315 −11.784 −10.605 1.00 9.52 | B C | |
| ATOM | 3700 CZ PHE H 32 | −20.027 −12.905 −10.989 1.00 9.82 | B C | |
| ATOM | 3701 CE2 PHE H 32 | −21.294 −13.127 −10.472 1.00 10.13 | B C | |
| ATOM | 3702 CD2 PHE H 32 | −21.822 −12.250 −9.544 1.00 10.06 | B C | |

APPENDIX-continued (APPENDIX discloses SEQ ID NOS 29-32, 29-32 and 29-32, respectively, in order of appearance)

| | | | |
|---|---|---|---|
| ATOM | 3703 C PHE H 32 | −22.707 −8.941 −10.074 1.00 9.64 | B C |
| ATOM | 3704 O PHE H 32 | −23.887 −9.282 −10.159 1.00 9.84 | B O |
| ATOM | 3705 N TYR H 33 | −21.965 −8.638 −11.132 1.00 9.59 | B N |
| ATOM | 3706 CA TYR H 33 | −22.526 −8.672 −12.474 1.00 9.67 | B C |
| ATOM | 3707 CB TYR H 33 | −22.259 −7.360 −13.207 1.00 9.52 | B C |
| ATOM | 3708 CG TYR H 33 | −23.038 −6.196 −12.645 1.00 10.94 | B C |
| ATOM | 3709 CD1 TYR H 33 | −22.482 −5.372 −11.677 1.00 12.23 | B C |
| ATOM | 3710 CE1 TYR H 33 | −23.198 −4.323 −11.137 1.00 12.93 | B C |
| ATOM | 3711 CZ TYR H 33 | −24.510 −4.129 −11.510 1.00 13.47 | B C |
| ATOM | 3712 OH TYR H 33 | −25.231 −3.093 −10.963 1.00 14.54 | B O |
| ATOM | 3713 CE2 TYR H 33 | −25.100 −4.963 −12.436 1.00 13.56 | B C |
| ATOM | 3714 CD2 TYR H 33 | −24.373 −6.006 −12.976 1.00 12.96 | B C |
| ATOM | 3715 C TYR H 33 | −22.001 −9.853 −13.273 1.00 9.94 | B C |
| ATOM | 3716 O TYR H 33 | −20.998 −9.747 −13.978 1.00 10.16 | B O |
| ATOM | 3717 N GLN H 34 | −22.714 −10.969 −13.184 1.00 10.06 | B N |
| ATOM | 3718 CA GLN H 34 | −22.191 −12.249 −13.632 1.00 10.01 | B C |
| ATOM | 3719 CB GLN H 34 | −23.190 −13.361 −13.327 1.00 10.22 | B C |
| ATOM | 3720 CG GLN H 34 | −22.760 −14.720 −13.829 1.00 11.12 | B C |
| ATOM | 3721 CD GLN H 34 | −23.604 −15.836 −13.257 1.00 13.13 | B C |
| ATOM | 3722 OE1 GLN H 34 | −24.746 −16.042 −13.673 1.00 14.24 | B O |
| ATOM | 3723 NE2 GLN H 34 | −23.057 −16.550 −12.278 1.00 13.79 | B N |
| ATOM | 3724 C GLN H 34 | −21.889 −12.220 −15.123 1.00 9.94 | B C |
| ATOM | 3725 O GLN H 34 | −21.096 −13.018 −15.622 1.00 10.08 | B O |
| ATOM | 3726 N SER H 35 | −22.564 −11.324 −15.836 1.00 9.87 | B N |
| ATOM | 3727 CA SER H 35 | −22.458 −11.253 −17.290 1.00 9.91 | B C |
| ATOM | 3728 CB SER H 35 | −23.743 −10.676 −17.889 1.00 10.03 | B C |
| ATOM | 3729 OG SER H 35 | −24.034 −9.401 −17.343 1.00 10.81 | B O |
| ATOM | 3730 C SER H 35 | −21.256 −10.410 −17.713 1.00 9.56 | B C |
| ATOM | 3731 O SER H 35 | −21.002 −10.214 −18.903 1.00 9.59 | B O |
| ATOM | 3732 N THR H 36 | −20.539 −9.892 −16.724 1.00 9.21 | B N |
| ATOM | 3733 CA THR H 36 | −19.420 −8.996 −16.964 1.00 9.06 | B C |
| ATOM | 3734 CB THR H 36 | −19.817 −7.536 −16.686 1.00 9.49 | B C |
| ATOM | 3735 OG1 THR H 36 | −20.874 −7.149 −17.573 1.00 10.82 | B O |
| ATOM | 3736 CG2 THR H 36 | −18.629 −6.609 −16.883 1.00 9.45 | B C |
| ATOM | 3737 C THR H 36 | −18.292 −9.403 −16.029 1.00 8.77 | B C |
| ATOM | 3738 O THR H 36 | −17.298 −8.693 −15.882 1.00 8.60 | B O |
| ATOM | 3739 N CYS H 37 | −18.457 −10.572 −15.415 1.00 8.69 | B N |
| ATOM | 3740 CA CYS H 37 | −17.594 −11.011 −14.327 1.00 8.69 | B C |
| ATOM | 3741 CB CYS H 37 | −16.509 −11.955 −14.846 1.00 8.81 | B C |
| ATOM | 3742 SG CYS H 37 | −15.737 −12.977 −13.569 1.00 10.80 | B S |
| ATOM | 3743 C CYS H 37 | −16.958 −9.820 −13.631 1.00 8.27 | B C |
| ATOM | 3744 O CYS H 37 | −15.735 −9.671 −13.628 1.00 8.27 | B O |
| ATOM | 3745 N SER H 38 | −17.796 −8.950 −13.080 1.00 7.92 | B N |
| ATOM | 3746 CA SER H 38 | −17.309 −7.784 −12.360 1.00 7.51 | B C |
| ATOM | 3747 CB SER H 38 | −17.130 −6.595 −13.308 1.00 7.63 | B C |
| ATOM | 3748 OG SER H 38 | −18.369 −6.193 −13.864 1.00 8.54 | B O |
| ATOM | 3749 C SER H 38 | −18.227 −7.411 −11.207 1.00 7.02 | B C |
| ATOM | 3750 O SER H 38 | −19.404 −7.771 −11.192 1.00 6.83 | B O |
| ATOM | 3751 N ALA H 39 | −17.647 −6.784 −10.191 1.00 6.64 | B N |
| ATOM | 3752 CA ALA H 39 | −18.371 −6.478 −8.969 1.00 6.58 | B C |
| ATOM | 3753 CB ALA H 39 | −17.843 −7.320 −7.817 1.00 6.67 | B C |
| ATOM | 3754 C ALA H 39 | −18.242 −4.995 −8.651 1.00 6.93 | B C |
| ATOM | 3755 O ALA H 39 | −17.217 −4.378 −8.944 1.00 7.38 | B O |
| ATOM | 3756 N VAL H 40 | −19.333 −4.401 −8.179 1.00 6.87 | B N |
| ATOM | 3757 CA VAL H 40 | −19.316 −3.008 −7.746 1.00 6.55 | B C |
| ATOM | 3758 CB VAL H 40 | −20.208 −2.122 −8.635 1.00 6.22 | B C |
| ATOM | 3759 CG1 VAL H 40 | −20.465 −0.783 −7.959 1.00 6.52 | B C |
| ATOM | 3760 CG2 VAL H 40 | −19.564 −1.921 −9.998 1.00 6.62 | B C |
| ATOM | 3761 C VAL H 40 | −19.743 −2.862 −6.290 1.00 6.73 | B C |
| ATOM | 3762 O VAL H 40 | −20.805 −3.340 −5.891 1.00 6.83 | B O |
| ATOM | 3763 N SER H 41 | −18.883 −2.240 −5.492 1.00 6.86 | B N |
| ATOM | 3764 CA SER H 41 | −19.251 −1.825 −4.148 1.00 6.75 | B C |
| ATOM | 3765 CB SER H 41 | −18.020 −1.779 −3.242 1.00 7.06 | B C |
| ATOM | 3766 OG SER H 41 | −16.905 −2.388 −3.866 1.00 7.50 | B O |
| ATOM | 3767 C SER H 41 | −19.922 −0.461 −4.180 1.00 6.56 | B C |
| ATOM | 3768 O SER H 41 | −19.392 0.490 −4.756 1.00 6.08 | B O |
| ATOM | 3769 N LYS H 42 | −21.097 −0.378 −3.565 1.00 7.02 | B N |
| ATOM | 3770 CA LYS H 42 | −21.938 0.810 −3.662 1.00 7.83 | B C |
| ATOM | 3771 CB LYS H 42 | −23.296 0.459 −4.269 1.00 8.15 | B C |
| ATOM | 3772 CG LYS H 42 | −23.226 −0.171 −5.641 1.00 9.75 | B C |
| ATOM | 3773 CD LYS H 42 | −24.621 −0.473 −6.153 1.00 12.62 | B C |
| ATOM | 3774 CE LYS H 42 | −24.579 −1.069 −7.548 1.00 14.04 | B C |
| ATOM | 3775 NZ LYS H 42 | −25.858 −0.856 −8.279 1.00 14.96 | B N |
| ATOM | 3776 C LYS H 42 | −22.143 1.444 −2.290 1.00 7.80 | B C |
| ATOM | 3777 O LYS H 42 | −21.947 0.798 −1.258 1.00 8.15 | B O |
| ATOM | 3778 N GLY H 43 | −22.594 2.696 −2.290 1.00 7.59 | B N |
| ATOM | 3779 CA GLY H 43 | −23.140 3.321 −1.090 1.00 7.35 | B C |

APPENDIX-continued (APPENDIX discloses SEQ ID NOS 29-32, 29-32 and 29-32, respectively, in order of appearance)

| | | | |
|---|---|---|---|
| ATOM | 3780 C GLY H 43 | −22.131 4.200 −0.378 1.00 7.10 | B C |
| ATOM | 3781 O GLY H 43 | −22.239 4.439 0.824 1.00 7.13 | B O |
| ATOM | 3782 N TYR H 44 | −21.173 4.723 −1.136 1.00 7.01 | B N |
| ATOM | 3783 CA TYR H 44 | −20.106 5.549 −0.577 1.00 6.89 | B C |
| ATOM | 3784 CB TYR H 44 | −18.755 5.125 −1.160 1.00 6.88 | B C |
| ATOM | 3785 CG TYR H 44 | −18.296 3.748 −0.732 1.00 6.41 | B C |
| ATOM | 3786 CD1 TYR H 44 | −18.340 2.676 −1.615 1.00 6.62 | B C |
| ATOM | 3787 CE1 TYR H 44 | −17.871 1.427 −1.245 1.00 6.48 | B C |
| ATOM | 3788 CZ TYR H 44 | −17.312 1.253 0.005 1.00 6.88 | B C |
| ATOM | 3789 OH TYR H 44 | −16.834 0.020 0.386 1.00 7.50 | B O |
| ATOM | 3790 CE2 TYR H 44 | −17.197 2.318 0.870 1.00 6.68 | B C |
| ATOM | 3791 CD2 TYR H 44 | −17.670 3.559 0.492 1.00 5.91 | B C |
| ATOM | 3792 C TYR H 44 | −20.357 7.026 −0.886 1.00 6.86 | B C |
| ATOM | 3793 O TYR H 44 | −20.912 7.354 −1.933 1.00 7.14 | B O |
| ATOM | 3794 N LEU H 45 | −19.834 7.916 −0.045 1.00 6.44 | B N |
| ATOM | 3795 CA LEU H 45 | −20.073 9.356 −0.205 1.00 6.12 | B C |
| ATOM | 3796 CB LEU H 45 | −20.896 9.917 0.966 1.00 6.31 | B C |
| ATOM | 3797 CG LEU H 45 | −22.355 9.463 1.108 1.00 6.38 | B C |
| ATOM | 3798 CD1 LEU H 45 | −22.859 9.699 2.524 1.00 7.05 | B C |
| ATOM | 3799 CD2 LEU H 45 | −23.256 10.158 0.096 1.00 7.05 | B C |
| ATOM | 3800 C LEU H 45 | −18.791 10.173 −0.413 1.00 5.84 | B C |
| ATOM | 3801 O LEU H 45 | −17.966 10.289 0.493 1.00 5.94 | B O |
| ATOM | 3802 N SER H 46 | −18.764 10.924 −1.512 1.00 5.43 | B N |
| ATOM | 3803 CA SER H 46 | −17.528 11.442 −2.112 1.00 5.26 | B C |
| ATOM | 3804 CB SER H 46 | −17.801 11.821 −3.568 1.00 5.21 | B C |
| ATOM | 3805 OG SER H 46 | −18.827 12.800 −3.647 1.00 4.95 | B O |
| ATOM | 3806 C SER H 46 | −17.113 12.696 −1.355 1.00 5.51 | B C |
| ATOM | 3807 O SER H 46 | −17.968 13.359 −0.771 1.00 6.03 | B O |
| ATOM | 3808 N ALA H 47 | −15.850 13.103 −1.424 1.00 5.24 | B N |
| ATOM | 3809 CA ALA H 47 | −15.530 14.323 −0.704 1.00 4.83 | B C |
| ATOM | 3810 CB ALA H 47 | −16.269 14.344 0.622 1.00 5.01 | B C |
| ATOM | 3811 C ALA H 47 | −14.089 14.763 −0.512 1.00 4.35 | B C |
| ATOM | 3812 O ALA H 47 | −13.178 13.936 −0.449 1.00 4.45 | B O |
| ATOM | 3813 N LEU H 48 | −13.989 15.994 −0.016 1.00 3.67 | B N |
| ATOM | 3814 CA LEU H 48 | −12.719 16.625 0.308 1.00 3.15 | B C |
| ATOM | 3815 CB LEU H 48 | −12.390 17.712 −0.720 1.00 2.78 | B C |
| ATOM | 3816 CG LEU H 48 | −12.856 17.464 −2.159 1.00 2.18 | B C |
| ATOM | 3817 CD1 LEU H 48 | −12.396 18.583 −3.082 1.00 2.00 | B C |
| ATOM | 3818 CD2 LEU H 48 | −12.378 16.109 −2.666 1.00 3.94 | B C |
| ATOM | 3819 C LEU H 48 | −12.768 17.232 1.707 1.00 3.06 | B C |
| ATOM | 3820 O LEU H 48 | −13.519 18.174 1.961 1.00 3.27 | B O |
| ATOM | 3821 N ARG H 49 | −11.879 16.758 2.571 1.00 2.91 | B N |
| ATOM | 3822 CA ARG H 49 | −11.733 17.305 3.912 1.00 2.88 | B C |
| ATOM | 3823 CB ARG H 49 | −10.649 16.538 4.668 1.00 2.69 | B C |
| ATOM | 3824 CG ARG H 49 | −11.032 16.140 6.075 1.00 2.15 | B C |
| ATOM | 3825 CD ARG H 49 | −9.882 16.395 7.026 1.00 2.00 | B C |
| ATOM | 3826 NE ARG H 49 | −9.728 17.816 7.320 1.00 5.18 | B N |
| ATOM | 3827 CZ ARG H 49 | −8.580 18.478 7.231 1.00 7.68 | B C |
| ATOM | 3828 NH1 ARG H 49 | −7.481 17.849 6.838 1.00 8.32 | B N |
| ATOM | 3829 NH2 ARG H 49 | −8.521 19.756 7.575 1.00 8.12 | B N |
| ATOM | 3830 C ARG H 49 | −11.364 18.780 3.843 1.00 3.09 | B C |
| ATOM | 3831 O ARG H 49 | −10.497 19.175 3.064 1.00 3.08 | B O |
| ATOM | 3832 N THR H 50 | −12.022 19.593 4.661 1.00 3.37 | B N |
| ATOM | 3833 CA THR H 50 | −11.594 20.970 4.855 1.00 3.55 | B C |
| ATOM | 3834 CB THR H 50 | −12.413 21.946 3.998 1.00 3.25 | B C |
| ATOM | 3835 OG1 THR H 50 | −13.807 21.633 4.109 1.00 2.66 | B O |
| ATOM | 3836 CG2 THR H 50 | −11.992 21.844 2.543 1.00 3.46 | B C |
| ATOM | 3837 C THR H 50 | −11.665 21.395 6.313 1.00 4.07 | B C |
| ATOM | 3838 O THR H 50 | −11.171 22.462 6.678 1.00 4.35 | B O |
| ATOM | 3840 CA GLY H 51 | −13.255 22.675 6.821 1.00 4.78 | B C |
| ATOM | 3841 C GLY H 51 | −11.930 22.228 7.407 1.00 4.98 | B C |
| ATOM | 3842 O GLY H 51 | −11.589 21.046 7.365 1.00 5.00 | B O |
| ATOM | 3843 N TRP H 52 | −11.162 23.180 7.925 1.00 5.34 | B N |
| ATOM | 3844 CA TRP H 52 | −9.845 22.878 8.465 1.00 5.42 | B C |
| ATOM | 3845 CB TRP H 52 | −8.754 23.540 7.632 1.00 5.75 | B C |
| ATOM | 3846 CG TRP H 52 | −8.691 23.029 6.243 1.00 6.38 | B C |
| ATOM | 3847 CD1 TRP H 52 | −9.100 23.678 5.117 1.00 7.27 | B C |
| ATOM | 3848 NE1 TRP H 52 | −8.926 22.875 4.019 1.00 7.46 | B N |
| ATOM | 3849 CE2 TRP H 52 | −8.445 21.660 4.430 1.00 7.15 | B C |
| ATOM | 3850 CD2 TRP H 52 | −8.315 21.710 5.832 1.00 7.02 | B C |
| ATOM | 3851 CE3 TRP H 52 | −7.799 20.595 6.500 1.00 6.83 | B C |
| ATOM | 3852 CZ3 TRP H 52 | −7.466 19.473 5.761 1.00 6.73 | B C |
| ATOM | 3853 CH2 TRP H 52 | −7.634 19.445 4.372 1.00 7.13 | B C |
| ATOM | 3854 CZ2 TRP H 52 | −8.111 20.529 3.689 1.00 6.82 | B C |
| ATOM | 3855 C TRP H 52 | −9.723 23.329 9.905 1.00 5.34 | B C |
| ATOM | 3856 O TRP H 52 | −10.279 24.359 10.289 1.00 5.47 | B O |
| ATOM | 3857 N TYR H 53 | −8.800 22.695 10.615 1.00 5.29 | B N |

APPENDIX-continued (APPENDIX discloses SEQ ID NOS 29-32, 29-32 and 29-32, respectively, in order of appearance)

| | | | |
|---|---|---|---|
| ATOM | 3858 CA TYR H 53 | −8.531 23.038 11.997 1.00 5.58 | B C |
| ATOM | 3859 CB TYR H 53 | −9.040 21.934 12.919 1.00 5.51 | B C |
| ATOM | 3860 CG TYR H 53 | −8.759 22.187 14.377 1.00 6.59 | B C |
| ATOM | 3861 CD1 TYR H 53 | −9.668 22.879 15.169 1.00 8.25 | B C |
| ATOM | 3862 CE1 TYR H 53 | −9.440 23.068 16.521 1.00 9.40 | B C |
| ATOM | 3863 CZ TYR H 53 | −8.293 22.555 17.096 1.00 9.24 | B C |
| ATOM | 3864 OH TYR H 53 | −8.053 22.750 18.439 1.00 9.61 | B O |
| ATOM | 3865 CE2 TYR H 53 | −7.360 21.893 16.321 1.00 8.78 | B C |
| ATOM | 3866 CD2 TYR H 53 | −7.600 21.709 14.971 1.00 7.93 | B C |
| ATOM | 3867 C TYR H 53 | −7.042 23.256 12.214 1.00 5.74 | B C |
| ATOM | 3868 O TYR H 53 | −6.259 22.306 12.223 1.00 6.19 | B O |
| ATOM | 3869 N THR H 54 | −6.645 24.521 12.296 1.00 6.04 | B N |
| ATOM | 3870 CA THR H 54 | −5.249 24.869 12.519 1.00 6.67 | B C |
| ATOM | 3871 CB THR H 54 | −5.032 26.391 12.438 1.00 6.97 | B C |
| ATOM | 3872 OG1 THR H 54 | −4.958 26.793 11.064 1.00 7.51 | B O |
| ATOM | 3873 CG2 THR H 54 | −3.747 26.788 13.147 1.00 7.98 | B C |
| ATOM | 3874 C THR H 54 | −4.775 24.360 13.877 1.00 6.97 | B C |
| ATOM | 3875 O THR H 54 | −5.576 24.173 14.792 1.00 7.32 | B O |
| ATOM | 3876 N SER H 55 | −3.479 24.086 13.987 1.00 7.24 | B N |
| ATOM | 3877 CA SER H 55 | −2.811 24.106 15.282 1.00 7.65 | B C |
| ATOM | 3878 CB SER H 55 | −3.110 22.830 16.072 1.00 7.69 | B C |
| ATOM | 3879 OG SER H 55 | −2.308 22.754 17.238 1.00 7.51 | B O |
| ATOM | 3880 C SER H 55 | −1.308 24.309 15.154 1.00 8.03 | B C |
| ATOM | 3881 O SER H 55 | −0.654 23.695 14.311 1.00 8.43 | B O |
| ATOM | 3882 N VAL H 56 | −0.760 25.106 16.063 1.00 8.14 | B N |
| ATOM | 3883 CA VAL H 56 | 0.600 25.601 15.930 1.00 8.41 | B C |
| ATOM | 3884 CB VAL H 56 | 0.672 27.116 16.193 1.00 8.72 | B C |
| ATOM | 3885 CG1 VAL H 56 | 1.868 27.723 15.477 1.00 9.29 | B C |
| ATOM | 3886 CG2 VAL H 56 | −0.619 27.792 15.756 1.00 9.51 | B C |
| ATOM | 3887 C VAL H 56 | 1.509 24.884 16.917 1.00 8.19 | B C |
| ATOM | 3888 O VAL H 56 | 1.348 25.011 18.129 1.00 8.54 | B O |
| ATOM | 3889 N ILE H 57 | 2.428 24.086 16.389 1.00 7.91 | B N |
| ATOM | 3890 CA ILE H 57 | 3.224 23.192 17.214 1.00 7.64 | B C |
| ATOM | 3891 CB ILE H 57 | 3.175 21.749 16.674 1.00 7.35 | B C |
| ATOM | 3892 CG1 ILE H 57 | 1.726 21.302 16.462 1.00 7.25 | B C |
| ATOM | 3893 CD1 ILE H 57 | 1.593 19.930 15.834 1.00 8.42 | B C |
| ATOM | 3894 CG2 ILE H 57 | 3.915 20.799 17.603 1.00 7.52 | B C |
| ATOM | 3895 C ILE H 57 | 4.670 23.670 17.258 1.00 7.69 | B C |
| ATOM | 3896 O ILE H 57 | 5.272 23.936 16.219 1.00 7.79 | B O |
| ATOM | 3897 N THR H 58 | 5.175 23.897 18.467 1.00 7.85 | B N |
| ATOM | 3898 CA THR H 58 | 6.465 24.554 18.659 1.00 8.15 | B C |
| ATOM | 3899 CB THR H 58 | 6.297 25.903 19.383 1.00 8.14 | B C |
| ATOM | 3900 OG1 THR H 58 | 4.946 26.360 19.239 1.00 8.62 | B O |
| ATOM | 3901 CG2 THR H 58 | 7.246 26.943 18.806 1.00 7.94 | B C |
| ATOM | 3902 C THR H 58 | 7.393 23.666 19.485 1.00 8.20 | B C |
| ATOM | 3903 O THR H 58 | 7.051 23.281 20.600 1.00 8.18 | B O |
| ATOM | 3904 N ILE H 59 | 8.565 23.351 18.941 1.00 8.54 | B N |
| ATOM | 3905 CA ILE H 59 | 9.482 22.397 19.572 1.00 9.23 | B C |
| ATOM | 3906 CB ILE H 59 | 9.604 21.112 18.729 1.00 8.92 | B C |
| ATOM | 3907 CG1 ILE H 59 | 8.231 20.482 18.496 1.00 9.27 | B C |
| ATOM | 3908 CD1 ILE H 59 | 8.253 19.315 17.533 1.00 10.89 | B C |
| ATOM | 3909 CG2 ILE H 59 | 10.559 20.130 19.387 1.00 8.74 | B C |
| ATOM | 3910 C ILE H 59 | 10.880 23.004 19.691 1.00 10.02 | B C |
| ATOM | 3911 O ILE H 59 | 11.474 23.380 18.684 1.00 10.20 | B O |
| ATOM | 3912 N GLU H 60 | 11.434 23.059 20.898 1.00 10.95 | B N |
| ATOM | 3913 CA GLU H 60 | 12.592 23.923 21.138 1.00 12.13 | B C |
| ATOM | 3914 CB GLU H 60 | 12.914 23.976 22.634 1.00 12.44 | B C |
| ATOM | 3915 CG GLU H 60 | 11.854 24.705 23.444 1.00 15.04 | B C |
| ATOM | 3916 CD GLU H 60 | 12.365 25.173 24.793 1.00 19.34 | B C |
| ATOM | 3917 OE1 GLU H 60 | 12.659 24.309 25.647 1.00 20.63 | B O |
| ATOM | 3918 OE2 GLU H 60 | 12.495 26.401 24.990 1.00 21.19 | B O |
| ATOM | 3919 C GLU H 60 | 13.816 23.509 20.301 1.00 12.46 | B C |
| ATOM | 3920 O GLU H 60 | 14.196 22.336 20.316 1.00 12.68 | B O |
| ATOM | 3921 N LEU H 61 | 14.390 24.428 19.510 1.00 12.80 | B N |
| ATOM | 3922 CA LEU H 61 | 15.786 24.207 19.132 1.00 12.71 | B C |
| ATOM | 3923 CB LEU H 61 | 16.470 25.295 18.316 1.00 12.55 | B C |
| ATOM | 3924 CG LEU H 61 | 17.932 24.803 18.355 1.00 12.39 | B C |
| ATOM | 3925 CD1 LEU H 61 | 18.053 23.370 17.848 1.00 13.14 | B C |
| ATOM | 3926 CD2 LEU H 61 | 18.944 25.717 17.683 1.00 12.50 | B C |
| ATOM | 3927 C LEU H 61 | 16.459 24.114 20.455 1.00 12.94 | B C |
| ATOM | 3928 O LEU H 61 | 16.827 25.135 21.048 1.00 12.78 | B O |
| ATOM | 3929 N SER H 62 | 16.080 23.014 21.081 1.00 13.61 | B N |
| ATOM | 3930 CA SER H 62 | 16.441 22.760 22.447 1.00 14.70 | B C |
| ATOM | 3931 CB SER H 62 | 15.805 21.454 22.924 1.00 14.52 | B C |
| ATOM | 3932 OG SER H 62 | 14.398 21.584 23.034 1.00 14.80 | B O |
| ATOM | 3933 C SER H 62 | 17.947 22.650 22.469 1.00 15.48 | B C |
| ATOM | 3934 O SER H 62 | 18.498 21.677 21.961 1.00 15.50 | B O |

APPENDIX-continued (APPENDIX discloses SEQ ID NOS 29-32, 29-32 and 29-32, respectively, in order of appearance)

| | | | |
|---|---|---|---|
| ATOM | 3935 N ASN H 63 | 18.597 23.777 22.721 1.00 16.61 | B N |
| ATOM | 3936 CA ASN H 63 | 20.030 23.839 22.523 1.00 17.77 | B C |
| ATOM | 3937 CB ASN H 63 | 20.519 25.279 22.439 1.00 17.73 | B C |
| ATOM | 3938 CG ASN H 63 | 21.686 25.433 21.493 1.00 18.52 | B C |
| ATOM | 3939 OD1 ASN H 63 | 22.559 24.567 21.428 1.00 18.29 | B O |
| ATOM | 3940 ND2 ASN H 63 | 21.641 26.467 20.665 1.00 19.40 | B N |
| ATOM | 3941 C ASN H 63 | 20.795 23.070 23.587 1.00 18.53 | B C |
| ATOM | 3942 O ASN H 63 | 20.356 22.967 24.732 1.00 18.82 | B O |
| ATOM | 3943 N ILE H 64 | 21.887 22.440 23.169 1.00 19.60 | B N |
| ATOM | 3944 CA ILE H 64 | 22.830 21.832 24.096 1.00 21.04 | B C |
| ATOM | 3945 CB ILE H 64 | 23.599 20.680 23.429 1.00 20.60 | B C |
| ATOM | 3946 CG1 ILE H 64 | 22.650 19.824 22.590 1.00 20.13 | B C |
| ATOM | 3947 CD1 ILE H 64 | 23.355 18.820 21.712 1.00 20.19 | B C |
| ATOM | 3948 CG2 ILE H 64 | 24.321 19.843 24.474 1.00 20.74 | B C |
| ATOM | 3949 C ILE H 64 | 23.837 22.859 24.601 1.00 22.58 | B C |
| ATOM | 3950 O ILE H 64 | 24.450 23.577 23.811 1.00 23.07 | B O |
| ATOM | 3951 N LYS H 65 | 24.104 22.827 25.903 1.00 24.21 | B N |
| ATOM | 3952 CA LYS H 65 | 25.356 23.354 26.435 1.00 25.86 | B C |
| ATOM | 3953 CB LYS H 65 | 25.109 24.202 27.686 1.00 25.90 | B C |
| ATOM | 3954 CG LYS H 65 | 23.736 24.015 28.312 1.00 26.69 | B C |
| ATOM | 3955 CD LYS H 65 | 23.556 22.597 28.830 1.00 28.26 | B C |
| ATOM | 3956 CE LYS H 65 | 23.104 22.591 30.281 1.00 28.67 | B C |
| ATOM | 3957 NZ LYS H 65 | 23.397 21.291 30.946 1.00 28.95 | B N |
| ATOM | 3958 C LYS H 65 | 26.377 22.252 26.719 1.00 26.81 | B C |
| ATOM | 3959 O LYS H 65 | 26.297 21.561 27.736 1.00 26.72 | B O |
| ATOM | 3960 N GLU H 66 | 27.382 22.159 25.852 1.00 27.90 | B N |
| ATOM | 3961 CA GLU H 66 | 28.276 21.001 25.793 1.00 28.82 | B C |
| ATOM | 3962 CB GLU H 66 | 29.031 20.991 24.457 1.00 28.88 | B C |
| ATOM | 3963 CG GLU H 66 | 30.531 20.737 24.572 1.00 30.33 | B C |
| ATOM | 3964 CD GLU H 66 | 31.320 21.283 23.391 1.00 33.17 | B C |
| ATOM | 3965 OE1 GLU H 66 | 32.446 20.796 23.151 1.00 35.05 | B O |
| ATOM | 3966 OE2 GLU H 66 | 30.864 22.268 22.775 1.00 33.14 | B O |
| ATOM | 3967 C GLU H 66 | 29.267 21.029 26.954 1.00 29.12 | B C |
| ATOM | 3968 O GLU H 66 | 29.751 22.097 27.329 1.00 29.28 | B O |
| ATOM | 3969 N ASN H 67 | 29.545 19.871 27.547 1.00 29.32 | B N |
| ATOM | 3970 CA ASN H 67 | 30.326 19.847 28.783 1.00 29.39 | B C |
| ATOM | 3971 CB ASN H 67 | 29.525 19.250 29.941 1.00 29.62 | B C |
| ATOM | 3972 CG ASN H 67 | 28.892 20.317 30.814 1.00 29.84 | B C |
| ATOM | 3973 OD1 ASN H 67 | 29.589 21.032 31.534 1.00 29.93 | B O |
| ATOM | 3974 ND2 ASN H 67 | 27.597 20.540 30.625 1.00 29.22 | B N |
| ATOM | 3975 C ASN H 67 | 31.745 19.271 28.698 1.00 29.15 | B C |
| ATOM | 3976 O ASN H 67 | 31.977 18.111 29.044 1.00 29.06 | B O |
| ATOM | 3977 N LYS H 68 | 32.625 20.020 28.036 1.00 28.87 | B N |
| ATOM | 3978 CA LYS H 68 | 34.033 20.170 28.428 1.00 28.78 | B C |
| ATOM | 3979 CB LYS H 68 | 34.334 21.625 28.806 1.00 28.89 | B C |
| ATOM | 3980 CG LYS H 68 | 33.742 22.653 27.846 1.00 29.26 | B C |
| ATOM | 3981 CD LYS H 68 | 33.794 24.057 28.427 1.00 29.68 | B C |
| ATOM | 3982 CE LYS H 68 | 35.058 24.267 29.243 1.00 29.46 | B C |
| ATOM | 3983 NZ LYS H 68 | 35.195 25.675 29.705 1.00 29.58 | B N |
| ATOM | 3984 C LYS H 68 | 34.543 19.202 29.509 1.00 28.60 | B C |
| ATOM | 3985 O LYS H 68 | 34.879 19.622 30.618 1.00 28.64 | B O |
| ATOM | 3986 N CYS H 69 | 34.618 17.912 29.162 1.00 28.09 | B N |
| ATOM | 3987 CA CYS H 69 | 35.404 16.889 29.895 1.00 27.63 | B C |
| ATOM | 3988 CB CYS H 69 | 34.502 15.694 30.287 1.00 27.07 | B C |
| ATOM | 3989 SG CYS H 69 | 34.515 14.237 29.134 1.00 28.01 | B S |
| ATOM | 3990 C CYS H 69 | 36.550 16.388 29.003 1.00 27.69 | B C |
| ATOM | 3991 O CYS H 69 | 36.474 16.529 27.785 1.00 27.41 | B O |
| ATOM | 3992 N ASN H 70 | 37.563 15.732 29.576 1.00 28.06 | B N |
| ATOM | 3993 CA ASN H 70 | 38.498 14.929 28.760 1.00 28.87 | B C |
| ATOM | 3994 CB ASN H 70 | 39.930 15.507 28.746 1.00 30.52 | B C |
| ATOM | 3995 CG ASN H 70 | 40.024 16.921 29.323 1.00 39.60 | B C |
| ATOM | 3996 OD1 ASN H 70 | 39.691 17.905 28.661 1.00 44.97 | B O |
| ATOM | 3997 ND2 ASN H 70 | 40.562 17.019 30.542 1.00 51.04 | B N |
| ATOM | 3998 C ASN H 70 | 38.528 13.423 29.067 1.00 26.97 | B C |
| ATOM | 3999 O ASN H 70 | 39.060 13.009 30.096 1.00 26.50 | B O |
| ATOM | 4000 N GLY H 71 | 38.111 12.611 28.096 1.00 25.46 | B N |
| ATOM | 4001 CA GLY H 71 | 38.117 11.148 28.237 1.00 23.67 | B C |
| ATOM | 4002 C GLY H 71 | 39.357 10.485 27.657 1.00 22.81 | B C |
| ATOM | 4003 O GLY H 71 | 40.279 11.169 27.211 1.00 22.79 | B O |
| ATOM | 4004 N THR H 72 | 39.400 9.155 27.687 1.00 21.93 | B N |
| ATOM | 4005 CA THR H 72 | 40.517 8.418 27.100 1.00 21.30 | B C |
| ATOM | 4006 CB THR H 72 | 40.594 6.975 27.644 1.00 21.12 | B C |
| ATOM | 4007 OG1 THR H 72 | 39.700 6.131 26.909 1.00 19.87 | B O |
| ATOM | 4008 CG2 THR H 72 | 40.210 6.947 29.115 1.00 20.76 | B C |
| ATOM | 4009 C THR H 72 | 40.436 8.407 25.571 1.00 21.50 | B C |
| ATOM | 4010 O THR H 72 | 39.458 7.924 24.999 1.00 21.85 | B O |
| ATOM | 4011 N ASP H 73 | 41.391 9.077 24.927 1.00 21.43 | B N |

APPENDIX-continued (APPENDIX discloses SEQ ID NOS 29-32, 29-32 and 29-32, respectively, in order of appearance)

| | | | |
|---|---|---|---|
| ATOM | 4012 CA ASP H 73 | 41.246 9.509 23.534 1.00 21.46 | B C |
| ATOM | 4013 CB ASP H 73 | 41.137 8.304 22.598 1.00 21.69 | B C |
| ATOM | 4014 CG ASP H 73 | 40.965 8.708 21.150 1.00 22.46 | B C |
| ATOM | 4015 OD1 ASP H 73 | 40.678 9.896 20.894 1.00 23.01 | B O |
| ATOM | 4016 OD2 ASP H 73 | 41.102 7.835 20.269 1.00 23.09 | B O |
| ATOM | 4017 C ASP H 73 | 40.060 10.451 23.324 1.00 20.96 | B C |
| ATOM | 4018 O ASP H 73 | 38.909 10.066 23.530 1.00 20.61 | B O |
| ATOM | 4019 N ALA H 74 | 40.342 11.642 22.802 1.00 20.42 | B N |
| ATOM | 4020 CA ALA H 74 | 39.342 12.698 22.730 1.00 20.38 | B C |
| ATOM | 4021 CB ALA H 74 | 39.707 13.839 23.670 1.00 20.11 | B C |
| ATOM | 4022 C ALA H 74 | 39.133 13.223 21.310 1.00 20.45 | B C |
| ATOM | 4023 O ALA H 74 | 38.545 14.286 21.121 1.00 20.46 | B O |
| ATOM | 4024 N LYS H 75 | 39.659 12.513 20.318 1.00 20.67 | B N |
| ATOM | 4025 CA LYS H 75 | 39.416 12.887 18.929 1.00 20.99 | B C |
| ATOM | 4026 CB LYS H 75 | 40.195 11.977 17.978 1.00 21.20 | B C |
| ATOM | 4027 CG LYS H 75 | 41.704 12.110 18.091 1.00 22.02 | B C |
| ATOM | 4028 CD LYS H 75 | 42.349 10.782 18.451 1.00 23.66 | B C |
| ATOM | 4029 CE LYS H 75 | 43.483 10.971 19.447 1.00 24.93 | B C |
| ATOM | 4030 NZ LYS H 75 | 43.559 9.859 20.434 1.00 25.55 | B N |
| ATOM | 4031 C LYS H 75 | 37.925 12.790 18.645 1.00 20.92 | B C |
| ATOM | 4032 O LYS H 75 | 37.397 13.474 17.768 1.00 20.92 | B O |
| ATOM | 4033 N VAL H 76 | 37.265 11.904 19.382 1.00 20.63 | B N |
| ATOM | 4034 CA VAL H 76 | 35.813 11.844 19.414 1.00 20.36 | B C |
| ATOM | 4035 CB VAL H 76 | 35.326 10.521 20.029 1.00 20.25 | B C |
| ATOM | 4036 CG1 VAL H 76 | 33.817 10.537 20.157 1.00 20.82 | B C |
| ATOM | 4037 CG2 VAL H 76 | 35.769 9.341 19.175 1.00 20.09 | B C |
| ATOM | 4038 C VAL H 76 | 35.234 13.006 20.213 1.00 20.29 | B C |
| ATOM | 4039 O VAL H 76 | 35.629 13.244 21.356 1.00 20.21 | B O |
| ATOM | 4040 N LYS H 77 | 34.284 13.715 19.613 1.00 20.17 | B N |
| ATOM | 4041 CA LYS H 77 | 33.726 14.916 20.224 1.00 20.17 | B C |
| ATOM | 4042 CB LYS H 77 | 34.593 16.136 19.904 1.00 20.62 | B C |
| ATOM | 4043 CG LYS H 77 | 35.797 16.307 20.825 1.00 23.31 | B C |
| ATOM | 4044 CD LYS H 77 | 36.952 16.989 20.103 1.00 26.74 | B C |
| ATOM | 4045 CE LYS H 77 | 38.196 17.046 20.971 1.00 28.32 | B C |
| ATOM | 4046 NZ LYS H 77 | 39.203 18.004 20.436 1.00 29.66 | B N |
| ATOM | 4047 C LYS H 77 | 32.294 15.141 19.759 1.00 19.45 | B C |
| ATOM | 4048 O LYS H 77 | 31.971 16.170 19.165 1.00 19.36 | B O |
| ATOM | 4049 N LEU H 78 | 31.441 14.162 20.033 1.00 18.70 | B N |
| ATOM | 4050 CA LEU H 78 | 30.155 14.056 19.365 1.00 17.98 | B C |
| ATOM | 4051 CB LEU H 78 | 29.356 12.892 19.945 1.00 17.72 | B C |
| ATOM | 4052 CG LEU H 78 | 30.168 11.596 20.034 1.00 17.51 | B C |
| ATOM | 4053 CD1 LEU H 78 | 29.321 10.446 20.554 1.00 17.41 | B C |
| ATOM | 4054 CD2 LEU H 78 | 30.802 11.249 18.690 1.00 17.62 | B C |
| ATOM | 4055 C LEU H 78 | 29.354 15.355 19.422 1.00 17.77 | B C |
| ATOM | 4056 O LEU H 78 | 28.996 15.911 18.384 1.00 17.89 | B O |
| ATOM | 4057 N ILE H 79 | 29.145 15.882 20.624 1.00 17.29 | B N |
| ATOM | 4058 CA ILE H 79 | 28.336 17.086 20.778 1.00 17.00 | B C |
| ATOM | 4059 CB ILE H 79 | 28.194 17.527 22.256 1.00 16.96 | B C |
| ATOM | 4060 CG1 ILE H 79 | 27.588 16.401 23.098 1.00 17.21 | B C |
| ATOM | 4061 CD1 ILE H 79 | 27.086 16.855 24.459 1.00 17.51 | B C |
| ATOM | 4062 CG2 ILE H 79 | 27.307 18.762 22.359 1.00 17.30 | B C |
| ATOM | 4063 C ILE H 79 | 28.854 18.238 19.911 1.00 16.83 | B C |
| ATOM | 4064 O ILE H 79 | 28.119 18.753 19.065 1.00 17.02 | B O |
| ATOM | 4065 N LYS H 80 | 30.124 18.571 19.800 1.00 16.55 | B N |
| ATOM | 4066 CA LYS H 80 | 30.366 19.684 18.841 1.00 16.38 | B C |
| ATOM | 4067 CB LYS H 80 | 31.861 20.021 18.833 1.00 16.73 | B C |
| ATOM | 4068 CG LYS H 80 | 32.255 21.150 17.895 1.00 17.99 | B C |
| ATOM | 4069 CD LYS H 80 | 32.343 22.475 18.640 1.00 20.71 | B C |
| ATOM | 4070 CE LYS H 80 | 32.566 23.632 17.681 1.00 22.92 | B C |
| ATOM | 4071 NZ LYS H 80 | 31.339 23.929 16.886 1.00 24.75 | B N |
| ATOM | 4072 C LYS H 80 | 29.884 19.466 17.349 1.00 15.79 | B C |
| ATOM | 4073 O LYS H 80 | 29.216 20.348 16.717 1.00 15.32 | B O |
| ATOM | 4074 N GLN H 81 | 30.177 18.286 16.806 1.00 15.48 | B N |
| ATOM | 4075 CA GLN H 81 | 29.878 17.961 15.401 1.00 15.33 | B C |
| ATOM | 4076 CB GLN H 81 | 30.465 16.593 15.049 1.00 15.70 | B C |
| ATOM | 4077 CG GLN H 81 | 31.870 16.364 15.565 1.00 17.88 | B C |
| ATOM | 4078 CD GLN H 81 | 32.301 14.917 15.435 1.00 20.46 | B C |
| ATOM | 4079 OE1 GLN H 81 | 31.670 14.133 14.730 1.00 21.59 | B O |
| ATOM | 4080 NE2 GLN H 81 | 33.378 14.554 16.123 1.00 20.26 | B N |
| ATOM | 4081 C GLN H 81 | 28.388 17.966 15.047 1.00 14.63 | B C |
| ATOM | 4082 O GLN H 81 | 27.972 18.429 13.962 1.00 14.60 | B O |
| ATOM | 4083 N GLU H 82 | 27.589 17.434 15.964 1.00 13.81 | B N |
| ATOM | 4084 CA GLU H 82 | 26.157 17.373 15.759 1.00 13.37 | B C |
| ATOM | 4085 CB GLU H 82 | 25.479 16.677 16.938 1.00 13.20 | B C |
| ATOM | 4086 CG GLU H 82 | 25.315 15.176 16.781 1.00 15.04 | B C |
| ATOM | 4087 CD GLU H 82 | 24.344 14.824 15.669 1.00 17.51 | B C |
| ATOM | 4088 OE1 GLU H 82 | 23.130 15.074 15.841 1.00 18.22 | B O |

APPENDIX-continued (APPENDIX discloses SEQ ID NOS 29-32, 29-32 and 29-32, respectively, in order of appearance)

| | | | |
|---|---|---|---|
| ATOM | 4089 OE2 GLU H 82 | 24.789 14.286 14.632 1.00 17.87 | B O |
| ATOM | 4090 C GLU H 82 | 25.650 18.794 15.638 1.00 12.99 | B C |
| ATOM | 4091 O GLU H 82 | 24.834 19.102 14.767 1.00 12.89 | B O |
| ATOM | 4092 N LEU H 83 | 26.174 19.677 16.482 1.00 12.89 | B N |
| ATOM | 4093 CA LEU H 83 | 25.727 21.057 16.454 1.00 13.08 | B C |
| ATOM | 4094 CB LEU H 83 | 26.419 21.865 17.552 1.00 13.26 | B C |
| ATOM | 4095 CG LEU H 83 | 26.057 21.498 18.994 1.00 14.18 | B C |
| ATOM | 4096 CD1 LEU H 83 | 26.535 22.566 19.968 1.00 15.11 | B C |
| ATOM | 4097 CD2 LEU H 83 | 24.558 21.282 19.117 1.00 14.79 | B C |
| ATOM | 4098 C LEU H 83 | 26.032 21.656 15.092 1.00 13.18 | B C |
| ATOM | 4099 O LEU H 83 | 25.150 22.261 14.459 1.00 13.05 | B O |
| ATOM | 4100 N ASP H 84 | 27.239 21.416 14.581 1.00 13.56 | B N |
| ATOM | 4101 CA ASP H 84 | 27.527 21.999 13.258 1.00 14.15 | B C |
| ATOM | 4102 CB ASP H 84 | 28.982 21.729 12.856 1.00 14.80 | B C |
| ATOM | 4103 CG ASP H 84 | 29.949 21.873 14.018 1.00 18.26 | B C |
| ATOM | 4104 OD1 ASP H 84 | 30.237 23.025 14.417 1.00 21.11 | B O |
| ATOM | 4105 OD2 ASP H 84 | 30.439 20.837 14.522 1.00 22.12 | B O |
| ATOM | 4106 C ASP H 84 | 26.572 21.490 12.150 1.00 13.56 | B C |
| ATOM | 4107 O ASP H 84 | 26.023 22.286 11.326 1.00 13.70 | B O |
| ATOM | 4108 N LYS H 85 | 26.328 20.180 12.146 1.00 12.87 | B N |
| ATOM | 4109 CA LYS H 85 | 25.458 19.616 11.106 1.00 12.31 | B C |
| ATOM | 4110 CB LYS H 85 | 25.412 18.090 11.210 1.00 12.41 | B C |
| ATOM | 4111 CG LYS H 85 | 24.611 17.417 10.110 1.00 12.26 | B C |
| ATOM | 4112 CD LYS H 85 | 24.213 16.002 10.506 1.00 12.72 | B C |
| ATOM | 4113 CE LYS H 85 | 23.359 16.018 11.762 1.00 14.40 | B C |
| ATOM | 4114 NZ LYS H 85 | 22.929 14.654 12.180 1.00 16.45 | B N |
| ATOM | 4115 C LYS H 85 | 24.038 20.192 11.202 1.00 11.85 | B C |
| ATOM | 4116 O LYS H 85 | 23.384 20.522 10.179 1.00 11.66 | B O |
| ATOM | 4117 N TYR H 86 | 23.571 20.318 12.442 1.00 11.32 | B N |
| ATOM | 4118 CA TYR H 86 | 22.232 20.825 12.683 1.00 11.07 | B C |
| ATOM | 4119 CB TYR H 86 | 21.875 20.784 14.167 1.00 11.12 | B C |
| ATOM | 4120 CG TYR H 86 | 20.899 21.871 14.551 1.00 11.30 | B C |
| ATOM | 4121 CD1 TYR H 86 | 19.564 21.805 14.169 1.00 12.16 | B C |
| ATOM | 4122 CE1 TYR H 86 | 18.672 22.804 14.514 1.00 12.39 | B C |
| ATOM | 4123 CZ TYR H 86 | 19.106 23.886 15.243 1.00 12.62 | B C |
| ATOM | 4124 OH TYR H 86 | 18.218 24.880 15.587 1.00 12.72 | B O |
| ATOM | 4125 CE2 TYR H 86 | 20.428 23.980 15.632 1.00 11.38 | B C |
| ATOM | 4126 CD2 TYR H 86 | 21.315 22.979 15.284 1.00 11.05 | B C |
| ATOM | 4127 C TYR H 86 | 22.120 22.247 12.181 1.00 10.75 | B C |
| ATOM | 4128 O TYR H 86 | 21.114 22.622 11.573 1.00 10.45 | B O |
| ATOM | 4129 N LYS H 87 | 23.155 23.046 12.419 1.00 10.66 | B N |
| ATOM | 4130 CA LYS H 87 | 23.093 24.423 11.971 1.00 11.03 | B C |
| ATOM | 4131 CB LYS H 87 | 24.333 25.191 12.407 1.00 11.36 | B C |
| ATOM | 4132 CG LYS H 87 | 24.600 25.106 13.890 1.00 12.79 | B C |
| ATOM | 4133 CD LYS H 87 | 25.805 25.931 14.269 1.00 14.76 | B C |
| ATOM | 4134 CE LYS H 87 | 25.989 25.979 15.771 1.00 15.29 | B C |
| ATOM | 4135 NZ LYS H 87 | 27.137 26.849 16.138 1.00 16.27 | B N |
| ATOM | 4136 C LYS H 87 | 22.961 24.455 10.457 1.00 10.83 | B C |
| ATOM | 4137 O LYS H 87 | 22.122 25.189 9.920 1.00 11.11 | B O |
| ATOM | 4138 N ASN H 88 | 23.724 23.621 9.755 1.00 10.52 | B N |
| ATOM | 4139 CA ASN H 88 | 23.568 23.646 8.297 1.00 10.21 | B C |
| ATOM | 4140 CB ASN H 88 | 24.586 22.715 7.640 1.00 10.61 | B C |
| ATOM | 4141 CG ASN H 88 | 24.426 22.646 6.134 1.00 11.81 | B C |
| ATOM | 4142 OD1 ASN H 88 | 24.215 23.664 5.474 1.00 12.97 | B O |
| ATOM | 4143 ND2 ASN H 88 | 24.515 21.443 5.585 1.00 13.82 | B N |
| ATOM | 4144 C ASN H 88 | 22.142 23.279 7.825 1.00 9.42 | B C |
| ATOM | 4145 O ASN H 88 | 21.538 23.959 6.939 1.00 8.94 | B O |
| ATOM | 4146 N ALA H 89 | 21.576 22.237 8.435 1.00 8.77 | B N |
| ATOM | 4147 CA ALA H 89 | 20.225 21.834 8.022 1.00 8.21 | B C |
| ATOM | 4148 CB ALA H 89 | 19.811 20.551 8.725 1.00 7.99 | B C |
| ATOM | 4149 C ALA H 89 | 19.208 22.951 8.293 1.00 7.78 | B C |
| ATOM | 4150 O ALA H 89 | 18.307 23.249 7.472 1.00 7.88 | B O |
| ATOM | 4151 N VAL H 90 | 19.383 23.581 9.449 1.00 7.01 | B N |
| ATOM | 4152 CA VAL H 90 | 18.493 24.639 9.880 1.00 6.26 | B C |
| ATOM | 4153 CB VAL H 90 | 18.866 25.140 11.289 1.00 5.91 | B C |
| ATOM | 4154 CG1 VAL H 90 | 18.089 26.401 11.626 1.00 5.92 | B C |
| ATOM | 4155 CG2 VAL H 90 | 18.608 24.054 12.318 1.00 5.26 | B C |
| ATOM | 4156 C VAL H 90 | 18.565 25.785 8.894 1.00 6.25 | B C |
| ATOM | 4157 O VAL H 90 | 17.547 26.368 8.538 1.00 6.32 | B O |
| ATOM | 4158 N THR H 91 | 19.771 26.092 8.434 1.00 6.24 | B N |
| ATOM | 4159 CA THR H 91 | 19.956 27.171 7.478 1.00 6.68 | B C |
| ATOM | 4160 CB THR H 91 | 21.444 27.375 7.139 1.00 6.62 | B C |
| ATOM | 4161 OG1 THR H 91 | 22.183 27.602 8.345 1.00 7.19 | B O |
| ATOM | 4162 CG2 THR H 91 | 21.619 28.565 6.210 1.00 7.27 | B C |
| ATOM | 4163 C THR H 91 | 19.203 26.886 6.180 1.00 7.02 | B C |
| ATOM | 4164 O THR H 91 | 18.505 27.767 5.661 1.00 7.16 | B O |
| ATOM | 4165 N GLU H 92 | 19.285 25.654 5.679 1.00 7.31 | B N |

APPENDIX-continued (APPENDIX discloses SEQ ID NOS 29-32, 29-32 and 29-32, respectively, in order of appearance)

| | | | |
|---|---|---|---|
| ATOM | 4166 CA GLU H 92 | 18.529 25.358 4.446 1.00 7.81 | B C |
| ATOM | 4167 CB GLU H 92 | 18.838 23.939 3.965 1.00 8.23 | B C |
| ATOM | 4168 CG GLU H 92 | 20.139 23.800 3.192 1.00 10.91 | B C |
| ATOM | 4169 CD GLU H 92 | 20.104 24.541 1.870 1.00 14.95 | B C |
| ATOM | 4170 OE1 GLU H 92 | 19.434 24.052 0.934 1.00 16.14 | B O |
| ATOM | 4171 OE2 GLU H 92 | 20.751 25.605 1.762 1.00 16.53 | B O |
| ATOM | 4172 C GLU H 92 | 17.003 25.530 4.644 1.00 7.47 | B C |
| ATOM | 4173 O GLU H 92 | 16.248 26.099 3.776 1.00 7.32 | B O |
| ATOM | 4174 N LEU H 93 | 16.541 25.053 5.800 1.00 7.30 | B N |
| ATOM | 4175 CA LEU H 93 | 15.117 25.171 6.098 1.00 7.47 | B C |
| ATOM | 4176 CB LEU H 93 | 14.760 24.426 7.385 1.00 7.15 | B C |
| ATOM | 4177 CG LEU H 93 | 14.797 22.898 7.297 1.00 7.20 | B C |
| ATOM | 4178 CD1 LEU H 93 | 14.346 22.282 8.610 1.00 7.93 | B C |
| ATOM | 4179 CD2 LEU H 93 | 13.941 22.397 6.141 1.00 6.91 | B C |
| ATOM | 4180 C LEU H 93 | 14.686 26.639 6.179 1.00 7.89 | B C |
| ATOM | 4181 O LEU H 93 | 13.626 27.012 5.675 1.00 7.94 | B O |
| ATOM | 4182 N GLN H 94 | 15.527 27.464 6.797 1.00 8.31 | B N |
| ATOM | 4183 CA GLN H 94 | 15.259 28.893 6.952 1.00 9.05 | B C |
| ATOM | 4184 CB GLN H 94 | 16.325 29.554 7.831 1.00 9.18 | B C |
| ATOM | 4185 CG GLN H 94 | 16.331 29.049 9.271 1.00 10.79 | B C |
| ATOM | 4186 CD GLN H 94 | 17.231 29.868 10.179 1.00 13.82 | B C |
| ATOM | 4187 OE1 GLN H 94 | 17.866 30.828 9.741 1.00 14.98 | B O |
| ATOM | 4188 NE2 GLN H 94 | 17.289 29.493 11.452 1.00 15.25 | B N |
| ATOM | 4189 C GLN H 94 | 15.190 29.545 5.576 1.00 9.25 | B C |
| ATOM | 4190 O GLN H 94 | 14.389 30.446 5.329 1.00 9.43 | B O |
| ATOM | 4191 N LEU H 95 | 16.050 29.058 4.691 1.00 9.55 | B N |
| ATOM | 4192 CA LEU H 95 | 16.140 29.479 3.294 1.00 10.17 | B C |
| ATOM | 4193 CB LEU H 95 | 17.327 28.800 2.605 1.00 9.79 | B C |
| ATOM | 4194 CG LEU H 95 | 18.721 29.321 2.958 1.00 8.86 | B C |
| ATOM | 4195 CD1 LEU H 95 | 19.789 28.548 2.198 1.00 8.31 | B C |
| ATOM | 4196 CD2 LEU H 95 | 18.823 30.809 2.667 1.00 7.62 | B C |
| ATOM | 4197 C LEU H 95 | 14.865 29.250 2.467 1.00 11.22 | B C |
| ATOM | 4198 O LEU H 95 | 14.579 30.030 1.560 1.00 11.55 | B O |
| ATOM | 4199 N LEU H 96 | 14.105 28.190 2.748 1.00 12.40 | B N |
| ATOM | 4200 CA LEU H 96 | 12.870 27.931 1.929 1.00 13.66 | B C |
| ATOM | 4201 CB LEU H 96 | 12.338 26.527 2.247 1.00 13.38 | B C |
| ATOM | 4202 CG LEU H 96 | 13.163 25.359 1.709 1.00 13.32 | B C |
| ATOM | 4203 CD1 LEU H 96 | 12.554 24.028 2.122 1.00 12.84 | B C |
| ATOM | 4204 CD2 LEU H 96 | 13.281 25.453 0.197 1.00 13.38 | B C |
| ATOM | 4205 C LEU H 96 | 11.631 28.927 1.839 1.00 14.97 | B C |
| ATOM | 4206 O LEU H 96 | 10.836 28.843 0.903 1.00 15.21 | B O |
| ATOM | 4207 N MET H 97 | 11.500 29.832 2.808 1.00 16.74 | B N |
| ATOM | 4208 CA MET H 97 | 10.348 30.575 3.317 1.00 18.96 | B C |
| ATOM | 4209 CB MET H 97 | 10.619 31.113 4.726 1.00 19.12 | B C |
| ATOM | 4210 CG MET H 97 | 10.944 30.037 5.758 1.00 21.87 | B C |
| ATOM | 4211 SD MET H 97 | 9.537 28.994 6.201 1.00 27.46 | B S |
| ATOM | 4212 CE MET H 97 | 8.667 28.891 4.638 1.00 24.25 | B C |
| ATOM | 4213 C MET H 97 | 9.912 31.705 2.386 1.00 20.09 | B C |
| ATOM | 4214 O MET H 97 | 8.725 32.019 2.294 1.00 20.58 | B O |
| ATOM | 4215 N GLN H 98 | 10.867 32.274 1.658 1.00 21.33 | B N |
| ATOM | 4216 CA GLN H 98 | 10.593 33.429 0.809 1.00 22.21 | B C |
| ATOM | 4217 CB GLN H 98 | 11.279 34.679 1.364 1.00 22.53 | B C |
| ATOM | 4218 CG GLN H 98 | 11.165 34.831 2.872 1.00 23.85 | B C |
| ATOM | 4219 CD GLN H 98 | 12.329 34.200 3.612 1.00 25.21 | B C |
| ATOM | 4220 OE1 GLN H 98 | 12.539 32.989 3.544 1.00 24.47 | B O |
| ATOM | 4221 NE2 GLN H 98 | 13.058 35.012 4.369 1.00 24.85 | B N |
| ATOM | 4222 C GLN H 98 | 11.035 33.183 −0.629 1.00 22.15 | B C |
| ATOM | 4223 O GLN H 98 | 11.448 32.080 −0.982 1.00 21.77 | B O |
| ATOM | 4224 N PHE H 137 | 5.312 39.031 −3.961 1.00 33.25 | B N |
| ATOM | 4225 CA PHE H 137 | 5.277 37.601 −4.244 1.00 36.79 | B C |
| ATOM | 4226 CB PHE H 137 | 3.903 37.193 −4.778 1.00 20.00 | B C |
| ATOM | 4227 CG PHE H 137 | 2.795 37.350 −3.779 1.00 20.00 | B C |
| ATOM | 4228 CD1 PHE H 137 | 2.542 36.360 −2.843 1.00 20.00 | B C |
| ATOM | 4229 CE1 PHE H 137 | 1.524 36.503 −1.920 1.00 20.00 | B C |
| ATOM | 4230 CZ PHE H 137 | 0.751 37.645 −1.920 1.00 20.00 | B C |
| ATOM | 4231 CE2 PHE H 137 | 1.003 38.646 −2.836 1.00 20.00 | B C |
| ATOM | 4232 CD2 PHE H 137 | 2.015 38.493 −3.764 1.00 20.00 | B C |
| ATOM | 4233 C PHE H 137 | 6.359 37.207 −5.241 1.00 48.73 | B C |
| ATOM | 4234 O PHE H 137 | 6.595 36.022 −5.477 1.00 49.28 | B O |
| ATOM | 4235 N LEU H 138 | 6.975 38.204 −5.868 1.00 42.04 | B N |
| ATOM | 4236 CA LEU H 138 | 8.094 37.959 −6.768 1.00 44.26 | B C |
| ATOM | 4237 CB LEU H 138 | 8.582 39.268 −7.389 1.00 20.00 | B C |
| ATOM | 4238 CG LEU H 138 | 7.578 40.005 −8.278 1.00 20.00 | B C |
| ATOM | 4239 CD1 LEU H 138 | 8.178 41.296 −8.816 1.00 20.00 | B C |
| ATOM | 4240 CD2 LEU H 138 | 7.101 39.112 −9.411 1.00 20.00 | B C |
| ATOM | 4241 C LEU H 138 | 9.234 37.274 −6.025 1.00 43.68 | B C |
| ATOM | 4242 O LEU H 138 | 10.107 36.658 −6.636 1.00 50.27 | B O |

APPENDIX-continued (APPENDIX discloses SEQ ID NOS 29-32, 29-32 and 29-32, respectively, in order of appearance)

| | | | |
|---|---|---|---|
| ATOM | 4243 N GLY H 139 | 9.188 37.343 −4.698 1.00 38.56 | B N |
| ATOM | 4244 CA GLY H 139 | 10.191 36.699 −3.860 1.00 47.99 | B C |
| ATOM | 4245 C GLY H 139 | 10.260 35.202 −4.081 1.00 44.53 | B C |
| ATOM | 4246 O GLY H 139 | 11.284 34.575 −3.815 1.00 32.21 | B O |
| ATOM | 4247 N PHE H 140 | 9.173 34.630 −4.590 1.00 46.33 | B N |
| ATOM | 4248 CA PHE H 140 | 9.070 33.183 −4.735 1.00 42.95 | B C |
| ATOM | 4249 CB PHE H 140 | 7.618 32.723 −4.576 1.00 20.00 | B C |
| ATOM | 4250 CG PHE H 140 | 7.058 32.941 −3.201 1.00 20.00 | B C |
| ATOM | 4251 CD1 PHE H 140 | 7.285 32.021 −2.190 1.00 20.00 | B C |
| ATOM | 4252 CE1 PHE H 140 | 6.763 32.217 −0.926 1.00 20.00 | B C |
| ATOM | 4253 CZ PHE H 140 | 5.992 33.332 −0.664 1.00 20.00 | B C |
| ATOM | 4254 CE2 PHE H 140 | 5.747 34.249 −1.667 1.00 20.00 | B C |
| ATOM | 4255 CD2 PHE H 140 | 6.271 34.047 −2.929 1.00 20.00 | B C |
| ATOM | 4256 C PHE H 140 | 9.632 32.695 −6.071 1.00 38.13 | B C |
| ATOM | 4257 O PHE H 140 | 9.693 31.490 −6.322 1.00 57.33 | B O |
| ATOM | 4258 N LEU H 141 | 10.017 33.631 −6.934 1.00 35.20 | B N |
| ATOM | 4259 CA LEU H 141 | 10.453 33.294 −8.288 1.00 27.01 | B C |
| ATOM | 4260 CB LEU H 141 | 11.557 32.235 −8.254 1.00 20.00 | B C |
| ATOM | 4261 CG LEU H 141 | 12.886 32.672 −7.636 1.00 20.00 | B C |
| ATOM | 4262 CD1 LEU H 141 | 13.836 31.493 −7.513 1.00 20.00 | B C |
| ATOM | 4263 CD2 LEU H 141 | 13.520 33.794 −8.445 1.00 20.00 | B C |
| ATOM | 4264 C LEU H 141 | 9.287 32.812 −9.144 1.00 35.79 | B C |
| ATOM | 4265 O LEU H 141 | 8.355 33.567 −9.417 1.00 46.92 | B O |
| ATOM | 4266 N LEU H 142 | 9.342 31.555 −9.570 1.00 38.67 | B N |
| ATOM | 4267 CA LEU H 142 | 8.195 30.927 −10.207 1.00 33.84 | B C |
| ATOM | 4268 CB LEU H 142 | 8.610 30.262 −11.517 1.00 20.00 | B C |
| ATOM | 4269 CG LEU H 142 | 9.069 31.205 −12.629 1.00 20.00 | B C |
| ATOM | 4270 CD1 LEU H 142 | 9.474 30.415 −13.865 1.00 20.00 | B C |
| ATOM | 4271 CD2 LEU H 142 | 7.974 32.209 −12.964 1.00 20.00 | B C |
| ATOM | 4272 C LEU H 142 | 7.541 29.910 −9.278 1.00 36.89 | B C |
| ATOM | 4273 O LEU H 142 | 8.215 29.038 −8.729 1.00 45.42 | B O |
| ATOM | 4274 N GLY H 143 | 6.268 30.132 −8.975 1.00 26.84 | B N |
| ATOM | 4275 CA GLY H 143 | 5.577 29.350 −7.958 1.00 27.41 | B C |
| ATOM | 4276 C GLY H 143 | 4.243 28.849 −8.463 1.00 29.08 | B C |
| ATOM | 4277 O GLY H 143 | 3.592 29.504 −9.277 1.00 40.24 | B O |
| ATOM | 4278 N VAL H 144 | 3.848 27.665 −8.010 1.00 30.17 | B N |
| ATOM | 4279 CA VAL H 144 | 2.550 27.121 −8.373 1.00 34.15 | B C |
| ATOM | 4280 CB VAL H 144 | 2.497 25.596 −8.195 1.00 20.00 | B C |
| ATOM | 4281 CG1 VAL H 144 | 1.073 25.102 −8.370 1.00 20.00 | B C |
| ATOM | 4282 CG2 VAL H 144 | 3.426 24.913 −9.187 1.00 20.00 | B C |
| ATOM | 4283 C VAL H 144 | 1.449 27.759 −7.538 1.00 36.67 | B C |
| ATOM | 4284 O VAL H 144 | 1.723 28.490 −6.587 1.00 42.49 | B O |
| ATOM | 4285 N GLY H 145 | 0.204 27.526 −7.938 1.00 47.09 | B N |
| ATOM | 4286 CA GLY H 145 | −0.946 27.979 −7.166 1.00 44.51 | B C |
| ATOM | 4287 C GLY H 145 | −0.857 27.562 −5.712 1.00 44.94 | B C |
| ATOM | 4288 O GLY H 145 | −1.097 28.365 −4.810 1.00 40.58 | B O |
| ATOM | 4289 N SER H 146 | −0.529 26.297 −5.473 1.00 42.06 | B N |
| ATOM | 4290 CA SER H 146 | −0.433 25.788 −4.109 1.00 47.39 | B C |
| ATOM | 4291 CB SER H 146 | −0.198 24.275 −4.119 1.00 20.00 | B C |
| ATOM | 4292 OG SER H 146 | 1.004 23.951 −4.796 1.00 20.00 | B O |
| ATOM | 4293 C SER H 146 | 0.665 26.482 −3.307 1.00 51.48 | B C |
| ATOM | 4294 O SER H 146 | 0.481 26.809 −2.131 1.00 47.45 | B O |
| ATOM | 4295 N ALA H 147 | 1.807 26.710 −3.949 1.00 39.51 | B N |
| ATOM | 4296 CA ALA H 147 | 2.943 27.334 −3.282 1.00 43.38 | B C |
| ATOM | 4297 CB ALA H 147 | 4.162 27.326 −4.194 1.00 20.00 | B C |
| ATOM | 4298 C ALA H 147 | 2.633 28.754 −2.821 1.00 47.39 | B C |
| ATOM | 4299 O ALA H 147 | 2.997 29.147 −1.713 1.00 50.18 | B O |
| ATOM | 4300 N ILE H 148 | 1.952 29.520 −3.668 1.00 44.67 | B N |
| ATOM | 4301 CA ILE H 148 | 1.602 30.892 −3.323 1.00 43.56 | B C |
| ATOM | 4302 CB ILE H 148 | 0.921 31.615 −4.499 1.00 20.00 | B C |
| ATOM | 4303 CG1 ILE H 148 | 1.854 31.657 −5.711 1.00 20.00 | B C |
| ATOM | 4304 CD1 ILE H 148 | 1.259 32.353 −6.916 1.00 20.00 | B C |
| ATOM | 4305 CG2 ILE H 148 | 0.504 33.020 −4.092 1.00 20.00 | B C |
| ATOM | 4306 C ILE H 148 | 0.672 30.913 −2.117 1.00 51.18 | B C |
| ATOM | 4307 O ILE H 148 | 0.830 31.730 −1.208 1.00 39.17 | B O |
| ATOM | 4308 N ALA H 149 | −0.289 29.995 −2.109 1.00 42.17 | B N |
| ATOM | 4309 CA ALA H 149 | −1.233 29.895 −1.007 1.00 36.76 | B C |
| ATOM | 4310 CB ALA H 149 | −2.297 28.854 −1.312 1.00 20.00 | B C |
| ATOM | 4311 C ALA H 149 | −0.490 29.541 0.272 1.00 45.19 | B C |
| ATOM | 4312 O ALA H 149 | −0.771 30.090 1.340 1.00 47.83 | B O |
| ATOM | 4313 N SER H 150 | 0.471 28.630 0.157 1.00 43.64 | B N |
| ATOM | 4314 CA SER H 150 | 1.250 28.218 1.315 1.00 43.46 | B C |
| ATOM | 4315 CB SER H 150 | 2.211 27.088 0.943 1.00 20.00 | B C |
| ATOM | 4316 OG SER H 150 | 3.113 27.499 −0.069 1.00 20.00 | B O |
| ATOM | 4317 C SER H 150 | 2.024 29.408 1.865 1.00 44.80 | B C |
| ATOM | 4318 O SER H 150 | 2.095 29.610 3.077 1.00 41.55 | B O |
| ATOM | 4319 N GLY H 151 | 2.590 30.205 0.964 1.00 27.01 | B N |

APPENDIX-continued (APPENDIX discloses SEQ ID NOS 29-32, 29-32 and 29-32, respectively, in order of appearance)

| | | | |
|---|---|---|---|
| ATOM | 4320 CA GLY H 151 | 3.342 31.379 1.362 1.00 35.21 | B C |
| ATOM | 4321 C GLY H 151 | 2.454 32.375 2.078 1.00 42.40 | B C |
| ATOM | 4322 O GLY H 151 | 2.849 32.969 3.083 1.00 45.11 | B O |
| ATOM | 4323 N VAL H 152 | 1.241 32.551 1.563 1.00 40.20 | B N |
| ATOM | 4324 CA VAL H 152 | 0.293 33.471 2.174 1.00 46.73 | B C |
| ATOM | 4325 CB VAL H 152 | −1.000 33.585 1.346 1.00 20.00 | B C |
| ATOM | 4326 CG1 VAL H 152 | −1.970 34.551 2.009 1.00 20.00 | B C |
| ATOM | 4327 CG2 VAL H 152 | −0.682 34.029 −0.073 1.00 20.00 | B C |
| ATOM | 4328 C VAL H 152 | −0.052 32.995 3.579 1.00 48.62 | B C |
| ATOM | 4329 O VAL H 152 | −0.133 33.792 4.517 1.00 49.32 | B O |
| ATOM | 4330 N ALA H 153 | −0.239 31.686 3.722 1.00 35.09 | B N |
| ATOM | 4331 CA ALA H 153 | −0.567 31.112 5.018 1.00 42.37 | B C |
| ATOM | 4332 CB ALA H 153 | −0.849 29.625 4.885 1.00 20.00 | B C |
| ATOM | 4333 C ALA H 153 | 0.578 31.353 5.992 1.00 37.79 | B C |
| ATOM | 4334 O ALA H 153 | 0.359 31.696 7.154 1.00 39.25 | B O |
| ATOM | 4335 N VAL H 154 | 1.802 31.189 5.502 1.00 38.88 | B N |
| ATOM | 4336 CA VAL H 154 | 2.982 31.394 6.328 1.00 35.53 | B C |
| ATOM | 4337 CB VAL H 154 | 4.274 31.042 5.568 1.00 20.00 | B C |
| ATOM | 4338 CG1 VAL H 154 | 5.489 31.267 6.454 1.00 20.00 | B C |
| ATOM | 4339 CG2 VAL H 154 | 4.223 29.605 5.074 1.00 20.00 | B C |
| ATOM | 4340 C VAL H 154 | 3.053 32.842 6.791 1.00 41.00 | B C |
| ATOM | 4341 O VAL H 154 | 3.380 33.118 7.945 1.00 50.08 | B O |
| ATOM | 4342 N SER H 155 | 2.742 33.766 5.888 1.00 37.82 | B N |
| ATOM | 4343 CA SER H 155 | 2.753 35.181 6.232 1.00 44.68 | B C |
| ATOM | 4344 CB SER H 155 | 2.496 36.038 4.991 1.00 20.00 | B C |
| ATOM | 4345 OG SER H 155 | 1.238 35.736 4.414 1.00 20.00 | B O |
| ATOM | 4346 C SER H 155 | 1.706 35.477 7.300 1.00 41.82 | B C |
| ATOM | 4347 O SER H 155 | 1.960 36.224 8.245 1.00 49.37 | B O |
| ATOM | 4348 N LYS H 156 | 0.528 34.880 7.144 1.00 36.99 | B N |
| ATOM | 4349 CA LYS H 156 | −0.559 35.059 8.102 1.00 35.11 | B C |
| ATOM | 4350 CB LYS H 156 | −1.843 34.411 7.579 1.00 20.00 | B C |
| ATOM | 4351 CG LYS H 156 | −2.334 34.983 6.259 1.00 20.00 | B C |
| ATOM | 4352 CD LYS H 156 | −3.611 34.297 5.801 1.00 20.00 | B C |
| ATOM | 4353 CE LYS H 156 | −4.102 34.869 4.481 1.00 20.00 | B C |
| ATOM | 4354 NZ LYS H 156 | −5.353 34.206 4.020 1.00 20.00 | B N |
| ATOM | 4355 C LYS H 156 | −0.210 34.493 9.476 1.00 35.98 | B C |
| ATOM | 4356 O LYS H 156 | −0.535 35.081 10.507 1.00 42.31 | B O |
| ATOM | 4357 N VAL H 157 | 0.448 33.339 9.470 1.00 37.88 | B N |
| ATOM | 4358 CA VAL H 157 | 0.794 32.617 10.689 1.00 50.94 | B C |
| ATOM | 4359 CB VAL H 157 | 1.143 31.145 10.396 1.00 20.00 | B C |
| ATOM | 4360 CG1 VAL H 157 | 1.572 30.439 11.672 1.00 20.00 | B C |
| ATOM | 4361 CG2 VAL H 157 | −0.043 30.435 9.762 1.00 20.00 | B C |
| ATOM | 4362 C VAL H 157 | 1.962 33.277 11.415 1.00 47.82 | B C |
| ATOM | 4363 O VAL H 157 | 2.296 32.905 12.541 1.00 56.87 | B O |
| ATOM | 4364 N LEU H 158 | 2.533 34.304 10.794 1.00 39.52 | B N |
| ATOM | 4365 CA LEU H 158 | 3.727 34.956 11.320 1.00 50.27 | B C |
| ATOM | 4366 CB LEU H 158 | 4.080 36.188 10.484 1.00 20.00 | B C |
| ATOM | 4367 CG LEU H 158 | 4.493 35.927 9.034 1.00 20.00 | B C |
| ATOM | 4368 CD1 LEU H 158 | 4.688 37.237 8.287 1.00 20.00 | B C |
| ATOM | 4369 CD2 LEU H 158 | 5.754 35.079 8.976 1.00 20.00 | B C |
| ATOM | 4370 C LEU H 158 | 3.589 35.334 12.794 1.00 54.47 | B C |
| ATOM | 4371 O LEU H 158 | 4.512 35.127 13.582 1.00 49.26 | B O |
| ATOM | 4372 N HIS H 159 | 2.448 35.754 13.309 1.00 59.45 | B N |
| ATOM | 4373 CA HIS H 159 | 2.473 36.028 14.762 1.00 49.11 | B C |
| ATOM | 4374 CB HIS H 159 | 1.136 36.614 15.221 1.00 20.00 | B C |
| ATOM | 4375 CG HIS H 159 | 0.780 37.903 14.548 1.00 20.00 | B C |
| ATOM | 4376 ND1 HIS H 159 | 1.149 39.132 15.051 1.00 20.00 | B N |
| ATOM | 4377 CE1 HIS H 159 | 0.699 40.085 14.254 1.00 20.00 | B C |
| ATOM | 4378 NE2 HIS H 159 | 0.052 39.519 13.252 1.00 20.00 | B N |
| ATOM | 4379 CD2 HIS H 159 | 0.087 38.155 13.412 1.00 20.00 | B C |
| ATOM | 4380 C HIS H 159 | 2.830 34.775 15.616 1.00 44.09 | B C |
| ATOM | 4381 O HIS H 159 | 3.627 34.822 16.600 1.00 42.13 | B O |
| ATOM | 4382 N LEU H 160 | 2.261 33.646 15.207 1.00 37.55 | B N |
| ATOM | 4383 CA LEU H 160 | 2.402 32.391 15.934 1.00 43.52 | B C |
| ATOM | 4384 CB LEU H 160 | 1.521 31.310 15.302 1.00 20.00 | B C |
| ATOM | 4385 CG LEU H 160 | 0.018 31.596 15.268 1.00 20.00 | B C |
| ATOM | 4386 CD1 LEU H 160 | −0.734 30.443 14.620 1.00 20.00 | B C |
| ATOM | 4387 CD2 LEU H 160 | −0.509 31.865 16.668 1.00 20.00 | B C |
| ATOM | 4388 C LEU H 160 | 3.839 31.887 16.044 1.00 47.22 | B C |
| ATOM | 4389 O LEU H 160 | 4.233 31.383 17.091 1.00 43.25 | B O |
| ATOM | 4390 N GLU H 161 | 4.620 32.011 14.976 1.00 40.88 | B N |
| ATOM | 4391 CA GLU H 161 | 5.996 31.524 15.008 1.00 40.61 | B C |
| ATOM | 4392 CB GLU H 161 | 6.644 31.658 13.628 1.00 20.00 | B C |
| ATOM | 4393 CG GLU H 161 | 5.936 30.878 12.532 1.00 20.00 | B C |
| ATOM | 4394 CD GLU H 161 | 6.606 31.031 11.181 1.00 20.00 | B C |
| ATOM | 4395 OE1 GLU H 161 | 6.113 30.437 10.200 1.00 20.00 | B O |
| ATOM | 4396 OE2 GLU H 161 | 7.628 31.745 11.101 1.00 20.00 | B O |

APPENDIX-continued (APPENDIX discloses SEQ ID NOS 29-32, 29-32 and 29-32, respectively, in order of appearance)

| | | | |
|---|---|---|---|
| ATOM | 4397 C GLU H 161 | 6.833 32.259 16.054 1.00 39.76 | B C |
| ATOM | 4398 O GLU H 161 | 7.606 31.642 16.795 1.00 44.02 | B O |
| ATOM | 4399 N GLY H 162 | 6.679 33.566 16.211 1.00 34.18 | B N |
| ATOM | 4400 CA GLY H 162 | 7.497 34.204 17.230 1.00 35.01 | B C |
| ATOM | 4401 C GLY H 162 | 7.170 33.593 18.586 1.00 34.86 | B C |
| ATOM | 4402 O GLY H 162 | 8.065 33.226 19.372 1.00 47.81 | B O |
| ATOM | 4403 N GLU H 163 | 5.875 33.431 18.838 1.00 40.78 | B N |
| ATOM | 4404 CA GLU H 163 | 5.403 32.797 20.058 1.00 37.20 | B C |
| ATOM | 4405 CB GLU H 163 | 3.877 32.847 20.137 1.00 20.00 | B C |
| ATOM | 4406 CG GLU H 163 | 3.301 34.254 20.134 1.00 20.00 | B C |
| ATOM | 4407 CD GLU H 163 | 1.788 34.264 20.214 1.00 20.00 | B C |
| ATOM | 4408 OE1 GLU H 163 | 1.199 35.365 20.219 1.00 20.00 | B O |
| ATOM | 4409 OE2 GLU H 163 | 1.186 33.171 20.273 1.00 20.00 | B O |
| ATOM | 4410 C GLU H 163 | 5.884 31.355 20.065 1.00 46.12 | B C |
| ATOM | 4411 O GLU H 163 | 6.295 30.824 21.098 1.00 58.66 | B O |
| ATOM | 4412 N VAL H 164 | 5.832 30.731 18.893 1.00 42.23 | B N |
| ATOM | 4413 CA VAL H 164 | 6.270 29.353 18.740 1.00 35.45 | B C |
| ATOM | 4414 CB VAL H 164 | 6.021 28.836 17.311 1.00 20.00 | B C |
| ATOM | 4415 CG1 VAL H 164 | 6.488 27.394 17.181 1.00 20.00 | B C |
| ATOM | 4416 CG2 VAL H 164 | 4.549 28.962 16.951 1.00 20.00 | B C |
| ATOM | 4417 C VAL H 164 | 7.753 29.241 19.061 1.00 46.32 | B C |
| ATOM | 4418 O VAL H 164 | 8.180 28.290 19.709 1.00 45.08 | B O |
| ATOM | 4419 N ASN H 165 | 8.536 30.217 18.611 1.00 40.82 | B N |
| ATOM | 4420 CA ASN H 165 | 9.966 30.227 18.891 1.00 46.48 | B C |
| ATOM | 4421 CB ASN H 165 | 10.653 31.372 18.145 1.00 20.00 | B C |
| ATOM | 4422 CG ASN H 165 | 10.488 31.270 16.642 1.00 20.00 | B C |
| ATOM | 4423 OD1 ASN H 165 | 10.982 32.113 15.893 1.00 20.00 | B O |
| ATOM | 4424 ND2 ASN H 165 | 9.792 30.232 16.192 1.00 20.00 | B N |
| ATOM | 4425 C ASN H 165 | 10.227 30.342 20.389 1.00 50.90 | B C |
| ATOM | 4426 O ASN H 165 | 11.099 29.655 20.941 1.00 47.11 | B O |
| ATOM | 4427 N LYS H 166 | 9.453 31.198 21.052 1.00 48.36 | B N |
| ATOM | 4428 CA LYS H 166 | 9.605 31.351 22.495 1.00 38.71 | B C |
| ATOM | 4429 CB LYS H 166 | 8.692 32.461 23.019 1.00 20.00 | B C |
| ATOM | 4430 CG LYS H 166 | 8.968 33.828 22.414 1.00 20.00 | B C |
| ATOM | 4431 CD LYS H 166 | 8.030 34.881 22.980 1.00 20.00 | B C |
| ATOM | 4432 CE LYS H 166 | 8.306 36.249 22.376 1.00 20.00 | B C |
| ATOM | 4433 NZ LYS H 166 | 7.396 37.292 22.923 1.00 20.00 | B N |
| ATOM | 4434 C LYS H 166 | 9.284 30.029 23.192 1.00 45.07 | B C |
| ATOM | 4435 O LYS H 166 | 9.977 29.609 24.131 1.00 56.09 | B O |
| ATOM | 4436 N ILE H 167 | 8.238 29.366 22.709 1.00 42.02 | B N |
| ATOM | 4437 CA ILE H 167 | 7.817 28.091 23.272 1.00 43.86 | B C |
| ATOM | 4438 CB ILE H 167 | 6.527 27.577 22.607 1.00 20.00 | B C |
| ATOM | 4439 CG1 ILE H 167 | 5.388 28.580 22.807 1.00 20.00 | B C |
| ATOM | 4440 CD1 ILE H 167 | 4.079 28.150 22.181 1.00 20.00 | B C |
| ATOM | 4441 CG2 ILE H 167 | 6.147 26.214 23.164 1.00 20.00 | B C |
| ATOM | 4442 C ILE H 167 | 8.916 27.053 23.099 1.00 49.02 | B C |
| ATOM | 4443 O ILE H 167 | 9.178 26.260 23.998 1.00 37.71 | B O |
| ATOM | 4444 N LYS H 168 | 9.557 27.068 21.935 1.00 33.87 | B N |
| ATOM | 4445 CA LYS H 168 | 10.644 26.146 21.640 1.00 35.11 | B C |
| ATOM | 4446 CB LYS H 168 | 11.103 26.304 20.189 1.00 20.00 | B C |
| ATOM | 4447 CG LYS H 168 | 10.014 26.040 19.162 1.00 20.00 | B C |
| ATOM | 4448 CD LYS H 168 | 10.535 26.220 17.746 1.00 20.00 | B C |
| ATOM | 4449 CE LYS H 168 | 9.445 25.959 16.719 1.00 20.00 | B C |
| ATOM | 4450 NZ LYS H 168 | 9.941 26.134 15.326 1.00 20.00 | B N |
| ATOM | 4451 C LYS H 168 | 11.813 26.380 22.588 1.00 39.27 | B C |
| ATOM | 4452 O LYS H 168 | 12.422 25.429 23.078 1.00 32.39 | B O |
| ATOM | 4453 N SER H 169 | 12.121 27.647 22.854 1.00 41.30 | B N |
| ATOM | 4454 CA SER H 169 | 13.203 27.963 23.783 1.00 43.23 | B C |
| ATOM | 4455 CB SER H 169 | 13.446 29.472 23.832 1.00 20.00 | B C |
| ATOM | 4456 OG SER H 169 | 12.284 30.162 24.259 1.00 20.00 | B O |
| ATOM | 4457 C SER H 169 | 12.865 27.436 25.178 1.00 41.44 | B C |
| ATOM | 4458 O SER H 169 | 13.723 26.871 25.883 1.00 44.82 | B O |
| ATOM | 4459 N ALA H 170 | 11.604 27.605 25.566 1.00 39.78 | B N |
| ATOM | 4460 CA ALA H 170 | 11.161 27.131 26.870 1.00 41.01 | B C |
| ATOM | 4461 CB ALA H 170 | 9.720 27.541 27.124 1.00 20.00 | B C |
| ATOM | 4462 C ALA H 170 | 11.308 25.615 26.948 1.00 46.04 | B C |
| ATOM | 4463 O ALA H 170 | 11.743 25.072 27.964 1.00 46.67 | B O |
| ATOM | 4464 N LEU H 171 | 10.955 24.940 25.859 1.00 34.26 | B N |
| ATOM | 4465 CA LEU H 171 | 11.050 23.489 25.782 1.00 37.69 | B C |
| ATOM | 4466 CB LEU H 171 | 10.458 22.982 24.466 1.00 20.00 | B C |
| ATOM | 4467 CG LEU H 171 | 8.984 23.305 24.216 1.00 20.00 | B C |
| ATOM | 4468 CD1 LEU H 171 | 8.529 22.743 22.878 1.00 20.00 | B C |
| ATOM | 4469 CD2 LEU H 171 | 8.118 22.773 25.348 1.00 20.00 | B C |
| ATOM | 4470 C LEU H 171 | 12.499 23.044 25.912 1.00 44.67 | B C |
| ATOM | 4471 O LEU H 171 | 12.797 22.054 26.579 1.00 34.27 | B O |
| ATOM | 4472 N LEU H 172 | 13.400 23.783 25.272 1.00 34.80 | B N |
| ATOM | 4473 CA LEU H 172 | 14.817 23.464 25.344 1.00 28.87 | B C |

APPENDIX-continued (APPENDIX discloses SEQ ID NOS 29-32, 29-32 and 29-32, respectively, in order of appearance)

| | | | | | | | | | |
|---|---|---|---|---|---|---|---|---|---|
| ATOM | 4474 CB LEU H 172 | 15.626 24.402 24.447 1.00 20.00 | B C |
| ATOM | 4475 CG LEU H 172 | 15.281 24.379 22.956 1.00 20.00 | B C |
| ATOM | 4476 CD1 LEU H 172 | 16.158 25.355 22.186 1.00 20.00 | B C |
| ATOM | 4477 CD2 LEU H 172 | 15.416 22.972 22.395 1.00 20.00 | B C |
| ATOM | 4478 C LEU H 172 | 15.291 23.577 26.786 1.00 29.90 | B C |
| ATOM | 4479 O LEU H 172 | 16.022 22.714 27.272 1.00 41.09 | B O |
| ATOM | 4480 N SER H 173 | 14.862 24.629 27.480 1.00 35.08 | B N |
| ATOM | 4481 CA SER H 173 | 15.184 24.754 28.902 1.00 35.53 | B C |
| ATOM | 4482 CB SER H 173 | 14.727 26.109 29.442 1.00 20.00 | B C |
| ATOM | 4483 OG SER H 173 | 13.328 26.272 29.294 1.00 20.00 | B O |
| ATOM | 4484 C SER H 173 | 14.506 23.618 29.673 1.00 35.07 | B C |
| ATOM | 4485 O SER H 173 | 15.056 23.037 30.609 1.00 51.28 | B O |
| ATOM | 4486 N THR H 174 | 13.286 23.341 29.234 1.00 46.35 | B N |
| ATOM | 4487 CA THR H 174 | 12.335 22.383 29.786 1.00 43.83 | B C |
| ATOM | 4488 CB THR H 174 | 10.885 22.764 29.429 1.00 20.00 | B C |
| ATOM | 4489 OG1 THR H 174 | 10.725 22.762 28.004 1.00 20.00 | B O |
| ATOM | 4490 CG2 THR H 174 | 10.547 24.144 29.971 1.00 20.00 | B C |
| ATOM | 4491 C THR H 174 | 12.616 20.979 29.263 1.00 52.54 | B C |
| ATOM | 4492 O THR H 174 | 12.523 20.726 28.063 1.00 64.10 | B O |
| ATOM | 4493 N ASN H 175 | 12.974 20.071 30.165 1.00 55.57 | B N |
| ATOM | 4494 CA ASN H 175 | 13.072 18.660 29.817 1.00 40.58 | B C |
| ATOM | 4495 CB ASN H 175 | 13.942 17.915 30.831 1.00 20.00 | B C |
| ATOM | 4496 CG ASN H 175 | 15.405 18.303 30.740 1.00 20.00 | B C |
| ATOM | 4497 OD1 ASN H 175 | 15.868 18.788 29.708 1.00 20.00 | B O |
| ATOM | 4498 ND2 ASN H 175 | 16.139 18.099 31.827 1.00 20.00 | B N |
| ATOM | 4499 C ASN H 175 | 11.695 18.009 29.714 1.00 43.65 | B C |
| ATOM | 4500 O ASN H 175 | 10.972 17.912 30.705 1.00 53.11 | B O |
| ATOM | 4501 N LYS H 176 | 11.296 17.666 28.491 1.00 44.89 | B N |
| ATOM | 4502 CA LYS H 176 | 9.986 17.068 28.250 1.00 46.42 | B C |
| ATOM | 4503 CB LYS H 176 | 8.873 18.052 28.618 1.00 20.00 | B C |
| ATOM | 4504 CG LYS H 176 | 8.873 18.468 30.088 1.00 20.00 | B C |
| ATOM | 4505 CD LYS H 176 | 7.844 19.557 30.362 1.00 20.00 | B C |
| ATOM | 4506 CE LYS H 176 | 7.773 19.904 31.841 1.00 20.00 | B C |
| ATOM | 4507 NZ LYS H 176 | 6.701 20.899 32.121 1.00 20.00 | B N |
| ATOM | 4508 C LYS H 176 | 9.829 16.596 26.806 1.00 45.00 | B C |
| ATOM | 4509 O LYS H 176 | 10.272 17.264 25.871 1.00 60.64 | B O |
| ATOM | 4510 N ALA H 177 | 9.245 15.415 26.634 1.00 46.01 | B N |
| ATOM | 4511 CA ALA H 177 | 8.914 14.913 25.306 1.00 43.65 | B C |
| ATOM | 4512 CB ALA H 177 | 8.530 13.442 25.374 1.00 20.00 | B C |
| ATOM | 4513 C ALA H 177 | 7.789 15.731 24.686 1.00 41.42 | B C |
| ATOM | 4514 O ALA H 177 | 7.894 16.184 23.547 1.00 45.37 | B O |
| ATOM | 4515 N VAL H 178 | 6.736 15.960 25.463 1.00 35.70 | B N |
| ATOM | 4516 CA VAL H 178 | 5.642 16.820 25.037 1.00 43.93 | B C |
| ATOM | 4517 CB VAL H 178 | 4.383 15.999 24.710 1.00 20.00 | B C |
| ATOM | 4518 CG1 VAL H 178 | 3.229 16.919 24.341 1.00 20.00 | B C |
| ATOM | 4519 CG2 VAL H 178 | 4.672 15.014 23.585 1.00 20.00 | B C |
| ATOM | 4520 C VAL H 178 | 5.313 17.836 26.124 1.00 34.16 | B C |
| ATOM | 4521 O VAL H 178 | 5.395 17.527 27.311 1.00 44.45 | B O |
| ATOM | 4522 N VAL H 179 | 5.028 19.069 25.717 1.00 44.87 | B N |
| ATOM | 4523 CA VAL H 179 | 4.818 20.155 26.667 1.00 38.47 | B C |
| ATOM | 4524 CB VAL H 179 | 6.150 20.766 27.131 1.00 20.00 | B C |
| ATOM | 4525 CG1 VAL H 179 | 5.908 21.808 28.221 1.00 20.00 | B C |
| ATOM | 4526 CG2 VAL H 179 | 7.097 19.678 27.609 1.00 20.00 | B C |
| ATOM | 4527 C VAL H 179 | 3.967 21.265 26.070 1.00 44.79 | B C |
| ATOM | 4528 O VAL H 179 | 4.226 21.727 24.959 1.00 51.88 | B O |
| ATOM | 4529 N SER H 180 | 3.025 21.765 26.862 1.00 45.23 | B N |
| ATOM | 4530 CA SER H 180 | 2.226 22.915 26.463 1.00 48.99 | B C |
| ATOM | 4531 CB SER H 180 | 0.976 23.033 27.340 1.00 20.00 | B C |
| ATOM | 4532 OG SER H 180 | 1.321 23.322 28.683 1.00 20.00 | B O |
| ATOM | 4533 C SER H 180 | 3.047 24.198 26.532 1.00 48.15 | B C |
| ATOM | 4534 O SER H 180 | 3.568 24.553 27.589 1.00 60.42 | B O |
| ATOM | 4535 N LEU H 181 | 3.261 24.821 25.378 1.00 42.42 | B N |
| ATOM | 4536 CA LEU H 181 | 3.872 26.143 25.325 1.00 43.22 | B C |
| ATOM | 4537 CB LEU H 181 | 4.252 26.498 23.888 1.00 20.00 | B C |
| ATOM | 4538 CG LEU H 181 | 5.279 25.577 23.233 1.00 20.00 | B C |
| ATOM | 4539 CD1 LEU H 181 | 5.583 26.043 21.818 1.00 20.00 | B C |
| ATOM | 4540 CD2 LEU H 181 | 6.541 25.519 24.073 1.00 20.00 | B C |
| ATOM | 4541 C LEU H 181 | 2.929 27.199 25.884 1.00 29.14 | B C |
| ATOM | 4542 O LEU H 181 | 1.891 27.494 25.291 1.00 43.42 | B O |
| ATOM | 4543 N SER H 182 | 3.271 27.735 27.051 1.00 41.83 | B N |
| ATOM | 4544 CA SER H 182 | 2.365 28.619 27.770 1.00 53.52 | B C |
| ATOM | 4545 CB SER H 182 | 2.034 28.053 29.152 1.00 20.00 | B C |
| ATOM | 4546 OG SER H 182 | 3.184 28.019 29.978 1.00 20.00 | B O |
| ATOM | 4547 C SER H 182 | 2.914 30.036 27.891 1.00 44.76 | B C |
| ATOM | 4548 O SER H 182 | 4.095 30.236 28.178 1.00 37.73 | B O |
| ATOM | 4549 N ASN H 183 | 2.072 31.008 27.556 1.00 47.84 | B N |
| ATOM | 4550 CA ASN H 183 | 2.258 32.384 27.996 1.00 59.45 | B C |

APPENDIX-continued (APPENDIX discloses SEQ ID NOS 29-32, 29-32 and 29-32, respectively, in order of appearance)

| | | | | | | | | | | | | |
|---|---|---|---|---|---|---|---|---|---|---|---|---|
| ATOM | 4551 | CB | ASN | H | 183 | 2.304 | 33.316 | 26.782 | 1.00 | 20.00 | B | C |
| ATOM | 4552 | CG | ASN | H | 183 | 3.512 | 33.066 | 25.897 | 1.00 | 20.00 | B | C |
| ATOM | 4553 | OD1 | ASN | H | 183 | 4.574 | 32.671 | 26.379 | 1.00 | 20.00 | B | O |
| ATOM | 4554 | ND2 | ASN | H | 183 | 3.384 | 33.386 | 24.615 | 1.00 | 20.00 | B | N |
| ATOM | 4555 | C | ASN | H | 183 | 1.117 | 32.791 | 28.924 | 1.00 | 75.41 | B | C |
| ATOM | 4556 | O | ASN | H | 183 | −0.008 | 32.318 | 28.769 | 1.00 | 102.31 | B | O |
| ATOM | 4557 | N | GLY | H | 184 | 1.432 | 33.563 | 29.959 | 1.00 | 79.30 | B | N |
| ATOM | 4558 | CA | GLY | H | 184 | 0.435 | 33.947 | 30.957 | 1.00 | 88.92 | B | C |
| ATOM | 4559 | C | GLY | H | 184 | −0.954 | 33.397 | 30.674 | 1.00 | 101.85 | B | C |
| ATOM | 4560 | O | GLY | H | 184 | −1.760 | 34.037 | 29.999 | 1.00 | 113.48 | B | O |
| ATOM | 4561 | N | VAL | H | 185 | −1.218 | 32.190 | 31.167 | 1.00 | 86.84 | B | N |
| ATOM | 4562 | CA | VAL | H | 185 | −2.573 | 31.636 | 31.236 | 1.00 | 81.80 | B | C |
| ATOM | 4563 | CB | VAL | H | 185 | −3.558 | 32.579 | 31.958 | 1.00 | 20.00 | B | C |
| ATOM | 4564 | CG1 | VAL | H | 185 | −4.974 | 32.022 | 31.887 | 1.00 | 20.00 | B | C |
| ATOM | 4565 | CG2 | VAL | H | 185 | −3.135 | 32.783 | 33.405 | 1.00 | 20.00 | B | C |
| ATOM | 4566 | C | VAL | H | 185 | −3.164 | 31.228 | 29.887 | 1.00 | 81.69 | B | C |
| ATOM | 4567 | O | VAL | H | 185 | −4.347 | 30.900 | 29.801 | 1.00 | 99.84 | B | O |
| ATOM | 4568 | N | SER | H | 186 | −2.336 | 31.193 | 28.848 | 1.00 | 70.63 | B | N |
| ATOM | 4569 | CA | SER | H | 186 | −2.819 | 30.830 | 27.519 | 1.00 | 72.29 | B | C |
| ATOM | 4570 | CB | SER | H | 186 | −3.084 | 32.081 | 26.679 | 1.00 | 20.00 | B | C |
| ATOM | 4571 | OG | SER | H | 186 | −1.884 | 32.787 | 26.420 | 1.00 | 20.00 | B | O |
| ATOM | 4572 | C | SER | H | 186 | −1.865 | 29.891 | 26.789 | 1.00 | 62.99 | B | C |
| ATOM | 4573 | O | SER | H | 186 | −0.655 | 30.115 | 26.765 | 1.00 | 58.35 | B | O |
| ATOM | 4574 | N | VAL | H | 187 | −2.422 | 28.851 | 26.177 | 1.00 | 66.49 | B | N |
| ATOM | 4575 | CA | VAL | H | 187 | −1.627 | 27.877 | 25.438 | 1.00 | 57.36 | B | C |
| ATOM | 4576 | CB | VAL | H | 187 | −2.284 | 26.484 | 25.457 | 1.00 | 20.00 | B | C |
| ATOM | 4577 | CG1 | VAL | H | 187 | −1.504 | 25.516 | 24.583 | 1.00 | 20.00 | B | C |
| ATOM | 4578 | CG2 | VAL | H | 187 | −2.383 | 25.963 | 26.883 | 1.00 | 20.00 | B | C |
| ATOM | 4579 | C | VAL | H | 187 | −1.432 | 28.317 | 23.991 | 1.00 | 53.67 | B | C |
| ATOM | 4580 | O | VAL | H | 187 | −2.401 | 28.531 | 23.262 | 1.00 | 50.10 | B | O |
| ATOM | 4581 | N | LEU | H | 188 | −0.176 | 28.476 | 23.588 | 1.00 | 43.20 | B | N |
| ATOM | 4582 | CA | LEU | H | 188 | 0.143 | 28.854 | 22.217 | 1.00 | 41.76 | B | C |
| ATOM | 4583 | CB | LEU | H | 188 | 1.487 | 29.581 | 22.160 | 1.00 | 20.00 | B | C |
| ATOM | 4584 | CG | LEU | H | 188 | 1.549 | 30.938 | 22.862 | 1.00 | 20.00 | B | C |
| ATOM | 4585 | CD1 | LEU | H | 188 | 2.957 | 31.507 | 22.799 | 1.00 | 20.00 | B | C |
| ATOM | 4586 | CD2 | LEU | H | 188 | 0.548 | 31.907 | 22.250 | 1.00 | 20.00 | B | C |
| ATOM | 4587 | C | LEU | H | 188 | 0.166 | 27.634 | 21.304 | 1.00 | 44.75 | B | C |
| ATOM | 4588 | O | LEU | H | 188 | −0.074 | 27.743 | 20.102 | 1.00 | 45.28 | B | O |
| ATOM | 4589 | N | THR | H | 189 | 0.390 | 26.466 | 21.897 | 1.00 | 39.28 | B | N |
| ATOM | 4590 | CA | THR | H | 189 | 0.552 | 25.235 | 21.133 | 1.00 | 36.51 | B | C |
| ATOM | 4591 | CB | THR | H | 189 | 1.229 | 25.498 | 19.774 | 1.00 | 20.00 | B | C |
| ATOM | 4592 | OG1 | THR | H | 189 | 2.554 | 26.001 | 19.986 | 1.00 | 20.00 | B | O |
| ATOM | 4593 | CG2 | THR | H | 189 | 0.430 | 26.512 | 18.968 | 1.00 | 20.00 | B | C |
| ATOM | 4594 | C | THR | H | 189 | 1.362 | 24.208 | 21.926 | 1.00 | 45.83 | B | C |
| ATOM | 4595 | O | THR | H | 189 | 1.419 | 24.267 | 23.154 | 1.00 | 42.57 | B | O |
| ATOM | 4596 | N | SER | H | 190 | 1.947 | 23.241 | 21.226 | 1.00 | 40.44 | B | N |
| ATOM | 4597 | CA | SER | H | 190 | 2.691 | 22.171 | 21.881 | 1.00 | 41.82 | B | C |
| ATOM | 4598 | CB | SER | H | 190 | 2.022 | 20.815 | 21.632 | 1.00 | 20.00 | B | C |
| ATOM | 4599 | OG | SER | H | 190 | 2.225 | 20.376 | 20.300 | 1.00 | 20.00 | B | O |
| ATOM | 4600 | C | SER | H | 190 | 4.152 | 22.141 | 21.437 | 1.00 | 33.81 | B | C |
| ATOM | 4601 | O | SER | H | 190 | 4.473 | 22.505 | 20.306 | 1.00 | 49.61 | B | O |
| ATOM | 4602 | N | LYS | H | 191 | 5.040 | 21.855 | 22.385 | 1.00 | 37.37 | B | N |
| ATOM | 4603 | CA | LYS | H | 191 | 6.463 | 21.711 | 22.098 | 1.00 | 41.23 | B | C |
| ATOM | 4604 | CB | LYS | H | 191 | 7.285 | 22.617 | 23.021 | 1.00 | 20.00 | B | C |
| ATOM | 4605 | CG | LYS | H | 191 | 7.104 | 24.102 | 22.750 | 1.00 | 20.00 | B | C |
| ATOM | 4606 | CD | LYS | H | 191 | 7.981 | 24.949 | 23.658 | 1.00 | 20.00 | B | C |
| ATOM | 4607 | CE | LYS | H | 191 | 7.790 | 26.435 | 23.369 | 1.00 | 20.00 | B | C |
| ATOM | 4608 | NZ | LYS | H | 191 | 8.364 | 27.306 | 24.434 | 1.00 | 20.00 | B | N |
| ATOM | 4609 | C | LYS | H | 191 | 6.906 | 20.260 | 22.268 | 1.00 | 35.03 | B | C |
| ATOM | 4610 | O | LYS | H | 191 | 6.828 | 19.710 | 23.365 | 1.00 | 40.06 | B | O |
| ATOM | 4611 | N | VAL | H | 192 | 7.443 | 19.670 | 21.205 | 1.00 | 33.70 | B | N |
| ATOM | 4612 | CA | VAL | H | 192 | 7.787 | 18.250 | 21.221 | 1.00 | 27.61 | B | C |
| ATOM | 4613 | CB | VAL | H | 192 | 6.974 | 17.456 | 20.182 | 1.00 | 20.00 | B | C |
| ATOM | 4614 | CG1 | VAL | H | 192 | 7.313 | 15.975 | 20.263 | 1.00 | 20.00 | B | C |
| ATOM | 4615 | CG2 | VAL | H | 192 | 5.487 | 17.679 | 20.391 | 1.00 | 20.00 | B | C |
| ATOM | 4616 | C | VAL | H | 192 | 9.277 | 18.011 | 20.985 | 1.00 | 31.74 | B | C |
| ATOM | 4617 | O | VAL | H | 192 | 9.931 | 18.771 | 20.272 | 1.00 | 25.58 | B | O |
| ATOM | 4618 | N | LEU | H | 193 | 9.792 | 16.921 | 21.550 | 1.00 | 28.88 | B | N |
| ATOM | 4619 | CA | LEU | H | 193 | 11.190 | 16.530 | 21.360 | 1.00 | 34.36 | B | C |
| ATOM | 4620 | CB | LEU | H | 193 | 12.061 | 17.069 | 22.505 | 1.00 | 20.00 | B | C |
| ATOM | 4621 | CG | LEU | H | 193 | 12.332 | 18.577 | 22.614 | 1.00 | 20.00 | B | C |
| ATOM | 4622 | CD1 | LEU | H | 193 | 12.987 | 18.914 | 23.949 | 1.00 | 20.00 | B | C |
| ATOM | 4623 | CD2 | LEU | H | 193 | 13.194 | 19.076 | 21.459 | 1.00 | 20.00 | B | C |
| ATOM | 4624 | C | LEU | H | 193 | 11.335 | 15.008 | 21.281 | 1.00 | 33.03 | B | C |
| ATOM | 4625 | O | LEU | H | 193 | 11.373 | 14.331 | 22.310 | 1.00 | 44.93 | B | O |
| ATOM | 4626 | N | ASP | H | 194 | 11.579 | 14.498 | 20.077 | 1.00 | 35.09 | B | N |
| ATOM | 4627 | CA | ASP | H | 194 | 11.209 | 13.127 | 19.730 | 1.00 | 41.39 | B | C |

APPENDIX-continued (APPENDIX discloses SEQ ID NOS 29-32, 29-32 and 29-32, respectively, in order of appearance)

| | | | | | | | | | | | |
|---|---|---|---|---|---|---|---|---|---|---|---|
| ATOM | 4628 | CB | ASP | H | 194 | 11.269 | 12.925 | 18.214 | 1.00 | 20.00 | B C |
| ATOM | 4629 | CG | ASP | H | 194 | 10.132 | 13.626 | 17.485 | 1.00 | 20.00 | B C |
| ATOM | 4630 | OD1 | ASP | H | 194 | 9.081 | 13.873 | 18.115 | 1.00 | 20.00 | B O |
| ATOM | 4631 | OD2 | ASP | H | 194 | 10.305 | 13.969 | 16.296 | 1.00 | 20.00 | B O |
| ATOM | 4632 | C | ASP | H | 194 | 12.091 | 12.100 | 20.433 | 1.00 | 38.04 | B C |
| ATOM | 4633 | O | ASP | H | 194 | 11.796 | 10.904 | 20.429 | 1.00 | 48.03 | B O |
| ATOM | 4634 | N | LEU | H | 195 | 13.174 | 12.576 | 21.039 | 1.00 | 43.64 | B N |
| ATOM | 4635 | CA | LEU | H | 195 | 14.206 | 11.690 | 21.555 | 1.00 | 35.97 | B C |
| ATOM | 4636 | CB | LEU | H | 195 | 15.532 | 11.935 | 20.832 | 1.00 | 20.00 | B C |
| ATOM | 4637 | CG | LEU | H | 195 | 15.563 | 11.586 | 19.340 | 1.00 | 20.00 | B C |
| ATOM | 4638 | CD1 | LEU | H | 195 | 16.947 | 11.852 | 18.750 | 1.00 | 20.00 | B C |
| ATOM | 4639 | CD2 | LEU | H | 195 | 15.118 | 10.144 | 19.081 | 1.00 | 20.00 | B C |
| ATOM | 4640 | C | LEU | H | 195 | 14.386 | 11.839 | 23.063 | 1.00 | 43.63 | B C |
| ATOM | 4641 | O | LEU | H | 195 | 15.068 | 11.036 | 23.699 | 1.00 | 34.71 | B O |
| ATOM | 4642 | N | ASN | H | 196 | 13.689 | 12.808 | 23.645 | 1.00 | 44.30 | B N |
| ATOM | 4643 | CA | ASN | H | 196 | 13.886 | 13.151 | 25.047 | 1.00 | 42.38 | B C |
| ATOM | 4644 | CB | ASN | H | 196 | 12.955 | 14.290 | 25.454 | 1.00 | 20.00 | B C |
| ATOM | 4645 | CG | ASN | H | 196 | 13.376 | 15.618 | 24.868 | 1.00 | 20.00 | B C |
| ATOM | 4646 | OD1 | ASN | H | 196 | 14.538 | 15.815 | 24.513 | 1.00 | 20.00 | B O |
| ATOM | 4647 | ND2 | ASN | H | 196 | 12.439 | 16.555 | 24.800 | 1.00 | 20.00 | B N |
| ATOM | 4648 | C | ASN | H | 196 | 13.721 | 11.972 | 26.000 | 1.00 | 43.66 | B C |
| ATOM | 4649 | O | ASN | H | 196 | 14.499 | 11.814 | 26.940 | 1.00 | 33.62 | B O |
| ATOM | 4650 | N | ASN | H | 197 | 12.649 | 11.208 | 25.817 | 1.00 | 34.31 | B N |
| ATOM | 4651 | CA | ASN | H | 197 | 12.370 | 10.074 | 26.691 | 1.00 | 38.83 | B C |
| ATOM | 4652 | CB | ASN | H | 197 | 11.043 | 9.417 | 26.318 | 1.00 | 20.00 | B C |
| ATOM | 4653 | CG | ASN | H | 197 | 9.848 | 10.251 | 26.729 | 1.00 | 20.00 | B C |
| ATOM | 4654 | OD1 | ASN | H | 197 | 9.957 | 11.129 | 27.585 | 1.00 | 20.00 | B O |
| ATOM | 4655 | ND2 | ASN | H | 197 | 8.722 | 10.042 | 26.059 | 1.00 | 20.00 | B N |
| ATOM | 4656 | C | ASN | H | 197 | 13.492 | 9.042 | 26.685 | 1.00 | 39.90 | B C |
| ATOM | 4657 | O | ASN | H | 197 | 14.026 | 8.687 | 27.735 | 1.00 | 39.04 | B O |
| ATOM | 4658 | N | TYR | H | 198 | 13.871 | 8.590 | 25.495 | 1.00 | 35.09 | B N |
| ATOM | 4659 | CA | TYR | H | 198 | 14.992 | 7.672 | 25.355 | 1.00 | 41.03 | B C |
| ATOM | 4660 | CB | TYR | H | 198 | 15.246 | 7.355 | 23.882 | 1.00 | 20.00 | B C |
| ATOM | 4661 | CG | TYR | H | 198 | 14.109 | 6.617 | 23.218 | 1.00 | 20.00 | B C |
| ATOM | 4662 | CD1 | TYR | H | 198 | 14.014 | 5.235 | 23.294 | 1.00 | 20.00 | B C |
| ATOM | 4663 | CE1 | TYR | H | 198 | 12.963 | 4.558 | 22.712 | 1.00 | 20.00 | B C |
| ATOM | 4664 | CZ | TYR | H | 198 | 11.999 | 5.265 | 22.024 | 1.00 | 20.00 | B C |
| ATOM | 4665 | OH | TYR | H | 198 | 10.967 | 4.598 | 21.403 | 1.00 | 20.00 | B O |
| ATOM | 4666 | CE2 | TYR | H | 198 | 12.073 | 6.638 | 21.934 | 1.00 | 20.00 | B C |
| ATOM | 4667 | CD2 | TYR | H | 198 | 13.120 | 7.305 | 22.533 | 1.00 | 20.00 | B C |
| ATOM | 4668 | C | TYR | H | 198 | 16.252 | 8.234 | 26.002 | 1.00 | 43.65 | B C |
| ATOM | 4669 | O | TYR | H | 198 | 16.940 | 7.533 | 26.744 | 1.00 | 52.37 | B O |
| ATOM | 4670 | N | ILE | H | 199 | 16.464 | 9.537 | 25.831 | 1.00 | 35.86 | B N |
| ATOM | 4671 | CA | ILE | H | 199 | 17.634 | 10.219 | 26.386 | 1.00 | 45.39 | B C |
| ATOM | 4672 | CB | ILE | H | 199 | 17.722 | 11.682 | 25.904 | 1.00 | 20.00 | B C |
| ATOM | 4673 | CG1 | ILE | H | 199 | 18.102 | 11.741 | 24.425 | 1.00 | 20.00 | B C |
| ATOM | 4674 | CD1 | ILE | H | 199 | 18.674 | 13.078 | 24.004 | 1.00 | 20.00 | B C |
| ATOM | 4675 | CG2 | ILE | H | 199 | 18.730 | 12.457 | 26.735 | 1.00 | 20.00 | B C |
| ATOM | 4676 | C | ILE | H | 199 | 17.639 | 10.200 | 27.912 | 1.00 | 37.89 | B C |
| ATOM | 4677 | O | ILE | H | 199 | 18.667 | 9.941 | 28.538 | 1.00 | 45.28 | B O |
| ATOM | 4678 | N | ASP | H | 200 | 16.492 | 10.508 | 28.505 | 1.00 | 37.36 | B N |
| ATOM | 4679 | CA | ASP | H | 200 | 16.368 | 10.551 | 29.954 | 1.00 | 46.66 | B C |
| ATOM | 4680 | CB | ASP | H | 200 | 14.992 | 11.080 | 30.354 | 1.00 | 20.00 | B C |
| ATOM | 4681 | CG | ASP | H | 200 | 14.837 | 12.564 | 30.083 | 1.00 | 20.00 | B C |
| ATOM | 4682 | OD1 | ASP | H | 200 | 15.826 | 13.308 | 30.264 | 1.00 | 20.00 | B O |
| ATOM | 4683 | OD2 | ASP | H | 200 | 13.718 | 12.992 | 29.721 | 1.00 | 20.00 | B O |
| ATOM | 4684 | C | ASP | H | 200 | 16.600 | 9.181 | 30.581 | 1.00 | 51.05 | B C |
| ATOM | 4685 | O | ASP | H | 200 | 16.986 | 9.081 | 31.745 | 1.00 | 57.39 | B O |
| ATOM | 4686 | N | LYS | H | 201 | 16.346 | 8.129 | 29.810 | 1.00 | 57.68 | B N |
| ATOM | 4687 | CA | LYS | H | 201 | 16.517 | 6.766 | 30.299 | 1.00 | 44.02 | B C |
| ATOM | 4688 | CB | LYS | H | 201 | 15.747 | 5.778 | 29.423 | 1.00 | 20.00 | B C |
| ATOM | 4689 | CG | LYS | H | 201 | 14.242 | 5.854 | 29.602 | 1.00 | 20.00 | B C |
| ATOM | 4690 | CD | LYS | H | 201 | 13.531 | 4.795 | 28.781 | 1.00 | 20.00 | B C |
| ATOM | 4691 | CE | LYS | H | 201 | 12.030 | 5.042 | 28.737 | 1.00 | 20.00 | B C |
| ATOM | 4692 | NZ | LYS | H | 201 | 11.346 | 4.192 | 27.722 | 1.00 | 20.00 | B N |
| ATOM | 4693 | C | LYS | H | 201 | 17.985 | 6.366 | 30.373 | 1.00 | 43.56 | B C |
| ATOM | 4694 | O | LYS | H | 201 | 18.348 | 5.447 | 31.105 | 1.00 | 51.34 | B O |
| ATOM | 4695 | N | GLN | H | 202 | 18.832 | 7.074 | 29.633 | 1.00 | 46.06 | B N |
| ATOM | 4696 | CA | GLN | H | 202 | 20.216 | 6.648 | 29.445 | 1.00 | 44.95 | B C |
| ATOM | 4697 | CB | GLN | H | 202 | 20.507 | 6.398 | 27.963 | 1.00 | 20.00 | B C |
| ATOM | 4698 | CG | GLN | H | 202 | 19.685 | 5.270 | 27.351 | 1.00 | 20.00 | B C |
| ATOM | 4699 | CD | GLN | H | 202 | 19.894 | 5.134 | 25.853 | 1.00 | 20.00 | B C |
| ATOM | 4700 | OE1 | GLN | H | 202 | 20.323 | 6.075 | 25.184 | 1.00 | 20.00 | B O |
| ATOM | 4701 | NE2 | GLN | H | 202 | 19.513 | 3.984 | 25.309 | 1.00 | 20.00 | B N |
| ATOM | 4702 | C | GLN | H | 202 | 21.245 | 7.616 | 30.044 | 1.00 | 42.35 | B C |
| ATOM | 4703 | O | GLN | H | 202 | 22.376 | 7.224 | 30.335 | 1.00 | 47.00 | B O |
| ATOM | 4704 | N | LEU | H | 203 | 20.852 | 8.874 | 30.228 | 1.00 | 49.55 | B N |

APPENDIX-continued (APPENDIX discloses SEQ ID NOS 29-32, 29-32 and 29-32, respectively, in order of appearance)

| | | | |
|---|---|---|---|
| ATOM | 4705 CA LEU H 203 | 21.762 9.902 30.735 1.00 50.77 | B C |
| ATOM | 4706 CB LEU H 203 | 21.119 11.283 30.618 1.00 20.00 | B C |
| ATOM | 4707 CG LEU H 203 | 20.836 11.775 29.202 1.00 20.00 | B C |
| ATOM | 4708 CD1 LEU H 203 | 20.093 13.100 29.256 1.00 20.00 | B C |
| ATOM | 4709 CD2 LEU H 203 | 22.134 11.910 28.422 1.00 20.00 | B C |
| ATOM | 4710 C LEU H 203 | 22.148 9.656 32.190 1.00 52.51 | B C |
| ATOM | 4711 O LEU H 203 | 21.273 9.564 33.050 1.00 46.02 | B O |
| ATOM | 4712 N LEU H 204 | 23.439 9.786 32.490 1.00 51.45 | B N |
| ATOM | 4713 CA LEU H 204 | 23.928 9.661 33.865 1.00 58.44 | B C |
| ATOM | 4714 CB LEU H 204 | 25.423 9.333 33.885 1.00 20.00 | B C |
| ATOM | 4715 CG LEU H 204 | 25.848 7.919 33.484 1.00 20.00 | B C |
| ATOM | 4716 CD1 LEU H 204 | 27.346 7.764 33.658 1.00 20.00 | B C |
| ATOM | 4717 CD2 LEU H 204 | 25.112 6.874 34.306 1.00 20.00 | B C |
| ATOM | 4718 C LEU H 204 | 23.661 10.930 34.667 1.00 54.99 | B C |
| ATOM | 4719 O LEU H 204 | 23.740 12.035 34.131 1.00 55.13 | B O |
| ATOM | 4720 N PRO H 205 | 23.414 10.775 35.977 1.00 58.64 | B N |
| ATOM | 4721 CA PRO H 205 | 22.981 11.935 36.734 1.00 52.19 | B C |
| ATOM | 4722 CB PRO H 205 | 22.776 11.363 38.137 1.00 20.00 | B C |
| ATOM | 4723 CG PRO H 205 | 23.735 10.190 38.219 1.00 20.00 | B C |
| ATOM | 4724 CD PRO H 205 | 24.191 9.850 36.818 1.00 20.00 | B C |
| ATOM | 4725 C PRO H 205 | 24.112 12.948 36.754 1.00 54.30 | B C |
| ATOM | 4726 O PRO H 205 | 23.898 14.128 37.030 1.00 70.22 | B O |
| ATOM | 4727 N ILE H 206 | 25.316 12.460 36.481 1.00 62.70 | B N |
| ATOM | 4728 CA ILE H 206 | 26.487 13.308 36.354 1.00 68.19 | B C |
| ATOM | 4729 CB ILE H 206 | 27.225 13.445 37.696 1.00 20.00 | B C |
| ATOM | 4730 CG1 ILE H 206 | 26.350 14.186 38.709 1.00 20.00 | B C |
| ATOM | 4731 CD1 ILE H 206 | 26.843 14.078 40.136 1.00 20.00 | B C |
| ATOM | 4732 CG2 ILE H 206 | 28.553 14.161 37.505 1.00 20.00 | B C |
| ATOM | 4733 C ILE H 206 | 27.439 12.723 35.321 1.00 62.35 | B C |
| ATOM | 4734 O ILE H 206 | 27.594 11.505 35.221 1.00 67.16 | B O |
| ATOM | 4735 N VAL H 207 | 28.023 13.596 34.510 1.00 52.22 | B N |
| ATOM | 4736 CA VAL H 207 | 28.952 13.168 33.480 1.00 51.31 | B C |
| ATOM | 4737 CB VAL H 207 | 28.568 13.742 32.111 1.00 20.00 | B C |
| ATOM | 4738 CG1 VAL H 207 | 29.545 13.261 31.047 1.00 20.00 | B C |
| ATOM | 4739 CG2 VAL H 207 | 27.136 13.356 31.758 1.00 20.00 | B C |
| ATOM | 4740 C VAL H 207 | 30.378 13.582 33.821 1.00 62.09 | B C |
| ATOM | 4741 O VAL H 207 | 30.751 14.746 33.673 1.00 58.88 | B O |
| ATOM | 4742 N ASN H 208 | 31.140 12.641 34.367 1.00 71.72 | B N |
| ATOM | 4743 CA ASN H 208 | 32.533 12.886 34.707 1.00 70.92 | B C |
| ATOM | 4744 CB ASN H 208 | 32.855 12.307 36.086 1.00 20.00 | B C |
| ATOM | 4745 CG ASN H 208 | 32.187 13.074 37.209 1.00 20.00 | B C |
| ATOM | 4746 OD1 ASN H 208 | 31.862 14.252 37.065 1.00 20.00 | B O |
| ATOM | 4747 ND2 ASN H 208 | 31.993 12.411 38.344 1.00 20.00 | B N |
| ATOM | 4748 C ASN H 208 | 33.484 12.312 33.665 1.00 63.05 | B C |
| ATOM | 4749 O ASN H 208 | 33.051 11.778 32.645 1.00 61.34 | B O |
| ATOM | 4750 N LYS H 209 | 34.776 12.337 33.979 1.00 68.91 | B N |
| ATOM | 4751 CA LYS H 209 | 35.811 11.927 33.037 1.00 59.11 | B C |
| ATOM | 4752 CB LYS H 209 | 37.190 12.378 33.528 1.00 20.00 | B C |
| ATOM | 4753 CG LYS H 209 | 37.362 13.888 33.639 1.00 20.00 | B C |
| ATOM | 4754 CD LYS H 209 | 38.689 14.243 34.302 1.00 20.00 | B C |
| ATOM | 4755 CE LYS H 209 | 38.914 15.748 34.344 1.00 20.00 | B C |
| ATOM | 4756 NZ LYS H 209 | 40.286 16.091 34.815 1.00 20.00 | B N |
| ATOM | 4757 C LYS H 209 | 35.810 10.415 32.817 1.00 50.69 | B C |
| ATOM | 4758 O LYS H 209 | 36.500 9.910 31.932 1.00 51.01 | B O |
| ATOM | 4759 N GLN H 210 | 35.116 9.691 33.689 1.00 44.68 | B N |
| ATOM | 4760 CA GLN H 210 | 34.957 8.249 33.528 1.00 49.52 | B C |
| ATOM | 4761 CB GLN H 210 | 34.767 7.581 34.890 1.00 20.00 | B C |
| ATOM | 4762 CG GLN H 210 | 35.976 7.671 35.803 1.00 20.00 | B C |
| ATOM | 4763 CD GLN H 210 | 35.727 7.036 37.156 1.00 20.00 | B C |
| ATOM | 4764 OE1 GLN H 210 | 34.591 6.983 37.629 1.00 20.00 | B O |
| ATOM | 4765 NE2 GLN H 210 | 36.792 6.571 37.798 1.00 20.00 | B N |
| ATOM | 4766 C GLN H 210 | 33.765 7.937 32.632 1.00 62.08 | B C |
| ATOM | 4767 O GLN H 210 | 33.906 7.310 31.580 1.00 80.43 | B O |
| ATOM | 4768 N SER H 211 | 32.599 8.424 33.040 1.00 58.92 | B N |
| ATOM | 4769 CA SER H 211 | 31.384 8.297 32.251 1.00 47.88 | B C |
| ATOM | 4770 CB SER H 211 | 30.270 9.156 32.857 1.00 20.00 | B C |
| ATOM | 4771 OG SER H 211 | 30.733 10.462 33.169 1.00 20.00 | B O |
| ATOM | 4772 C SER H 211 | 31.609 8.665 30.783 1.00 57.32 | B C |
| ATOM | 4773 O SER H 211 | 31.138 7.967 29.884 1.00 50.74 | B O |
| ATOM | 4774 N CYS H 212 | 32.412 9.699 30.545 1.00 44.34 | B N |
| ATOM | 4775 CA CYS H 212 | 32.520 10.292 29.213 1.00 57.52 | B C |
| ATOM | 4776 CB CYS H 212 | 33.762 11.204 29.075 1.00 20.00 | B C |
| ATOM | 4777 SG CYS H 212 | 33.808 12.659 30.229 1.00 20.00 | B S |
| ATOM | 4778 C CYS H 212 | 32.395 9.264 28.073 1.00 60.91 | B C |
| ATOM | 4779 O CYS H 212 | 31.468 9.353 27.272 1.00 52.17 | B O |
| ATOM | 4780 N SER H 213 | 33.381 8.374 27.965 1.00 21.55 | B N |
| ATOM | 4781 CA SER H 213 | 33.462 7.484 26.814 1.00 21.67 | B C |

APPENDIX-continued (APPENDIX discloses SEQ ID NOS 29-32, 29-32 and 29-32, respectively, in order of appearance)

| | | | |
|---|---|---|---|
| ATOM | 4782 CB SER H 213 | 34.765 6.678 26.855 1.00 21.81 | B C |
| ATOM | 4783 OG SER H 213 | 35.892 7.530 26.960 1.00 23.00 | B O |
| ATOM | 4784 C SER H 213 | 32.284 6.537 26.686 1.00 21.45 | B C |
| ATOM | 4785 O SER H 213 | 31.711 6.410 25.603 1.00 21.98 | B O |
| ATOM | 4786 N ILE H 214 | 31.895 5.885 27.776 1.00 20.90 | B N |
| ATOM | 4787 CA ILE H 214 | 30.691 5.081 27.699 1.00 20.45 | B C |
| ATOM | 4788 CB ILE H 214 | 30.475 4.234 28.960 1.00 20.53 | B C |
| ATOM | 4789 CG1 ILE H 214 | 31.411 3.025 28.946 1.00 20.46 | B C |
| ATOM | 4790 CD1 ILE H 214 | 31.049 1.951 29.952 1.00 21.75 | B C |
| ATOM | 4791 CG2 ILE H 214 | 29.021 3.787 29.052 1.00 20.34 | B C |
| ATOM | 4792 C ILE H 214 | 29.526 6.035 27.523 1.00 20.15 | B C |
| ATOM | 4793 O ILE H 214 | 28.694 5.870 26.631 1.00 19.91 | B O |
| ATOM | 4794 N SER H 215 | 29.528 7.080 28.346 1.00 19.84 | B N |
| ATOM | 4795 CA SER H 215 | 28.475 8.080 28.330 1.00 19.58 | B C |
| ATOM | 4796 CB SER H 215 | 28.663 9.070 29.478 1.00 19.76 | B C |
| ATOM | 4797 OG SER H 215 | 27.637 10.048 29.470 1.00 19.97 | B O |
| ATOM | 4798 C SER H 215 | 28.460 8.825 27.017 1.00 19.34 | B C |
| ATOM | 4799 O SER H 215 | 27.406 9.053 26.446 1.00 19.54 | B O |
| ATOM | 4800 N ASN H 216 | 29.638 9.187 26.527 1.00 18.80 | B N |
| ATOM | 4801 CA ASN H 216 | 29.724 9.885 25.258 1.00 18.36 | B C |
| ATOM | 4802 CB ASN H 216 | 31.156 10.336 24.972 1.00 18.41 | B C |
| ATOM | 4803 CG ASN H 216 | 31.647 11.377 25.959 1.00 19.55 | B C |
| ATOM | 4804 OD1 ASN H 216 | 31.028 12.428 26.133 1.00 20.52 | B O |
| ATOM | 4805 ND2 ASN H 216 | 32.779 11.100 26.597 1.00 20.43 | B N |
| ATOM | 4806 C ASN H 216 | 29.211 9.010 24.129 1.00 17.78 | B C |
| ATOM | 4807 O ASN H 216 | 28.481 9.479 23.255 1.00 17.91 | B O |
| ATOM | 4808 N ILE H 217 | 29.570 7.730 24.150 1.00 17.02 | B N |
| ATOM | 4809 CA ILE H 217 | 29.110 6.845 23.095 1.00 16.60 | B C |
| ATOM | 4810 CB ILE H 217 | 29.718 5.439 23.210 1.00 16.46 | B C |
| ATOM | 4811 CG1 ILE H 217 | 31.093 5.403 22.540 1.00 16.26 | B C |
| ATOM | 4812 CD1 ILE H 217 | 31.610 4.001 22.276 1.00 16.44 | B C |
| ATOM | 4813 CG2 ILE H 217 | 28.791 4.408 22.591 1.00 16.70 | B C |
| ATOM | 4814 C ILE H 217 | 27.599 6.750 23.148 1.00 16.73 | B C |
| ATOM | 4815 O ILE H 217 | 26.923 6.809 22.116 1.00 16.80 | B O |
| ATOM | 4816 N GLU H 218 | 27.064 6.639 24.360 1.00 17.02 | B N |
| ATOM | 4817 CA GLU H 218 | 25.631 6.500 24.526 1.00 17.70 | B C |
| ATOM | 4818 CB GLU H 218 | 25.266 6.321 26.000 1.00 18.20 | B C |
| ATOM | 4819 CG GLU H 218 | 25.955 5.155 26.685 1.00 21.31 | B C |
| ATOM | 4820 CD GLU H 218 | 25.270 4.774 27.986 1.00 25.72 | B C |
| ATOM | 4821 OE1 GLU H 218 | 25.558 5.409 29.023 1.00 26.96 | B O |
| ATOM | 4822 OE2 GLU H 218 | 24.447 3.835 27.975 1.00 27.07 | B O |
| ATOM | 4823 C GLU H 218 | 24.951 7.742 23.995 1.00 17.29 | B C |
| ATOM | 4824 O GLU H 218 | 23.942 7.660 23.312 1.00 17.62 | B O |
| ATOM | 4825 N THR H 219 | 25.482 8.931 24.255 1.00 16.62 | B N |
| ATOM | 4826 CA THR H 219 | 24.786 10.141 23.789 1.00 15.95 | B C |
| ATOM | 4827 CB THR H 219 | 25.475 11.413 24.325 1.00 15.95 | B C |
| ATOM | 4828 OG1 THR H 219 | 25.394 11.438 25.756 1.00 15.63 | B O |
| ATOM | 4829 CG2 THR H 219 | 24.814 12.661 23.759 1.00 15.97 | B C |
| ATOM | 4830 C THR H 219 | 24.646 10.261 22.254 1.00 15.64 | B C |
| ATOM | 4831 O THR H 219 | 23.557 10.569 21.720 1.00 15.93 | B O |
| ATOM | 4832 N VAL H 220 | 25.737 9.974 21.550 1.00 14.98 | B N |
| ATOM | 4833 CA VAL H 220 | 25.773 10.074 20.093 1.00 14.51 | B C |
| ATOM | 4834 CB VAL H 220 | 27.177 9.738 19.559 1.00 14.29 | B C |
| ATOM | 4835 CG1 VAL H 220 | 27.191 9.771 18.041 1.00 14.24 | B C |
| ATOM | 4836 CG2 VAL H 220 | 28.213 10.693 20.137 1.00 14.10 | B C |
| ATOM | 4837 C VAL H 220 | 24.779 9.088 19.498 1.00 14.64 | B C |
| ATOM | 4838 O VAL H 220 | 24.030 9.390 18.544 1.00 14.79 | B O |
| ATOM | 4839 N ILE H 221 | 24.762 7.904 20.097 1.00 14.43 | B N |
| ATOM | 4840 CA ILE H 221 | 23.860 6.856 19.674 1.00 14.36 | B C |
| ATOM | 4841 CB ILE H 221 | 24.067 5.569 20.487 1.00 14.03 | B C |
| ATOM | 4842 CG1 ILE H 221 | 25.394 4.909 20.110 1.00 13.72 | B C |
| ATOM | 4843 CD1 ILE H 221 | 25.493 4.526 18.649 1.00 14.17 | B C |
| ATOM | 4844 CG2 ILE H 221 | 22.908 4.611 20.267 1.00 13.91 | B C |
| ATOM | 4845 C ILE H 221 | 22.443 7.351 19.869 1.00 14.82 | B C |
| ATOM | 4846 O ILE H 221 | 21.589 7.132 19.023 1.00 14.82 | B O |
| ATOM | 4847 N GLU H 222 | 22.195 8.039 20.978 1.00 15.51 | B N |
| ATOM | 4848 CA GLU H 222 | 20.857 8.551 21.246 1.00 16.52 | B C |
| ATOM | 4849 CB GLU H 222 | 20.733 9.113 22.663 1.00 16.80 | B C |
| ATOM | 4850 CG GLU H 222 | 20.725 8.043 23.747 1.00 19.14 | B C |
| ATOM | 4851 CD GLU H 222 | 19.637 8.267 24.780 1.00 22.62 | B C |
| ATOM | 4852 OE1 GLU H 222 | 19.965 8.662 25.919 1.00 24.35 | B O |
| ATOM | 4853 OE2 GLU H 222 | 18.453 8.039 24.454 1.00 23.98 | B O |
| ATOM | 4854 C GLU H 222 | 20.400 9.566 20.199 1.00 16.65 | B C |
| ATOM | 4855 O GLU H 222 | 19.255 9.541 19.792 1.00 16.95 | B O |
| ATOM | 4856 N PHE H 223 | 21.292 10.444 19.752 1.00 16.70 | B N |
| ATOM | 4857 CA PHE H 223 | 20.971 11.413 18.690 1.00 16.95 | B C |
| ATOM | 4858 CB PHE H 223 | 22.259 12.227 18.509 1.00 16.85 | B C |

APPENDIX-continued (APPENDIX discloses SEQ ID NOS 29-32, 29-32 and 29-32, respectively, in order of appearance)

| | | | | |
|---|---|---|---|---|
| ATOM | 4859 CG PHE H 223 | 22.154 13.406 17.593 1.00 17.23 | B C |
| ATOM | 4860 CD1 PHE H 223 | 21.522 14.570 17.995 1.00 17.98 | B C |
| ATOM | 4861 CE1 PHE H 223 | 21.467 15.667 17.155 1.00 18.28 | B C |
| ATOM | 4862 CZ PHE H 223 | 22.071 15.616 15.914 1.00 18.19 | B C |
| ATOM | 4863 CE2 PHE H 223 | 22.726 14.469 15.516 1.00 18.14 | B C |
| ATOM | 4864 CD2 PHE H 223 | 22.776 13.380 16.357 1.00 17.75 | B C |
| ATOM | 4865 C PHE H 223 | 20.601 10.675 17.371 1.00 17.28 | B C |
| ATOM | 4866 O PHE H 223 | 19.564 10.951 16.650 1.00 17.17 | B O |
| ATOM | 4867 N GLN H 224 | 21.422 9.671 17.091 1.00 17.62 | B N |
| ATOM | 4868 CA GLN H 224 | 21.209 8.880 15.894 1.00 18.16 | B C |
| ATOM | 4869 CB GLN H 224 | 22.390 7.930 15.652 1.00 18.51 | B C |
| ATOM | 4870 CG GLN H 224 | 23.751 8.594 15.888 1.00 20.06 | B C |
| ATOM | 4871 CD GLN H 224 | 24.867 8.009 15.039 1.00 22.03 | B C |
| ATOM | 4872 OE1 GLN H 224 | 24.920 6.800 14.806 1.00 22.15 | B O |
| ATOM | 4873 NE2 GLN H 224 | 25.783 8.864 14.595 1.00 22.11 | B N |
| ATOM | 4874 C GLN H 224 | 19.855 8.158 15.956 1.00 18.04 | B C |
| ATOM | 4875 O GLN H 224 | 19.196 7.981 14.932 1.00 18.17 | B O |
| ATOM | 4876 N GLN H 225 | 19.488 7.701 17.156 1.00 17.90 | B N |
| ATOM | 4877 CA GLN H 225 | 18.192 7.079 17.492 1.00 17.95 | B C |
| ATOM | 4878 CB GLN H 225 | 18.271 6.408 18.861 1.00 18.13 | B C |
| ATOM | 4879 CG GLN H 225 | 19.251 5.257 18.893 1.00 19.04 | B C |
| ATOM | 4880 CD GLN H 225 | 18.854 4.196 19.891 1.00 21.22 | B C |
| ATOM | 4881 OE1 GLN H 225 | 17.834 4.321 20.569 1.00 22.55 | B O |
| ATOM | 4882 NE2 GLN H 225 | 19.651 3.142 19.985 1.00 22.48 | B N |
| ATOM | 4883 C GLN H 225 | 16.993 8.032 17.430 1.00 17.84 | B C |
| ATOM | 4884 O GLN H 225 | 15.872 7.657 17.090 1.00 17.71 | B O |
| ATOM | 4885 N LYS H 226 | 18.593 9.729 17.758 1.00 17.95 | B N |
| ATOM | 4886 CA LYS H 226 | 17.704 10.870 17.777 1.00 18.00 | B C |
| ATOM | 4887 CB LYS H 226 | 18.471 12.167 18.045 1.00 18.21 | B C |
| ATOM | 4888 CG LYS H 226 | 19.258 12.240 19.342 1.00 18.50 | B C |
| ATOM | 4889 CD LYS H 226 | 18.743 13.353 20.242 1.00 19.87 | B C |
| ATOM | 4890 CE LYS H 226 | 19.762 13.696 21.316 1.00 21.36 | B C |
| ATOM | 4891 NZ LYS H 226 | 19.374 14.909 22.085 1.00 21.83 | B N |
| ATOM | 4892 C LYS H 226 | 17.251 10.914 16.350 1.00 17.84 | B C |
| ATOM | 4893 O LYS H 226 | 16.195 11.458 16.046 1.00 17.94 | B O |
| ATOM | 4894 N ASN H 227 | 18.025 10.304 15.460 1.00 17.70 | B N |
| ATOM | 4895 CA ASN H 227 | 17.467 10.197 14.086 1.00 17.66 | B C |
| ATOM | 4896 CB ASN H 227 | 18.366 9.273 13.270 1.00 17.36 | B C |
| ATOM | 4897 CG ASN H 227 | 19.700 9.884 12.927 1.00 17.40 | B C |
| ATOM | 4898 OD1 ASN H 227 | 20.438 9.337 12.107 1.00 17.84 | B O |
| ATOM | 4899 ND2 ASN H 227 | 20.025 11.011 13.545 1.00 17.22 | B N |
| ATOM | 4900 C ASN H 227 | 16.016 9.596 13.857 1.00 17.76 | B C |
| ATOM | 4901 O ASN H 227 | 15.214 10.239 13.175 1.00 17.92 | B O |
| ATOM | 4902 N ASN H 228 | 15.655 8.431 14.418 1.00 17.78 | B N |
| ATOM | 4903 CA ASN H 228 | 14.290 7.922 14.435 1.00 17.59 | B C |
| ATOM | 4904 CB ASN H 228 | 14.003 7.185 15.743 1.00 17.89 | B C |
| ATOM | 4905 CG ASN H 228 | 14.845 5.934 15.903 1.00 18.43 | B C |
| ATOM | 4906 OD1 ASN H 228 | 15.432 5.698 16.959 1.00 18.74 | B O |
| ATOM | 4907 ND2 ASN H 228 | 14.908 5.124 14.852 1.00 18.61 | B N |
| ATOM | 4908 C ASN H 228 | 13.335 9.091 14.265 1.00 17.09 | B C |
| ATOM | 4909 O ASN H 228 | 12.380 9.032 13.490 1.00 17.17 | B O |
| ATOM | 4910 N ARG H 229 | 13.267 9.880 15.306 1.00 16.33 | B N |
| ATOM | 4911 CA ARG H 229 | 12.252 10.885 15.298 1.00 15.76 | B C |
| ATOM | 4912 CB ARG H 229 | 11.906 11.215 16.758 1.00 15.70 | B C |
| ATOM | 4913 CG ARG H 229 | 11.667 9.916 17.580 1.00 14.99 | B C |
| ATOM | 4914 CD ARG H 229 | 11.240 10.128 19.039 1.00 15.33 | B C |
| ATOM | 4915 NE ARG H 229 | 12.372 10.516 19.868 1.00 15.59 | B N |
| ATOM | 4916 CZ ARG H 229 | 13.209 9.663 20.448 1.00 15.85 | B C |
| ATOM | 4917 NH1 ARG H 229 | 13.045 8.350 20.313 1.00 16.20 | B N |
| ATOM | 4918 NH2 ARG H 229 | 14.216 10.134 21.168 1.00 16.63 | B N |
| ATOM | 4919 C ARG H 229 | 12.960 11.937 14.490 1.00 15.62 | B C |
| ATOM | 4920 O ARG H 229 | 12.436 12.586 13.561 1.00 15.73 | B O |
| ATOM | 4921 N LEU H 230 | 14.249 11.935 14.783 1.00 15.46 | B N |
| ATOM | 4922 CA LEU H 230 | 15.146 12.972 14.402 1.00 15.22 | B C |
| ATOM | 4923 CB LEU H 230 | 16.334 12.863 15.348 1.00 15.08 | B C |
| ATOM | 4924 CG LEU H 230 | 17.100 14.054 15.896 1.00 14.70 | B C |
| ATOM | 4925 CD1 LEU H 230 | 16.465 14.590 17.171 1.00 15.19 | B C |
| ATOM | 4926 CD2 LEU H 230 | 18.500 13.564 16.165 1.00 15.46 | B C |
| ATOM | 4927 C LEU H 230 | 15.658 12.853 12.989 1.00 15.31 | B C |
| ATOM | 4928 O LEU H 230 | 15.224 13.608 12.133 1.00 15.46 | B O |
| ATOM | 4929 N LEU H 231 | 16.533 11.890 12.727 1.00 15.48 | B N |
| ATOM | 4930 CA LEU H 231 | 17.158 11.825 11.423 1.00 15.75 | B C |
| ATOM | 4931 CB LEU H 231 | 18.215 10.722 11.423 1.00 15.90 | B C |
| ATOM | 4932 CG LEU H 231 | 19.366 10.875 12.416 1.00 16.63 | B C |
| ATOM | 4933 CD1 LEU H 231 | 20.443 9.836 12.133 1.00 18.45 | B C |
| ATOM | 4934 CD2 LEU H 231 | 19.953 12.276 12.366 1.00 16.67 | B C |
| ATOM | 4935 C LEU H 231 | 16.139 11.575 10.324 1.00 15.76 | B C |

APPENDIX-continued (APPENDIX discloses SEQ ID NOS 29-32, 29-32 and 29-32, respectively, in order of appearance)

| | | | |
|---|---|---|---|
| ATOM | 4936 O LEU H 231 | 16.121 12.269 9.309 1.00 15.84 | B O |
| ATOM | 4937 N GLU H 232 | 15.249 10.617 10.561 1.00 15.71 | B N |
| ATOM | 4938 CA GLU H 232 | 14.200 10.308 9.607 1.00 15.93 | B C |
| ATOM | 4939 CB GLU H 232 | 13.470 9.012 10.001 1.00 16.15 | B C |
| ATOM | 4940 CG GLU H 232 | 14.389 7.801 10.158 1.00 18.59 | B C |
| ATOM | 4941 CD GLU H 232 | 14.567 6.988 8.876 1.00 21.47 | B C |
| ATOM | 4942 OE1 GLU H 232 | 13.976 7.355 7.839 1.00 22.14 | B O |
| ATOM | 4943 OE2 GLU H 232 | 15.298 5.973 8.907 1.00 23.34 | B O |
| ATOM | 4944 C GLU H 232 | 13.241 11.482 9.456 1.00 15.45 | B C |
| ATOM | 4945 O GLU H 232 | 12.881 11.860 8.328 1.00 15.95 | B O |
| ATOM | 4946 N ILE H 233 | 12.855 12.113 10.564 1.00 14.54 | B N |
| ATOM | 4947 CA ILE H 233 | 11.941 13.221 10.375 1.00 13.69 | B C |
| ATOM | 4948 CB ILE H 233 | 11.444 13.775 11.699 1.00 13.63 | B C |
| ATOM | 4949 CG1 ILE H 233 | 10.497 12.763 12.326 1.00 13.58 | B C |
| ATOM | 4950 CD1 ILE H 233 | 9.817 13.280 13.532 1.00 13.55 | B C |
| ATOM | 4951 CG2 ILE H 233 | 10.682 15.070 11.490 1.00 13.88 | B C |
| ATOM | 4952 C ILE H 233 | 12.605 14.309 9.526 1.00 13.28 | B C |
| ATOM | 4953 O ILE H 233 | 11.972 14.914 8.653 1.00 13.04 | B O |
| ATOM | 4954 N THR H 234 | 13.888 14.544 9.773 1.00 13.18 | B N |
| ATOM | 4955 CA THR H 234 | 14.620 15.575 9.063 1.00 13.39 | B C |
| ATOM | 4956 CB THR H 234 | 16.082 15.655 9.574 1.00 13.21 | B C |
| ATOM | 4957 OG1 THR H 234 | 16.099 15.927 10.978 1.00 13.15 | B O |
| ATOM | 4958 CG2 THR H 234 | 16.870 16.740 8.846 1.00 13.22 | B C |
| ATOM | 4959 C THR H 234 | 14.686 15.273 7.577 1.00 13.76 | B C |
| ATOM | 4960 O THR H 234 | 14.434 16.152 6.738 1.00 13.95 | B O |
| ATOM | 4961 N ARG H 235 | 14.994 14.024 7.240 1.00 14.26 | B N |
| ATOM | 4962 CA ARG H 235 | 15.119 13.686 5.831 1.00 14.92 | B C |
| ATOM | 4963 CB ARG H 235 | 15.574 12.242 5.661 1.00 15.30 | B C |
| ATOM | 4964 CG ARG H 235 | 14.532 11.325 5.054 1.00 16.27 | B C |
| ATOM | 4965 CD ARG H 235 | 14.829 9.882 5.408 1.00 18.52 | B C |
| ATOM | 4966 NE ARG H 235 | 16.234 9.676 5.746 1.00 17.86 | B N |
| ATOM | 4967 CZ ARG H 235 | 17.190 9.425 4.858 1.00 16.91 | B C |
| ATOM | 4968 NH1 ARG H 235 | 16.898 9.354 3.566 1.00 16.59 | B N |
| ATOM | 4969 NH2 ARG H 235 | 18.438 9.249 5.267 1.00 16.86 | B N |
| ATOM | 4970 C ARG H 235 | 13.766 13.887 5.176 1.00 15.05 | B C |
| ATOM | 4971 O ARG H 235 | 13.663 14.432 4.073 1.00 15.15 | B O |
| ATOM | 4972 N GLU H 236 | 12.727 13.474 5.894 1.00 15.18 | B N |
| ATOM | 4973 CA GLU H 236 | 11.375 13.527 5.376 1.00 15.24 | B C |
| ATOM | 4974 CB GLU H 236 | 10.415 12.920 6.403 1.00 15.69 | B C |
| ATOM | 4975 CG GLU H 236 | 9.176 12.265 5.822 1.00 18.22 | B C |
| ATOM | 4976 CD GLU H 236 | 8.355 11.543 6.875 1.00 21.59 | B C |
| ATOM | 4977 OE1 GLU H 236 | 7.200 11.178 6.581 1.00 24.41 | B O |
| ATOM | 4978 OE2 GLU H 236 | 8.857 11.345 8.000 1.00 21.59 | B O |
| ATOM | 4979 C GLU H 236 | 10.987 14.971 5.073 1.00 14.61 | B C |
| ATOM | 4980 O GLU H 236 | 10.396 15.253 4.031 1.00 14.82 | B O |
| ATOM | 4981 N PHE H 237 | 11.333 15.877 5.985 1.00 14.05 | B N |
| ATOM | 4982 CA PHE H 237 | 11.053 17.296 5.809 1.00 13.84 | B C |
| ATOM | 4983 CB PHE H 237 | 11.316 18.065 7.105 1.00 14.04 | B C |
| ATOM | 4984 CG PHE H 237 | 10.142 18.087 8.038 1.00 14.84 | B C |
| ATOM | 4985 CD1 PHE H 237 | 10.224 17.516 9.297 1.00 15.30 | B C |
| ATOM | 4986 CE1 PHE H 237 | 9.142 17.542 10.153 1.00 15.15 | B C |
| ATOM | 4987 CZ PHE H 237 | 7.961 18.135 9.755 1.00 15.19 | B C |
| ATOM | 4988 CE2 PHE H 237 | 7.864 18.704 8.502 1.00 15.02 | B C |
| ATOM | 4989 CD2 PHE H 237 | 8.949 18.677 7.651 1.00 15.03 | B C |
| ATOM | 4990 C PHE H 237 | 11.830 17.909 4.654 1.00 13.51 | B C |
| ATOM | 4991 O PHE H 237 | 11.293 18.687 3.866 1.00 13.43 | B O |
| ATOM | 4992 N SER H 238 | 13.100 17.534 4.554 1.00 13.11 | B N |
| ATOM | 4993 CA SER H 238 | 13.972 18.065 3.516 1.00 12.82 | B C |
| ATOM | 4994 CB SER H 238 | 15.404 17.546 3.691 1.00 12.86 | B C |
| ATOM | 4995 OG SER H 238 | 15.976 17.981 4.916 1.00 12.76 | B O |
| ATOM | 4996 C SER H 238 | 13.411 17.654 2.164 1.00 12.69 | B C |
| ATOM | 4997 O SER H 238 | 13.437 18.425 1.202 1.00 12.63 | B O |
| ATOM | 4998 N VAL H 239 | 12.910 16.426 2.107 1.00 12.59 | B N |
| ATOM | 4999 CA VAL H 239 | 12.361 15.865 0.883 1.00 12.80 | B C |
| ATOM | 5000 CB VAL H 239 | 12.065 14.358 1.041 1.00 12.71 | B C |
| ATOM | 5001 CG1 VAL H 239 | 11.359 13.819 −0.193 1.00 13.63 | B C |
| ATOM | 5002 CG2 VAL H 239 | 13.349 13.588 1.316 1.00 13.57 | B C |
| ATOM | 5003 C VAL H 239 | 11.094 16.596 0.443 1.00 12.94 | B C |
| ATOM | 5004 O VAL H 239 | 10.722 16.546 −0.728 1.00 13.10 | B O |
| ATOM | 5005 N ASN H 240 | 10.430 17.274 1.372 1.00 4.15 | B N |
| ATOM | 5006 CA ASN H 240 | 9.074 17.741 1.109 1.00 4.33 | B C |
| ATOM | 5007 CB ASN H 240 | 8.110 17.268 2.199 1.00 4.59 | B C |
| ATOM | 5008 CG ASN H 240 | 7.810 15.784 2.106 1.00 5.36 | B C |
| ATOM | 5009 OD1 ASN H 240 | 7.128 15.331 1.188 1.00 6.27 | B O |
| ATOM | 5010 ND2 ASN H 240 | 8.343 15.016 3.047 1.00 7.15 | B N |
| ATOM | 5011 C ASN H 240 | 8.924 19.242 0.853 1.00 4.19 | B C |
| ATOM | 5012 O ASN H 240 | 7.843 19.707 0.490 1.00 4.19 | B O |

APPENDIX-continued (APPENDIX discloses SEQ ID NOS 29-32, 29-32 and 29-32, respectively, in order of appearance)

| | | | |
|---|---|---|---|
| ATOM | 5013 N ALA H 241 | 10.014 19.990 0.995 1.00 3.93 | B N |
| ATOM | 5014 CA ALA H 241 | 9.948 21.447 0.930 1.00 3.90 | B C |
| ATOM | 5015 CB ALA H 241 | 9.784 21.908 −0.511 1.00 3.86 | B C |
| ATOM | 5016 C ALA H 241 | 8.812 21.985 1.798 1.00 4.22 | B C |
| ATOM | 5017 O ALA H 241 | 7.932 22.697 1.314 1.00 4.47 | B O |
| ATOM | 5018 N GLY H 242 | 8.772 21.540 3.049 1.00 4.53 | B N |
| ATOM | 5019 CA GLY H 242 | 8.055 22.258 4.097 1.00 4.65 | B C |
| ATOM | 5020 C GLY H 242 | 6.563 21.980 4.122 1.00 4.67 | B C |
| ATOM | 5021 O GLY H 242 | 5.792 22.759 4.683 1.00 5.27 | B O |
| ATOM | 5022 N VAL H 243 | 6.159 20.841 3.570 1.00 4.37 | B N |
| ATOM | 5023 CA VAL H 243 | 4.755 20.449 3.577 1.00 4.32 | B C |
| ATOM | 5024 CB VAL H 243 | 3.961 21.182 2.477 1.00 3.99 | B C |
| ATOM | 5025 CG1 VAL H 243 | 2.519 21.398 2.915 1.00 4.22 | B C |
| ATOM | 5026 CG2 VAL H 243 | 4.629 22.508 2.131 1.00 3.85 | B C |
| ATOM | 5027 C VAL H 243 | 4.595 18.943 3.393 1.00 4.61 | B C |
| ATOM | 5028 O VAL H 243 | 5.201 18.350 2.501 1.00 4.89 | B O |
| ATOM | 5029 N THR H 244 | 3.764 18.333 4.231 1.00 4.95 | B N |
| ATOM | 5030 CA THR H 244 | 3.600 16.886 4.220 1.00 5.71 | B C |
| ATOM | 5031 CB THR H 244 | 4.318 16.226 5.410 1.00 6.11 | B C |
| ATOM | 5032 OG1 THR H 244 | 5.051 17.217 6.140 1.00 7.17 | B O |
| ATOM | 5033 CG2 THR H 244 | 5.273 15.147 4.925 1.00 7.55 | B C |
| ATOM | 5034 C THR H 244 | 2.129 16.505 4.268 1.00 5.61 | B C |
| ATOM | 5035 O THR H 244 | 1.359 17.073 5.042 1.00 5.85 | B O |
| ATOM | 5036 N THR H 245 | 1.786 15.428 3.575 1.00 5.53 | B N |
| ATOM | 5037 CA THR H 245 | 0.617 14.647 3.939 1.00 5.81 | B C |
| ATOM | 5038 CB THR H 245 | −0.404 14.592 2.788 1.00 6.13 | B C |
| ATOM | 5039 OG1 THR H 245 | −0.888 15.915 2.517 1.00 8.11 | B O |
| ATOM | 5040 CG2 THR H 245 | −1.577 13.695 3.154 1.00 6.63 | B C |
| ATOM | 5041 C THR H 245 | 1.032 13.245 4.370 1.00 5.73 | B C |
| ATOM | 5042 O THR H 245 | 2.189 12.861 4.202 1.00 5.86 | B O |
| ATOM | 5043 N PRO H 246 | 0.060 12.433 4.804 1.00 5.68 | B N |
| ATOM | 5044 CA PRO H 246 | 0.078 11.993 6.186 1.00 5.11 | B C |
| ATOM | 5045 CB PRO H 246 | 0.753 10.626 6.084 1.00 5.19 | B C |
| ATOM | 5046 CG PRO H 246 | 0.360 10.124 4.675 1.00 5.90 | B C |
| ATOM | 5047 CD PRO H 246 | −0.256 11.297 3.926 1.00 6.36 | B C |
| ATOM | 5048 C PRO H 246 | 0.830 12.916 7.140 1.00 4.85 | B C |
| ATOM | 5049 O PRO H 246 | 1.927 13.379 6.825 1.00 5.25 | B O |
| ATOM | 5050 N VAL H 247 | 0.144 13.323 8.205 1.00 4.35 | B N |
| ATOM | 5051 CA VAL H 247 | 0.792 13.950 9.347 1.00 3.82 | B C |
| ATOM | 5052 CB VAL H 247 | −0.198 14.817 10.157 1.00 3.52 | B C |
| ATOM | 5053 CG1 VAL H 247 | 0.558 15.754 11.087 1.00 3.62 | B C |
| ATOM | 5054 CG2 VAL H 247 | −1.091 15.615 9.217 1.00 3.60 | B C |
| ATOM | 5055 C VAL H 247 | 1.447 12.899 10.242 1.00 3.69 | B C |
| ATOM | 5056 O VAL H 247 | 0.761 12.124 10.913 1.00 3.36 | B O |
| ATOM | 5057 N SER H 248 | 2.748 12.721 10.040 1.00 3.72 | B N |
| ATOM | 5058 CA SER H 248 | 3.496 11.654 10.686 1.00 3.96 | B C |
| ATOM | 5059 CB SER H 248 | 4.995 11.840 10.451 1.00 4.07 | B C |
| ATOM | 5060 OG SER H 248 | 5.525 12.834 11.310 1.00 4.13 | B O |
| ATOM | 5061 C SER H 248 | 3.211 11.615 12.180 1.00 4.35 | B C |
| ATOM | 5062 O SER H 248 | 2.890 12.635 12.788 1.00 4.36 | B O |
| ATOM | 5063 N THR H 249 | 3.458 10.460 12.784 1.00 4.53 | B N |
| ATOM | 5064 CA THR H 249 | 3.489 10.350 14.231 1.00 4.61 | B C |
| ATOM | 5065 CB THR H 249 | 3.682 8.893 14.677 1.00 4.70 | B C |
| ATOM | 5066 OG1 THR H 249 | 5.018 8.473 14.374 1.00 5.42 | B O |
| ATOM | 5067 CG2 THR H 249 | 2.695 7.984 13.961 1.00 4.88 | B C |
| ATOM | 5068 C THR H 249 | 4.589 11.215 14.839 1.00 4.47 | B C |
| ATOM | 5069 O THR H 249 | 4.570 11.491 16.039 1.00 4.74 | B O |
| ATOM | 5070 N TYR H 250 | 5.518 11.684 14.009 1.00 4.32 | B N |
| ATOM | 5071 CA TYR H 250 | 6.544 12.619 14.475 1.00 4.42 | B C |
| ATOM | 5072 CB TYR H 250 | 7.811 12.531 13.625 1.00 4.91 | B C |
| ATOM | 5073 CG TYR H 250 | 8.409 11.148 13.525 1.00 6.81 | B C |
| ATOM | 5074 CD1 TYR H 250 | 8.844 10.657 12.302 1.00 8.89 | B C |
| ATOM | 5075 CE1 TYR H 250 | 9.480 9.437 12.205 1.00 10.73 | B C |
| ATOM | 5076 CZ TYR H 250 | 9.685 8.685 13.341 1.00 12.28 | B C |
| ATOM | 5077 OH TYR H 250 | 10.305 7.460 13.251 1.00 12.24 | B O |
| ATOM | 5078 CE2 TYR H 250 | 9.284 9.161 14.571 1.00 12.15 | B C |
| ATOM | 5079 CD2 TYR H 250 | 8.689 10.405 14.662 1.00 9.81 | B C |
| ATOM | 5080 C TYR H 250 | 6.053 14.064 14.516 1.00 4.21 | B C |
| ATOM | 5081 O TYR H 250 | 6.596 14.883 15.259 1.00 4.20 | B O |
| ATOM | 5082 N MET H 251 | 5.148 14.413 13.605 1.00 4.14 | B N |
| ATOM | 5083 CA MET H 251 | 4.517 15.732 13.632 1.00 4.15 | B C |
| ATOM | 5084 CB MET H 251 | 3.798 16.014 12.313 1.00 4.14 | B C |
| ATOM | 5085 CG MET H 251 | 4.720 16.097 11.115 1.00 4.51 | B C |
| ATOM | 5086 SD MET H 251 | 5.733 17.587 11.115 1.00 3.81 | B S |
| ATOM | 5087 CE MET H 251 | 5.601 18.077 9.395 1.00 4.55 | B C |
| ATOM | 5088 C MET H 251 | 3.519 15.806 14.775 1.00 4.13 | B C |
| ATOM | 5089 O MET H 251 | 3.510 16.759 15.555 1.00 4.24 | B O |

APPENDIX-continued (APPENDIX discloses SEQ ID NOS 29-32, 29-32 and 29-32, respectively, in order of appearance)

| | | | |
|---|---|---|---|
| ATOM | 5090 N LEU H 252 | 2.692 14.773 14.874 1.00 4.23 | B N |
| ATOM | 5091 CA LEU H 252 | 1.708 14.681 15.934 1.00 4.22 | B C |
| ATOM | 5092 CB LEU H 252 | 0.302 14.881 15.369 1.00 4.14 | B C |
| ATOM | 5093 CG LEU H 252 | −0.295 16.282 15.515 1.00 4.05 | B C |
| ATOM | 5094 CD1 LEU H 252 | −1.813 16.216 15.561 1.00 5.22 | B C |
| ATOM | 5095 CD2 LEU H 252 | 0.245 16.972 16.756 1.00 6.20 | B C |
| ATOM | 5096 C LEU H 252 | 1.818 13.314 16.589 1.00 4.62 | B C |
| ATOM | 5097 O LEU H 252 | 1.906 12.295 15.903 1.00 4.97 | B O |
| ATOM | 5098 N THR H 253 | 1.986 13.314 17.906 1.00 4.90 | B N |
| ATOM | 5099 CA THR H 253 | 1.718 12.126 18.704 1.00 5.57 | B C |
| ATOM | 5100 CB THR H 253 | 2.147 12.323 20.168 1.00 5.55 | B C |
| ATOM | 5101 OG1 THR H 253 | 3.369 13.068 20.214 1.00 6.43 | B O |
| ATOM | 5102 CG2 THR H 253 | 2.362 10.978 20.842 1.00 6.28 | B C |
| ATOM | 5103 C THR H 253 | 0.235 11.775 18.673 1.00 6.03 | B C |
| ATOM | 5104 O THR H 253 | −0.621 12.663 18.679 1.00 6.68 | B O |
| ATOM | 5105 N ASN H 254 | −0.066 10.483 18.746 1.00 6.39 | B N |
| ATOM | 5106 CA ASN H 254 | −1.396 10.040 19.141 1.00 6.79 | B C |
| ATOM | 5107 CB ASN H 254 | −1.375 8.564 19.534 1.00 6.85 | B C |
| ATOM | 5108 CG ASN H 254 | −2.758 7.954 19.571 1.00 6.81 | B C |
| ATOM | 5109 OD1 ASN H 254 | −3.395 7.771 18.534 1.00 7.67 | B O |
| ATOM | 5110 ND2 ASN H 254 | −3.252 7.682 20.773 1.00 6.19 | B N |
| ATOM | 5111 C ASN H 254 | −1.956 10.882 20.284 1.00 7.08 | B C |
| ATOM | 5112 O ASN H 254 | −2.968 11.565 20.125 1.00 6.90 | B O |
| ATOM | 5113 N SER H 255 | −1.282 10.843 21.430 1.00 7.21 | B N |
| ATOM | 5114 CA SER H 255 | −1.689 11.633 22.588 1.00 7.37 | B C |
| ATOM | 5115 CB SER H 255 | −0.561 11.714 23.619 1.00 8.09 | B C |
| ATOM | 5116 OG SER H 255 | 0.228 10.539 23.617 1.00 10.47 | B O |
| ATOM | 5117 C SER H 255 | −2.102 13.036 22.163 1.00 6.82 | B C |
| ATOM | 5118 O SER H 255 | −3.192 13.499 22.496 1.00 6.99 | B O |
| ATOM | 5119 N GLU H 256 | −1.229 13.704 21.415 1.00 6.17 | B N |
| ATOM | 5120 CA GLU H 256 | −1.485 15.072 20.981 1.00 6.13 | B C |
| ATOM | 5121 CB GLU H 256 | −0.274 15.644 20.243 1.00 6.22 | B C |
| ATOM | 5122 CG GLU H 256 | 0.847 16.110 21.152 1.00 8.41 | B C |
| ATOM | 5123 CD GLU H 256 | 2.209 15.761 20.596 1.00 10.26 | B C |
| ATOM | 5124 OE1 GLU H 256 | 2.292 15.472 19.384 1.00 11.90 | B O |
| ATOM | 5125 OE2 GLU H 256 | 3.162 15.626 21.392 1.00 9.55 | B O |
| ATOM | 5126 C GLU H 256 | −2.706 15.126 20.079 1.00 5.76 | B C |
| ATOM | 5127 O GLU H 256 | −3.684 15.810 20.380 1.00 5.93 | B O |
| ATOM | 5128 N LEU H 257 | −2.633 14.420 18.956 1.00 5.67 | B N |
| ATOM | 5129 CA LEU H 257 | −3.729 14.411 18.002 1.00 5.37 | B C |
| ATOM | 5130 CB LEU H 257 | −3.543 13.299 16.970 1.00 5.03 | B C |
| ATOM | 5131 CG LEU H 257 | −4.781 13.003 16.121 1.00 3.65 | B C |
| ATOM | 5132 CD1 LEU H 257 | −5.114 14.184 15.222 1.00 2.00 | B C |
| ATOM | 5133 CD2 LEU H 257 | −4.592 11.737 15.305 1.00 2.14 | B C |
| ATOM | 5134 C LEU H 257 | −5.050 14.223 18.732 1.00 5.64 | B C |
| ATOM | 5135 O LEU H 257 | −6.020 14.934 18.475 1.00 5.81 | B O |
| ATOM | 5136 N LEU H 258 | −5.061 13.300 19.687 1.00 5.75 | B N |
| ATOM | 5137 CA LEU H 258 | −6.297 12.905 20.344 1.00 5.91 | B C |
| ATOM | 5138 CB LEU H 258 | −6.063 11.693 21.242 1.00 6.10 | B C |
| ATOM | 5139 CG LEU H 258 | −6.438 10.358 20.605 1.00 5.75 | B C |
| ATOM | 5140 CD1 LEU H 258 | −5.970 9.206 21.477 1.00 6.33 | B C |
| ATOM | 5141 CD2 LEU H 258 | −7.939 10.287 20.372 1.00 7.33 | B C |
| ATOM | 5142 C LEU H 258 | −6.908 14.049 21.142 1.00 6.03 | B C |
| ATOM | 5143 O LEU H 258 | −8.113 14.290 21.071 1.00 5.73 | B O |
| ATOM | 5144 N SER H 259 | −6.076 14.745 21.910 1.00 6.47 | B N |
| ATOM | 5145 CA SER H 259 | −6.537 15.883 22.695 1.00 6.95 | B C |
| ATOM | 5146 CB SER H 259 | −5.521 16.237 23.784 1.00 7.05 | B C |
| ATOM | 5147 OG SER H 259 | −4.695 17.317 23.383 1.00 6.86 | B O |
| ATOM | 5148 C SER H 259 | −6.782 17.086 21.795 1.00 6.74 | B C |
| ATOM | 5149 O SER H 259 | −7.592 17.959 22.110 1.00 6.86 | B O |
| ATOM | 5150 N LEU H 260 | −6.074 17.125 20.670 1.00 6.31 | B N |
| ATOM | 5151 CA LEU H 260 | −6.295 18.149 19.657 1.00 6.09 | B C |
| ATOM | 5152 CB LEU H 260 | −5.239 18.052 18.552 1.00 6.09 | B C |
| ATOM | 5153 CG LEU H 260 | −4.235 19.203 18.446 1.00 6.24 | B C |
| ATOM | 5154 CD1 LEU H 260 | −3.350 19.030 17.222 1.00 6.53 | B C |
| ATOM | 5155 CD2 LEU H 260 | −4.944 20.549 18.407 1.00 5.98 | B C |
| ATOM | 5156 C LEU H 260 | −7.692 18.026 19.056 1.00 6.25 | B C |
| ATOM | 5157 O LEU H 260 | −8.428 19.010 18.963 1.00 6.37 | B O |
| ATOM | 5158 N ILE H 261 | −8.024 16.825 18.596 1.00 6.63 | B N |
| ATOM | 5159 CA ILE H 261 | −9.395 16.490 18.245 1.00 7.19 | B C |
| ATOM | 5160 CB ILE H 261 | −9.568 14.975 18.078 1.00 7.09 | B C |
| ATOM | 5161 CG1 ILE H 261 | −9.037 14.528 16.715 1.00 7.46 | B C |
| ATOM | 5162 CD1 ILE H 261 | −8.132 13.315 16.782 1.00 8.38 | B C |
| ATOM | 5163 CG2 ILE H 261 | −11.024 14.579 18.262 1.00 6.61 | B C |
| ATOM | 5164 C ILE H 261 | −10.352 16.980 19.322 1.00 8.01 | B C |
| ATOM | 5165 O ILE H 261 | −11.255 17.770 19.051 1.00 8.26 | B O |
| ATOM | 5166 N ASN H 262 | −10.081 16.586 20.560 1.00 9.05 | B N |

APPENDIX-continued (APPENDIX discloses SEQ ID NOS 29-32, 29-32 and 29-32, respectively, in order of appearance)

| | | | |
|---|---|---|---|
| ATOM | 5167 CA ASN H 262 | −10.896 17.006 21.689 1.00 9.88 | B C |
| ATOM | 5168 CB ASN H 262 | −10.175 16.714 23.001 1.00 9.99 | B C |
| ATOM | 5169 CG ASN H 262 | −11.127 16.353 24.111 1.00 11.16 | B C |
| ATOM | 5170 OD1 ASN H 262 | −12.345 16.408 23.936 1.00 12.70 | B O |
| ATOM | 5171 ND2 ASN H 262 | −10.583 15.980 25.264 1.00 13.20 | B N |
| ATOM | 5172 C ASN H 262 | −11.258 18.482 21.619 1.00 10.17 | B C |
| ATOM | 5173 O ASN H 262 | −12.347 18.887 22.027 1.00 10.52 | B O |
| ATOM | 5174 N ASP H 263 | −10.310 19.289 21.158 1.00 10.62 | B N |
| ATOM | 5175 CA ASP H 263 | −10.437 20.734 21.247 1.00 11.02 | B C |
| ATOM | 5176 CB ASP H 263 | −9.057 21.395 21.285 1.00 11.49 | B C |
| ATOM | 5177 CG ASP H 263 | −9.138 22.905 21.401 1.00 12.80 | B C |
| ATOM | 5178 OD1 ASP H 263 | −9.972 23.401 22.188 1.00 14.72 | B O |
| ATOM | 5179 OD2 ASP H 263 | −8.354 23.596 20.717 1.00 13.88 | B O |
| ATOM | 5180 C ASP H 263 | −11.261 21.293 20.091 1.00 10.92 | B C |
| ATOM | 5181 O ASP H 263 | −11.686 22.446 20.130 1.00 10.96 | B O |
| ATOM | 5182 N MET H 264 | −11.539 20.453 19.097 1.00 10.91 | B N |
| ATOM | 5183 CA MET H 264 | −12.199 20.904 17.871 1.00 10.78 | B C |
| ATOM | 5184 CB MET H 264 | −12.091 19.840 16.770 1.00 10.51 | B C |
| ATOM | 5185 CG MET H 264 | −10.664 19.427 16.425 1.00 11.26 | B C |
| ATOM | 5186 SD MET H 264 | −10.510 18.571 14.840 1.00 12.70 | B S |
| ATOM | 5187 CE MET H 264 | −11.715 17.260 15.021 1.00 13.92 | B C |
| ATOM | 5188 C MET H 264 | −13.666 21.240 18.119 1.00 10.85 | B C |
| ATOM | 5189 O MET H 264 | −14.369 20.489 18.795 1.00 11.03 | B O |
| ATOM | 5190 N PRO H 265 | −14.146 22.342 17.517 1.00 10.88 | B N |
| ATOM | 5191 CA PRO H 265 | −15.522 22.802 17.700 1.00 11.09 | B C |
| ATOM | 5192 CB PRO H 265 | −15.515 24.198 17.060 1.00 11.28 | B C |
| ATOM | 5193 CG PRO H 265 | −14.322 24.216 16.167 1.00 11.24 | B C |
| ATOM | 5194 CD PRO H 265 | −13.313 23.356 16.849 1.00 11.03 | B C |
| ATOM | 5195 C PRO H 265 | −16.546 21.912 17.003 1.00 11.19 | B C |
| ATOM | 5196 O PRO H 265 | −17.320 22.395 16.177 1.00 11.47 | B O |
| ATOM | 5197 N ILE H 266 | −16.633 20.655 17.425 1.00 11.54 | B N |
| ATOM | 5198 CA ILE H 266 | −17.540 19.710 16.786 1.00 12.15 | B C |
| ATOM | 5199 CB ILE H 266 | −16.794 18.757 15.828 1.00 12.22 | B C |
| ATOM | 5200 CG1 ILE H 266 | −15.611 18.088 16.536 1.00 12.53 | B C |
| ATOM | 5201 CD1 ILE H 266 | −15.044 16.895 15.789 1.00 12.40 | B C |
| ATOM | 5202 CG2 ILE H 266 | −16.337 19.507 14.588 1.00 12.74 | B C |
| ATOM | 5203 C ILE H 266 | −18.353 18.902 17.793 1.00 12.29 | B C |
| ATOM | 5204 O ILE H 266 | −18.068 18.913 18.991 1.00 12.36 | B O |
| ATOM | 5205 N THR H 267 | −19.404 18.252 17.303 1.00 12.29 | B N |
| ATOM | 5206 CA THR H 267 | −20.248 17.414 18.148 1.00 12.43 | B C |
| ATOM | 5207 CB THR H 267 | −21.440 16.821 17.366 1.00 12.40 | B C |
| ATOM | 5208 OG1 THR H 267 | −21.299 15.397 17.278 1.00 13.21 | B O |
| ATOM | 5209 CG2 THR H 267 | −21.509 17.405 15.968 1.00 12.21 | B C |
| ATOM | 5210 C THR H 267 | −19.432 16.276 18.740 1.00 12.37 | B C |
| ATOM | 5211 O THR H 267 | −18.246 16.134 18.446 1.00 12.29 | B O |
| ATOM | 5212 N ASN H 268 | −20.058 15.490 19.605 1.00 12.47 | B N |
| ATOM | 5213 CA ASN H 268 | −19.325 14.501 20.377 1.00 12.57 | B C |
| ATOM | 5214 CB ASN H 268 | −20.025 14.218 21.701 1.00 12.69 | B C |
| ATOM | 5215 CG ASN H 268 | −19.461 15.041 22.832 1.00 13.65 | B C |
| ATOM | 5216 OD1 ASN H 268 | −18.555 15.851 22.631 1.00 14.37 | B O |
| ATOM | 5217 ND2 ASN H 268 | −20.005 14.856 24.028 1.00 15.74 | B N |
| ATOM | 5218 C ASN H 268 | −19.084 13.207 19.621 1.00 12.43 | B C |
| ATOM | 5219 O ASN H 268 | −18.038 12.576 19.776 1.00 12.51 | B O |
| ATOM | 5220 N ASP H 269 | −20.107 12.747 18.912 1.00 12.34 | B N |
| ATOM | 5221 CA ASP H 269 | −19.976 11.565 18.077 1.00 12.33 | B C |
| ATOM | 5222 CB ASP H 269 | −21.316 11.222 17.431 1.00 12.89 | B C |
| ATOM | 5223 CG ASP H 269 | −22.404 10.959 18.456 1.00 14.84 | B C |
| ATOM | 5224 OD1 ASP H 269 | −22.145 10.209 19.422 1.00 16.90 | B O |
| ATOM | 5225 OD2 ASP H 269 | −23.487 11.573 18.346 1.00 17.65 | B O |
| ATOM | 5226 C ASP H 269 | −18.916 11.780 17.008 1.00 11.60 | B C |
| ATOM | 5227 O ASP H 269 | −18.073 10.914 16.774 1.00 11.65 | B O |
| ATOM | 5228 N GLN H 270 | −18.924 12.963 16.405 1.00 10.62 | B N |
| ATOM | 5229 CA GLN H 270 | −17.836 13.371 15.530 1.00 10.01 | B C |
| ATOM | 5230 CB GLN H 270 | −17.958 14.851 15.179 1.00 10.18 | B C |
| ATOM | 5231 CG GLN H 270 | −17.709 15.154 13.718 1.00 11.49 | B C |
| ATOM | 5232 CD GLN H 270 | −18.572 16.286 13.213 1.00 14.38 | B C |
| ATOM | 5233 OE1 GLN H 270 | −18.076 17.238 12.613 1.00 16.38 | B O |
| ATOM | 5234 NE2 GLN H 270 | −19.866 16.215 13.496 1.00 15.41 | B N |
| ATOM | 5235 C GLN H 270 | −16.486 13.097 16.181 1.00 9.48 | B C |
| ATOM | 5236 O GLN H 270 | −15.696 12.296 15.682 1.00 9.12 | B O |
| ATOM | 5237 N LYS H 271 | −16.229 13.763 17.301 1.00 9.19 | B N |
| ATOM | 5238 CA LYS H 271 | −15.004 13.541 18.056 1.00 8.89 | B C |
| ATOM | 5239 CB LYS H 271 | −15.117 14.168 19.448 1.00 8.52 | B C |
| ATOM | 5240 CG LYS H 271 | −15.410 15.663 19.445 1.00 9.14 | B C |
| ATOM | 5241 CD LYS H 271 | −14.906 16.316 20.726 1.00 10.72 | B C |
| ATOM | 5242 CE LYS H 271 | −15.469 17.718 20.900 1.00 10.79 | B C |
| ATOM | 5243 NZ LYS H 271 | −14.711 18.506 21.916 1.00 9.77 | B N |

APPENDIX-continued (APPENDIX discloses SEQ ID NOS 29-32, 29-32 and 29-32, respectively, in order of appearance)

| | | | |
|---|---|---|---|
| ATOM | 5244 C LYS H 271 | −14.699 12.049 18.175 1.00 8.83 | B C |
| ATOM | 5245 O LYS H 271 | −13.660 11.577 17.713 1.00 9.05 | B O |
| ATOM | 5246 N LYS H 272 | −15.653 11.301 18.719 1.00 8.65 | B N |
| ATOM | 5247 CA LYS H 272 | −15.485 9.868 18.899 1.00 8.50 | B C |
| ATOM | 5248 CB LYS H 272 | −16.766 9.240 19.443 1.00 9.14 | B C |
| ATOM | 5249 CG LYS H 272 | −16.762 7.726 19.397 1.00 11.58 | B C |
| ATOM | 5250 CD LYS H 272 | −18.170 7.167 19.394 1.00 15.78 | B C |
| ATOM | 5251 CE LYS H 272 | −18.151 5.663 19.599 1.00 17.65 | B C |
| ATOM | 5252 NZ LYS H 272 | −19.476 5.142 20.029 1.00 19.68 | B N |
| ATOM | 5253 C LYS H 272 | −15.083 9.185 17.598 1.00 7.88 | B C |
| ATOM | 5254 O LYS H 272 | −14.195 8.332 17.587 1.00 8.12 | B O |
| ATOM | 5255 N LEU H 273 | −15.787 9.506 16.517 1.00 6.95 | B N |
| ATOM | 5256 CA LEU H 273 | −15.456 8.939 15.216 1.00 5.70 | B C |
| ATOM | 5257 CB LEU H 273 | −16.366 9.490 14.116 1.00 5.85 | B C |
| ATOM | 5258 CG LEU H 273 | −15.894 9.204 12.683 1.00 4.65 | B C |
| ATOM | 5259 CD1 LEU H 273 | −16.085 7.739 12.312 1.00 4.57 | B C |
| ATOM | 5260 CD2 LEU H 273 | −16.569 10.123 11.669 1.00 3.69 | B C |
| ATOM | 5261 C LEU H 273 | −14.005 9.227 14.877 1.00 5.14 | B C |
| ATOM | 5262 O LEU H 273 | −13.188 8.312 14.795 1.00 5.25 | B O |
| ATOM | 5263 N MET H 274 | −13.668 10.509 14.775 1.00 4.52 | B N |
| ATOM | 5264 CA MET H 274 | −12.307 10.910 14.447 1.00 4.59 | B C |
| ATOM | 5265 CB MET H 274 | −12.147 12.429 14.567 1.00 4.35 | B C |
| ATOM | 5266 CG MET H 274 | −12.862 13.219 13.479 1.00 4.50 | B C |
| ATOM | 5267 SD MET H 274 | −12.547 14.992 13.574 1.00 5.51 | B S |
| ATOM | 5268 CE MET H 274 | −10.875 15.078 12.935 1.00 5.26 | B C |
| ATOM | 5269 C MET H 274 | −11.294 10.190 15.334 1.00 5.18 | B C |
| ATOM | 5270 O MET H 274 | −10.272 9.703 14.851 1.00 5.61 | B O |
| ATOM | 5271 N SER H 275 | −11.652 10.006 16.601 1.00 5.89 | B N |
| ATOM | 5272 CA SER H 275 | −10.752 9.380 17.557 1.00 6.18 | B C |
| ATOM | 5273 CB SER H 275 | −11.237 9.619 18.988 1.00 6.33 | B C |
| ATOM | 5274 OG SER H 275 | −11.029 10.969 19.371 1.00 5.91 | B O |
| ATOM | 5275 C SER H 275 | −10.583 7.886 17.288 1.00 6.58 | B C |
| ATOM | 5276 O SER H 275 | −9.519 7.318 17.544 1.00 7.03 | B O |
| ATOM | 5277 N ASN H 276 | −11.607 7.268 16.711 1.00 7.07 | B N |
| ATOM | 5278 CA ASN H 276 | −11.525 5.857 16.369 1.00 7.86 | B C |
| ATOM | 5279 CB ASN H 276 | −12.885 5.173 16.547 1.00 8.34 | B C |
| ATOM | 5280 CG ASN H 276 | −13.108 4.676 17.969 1.00 9.77 | B C |
| ATOM | 5281 OD1 ASN H 276 | −12.161 4.307 18.666 1.00 11.84 | B O |
| ATOM | 5282 ND2 ASN H 276 | −14.351 4.748 18.433 1.00 11.15 | B N |
| ATOM | 5283 C ASN H 276 | −10.959 5.605 14.971 1.00 7.71 | B C |
| ATOM | 5284 O ASN H 276 | −10.950 4.468 14.498 1.00 7.84 | B O |
| ATOM | 5285 N ASN H 277 | −10.386 6.643 14.363 1.00 7.77 | B N |
| ATOM | 5286 CA ASN H 277 | −10.026 6.597 12.943 1.00 7.85 | B C |
| ATOM | 5287 CB ASN H 277 | −11.209 7.021 12.073 1.00 7.58 | B C |
| ATOM | 5288 CG ASN H 277 | −12.197 5.896 11.846 1.00 8.29 | B C |
| ATOM | 5289 OD1 ASN H 277 | −11.932 4.970 11.079 1.00 9.04 | B O |
| ATOM | 5290 ND2 ASN H 277 | −13.297 5.915 12.592 1.00 9.57 | B N |
| ATOM | 5291 C ASN H 277 | −8.792 7.426 12.585 1.00 7.86 | B C |
| ATOM | 5292 O ASN H 277 | −8.614 7.832 11.435 1.00 7.85 | B O |
| ATOM | 5293 N VAL H 278 | −8.003 7.754 13.603 1.00 7.67 | B N |
| ATOM | 5294 CA VAL H 278 | −6.682 8.354 13.425 1.00 7.77 | B C |
| ATOM | 5295 CB VAL H 278 | −5.677 7.813 14.459 1.00 7.98 | B C |
| ATOM | 5296 CG1 VAL H 278 | −5.763 8.615 15.749 1.00 7.21 | B C |
| ATOM | 5297 CG2 VAL H 278 | −5.932 6.336 14.725 1.00 8.99 | B C |
| ATOM | 5298 C VAL H 278 | −6.095 8.223 12.019 1.00 7.76 | B C |
| ATOM | 5299 O VAL H 278 | −5.641 9.211 11.444 1.00 7.84 | B O |
| ATOM | 5300 N GLN H 279 | −5.935 6.989 11.553 1.00 7.47 | B N |
| ATOM | 5301 CA GLN H 279 | −5.162 6.725 10.343 1.00 7.07 | B C |
| ATOM | 5302 CB GLN H 279 | −5.291 5.256 9.938 1.00 7.62 | B C |
| ATOM | 5303 CG GLN H 279 | −3.986 4.621 9.497 1.00 10.35 | B C |
| ATOM | 5304 CD GLN H 279 | −4.194 3.335 8.725 1.00 13.70 | B C |
| ATOM | 5305 OE1 GLN H 279 | −5.319 2.986 8.367 1.00 15.06 | B O |
| ATOM | 5306 NE2 GLN H 279 | −3.105 2.622 8.460 1.00 13.97 | B N |
| ATOM | 5307 C GLN H 279 | −5.610 7.621 9.192 1.00 6.02 | B C |
| ATOM | 5308 O GLN H 279 | −4.795 8.297 8.563 1.00 5.45 | B O |
| ATOM | 5309 N ILE H 280 | −6.881 7.492 8.829 1.00 5.25 | B N |
| ATOM | 5310 CA ILE H 280 | −7.499 8.346 7.822 1.00 4.74 | B C |
| ATOM | 5311 CB ILE H 280 | −9.022 8.133 7.775 1.00 4.58 | B C |
| ATOM | 5312 CG1 ILE H 280 | −9.349 6.641 7.685 1.00 4.16 | B C |
| ATOM | 5313 CD1 ILE H 280 | −8.986 6.014 6.357 1.00 3.88 | B C |
| ATOM | 5314 CG2 ILE H 280 | −9.636 8.897 6.612 1.00 3.92 | B C |
| ATOM | 5315 C ILE H 280 | −7.225 9.818 8.101 1.00 4.43 | B C |
| ATOM | 5316 O ILE H 280 | −6.655 10.522 7.268 1.00 4.39 | B O |
| ATOM | 5317 N VAL H 281 | −7.745 10.301 9.224 1.00 4.05 | B N |
| ATOM | 5318 CA VAL H 281 | −7.502 11.671 9.651 1.00 3.58 | B C |
| ATOM | 5319 CB VAL H 281 | −7.705 11.833 11.170 1.00 3.13 | B C |
| ATOM | 5320 CG1 VAL H 281 | −7.901 13.299 11.526 1.00 2.34 | B C |

APPENDIX-continued (APPENDIX discloses SEQ ID NOS 29-32, 29-32 and 29-32, respectively, in order of appearance)

| | | | |
|---|---|---|---|
| ATOM | 5321 CG2 VAL H 281 | −8.890 11.002 11.638 1.00 2.21 | B C |
| ATOM | 5322 C VAL H 281 | −6.089 12.110 9.280 1.00 3.96 | B C |
| ATOM | 5323 O VAL H 281 | −5.905 13.063 8.522 1.00 4.15 | B O |
| ATOM | 5324 N ARG H 282 | −5.096 11.377 9.777 1.00 4.23 | B N |
| ATOM | 5325 CA ARG H 282 | −3.697 11.649 9.454 1.00 4.45 | B C |
| ATOM | 5326 CB ARG H 282 | −2.799 10.506 9.941 1.00 3.96 | B C |
| ATOM | 5327 CG ARG H 282 | −2.843 10.255 11.440 1.00 2.99 | B C |
| ATOM | 5328 CD ARG H 282 | −1.441 10.173 12.028 1.00 2.28 | B C |
| ATOM | 5329 NE ARG H 282 | −1.470 9.891 13.460 1.00 2.00 | B N |
| ATOM | 5330 CZ ARG H 282 | −0.687 10.483 14.358 1.00 2.44 | B C |
| ATOM | 5331 NH1 ARG H 282 | 0.219 11.371 13.970 1.00 2.04 | B N |
| ATOM | 5332 NH2 ARG H 282 | −0.770 10.140 15.636 1.00 3.44 | B N |
| ATOM | 5333 C ARG H 282 | −3.530 11.813 7.953 1.00 5.32 | B C |
| ATOM | 5334 O ARG H 282 | −2.952 12.793 7.482 1.00 5.95 | B O |
| ATOM | 5335 N GLN H 283 | −3.946 10.791 7.214 1.00 5.50 | B N |
| ATOM | 5336 CA GLN H 283 | −3.837 10.802 5.766 1.00 5.80 | B C |
| ATOM | 5337 CB GLN H 283 | −4.404 9.511 5.178 1.00 6.19 | B C |
| ATOM | 5338 CG GLN H 283 | −3.531 8.297 5.431 1.00 9.68 | B C |
| ATOM | 5339 CD GLN H 283 | −4.248 6.994 5.156 1.00 13.92 | B C |
| ATOM | 5340 OE1 GLN H 283 | −5.408 6.984 4.745 1.00 16.20 | B O |
| ATOM | 5341 NE2 GLN H 283 | −3.549 5.883 5.354 1.00 14.17 | B N |
| ATOM | 5342 C GLN H 283 | −4.552 12.008 5.175 1.00 5.44 | B C |
| ATOM | 5343 O GLN H 283 | −4.187 12.493 4.104 1.00 5.43 | B O |
| ATOM | 5344 N GLN H 284 | −5.532 12.527 5.905 1.00 5.26 | B N |
| ATOM | 5345 CA GLN H 284 | −6.361 13.609 5.396 1.00 5.18 | B C |
| ATOM | 5346 CB GLN H 284 | −7.799 13.451 5.877 1.00 5.32 | B C |
| ATOM | 5347 CG GLN H 284 | −8.666 12.649 4.933 1.00 6.85 | B C |
| ATOM | 5348 CD GLN H 284 | −10.091 12.547 5.415 1.00 9.21 | B C |
| ATOM | 5349 OE1 GLN H 284 | −10.340 12.297 6.595 1.00 9.74 | B O |
| ATOM | 5350 NE2 GLN H 284 | −11.034 12.860 4.537 1.00 9.79 | B N |
| ATOM | 5351 C GLN H 284 | −5.817 14.967 5.813 1.00 4.67 | B C |
| ATOM | 5352 O GLN H 284 | −6.336 16.006 5.406 1.00 4.19 | B O |
| ATOM | 5353 N SER H 285 | −4.758 14.950 6.614 1.00 4.51 | B N |
| ATOM | 5354 CA SER H 285 | −4.240 16.170 7.212 1.00 4.39 | B C |
| ATOM | 5355 CB SER H 285 | −4.020 15.979 8.713 1.00 4.13 | B C |
| ATOM | 5356 OG SER H 285 | −5.177 15.446 9.334 1.00 4.40 | B O |
| ATOM | 5357 C SER H 285 | −2.943 16.598 6.540 1.00 4.44 | B C |
| ATOM | 5358 O SER H 285 | −2.286 15.804 5.866 1.00 4.82 | B O |
| ATOM | 5359 N TYR H 286 | −2.600 17.870 6.704 1.00 4.53 | B N |
| ATOM | 5360 CA TYR H 286 | −1.328 18.388 6.228 1.00 4.80 | B C |
| ATOM | 5361 CB TYR H 286 | −1.560 19.527 5.236 1.00 4.88 | B C |
| ATOM | 5362 CG TYR H 286 | −2.163 19.083 3.923 1.00 5.68 | B C |
| ATOM | 5363 CD1 TYR H 286 | −3.448 18.558 3.868 1.00 7.34 | B C |
| ATOM | 5364 CE1 TYR H 286 | −4.003 18.153 2.668 1.00 9.02 | B C |
| ATOM | 5365 CZ TYR H 286 | −3.279 18.287 1.502 1.00 9.40 | B C |
| ATOM | 5366 OH TYR H 286 | −3.829 17.892 0.304 1.00 10.44 | B O |
| ATOM | 5367 CE2 TYR H 286 | −2.006 18.817 1.530 1.00 9.38 | B C |
| ATOM | 5368 CD2 TYR H 286 | −1.458 19.214 2.735 1.00 7.39 | B C |
| ATOM | 5369 C TYR H 286 | −0.501 18.884 7.404 1.00 4.76 | B C |
| ATOM | 5370 O TYR H 286 | −1.036 19.160 8.478 1.00 5.25 | B O |
| ATOM | 5371 N SER H 287 | 0.803 19.011 7.194 1.00 4.52 | B N |
| ATOM | 5372 CA SER H 287 | 1.649 19.738 8.125 1.00 4.45 | B C |
| ATOM | 5373 CB SER H 287 | 2.518 18.768 8.927 1.00 4.57 | B C |
| ATOM | 5374 OG SER H 287 | 3.602 19.441 9.544 1.00 4.38 | B O |
| ATOM | 5375 C SER H 287 | 2.515 20.758 7.396 1.00 4.61 | B C |
| ATOM | 5376 O SER H 287 | 3.264 20.409 6.483 1.00 4.40 | B O |
| ATOM | 5377 N ILE H 288 | 2.294 22.033 7.710 1.00 5.11 | B N |
| ATOM | 5378 CA ILE H 288 | 3.067 23.130 7.131 1.00 5.81 | B C |
| ATOM | 5379 CB ILE H 288 | 2.176 24.349 6.825 1.00 5.52 | B C |
| ATOM | 5380 CG1 ILE H 288 | 0.730 23.913 6.578 1.00 5.47 | B C |
| ATOM | 5381 CD1 ILE H 288 | 0.479 23.356 5.196 1.00 6.23 | B C |
| ATOM | 5382 CG2 ILE H 288 | 2.733 25.142 5.651 1.00 6.22 | B C |
| ATOM | 5383 C ILE H 288 | 4.170 23.581 8.080 1.00 6.71 | B C |
| ATOM | 5384 O ILE H 288 | 3.902 23.948 9.224 1.00 7.30 | B O |
| ATOM | 5385 N MET H 289 | 5.380 23.699 7.548 1.00 7.71 | B N |
| ATOM | 5386 CA MET H 289 | 6.487 24.307 8.274 1.00 8.57 | B C |
| ATOM | 5387 CB MET H 289 | 7.781 24.096 7.492 1.00 8.71 | B C |
| ATOM | 5388 CG MET H 289 | 9.038 24.181 8.326 1.00 9.70 | B C |
| ATOM | 5389 SD MET H 289 | 10.511 24.120 7.292 1.00 12.59 | B S |
| ATOM | 5390 CE MET H 289 | 10.168 25.446 6.138 1.00 12.41 | B C |
| ATOM | 5391 C MET H 289 | 6.245 25.801 8.468 1.00 9.12 | B C |
| ATOM | 5392 O MET H 289 | 5.976 26.513 7.501 1.00 9.31 | B O |
| ATOM | 5393 N SER H 290 | 6.457 26.293 9.688 1.00 9.80 | B N |
| ATOM | 5394 CA SER H 290 | 6.140 27.688 10.021 1.00 10.49 | B C |
| ATOM | 5395 CB SER H 290 | 5.283 27.777 11.287 1.00 10.64 | B C |
| ATOM | 5396 OG SER H 290 | 4.906 29.117 11.560 1.00 11.99 | B O |
| ATOM | 5397 C SER H 290 | 7.372 28.582 10.146 1.00 10.75 | B C |

APPENDIX-continued (APPENDIX discloses SEQ ID NOS 29-32, 29-32 and 29-32, respectively, in order of appearance)

| | | | |
|---|---|---|---|
| ATOM | 5398 O SER H 290 | 7.635 29.401 9.265 1.00 10.89 | B O |
| ATOM | 5399 N ILE H 291 | 8.095 28.469 11.258 1.00 11.04 | B N |
| ATOM | 5400 CA ILE H 291 | 9.405 29.112 11.361 1.00 11.41 | B C |
| ATOM | 5401 CB ILE H 291 | 9.335 30.523 11.981 1.00 11.80 | B C |
| ATOM | 5402 CG1 ILE H 291 | 8.071 30.680 12.828 1.00 11.81 | B C |
| ATOM | 5403 CD1 ILE H 291 | 8.273 30.362 14.291 1.00 11.76 | B C |
| ATOM | 5404 CG2 ILE H 291 | 9.390 31.586 10.891 1.00 12.39 | B C |
| ATOM | 5405 C ILE H 291 | 10.510 28.289 12.022 1.00 11.13 | B C |
| ATOM | 5406 O ILE H 291 | 10.337 27.742 13.111 1.00 10.55 | B O |
| ATOM | 5407 N ILE H 292 | 11.678 28.302 11.388 1.00 11.36 | B N |
| ATOM | 5408 CA ILE H 292 | 12.827 27.544 11.855 1.00 11.82 | B C |
| ATOM | 5409 CB ILE H 292 | 13.483 26.752 10.710 1.00 11.86 | B C |
| ATOM | 5410 CG1 ILE H 292 | 12.770 27.030 9.386 1.00 13.42 | B C |
| ATOM | 5411 CD1 ILE H 292 | 11.373 27.593 9.542 1.00 15.86 | B C |
| ATOM | 5412 CG2 ILE H 292 | 13.500 25.262 11.022 1.00 10.85 | B C |
| ATOM | 5413 C ILE H 292 | 13.867 28.476 12.454 1.00 11.72 | B C |
| ATOM | 5414 O ILE H 292 | 14.414 29.343 11.771 1.00 11.28 | B O |
| ATOM | 5415 N LYS H 293 | 14.150 28.269 13.733 1.00 12.11 | B N |
| ATOM | 5416 CA LYS H 293 | 15.287 28.894 14.382 1.00 12.92 | B C |
| ATOM | 5417 CB LYS H 293 | 14.812 29.763 15.544 1.00 13.15 | B C |
| ATOM | 5418 CG LYS H 293 | 13.615 30.634 15.208 1.00 14.17 | B C |
| ATOM | 5419 CD LYS H 293 | 13.793 32.037 15.758 1.00 15.37 | B C |
| ATOM | 5420 CE LYS H 293 | 12.940 33.041 15.001 1.00 16.68 | B C |
| ATOM | 5421 NZ LYS H 293 | 13.111 34.421 15.532 1.00 18.18 | B N |
| ATOM | 5422 C LYS H 293 | 16.224 27.813 14.894 1.00 13.32 | B C |
| ATOM | 5423 O LYS H 293 | 15.800 26.689 15.167 1.00 13.17 | B O |
| ATOM | 5424 N GLU H 294 | 17.511 28.132 14.944 1.00 14.07 | B N |
| ATOM | 5425 CA GLU H 294 | 18.518 27.147 15.302 1.00 15.07 | B C |
| ATOM | 5426 CB GLU H 294 | 19.847 27.831 15.624 1.00 15.94 | B C |
| ATOM | 5427 CG GLU H 294 | 20.563 28.399 14.409 1.00 19.87 | B C |
| ATOM | 5428 CD GLU H 294 | 21.978 28.849 14.721 1.00 23.88 | B C |
| ATOM | 5429 OE1 GLU H 294 | 22.830 27.983 15.010 1.00 23.75 | B O |
| ATOM | 5430 OE2 GLU H 294 | 22.247 30.066 14.640 1.00 25.81 | B O |
| ATOM | 5431 C GLU H 294 | 18.056 26.299 16.482 1.00 14.40 | B C |
| ATOM | 5432 O GLU H 294 | 18.348 25.106 16.546 1.00 14.33 | B O |
| ATOM | 5433 N GLU H 295 | 17.279 26.904 17.378 1.00 13.97 | B N |
| ATOM | 5434 CA GLU H 295 | 16.914 26.255 18.635 1.00 13.84 | B C |
| ATOM | 5435 CB GLU H 295 | 17.570 26.953 19.830 1.00 14.67 | B C |
| ATOM | 5436 CG GLU H 295 | 18.047 28.366 19.550 1.00 17.56 | B C |
| ATOM | 5437 CD GLU H 295 | 16.928 29.281 19.096 1.00 21.41 | B C |
| ATOM | 5438 OE1 GLU H 295 | 16.816 29.524 17.876 1.00 22.35 | B O |
| ATOM | 5439 OE2 GLU H 295 | 16.190 29.795 19.962 1.00 23.20 | B O |
| ATOM | 5440 C GLU H 295 | 15.406 26.155 18.851 1.00 12.77 | B C |
| ATOM | 5441 O GLU H 295 | 14.956 25.743 19.919 1.00 12.58 | B O |
| ATOM | 5442 N VAL H 296 | 14.627 26.533 17.845 1.00 11.72 | B N |
| ATOM | 5443 CA VAL H 296 | 13.195 26.268 17.870 1.00 10.65 | B C |
| ATOM | 5444 CB VAL H 296 | 12.418 27.396 18.571 1.00 10.47 | B C |
| ATOM | 5445 CG1 VAL H 296 | 10.974 26.983 18.804 1.00 9.77 | B C |
| ATOM | 5446 CG2 VAL H 296 | 13.090 27.760 19.884 1.00 11.31 | B C |
| ATOM | 5447 C VAL H 296 | 12.632 26.053 16.473 1.00 10.26 | B C |
| ATOM | 5448 O VAL H 296 | 12.887 26.838 15.561 1.00 10.09 | B O |
| ATOM | 5449 N LEU H 297 | 11.781 25.042 16.345 1.00 9.77 | B N |
| ATOM | 5450 CA LEU H 297 | 11.034 24.815 15.119 1.00 8.97 | B C |
| ATOM | 5451 CB LEU H 297 | 11.386 23.448 14.534 1.00 8.64 | B C |
| ATOM | 5452 CG LEU H 297 | 10.442 22.948 13.442 1.00 9.01 | B C |
| ATOM | 5453 CD1 LEU H 297 | 10.243 24.018 12.373 1.00 9.79 | B C |
| ATOM | 5454 CD2 LEU H 297 | 10.960 21.648 12.834 1.00 9.43 | B C |
| ATOM | 5455 C LEU H 297 | 9.535 24.885 15.388 1.00 8.34 | B C |
| ATOM | 5456 O LEU H 297 | 9.006 24.129 16.205 1.00 8.64 | B O |
| ATOM | 5457 N ALA H 298 | 8.848 25.771 14.675 1.00 7.21 | B N |
| ATOM | 5458 CA ALA H 298 | 7.396 25.872 14.777 1.00 6.33 | B C |
| ATOM | 5459 CB ALA H 298 | 6.987 27.268 15.238 1.00 6.68 | B C |
| ATOM | 5460 C ALA H 298 | 6.749 25.537 13.441 1.00 5.85 | B C |
| ATOM | 5461 O ALA H 298 | 7.310 25.823 12.384 1.00 5.96 | B O |
| ATOM | 5462 N TYR H 299 | 5.653 24.793 13.492 1.00 5.28 | B N |
| ATOM | 5463 CA TYR H 299 | 4.928 24.443 12.282 1.00 4.63 | B C |
| ATOM | 5464 CB TYR H 299 | 5.468 23.142 11.691 1.00 4.36 | B C |
| ATOM | 5465 CG TYR H 299 | 5.432 21.978 12.652 1.00 4.34 | B C |
| ATOM | 5466 CD1 TYR H 299 | 4.330 21.136 12.711 1.00 4.48 | B C |
| ATOM | 5467 CE1 TYR H 299 | 4.299 20.061 13.578 1.00 4.55 | B C |
| ATOM | 5468 CZ TYR H 299 | 5.373 19.826 14.410 1.00 3.72 | B C |
| ATOM | 5469 OH TYR H 299 | 5.343 18.762 15.282 1.00 2.38 | B O |
| ATOM | 5470 CE2 TYR H 299 | 6.475 20.651 14.374 1.00 4.13 | B C |
| ATOM | 5471 CD2 TYR H 299 | 6.494 21.727 13.509 1.00 4.38 | B C |
| ATOM | 5472 C TYR H 299 | 3.443 24.308 12.563 1.00 4.32 | B C |
| ATOM | 5473 O TYR H 299 | 3.034 24.068 13.699 1.00 4.67 | B O |
| ATOM | 5474 N VAL H 300 | 2.638 24.454 11.519 1.00 3.87 | B N |

APPENDIX-continued (APPENDIX discloses SEQ ID NOS 29-32, 29-32 and 29-32, respectively, in order of appearance)

| | | | |
|---|---|---|---|
| ATOM | 5475 CA VAL H 300 | 1.193 24.395 11.664 1.00 3.57 | B C |
| ATOM | 5476 CB VAL H 300 | 0.501 25.518 10.873 1.00 3.52 | B C |
| ATOM | 5477 CG1 VAL H 300 | −0.990 25.241 10.751 1.00 3.44 | B C |
| ATOM | 5478 CG2 VAL H 300 | 0.743 26.861 11.544 1.00 3.90 | B C |
| ATOM | 5479 C VAL H 300 | 0.654 23.049 11.203 1.00 3.53 | B C |
| ATOM | 5480 O VAL H 300 | 0.858 22.647 10.058 1.00 3.68 | B O |
| ATOM | 5481 N VAL H 301 | −0.061 22.370 12.092 1.00 3.41 | B N |
| ATOM | 5482 CA VAL H 301 | −0.857 21.216 11.704 1.00 3.36 | B C |
| ATOM | 5483 CB VAL H 301 | −1.038 20.233 12.873 1.00 3.24 | B C |
| ATOM | 5484 CG1 VAL H 301 | −2.141 19.235 12.559 1.00 3.76 | B C |
| ATOM | 5485 CG2 VAL H 301 | 0.270 19.516 13.169 1.00 3.10 | B C |
| ATOM | 5486 C VAL H 301 | −2.223 21.641 11.183 1.00 3.48 | B C |
| ATOM | 5487 O VAL H 301 | −2.772 22.661 11.602 1.00 3.92 | B O |
| ATOM | 5488 N GLN H 302 | −2.766 20.845 10.270 1.00 3.21 | B N |
| ATOM | 5489 CA GLN H 302 | −3.989 21.201 9.569 1.00 3.01 | B C |
| ATOM | 5490 CB GLN H 302 | −3.662 21.767 8.188 1.00 3.24 | B C |
| ATOM | 5491 CG GLN H 302 | −4.875 21.992 7.307 1.00 5.21 | B C |
| ATOM | 5492 CD GLN H 302 | −4.603 22.977 6.191 1.00 7.54 | B C |
| ATOM | 5493 OE1 GLN H 302 | −3.715 23.822 6.297 1.00 7.28 | B O |
| ATOM | 5494 NE2 GLN H 302 | −5.364 22.870 5.108 1.00 9.27 | B N |
| ATOM | 5495 C GLN H 302 | −4.885 19.978 9.434 1.00 2.42 | B C |
| ATOM | 5496 O GLN H 302 | −4.564 19.038 8.706 1.00 2.40 | B O |
| ATOM | 5497 N LEU H 303 | −5.964 19.959 10.207 1.00 2.00 | B N |
| ATOM | 5498 CA LEU H 303 | −6.802 18.775 10.329 1.00 2.00 | B C |
| ATOM | 5499 CB LEU H 303 | −6.945 18.389 11.802 1.00 2.00 | B C |
| ATOM | 5500 CG LEU H 303 | −5.634 18.464 12.590 1.00 2.00 | B C |
| ATOM | 5501 CD1 LEU H 303 | −5.840 18.189 14.073 1.00 2.00 | B C |
| ATOM | 5502 CD2 LEU H 303 | −4.598 17.517 11.999 1.00 2.00 | B C |
| ATOM | 5503 C LEU H 303 | −8.172 19.024 9.704 1.00 2.00 | B C |
| ATOM | 5504 O LEU H 303 | −8.499 20.159 9.359 1.00 2.45 | B O |
| ATOM | 5505 N PRO H 304 | −8.955 17.949 9.506 1.00 2.00 | B N |
| ATOM | 5506 CA PRO H 304 | −10.222 18.040 8.763 1.00 2.07 | B C |
| ATOM | 5507 CB PRO H 304 | −10.407 16.623 8.206 1.00 2.00 | B C |
| ATOM | 5508 CG PRO H 304 | −9.560 15.748 9.074 1.00 2.00 | B C |
| ATOM | 5509 CD PRO H 304 | −8.390 16.589 9.469 1.00 2.06 | B C |
| ATOM | 5510 C PRO H 304 | −11.449 18.462 9.590 1.00 2.11 | B C |
| ATOM | 5511 O PRO H 304 | −11.353 18.606 10.812 1.00 2.13 | B O |
| ATOM | 5512 N ALA H 305 | −12.622 18.425 8.953 1.00 30.00 | B N |
| ATOM | 5513 CA ALA H 305 | −12.858 19.173 7.708 1.00 30.00 | B C |
| ATOM | 5514 CB ALA H 305 | −11.532 19.487 7.023 1.00 30.00 | B C |
| ATOM | 5515 C ALA H 305 | −13.809 18.445 6.733 1.00 30.00 | B C |
| ATOM | 5516 O ALA H 305 | −13.601 17.265 6.429 1.00 30.00 | B O |
| ATOM | 5517 N TYR H 306 | −14.925 19.101 6.370 1.00 13.49 | B N |
| ATOM | 5518 CA TYR H 306 | −15.658 18.816 5.101 1.00 13.70 | B C |
| ATOM | 5519 CB TYR H 306 | −16.947 18.016 5.303 1.00 13.93 | B C |
| ATOM | 5520 CG TYR H 306 | −17.614 18.033 6.640 1.00 14.08 | B C |
| ATOM | 5521 CD1 TYR H 306 | −18.719 18.859 6.857 1.00 14.59 | B C |
| ATOM | 5522 CE1 TYR H 306 | −19.825 18.384 7.554 1.00 14.82 | B C |
| ATOM | 5523 CZ TYR H 306 | −19.818 17.083 8.031 1.00 14.52 | B C |
| ATOM | 5524 OH TYR H 306 | −20.780 16.679 8.925 1.00 13.02 | B O |
| ATOM | 5525 CE2 TYR H 306 | −18.727 16.282 7.818 1.00 15.22 | B C |
| ATOM | 5526 CD2 TYR H 306 | −17.583 16.855 7.363 1.00 14.61 | B C |
| ATOM | 5527 C TYR H 306 | −16.111 19.916 4.144 1.00 13.68 | B C |
| ATOM | 5528 O TYR H 306 | −15.500 20.982 4.051 1.00 13.95 | B O |
| ATOM | 5529 N GLY H 307 | −17.412 19.756 3.831 1.00 13.54 | B N |
| ATOM | 5530 CA GLY H 307 | −18.190 20.428 2.747 1.00 13.37 | B C |
| ATOM | 5531 C GLY H 307 | −18.295 19.776 1.353 1.00 13.47 | B C |
| ATOM | 5532 O GLY H 307 | −17.282 19.701 0.658 1.00 13.90 | B O |
| ATOM | 5533 N VAL H 308 | −19.505 19.569 0.815 1.00 13.31 | B N |
| ATOM | 5534 CA VAL H 308 | −19.608 19.371 −0.649 1.00 13.30 | B C |
| ATOM | 5535 CB VAL H 308 | −18.352 18.643 −1.188 1.00 13.03 | B C |
| ATOM | 5536 CG1 VAL H 308 | −17.948 19.190 −2.545 1.00 13.62 | B C |
| ATOM | 5537 CG2 VAL H 308 | −17.209 18.740 −0.205 1.00 12.86 | B C |
| ATOM | 5538 C VAL H 308 | −20.720 18.501 −1.196 1.00 13.58 | B C |
| ATOM | 5539 O VAL H 308 | −21.809 18.418 −0.627 1.00 13.71 | B O |
| ATOM | 5540 N ILE H 309 | −20.173 17.489 −1.845 1.00 4.08 | B N |
| ATOM | 5541 CA ILE H 309 | −19.600 16.440 −1.057 1.00 4.84 | B C |
| ATOM | 5542 CB ILE H 309 | −19.530 16.902 0.426 1.00 4.89 | B C |
| ATOM | 5543 CG1 ILE H 309 | −18.554 18.070 0.585 1.00 5.85 | B C |
| ATOM | 5544 CD1 ILE H 309 | −17.312 17.711 1.373 1.00 8.12 | B C |
| ATOM | 5545 CG2 ILE H 309 | −19.121 15.756 1.332 1.00 4.44 | B C |
| ATOM | 5546 C ILE H 309 | −20.750 15.497 −1.251 1.00 5.23 | B C |
| ATOM | 5547 O ILE H 309 | −21.670 15.818 −1.998 1.00 5.92 | B O |
| ATOM | 5548 N ASP H 310 | −20.752 14.358 −0.584 1.00 5.33 | B N |
| ATOM | 5549 CA ASP H 310 | −21.992 13.604 −0.482 1.00 5.83 | B C |
| ATOM | 5550 CB ASP H 310 | −23.072 14.462 0.188 1.00 6.21 | B C |
| ATOM | 5551 CG ASP H 310 | −22.698 14.894 1.595 1.00 7.19 | B C |

APPENDIX-continued (APPENDIX discloses SEQ ID NOS 29-32, 29-32 and 29-32, respectively, in order of appearance)

| | | | |
|---|---|---|---|
| ATOM | 5552 OD1 ASP H 310 | −22.903 16.084 1.920 1.00 7.74 | B O |
| ATOM | 5553 OD2 ASP H 310 | −22.425 14.005 2.428 1.00 7.58 | B O |
| ATOM | 5554 C ASP H 310 | −22.524 13.115 −1.841 1.00 6.02 | B C |
| ATOM | 5555 O ASP H 310 | −23.670 12.673 −1.927 1.00 6.05 | B O |
| ATOM | 5556 N THR H 311 | −21.716 13.207 −2.897 1.00 6.24 | B N |
| ATOM | 5557 CA THR H 311 | −22.015 12.488 −4.140 1.00 6.14 | B C |
| ATOM | 5558 CB THR H 311 | −21.097 12.933 −5.305 1.00 5.69 | B C |
| ATOM | 5559 OG1 THR H 311 | −20.497 14.196 −4.994 1.00 5.34 | B O |
| ATOM | 5560 CG2 THR H 311 | −21.891 13.063 −6.599 1.00 7.10 | B C |
| ATOM | 5561 C THR H 311 | −21.832 10.990 −3.911 1.00 6.78 | B C |
| ATOM | 5562 O THR H 311 | −20.946 10.587 −3.160 1.00 7.33 | B O |
| ATOM | 5563 N PRO H 312 | −22.611 10.155 −4.621 1.00 7.00 | B N |
| ATOM | 5564 CA PRO H 312 | −22.351 8.718 −4.567 1.00 7.23 | B C |
| ATOM | 5565 CB PRO H 312 | −23.560 8.115 −5.289 1.00 7.00 | B C |
| ATOM | 5566 CG PRO H 312 | −24.053 9.200 −6.178 1.00 6.59 | B C |
| ATOM | 5567 CD PRO H 312 | −23.800 10.475 −5.432 1.00 6.99 | B C |
| ATOM | 5568 C PRO H 312 | −21.061 8.352 −5.298 1.00 7.69 | B C |
| ATOM | 5569 O PRO H 312 | −20.796 8.881 −6.377 1.00 7.55 | B O |
| ATOM | 5570 N CYS H 313 | −20.259 7.469 −4.712 1.00 8.10 | B N |
| ATOM | 5571 CA CYS H 313 | −19.271 6.730 −5.491 1.00 8.54 | B C |
| ATOM | 5572 CB CYS H 313 | −17.840 7.078 −5.071 1.00 8.77 | B C |
| ATOM | 5573 SG CYS H 313 | −17.635 8.680 −4.269 1.00 10.74 | B S |
| ATOM | 5574 C CYS H 313 | −19.470 5.222 −5.446 1.00 8.19 | B C |
| ATOM | 5575 O CYS H 313 | −20.334 4.712 −4.734 1.00 8.07 | B O |
| ATOM | 5576 N TRP H 314 | −18.571 4.517 −6.121 1.00 7.93 | B N |
| ATOM | 5577 CA TRP H 314 | −18.564 3.067 −6.116 1.00 7.80 | B C |
| ATOM | 5578 CB TRP H 314 | −19.648 2.528 −7.050 1.00 8.13 | B C |
| ATOM | 5579 CG TRP H 314 | −19.582 3.091 −8.436 1.00 9.09 | B C |
| ATOM | 5580 CD1 TRP H 314 | −19.041 2.490 −9.536 1.00 10.26 | B C |
| ATOM | 5581 NE1 TRP H 314 | −19.247 3.268 −10.650 1.00 10.86 | B N |
| ATOM | 5582 CE2 TRP H 314 | −19.940 4.392 −10.285 1.00 10.68 | B C |
| ATOM | 5583 CD2 TRP H 314 | −20.172 4.313 −8.897 1.00 10.49 | B C |
| ATOM | 5584 CE3 TRP H 314 | −20.877 5.347 −8.271 1.00 11.67 | B C |
| ATOM | 5585 CZ3 TRP H 314 | −21.301 6.419 −9.037 1.00 12.98 | B C |
| ATOM | 5586 CH2 TRP H 314 | −21.048 6.472 −10.413 1.00 12.74 | B C |
| ATOM | 5587 CZ2 TRP H 314 | −20.369 5.472 −11.054 1.00 11.73 | B C |
| ATOM | 5588 C TRP H 314 | −17.198 2.576 −6.563 1.00 7.34 | B C |
| ATOM | 5589 O TRP H 314 | −16.485 3.272 −7.288 1.00 7.47 | B O |
| ATOM | 5590 N LYS H 315 | −16.791 1.426 −6.041 1.00 6.75 | B N |
| ATOM | 5591 CA LYS H 315 | −15.547 0.807 −6.462 1.00 6.37 | B C |
| ATOM | 5592 CB LYS H 315 | −14.741 0.337 −5.252 1.00 6.38 | B C |
| ATOM | 5593 CG LYS H 315 | −13.277 0.071 −5.554 1.00 6.55 | B C |
| ATOM | 5594 CD LYS H 315 | −12.509 −0.282 −4.292 1.00 8.01 | B C |
| ATOM | 5595 CE LYS H 315 | −11.014 −0.331 −4.556 1.00 8.78 | B C |
| ATOM | 5596 NZ LYS H 315 | −10.337 −1.364 −3.726 1.00 10.21 | B N |
| ATOM | 5597 C LYS H 315 | −15.825 −0.361 −7.392 1.00 6.32 | B C |
| ATOM | 5598 O LYS H 315 | −16.746 −1.145 −7.164 1.00 6.21 | B O |
| ATOM | 5599 N LEU H 316 | −15.089 −0.411 −8.495 1.00 6.58 | B N |
| ATOM | 5600 CA LEU H 316 | −15.304 −1.435 −9.502 1.00 7.02 | B C |
| ATOM | 5601 CB LEU H 316 | −15.491 −0.801 −10.880 1.00 6.64 | B C |
| ATOM | 5602 CG LEU H 316 | −15.452 −1.767 −12.065 1.00 6.21 | B C |
| ATOM | 5603 CD1 LEU H 316 | −16.540 −2.822 −11.936 1.00 5.94 | B C |
| ATOM | 5604 CD2 LEU H 316 | −15.590 −1.011 −13.378 1.00 6.57 | B C |
| ATOM | 5605 C LEU H 316 | −14.138 −2.409 −9.525 1.00 7.77 | B C |
| ATOM | 5606 O LEU H 316 | −12.999 −2.024 −9.792 1.00 8.47 | B O |
| ATOM | 5607 N HIS H 317 | −14.414 −3.656 −9.168 1.00 8.05 | B N |
| ATOM | 5608 CA HIS H 317 | −13.460 −4.725 −9.388 1.00 8.21 | B C |
| ATOM | 5609 CB HIS H 317 | −13.266 −5.547 −8.116 1.00 9.04 | B C |
| ATOM | 5610 CG HIS H 317 | −13.449 −4.761 −6.856 1.00 11.41 | B C |
| ATOM | 5611 ND1 HIS H 317 | −12.392 −4.368 −6.063 1.00 13.62 | B N |
| ATOM | 5612 CE1 HIS H 317 | −12.854 −3.746 −4.993 1.00 14.91 | B C |
| ATOM | 5613 NE2 HIS H 317 | −14.172 −3.725 −5.060 1.00 14.25 | B N |
| ATOM | 5614 CD2 HIS H 317 | −14.570 −4.352 −6.216 1.00 12.67 | B C |
| ATOM | 5615 C HIS H 317 | −13.904 −5.625 −10.528 1.00 7.39 | B C |
| ATOM | 5616 O HIS H 317 | −15.085 −5.677 −10.870 1.00 7.23 | B O |
| ATOM | 5617 N THR H 318 | −12.976 −6.451 −10.993 1.00 7.11 | B N |
| ATOM | 5618 CA THR H 318 | −12.973 −6.913 −12.372 1.00 6.56 | B C |
| ATOM | 5619 CB THR H 318 | −12.242 −5.919 −13.295 1.00 6.28 | B C |
| ATOM | 5620 OG1 THR H 318 | −13.197 −5.193 −14.078 1.00 6.33 | B O |
| ATOM | 5621 CG2 THR H 318 | −11.296 −6.662 −14.224 1.00 6.52 | B C |
| ATOM | 5622 C THR H 318 | −12.254 −8.251 −12.438 1.00 6.58 | B C |
| ATOM | 5623 O THR H 318 | −11.142 −8.393 −11.930 1.00 6.67 | B O |
| ATOM | 5624 N SER H 319 | −12.919 −9.252 −13.001 1.00 6.81 | B N |
| ATOM | 5625 CA SER H 319 | −12.328 −10.578 −13.115 1.00 7.31 | B C |
| ATOM | 5626 CB SER H 319 | −12.902 −11.513 −12.047 1.00 7.14 | B C |
| ATOM | 5627 OG SER H 319 | −12.244 −12.769 −12.052 1.00 6.84 | B O |
| ATOM | 5628 C SER H 319 | −12.533 −11.169 −14.509 1.00 7.93 | B C |

APPENDIX-continued (APPENDIX discloses SEQ ID NOS 29-32, 29-32 and 29-32, respectively, in order of appearance)

| | | | | |
|---|---|---|---|---|
| ATOM | 5629 O SER H 319 | −13.583 −10.975 −15.124 1.00 8.65 | B O |
| ATOM | 5630 N PRO H 320 | −11.534 −11.917 −15.002 1.00 8.08 | B N |
| ATOM | 5631 CA PRO H 320 | −11.592 −12.459 −16.354 1.00 8.34 | B C |
| ATOM | 5632 CB PRO H 320 | −10.339 −13.342 −16.442 1.00 7.99 | B C |
| ATOM | 5633 CG PRO H 320 | −9.773 −13.404 −15.045 1.00 8.01 | B C |
| ATOM | 5634 CD PRO H 320 | −10.230 −12.163 −14.367 1.00 8.10 | B C |
| ATOM | 5635 C PRO H 320 | −12.848 −13.288 −16.610 1.00 9.03 | B C |
| ATOM | 5636 O PRO H 320 | −13.372 −13.928 −15.697 1.00 8.74 | B O |
| ATOM | 5637 N LEU H 321 | −13.224 −13.384 −17.881 1.00 10.31 | B N |
| ATOM | 5638 CA LEU H 321 | −14.514 −13.933 −18.284 1.00 11.63 | B C |
| ATOM | 5639 CB LEU H 321 | −15.543 −12.807 −18.448 1.00 11.31 | B C |
| ATOM | 5640 CG LEU H 321 | −17.032 −13.163 −18.454 1.00 10.97 | B C |
| ATOM | 5641 CD1 LEU H 321 | −17.828 −12.071 −19.154 1.00 10.04 | B C |
| ATOM | 5642 CD2 LEU H 321 | −17.273 −14.514 −19.113 1.00 10.69 | B C |
| ATOM | 5643 C LEU H 321 | −14.359 −14.687 −19.603 1.00 12.92 | B C |
| ATOM | 5644 O LEU H 321 | −13.871 −14.135 −20.591 1.00 13.29 | B O |
| ATOM | 5645 N CYS H 322 | −14.788 −15.947 −19.611 1.00 13.39 | B N |
| ATOM | 5646 CA CYS H 322 | −14.579 −16.836 −20.751 1.00 14.16 | B C |
| ATOM | 5647 CB CYS H 322 | −13.459 −17.833 −20.451 1.00 13.72 | B C |
| ATOM | 5648 SG CYS H 322 | −11.996 −17.091 −19.704 1.00 13.42 | B S |
| ATOM | 5649 C CYS H 322 | −15.859 −17.589 −21.115 1.00 15.46 | B C |
| ATOM | 5650 O CYS H 322 | −16.561 −18.099 −20.241 1.00 15.94 | B O |
| ATOM | 5651 N THR H 323 | −16.097 −17.735 −22.415 1.00 16.70 | B N |
| ATOM | 5652 CA THR H 323 | −17.059 −18.703 −22.940 1.00 17.84 | B C |
| ATOM | 5653 CB THR H 323 | −17.054 −18.690 −24.477 1.00 17.50 | B C |
| ATOM | 5654 OG1 THR H 323 | −15.767 −18.268 −24.947 1.00 15.70 | B O |
| ATOM | 5655 CG2 THR H 323 | −18.118 −17.740 −25.005 1.00 18.05 | B C |
| ATOM | 5656 C THR H 323 | −16.755 −20.125 −22.469 1.00 19.54 | B C |
| ATOM | 5657 O THR H 323 | −15.670 −20.389 −21.950 1.00 19.84 | B O |
| ATOM | 5658 N THR H 324 | −17.625 −21.068 −22.825 1.00 21.17 | B N |
| ATOM | 5659 CA THR H 324 | −17.251 −22.481 −22.774 1.00 22.89 | B C |
| ATOM | 5660 CB THR H 324 | −17.589 −23.138 −21.426 1.00 22.69 | B C |
| ATOM | 5661 OG1 THR H 324 | −18.025 −22.141 −20.494 1.00 22.10 | B O |
| ATOM | 5662 CG2 THR H 324 | −16.365 −23.854 −20.871 1.00 22.03 | B C |
| ATOM | 5663 C THR H 324 | −17.737 −23.375 −23.915 1.00 24.39 | B C |
| ATOM | 5664 O THR H 324 | −17.251 −24.495 −24.070 1.00 24.53 | B O |
| ATOM | 5665 N ASN H 325 | −18.633 −22.866 −24.755 1.00 25.72 | B N |
| ATOM | 5666 CA ASN H 325 | −18.864 −23.475 −26.064 1.00 27.01 | B C |
| ATOM | 5667 CB ASN H 325 | −19.924 −24.578 −25.977 1.00 27.37 | B C |
| ATOM | 5668 CG ASN H 325 | −19.337 −25.925 −25.593 1.00 28.46 | B C |
| ATOM | 5669 OD1 ASN H 325 | −19.134 −26.792 −26.443 1.00 30.37 | B O |
| ATOM | 5670 ND2 ASN H 325 | −19.086 −26.114 −24.303 1.00 28.78 | B N |
| ATOM | 5671 C ASN H 325 | −19.246 −22.460 −27.136 1.00 27.36 | B C |
| ATOM | 5672 O ASN H 325 | −19.634 −21.334 −26.829 1.00 27.94 | B O |
| ATOM | 5673 N SER H 330 | −15.365 −21.167 −24.863 1.00 35.76 | B N |
| ATOM | 5674 CA SER H 330 | −14.200 −21.669 −25.580 1.00 35.01 | B C |
| ATOM | 5675 CB SER H 330 | −14.630 −22.631 −26.690 1.00 35.47 | B C |
| ATOM | 5676 OG SER H 330 | −15.521 −22.000 −27.595 1.00 33.31 | B O |
| ATOM | 5677 C SER H 330 | −13.383 −20.522 −26.168 1.00 34.35 | B C |
| ATOM | 5678 O SER H 330 | −13.938 −19.509 −26.593 1.00 34.33 | B O |
| ATOM | 5679 N ASN H 331 | −12.062 −20.653 −26.123 1.00 32.48 | B N |
| ATOM | 5680 CA ASN H 331 | −11.191 −19.933 −27.046 1.00 30.72 | B C |
| ATOM | 5681 CB ASN H 331 | −11.577 −20.233 −28.504 1.00 31.31 | B C |
| ATOM | 5682 CG ASN H 331 | −11.276 −21.670 −28.918 1.00 32.11 | B C |
| ATOM | 5683 OD1 ASN H 331 | −10.553 −22.391 −28.229 1.00 32.54 | B O |
| ATOM | 5684 ND2 ASN H 331 | −11.753 −22.055 −30.097 1.00 31.30 | B N |
| ATOM | 5685 C ASN H 331 | −11.120 −18.411 −26.826 1.00 28.71 | B C |
| ATOM | 5686 O ASN H 331 | −10.495 −17.710 −27.621 1.00 29.07 | B O |
| ATOM | 5687 N ILE H 332 | −11.797 −17.887 −25.802 1.00 25.44 | B N |
| ATOM | 5688 CA ILE H 332 | −11.904 −16.424 −25.638 1.00 21.83 | B C |
| ATOM | 5689 CB ILE H 332 | −12.919 −15.806 −26.624 1.00 21.42 | B C |
| ATOM | 5690 CG1 ILE H 332 | −12.916 −14.280 −26.511 1.00 19.89 | B C |
| ATOM | 5691 CD1 ILE H 332 | −11.986 −13.596 −27.488 1.00 17.67 | B C |
| ATOM | 5692 CG2 ILE H 332 | −14.314 −16.360 −26.374 1.00 20.61 | B C |
| ATOM | 5693 C ILE H 332 | −12.204 −15.918 −24.217 1.00 20.37 | B C |
| ATOM | 5694 O ILE H 332 | −13.219 −16.290 −23.624 1.00 19.95 | B O |
| ATOM | 5695 N CYS H 333 | −11.425 −14.935 −23.761 1.00 18.27 | B N |
| ATOM | 5696 CA CYS H 333 | −11.681 −14.282 −22.474 1.00 16.47 | B C |
| ATOM | 5697 CB CYS H 333 | −10.802 −14.873 −21.371 1.00 16.14 | B C |
| ATOM | 5698 SG CYS H 333 | −10.807 −16.672 −21.295 1.00 17.09 | B S |
| ATOM | 5699 C CYS H 333 | −11.542 −12.763 −22.482 1.00 15.73 | B C |
| ATOM | 5700 O CYS H 333 | −10.707 −12.206 −23.197 1.00 15.43 | B O |
| ATOM | 5701 N LEU H 334 | −12.154 −12.155 −21.470 1.00 15.06 | B N |
| ATOM | 5702 CA LEU H 334 | −12.256 −10.708 −21.353 1.00 13.79 | B C |
| ATOM | 5703 CB LEU H 334 | −13.702 −10.264 −21.588 1.00 13.39 | B C |
| ATOM | 5704 CG LEU H 334 | −14.262 −10.341 −23.008 1.00 13.93 | B C |
| ATOM | 5705 CD1 LEU H 334 | −15.276 −9.230 −23.235 1.00 14.20 | B C |

APPENDIX-continued

| (APPENDIX discloses SEQ ID NOS 29-32, 29-32 and 29-32, respectively, in order of appearance) | | | |
|---|---|---|---|
| ATOM | 5706 CD2 LEU H 334 | −13.143 −10.266 −24.035 1.00 14.52 | B C |
| ATOM | 5707 C LEU H 334 | −11.868 −10.345 −19.930 1.00 13.22 | B C |
| ATOM | 5708 O LEU H 334 | −12.324 −10.980 −18.980 1.00 13.31 | B O |
| ATOM | 5709 N THR H 335 | −11.141 −9.246 −19.776 1.00 12.58 | B N |
| ATOM | 5710 CA THR H 335 | −11.033 −8.596 −18.478 1.00 12.17 | B C |
| ATOM | 5711 CB THR H 335 | −9.677 −8.904 −17.798 1.00 12.02 | B C |
| ATOM | 5712 OG1 THR H 335 | −9.207 −10.191 −18.219 1.00 12.64 | B O |
| ATOM | 5713 CG2 THR H 335 | −9.817 −8.893 −16.280 1.00 11.47 | B C |
| ATOM | 5714 C THR H 335 | −11.203 −7.092 −18.639 1.00 11.97 | B C |
| ATOM | 5715 O THR H 335 | −10.637 −6.493 −19.553 1.00 11.93 | B O |
| ATOM | 5716 N ARG H 336 | −12.130 −6.526 −17.874 1.00 11.60 | B N |
| ATOM | 5717 CA ARG H 336 | −12.411 −5.098 −17.949 1.00 12.15 | B C |
| ATOM | 5718 CB ARG H 336 | −13.716 −4.767 −17.215 1.00 12.16 | B C |
| ATOM | 5719 CG ARG H 336 | −14.525 −3.643 −17.849 1.00 12.67 | B C |
| ATOM | 5720 CD ARG H 336 | −15.993 −4.018 −17.970 1.00 12.52 | B C |
| ATOM | 5721 NE ARG H 336 | −16.736 −3.718 −16.750 1.00 12.35 | B N |
| ATOM | 5722 CZ ARG H 336 | −17.058 −2.490 −16.355 1.00 12.54 | B C |
| ATOM | 5723 NH1 ARG H 336 | −16.665 −1.439 −17.062 1.00 12.38 | B N |
| ATOM | 5724 NH2 ARG H 336 | −17.761 −2.312 −15.246 1.00 12.48 | B N |
| ATOM | 5725 C ARG H 336 | −11.252 −4.295 −17.361 1.00 12.71 | B C |
| ATOM | 5726 O ARG H 336 | −10.891 −4.475 −16.198 1.00 12.62 | B O |
| ATOM | 5727 N THR H 337 | −10.615 −3.475 −18.192 1.00 13.70 | B N |
| ATOM | 5728 CA THR H 337 | −9.431 −2.733 −17.766 1.00 14.91 | B C |
| ATOM | 5729 CB THR H 337 | −8.736 −2.032 −18.949 1.00 15.27 | B C |
| ATOM | 5730 OG1 THR H 337 | −8.620 −2.946 −20.046 1.00 16.65 | B O |
| ATOM | 5731 CG2 THR H 337 | −7.347 −1.560 −18.546 1.00 15.94 | B C |
| ATOM | 5732 C THR H 337 | −9.759 −1.707 −16.681 1.00 15.16 | B C |
| ATOM | 5733 O THR H 337 | −9.100 −1.659 −15.643 1.00 15.60 | B O |
| ATOM | 5734 N ASP H 338 | −10.770 −0.880 −16.934 1.00 15.15 | B N |
| ATOM | 5735 CA ASP H 338 | −10.988 0.325 −16.143 1.00 15.52 | B C |
| ATOM | 5736 CB ASP H 338 | −11.999 1.250 −16.828 1.00 16.81 | B C |
| ATOM | 5737 CG ASP H 338 | −13.028 0.489 −17.642 1.00 20.57 | B C |
| ATOM | 5738 OD1 ASP H 338 | −13.670 1.103 −18.519 1.00 23.00 | B O |
| ATOM | 5739 OD2 ASP H 338 | −13.224 −0.716 −17.378 1.00 22.92 | B O |
| ATOM | 5740 C ASP H 338 | −11.453 −0.022 −14.733 1.00 14.21 | B C |
| ATOM | 5741 O ASP H 338 | −12.651 −0.171 −14.482 1.00 14.00 | B O |
| ATOM | 5742 N ARG H 339 | −10.494 −0.189 −13.827 1.00 12.79 | B N |
| ATOM | 5743 CA ARG H 339 | −10.792 −0.528 −12.440 1.00 11.71 | B C |
| ATOM | 5744 CB ARG H 339 | −9.866 −1.630 −11.950 1.00 11.73 | B C |
| ATOM | 5745 CG ARG H 339 | −9.941 −2.905 −12.727 1.00 12.49 | B C |
| ATOM | 5746 CD ARG H 339 | −9.329 −3.991 −11.895 1.00 13.24 | B C |
| ATOM | 5747 NE ARG H 339 | −8.677 −5.006 −12.705 1.00 12.04 | B N |
| ATOM | 5748 CZ ARG H 339 | −8.332 −6.200 −12.239 1.00 11.74 | B C |
| ATOM | 5749 NH1 ARG H 339 | −8.540 −6.498 −10.964 1.00 13.43 | B N |
| ATOM | 5750 NH2 ARG H 339 | −7.784 −7.097 −13.045 1.00 9.80 | B N |
| ATOM | 5751 C ARG H 339 | −10.626 0.666 −11.519 1.00 11.16 | B C |
| ATOM | 5752 O ARG H 339 | −9.690 1.448 −11.681 1.00 11.37 | B O |
| ATOM | 5753 N GLY H 340 | −11.290 0.573 −10.373 1.00 10.43 | B N |
| ATOM | 5754 CA GLY H 340 | −11.038 1.481 −9.269 1.00 9.52 | B C |
| ATOM | 5755 C GLY H 340 | −12.279 2.268 −8.916 1.00 8.80 | B C |
| ATOM | 5756 O GLY H 340 | −13.397 1.759 −8.996 1.00 8.56 | B O |
| ATOM | 5757 N TRP H 341 | −12.077 3.513 −8.506 1.00 8.25 | B N |
| ATOM | 5758 CA TRP H 341 | −13.156 4.309 −7.953 1.00 7.98 | B C |
| ATOM | 5759 CB TRP H 341 | −12.629 5.235 −6.865 1.00 7.79 | B C |
| ATOM | 5760 CG TRP H 341 | −12.435 4.538 −5.579 1.00 7.67 | B C |
| ATOM | 5761 CD1 TRP H 341 | −11.275 3.990 −5.119 1.00 8.12 | B C |
| ATOM | 5762 NE1 TRP H 341 | −11.496 3.346 −3.928 1.00 8.60 | B N |
| ATOM | 5763 CE2 TRP H 341 | −12.834 3.401 −3.639 1.00 7.57 | B C |
| ATOM | 5764 CD2 TRP H 341 | −13.464 4.093 −4.691 1.00 7.52 | B C |
| ATOM | 5765 CE3 TRP H 341 | −14.848 4.291 −4.636 1.00 7.86 | B C |
| ATOM | 5766 CZ3 TRP H 341 | −15.545 3.797 −3.548 1.00 7.14 | B C |
| ATOM | 5767 CH2 TRP H 341 | −14.890 3.105 −2.522 1.00 6.39 | B C |
| ATOM | 5768 CZ2 TRP H 341 | −13.538 2.903 −2.546 1.00 7.30 | B C |
| ATOM | 5769 C TRP H 341 | −13.835 5.117 −9.037 1.00 8.26 | B C |
| ATOM | 5770 O TRP H 341 | −13.222 5.978 −9.666 1.00 8.35 | B O |
| ATOM | 5771 N TYR H 342 | −15.113 4.840 −9.244 1.00 8.44 | B N |
| ATOM | 5772 CA TYR H 342 | −16.000 5.809 −9.847 1.00 8.53 | B C |
| ATOM | 5773 CB TYR H 342 | −16.948 5.116 −10.814 1.00 8.43 | B C |
| ATOM | 5774 CG TYR H 342 | −16.214 4.338 −11.870 1.00 9.17 | B C |
| ATOM | 5775 CD1 TYR H 342 | −15.551 3.163 −11.540 1.00 10.32 | B C |
| ATOM | 5776 CE1 TYR H 342 | −14.766 2.503 −12.465 1.00 10.99 | B C |
| ATOM | 5777 CZ TYR H 342 | −14.566 3.063 −13.709 1.00 11.00 | B C |
| ATOM | 5778 OH TYR H 342 | −13.828 2.387 −14.653 1.00 12.82 | B O |
| ATOM | 5779 CE2 TYR H 342 | −15.115 4.288 −14.019 1.00 10.67 | B C |
| ATOM | 5780 CD2 TYR H 342 | −15.913 4.930 −13.091 1.00 10.41 | B C |
| ATOM | 5781 C TYR H 342 | −16.781 6.535 −8.778 1.00 8.64 | B C |
| ATOM | 5782 O TYR H 342 | −16.830 6.103 −7.628 1.00 8.40 | B O |

APPENDIX-continued (APPENDIX discloses SEQ ID NOS 29-32, 29-32 and 29-32, respectively, in order of appearance)

| | | | |
|---|---|---|---|
| ATOM | 5783 N CYS H 343 | −17.373 7.657 −9.157 1.00 8.87 | B N |
| ATOM | 5784 CA CYS H 343 | −17.812 8.625 −8.178 1.00 9.35 | B C |
| ATOM | 5785 CB CYS H 343 | −16.702 8.901 −7.160 1.00 9.17 | B C |
| ATOM | 5786 SG CYS H 343 | −17.204 9.963 −5.787 1.00 11.88 | B S |
| ATOM | 5787 C CYS H 343 | −18.258 9.907 −8.863 1.00 9.42 | B C |
| ATOM | 5788 O CYS H 343 | −17.552 10.444 −9.717 1.00 9.96 | B O |
| ATOM | 5789 N ASP H 344 | −19.523 10.250 −8.643 1.00 9.36 | B N |
| ATOM | 5790 CA ASP H 344 | −20.231 11.213 −9.477 1.00 9.24 | B C |
| ATOM | 5791 CB ASP H 344 | −21.712 11.250 −9.097 1.00 9.34 | B C |
| ATOM | 5792 CG ASP H 344 | −22.555 10.320 −9.943 1.00 10.72 | B C |
| ATOM | 5793 OD1 ASP H 344 | −22.582 10.500 −11.178 1.00 13.93 | B O |
| ATOM | 5794 OD2 ASP H 344 | −23.246 9.453 −9.367 1.00 11.87 | B O |
| ATOM | 5795 C ASP H 344 | −19.632 12.607 −9.330 1.00 9.09 | B C |
| ATOM | 5796 O ASP H 344 | −19.454 13.101 −8.216 1.00 9.39 | B O |
| ATOM | 5797 N ASN H 345 | −19.416 13.274 −10.457 1.00 9.13 | B N |
| ATOM | 5798 CA ASN H 345 | −19.165 14.709 −10.461 1.00 9.52 | B C |
| ATOM | 5799 CB ASN H 345 | −17.833 15.011 −11.149 1.00 9.61 | B C |
| ATOM | 5800 CG ASN H 345 | −17.166 16.258 −10.606 1.00 9.21 | B C |
| ATOM | 5801 OD1 ASN H 345 | −16.787 16.316 −9.437 1.00 6.21 | B O |
| ATOM | 5802 ND2 ASN H 345 | −17.023 17.268 −11.456 1.00 11.05 | B N |
| ATOM | 5803 C ASN H 345 | −20.303 15.452 −11.152 1.00 10.06 | B C |
| ATOM | 5804 O ASN H 345 | −21.347 14.867 −11.441 1.00 11.10 | B O |
| ATOM | 5805 N ALA H 346 | −20.133 16.755 −11.352 1.00 9.74 | B N |
| ATOM | 5806 CA ALA H 346 | −21.211 17.584 −11.877 1.00 9.58 | B C |
| ATOM | 5807 CB ALA H 346 | −20.708 18.991 −12.164 1.00 9.60 | B C |
| ATOM | 5808 C ALA H 346 | −21.825 16.968 −13.133 1.00 9.66 | B C |
| ATOM | 5809 O ALA H 346 | −21.347 17.196 −14.244 1.00 9.39 | B O |
| ATOM | 5810 N GLY H 347 | −22.883 16.182 −12.948 1.00 10.04 | B N |
| ATOM | 5811 CA GLY H 347 | −23.684 15.689 −14.067 1.00 10.68 | B C |
| ATOM | 5812 C GLY H 347 | −22.964 14.606 −14.846 1.00 10.90 | B C |
| ATOM | 5813 O GLY H 347 | −23.490 14.064 −15.819 1.00 11.46 | B O |
| ATOM | 5814 N SER H 348 | −21.714 14.370 −14.467 1.00 10.30 | B N |
| ATOM | 5815 CA SER H 348 | −20.844 13.436 −15.165 1.00 9.94 | B C |
| ATOM | 5816 CB SER H 348 | −19.833 14.200 −16.022 1.00 9.88 | B C |
| ATOM | 5817 OG SER H 348 | −20.488 15.064 −16.934 1.00 10.09 | B O |
| ATOM | 5818 C SER H 348 | −20.120 12.619 −14.104 1.00 9.60 | B C |
| ATOM | 5819 O SER H 348 | −20.367 12.796 −12.912 1.00 9.59 | B O |
| ATOM | 5820 N VAL H 349 | −19.286 11.677 −14.528 1.00 9.54 | B N |
| ATOM | 5821 CA VAL H 349 | −18.647 10.766 −13.581 1.00 9.56 | B C |
| ATOM | 5822 CB VAL H 349 | −19.075 9.305 −13.809 1.00 9.28 | B C |
| ATOM | 5823 CG1 VAL H 349 | −18.659 8.442 −12.626 1.00 9.24 | B C |
| ATOM | 5824 CG2 VAL H 349 | −20.576 9.222 −14.033 1.00 9.94 | B C |
| ATOM | 5825 C VAL H 349 | −17.126 10.861 −13.619 1.00 9.59 | B C |
| ATOM | 5826 O VAL H 349 | −16.513 10.752 −14.681 1.00 9.69 | B O |
| ATOM | 5827 N SER H 350 | −16.520 11.027 −12.449 1.00 9.93 | B N |
| ATOM | 5828 CA SER H 350 | −15.073 11.104 −12.357 1.00 10.44 | B C |
| ATOM | 5829 CB SER H 350 | −14.646 12.227 −11.408 1.00 10.04 | B C |
| ATOM | 5830 OG SER H 350 | −14.584 13.468 −12.090 1.00 8.41 | B O |
| ATOM | 5831 C SER H 350 | −14.459 9.773 −11.938 1.00 11.45 | B C |
| ATOM | 5832 O SER H 350 | −15.000 9.062 −11.089 1.00 11.58 | B O |
| ATOM | 5833 N PHE H 351 | −13.354 9.424 −12.587 1.00 12.28 | B N |
| ATOM | 5834 CA PHE H 351 | −12.717 8.129 −12.403 1.00 13.04 | B C |
| ATOM | 5835 CB PHE H 351 | −12.800 7.315 −13.697 1.00 12.87 | B C |
| ATOM | 5836 CG PHE H 351 | −11.985 6.052 −13.677 1.00 13.52 | B C |
| ATOM | 5837 CD1 PHE H 351 | −12.081 5.165 −12.615 1.00 13.76 | B C |
| ATOM | 5838 CE1 PHE H 351 | −11.300 4.022 −12.574 1.00 14.10 | B C |
| ATOM | 5839 CZ PHE H 351 | −10.453 3.726 −13.629 1.00 14.07 | B C |
| ATOM | 5840 CE2 PHE H 351 | −10.381 4.583 −14.715 1.00 14.14 | B C |
| ATOM | 5841 CD2 PHE H 351 | −11.134 5.744 −14.728 1.00 13.92 | B C |
| ATOM | 5842 C PHE H 351 | −11.262 8.315 −11.993 1.00 13.84 | B C |
| ATOM | 5843 O PHE H 351 | −10.528 9.090 −12.608 1.00 13.96 | B O |
| ATOM | 5844 N PHE H 352 | −10.866 7.641 −10.919 1.00 14.72 | B N |
| ATOM | 5845 CA PHE H 352 | −9.500 7.717 −10.418 1.00 15.98 | B C |
| ATOM | 5846 CB PHE H 352 | −9.490 8.210 −8.966 1.00 15.75 | B C |
| ATOM | 5847 CG PHE H 352 | −10.600 9.176 −8.638 1.00 15.51 | B C |
| ATOM | 5848 CD1 PHE H 352 | −11.835 8.713 −8.210 1.00 15.05 | B C |
| ATOM | 5849 CE1 PHE H 352 | −12.836 9.597 −7.837 1.00 14.05 | B C |
| ATOM | 5850 CZ PHE H 352 | −12.592 10.955 −7.844 1.00 13.28 | B C |
| ATOM | 5851 CE2 PHE H 352 | −11.343 11.426 −8.201 1.00 13.71 | B C |
| ATOM | 5852 CD2 PHE H 352 | −10.347 10.536 −8.570 1.00 14.94 | B C |
| ATOM | 5853 C PHE H 352 | −8.820 6.350 −10.511 1.00 17.56 | B C |
| ATOM | 5854 O PHE H 352 | −9.259 5.390 −9.880 1.00 17.74 | B O |
| ATOM | 5855 N PRO H 353 | −7.728 6.266 −11.288 1.00 19.05 | B N |
| ATOM | 5856 CA PRO H 353 | −7.203 5.002 −11.802 1.00 20.40 | B C |
| ATOM | 5857 CB PRO H 353 | −6.180 5.443 −12.859 1.00 20.26 | B C |
| ATOM | 5858 CG PRO H 353 | −6.492 6.878 −13.145 1.00 19.71 | B C |
| ATOM | 5859 CD PRO H 353 | −7.032 7.424 −11.869 1.00 18.97 | B C |

APPENDIX-continued (APPENDIX discloses SEQ ID NOS 29-32, 29-32 and 29-32, respectively, in order of appearance)

| | | | |
|---|---|---|---|
| ATOM | 5860 C PRO H 353 | −6.522 4.135 −10.743 1.00 21.94 | B C |
| ATOM | 5861 O PRO H 353 | −6.511 2.911 −10.873 1.00 22.29 | B O |
| ATOM | 5862 N GLN H 354 | −5.904 4.757 −9.742 1.00 23.38 | B N |
| ATOM | 5863 CA GLN H 354 | −5.118 4.007 −8.760 1.00 24.64 | B C |
| ATOM | 5864 CB GLN H 354 | −3.621 4.108 −9.064 1.00 24.93 | B C |
| ATOM | 5865 CG GLN H 354 | −3.259 5.210 −10.038 1.00 26.00 | B C |
| ATOM | 5866 CD GLN H 354 | −3.331 6.581 −9.407 1.00 25.92 | B C |
| ATOM | 5867 OE1 GLN H 354 | −2.732 6.830 −8.360 1.00 25.67 | B O |
| ATOM | 5868 NE2 GLN H 354 | −4.094 7.475 −10.025 1.00 24.27 | B N |
| ATOM | 5869 C GLN H 354 | −5.393 4.393 −7.307 1.00 24.85 | B C |
| ATOM | 5870 O GLN H 354 | −5.653 5.558 −7.007 1.00 24.51 | B O |
| ATOM | 5871 N ALA H 355 | −5.162 3.446 −6.399 1.00 25.22 | B N |
| ATOM | 5872 CA ALA H 355 | −5.563 3.599 −4.997 1.00 25.34 | B C |
| ATOM | 5873 CB ALA H 355 | −5.112 2.400 −4.173 1.00 25.09 | B C |
| ATOM | 5874 C ALA H 355 | −5.092 4.910 −4.354 1.00 24.92 | B C |
| ATOM | 5875 O ALA H 355 | −5.901 5.647 −3.790 1.00 25.23 | B O |
| ATOM | 5876 N GLU H 356 | −3.775 5.074 −4.242 1.00 23.93 | B N |
| ATOM | 5877 CA GLU H 356 | −3.138 6.394 −4.141 1.00 22.77 | B C |
| ATOM | 5878 CB GLU H 356 | −2.214 6.635 −5.339 1.00 23.22 | B C |
| ATOM | 5879 CG GLU H 356 | −0.973 5.756 −5.344 1.00 26.33 | B C |
| ATOM | 5880 CD GLU H 356 | −0.571 5.312 −3.948 1.00 30.93 | B C |
| ATOM | 5881 OE1 GLU H 356 | −1.012 4.225 −3.516 1.00 31.97 | B O |
| ATOM | 5882 OE2 GLU H 356 | 0.074 6.111 −3.237 1.00 32.21 | B O |
| ATOM | 5883 C GLU H 356 | −4.114 7.558 −3.990 1.00 21.31 | B C |
| ATOM | 5884 O GLU H 356 | −4.098 8.270 −2.985 1.00 21.01 | B O |
| ATOM | 5885 N THR H 357 | −4.868 7.819 −5.052 1.00 19.51 | B N |
| ATOM | 5886 CA THR H 357 | −5.718 9.000 −5.138 1.00 17.55 | B C |
| ATOM | 5887 CB THR H 357 | −6.391 9.086 −6.519 1.00 17.30 | B C |
| ATOM | 5888 OG1 THR H 357 | −5.644 8.305 −7.462 1.00 17.32 | B O |
| ATOM | 5889 CG2 THR H 357 | −6.472 10.531 −6.997 1.00 17.72 | B C |
| ATOM | 5890 C THR H 357 | −6.801 9.006 −4.063 1.00 16.62 | B C |
| ATOM | 5891 O THR H 357 | −7.346 10.058 −3.730 1.00 17.29 | B O |
| ATOM | 5892 N CYS H 358 | −7.179 7.822 −3.594 1.00 14.88 | B N |
| ATOM | 5893 CA CYS H 358 | −8.414 7.676 −2.833 1.00 13.15 | B C |
| ATOM | 5894 CB CYS H 358 | −9.479 6.949 −3.655 1.00 13.04 | B C |
| ATOM | 5895 SG CYS H 358 | −10.003 7.836 −5.144 1.00 14.02 | B S |
| ATOM | 5896 C CYS H 358 | −8.202 6.982 −1.492 1.00 12.08 | B C |
| ATOM | 5897 O CYS H 358 | −7.521 5.959 −1.408 1.00 12.15 | B O |
| ATOM | 5898 N LYS H 359 | −8.741 7.585 −0.438 1.00 11.35 | B N |
| ATOM | 5899 CA LYS H 359 | −8.861 6.922 0.853 1.00 11.01 | B C |
| ATOM | 5900 CB LYS H 359 | −8.119 7.713 1.931 1.00 11.16 | B C |
| ATOM | 5901 CG LYS H 359 | −7.413 8.953 1.414 1.00 13.28 | B C |
| ATOM | 5902 CD LYS H 359 | −5.907 8.816 1.540 1.00 16.11 | B C |
| ATOM | 5903 CE LYS H 359 | −5.199 10.088 1.104 1.00 17.91 | B C |
| ATOM | 5904 NZ LYS H 359 | −3.719 9.952 1.184 1.00 20.99 | B N |
| ATOM | 5905 C LYS H 359 | −10.325 6.777 1.242 1.00 10.46 | B C |
| ATOM | 5906 O LYS H 359 | −11.191 7.462 0.697 1.00 10.70 | B O |
| ATOM | 5907 N VAL H 360 | −10.579 5.977 2.270 1.00 9.99 | B N |
| ATOM | 5908 CA VAL H 360 | −11.939 5.576 2.592 1.00 9.84 | B C |
| ATOM | 5909 CB VAL H 360 | −12.406 4.401 1.712 1.00 9.42 | B C |
| ATOM | 5910 CG1 VAL H 360 | −11.411 3.253 1.784 1.00 10.07 | B C |
| ATOM | 5911 CG2 VAL H 360 | −13.796 3.944 2.125 1.00 9.56 | B C |
| ATOM | 5912 C VAL H 360 | −12.087 5.214 4.063 1.00 9.98 | B C |
| ATOM | 5913 O VAL H 360 | −11.267 4.485 4.622 1.00 9.96 | B O |
| ATOM | 5914 N GLN H 361 | −13.109 5.780 4.696 1.00 10.39 | B N |
| ATOM | 5915 CA GLN H 361 | −13.322 5.606 6.125 1.00 11.53 | B C |
| ATOM | 5916 CB GLN H 361 | −12.858 6.851 6.883 1.00 12.03 | B C |
| ATOM | 5917 CG GLN H 361 | −13.051 6.769 8.385 1.00 16.44 | B C |
| ATOM | 5918 CD GLN H 361 | −11.812 7.176 9.152 1.00 25.16 | B C |
| ATOM | 5919 OE1 GLN H 361 | −11.763 8.257 9.738 1.00 29.01 | B O |
| ATOM | 5920 NE2 GLN H 361 | −10.773 6.352 9.080 1.00 27.20 | B N |
| ATOM | 5921 C GLN H 361 | −14.795 5.340 6.415 1.00 11.15 | B C |
| ATOM | 5922 O GLN H 361 | −15.620 6.253 6.355 1.00 11.80 | B O |
| ATOM | 5923 N SER H 362 | −15.136 4.078 6.650 1.00 10.90 | B N |
| ATOM | 5924 CA SER H 362 | −16.529 3.677 6.634 1.00 10.30 | B C |
| ATOM | 5925 CB SER H 362 | −17.326 4.548 7.603 1.00 10.47 | B C |
| ATOM | 5926 OG SER H 362 | −18.616 4.011 7.823 1.00 11.17 | B O |
| ATOM | 5927 C SER H 362 | −17.074 3.846 5.224 1.00 9.58 | B C |
| ATOM | 5928 O SER H 362 | −16.419 3.474 4.250 1.00 9.48 | B O |
| ATOM | 5929 N ASN H 363 | −18.182 4.569 5.115 1.00 9.12 | B N |
| ATOM | 5930 CA ASN H 363 | −18.810 4.826 3.826 1.00 8.73 | B C |
| ATOM | 5931 CB ASN H 363 | −20.329 4.778 3.972 1.00 9.01 | B C |
| ATOM | 5932 CG ASN H 363 | −20.850 5.801 4.965 1.00 9.29 | B C |
| ATOM | 5933 OD1 ASN H 363 | −20.079 6.555 5.561 1.00 9.82 | B O |
| ATOM | 5934 ND2 ASN H 363 | −22.162 5.818 5.163 1.00 10.08 | B N |
| ATOM | 5935 C ASN H 363 | −18.382 6.185 3.277 1.00 8.12 | B C |
| ATOM | 5936 O ASN H 363 | −18.996 6.720 2.352 1.00 8.10 | B O |

APPENDIX-continued (APPENDIX discloses SEQ ID NOS 29-32, 29-32 and 29-32, respectively, in order of appearance)

| | | | |
|---|---|---|---|
| ATOM | 5937 N ARG H 364 | −17.346 6.749 3.890 1.00 7.20 | B N |
| ATOM | 5938 CA ARG H 364 | −16.777 8.017 3.457 1.00 6.82 | B C |
| ATOM | 5939 CB ARG H 364 | −16.307 8.821 4.671 1.00 6.91 | B C |
| ATOM | 5940 CG ARG H 364 | −16.741 10.271 4.655 1.00 7.92 | B C |
| ATOM | 5941 CD ARG H 364 | −18.197 10.397 4.249 1.00 8.20 | B C |
| ATOM | 5942 NE ARG H 364 | −18.377 11.314 3.127 1.00 8.70 | B N |
| ATOM | 5943 CZ ARG H 364 | −19.450 12.077 2.958 1.00 8.88 | B C |
| ATOM | 5944 NH1 ARG H 364 | −20.420 12.062 3.862 1.00 8.57 | B N |
| ATOM | 5945 NH2 ARG H 364 | −19.546 12.867 1.897 1.00 10.59 | B N |
| ATOM | 5946 C ARG H 364 | −15.603 7.775 2.519 1.00 6.58 | B C |
| ATOM | 5947 O ARG H 364 | −14.680 7.030 2.847 1.00 6.65 | B O |
| ATOM | 5948 N VAL H 365 | −15.619 8.448 1.375 1.00 6.64 | B N |
| ATOM | 5949 CA VAL H 365 | −14.526 8.350 0.419 1.00 6.54 | B C |
| ATOM | 5950 CB VAL H 365 | −15.000 7.763 −0.922 1.00 5.95 | B C |
| ATOM | 5951 CG1 VAL H 365 | −13.934 7.950 −1.990 1.00 5.48 | B C |
| ATOM | 5952 CG2 VAL H 365 | −15.350 6.292 −0.762 1.00 6.22 | B C |
| ATOM | 5953 C VAL H 365 | −13.914 9.719 0.166 1.00 7.35 | B C |
| ATOM | 5954 O VAL H 365 | −14.617 10.729 0.128 1.00 8.33 | B O |
| ATOM | 5955 N PHE H 366 | −12.611 9.733 −0.081 1.00 7.37 | B N |
| ATOM | 5956 CA PHE H 366 | −11.904 10.969 −0.360 1.00 7.44 | B C |
| ATOM | 5957 CB PHE H 366 | −11.137 11.431 0.874 1.00 7.30 | B C |
| ATOM | 5958 CG PHE H 366 | −12.009 11.714 2.054 1.00 6.70 | B C |
| ATOM | 5959 CD1 PHE H 366 | −12.571 10.677 2.778 1.00 6.70 | B C |
| ATOM | 5960 CE1 PHE H 366 | −13.347 10.932 3.894 1.00 5.94 | B C |
| ATOM | 5961 CZ PHE H 366 | −13.546 12.236 4.311 1.00 5.71 | B C |
| ATOM | 5962 CE2 PHE H 366 | −12.990 13.279 3.593 1.00 5.96 | B C |
| ATOM | 5963 CD2 PHE H 366 | −12.235 13.015 2.467 1.00 6.52 | B C |
| ATOM | 5964 C PHE H 366 | −10.939 10.777 −1.511 1.00 7.45 | B C |
| ATOM | 5965 O PHE H 366 | −9.931 10.082 −1.381 1.00 7.45 | B O |
| ATOM | 5966 N CYS H 367 | −11.212 11.453 −2.618 1.00 8.00 | B N |
| ATOM | 5967 CA CYS H 367 | −10.408 11.281 −3.809 1.00 8.90 | B C |
| ATOM | 5968 CB CYS H 367 | −11.217 10.596 −4.909 1.00 9.46 | B C |
| ATOM | 5969 SG CYS H 367 | −11.640 8.877 −4.545 1.00 10.79 | B S |
| ATOM | 5970 C CYS H 367 | −9.870 12.612 −4.297 1.00 9.09 | B C |
| ATOM | 5971 O CYS H 367 | −10.363 13.674 −3.919 1.00 9.24 | B O |
| ATOM | 5972 N ASP H 368 | −8.892 12.540 −5.188 1.00 9.54 | B N |
| ATOM | 5973 CA ASP H 368 | −8.190 13.724 −5.637 1.00 10.55 | B C |
| ATOM | 5974 CB ASP H 368 | −6.693 13.584 −5.372 1.00 10.53 | B C |
| ATOM | 5975 CG ASP H 368 | −5.983 14.917 −5.352 1.00 11.11 | B C |
| ATOM | 5976 OD1 ASP H 368 | −6.335 15.787 −6.177 1.00 11.42 | B O |
| ATOM | 5977 OD2 ASP H 368 | −5.158 15.138 −4.441 1.00 11.35 | B O |
| ATOM | 5978 C ASP H 368 | −8.442 13.949 −7.118 1.00 11.45 | B C |
| ATOM | 5979 O ASP H 368 | −8.036 13.143 −7.955 1.00 12.05 | B O |
| ATOM | 5980 N THR H 369 | −9.222 14.980 −7.425 1.00 12.41 | B N |
| ATOM | 5981 CA THR H 369 | −9.359 15.444 −8.796 1.00 13.00 | B C |
| ATOM | 5982 CB THR H 369 | −9.723 16.934 −8.846 1.00 12.69 | B C |
| ATOM | 5983 OG1 THR H 369 | −10.937 17.158 −8.117 1.00 11.72 | B O |
| ATOM | 5984 CG2 THR H 369 | −9.896 17.390 −10.289 1.00 13.33 | B C |
| ATOM | 5985 C THR H 369 | −8.052 15.254 −9.548 1.00 14.13 | B C |
| ATOM | 5986 O THR H 369 | −7.986 14.504 −10.520 1.00 14.72 | B O |
| ATOM | 5987 N MET H 370 | −6.996 15.868 −9.029 1.00 15.25 | B N |
| ATOM | 5988 CA MET H 370 | −5.822 16.195 −9.825 1.00 16.60 | B C |
| ATOM | 5989 CB MET H 370 | −4.542 15.983 −9.019 1.00 17.42 | B C |
| ATOM | 5990 CG MET H 370 | −3.815 17.270 −8.673 1.00 20.31 | B C |
| ATOM | 5991 SD MET H 370 | −3.256 18.144 −10.144 1.00 26.43 | B S |
| ATOM | 5992 CE MET H 370 | −4.817 18.449 −10.970 1.00 24.07 | B C |
| ATOM | 5993 C MET H 370 | −5.752 15.466 −11.165 1.00 16.54 | B C |
| ATOM | 5994 O MET H 370 | −5.659 16.108 −12.209 1.00 16.74 | B O |
| ATOM | 5995 N ASN H 371 | −5.730 14.137 −11.146 1.00 16.35 | B N |
| ATOM | 5996 CA ASN H 371 | −5.564 13.390 −12.394 1.00 16.07 | B C |
| ATOM | 5997 CB ASN H 371 | −4.271 12.573 −12.386 1.00 16.41 | B C |
| ATOM | 5998 CG ASN H 371 | −3.047 13.428 −12.644 1.00 16.71 | B C |
| ATOM | 5999 OD1 ASN H 371 | −2.747 13.766 −13.790 1.00 15.75 | B O |
| ATOM | 6000 ND2 ASN H 371 | −2.401 13.874 −11.572 1.00 17.76 | B N |
| ATOM | 6001 C ASN H 371 | −6.767 12.552 −12.827 1.00 15.55 | B C |
| ATOM | 6002 O ASN H 371 | −6.757 11.959 −13.907 1.00 15.84 | B O |
| ATOM | 6003 N SER H 372 | −7.879 12.750 −12.126 1.00 14.76 | B N |
| ATOM | 6004 CA SER H 372 | −9.165 12.189 −12.526 1.00 13.91 | B C |
| ATOM | 6005 CB SER H 372 | −10.309 12.932 −11.832 1.00 14.04 | B C |
| ATOM | 6006 OG SER H 372 | −10.226 14.328 −12.061 1.00 15.09 | B O |
| ATOM | 6007 C SER H 372 | −9.372 12.202 −14.037 1.00 13.07 | B C |
| ATOM | 6008 O SER H 372 | −8.839 13.056 −14.743 1.00 13.02 | B O |
| ATOM | 6009 N LEU H 373 | −10.112 11.213 −14.526 1.00 12.23 | B N |
| ATOM | 6010 CA LEU H 373 | −10.687 11.256 −15.864 1.00 11.45 | B C |
| ATOM | 6011 CB LEU H 373 | −10.417 9.939 −16.594 1.00 11.43 | B C |
| ATOM | 6012 CG LEU H 373 | −9.204 9.880 −17.524 1.00 11.04 | B C |
| ATOM | 6013 CD1 LEU H 373 | −7.988 10.551 −16.888 1.00 11.76 | B C |

APPENDIX-continued (APPENDIX discloses SEQ ID NOS 29-32, 29-32 and 29-32, respectively, in order of appearance)

| | | | |
|---|---|---|---|
| ATOM | 6014 CD2 LEU H 373 | −8.894 8.435 −17.915 1.00 10.49 | B C |
| ATOM | 6015 C LEU H 373 | −12.188 11.472 −15.762 1.00 11.17 | B C |
| ATOM | 6016 O LEU H 373 | −12.847 10.886 −14.904 1.00 11.27 | B O |
| ATOM | 6017 N THR H 374 | −12.733 12.289 −16.655 1.00 10.70 | B N |
| ATOM | 6018 CA THR H 374 | −14.144 12.637 −16.586 1.00 10.23 | B C |
| ATOM | 6019 CB THR H 374 | −14.367 14.151 −16.730 1.00 10.24 | B C |
| ATOM | 6020 OG1 THR H 374 | −13.177 14.850 −16.344 1.00 11.25 | B O |
| ATOM | 6021 CG2 THR H 374 | −15.521 14.604 −15.849 1.00 10.52 | B C |
| ATOM | 6022 C THR H 374 | −14.953 11.896 −17.641 1.00 9.54 | B C |
| ATOM | 6023 O THR H 374 | −14.580 11.855 −18.813 1.00 9.70 | B O |
| ATOM | 6024 N LEU H 375 | −16.035 11.266 −17.198 1.00 8.83 | B N |
| ATOM | 6025 CA LEU H 375 | −16.731 10.270 −18.000 1.00 7.83 | B C |
| ATOM | 6026 CB LEU H 375 | −16.360 8.861 −17.540 1.00 7.38 | B C |
| ATOM | 6027 CG LEU H 375 | −14.878 8.495 −17.551 1.00 5.06 | B C |
| ATOM | 6028 CD1 LEU H 375 | −14.710 7.045 −17.124 1.00 2.41 | B C |
| ATOM | 6029 CD2 LEU H 375 | −14.288 8.729 −18.934 1.00 4.31 | B C |
| ATOM | 6030 C LEU H 375 | −18.236 10.456 −17.878 1.00 7.79 | B C |
| ATOM | 6031 O LEU H 375 | −18.724 10.928 −16.850 1.00 7.92 | B O |
| ATOM | 6032 N PRO H 376 | −18.982 9.954 −18.871 1.00 7.51 | B N |
| ATOM | 6033 CA PRO H 376 | −20.439 10.009 −18.882 1.00 7.90 | B C |
| ATOM | 6034 CB PRO H 376 | −20.780 9.837 −20.362 1.00 7.90 | B C |
| ATOM | 6035 CG PRO H 376 | −19.657 9.033 −20.908 1.00 7.97 | B C |
| ATOM | 6036 CD PRO H 376 | −18.435 9.468 −20.150 1.00 7.40 | B C |
| ATOM | 6037 C PRO H 376 | −21.063 8.881 −18.064 1.00 8.35 | B C |
| ATOM | 6038 O PRO H 376 | −20.569 7.753 −18.085 1.00 8.71 | B O |
| ATOM | 6039 N SER H 377 | −22.190 9.172 −17.421 1.00 9.11 | B N |
| ATOM | 6040 CA SER H 377 | −22.937 8.165 −16.673 1.00 9.91 | B C |
| ATOM | 6041 CB SER H 377 | −24.272 8.737 −16.191 1.00 10.23 | B C |
| ATOM | 6042 OG SER H 377 | −24.293 10.150 −16.304 1.00 10.90 | B O |
| ATOM | 6043 C SER H 377 | −23.180 6.915 −17.513 1.00 10.14 | B C |
| ATOM | 6044 O SER H 377 | −23.678 5.906 −17.013 1.00 10.08 | B O |
| ATOM | 6045 N GLU H 378 | −22.875 7.010 −18.803 1.00 10.71 | B N |
| ATOM | 6046 CA GLU H 378 | −23.057 5.893 −19.721 1.00 11.40 | B C |
| ATOM | 6047 CB GLU H 378 | −22.970 6.377 −21.170 1.00 11.65 | B C |
| ATOM | 6048 CG GLU H 378 | −24.261 6.977 −21.706 1.00 13.46 | B C |
| ATOM | 6049 CD GLU H 378 | −24.671 8.241 −20.972 1.00 16.20 | B C |
| ATOM | 6050 OE1 GLU H 378 | −23.922 8.681 −20.074 1.00 15.73 | B O |
| ATOM | 6051 OE2 GLU H 378 | −25.749 8.788 −21.285 1.00 18.38 | B O |
| ATOM | 6052 C GLU H 378 | −22.019 4.805 −19.468 1.00 11.27 | B C |
| ATOM | 6053 O GLU H 378 | −22.196 3.657 −19.877 1.00 11.28 | B O |
| ATOM | 6054 N VAL H 379 | −20.943 5.170 −18.779 1.00 11.31 | B N |
| ATOM | 6055 CA VAL H 379 | −19.977 4.192 −18.296 1.00 11.59 | B C |
| ATOM | 6056 CB VAL H 379 | −18.973 4.824 −17.315 1.00 11.27 | B C |
| ATOM | 6057 CG1 VAL H 379 | −18.343 3.752 −16.440 1.00 11.60 | B C |
| ATOM | 6058 CG2 VAL H 379 | −17.905 5.597 −18.073 1.00 11.54 | B C |
| ATOM | 6059 C VAL H 379 | −20.675 3.023 −17.610 1.00 12.16 | B C |
| ATOM | 6060 O VAL H 379 | −20.260 1.872 −17.750 1.00 12.51 | B O |
| ATOM | 6061 N ASN H 380 | −21.769 3.317 −16.915 1.00 12.98 | B N |
| ATOM | 6062 CA ASN H 380 | −22.428 2.328 −16.068 1.00 14.00 | B C |
| ATOM | 6063 CB ASN H 380 | −23.553 2.973 −15.258 1.00 14.59 | B C |
| ATOM | 6064 CG ASN H 380 | −23.038 3.964 −14.234 1.00 17.09 | B C |
| ATOM | 6065 OD1 ASN H 380 | −22.893 3.637 −13.056 1.00 20.41 | B O |
| ATOM | 6066 ND2 ASN H 380 | −22.690 5.160 −14.693 1.00 18.86 | B N |
| ATOM | 6067 C ASN H 380 | −22.954 1.115 −16.833 1.00 13.96 | B C |
| ATOM | 6068 O ASN H 380 | −22.973 0.005 −16.302 1.00 14.38 | B O |
| ATOM | 6069 N LEU H 381 | −23.459 1.343 −18.042 1.00 13.61 | B N |
| ATOM | 6070 CA LEU H 381 | −24.024 0.261 −18.844 1.00 13.72 | B C |
| ATOM | 6071 CB LEU H 381 | −24.514 0.792 −20.191 1.00 13.79 | B C |
| ATOM | 6072 CG LEU H 381 | −25.004 2.240 −20.194 1.00 14.92 | B C |
| ATOM | 6073 CD1 LEU H 381 | −25.409 2.670 −21.595 1.00 15.56 | B C |
| ATOM | 6074 CD2 LEU H 381 | −26.157 2.422 −19.218 1.00 15.78 | B C |
| ATOM | 6075 C LEU H 381 | −22.982 −0.827 −19.060 1.00 13.62 | B C |
| ATOM | 6076 O LEU H 381 | −23.314 −1.973 −19.365 1.00 13.57 | B O |
| ATOM | 6077 N CYS H 382 | −21.729 −0.478 −18.796 1.00 13.47 | B N |
| ATOM | 6078 CA CYS H 382 | −20.615 −1.367 −19.068 1.00 13.57 | B C |
| ATOM | 6079 CB CYS H 382 | −19.321 −0.565 −19.165 1.00 13.62 | B C |
| ATOM | 6080 SG CYS H 382 | −18.814 −0.217 −20.852 1.00 15.64 | B S |
| ATOM | 6081 C CYS H 382 | −20.494 −2.432 −17.987 1.00 13.33 | B C |
| ATOM | 6082 O CYS H 382 | −19.948 −3.510 −18.224 1.00 13.57 | B O |
| ATOM | 6083 N ASN H 383 | −21.096 −2.163 −16.833 1.00 13.21 | B N |
| ATOM | 6084 CA ASN H 383 | −21.267 −3.181 −15.803 1.00 13.22 | B C |
| ATOM | 6085 CB ASN H 383 | −21.854 −2.568 −14.531 1.00 13.18 | B C |
| ATOM | 6086 CG ASN H 383 | −21.059 −1.381 −14.034 1.00 13.42 | B C |
| ATOM | 6087 OD1 ASN H 383 | −19.830 −1.418 −13.985 1.00 13.68 | B O |
| ATOM | 6088 ND2 ASN H 383 | −21.761 −0.330 −13.626 1.00 14.32 | B N |
| ATOM | 6089 C ASN H 383 | −22.159 −4.317 −16.277 1.00 13.28 | B C |
| ATOM | 6090 O ASN H 383 | −22.096 −5.428 −15.751 1.00 13.50 | B O |

APPENDIX-continued (APPENDIX discloses SEQ ID NOS 29-32, 29-32 and 29-32, respectively, in order of appearance)

| | | | | | | | | |
|---|---|---|---|---|---|---|---|---|
| ATOM | 6091 N VAL H 384 | −23.092 | −3.990 | −17.164 | 1.00 | 13.24 | B | N |
| ATOM | 6092 CA VAL H 384 | −24.065 | −4.964 | −17.630 | 1.00 | 13.29 | B | C |
| ATOM | 6093 CB VAL H 384 | −25.484 | −4.367 | −17.709 | 1.00 | 13.28 | B | C |
| ATOM | 6094 CG1 VAL H 384 | −26.371 | −5.222 | −18.601 | 1.00 | 13.73 | B | C |
| ATOM | 6095 CG2 VAL H 384 | −26.083 | −4.241 | −16.315 | 1.00 | 12.76 | B | C |
| ATOM | 6096 C VAL H 384 | −23.677 | −5.563 | −18.977 | 1.00 | 13.57 | B | C |
| ATOM | 6097 O VAL H 384 | −23.940 | −6.737 | −19.233 | 1.00 | 13.31 | B | O |
| ATOM | 6098 N ASP H 385 | −23.060 | −4.764 | −19.843 | 1.00 | 14.07 | B | N |
| ATOM | 6099 CA ASP H 385 | −22.923 | −5.172 | −21.238 | 1.00 | 14.61 | B | C |
| ATOM | 6100 CB ASP H 385 | −23.915 | −4.459 | −22.154 | 1.00 | 14.71 | B | C |
| ATOM | 6101 CG ASP H 385 | −24.584 | −5.410 | −23.130 | 1.00 | 16.69 | B | C |
| ATOM | 6102 OD1 ASP H 385 | −24.093 | −6.549 | −23.281 | 1.00 | 18.63 | B | O |
| ATOM | 6103 OD2 ASP H 385 | −25.614 | −5.030 | −23.724 | 1.00 | 19.10 | B | O |
| ATOM | 6104 C ASP H 385 | −21.525 | −5.244 | −21.851 | 1.00 | 14.63 | B | C |
| ATOM | 6105 O ASP H 385 | −21.203 | −6.221 | −22.526 | 1.00 | 14.34 | B | O |
| ATOM | 6106 N ILE H 386 | −20.722 | −4.198 | −21.691 | 1.00 | 14.54 | B | N |
| ATOM | 6107 CA ILE H 386 | −19.435 | −4.146 | −22.382 | 1.00 | 14.46 | B | C |
| ATOM | 6108 CB ILE H 386 | −18.772 | −5.540 | −22.417 | 1.00 | 13.83 | B | C |
| ATOM | 6109 CG1 ILE H 386 | −18.450 | −6.032 | −21.009 | 1.00 | 13.44 | B | C |
| ATOM | 6110 CD1 ILE H 386 | −18.701 | −7.516 | −20.821 | 1.00 | 12.39 | B | C |
| ATOM | 6111 CG2 ILE H 386 | −17.533 | −5.525 | −23.298 | 1.00 | 13.51 | B | C |
| ATOM | 6112 C ILE H 386 | −19.673 | −3.755 | −23.830 | 1.00 | 14.73 | B | C |
| ATOM | 6113 O ILE H 386 | −19.266 | −2.682 | −24.274 | 1.00 | 14.68 | B | O |
| ATOM | 6114 N PHE H 387 | −20.135 | −4.733 | −24.601 | 1.00 | 14.71 | B | N |
| ATOM | 6115 CA PHE H 387 | −20.696 | −4.482 | −25.915 | 1.00 | 14.78 | B | C |
| ATOM | 6116 CB PHE H 387 | −20.739 | −5.766 | −26.733 | 1.00 | 14.77 | B | C |
| ATOM | 6117 CG PHE H 387 | −19.482 | −6.569 | −26.647 | 1.00 | 14.75 | B | C |
| ATOM | 6118 CD1 PHE H 387 | −19.407 | −7.658 | −25.797 | 1.00 | 15.03 | B | C |
| ATOM | 6119 CE1 PHE H 387 | −18.229 | −8.368 | −25.662 | 1.00 | 14.62 | B | C |
| ATOM | 6120 CZ PHE H 387 | −17.093 | −7.943 | −26.318 | 1.00 | 14.55 | B | C |
| ATOM | 6121 CE2 PHE H 387 | −17.136 | −6.809 | −27.103 | 1.00 | 14.68 | B | C |
| ATOM | 6122 CD2 PHE H 387 | −18.316 | −6.103 | −27.227 | 1.00 | 14.61 | B | C |
| ATOM | 6123 C PHE H 387 | −22.080 | −3.871 | −25.821 | 1.00 | 14.91 | B | C |
| ATOM | 6124 O PHE H 387 | −22.992 | −4.445 | −25.228 | 1.00 | 14.86 | B | O |
| ATOM | 6125 N ASN H 388 | −22.144 | −2.610 | −26.216 | 1.00 | 15.11 | B | N |
| ATOM | 6126 CA ASN H 388 | −23.383 | −1.869 | −26.295 | 1.00 | 15.38 | B | C |
| ATOM | 6127 CB ASN H 388 | −23.968 | −1.663 | −24.897 | 1.00 | 14.86 | B | C |
| ATOM | 6128 CG ASN H 388 | −23.005 | −0.958 | −23.963 | 1.00 | 14.86 | B | C |
| ATOM | 6129 OD1 ASN H 388 | −22.936 | 0.270 | −23.935 | 1.00 | 12.80 | B | O |
| ATOM | 6130 ND2 ASN H 388 | −22.213 | −1.736 | −23.234 | 1.00 | 15.97 | B | N |
| ATOM | 6131 C ASN H 388 | −23.023 | −0.526 | −26.906 | 1.00 | 16.11 | B | C |
| ATOM | 6132 O ASN H 388 | −21.965 | 0.024 | −26.599 | 1.00 | 15.92 | B | O |
| ATOM | 6133 N PRO H 389 | −23.772 | −0.117 | −27.935 | 1.00 | 16.99 | B | N |
| ATOM | 6134 CA PRO H 389 | −23.716 | 1.289 | −28.309 | 1.00 | 17.40 | B | C |
| ATOM | 6135 CB PRO H 389 | −24.965 | 1.468 | −29.176 | 1.00 | 17.72 | B | C |
| ATOM | 6136 CG PRO H 389 | −25.904 | 0.425 | −28.694 | 1.00 | 17.47 | B | C |
| ATOM | 6137 CD PRO H 389 | −25.041 | −0.747 | −28.339 | 1.00 | 17.05 | B | C |
| ATOM | 6138 C PRO H 389 | −23.810 | 2.170 | −27.071 | 1.00 | 17.86 | B | C |
| ATOM | 6139 O PRO H 389 | −24.276 | 1.718 | −26.025 | 1.00 | 18.45 | B | O |
| ATOM | 6140 N LYS H 390 | −23.335 | 3.406 | −27.180 | 1.00 | 17.97 | B | N |
| ATOM | 6141 CA LYS H 390 | −23.325 | 4.318 | −26.045 | 1.00 | 18.06 | B | C |
| ATOM | 6142 CB LYS H 390 | −24.373 | 3.904 | −25.009 | 1.00 | 17.92 | B | C |
| ATOM | 6143 CG LYS H 390 | −25.807 | 4.197 | −25.424 | 1.00 | 18.58 | B | C |
| ATOM | 6144 CD LYS H 390 | −26.259 | 5.564 | −24.935 | 1.00 | 20.61 | B | C |
| ATOM | 6145 CE LYS H 390 | −27.775 | 5.656 | −24.875 | 1.00 | 21.48 | B | C |
| ATOM | 6146 NZ LYS H 390 | −28.387 | 5.669 | −26.232 | 1.00 | 23.16 | B | N |
| ATOM | 6147 C LYS H 390 | −21.946 | 4.403 | −25.400 | 1.00 | 18.01 | B | C |
| ATOM | 6148 O LYS H 390 | −21.382 | 5.490 | −25.279 | 1.00 | 18.43 | B | O |
| ATOM | 6149 N TYR H 391 | −21.391 | 3.261 | −25.011 | 1.00 | 17.68 | B | N |
| ATOM | 6150 CA TYR H 391 | −20.012 | 3.232 | −24.539 | 1.00 | 17.33 | B | C |
| ATOM | 6151 CB TYR H 391 | −19.948 | 3.140 | −23.015 | 1.00 | 17.42 | B | C |
| ATOM | 6152 CG TYR H 391 | −18.847 | 3.986 | −22.423 | 1.00 | 17.27 | B | C |
| ATOM | 6153 CD1 TYR H 391 | −18.602 | 5.263 | −22.911 | 1.00 | 17.29 | B | C |
| ATOM | 6154 CE1 TYR H 391 | −17.553 | 6.021 | −22.434 | 1.00 | 17.32 | B | C |
| ATOM | 6155 CZ TYR H 391 | −16.698 | 5.486 | −21.496 | 1.00 | 16.51 | B | C |
| ATOM | 6156 OH TYR H 391 | −15.654 | 6.241 | −21.015 | 1.00 | 16.65 | B | O |
| ATOM | 6157 CE2 TYR H 391 | −16.878 | 4.195 | −21.045 | 1.00 | 16.52 | B | C |
| ATOM | 6158 CD2 TYR H 391 | −17.933 | 3.444 | −21.530 | 1.00 | 17.24 | B | C |
| ATOM | 6159 C TYR H 391 | −19.179 | 2.130 | −25.176 | 1.00 | 17.43 | B | C |
| ATOM | 6160 O TYR H 391 | −19.459 | 0.946 | −24.993 | 1.00 | 17.70 | B | O |
| ATOM | 6161 N ASP H 392 | −18.075 | 2.522 | −25.804 | 1.00 | 17.56 | B | N |
| ATOM | 6162 CA ASP H 392 | −16.973 | 1.599 | −26.012 | 1.00 | 17.69 | B | C |
| ATOM | 6163 CB ASP H 392 | −16.119 | 2.003 | −27.214 | 1.00 | 17.89 | B | C |
| ATOM | 6164 CG ASP H 392 | −16.587 | 3.290 | −27.853 | 1.00 | 18.86 | B | C |
| ATOM | 6165 OD1 ASP H 392 | −16.582 | 4.332 | −27.165 | 1.00 | 20.34 | B | O |
| ATOM | 6166 OD2 ASP H 392 | −16.931 | 3.269 | −29.053 | 1.00 | 18.51 | B | O |
| ATOM | 6167 C ASP H 392 | −16.115 | 1.473 | −24.767 | 1.00 | 17.11 | B | C |

APPENDIX-continued (APPENDIX discloses SEQ ID NOS 29-32, 29-32 and 29-32, respectively, in order of appearance)

| | | | |
|---|---|---|---|
| ATOM | 6168 O ASP H 392 | −15.801 2.460 −24.101 1.00 17.04 | B O |
| ATOM | 6169 N CYS H 393 | −15.736 0.239 −24.468 1.00 16.33 | B N |
| ATOM | 6170 CA CYS H 393 | −15.683 −0.240 −23.102 1.00 16.17 | B C |
| ATOM | 6171 CB CYS H 393 | −16.818 −1.230 −22.851 1.00 16.11 | B C |
| ATOM | 6172 SG CYS H 393 | −17.226 −1.449 −21.117 1.00 20.23 | B S |
| ATOM | 6173 C CYS H 393 | −14.355 −0.941 −22.926 1.00 15.37 | B C |
| ATOM | 6174 O CYS H 393 | −14.044 −1.876 −23.663 1.00 15.15 | B O |
| ATOM | 6175 N LYS H 394 | −13.482 −0.332 −22.138 1.00 14.91 | B N |
| ATOM | 6176 CA LYS H 394 | −12.100 −0.755 −22.107 1.00 14.50 | B C |
| ATOM | 6177 CB LYS H 394 | −11.242 0.294 −21.405 1.00 14.60 | B C |
| ATOM | 6178 CG LYS H 394 | −11.613 1.723 −21.788 1.00 16.44 | B C |
| ATOM | 6179 CD LYS H 394 | −10.460 2.688 −21.576 1.00 20.45 | B C |
| ATOM | 6180 CE LYS H 394 | −10.252 2.974 −20.099 1.00 23.05 | B C |
| ATOM | 6181 NZ LYS H 394 | −9.330 1.988 −19.467 1.00 24.13 | B N |
| ATOM | 6182 C LYS H 394 | −11.955 −2.130 −21.463 1.00 14.00 | B C |
| ATOM | 6183 O LYS H 394 | −12.593 −2.434 −20.454 1.00 14.14 | B O |
| ATOM | 6184 N ILE H 395 | −11.118 −2.957 −22.077 1.00 13.28 | B N |
| ATOM | 6185 CA ILE H 395 | −11.238 −4.407 −22.026 1.00 12.89 | B C |
| ATOM | 6186 CB ILE H 395 | −12.208 −4.925 −23.106 1.00 12.75 | B C |
| ATOM | 6187 CG1 ILE H 395 | −13.660 −4.699 −22.690 1.00 13.58 | B C |
| ATOM | 6188 CD1 ILE H 395 | −14.633 −4.719 −23.849 1.00 15.33 | B C |
| ATOM | 6189 CG2 ILE H 395 | −11.947 −6.396 −23.399 1.00 12.16 | B C |
| ATOM | 6190 C ILE H 395 | −9.860 −4.906 −22.407 1.00 13.15 | B C |
| ATOM | 6191 O ILE H 395 | −9.242 −4.353 −23.312 1.00 13.45 | B O |
| ATOM | 6192 N MET H 396 | −9.462 −6.054 −21.877 1.00 13.06 | B N |
| ATOM | 6193 CA MET H 396 | −8.356 −6.773 −22.482 1.00 13.00 | B C |
| ATOM | 6194 CB MET H 396 | −7.104 −6.717 −21.605 1.00 13.34 | B C |
| ATOM | 6195 CG MET H 396 | −7.052 −7.752 −20.500 1.00 14.30 | B C |
| ATOM | 6196 SD MET H 396 | −5.571 −7.581 −19.484 1.00 18.50 | B S |
| ATOM | 6197 CE MET H 396 | −5.752 −5.895 −18.904 1.00 17.80 | B C |
| ATOM | 6198 C MET H 396 | −8.702 −8.200 −22.867 1.00 12.96 | B C |
| ATOM | 6199 O MET H 396 | −9.615 −8.808 −22.309 1.00 13.04 | B O |
| ATOM | 6200 N THR H 397 | −7.935 −8.734 −23.808 1.00 12.78 | B N |
| ATOM | 6201 CA THR H 397 | −8.350 −9.888 −24.585 1.00 12.51 | B C |
| ATOM | 6202 CB THR H 397 | −8.389 −9.563 −26.087 1.00 12.39 | B C |
| ATOM | 6203 OG1 THR H 397 | −9.593 −8.851 −26.394 1.00 12.50 | B O |
| ATOM | 6204 CG2 THR H 397 | −8.335 −10.839 −26.912 1.00 12.55 | B C |
| ATOM | 6205 C THR H 397 | −7.350 −11.005 −24.366 1.00 12.58 | B C |
| ATOM | 6206 O THR H 397 | −6.143 −10.772 −24.327 1.00 12.88 | B O |
| ATOM | 6207 N SER H 398 | −7.859 −12.210 −24.165 1.00 12.55 | B N |
| ATOM | 6208 CA SER H 398 | −7.082 −13.401 −24.410 1.00 12.76 | B C |
| ATOM | 6209 CB SER H 398 | −6.083 −13.627 −23.273 1.00 12.52 | B C |
| ATOM | 6210 OG SER H 398 | −5.764 −15.001 −23.133 1.00 12.72 | B O |
| ATOM | 6211 C SER H 398 | −8.070 −14.539 −24.456 1.00 12.99 | B C |
| ATOM | 6212 O SER H 398 | −8.838 −14.672 −25.410 1.00 13.13 | B O |
| ATOM | 6213 N LYS H 399 | −8.182 −15.232 −23.330 1.00 13.01 | B N |
| ATOM | 6214 CA LYS H 399 | −7.890 −16.651 −23.342 1.00 13.29 | B C |
| ATOM | 6215 CB LYS H 399 | −6.739 −17.020 −24.279 1.00 13.79 | B C |
| ATOM | 6216 CG LYS H 399 | −6.786 −16.279 −25.618 1.00 14.34 | B C |
| ATOM | 6217 CD LYS H 399 | −7.835 −16.868 −26.552 1.00 16.43 | B C |
| ATOM | 6218 CE LYS H 399 | −7.864 −16.139 −27.889 1.00 17.37 | B C |
| ATOM | 6219 NZ LYS H 399 | −8.770 −16.802 −28.867 1.00 16.62 | B N |
| ATOM | 6220 C LYS H 399 | −8.128 −17.609 −22.171 1.00 13.09 | B C |
| ATOM | 6221 O LYS H 399 | −9.087 −18.376 −22.216 1.00 12.87 | B O |
| ATOM | 6222 N THR H 400 | −7.140 −17.783 −21.300 1.00 13.04 | B N |
| ATOM | 6223 CA THR H 400 | −7.133 −18.953 −20.420 1.00 13.38 | B C |
| ATOM | 6224 CB THR H 400 | −5.703 −19.453 −20.133 1.00 13.74 | B C |
| ATOM | 6225 OG1 THR H 400 | −4.773 −18.763 −20.977 1.00 14.38 | B O |
| ATOM | 6226 CG2 THR H 400 | −5.601 −20.950 −20.394 1.00 14.32 | B C |
| ATOM | 6227 C THR H 400 | −7.866 −18.687 −19.104 1.00 13.20 | B C |
| ATOM | 6228 O THR H 400 | −7.913 −17.551 −18.630 1.00 13.12 | B O |
| ATOM | 6229 N ASP H 401 | −8.478 −19.728 −18.545 1.00 12.97 | B N |
| ATOM | 6230 CA ASP H 401 | −8.896 −19.715 −17.145 1.00 12.50 | B C |
| ATOM | 6231 CB ASP H 401 | −9.622 −21.022 −16.798 1.00 12.73 | B C |
| ATOM | 6232 CG ASP H 401 | −10.854 −21.261 −17.651 1.00 13.98 | B C |
| ATOM | 6233 OD1 ASP H 401 | −10.870 −20.793 −18.808 1.00 16.55 | B O |
| ATOM | 6234 OD2 ASP H 401 | −11.708 −22.076 −17.236 1.00 14.80 | B O |
| ATOM | 6235 C ASP H 401 | −7.683 −19.567 −16.222 1.00 12.13 | B C |
| ATOM | 6236 O ASP H 401 | −6.906 −20.508 −16.071 1.00 12.31 | B O |
| ATOM | 6237 N VAL H 402 | −7.609 −18.459 −15.489 1.00 11.49 | B N |
| ATOM | 6238 CA VAL H 402 | −7.400 −18.523 −14.044 1.00 10.74 | B C |
| ATOM | 6239 CB VAL H 402 | −7.004 −17.151 −13.456 1.00 10.60 | B C |
| ATOM | 6240 CG1 VAL H 402 | −7.433 −17.045 −11.998 1.00 11.26 | B C |
| ATOM | 6241 CG2 VAL H 402 | −5.504 −16.918 −13.602 1.00 10.99 | B C |
| ATOM | 6242 C VAL H 402 | −8.707 −18.986 −13.423 1.00 10.24 | B C |
| ATOM | 6243 O VAL H 402 | −9.515 −19.616 −14.104 1.00 10.30 | B O |
| ATOM | 6244 N SER H 403 | −9.015 −18.516 −12.218 1.00 9.76 | B N |

(APPENDIX discloses SEQ ID NOS 29-32, 29-32 and 29-32, respectively, in order of appearance)

| | | | |
|---|---|---|---|
| ATOM | 6245 CA SER H 403 | −10.286 −18.897 −11.605 1.00 9.18 | B C |
| ATOM | 6246 CB SER H 403 | −10.485 −20.406 −11.726 1.00 9.41 | B C |
| ATOM | 6247 OG SER H 403 | −9.349 −21.015 −12.313 1.00 10.82 | B O |
| ATOM | 6248 C SER H 403 | −10.528 −18.449 −10.162 1.00 8.51 | B C |
| ATOM | 6249 O SER H 403 | −9.701 −18.699 −9.285 1.00 8.30 | B O |
| ATOM | 6250 N SER H 404 | −11.773 −18.053 −9.888 1.00 8.35 | B N |
| ATOM | 6251 CA SER H 404 | −12.352 −18.148 −8.541 1.00 8.18 | B C |
| ATOM | 6252 CB SER H 404 | −11.585 −17.257 −7.564 1.00 8.18 | B C |
| ATOM | 6253 OG SER H 404 | −12.250 −16.019 −7.382 1.00 8.83 | B O |
| ATOM | 6254 C SER H 404 | −13.841 −17.789 −8.505 1.00 7.62 | B C |
| ATOM | 6255 O SER H 404 | −14.505 −17.759 −9.541 1.00 7.57 | B O |
| ATOM | 6256 N SER H 405 | −14.357 −17.506 −7.310 1.00 7.08 | B N |
| ATOM | 6257 CA SER H 405 | −15.777 −17.210 −7.151 1.00 6.53 | B C |
| ATOM | 6258 CB SER H 405 | −16.568 −18.475 −6.802 1.00 6.42 | B C |
| ATOM | 6259 OG SER H 405 | −17.786 −18.156 −6.146 1.00 5.66 | B O |
| ATOM | 6260 C SER H 405 | −16.070 −16.101 −6.144 1.00 6.28 | B C |
| ATOM | 6261 O SER H 405 | −15.289 −15.847 −5.226 1.00 5.98 | B O |
| ATOM | 6262 N VAL H 406 | −17.254 −15.514 −6.281 1.00 6.22 | B N |
| ATOM | 6263 CA VAL H 406 | −17.629 −14.309 −5.557 1.00 6.50 | B C |
| ATOM | 6264 CB VAL H 406 | −17.390 −13.053 −6.414 1.00 6.45 | B C |
| ATOM | 6265 CG1 VAL H 406 | −17.384 −11.811 −5.546 1.00 7.66 | B C |
| ATOM | 6266 CG2 VAL H 406 | −16.090 −13.177 −7.191 1.00 7.38 | B C |
| ATOM | 6267 C VAL H 406 | −19.115 −14.377 −5.237 1.00 6.24 | B C |
| ATOM | 6268 O VAL H 406 | −19.946 −14.488 −6.138 1.00 6.14 | B O |
| ATOM | 6269 N ILE H 407 | −19.450 −14.313 −3.955 1.00 6.32 | B N |
| ATOM | 6270 CA ILE H 407 | −20.831 −14.478 −3.534 1.00 6.60 | B C |
| ATOM | 6271 CB ILE H 407 | −20.925 −15.154 −2.163 1.00 6.27 | B C |
| ATOM | 6272 CG1 ILE H 407 | −20.643 −16.651 −2.296 1.00 6.19 | B C |
| ATOM | 6273 CD1 ILE H 407 | −21.477 −17.514 −1.376 1.00 8.34 | B C |
| ATOM | 6274 CG2 ILE H 407 | −22.294 −14.923 −1.550 1.00 6.42 | B C |
| ATOM | 6275 C ILE H 407 | −21.570 −13.149 −3.497 1.00 7.20 | B C |
| ATOM | 6276 O ILE H 407 | −21.094 −12.176 −2.913 1.00 7.42 | B O |
| ATOM | 6277 N THR H 408 | −22.792 −13.155 −4.016 1.00 7.57 | B N |
| ATOM | 6278 CA THR H 408 | −23.563 −11.933 −4.148 1.00 8.19 | B C |
| ATOM | 6279 CB THR H 408 | −24.066 −11.739 −5.587 1.00 8.15 | B C |
| ATOM | 6280 OG1 THR H 408 | −24.863 −12.866 −5.971 1.00 8.88 | B O |
| ATOM | 6281 CG2 THR H 408 | −22.893 −11.606 −6.542 1.00 7.93 | B C |
| ATOM | 6282 C THR H 408 | −24.753 −11.933 −3.203 1.00 8.55 | B C |
| ATOM | 6283 O THR H 408 | −24.998 −12.905 −2.488 1.00 9.07 | B O |
| ATOM | 6284 N SER H 409 | −25.513 −10.844 −3.238 1.00 8.70 | B N |
| ATOM | 6285 CA SER H 409 | −26.644 −10.667 −2.344 1.00 9.20 | B C |
| ATOM | 6286 CB SER H 409 | −27.266 −9.284 −2.543 1.00 9.72 | B C |
| ATOM | 6287 OG SER H 409 | −26.279 −8.269 −2.491 1.00 10.75 | B O |
| ATOM | 6288 C SER H 409 | −27.686 −11.747 −2.596 1.00 9.01 | B C |
| ATOM | 6289 O SER H 409 | −28.360 −12.203 −1.671 1.00 9.02 | B O |
| ATOM | 6290 N LEU H 410 | −27.804 −12.160 −3.853 1.00 8.91 | B N |
| ATOM | 6291 CA LEU H 410 | −28.962 −12.921 −4.302 1.00 9.29 | B C |
| ATOM | 6292 CB LEU H 410 | −29.901 −12.033 −5.118 1.00 9.61 | B C |
| ATOM | 6293 CG LEU H 410 | −31.317 −11.873 −4.558 1.00 9.70 | B C |
| ATOM | 6294 CD1 LEU H 410 | −31.289 −11.183 −3.203 1.00 11.11 | B C |
| ATOM | 6295 CD2 LEU H 410 | −32.204 −11.113 −5.532 1.00 9.16 | B C |
| ATOM | 6296 C LEU H 410 | −28.533 −14.134 −5.119 1.00 9.12 | B C |
| ATOM | 6297 O LEU H 410 | −29.364 −14.840 −5.690 1.00 9.08 | B O |
| ATOM | 6298 N GLY H 411 | −27.228 −14.365 −5.173 1.00 9.03 | B N |
| ATOM | 6299 CA GLY H 411 | −26.691 −15.606 −5.706 1.00 8.44 | B C |
| ATOM | 6300 C GLY H 411 | −25.180 −15.615 −5.632 1.00 7.91 | B C |
| ATOM | 6301 O GLY H 411 | −24.594 −15.123 −4.668 1.00 7.85 | B O |
| ATOM | 6302 N ALA H 412 | −24.546 −16.095 −6.694 1.00 7.30 | B N |
| ATOM | 6303 CA ALA H 412 | −23.095 −16.167 −6.738 1.00 6.92 | B C |
| ATOM | 6304 CB ALA H 412 | −22.607 −17.439 −6.062 1.00 6.90 | B C |
| ATOM | 6305 C ALA H 412 | −22.593 −16.098 −8.173 1.00 6.99 | B C |
| ATOM | 6306 O ALA H 412 | −23.277 −16.525 −9.102 1.00 6.94 | B O |
| ATOM | 6307 N ILE H 413 | −21.415 −15.510 −8.349 1.00 7.29 | B N |
| ATOM | 6308 CA ILE H 413 | −20.705 −15.567 −9.622 1.00 7.49 | B C |
| ATOM | 6309 CB ILE H 413 | −20.073 −14.207 −9.961 1.00 7.24 | B C |
| ATOM | 6310 CG1 ILE H 413 | −21.142 −13.236 −10.466 1.00 7.18 | B C |
| ATOM | 6311 CD1 ILE H 413 | −20.589 −12.045 −11.233 1.00 7.70 | B C |
| ATOM | 6312 CG2 ILE H 413 | −18.958 −14.377 −10.983 1.00 7.70 | B C |
| ATOM | 6313 C ILE H 413 | −19.596 −16.608 −9.554 1.00 7.94 | B C |
| ATOM | 6314 O ILE H 413 | −18.965 −16.775 −8.512 1.00 8.39 | B O |
| ATOM | 6315 N VAL H 414 | −19.276 −17.221 −10.687 1.00 8.22 | B N |
| ATOM | 6316 CA VAL H 414 | −18.141 −18.134 −10.734 1.00 8.77 | B C |
| ATOM | 6317 CB VAL H 414 | −18.558 −19.593 −10.482 1.00 8.57 | B C |
| ATOM | 6318 CG1 VAL H 414 | −19.806 −19.936 −11.279 1.00 9.12 | B C |
| ATOM | 6319 CG2 VAL H 414 | −17.416 −20.538 −10.825 1.00 8.90 | B C |
| ATOM | 6320 C VAL H 414 | −17.323 −18.031 −12.015 1.00 8.92 | B C |
| ATOM | 6321 O VAL H 414 | −17.803 −18.347 −13.105 1.00 9.00 | B O |

APPENDIX-continued (APPENDIX discloses SEQ ID NOS 29-32, 29-32 and 29-32, respectively, in order of appearance)

| | | | | | | | | | | | | | |
|---|---|---|---|---|---|---|---|---|---|---|---|---|---|
| ATOM | 6322 | N | SER | H | 415 | −16.058 | −17.659 | −11.853 | 1.00 | 8.97 | B | N |
| ATOM | 6323 | CA | SER | H | 415 | −15.120 | −17.594 | −12.962 | 1.00 | 9.02 | B | C |
| ATOM | 6324 | CB | SER | H | 415 | −14.260 | −16.335 | −12.855 | 1.00 | 8.98 | B | C |
| ATOM | 6325 | OG | SER | H | 415 | −15.043 | −15.218 | −12.473 | 1.00 | 9.54 | B | O |
| ATOM | 6326 | C | SER | H | 415 | −14.235 | −18.832 | −12.987 | 1.00 | 9.36 | B | C |
| ATOM | 6327 | O | SER | H | 415 | −13.326 | −18.975 | −12.170 | 1.00 | 9.61 | B | O |
| ATOM | 6328 | N | CYS | H | 416 | −14.602 | −19.786 | −13.834 | 1.00 | 9.57 | B | N |
| ATOM | 6329 | CA | CYS | H | 416 | −13.851 | −21.023 | −13.963 | 1.00 | 9.61 | B | C |
| ATOM | 6330 | CB | CYS | H | 416 | −14.801 | −22.216 | −14.038 | 1.00 | 9.62 | B | C |
| ATOM | 6331 | SG | CYS | H | 416 | −14.118 | −23.727 | −13.341 | 1.00 | 11.33 | B | S |
| ATOM | 6332 | C | CYS | H | 416 | −12.998 | −20.973 | −15.215 | 1.00 | 9.61 | B | C |
| ATOM | 6333 | O | CYS | H | 416 | −13.519 | −20.829 | −16.320 | 1.00 | 9.80 | B | O |
| ATOM | 6334 | N | TYR | H | 417 | −11.684 | −20.941 | −15.027 | 1.00 | 9.48 | B | N |
| ATOM | 6335 | CA | TYR | H | 417 | −10.772 | −20.739 | −16.142 | 1.00 | 9.28 | B | C |
| ATOM | 6336 | CB | TYR | H | 417 | −10.307 | −19.281 | −16.205 | 1.00 | 9.17 | B | C |
| ATOM | 6337 | CG | TYR | H | 417 | −11.358 | −18.318 | −16.714 | 1.00 | 8.71 | B | C |
| ATOM | 6338 | CD1 | TYR | H | 417 | −11.483 | −17.048 | −16.167 | 1.00 | 8.54 | B | C |
| ATOM | 6339 | CE1 | TYR | H | 417 | −12.425 | −16.159 | −16.635 | 1.00 | 9.56 | B | C |
| ATOM | 6340 | CZ | TYR | H | 417 | −13.230 | −16.516 | −17.693 | 1.00 | 9.83 | B | C |
| ATOM | 6341 | OH | TYR | H | 417 | −14.184 | −15.638 | −18.143 | 1.00 | 10.51 | B | O |
| ATOM | 6342 | CE2 | TYR | H | 417 | −13.122 | −17.765 | −18.263 | 1.00 | 9.36 | B | C |
| ATOM | 6343 | CD2 | TYR | H | 417 | −12.177 | −18.651 | −17.786 | 1.00 | 8.95 | B | C |
| ATOM | 6344 | C | TYR | H | 417 | −9.572 | −21.677 | −16.068 | 1.00 | 9.35 | B | C |
| ATOM | 6345 | O | TYR | H | 417 | −9.336 | −22.318 | −15.044 | 1.00 | 9.11 | B | O |
| ATOM | 6346 | N | GLY | H | 418 | −8.830 | −21.762 | −17.169 | 1.00 | 9.71 | B | N |
| ATOM | 6347 | CA | GLY | H | 418 | −7.678 | −22.656 | −17.263 | 1.00 | 9.95 | B | C |
| ATOM | 6348 | C | GLY | H | 418 | −8.045 | −24.101 | −16.993 | 1.00 | 10.09 | B | C |
| ATOM | 6349 | O | GLY | H | 418 | −9.082 | −24.584 | −17.450 | 1.00 | 10.17 | B | O |
| ATOM | 6350 | N | LYS | H | 419 | −7.251 | −24.756 | −16.154 | 1.00 | 10.17 | B | N |
| ATOM | 6351 | CA | LYS | H | 419 | −7.426 | −26.177 | −15.896 | 1.00 | 10.50 | B | C |
| ATOM | 6352 | CB | LYS | H | 419 | −6.086 | −26.827 | −15.545 | 1.00 | 11.09 | B | C |
| ATOM | 6353 | CG | LYS | H | 419 | −5.332 | −27.389 | −16.738 | 1.00 | 12.94 | B | C |
| ATOM | 6354 | CD | LYS | H | 419 | −4.265 | −28.377 | −16.297 | 1.00 | 15.52 | B | C |
| ATOM | 6355 | CE | LYS | H | 419 | −3.705 | −29.152 | −17.479 | 1.00 | 17.07 | B | C |
| ATOM | 6356 | NZ | LYS | H | 419 | −3.179 | −28.247 | −18.538 | 1.00 | 19.30 | B | N |
| ATOM | 6357 | C | LYS | H | 419 | −8.447 | −26.465 | −14.798 | 1.00 | 10.23 | B | C |
| ATOM | 6358 | O | LYS | H | 419 | −8.613 | −27.616 | −14.398 | 1.00 | 10.58 | B | O |
| ATOM | 6359 | N | THR | H | 420 | −9.070 | −25.426 | −14.250 | 1.00 | 10.10 | B | N |
| ATOM | 6360 | CA | THR | H | 420 | −9.805 | −25.587 | −12.997 | 1.00 | 9.74 | B | C |
| ATOM | 6361 | CB | THR | H | 420 | −9.938 | −24.270 | −12.223 | 1.00 | 9.28 | B | C |
| ATOM | 6362 | OG1 | THR | H | 420 | −9.022 | −23.306 | −12.754 | 1.00 | 9.21 | B | O |
| ATOM | 6363 | CG2 | THR | H | 420 | −9.633 | −24.499 | −10.752 | 1.00 | 9.03 | B | C |
| ATOM | 6364 | C | THR | H | 420 | −11.181 | −26.223 | −13.168 | 1.00 | 9.95 | B | C |
| ATOM | 6365 | O | THR | H | 420 | −11.779 | −26.160 | −14.242 | 1.00 | 10.35 | B | O |
| ATOM | 6366 | N | LYS | H | 421 | −11.652 | −26.879 | −12.111 | 1.00 | 10.07 | B | N |
| ATOM | 6367 | CA | LYS | H | 421 | −12.961 | −27.527 | −12.115 | 1.00 | 10.21 | B | C |
| ATOM | 6368 | CB | LYS | H | 421 | −12.835 | −28.979 | −11.649 | 1.00 | 10.30 | B | C |
| ATOM | 6369 | CG | LYS | H | 421 | −12.705 | −29.989 | −12.776 | 1.00 | 12.43 | B | C |
| ATOM | 6370 | CD | LYS | H | 421 | −12.482 | −31.391 | −12.234 | 1.00 | 15.12 | B | C |
| ATOM | 6371 | CE | LYS | H | 421 | −11.769 | −32.267 | −13.251 | 1.00 | 15.21 | B | C |
| ATOM | 6372 | NZ | LYS | H | 421 | −11.047 | −33.396 | −12.601 | 1.00 | 15.98 | B | N |
| ATOM | 6373 | C | LYS | H | 421 | −13.933 | −26.782 | −11.206 | 1.00 | 10.09 | B | C |
| ATOM | 6374 | O | LYS | H | 421 | −13.600 | −26.456 | −10.067 | 1.00 | 10.36 | B | O |
| ATOM | 6375 | N | CYS | H | 422 | −15.155 | −26.574 | −11.685 | 1.00 | 9.81 | B | N |
| ATOM | 6376 | CA | CYS | H | 422 | −16.153 | −25.863 | −10.898 | 1.00 | 9.56 | B | C |
| ATOM | 6377 | CB | CYS | H | 422 | −16.222 | −24.392 | −11.302 | 1.00 | 9.72 | B | C |
| ATOM | 6378 | SG | CYS | H | 422 | −14.611 | −23.591 | −11.379 | 1.00 | 11.42 | B | S |
| ATOM | 6379 | C | CYS | H | 422 | −17.535 | −26.499 | −10.939 | 1.00 | 9.18 | B | C |
| ATOM | 6380 | O | CYS | H | 422 | −17.952 | −27.056 | −11.954 | 1.00 | 9.27 | B | O |
| ATOM | 6381 | N | THR | H | 423 | −18.273 | −26.311 | −9.851 | 1.00 | 8.93 | B | N |
| ATOM | 6382 | CA | THR | H | 423 | −19.417 | −27.147 | −9.527 | 1.00 | 8.64 | B | C |
| ATOM | 6383 | CB | THR | H | 423 | −19.014 | −28.315 | −8.606 | 1.00 | 8.32 | B | C |
| ATOM | 6384 | OG1 | THR | H | 423 | −17.878 | −28.993 | −9.154 | 1.00 | 7.97 | B | O |
| ATOM | 6385 | CG2 | THR | H | 423 | −20.165 | −29.297 | −8.456 | 1.00 | 8.36 | B | C |
| ATOM | 6386 | C | THR | H | 423 | −20.441 | −26.297 | −8.791 | 1.00 | 8.86 | B | C |
| ATOM | 6387 | O | THR | H | 423 | −20.133 | −25.694 | −7.763 | 1.00 | 9.26 | B | O |
| ATOM | 6388 | N | ALA | H | 424 | −21.676 | −26.306 | −9.279 | 1.00 | 8.74 | B | N |
| ATOM | 6389 | CA | ALA | H | 424 | −22.803 | −25.836 | −8.487 | 1.00 | 8.79 | B | C |
| ATOM | 6390 | CB | ALA | H | 424 | −23.693 | −24.926 | −9.317 | 1.00 | 8.94 | B | C |
| ATOM | 6391 | C | ALA | H | 424 | −23.605 | −27.008 | −7.932 | 1.00 | 8.84 | B | C |
| ATOM | 6392 | O | ALA | H | 424 | −24.158 | −27.807 | −8.687 | 1.00 | 9.24 | B | O |
| ATOM | 6393 | N | SER | H | 425 | −23.649 | −27.113 | −6.608 | 1.00 | 8.81 | B | N |
| ATOM | 6394 | CA | SER | H | 425 | −24.412 | −28.166 | −5.950 | 1.00 | 8.85 | B | C |
| ATOM | 6395 | CB | SER | H | 425 | −23.530 | −28.925 | −4.957 | 1.00 | 8.94 | B | C |
| ATOM | 6396 | OG | SER | H | 425 | −22.166 | −28.871 | −5.341 | 1.00 | 7.69 | B | O |
| ATOM | 6397 | C | SER | H | 425 | −25.626 | −27.584 | −5.235 | 1.00 | 9.01 | B | C |
| ATOM | 6398 | O | SER | H | 425 | −25.593 | −26.447 | −4.763 | 1.00 | 8.63 | B | O |

APPENDIX-continued (APPENDIX discloses SEQ ID NOS 29-32, 29-32 and 29-32, respectively, in order of appearance)

| | | | | | | | | | | | | | |
|---|---|---|---|---|---|---|---|---|---|---|---|---|---|
| ATOM | 6399 | N | ASN | H | 426 | −26.716 | −28.345 | −5.208 | 1.00 | 9.54 | B | N |
| ATOM | 6400 | CA | ASN | H | 426 | −27.971 | −27.851 | −4.658 | 1.00 | 10.19 | B | C |
| ATOM | 6401 | CB | ASN | H | 426 | −29.166 | −28.508 | −5.356 | 1.00 | 9.77 | B | C |
| ATOM | 6402 | CG | ASN | H | 426 | −29.499 | −29.874 | −4.787 | 1.00 | 9.43 | B | C |
| ATOM | 6403 | OD1 | ASN | H | 426 | −28.998 | −30.259 | −3.730 | 1.00 | 9.01 | B | O |
| ATOM | 6404 | ND2 | ASN | H | 426 | −30.349 | −30.615 | −5.488 | 1.00 | 9.01 | B | N |
| ATOM | 6405 | C | ASN | H | 426 | −28.074 | −28.031 | −3.146 | 1.00 | 11.16 | B | C |
| ATOM | 6406 | O | ASN | H | 426 | −27.072 | −28.247 | −2.463 | 1.00 | 11.06 | B | O |
| ATOM | 6407 | N | LYS | H | 427 | −29.285 | −27.847 | −2.628 | 1.00 | 12.38 | B | N |
| ATOM | 6408 | CA | LYS | H | 427 | −29.569 | −27.993 | −1.203 | 1.00 | 13.52 | B | C |
| ATOM | 6409 | CB | LYS | H | 427 | −31.082 | −28.017 | −0.968 | 1.00 | 14.00 | B | C |
| ATOM | 6410 | CG | LYS | H | 427 | −31.681 | −26.675 | −0.585 | 1.00 | 16.18 | B | C |
| ATOM | 6411 | CD | LYS | H | 427 | −33.105 | −26.838 | −0.078 | 1.00 | 18.24 | B | C |
| ATOM | 6412 | CE | LYS | H | 427 | −33.487 | −25.714 | 0.870 | 1.00 | 19.72 | B | C |
| ATOM | 6413 | NZ | LYS | H | 427 | −32.873 | −25.888 | 2.216 | 1.00 | 21.43 | B | N |
| ATOM | 6414 | C | LYS | H | 427 | −28.943 | −29.256 | −0.621 | 1.00 | 13.71 | B | C |
| ATOM | 6415 | O | LYS | H | 427 | −28.329 | −29.220 | 0.446 | 1.00 | 13.63 | B | O |
| ATOM | 6416 | N | ASN | H | 428 | −29.233 | −30.390 | −1.252 | 1.00 | 14.28 | B | N |
| ATOM | 6417 | CA | ASN | H | 428 | −28.838 | −31.694 | −0.729 | 1.00 | 14.60 | B | C |
| ATOM | 6418 | CB | ASN | H | 428 | −29.715 | −32.800 | −1.324 | 1.00 | 14.57 | B | C |
| ATOM | 6419 | CG | ASN | H | 428 | −31.103 | −32.312 | −1.690 | 1.00 | 13.24 | B | C |
| ATOM | 6420 | OD1 | ASN | H | 428 | −31.832 | −31.790 | −0.846 | 1.00 | 9.74 | B | O |
| ATOM | 6421 | ND2 | ASN | H | 428 | −31.503 | −32.546 | −2.935 | 1.00 | 12.83 | B | N |
| ATOM | 6422 | C | ASN | H | 428 | −27.367 | −32.009 | −0.984 | 1.00 | 14.83 | B | C |
| ATOM | 6423 | O | ASN | H | 428 | −26.834 | −32.982 | −0.451 | 1.00 | 15.25 | B | O |
| ATOM | 6424 | N | ARG | H | 429 | −26.755 | −31.260 | −1.895 | 1.00 | 14.78 | B | N |
| ATOM | 6425 | CA | ARG | H | 429 | −25.364 | −31.488 | −2.275 | 1.00 | 14.74 | B | C |
| ATOM | 6426 | CB | ARG | H | 429 | −24.626 | −32.268 | −1.184 | 1.00 | 14.93 | B | C |
| ATOM | 6427 | CG | ARG | H | 429 | −24.252 | −31.435 | 0.031 | 1.00 | 16.26 | B | C |
| ATOM | 6428 | CD | ARG | H | 429 | −22.869 | −30.821 | −0.119 | 1.00 | 19.79 | B | C |
| ATOM | 6429 | NE | ARG | H | 429 | −22.634 | −29.760 | 0.857 | 1.00 | 22.68 | B | N |
| ATOM | 6430 | CZ | ARG | H | 429 | −22.532 | −29.958 | 2.167 | 1.00 | 23.54 | B | C |
| ATOM | 6431 | NH1 | ARG | H | 429 | −22.640 | −31.182 | 2.667 | 1.00 | 22.87 | B | N |
| ATOM | 6432 | NH2 | ARG | H | 429 | −22.321 | −28.932 | 2.980 | 1.00 | 23.53 | B | N |
| ATOM | 6433 | C | ARG | H | 429 | −25.252 | −32.217 | −3.611 | 1.00 | 14.35 | B | C |
| ATOM | 6434 | O | ARG | H | 429 | −24.175 | −32.285 | −4.203 | 1.00 | 14.62 | B | O |
| ATOM | 6435 | N | GLY | H | 430 | −26.373 | −32.752 | −4.085 | 1.00 | 13.67 | B | N |
| ATOM | 6436 | CA | GLY | H | 430 | −26.519 | −33.087 | −5.496 | 1.00 | 12.80 | B | C |
| ATOM | 6437 | C | GLY | H | 430 | −26.014 | −31.977 | −6.397 | 1.00 | 12.11 | B | C |
| ATOM | 6438 | O | GLY | H | 430 | −26.326 | −30.805 | −6.188 | 1.00 | 12.18 | B | O |
| ATOM | 6439 | N | ILE | H | 431 | −25.216 | −32.346 | −7.393 | 1.00 | 11.58 | B | N |
| ATOM | 6440 | CA | ILE | H | 431 | −24.551 | −31.372 | −8.251 | 1.00 | 10.76 | B | C |
| ATOM | 6441 | CB | ILE | H | 431 | −23.175 | −31.896 | −8.715 | 1.00 | 10.43 | B | C |
| ATOM | 6442 | CG1 | ILE | H | 431 | −22.220 | −32.024 | −7.527 | 1.00 | 10.95 | B | C |
| ATOM | 6443 | CD1 | ILE | H | 431 | −21.220 | −33.153 | −7.665 | 1.00 | 12.08 | B | C |
| ATOM | 6444 | CG2 | ILE | H | 431 | −22.592 | −30.993 | −9.791 | 1.00 | 10.07 | B | C |
| ATOM | 6445 | C | ILE | H | 431 | −25.406 | −31.085 | −9.484 | 1.00 | 10.68 | B | C |
| ATOM | 6446 | O | ILE | H | 431 | −25.703 | −31.994 | −10.258 | 1.00 | 10.40 | B | O |
| ATOM | 6447 | N | ILE | H | 432 | −25.852 | −29.840 | −9.636 | 1.00 | 10.90 | B | N |
| ATOM | 6448 | CA | ILE | H | 432 | −26.692 | −29.481 | −10.779 | 1.00 | 11.42 | B | C |
| ATOM | 6449 | CB | ILE | H | 432 | −27.709 | −28.375 | −10.448 | 1.00 | 11.63 | B | C |
| ATOM | 6450 | CG1 | ILE | H | 432 | −27.875 | −28.224 | −8.936 | 1.00 | 12.68 | B | C |
| ATOM | 6451 | CD1 | ILE | H | 432 | −28.514 | −26.915 | −8.524 | 1.00 | 13.89 | B | C |
| ATOM | 6452 | CG2 | ILE | H | 432 | −29.046 | −28.664 | −11.116 | 1.00 | 12.24 | B | C |
| ATOM | 6453 | C | ILE | H | 432 | −25.884 | −29.045 | −11.993 | 1.00 | 11.41 | B | C |
| ATOM | 6454 | O | ILE | H | 432 | −26.225 | −29.395 | −13.123 | 1.00 | 11.63 | B | O |
| ATOM | 6455 | N | LYS | H | 433 | −24.982 | −28.093 | −11.782 | 1.00 | 11.52 | B | N |
| ATOM | 6456 | CA | LYS | H | 433 | −24.226 | −27.523 | −12.888 | 1.00 | 11.96 | B | C |
| ATOM | 6457 | CB | LYS | H | 433 | −24.433 | −26.010 | −12.976 | 1.00 | 12.31 | B | C |
| ATOM | 6458 | CG | LYS | H | 433 | −23.850 | −25.387 | −14.237 | 1.00 | 14.42 | B | C |
| ATOM | 6459 | CD | LYS | H | 433 | −24.649 | −24.175 | −14.685 | 1.00 | 16.74 | B | C |
| ATOM | 6460 | CE | LYS | H | 433 | −24.112 | −23.613 | −15.993 | 1.00 | 17.08 | B | C |
| ATOM | 6461 | NZ | LYS | H | 433 | −24.993 | −23.949 | −17.146 | 1.00 | 17.30 | B | N |
| ATOM | 6462 | C | LYS | H | 433 | −22.743 | −27.850 | −12.793 | 1.00 | 11.65 | B | C |
| ATOM | 6463 | O | LYS | H | 433 | −22.248 | −28.250 | −11.740 | 1.00 | 11.48 | B | O |
| ATOM | 6464 | N | THR | H | 434 | −22.052 | −27.731 | −13.921 | 1.00 | 11.28 | B | N |
| ATOM | 6465 | CA | THR | H | 434 | −20.617 | −27.970 | −13.975 | 1.00 | 11.21 | B | C |
| ATOM | 6466 | CB | THR | H | 434 | −20.308 | −29.467 | −14.165 | 1.00 | 11.30 | B | C |
| ATOM | 6467 | OG1 | THR | H | 434 | −18.945 | −29.629 | −14.574 | 1.00 | 11.83 | B | O |
| ATOM | 6468 | CG2 | THR | H | 434 | −21.224 | −30.071 | −15.220 | 1.00 | 11.84 | B | C |
| ATOM | 6469 | C | THR | H | 434 | −20.009 | −27.185 | −15.131 | 1.00 | 10.94 | B | C |
| ATOM | 6470 | O | THR | H | 434 | −20.623 | −27.060 | −16.190 | 1.00 | 10.93 | B | O |
| ATOM | 6471 | N | PHE | H | 435 | −18.867 | −26.549 | −14.886 | 1.00 | 11.10 | B | N |
| ATOM | 6472 | CA | PHE | H | 435 | −18.610 | −25.235 | −15.464 | 1.00 | 11.96 | B | C |
| ATOM | 6473 | CB | PHE | H | 435 | −18.186 | −24.223 | −14.401 | 1.00 | 11.51 | B | C |
| ATOM | 6474 | CG | PHE | H | 435 | −19.344 | −23.561 | −13.710 | 1.00 | 11.19 | B | C |
| ATOM | 6475 | CD1 | PHE | H | 435 | −19.580 | −23.788 | −12.365 | 1.00 | 10.86 | B | C |

APPENDIX-continued (APPENDIX discloses SEQ ID NOS 29-32, 29-32 and 29-32, respectively, in order of appearance)

| | | | |
|---|---|---|---|
| ATOM | 6476 CE1 PHE H 435 | −20.692 −23.253 −11.741 1.00 10.24 | B C |
| ATOM | 6477 CZ PHE H 435 | −21.613 −22.532 −12.474 1.00 9.89 | B C |
| ATOM | 6478 CE2 PHE H 435 | −21.420 −22.347 −13.828 1.00 10.78 | B C |
| ATOM | 6479 CD2 PHE H 435 | −20.304 −22.884 −14.445 1.00 11.14 | B C |
| ATOM | 6480 C PHE H 435 | −17.694 −25.202 −16.684 1.00 13.00 | B C |
| ATOM | 6481 O PHE H 435 | −16.525 −25.587 −16.618 1.00 13.03 | B O |
| ATOM | 6482 N SER H 436 | −18.199 −24.569 −17.738 1.00 13.89 | B N |
| ATOM | 6483 CA SER H 436 | −17.549 −24.549 −19.039 1.00 14.67 | B C |
| ATOM | 6484 CB SER H 436 | −18.601 −24.438 −20.145 1.00 15.04 | B C |
| ATOM | 6485 OG SER H 436 | −18.532 −25.539 −21.033 1.00 16.58 | B O |
| ATOM | 6486 C SER H 436 | −16.586 −23.371 −19.134 1.00 14.75 | B C |
| ATOM | 6487 O SER H 436 | −16.849 −22.398 −19.841 1.00 14.75 | B O |
| ATOM | 6488 N ASN H 437 | −15.480 −23.451 −18.405 1.00 14.44 | B N |
| ATOM | 6489 CA ASN H 437 | −14.306 −22.659 −18.736 1.00 14.35 | B C |
| ATOM | 6490 CB ASN H 437 | −13.508 −23.354 −19.840 1.00 14.75 | B C |
| ATOM | 6491 CG ASN H 437 | −12.101 −22.822 −19.966 1.00 15.51 | B C |
| ATOM | 6492 OD1 ASN H 437 | −11.290 −22.960 −19.049 1.00 16.85 | B O |
| ATOM | 6493 ND2 ASN H 437 | −11.757 −22.358 −21.162 1.00 16.10 | B N |
| ATOM | 6494 C ASN H 437 | −14.692 −21.239 −19.161 1.00 13.69 | B C |
| ATOM | 6495 O ASN H 437 | −14.402 −20.814 −20.280 1.00 13.40 | B O |
| ATOM | 6496 N GLY H 438 | −15.374 −20.527 −18.267 1.00 13.39 | B N |
| ATOM | 6497 CA GLY H 438 | −15.942 −19.216 −18.573 1.00 12.92 | B C |
| ATOM | 6498 C GLY H 438 | −16.310 −18.455 −17.311 1.00 12.72 | B C |
| ATOM | 6499 O GLY H 438 | −15.574 −18.495 −16.324 1.00 12.83 | B O |
| ATOM | 6500 N CYS H 439 | −17.502 −17.863 −17.297 1.00 12.17 | B N |
| ATOM | 6501 CA CYS H 439 | −17.969 −17.110 −16.134 1.00 11.52 | B C |
| ATOM | 6502 CB CYS H 439 | −17.353 −15.712 −16.124 1.00 11.68 | B C |
| ATOM | 6503 SG CYS H 439 | −18.500 −14.404 −16.619 1.00 12.89 | B S |
| ATOM | 6504 C CYS H 439 | −19.492 −17.006 −16.079 1.00 10.95 | B C |
| ATOM | 6505 O CYS H 439 | −20.102 −16.298 −16.880 1.00 10.77 | B O |
| ATOM | 6506 N ASP H 440 | −20.089 −17.630 −15.066 1.00 10.41 | B N |
| ATOM | 6507 CA ASP H 440 | −21.541 −17.762 −14.987 1.00 10.06 | B C |
| ATOM | 6508 CB ASP H 440 | −21.953 −19.232 −15.091 1.00 10.85 | B C |
| ATOM | 6509 CG ASP H 440 | −22.561 −19.576 −16.438 1.00 13.11 | B C |
| ATOM | 6510 OD1 ASP H 440 | −23.750 −19.260 −16.654 1.00 14.97 | B O |
| ATOM | 6511 OD2 ASP H 440 | −21.872 −20.227 −17.251 1.00 15.27 | B O |
| ATOM | 6512 C ASP H 440 | −22.098 −17.161 −13.700 1.00 9.01 | B C |
| ATOM | 6513 O ASP H 440 | −21.345 −16.790 −12.798 1.00 9.09 | B O |
| ATOM | 6514 N TYR H 441 | −23.422 −17.184 −13.580 1.00 7.92 | B N |
| ATOM | 6515 CA TYR H 441 | −24.117 −16.707 −12.387 1.00 7.24 | B C |
| ATOM | 6516 CB TYR H 441 | −24.810 −15.371 −12.683 1.00 7.04 | B C |
| ATOM | 6517 CG TYR H 441 | −25.669 −14.849 −11.556 1.00 6.77 | B C |
| ATOM | 6518 CD1 TYR H 441 | −25.145 −13.986 −10.605 1.00 7.41 | B C |
| ATOM | 6519 CE1 TYR H 441 | −25.927 −13.498 −9.579 1.00 6.79 | B C |
| ATOM | 6520 CZ TYR H 441 | −27.270 −13.809 −9.539 1.00 6.49 | B C |
| ATOM | 6521 OH TYR H 441 | −28.049 −13.340 −8.507 1.00 5.09 | B O |
| ATOM | 6522 CE2 TYR H 441 | −27.823 −14.634 −10.494 1.00 7.52 | B C |
| ATOM | 6523 CD2 TYR H 441 | −27.029 −15.122 −11.512 1.00 7.12 | B C |
| ATOM | 6524 C TYR H 441 | −25.153 −17.748 −11.974 1.00 6.89 | B C |
| ATOM | 6525 O TYR H 441 | −25.720 −18.436 −12.823 1.00 7.12 | B O |
| ATOM | 6526 N VAL H 442 | −25.353 −17.906 −10.670 1.00 6.73 | B N |
| ATOM | 6527 CA VAL H 442 | −26.400 −18.784 −10.159 1.00 6.78 | B C |
| ATOM | 6528 CB VAL H 442 | −25.808 −20.089 −9.596 1.00 6.51 | B C |
| ATOM | 6529 CG1 VAL H 442 | −25.394 −21.017 −10.729 1.00 7.38 | B C |
| ATOM | 6530 CG2 VAL H 442 | −24.625 −19.786 −8.688 1.00 6.00 | B C |
| ATOM | 6531 C VAL H 442 | −27.167 −18.062 −9.059 1.00 7.13 | B C |
| ATOM | 6532 O VAL H 442 | −26.774 −16.973 −8.643 1.00 7.77 | B O |
| ATOM | 6533 N SER H 443 | −28.229 −18.679 −8.552 1.00 7.12 | B N |
| ATOM | 6534 CA SER H 443 | −29.017 −18.039 −7.504 1.00 7.64 | B C |
| ATOM | 6535 CB SER H 443 | −30.184 −17.252 −8.104 1.00 7.83 | B C |
| ATOM | 6536 OG SER H 443 | −31.411 −17.936 −7.922 1.00 7.99 | B O |
| ATOM | 6537 C SER H 443 | −29.508 −18.989 −6.415 1.00 8.16 | B C |
| ATOM | 6538 O SER H 443 | −29.421 −20.210 −6.552 1.00 8.69 | B O |
| ATOM | 6539 N ASN H 444 | −29.959 −18.412 −5.306 1.00 8.73 | B N |
| ATOM | 6540 CA ASN H 444 | −30.539 −19.184 −4.213 1.00 9.50 | B C |
| ATOM | 6541 CB ASN H 444 | −30.766 −18.297 −2.984 1.00 9.65 | B C |
| ATOM | 6542 CG ASN H 444 | −29.895 −17.053 −2.990 1.00 10.64 | B C |
| ATOM | 6543 OD1 ASN H 444 | −28.780 −17.060 −3.516 1.00 12.28 | B O |
| ATOM | 6544 ND2 ASN H 444 | −30.414 −15.966 −2.426 1.00 11.75 | B N |
| ATOM | 6545 C ASN H 444 | −31.843 −19.863 −4.618 1.00 10.24 | B C |
| ATOM | 6546 O ASN H 444 | −32.618 −19.317 −5.403 1.00 9.89 | B O |
| ATOM | 6547 N LYS H 445 | −32.146 −20.975 −3.955 1.00 11.63 | B N |
| ATOM | 6548 CA LYS H 445 | −32.826 −22.105 −4.588 1.00 13.07 | B C |
| ATOM | 6549 CB LYS H 445 | −34.344 −21.990 −4.421 1.00 13.70 | B C |
| ATOM | 6550 CG LYS H 445 | −35.131 −23.200 −4.915 1.00 15.80 | B C |
| ATOM | 6551 CD LYS H 445 | −34.354 −24.501 −4.753 1.00 18.31 | B C |
| ATOM | 6552 CE LYS H 445 | −33.508 −24.498 −3.490 1.00 19.03 | B C |

APPENDIX-continued (APPENDIX discloses SEQ ID NOS 29-32, 29-32 and 29-32, respectively, in order of appearance)

| | | | | |
|---|---|---|---|---|
| ATOM | 6553 NZ LYS H 445 | −34.316 −24.206 −2.274 1.00 20.02 | B N |
| ATOM | 6554 C LYS H 445 | −32.459 −22.265 −6.060 1.00 12.96 | B C |
| ATOM | 6555 O LYS H 445 | −32.290 −21.282 −6.780 1.00 13.24 | B O |
| ATOM | 6556 N GLY H 446 | −32.350 −23.513 −6.504 1.00 13.08 | B N |
| ATOM | 6557 CA GLY H 446 | −31.215 −23.936 −7.312 1.00 12.42 | B C |
| ATOM | 6558 C GLY H 446 | −29.988 −24.163 −6.453 1.00 11.83 | B C |
| ATOM | 6559 O GLY H 446 | −29.855 −25.209 −5.819 1.00 12.44 | B O |
| ATOM | 6560 N VAL H 447 | −29.191 −23.114 −6.285 1.00 10.63 | B N |
| ATOM | 6561 CA VAL H 447 | −27.809 −23.277 −5.857 1.00 10.01 | B C |
| ATOM | 6562 CB VAL H 447 | −26.839 −22.442 −6.711 1.00 9.97 | B C |
| ATOM | 6563 CG1 VAL H 447 | −25.405 −22.896 −6.479 1.00 10.51 | B C |
| ATOM | 6564 CG2 VAL H 447 | −27.204 −22.551 −8.183 1.00 10.50 | B C |
| ATOM | 6565 C VAL H 447 | −27.603 −22.962 −4.380 1.00 9.53 | B C |
| ATOM | 6566 O VAL H 447 | −28.099 −21.957 −3.868 1.00 9.61 | B O |
| ATOM | 6567 N ASP H 448 | −26.719 −23.735 −3.760 1.00 9.16 | B N |
| ATOM | 6568 CA ASP H 448 | −26.522 −23.714 −2.318 1.00 8.75 | B C |
| ATOM | 6569 CB ASP H 448 | −27.139 −24.971 −1.698 1.00 9.22 | B C |
| ATOM | 6570 CG ASP H 448 | −27.482 −24.795 −0.234 1.00 11.44 | B C |
| ATOM | 6571 OD1 ASP H 448 | −26.877 −23.921 0.421 1.00 13.83 | B O |
| ATOM | 6572 OD2 ASP H 448 | −28.319 −25.568 0.276 1.00 14.13 | B O |
| ATOM | 6573 C ASP H 448 | −25.020 −23.714 −2.076 1.00 8.18 | B C |
| ATOM | 6574 O ASP H 448 | −24.528 −23.151 −1.098 1.00 8.06 | B O |
| ATOM | 6575 N THR H 449 | −24.298 −24.280 −3.036 1.00 7.63 | B N |
| ATOM | 6576 CA THR H 449 | −22.858 −24.437 −2.940 1.00 6.80 | B C |
| ATOM | 6577 CB THR H 449 | −22.485 −25.824 −2.386 1.00 6.89 | B C |
| ATOM | 6578 OG1 THR H 449 | −22.377 −25.758 −0.959 1.00 6.16 | B O |
| ATOM | 6579 CG2 THR H 449 | −21.163 −26.296 −2.970 1.00 7.55 | B C |
| ATOM | 6580 C THR H 449 | −22.265 −24.297 −4.333 1.00 6.53 | B C |
| ATOM | 6581 O THR H 449 | −22.828 −24.792 −5.309 1.00 6.59 | B O |
| ATOM | 6582 N VAL H 450 | −21.145 −23.594 −4.428 1.00 6.07 | B N |
| ATOM | 6583 CA VAL H 450 | −20.209 −23.829 −5.512 1.00 6.02 | B C |
| ATOM | 6584 CB VAL H 450 | −20.064 −22.597 −6.420 1.00 5.61 | B C |
| ATOM | 6585 CG1 VAL H 450 | −21.429 −22.130 −6.904 1.00 5.32 | B C |
| ATOM | 6586 CG2 VAL H 450 | −19.339 −21.481 −5.687 1.00 5.55 | B C |
| ATOM | 6587 C VAL H 450 | −18.853 −24.210 −4.950 1.00 6.37 | B C |
| ATOM | 6588 O VAL H 450 | −18.503 −23.827 −3.833 1.00 6.54 | B O |
| ATOM | 6589 N SER H 451 | −18.176 −25.110 −5.649 1.00 6.41 | B N |
| ATOM | 6590 CA SER H 451 | −16.786 −25.397 −5.362 1.00 6.70 | B C |
| ATOM | 6591 CB SER H 451 | −16.602 −26.886 −5.069 1.00 7.13 | B C |
| ATOM | 6592 OG SER H 451 | −17.729 −27.629 −5.498 1.00 9.26 | B O |
| ATOM | 6593 C SER H 451 | −15.944 −24.990 −6.555 1.00 6.47 | B C |
| ATOM | 6594 O SER H 451 | −16.363 −25.147 −7.701 1.00 6.54 | B O |
| ATOM | 6595 N VAL H 452 | −14.861 −24.277 −6.276 1.00 6.56 | B N |
| ATOM | 6596 CA VAL H 452 | −13.801 −24.112 −7.251 1.00 6.31 | B C |
| ATOM | 6597 CB VAL H 452 | −13.469 −22.625 −7.471 1.00 5.74 | B C |
| ATOM | 6598 CG1 VAL H 452 | −12.757 −22.433 −8.801 1.00 5.06 | B C |
| ATOM | 6599 CG2 VAL H 452 | −14.740 −21.787 −7.420 1.00 5.56 | B C |
| ATOM | 6600 C VAL H 452 | −12.558 −24.861 −6.791 1.00 6.60 | B C |
| ATOM | 6601 O VAL H 452 | −12.130 −24.726 −5.644 1.00 7.04 | B O |
| ATOM | 6602 N GLY H 453 | −12.047 −25.732 −7.654 1.00 6.54 | B N |
| ATOM | 6603 CA GLY H 453 | −11.013 −26.672 −7.250 1.00 6.43 | B C |
| ATOM | 6604 C GLY H 453 | −11.329 −27.255 −5.889 1.00 6.09 | B C |
| ATOM | 6605 O GLY H 453 | −12.396 −27.836 −5.690 1.00 5.90 | B O |
| ATOM | 6606 N ASN H 454 | −10.479 −26.962 −4.913 1.00 6.02 | B N |
| ATOM | 6607 CA ASN H 454 | −10.646 −27.533 −3.585 1.00 6.39 | B C |
| ATOM | 6608 CB ASN H 454 | −9.330 −28.111 −3.073 1.00 6.81 | B C |
| ATOM | 6609 CG ASN H 454 | −9.190 −29.585 −3.382 1.00 8.99 | B C |
| ATOM | 6610 OD1 ASN H 454 | −9.587 −30.433 −2.584 1.00 11.67 | B O |
| ATOM | 6611 ND2 ASN H 454 | −8.782 −29.893 −4.609 1.00 10.25 | B N |
| ATOM | 6612 C ASN H 454 | −11.235 −26.563 −2.573 1.00 6.15 | B C |
| ATOM | 6613 O ASN H 454 | −11.623 −26.963 −1.475 1.00 6.47 | B O |
| ATOM | 6614 N THR H 455 | −11.406 −25.312 −2.985 1.00 5.40 | B N |
| ATOM | 6615 CA THR H 455 | −12.129 −24.347 −2.172 1.00 4.53 | B C |
| ATOM | 6616 CB THR H 455 | −11.775 −22.902 −2.551 1.00 4.70 | B C |
| ATOM | 6617 OG1 THR H 455 | −10.351 −22.746 −2.567 1.00 5.28 | B O |
| ATOM | 6618 CG2 THR H 455 | −12.374 −21.928 −1.542 1.00 5.57 | B C |
| ATOM | 6619 C THR H 455 | −13.632 −24.543 −2.293 1.00 4.01 | B C |
| ATOM | 6620 O THR H 455 | −14.139 −24.921 −3.349 1.00 3.78 | B O |
| ATOM | 6621 N LEU H 456 | −14.338 −24.306 −1.194 1.00 3.87 | B N |
| ATOM | 6622 CA LEU H 456 | −15.787 −24.419 −1.181 1.00 4.05 | B C |
| ATOM | 6623 CB LEU H 456 | −16.232 −25.520 −0.219 1.00 3.95 | B C |
| ATOM | 6624 CG LEU H 456 | −17.708 −25.915 −0.306 1.00 3.76 | B C |
| ATOM | 6625 CD1 LEU H 456 | −18.042 −26.440 −1.694 1.00 5.35 | B C |
| ATOM | 6626 CD2 LEU H 456 | −18.053 −26.944 0.758 1.00 4.10 | B C |
| ATOM | 6627 C LEU H 456 | −16.439 −23.097 −0.802 1.00 4.47 | B C |
| ATOM | 6628 O LEU H 456 | −16.186 −22.551 0.272 1.00 4.94 | B O |
| ATOM | 6629 N TYR H 457 | −17.343 −22.634 −1.657 1.00 4.59 | B N |

APPENDIX-continued (APPENDIX discloses SEQ ID NOS 29-32, 29-32 and 29-32, respectively, in order of appearance)

| | | | |
|---|---|---|---|
| ATOM | 6630 CA TYR H 457 | −18.102 −21.425 −1.386 1.00 4.60 | B C |
| ATOM | 6631 CB TYR H 457 | −17.996 −20.463 −2.570 1.00 4.71 | B C |
| ATOM | 6632 CG TYR H 457 | −16.594 −19.949 −2.820 1.00 5.62 | B C |
| ATOM | 6633 CD1 TYR H 457 | −15.657 −20.727 −3.485 1.00 7.09 | B C |
| ATOM | 6634 CE1 TYR H 457 | −14.388 −20.247 −3.748 1.00 8.22 | B C |
| ATOM | 6635 CZ TYR H 457 | −14.029 −18.994 −3.305 1.00 8.06 | B C |
| ATOM | 6636 OH TYR H 457 | −12.763 −18.520 −3.550 1.00 8.80 | B O |
| ATOM | 6637 CE2 TYR H 457 | −14.933 −18.212 −2.622 1.00 7.18 | B C |
| ATOM | 6638 CD2 TYR H 457 | −16.203 −18.694 −2.375 1.00 6.66 | B C |
| ATOM | 6639 C TYR H 457 | −19.565 −21.758 −1.099 1.00 4.46 | B C |
| ATOM | 6640 O TYR H 457 | −20.180 −22.551 −1.811 1.00 4.92 | B O |
| ATOM | 6641 N TYR H 458 | −20.098 −21.196 −0.017 1.00 3.90 | B N |
| ATOM | 6642 CA TYR H 458 | −21.496 −21.408 0.366 1.00 3.26 | B C |
| ATOM | 6643 CB TYR H 458 | −21.610 −21.544 1.885 1.00 3.16 | B C |
| ATOM | 6644 CG TYR H 458 | −20.863 −22.722 2.457 1.00 3.29 | B C |
| ATOM | 6645 CD1 TYR H 458 | −19.547 −22.597 2.881 1.00 3.93 | B C |
| ATOM | 6646 CE1 TYR H 458 | −18.866 −23.672 3.419 1.00 4.90 | B C |
| ATOM | 6647 CZ TYR H 458 | −19.501 −24.890 3.535 1.00 5.12 | B C |
| ATOM | 6648 OH TYR H 458 | −18.826 −25.967 4.062 1.00 5.42 | B O |
| ATOM | 6649 CE2 TYR H 458 | −20.810 −25.036 3.128 1.00 4.72 | B C |
| ATOM | 6650 CD2 TYR H 458 | −21.483 −23.955 2.598 1.00 3.89 | B C |
| ATOM | 6651 C TYR H 458 | −22.372 −20.242 −0.085 1.00 3.04 | B C |
| ATOM | 6652 O TYR H 458 | −22.185 −19.119 0.378 1.00 3.37 | B O |
| ATOM | 6653 N VAL H 459 | −23.453 −20.542 −0.800 1.00 2.71 | B N |
| ATOM | 6654 CA VAL H 459 | −24.073 −19.546 −1.678 1.00 2.61 | B C |
| ATOM | 6655 CB VAL H 459 | −24.381 −20.115 −3.067 1.00 2.22 | B C |
| ATOM | 6656 CG1 VAL H 459 | −25.021 −19.042 −3.938 1.00 2.62 | B C |
| ATOM | 6657 CG2 VAL H 459 | −23.123 −20.656 −3.716 1.00 2.61 | B C |
| ATOM | 6658 C VAL H 459 | −25.372 −18.924 −1.190 1.00 3.03 | B C |
| ATOM | 6659 O VAL H 459 | −25.418 −18.348 −0.103 1.00 3.21 | B O |
| ATOM | 6660 N ASN H 460 | −26.215 −18.648 −2.185 1.00106.93 | B N |
| ATOM | 6661 CA ASN H 460 | −27.625 −18.431 −1.941 1.00 95.54 | B C |
| ATOM | 6662 CB ASN H 460 | −27.810 −17.878 −0.542 1.00 20.00 | B C |
| ATOM | 6663 CG ASN H 460 | −28.967 −18.507 0.162 1.00 20.00 | B C |
| ATOM | 6664 OD1 ASN H 460 | −29.655 −19.349 −0.416 1.00 20.00 | B O |
| ATOM | 6665 ND2 ASN H 460 | −29.359 −17.912 1.280 1.00 20.00 | B N |
| ATOM | 6666 C ASN H 460 | −28.426 −17.612 −2.969 1.00 99.41 | B C |
| ATOM | 6667 O ASN H 460 | −29.222 −18.178 −3.718 1.00 108.91 | B O |
| ATOM | 6668 N LYS H 461 | −28.370 −16.283 −2.861 1.00 97.04 | B N |
| ATOM | 6669 CA LYS H 461 | −29.458 −15.387 −3.306 1.00105.93 | B C |
| ATOM | 6670 CB LYS H 461 | −29.011 −13.925 −3.219 1.00 20.00 | B C |
| ATOM | 6671 CG LYS H 461 | −28.633 −13.460 −1.820 1.00 20.00 | B C |
| ATOM | 6672 CD LYS H 461 | −27.794 −12.187 −1.865 1.00 20.00 | B C |
| ATOM | 6673 CE LYS H 461 | −27.646 −11.565 −0.482 1.00 20.00 | B C |
| ATOM | 6674 NZ LYS H 461 | −26.746 −10.375 −0.482 1.00 20.00 | B N |
| ATOM | 6675 C LYS H 461 | −30.025 −15.676 −4.708 1.00102.28 | B C |
| ATOM | 6676 O LYS H 461 | −29.779 −16.739 −5.276 1.00105.02 | B O |
| ATOM | 6677 N GLN H 462 | −30.766 −14.715 −5.266 1.00 96.68 | B N |
| ATOM | 6678 CA GLN H 462 | −31.286 −14.810 −6.641 1.00105.71 | B C |
| ATOM | 6679 CB GLN H 462 | −32.787 −15.128 −6.624 1.00 20.00 | B C |
| ATOM | 6680 CG GLN H 462 | −33.142 −16.522 −6.122 1.00 20.00 | B C |
| ATOM | 6681 CD GLN H 462 | −34.637 −16.794 −6.159 1.00 20.00 | B C |
| ATOM | 6682 OE1 GLN H 462 | −35.450 −15.870 −6.115 1.00 20.00 | B O |
| ATOM | 6683 NE2 GLN H 462 | −35.006 −18.068 −6.230 1.00 20.00 | B N |
| ATOM | 6684 C GLN H 462 | −31.052 −13.514 −7.429 1.00101.50 | B C |
| ATOM | 6685 O GLN H 462 | −31.398 −12.430 −6.960 1.00105.94 | B O |
| ATOM | 6686 N GLU H 463 | −30.565 −13.634 −8.663 1.00 98.92 | B N |
| ATOM | 6687 CA GLU H 463 | −30.241 −12.453 −9.465 1.00108.59 | B C |
| ATOM | 6688 CB GLU H 463 | −28.792 −12.505 −9.966 1.00 20.00 | B C |
| ATOM | 6689 CG GLU H 463 | −27.767 −11.973 −8.957 1.00 20.00 | B C |
| ATOM | 6690 CD GLU H 463 | −26.341 −11.973 −9.490 1.00 20.00 | B C |
| ATOM | 6691 OE1 GLU H 463 | −26.167 −11.917 −10.729 1.00 20.00 | B O |
| ATOM | 6692 OE2 GLU H 463 | −25.399 −11.890 −8.672 1.00 20.00 | B O |
| ATOM | 6693 C GLU H 463 | −31.208 −12.245 −10.629 1.00116.39 | B C |
| ATOM | 6694 O GLU H 463 | −31.442 −13.153 −11.426 1.00118.70 | B O |
| ATOM | 6695 N GLY H 464 | −31.759 −11.039 −10.722 1.00127.70 | B N |
| ATOM | 6696 CA GLY H 464 | −32.671 −10.693 −11.806 1.00143.17 | B C |
| ATOM | 6697 C GLY H 464 | −31.941 −10.347 −13.089 1.00149.77 | B C |
| ATOM | 6698 O GLY H 464 | −30.719 −10.197 −13.098 1.00155.06 | B O |
| ATOM | 6699 N LYS H 465 | −32.694 −10.223 −14.178 1.00153.73 | B N |
| ATOM | 6700 CA LYS H 465 | −32.115 −9.929 −15.484 1.00153.69 | B C |
| ATOM | 6701 CB LYS H 465 | −31.275 −8.651 −15.424 1.00 20.00 | B C |
| ATOM | 6702 CG LYS H 465 | −32.085 −7.385 −15.193 1.00 20.00 | B C |
| ATOM | 6703 CD LYS H 465 | −31.186 −6.163 −15.106 1.00 20.00 | B C |
| ATOM | 6704 CE LYS H 465 | −31.995 −4.898 −14.868 1.00 20.00 | B C |
| ATOM | 6705 NZ LYS H 465 | −31.127 −3.692 −14.776 1.00 20.00 | B N |
| ATOM | 6706 C LYS H 465 | −31.267 −11.091 −15.990 1.00155.37 | B C |

APPENDIX-continued (APPENDIX discloses SEQ ID NOS 29-32, 29-32 and 29-32, respectively, in order of appearance)

| | | | | |
|---|---|---|---|---|
| ATOM | 6707 O LYS H 465 | −31.276 −11.407 −17.180 1.00155.20 | B O |
| ATOM | 6708 N GLU H 472 | −30.692 −9.899 −23.132 1.00145.47 | B N |
| ATOM | 6709 CA GLU H 472 | −30.214 −9.535 −24.461 1.00151.12 | B C |
| ATOM | 6710 CB GLU H 472 | −30.931 −8.281 −24.964 1.00 20.00 | B C |
| ATOM | 6711 CG GLU H 472 | −32.419 −8.472 −25.209 1.00 20.00 | B C |
| ATOM | 6712 CD GLU H 472 | −33.106 −7.192 −25.643 1.00 20.00 | B C |
| ATOM | 6713 OE1 GLU H 472 | −32.477 −6.117 −25.554 1.00 20.00 | B O |
| ATOM | 6714 OE2 GLU H 472 | −34.279 −7.260 −26.070 1.00 20.00 | B O |
| ATOM | 6715 C GLU H 472 | −28.705 −9.310 −24.462 1.00153.35 | B C |
| ATOM | 6716 O GLU H 472 | −28.208 −8.395 −23.805 1.00159.41 | B O |
| ATOM | 6717 N PRO H 473 | −27.971 −10.164 −25.188 1.00150.51 | B N |
| ATOM | 6718 CA PRO H 473 | −26.535 −10.028 −25.339 1.00141.97 | B C |
| ATOM | 6719 CB PRO H 473 | −26.035 −11.435 −25.011 1.00 20.00 | B C |
| ATOM | 6720 CG PRO H 473 | −27.175 −12.350 −25.428 1.00 20.00 | B C |
| ATOM | 6721 CD PRO H 473 | −28.424 −11.506 −25.583 1.00 20.00 | B C |
| ATOM | 6722 C PRO H 473 | −26.193 −9.688 −26.782 1.00 135.14 | B C |
| ATOM | 6723 O PRO H 473 | −26.968 −9.997 −27.687 1.00 144.93 | B O |
| ATOM | 6724 N ILE H 474 | −25.024 −9.096 −27.001 1.00 118.07 | B N |
| ATOM | 6725 CA ILE H 474 | −24.617 −8.700 −28.344 1.00 105.14 | B C |
| ATOM | 6726 CB ILE H 474 | −25.549 −7.614 −28.919 1.00 20.00 | B C |
| ATOM | 6727 CG1 ILE H 474 | −26.957 −8.174 −29.133 1.00 20.00 | B C |
| ATOM | 6728 CD1 ILE H 474 | −28.021 −7.109 −29.293 1.00 20.00 | B C |
| ATOM | 6729 CG2 ILE H 474 | −24.988 −7.064 −30.222 1.00 20.00 | B C |
| ATOM | 6730 C ILE H 474 | −23.184 −8.180 −28.352 1.00 104.75 | B C |
| ATOM | 6731 O ILE H 474 | −22.938 −7.013 −28.046 1.00 111.83 | B O |
| ATOM | 6732 N ILE H 475 | −22.242 −9.045 −28.716 1.00 94.65 | B N |
| ATOM | 6733 CA ILE H 475 | −20.826 −8.732 −28.565 1.00 79.88 | B C |
| ATOM | 6734 CB ILE H 475 | −20.175 −9.577 −27.453 1.00 20.00 | B C |
| ATOM | 6735 CG1 ILE H 475 | −20.674 −9.120 −26.079 1.00 20.00 | B C |
| ATOM | 6736 CD1 ILE H 475 | −20.434 −10.125 −24.972 1.00 20.00 | B C |
| ATOM | 6737 CG2 ILE H 475 | −18.658 −9.507 −27.545 1.00 20.00 | B C |
| ATOM | 6738 C ILE H 475 | −20.051 −8.909 −29.868 1.00 79.52 | B C |
| ATOM | 6739 O ILE H 475 | −19.808 −10.032 −30.310 1.00 82.70 | B O |
| ATOM | 6740 N ASN H 476 | −19.589 −7.793 −30.425 1.00 69.64 | B N |
| ATOM | 6741 CA ASN H 476 | −18.756 −7.812 −31.623 1.00 68.88 | B C |
| ATOM | 6742 CB ASN H 476 | −18.880 −6.487 −32.381 1.00 20.00 | B C |
| ATOM | 6743 CG ASN H 476 | −20.247 −6.299 −33.011 1.00 20.00 | B C |
| ATOM | 6744 OD1 ASN H 476 | −20.954 −7.268 −33.288 1.00 20.00 | B O |
| ATOM | 6745 ND2 ASN H 476 | −20.618 −5.048 −33.257 1.00 20.00 | B N |
| ATOM | 6746 C ASN H 476 | −17.290 −8.097 −31.306 1.00 67.13 | B C |
| ATOM | 6747 O ASN H 476 | −16.718 −7.507 −30.389 1.00 73.10 | B O |
| ATOM | 6748 N PHE H 477 | −16.677 −8.975 −32.096 1.00 64.95 | B N |
| ATOM | 6749 CA PHE H 477 | −15.288 −9.380 −31.879 1.00 68.13 | B C |
| ATOM | 6750 CB PHE H 477 | −14.918 −10.567 −32.776 1.00 20.00 | B C |
| ATOM | 6751 CG PHE H 477 | −15.678 −11.822 −32.466 1.00 20.00 | B C |
| ATOM | 6752 CD1 PHE H 477 | −15.266 −12.666 −31.448 1.00 20.00 | B C |
| ATOM | 6753 CE1 PHE H 477 | −15.965 −13.820 −31.162 1.00 20.00 | B C |
| ATOM | 6754 CZ PHE H 477 | −17.069 −14.158 −31.915 1.00 20.00 | B C |
| ATOM | 6755 CE2 PHE H 477 | −17.473 −13.339 −32.949 1.00 20.00 | B C |
| ATOM | 6756 CD2 PHE H 477 | −16.778 −12.181 −33.222 1.00 20.00 | B C |
| ATOM | 6757 C PHE H 477 | −14.307 −8.232 −32.117 1.00 65.57 | B C |
| ATOM | 6758 O PHE H 477 | −13.094 −8.412 −31.999 1.00 49.83 | B O |
| ATOM | 6759 N TYR H 478 | −14.816 −7.113 −32.617 1.00 51.97 | B N |
| ATOM | 6760 CA TYR H 478 | −13.996 −5.920 −32.779 1.00 52.01 | B C |
| ATOM | 6761 CB TYR H 478 | −14.573 −5.017 −33.870 1.00 20.00 | B C |
| ATOM | 6762 CG TYR H 478 | −14.579 −5.653 −35.247 1.00 20.00 | B C |
| ATOM | 6763 CD1 TYR H 478 | −13.458 −5.593 −36.069 1.00 20.00 | B C |
| ATOM | 6764 CE1 TYR H 478 | −13.453 −6.195 −37.316 1.00 20.00 | B C |
| ATOM | 6765 CZ TYR H 478 | −14.585 −6.849 −37.766 1.00 20.00 | B C |
| ATOM | 6766 OH TYR H 478 | −14.597 −7.434 −39.013 1.00 20.00 | B O |
| ATOM | 6767 CE2 TYR H 478 | −15.689 −6.967 −36.948 1.00 20.00 | B C |
| ATOM | 6768 CD2 TYR H 478 | −15.687 −6.360 −35.703 1.00 20.00 | B C |
| ATOM | 6769 C TYR H 478 | −13.909 −5.178 −31.454 1.00 66.63 | B C |
| ATOM | 6770 O TYR H 478 | −13.401 −4.059 −31.383 1.00 63.45 | B O |
| ATOM | 6771 N ASP H 479 | −14.391 −5.828 −30.401 1.00 65.34 | B N |
| ATOM | 6772 CA ASP H 479 | −14.256 −5.311 −29.049 1.00 65.32 | B C |
| ATOM | 6773 CB ASP H 479 | −15.579 −5.450 −28.296 1.00 20.00 | B C |
| ATOM | 6774 CG ASP H 479 | −16.664 −4.552 −28.856 1.00 20.00 | B C |
| ATOM | 6775 OD1 ASP H 479 | −16.327 −3.593 −29.582 1.00 20.00 | B O |
| ATOM | 6776 OD2 ASP H 479 | −17.854 −4.799 −28.568 1.00 20.00 | B O |
| ATOM | 6777 C ASP H 479 | −13.144 −6.036 −28.300 1.00 64.83 | B C |
| ATOM | 6778 O ASP H 479 | −12.738 −5.609 −27.220 1.00 60.42 | B O |
| ATOM | 6779 N PRO H 480 | −12.610 −7.108 −28.903 1.00 47.60 | B N |
| ATOM | 6780 CA PRO H 480 | −11.568 −7.902 −28.282 1.00 46.52 | B C |
| ATOM | 6781 CB PRO H 480 | −11.905 −9.318 −28.742 1.00 20.00 | B C |
| ATOM | 6782 CG PRO H 480 | −12.596 −9.131 −30.072 1.00 20.00 | B C |
| ATOM | 6783 CD PRO H 480 | −13.021 −7.682 −30.193 1.00 20.00 | B C |

APPENDIX-continued (APPENDIX discloses SEQ ID NOS 29-32, 29-32 and 29-32, respectively, in order of appearance)

| | | | |
|---|---|---|---|
| ATOM | 6784 C PRO H 480 | −10.199 −7.497 −28.809 1.00 52.36 | B C |
| ATOM | 6785 O PRO H 480 | −9.736 −8.035 −29.815 1.00 64.15 | B O |
| ATOM | 6786 N LEU H 481 | −9.618 −6.472 −28.197 1.00 62.90 | B N |
| ATOM | 6787 CA LEU H 481 | −8.285 −6.015 −28.562 1.00 54.24 | B C |
| ATOM | 6788 CB LEU H 481 | −8.322 −4.544 −28.982 1.00 20.00 | B C |
| ATOM | 6789 CG LEU H 481 | −9.202 −4.212 −30.186 1.00 20.00 | B C |
| ATOM | 6790 CD1 LEU H 481 | −9.255 −2.706 −30.408 1.00 20.00 | B C |
| ATOM | 6791 CD2 LEU H 481 | −8.698 −4.931 −31.425 1.00 20.00 | B C |
| ATOM | 6792 C LEU H 481 | −7.315 −6.203 −27.402 1.00 59.81 | B C |
| ATOM | 6793 O LEU H 481 | −7.682 −6.724 −26.348 1.00 64.98 | B O |
| ATOM | 6794 N VAL H 482 | −6.058 −5.840 −27.628 1.00 59.66 | B N |
| ATOM | 6795 CA VAL H 482 | −5.084 −5.781 −26.549 1.00 49.67 | B C |
| ATOM | 6796 CB VAL H 482 | −3.786 −6.531 −26.911 1.00 20.00 | B C |
| ATOM | 6797 CG1 VAL H 482 | −2.811 −6.492 −25.742 1.00 20.00 | B C |
| ATOM | 6798 CG2 VAL H 482 | −4.097 −7.973 −27.288 1.00 20.00 | B C |
| ATOM | 6799 C VAL H 482 | −4.762 −4.337 −26.191 1.00 53.03 | B C |
| ATOM | 6800 O VAL H 482 | −4.706 −3.472 −27.064 1.00 46.27 | B O |
| ATOM | 6801 N PHE H 483 | −4.641 −4.070 −24.894 1.00 61.61 | B N |
| ATOM | 6802 CA PHE H 483 | −4.311 −2.732 −24.415 1.00 65.03 | B C |
| ATOM | 6803 CB PHE H 483 | −5.338 −2.259 −23.391 1.00 20.00 | B C |
| ATOM | 6804 CG PHE H 483 | −6.714 −2.064 −23.966 1.00 20.00 | B C |
| ATOM | 6805 CD1 PHE H 483 | −7.021 −0.928 −24.695 1.00 20.00 | B C |
| ATOM | 6806 CE1 PHE H 483 | −8.294 −0.739 −25.209 1.00 20.00 | B C |
| ATOM | 6807 CZ PHE H 483 | −9.246 −1.731 −25.077 1.00 20.00 | B C |
| ATOM | 6808 CE2 PHE H 483 | −8.937 −2.888 −24.397 1.00 20.00 | B C |
| ATOM | 6809 CD2 PHE H 483 | −7.667 −3.065 −23.872 1.00 20.00 | B C |
| ATOM | 6810 C PHE H 483 | −2.897 −2.662 −23.852 1.00 71.00 | B C |
| ATOM | 6811 O PHE H 483 | −2.704 −2.417 −22.659 1.00100.44 | B O |
| ATOM | 6812 N PRO H 484 | −1.909 −2.972 −24.705 1.00 54.44 | B N |
| ATOM | 6813 CA PRO H 484 | −0.512 −3.000 −24.329 1.00 47.46 | B C |
| ATOM | 6814 CB PRO H 484 | −0.179 −4.492 −24.438 1.00 20.00 | B C |
| ATOM | 6815 CG PRO H 484 | −1.142 −5.021 −25.513 1.00 20.00 | B C |
| ATOM | 6816 CD PRO H 484 | −2.157 −3.926 −25.796 1.00 20.00 | B C |
| ATOM | 6817 C PRO H 484 | 0.323 −2.225 −25.346 1.00 41.56 | B C |
| ATOM | 6818 O PRO H 484 | 0.278 −2.527 −26.539 1.00 46.53 | B O |
| ATOM | 6819 N SER H 485 | 1.033 −1.202 −24.883 1.00 46.30 | B N |
| ATOM | 6820 CA SER H 485 | 1.824 −0.355 −25.768 1.00 49.30 | B C |
| ATOM | 6821 CB SER H 485 | 3.010 0.252 −25.015 1.00 20.00 | B C |
| ATOM | 6822 OG SER H 485 | 3.864 −0.754 −24.502 1.00 20.00 | B O |
| ATOM | 6823 C SER H 485 | 2.307 −1.112 −27.003 1.00 41.24 | B C |
| ATOM | 6824 O SER H 485 | 1.964 −0.755 −28.131 1.00 46.93 | B O |
| ATOM | 6825 N ASP H 486 | 3.108 −2.150 −26.785 1.00 49.48 | B N |
| ATOM | 6826 CA ASP H 486 | 3.700 −2.909 −27.881 1.00 37.44 | B C |
| ATOM | 6827 CB ASP H 486 | 4.552 −4.054 −27.333 1.00 20.00 | B C |
| ATOM | 6828 CG ASP H 486 | 5.885 −3.576 −26.790 1.00 20.00 | B C |
| ATOM | 6829 OD1 ASP H 486 | 6.284 −2.437 −27.115 1.00 20.00 | B O |
| ATOM | 6830 OD2 ASP H 486 | 6.556 −4.355 −26.080 1.00 20.00 | B O |
| ATOM | 6831 C ASP H 486 | 2.628 −3.456 −28.818 1.00 45.66 | B C |
| ATOM | 6832 O ASP H 486 | 2.683 −3.252 −30.034 1.00 39.86 | B O |
| ATOM | 6833 N GLU H 487 | 1.627 −4.107 −28.238 1.00 49.20 | B N |
| ATOM | 6834 CA GLU H 487 | 0.525 −4.652 −29.013 1.00 45.70 | B C |
| ATOM | 6835 CB GLU H 487 | −0.444 −5.410 −28.105 1.00 20.00 | B C |
| ATOM | 6836 CG GLU H 487 | 0.156 −6.664 −27.483 1.00 20.00 | B C |
| ATOM | 6837 CD GLU H 487 | −0.814 −7.393 −26.576 1.00 20.00 | B C |
| ATOM | 6838 OE1 GLU H 487 | −1.852 −6.804 −26.214 1.00 20.00 | B O |
| ATOM | 6839 OE2 GLU H 487 | −0.514 −8.540 −26.183 1.00 20.00 | B O |
| ATOM | 6840 C GLU H 487 | −0.203 −3.556 −29.783 1.00 41.48 | B C |
| ATOM | 6841 O GLU H 487 | −0.411 −3.674 −30.989 1.00 48.92 | B O |
| ATOM | 6842 N PHE H 488 | −0.486 −2.447 −29.110 1.00 42.16 | B N |
| ATOM | 6843 CA PHE H 488 | −1.183 −1.339 −29.747 1.00 39.33 | B C |
| ATOM | 6844 CB PHE H 488 | −1.438 −0.219 −28.745 1.00 20.00 | B C |
| ATOM | 6845 CG PHE H 488 | −2.369 −0.602 −27.638 1.00 20.00 | B C |
| ATOM | 6846 CD1 PHE H 488 | −3.739 −0.595 −27.833 1.00 20.00 | B C |
| ATOM | 6847 CE1 PHE H 488 | −4.602 −0.873 −26.789 1.00 20.00 | B C |
| ATOM | 6848 CZ PHE H 488 | −4.095 −1.193 −25.546 1.00 20.00 | B C |
| ATOM | 6849 CE2 PHE H 488 | −2.731 −1.192 −25.340 1.00 20.00 | B C |
| ATOM | 6850 CD2 PHE H 488 | −1.876 −0.912 −26.385 1.00 20.00 | B C |
| ATOM | 6851 C PHE H 488 | −0.401 −0.804 −30.939 1.00 43.06 | B C |
| ATOM | 6852 O PHE H 488 | −0.977 −0.505 −31.984 1.00 61.71 | B O |
| ATOM | 6853 N ASP H 489 | 0.915 −0.700 −30.782 1.00 41.95 | B N |
| ATOM | 6854 CA ASP H 489 | 1.766 −0.104 −31.808 1.00 42.75 | B C |
| ATOM | 6855 CB ASP H 489 | 3.172 0.134 −31.262 1.00 20.00 | B C |
| ATOM | 6856 CG ASP H 489 | 3.235 1.317 −30.327 1.00 20.00 | B C |
| ATOM | 6857 OD1 ASP H 489 | 2.256 2.089 −30.288 1.00 20.00 | B O |
| ATOM | 6858 OD2 ASP H 489 | 4.252 1.462 −29.617 1.00 20.00 | B O |
| ATOM | 6859 C ASP H 489 | 1.837 −0.980 −33.054 1.00 45.61 | B C |
| ATOM | 6860 O ASP H 489 | 2.110 −0.495 −34.154 1.00 54.39 | B O |

APPENDIX-continued (APPENDIX discloses SEQ ID NOS 29-32, 29-32 and 29-32, respectively, in order of appearance)

| | | | |
|---|---|---|---|
| ATOM | 6861 N ALA H 490 | 1.702 −2.287 −32.853 1.00 42.89 | B N |
| ATOM | 6862 CA ALA H 490 | 1.705 −3.238 −33.957 1.00 38.40 | B C |
| ATOM | 6863 CB ALA H 490 | 1.928 −4.653 −33.436 1.00 20.00 | B C |
| ATOM | 6864 C ALA H 490 | 0.413 −3.160 −34.770 1.00 39.67 | B C |
| ATOM | 6865 O ALA H 490 | 0.443 −3.194 −35.998 1.00 56.80 | B O |
| ATOM | 6866 N SER H 491 | −0.717 −3.050 −34.080 1.00 40.38 | B N |
| ATOM | 6867 CA SER H 491 | −2.003 −2.833 −34.737 1.00 41.77 | B C |
| ATOM | 6868 CB SER H 491 | −3.155 −2.963 −33.731 1.00 20.00 | B C |
| ATOM | 6869 OG SER H 491 | −3.173 −1.878 −32.817 1.00 20.00 | B O |
| ATOM | 6870 C SER H 491 | −2.056 −1.474 −35.432 1.00 39.01 | B C |
| ATOM | 6871 O SER H 491 | −2.701 −1.325 −36.472 1.00 36.91 | B O |
| ATOM | 6872 N ILE H 492 | −1.440 −0.470 −34.812 1.00 38.11 | B N |
| ATOM | 6873 CA ILE H 492 | −1.342 0.863 −35.402 1.00 41.21 | B C |
| ATOM | 6874 CB ILE H 492 | −0.651 1.856 −34.446 1.00 20.00 | B C |
| ATOM | 6875 CG1 ILE H 492 | −1.506 2.097 −33.203 1.00 20.00 | B C |
| ATOM | 6876 CD1 ILE H 492 | −0.883 3.081 −32.232 1.00 20.00 | B C |
| ATOM | 6877 CG2 ILE H 492 | −0.363 3.173 −35.150 1.00 20.00 | B C |
| ATOM | 6878 C ILE H 492 | −0.561 0.826 −36.714 1.00 39.22 | B C |
| ATOM | 6879 O ILE H 492 | −0.943 1.466 −37.696 1.00 47.54 | B O |
| ATOM | 6880 N SER H 493 | 0.535 0.073 −36.718 1.00 41.64 | B N |
| ATOM | 6881 CA SER H 493 | 1.307 −0.161 −37.933 1.00 35.15 | B C |
| ATOM | 6882 CB SER H 493 | 2.587 −0.944 −37.618 1.00 20.00 | B C |
| ATOM | 6883 OG SER H 493 | 2.296 −2.250 −37.147 1.00 20.00 | B O |
| ATOM | 6884 C SER H 493 | 0.486 −0.880 −39.011 1.00 47.90 | B C |
| ATOM | 6885 O SER H 493 | 0.565 −0.538 −40.191 1.00 50.94 | B O |
| ATOM | 6886 N GLN H 494 | −0.321 −1.855 −38.596 1.00 42.51 | B N |
| ATOM | 6887 CA GLN H 494 | −1.175 −2.611 −39.517 1.00 41.96 | B C |
| ATOM | 6888 CB GLN H 494 | −1.822 −3.801 −38.795 1.00 20.00 | B C |
| ATOM | 6889 CG GLN H 494 | −0.843 −4.905 −38.423 1.00 20.00 | B C |
| ATOM | 6890 CD GLN H 494 | −1.489 −6.019 −37.630 1.00 20.00 | B C |
| ATOM | 6891 OE1 GLN H 494 | −2.536 −5.830 −37.011 1.00 20.00 | B O |
| ATOM | 6892 NE2 GLN H 494 | −0.893 −7.205 −37.684 1.00 20.00 | B N |
| ATOM | 6893 C GLN H 494 | −2.254 −1.721 −40.130 1.00 33.86 | B C |
| ATOM | 6894 O GLN H 494 | −2.479 −1.743 −41.340 1.00 54.89 | B O |
| ATOM | 6895 N VAL H 495 | −2.973 −1.005 −39.272 1.00 34.99 | B N |
| ATOM | 6896 CA VAL H 495 | −3.955 −0.025 −39.718 1.00 38.42 | B C |
| ATOM | 6897 CB VAL H 495 | −4.485 0.807 −38.536 1.00 20.00 | B C |
| ATOM | 6898 CG1 VAL H 495 | −5.501 1.828 −39.016 1.00 20.00 | B C |
| ATOM | 6899 CG2 VAL H 495 | −5.088 −0.101 −37.479 1.00 20.00 | B C |
| ATOM | 6900 C VAL H 495 | −3.344 0.912 −40.751 1.00 42.74 | B C |
| ATOM | 6901 O VAL H 495 | −3.876 1.069 −41.850 1.00 44.00 | B O |
| ATOM | 6902 N ASN H 496 | −2.171 1.447 −40.434 1.00 42.45 | B N |
| ATOM | 6903 CA ASN H 496 | −1.500 2.382 −41.323 1.00 43.01 | B C |
| ATOM | 6904 CB ASN H 496 | −0.202 2.880 −40.692 1.00 20.00 | B C |
| ATOM | 6905 CG ASN H 496 | −0.446 3.770 −39.497 1.00 20.00 | B C |
| ATOM | 6906 OD1 ASN H 496 | −1.517 4.360 −39.358 1.00 20.00 | B O |
| ATOM | 6907 ND2 ASN H 496 | 0.537 3.849 −38.608 1.00 20.00 | B N |
| ATOM | 6908 C ASN H 496 | −1.227 1.780 −42.695 1.00 43.13 | B C |
| ATOM | 6909 O ASN H 496 | −1.502 2.404 −43.720 1.00 54.76 | B O |
| ATOM | 6910 N GLU H 497 | −0.737 0.544 −42.708 1.00 42.08 | B N |
| ATOM | 6911 CA GLU H 497 | −0.453 −0.150 −43.957 1.00 43.13 | B C |
| ATOM | 6912 CB GLU H 497 | 0.151 −1.525 −43.678 1.00 20.00 | B C |
| ATOM | 6913 CG GLU H 497 | 1.651 −1.515 −43.476 1.00 20.00 | B C |
| ATOM | 6914 CD GLU H 497 | 2.193 −2.884 −43.108 1.00 20.00 | B C |
| ATOM | 6915 OE1 GLU H 497 | 1.402 −3.851 −43.058 1.00 20.00 | B O |
| ATOM | 6916 OE2 GLU H 497 | 3.419 −3.001 −42.899 1.00 20.00 | B O |
| ATOM | 6917 C GLU H 497 | −1.724 −0.306 −44.781 1.00 49.77 | B C |
| ATOM | 6918 O GLU H 497 | −1.680 −0.352 −46.011 1.00 42.88 | B O |
| ATOM | 6919 N LYS H 498 | −2.846 −0.477 −44.088 1.00 41.82 | B N |
| ATOM | 6920 CA LYS H 498 | −4.141 −0.621 −44.741 1.00 53.60 | B C |
| ATOM | 6921 CB LYS H 498 | −5.174 −1.179 −43.761 1.00 20.00 | B C |
| ATOM | 6922 CG LYS H 498 | −4.967 −2.641 −43.403 1.00 20.00 | B C |
| ATOM | 6923 CD LYS H 498 | −6.078 −3.148 −42.491 1.00 20.00 | B C |
| ATOM | 6924 CE LYS H 498 | −5.896 −4.624 −42.160 1.00 20.00 | B C |
| ATOM | 6925 NZ LYS H 498 | −6.862 −5.090 −41.127 1.00 20.00 | B N |
| ATOM | 6926 C LYS H 498 | −4.622 0.716 −45.298 1.00 55.29 | B C |
| ATOM | 6927 O LYS H 498 | −5.273 0.766 −46.340 1.00 61.06 | B O |
| ATOM | 6928 N ILE H 499 | −4.359 1.789 −44.558 1.00 52.22 | B N |
| ATOM | 6929 CA ILE H 499 | −4.606 3.140 −45.052 1.00 48.26 | B C |
| ATOM | 6930 CB ILE H 499 | −4.213 4.205 −44.012 1.00 20.00 | B C |
| ATOM | 6931 CG1 ILE H 499 | −5.137 4.139 −42.797 1.00 20.00 | B C |
| ATOM | 6932 CD1 ILE H 499 | −4.719 5.058 −41.669 1.00 20.00 | B C |
| ATOM | 6933 CG2 ILE H 499 | −4.246 5.594 −44.631 1.00 20.00 | B C |
| ATOM | 6934 C ILE H 499 | −3.809 3.400 −46.323 1.00 49.07 | B C |
| ATOM | 6935 O ILE H 499 | −4.273 4.090 −47.232 1.00 58.45 | B O |
| ATOM | 6936 N ASN H 500 | −2.600 2.849 −46.371 1.00 51.02 | B N |
| ATOM | 6937 CA ASN H 500 | −1.718 3.000 −47.524 1.00 52.06 | B C |

APPENDIX-continued (APPENDIX discloses SEQ ID NOS 29-32, 29-32 and 29-32, respectively, in order of appearance)

| | | | |
|---|---|---|---|
| ATOM | 6938 CB ASN H 500 | −0.284 2.663 −47.120 1.00 20.00 | B C |
| ATOM | 6939 CG ASN H 500 | 0.707 2.898 −48.233 1.00 20.00 | B C |
| ATOM | 6940 OD1 ASN H 500 | 0.607 3.875 −48.973 1.00 20.00 | B O |
| ATOM | 6941 ND2 ASN H 500 | 1.740 2.071 −48.275 1.00 20.00 | B N |
| ATOM | 6942 C ASN H 500 | −2.151 2.149 −48.719 1.00 48.31 | B C |
| ATOM | 6943 O ASN H 500 | −1.841 2.469 −49.867 1.00 56.89 | B O |
| ATOM | 6944 N GLN H 501 | −2.872 1.067 −48.438 1.00 55.87 | B N |
| ATOM | 6945 CA GLN H 501 | −3.511 0.269 −49.480 1.00 53.55 | B C |
| ATOM | 6946 CB GLN H 501 | −3.879 −1.116 −48.940 1.00 20.00 | B C |
| ATOM | 6947 CG GLN H 501 | −2.685 −1.963 −48.513 1.00 20.00 | B C |
| ATOM | 6948 CD GLN H 501 | −3.093 −3.333 −47.996 1.00 20.00 | B C |
| ATOM | 6949 OE1 GLN H 501 | −4.169 −3.495 −47.420 1.00 20.00 | B O |
| ATOM | 6950 NE2 GLN H 501 | −2.215 −4.317 −48.162 1.00 20.00 | B N |
| ATOM | 6951 C GLN H 501 | −4.755 0.964 −50.023 1.00 45.67 | B C |
| ATOM | 6952 O GLN H 501 | −4.984 0.994 −51.232 1.00 58.31 | B O |
| ATOM | 6953 N SER H 502 | −5.525 1.570 −49.124 1.00 43.44 | B N |
| ATOM | 6954 CA SER H 502 | −6.702 2.345 −49.508 1.00 45.40 | B C |
| ATOM | 6955 CB SER H 502 | −7.471 2.800 −48.264 1.00 20.00 | B C |
| ATOM | 6956 OG SER H 502 | −6.684 3.664 −47.464 1.00 20.00 | B O |
| ATOM | 6957 C SER H 502 | −6.319 3.555 −50.358 1.00 55.15 | B C |
| ATOM | 6958 O SER H 502 | −7.049 3.943 −51.270 1.00 52.57 | B O |
| ATOM | 6959 N LEU H 503 | −5.160 4.135 −50.060 1.00 55.35 | B N |
| ATOM | 6960 CA LEU H 503 | −4.662 5.286 −50.805 1.00 52.12 | B C |
| ATOM | 6961 CB LEU H 503 | −3.529 5.973 −50.037 1.00 20.00 | B C |
| ATOM | 6962 CG LEU H 503 | −3.896 6.598 −48.688 1.00 20.00 | B C |
| ATOM | 6963 CD1 LEU H 503 | −2.646 7.032 −47.948 1.00 20.00 | B C |
| ATOM | 6964 CD2 LEU H 503 | −4.847 7.769 −48.868 1.00 20.00 | B C |
| ATOM | 6965 C LEU H 503 | −4.187 4.882 −52.197 1.00 55.74 | B C |
| ATOM | 6966 O LEU H 503 | −4.339 5.636 −53.159 1.00 57.75 | B O |
| ATOM | 6967 N ALA H 504 | −3.608 3.691 −52.295 1.00 57.22 | B N |
| ATOM | 6968 CA ALA H 504 | −3.204 3.150 −53.584 1.00 59.12 | B C |
| ATOM | 6969 CB ALA H 504 | −2.319 1.930 −53.394 1.00 20.00 | B C |
| ATOM | 6970 C ALA H 504 | −4.423 2.802 −54.427 1.00 58.10 | B C |
| ATOM | 6971 O ALA H 504 | −4.488 3.145 −55.608 1.00 63.64 | B O |
| ATOM | 6972 N PHE H 505 | −5.421 2.194 −53.793 1.00 58.17 | B N |
| ATOM | 6973 CA PHE H 505 | −6.683 1.909 −54.464 1.00 56.56 | B C |
| ATOM | 6974 CB PHE H 505 | −7.657 1.198 −53.517 1.00 20.00 | B C |
| ATOM | 6975 CG PHE H 505 | −7.174 −0.142 −53.045 1.00 20.00 | B C |
| ATOM | 6976 CD1 PHE H 505 | −7.297 −1.263 −53.851 1.00 20.00 | B C |
| ATOM | 6977 CE1 PHE H 505 | −6.817 −2.490 −53.432 1.00 20.00 | B C |
| ATOM | 6978 CZ PHE H 505 | −6.236 −2.610 −52.183 1.00 20.00 | B C |
| ATOM | 6979 CE2 PHE H 505 | −6.106 −1.497 −51.373 1.00 20.00 | B C |
| ATOM | 6980 CD2 PHE H 505 | −6.566 −0.272 −51.809 1.00 20.00 | B C |
| ATOM | 6981 C PHE H 505 | −7.307 3.189 −55.020 1.00 60.12 | B C |
| ATOM | 6982 O PHE H 505 | −7.761 3.223 −56.166 1.00 65.46 | B O |
| ATOM | 6983 N ILE H 506 | −7.214 4.267 −54.247 1.00 56.10 | B N |
| ATOM | 6984 CA ILE H 506 | −7.762 5.552 −54.667 1.00 57.32 | B C |
| ATOM | 6985 CB ILE H 506 | −7.716 6.599 −53.536 1.00 20.00 | B C |
| ATOM | 6986 CG1 ILE H 506 | −8.610 6.163 −52.376 1.00 20.00 | B C |
| ATOM | 6987 CD1 ILE H 506 | −8.728 7.191 −51.274 1.00 20.00 | B C |
| ATOM | 6988 CG2 ILE H 506 | −8.177 7.956 −54.049 1.00 20.00 | B C |
| ATOM | 6989 C ILE H 506 | −7.013 6.084 −55.883 1.00 67.33 | B C |
| ATOM | 6990 O ILE H 506 | −7.625 6.563 −56.839 1.00 76.99 | B O |
| ATOM | 6991 N ARG H 507 | −5.694 5.913 −55.876 1.00 67.87 | B N |
| ATOM | 6992 CA ARG H 507 | −4.858 6.338 −56.993 1.00 62.11 | B C |
| ATOM | 6993 CB ARG H 507 | −3.381 6.153 −56.657 1.00 20.00 | B C |
| ATOM | 6994 CG ARG H 507 | −2.862 7.130 −55.630 1.00 20.00 | B C |
| ATOM | 6995 CD ARG H 507 | −1.380 6.930 −55.386 1.00 20.00 | B C |
| ATOM | 6996 NE ARG H 507 | −0.903 7.783 −54.303 1.00 20.00 | B N |
| ATOM | 6997 CZ ARG H 507 | 0.322 7.729 −53.792 1.00 20.00 | B C |
| ATOM | 6998 NH1 ARG H 507 | 1.215 6.883 −54.288 1.00 20.00 | B N |
| ATOM | 6999 NH2 ARG H 507 | 0.656 8.530 −52.791 1.00 20.00 | B N |
| ATOM | 7000 C ARG H 507 | −5.191 5.565 −58.258 1.00 67.30 | B C |
| ATOM | 7001 O ARG H 507 | −5.255 6.139 −59.344 1.00 67.02 | B O |
| ATOM | 7002 N LYS H 508 | −5.222 4.243 −58.139 1.00 66.83 | B N |
| ATOM | 7003 CA LYS H 508 | −5.694 3.391 −59.220 1.00 68.12 | B C |
| ATOM | 7004 CB LYS H 508 | −5.743 1.932 −58.763 1.00 20.00 | B C |
| ATOM | 7005 CG LYS H 508 | −4.368 1.325 −58.543 1.00 20.00 | B C |
| ATOM | 7006 CD LYS H 508 | −4.433 −0.159 −58.230 1.00 20.00 | B C |
| ATOM | 7007 CE LYS H 508 | −3.037 −0.710 −57.973 1.00 20.00 | B C |
| ATOM | 7008 NZ LYS H 508 | −3.053 −2.129 −57.525 1.00 20.00 | B N |
| ATOM | 7009 C LYS H 508 | −7.065 3.839 −59.705 1.00 65.22 | B C |
| ATOM | 7010 O LYS H 508 | −7.245 4.154 −60.881 1.00 72.34 | B O |
| ATOM | 7011 N SER H 509 | −7.996 3.977 −58.767 1.00 64.87 | B N |
| ATOM | 7012 CA SER H 509 | −9.366 4.349 −59.095 1.00 56.47 | B C |
| ATOM | 7013 CB SER H 509 | −10.227 4.420 −57.832 1.00 20.00 | B C |
| ATOM | 7014 OG SER H 509 | −9.862 5.523 −57.023 1.00 20.00 | B O |

APPENDIX-continued (APPENDIX discloses SEQ ID NOS 29-32, 29-32 and 29-32, respectively, in order of appearance)

| | | | |
|---|---|---|---|
| ATOM | 7015 C SER H 509 | −9.418 5.673 −59.851 1.00 56.96 | B C |
| ATOM | 7016 O SER H 509 | −10.124 5.796 −60.854 1.00 65.57 | B O |
| ATOM | 7017 N ASP H 510 | −8.670 6.661 −59.368 1.00 64.34 | B N |
| ATOM | 7018 CA ASP H 510 | −8.624 7.971 −60.009 1.00 64.83 | B C |
| ATOM | 7019 CB ASP H 510 | −7.774 8.944 −59.192 1.00 20.00 | B C |
| ATOM | 7020 CG ASP H 510 | −8.421 9.315 −57.872 1.00 20.00 | B C |
| ATOM | 7021 OD1 ASP H 510 | −9.589 8.927 −57.652 1.00 20.00 | B O |
| ATOM | 7022 OD2 ASP H 510 | −7.729 9.904 −57.015 1.00 20.00 | B O |
| ATOM | 7023 C ASP H 510 | −8.087 7.873 −61.431 1.00 62.11 | B C |
| ATOM | 7024 O ASP H 510 | −8.711 8.358 −62.373 1.00 67.61 | B O |
| ATOM | 7025 N GLU H 511 | −6.939 7.222 −61.584 1.00 64.95 | B N |
| ATOM | 7026 CA GLU H 511 | −6.330 7.042 −62.896 1.00 60.64 | B C |
| ATOM | 7027 CB GLU H 511 | −5.117 6.109 −62.804 1.00 20.00 | B C |
| ATOM | 7028 CG GLU H 511 | −3.959 6.673 −61.982 1.00 20.00 | B C |
| ATOM | 7029 CD GLU H 511 | −2.858 5.655 −61.716 1.00 20.00 | B C |
| ATOM | 7030 OE1 GLU H 511 | −3.140 4.438 −61.756 1.00 20.00 | B O |
| ATOM | 7031 OE2 GLU H 511 | −1.749 6.076 −61.324 1.00 20.00 | B O |
| ATOM | 7032 C GLU H 511 | −7.340 6.528 −63.928 1.00 59.91 | B C |
| ATOM | 7033 O GLU H 511 | −7.417 7.043 −65.045 1.00 55.45 | B O |
| ATOM | 7034 N LEU H 512 | −8.137 5.537 −63.533 1.00 44.35 | B N |
| ATOM | 7035 CA LEU H 512 | −9.117 4.929 −64.432 1.00 49.60 | B C |
| ATOM | 7036 CB LEU H 512 | −9.744 3.682 −63.796 1.00 20.00 | B C |
| ATOM | 7037 CG LEU H 512 | −8.841 2.462 −63.572 1.00 20.00 | B C |
| ATOM | 7038 CD1 LEU H 512 | −9.594 1.368 −62.825 1.00 20.00 | B C |
| ATOM | 7039 CD2 LEU H 512 | −8.295 1.930 −64.892 1.00 20.00 | B C |
| ATOM | 7040 C LEU H 512 | −10.208 5.920 −64.821 1.00 58.00 | B C |
| ATOM | 7041 O LEU H 512 | −10.524 6.073 −66.000 1.00 55.11 | B O |
| ATOM | 7042 N LEU H 513 | −10.814 6.552 −63.820 1.00 57.91 | B N |
| ATOM | 7043 CA LEU H 513 | −11.866 7.536 −64.057 1.00 57.49 | B C |
| ATOM | 7044 CB LEU H 513 | −12.390 8.097 −62.733 1.00 20.00 | B C |
| ATOM | 7045 CG LEU H 513 | −13.077 7.088 −61.815 1.00 20.00 | B C |
| ATOM | 7046 CD1 LEU H 513 | −13.388 7.705 −60.461 1.00 20.00 | B C |
| ATOM | 7047 CD2 LEU H 513 | −14.336 6.556 −62.474 1.00 20.00 | B C |
| ATOM | 7048 C LEU H 513 | −11.384 8.676 −64.949 1.00 58.78 | B C |
| ATOM | 7049 O LEU H 513 | −12.154 9.220 −65.740 1.00 59.88 | B O |
| ATOM | 7050 N HIS H 514 | −10.131 9.086 −64.764 1.00 60.07 | B N |
| ATOM | 7051 CA HIS H 514 | −9.544 10.151 −65.578 1.00 62.82 | B C |
| ATOM | 7052 CB HIS H 514 | −8.240 10.665 −64.951 1.00 20.00 | B C |
| ATOM | 7053 CG HIS H 514 | −8.406 11.218 −63.567 1.00 20.00 | B C |
| ATOM | 7054 ND1 HIS H 514 | −9.083 12.390 −63.308 1.00 20.00 | B N |
| ATOM | 7055 CE1 HIS H 514 | −9.060 12.634 −62.010 1.00 20.00 | B C |
| ATOM | 7056 NE2 HIS H 514 | −8.393 11.660 −61.416 1.00 20.00 | B N |
| ATOM | 7057 CD2 HIS H 514 | −7.960 10.770 −62.368 1.00 20.00 | B C |
| ATOM | 7058 C HIS H 514 | −9.305 9.679 −67.014 1.00 65.10 | B C |
| ATOM | 7059 O HIS H 514 | −9.352 10.475 −67.953 1.00 66.73 | B O |
| ATOM | 7060 N ASN H 515 | −9.179 8.365 −67.187 1.00 63.45 | B N |
| ATOM | 7061 CA ASN H 515 | −9.028 7.768 −68.513 1.00 56.53 | B C |
| ATOM | 7062 CB ASN H 515 | −8.367 6.392 −68.409 1.00 20.00 | B C |
| ATOM | 7063 CG ASN H 515 | −6.901 6.476 −68.035 1.00 20.00 | B C |
| ATOM | 7064 OD1 ASN H 515 | −6.233 7.470 −68.319 1.00 20.00 | B O |
| ATOM | 7065 ND2 ASN H 515 | −6.375 5.399 −67.462 1.00 20.00 | B N |
| ATOM | 7066 C ASN H 515 | −10.357 7.651 −69.254 1.00 60.06 | B C |
| ATOM | 7067 O ASN H 515 | −10.414 7.816 −70.473 1.00 66.48 | B O |
| ATOM | 7068 N VAL H 516 | −11.402 7.275 −68.522 1.00 54.29 | B N |
| ATOM | 7069 CA VAL H 516 | −12.765 7.256 −69.056 1.00 52.70 | B C |
| ATOM | 7070 CB VAL H 516 | −13.775 6.751 −68.001 1.00 20.00 | B C |
| ATOM | 7071 CG1 VAL H 516 | −15.194 6.825 −68.541 1.00 20.00 | B C |
| ATOM | 7072 CG2 VAL H 516 | −13.431 5.333 −67.568 1.00 20.00 | B C |
| ATOM | 7073 C VAL H 516 | −13.206 8.633 −69.557 1.00 60.10 | B C |
| ATOM | 7074 O VAL H 516 | −13.761 8.759 −70.649 1.00 61.55 | B O |
| ATOM | 7075 N ASN H 517 | −12.957 9.661 −68.752 1.00 69.10 | B N |
| ATOM | 7076 CA ASN H 517 | −13.297 11.030 −69.125 1.00 67.75 | B C |
| ATOM | 7077 CB ASN H 517 | −12.850 12.012 −68.038 1.00 20.00 | B C |
| ATOM | 7078 CG ASN H 517 | −13.685 11.907 −66.774 1.00 20.00 | B C |
| ATOM | 7079 OD1 ASN H 517 | −14.835 11.471 −66.813 1.00 20.00 | B O |
| ATOM | 7080 ND2 ASN H 517 | −13.126 12.355 −65.653 1.00 20.00 | B N |
| ATOM | 7081 C ASN H 517 | −12.686 11.424 −70.465 1.00 71.17 | B C |
| ATOM | 7082 O ASN H 517 | −13.289 12.169 −71.238 1.00 66.42 | B O |
| ATOM | 7083 N ALA H 518 | −11.489 10.912 −70.739 1.00 72.11 | B N |
| ATOM | 7084 CA ALA H 518 | −10.794 11.202 −71.989 1.00 74.82 | B C |
| ATOM | 7085 CB ALA H 518 | −9.318 10.855 −71.867 1.00 20.00 | B C |
| ATOM | 7086 C ALA H 518 | −11.421 10.450 −73.155 1.00 70.11 | B C |
| ATOM | 7087 O ALA H 518 | −11.593 11.001 −74.242 1.00 65.18 | B O |
| ATOM | 7088 N GLY H 519 | −11.665 9.160 −72.952 1.00 56.07 | B N |
| ATOM | 7089 CA GLY H 519 | −12.395 8.360 −73.926 1.00 53.01 | B C |
| ATOM | 7090 C GLY H 519 | −13.763 8.941 −74.222 1.00 63.58 | B C |
| ATOM | 7091 O GLY H 519 | −14.203 8.960 −75.371 1.00 69.35 | B O |

APPENDIX-continued (APPENDIX discloses SEQ ID NOS 29-32, 29-32 and 29-32, respectively, in order of appearance)

| | | | | |
|---|---|---|---|---|
| ATOM | 7092 N LYS H 520 | −14.422 9.444 −73.183 1.00 58.33 | B N |
| ATOM | 7093 CA LYS H 520 | −15.716 10.101 −73.333 1.00 53.44 | B C |
| ATOM | 7094 CB LYS H 520 | −16.241 10.557 −71.975 1.00 20.00 | B C |
| ATOM | 7095 CG LYS H 520 | −16.441 9.429 −70.996 1.00 20.00 | B C |
| ATOM | 7096 CD LYS H 520 | −16.739 9.961 −69.616 1.00 20.00 | B C |
| ATOM | 7097 CE LYS H 520 | −17.296 8.868 −68.730 1.00 20.00 | B C |
| ATOM | 7098 NZ LYS H 520 | −17.807 9.424 −67.452 1.00 20.00 | B N |
| ATOM | 7099 C LYS H 520 | −15.623 11.296 −74.268 1.00 58.24 | B C |
| ATOM | 7100 O LYS H 520 | −16.579 11.621 −74.972 1.00 48.60 | B O |
| ATOM | 7101 N SER H 521 | −14.489 11.986 −74.219 1.00 67.19 | B N |
| ATOM | 7102 CA SER H 521 | −14.232 13.101 −75.120 1.00 60.42 | B C |
| ATOM | 7103 CB SER H 521 | −12.938 13.821 −74.727 1.00 20.00 | B C |
| ATOM | 7104 OG SER H 521 | −11.894 12.898 −74.459 1.00 20.00 | B O |
| ATOM | 7105 C SER H 521 | −14.167 12.636 −76.573 1.00 54.19 | B C |
| ATOM | 7106 O SER H 521 | −14.886 13.151 −77.430 1.00 65.36 | B O |
| ATOM | 7107 N THR H 522 | −13.362 11.609 −76.825 1.00 50.09 | B N |
| ATOM | 7108 CA THR H 522 | −13.259 11.025 −78.158 1.00 57.59 | B C |
| ATOM | 7109 CB THR H 522 | −12.299 9.817 −78.179 1.00 20.00 | B C |
| ATOM | 7110 OG1 THR H 522 | −12.774 8.810 −77.278 1.00 20.00 | B O |
| ATOM | 7111 CG2 THR H 522 | −10.894 10.235 −77.767 1.00 20.00 | B C |
| ATOM | 7112 C THR H 522 | −14.625 10.565 −78.646 1.00 59.16 | B C |
| ATOM | 7113 O THR H 522 | −15.044 10.893 −79.755 1.00 65.90 | B O |
| ATOM | 7114 N THR H 523 | −15.338 9.849 −77.783 1.00 52.59 | B N |
| ATOM | 7115 CA THR H 523 | −16.665 9.347 −78.112 1.00 42.19 | B C |
| ATOM | 7116 CB THR H 523 | −17.298 8.599 −76.922 1.00 20.00 | B C |
| ATOM | 7117 OG1 THR H 523 | −17.543 9.516 −75.848 1.00 20.00 | B O |
| ATOM | 7118 CG2 THR H 523 | −16.373 7.492 −76.435 1.00 20.00 | B C |
| ATOM | 7119 C THR H 523 | −17.596 10.466 −78.566 1.00 48.90 | B C |
| ATOM | 7120 O THR H 523 | −18.331 10.314 −79.541 1.00 63.19 | B O |
| ATOM | 7121 N ASN H 524 | −17.535 11.601 −77.881 1.00 52.51 | B N |
| ATOM | 7122 CA ASN H 524 | −18.341 12.752 −78.258 1.00 57.54 | B C |
| ATOM | 7123 CB ASN H 524 | −18.235 13.853 −77.202 1.00 20.00 | B C |
| ATOM | 7124 CG ASN H 524 | −19.015 13.528 −75.945 1.00 20.00 | B C |
| ATOM | 7125 OD1 ASN H 524 | −19.910 12.682 −75.959 1.00 20.00 | B O |
| ATOM | 7126 ND2 ASN H 524 | −18.683 14.203 −74.850 1.00 20.00 | B N |
| ATOM | 7127 C ASN H 524 | −17.956 13.287 −79.633 1.00 54.12 | B C |
| ATOM | 7128 O ASN H 524 | −18.812 13.463 −80.500 1.00 61.31 | B O |
| ATOM | 7129 N SER H 525 | −16.656 13.422 −79.866 1.00 48.97 | B N |
| ATOM | 7130 CA SER H 525 | −16.165 13.913 −81.145 1.00 64.81 | B C |
| ATOM | 7131 CB SER H 525 | −14.636 13.940 −81.151 1.00 61.22 | B C |
| ATOM | 7132 OG SER H 525 | −14.141 14.856 −80.191 1.00 85.90 | B O |
| ATOM | 7133 C SER H 525 | −16.689 13.053 −82.292 1.00 69.67 | B C |
| ATOM | 7134 O SER H 525 | −17.013 13.563 −83.367 1.00 72.60 | B O |
| ATOM | 7135 N LYS H 526 | −16.849 11.760 −82.029 1.00 66.06 | B N |
| ATOM | 7136 CA LYS H 526 | −17.335 10.831 −83.043 1.00 63.67 | B C |
| ATOM | 7137 CB LYS H 526 | −17.003 9.383 −82.660 1.00 70.55 | B C |
| ATOM | 7138 CG LYS H 526 | −15.562 8.963 −82.939 1.00 75.29 | B C |
| ATOM | 7139 CD LYS H 526 | −15.205 7.681 −82.194 1.00 85.03 | B C |
| ATOM | 7140 CE LYS H 526 | −13.700 7.525 −82.041 1.00 82.65 | B C |
| ATOM | 7141 NZ LYS H 526 | −13.347 6.537 −80.984 1.00 73.89 | B N |
| ATOM | 7142 C LYS H 526 | −18.838 10.987 −83.239 1.00 55.36 | B C |
| ATOM | 7143 O LYS H 526 | −19.333 10.950 −84.365 1.00 70.69 | B O |
| ATOM | 7144 N ILE H 527 | −19.560 11.149 −82.135 1.00 57.52 | B N |
| ATOM | 7145 CA ILE H 527 | −20.995 11.389 −82.189 1.00 58.48 | B C |
| ATOM | 7146 CB ILE H 527 | −21.569 11.642 −80.787 1.00 57.00 | B C |
| ATOM | 7147 CG1 ILE H 527 | −21.356 10.420 −79.891 1.00 49.07 | B C |
| ATOM | 7148 CD1 ILE H 527 | −21.790 9.118 −80.517 1.00 46.18 | B C |
| ATOM | 7149 CG2 ILE H 527 | −23.035 12.029 −80.872 1.00 52.63 | B C |
| ATOM | 7150 C ILE H 527 | −21.317 12.586 −83.075 1.00 65.20 | B C |
| ATOM | 7151 O ILE H 527 | −22.228 12.532 −83.900 1.00 66.48 | B O |
| ATOM | 7152 N TYR H 528 | −20.590 13.681 −82.870 1.00 69.78 | B N |
| ATOM | 7153 CA TYR H 528 | −20.780 14.884 −83.673 1.00 72.52 | B C |
| ATOM | 7154 CB TYR H 528 | −19.738 15.948 −83.316 1.00 73.16 | B C |
| ATOM | 7155 CG TYR H 528 | −19.707 16.343 −81.856 1.00 76.94 | B C |
| ATOM | 7156 CD1 TYR H 528 | −18.615 17.018 −81.327 1.00 70.95 | B C |
| ATOM | 7157 CE1 TYR H 528 | −18.584 17.406 −80.000 1.00 67.73 | B C |
| ATOM | 7158 CZ TYR H 528 | −19.653 17.114 −79.180 1.00 71.89 | B C |
| ATOM | 7159 OH TYR H 528 | −19.626 17.490 −77.856 1.00 75.44 | B O |
| ATOM | 7160 CE2 TYR H 528 | −20.759 16.464 −79.687 1.00 77.03 | B C |
| ATOM | 7161 CD2 TYR H 528 | −20.782 16.084 −81.018 1.00 77.84 | B C |
| ATOM | 7162 C TYR H 528 | −20.678 14.551 −85.157 1.00 71.63 | B C |
| ATOM | 7163 O TYR H 528 | −21.609 14.797 −85.925 1.00 84.20 | B O |
| ATOM | 7164 N HIS H 529 | −19.526 14.025 −85.559 1.00 67.69 | B N |
| ATOM | 7165 CA HIS H 529 | −19.265 13.733 −86.962 1.00 60.28 | B C |
| ATOM | 7166 CB HIS H 529 | −17.883 13.102 −87.131 1.00 67.84 | B C |
| ATOM | 7167 CG HIS H 529 | −16.752 14.042 −86.853 1.00 88.54 | B C |
| ATOM | 7168 ND1 HIS H 529 | −15.514 13.914 −87.444 1.00 93.34 | B N |

APPENDIX-continued (APPENDIX discloses SEQ ID NOS 29-32, 29-32 and 29-32, respectively, in order of appearance)

| | | | |
|---|---|---|---|
| ATOM | 7169 CE1 HIS H 529 | −14.718 14.874 −87.007 1.00 86.23 | B C |
| ATOM | 7170 NE2 HIS H 529 | −15.394 15.614 −86.145 1.00 91.95 | B N |
| ATOM | 7171 CD2 HIS H 529 | −16.667 15.110 −86.026 1.00 93.77 | B C |
| ATOM | 7172 C HIS H 529 | −20.333 12.817 −87.546 1.00 63.30 | B C |
| ATOM | 7173 O HIS H 529 | −20.803 13.034 −88.663 1.00 61.02 | B O |
| ATOM | 7174 N ILE H 530 | −20.710 11.791 −86.791 1.00 59.79 | B N |
| ATOM | 7175 CA ILE H 530 | −21.800 10.915 −87.201 1.00 45.70 | B C |
| ATOM | 7176 CB ILE H 530 | −22.019 9.780 −86.190 1.00 40.57 | B C |
| ATOM | 7177 CG1 ILE H 530 | −20.879 8.765 −86.292 1.00 42.86 | B C |
| ATOM | 7178 CD1 ILE H 530 | −20.826 7.775 −85.154 1.00 51.01 | B C |
| ATOM | 7179 CG2 ILE H 530 | −23.360 9.108 −86.437 1.00 35.31 | B C |
| ATOM | 7180 C ILE H 530 | −23.085 11.717 −87.331 1.00 57.52 | B C |
| ATOM | 7181 O ILE H 530 | −23.779 11.645 −88.345 1.00 71.18 | B O |
| ATOM | 7182 N GLU H 531 | −23.322 12.569 −86.341 1.00 67.55 | B N |
| ATOM | 7183 CA GLU H 531 | −24.479 13.449 −86.325 1.00 69.79 | B C |
| ATOM | 7184 CB GLU H 531 | −24.440 14.327 −85.074 1.00 84.02 | B C |
| ATOM | 7185 CG GLU H 531 | −25.803 14.718 −84.541 1.00 04.22 | B C |
| ATOM | 7186 CD GLU H 531 | −25.706 15.531 −83.270 1.00 16.08 | B C |
| ATOM | 7187 OE1 GLU H 531 | −25.017 15.079 −82.331 1.00 18.71 | B O |
| ATOM | 7188 OE2 GLU H 531 | −26.222 16.669 −83.251 1.00 19.69 | B O |
| ATOM | 7189 C GLU H 531 | −24.506 14.328 −87.569 1.00 64.87 | B C |
| ATOM | 7190 O GLU H 531 | −25.517 14.404 −88.269 1.00 55.58 | B O |
| ATOM | 7191 N ASN H 532 | −23.394 15.011 −87.821 1.00 65.70 | B N |
| ATOM | 7192 CA ASN H 532 | −23.273 15.890 −88.979 1.00 64.16 | B C |
| ATOM | 7193 CB ASN H 532 | −21.931 16.625 −88.953 1.00 60.58 | B C |
| ATOM | 7194 CG ASN H 532 | −21.793 17.621 −90.085 1.00 67.75 | B C |
| ATOM | 7195 OD1 ASN H 532 | −22.591 18.550 −90.206 1.00 53.59 | B O |
| ATOM | 7196 ND2 ASN H 532 | −20.822 17.392 −90.961 1.00 61.81 | B N |
| ATOM | 7197 C ASN H 532 | −23.418 15.119 −90.284 1.00 72.17 | B C |
| ATOM | 7198 O ASN H 532 | −24.041 15.593 −91.233 1.00 85.75 | B O |
| ATOM | 7199 N GLU H 533 | −22.870 13.909 −90.300 1.00 79.68 | B N |
| ATOM | 7200 CA GLU H 533 | −22.922 13.044 −91.468 1.00 71.96 | B C |
| ATOM | 7201 CB GLU H 533 | −22.010 11.837 −91.264 1.00 67.87 | B C |
| ATOM | 7202 CG GLU H 533 | −21.638 11.131 −92.547 1.00 81.94 | B C |
| ATOM | 7203 CD GLU H 533 | −20.906 12.037 −93.515 1.00 92.79 | B C |
| ATOM | 7204 OE1 GLU H 533 | −19.930 12.692 −93.094 1.00 95.90 | B O |
| ATOM | 7205 OE2 GLU H 533 | −21.247 12.025 −94.716 1.00 93.14 | B O |
| ATOM | 7206 C GLU H 533 | −24.342 12.570 −91.747 1.00 68.54 | B C |
| ATOM | 7207 O GLU H 533 | −24.667 12.175 −92.866 1.00 79.29 | B O |
| ATOM | 7208 N ILE H 534 | −25.137 12.470 −90.688 1.00 69.50 | B N |
| ATOM | 7209 CA ILE H 534 | −26.529 12.076 −90.817 1.00 72.55 | B C |
| ATOM | 7210 CB ILE H 534 | −27.056 11.467 −89.514 1.00 79.55 | B C |
| ATOM | 7211 CG1 ILE H 534 | −26.263 10.209 −89.164 1.00 80.41 | B C |
| ATOM | 7212 CD1 ILE H 534 | −25.562 9.592 −90.348 1.00 89.38 | B C |
| ATOM | 7213 CG2 ILE H 534 | −28.526 11.138 −89.645 1.00 78.63 | B C |
| ATOM | 7214 C ILE H 534 | −27.389 13.273 −91.189 1.00 74.92 | B C |
| ATOM | 7215 O ILE H 534 | −28.479 13.120 −91.740 1.00 81.01 | B O |
| ATOM | 7216 N ALA H 535 | −26.880 14.465 −90.903 1.00 79.52 | B N |
| ATOM | 7217 CA ALA H 535 | −27.559 15.690 −91.290 1.00 82.64 | B C |
| ATOM | 7218 CB ALA H 535 | −27.016 16.867 −90.498 1.00 75.39 | B C |
| ATOM | 7219 C ALA H 535 | −27.440 15.939 −92.795 1.00 81.39 | B C |
| ATOM | 7220 O ALA H 535 | −28.408 16.341 −93.443 1.00 85.54 | B O |
| ATOM | 7221 N ARG H 536 | −26.274 15.630 −93.358 1.00 78.41 | B N |
| ATOM | 7222 CA ARG H 536 | −26.044 15.812 −94.791 1.00 83.27 | B C |
| ATOM | 7223 CB ARG H 536 | −24.545 15.814 −95.106 1.00 84.58 | B C |
| ATOM | 7224 CG ARG H 536 | −23.776 16.993 −94.527 1.00103.24 | B C |
| ATOM | 7225 CD ARG H 536 | −22.638 17.422 −95.449 1.00114.72 | B C |
| ATOM | 7226 NE ARG H 536 | −21.692 16.343 −95.722 1.00117.80 | B N |
| ATOM | 7227 CZ ARG H 536 | −20.692 16.430 −96.594 1.00116.66 | B C |
| ATOM | 7228 NH1 ARG H 536 | −20.522 17.538 −97.303 1.00114.57 | B N |
| ATOM | 7229 NH2 ARG H 536 | −19.885 15.396 −96.786 1.00116.38 | B N |
| ATOM | 7230 C ARG H 536 | −26.744 14.727 −95.606 1.00 82.20 | B C |
| ATOM | 7231 O ARG H 536 | −27.369 15.011 −96.627 1.00 86.28 | B O |
| ATOM | 7232 N ILE H 537 | −26.598 13.479 −95.172 1.00 77.08 | B N |
| ATOM | 7233 CA ILE H 537 | −27.315 12.371 −95.782 1.00 66.79 | B C |
| ATOM | 7234 CB ILE H 537 | −26.955 11.038 −95.113 1.00 64.76 | B C |
| ATOM | 7235 CG1 ILE H 537 | −25.523 10.627 −95.476 1.00 66.92 | B C |
| ATOM | 7236 CD1 ILE H 537 | −24.906 9.625 −94.519 1.00 70.83 | B C |
| ATOM | 7237 CG2 ILE H 537 | −27.960 9.964 −95.497 1.00 51.02 | B C |
| ATOM | 7238 C ILE H 537 | −28.817 12.585 −95.674 1.00 74.94 | B C |
| ATOM | 7239 O ILE H 537 | −29.587 12.070 −96.482 1.00 97.16 | B O |
| ATOM | 7240 N LYS H 538 | −29.232 13.337 −94.661 1.00 75.09 | B N |
| ATOM | 7241 CA LYS H 538 | −30.640 13.666 −94.485 1.00 90.28 | B C |
| ATOM | 7242 CB LYS H 538 | −30.958 13.868 −93.003 1.00 93.73 | B C |
| ATOM | 7243 CG LYS H 538 | −32.344 13.390 −92.575 1.00 96.60 | B C |
| ATOM | 7244 CD LYS H 538 | −32.640 13.787 −91.126 1.00 95.37 | B C |
| ATOM | 7245 CE LYS H 538 | −34.127 13.714 −90.798 1.00100.63 | B C |

APPENDIX-continued (APPENDIX discloses SEQ ID NOS 29-32, 29-32 and 29-32, respectively, in order of appearance)

| | | | |
|---|---|---|---|
| ATOM | 7246 NZ LYS H 538 | −34.398 14.067 −89.375 1.00 99.58 | B N |
| ATOM | 7247 C LYS H 538 | −31.022 14.911 −95.284 1.00102.20 | B C |
| ATOM | 7248 O LYS H 538 | −32.166 15.360 −95.235 1.00112.11 | B O |
| ATOM | 7249 N LYS H 539 | −30.069 15.444 −96.043 1.00105.15 | B N |
| ATOM | 7250 CA LYS H 539 | −30.317 16.603 −96.899 1.00105.65 | B C |
| ATOM | 7251 CB LYS H 539 | −29.144 17.589 −96.823 1.00110.12 | B C |
| ATOM | 7252 CG LYS H 539 | −29.408 18.944 −97.481 1.00113.31 | B C |
| ATOM | 7253 CD LYS H 539 | −28.182 19.854 −97.435 1.00114.26 | B C |
| ATOM | 7254 CE LYS H 539 | −28.426 21.145 −98.205 1.00118.39 | B C |
| ATOM | 7255 NZ LYS H 539 | −27.168 21.897 −98.470 1.00121.77 | B N |
| ATOM | 7256 C LYS H 539 | −30.572 16.187 −98.347 1.00108.88 | B C |
| ATOM | 7257 O LYS H 539 | −30.886 17.021 −99.195 1.00110.77 | B O |
| ATOM | 7258 N LEU H 540 | −30.515 14.884 −98.605 1.00111.50 | B N |
| ATOM | 7259 CA LEU H 540 | −30.796 14.356 −99.935 1.00110.31 | B C |
| ATOM | 7260 CB LEU H 540 | −29.690 13.389 −100.368 1.00101.19 | B C |
| ATOM | 7261 CG LEU H 540 | −28.270 13.889 −100.078 1.00 94.26 | B C |
| ATOM | 7262 CD1 LEU H 540 | −27.249 12.769 −100.179 1.00 86.40 | B C |
| ATOM | 7263 CD2 LEU H 540 | −27.896 15.059 −100.984 1.00 84.54 | B C |
| ATOM | 7264 C LEU H 540 | −32.157 13.675 −99.961 1.00 118.37 | B C |
| ATOM | 7265 O LEU H 540 | −32.531 13.039 −100.945 1.00116.71 | B O |
| ATOM | 7266 N ILE H 541 | −32.923 13.883 −98.896 1.00130.80 | B N |
| ATOM | 7267 CA ILE H 541 | −34.267 13.339 −98.801 1.00140.48 | B C |
| ATOM | 7268 CB ILE H 541 | −34.250 11.862 −98.372 1.00138.99 | B C |
| ATOM | 7269 CG1 ILE H 541 | −33.319 11.059 −99.282 1.00133.30 | B C |
| ATOM | 7270 CD1 ILE H 541 | −33.895 10.789 −100.656 1.00136.26 | B C |
| ATOM | 7271 CG2 ILE H 541 | −35.653 11.281 −98.432 1.00136.12 | B C |
| ATOM | 7272 C ILE H 541 | −35.146 14.139 −97.839 1.00144.97 | B C |
| ATOM | 7273 O ILE H 541 | −36.372 14.063 −97.905 1.00145.83 | B O |
| ATOM | 7274 N GLY H 542 | −34.523 14.940 −96.979 1.00148.77 | B N |
| ATOM | 7275 CA GLY H 542 | −35.267 15.725 −95.991 1.00153.58 | B C |
| ATOM | 7276 C GLY H 542 | −35.358 17.210 −96.308 1.00160.45 | B C |
| ATOM | 7277 O GLY H 542 | −35.594 17.599 −97.454 1.00163.41 | B O |
| ATOM | 7278 N GLU H 543 | −35.275 18.034 −95.267 1.00163.83 | B N |
| ATOM | 7279 CA GLU H 543 | −35.152 19.480 −95.430 1.00165.52 | B C |
| ATOM | 7280 CB GLU H 543 | −35.727 20.205 −94.211 1.00158.94 | B C |
| ATOM | 7285 C GLU H 543 | −33.698 19.890 −95.644 1.00168.27 | B C |
| ATOM | 7286 O GLU H 543 | −32.778 19.116 −95.373 1.00167.37 | B O |
| ATOM | 7287 N GLN I 26 | 21.181 −26.937 −9.836 1.00 23.62 | C N |
| ATOM | 7288 CA GLN I 26 | 21.159 −25.618 −10.530 1.00 23.82 | C C |
| ATOM | 7289 CB GLN I 26 | 21.607 −24.503 −9.580 1.00 23.94 | C C |
| ATOM | 7290 CG GLN I 26 | 20.888 −24.492 −8.237 1.00 28.83 | C C |
| ATOM | 7291 CD GLN I 26 | 21.323 −25.626 −7.329 1.00 36.36 | C C |
| ATOM | 7292 OE1 GLN I 26 | 20.813 −26.740 −7.428 1.00 39.09 | C O |
| ATOM | 7293 NE2 GLN I 26 | 22.207 −25.325 −6.384 1.00 37.86 | C N |
| ATOM | 7294 C GLN I 26 | 22.043 −25.641 −11.774 1.00 23.09 | C C |
| ATOM | 7295 O GLN I 26 | 22.946 −26.471 −11.888 1.00 24.21 | C O |
| ATOM | 7296 N ASN I 27 | 21.670 −24.835 −12.765 1.00 20.98 | C N |
| ATOM | 7297 CA ASN I 27 | 22.435 −24.709 −14.004 1.00 19.70 | C C |
| ATOM | 7298 CB ASN I 27 | 22.165 −25.904 −14.928 1.00 20.41 | C C |
| ATOM | 7299 CG ASN I 27 | 22.952 −25.833 −16.231 1.00 23.56 | C C |
| ATOM | 7300 OD1 ASN I 27 | 24.156 −25.579 −16.199 1.00 24.42 | C O |
| ATOM | 7301 ND2 ASN I 27 | 22.227 −25.693 −17.339 1.00 27.70 | C N |
| ATOM | 7302 C ASN I 27 | 22.086 −23.414 −14.727 1.00 18.42 | C C |
| ATOM | 7303 O ASN I 27 | 21.539 −23.447 −15.830 1.00 18.47 | C O |
| ATOM | 7304 N ILE I 28 | 22.230 −22.288 −14.033 1.00 16.54 | C N |
| ATOM | 7305 CA ILE I 28 | 21.853 −21.004 −14.611 1.00 14.59 | C C |
| ATOM | 7306 CB ILE I 28 | 21.526 −19.932 −13.546 1.00 14.01 | C C |
| ATOM | 7307 CG1 ILE I 28 | 22.461 −20.055 −12.343 1.00 15.60 | C C |
| ATOM | 7308 CD1 ILE I 28 | 23.710 −19.205 −12.454 1.00 16.26 | C C |
| ATOM | 7309 CG2 ILE I 28 | 20.065 −20.023 −13.122 1.00 12.57 | C C |
| ATOM | 7310 C ILE I 28 | 22.915 −20.484 −15.561 1.00 13.86 | C C |
| ATOM | 7311 O ILE I 28 | 24.111 −20.702 −15.363 1.00 13.70 | C O |
| ATOM | 7312 N THR I 29 | 22.442 −20.013 −16.703 1.00 13.23 | C N |
| ATOM | 7313 CA THR I 29 | 23.301 −19.589 −17.786 1.00 12.65 | C C |
| ATOM | 7314 CB THR I 29 | 23.241 −20.586 −18.948 1.00 12.69 | C C |
| ATOM | 7315 OG1 THR I 29 | 22.805 −21.861 −18.463 1.00 12.62 | C O |
| ATOM | 7316 CG2 THR I 29 | 24.603 −20.727 −19.608 1.00 12.92 | C C |
| ATOM | 7317 C THR I 29 | 22.740 −18.277 −18.281 1.00 12.47 | C C |
| ATOM | 7318 O THR I 29 | 21.531 −18.051 −18.220 1.00 12.53 | C O |
| ATOM | 7319 N GLU I 30 | 23.596 −17.467 −18.884 1.00 11.98 | C N |
| ATOM | 7320 CA GLU I 30 | 23.135 −16.364 −19.702 1.00 11.68 | C C |
| ATOM | 7321 CB GLU I 30 | 23.508 −15.035 −19.049 1.00 11.98 | C C |
| ATOM | 7322 CG GLU I 30 | 22.537 −13.901 −19.321 1.00 13.38 | C C |
| ATOM | 7323 CD GLU I 30 | 22.687 −12.767 −18.325 1.00 16.03 | C C |
| ATOM | 7324 OE1 GLU I 30 | 23.820 −12.269 −18.155 1.00 16.65 | C O |
| ATOM | 7325 OE2 GLU I 30 | 21.684 −12.412 −17.673 1.00 17.06 | C O |
| ATOM | 7326 C GLU I 30 | 23.814 −16.480 −21.047 1.00 11.39 | C C |

APPENDIX-continued (APPENDIX discloses SEQ ID NOS 29-32, 29-32 and 29-32, respectively, in order of appearance)

| | | | |
|---|---|---|---|
| ATOM | 7327 O GLU I 30 | 25.000 −16.799 −21.124 1.00 11.50 | C O |
| ATOM | 7328 N GLU I 31 | 23.036 −16.344 −22.111 1.00 11.11 | C N |
| ATOM | 7329 CA GLU I 31 | 23.626 −16.233 −23.427 1.00 11.06 | C C |
| ATOM | 7330 CB GLU I 31 | 23.376 −17.494 −24.251 1.00 11.48 | C C |
| ATOM | 7331 CG GLU I 31 | 22.395 −17.322 −25.391 1.00 13.90 | C C |
| ATOM | 7332 CD GLU I 31 | 22.329 −18.546 −26.280 1.00 17.27 | C C |
| ATOM | 7333 OE1 GLU I 31 | 22.658 −18.428 −27.478 1.00 17.55 | C O |
| ATOM | 7334 OE2 GLU I 31 | 21.999 −19.638 −25.769 1.00 18.73 | C O |
| ATOM | 7335 C GLU I 31 | 23.177 −14.989 −24.167 1.00 10.47 | C C |
| ATOM | 7336 O GLU I 31 | 22.010 −14.597 −24.118 1.00 10.12 | C O |
| ATOM | 7337 N PHE I 32 | 24.139 −14.352 −24.816 1.00 10.15 | C N |
| ATOM | 7338 CA PHE I 32 | 23.986 −12.994 −25.289 1.00 9.62 | C C |
| ATOM | 7339 CB PHE I 32 | 25.267 −12.204 −25.017 1.00 9.42 | C C |
| ATOM | 7340 CG PHE I 32 | 25.384 −10.939 −25.822 1.00 9.27 | C C |
| ATOM | 7341 CD1 PHE I 32 | 24.529 −9.871 −25.585 1.00 9.37 | C C |
| ATOM | 7342 CE1 PHE I 32 | 24.614 −8.713 −26.339 1.00 9.52 | C C |
| ATOM | 7343 CZ PHE I 32 | 25.594 −8.593 −27.306 1.00 9.82 | C C |
| ATOM | 7344 CE2 PHE I 32 | 26.458 −9.651 −27.548 1.00 10.13 | C C |
| ATOM | 7345 CD2 PHE I 32 | 26.372 −10.802 −26.786 1.00 10.06 | C C |
| ATOM | 7346 C PHE I 32 | 23.715 −13.038 −26.782 1.00 9.64 | C C |
| ATOM | 7347 O PHE I 32 | 24.336 −13.811 −27.512 1.00 9.84 | C O |
| ATOM | 7348 N TYR I 33 | 22.764 −12.229 −27.228 1.00 9.59 | C N |
| ATOM | 7349 CA TYR I 33 | 22.384 −12.221 −28.629 1.00 9.67 | C C |
| ATOM | 7350 CB TYR I 33 | 20.874 −12.414 −28.771 1.00 9.52 | C C |
| ATOM | 7351 CG TYR I 33 | 20.408 −13.802 −28.397 1.00 10.94 | C C |
| ATOM | 7352 CD1 TYR I 33 | 19.978 −14.084 −27.107 1.00 12.23 | C C |
| ATOM | 7353 CE1 TYR I 33 | 19.587 −15.359 −26.750 1.00 12.93 | C C |
| ATOM | 7354 CZ TYR I 33 | 19.675 −16.381 −27.670 1.00 13.47 | C C |
| ATOM | 7355 OH TYR I 33 | 19.297 −17.656 −27.315 1.00 14.54 | C O |
| ATOM | 7356 CE2 TYR I 33 | 20.151 −16.137 −28.941 1.00 13.56 | C C |
| ATOM | 7357 CD2 TYR I 33 | 20.538 −14.858 −29.288 1.00 12.96 | C C |
| ATOM | 7358 C TYR I 33 | 22.832 −10.933 −29.306 1.00 9.94 | C C |
| ATOM | 7359 O TYR I 33 | 22.138 −9.917 −29.257 1.00 10.16 | C O |
| ATOM | 7360 N GLN I 34 | 24.036 −10.964 −29.865 1.00 10.06 | C N |
| ATOM | 7361 CA GLN I 34 | 24.713 −9.751 −30.294 1.00 10.01 | C C |
| ATOM | 7362 CB GLN I 34 | 26.105 −10.085 −30.819 1.00 10.22 | C C |
| ATOM | 7363 CG GLN I 34 | 26.862 −8.884 −31.336 1.00 11.12 | C C |
| ATOM | 7364 CD GLN I 34 | 28.323 −9.187 −31.577 1.00 13.13 | C C |
| ATOM | 7365 OE1 GLN I 34 | 28.674 −9.887 −32.528 1.00 14.24 | C O |
| ATOM | 7366 NE2 GLN I 34 | 29.183 −8.693 −30.693 1.00 13.79 | C N |
| ATOM | 7367 C GLN I 34 | 23.914 −9.028 −31.370 1.00 9.94 | C C |
| ATOM | 7368 O GLN I 34 | 24.051 −7.818 −31.550 1.00 10.08 | C O |
| ATOM | 7369 N SER I 35 | 23.079 −9.781 −32.081 1.00 9.87 | C N |
| ATOM | 7370 CA SER I 35 | 22.336 −9.255 −33.225 1.00 9.91 | C C |
| ATOM | 7371 CB SER I 35 | 21.995 −10.382 −34.206 1.00 10.03 | C C |
| ATOM | 7372 OG SER I 35 | 21.241 −11.403 −33.574 1.00 10.81 | C O |
| ATOM | 7373 C SER I 35 | 21.059 −8.555 −32.775 1.00 9.56 | C C |
| ATOM | 7374 O SER I 35 | 20.248 −8.124 −33.595 1.00 9.59 | C O |
| ATOM | 7375 N THR I 36 | 20.823 −8.581 −31.472 1.00 9.21 | C N |
| ATOM | 7376 CA THR I 36 | 19.592 −8.066 −30.903 1.00 9.06 | C C |
| ATOM | 7377 CB THR I 36 | 18.648 −9.214 −30.517 1.00 9.49 | C C |
| ATOM | 7378 OG1 THR I 36 | 18.292 −9.956 −31.691 1.00 10.82 | C O |
| ATOM | 7379 CG2 THR I 36 | 17.392 −8.673 −29.860 1.00 9.45 | C C |
| ATOM | 7380 C THR I 36 | 19.966 −7.274 −29.661 1.00 8.77 | C C |
| ATOM | 7381 O THR I 36 | 19.112 −6.915 −28.848 1.00 8.60 | C O |
| ATOM | 7382 N CYS I 37 | 21.266 −7.035 −29.515 1.00 8.69 | C N |
| ATOM | 7383 CA CYS I 37 | 21.818 −6.428 −28.314 1.00 8.69 | C C |
| ATOM | 7384 CB CYS I 37 | 21.917 −4.911 −28.490 1.00 8.81 | C C |
| ATOM | 7385 SG CYS I 37 | 23.280 −4.138 −27.602 1.00 10.80 | C S |
| ATOM | 7386 C CYS I 37 | 20.954 −6.758 −27.107 1.00 8.27 | C C |
| ATOM | 7387 O CYS I 37 | 20.341 −5.872 −26.513 1.00 8.27 | C O |
| ATOM | 7388 N SER I 38 | 20.825 −8.045 −26.808 1.00 7.92 | C N |
| ATOM | 7389 CA SER I 38 | 19.990 −8.476 −25.699 1.00 7.51 | C C |
| ATOM | 7390 CB SER I 38 | 18.537 −8.626 −26.150 1.00 7.63 | C C |
| ATOM | 7391 OG SER I 38 | 18.429 −9.583 −27.190 1.00 8.54 | C O |
| ATOM | 7392 C SER I 38 | 20.496 −9.784 −25.110 1.00 7.02 | C C |
| ATOM | 7393 O SER I 38 | 21.196 −10.546 −25.776 1.00 6.83 | C O |
| ATOM | 7394 N ALA I 39 | 20.214 −9.995 −23.830 1.00 6.64 | C N |
| ATOM | 7395 CA ALA I 39 | 20.727 −11.159 −23.127 1.00 6.58 | C C |
| ATOM | 7396 CB ALA I 39 | 21.834 −10.761 −22.174 1.00 6.67 | C C |
| ATOM | 7397 C ALA I 39 | 19.615 −11.885 −22.388 1.00 6.93 | C C |
| ATOM | 7398 O ALA I 39 | 18.683 −11.263 −21.878 1.00 7.38 | C O |
| ATOM | 7399 N VAL I 40 | 19.675 −13.211 −22.415 1.00 6.87 | C N |
| ATOM | 7400 CA VAL I 40 | 18.707 −14.034 −21.706 1.00 6.55 | C C |
| ATOM | 7401 CB VAL I 40 | 17.905 −14.928 −22.668 1.00 6.22 | C C |
| ATOM | 7402 CG1 VAL I 40 | 17.196 −16.031 −21.899 1.00 6.52 | C C |
| ATOM | 7403 CG2 VAL I 40 | 16.905 −14.098 −23.456 1.00 6.62 | C C |

APPENDIX-continued (APPENDIX discloses SEQ ID NOS 29-32, 29-32 and 29-32, respectively, in order of appearance)

| | | | |
|---|---|---|---|
| ATOM | 7404 C VAL I 40 | 19.394 −14.909 −20.670 1.00 6.73 | C C |
| ATOM | 7405 O VAL I 40 | 20.351 −15.620 −20.977 1.00 6.83 | C O |
| ATOM | 7406 N SER I 41 | 18.916 −14.822 −19.434 1.00 6.86 | C N |
| ATOM | 7407 CA SER I 41 | 19.298 −15.760 −18.388 1.00 6.75 | C C |
| ATOM | 7408 CB SER I 41 | 19.221 −15.082 −17.022 1.00 7.06 | C C |
| ATOM | 7409 OG SER I 41 | 18.745 −13.752 −17.148 1.00 7.50 | C O |
| ATOM | 7410 C SER I 41 | 18.399 −16.988 −18.409 1.00 6.56 | C C |
| ATOM | 7411 O SER I 41 | 17.174 −16.873 −18.403 1.00 6.08 | C O |
| ATOM | 7412 N LYS I 42 | 19.019 −18.163 −18.409 1.00 7.02 | C N |
| ATOM | 7413 CA LYS I 42 | 18.311 −19.409 −18.665 1.00 7.83 | C C |
| ATOM | 7414 CB LYS I 42 | 18.835 −20.066 −19.943 1.00 8.15 | C C |
| ATOM | 7415 CG LYS I 42 | 18.753 −19.192 −21.182 1.00 9.75 | C C |
| ATOM | 7416 CD LYS I 42 | 19.416 −19.872 −22.369 1.00 12.62 | C C |
| ATOM | 7417 CE LYS I 42 | 19.087 −19.162 −23.671 1.00 14.04 | C C |
| ATOM | 7418 NZ LYS I 42 | 19.298 −20.046 −24.851 1.00 14.96 | C N |
| ATOM | 7419 C LYS I 42 | 18.489 −20.367 −17.495 1.00 7.80 | C C |
| ATOM | 7420 O LYS I 42 | 19.512 −20.336 −16.810 1.00 8.15 | C O |
| ATOM | 7421 N GLY I 43 | 17.581 −21.330 −17.389 1.00 7.59 | C N |
| ATOM | 7422 CA GLY I 43 | 17.783 −22.472 −16.508 1.00 7.35 | C C |
| ATOM | 7423 C GLY I 43 | 17.031 −22.326 −15.202 1.00 7.10 | C C |
| ATOM | 7424 O GLY I 43 | 17.428 −22.883 −14.179 1.00 7.13 | C O |
| ATOM | 7425 N TYR I 44 | 15.907 −21.621 −15.253 1.00 7.01 | C N |
| ATOM | 7426 CA TYR I 44 | 15.095 −21.391 −14.066 1.00 6.89 | C C |
| ATOM | 7427 CB TYR I 44 | 14.678 −19.924 −13.982 1.00 6.88 | C C |
| ATOM | 7428 CG TYR I 44 | 15.828 −18.979 −13.738 1.00 6.41 | C C |
| ATOM | 7429 CD1 TYR I 44 | 16.374 −18.238 −14.776 1.00 6.62 | C C |
| ATOM | 7430 CE1 TYR I 44 | 17.430 −17.376 −14.558 1.00 6.48 | C C |
| ATOM | 7431 CZ TYR I 44 | 17.946 −17.240 −13.287 1.00 6.88 | C C |
| ATOM | 7432 OH TYR I 44 | 18.989 −16.371 −13.062 1.00 7.50 | C O |
| ATOM | 7433 CE2 TYR I 44 | 17.438 −17.984 −12.245 1.00 6.68 | C C |
| ATOM | 7434 CD2 TYR I 44 | 16.388 −18.851 −12.475 1.00 5.91 | C C |
| ATOM | 7435 C TYR I 44 | 13.859 −22.275 −14.065 1.00 6.86 | C C |
| ATOM | 7436 O TYR I 44 | 13.320 −22.602 −15.122 1.00 7.14 | C O |
| ATOM | 7437 N LEU I 45 | 13.309 −22.498 −12.875 1.00 6.44 | C N |
| ATOM | 7438 CA LEU I 45 | 12.131 −23.342 −12.733 1.00 6.12 | C C |
| ATOM | 7439 CB LEU I 45 | 12.479 −24.650 −12.019 1.00 6.31 | C C |
| ATOM | 7440 CG LEU I 45 | 13.457 −25.536 −12.798 1.00 6.38 | C C |
| ATOM | 7441 CD1 LEU I 45 | 14.250 −26.452 −11.877 1.00 7.05 | C C |
| ATOM | 7442 CD2 LEU I 45 | 12.736 −26.332 −13.874 1.00 7.05 | C C |
| ATOM | 7443 C LEU I 45 | 10.924 −22.641 −12.096 1.00 5.84 | C C |
| ATOM | 7444 O LEU I 45 | 10.954 −22.268 −10.921 1.00 5.94 | C O |
| ATOM | 7445 N SER I 46 | 9.806 −22.689 −12.821 1.00 5.43 | C N |
| ATOM | 7446 CA SER I 46 | 8.639 −21.822 −12.611 1.00 5.26 | C C |
| ATOM | 7447 CB SER I 46 | 7.803 −21.796 −13.891 1.00 5.21 | C C |
| ATOM | 7448 OG SER I 46 | 7.441 −23.112 −14.280 1.00 4.95 | C O |
| ATOM | 7449 C SER I 46 | 7.793 −22.404 −11.485 1.00 5.51 | C C |
| ATOM | 7450 O SER I 46 | 8.086 −23.500 −11.013 1.00 6.03 | C O |
| ATOM | 7451 N ALA I 47 | 6.787 −21.679 −11.001 1.00 5.24 | C N |
| ATOM | 7452 CA ALA I 47 | 6.265 −22.042 −9.688 1.00 4.83 | C C |
| ATOM | 7453 CB ALA I 47 | 7.391 −22.094 −8.675 1.00 5.01 | C C |
| ATOM | 7454 C ALA I 47 | 5.061 −21.315 −9.106 1.00 4.35 | C C |
| ATOM | 7455 O ALA I 47 | 5.100 −20.099 −8.920 1.00 4.45 | C O |
| ATOM | 7456 N LEU I 48 | 4.246 −22.119 −8.428 1.00 3.67 | C N |
| ATOM | 7457 CA LEU I 48 | 3.120 −21.630 −7.645 1.00 3.15 | C C |
| ATOM | 7458 CB LEU I 48 | 1.802 −21.948 −8.359 1.00 2.78 | C C |
| ATOM | 7459 CG LEU I 48 | 1.785 −21.864 −9.889 1.00 2.18 | C C |
| ATOM | 7460 CD1 LEU I 48 | 0.350 −21.834 −10.383 1.00 2.00 | C C |
| ATOM | 7461 CD2 LEU I 48 | 2.544 −20.643 −10.386 1.00 3.94 | C C |
| ATOM | 7462 C LEU I 48 | 3.128 −22.240 −6.239 1.00 3.06 | C C |
| ATOM | 7463 O LEU I 48 | 3.433 −23.422 −6.065 1.00 3.27 | C O |
| ATOM | 7464 N ARG I 49 | 2.926 −21.394 −5.233 1.00 2.91 | C N |
| ATOM | 7465 CA ARG I 49 | 2.903 −21.846 −3.846 1.00 2.88 | C C |
| ATOM | 7466 CB ARG I 49 | 3.036 −20.658 −2.887 1.00 2.69 | C C |
| ATOM | 7467 CG ARG I 49 | 3.904 −20.942 −1.663 1.00 2.15 | C C |
| ATOM | 7468 CD ARG I 49 | 3.321 −20.322 −0.404 1.00 2.00 | C C |
| ATOM | 7469 NE ARG I 49 | 2.284 −21.163 0.190 1.00 5.18 | C N |
| ATOM | 7470 CZ ARG I 49 | 1.050 −20.748 0.463 1.00 7.68 | C C |
| ATOM | 7471 NH1 ARG I 49 | 0.699 −19.492 0.217 1.00 8.32 | C N |
| ATOM | 7472 NH2 ARG I 49 | 0.181 −21.570 1.036 1.00 8.12 | C N |
| ATOM | 7473 C ARG I 49 | 1.625 −22.619 −3.544 1.00 3.09 | C C |
| ATOM | 7474 O ARG I 49 | 0.527 −22.170 −3.873 1.00 3.08 | C O |
| ATOM | 7475 N THR I 50 | 1.774 −23.803 −2.956 1.00 3.37 | C N |
| ATOM | 7476 CA THR I 50 | 0.625 −24.551 −2.456 1.00 3.55 | C C |
| ATOM | 7477 CB THR I 50 | 0.042 −25.503 −3.512 1.00 3.25 | C C |
| ATOM | 7478 OG1 THR I 50 | 1.091 −26.292 −4.086 1.00 2.66 | C O |
| ATOM | 7479 CG2 THR I 50 | −0.670 −24.723 −4.605 1.00 3.46 | C C |
| ATOM | 7480 C THR I 50 | 0.919 −25.349 −1.195 1.00 4.07 | C C |

APPENDIX-continued (APPENDIX discloses SEQ ID NOS 29-32, 29-32 and 29-32, respectively, in order of appearance)

| | | | |
|---|---|---|---|
| ATOM | 7481 O THR I 50 | 0.137 −25.308 −0.247 1.00 4.35 | C O |
| ATOM | 7482 N GLY I 51 | 1.892 −26.248 −1.274 1.00 4.24 | C N |
| ATOM | 7483 CA GLY I 51 | 2.393 −26.864 −0.060 1.00 4.78 | C C |
| ATOM | 7484 C GLY I 51 | 2.414 −25.769 0.981 1.00 4.98 | C C |
| ATOM | 7485 O GLY I 51 | 3.082 −24.754 0.786 1.00 5.00 | C O |
| ATOM | 7486 N TRP I 52 | 1.481 −25.829 1.923 1.00 5.34 | C N |
| ATOM | 7487 CA TRP I 52 | 1.440 −24.823 2.974 1.00 5.42 | C C |
| ATOM | 7488 CB TRP I 52 | 0.124 −24.048 2.951 1.00 5.75 | C C |
| ATOM | 7489 CG TRP I 52 | −0.090 −23.284 1.696 1.00 6.38 | C C |
| ATOM | 7490 CD1 TRP I 52 | −1.020 −23.544 0.734 1.00 7.27 | C C |
| ATOM | 7491 NE1 TRP I 52 | −0.899 −22.647 −0.297 1.00 7.46 | C N |
| ATOM | 7492 CE2 TRP I 52 | 0.129 −21.785 −0.018 1.00 7.15 | C C |
| ATOM | 7493 CD2 TRP I 52 | 0.671 −22.164 1.228 1.00 7.02 | C C |
| ATOM | 7494 CE3 TRP I 52 | 1.741 −21.428 1.752 1.00 6.83 | C C |
| ATOM | 7495 CZ3 TRP I 52 | 2.221 −20.347 1.027 1.00 6.73 | C C |
| ATOM | 7496 CH2 TRP I 52 | 1.664 −20.000 −0.214 1.00 7.13 | C C |
| ATOM | 7497 CZ2 TRP I 52 | 0.621 −20.706 −0.751 1.00 6.82 | C C |
| ATOM | 7498 C TRP I 52 | 1.680 −25.408 4.354 1.00 5.34 | C C |
| ATOM | 7499 O TRP I 52 | 1.222 −26.507 4.667 1.00 5.47 | C O |
| ATOM | 7500 N TYR I 53 | 2.237 −24.581 5.227 1.00 5.29 | C N |
| ATOM | 7501 CA TYR I 53 | 2.492 −24.977 6.598 1.00 5.58 | C C |
| ATOM | 7502 CB TYR I 53 | 4.002 −25.087 6.829 1.00 5.51 | C C |
| ATOM | 7503 CG TYR I 53 | 4.401 −25.463 8.239 1.00 6.59 | C C |
| ATOM | 7504 CD1 TYR I 53 | 4.613 −26.791 8.591 1.00 8.25 | C C |
| ATOM | 7505 CE1 TYR I 53 | 5.010 −27.136 9.872 1.00 9.40 | C C |
| ATOM | 7506 CZ TYR I 53 | 5.280 −26.145 10.790 1.00 9.24 | C C |
| ATOM | 7507 OH TYR I 53 | 5.693 −26.480 12.058 1.00 9.61 | C O |
| ATOM | 7508 CE2 TYR I 53 | 5.162 −24.818 10.437 1.00 8.78 | C C |
| ATOM | 7509 CD2 TYR I 53 | 4.758 −24.485 9.157 1.00 7.93 | C C |
| ATOM | 7510 C TYR I 53 | 1.869 −23.950 7.539 1.00 5.74 | C C |
| ATOM | 7511 O TYR I 53 | 2.281 −22.790 7.558 1.00 6.19 | C O |
| ATOM | 7512 N THR I 54 | 0.756 −24.328 8.159 1.00 6.04 | C N |
| ATOM | 7513 CA THR I 54 | 0.075 −23.456 9.109 1.00 6.67 | C C |
| ATOM | 7514 CB THR I 54 | −1.298 −24.028 9.513 1.00 6.97 | C C |
| ATOM | 7515 OG1 THR I 54 | −2.247 −23.782 8.467 1.00 7.51 | C O |
| ATOM | 7516 CG2 THR I 54 | −1.790 −23.384 10.800 1.00 7.98 | C C |
| ATOM | 7517 C THR I 54 | 0.928 −23.266 10.359 1.00 6.97 | C C |
| ATOM | 7518 O THR I 54 | 1.713 −24.141 10.723 1.00 7.32 | C O |
| ATOM | 7519 N SER I 55 | 0.775 −22.120 11.013 1.00 7.24 | C N |
| ATOM | 7520 CA SER I 55 | 1.085 −22.019 12.433 1.00 7.65 | C C |
| ATOM | 7521 CB SER I 55 | 2.589 −21.862 12.654 1.00 7.69 | C C |
| ATOM | 7522 OG SER I 55 | 2.868 −21.507 13.998 1.00 7.51 | C O |
| ATOM | 7523 C SER I 55 | 0.338 −20.878 13.104 1.00 8.03 | C C |
| ATOM | 7524 O SER I 55 | 0.238 −19.778 12.560 1.00 8.43 | C O |
| ATOM | 7525 N VAL I 56 | −0.094 −21.121 14.335 1.00 8.14 | C N |
| ATOM | 7526 CA VAL I 56 | −1.029 −20.234 15.006 1.00 8.41 | C C |
| ATOM | 7527 CB VAL I 56 | −2.209 −21.014 15.598 1.00 8.72 | C C |
| ATOM | 7528 CG1 VAL I 56 | −3.403 −20.094 15.787 1.00 9.29 | C C |
| ATOM | 7529 CG2 VAL I 56 | −2.569 −22.184 14.695 1.00 9.51 | C C |
| ATOM | 7530 C VAL I 56 | −0.331 −19.478 16.123 1.00 8.19 | C C |
| ATOM | 7531 O VAL I 56 | 0.075 −20.066 17.122 1.00 8.54 | C O |
| ATOM | 7532 N ILE I 57 | −0.187 −18.171 15.943 1.00 7.91 | C N |
| ATOM | 7533 CA ILE I 57 | 0.639 −17.368 16.832 1.00 7.64 | C C |
| ATOM | 7534 CB ILE I 57 | 1.675 −16.539 16.051 1.00 7.35 | C C |
| ATOM | 7535 CG1 ILE I 57 | 2.612 −17.461 15.262 1.00 7.25 | C C |
| ATOM | 7536 CD1 ILE I 57 | 3.526 −16.730 14.294 1.00 8.42 | C C |
| ATOM | 7537 CG2 ILE I 57 | 2.457 −15.632 16.993 1.00 7.52 | C C |
| ATOM | 7538 C ILE I 57 | −0.222 −16.445 17.680 1.00 7.69 | C C |
| ATOM | 7539 O ILE I 57 | −1.150 −15.810 17.178 1.00 7.79 | C O |
| ATOM | 7540 N THR I 58 | −0.024 −16.523 18.989 1.00 7.85 | C N |
| ATOM | 7541 CA THR I 58 | −0.929 −15.900 19.938 1.00 8.15 | C C |
| ATOM | 7542 CB THR I 58 | −1.660 −16.954 20.777 1.00 8.14 | C C |
| ATOM | 7543 OG1 THR I 58 | −1.584 −18.225 20.120 1.00 8.62 | C O |
| ATOM | 7544 CG2 THR I 58 | −3.116 −16.566 20.957 1.00 7.94 | C C |
| ATOM | 7545 C THR I 58 | −0.152 −14.983 20.869 1.00 8.20 | C C |
| ATOM | 7546 O THR I 58 | 0.808 −15.408 21.510 1.00 8.18 | C O |
| ATOM | 7547 N ILE I 59 | −0.539 −13.713 20.903 1.00 8.54 | C N |
| ATOM | 7548 CA ILE I 59 | 0.226 −12.694 21.616 1.00 9.23 | C C |
| ATOM | 7549 CB ILE I 59 | 0.863 −11.690 20.634 1.00 8.92 | C C |
| ATOM | 7550 CG1 ILE I 59 | 1.868 −12.391 19.717 1.00 9.27 | C C |
| ATOM | 7551 CD1 ILE I 59 | 2.587 −11.453 18.770 1.00 10.89 | C C |
| ATOM | 7552 CG2 ILE I 59 | 1.516 −10.544 21.390 1.00 8.74 | C C |
| ATOM | 7553 C ILE I 59 | −0.691 −11.920 22.553 1.00 10.02 | C C |
| ATOM | 7554 O ILE I 59 | −1.692 −11.357 22.113 1.00 10.20 | C O |
| ATOM | 7555 N GLU I 60 | −0.439 −12.007 23.853 1.00 10.95 | C N |
| ATOM | 7556 CA GLU I 60 | −1.462 −11.602 24.808 1.00 12.13 | C C |
| ATOM | 7557 CB GLU I 60 | −0.963 −11.829 26.248 1.00 12.44 | C C |

APPENDIX-continued

| (APPENDIX discloses SEQ ID NOS 29-32, 29-32 and 29-32, respectively, in order of appearance) | | | |
|---|---|---|---|
| ATOM | 7558 CG GLU I 60 | −0.554 −13.288 26.547 1.00 15.04 | C C |
| ATOM | 7559 CD GLU I 60 | −0.560 −13.630 28.036 1.00 19.34 | C C |
| ATOM | 7560 OE1 GLU I 60 | 0.413 −13.267 28.733 1.00 20.63 | C O |
| ATOM | 7561 OE2 GLU I 60 | −1.469 −14.368 28.478 1.00 21.19 | C O |
| ATOM | 7562 C GLU I 60 | −1.856 −10.131 24.547 1.00 12.46 | C C |
| ATOM | 7563 O GLU I 60 | −0.984 −9.259 24.567 1.00 12.68 | C O |
| ATOM | 7564 N LEU I 61 | −3.138 −9.818 24.298 1.00 12.80 | C N |
| ATOM | 7565 CA LEU I 61 | −3.535 −8.473 24.718 1.00 12.71 | C C |
| ATOM | 7566 CB LEU I 61 | −5.021 −8.120 24.699 1.00 12.55 | C C |
| ATOM | 7567 CG LEU I 61 | −5.052 −6.753 25.421 1.00 12.39 | C C |
| ATOM | 7568 CD1 LEU I 61 | −4.358 −5.650 24.625 1.00 13.14 | C C |
| ATOM | 7569 CD2 LEU I 61 | −6.421 −6.318 25.899 1.00 12.50 | C C |
| ATOM | 7570 C LEU I 61 | −3.097 −8.585 26.133 1.00 12.94 | C C |
| ATOM | 7571 O LEU I 61 | −3.578 −9.474 26.843 1.00 12.78 | C O |
| ATOM | 7572 N SER I 62 | −1.846 −8.190 26.260 1.00 13.61 | C N |
| ATOM | 7573 CA SER I 62 | −1.183 −8.231 27.527 1.00 14.70 | C C |
| ATOM | 7574 CB SER I 62 | 0.326 −8.252 27.325 1.00 14.52 | C C |
| ATOM | 7575 OG SER I 62 | 0.724 −9.440 26.664 1.00 14.80 | C O |
| ATOM | 7576 C SER I 62 | −1.605 −6.983 28.261 1.00 15.48 | C C |
| ATOM | 7577 O SER I 62 | −1.206 −5.880 27.893 1.00 15.50 | C O |
| ATOM | 7578 N ASN I 63 | −2.602 −7.135 29.121 1.00 16.61 | C N |
| ATOM | 7579 CA ASN I 63 | −3.232 −5.978 29.716 1.00 17.77 | C C |
| ATOM | 7580 CB ASN I 63 | −4.616 −6.314 30.263 1.00 17.73 | C C |
| ATOM | 7581 CG ASN I 63 | −5.566 −5.142 30.175 1.00 18.52 | C C |
| ATOM | 7582 OD1 ASN I 63 | −5.140 −3.987 30.185 1.00 18.29 | C O |
| ATOM | 7583 ND2 ASN I 63 | −6.837 −5.433 29.933 1.00 19.40 | C N |
| ATOM | 7584 C ASN I 63 | −2.369 −5.335 30.787 1.00 18.53 | C C |
| ATOM | 7585 O ASN I 63 | −1.589 −6.007 31.463 1.00 18.82 | C O |
| ATOM | 7586 N ILE I 64 | −2.403 −4.010 30.819 1.00 19.60 | C N |
| ATOM | 7587 CA ILE I 64 | −1.812 −3.252 31.908 1.00 21.04 | C C |
| ATOM | 7588 CB ILE I 64 | −1.433 −1.836 31.448 1.00 20.60 | C C |
| ATOM | 7589 CG1 ILE I 64 | −0.845 −1.878 30.038 1.00 20.13 | C C |
| ATOM | 7590 CD1 ILE I 64 | −0.383 −0.534 29.522 1.00 20.19 | C C |
| ATOM | 7591 CG2 ILE I 64 | −0.451 −1.211 32.416 1.00 20.74 | C C |
| ATOM | 7592 C ILE I 64 | −2.778 −3.148 33.082 1.00 22.58 | C C |
| ATOM | 7593 O ILE I 64 | −3.951 −2.832 32.900 1.00 23.07 | C O |
| ATOM | 7594 N LYS I 65 | −2.259 −3.322 34.292 1.00 24.21 | C N |
| ATOM | 7595 CA LYS I 65 | −2.904 −2.779 35.482 1.00 25.86 | C C |
| ATOM | 7596 CB LYS I 65 | −2.929 −3.822 36.602 1.00 25.90 | C C |
| ATOM | 7597 CG LYS I 65 | −2.083 −5.056 36.323 1.00 26.69 | C C |
| ATOM | 7598 CD LYS I 65 | −0.616 −4.698 36.160 1.00 28.26 | C C |
| ATOM | 7599 CE LYS I 65 | 0.273 −5.606 36.992 1.00 28.67 | C C |
| ATOM | 7600 NZ LYS I 65 | 1.600 −4.983 37.247 1.00 28.95 | C N |
| ATOM | 7601 C LYS I 65 | −2.215 −1.500 35.961 1.00 26.81 | C C |
| ATOM | 7602 O LYS I 65 | −1.160 −1.557 36.591 1.00 26.72 | C O |
| ATOM | 7603 N GLU I 66 | −2.903 −0.371 35.798 1.00 27.90 | C N |
| ATOM | 7604 CA GLU I 66 | −2.291 0.962 35.878 1.00 28.82 | C C |
| ATOM | 7605 CB GLU I 66 | −3.184 1.983 35.163 1.00 28.88 | C C |
| ATOM | 7606 CG GLU I 66 | −3.354 3.309 35.901 1.00 30.33 | C C |
| ATOM | 7607 CD GLU I 66 | −4.570 4.084 35.431 1.00 33.17 | C C |
| ATOM | 7608 OE1 GLU I 66 | −4.590 5.323 35.595 1.00 35.05 | C O |
| ATOM | 7609 OE2 GLU I 66 | −5.488 3.457 34.860 1.00 33.14 | C O |
| ATOM | 7610 C GLU I 66 | −2.102 1.393 37.333 1.00 29.12 | C C |
| ATOM | 7611 O GLU I 66 | −3.002 1.204 38.148 1.00 29.28 | C O |
| ATOM | 7612 N ASN I 67 | −0.975 2.029 37.653 1.00 29.32 | C N |
| ATOM | 7613 CA ASN I 67 | −0.630 2.266 39.065 1.00 29.39 | C C |
| ATOM | 7614 CB ASN I 67 | 0.664 1.550 39.473 1.00 29.62 | C C |
| ATOM | 7615 CG ASN I 67 | 0.399 0.206 40.133 1.00 29.84 | C C |
| ATOM | 7616 OD1 ASN I 67 | −0.154 0.147 41.233 1.00 29.93 | C O |
| ATOM | 7617 ND2 ASN I 67 | 0.655 −0.875 39.400 1.00 29.22 | C N |
| ATOM | 7618 C ASN I 67 | −0.670 3.712 39.571 1.00 29.15 | C C |
| ATOM | 7619 O ASN I 67 | 0.352 4.281 39.962 1.00 29.06 | C O |
| ATOM | 7620 N LYS I 68 | −1.872 4.284 39.584 1.00 28.87 | C N |
| ATOM | 7621 CA LYS I 68 | −2.302 5.212 40.630 1.00 28.78 | C C |
| ATOM | 7622 CB LYS I 68 | −3.436 4.596 41.454 1.00 28.89 | C C |
| ATOM | 7623 CG LYS I 68 | −4.461 3.838 40.617 1.00 29.26 | C C |
| ATOM | 7624 CD LYS I 68 | −5.357 2.964 41.483 1.00 29.68 | C C |
| ATOM | 7625 CE LYS I 68 | −5.626 3.615 42.835 1.00 29.46 | C C |
| ATOM | 7626 NZ LYS I 68 | −6.764 2.972 43.555 1.00 29.58 | C N |
| ATOM | 7627 C LYS I 68 | −1.171 5.722 41.535 1.00 28.60 | C C |
| ATOM | 7628 O LYS I 68 | −1.082 5.347 42.703 1.00 28.64 | C O |
| ATOM | 7629 N CYS I 69 | −0.274 6.525 40.961 1.00 28.09 | C N |
| ATOM | 7630 CA CYS I 69 | 0.585 7.455 41.715 1.00 27.63 | C C |
| ATOM | 7631 CB CYS I 69 | 2.068 7.270 41.326 1.00 27.07 | C C |
| ATOM | 7632 SG CYS I 69 | 2.742 8.433 40.058 1.00 28.01 | C S |
| ATOM | 7633 C CYS I 69 | 0.143 8.893 41.433 1.00 27.69 | C C |
| ATOM | 7634 O CYS I 69 | −0.588 9.134 40.473 1.00 27.41 | C O |

APPENDIX-continued (APPENDIX discloses SEQ ID NOS 29-32, 29-32 and 29-32, respectively, in order of appearance)

| | | | |
|---|---|---|---|
| ATOM | 7635 N ASN I 70 | 0.615 9.855 42.226 1.00 28.06 | C N |
| ATOM | 7636 CA ASN I 70 | 0.603 11.259 41.794 1.00 28.87 | C C |
| ATOM | 7637 CB ASN I 70 | −0.364 12.119 42.626 1.00 30.52 | C C |
| ATOM | 7638 CG ASN I 70 | −1.286 11.299 43.518 1.00 39.60 | C C |
| ATOM | 7639 OD1 ASN I 70 | −2.181 10.602 43.040 1.00 44.97 | C O |
| ATOM | 7640 ND2 ASN I 70 | −1.073 11.402 44.831 1.00 51.04 | C N |
| ATOM | 7641 C ASN I 70 | 1.978 11.934 41.727 1.00 26.97 | C C |
| ATOM | 7642 O ASN I 70 | 2.563 12.257 42.761 1.00 26.50 | C O |
| ATOM | 7643 N GLY I 71 | 2.371 12.349 40.523 1.00 25.46 | C N |
| ATOM | 7644 CA GLY I 71 | 3.643 13.052 40.316 1.00 23.67 | C C |
| ATOM | 7645 C GLY I 71 | 3.501 14.565 40.288 1.00 22.81 | C C |
| ATOM | 7646 O GLY I 71 | 2.415 15.094 40.516 1.00 22.79 | C O |
| ATOM | 7647 N THR I 72 | 4.585 15.268 39.975 1.00 21.93 | C N |
| ATOM | 7648 CA THR I 72 | 4.526 16.721 39.835 1.00 21.30 | C C |
| ATOM | 7649 CB THR I 72 | 5.923 17.363 39.940 1.00 21.12 | C C |
| ATOM | 7650 OG1 THR I 72 | 6.624 17.194 38.702 1.00 19.87 | C O |
| ATOM | 7651 CG2 THR I 72 | 6.725 16.723 41.063 1.00 20.76 | C C |
| ATOM | 7652 C THR I 72 | 3.864 17.132 38.518 1.00 21.50 | C C |
| ATOM | 7653 O THR I 72 | 4.384 16.852 37.438 1.00 21.85 | C O |
| ATOM | 7654 N ASP I 73 | 2.703 17.774 38.617 1.00 21.43 | C N |
| ATOM | 7655 CA ASP I 73 | 1.767 17.891 37.494 1.00 21.46 | C C |
| ATOM | 7656 CB ASP I 73 | 2.361 18.743 36.368 1.00 21.69 | C C |
| ATOM | 7657 CG ASP I 73 | 1.457 18.812 35.149 1.00 22.46 | C C |
| ATOM | 7658 OD1 ASP I 73 | 0.542 17.969 35.035 1.00 23.01 | C O |
| ATOM | 7659 OD2 ASP I 73 | 1.682 19.690 34.289 1.00 23.09 | C O |
| ATOM | 7660 C ASP I 73 | 1.323 16.536 36.950 1.00 20.96 | C C |
| ATOM | 7661 O ASP I 73 | 2.128 15.792 36.390 1.00 20.61 | C O |
| ATOM | 7662 N ALA I 74 | 0.019 16.285 36.989 1.00 20.42 | C N |
| ATOM | 7663 CA ALA I 74 | −0.512 14.977 36.622 1.00 20.38 | C C |
| ATOM | 7664 CB ALA I 74 | −1.027 14.248 37.855 1.00 20.11 | C C |
| ATOM | 7665 C ALA I 74 | −1.602 15.058 35.556 1.00 20.45 | C C |
| ATOM | 7666 O ALA I 74 | −2.490 14.208 35.509 1.00 20.46 | C O |
| ATOM | 7667 N LYS I 75 | −1.583 16.114 34.750 1.00 20.67 | C N |
| ATOM | 7668 CA LYS I 75 | −2.473 16.188 33.596 1.00 20.99 | C C |
| ATOM | 7669 CB LYS I 75 | −2.421 17.583 32.970 1.00 21.20 | C C |
| ATOM | 7670 CG LYS I 75 | −2.967 18.684 33.865 1.00 22.02 | C C |
| ATOM | 7671 CD LYS I 75 | −1.927 19.766 34.106 1.00 23.66 | C C |
| ATOM | 7672 CE LYS I 75 | −1.971 20.263 35.542 1.00 24.93 | C C |
| ATOM | 7673 NZ LYS I 75 | −0.622 20.658 36.036 1.00 25.55 | C N |
| ATOM | 7674 C LYS I 75 | −2.025 15.144 32.587 1.00 20.92 | C C |
| ATOM | 7675 O LYS I 75 | −2.801 14.680 31.751 1.00 20.92 | C O |
| ATOM | 7676 N VAL I 76 | −0.731 14.853 32.634 1.00 20.63 | C N |
| ATOM | 7677 CA VAL I 76 | −0.147 13.700 31.971 1.00 20.36 | C C |
| ATOM | 7678 CB VAL I 76 | 1.386 13.792 32.017 1.00 20.25 | C C |
| ATOM | 7679 CG1 VAL I 76 | 2.009 12.475 31.612 1.00 20.82 | C C |
| ATOM | 7680 CG2 VAL I 76 | 1.873 14.923 31.130 1.00 20.09 | C C |
| ATOM | 7681 C VAL I 76 | −0.586 12.393 32.629 1.00 20.29 | C C |
| ATOM | 7682 O VAL I 76 | −0.452 12.225 33.840 1.00 20.21 | C O |
| ATOM | 7683 N LYS I 77 | −1.106 11.471 31.826 1.00 20.17 | C N |
| ATOM | 7684 CA LYS I 77 | −1.642 10.218 32.348 1.00 20.17 | C C |
| ATOM | 7685 CB LYS I 77 | −3.103 10.393 32.760 1.00 20.62 | C C |
| ATOM | 7686 CG LYS I 77 | −3.297 10.767 34.215 1.00 23.31 | C C |
| ATOM | 7687 CD LYS I 77 | −4.508 11.664 34.388 1.00 26.74 | C C |
| ATOM | 7688 CE LYS I 77 | −4.529 12.291 35.767 1.00 28.32 | C C |
| ATOM | 7689 NZ LYS I 77 | −5.869 12.836 36.105 1.00 29.66 | C N |
| ATOM | 7690 C LYS I 77 | −1.523 9.105 31.317 1.00 19.45 | C C |
| ATOM | 7691 O LYS I 77 | −2.517 8.496 30.921 1.00 19.36 | C O |
| ATOM | 7692 N LEU I 78 | −0.297 8.863 30.871 1.00 18.70 | C N |
| ATOM | 7693 CA LEU I 78 | −0.064 8.098 29.659 1.00 17.98 | C C |
| ATOM | 7694 CB LEU I 78 | 1.419 7.775 29.528 1.00 17.72 | C C |
| ATOM | 7695 CG LEU I 78 | 2.275 9.033 29.591 1.00 17.51 | C C |
| ATOM | 7696 CD1 LEU I 78 | 3.746 8.676 29.494 1.00 17.41 | C C |
| ATOM | 7697 CD2 LEU I 78 | 1.859 9.984 28.480 1.00 17.62 | C C |
| ATOM | 7698 C LEU I 78 | −0.882 6.820 29.656 1.00 17.77 | C C |
| ATOM | 7699 O LEU I 78 | −1.665 6.576 28.739 1.00 17.89 | C O |
| ATOM | 7700 N ILE I 79 | −0.749 6.036 30.717 1.00 17.29 | C N |
| ATOM | 7701 CA ILE I 79 | −1.319 4.703 30.726 1.00 17.00 | C C |
| ATOM | 7702 CB ILE I 79 | −0.968 3.948 32.005 1.00 16.96 | C C |
| ATOM | 7703 CG1 ILE I 79 | 0.550 3.801 32.113 1.00 17.21 | C C |
| ATOM | 7704 CD1 ILE I 79 | 1.020 3.244 33.429 1.00 17.51 | C C |
| ATOM | 7705 CG2 ILE I 79 | −1.643 2.587 32.005 1.00 17.30 | C C |
| ATOM | 7706 C ILE I 79 | −2.828 4.750 30.547 1.00 16.83 | C C |
| ATOM | 7707 O ILE I 79 | −3.365 4.160 29.609 1.00 17.02 | C O |
| ATOM | 7708 N LYS I 80 | −3.616 5.565 31.220 1.00 16.55 | C N |
| ATOM | 7709 CA LYS I 80 | −5.043 5.447 30.835 1.00 16.38 | C C |
| ATOM | 7710 CB LYS I 80 | −5.918 6.332 31.725 1.00 16.73 | C C |
| ATOM | 7711 CG LYS I 80 | −7.025 7.055 30.971 1.00 17.99 | C C |

APPENDIX-continued (APPENDIX discloses SEQ ID NOS 29-32, 29-32 and 29-32, respectively, in order of appearance)

| | | | |
|---|---|---|---|
| ATOM | 7712 CD LYS I 80 | −8.237 7.295 31.854 1.00 20.71 | C C |
| ATOM | 7713 CE LYS I 80 | −9.171 6.094 31.833 1.00 22.92 | C C |
| ATOM | 7714 NZ LYS I 80 | −8.439 4.818 32.068 1.00 24.75 | C N |
| ATOM | 7715 C LYS I 80 | −5.386 5.716 29.328 1.00 15.79 | C C |
| ATOM | 7716 O LYS I 80 | −6.140 4.942 28.677 1.00 15.32 | C O |
| ATOM | 7717 N GLN I 81 | −4.802 6.770 28.763 1.00 15.48 | C N |
| ATOM | 7718 CA GLN I 81 | −5.092 7.178 27.383 1.00 15.33 | C C |
| ATOM | 7719 CB GLN I 81 | −4.378 8.495 27.068 1.00 15.70 | C C |
| ATOM | 7720 CG GLN I 81 | −4.522 9.557 28.146 1.00 17.88 | C C |
| ATOM | 7721 CD GLN I 81 | −3.631 10.759 27.903 1.00 20.46 | C C |
| ATOM | 7722 OE1 GLN I 81 | −3.065 10.916 26.822 1.00 21.59 | C O |
| ATOM | 7723 NE2 GLN I 81 | −3.498 11.613 28.913 1.00 20.26 | C N |
| ATOM | 7724 C GLN I 81 | −4.708 6.125 26.341 1.00 14.63 | C C |
| ATOM | 7725 O GLN I 81 | −5.438 5.881 25.360 1.00 14.60 | C O |
| ATOM | 7726 N GLU I 82 | −3.556 5.500 26.560 1.00 13.81 | C N |
| ATOM | 7727 CA GLU I 82 | −3.078 4.470 25.657 1.00 13.37 | C C |
| ATOM | 7728 CB GLU I 82 | −1.705 3.958 26.094 1.00 13.20 | C C |
| ATOM | 7729 CG GLU I 82 | −0.528 4.666 25.439 1.00 15.04 | C C |
| ATOM | 7730 CD GLU I 82 | −0.472 4.436 23.942 1.00 17.51 | C C |
| ATOM | 7731 OE1 GLU I 82 | 0.319 3.576 23.502 1.00 18.22 | C O |
| ATOM | 7732 OE2 GLU I 82 | −1.211 5.121 23.205 1.00 17.87 | C O |
| ATOM | 7733 C GLU I 82 | −4.079 3.333 25.659 1.00 12.99 | C C |
| ATOM | 7734 O GLU I 82 | −4.400 2.779 24.610 1.00 12.89 | C O |
| ATOM | 7735 N LEU I 83 | −4.593 3.001 26.838 1.00 12.89 | C N |
| ATOM | 7736 CA LEU I 83 | −5.558 1.919 26.944 1.00 13.08 | C C |
| ATOM | 7737 CB LEU I 83 | −5.923 1.668 28.407 1.00 13.26 | C C |
| ATOM | 7738 CG LEU I 83 | −4.774 1.250 29.325 1.00 14.18 | C C |
| ATOM | 7739 CD1 LEU I 83 | −5.293 0.948 30.721 1.00 15.11 | C C |
| ATOM | 7740 CD2 LEU I 83 | −4.036 0.051 28.748 1.00 14.79 | C C |
| ATOM | 7741 C LEU I 83 | −6.808 2.252 26.144 1.00 13.18 | C C |
| ATOM | 7742 O LEU I 83 | −7.310 1.410 25.386 1.00 13.05 | C O |
| ATOM | 7743 N ASP I 84 | −7.286 3.490 26.251 1.00 13.56 | C N |
| ATOM | 7744 CA ASP I 84 | −8.478 3.834 25.467 1.00 14.15 | C C |
| ATOM | 7745 CB ASP I 84 | −8.946 5.258 25.781 1.00 14.80 | C C |
| ATOM | 7746 CG ASP I 84 | −9.044 5.529 27.268 1.00 18.26 | C C |
| ATOM | 7747 OD1 ASP I 84 | −10.133 5.330 27.846 1.00 21.11 | C O |
| ATOM | 7748 OD2 ASP I 84 | −8.032 5.959 27.858 1.00 22.12 | C O |
| ATOM | 7749 C ASP I 84 | −8.226 3.703 23.954 1.00 13.56 | C C |
| ATOM | 7750 O ASP I 84 | −9.062 3.149 23.192 1.00 13.70 | C O |
| ATOM | 7751 N LYS I 85 | −7.062 4.182 23.517 1.00 12.87 | C N |
| ATOM | 7752 CA LYS I 85 | −6.752 4.121 22.089 1.00 12.31 | C C |
| ATOM | 7753 CB LYS I 85 | −5.424 4.816 21.793 1.00 12.41 | C C |
| ATOM | 7754 CG LYS I 85 | −5.118 4.954 20.308 1.00 12.26 | C C |
| ATOM | 7755 CD LYS I 85 | −3.659 5.305 20.076 1.00 12.72 | C C |
| ATOM | 7756 CE LYS I 85 | −2.751 4.171 20.519 1.00 14.40 | C C |
| ATOM | 7757 NZ LYS I 85 | −1.316 4.445 20.230 1.00 16.45 | C N |
| ATOM | 7758 C LYS I 85 | −6.691 2.671 21.621 1.00 11.85 | C C |
| ATOM | 7759 O LYS I 85 | −7.187 2.312 20.537 1.00 11.66 | C O |
| ATOM | 7760 N TYR I 86 | −6.085 1.836 22.457 1.00 11.32 | C N |
| ATOM | 7761 CA TYR I 86 | −5.931 0.432 22.135 1.00 11.07 | C C |
| ATOM | 7762 CB TYR I 86 | −5.115 −0.290 23.203 1.00 11.12 | C C |
| ATOM | 7763 CG TYR I 86 | −5.391 −1.773 23.243 1.00 11.30 | C C |
| ATOM | 7764 CD1 TYR I 86 | −4.884 −2.621 22.268 1.00 12.16 | C C |
| ATOM | 7765 CE1 TYR I 86 | −5.140 −3.977 22.297 1.00 12.39 | C C |
| ATOM | 7766 CZ TYR I 86 | −5.916 −4.500 23.308 1.00 12.62 | C C |
| ATOM | 7767 OH TYR I 86 | −6.174 −5.852 23.343 1.00 12.72 | C O |
| ATOM | 7768 CE2 TYR I 86 | −6.434 −3.680 24.286 1.00 11.38 | C C |
| ATOM | 7769 CD2 TYR I 86 | −6.173 −2.325 24.248 1.00 11.05 | C C |
| ATOM | 7770 C TYR I 86 | −7.290 −0.219 22.008 1.00 10.75 | C C |
| ATOM | 7771 O TYR I 86 | −7.517 −1.004 21.098 1.00 10.45 | C O |
| ATOM | 7772 N LYS I 87 | −8.204 0.123 22.908 1.00 10.66 | C N |
| ATOM | 7773 CA LYS I 87 | −9.533 −0.467 22.847 1.00 11.03 | C C |
| ATOM | 7774 CB LYS I 87 | −10.389 0.010 24.021 1.00 11.36 | C C |
| ATOM | 7775 CG LYS I 87 | −9.786 −0.270 25.384 1.00 12.79 | C C |
| ATOM | 7776 CD LYS I 87 | −10.675 0.264 26.495 1.00 14.76 | C C |
| ATOM | 7777 CE LYS I 87 | −10.068 −0.017 27.859 1.00 15.29 | C C |
| ATOM | 7778 NZ LYS I 87 | −10.924 0.485 28.970 1.00 16.27 | C N |
| ATOM | 7779 C LYS I 87 | −10.208 −0.098 21.530 1.00 10.83 | C C |
| ATOM | 7780 O LYS I 87 | −10.800 −0.963 20.857 1.00 11.11 | C O |
| ATOM | 7781 N ASN I 88 | −10.089 1.168 21.126 1.00 10.52 | C N |
| ATOM | 7782 CA ASN I 88 | −10.721 1.545 19.858 1.00 10.21 | C C |
| ATOM | 7783 CB ASN I 88 | −10.592 3.050 19.614 1.00 10.61 | C C |
| ATOM | 7784 CG ASN I 88 | −11.178 3.480 18.281 1.00 11.81 | C C |
| ATOM | 7785 OD1 ASN I 88 | −12.114 2.864 17.772 1.00 12.97 | C O |
| ATOM | 7786 ND2 ASN I 88 | −10.625 4.543 17.709 1.00 13.82 | C N |
| ATOM | 7787 C ASN I 88 | −10.128 0.767 18.674 1.00 9.42 | C C |
| ATOM | 7788 O ASN I 88 | −10.858 0.237 17.796 1.00 8.94 | C O |

APPENDIX-continued (APPENDIX discloses SEQ ID NOS 29-32, 29-32 and 29-32, respectively, in order of appearance)

| | | | |
|---|---|---|---|
| ATOM | 7789 N ALA I 89 | −8.802 0.652 18.677 1.00 8.77 | C N |
| ATOM | 7790 CA ALA I 89 | −8.130 −0.041 17.586 1.00 8.21 | C C |
| ATOM | 7791 CB ALA I 89 | −6.623 0.040 17.751 1.00 7.99 | C C |
| ATOM | 7792 C ALA I 89 | −8.588 −1.493 17.543 1.00 7.78 | C C |
| ATOM | 7793 O ALA I 89 | −8.826 −2.057 16.472 1.00 7.88 | C O |
| ATOM | 7794 N VAL I 90 | −8.718 −2.086 18.724 1.00 7.01 | C N |
| ATOM | 7795 CA VAL I 90 | −9.124 −3.474 18.849 1.00 6.26 | C C |
| ATOM | 7796 CB VAL I 90 | −9.079 −3.943 20.313 1.00 5.91 | C C |
| ATOM | 7797 CG1 VAL I 90 | −9.557 −5.381 20.422 1.00 5.92 | C C |
| ATOM | 7798 CG2 VAL I 90 | −7.671 −3.802 20.871 1.00 5.26 | C C |
| ATOM | 7799 C VAL I 90 | −10.524 −3.689 18.299 1.00 6.25 | C C |
| ATOM | 7800 O VAL I 90 | −10.765 −4.663 17.592 1.00 6.32 | C O |
| ATOM | 7801 N THR I 91 | −11.445 −2.776 18.592 1.00 6.24 | C N |
| ATOM | 7802 CA THR I 91 | −12.799 −2.932 18.065 1.00 6.68 | C C |
| ATOM | 7803 CB THR I 91 | −13.734 −1.829 18.584 1.00 6.62 | C C |
| ATOM | 7804 OG1 THR I 91 | −13.711 −1.819 20.017 1.00 7.19 | C O |
| ATOM | 7805 CG2 THR I 91 | −15.157 −2.071 18.106 1.00 7.27 | C C |
| ATOM | 7806 C THR I 91 | −12.768 −2.885 16.536 1.00 7.02 | C C |
| ATOM | 7807 O THR I 91 | −13.430 −3.703 15.833 1.00 7.16 | C O |
| ATOM | 7808 N GLU I 92 | −11.970 −1.955 16.011 1.00 7.31 | C N |
| ATOM | 7809 CA GLU I 92 | −11.889 −1.863 14.558 1.00 7.81 | C C |
| ATOM | 7810 CB GLU I 92 | −11.017 −0.680 14.131 1.00 8.23 | C C |
| ATOM | 7811 CG GLU I 92 | −11.774 0.630 13.973 1.00 10.91 | C C |
| ATOM | 7812 CD GLU I 92 | −12.907 0.529 12.969 1.00 14.95 | C C |
| ATOM | 7813 OE1 GLU I 92 | −12.739 1.010 11.830 1.00 16.14 | C O |
| ATOM | 7814 OE2 GLU I 92 | −13.968 −0.027 13.320 1.00 16.53 | C O |
| ATOM | 7815 C GLU I 92 | −11.349 −3.164 13.959 1.00 7.47 | C C |
| ATOM | 7816 O GLU I 92 | −11.911 −3.691 12.994 1.00 7.32 | C O |
| ATOM | 7817 N LEU I 93 | −10.303 −3.716 14.568 1.00 7.30 | C N |
| ATOM | 7818 CA LEU I 93 | −9.703 −4.950 14.062 1.00 7.47 | C C |
| ATOM | 7819 CB LEU I 93 | −8.429 −5.299 14.830 1.00 7.15 | C C |
| ATOM | 7820 CG LEU I 93 | −7.212 −4.438 14.490 1.00 7.20 | C C |
| ATOM | 7821 CD1 LEU I 93 | −5.977 −4.957 15.204 1.00 7.93 | C C |
| ATOM | 7822 CD2 LEU I 93 | −6.989 −4.392 12.984 1.00 6.91 | C C |
| ATOM | 7823 C LEU I 93 | −10.705 −6.097 14.123 1.00 7.89 | C C |
| ATOM | 7824 O LEU I 93 | −10.764 −6.947 13.235 1.00 7.94 | C O |
| ATOM | 7825 N GLN I 94 | −11.486 −6.094 15.193 1.00 8.31 | C N |
| ATOM | 7826 CA GLN I 94 | −12.514 −7.088 15.461 1.00 9.05 | C C |
| ATOM | 7827 CB GLN I 94 | −13.131 −6.862 16.845 1.00 9.18 | C C |
| ATOM | 7828 CG GLN I 94 | −12.158 −7.052 17.996 1.00 10.79 | C C |
| ATOM | 7829 CD GLN I 94 | −12.831 −6.966 19.353 1.00 13.82 | C C |
| ATOM | 7830 OE1 GLN I 94 | −14.042 −6.762 19.448 1.00 14.98 | C O |
| ATOM | 7831 NE2 GLN I 94 | −12.047 −7.125 20.412 1.00 15.25 | C N |
| ATOM | 7832 C GLN I 94 | −13.615 −7.127 14.405 1.00 9.25 | C C |
| ATOM | 7833 O GLN I 94 | −14.122 −8.204 14.093 1.00 9.43 | C O |
| ATOM | 7834 N LEU I 95 | −14.007 −5.977 13.858 1.00 9.55 | C N |
| ATOM | 7835 CA LEU I 95 | −15.128 −6.009 12.888 1.00 10.17 | C C |
| ATOM | 7836 CB LEU I 95 | −15.535 −4.582 12.510 1.00 9.79 | C C |
| ATOM | 7837 CG LEU I 95 | −16.117 −3.716 13.628 1.00 8.86 | C C |
| ATOM | 7838 CD1 LEU I 95 | −16.419 −2.315 13.117 1.00 8.31 | C C |
| ATOM | 7839 CD2 LEU I 95 | −17.367 −4.359 14.211 1.00 7.62 | C C |
| ATOM | 7840 C LEU I 95 | −14.958 −6.865 11.591 1.00 11.22 | C C |
| ATOM | 7841 O LEU I 95 | −15.902 −7.505 11.125 1.00 11.55 | C O |
| ATOM | 7842 N LEU I 96 | −13.751 −6.843 11.039 1.00 12.40 | C N |
| ATOM | 7843 CA LEU I 96 | −13.313 −7.374 9.755 1.00 13.66 | C C |
| ATOM | 7844 CB LEU I 96 | −11.796 −7.246 9.601 1.00 13.38 | C C |
| ATOM | 7845 CG LEU I 96 | −11.288 −5.847 9.244 1.00 13.32 | C C |
| ATOM | 7846 CD1 LEU I 96 | −9.901 −5.910 8.624 1.00 12.84 | C C |
| ATOM | 7847 CD2 LEU I 96 | −12.256 −5.161 8.301 1.00 13.38 | C C |
| ATOM | 7848 C LEU I 96 | −13.765 −8.817 9.534 1.00 14.97 | C C |
| ATOM | 7849 O LEU I 96 | −13.908 −9.257 8.395 1.00 15.21 | C O |
| ATOM | 7850 N MET I 97 | −14.125 −9.501 10.615 1.00 16.74 | C N |
| ATOM | 7851 CA MET I 97 | −14.122 −10.962 10.625 1.00 18.96 | C C |
| ATOM | 7852 CB MET I 97 | −13.987 −11.498 12.053 1.00 19.12 | C C |
| ATOM | 7853 CG MET I 97 | −12.742 −11.021 12.784 1.00 21.87 | C C |
| ATOM | 7854 SD MET I 97 | −11.220 −11.692 12.090 1.00 27.46 | C S |
| ATOM | 7855 CE MET I 97 | −11.585 −11.630 10.338 1.00 24.25 | C C |
| ATOM | 7856 C MET I 97 | −15.339 −11.576 9.929 1.00 20.09 | C C |
| ATOM | 7857 O MET I 97 | −15.246 −12.655 9.343 1.00 20.58 | C O |
| ATOM | 7858 N GLN I 98 | −16.462 −10.865 9.950 1.00 21.33 | C N |
| ATOM | 7859 CA GLN I 98 | −17.706 −11.392 9.401 1.00 22.21 | C C |
| ATOM | 7860 CB GLN I 98 | −18.708 −11.678 10.521 1.00 22.53 | C C |
| ATOM | 7861 CG GLN I 98 | −18.099 −12.341 11.742 1.00 23.85 | C C |
| ATOM | 7862 CD GLN I 98 | −17.673 −11.337 12.792 1.00 25.21 | C C |
| ATOM | 7863 OE1 GLN I 98 | −16.838 −10.469 12.535 1.00 24.47 | C O |
| ATOM | 7864 NE2 GLN I 98 | −18.199 −11.489 14.002 1.00 24.85 | C N |
| ATOM | 7865 C GLN I 98 | −18.318 −10.439 8.378 1.00 22.15 | C C |

APPENDIX-continued (APPENDIX discloses SEQ ID NOS 29-32, 29-32 and 29-32, respectively, in order of appearance)

| | | | |
|---|---|---|---|
| ATOM | 7866 O GLN I 98 | −17.765 −9.376 8.095 1.00 21.77 | C O |
| ATOM | 7867 N PHE I 137 | −22.709 −16.921 4.271 1.00 33.25 | C N |
| ATOM | 7868 CA PHE I 137 | −21.644 −16.142 3.651 1.00 36.79 | C C |
| ATOM | 7869 CB PHE I 137 | −21.061 −16.892 2.453 1.00 20.00 | C C |
| ATOM | 7870 CG PHE I 137 | −20.354 −18.166 2.825 1.00 20.00 | C C |
| ATOM | 7871 CD1 PHE I 137 | −19.059 −18.134 3.318 1.00 20.00 | C C |
| ATOM | 7872 CE1 PHE I 137 | −18.416 −19.301 3.700 1.00 20.00 | C C |
| ATOM | 7873 CZ PHE I 137 | −19.092 −20.504 3.660 1.00 20.00 | C C |
| ATOM | 7874 CE2 PHE I 137 | −20.414 −20.534 3.260 1.00 20.00 | C C |
| ATOM | 7875 CD2 PHE I 137 | −21.046 −19.365 2.871 1.00 20.00 | C C |
| ATOM | 7876 C PHE I 137 | −22.138 −14.765 3.226 1.00 48.73 | C C |
| ATOM | 7877 O PHE I 137 | −21.342 −13.888 2.890 1.00 49.28 | C O |
| ATOM | 7878 N LEU I 138 | −23.454 −14.580 3.253 1.00 42.04 | C N |
| ATOM | 7879 CA LEU I 138 | −24.055 −13.275 2.999 1.00 44.26 | C C |
| ATOM | 7880 CB LEU I 138 | −25.581 −13.366 3.047 1.00 20.00 | C C |
| ATOM | 7881 CG LEU I 138 | −26.248 −14.219 1.966 1.00 20.00 | C C |
| ATOM | 7882 CD1 LEU I 138 | −27.748 −14.301 2.197 1.00 20.00 | C C |
| ATOM | 7883 CD2 LEU I 138 | −25.944 −13.673 0.580 1.00 20.00 | C C |
| ATOM | 7884 C LEU I 138 | −23.565 −12.242 4.006 1.00 43.68 | C C |
| ATOM | 7885 O LEU I 138 | −23.730 −11.038 3.804 1.00 50.27 | C O |
| ATOM | 7886 N GLY I 139 | −22.983 −12.724 5.100 1.00 38.56 | C N |
| ATOM | 7887 CA GLY I 139 | −22.415 −11.853 6.126 1.00 47.99 | C C |
| ATOM | 7888 C GLY I 139 | −21.274 −10.985 5.625 1.00 44.53 | C C |
| ATOM | 7889 O GLY I 139 | −20.971 −9.947 6.213 1.00 32.21 | C O |
| ATOM | 7890 N PHE I 140 | −20.649 −11.402 4.528 1.00 46.33 | C N |
| ATOM | 7891 CA PHE I 140 | −19.494 −10.693 3.986 1.00 42.95 | C C |
| ATOM | 7892 CB PHE I 140 | −18.549 −11.668 3.281 1.00 20.00 | C C |
| ATOM | 7893 CG PHE I 140 | −17.916 −12.677 4.202 1.00 20.00 | C C |
| ATOM | 7894 CD1 PHE I 140 | −16.781 −12.356 4.929 1.00 20.00 | C C |
| ATOM | 7895 CE1 PHE I 140 | −16.194 −13.284 5.769 1.00 20.00 | C C |
| ATOM | 7896 CZ PHE I 140 | −16.731 −14.551 5.879 1.00 20.00 | C C |
| ATOM | 7897 CE2 PHE I 140 | −17.854 −14.888 5.150 1.00 20.00 | C C |
| ATOM | 7898 CD2 PHE I 140 | −18.434 −13.958 4.308 1.00 20.00 | C C |
| ATOM | 7899 C PHE I 140 | −19.898 −9.568 3.032 1.00 38.13 | C C |
| ATOM | 7900 O PHE I 140 | −19.052 −8.795 2.581 1.00 57.33 | C O |
| ATOM | 7901 N LEU I 141 | −21.191 −9.475 2.736 1.00 35.20 | C N |
| ATOM | 7902 CA LEU I 141 | −21.690 −8.512 1.759 1.00 27.01 | C C |
| ATOM | 7903 CB LEU I 141 | −21.184 −7.103 2.079 1.00 20.00 | C C |
| ATOM | 7904 CG LEU I 141 | −21.717 −6.450 3.356 1.00 20.00 | C C |
| ATOM | 7905 CD1 LEU I 141 | −20.991 −5.144 3.632 1.00 20.00 | C C |
| ATOM | 7906 CD2 LEU I 141 | −23.216 −6.216 3.252 1.00 20.00 | C C |
| ATOM | 7907 C LEU I 141 | −21.292 −8.918 0.341 1.00 35.79 | C C |
| ATOM | 7908 O LEU I 141 | −21.674 −9.989 −0.130 1.00 46.92 | C O |
| ATOM | 7909 N LEU I 142 | −20.469 −8.099 −0.306 1.00 38.67 | C N |
| ATOM | 7910 CA LEU I 142 | −19.832 −8.492 −1.559 1.00 33.84 | C C |
| ATOM | 7911 CB LEU I 142 | −20.017 −7.408 −2.618 1.00 20.00 | C C |
| ATOM | 7912 CG LEU I 142 | −21.465 −7.163 −3.040 1.00 20.00 | C C |
| ATOM | 7913 CD1 LEU I 142 | −21.584 −5.883 −3.848 1.00 20.00 | C C |
| ATOM | 7914 CD2 LEU I 142 | −21.999 −8.350 −3.827 1.00 20.00 | C C |
| ATOM | 7915 C LEU I 142 | −18.352 −8.799 −1.363 1.00 36.89 | C C |
| ATOM | 7916 O LEU I 142 | −17.604 −7.979 −0.831 1.00 45.42 | C O |
| ATOM | 7917 N GLY I 143 | −17.970 −10.034 −1.673 1.00 26.84 | C N |
| ATOM | 7918 CA GLY I 143 | −16.624 −10.516 −1.387 1.00 27.41 | C C |
| ATOM | 7919 C GLY I 143 | −15.977 −11.154 −2.599 1.00 29.08 | C C |
| ATOM | 7920 O GLY I 143 | −16.645 −11.813 −3.396 1.00 40.24 | C O |
| ATOM | 7921 N VAL I 144 | −14.672 −10.957 −2.742 1.00 30.17 | C N |
| ATOM | 7922 CA VAL I 144 | −13.928 −11.605 −3.814 1.00 34.15 | C C |
| ATOM | 7923 CB VAL I 144 | −12.559 −10.921 −4.058 1.00 20.00 | C C |
| ATOM | 7924 CG1 VAL I 144 | −11.826 −11.591 −5.212 1.00 20.00 | C C |
| ATOM | 7925 CG2 VAL I 144 | −12.750 −9.434 −4.339 1.00 20.00 | C C |
| ATOM | 7926 C VAL I 144 | −13.732 −13.091 −3.508 1.00 36.67 | C C |
| ATOM | 7927 O VAL I 144 | −14.071 −13.558 −2.419 1.00 42.49 | C O |
| ATOM | 7928 N GLY I 145 | −13.320 −13.847 −4.521 1.00 47.09 | C N |
| ATOM | 7929 CA GLY I 145 | −12.893 −15.227 −4.321 1.00 44.51 | C C |
| ATOM | 7930 C GLY I 145 | −11.950 −15.377 −3.141 1.00 44.94 | C C |
| ATOM | 7931 O GLY I 145 | −12.181 −16.196 −2.253 1.00 40.58 | C O |
| ATOM | 7932 N SER I 146 | −10.905 −14.560 −3.085 1.00 42.06 | C N |
| ATOM | 7933 CA SER I 146 | −9.931 −14.673 −2.000 1.00 47.39 | C C |
| ATOM | 7934 CB SER I 146 | −8.758 −13.718 −2.236 1.00 20.00 | C C |
| ATOM | 7935 OG SER I 146 | −9.200 −12.373 −2.297 1.00 20.00 | C O |
| ATOM | 7936 C SER I 146 | −10.535 −14.425 −0.613 1.00 51.48 | C C |
| ATOM | 7937 O SER I 146 | −10.211 −15.129 0.351 1.00 47.45 | C O |
| ATOM | 7938 N ALA I 147 | −11.415 −13.434 −0.514 1.00 39.51 | C N |
| ATOM | 7939 CA ALA I 147 | −12.026 −13.082 0.766 1.00 43.38 | C C |
| ATOM | 7940 CB ALA I 147 | −12.866 −11.821 0.621 1.00 20.00 | C C |
| ATOM | 7941 C ALA I 147 | −12.865 −14.218 1.348 1.00 47.39 | C C |
| ATOM | 7942 O ALA I 147 | −12.823 −14.476 2.554 1.00 50.18 | C O |

APPENDIX-continued (APPENDIX discloses SEQ ID NOS 29-32, 29-32 and 29-32, respectively, in order of appearance)

| | | | |
|---|---|---|---|
| ATOM | 7943 N ILE I 148 | −13.624 −14.894 0.492 1.00 44.67 | C N |
| ATOM | 7944 CA ILE I 148 | −14.453 −16.007 0.937 1.00 43.56 | C C |
| ATOM | 7945 CB ILE I 148 | −15.322 −16.558 −0.208 1.00 20.00 | C C |
| ATOM | 7946 CG1 ILE I 148 | −16.249 −15.466 −0.746 1.00 20.00 | C C |
| ATOM | 7947 CD1 ILE I 148 | −17.141 −15.925 −1.878 1.00 20.00 | C C |
| ATOM | 7948 CG2 ILE I 148 | −16.127 −17.759 0.265 1.00 20.00 | C C |
| ATOM | 7949 C ILE I 148 | −13.575 −17.126 1.483 1.00 51.18 | C C |
| ATOM | 7950 O ILE I 148 | −13.886 −17.736 2.510 1.00 39.17 | C O |
| ATOM | 7951 N ALA I 149 | −12.468 −17.382 0.794 1.00 42.17 | C N |
| ATOM | 7952 CA ALA I 149 | −11.531 −18.412 1.217 1.00 36.76 | C C |
| ATOM | 7953 CB ALA I 149 | −10.424 −18.578 0.189 1.00 20.00 | C C |
| ATOM | 7954 C ALA I 149 | −10.949 −18.044 2.574 1.00 45.19 | C C |
| ATOM | 7955 O ALA I 149 | −10.806 −18.897 3.451 1.00 47.83 | C O |
| ATOM | 7956 N SER I 150 | −10.632 −16.765 2.748 1.00 43.64 | C N |
| ATOM | 7957 CA SER I 150 | −10.084 −16.296 4.014 1.00 43.46 | C C |
| ATOM | 7958 CB SER I 150 | −9.701 −14.818 3.919 1.00 20.00 | C C |
| ATOM | 7959 OG SER I 150 | −10.828 −14.018 3.605 1.00 20.00 | C O |
| ATOM | 7960 C SER I 150 | −11.093 −16.507 5.138 1.00 44.80 | C C |
| ATOM | 7961 O SER I 150 | −10.733 −16.932 6.238 1.00 41.55 | C O |
| ATOM | 7962 N GLY I 151 | −12.361 −16.222 4.854 1.00 27.01 | C N |
| ATOM | 7963 CA GLY I 151 | −13.413 −16.410 5.836 1.00 35.21 | C C |
| ATOM | 7964 C GLY I 151 | −13.553 −17.871 6.219 1.00 42.40 | C C |
| ATOM | 7965 O GLY I 151 | −13.742 −18.212 7.394 1.00 45.11 | C O |
| ATOM | 7966 N VAL I 152 | −13.454 −18.742 5.219 1.00 40.20 | C N |
| ATOM | 7967 CA VAL I 152 | −13.548 −20.175 5.458 1.00 46.73 | C C |
| ATOM | 7968 CB VAL I 152 | −13.505 −20.973 4.144 1.00 20.00 | C C |
| ATOM | 7969 CG1 VAL I 152 | −13.606 −22.464 4.426 1.00 20.00 | C C |
| ATOM | 7970 CG2 VAL I 152 | −14.621 −20.523 3.214 1.00 20.00 | C C |
| ATOM | 7971 C VAL I 152 | −12.396 −20.615 6.351 1.00 48.62 | C C |
| ATOM | 7972 O VAL I 152 | −12.579 −21.411 7.273 1.00 49.32 | C O |
| ATOM | 7973 N ALA I 153 | −11.212 −20.074 6.083 1.00 35.09 | C N |
| ATOM | 7974 CA ALA I 153 | −10.030 −20.403 6.867 1.00 42.37 | C C |
| ATOM | 7975 CB ALA I 153 | −8.798 −19.741 6.274 1.00 20.00 | C C |
| ATOM | 7976 C ALA I 153 | −10.231 −19.965 8.310 1.00 37.79 | C C |
| ATOM | 7977 O ALA I 153 | −9.860 −20.676 9.244 1.00 39.25 | C O |
| ATOM | 7978 N VAL I 154 | −10.825 −18.789 8.486 1.00 38.88 | C N |
| ATOM | 7979 CA VAL I 154 | −11.100 −18.270 9.819 1.00 35.53 | C C |
| ATOM | 7980 CB VAL I 154 | −11.680 −16.845 9.762 1.00 20.00 | C C |
| ATOM | 7981 CG1 VAL I 154 | −11.955 −16.328 11.165 1.00 20.00 | C C |
| ATOM | 7982 CG2 VAL I 154 | −10.731 −15.916 9.021 1.00 20.00 | C C |
| ATOM | 7983 C VAL I 154 | −12.071 −19.175 10.572 1.00 41.00 | C C |
| ATOM | 7984 O VAL I 154 | −11.884 −19.441 11.759 1.00 50.08 | C O |
| ATOM | 7985 N SER I 155 | −13.105 −19.652 9.882 1.00 37.82 | C N |
| ATOM | 7986 CA SER I 155 | −14.071 −20.556 10.508 1.00 44.68 | C C |
| ATOM | 7987 CB SER I 155 | −15.239 −20.834 9.561 1.00 20.00 | C C |
| ATOM | 7988 OG SER I 155 | −14.790 −21.436 8.360 1.00 20.00 | C O |
| ATOM | 7989 C SER I 155 | −13.400 −21.867 10.917 1.00 41.82 | C C |
| ATOM | 7990 O SER I 155 | −13.667 −22.425 11.982 1.00 49.37 | C O |
| ATOM | 7991 N LYS I 156 | −12.525 −22.338 10.038 1.00 36.99 | C N |
| ATOM | 7992 CA LYS I 156 | −11.772 −23.575 10.184 1.00 35.11 | C C |
| ATOM | 7993 CB LYS I 156 | −11.122 −23.965 8.856 1.00 20.00 | C C |
| ATOM | 7994 CG LYS I 156 | −12.116 −24.339 7.768 1.00 20.00 | C C |
| ATOM | 7995 CD LYS I 156 | −11.408 −24.786 6.499 1.00 20.00 | C C |
| ATOM | 7996 CE LYS I 156 | −12.400 −25.265 5.452 1.00 20.00 | C C |
| ATOM | 7997 NZ LYS I 156 | −11.733 −25.581 4.158 1.00 20.00 | C N |
| ATOM | 7998 C LYS I 156 | −10.715 −23.451 11.275 1.00 35.98 | C C |
| ATOM | 7999 O LYS I 156 | −10.361 −24.436 11.922 1.00 42.31 | C O |
| ATOM | 8000 N VAL I 157 | −10.260 −22.224 11.514 1.00 37.88 | C N |
| ATOM | 8001 CA VAL I 157 | −9.225 −21.960 12.515 1.00 50.94 | C C |
| ATOM | 8002 CB VAL I 157 | −8.267 −20.831 12.062 1.00 20.00 | C C |
| ATOM | 8003 CG1 VAL I 157 | −7.261 −20.505 13.162 1.00 20.00 | C C |
| ATOM | 8004 CG2 VAL I 157 | −7.552 −21.219 10.771 1.00 20.00 | C C |
| ATOM | 8005 C VAL I 157 | −9.832 −21.596 13.871 1.00 47.82 | C C |
| ATOM | 8006 O VAL I 157 | −9.116 −21.443 14.863 1.00 56.87 | C O |
| ATOM | 8007 N LEU I 158 | −11.156 −21.533 13.947 1.00 39.52 | C N |
| ATOM | 8008 CA LEU I 158 | −11.838 −20.969 15.112 1.00 50.27 | C C |
| ATOM | 8009 CB LEU I 158 | −13.351 −20.935 14.869 1.00 20.00 | C C |
| ATOM | 8010 CG LEU I 158 | −13.827 −20.109 13.673 1.00 20.00 | C C |
| ATOM | 8011 CD1 LEU I 158 | −15.343 −20.163 13.552 1.00 20.00 | C C |
| ATOM | 8012 CD2 LEU I 158 | −13.346 −18.671 13.788 1.00 20.00 | C C |
| ATOM | 8013 C LEU I 158 | −11.550 −21.631 16.465 1.00 54.47 | C C |
| ATOM | 8014 O LEU I 158 | −11.417 −20.934 17.477 1.00 49.26 | C O |
| ATOM | 8015 N HIS I 159 | −11.447 −22.954 16.501 1.00 59.45 | C N |
| ATOM | 8016 CA HIS I 159 | −11.205 −23.636 17.768 1.00 49.11 | C C |
| ATOM | 8017 CB HIS I 159 | −11.225 −25.153 17.573 1.00 20.00 | C C |
| ATOM | 8018 CG HIS I 159 | −12.522 −25.676 17.038 1.00 20.00 | C C |
| ATOM | 8019 ND1 HIS I 159 | −13.559 −26.070 17.855 1.00 20.00 | C N |

(APPENDIX discloses SEQ ID NOS 29-32, 29-32 and 29-32, respectively, in order of appearance)

| | | | | |
|---|---|---|---|---|
| ATOM | 8020 CE1 HIS I 159 | −14.570 −26.484 17.112 1.00 20.00 | C C |
| ATOM | 8021 NE2 HIS I 159 | −14.225 −26.373 15.842 1.00 20.00 | C N |
| ATOM | 8022 CD2 HIS I 159 | −12.949 −25.871 15.768 1.00 20.00 | C C |
| ATOM | 8023 C HIS I 159 | −9.874 −23.203 18.385 1.00 44.09 | C C |
| ATOM | 8024 O HIS I 159 | −9.780 −22.977 19.596 1.00 42.13 | C O |
| ATOM | 8025 N LEU I 160 | −8.851 −23.072 17.546 1.00 37.55 | C N |
| ATOM | 8026 CA LEU I 160 | −7.536 −22.649 18.011 1.00 43.52 | C C |
| ATOM | 8027 CB LEU I 160 | −6.520 −22.704 16.869 1.00 20.00 | C C |
| ATOM | 8028 CG LEU I 160 | −6.299 −24.073 16.224 1.00 20.00 | C C |
| ATOM | 8029 CD1 LEU I 160 | −5.268 −23.982 15.109 1.00 20.00 | C C |
| ATOM | 8030 CD2 LEU I 160 | −5.877 −25.097 17.266 1.00 20.00 | C C |
| ATOM | 8031 C LEU I 160 | −7.599 −21.240 18.591 1.00 47.22 | C C |
| ATOM | 8032 O LEU I 160 | −6.984 −20.951 19.619 1.00 43.25 | C O |
| ATOM | 8033 N GLU I 161 | −8.351 −20.368 17.927 1.00 40.88 | C N |
| ATOM | 8034 CA GLU I 161 | −8.512 −18.996 18.388 1.00 40.61 | C C |
| ATOM | 8035 CB GLU I 161 | −9.325 −18.182 17.381 1.00 20.00 | C C |
| ATOM | 8036 CG GLU I 161 | −8.702 −18.104 15.997 1.00 20.00 | C C |
| ATOM | 8037 CD GLU I 161 | −9.537 −17.292 15.027 1.00 20.00 | C C |
| ATOM | 8038 OE1 GLU I 161 | −9.126 −17.158 13.855 1.00 20.00 | C O |
| ATOM | 8039 OE2 GLU I 161 | −10.604 −16.788 15.436 1.00 20.00 | C O |
| ATOM | 8040 C GLU I 161 | −9.195 −18.983 19.749 1.00 39.76 | C C |
| ATOM | 8041 O GLU I 161 | −8.816 −18.221 20.642 1.00 44.02 | C O |
| ATOM | 8042 N GLY I 162 | −10.199 −19.840 19.906 1.00 34.18 | C N |
| ATOM | 8043 CA GLY I 162 | −10.907 −19.934 21.169 1.00 35.01 | C C |
| ATOM | 8044 C GLY I 162 | −9.967 −20.387 22.269 1.00 34.86 | C C |
| ATOM | 8045 O GLY I 162 | −9.997 −19.864 23.386 1.00 47.81 | C O |
| ATOM | 8046 N GLU I 163 | −9.112 −21.352 21.945 1.00 40.78 | C N |
| ATOM | 8047 CA GLU I 163 | −8.143 −21.856 22.911 1.00 37.20 | C C |
| ATOM | 8048 CB GLU I 163 | −7.365 −23.036 22.326 1.00 20.00 | C C |
| ATOM | 8049 CG GLU I 163 | −8.235 −24.218 21.931 1.00 20.00 | C C |
| ATOM | 8050 CD GLU I 163 | −7.430 −25.368 21.357 1.00 20.00 | C C |
| ATOM | 8051 OE1 GLU I 163 | −8.037 −26.397 20.995 1.00 20.00 | C O |
| ATOM | 8052 OE2 GLU I 163 | −6.191 −25.241 21.268 1.00 20.00 | C O |
| ATOM | 8053 C GLU I 163 | −7.183 −20.745 23.324 1.00 46.12 | C C |
| ATOM | 8054 O GLU I 163 | −6.837 −20.611 24.501 1.00 58.66 | C O |
| ATOM | 8055 N VAL I 164 | −6.761 −19.944 22.350 1.00 42.23 | C N |
| ATOM | 8056 CA VAL I 164 | −5.857 −18.834 22.620 1.00 35.45 | C C |
| ATOM | 8057 CB VAL I 164 | −5.429 −18.124 21.323 1.00 20.00 | C C |
| ATOM | 8058 CG1 VAL I 164 | −4.487 −16.971 21.635 1.00 20.00 | C C |
| ATOM | 8059 CG2 VAL I 164 | −4.775 −19.112 20.369 1.00 20.00 | C C |
| ATOM | 8060 C VAL I 164 | −6.522 −17.823 23.548 1.00 46.32 | C C |
| ATOM | 8061 O VAL I 164 | −5.892 −17.301 24.472 1.00 45.08 | C O |
| ATOM | 8062 N ASN I 165 | −7.802 −17.558 23.304 1.00 40.82 | C N |
| ATOM | 8063 CA ASN I 165 | −8.548 −16.631 24.144 1.00 46.48 | C C |
| ATOM | 8064 CB ASN I 165 | −9.952 −16.403 23.581 1.00 20.00 | C C |
| ATOM | 8065 CG ASN I 165 | −9.930 −15.822 22.181 1.00 20.00 | C C |
| ATOM | 8066 OD1 ASN I 165 | −10.975 −15.504 21.612 1.00 20.00 | C O |
| ATOM | 8067 ND2 ASN I 165 | −8.736 −15.681 21.617 1.00 20.00 | C N |
| ATOM | 8068 C ASN I 165 | −8.631 −17.160 25.569 1.00 50.90 | C C |
| ATOM | 8069 O ASN I 165 | −8.474 −16.412 26.536 1.00 47.11 | C O |
| ATOM | 8070 N LYS I 166 | −8.857 −18.464 25.688 1.00 48.36 | C N |
| ATOM | 8071 CA LYS I 166 | −8.945 −19.120 26.986 1.00 38.71 | C C |
| ATOM | 8072 CB LYS I 166 | −9.329 −20.592 26.818 1.00 20.00 | C C |
| ATOM | 8073 CG LYS I 166 | −10.649 −20.811 26.097 1.00 20.00 | C C |
| ATOM | 8074 CD LYS I 166 | −10.952 −22.292 25.936 1.00 20.00 | C C |
| ATOM | 8075 CE LYS I 166 | −12.264 −22.511 25.200 1.00 20.00 | C C |
| ATOM | 8076 NZ LYS I 166 | −12.569 −23.958 25.028 1.00 20.00 | C N |
| ATOM | 8077 C LYS I 166 | −7.623 −19.006 27.738 1.00 45.07 | C C |
| ATOM | 8078 O LYS I 166 | −7.600 −18.823 28.955 1.00 56.09 | C O |
| ATOM | 8079 N ILE I 167 | −6.525 −19.121 26.999 1.00 42.02 | C N |
| ATOM | 8080 CA ILE I 167 | −5.184 −19.080 27.576 1.00 43.86 | C C |
| ATOM | 8081 CB ILE I 167 | −4.207 −19.975 26.789 1.00 20.00 | C C |
| ATOM | 8082 CG1 ILE I 167 | −4.685 −21.429 26.804 1.00 20.00 | C C |
| ATOM | 8083 CD1 ILE I 167 | −3.778 −22.377 26.050 1.00 20.00 | C C |
| ATOM | 8084 CG2 ILE I 167 | −2.803 −19.865 27.362 1.00 20.00 | C C |
| ATOM | 8085 C ILE I 167 | −4.599 −17.669 27.665 1.00 49.02 | C C |
| ATOM | 8086 O ILE I 167 | −3.448 −17.497 28.066 1.00 37.71 | C O |
| ATOM | 8087 N LYS I 168 | −5.382 −16.664 27.282 1.00 33.87 | C N |
| ATOM | 8088 CA LYS I 168 | −4.890 −15.285 27.251 1.00 35.11 | C C |
| ATOM | 8089 CB LYS I 168 | −5.939 −14.363 26.622 1.00 20.00 | C C |
| ATOM | 8090 CG LYS I 168 | −6.275 −14.698 25.178 1.00 20.00 | C C |
| ATOM | 8091 CD LYS I 168 | −7.292 −13.723 24.607 1.00 20.00 | C C |
| ATOM | 8092 CE LYS I 168 | −7.612 −14.046 23.157 1.00 20.00 | C C |
| ATOM | 8093 NZ LYS I 168 | −8.599 −13.092 22.580 1.00 20.00 | C N |
| ATOM | 8094 C LYS I 168 | −4.431 −14.704 28.600 1.00 39.27 | C C |
| ATOM | 8095 O LYS I 168 | −3.414 −14.012 28.655 1.00 32.39 | C O |
| ATOM | 8096 N SER I 169 | −5.164 −14.973 29.677 1.00 41.30 | C N |

APPENDIX-continued (APPENDIX discloses SEQ ID NOS 29-32, 29-32 and 29-32, respectively, in order of appearance)

| | | | |
|---|---|---|---|
| ATOM | 8097 CA SER I 169 | −4.797 −14.446 30.987 1.00 43.23 | C C |
| ATOM | 8098 CB SER I 169 | −5.756 −14.957 32.064 1.00 20.00 | C C |
| ATOM | 8099 OG SER I 169 | −5.739 −16.371 32.127 1.00 20.00 | C O |
| ATOM | 8100 C SER I 169 | −3.359 −14.795 31.353 1.00 41.44 | C C |
| ATOM | 8101 O SER I 169 | −2.580 −13.924 31.740 1.00 44.82 | C O |
| ATOM | 8102 N ALA I 170 | −3.013 −16.072 31.235 1.00 39.78 | C N |
| ATOM | 8103 CA ALA I 170 | −1.644 −16.517 31.469 1.00 41.01 | C C |
| ATOM | 8104 CB ALA I 170 | −1.541 −18.025 31.320 1.00 20.00 | C C |
| ATOM | 8105 C ALA I 170 | −0.674 −15.820 30.523 1.00 46.04 | C C |
| ATOM | 8106 O ALA I 170 | 0.396 −15.373 30.935 1.00 46.67 | C O |
| ATOM | 8107 N LEU I 171 | −1.061 −15.718 29.258 1.00 34.26 | C N |
| ATOM | 8108 CA LEU I 171 | −0.245 −15.030 28.269 1.00 37.69 | C C |
| ATOM | 8109 CB LEU I 171 | −0.942 −15.036 26.912 1.00 20.00 | C C |
| ATOM | 8110 CG LEU I 171 | −1.226 −16.424 26.346 1.00 20.00 | C C |
| ATOM | 8111 CD1 LEU I 171 | −1.873 −16.311 24.972 1.00 20.00 | C C |
| ATOM | 8112 CD2 LEU I 171 | 0.060 −17.242 26.293 1.00 20.00 | C C |
| ATOM | 8113 C LEU I 171 | 0.053 −13.598 28.702 1.00 44.67 | C C |
| ATOM | 8114 O LEU I 171 | 1.173 −13.109 28.538 1.00 34.27 | C O |
| ATOM | 8115 N LEU I 172 | −0.935 −12.955 29.314 1.00 34.80 | C N |
| ATOM | 8116 CA LEU I 172 | −0.817 −11.555 29.692 1.00 28.87 | C C |
| ATOM | 8117 CB LEU I 172 | −2.199 −10.971 29.993 1.00 20.00 | C C |
| ATOM | 8118 CG LEU I 172 | −3.198 −10.968 28.835 1.00 20.00 | C C |
| ATOM | 8119 CD1 LEU I 172 | −4.534 −10.393 29.283 1.00 20.00 | C C |
| ATOM | 8120 CD2 LEU I 172 | −2.643 −10.187 27.668 1.00 20.00 | C C |
| ATOM | 8121 C LEU I 172 | 0.099 −11.400 30.901 1.00 29.90 | C C |
| ATOM | 8122 O LEU I 172 | 0.896 −10.462 30.972 1.00 41.09 | C O |
| ATOM | 8123 N SER I 173 | 0.016 −12.355 31.824 1.00 35.08 | C N |
| ATOM | 8124 CA SER I 173 | 0.740 −12.276 33.092 1.00 35.53 | C C |
| ATOM | 8125 CB SER I 173 | 0.110 −13.206 34.132 1.00 20.00 | C C |
| ATOM | 8126 OG SER I 173 | 0.148 −14.555 33.701 1.00 20.00 | C O |
| ATOM | 8127 C SER I 173 | 2.218 −12.610 32.919 1.00 35.07 | C C |
| ATOM | 8128 O SER I 173 | 3.042 −12.300 33.779 1.00 51.28 | C O |
| ATOM | 8129 N THR I 174 | 2.537 −13.275 31.817 1.00 46.35 | C N |
| ATOM | 8130 CA THR I 174 | 3.894 −13.733 31.561 1.00 43.83 | C C |
| ATOM | 8131 CB THR I 174 | 3.889 −14.970 30.641 1.00 20.00 | C C |
| ATOM | 8132 OG1 THR I 174 | 3.327 −14.620 29.371 1.00 20.00 | C O |
| ATOM | 8133 CG2 THR I 174 | 3.056 −16.081 31.260 1.00 20.00 | C C |
| ATOM | 8134 C THR I 174 | 4.722 −12.626 30.910 1.00 52.54 | C C |
| ATOM | 8135 O THR I 174 | 4.393 −12.154 29.821 1.00 64.10 | C O |
| ATOM | 8136 N ASN I 175 | 5.771 −12.188 31.599 1.00 55.57 | C N |
| ATOM | 8137 CA ASN I 175 | 6.735 −11.267 31.008 1.00 40.58 | C C |
| ATOM | 8138 CB ASN I 175 | 7.507 −10.521 32.099 1.00 20.00 | C C |
| ATOM | 8139 CG ASN I 175 | 6.646 −9.518 32.845 1.00 20.00 | C C |
| ATOM | 8140 OD1 ASN I 175 | 5.640 −9.033 32.324 1.00 20.00 | C O |
| ATOM | 8141 ND2 ASN I 175 | 7.043 −9.196 34.072 1.00 20.00 | C N |
| ATOM | 8142 C ASN I 175 | 7.708 −11.986 30.075 1.00 43.65 | C C |
| ATOM | 8143 O ASN I 175 | 8.525 −12.793 30.521 1.00 53.11 | C O |
| ATOM | 8144 N LYS I 176 | 7.546 −11.768 28.773 1.00 44.89 | C N |
| ATOM | 8145 CA LYS I 176 | 8.402 −12.407 27.776 1.00 46.42 | C C |
| ATOM | 8146 CB LYS I 176 | 8.150 −13.917 27.740 1.00 20.00 | C C |
| ATOM | 8147 CG LYS I 176 | 8.510 −14.625 29.034 1.00 20.00 | C C |
| ATOM | 8148 CD LYS I 176 | 8.270 −16.122 28.943 1.00 20.00 | C C |
| ATOM | 8149 CE LYS I 176 | 8.994 −16.863 30.063 1.00 20.00 | C C |
| ATOM | 8150 NZ LYS I 176 | 9.447 −18.223 29.648 1.00 20.00 | C N |
| ATOM | 8151 C LYS I 176 | 8.192 −11.798 26.392 1.00 45.00 | C C |
| ATOM | 8152 O LYS I 176 | 7.084 −11.379 26.053 1.00 60.64 | C O |
| ATOM | 8153 N ALA I 177 | 9.280 −11.645 25.643 1.00 46.01 | C N |
| ATOM | 8154 CA ALA I 177 | 9.189 −11.237 24.242 1.00 43.65 | C C |
| ATOM | 8155 CB ALA I 177 | 10.555 −10.847 23.706 1.00 20.00 | C C |
| ATOM | 8156 C ALA I 177 | 8.592 −12.349 23.395 1.00 41.42 | C C |
| ATOM | 8157 O ALA I 177 | 7.695 −12.116 22.584 1.00 45.37 | C O |
| ATOM | 8158 N VAL I 178 | 9.140 −13.549 23.545 1.00 35.70 | C N |
| ATOM | 8159 CA VAL I 178 | 8.580 −14.725 22.902 1.00 43.93 | C C |
| ATOM | 8160 CB VAL I 178 | 9.495 −15.243 21.780 1.00 20.00 | C C |
| ATOM | 8161 CG1 VAL I 178 | 8.898 −16.490 21.143 1.00 20.00 | C C |
| ATOM | 8162 CG2 VAL I 178 | 9.714 −14.159 20.734 1.00 20.00 | C C |
| ATOM | 8163 C VAL I 178 | 8.363 −15.829 23.922 1.00 34.16 | C C |
| ATOM | 8164 O VAL I 178 | 9.115 −15.950 24.889 1.00 44.45 | C O |
| ATOM | 8165 N VAL I 179 | 7.271 −16.565 23.760 1.00 44.87 | C N |
| ATOM | 8166 CA VAL I 179 | 6.916 −17.608 24.708 1.00 38.47 | C C |
| ATOM | 8167 CB VAL I 179 | 6.234 −17.027 25.960 1.00 20.00 | C C |
| ATOM | 8168 CG1 VAL I 179 | 5.785 −18.147 26.887 1.00 20.00 | C C |
| ATOM | 8169 CG2 VAL I 179 | 7.174 −16.076 26.680 1.00 20.00 | C C |
| ATOM | 8170 C VAL I 179 | 6.003 −18.648 24.074 1.00 44.79 | C C |
| ATOM | 8171 O VAL I 179 | 5.097 −18.317 23.310 1.00 51.88 | C O |
| ATOM | 8172 N SER I 180 | 6.270 −19.911 24.378 1.00 45.23 | C N |
| ATOM | 8173 CA SER I 180 | 5.428 −21.002 23.914 1.00 48.99 | C C |

APPENDIX-continued (APPENDIX discloses SEQ ID NOS 29-32, 29-32 and 29-32, respectively, in order of appearance)

| | | | |
|---|---|---|---|
| ATOM | 8174 CB SER I 180 | 6.171 −22.334 24.038 1.00 20.00 | C C |
| ATOM | 8175 OG SER I 180 | 6.627 −22.542 25.364 1.00 20.00 | C O |
| ATOM | 8176 C SER I 180 | 4.118 −21.053 24.698 1.00 48.15 | C C |
| ATOM | 8177 O SER I 180 | 4.116 −21.309 25.901 1.00 60.42 | C O |
| ATOM | 8178 N LEU I 181 | 3.009 −20.782 24.016 1.00 42.42 | C N |
| ATOM | 8179 CA LEU I 181 | 1.684 −20.959 24.605 1.00 43.22 | C C |
| ATOM | 8180 CB LEU I 181 | 0.610 −20.369 23.693 1.00 20.00 | C C |
| ATOM | 8181 CG LEU I 181 | 0.738 −18.866 23.467 1.00 20.00 | C C |
| ATOM | 8182 CD1 LEU I 181 | −0.514 −18.314 22.808 1.00 20.00 | C C |
| ATOM | 8183 CD2 LEU I 181 | 1.008 −18.184 24.795 1.00 20.00 | C C |
| ATOM | 8184 C LEU I 181 | 1.388 −22.428 24.863 1.00 29.14 | C C |
| ATOM | 8185 O LEU I 181 | 1.144 −23.194 23.931 1.00 43.42 | C O |
| ATOM | 8186 N SER I 182 | 1.361 −22.807 26.136 1.00 41.83 | C N |
| ATOM | 8187 CA SER I 182 | 1.272 −24.214 26.503 1.00 53.52 | C C |
| ATOM | 8188 CB SER I 182 | 2.491 −24.642 27.324 1.00 20.00 | C C |
| ATOM | 8189 OG SER I 182 | 2.601 −23.890 28.521 1.00 20.00 | C O |
| ATOM | 8190 C SER I 182 | −0.025 −24.557 27.236 1.00 44.76 | C C |
| ATOM | 8191 O SER I 182 | −0.492 −23.802 28.090 1.00 37.73 | C O |
| ATOM | 8192 N ASN I 183 | −0.652 −25.649 26.815 1.00 47.84 | C N |
| ATOM | 8193 CA ASN I 183 | −1.684 −26.308 27.603 1.00 59.45 | C C |
| ATOM | 8194 CB ASN I 183 | −3.002 −26.334 26.822 1.00 20.00 | C C |
| ATOM | 8195 CG ASN I 183 | −3.598 −24.951 26.632 1.00 20.00 | C C |
| ATOM | 8196 OD1 ASN I 183 | −3.426 −24.069 27.473 1.00 20.00 | C O |
| ATOM | 8197 ND2 ASN I 183 | −4.381 −24.785 25.572 1.00 20.00 | C N |
| ATOM | 8198 C ASN I 183 | −1.232 −27.732 27.905 1.00 75.41 | C C |
| ATOM | 8199 O ASN I 183 | −0.535 −28.342 27.096 1.00 102.31 | C O |
| ATOM | 8200 N GLY I 184 | −1.489 −28.200 29.121 1.00 79.30 | C N |
| ATOM | 8201 CA GLY I 184 | −1.001 −29.510 29.549 1.00 88.92 | C C |
| ATOM | 8202 C GLY I 184 | −0.204 −30.239 28.479 1.00101.85 | C C |
| ATOM | 8203 O GLY I 184 | −0.764 −30.990 27.680 1.00113.48 | C O |
| ATOM | 8204 N VAL I 185 | 1.103 −29.994 28.448 1.00 86.84 | C N |
| ATOM | 8205 CA VAL I 185 | 2.047 −30.825 27.696 1.00 81.80 | C C |
| ATOM | 8206 CB VAL I 185 | 1.899 −32.323 28.027 1.00 20.00 | C C |
| ATOM | 8207 CG1 VAL I 185 | 2.803 −33.155 27.126 1.00 20.00 | C C |
| ATOM | 8208 CG2 VAL I 185 | 2.219 −32.578 29.491 1.00 20.00 | C C |
| ATOM | 8209 C VAL I 185 | 1.997 −30.638 26.179 1.00 81.69 | C C |
| ATOM | 8210 O VAL I 185 | 2.634 −31.388 25.439 1.00 99.84 | C O |
| ATOM | 8211 N SER I 186 | 1.282 −29.618 25.718 1.00 70.63 | C N |
| ATOM | 8212 CA SER I 186 | 1.132 −29.398 24.284 1.00 72.29 | C C |
| ATOM | 8213 CB SER I 186 | −0.201 −29.962 23.792 1.00 20.00 | C C |
| ATOM | 8214 OG SER I 186 | −1.291 −29.357 24.467 1.00 20.00 | C O |
| ATOM | 8215 C SER I 186 | 1.247 −27.923 23.915 1.00 62.99 | C C |
| ATOM | 8216 O SER I 186 | 0.649 −27.064 24.565 1.00 58.35 | C O |
| ATOM | 8217 N VAL I 187 | 2.013 −27.638 22.865 1.00 66.49 | C N |
| ATOM | 8218 CA VAL I 187 | 2.203 −26.266 22.398 1.00 57.36 | C C |
| ATOM | 8219 CB VAL I 187 | 3.581 −26.078 21.735 1.00 20.00 | C C |
| ATOM | 8220 CG1 VAL I 187 | 3.748 −24.643 21.256 1.00 20.00 | C C |
| ATOM | 8221 CG2 VAL I 187 | 4.691 −26.452 22.699 1.00 20.00 | C C |
| ATOM | 8222 C VAL I 187 | 1.116 −25.863 21.405 1.00 53.67 | C C |
| ATOM | 8223 O VAL I 187 | 0.949 −26.501 20.365 1.00 50.10 | C O |
| ATOM | 8224 N LEU I 188 | 0.381 −24.803 21.731 1.00 43.20 | C N |
| ATOM | 8225 CA LEU I 188 | −0.676 −24.302 20.858 1.00 41.76 | C C |
| ATOM | 8226 CB LEU I 188 | −1.749 −23.580 21.674 1.00 20.00 | C C |
| ATOM | 8227 CG LEU I 188 | −2.557 −24.455 22.632 1.00 20.00 | C C |
| ATOM | 8228 CD1 LEU I 188 | −3.533 −23.609 23.429 1.00 20.00 | C C |
| ATOM | 8229 CD2 LEU I 188 | −3.287 −25.542 21.865 1.00 20.00 | C C |
| ATOM | 8230 C LEU I 188 | −0.102 −23.361 19.813 1.00 44.75 | C C |
| ATOM | 8231 O LEU I 188 | −0.674 −23.184 18.738 1.00 45.28 | C O |
| ATOM | 8232 N THR I 189 | 1.054 −22.786 20.124 1.00 39.28 | C N |
| ATOM | 8233 CA THR I 189 | 1.675 −21.805 19.250 1.00 36.51 | C C |
| ATOM | 8234 CB THR I 189 | 0.614 −20.957 18.526 1.00 20.00 | C C |
| ATOM | 8235 OG1 THR I 189 | −0.113 −20.177 19.481 1.00 20.00 | C O |
| ATOM | 8236 CG2 THR I 189 | −0.360 −21.858 17.785 1.00 20.00 | C C |
| ATOM | 8237 C THR I 189 | 2.615 −20.901 20.039 1.00 45.83 | C C |
| ATOM | 8238 O THR I 189 | 3.150 −21.304 21.072 1.00 42.57 | C O |
| ATOM | 8239 N SER I 190 | 2.853 −19.698 19.530 1.00 40.44 | C N |
| ATOM | 8240 CA SER I 190 | 3.792 −18.785 20.166 1.00 41.82 | C C |
| ATOM | 8241 CB SER I 190 | 5.022 −18.584 19.283 1.00 20.00 | C C |
| ATOM | 8242 OG SER I 190 | 4.664 −18.015 18.038 1.00 20.00 | C O |
| ATOM | 8243 C SER I 190 | 3.146 −17.444 20.491 1.00 33.81 | C C |
| ATOM | 8244 O SER I 190 | 2.391 −16.897 19.687 1.00 49.61 | C O |
| ATOM | 8245 N LYS I 191 | 3.454 −16.920 21.674 1.00 37.37 | C N |
| ATOM | 8246 CA LYS I 191 | 2.986 −15.598 22.086 1.00 41.23 | C C |
| ATOM | 8247 CB LYS I 191 | 2.358 −15.664 23.478 1.00 20.00 | C C |
| ATOM | 8248 CG LYS I 191 | 1.069 −16.459 23.525 1.00 20.00 | C C |
| ATOM | 8249 CD LYS I 191 | 0.505 −16.514 24.931 1.00 20.00 | C C |
| ATOM | 8250 CE LYS I 191 | −0.626 −17.531 25.037 1.00 20.00 | C C |

APPENDIX-continued (APPENDIX discloses SEQ ID NOS 29-32, 29-32 and 29-32, respectively, in order of appearance)

| | | | |
|---|---|---|---|
| ATOM | 8251 NZ LYS I 191 | −0.791 −18.032 26.435 1.00 20.00 | C N |
| ATOM | 8252 C LYS I 191 | 4.112 −14.568 22.069 1.00 35.03 | C C |
| ATOM | 8253 O LYS I 191 | 5.120 −14.728 22.757 1.00 40.06 | C O |
| ATOM | 8254 N VAL I 192 | 3.920 −13.495 21.308 1.00 33.70 | C N |
| ATOM | 8255 CA VAL I 192 | 4.967 −12.498 21.120 1.00 27.61 | C C |
| ATOM | 8256 CB VAL I 192 | 5.392 −12.392 19.646 1.00 20.00 | C C |
| ATOM | 8257 CG1 VAL I 192 | 6.395 −11.267 19.465 1.00 20.00 | C C |
| ATOM | 8258 CG2 VAL I 192 | 5.972 −13.709 19.165 1.00 20.00 | C C |
| ATOM | 8259 C VAL I 192 | 4.550 −11.121 21.624 1.00 31.74 | C C |
| ATOM | 8260 O VAL I 192 | 3.376 −10.755 21.573 1.00 25.58 | C O |
| ATOM | 8261 N LEU I 193 | 5.526 −10.364 22.114 1.00 28.88 | C N |
| ATOM | 8262 CA LEU I 193 | 5.316 −8.973 22.488 1.00 34.36 | C C |
| ATOM | 8263 CB LEU I 193 | 5.118 −8.855 23.998 1.00 20.00 | C C |
| ATOM | 8264 CG LEU I 193 | 3.893 −9.566 24.567 1.00 20.00 | C C |
| ATOM | 8265 CD1 LEU I 193 | 3.915 −9.514 26.084 1.00 20.00 | C C |
| ATOM | 8266 CD2 LEU I 193 | 2.623 −8.947 24.019 1.00 20.00 | C C |
| ATOM | 8267 C LEU I 193 | 6.507 −8.126 22.059 1.00 33.03 | C C |
| ATOM | 8268 O LEU I 193 | 7.592 −8.238 22.627 1.00 44.93 | C O |
| ATOM | 8269 N ASP I 194 | 6.304 −7.294 21.042 1.00 35.09 | C N |
| ATOM | 8270 CA ASP I 194 | 7.409 −6.702 20.288 1.00 41.39 | C C |
| ATOM | 8271 CB ASP I 194 | 6.892 −6.027 19.014 1.00 20.00 | C C |
| ATOM | 8272 CG ASP I 194 | 6.375 −7.023 17.994 1.00 20.00 | C C |
| ATOM | 8273 OD1 ASP I 194 | 6.659 −8.229 18.141 1.00 20.00 | C O |
| ATOM | 8274 OD2 ASP I 194 | 5.654 −6.606 17.064 1.00 20.00 | C O |
| ATOM | 8275 C ASP I 194 | 8.255 −5.712 21.094 1.00 38.04 | C C |
| ATOM | 8276 O ASP I 194 | 9.349 −5.339 20.670 1.00 48.03 | C O |
| ATOM | 8277 N LEU I 195 | 7.723 −5.232 22.215 1.00 43.64 | C N |
| ATOM | 8278 CA LEU I 195 | 8.360 −4.139 22.947 1.00 35.97 | C C |
| ATOM | 8279 CB LEU I 195 | 7.417 −2.935 23.045 1.00 20.00 | C C |
| ATOM | 8280 CG LEU I 195 | 7.024 −2.281 21.714 1.00 20.00 | C C |
| ATOM | 8281 CD1 LEU I 195 | 5.965 −1.195 21.915 1.00 20.00 | C C |
| ATOM | 8282 CD2 LEU I 195 | 8.249 −1.730 20.980 1.00 20.00 | C C |
| ATOM | 8283 C LEU I 195 | 8.858 −4.546 24.335 1.00 43.63 | C C |
| ATOM | 8284 O LEU I 195 | 9.609 −3.811 24.972 1.00 34.71 | C O |
| ATOM | 8285 N ASN I 196 | 8.535 −5.769 24.742 1.00 44.30 | C N |
| ATOM | 8286 CA ASN I 196 | 8.824 −6.238 26.095 1.00 42.38 | C C |
| ATOM | 8287 CB ASN I 196 | 8.399 −7.701 26.254 1.00 20.00 | C C |
| ATOM | 8288 CG ASN I 196 | 6.892 −7.874 26.221 1.00 20.00 | C C |
| ATOM | 8289 OD1 ASN I 196 | 6.146 −6.952 26.545 1.00 20.00 | C O |
| ATOM | 8290 ND2 ASN I 196 | 6.438 −9.055 25.817 1.00 20.00 | C N |
| ATOM | 8291 C ASN I 196 | 10.282 −6.058 26.511 1.00 43.66 | C C |
| ATOM | 8292 O ASN I 196 | 10.568 −5.610 27.622 1.00 33.62 | C O |
| ATOM | 8293 N ASN I 197 | 11.199 −6.448 25.633 1.00 34.31 | C N |
| ATOM | 8294 CA ASN I 197 | 12.621 −6.414 25.950 1.00 38.83 | C C |
| ATOM | 8295 CB ASN I 197 | 13.437 −7.021 24.812 1.00 20.00 | C C |
| ATOM | 8296 CG ASN I 197 | 13.306 −8.527 24.747 1.00 20.00 | C C |
| ATOM | 8297 OD1 ASN I 197 | 13.064 −9.180 25.764 1.00 20.00 | C O |
| ATOM | 8298 ND2 ASN I 197 | 13.315 −9.069 23.533 1.00 20.00 | C N |
| ATOM | 8299 C ASN I 197 | 13.106 −5.005 26.239 1.00 39.90 | C C |
| ATOM | 8300 O ASN I 197 | 13.745 −4.752 27.261 1.00 39.04 | C O |
| ATOM | 8301 N TYR I 198 | 12.824 −4.095 25.314 1.00 35.09 | C N |
| ATOM | 8302 CA TYR I 198 | 13.109 −2.682 25.518 1.00 41.03 | C C |
| ATOM | 8303 CB TYR I 198 | 12.610 −1.859 24.332 1.00 20.00 | C C |
| ATOM | 8304 CG TYR I 198 | 13.298 −2.189 23.031 1.00 20.00 | C C |
| ATOM | 8305 CD1 TYR I 198 | 14.497 −1.579 22.687 1.00 20.00 | C C |
| ATOM | 8306 CE1 TYR I 198 | 15.110 −1.847 21.488 1.00 20.00 | C C |
| ATOM | 8307 CZ TYR I 198 | 14.536 −2.752 20.620 1.00 20.00 | C C |
| ATOM | 8308 OH TYR I 198 | 15.138 −3.016 19.411 1.00 20.00 | C O |
| ATOM | 8309 CE2 TYR I 198 | 13.349 −3.378 20.941 1.00 20.00 | C C |
| ATOM | 8310 CD2 TYR I 198 | 12.749 −3.109 22.148 1.00 20.00 | C C |
| ATOM | 8311 C TYR I 198 | 12.490 −2.163 26.811 1.00 43.65 | C C |
| ATOM | 8312 O TYR I 198 | 13.128 −1.410 27.549 1.00 52.37 | C O |
| ATOM | 8313 N ILE I 199 | 11.279 −2.622 27.115 1.00 35.86 | C N |
| ATOM | 8314 CA ILE I 199 | 10.573 −2.185 28.316 1.00 45.39 | C C |
| ATOM | 8315 CB ILE I 199 | 9.108 −2.624 28.306 1.00 20.00 | C C |
| ATOM | 8316 CG1 ILE I 199 | 8.330 −1.808 27.272 1.00 20.00 | C C |
| ATOM | 8317 CD1 ILE I 199 | 7.307 −2.607 26.505 1.00 20.00 | C C |
| ATOM | 8318 CG2 ILE I 199 | 8.502 −2.461 29.691 1.00 20.00 | C C |
| ATOM | 8319 C ILE I 199 | 11.232 −2.684 29.595 1.00 37.89 | C C |
| ATOM | 8320 O ILE I 199 | 11.344 −1.943 30.572 1.00 45.28 | C O |
| ATOM | 8321 N ASP I 200 | 11.628 −3.953 29.597 1.00 37.36 | C N |
| ATOM | 8322 CA ASP I 200 | 12.325 −4.543 30.737 1.00 46.66 | C C |
| ATOM | 8323 CB ASP I 200 | 12.549 −6.040 30.507 1.00 20.00 | C C |
| ATOM | 8324 CG ASP I 200 | 11.269 −6.841 30.616 1.00 20.00 | C C |
| ATOM | 8325 OD1 ASP I 200 | 10.283 −6.314 31.172 1.00 20.00 | C O |
| ATOM | 8326 OD2 ASP I 200 | 11.248 −7.996 30.143 1.00 20.00 | C O |
| ATOM | 8327 C ASP I 200 | 13.655 −3.842 31.033 1.00 51.05 | C C |

APPENDIX-continued (APPENDIX discloses SEQ ID NOS 29-32, 29-32 and 29-32, respectively, in order of appearance)

| | | | | |
|---|---|---|---|---|
| ATOM | 8328 O ASP I 200 | 14.077 −3.753 32.188 1.00 57.39 | C O |
| ATOM | 8329 N LYS I 201 | 14.284 −3.306 29.989 1.00 57.68 | C N |
| ATOM | 8330 CA LYS I 201 | 15.560 −2.605 30.126 1.00 44.02 | C C |
| ATOM | 8331 CB LYS I 201 | 16.228 −2.417 28.760 1.00 20.00 | C C |
| ATOM | 8332 CG LYS I 201 | 16.590 −3.716 28.055 1.00 20.00 | C C |
| ATOM | 8333 CD LYS I 201 | 17.363 −3.463 26.764 1.00 20.00 | C C |
| ATOM | 8334 CE LYS I 201 | 17.644 −4.764 26.018 1.00 20.00 | C C |
| ATOM | 8335 NZ LYS I 201 | 18.195 −4.531 24.654 1.00 20.00 | C N |
| ATOM | 8336 C LYS I 201 | 15.409 −1.254 30.827 1.00 43.56 | C C |
| ATOM | 8337 O LYS I 201 | 16.366 −0.743 31.407 1.00 51.34 | C O |
| ATOM | 8338 N GLN I 202 | 14.202 −0.694 30.795 1.00 46.06 | C N |
| ATOM | 8339 CA GLN I 202 | 13.987 0.689 31.223 1.00 44.95 | C C |
| ATOM | 8340 CB GLN I 202 | 13.366 1.518 30.101 1.00 20.00 | C C |
| ATOM | 8341 CG GLN I 202 | 14.344 1.932 29.024 1.00 20.00 | C C |
| ATOM | 8342 CD GLN I 202 | 13.660 2.551 27.823 1.00 20.00 | C C |
| ATOM | 8343 OE1 GLN I 202 | 12.435 2.519 27.702 1.00 20.00 | C O |
| ATOM | 8344 NE2 GLN I 202 | 14.452 3.135 26.932 1.00 20.00 | C N |
| ATOM | 8345 C GLN I 202 | 13.142 0.816 32.489 1.00 42.35 | C C |
| ATOM | 8346 O GLN I 202 | 13.166 1.853 33.151 1.00 47.00 | C O |
| ATOM | 8347 N LEU I 203 | 12.318 −0.189 32.766 1.00 49.55 | C N |
| ATOM | 8348 CA LEU I 203 | 11.397 −0.111 33.895 1.00 50.77 | C C |
| ATOM | 8349 CB LEU I 203 | 10.332 −1.205 33.796 1.00 20.00 | C C |
| ATOM | 8350 CG LEU I 203 | 9.392 −1.066 32.594 1.00 20.00 | C C |
| ATOM | 8351 CD1 LEU I 203 | 8.616 −2.347 32.316 1.00 20.00 | C C |
| ATOM | 8352 CD2 LEU I 203 | 8.447 0.111 32.787 1.00 20.00 | C C |
| ATOM | 8353 C LEU I 203 | 12.134 −0.184 35.231 1.00 52.51 | C C |
| ATOM | 8354 O LEU I 203 | 13.096 −0.937 35.379 1.00 46.02 | C O |
| ATOM | 8355 N LEU I 204 | 11.747 0.686 36.159 1.00 51.45 | C N |
| ATOM | 8356 CA LEU I 204 | 12.308 0.682 37.507 1.00 58.44 | C C |
| ATOM | 8357 CB LEU I 204 | 12.055 2.021 38.187 1.00 20.00 | C C |
| ATOM | 8358 CG LEU I 204 | 12.780 3.206 37.565 1.00 20.00 | C C |
| ATOM | 8359 CD1 LEU I 204 | 12.380 4.480 38.291 1.00 20.00 | C C |
| ATOM | 8360 CD2 LEU I 204 | 14.286 2.982 37.637 1.00 20.00 | C C |
| ATOM | 8361 C LEU I 204 | 11.700 −0.425 38.354 1.00 54.99 | C C |
| ATOM | 8362 O LEU I 204 | 10.489 −0.633 38.319 1.00 55.13 | C O |
| ATOM | 8363 N PRO I 205 | 12.498 −0.979 39.277 1.00 58.64 | C N |
| ATOM | 8364 CA PRO I 205 | 12.014 −2.145 39.995 1.00 52.19 | C C |
| ATOM | 8365 CB PRO I 205 | 13.198 −2.496 40.896 1.00 20.00 | C C |
| ATOM | 8366 CG PRO I 205 | 13.924 −1.175 41.116 1.00 20.00 | C C |
| ATOM | 8367 CD PRO I 205 | 13.404 −0.175 40.112 1.00 20.00 | C C |
| ATOM | 8368 C PRO I 205 | 10.799 −1.765 40.840 1.00 54.30 | C C |
| ATOM | 8369 O PRO I 205 | 10.014 −2.630 41.235 1.00 70.22 | C O |
| ATOM | 8370 N ILE I 206 | 10.656 −0.465 41.096 1.00 62.70 | C N |
| ATOM | 8371 CA ILE I 206 | 9.491 0.087 41.787 1.00 68.19 | C C |
| ATOM | 8372 CB ILE I 206 | 9.725 0.181 43.311 1.00 20.00 | C C |
| ATOM | 8373 CG1 ILE I 206 | 9.753 −1.214 43.941 1.00 20.00 | C C |
| ATOM | 8374 CD1 ILE I 206 | 10.200 −1.220 45.389 1.00 20.00 | C C |
| ATOM | 8375 CG2 ILE I 206 | 8.656 1.047 43.966 1.00 20.00 | C C |
| ATOM | 8376 C ILE I 206 | 9.175 1.484 41.253 1.00 62.35 | C C |
| ATOM | 8377 O ILE I 206 | 10.081 2.268 40.973 1.00 67.16 | C O |
| ATOM | 8378 N VAL I 207 | 7.894 1.749 41.015 1.00 52.22 | C N |
| ATOM | 8379 CA VAL I 207 | 7.461 3.050 40.521 1.00 51.31 | C C |
| ATOM | 8380 CB VAL I 207 | 6.469 2.918 39.345 1.00 20.00 | C C |
| ATOM | 8381 CG1 VAL I 207 | 5.891 4.279 38.984 1.00 20.00 | C C |
| ATOM | 8382 CG2 VAL I 207 | 7.149 2.291 38.139 1.00 20.00 | C C |
| ATOM | 8383 C VAL I 207 | 6.800 3.846 41.634 1.00 62.09 | C C |
| ATOM | 8384 O VAL I 207 | 5.644 3.607 41.980 1.00 58.88 | C O |
| ATOM | 8385 N ASN I 208 | 7.557 4.759 42.229 1.00 71.72 | C N |
| ATOM | 8386 CA ASN I 208 | 7.023 5.625 43.267 1.00 70.92 | C C |
| ATOM | 8387 CB ASN I 208 | 8.004 5.721 44.433 1.00 20.00 | C C |
| ATOM | 8388 CG ASN I 208 | 8.100 4.428 45.222 1.00 20.00 | C C |
| ATOM | 8389 OD1 ASN I 208 | 7.170 3.620 45.228 1.00 20.00 | C O |
| ATOM | 8390 ND2 ASN I 208 | 9.234 4.221 45.884 1.00 20.00 | C N |
| ATOM | 8391 C ASN I 208 | 6.699 7.015 42.735 1.00 63.05 | C C |
| ATOM | 8392 O ASN I 208 | 6.780 7.264 41.532 1.00 61.34 | C O |
| ATOM | 8393 N LYS I 209 | 6.391 7.933 43.645 1.00 68.91 | C N |
| ATOM | 8394 CA LYS I 209 | 5.953 9.273 43.274 1.00 59.11 | C C |
| ATOM | 8395 CB LYS I 209 | 5.349 9.992 44.482 1.00 20.00 | C C |
| ATOM | 8396 CG LYS I 209 | 4.044 9.391 44.979 1.00 20.00 | C C |
| ATOM | 8397 CD LYS I 209 | 3.507 10.158 46.179 1.00 20.00 | C C |
| ATOM | 8398 CE LYS I 209 | 2.159 9.612 46.629 1.00 20.00 | C C |
| ATOM | 8399 NZ LYS I 209 | 1.583 10.385 47.765 1.00 20.00 | C N |
| ATOM | 8400 C LYS I 209 | 7.100 10.100 42.702 1.00 50.69 | C C |
| ATOM | 8401 O LYS I 209 | 6.883 11.178 42.152 1.00 51.01 | C O |
| ATOM | 8402 N GLN I 210 | 8.326 9.638 42.920 1.00 44.68 | C N |
| ATOM | 8403 CA GLN I 210 | 9.495 10.293 42.349 1.00 49.52 | C C |
| ATOM | 8404 CB GLN I 210 | 10.724 10.052 43.223 1.00 20.00 | C C |

APPENDIX-continued (APPENDIX discloses SEQ ID NOS 29-32, 29-32 and 29-32, respectively, in order of appearance)

| | | | |
|---|---|---|---|
| ATOM | 8405 CG GLN I 210 | 10.667 10.739 44.573 1.00 20.00 | C C |
| ATOM | 8406 CD GLN I 210 | 11.865 10.409 45.435 1.00 20.00 | C C |
| ATOM | 8407 OE1 GLN I 210 | 12.517 9.385 45.239 1.00 20.00 | C O |
| ATOM | 8408 NE2 GLN I 210 | 12.173 11.286 46.383 1.00 20.00 | C N |
| ATOM | 8409 C GLN I 210 | 9.755 9.786 40.938 1.00 62.08 | C C |
| ATOM | 8410 O GLN I 210 | 9.786 10.560 39.983 1.00 80.43 | C O |
| ATOM | 8411 N SER I 211 | 9.902 8.472 40.813 1.00 58.92 | C N |
| ATOM | 8412 CA SER I 211 | 10.076 7.840 39.514 1.00 47.88 | C C |
| ATOM | 8413 CB SER I 211 | 9.987 6.319 39.647 1.00 20.00 | C C |
| ATOM | 8414 OG SER I 211 | 8.735 5.930 40.184 1.00 20.00 | C O |
| ATOM | 8415 C SER I 211 | 9.050 8.344 38.503 1.00 57.32 | C C |
| ATOM | 8416 O SER I 211 | 9.372 8.538 37.331 1.00 50.74 | C O |
| ATOM | 8417 N CYS I 212 | 7.845 8.647 38.979 1.00 44.34 | C N |
| ATOM | 8418 CA CYS I 212 | 6.690 8.758 38.095 1.00 57.52 | C C |
| ATOM | 8419 CB CYS I 212 | 5.453 9.307 38.834 1.00 20.00 | C C |
| ATOM | 8420 SG CYS I 212 | 4.771 8.198 40.141 1.00 20.00 | C S |
| ATOM | 8421 C CYS I 212 | 7.005 9.537 36.808 1.00 60.91 | C C |
| ATOM | 8422 O CYS I 212 | 6.991 8.952 35.727 1.00 52.17 | C O |
| ATOM | 8423 N SER I 213 | 7.305 10.827 36.916 1.00 21.55 | C N |
| ATOM | 8424 CA SER I 213 | 7.501 11.624 35.711 1.00 21.67 | C C |
| ATOM | 8425 CB SER I 213 | 7.747 13.090 36.075 1.00 21.81 | C C |
| ATOM | 8426 OG SER I 213 | 6.648 13.630 36.788 1.00 23.00 | C O |
| ATOM | 8427 C SER I 213 | 8.650 11.098 34.858 1.00 21.45 | C C |
| ATOM | 8428 O SER I 213 | 8.509 10.969 33.640 1.00 21.98 | C O |
| ATOM | 8429 N ILE I 214 | 9.775 10.772 35.484 1.00 20.90 | C N |
| ATOM | 8430 CA ILE I 214 | 10.875 10.168 34.746 1.00 20.45 | C C |
| ATOM | 8431 CB ILE I 214 | 12.127 10.002 35.624 1.00 20.53 | C C |
| ATOM | 8432 CG1 ILE I 214 | 12.599 11.363 36.141 1.00 20.46 | C C |
| ATOM | 8433 CD1 ILE I 214 | 13.831 11.289 37.016 1.00 21.75 | C C |
| ATOM | 8434 CG2 ILE I 214 | 13.235 9.309 34.846 1.00 20.34 | C C |
| ATOM | 8435 C ILE I 214 | 10.423 8.802 34.247 1.00 20.15 | C C |
| ATOM | 8436 O ILE I 214 | 10.647 8.427 33.090 1.00 19.91 | C O |
| ATOM | 8437 N SER I 215 | 9.751 8.075 35.136 1.00 19.84 | C N |
| ATOM | 8438 CA SER I 215 | 9.240 6.749 34.827 1.00 19.58 | C C |
| ATOM | 8439 CB SER I 215 | 8.632 6.104 36.073 1.00 19.76 | C C |
| ATOM | 8440 OG SER I 215 | 8.132 4.810 35.785 1.00 19.97 | C O |
| ATOM | 8441 C SER I 215 | 8.201 6.841 33.724 1.00 19.34 | C C |
| ATOM | 8442 O SER I 215 | 8.172 6.013 32.818 1.00 19.54 | C O |
| ATOM | 8443 N ASN I 216 | 7.351 7.858 33.804 1.00 18.80 | C N |
| ATOM | 8444 CA ASN I 216 | 6.324 8.059 32.796 1.00 18.36 | C C |
| ATOM | 8445 CB ASN I 216 | 5.406 9.218 33.187 1.00 18.41 | C C |
| ATOM | 8446 CG ASN I 216 | 4.701 8.983 34.508 1.00 19.55 | C C |
| ATOM | 8447 OD1 ASN I 216 | 3.922 9.819 34.967 1.00 20.52 | C O |
| ATOM | 8448 ND2 ASN I 216 | 4.971 7.840 35.128 1.00 20.43 | C N |
| ATOM | 8449 C ASN I 216 | 6.958 8.324 31.440 1.00 17.78 | C C |
| ATOM | 8450 O ASN I 216 | 6.509 7.800 30.421 1.00 17.91 | C O |
| ATOM | 8451 N ILE I 217 | 8.016 9.130 31.433 1.00 17.02 | C N |
| ATOM | 8452 CA ILE I 217 | 8.714 9.439 30.194 1.00 16.60 | C C |
| ATOM | 8453 CB ILE I 217 | 9.833 10.472 30.417 1.00 16.46 | C C |
| ATOM | 8454 CG1 ILE I 217 | 9.252 11.776 30.969 1.00 16.26 | C C |
| ATOM | 8455 CD1 ILE I 217 | 10.289 12.849 31.217 1.00 16.44 | C C |
| ATOM | 8456 CG2 ILE I 217 | 10.589 10.727 29.122 1.00 16.70 | C C |
| ATOM | 8457 C ILE I 217 | 9.314 8.168 29.609 1.00 16.73 | C C |
| ATOM | 8458 O ILE I 217 | 9.247 7.931 28.398 1.00 16.80 | C O |
| ATOM | 8459 N GLU I 218 | 9.885 7.339 30.478 1.00 17.02 | C N |
| ATOM | 8460 CA GLU I 218 | 10.485 6.090 30.031 1.00 17.70 | C C |
| ATOM | 8461 CB GLU I 218 | 11.172 5.376 31.197 1.00 18.20 | C C |
| ATOM | 8462 CG GLU I 218 | 12.289 6.178 31.844 1.00 21.31 | C C |
| ATOM | 8463 CD GLU I 218 | 12.951 5.437 32.989 1.00 25.72 | C C |
| ATOM | 8464 OE1 GLU I 218 | 13.884 5.998 33.602 1.00 26.96 | C O |
| ATOM | 8465 OE2 GLU I 218 | 12.538 4.294 33.277 1.00 27.07 | C O |
| ATOM | 8466 C GLU I 218 | 9.419 5.192 29.418 1.00 17.29 | C C |
| ATOM | 8467 O GLU I 218 | 9.642 4.555 28.387 1.00 17.62 | C O |
| ATOM | 8468 N THR I 219 | 8.253 5.156 30.055 1.00 16.62 | C N |
| ATOM | 8469 CA THR I 219 | 7.146 4.342 29.577 1.00 15.95 | C C |
| ATOM | 8470 CB THR I 219 | 5.952 4.387 30.547 1.00 15.95 | C C |
| ATOM | 8471 OG1 THR I 219 | 6.356 3.894 31.831 1.00 15.63 | C O |
| ATOM | 8472 CG2 THR I 219 | 4.806 3.536 30.021 1.00 15.97 | C C |
| ATOM | 8473 C THR I 219 | 6.696 4.825 28.207 1.00 15.64 | C C |
| ATOM | 8474 O THR I 219 | 6.414 4.022 27.321 1.00 15.93 | C O |
| ATOM | 8475 N VAL I 220 | 6.639 6.141 28.037 1.00 14.98 | C N |
| ATOM | 8476 CA VAL I 220 | 6.235 6.720 26.764 1.00 14.51 | C C |
| ATOM | 8477 CB VAL I 220 | 6.143 8.254 26.844 1.00 14.29 | C C |
| ATOM | 8478 CG1 VAL I 220 | 5.716 8.830 25.502 1.00 14.24 | C C |
| ATOM | 8479 CG2 VAL I 220 | 5.176 8.671 27.942 1.00 14.10 | C C |
| ATOM | 8480 C VAL I 220 | 7.233 6.334 25.682 1.00 14.64 | C C |
| ATOM | 8481 O VAL I 220 | 6.850 5.992 24.560 1.00 14.79 | C O |

APPENDIX-continued (APPENDIX discloses SEQ ID NOS 29-32, 29-32 and 29-32, respectively, in order of appearance)

| | | | |
|---|---|---|---|
| ATOM | 8482 N ILE I 221 | 8.516 6.375 26.028 1.00 14.43 | C N |
| ATOM | 8483 CA ILE I 221 | 9.556 6.013 25.075 1.00 14.36 | C C |
| ATOM | 8484 CB ILE I 221 | 10.962 6.235 25.661 1.00 14.03 | C C |
| ATOM | 8485 CG1 ILE I 221 | 11.156 7.704 26.041 1.00 13.72 | C C |
| ATOM | 8486 CD1 ILE I 221 | 11.011 8.660 24.877 1.00 14.17 | C C |
| ATOM | 8487 CG2 ILE I 221 | 12.027 5.791 24.671 1.00 13.91 | C C |
| ATOM | 8488 C ILE I 221 | 9.404 4.552 24.672 1.00 14.82 | C C |
| ATOM | 8489 O ILE I 221 | 9.531 4.204 23.496 1.00 14.82 | C O |
| ATOM | 8490 N GLU I 222 | 9.112 3.703 25.652 1.00 15.51 | C N |
| ATOM | 8491 CA GLU I 222 | 8.936 2.281 25.392 1.00 16.52 | C C |
| ATOM | 8492 CB GLU I 222 | 8.730 1.517 26.701 1.00 16.80 | C C |
| ATOM | 8493 CG GLU I 222 | 9.889 1.635 27.677 1.00 19.14 | C C |
| ATOM | 8494 CD GLU I 222 | 9.653 0.861 28.959 1.00 22.62 | C C |
| ATOM | 8495 OE1 GLU I 222 | 10.539 0.882 29.840 1.00 24.35 | C O |
| ATOM | 8496 OE2 GLU I 222 | 8.583 0.230 29.086 1.00 23.98 | C O |
| ATOM | 8497 C GLU I 222 | 7.750 2.064 24.464 1.00 16.65 | C C |
| ATOM | 8498 O GLU I 222 | 7.802 1.238 23.553 1.00 16.95 | C O |
| ATOM | 8499 N PHE I 223 | 6.681 2.817 24.701 1.00 16.70 | C N |
| ATOM | 8500 CA PHE I 223 | 5.482 2.717 23.885 1.00 16.95 | C C |
| ATOM | 8501 CB PHE I 223 | 4.370 3.600 24.453 1.00 16.85 | C C |
| ATOM | 8502 CG PHE I 223 | 3.058 3.460 23.736 1.00 17.23 | C C |
| ATOM | 8503 CD1 PHE I 223 | 2.127 2.519 24.145 1.00 17.98 | C C |
| ATOM | 8504 CE1 PHE I 223 | 0.919 2.387 23.488 1.00 18.28 | C C |
| ATOM | 8505 CZ PHE I 223 | 0.629 3.199 22.409 1.00 18.19 | C C |
| ATOM | 8506 CE2 PHE I 223 | 1.548 4.140 21.991 1.00 18.14 | C C |
| ATOM | 8507 CD2 PHE I 223 | 2.755 4.267 22.653 1.00 17.75 | C C |
| ATOM | 8508 C PHE I 223 | 5.790 3.119 22.450 1.00 17.28 | C C |
| ATOM | 8509 O PHE I 223 | 5.324 2.482 21.506 1.00 17.17 | C O |
| ATOM | 8510 N GLN I 224 | 6.581 4.175 22.287 1.00 17.62 | C N |
| ATOM | 8511 CA GLN I 224 | 6.954 4.619 20.952 1.00 18.16 | C C |
| ATOM | 8512 CB GLN I 224 | 7.759 5.918 21.021 1.00 18.51 | C C |
| ATOM | 8513 CG GLN I 224 | 7.015 7.075 21.669 1.00 20.06 | C C |
| ATOM | 8514 CD GLN I 224 | 7.842 8.344 21.718 1.00 22.03 | C C |
| ATOM | 8515 OE1 GLN I 224 | 7.387 9.376 22.214 1.00 22.15 | C O |
| ATOM | 8516 NE2 GLN I 224 | 9.064 8.275 21.203 1.00 22.11 | C N |
| ATOM | 8517 C GLN I 224 | 7.767 3.532 20.261 1.00 18.04 | C C |
| ATOM | 8518 O GLN I 224 | 7.561 3.238 19.083 1.00 18.17 | C O |
| ATOM | 8519 N GLN I 225 | 8.688 2.933 21.009 1.00 17.90 | C N |
| ATOM | 8520 CA GLN I 225 | 9.508 1.840 20.500 1.00 17.95 | C C |
| ATOM | 8521 CB GLN I 225 | 10.599 1.474 21.509 1.00 18.13 | C C |
| ATOM | 8522 CG GLN I 225 | 11.551 2.613 21.833 1.00 19.04 | C C |
| ATOM | 8523 CD GLN I 225 | 12.619 2.213 22.831 1.00 21.22 | C C |
| ATOM | 8524 OE1 GLN I 225 | 12.659 1.072 23.292 1.00 22.55 | C O |
| ATOM | 8525 NE2 GLN I 225 | 13.493 3.154 23.172 1.00 22.48 | C N |
| ATOM | 8526 C GLN I 225 | 8.664 0.611 20.172 1.00 17.84 | C C |
| ATOM | 8527 O GLN I 225 | 8.892 −0.068 19.171 1.00 17.71 | C O |
| ATOM | 8528 N LYS I 226 | 7.693 0.334 21.036 1.00 17.95 | C N |
| ATOM | 8529 CA LYS I 226 | 6.848 −0.831 20.912 1.00 18.00 | C C |
| ATOM | 8530 CB LYS I 226 | 6.821 −1.593 22.234 1.00 18.21 | C C |
| ATOM | 8531 CG LYS I 226 | 8.189 −1.697 22.905 1.00 18.50 | C C |
| ATOM | 8532 CD LYS I 226 | 8.132 −2.591 24.132 1.00 19.87 | C C |
| ATOM | 8533 CE LYS I 226 | 9.357 −2.411 25.004 1.00 21.36 | C C |
| ATOM | 8534 NZ LYS I 226 | 9.268 −3.230 26.248 1.00 21.83 | C N |
| ATOM | 8535 C LYS I 226 | 5.446 −0.408 20.499 1.00 17.84 | C C |
| ATOM | 8536 O LYS I 226 | 4.672 −1.220 19.998 1.00 17.94 | C O |
| ATOM | 8537 N ASN I 227 | 5.209 0.900 20.514 1.00 17.70 | C N |
| ATOM | 8538 CA ASN I 227 | 4.173 1.494 19.683 1.00 17.66 | C C |
| ATOM | 8539 CB ASN I 227 | 3.153 2.256 20.549 1.00 17.36 | C C |
| ATOM | 8540 CG ASN I 227 | 2.612 1.411 21.710 1.00 17.40 | C C |
| ATOM | 8541 OD1 ASN I 227 | 2.451 0.196 21.589 1.00 17.84 | C O |
| ATOM | 8542 ND2 ASN I 227 | 2.333 2.059 22.834 1.00 17.22 | C N |
| ATOM | 8543 C ASN I 227 | 4.713 2.343 18.506 1.00 17.76 | C C |
| ATOM | 8544 O ASN I 227 | 3.943 2.750 17.635 1.00 17.92 | C O |
| ATOM | 8545 N ASN I 228 | 6.045 2.460 18.398 1.00 17.78 | C N |
| ATOM | 8546 CA ASN I 228 | 6.734 2.532 17.084 1.00 17.59 | C C |
| ATOM | 8547 CB ASN I 228 | 8.170 3.085 17.155 1.00 17.89 | C C |
| ATOM | 8548 CG ASN I 228 | 8.870 3.082 15.779 1.00 18.43 | C C |
| ATOM | 8549 OD1 ASN I 228 | 9.451 2.077 15.366 1.00 18.74 | C O |
| ATOM | 8550 ND2 ASN I 228 | 8.682 4.157 15.022 1.00 18.61 | C N |
| ATOM | 8551 C ASN I 228 | 6.765 1.204 16.358 1.00 17.09 | C C |
| ATOM | 8552 O ASN I 228 | 6.004 0.992 15.417 1.00 17.17 | C O |
| ATOM | 8553 N ARG I 229 | 7.685 0.328 16.745 1.00 16.33 | C N |
| ATOM | 8554 CA ARG I 229 | 7.664 −1.016 16.195 1.00 15.76 | C C |
| ATOM | 8555 CB ARG I 229 | 8.624 −1.952 16.933 1.00 15.70 | C C |
| ATOM | 8556 CG ARG I 229 | 9.369 −2.904 16.000 1.00 14.99 | C C |
| ATOM | 8557 CD ARG I 229 | 9.887 −4.135 16.728 1.00 15.33 | C C |
| ATOM | 8558 NE ARG I 229 | 9.601 −5.376 16.008 1.00 15.59 | C N |

APPENDIX-continued (APPENDIX discloses SEQ ID NOS 29-32, 29-32 and 29-32, respectively, in order of appearance)

| | | | |
|---|---|---|---|
| ATOM | 8559 CZ ARG I 229 | 9.926 −6.587 16.451 1.00 15.85 | C C |
| ATOM | 8560 NH1 ARG I 229 | 10.559 −6.725 17.609 1.00 16.20 | C N |
| ATOM | 8561 NH2 ARG I 229 | 9.650 −7.660 15.722 1.00 16.63 | C N |
| ATOM | 8562 C ARG I 229 | 6.238 −1.559 16.223 1.00 15.62 | C C |
| ATOM | 8563 O ARG I 229 | 5.666 −1.860 15.175 1.00 15.73 | C O |
| ATOM | 8564 N LEU I 230 | 5.601 −1.468 17.387 1.00 15.46 | C N |
| ATOM | 8565 CA LEU I 230 | 4.191 −1.829 17.511 1.00 15.22 | C C |
| ATOM | 8566 CB LEU I 230 | 3.735 −1.792 18.974 1.00 15.08 | C C |
| ATOM | 8567 CG LEU I 230 | 2.252 −2.079 19.224 1.00 14.70 | C C |
| ATOM | 8568 CD1 LEU I 230 | 2.003 −3.572 19.359 1.00 15.19 | C C |
| ATOM | 8569 CD2 LEU I 230 | 1.743 −1.335 20.449 1.00 15.46 | C C |
| ATOM | 8570 C LEU I 230 | 3.302 −0.931 16.655 1.00 15.31 | C C |
| ATOM | 8571 O LEU I 230 | 2.417 −1.415 15.950 1.00 15.46 | C O |
| ATOM | 8572 N LEU I 231 | 3.519 0.377 16.745 1.00 15.48 | C N |
| ATOM | 8573 CA LEU I 231 | 2.678 1.338 16.038 1.00 15.75 | C C |
| ATOM | 8574 CB LEU I 231 | 3.187 2.763 16.257 1.00 15.90 | C C |
| ATOM | 8575 CG LEU I 231 | 2.906 3.379 17.628 1.00 16.63 | C C |
| ATOM | 8576 CD1 LEU I 231 | 3.382 4.819 17.676 1.00 18.45 | C C |
| ATOM | 8577 CD2 LEU I 231 | 1.425 3.292 17.961 1.00 16.67 | C C |
| ATOM | 8578 C LEU I 231 | 2.653 1.025 14.551 1.00 15.76 | C C |
| ATOM | 8579 O LEU I 231 | 1.606 1.092 13.908 1.00 15.84 | C O |
| ATOM | 8580 N GLU I 232 | 3.828 0.750 13.997 1.00 15.71 | C N |
| ATOM | 8581 CA GLU I 232 | 3.973 0.563 12.562 1.00 15.93 | C C |
| ATOM | 8582 CB GLU I 232 | 5.447 0.626 12.163 1.00 16.15 | C C |
| ATOM | 8583 CG GLU I 232 | 6.142 1.913 12.568 1.00 18.59 | C C |
| ATOM | 8584 CD GLU I 232 | 6.407 2.823 11.387 1.00 21.47 | C C |
| ATOM | 8585 OE1 GLU I 232 | 5.892 2.532 10.286 1.00 22.14 | C O |
| ATOM | 8586 OE2 GLU I 232 | 7.214 3.765 11.530 1.00 23.34 | C O |
| ATOM | 8587 C GLU I 232 | 3.377 −0.767 12.124 1.00 15.45 | C C |
| ATOM | 8588 O GLU I 232 | 2.921 −0.908 10.990 1.00 15.95 | C O |
| ATOM | 8589 N ILE I 233 | 3.432 −1.757 13.007 1.00 14.54 | C N |
| ATOM | 8590 CA ILE I 233 | 2.713 −3.000 12.776 1.00 13.69 | C C |
| ATOM | 8591 CB ILE I 233 | 2.998 −4.028 13.873 1.00 13.63 | C C |
| ATOM | 8592 CG1 ILE I 233 | 4.500 −4.093 14.151 1.00 13.58 | C C |
| ATOM | 8593 CD1 ILE I 233 | 4.854 −4.786 15.444 1.00 13.55 | C C |
| ATOM | 8594 CG2 ILE I 233 | 2.458 −5.392 13.469 1.00 13.88 | C C |
| ATOM | 8595 C ILE I 233 | 1.219 −2.728 12.735 1.00 13.28 | C C |
| ATOM | 8596 O ILE I 233 | 0.528 −3.137 11.802 1.00 13.04 | C O |
| ATOM | 8597 N THR I 234 | 0.764 −1.898 13.667 1.00 13.18 | C N |
| ATOM | 8598 CA THR I 234 | −0.651 −1.590 13.796 1.00 13.39 | C C |
| ATOM | 8599 CB THR I 234 | −0.913 −0.636 14.974 1.00 13.21 | C C |
| ATOM | 8600 OG1 THR I 234 | −0.476 −1.248 16.193 1.00 13.15 | C O |
| ATOM | 8601 CG2 THR I 234 | −2.395 −0.311 15.078 1.00 13.22 | C C |
| ATOM | 8602 C THR I 234 | −1.208 −0.981 12.514 1.00 13.76 | C C |
| ATOM | 8603 O THR I 234 | −2.230 −1.432 11.997 1.00 13.95 | C O |
| ATOM | 8604 N ARG I 235 | −0.535 0.045 12.003 1.00 14.26 | C N |
| ATOM | 8605 CA ARG I 235 | −0.945 0.670 10.752 1.00 14.92 | C C |
| ATOM | 8606 CB ARG I 235 | −0.051 1.874 10.432 1.00 15.30 | C C |
| ATOM | 8607 CG ARG I 235 | 0.875 1.681 9.240 1.00 16.27 | C C |
| ATOM | 8608 CD ARG I 235 | 2.190 2.436 9.413 1.00 18.52 | C C |
| ATOM | 8609 NE ARG I 235 | 2.083 3.558 10.344 1.00 17.86 | C N |
| ATOM | 8610 CZ ARG I 235 | 1.516 4.724 10.051 1.00 16.91 | C C |
| ATOM | 8611 NH1 ARG I 235 | 0.855 4.874 8.912 1.00 16.59 | C N |
| ATOM | 8612 NH2 ARG I 235 | 1.511 5.703 10.946 1.00 16.86 | C N |
| ATOM | 8613 C ARG I 235 | −0.904 −0.353 9.620 1.00 15.05 | C C |
| ATOM | 8614 O ARG I 235 | −1.939 −0.693 9.045 1.00 15.15 | C O |
| ATOM | 8615 N GLU I 236 | 0.240 −1.020 9.504 1.00 15.18 | C N |
| ATOM | 8616 CA GLU I 236 | 0.451 −2.047 8.490 1.00 15.24 | C C |
| ATOM | 8617 CB GLU I 236 | 1.725 −2.835 8.801 1.00 15.69 | C C |
| ATOM | 8618 CG GLU I 236 | 2.432 −3.396 7.580 1.00 18.22 | C C |
| ATOM | 8619 CD GLU I 236 | 3.760 −4.040 7.926 1.00 21.59 | C C |
| ATOM | 8620 OE1 GLU I 236 | 4.381 −4.645 7.027 1.00 24.41 | C O |
| ATOM | 8621 OE2 GLU I 236 | 4.182 −3.944 9.097 1.00 21.59 | C O |
| ATOM | 8622 C GLU I 236 | −0.735 −2.999 8.400 1.00 14.61 | C C |
| ATOM | 8623 O GLU I 236 | −1.191 −3.334 7.307 1.00 14.82 | C O |
| ATOM | 8624 N PHE I 237 | −1.184 −3.485 9.552 1.00 14.05 | C N |
| ATOM | 8625 CA PHE I 237 | −2.318 −4.397 9.602 1.00 13.84 | C C |
| ATOM | 8626 CB PHE I 237 | −2.466 −4.996 11.003 1.00 14.04 | C C |
| ATOM | 8627 CG PHE I 237 | −1.643 −6.235 11.225 1.00 14.84 | C C |
| ATOM | 8628 CD1 PHE I 237 | −0.734 −6.296 12.267 1.00 15.30 | C C |
| ATOM | 8629 CE1 PHE I 237 | −0.006 −7.446 12.503 1.00 15.15 | C C |
| ATOM | 8630 CZ PHE I 237 | −0.197 −8.557 11.708 1.00 15.19 | C C |
| ATOM | 8631 CE2 PHE I 237 | −1.110 −8.514 10.673 1.00 15.02 | C C |
| ATOM | 8632 CD2 PHE I 237 | −1.831 −7.360 10.439 1.00 15.03 | C C |
| ATOM | 8633 C PHE I 237 | −3.607 −3.689 9.195 1.00 13.51 | C C |
| ATOM | 8634 O PHE I 237 | −4.387 −4.213 8.399 1.00 13.43 | C O |
| ATOM | 8635 N SER I 238 | −3.830 −2.503 9.754 1.00 13.11 | C N |

APPENDIX-continued (APPENDIX discloses SEQ ID NOS 29-32, 29-32 and 29-32, respectively, in order of appearance)

| | | | |
|---|---|---|---|
| ATOM | 8636 CA SER I 238 | −5.032 −1.729 9.460 1.00 12.82 | C C |
| ATOM | 8637 CB SER I 238 | −5.049 −0.438 10.279 1.00 12.86 | C C |
| ATOM | 8638 OG SER I 238 | −5.205 −0.711 11.660 1.00 12.76 | C O |
| ATOM | 8639 C SER I 238 | −5.104 −1.400 7.977 1.00 12.69 | C C |
| ATOM | 8640 O SER I 238 | −6.187 −1.237 7.414 1.00 12.63 | C O |
| ATOM | 8641 N VAL I 239 | −3.937 −1.313 7.349 1.00 12.59 | C N |
| ATOM | 8642 CA VAL I 239 | −3.858 −1.042 5.923 1.00 12.80 | C C |
| ATOM | 8643 CB VAL I 239 | −2.482 −0.473 5.524 1.00 12.71 | C C |
| ATOM | 8644 CG1 VAL I 239 | −2.390 −0.321 4.012 1.00 13.63 | C C |
| ATOM | 8645 CG2 VAL I 239 | −2.239 0.859 6.214 1.00 13.57 | C C |
| ATOM | 8646 C VAL I 239 | −4.144 −2.286 5.090 1.00 12.94 | C C |
| ATOM | 8647 O VAL I 239 | −4.320 −2.190 3.877 1.00 13.10 | C O |
| ATOM | 8648 N ASN I 240 | −4.139 −3.458 5.721 1.00 4.15 | C N |
| ATOM | 8649 CA ASN I 240 | −4.166 −4.709 4.966 1.00 4.33 | C C |
| ATOM | 8650 CB ASN I 240 | −2.941 −5.569 5.281 1.00 4.59 | C C |
| ATOM | 8651 CG ASN I 240 | −1.674 −5.027 4.647 1.00 5.36 | C C |
| ATOM | 8652 OD1 ASN I 240 | −1.524 −5.043 3.423 1.00 6.27 | C O |
| ATOM | 8653 ND2 ASN I 240 | −0.816 −4.427 5.465 1.00 7.15 | C N |
| ATOM | 8654 C ASN I 240 | −5.454 −5.529 5.074 1.00 4.19 | C C |
| ATOM | 8655 O ASN I 240 | −5.634 −6.507 4.347 1.00 4.19 | C O |
| ATOM | 8656 N ALA I 241 | −6.385 −5.073 5.904 1.00 3.93 | C N |
| ATOM | 8657 CA ALA I 241 | −7.593 −5.840 6.186 1.00 3.90 | C C |
| ATOM | 8658 CB ALA I 241 | −8.563 −5.749 5.020 1.00 3.86 | C C |
| ATOM | 8659 C ALA I 241 | −7.253 −7.297 6.491 1.00 4.22 | C C |
| ATOM | 8660 O ALA I 241 | −7.778 −8.212 5.856 1.00 4.47 | C O |
| ATOM | 8661 N GLY I 242 | −6.289 −7.497 7.386 1.00 4.53 | C N |
| ATOM | 8662 CA GLY I 242 | −6.124 −8.774 8.078 1.00 4.65 | C C |
| ATOM | 8663 C GLY I 242 | −5.398 −9.848 7.282 1.00 4.67 | C C |
| ATOM | 8664 O GLY I 242 | −5.496 −11.034 7.600 1.00 5.27 | C O |
| ATOM | 8665 N VAL I 243 | −4.611 −9.433 6.292 1.00 4.37 | C N |
| ATOM | 8666 CA VAL I 243 | −3.780 −10.366 5.531 1.00 4.32 | C C |
| ATOM | 8667 CB VAL I 243 | −4.570 −11.042 4.389 1.00 3.99 | C C |
| ATOM | 8668 CG1 VAL I 243 | −3.987 −12.411 4.078 1.00 4.22 | C C |
| ATOM | 8669 CG2 VAL I 243 | −6.042 −11.154 4.748 1.00 3.85 | C C |
| ATOM | 8670 C VAL I 243 | −2.571 −9.658 4.932 1.00 4.61 | C C |
| ATOM | 8671 O VAL I 243 | −2.704 −8.607 4.308 1.00 4.89 | C O |
| ATOM | 8672 N THR I 244 | −1.402 −10.269 5.072 1.00 4.95 | C N |
| ATOM | 8673 CA THR I 244 | −0.168 −9.654 4.604 1.00 5.71 | C C |
| ATOM | 8674 CB THR I 244 | 0.678 −9.128 5.775 1.00 6.11 | C C |
| ATOM | 8675 OG1 THR I 244 | −0.078 −9.209 6.989 1.00 7.17 | C O |
| ATOM | 8676 CG2 THR I 244 | 1.091 −7.686 5.532 1.00 7.55 | C C |
| ATOM | 8677 C THR I 244 | 0.664 −10.649 3.813 1.00 5.61 | C C |
| ATOM | 8678 O THR I 244 | 0.811 −11.803 4.214 1.00 5.85 | C O |
| ATOM | 8679 N THR I 245 | 1.346 −10.150 2.791 1.00 5.53 | C N |
| ATOM | 8680 CA THR I 245 | 2.556 −10.791 2.308 1.00 5.81 | C C |
| ATOM | 8681 CB THR I 245 | 2.426 −11.170 0.818 1.00 6.13 | C C |
| ATOM | 8682 OG1 THR I 245 | 1.421 −12.181 0.668 1.00 8.11 | C O |
| ATOM | 8683 CG2 THR I 245 | 3.746 −11.696 0.281 1.00 6.63 | C C |
| ATOM | 8684 C THR I 245 | 3.748 −9.865 2.542 1.00 5.73 | C C |
| ATOM | 8685 O THR I 245 | 3.568 −8.705 2.916 1.00 5.86 | C O |
| ATOM | 8686 N PRO I 246 | 4.963 −10.337 2.223 1.00 5.68 | C N |
| ATOM | 8687 CA PRO I 246 | 5.942 −10.579 3.269 1.00 5.11 | C C |
| ATOM | 8688 CB PRO I 246 | 6.802 −9.317 3.210 1.00 5.19 | C C |
| ATOM | 8689 CG PRO I 246 | 6.717 −8.878 1.734 1.00 5.90 | C C |
| ATOM | 8690 CD PRO I 246 | 5.613 −9.691 1.074 1.00 6.36 | C C |
| ATOM | 8691 C PRO I 246 | 5.360 −10.786 4.664 1.00 4.85 | C C |
| ATOM | 8692 O PRO I 246 | 4.465 −10.053 5.084 1.00 5.25 | C O |
| ATOM | 8693 N VAL I 247 | 5.795 −11.859 5.316 1.00 4.35 | C N |
| ATOM | 8694 CA VAL I 247 | 5.555 −12.048 6.739 1.00 3.82 | C C |
| ATOM | 8695 CB VAL I 247 | 5.603 −13.536 7.127 1.00 3.52 | C C |
| ATOM | 8696 CG1 VAL I 247 | 5.206 −13.717 8.584 1.00 3.62 | C C |
| ATOM | 8697 CG2 VAL I 247 | 4.694 −14.347 6.218 1.00 3.60 | C C |
| ATOM | 8698 C VAL I 247 | 6.576 −11.271 7.558 1.00 3.69 | C C |
| ATOM | 8699 O VAL I 247 | 7.744 −11.653 7.641 1.00 3.36 | C O |
| ATOM | 8700 N SER I 248 | 6.172 −10.077 7.973 1.00 3.72 | C N |
| ATOM | 8701 CA SER I 248 | 7.077 −9.138 8.611 1.00 3.96 | C C |
| ATOM | 8702 CB SER I 248 | 6.291 −7.973 9.214 1.00 4.07 | C C |
| ATOM | 8703 OG SER I 248 | 5.661 −8.356 10.425 1.00 4.13 | C O |
| ATOM | 8704 C SER I 248 | 7.885 −9.830 9.695 1.00 4.35 | C C |
| ATOM | 8705 O SER I 248 | 7.453 −10.838 10.257 1.00 4.36 | C O |
| ATOM | 8706 N THR I 249 | 9.008 −9.223 10.057 1.00 4.53 | C N |
| ATOM | 8707 CA THR I 249 | 9.752 −9.638 11.235 1.00 4.61 | C C |
| ATOM | 8708 CB THR I 249 | 11.104 −8.916 11.329 1.00 4.70 | C C |
| ATOM | 8709 OG1 THR I 249 | 10.889 −7.544 11.679 1.00 5.42 | C O |
| ATOM | 8710 CG2 THR I 249 | 11.833 −8.984 9.999 1.00 4.88 | C C |
| ATOM | 8711 C THR I 249 | 8.955 −9.383 12.509 1.00 4.47 | C C |
| ATOM | 8712 O THR I 249 | 9.321 −9.861 13.584 1.00 4.74 | C O |

APPENDIX-continued (APPENDIX discloses SEQ ID NOS 29-32, 29-32 and 29-32, respectively, in order of appearance)

| | | | |
|---|---|---|---|
| ATOM | 8713 N TYR I 250 | 7.864 −8.633 12.388 1.00 4.32 | C N |
| ATOM | 8714 CA TYR I 250 | 6.956 −8.435 13.512 1.00 4.42 | C C |
| ATOM | 8715 CB TYR I 250 | 6.195 −7.113 13.381 1.00 4.91 | C C |
| ATOM | 8716 CG TYR I 250 | 7.072 −5.881 13.272 1.00 6.81 | C C |
| ATOM | 8717 CD1 TYR I 250 | 6.791 −4.897 12.333 1.00 8.89 | C C |
| ATOM | 8718 CE1 TYR I 250 | 7.556 −3.752 12.243 1.00 10.73 | C C |
| ATOM | 8719 CZ TYR I 250 | 8.587 −3.549 13.137 1.00 12.28 | C C |
| ATOM | 8720 OH TYR I 250 | 9.370 −2.421 13.032 1.00 12.24 | C O |
| ATOM | 8721 CE2 TYR I 250 | 8.851 −4.483 14.121 1.00 12.15 | C C |
| ATOM | 8722 CD2 TYR I 250 | 8.067 −5.621 14.209 1.00 9.81 | C C |
| ATOM | 8723 C TYR I 250 | 5.973 −9.592 13.662 1.00 4.21 | C C |
| ATOM | 8724 O TYR I 250 | 5.525 −9.893 14.768 1.00 4.20 | C O |
| ATOM | 8725 N MET I 251 | 5.574 −10.183 12.541 1.00 4.14 | C N |
| ATOM | 8726 CA MET I 251 | 4.731 −11.372 12.574 1.00 4.15 | C C |
| ATOM | 8727 CB MET I 251 | 4.160 −11.662 11.187 1.00 4.14 | C C |
| ATOM | 8728 CG MET I 251 | 3.297 −10.547 10.630 1.00 4.51 | C C |
| ATOM | 8729 SD MET I 251 | 1.731 −10.386 11.505 1.00 3.81 | C S |
| ATOM | 8730 CE MET I 251 | 0.800 −9.412 10.327 1.00 4.55 | C C |
| ATOM | 8731 C MET I 251 | 5.540 −12.565 13.057 1.00 4.13 | C C |
| ATOM | 8732 O MET I 251 | 5.127 −13.289 13.964 1.00 4.24 | C O |
| ATOM | 8733 N LEU I 252 | 6.728 −12.718 12.487 1.00 4.23 | C N |
| ATOM | 8734 CA LEU I 252 | 7.586 −13.848 12.792 1.00 4.22 | C C |
| ATOM | 8735 CB LEU I 252 | 7.586 −14.839 11.631 1.00 4.14 | C C |
| ATOM | 8736 CG LEU I 252 | 6.703 −16.071 11.816 1.00 4.05 | C C |
| ATOM | 8737 CD1 LEU I 252 | 7.171 −17.204 10.918 1.00 5.22 | C C |
| ATOM | 8738 CD2 LEU I 252 | 6.692 −16.508 13.273 1.00 6.20 | C C |
| ATOM | 8739 C LEU I 252 | 8.998 −13.356 13.040 1.00 4.62 | C C |
| ATOM | 8740 O LEU I 252 | 9.599 −12.712 12.182 1.00 4.97 | C O |
| ATOM | 8741 N THR I 253 | 9.531 −13.670 14.212 1.00 4.90 | C N |
| ATOM | 8742 CA THR I 253 | 10.942 −13.463 14.472 1.00 5.57 | C C |
| ATOM | 8743 CB THR I 253 | 11.265 −13.708 15.946 1.00 5.55 | C C |
| ATOM | 8744 OG1 THR I 253 | 10.337 −12.987 16.765 1.00 6.43 | C O |
| ATOM | 8745 CG2 THR I 253 | 12.673 −13.251 16.259 1.00 6.28 | C C |
| ATOM | 8746 C THR I 253 | 11.753 −14.424 13.622 1.00 6.03 | C C |
| ATOM | 8747 O THR I 253 | 11.315 −15.541 13.349 1.00 6.68 | C O |
| ATOM | 8748 N ASN I 254 | 12.961 −14.015 13.255 1.00 6.39 | C N |
| ATOM | 8749 CA ASN I 254 | 13.951 −14.973 12.800 1.00 6.79 | C C |
| ATOM | 8750 CB ASN I 254 | 15.341 −14.348 12.762 1.00 6.85 | C C |
| ATOM | 8751 CG ASN I 254 | 16.324 −15.177 11.964 1.00 6.81 | C C |
| ATOM | 8752 OD1 ASN I 254 | 16.152 −15.366 10.760 1.00 7.67 | C O |
| ATOM | 8753 ND2 ASN I 254 | 17.271 −15.799 12.657 1.00 6.19 | C N |
| ATOM | 8754 C ASN I 254 | 13.964 −16.211 13.686 1.00 7.08 | C C |
| ATOM | 8755 O ASN I 254 | 13.654 −17.312 13.231 1.00 6.90 | C O |
| ATOM | 8756 N SER I 255 | 14.283 −16.017 14.962 1.00 7.21 | C N |
| ATOM | 8757 CA SER I 255 | 14.292 −17.112 15.929 1.00 7.37 | C C |
| ATOM | 8758 CB SER I 255 | 14.338 −16.568 17.360 1.00 8.09 | C C |
| ATOM | 8759 OG SER I 255 | 14.953 −15.293 17.407 1.00 10.47 | C O |
| ATOM | 8760 C SER I 255 | 13.078 −18.024 15.750 1.00 6.82 | C C |
| ATOM | 8761 O SER I 255 | 13.205 −19.249 15.768 1.00 6.99 | C O |
| ATOM | 8762 N GLU I 256 | 11.901 −17.422 15.611 1.00 6.17 | C N |
| ATOM | 8763 CA GLU I 256 | 10.658 −18.184 15.544 1.00 6.13 | C C |
| ATOM | 8764 CB GLU I 256 | 9.452 −17.266 15.742 1.00 6.22 | C C |
| ATOM | 8765 CG GLU I 256 | 9.210 −16.863 17.185 1.00 8.41 | C C |
| ATOM | 8766 CD GLU I 256 | 8.527 −15.516 17.299 1.00 10.26 | C C |
| ATOM | 8767 OE1 GLU I 256 | 8.232 −14.907 16.248 1.00 11.90 | C O |
| ATOM | 8768 OE2 GLU I 256 | 8.275 −15.070 18.437 1.00 9.55 | C O |
| ATOM | 8769 C GLU I 256 | 10.535 −18.895 14.209 1.00 5.76 | C C |
| ATOM | 8770 O GLU I 256 | 10.154 −20.064 14.154 1.00 5.93 | C O |
| ATOM | 8771 N LEU I 257 | 10.669 −18.124 13.134 1.00 5.67 | C N |
| ATOM | 8772 CA LEU I 257 | 10.638 −18.679 11.787 1.00 5.37 | C C |
| ATOM | 8773 CB LEU I 257 | 11.010 −17.613 10.753 1.00 5.03 | C C |
| ATOM | 8774 CG LEU I 257 | 11.316 −18.130 9.344 1.00 3.65 | C C |
| ATOM | 8775 CD1 LEU I 257 | 10.067 −18.702 8.689 1.00 2.00 | C C |
| ATOM | 8776 CD2 LEU I 257 | 11.917 −17.030 8.485 1.00 2.14 | C C |
| ATOM | 8777 C LEU I 257 | 11.580 −19.871 11.670 1.00 5.64 | C C |
| ATOM | 8778 O LEU I 257 | 11.234 −20.895 11.079 1.00 5.81 | C O |
| ATOM | 8779 N LEU I 258 | 12.764 −19.741 12.259 1.00 5.75 | C N |
| ATOM | 8780 CA LEU I 258 | 13.808 −20.739 12.081 1.00 5.91 | C C |
| ATOM | 8781 CB LEU I 258 | 15.156 −20.215 12.583 1.00 6.10 | C C |
| ATOM | 8782 CG LEU I 258 | 16.059 −19.626 11.495 1.00 5.75 | C C |
| ATOM | 8783 CD1 LEU I 258 | 17.208 −18.836 12.101 1.00 6.33 | C C |
| ATOM | 8784 CD2 LEU I 258 | 16.577 −20.724 10.577 1.00 7.33 | C C |
| ATOM | 8785 C LEU I 258 | 13.464 −22.074 12.736 1.00 6.03 | C C |
| ATOM | 8786 O LEU I 258 | 13.589 −23.125 12.109 1.00 5.73 | C O |
| ATOM | 8787 N SER I 259 | 12.980 −22.030 13.974 1.00 6.47 | C N |
| ATOM | 8788 CA SER I 259 | 12.538 −23.243 14.662 1.00 6.95 | C C |
| ATOM | 8789 CB SER I 259 | 12.400 −23.000 16.168 1.00 7.05 | C C |

APPENDIX-continued (APPENDIX discloses SEQ ID NOS 29-32, 29-32 and 29-32, respectively, in order of appearance)

| | | | |
|---|---|---|---|
| ATOM | 8790 OG SER I 259 | 11.147 −23.460 16.650 1.00 6.86 | C O |
| ATOM | 8791 C SER I 259 | 11.220 −23.759 14.097 1.00 6.74 | C C |
| ATOM | 8792 O SER I 259 | 10.905 −24.943 14.213 1.00 6.86 | C O |
| ATOM | 8793 N LEU I 260 | 10.411 −22.844 13.576 1.00 6.31 | C N |
| ATOM | 8794 CA LEU I 260 | 9.188 −23.211 12.880 1.00 6.09 | C C |
| ATOM | 8795 CB LEU I 260 | 8.407 −21.957 12.484 1.00 6.09 | C C |
| ATOM | 8796 CG LEU I 260 | 7.140 −21.665 13.291 1.00 6.24 | C C |
| ATOM | 8797 CD1 LEU I 260 | 6.291 −20.595 12.611 1.00 6.53 | C C |
| ATOM | 8798 CD2 LEU I 260 | 6.337 −22.944 13.521 1.00 5.98 | C C |
| ATOM | 8799 C LEU I 260 | 9.497 −24.047 11.644 1.00 6.25 | C C |
| ATOM | 8800 O LEU I 260 | 8.809 −25.028 11.361 1.00 6.37 | C O |
| ATOM | 8801 N ILE I 261 | 10.452 −23.580 10.847 1.00 6.63 | C N |
| ATOM | 8802 CA ILE I 261 | 10.952 −24.360 9.723 1.00 7.19 | C C |
| ATOM | 8803 CB ILE I 261 | 12.165 −23.681 9.061 1.00 7.09 | C C |
| ATOM | 8804 CG1 ILE I 261 | 11.703 −22.635 8.046 1.00 7.46 | C C |
| ATOM | 8805 CD1 ILE I 261 | 12.646 −21.460 7.909 1.00 8.38 | C C |
| ATOM | 8806 CG2 ILE I 261 | 13.055 −24.718 8.391 1.00 6.61 | C C |
| ATOM | 8807 C ILE I 261 | 11.389 −25.723 10.228 1.00 8.01 | C C |
| ATOM | 8808 O ILE I 261 | 10.967 −26.758 9.713 1.00 8.26 | C O |
| ATOM | 8809 N ASN I 262 | 12.206 −25.708 11.273 1.00 9.05 | C N |
| ATOM | 8810 CA ASN I 262 | 12.640 −26.935 11.912 1.00 9.88 | C C |
| ATOM | 8811 CB ASN I 262 | 13.220 −26.636 13.292 1.00 9.99 | C C |
| ATOM | 8812 CG ASN I 262 | 14.327 −27.590 13.672 1.00 11.16 | C C |
| ATOM | 8813 OD1 ASN I 262 | 14.709 −28.457 12.886 1.00 12.70 | C O |
| ATOM | 8814 ND2 ASN I 262 | 14.912 −27.379 14.844 1.00 13.20 | C N |
| ATOM | 8815 C ASN I 262 | 11.500 −27.939 12.023 1.00 10.17 | C C |
| ATOM | 8816 O ASN I 262 | 11.661 −29.108 11.675 1.00 10.52 | C O |
| ATOM | 8817 N ASP I 263 | 10.315 −27.444 12.368 1.00 10.62 | C N |
| ATOM | 8818 CA ASP I 263 | 9.203 −28.311 12.741 1.00 11.02 | C C |
| ATOM | 8819 CB ASP I 263 | 8.230 −27.584 13.675 1.00 11.49 | C C |
| ATOM | 8820 CG ASP I 263 | 7.026 −28.435 14.040 1.00 12.80 | C C |
| ATOM | 8821 OD1 ASP I 263 | 7.219 −29.586 14.487 1.00 14.72 | C O |
| ATOM | 8822 OD2 ASP I 263 | 5.886 −27.978 13.811 1.00 13.88 | C O |
| ATOM | 8823 C ASP I 263 | 8.460 −28.855 11.520 1.00 10.92 | C C |
| ATOM | 8824 O ASP I 263 | 7.619 −29.748 11.642 1.00 10.96 | C O |
| ATOM | 8825 N MET I 264 | 8.807 −28.346 10.341 1.00 10.91 | C N |
| ATOM | 8826 CA MET I 264 | 8.105 −28.707 9.110 1.00 10.78 | C C |
| ATOM | 8827 CB MET I 264 | 8.397 −27.687 8.007 1.00 10.51 | C C |
| ATOM | 8828 CG MET I 264 | 7.934 −26.276 8.329 1.00 11.26 | C C |
| ATOM | 8829 SD MET I 264 | 8.142 −25.144 6.942 1.00 12.70 | C S |
| ATOM | 8830 CE MET I 264 | 9.799 −25.565 6.411 1.00 13.92 | C C |
| ATOM | 8831 C MET I 264 | 8.466 −30.116 8.631 1.00 10.85 | C C |
| ATOM | 8832 O MET I 264 | 9.644 −30.472 8.578 1.00 11.03 | C O |
| ATOM | 8833 N PRO I 265 | 7.451 −30.900 8.230 1.00 10.88 | C N |
| ATOM | 8834 CA PRO I 265 | 7.647 −32.293 7.841 1.00 11.09 | C C |
| ATOM | 8835 CB PRO I 265 | 6.215 −32.820 7.685 1.00 11.28 | C C |
| ATOM | 8836 CG PRO I 265 | 5.387 −31.612 7.438 1.00 11.24 | C C |
| ATOM | 8837 CD PRO I 265 | 6.025 −30.534 8.255 1.00 11.03 | C C |
| ATOM | 8838 C PRO I 265 | 8.400 −32.420 6.521 1.00 11.19 | C C |
| ATOM | 8839 O PRO I 265 | 7.889 −33.027 5.580 1.00 11.47 | C O |
| ATOM | 8840 N ILE I 266 | 9.642 −31.940 6.488 1.00 11.54 | C N |
| ATOM | 8841 CA ILE I 266 | 10.448 −31.980 5.266 1.00 12.15 | C C |
| ATOM | 8842 CB ILE I 266 | 10.586 −30.587 4.621 1.00 12.22 | C C |
| ATOM | 8843 CG1 ILE I 266 | 11.051 −29.559 5.654 1.00 12.53 | C C |
| ATOM | 8844 CD1 ILE I 266 | 11.557 −28.269 5.047 1.00 12.40 | C C |
| ATOM | 8845 CG2 ILE I 266 | 9.271 −30.157 3.984 1.00 12.74 | C C |
| ATOM | 8846 C ILE I 266 | 11.839 −32.574 5.485 1.00 12.29 | C C |
| ATOM | 8847 O ILE I 266 | 12.291 −32.724 6.619 1.00 12.36 | C O |
| ATOM | 8848 N THR I 267 | 12.498 −32.936 4.388 1.00 12.29 | C N |
| ATOM | 8849 CA THR I 267 | 13.868 −33.435 4.440 1.00 12.43 | C C |
| ATOM | 8850 CB THR I 267 | 14.386 −33.809 3.039 1.00 12.40 | C C |
| ATOM | 8851 OG1 THR I 267 | 15.460 −32.934 2.674 1.00 13.21 | C O |
| ATOM | 8852 CG2 THR I 267 | 13.274 −33.699 2.010 1.00 12.21 | C C |
| ATOM | 8853 C THR I 267 | 14.797 −32.391 5.046 1.00 12.37 | C C |
| ATOM | 8854 O THR I 267 | 14.403 −31.244 5.251 1.00 12.29 | C O |
| ATOM | 8855 N ASN I 268 | 16.045 −32.779 5.282 1.00 12.47 | C N |
| ATOM | 8856 CA ASN I 268 | 16.965 −31.945 6.045 1.00 12.57 | C C |
| ATOM | 8857 CB ASN I 268 | 18.041 −32.800 6.715 1.00 12.69 | C C |
| ATOM | 8858 CG ASN I 268 | 17.682 −33.171 8.138 1.00 13.65 | C C |
| ATOM | 8859 OD1 ASN I 268 | 16.611 −32.820 8.631 1.00 14.37 | C O |
| ATOM | 8860 ND2 ASN I 268 | 18.569 −33.905 8.800 1.00 15.74 | C N |
| ATOM | 8861 C ASN I 268 | 17.608 −30.843 5.211 1.00 12.43 | C C |
| ATOM | 8862 O ASN I 268 | 17.775 −29.717 5.680 1.00 12.51 | C O |
| ATOM | 8863 N ASP I 269 | 18.038 −31.194 4.005 1.00 12.34 | C N |
| ATOM | 8864 CA ASP I 269 | 18.574 −30.211 3.072 1.00 12.33 | C C |
| ATOM | 8865 CB ASP I 269 | 19.015 −30.891 1.777 1.00 12.89 | C C |
| ATOM | 8866 CG ASP I 269 | 20.071 −31.950 2.007 1.00 14.84 | C C |

APPENDIX-continued (APPENDIX discloses SEQ ID NOS 29-32, 29-32 and 29-32, respectively, in order of appearance)

| | | | |
|---|---|---|---|
| ATOM | 8867 OD1 ASP I 269 | 21.002 −31.699 2.800 1.00 16.90 | C O |
| ATOM | 8868 OD2 ASP I 269 | 19.952 −33.047 1.422 1.00 17.65 | C O |
| ATOM | 8869 C ASP I 269 | 17.539 −29.138 2.769 1.00 11.60 | C C |
| ATOM | 8870 O ASP I 269 | 17.861 −27.952 2.696 1.00 11.65 | C O |
| ATOM | 8871 N GLN I 270 | 16.295 −29.564 2.585 1.00 10.62 | C N |
| ATOM | 8872 CA GLN I 270 | 15.182 −28.633 2.501 1.00 10.01 | C C |
| ATOM | 8873 CB GLN I 270 | 13.853 −29.384 2.525 1.00 10.18 | C C |
| ATOM | 8874 CG GLN I 270 | 12.845 −28.862 1.525 1.00 11.49 | C C |
| ATOM | 8875 CD GLN I 270 | 12.012 −29.968 0.918 1.00 14.38 | C C |
| ATOM | 8876 OE1 GLN I 270 | 10.789 −29.863 0.836 1.00 16.38 | C O |
| ATOM | 8877 NE2 GLN I 270 | 12.665 −31.057 0.530 1.00 15.41 | C N |
| ATOM | 8878 C GLN I 270 | 15.228 −27.620 3.636 1.00 9.48 | C C |
| ATOM | 8879 O GLN I 270 | 15.310 −26.415 3.400 1.00 9.12 | C O |
| ATOM | 8880 N LYS I 271 | 15.170 −28.112 4.868 1.00 9.19 | C N |
| ATOM | 8881 CA LYS I 271 | 15.211 −27.240 6.035 1.00 8.89 | C C |
| ATOM | 8882 CB LYS I 271 | 15.253 −28.064 7.322 1.00 8.52 | C C |
| ATOM | 8883 CG LYS I 271 | 13.948 −28.773 7.643 1.00 9.14 | C C |
| ATOM | 8884 CD LYS I 271 | 13.927 −29.280 9.076 1.00 10.72 | C C |
| ATOM | 8885 CE LYS I 271 | 13.274 −30.648 9.163 1.00 10.79 | C C |
| ATOM | 8886 NZ LYS I 271 | 12.712 −30.914 10.514 1.00 9.77 | C N |
| ATOM | 8887 C LYS I 271 | 16.405 −26.295 5.973 1.00 8.83 | C C |
| ATOM | 8888 O LYS I 271 | 16.257 −25.082 6.127 1.00 9.05 | C O |
| ATOM | 8889 N LYS I 272 | 17.583 −26.854 5.707 1.00 8.65 | C N |
| ATOM | 8890 CA LYS I 272 | 18.796 −26.058 5.548 1.00 8.50 | C C |
| ATOM | 8891 CB LYS I 272 | 19.977 −26.948 5.145 1.00 9.14 | C C |
| ATOM | 8892 CG LYS I 272 | 21.158 −26.189 4.547 1.00 11.58 | C C |
| ATOM | 8893 CD LYS I 272 | 22.213 −27.138 3.991 1.00 15.78 | C C |
| ATOM | 8894 CE LYS I 272 | 23.576 −26.464 3.891 1.00 17.65 | C C |
| ATOM | 8895 NZ LYS I 272 | 24.667 −27.446 3.641 1.00 19.68 | C N |
| ATOM | 8896 C LYS I 272 | 18.599 −24.956 4.514 1.00 7.88 | C C |
| ATOM | 8897 O LYS I 272 | 18.919 −23.794 4.761 1.00 8.12 | C O |
| ATOM | 8898 N LEU I 273 | 18.111 −25.336 3.338 1.00 6.95 | C N |
| ATOM | 8899 CA LEU I 273 | 17.867 −24.375 2.271 1.00 5.70 | C C |
| ATOM | 8900 CB LEU I 273 | 17.235 −25.063 1.060 1.00 5.85 | C C |
| ATOM | 8901 CG LEU I 273 | 16.754 −24.131 −0.054 1.00 4.65 | C C |
| ATOM | 8902 CD1 LEU I 273 | 17.928 −23.571 −0.841 1.00 4.57 | C C |
| ATOM | 8903 CD2 LEU I 273 | 15.777 −24.846 −0.972 1.00 3.69 | C C |
| ATOM | 8904 C LEU I 273 | 16.969 −23.244 2.755 1.00 5.14 | C C |
| ATOM | 8905 O LEU I 273 | 17.345 −22.074 2.702 1.00 5.25 | C O |
| ATOM | 8906 N MET I 274 | 15.776 −23.601 3.221 1.00 4.52 | C N |
| ATOM | 8907 CA MET I 274 | 14.828 −22.616 3.723 1.00 4.59 | C C |
| ATOM | 8908 CB MET I 274 | 13.599 −23.308 4.314 1.00 4.35 | C C |
| ATOM | 8909 CG MET I 274 | 12.709 −23.975 3.279 1.00 4.50 | C C |
| ATOM | 8910 SD MET I 274 | 11.194 −24.645 3.989 1.00 5.51 | C S |
| ATOM | 8911 CE MET I 274 | 10.326 −23.138 4.417 1.00 5.26 | C C |
| ATOM | 8912 C MET I 274 | 15.479 −21.720 4.768 1.00 5.18 | C C |
| ATOM | 8913 O MET I 274 | 15.279 −20.505 4.771 1.00 5.61 | C O |
| ATOM | 8914 N SER I 275 | 16.315 −22.319 5.610 1.00 5.89 | C N |
| ATOM | 8915 CA SER I 275 | 16.961 −21.588 6.688 1.00 6.18 | C C |
| ATOM | 8916 CB SER I 275 | 17.607 −22.555 7.682 1.00 6.33 | C C |
| ATOM | 8917 OG SER I 275 | 16.654 −23.470 8.193 1.00 5.91 | C O |
| ATOM | 8918 C SER I 275 | 17.996 −20.603 6.157 1.00 6.58 | C C |
| ATOM | 8919 O SER I 275 | 18.181 −19.526 6.721 1.00 7.03 | C O |
| ATOM | 8920 N ASN I 276 | 18.615 −20.940 5.030 1.00 7.07 | C N |
| ATOM | 8921 CA ASN I 276 | 19.593 −20.050 4.412 1.00 7.86 | C C |
| ATOM | 8922 CB ASN I 276 | 20.696 −20.854 3.711 1.00 8.34 | C C |
| ATOM | 8923 CG ASN I 276 | 21.868 −21.177 4.633 1.00 9.77 | C C |
| ATOM | 8924 OD1 ASN I 276 | 22.167 −20.430 5.567 1.00 11.84 | C O |
| ATOM | 8925 ND2 ASN I 276 | 22.557 −22.278 4.349 1.00 11.15 | C N |
| ATOM | 8926 C ASN I 276 | 18.976 −19.029 3.453 1.00 7.71 | C C |
| ATOM | 8927 O ASN I 276 | 19.695 −18.349 2.722 1.00 7.84 | C O |
| ATOM | 8928 N ASN I 277 | 17.655 −18.870 3.509 1.00 7.77 | C N |
| ATOM | 8929 CA ASN I 277 | 16.938 −18.098 2.491 1.00 7.85 | C C |
| ATOM | 8930 CB ASN I 277 | 16.575 −18.987 1.304 1.00 7.58 | C C |
| ATOM | 8931 CG ASN I 277 | 17.725 −19.157 0.335 1.00 8.29 | C C |
| ATOM | 8932 OD1 ASN I 277 | 18.053 −18.240 −0.417 1.00 9.04 | C O |
| ATOM | 8933 ND2 ASN I 277 | 18.427 −20.279 0.443 1.00 9.57 | C N |
| ATOM | 8934 C ASN I 277 | 15.697 −17.371 3.006 1.00 7.86 | C C |
| ATOM | 8935 O ASN I 277 | 14.826 −16.977 2.229 1.00 7.85 | C O |
| ATOM | 8936 N VAL I 278 | 15.593 −17.272 4.328 1.00 7.67 | C N |
| ATOM | 8937 CA VAL I 278 | 14.554 −16.489 4.998 1.00 7.77 | C C |
| ATOM | 8938 CB VAL I 278 | 15.120 −15.739 6.215 1.00 7.98 | C C |
| ATOM | 8939 CG1 VAL I 278 | 15.116 −16.638 7.440 1.00 7.21 | C C |
| ATOM | 8940 CG2 VAL I 278 | 16.524 −15.234 5.918 1.00 8.99 | C C |
| ATOM | 8941 C VAL I 278 | 13.813 −15.497 4.105 1.00 7.76 | C C |
| ATOM | 8942 O VAL I 278 | 12.583 −15.441 4.123 1.00 7.84 | C O |
| ATOM | 8943 N GLN I 279 | 14.562 −14.581 3.501 1.00 7.47 | C N |

APPENDIX-continued

| (APPENDIX discloses SEQ ID NOS 29-32, 29-32 and 29-32, respectively, in order of appearance) | | | |
|---|---|---|---|
| ATOM | 8944 CA GLN I 279 | 13.966 −13.446 2.809 1.00 7.07 | C C |
| ATOM | 8945 CB GLN I 279 | 15.038 −12.668 2.045 1.00 7.62 | C C |
| ATOM | 8946 CG GLN I 279 | 14.870 −11.159 2.116 1.00 10.35 | C C |
| ATOM | 8947 CD GLN I 279 | 15.712 −10.430 1.091 1.00 13.70 | C C |
| ATOM | 8948 OE1 GLN I 279 | 16.199 −11.027 0.132 1.00 15.06 | C O |
| ATOM | 8949 NE2 GLN I 279 | 15.865 −9.124 1.275 1.00 13.97 | C N |
| ATOM | 8950 C GLN I 279 | 12.868 −13.901 1.851 1.00 6.02 | C C |
| ATOM | 8951 O GLN I 279 | 11.734 −13.423 1.912 1.00 5.45 | C O |
| ATOM | 8952 N ILE I 280 | 13.249 −14.748 0.901 1.00 5.25 | C N |
| ATOM | 8953 CA ILE I 280 | 12.304 −15.343 −0.031 1.00 4.74 | C C |
| ATOM | 8954 CB ILE I 280 | 12.978 −16.451 −0.860 1.00 4.58 | C C |
| ATOM | 8955 CG1 ILE I 280 | 14.333 −15.973 −1.385 1.00 4.16 | C C |
| ATOM | 8956 CD1 ILE I 280 | 14.238 −15.065 −2.587 1.00 3.88 | C C |
| ATOM | 8957 CG2 ILE I 280 | 12.065 −16.900 −1.996 1.00 3.92 | C C |
| ATOM | 8958 C ILE I 280 | 11.122 −15.946 0.716 1.00 4.43 | C C |
| ATOM | 8959 O ILE I 280 | 9.972 −15.547 0.516 1.00 4.39 | C O |
| ATOM | 8960 N VAL I 281 | 11.409 −16.970 1.513 1.00 4.05 | C N |
| ATOM | 8961 CA VAL I 281 | 10.390 −17.623 2.319 1.00 3.58 | C C |
| ATOM | 8962 CB VAL I 281 | 11.010 −18.335 3.534 1.00 3.13 | C C |
| ATOM | 8963 CG1 VAL I 281 | 10.006 −19.291 4.158 1.00 2.34 | C C |
| ATOM | 8964 CG2 VAL I 281 | 12.277 −19.073 3.127 1.00 2.21 | C C |
| ATOM | 8965 C VAL I 281 | 9.373 −16.601 2.806 1.00 3.96 | C C |
| ATOM | 8966 O VAL I 281 | 8.186 −16.694 2.495 1.00 4.15 | C O |
| ATOM | 8967 N ARG I 282 | 9.857 −15.593 3.522 1.00 4.23 | C N |
| ATOM | 8968 CA ARG I 282 | 8.995 −14.530 4.016 1.00 4.45 | C C |
| ATOM | 8969 CB ARG I 282 | 9.829 −13.427 4.656 1.00 3.96 | C C |
| ATOM | 8970 CG ARG I 282 | 10.637 −13.896 5.841 1.00 2.99 | C C |
| ATOM | 8971 CD ARG I 282 | 10.550 −12.909 6.979 1.00 2.28 | C C |
| ATOM | 8972 NE ARG I 282 | 11.505 −13.236 8.029 1.00 2.00 | C N |
| ATOM | 8973 CZ ARG I 282 | 11.175 −13.463 9.297 1.00 2.44 | C C |
| ATOM | 8974 NH1 ARG I 282 | 9.914 −13.339 9.690 1.00 2.04 | C N |
| ATOM | 8975 NH2 ARG I 282 | 12.099 −13.847 10.167 1.00 3.44 | C N |
| ATOM | 8976 C ARG I 282 | 8.144 −13.952 2.898 1.00 5.32 | C C |
| ATOM | 8977 O ARG I 282 | 6.924 −13.854 3.022 1.00 5.95 | C O |
| ATOM | 8978 N GLN I 283 | 8.794 −13.551 1.812 1.00 5.50 | C N |
| ATOM | 8979 CA GLN I 283 | 8.083 −12.995 0.671 1.00 5.80 | C C |
| ATOM | 8980 CB GLN I 283 | 9.064 −12.580 −0.421 1.00 6.19 | C C |
| ATOM | 8981 CG GLN I 283 | 9.908 −11.381 −0.047 1.00 9.68 | C C |
| ATOM | 8982 CD GLN I 283 | 11.088 −11.192 −0.971 1.00 13.92 | C C |
| ATOM | 8983 OE1 GLN I 283 | 11.266 −11.939 −1.934 1.00 16.20 | C O |
| ATOM | 8984 NE2 GLN I 283 | 11.885 −10.164 −0.706 1.00 14.17 | C N |
| ATOM | 8985 C GLN I 283 | 7.071 −13.988 0.120 1.00 5.44 | C C |
| ATOM | 8986 O GLN I 283 | 6.069 −13.598 −0.479 1.00 5.43 | C O |
| ATOM | 8987 N GLN I 284 | 7.302 −15.269 0.387 1.00 5.26 | C N |
| ATOM | 8988 CA GLN I 284 | 6.465 −16.321 −0.172 1.00 5.18 | C C |
| ATOM | 8989 CB GLN I 284 | 7.303 −17.549 −0.517 1.00 5.32 | C C |
| ATOM | 8990 CG GLN I 284 | 7.689 −17.619 −1.981 1.00 6.85 | C C |
| ATOM | 8991 CD GLN I 284 | 8.548 −18.821 −2.304 1.00 9.21 | C C |
| ATOM | 8992 OE1 GLN I 284 | 9.398 −19.227 −1.511 1.00 9.74 | C O |
| ATOM | 8993 NE2 GLN I 284 | 8.332 −19.400 −3.477 1.00 9.79 | C N |
| ATOM | 8994 C GLN I 284 | 5.345 −16.705 0.779 1.00 4.67 | C C |
| ATOM | 8995 O GLN I 284 | 4.485 −17.520 0.447 1.00 4.19 | C O |
| ATOM | 8996 N SER I 285 | 5.367 −16.116 1.968 1.00 4.51 | C N |
| ATOM | 8997 CA SER I 285 | 4.457 −16.516 3.027 1.00 4.39 | C C |
| ATOM | 8998 CB SER I 285 | 5.218 −16.729 4.336 1.00 4.13 | C C |
| ATOM | 8999 OG SER I 285 | 6.328 −17.588 4.146 1.00 4.40 | C O |
| ATOM | 9000 C SER I 285 | 3.359 −15.481 3.220 1.00 4.44 | C C |
| ATOM | 9001 O SER I 285 | 3.483 −14.335 2.785 1.00 4.82 | C O |
| ATOM | 9002 N TYR I 286 | 2.268 −15.908 3.842 1.00 4.53 | C N |
| ATOM | 9003 CA TYR I 286 | 1.194 −15.002 4.213 1.00 4.80 | C C |
| ATOM | 9004 CB TYR I 286 | −0.116 −15.441 3.559 1.00 4.88 | C C |
| ATOM | 9005 CG TYR I 286 | −0.135 −15.272 2.059 1.00 5.68 | C C |
| ATOM | 9006 CD1 TYR I 286 | 0.713 −16.013 1.245 1.00 7.34 | C C |
| ATOM | 9007 CE1 TYR I 286 | 0.695 −15.864 −0.126 1.00 9.02 | C C |
| ATOM | 9008 CZ TYR I 286 | −0.190 −14.979 −0.701 1.00 9.40 | C C |
| ATOM | 9009 OH TYR I 286 | −0.206 −14.824 −2.066 1.00 10.44 | C O |
| ATOM | 9010 CE2 TYR I 286 | −1.054 −14.244 0.083 1.00 9.38 | C C |
| ATOM | 9011 CD2 TYR I 286 | −1.024 −14.395 1.453 1.00 7.39 | C C |
| ATOM | 9012 C TYR I 286 | 1.037 −14.978 5.726 1.00 4.76 | C C |
| ATOM | 9013 O TYR I 286 | 1.499 −15.883 6.421 1.00 5.25 | C O |
| ATOM | 9014 N SER I 287 | 0.403 −13.929 6.234 1.00 4.52 | C N |
| ATOM | 9015 CA SER I 287 | −0.072 −13.924 7.609 1.00 4.45 | C C |
| ATOM | 9016 CB SER I 287 | 0.779 −12.989 8.470 1.00 4.57 | C C |
| ATOM | 9017 OG SER I 287 | 0.113 −12.662 9.678 1.00 4.38 | C O |
| ATOM | 9018 C SER I 287 | −1.535 −13.516 7.675 1.00 4.61 | C C |
| ATOM | 9019 O SER I 287 | −1.920 −12.460 7.172 1.00 4.40 | C O |
| ATOM | 9020 N ILE I 288 | −2.364 −14.425 8.171 1.00 5.11 | C N |

APPENDIX-continued (APPENDIX discloses SEQ ID NOS 29-32, 29-32 and 29-32, respectively, in order of appearance)

| | | | |
|---|---|---|---|
| ATOM | 9021 CA ILE I 288 | −3.788 −14.171 8.302 1.00 5.81 | C C |
| ATOM | 9022 CB ILE I 288 | −4.610 −15.393 7.863 1.00 5.52 | C C |
| ATOM | 9023 CG1 ILE I 288 | −3.811 −16.253 6.878 1.00 5.47 | C C |
| ATOM | 9024 CD1 ILE I 288 | −3.975 −15.852 5.429 1.00 6.23 | C C |
| ATOM | 9025 CG2 ILE I 288 | −5.939 −14.957 7.271 1.00 6.22 | C C |
| ATOM | 9026 C ILE I 288 | −4.123 −13.848 9.750 1.00 6.71 | C C |
| ATOM | 9027 O ILE I 288 | −3.759 −14.593 10.660 1.00 7.30 | C O |
| ATOM | 9028 N MET I 289 | −4.874 −12.771 9.952 1.00 7.71 | C N |
| ATOM | 9029 CA MET I 289 | −5.451 −12.476 11.257 1.00 8.57 | C C |
| ATOM | 9030 CB MET I 289 | −6.099 −11.090 11.246 1.00 8.71 | C C |
| ATOM | 9031 CG MET I 289 | −6.131 −10.412 12.603 1.00 9.70 | C C |
| ATOM | 9032 SD MET I 289 | −7.100 −8.895 12.581 1.00 12.59 | C S |
| ATOM | 9033 CE MET I 289 | −8.569 −9.452 11.721 1.00 12.41 | C C |
| ATOM | 9034 C MET I 289 | −6.477 −13.538 11.658 1.00 9.12 | C C |
| ATOM | 9035 O MET I 289 | −7.322 −13.925 10.851 1.00 9.31 | C O |
| ATOM | 9036 N SER I 290 | −6.406 −13.998 12.907 1.00 9.80 | C N |
| ATOM | 9037 CA SER I 290 | −7.290 −15.062 13.388 1.00 10.49 | C C |
| ATOM | 9038 CB SER I 290 | −6.494 −16.195 14.035 1.00 10.64 | C C |
| ATOM | 9039 OG SER I 290 | −7.316 −17.328 14.257 1.00 11.99 | C O |
| ATOM | 9040 C SER I 290 | −8.385 −14.573 14.335 1.00 10.75 | C C |
| ATOM | 9041 O SER I 290 | −9.563 −14.595 13.980 1.00 10.89 | C O |
| ATOM | 9042 N ILE I 291 | −8.018 −14.243 15.571 1.00 11.04 | C N |
| ATOM | 9043 CA ILE I 291 | −8.955 −13.562 16.461 1.00 11.41 | C C |
| ATOM | 9044 CB ILE I 291 | −9.796 −14.539 17.305 1.00 11.80 | C C |
| ATOM | 9045 CG1 ILE I 291 | −9.096 −15.893 17.419 1.00 11.81 | C C |
| ATOM | 9046 CD1 ILE I 291 | −8.227 −16.028 18.647 1.00 11.76 | C C |
| ATOM | 9047 CG2 ILE I 291 | −11.179 −14.707 16.700 1.00 12.39 | C C |
| ATOM | 9048 C ILE I 291 | −8.349 −12.481 17.346 1.00 11.13 | C C |
| ATOM | 9049 O ILE I 291 | −7.316 −12.681 17.986 1.00 10.55 | C O |
| ATOM | 9050 N ILE I 292 | −9.034 −11.343 17.398 1.00 11.36 | C N |
| ATOM | 9051 CA ILE I 292 | −8.605 −10.215 18.211 1.00 11.82 | C C |
| ATOM | 9052 CB ILE I 292 | −8.651 −8.884 17.421 1.00 11.86 | C C |
| ATOM | 9053 CG1 ILE I 292 | −9.052 −9.127 15.963 1.00 13.42 | C C |
| ATOM | 9054 CD1 ILE I 292 | −7.968 −9.771 15.126 1.00 15.86 | C C |
| ATOM | 9055 CG2 ILE I 292 | −7.311 −8.160 17.508 1.00 10.85 | C C |
| ATOM | 9056 C ILE I 292 | −9.486 −10.092 19.444 1.00 11.72 | C C |
| ATOM | 9057 O ILE I 292 | −10.713 −10.029 19.346 1.00 11.28 | C O |
| ATOM | 9058 N LYS I 293 | −8.857 −10.180 20.607 1.00 12.11 | C N |
| ATOM | 9059 CA LYS I 293 | −9.479 −9.728 21.834 1.00 12.92 | C C |
| ATOM | 9060 CB LYS I 293 | −9.599 −10.889 22.820 1.00 13.15 | C C |
| ATOM | 9061 CG LYS I 293 | −10.034 −12.194 22.174 1.00 14.17 | C C |
| ATOM | 9062 CD LYS I 293 | −10.958 −12.974 23.091 1.00 15.37 | C C |
| ATOM | 9063 CE LYS I 293 | −11.869 −13.899 22.305 1.00 16.68 | C C |
| ATOM | 9064 NZ LYS I 293 | −12.822 −14.614 23.197 1.00 18.18 | C N |
| ATOM | 9065 C LYS I 293 | −8.670 −8.584 22.433 1.00 13.32 | C C |
| ATOM | 9066 O LYS I 293 | −7.518 −8.366 22.055 1.00 13.17 | C O |
| ATOM | 9067 N GLU I 294 | −9.337 −7.759 23.233 1.00 14.07 | C N |
| ATOM | 9068 CA GLU I 294 | −8.714 −6.572 23.805 1.00 15.07 | C C |
| ATOM | 9069 CB GLU I 294 | −9.608 −5.975 24.896 1.00 15.94 | C C |
| ATOM | 9070 CG GLU I 294 | −10.872 −5.307 24.373 1.00 19.87 | C C |
| ATOM | 9071 CD GLU I 294 | −11.569 −4.471 25.427 1.00 23.88 | C C |
| ATOM | 9072 OE1 GLU I 294 | −10.994 −3.449 25.854 1.00 23.75 | C O |
| ATOM | 9073 OE2 GLU I 294 | −12.723 −4.799 25.777 1.00 25.81 | C O |
| ATOM | 9074 C GLU I 294 | −7.324 −6.878 24.362 1.00 14.40 | C C |
| ATOM | 9075 O GLU I 294 | −6.433 −6.031 24.319 1.00 14.33 | C O |
| ATOM | 9076 N GLU I 295 | −7.144 −8.092 24.879 1.00 13.97 | C N |
| ATOM | 9077 CA GLU I 295 | −5.908 −8.452 25.568 1.00 13.84 | C C |
| ATOM | 9078 CB GLU I 295 | −6.161 −8.721 27.055 1.00 14.67 | C C |
| ATOM | 9079 CG GLU I 295 | −7.620 −8.914 27.427 1.00 17.56 | C C |
| ATOM | 9080 CD GLU I 295 | −8.245 −10.112 26.743 1.00 21.41 | C C |
| ATOM | 9081 OE1 GLU I 295 | −8.990 −9.909 25.761 1.00 22.35 | C O |
| ATOM | 9082 OE2 GLU I 295 | −8.090 −11.241 27.257 1.00 23.20 | C O |
| ATOM | 9083 C GLU I 295 | −5.166 −9.630 24.933 1.00 12.77 | C C |
| ATOM | 9084 O GLU I 295 | −4.166 −10.100 25.476 1.00 12.58 | C O |
| ATOM | 9085 N VAL I 296 | −5.701 −10.162 23.838 1.00 11.72 | C N |
| ATOM | 9086 CA VAL I 296 | −4.970 −11.150 23.051 1.00 10.65 | C C |
| ATOM | 9087 CB VAL I 296 | −5.245 −12.589 23.517 1.00 10.47 | C C |
| ATOM | 9088 CG1 VAL I 296 | −4.277 −13.546 22.846 1.00 9.77 | C C |
| ATOM | 9089 CG2 VAL I 296 | −5.118 −12.688 25.026 1.00 11.31 | C C |
| ATOM | 9090 C VAL I 296 | −5.245 −11.039 21.562 1.00 10.26 | C C |
| ATOM | 9091 O VAL I 296 | −6.395 −10.940 21.133 1.00 10.09 | C O |
| ATOM | 9092 N LEU I 297 | −4.184 −11.178 20.777 1.00 9.77 | C N |
| ATOM | 9093 CA LEU I 297 | −4.302 −11.269 19.332 1.00 8.97 | C C |
| ATOM | 9094 CB LEU I 297 | −3.577 −10.097 18.672 1.00 8.64 | C C |
| ATOM | 9095 CG LEU I 297 | −3.382 −10.209 17.160 1.00 9.01 | C C |
| ATOM | 9096 CD1 LEU I 297 | −4.721 −10.384 16.459 1.00 9.79 | C C |
| ATOM | 9097 CD2 LEU I 297 | −2.645 −8.994 16.620 1.00 9.43 | C C |

APPENDIX-continued (APPENDIX discloses SEQ ID NOS 29-32, 29-32 and 29-32, respectively, in order of appearance)

| | | | |
|---|---|---|---|
| ATOM | 9098 C LEU I 297 | −3.725 −12.587 18.829 1.00 8.34 | C C |
| ATOM | 9099 O LEU I 297 | −2.565 −12.908 19.089 1.00 8.64 | C O |
| ATOM | 9100 N ALA I 298 | −4.545 −13.352 18.116 1.00 7.21 | C N |
| ATOM | 9101 CA ALA I 298 | −4.095 −14.600 17.515 1.00 6.33 | C C |
| ATOM | 9102 CB ALA I 298 | −4.908 −15.770 18.047 1.00 6.68 | C C |
| ATOM | 9103 C ALA I 298 | −4.207 −14.524 16.002 1.00 5.85 | C C |
| ATOM | 9104 O ALA I 298 | −5.179 −13.991 15.468 1.00 5.96 | C O |
| ATOM | 9105 N TYR I 299 | −3.197 −15.040 15.314 1.00 5.28 | C N |
| ATOM | 9106 CA TYR I 299 | −3.197 −15.042 13.861 1.00 4.63 | C C |
| ATOM | 9107 CB TYR I 299 | −2.583 −13.749 13.324 1.00 4.36 | C C |
| ATOM | 9108 CG TYR I 299 | −1.177 −13.490 13.812 1.00 4.34 | C C |
| ATOM | 9109 CD1 TYR I 299 | −0.080 −13.970 13.110 1.00 4.48 | C C |
| ATOM | 9110 CE1 TYR I 299 | 1.207 −13.733 13.549 1.00 4.55 | C C |
| ATOM | 9111 CZ TYR I 299 | 1.409 −13.011 14.705 1.00 3.72 | C C |
| ATOM | 9112 OH TYR I 299 | 2.690 −12.775 15.149 1.00 2.38 | C O |
| ATOM | 9113 CE2 TYR I 299 | 0.336 −12.526 15.422 1.00 4.13 | C C |
| ATOM | 9114 CD2 TYR I 299 | −0.947 −12.767 14.975 1.00 4.38 | C C |
| ATOM | 9115 C TYR I 299 | −2.440 −16.243 13.322 1.00 4.32 | C C |
| ATOM | 9116 O TYR I 299 | −1.602 −16.822 14.012 1.00 4.67 | C O |
| ATOM | 9117 N VAL I 300 | −2.746 −16.622 12.087 1.00 3.87 | C N |
| ATOM | 9118 CA VAL I 300 | −2.130 −17.792 11.486 1.00 3.57 | C C |
| ATOM | 9119 CB VAL I 300 | −3.169 −18.702 10.805 1.00 3.52 | C C |
| ATOM | 9120 CG1 VAL I 300 | −2.475 −19.749 9.943 1.00 3.44 | C C |
| ATOM | 9121 CG2 VAL I 300 | −4.053 −19.368 11.851 1.00 3.90 | C C |
| ATOM | 9122 C VAL I 300 | −1.060 −17.392 10.482 1.00 3.53 | C C |
| ATOM | 9123 O VAL I 300 | −1.299 −16.575 9.593 1.00 3.68 | C O |
| ATOM | 9124 N VAL I 301 | 0.148 −17.899 10.695 1.00 3.41 | C N |
| ATOM | 9125 CA VAL I 301 | 1.193 −17.816 9.689 1.00 3.36 | C C |
| ATOM | 9126 CB VAL I 301 | 2.593 −17.825 10.324 1.00 3.24 | C C |
| ATOM | 9127 CG1 VAL I 301 | 3.655 −18.061 9.261 1.00 3.76 | C C |
| ATOM | 9128 CG2 VAL I 301 | 2.849 −16.519 11.059 1.00 3.10 | C C |
| ATOM | 9129 C VAL I 301 | 1.084 −18.962 8.695 1.00 3.48 | C C |
| ATOM | 9130 O VAL I 301 | 0.647 −20.061 9.037 1.00 3.92 | C O |
| ATOM | 9131 N GLN I 302 | 1.466 −18.684 7.456 1.00 3.21 | C N |
| ATOM | 9132 CA GLN I 302 | 1.274 −19.625 6.368 1.00 3.01 | C C |
| ATOM | 9133 CB GLN I 302 | 0.090 −19.202 5.504 1.00 3.24 | C C |
| ATOM | 9134 CG GLN I 302 | −0.067 −20.021 4.239 1.00 5.21 | C C |
| ATOM | 9135 CD GLN I 302 | −1.479 −19.984 3.701 1.00 7.54 | C C |
| ATOM | 9136 OE1 GLN I 302 | −2.435 −19.784 4.449 1.00 7.28 | C O |
| ATOM | 9137 NE2 GLN I 302 | −1.616 −20.143 2.390 1.00 9.27 | C N |
| ATOM | 9138 C GLN I 302 | 2.533 −19.693 5.523 1.00 2.42 | C C |
| ATOM | 9139 O GLN I 302 | 2.881 −18.736 4.832 1.00 2.40 | C O |
| ATOM | 9140 N LEU I 303 | 3.292 −20.765 5.707 1.00 2.00 | C N |
| ATOM | 9141 CA LEU I 303 | 4.607 −20.868 5.104 1.00 2.00 | C C |
| ATOM | 9142 CB LEU I 303 | 5.628 −21.358 6.130 1.00 2.00 | C C |
| ATOM | 9143 CG LEU I 303 | 5.663 −20.559 7.434 1.00 2.00 | C C |
| ATOM | 9144 CD1 LEU I 303 | 6.712 −21.118 8.382 1.00 2.00 | C C |
| ATOM | 9145 CD2 LEU I 303 | 5.918 −19.085 7.154 1.00 2.00 | C C |
| ATOM | 9146 C LEU I 303 | 4.564 −21.805 3.909 1.00 2.00 | C C |
| ATOM | 9147 O LEU I 303 | 3.658 −22.630 3.794 1.00 2.45 | C O |
| ATOM | 9148 N PRO I 304 | 5.499 −21.620 2.970 1.00 2.00 | C N |
| ATOM | 9149 CA PRO I 304 | 5.617 −22.519 1.840 1.00 2.07 | C C |
| ATOM | 9150 CB PRO I 304 | 6.326 −21.656 0.803 1.00 2.00 | C C |
| ATOM | 9151 CG PRO I 304 | 7.221 −20.775 1.620 1.00 2.00 | C C |
| ATOM | 9152 CD PRO I 304 | 6.564 −20.601 2.973 1.00 2.06 | C C |
| ATOM | 9153 C PRO I 304 | 6.492 −23.711 2.194 1.00 2.11 | C C |
| ATOM | 9154 O PRO I 304 | 7.544 −23.530 2.809 1.00 2.13 | C O |
| ATOM | 9155 N ALA I 305 | 5.903 −24.902 2.097 1.00 30.00 | C N |
| ATOM | 9156 CA ALA I 305 | 6.371 −25.959 1.180 1.00 30.00 | C C |
| ATOM | 9157 CB ALA I 305 | 5.841 −27.314 1.627 1.00 30.00 | C C |
| ATOM | 9158 C ALA I 305 | 6.011 −25.690 −0.310 1.00 30.00 | C C |
| ATOM | 9159 O ALA I 305 | 5.614 −24.571 −0.624 1.00 30.00 | C O |
| ATOM | 9160 N TYR I 306 | 5.840 −26.756 −1.125 1.00 13.49 | C N |
| ATOM | 9161 CA TYR I 306 | 6.433 −26.943 −2.522 1.00 13.70 | C C |
| ATOM | 9162 CB TYR I 306 | 7.412 −28.117 −2.435 1.00 13.93 | C C |
| ATOM | 9163 CG TYR I 306 | 8.486 −28.217 −3.491 1.00 14.08 | C C |
| ATOM | 9164 CD1 TYR I 306 | 8.717 −29.447 −4.102 1.00 14.59 | C C |
| ATOM | 9165 CE1 TYR I 306 | 9.982 −29.819 −4.531 1.00 14.82 | C C |
| ATOM | 9166 CZ TYR I 306 | 11.002 −28.893 −4.523 1.00 14.52 | C C |
| ATOM | 9167 OH TYR I 306 | 12.189 −29.164 −5.167 1.00 13.02 | C O |
| ATOM | 9168 CE2 TYR I 306 | 10.781 −27.632 −4.011 1.00 15.22 | C C |
| ATOM | 9169 CD2 TYR I 306 | 9.534 −27.303 −3.495 1.00 14.61 | C C |
| ATOM | 9170 C TYR I 306 | 5.391 −27.297 −3.661 1.00 13.68 | C C |
| ATOM | 9171 O TYR I 306 | 4.296 −27.738 −3.325 1.00 13.95 | C O |
| ATOM | 9172 N GLY I 307 | 5.786 −27.316 −4.962 1.00 13.54 | C N |
| ATOM | 9173 CA GLY I 307 | 5.057 −28.108 −6.046 1.00 13.37 | C C |
| ATOM | 9174 C GLY I 307 | 5.290 −27.995 −7.585 1.00 13.47 | C C |

APPENDIX-continued

| (APPENDIX discloses SEQ ID NOS 29-32, 29-32 and 29-32, respectively, in order of appearance) | | | |
|---|---|---|---|
| ATOM | 9175 O GLY I 307 | 5.871 −27.017 −8.054 1.00 13.90 | C O |
| ATOM | 9176 N VAL I 308 | 4.808 −28.976 −8.370 1.00 13.31 | C N |
| ATOM | 9177 CA VAL I 308 | 3.931 −28.717 −9.548 1.00 13.30 | C C |
| ATOM | 9178 CB VAL I 308 | 3.187 −27.383 −9.404 1.00 13.03 | C C |
| ATOM | 9179 CG1 VAL I 308 | 1.935 −27.380 −10.261 1.00 13.62 | C C |
| ATOM | 9180 CG2 VAL I 308 | 2.849 −27.116 −7.951 1.00 12.86 | C C |
| ATOM | 9181 C VAL I 308 | 4.596 −28.668 −10.927 1.00 13.58 | C C |
| ATOM | 9182 O VAL I 308 | 5.407 −29.530 −11.271 1.00 13.71 | C O |
| ATOM | 9183 N ILE I 309 | 4.541 −27.470 −11.498 1.00 4.08 | C N |
| ATOM | 9184 CA ILE I 309 | 5.611 −26.532 −11.251 1.00 4.84 | C C |
| ATOM | 9185 CB ILE I 309 | 6.204 −26.810 −9.854 1.00 4.89 | C C |
| ATOM | 9186 CG1 ILE I 309 | 5.086 −26.815 −8.801 1.00 5.85 | C C |
| ATOM | 9187 CD1 ILE I 309 | 4.233 −25.561 −8.803 1.00 8.12 | C C |
| ATOM | 9188 CG2 ILE I 309 | 7.308 −25.817 −9.517 1.00 4.44 | C C |
| ATOM | 9189 C ILE I 309 | 6.637 −26.814 −12.345 1.00 5.23 | C C |
| ATOM | 9190 O ILE I 309 | 6.299 −27.437 −13.352 1.00 5.92 | C O |
| ATOM | 9191 N ASP I 310 | 7.864 −26.330 −12.187 1.00 5.33 | C N |
| ATOM | 9192 CA ASP I 310 | 9.004 −26.924 −12.889 1.00 5.83 | C C |
| ATOM | 9193 CB ASP I 310 | 9.086 −28.423 −12.589 1.00 6.21 | C C |
| ATOM | 9194 CG ASP I 310 | 9.193 −28.716 −11.104 1.00 7.19 | C C |
| ATOM | 9195 OD1 ASP I 310 | 8.350 −29.478 −10.583 1.00 7.74 | C O |
| ATOM | 9196 OD2 ASP I 310 | 10.151 −28.228 −10.467 1.00 7.58 | C O |
| ATOM | 9197 C ASP I 310 | 8.997 −26.705 −14.408 1.00 6.02 | C C |
| ATOM | 9198 O ASP I 310 | 9.656 −27.438 −15.146 1.00 6.05 | C O |
| ATOM | 9199 N THR I 311 | 8.273 −25.687 −14.866 1.00 6.24 | C N |
| ATOM | 9200 CA THR I 311 | 8.429 −25.173 −16.229 1.00 6.14 | C C |
| ATOM | 9201 CB THR I 311 | 7.231 −24.299 −16.630 1.00 5.69 | C C |
| ATOM | 9202 OG1 THR I 311 | 6.093 −24.646 −15.830 1.00 5.34 | C O |
| ATOM | 9203 CG2 THR I 311 | 6.897 −24.500 −18.092 1.00 7.10 | C C |
| ATOM | 9204 C THR I 311 | 9.682 −24.313 −16.335 1.00 6.78 | C C |
| ATOM | 9205 O THR I 311 | 9.970 −23.530 −15.430 1.00 7.33 | C O |
| ATOM | 9206 N PRO I 312 | 10.330 −24.318 −17.509 1.00 7.00 | C N |
| ATOM | 9207 CA PRO I 312 | 11.470 −23.419 −17.668 1.00 7.23 | C C |
| ATOM | 9208 CB PRO I 312 | 12.060 −23.834 −19.020 1.00 7.00 | C C |
| ATOM | 9209 CG PRO I 312 | 10.936 −24.505 −19.747 1.00 6.59 | C C |
| ATOM | 9210 CD PRO I 312 | 10.098 −25.159 −18.697 1.00 6.99 | C C |
| ATOM | 9211 C PRO I 312 | 11.016 −21.962 −17.703 1.00 7.69 | C C |
| ATOM | 9212 O PRO I 312 | 9.943 −21.670 −18.228 1.00 7.55 | C O |
| ATOM | 9213 N CYS I 313 | 11.755 −21.077 −17.041 1.00 8.10 | C N |
| ATOM | 9214 CA CYS I 313 | 11.668 −19.654 −17.353 1.00 8.54 | C C |
| ATOM | 9215 CB CYS I 313 | 11.082 −18.852 −16.186 1.00 8.77 | C C |
| ATOM | 9216 SG CYS I 313 | 10.025 −19.785 −15.057 1.00 10.74 | C S |
| ATOM | 9217 C CYS I 313 | 13.000 −19.058 −17.780 1.00 8.19 | C C |
| ATOM | 9218 O CYS I 313 | 14.035 −19.725 −17.760 1.00 8.07 | C O |
| ATOM | 9219 N TRP I 314 | 12.964 −17.777 −18.126 1.00 7.93 | C N |
| ATOM | 9220 CA TRP I 314 | 14.162 −17.035 −18.473 1.00 7.80 | C C |
| ATOM | 9221 CB TRP I 314 | 14.563 −17.322 −19.919 1.00 8.13 | C C |
| ATOM | 9222 CG TRP I 314 | 13.457 −17.091 −20.902 1.00 9.09 | C C |
| ATOM | 9223 CD1 TRP I 314 | 13.295 −16.003 −21.710 1.00 10.26 | C C |
| ATOM | 9224 NE1 TRP I 314 | 12.219 −16.189 −22.546 1.00 10.86 | C N |
| ATOM | 9225 CE2 TRP I 314 | 11.671 −17.421 −22.298 1.00 10.68 | C C |
| ATOM | 9226 CD2 TRP I 314 | 12.426 −18.020 −21.269 1.00 10.49 | C C |
| ATOM | 9227 CE3 TRP I 314 | 12.083 −19.308 −20.842 1.00 11.67 | C C |
| ATOM | 9228 CZ3 TRP I 314 | 11.009 −19.946 −21.447 1.00 12.98 | C C |
| ATOM | 9229 CH2 TRP I 314 | 10.268 −19.318 −22.457 1.00 12.74 | C C |
| ATOM | 9230 CZ2 TRP I 314 | 10.580 −18.059 −22.895 1.00 11.73 | C C |
| ATOM | 9231 C TRP I 314 | 13.899 −15.550 −18.298 1.00 7.34 | C C |
| ATOM | 9232 O TRP I 314 | 12.764 −15.091 −18.427 1.00 7.47 | C O |
| ATOM | 9233 N LYS I 315 | 14.936 −14.815 −17.920 1.00 6.75 | C N |
| ATOM | 9234 CA LYS I 315 | 14.833 −13.372 −17.823 1.00 6.37 | C C |
| ATOM | 9235 CB LYS I 315 | 15.493 −12.875 −16.541 1.00 6.38 | C C |
| ATOM | 9236 CG LYS I 315 | 14.992 −11.522 −16.065 1.00 6.55 | C C |
| ATOM | 9237 CD LYS I 315 | 15.692 −11.117 −14.778 1.00 8.01 | C C |
| ATOM | 9238 CE LYS I 315 | 15.198 −9.776 −14.269 1.00 8.78 | C C |
| ATOM | 9239 NZ LYS I 315 | 16.141 −9.189 −13.276 1.00 10.21 | C N |
| ATOM | 9240 C LYS I 315 | 15.468 −12.711 −19.036 1.00 6.32 | C C |
| ATOM | 9241 O LYS I 315 | 16.510 −13.153 −19.523 1.00 6.21 | C O |
| ATOM | 9242 N LEU I 316 | 14.766 −11.724 −19.584 1.00 6.58 | C N |
| ATOM | 9243 CA LEU I 316 | 15.231 −10.992 −20.758 1.00 7.02 | C C |
| ATOM | 9244 CB LEU I 316 | 14.122 −10.908 −21.809 1.00 6.64 | C C |
| ATOM | 9245 CG LEU I 316 | 14.308 −9.874 −22.922 1.00 6.21 | C C |
| ATOM | 9246 CD1 LEU I 316 | 15.563 −10.150 −23.731 1.00 5.94 | C C |
| ATOM | 9247 CD2 LEU I 316 | 13.082 −9.824 −23.819 1.00 6.57 | C C |
| ATOM | 9248 C LEU I 316 | 15.675 −9.588 −20.372 1.00 7.77 | C C |
| ATOM | 9249 O LEU I 316 | 14.865 −8.768 −19.941 1.00 8.47 | C O |
| ATOM | 9250 N HIS I 317 | 16.956 −9.302 −20.563 1.00 8.05 | C N |
| ATOM | 9251 CA HIS I 317 | 17.422 −7.929 −20.547 1.00 8.21 | C C |

APPENDIX-continued (APPENDIX discloses SEQ ID NOS 29-32, 29-32 and 29-32, respectively, in order of appearance)

| | | | |
|---|---|---|---|
| ATOM | 9252 CB HIS I 317 | 18.641 −7.786 −19.640 1.00 9.04 | C C |
| ATOM | 9253 CG HIS I 317 | 18.644 −8.734 −18.483 1.00 11.41 | C C |
| ATOM | 9254 ND1 HIS I 317 | 18.314 −8.347 −17.202 1.00 13.62 | C N |
| ATOM | 9255 CE1 HIS I 317 | 18.423 −9.383 −16.389 1.00 14.91 | C C |
| ATOM | 9256 NE2 HIS I 317 | 18.811 −10.428 −17.097 1.00 14.25 | C N |
| ATOM | 9257 CD2 HIS I 317 | 18.960 −10.048 −18.409 1.00 12.67 | C C |
| ATOM | 9258 C HIS I 317 | 17.760 −7.469 −21.950 1.00 7.39 | C C |
| ATOM | 9259 O HIS I 317 | 17.881 −8.278 −22.869 1.00 7.23 | C O |
| ATOM | 9260 N THR I 318 | 17.997 −6.172 −22.086 1.00 7.11 | C N |
| ATOM | 9261 CA THR I 318 | 17.745 −5.476 −23.333 1.00 6.56 | C C |
| ATOM | 9262 CB THR I 318 | 16.268 −5.093 −23.468 1.00 6.28 | C C |
| ATOM | 9263 OG1 THR I 318 | 15.652 −5.909 −24.471 1.00 6.33 | C O |
| ATOM | 9264 CG2 THR I 318 | 16.141 −3.634 −23.866 1.00 6.52 | C C |
| ATOM | 9265 C THR I 318 | 18.563 −4.201 −23.357 1.00 6.58 | C C |
| ATOM | 9266 O THR I 318 | 18.437 −3.356 −22.472 1.00 6.67 | C O |
| ATOM | 9267 N SER I 319 | 19.378 −4.044 −24.390 1.00 6.81 | C N |
| ATOM | 9268 CA SER I 319 | 20.173 −2.837 −24.533 1.00 7.31 | C C |
| ATOM | 9269 CB SER I 319 | 21.633 −3.105 −24.159 1.00 7.14 | C C |
| ATOM | 9270 OG SER I 319 | 22.309 −1.904 −23.825 1.00 6.84 | C O |
| ATOM | 9271 C SER I 319 | 20.069 −2.273 −25.945 1.00 7.93 | C C |
| ATOM | 9272 O SER I 319 | 19.736 −2.996 −26.887 1.00 8.65 | C O |
| ATOM | 9273 N PRO I 320 | 20.242 −0.952 −26.075 1.00 8.08 | C N |
| ATOM | 9274 CA PRO I 320 | 20.052 −0.299 −27.363 1.00 8.34 | C C |
| ATOM | 9275 CB PRO I 320 | 20.263 1.187 −27.047 1.00 7.99 | C C |
| ATOM | 9276 CG PRO I 320 | 20.887 1.228 −25.680 1.00 8.01 | C C |
| ATOM | 9277 CD PRO I 320 | 20.384 0.015 −24.977 1.00 8.10 | C C |
| ATOM | 9278 C PRO I 320 | 21.061 −0.770 −28.400 1.00 9.03 | C C |
| ATOM | 9279 O PRO I 320 | 22.135 −1.262 −28.053 1.00 8.74 | C O |
| ATOM | 9280 N LEU I 321 | 20.711 −0.594 −29.669 1.00 10.31 | C N |
| ATOM | 9281 CA LEU I 321 | 21.427 −1.228 −30.766 1.00 11.63 | C C |
| ATOM | 9282 CB LEU I 321 | 20.792 −2.576 −31.105 1.00 11.31 | C C |
| ATOM | 9283 CG LEU I 321 | 21.681 −3.600 −31.812 1.00 10.97 | C C |
| ATOM | 9284 CD1 LEU I 321 | 20.835 −4.621 −32.549 1.00 10.04 | C C |
| ATOM | 9285 CD2 LEU I 321 | 22.652 −2.914 −32.761 1.00 10.69 | C C |
| ATOM | 9286 C LEU I 321 | 21.412 −0.317 −31.989 1.00 12.92 | C C |
| ATOM | 9287 O LEU I 321 | 20.351 0.114 −32.441 1.00 13.29 | C O |
| ATOM | 9288 N CYS I 322 | 22.601 0.013 −32.486 1.00 13.39 | C N |
| ATOM | 9289 CA CYS I 322 | 22.751 0.987 −33.563 1.00 14.16 | C C |
| ATOM | 9290 CB CYS I 322 | 23.359 2.288 −33.036 1.00 13.72 | C C |
| ATOM | 9291 SG CYS I 322 | 22.632 2.898 −31.504 1.00 13.42 | C S |
| ATOM | 9292 C CYS I 322 | 23.622 0.441 −34.690 1.00 15.46 | C C |
| ATOM | 9293 O CYS I 322 | 24.646 −0.196 −34.446 1.00 15.94 | C O |
| ATOM | 9294 N THR I 323 | 23.265 0.802 −35.919 1.00 16.70 | C N |
| ATOM | 9295 CA THR I 323 | 24.152 0.675 −37.075 1.00 17.84 | C C |
| ATOM | 9296 CB THR I 323 | 23.429 1.117 −38.359 1.00 17.50 | C C |
| ATOM | 9297 OG1 THR I 323 | 22.416 2.076 −38.031 1.00 15.70 | C O |
| ATOM | 9298 CG2 THR I 323 | 22.786 −0.076 −39.047 1.00 18.05 | C C |
| ATOM | 9299 C THR I 323 | 25.403 1.536 −36.918 1.00 19.54 | C C |
| ATOM | 9300 O THR I 323 | 25.408 2.477 −36.124 1.00 19.84 | C O |
| ATOM | 9301 N THR I 324 | 26.352 1.379 −37.840 1.00 21.17 | C N |
| ATOM | 9302 CA THR I 324 | 27.430 2.358 −37.967 1.00 22.89 | C C |
| ATOM | 9303 CB THR I 324 | 28.687 1.950 −37.188 1.00 22.69 | C C |
| ATOM | 9304 OG1 THR I 324 | 28.403 0.800 −36.381 1.00 22.10 | C O |
| ATOM | 9305 CG2 THR I 324 | 29.150 3.094 −36.300 1.00 22.03 | C C |
| ATOM | 9306 C THR I 324 | 27.815 2.806 −39.378 1.00 24.39 | C C |
| ATOM | 9307 O THR I 324 | 28.495 3.820 −39.537 1.00 24.53 | C O |
| ATOM | 9308 N ASN I 325 | 27.330 2.106 −40.398 1.00 25.72 | C N |
| ATOM | 9309 CA ASN I 325 | 27.321 2.661 −41.751 1.00 27.01 | C C |
| ATOM | 9310 CB ASN I 325 | 28.628 2.344 −42.484 1.00 27.37 | C C |
| ATOM | 9311 CG ASN I 325 | 29.720 3.360 −42.199 1.00 28.46 | C C |
| ATOM | 9312 OD1 ASN I 325 | 29.982 4.252 −43.007 1.00 30.37 | C O |
| ATOM | 9313 ND2 ASN I 325 | 30.364 3.229 −41.045 1.00 28.78 | C N |
| ATOM | 9314 C ASN I 325 | 26.125 2.199 −42.576 1.00 27.36 | C C |
| ATOM | 9315 O ASN I 325 | 25.455 1.228 −42.226 1.00 27.94 | C O |
| ATOM | 9316 N SER I 330 | 24.776 3.883 −38.461 1.00 35.76 | C N |
| ATOM | 9317 CA SER I 330 | 24.479 5.303 −38.606 1.00 35.01 | C C |
| ATOM | 9318 CB SER I 330 | 24.922 5.803 −39.983 1.00 35.47 | C C |
| ATOM | 9319 OG SER I 330 | 24.296 5.067 −41.019 1.00 33.31 | C O |
| ATOM | 9320 C SER I 330 | 22.992 5.574 −38.405 1.00 34.35 | C C |
| ATOM | 9321 O SER I 330 | 22.148 4.769 −38.798 1.00 34.33 | C O |
| ATOM | 9322 N ASN I 331 | 22.677 6.688 −37.752 1.00 32.48 | C N |
| ATOM | 9323 CA ASN I 331 | 21.365 7.314 −37.886 1.00 30.72 | C C |
| ATOM | 9324 CB ASN I 331 | 21.065 7.642 −39.357 1.00 31.31 | C C |
| ATOM | 9325 CG ASN I 331 | 21.961 8.740 −39.916 1.00 32.11 | C C |
| ATOM | 9326 OD1 ASN I 331 | 22.615 9.469 −39.170 1.00 32.54 | C O |
| ATOM | 9327 ND2 ASN I 331 | 21.941 8.901 −41.235 1.00 31.30 | C N |
| ATOM | 9328 C ASN I 331 | 20.188 6.532 −37.282 1.00 28.71 | C C |

APPENDIX-continued (APPENDIX discloses SEQ ID NOS 29-32, 29-32 and 29-32, respectively, in order of appearance)

| | | | |
|---|---|---|---|
| ATOM | 9329 O ASN I 331 | 19.038 6.940 −37.444 1.00 29.07 | C O |
| ATOM | 9330 N ILE I 332 | 20.450 5.399 −36.629 1.00 25.44 | C N |
| ATOM | 9331 CA ILE I 332 | 19.354 4.517 −36.200 1.00 21.83 | C C |
| ATOM | 9332 CB ILE I 332 | 18.777 3.711 −37.387 1.00 21.42 | C C |
| ATOM | 9333 CG1 ILE I 332 | 17.534 2.929 −36.961 1.00 19.89 | C C |
| ATOM | 9334 CD1 ILE I 332 | 16.273 3.385 −37.652 1.00 17.67 | C C |
| ATOM | 9335 CG2 ILE I 332 | 19.828 2.777 −37.965 1.00 20.61 | C C |
| ATOM | 9336 C ILE I 332 | 19.679 3.570 −35.035 1.00 20.37 | C C |
| ATOM | 9337 O ILE I 332 | 20.593 2.751 −35.134 1.00 19.95 | C O |
| ATOM | 9338 N CYS I 333 | 18.816 3.561 −34.019 1.00 18.27 | C N |
| ATOM | 9339 CA CYS I 333 | 18.930 2.597 −32.921 1.00 16.47 | C C |
| ATOM | 9340 CB CYS I 333 | 19.646 3.216 −31.720 1.00 16.14 | C C |
| ATOM | 9341 SG CYS I 333 | 21.144 4.124 −32.136 1.00 17.09 | C S |
| ATOM | 9342 C CYS I 333 | 17.615 1.958 −32.475 1.00 15.73 | C C |
| ATOM | 9343 O CYS I 333 | 16.556 2.586 −32.511 1.00 15.43 | C O |
| ATOM | 9344 N LEU I 334 | 17.761 0.811 −31.819 1.00 15.06 | C N |
| ATOM | 9345 CA LEU I 334 | 16.643 −0.021 −31.394 1.00 13.79 | C C |
| ATOM | 9346 CB LEU I 334 | 16.607 −1.319 −32.203 1.00 13.39 | C C |
| ATOM | 9347 CG LEU I 334 | 16.482 −1.230 −33.725 1.00 13.93 | C C |
| ATOM | 9348 CD1 LEU I 334 | 15.861 −2.496 −34.287 1.00 14.20 | C C |
| ATOM | 9349 CD2 LEU I 334 | 15.686 −0.009 −34.151 1.00 14.52 | C C |
| ATOM | 9350 C LEU I 334 | 16.852 −0.366 −29.928 1.00 13.22 | C C |
| ATOM | 9351 O LEU I 334 | 17.968 −0.685 −29.520 1.00 13.31 | C O |
| ATOM | 9352 N THR I 335 | 15.768 −0.423 −29.167 1.00 12.58 | C N |
| ATOM | 9353 CA THR I 335 | 15.790 −1.126 −27.892 1.00 12.17 | C C |
| ATOM | 9354 CB THR I 335 | 15.955 −0.158 −26.706 1.00 12.02 | C C |
| ATOM | 9355 OG1 THR I 335 | 16.652 1.018 −27.139 1.00 12.64 | C O |
| ATOM | 9356 CG2 THR I 335 | 16.739 −0.825 −25.582 1.00 11.47 | C C |
| ATOM | 9357 C THR I 335 | 14.523 −1.942 −27.703 1.00 11.97 | C C |
| ATOM | 9358 O THR I 335 | 13.423 −1.471 −27.990 1.00 11.93 | C O |
| ATOM | 9359 N ARG I 336 | 14.700 −3.216 −27.379 1.00 11.60 | C N |
| ATOM | 9360 CA ARG I 336 | 13.573 −4.131 −27.260 1.00 12.15 | C C |
| ATOM | 9361 CB ARG I 336 | 14.066 −5.579 −27.235 1.00 12.16 | C C |
| ATOM | 9362 CG ARG I 336 | 13.124 −6.566 −27.906 1.00 12.67 | C C |
| ATOM | 9363 CD ARG I 336 | 13.876 −7.491 −28.846 1.00 12.52 | C C |
| ATOM | 9364 NE ARG I 336 | 14.414 −8.649 −28.144 1.00 12.35 | C N |
| ATOM | 9365 CZ ARG I 336 | 13.675 −9.665 −27.713 1.00 12.54 | C C |
| ATOM | 9366 NH1 ARG I 336 | 12.384 −9.718 −28.013 1.00 12.38 | C N |
| ATOM | 9367 NH2 ARG I 336 | 14.249 −10.681 −27.084 1.00 12.48 | C N |
| ATOM | 9368 C ARG I 336 | 12.761 −3.833 −26.004 1.00 12.71 | C C |
| ATOM | 9369 O ARG I 336 | 13.272 −3.932 −24.890 1.00 12.62 | C O |
| ATOM | 9370 N THR I 337 | 11.501 −3.457 −26.186 1.00 13.70 | C N |
| ATOM | 9371 CA THR I 337 | 10.696 −2.998 −25.065 1.00 14.91 | C C |
| ATOM | 9372 CB THR I 337 | 9.353 −2.405 −25.516 1.00 15.27 | C C |
| ATOM | 9373 OG1 THR I 337 | 9.571 −1.474 −26.584 1.00 16.65 | C O |
| ATOM | 9374 CG2 THR I 337 | 8.694 −1.678 −24.356 1.00 15.94 | C C |
| ATOM | 9375 C THR I 337 | 10.438 −4.115 −24.064 1.00 15.16 | C C |
| ATOM | 9376 O THR I 337 | 10.515 −3.902 −22.857 1.00 15.60 | C O |
| ATOM | 9377 N ASP I 338 | 10.036 −5.277 −24.566 1.00 15.15 | C N |
| ATOM | 9378 CA ASP I 338 | 9.394 −6.289 −23.732 1.00 15.52 | C C |
| ATOM | 9379 CB ASP I 338 | 8.653 −7.306 −24.602 1.00 16.81 | C C |
| ATOM | 9380 CG ASP I 338 | 9.242 −7.417 −26.000 1.00 20.57 | C C |
| ATOM | 9381 OD1 ASP I 338 | 8.554 −7.950 −26.895 1.00 23.00 | C O |
| ATOM | 9382 OD2 ASP I 338 | 10.395 −6.981 −26.200 1.00 22.92 | C O |
| ATOM | 9383 C ASP I 338 | 10.402 −7.004 −22.837 1.00 14.21 | C C |
| ATOM | 9384 O ASP I 338 | 10.930 −8.057 −23.196 1.00 14.00 | C O |
| ATOM | 9385 N ARG I 339 | 10.654 −6.432 −21.664 1.00 12.79 | C N |
| ATOM | 9386 CA ARG I 339 | 11.678 −6.949 −20.764 1.00 11.71 | C C |
| ATOM | 9387 CB ARG I 339 | 12.488 −5.810 −20.163 1.00 11.73 | C C |
| ATOM | 9388 CG ARG I 339 | 13.374 −5.080 −21.129 1.00 12.49 | C C |
| ATOM | 9389 CD ARG I 339 | 14.312 −4.211 −20.346 1.00 13.24 | C C |
| ATOM | 9390 NE ARG I 339 | 14.580 −2.944 −21.005 1.00 12.04 | C N |
| ATOM | 9391 CZ ARG I 339 | 15.717 −2.282 −20.858 1.00 11.74 | C C |
| ATOM | 9392 NH1 ARG I 339 | 16.664 −2.771 −20.072 1.00 13.43 | C N |
| ATOM | 9393 NH2 ARG I 339 | 15.904 −1.125 −21.475 1.00 9.80 | C N |
| ATOM | 9394 C ARG I 339 | 11.062 −7.727 −19.622 1.00 11.16 | C C |
| ATOM | 9395 O ARG I 339 | 10.029 −7.326 −19.087 1.00 11.37 | C O |
| ATOM | 9396 N GLY I 340 | 11.892 −8.572 −19.027 1.00 10.43 | C N |
| ATOM | 9397 CA GLY I 340 | 11.574 −9.178 −17.749 1.00 9.52 | C C |
| ATOM | 9398 C GLY I 340 | 11.463 −10.678 −17.876 1.00 8.80 | C C |
| ATOM | 9399 O GLY I 340 | 12.269 −11.313 −18.555 1.00 8.56 | C O |
| ATOM | 9400 N TRP I 341 | 10.532 −11.257 −17.129 1.00 8.25 | C N |
| ATOM | 9401 CA TRP I 341 | 10.462 −12.699 −17.005 1.00 7.98 | C C |
| ATOM | 9402 CB TRP I 341 | 10.018 −13.097 −15.605 1.00 7.79 | C C |
| ATOM | 9403 CG TRP I 341 | 11.120 −13.020 −14.622 1.00 7.67 | C C |
| ATOM | 9404 CD1 TRP I 341 | 11.382 −11.986 −13.775 1.00 8.12 | C C |
| ATOM | 9405 NE1 TRP I 341 | 12.511 −12.252 −13.042 1.00 8.60 | C N |

APPENDIX-continued (APPENDIX discloses SEQ ID NOS 29-32, 29-32 and 29-32, respectively, in order of appearance)

| | | | |
|---|---|---|---|
| ATOM | 9406 CE2 TRP I 341 | 13.037 −13.447 −13.459 1.00 7.57 | C C |
| ATOM | 9407 CD2 TRP I 341 | 12.217 −13.931 −14.495 1.00 7.52 | C C |
| ATOM | 9408 CE3 TRP I 341 | 12.541 −15.150 −15.098 1.00 7.86 | C C |
| ATOM | 9409 CZ3 TRP I 341 | 13.653 −15.837 −14.650 1.00 7.14 | C C |
| ATOM | 9410 CH2 TRP I 341 | 14.457 −15.323 −13.625 1.00 6.39 | C C |
| ATOM | 9411 CZ2 TRP I 341 | 14.164 −14.134 −13.017 1.00 7.30 | C C |
| ATOM | 9412 C TRP I 341 | 9.525 −13.288 −18.037 1.00 8.26 | C C |
| ATOM | 9413 O TRP I 341 | 8.322 −13.022 −18.031 1.00 8.35 | C O |
| ATOM | 9414 N TYR I 342 | 10.085 −14.100 −18.922 1.00 8.44 | C N |
| ATOM | 9415 CA TYR I 342 | 9.308 −15.102 −19.616 1.00 8.53 | C C |
| ATOM | 9416 CB TYR I 342 | 9.755 −15.202 −21.069 1.00 8.43 | C C |
| ATOM | 9417 CG TYR I 342 | 9.687 −13.885 −21.793 1.00 9.17 | C C |
| ATOM | 9418 CD1 TYR I 342 | 10.592 −12.874 −21.499 1.00 10.32 | C C |
| ATOM | 9419 CE1 TYR I 342 | 10.474 −11.625 −22.068 1.00 10.99 | C C |
| ATOM | 9420 CZ TYR I 342 | 9.395 −11.349 −22.873 1.00 11.00 | C C |
| ATOM | 9421 OH TYR I 342 | 9.267 −10.102 −23.435 1.00 12.82 | C O |
| ATOM | 9422 CE2 TYR I 342 | 8.433 −12.307 −23.105 1.00 10.67 | C C |
| ATOM | 9423 CD2 TYR I 342 | 8.569 −13.555 −22.542 1.00 10.41 | C C |
| ATOM | 9424 C TYR I 342 | 9.469 −16.437 −18.925 1.00 8.64 | C C |
| ATOM | 9425 O TYR I 342 | 10.376 −16.628 −18.115 1.00 8.40 | C O |
| ATOM | 9426 N CYS I 343 | 8.558 −17.351 −19.224 1.00 8.87 | C N |
| ATOM | 9427 CA CYS I 343 | 8.370 −18.516 −18.389 1.00 9.35 | C C |
| ATOM | 9428 CB CYS I 343 | 8.266 −18.116 −16.915 1.00 9.17 | C C |
| ATOM | 9429 SG CYS I 343 | 8.138 −19.512 −15.769 1.00 11.88 | C S |
| ATOM | 9430 C CYS I 343 | 7.151 −19.312 −18.831 1.00 9.42 | C C |
| ATOM | 9431 O CYS I 343 | 6.039 −18.788 −18.900 1.00 9.96 | C O |
| ATOM | 9432 N ASP I 344 | 7.408 −20.545 −19.254 1.00 9.36 | C N |
| ATOM | 9433 CA ASP I 344 | 6.483 −21.302 −20.083 1.00 9.24 | C C |
| ATOM | 9434 CB ASP I 344 | 7.122 −22.628 −20.500 1.00 9.34 | C C |
| ATOM | 9435 CG ASP I 344 | 7.796 −22.551 −21.856 1.00 10.72 | C C |
| ATOM | 9436 OD1 ASP I 344 | 7.123 −22.161 −22.833 1.00 13.93 | C O |
| ATOM | 9437 OD2 ASP I 344 | 9.003 −22.864 −21.942 1.00 11.87 | C O |
| ATOM | 9438 C ASP I 344 | 5.198 −21.576 −19.320 1.00 9.09 | C C |
| ATOM | 9439 O ASP I 344 | 5.233 −22.061 −18.192 1.00 9.39 | C O |
| ATOM | 9440 N ASN I 345 | 4.067 −21.385 −19.988 1.00 9.13 | C N |
| ATOM | 9441 CA ASN I 345 | 2.801 −21.924 −19.510 1.00 9.52 | C C |
| ATOM | 9442 CB ASN I 345 | 1.770 −20.804 −19.361 1.00 9.61 | C C |
| ATOM | 9443 CG ASN I 345 | 0.742 −21.101 −18.293 1.00 9.21 | C C |
| ATOM | 9444 OD1 ASN I 345 | 1.075 −21.251 −17.118 1.00 6.21 | C O |
| ATOM | 9445 ND2 ASN I 345 | −0.511 −21.247 −18.706 1.00 11.05 | C N |
| ATOM | 9446 C ASN I 345 | 2.271 −23.022 −20.427 1.00 10.06 | C C |
| ATOM | 9447 O ASN I 345 | 3.005 −23.546 −21.267 1.00 11.10 | C O |
| ATOM | 9448 N ALA I 346 | 1.017 −23.411 −20.223 1.00 9.74 | C N |
| ATOM | 9449 CA ALA I 346 | 0.416 −24.492 −20.998 1.00 9.58 | C C |
| ATOM | 9450 CB ALA I 346 | −1.062 −24.635 −20.650 1.00 9.60 | C C |
| ATOM | 9451 C ALA I 346 | 0.593 −24.278 −22.502 1.00 9.66 | C C |
| ATOM | 9452 O ALA I 346 | −0.241 −23.639 −23.145 1.00 9.39 | C O |
| ATOM | 9453 N GLY I 347 | 1.655 −24.849 −23.065 1.00 10.04 | C N |
| ATOM | 9454 CA GLY I 347 | 1.836 −24.857 −24.513 1.00 10.68 | C C |
| ATOM | 9455 C GLY I 347 | 1.879 −23.454 −25.085 1.00 10.90 | C C |
| ATOM | 9456 O GLY I 347 | 1.661 −23.251 −26.280 1.00 11.46 | C O |
| ATOM | 9457 N SER I 348 | 2.016 −22.477 −24.193 1.00 10.30 | C N |
| ATOM | 9458 CA SER I 348 | 2.256 −21.088 −24.567 1.00 9.94 | C C |
| ATOM | 9459 CB SER I 348 | 0.933 −20.322 −24.613 1.00 9.88 | C C |
| ATOM | 9460 OG SER I 348 | 0.000 −20.969 −25.461 1.00 10.09 | C O |
| ATOM | 9461 C SER I 348 | 3.194 −20.462 −23.538 1.00 9.60 | C C |
| ATOM | 9462 O SER I 348 | 3.700 −21.157 −22.660 1.00 9.59 | C O |
| ATOM | 9463 N VAL I 349 | 3.494 −19.178 −23.689 1.00 9.54 | C N |
| ATOM | 9464 CA VAL I 349 | 4.452 −18.532 −22.800 1.00 9.56 | C C |
| ATOM | 9465 CB VAL I 349 | 5.700 −18.047 −23.558 1.00 9.28 | C C |
| ATOM | 9466 CG1 VAL I 349 | 6.722 −17.476 −22.589 1.00 9.24 | C C |
| ATOM | 9467 CG2 VAL I 349 | 6.303 −19.183 −24.370 1.00 9.94 | C C |
| ATOM | 9468 C VAL I 349 | 3.832 −17.367 −22.041 1.00 9.59 | C C |
| ATOM | 9469 O VAL I 349 | 3.179 −16.506 −22.631 1.00 9.69 | C O |
| ATOM | 9470 N SER I 350 | 4.073 −17.326 −20.735 1.00 9.93 | C N |
| ATOM | 9471 CA SER I 350 | 3.559 −16.252 −19.896 1.00 10.44 | C C |
| ATOM | 9472 CB SER I 350 | 2.926 −16.815 −18.620 1.00 10.04 | C C |
| ATOM | 9473 OG SER I 350 | 1.578 −17.196 −18.841 1.00 8.41 | C O |
| ATOM | 9474 C SER I 350 | 4.629 −15.218 −19.557 1.00 11.45 | C C |
| ATOM | 9475 O SER I 350 | 5.746 −15.561 −19.168 1.00 11.58 | C O |
| ATOM | 9476 N PHE I 351 | 4.259 −13.948 −19.679 1.00 12.28 | C N |
| ATOM | 9477 CA PHE I 351 | 5.200 −12.847 −19.543 1.00 13.04 | C C |
| ATOM | 9478 CB PHE I 351 | 5.320 −12.089 −20.867 1.00 12.87 | C C |
| ATOM | 9479 CG PHE I 351 | 6.094 −10.809 −20.763 1.00 13.52 | C C |
| ATOM | 9480 CD1 PHE I 351 | 7.344 −10.788 −20.172 1.00 13.76 | C C |
| ATOM | 9481 CE1 PHE I 351 | 8.066 −9.613 −20.085 1.00 14.10 | C C |
| ATOM | 9482 CZ PHE I 351 | 7.541 −8.442 −20.588 1.00 14.07 | C C |

APPENDIX-continued (APPENDIX discloses SEQ ID NOS 29-32, 29-32 and 29-32, respectively, in order of appearance)

| | | | |
|---|---|---|---|
| ATOM | 9483 CE2 PHE I 351 | 6.305 −8.452 −21.197 1.00 14.14 | C C |
| ATOM | 9484 CD2 PHE I 351 | 5.580 −9.629 −21.270 1.00 13.92 | C C |
| ATOM | 9485 C PHE I 351 | 4.742 −11.899 −18.441 1.00 13.84 | C C |
| ATOM | 9486 O PHE I 351 | 3.579 −11.499 −18.394 1.00 13.96 | C O |
| ATOM | 9487 N PHE I 352 | 5.655 −11.574 −17.534 1.00 14.72 | C N |
| ATOM | 9488 CA PHE I 352 | 5.344 −10.699 −16.412 1.00 15.98 | C C |
| ATOM | 9489 CB PHE I 352 | 5.570 −11.435 −15.093 1.00 15.75 | C C |
| ATOM | 9490 CG PHE I 352 | 5.295 −12.909 −15.169 1.00 15.51 | C C |
| ATOM | 9491 CD1 PHE I 352 | 6.188 −13.762 −15.803 1.00 15.05 | C C |
| ATOM | 9492 CE1 PHE I 352 | 5.926 −15.116 −15.902 1.00 14.05 | C C |
| ATOM | 9493 CZ PHE I 352 | 4.745 −15.624 −15.402 1.00 13.28 | C C |
| ATOM | 9494 CE2 PHE I 352 | 3.833 −14.777 −14.796 1.00 13.71 | C C |
| ATOM | 9495 CD2 PHE I 352 | 4.099 −13.425 −14.704 1.00 14.94 | C C |
| ATOM | 9496 C PHE I 352 | 6.195 −9.438 −16.453 1.00 17.56 | C C |
| ATOM | 9497 O PHE I 352 | 7.419 −9.509 −16.360 1.00 17.74 | C O |
| ATOM | 9498 N PRO I 353 | 5.541 −8.271 −16.525 1.00 19.05 | C N |
| ATOM | 9499 CA PRO I 353 | 6.188 −7.074 −17.055 1.00 20.40 | C C |
| ATOM | 9500 CB PRO I 353 | 5.010 −6.146 −17.365 1.00 20.26 | C C |
| ATOM | 9501 CG PRO I 353 | 3.839 −7.052 −17.522 1.00 19.71 | C C |
| ATOM | 9502 CD PRO I 353 | 4.073 −8.155 −16.545 1.00 18.97 | C C |
| ATOM | 9503 C PRO I 353 | 7.136 −6.408 −16.058 1.00 21.94 | C C |
| ATOM | 9504 O PRO I 353 | 8.087 −5.745 −16.470 1.00 22.29 | C O |
| ATOM | 9505 N GLN I 354 | 6.858 −6.544 −14.763 1.00 23.38 | C N |
| ATOM | 9506 CA GLN I 354 | 7.646 −5.847 −13.743 1.00 24.64 | C C |
| ATOM | 9507 CB GLN I 354 | 6.943 −4.569 −13.274 1.00 24.93 | C C |
| ATOM | 9508 CG GLN I 354 | 5.458 −4.509 −13.587 1.00 26.00 | C C |
| ATOM | 9509 CD GLN I 354 | 4.646 −5.481 −12.756 1.00 25.92 | C C |
| ATOM | 9510 OE1 GLN I 354 | 4.710 −5.474 −11.527 1.00 25.67 | C O |
| ATOM | 9511 NE2 GLN I 354 | 3.870 −6.324 −13.427 1.00 24.27 | C N |
| ATOM | 9512 C GLN I 354 | 8.048 −6.707 −12.543 1.00 24.85 | C C |
| ATOM | 9513 O GLN I 354 | 7.280 −7.556 −12.088 1.00 24.51 | C O |
| ATOM | 9514 N ALA I 355 | 9.200 −6.384 −11.959 1.00 25.22 | C N |
| ATOM | 9515 CA ALA I 355 | 9.818 −7.215 −10.926 1.00 25.34 | C C |
| ATOM | 9516 CB ALA I 355 | 10.949 −6.458 −10.245 1.00 25.09 | C C |
| ATOM | 9517 C ALA I 355 | 8.809 −7.711 −9.892 1.00 24.92 | C C |
| ATOM | 9518 O ALA I 355 | 8.679 −8.915 −9.669 1.00 25.23 | C O |
| ATOM | 9519 N GLU I 356 | 8.278 −6.771 −9.115 1.00 23.93 | C N |
| ATOM | 9520 CA GLU I 356 | 7.089 −6.998 −8.295 1.00 22.77 | C C |
| ATOM | 9521 CB GLU I 356 | 5.993 −5.995 −8.658 1.00 23.22 | C C |
| ATOM | 9522 CG GLU I 356 | 6.412 −4.545 −8.500 1.00 26.33 | C C |
| ATOM | 9523 CD GLU I 356 | 7.250 −4.314 −7.258 1.00 30.93 | C C |
| ATOM | 9524 OE1 GLU I 356 | 8.490 −4.231 −7.380 1.00 31.97 | C O |
| ATOM | 9525 OE2 GLU I 356 | 6.668 −4.227 −6.156 1.00 32.21 | C O |
| ATOM | 9526 C GLU I 356 | 6.547 −8.419 −8.377 1.00 21.31 | C C |
| ATOM | 9527 O GLU I 356 | 6.338 −9.070 −7.354 1.00 21.01 | C O |
| ATOM | 9528 N THR I 357 | 6.137 −8.809 −9.577 1.00 19.51 | C N |
| ATOM | 9529 CA THR I 357 | 5.358 −10.023 −9.766 1.00 17.55 | C C |
| ATOM | 9530 CB THR I 357 | 4.829 −10.115 −11.207 1.00 17.30 | C C |
| ATOM | 9531 OG1 THR I 357 | 5.071 −8.873 −11.882 1.00 17.32 | C O |
| ATOM | 9532 CG2 THR I 357 | 3.335 −10.387 −11.203 1.00 17.72 | C C |
| ATOM | 9533 C THR I 357 | 6.178 −11.268 −9.433 1.00 16.62 | C C |
| ATOM | 9534 O THR I 357 | 5.631 −12.286 −9.008 1.00 17.29 | C O |
| ATOM | 9535 N CYS I 358 | 7.498 −11.146 −9.526 1.00 14.88 | C N |
| ATOM | 9536 CA CYS I 358 | 8.365 −12.317 −9.566 1.00 13.15 | C C |
| ATOM | 9537 CB CYS I 358 | 8.955 −12.501 −10.961 1.00 13.04 | C C |
| ATOM | 9538 SG CYS I 358 | 7.735 −12.899 −12.228 1.00 14.02 | C S |
| ATOM | 9539 C CYS I 358 | 9.478 −12.255 −8.529 1.00 12.08 | C C |
| ATOM | 9540 O CYS I 358 | 10.186 −11.252 −8.417 1.00 12.15 | C O |
| ATOM | 9541 N LYS I 359 | 9.640 −13.345 −7.788 1.00 11.35 | C N |
| ATOM | 9542 CA LYS I 359 | 10.793 −13.519 −6.918 1.00 11.01 | C C |
| ATOM | 9543 CB LYS I 359 | 10.349 −13.675 −5.460 1.00 11.16 | C C |
| ATOM | 9544 CG LYS I 359 | 8.858 −13.470 −5.229 1.00 13.28 | C C |
| ATOM | 9545 CD LYS I 359 | 8.607 −12.427 −4.150 1.00 16.11 | C C |
| ATOM | 9546 CE LYS I 359 | 7.124 −12.287 −3.850 1.00 17.91 | C C |
| ATOM | 9547 NZ LYS I 359 | 6.818 −11.012 −3.145 1.00 20.99 | C N |
| ATOM | 9548 C LYS I 359 | 11.592 −14.739 −7.349 1.00 10.46 | C C |
| ATOM | 9549 O LYS I 359 | 11.091 −15.589 −8.085 1.00 10.70 | C O |
| ATOM | 9550 N VAL I 360 | 12.791 −14.880 −6.798 1.00 9.99 | C N |
| ATOM | 9551 CA VAL I 360 | 13.720 −15.885 −7.282 1.00 9.84 | C C |
| ATOM | 9552 CB VAL I 360 | 14.452 −15.412 −8.541 1.00 9.42 | C C |
| ATOM | 9553 CG1 VAL I 360 | 15.135 −14.066 −8.288 1.00 10.07 | C C |
| ATOM | 9554 CG2 VAL I 360 | 15.454 −16.473 −8.996 1.00 9.56 | C C |
| ATOM | 9555 C VAL I 360 | 14.738 −16.297 −6.229 1.00 9.98 | C C |
| ATOM | 9556 O VAL I 360 | 15.380 −15.457 −5.598 1.00 9.96 | C O |
| ATOM | 9557 N GLN I 361 | 14.900 −17.604 −6.071 1.00 10.39 | C N |
| ATOM | 9558 CA GLN I 361 | 15.781 −18.150 −5.052 1.00 11.53 | C C |
| ATOM | 9559 CB GLN I 361 | 14.966 −18.692 −3.880 1.00 12.03 | C C |

APPENDIX-continued (APPENDIX discloses SEQ ID NOS 29-32, 29-32 and 29-32, respectively, in order of appearance)

| | | | |
|---|---|---|---|
| ATOM | 9560 CG GLN I 361 | 15.810 −19.254 −2.750 1.00 16.44 | C C |
| ATOM | 9561 CD GLN I 361 | 15.388 −18.722 −1.398 1.00 25.16 | C C |
| ATOM | 9562 OE1 GLN I 361 | 14.773 −19.434 −0.604 1.00 29.01 | C O |
| ATOM | 9563 NE2 GLN I 361 | 15.686 −17.453 −1.141 1.00 27.20 | C N |
| ATOM | 9564 C GLN I 361 | 16.613 −19.271 −5.641 1.00 11.15 | C C |
| ATOM | 9565 O GLN I 361 | 16.114 −20.375 −5.854 1.00 11.80 | C O |
| ATOM | 9566 N SER I 362 | 17.877 −18.986 −5.925 1.00 10.90 | C N |
| ATOM | 9567 CA SER I 362 | 18.671 −19.921 −6.695 1.00 10.30 | C C |
| ATOM | 9568 CB SER I 362 | 18.610 −21.302 −6.040 1.00 10.47 | C C |
| ATOM | 9569 OG SER I 362 | 19.659 −22.138 −6.491 1.00 11.17 | C O |
| ATOM | 9570 C SER I 362 | 18.088 −19.980 −8.103 1.00 9.58 | C C |
| ATOM | 9571 O SER I 362 | 17.759 −18.946 −8.683 1.00 9.48 | C O |
| ATOM | 9572 N ASN I 363 | 17.806 −21.188 −8.577 1.00 9.12 | C N |
| ATOM | 9573 CA ASN I 363 | 17.229 −21.365 −9.904 1.00 8.73 | C C |
| ATOM | 9574 CB ASN I 363 | 17.821 −22.602 −10.568 1.00 9.01 | C C |
| ATOM | 9575 CG ASN I 363 | 17.547 −23.864 −9.781 1.00 9.29 | C C |
| ATOM | 9576 OD1 ASN I 363 | 16.903 −23.826 −8.732 1.00 9.82 | C O |
| ATOM | 9577 ND2 ASN I 363 | 17.981 −25.000 −10.314 1.00 10.08 | C N |
| ATOM | 9578 C ASN I 363 | 15.716 −21.503 −9.827 1.00 8.12 | C C |
| ATOM | 9579 O ASN I 363 | 15.084 −22.042 −10.736 1.00 8.10 | C O |
| ATOM | 9580 N ARG I 364 | 15.168 −21.165 −8.665 1.00 7.20 | C N |
| ATOM | 9581 CA ARG I 364 | 13.731 −21.222 −8.445 1.00 6.82 | C C |
| ATOM | 9582 CB ARG I 364 | 13.427 −21.658 −7.012 1.00 6.91 | C C |
| ATOM | 9583 CG ARG I 364 | 12.287 −22.649 −6.908 1.00 7.92 | C C |
| ATOM | 9584 CD ARG I 364 | 12.520 −23.817 −7.843 1.00 8.20 | C C |
| ATOM | 9585 NE ARG I 364 | 11.374 −24.061 −8.711 1.00 8.70 | C N |
| ATOM | 9586 CZ ARG I 364 | 11.056 −25.255 −9.196 1.00 8.88 | C C |
| ATOM | 9587 NH1 ARG I 364 | 11.800 −26.309 −8.894 1.00 8.57 | C N |
| ATOM | 9588 NH2 ARG I 364 | 9.976 −25.403 −9.950 1.00 10.59 | C N |
| ATOM | 9589 C ARG I 364 | 13.110 −19.861 −8.694 1.00 6.58 | C C |
| ATOM | 9590 O ARG I 364 | 13.540 −18.861 −8.121 1.00 6.65 | C O |
| ATOM | 9591 N VAL I 365 | 12.031 −19.846 −9.466 1.00 6.64 | C N |
| ATOM | 9592 CA VAL I 365 | 11.325 −18.609 −9.756 1.00 6.54 | C C |
| ATOM | 9593 CB VAL I 365 | 11.399 −18.261 −11.254 1.00 5.95 | C C |
| ATOM | 9594 CG1 VAL I 365 | 10.374 −17.196 −11.608 1.00 5.48 | C C |
| ATOM | 9595 CG2 VAL I 365 | 12.801 −17.804 −11.623 1.00 6.22 | C C |
| ATOM | 9596 C VAL I 365 | 9.866 −18.723 −9.335 1.00 7.35 | C C |
| ATOM | 9597 O VAL I 365 | 9.271 −19.799 −9.416 1.00 8.33 | C O |
| ATOM | 9598 N PHE I 366 | 9.309 −17.619 −8.843 1.00 7.37 | C N |
| ATOM | 9599 CA PHE I 366 | 7.919 −17.584 −8.401 1.00 7.44 | C C |
| ATOM | 9600 CB PHE I 366 | 7.840 −17.604 −6.875 1.00 7.30 | C C |
| ATOM | 9601 CG PHE I 366 | 8.426 −18.834 −6.255 1.00 6.70 | C C |
| ATOM | 9602 CD1 PHE I 366 | 9.799 −18.991 −6.163 1.00 6.70 | C C |
| ATOM | 9603 CE1 PHE I 366 | 10.345 −20.120 −5.588 1.00 5.94 | C C |
| ATOM | 9604 CZ PHE I 366 | 9.520 −21.083 −5.055 1.00 5.71 | C C |
| ATOM | 9605 CE2 PHE I 366 | 8.149 −20.934 −5.130 1.00 5.96 | C C |
| ATOM | 9606 CD2 PHE I 366 | 7.609 −19.805 −5.710 1.00 6.52 | C C |
| ATOM | 9607 C PHE I 366 | 7.236 −16.335 −8.919 1.00 7.45 | C C |
| ATOM | 9608 O PHE I 366 | 7.530 −15.225 −8.476 1.00 7.45 | C O |
| ATOM | 9609 N CYS I 367 | 6.282 −16.524 −9.819 1.00 8.00 | C N |
| ATOM | 9610 CA CYS I 367 | 5.626 −15.400 −10.450 1.00 8.90 | C C |
| ATOM | 9611 CB CYS I 367 | 5.985 −15.338 −11.934 1.00 9.46 | C C |
| ATOM | 9612 SG CYS I 367 | 7.712 −14.929 −12.259 1.00 10.79 | C S |
| ATOM | 9613 C CYS I 367 | 4.121 −15.484 −10.268 1.00 9.09 | C C |
| ATOM | 9614 O CYS I 367 | 3.591 −16.493 −9.799 1.00 9.24 | C O |
| ATOM | 9615 N ASP I 368 | 3.449 −14.382 −10.568 1.00 9.54 | C N |
| ATOM | 9616 CA ASP I 368 | 2.034 −14.255 −10.285 1.00 10.55 | C C |
| ATOM | 9617 CB ASP I 368 | 1.792 −13.067 −9.349 1.00 10.53 | C C |
| ATOM | 9618 CG ASP I 368 | 0.421 −13.102 −8.698 1.00 11.11 | C C |
| ATOM | 9619 OD1 ASP I 368 | −0.574 −13.335 −9.415 1.00 11.42 | C O |
| ATOM | 9620 OD2 ASP I 368 | 0.323 −12.765 −7.499 1.00 11.35 | C O |
| ATOM | 9621 C ASP I 368 | 1.266 −14.073 −11.590 1.00 11.45 | C C |
| ATOM | 9622 O ASP I 368 | 1.418 −13.061 −12.274 1.00 12.05 | C O |
| ATOM | 9623 N THR I 369 | 0.563 −15.122 −12.003 1.00 12.41 | C N |
| ATOM | 9624 CA THR I 369 | −0.399 −15.013 −13.089 1.00 13.00 | C C |
| ATOM | 9625 CB THR I 369 | −1.513 −16.063 −12.953 1.00 12.69 | C C |
| ATOM | 9626 OG1 THR I 369 | −0.935 −17.374 −12.929 1.00 11.72 | C O |
| ATOM | 9627 CG2 THR I 369 | −2.488 −15.962 −14.115 1.00 13.33 | C C |
| ATOM | 9628 C THR I 369 | −1.034 −13.632 −13.093 1.00 14.13 | C C |
| ATOM | 9629 O THR I 369 | −0.895 −12.874 −14.051 1.00 14.72 | C O |
| ATOM | 9630 N MET I 370 | −1.675 −13.289 −11.984 1.00 15.25 | C N |
| ATOM | 9631 CA MET I 370 | −2.681 −12.240 −11.975 1.00 16.60 | C C |
| ATOM | 9632 CB MET I 370 | −2.538 −11.361 −10.734 1.00 17.42 | C C |
| ATOM | 9633 CG MET I 370 | −3.744 −11.411 −9.811 1.00 20.31 | C C |
| ATOM | 9634 SD MET I 370 | −5.284 −10.974 −10.642 1.00 26.43 | C S |
| ATOM | 9635 CE MET I 370 | −5.320 −12.185 −11.963 1.00 24.07 | C C |
| ATOM | 9636 C MET I 370 | −2.700 −11.396 −13.249 1.00 16.54 | C C |

APPENDIX-continued (APPENDIX discloses SEQ ID NOS 29-32, 29-32 and 29-32, respectively, in order of appearance)

| | | | | |
|---|---|---|---|---|
| ATOM | 9637 O MET I 370 | −3.707 −11.367 −13.953 1.00 16.74 | C O |
| ATOM | 9638 N ASN I 371 | −1.610 −10.691 −13.540 1.00 16.35 | C N |
| ATOM | 9639 CA ASN I 371 | −1.614 −9.772 −14.680 1.00 16.07 | C C |
| ATOM | 9640 CB ASN I 371 | −1.375 −8.326 −14.232 1.00 16.41 | C C |
| ATOM | 9641 CG ASN I 371 | −2.619 −7.690 −13.634 1.00 16.71 | C C |
| ATOM | 9642 OD1 ASN I 371 | −3.501 −7.228 −14.356 1.00 15.75 | C O |
| ATOM | 9643 ND2 ASN I 371 | −2.722 −7.724 −12.310 1.00 17.76 | C N |
| ATOM | 9644 C ASN I 371 | −0.698 −10.167 −15.842 1.00 15.55 | C C |
| ATOM | 9645 O ASN I 371 | −0.650 −9.478 −16.862 1.00 15.84 | C O |
| ATOM | 9646 N SER I 372 | −0.166 −11.383 −15.771 1.00 14.76 | C N |
| ATOM | 9647 CA SER I 372 | 0.540 −11.990 −16.894 1.00 13.91 | C C |
| ATOM | 9648 CB SER I 372 | 0.561 −13.512 −16.746 1.00 14.04 | C C |
| ATOM | 9649 OG SER I 372 | −0.696 −14.071 −17.084 1.00 15.09 | C O |
| ATOM | 9650 C SER I 372 | −0.071 −11.614 −18.242 1.00 13.07 | C C |
| ATOM | 9651 O SER I 372 | −1.291 −11.511 −18.373 1.00 13.02 | C O |
| ATOM | 9652 N LEU I 373 | 0.781 −11.525 −19.263 1.00 12.23 | C N |
| ATOM | 9653 CA LEU I 373 | 0.352 −11.621 −20.658 1.00 11.45 | C C |
| ATOM | 9654 CB LEU I 373 | 0.999 −10.504 −21.485 1.00 11.43 | C C |
| ATOM | 9655 CG LEU I 373 | 0.250 −9.176 −21.636 1.00 11.04 | C C |
| ATOM | 9656 CD1 LEU I 373 | −0.580 −8.867 −20.406 1.00 11.76 | C C |
| ATOM | 9657 CD2 LEU I 373 | 1.213 −8.035 −21.928 1.00 10.49 | C C |
| ATOM | 9658 C LEU I 373 | 0.727 −12.982 −21.247 1.00 11.17 | C C |
| ATOM | 9659 O LEU I 373 | 1.819 −13.492 −21.000 1.00 11.27 | C O |
| ATOM | 9660 N THR I 374 | −0.164 −13.546 −22.056 1.00 10.70 | C N |
| ATOM | 9661 CA THR I 374 | 0.062 −14.869 −22.633 1.00 10.23 | C C |
| ATOM | 9662 CB THR I 374 | −1.187 −15.768 −22.531 1.00 10.24 | C C |
| ATOM | 9663 OG1 THR I 374 | −1.999 −15.346 −21.429 1.00 11.25 | C O |
| ATOM | 9664 CG2 THR I 374 | −0.785 −17.224 −22.338 1.00 10.52 | C C |
| ATOM | 9665 C THR I 374 | 0.481 −14.772 −24.091 1.00 9.54 | C C |
| ATOM | 9666 O THR I 374 | −0.164 −14.097 −24.893 1.00 9.70 | C O |
| ATOM | 9667 N LEU I 375 | 1.576 −15.444 −24.422 1.00 8.83 | C N |
| ATOM | 9668 CA LEU I 375 | 2.236 −15.253 −25.704 1.00 7.83 | C C |
| ATOM | 9669 CB LEU I 375 | 3.470 −14.361 −25.547 1.00 7.38 | C C |
| ATOM | 9670 CG LEU I 375 | 3.309 −13.047 −24.780 1.00 5.06 | C C |
| ATOM | 9671 CD1 LEU I 375 | 4.669 −12.411 −24.533 1.00 2.41 | C C |
| ATOM | 9672 CD2 LEU I 375 | 2.397 −12.098 −25.535 1.00 4.31 | C C |
| ATOM | 9673 C LEU I 375 | 2.644 −16.600 −26.283 1.00 7.79 | C C |
| ATOM | 9674 O LEU I 375 | 2.703 −17.598 −25.565 1.00 7.92 | C O |
| ATOM | 9675 N PRO I 376 | 2.914 −16.629 −27.595 1.00 7.51 | C N |
| ATOM | 9676 CA PRO I 376 | 3.325 −17.826 −28.323 1.00 7.90 | C C |
| ATOM | 9677 CB PRO I 376 | 2.852 −17.538 −29.748 1.00 7.90 | C C |
| ATOM | 9678 CG PRO I 376 | 2.913 −16.062 −29.858 1.00 7.97 | C C |
| ATOM | 9679 CD PRO I 376 | 2.537 −15.534 −28.505 1.00 7.40 | C C |
| ATOM | 9680 C PRO I 376 | 4.838 −18.023 −28.310 1.00 8.35 | C C |
| ATOM | 9681 O PRO I 376 | 5.589 −17.062 −28.484 1.00 8.71 | C O |
| ATOM | 9682 N SER I 377 | 5.263 −19.283 −28.263 1.00 9.11 | C N |
| ATOM | 9683 CA SER I 377 | 6.682 −19.622 −28.207 1.00 9.91 | C C |
| ATOM | 9684 CB SER I 377 | 6.880 −21.137 −28.330 1.00 10.23 | C C |
| ATOM | 9685 OG SER I 377 | 5.713 −21.842 −27.939 1.00 10.90 | C O |
| ATOM | 9686 C SER I 377 | 7.438 −18.911 −29.319 1.00 10.14 | C C |
| ATOM | 9687 O SER I 377 | 8.660 −19.024 −29.425 1.00 10.08 | C O |
| ATOM | 9688 N GLU I 378 | 6.683 −18.286 −30.215 1.00 10.71 | C N |
| ATOM | 9689 CA GLU I 378 | 7.256 −17.563 −31.339 1.00 11.40 | C C |
| ATOM | 9690 CB GLU I 378 | 6.177 −17.256 −32.379 1.00 11.65 | C C |
| ATOM | 9691 CG GLU I 378 | 5.858 −18.418 −33.312 1.00 13.46 | C C |
| ATOM | 9692 CD GLU I 378 | 5.249 −19.608 −32.588 1.00 16.20 | C C |
| ATOM | 9693 OE1 GLU I 378 | 4.999 −19.505 −31.368 1.00 15.73 | C O |
| ATOM | 9694 OE2 GLU I 378 | 4.989 −20.636 −33.250 1.00 18.38 | C O |
| ATOM | 9695 C GLU I 378 | 7.922 −16.274 −30.873 1.00 11.27 | C C |
| ATOM | 9696 O GLU I 378 | 8.776 −15.722 −31.567 1.00 11.28 | C O |
| ATOM | 9697 N VAL I 379 | 7.570 −15.827 −29.672 1.00 11.31 | C N |
| ATOM | 9698 CA VAL I 379 | 8.268 −14.708 −29.056 1.00 11.59 | C C |
| ATOM | 9699 CB VAL I 379 | 7.849 −14.504 −27.591 1.00 11.27 | C C |
| ATOM | 9700 CG1 VAL I 379 | 8.894 −13.674 −26.858 1.00 11.60 | C C |
| ATOM | 9701 CG2 VAL I 379 | 6.486 −13.833 −27.520 1.00 11.54 | C C |
| ATOM | 9702 C VAL I 379 | 9.779 −14.907 −29.124 1.00 12.16 | C C |
| ATOM | 9703 O VAL I 379 | 10.533 −13.943 −29.255 1.00 12.51 | C O |
| ATOM | 9704 N ASN I 380 | 10.219 −16.158 −29.030 1.00 12.98 | C N |
| ATOM | 9705 CA ASN I 380 | 11.637 −16.453 −28.854 1.00 14.00 | C C |
| ATOM | 9706 CB ASN I 380 | 11.854 −17.947 −28.579 1.00 14.59 | C C |
| ATOM | 9707 CG ASN I 380 | 11.318 −18.381 −27.224 1.00 17.09 | C C |
| ATOM | 9708 OD1 ASN I 380 | 12.070 −18.488 −26.256 1.00 20.41 | C O |
| ATOM | 9709 ND2 ASN I 380 | 10.045 −18.763 −27.186 1.00 18.86 | C N |
| ATOM | 9710 C ASN I 380 | 12.477 −16.006 −30.051 1.00 13.96 | C C |
| ATOM | 9711 O ASN I 380 | 13.619 −15.576 −29.890 1.00 14.38 | C O |
| ATOM | 9712 N LEU I 381 | 11.925 −16.159 −31.252 1.00 13.61 | C N |
| ATOM | 9713 CA LEU I 381 | 12.638 −15.798 −32.475 1.00 13.72 | C C |

APPENDIX-continued (APPENDIX discloses SEQ ID NOS 29-32, 29-32 and 29-32, respectively, in order of appearance)

| | | | |
|---|---|---|---|
| ATOM | 9714 CB LEU I 381 | 11.742 −15.996 −33.698 1.00 13.79 | C C |
| ATOM | 9715 CG LEU I 381 | 10.720 −17.130 −33.607 1.00 14.92 | C C |
| ATOM | 9716 CD1 LEU I 381 | 9.817 −17.138 −34.830 1.00 15.56 | C C |
| ATOM | 9717 CD2 LEU I 381 | 11.421 −18.470 −33.446 1.00 15.78 | C C |
| ATOM | 9718 C LEU I 381 | 13.093 −14.349 −32.401 1.00 13.62 | C C |
| ATOM | 9719 O LEU I 381 | 14.017 −13.934 −33.100 1.00 13.57 | C O |
| ATOM | 9720 N CYS I 382 | 12.473 −13.607 −31.494 1.00 13.47 | C N |
| ATOM | 9721 CA CYS I 382 | 12.727 −12.187 −31.357 1.00 13.57 | C C |
| ATOM | 9722 CB CYS I 382 | 11.613 −11.538 −30.545 1.00 13.62 | C C |
| ATOM | 9723 SG CYS I 382 | 10.346 −10.770 −31.551 1.00 15.64 | C S |
| ATOM | 9724 C CYS I 382 | 14.073 −11.928 −30.696 1.00 13.33 | C C |
| ATOM | 9725 O CYS I 382 | 14.690 −10.887 −30.923 1.00 13.57 | C O |
| ATOM | 9726 N ASN I 383 | 14.565 −12.914 −29.948 1.00 13.21 | C N |
| ATOM | 9727 CA ASN I 383 | 15.925 −12.865 −29.415 1.00 13.22 | C C |
| ATOM | 9728 CB ASN I 383 | 16.191 −14.054 −28.491 1.00 13.18 | C C |
| ATOM | 9729 CG ASN I 383 | 15.154 −14.186 −27.400 1.00 13.42 | C C |
| ATOM | 9730 OD1 ASN I 383 | 14.774 −13.202 −26.769 1.00 13.68 | C O |
| ATOM | 9731 ND2 ASN I 383 | 14.660 −15.402 −27.199 1.00 14.32 | C N |
| ATOM | 9732 C ASN I 383 | 16.959 −12.845 −30.530 1.00 13.28 | C C |
| ATOM | 9733 O ASN I 383 | 18.081 −12.374 −30.344 1.00 13.50 | C O |
| ATOM | 9734 N VAL I 384 | 16.605 −13.451 −31.657 1.00 13.24 | C N |
| ATOM | 9735 CA VAL I 384 | 17.532 −13.584 −32.767 1.00 13.29 | C C |
| ATOM | 9736 CB VAL I 384 | 17.484 −14.992 −33.387 1.00 13.28 | C C |
| ATOM | 9737 CG1 VAL I 384 | 18.046 −14.970 −34.800 1.00 13.73 | C C |
| ATOM | 9738 CG2 VAL I 384 | 18.251 −15.977 −32.518 1.00 12.76 | C C |
| ATOM | 9739 C VAL I 384 | 17.292 −12.529 −33.842 1.00 13.57 | C C |
| ATOM | 9740 O VAL I 384 | 18.239 −12.070 −34.480 1.00 13.31 | C O |
| ATOM | 9741 N ASP I 385 | 16.038 −12.140 −34.049 1.00 14.07 | C N |
| ATOM | 9742 CA ASP I 385 | 15.711 −11.380 −35.249 1.00 14.61 | C C |
| ATOM | 9743 CB ASP I 385 | 15.049 −12.246 −36.318 1.00 14.71 | C C |
| ATOM | 9744 CG ASP I 385 | 15.608 −11.980 −37.701 1.00 16.69 | C C |
| ATOM | 9745 OD1 ASP I 385 | 16.308 −10.959 −37.872 1.00 18.63 | C O |
| ATOM | 9746 OD2 ASP I 385 | 15.367 −12.800 −38.612 1.00 19.10 | C O |
| ATOM | 9747 C ASP I 385 | 15.014 −10.029 −35.092 1.00 14.63 | C C |
| ATOM | 9748 O ASP I 385 | 15.412 −9.054 −35.728 1.00 14.34 | C O |
| ATOM | 9749 N ILE I 386 | 13.937 −9.980 −34.314 1.00 14.54 | C N |
| ATOM | 9750 CA ILE I 386 | 13.154 −8.752 −34.212 1.00 14.46 | C C |
| ATOM | 9751 CB ILE I 386 | 14.074 −7.521 −34.137 1.00 13.83 | C C |
| ATOM | 9752 CG1 ILE I 386 | 14.932 −7.584 −32.875 1.00 13.44 | C C |
| ATOM | 9753 CD1 ILE I 386 | 16.315 −7.018 −33.048 1.00 12.39 | C C |
| ATOM | 9754 CG2 ILE I 386 | 13.253 −6.241 −34.161 1.00 13.51 | C C |
| ATOM | 9755 C ILE I 386 | 12.274 −8.602 −35.443 1.00 14.73 | C C |
| ATOM | 9756 O ILE I 386 | 11.048 −8.692 −35.369 1.00 14.68 | C O |
| ATOM | 9757 N PHE I 387 | 12.917 −8.301 −36.564 1.00 14.71 | C N |
| ATOM | 9758 CA PHE I 387 | 12.294 −8.428 −37.868 1.00 14.78 | C C |
| ATOM | 9759 CB PHE I 387 | 12.993 −7.528 −38.876 1.00 14.77 | C C |
| ATOM | 9760 CG PHE I 387 | 13.269 −6.154 −38.354 1.00 14.75 | C C |
| ATOM | 9761 CD1 PHE I 387 | 14.538 −5.818 −37.909 1.00 15.03 | C C |
| ATOM | 9762 CE1 PHE I 387 | 14.790 −4.572 −37.366 1.00 14.62 | C C |
| ATOM | 9763 CZ PHE I 387 | 13.743 −3.702 −37.131 1.00 14.55 | C C |
| ATOM | 9764 CE2 PHE I 387 | 12.452 −4.074 −37.463 1.00 14.68 | C C |
| ATOM | 9765 CD2 PHE I 387 | 12.219 −5.303 −38.052 1.00 14.61 | C C |
| ATOM | 9766 C PHE I 387 | 12.291 −9.864 −38.352 1.00 14.91 | C C |
| ATOM | 9767 O PHE I 387 | 13.339 −10.461 −38.604 1.00 14.86 | C O |
| ATOM | 9768 N ASN I 388 | 11.102 −10.448 −38.325 1.00 15.11 | C N |
| ATOM | 9769 CA ASN I 388 | 10.866 −11.776 −38.850 1.00 15.38 | C C |
| ATOM | 9770 CB ASN I 388 | 11.522 −12.817 −37.947 1.00 14.86 | C C |
| ATOM | 9771 CG ASN I 388 | 11.029 −12.733 −36.519 1.00 14.86 | C C |
| ATOM | 9772 OD1 ASN I 388 | 10.004 −13.318 −36.170 1.00 12.80 | C O |
| ATOM | 9773 ND2 ASN I 388 | 11.708 −11.934 −35.707 1.00 15.97 | C N |
| ATOM | 9774 C ASN I 388 | 9.363 −11.982 −38.843 1.00 16.11 | C C |
| ATOM | 9775 O ASN I 388 | 8.688 −11.570 −37.902 1.00 15.92 | C O |
| ATOM | 9776 N PRO I 389 | 8.817 −12.450 −39.969 1.00 16.99 | C N |
| ATOM | 9777 CA PRO I 389 | 7.464 −12.988 −39.920 1.00 17.40 | C C |
| ATOM | 9778 CB PRO I 389 | 7.376 −13.815 −41.204 1.00 17.72 | C C |
| ATOM | 9779 CG PRO I 389 | 8.776 −14.223 −41.477 1.00 17.47 | C C |
| ATOM | 9780 CD PRO I 389 | 9.618 −13.063 −41.043 1.00 17.05 | C C |
| ATOM | 9781 C PRO I 389 | 7.304 −13.894 −38.706 1.00 17.86 | C C |
| ATOM | 9782 O PRO I 389 | 8.297 −14.397 −38.181 1.00 18.45 | C O |
| ATOM | 9783 N LYS I 390 | 6.068 −14.106 −38.269 1.00 17.97 | C N |
| ATOM | 9784 CA LYS I 390 | 5.813 −14.937 −37.098 1.00 18.06 | C C |
| ATOM | 9785 CB LYS I 390 | 6.986 −15.889 −36.844 1.00 17.92 | C C |
| ATOM | 9786 CG LYS I 390 | 7.066 −17.065 −37.806 1.00 18.58 | C C |
| ATOM | 9787 CD LYS I 390 | 6.331 −18.283 −37.264 1.00 20.61 | C C |
| ATOM | 9788 CE LYS I 390 | 6.758 −19.556 −37.982 1.00 21.48 | C C |
| ATOM | 9789 NZ LYS I 390 | 6.197 −19.645 −39.360 1.00 23.16 | C N |
| ATOM | 9790 C LYS I 390 | 5.557 −14.087 −35.858 1.00 18.01 | C C |

APPENDIX-continued (APPENDIX discloses SEQ ID NOS 29-32, 29-32 and 29-32, respectively, in order of appearance)

| | | | | |
|---|---|---|---|---|
| ATOM | 9791 O LYS I 390 | 4.552 −14.267 −35.171 1.00 18.43 | C O |
| ATOM | 9792 N TYR I 391 | 6.490 −13.192 −35.548 1.00 17.68 | C N |
| ATOM | 9793 CA TYR I 391 | 6.267 −12.216 −34.492 1.00 17.33 | C C |
| ATOM | 9794 CB TYR I 391 | 7.026 −12.599 −33.224 1.00 17.42 | C C |
| ATOM | 9795 CG TYR I 391 | 6.220 −12.376 −31.971 1.00 17.27 | C C |
| ATOM | 9796 CD1 TYR I 391 | 4.863 −12.657 −31.951 1.00 17.29 | C C |
| ATOM | 9797 CE1 TYR I 391 | 4.108 −12.437 −30.822 1.00 17.32 | C C |
| ATOM | 9798 CZ TYR I 391 | 4.678 −11.809 −29.739 1.00 16.51 | C C |
| ATOM | 9799 OH TYR I 391 | 3.934 −11.601 −28.602 1.00 16.65 | C O |
| ATOM | 9800 CE2 TYR I 391 | 6.005 −11.441 −29.765 1.00 16.52 | C C |
| ATOM | 9801 CD2 TYR I 391 | 6.756 −11.689 −30.893 1.00 17.24 | C C |
| ATOM | 9802 C TYR I 391 | 6.623 −10.796 −34.910 1.00 17.43 | C C |
| ATOM | 9803 O TYR I 391 | 7.786 −10.491 −35.175 1.00 17.70 | C O |
| ATOM | 9804 N ASP I 392 | 5.647 −9.899 −34.813 1.00 17.56 | C N |
| ATOM | 9805 CA ASP I 392 | 5.944 −8.487 −34.609 1.00 17.69 | C C |
| ATOM | 9806 CB ASP I 392 | 4.779 −7.590 −35.045 1.00 17.89 | C C |
| ATOM | 9807 CG ASP I 392 | 3.556 −8.380 −35.472 1.00 18.86 | C C |
| ATOM | 9808 OD1 ASP I 392 | 2.911 −8.993 −34.596 1.00 20.34 | C O |
| ATOM | 9809 OD2 ASP I 392 | 3.162 −8.272 −36.653 1.00 18.51 | C O |
| ATOM | 9810 C ASP I 392 | 6.342 −8.188 −33.169 1.00 17.11 | C C |
| ATOM | 9811 O ASP I 392 | 5.674 −8.609 −32.222 1.00 17.04 | C O |
| ATOM | 9812 N CYS I 393 | 7.356 −7.342 −33.026 1.00 16.33 | C N |
| ATOM | 9813 CA CYS I 393 | 8.347 −7.491 −31.975 1.00 16.17 | C C |
| ATOM | 9814 CB CYS I 393 | 9.656 −8.022 −32.554 1.00 16.11 | C C |
| ATOM | 9815 SG CYS I 393 | 10.738 −8.792 −31.342 1.00 20.23 | C S |
| ATOM | 9816 C CYS I 393 | 8.587 −6.139 −31.330 1.00 15.37 | C C |
| ATOM | 9817 O CYS I 393 | 9.066 −5.209 −31.980 1.00 15.15 | C O |
| ATOM | 9818 N LYS I 394 | 8.077 −5.982 −30.115 1.00 14.91 | C N |
| ATOM | 9819 CA LYS I 394 | 7.988 −4.668 −29.502 1.00 14.50 | C C |
| ATOM | 9820 CB LYS I 394 | 7.163 −4.724 −28.214 1.00 14.60 | C C |
| ATOM | 9821 CG LYS I 394 | 5.909 −5.591 −28.313 1.00 16.44 | C C |
| ATOM | 9822 CD LYS I 394 | 4.799 −5.101 −27.382 1.00 20.45 | C C |
| ATOM | 9823 CE LYS I 394 | 4.989 −5.604 −25.955 1.00 23.05 | C C |
| ATOM | 9824 NZ LYS I 394 | 5.685 −4.608 −25.094 1.00 24.13 | C N |
| ATOM | 9825 C LYS I 394 | 9.370 −4.087 −29.239 1.00 14.00 | C C |
| ATOM | 9826 O LYS I 394 | 10.260 −4.760 −28.720 1.00 14.14 | C O |
| ATOM | 9827 N ILE I 395 | 9.497 −2.797 −29.507 1.00 13.28 | C N |
| ATOM | 9828 CA ILE I 395 | 10.750 −2.193 −29.919 1.00 12.89 | C C |
| ATOM | 9829 CB ILE I 395 | 10.960 −2.334 −31.435 1.00 12.75 | C C |
| ATOM | 9830 CG1 ILE I 395 | 11.556 −3.695 −31.786 1.00 13.58 | C C |
| ATOM | 9831 CD1 ILE I 395 | 11.347 −4.084 −33.236 1.00 15.33 | C C |
| ATOM | 9832 CG2 ILE I 395 | 11.838 −1.216 −31.951 1.00 12.16 | C C |
| ATOM | 9833 C ILE I 395 | 10.534 −0.722 −29.648 1.00 13.15 | C C |
| ATOM | 9834 O ILE I 395 | 9.437 −0.210 −29.867 1.00 13.45 | C O |
| ATOM | 9835 N MET I 396 | 11.597 −0.002 −29.330 1.00 13.06 | C N |
| ATOM | 9836 CA MET I 396 | 11.526 1.433 −29.454 1.00 13.00 | C C |
| ATOM | 9837 CB MET I 396 | 11.421 2.114 −28.088 1.00 13.34 | C C |
| ATOM | 9838 CG MET I 396 | 12.738 2.594 −27.506 1.00 14.30 | C C |
| ATOM | 9839 SD MET I 396 | 12.483 3.421 −25.925 1.00 18.50 | C S |
| ATOM | 9840 CE MET I 396 | 11.067 2.515 −25.304 1.00 17.80 | C C |
| ATOM | 9841 C MET I 396 | 12.646 2.009 −30.288 1.00 12.96 | C C |
| ATOM | 9842 O MET I 396 | 13.704 1.405 −30.453 1.00 13.04 | C O |
| ATOM | 9843 N THR I 397 | 12.360 3.167 −30.862 1.00 12.78 | C N |
| ATOM | 9844 CA THR I 397 | 13.158 3.744 −31.917 1.00 12.51 | C C |
| ATOM | 9845 CB THR I 397 | 12.261 4.048 −33.134 1.00 12.39 | C C |
| ATOM | 9846 OG1 THR I 397 | 12.048 2.845 −33.883 1.00 12.50 | C O |
| ATOM | 9847 CG2 THR I 397 | 12.895 5.107 −34.026 1.00 12.55 | C C |
| ATOM | 9848 C THR I 397 | 13.633 5.062 −31.330 1.00 12.58 | C C |
| ATOM | 9849 O THR I 397 | 12.815 5.911 −31.001 1.00 12.88 | C O |
| ATOM | 9850 N SER I 398 | 14.919 5.217 −31.088 1.00 12.55 | C N |
| ATOM | 9851 CA SER I 398 | 15.538 6.442 −31.506 1.00 12.76 | C C |
| ATOM | 9852 CB SER I 398 | 16.509 6.920 −30.432 1.00 12.52 | C C |
| ATOM | 9853 OG SER I 398 | 17.486 7.787 −30.978 1.00 12.72 | C O |
| ATOM | 9854 C SER I 398 | 16.262 5.826 −32.632 1.00 12.99 | C C |
| ATOM | 9855 O SER I 398 | 16.219 6.314 −33.761 1.00 13.13 | C O |
| ATOM | 9856 N LYS I 399 | 16.463 4.540 −32.418 1.00 13.01 | C N |
| ATOM | 9857 CA LYS I 399 | 17.619 4.000 −32.989 1.00 13.29 | C C |
| ATOM | 9858 CB LYS I 399 | 17.475 4.221 −34.500 1.00 13.79 | C C |
| ATOM | 9859 CG LYS I 399 | 15.997 4.359 −34.942 1.00 14.34 | C C |
| ATOM | 9860 CD LYS I 399 | 15.854 4.556 −36.445 1.00 16.43 | C C |
| ATOM | 9861 CE LYS I 399 | 15.114 3.394 −37.093 1.00 17.37 | C C |
| ATOM | 9862 NZ LYS I 399 | 15.524 3.199 −38.511 1.00 16.62 | C N |
| ATOM | 9863 C LYS I 399 | 18.632 4.961 −32.349 1.00 13.09 | C C |
| ATOM | 9864 O LYS I 399 | 19.670 5.257 −32.934 1.00 12.87 | C O |
| ATOM | 9865 N THR I 400 | 18.236 5.572 −31.225 1.00 13.04 | C N |
| ATOM | 9866 CA THR I 400 | 19.072 6.571 −30.513 1.00 13.38 | C C |
| ATOM | 9867 CB THR I 400 | 18.218 7.723 −29.906 1.00 13.74 | C C |

APPENDIX-continued (APPENDIX discloses SEQ ID NOS 29-32, 29-32 and 29-32, respectively, in order of appearance)

| | | | |
|---|---|---|---|
| ATOM | 9868 OG1 THR I 400 | 16.861 7.632 −30.365 1.00 14.38 | C O |
| ATOM | 9869 CG2 THR I 400 | 18.798 9.072 −30.296 1.00 14.32 | C C |
| ATOM | 9870 C THR I 400 | 19.991 5.980 −29.408 1.00 13.20 | C C |
| ATOM | 9871 O THR I 400 | 19.748 4.866 −28.945 1.00 13.12 | C O |
| ATOM | 9872 N ASP I 401 | 20.881 6.801 −28.834 1.00 12.97 | C N |
| ATOM | 9873 CA ASP I 401 | 22.197 6.333 −28.331 1.00 12.50 | C C |
| ATOM | 9874 CB ASP I 401 | 23.307 7.270 −28.816 1.00 12.73 | C C |
| ATOM | 9875 CG ASP I 401 | 24.212 6.623 −29.841 1.00 13.98 | C C |
| ATOM | 9876 OD1 ASP I 401 | 23.677 6.029 −30.801 1.00 16.55 | C O |
| ATOM | 9877 OD2 ASP I 401 | 25.430 6.903 −29.814 1.00 14.80 | C O |
| ATOM | 9878 C ASP I 401 | 22.414 6.066 −26.816 1.00 12.13 | C C |
| ATOM | 9879 O ASP I 401 | 21.541 6.376 −26.002 1.00 12.31 | C O |
| ATOM | 9880 N VAL I 402 | 23.721 6.022 −26.502 1.00 11.49 | C N |
| ATOM | 9881 CA VAL I 402 | 24.382 5.380 −25.316 1.00 10.74 | C C |
| ATOM | 9882 CB VAL I 402 | 23.454 5.112 −24.128 1.00 10.60 | C C |
| ATOM | 9883 CG1 VAL I 402 | 24.200 4.335 −23.060 1.00 11.26 | C C |
| ATOM | 9884 CG2 VAL I 402 | 22.942 6.425 −23.556 1.00 10.99 | C C |
| ATOM | 9885 C VAL I 402 | 25.452 4.251 −25.504 1.00 10.24 | C C |
| ATOM | 9886 O VAL I 402 | 25.773 3.895 −26.638 1.00 10.30 | C O |
| ATOM | 9887 N SER I 403 | 25.962 3.665 −24.400 1.00 9.76 | C N |
| ATOM | 9888 CA SER I 403 | 27.019 2.595 −24.456 1.00 9.18 | C C |
| ATOM | 9889 CB SER I 403 | 28.324 3.145 −25.036 1.00 9.41 | C C |
| ATOM | 9890 OG SER I 403 | 28.274 4.554 −25.165 1.00 10.82 | C O |
| ATOM | 9891 C SER I 403 | 27.325 1.652 −23.238 1.00 8.51 | C C |
| ATOM | 9892 O SER I 403 | 27.347 2.099 −22.088 1.00 8.30 | C O |
| ATOM | 9893 N SER I 404 | 27.642 0.376 −23.530 1.00 8.35 | C N |
| ATOM | 9894 CA SER I 404 | 28.574 −0.482 −22.733 1.00 8.18 | C C |
| ATOM | 9895 CB SER I 404 | 28.123 −0.585 −21.276 1.00 8.18 | C C |
| ATOM | 9896 OG SER I 404 | 27.698 −1.901 −20.968 1.00 8.83 | C O |
| ATOM | 9897 C SER I 404 | 28.789 −1.907 −23.310 1.00 7.62 | C C |
| ATOM | 9898 O SER I 404 | 28.422 −2.171 −24.455 1.00 7.57 | C O |
| ATOM | 9899 N SER I 405 | 29.368 −2.817 −22.514 1.00 7.08 | C N |
| ATOM | 9900 CA SER I 405 | 29.672 −4.192 −22.973 1.00 6.53 | C C |
| ATOM | 9901 CB SER I 405 | 31.139 −4.335 −23.400 1.00 6.42 | C C |
| ATOM | 9902 OG SER I 405 | 31.467 −5.695 −23.651 1.00 5.66 | C O |
| ATOM | 9903 C SER I 405 | 29.300 −5.333 −22.012 1.00 6.28 | C C |
| ATOM | 9904 O SER I 405 | 29.334 −5.169 −20.791 1.00 5.98 | C O |
| ATOM | 9905 N VAL I 406 | 29.215 −6.535 −22.576 1.00 6.22 | C N |
| ATOM | 9906 CA VAL I 406 | 28.714 −7.705 −21.866 1.00 6.50 | C C |
| ATOM | 9907 CB VAL I 406 | 27.208 −7.894 −22.099 1.00 6.45 | C C |
| ATOM | 9908 CG1 VAL I 406 | 26.661 −8.972 −21.181 1.00 7.66 | C C |
| ATOM | 9909 CG2 VAL I 406 | 26.470 −6.577 −21.903 1.00 7.38 | C C |
| ATOM | 9910 C VAL I 406 | 29.424 −8.942 −22.388 1.00 6.24 | C C |
| ATOM | 9911 O VAL I 406 | 29.397 −9.228 −23.584 1.00 6.14 | C O |
| ATOM | 9912 N ILE I 407 | 30.041 −9.689 −21.485 1.00 6.32 | C N |
| ATOM | 9913 CA ILE I 407 | 30.831 −10.838 −21.881 1.00 6.60 | C C |
| ATOM | 9914 CB ILE I 407 | 32.035 −11.021 −20.959 1.00 6.27 | C C |
| ATOM | 9915 CG1 ILE I 407 | 33.112 −9.989 −21.295 1.00 6.19 | C C |
| ATOM | 9916 CD1 ILE I 407 | 33.720 −9.323 −20.073 1.00 8.34 | C C |
| ATOM | 9917 CG2 ILE I 407 | 32.567 −12.438 −21.053 1.00 6.42 | C C |
| ATOM | 9918 C ILE I 407 | 29.995 −12.110 −21.882 1.00 7.20 | C C |
| ATOM | 9919 O ILE I 407 | 29.246 −12.376 −20.944 1.00 7.42 | C O |
| ATOM | 9920 N THR I 408 | 30.163 −12.914 −22.925 1.00 7.57 | C N |
| ATOM | 9921 CA THR I 408 | 29.355 −14.113 −23.103 1.00 8.19 | C C |
| ATOM | 9922 CB THR I 408 | 28.681 −14.138 −24.483 1.00 8.15 | C C |
| ATOM | 9923 OG1 THR I 408 | 29.684 −14.218 −25.503 1.00 8.88 | C O |
| ATOM | 9924 CG2 THR I 408 | 27.853 −12.888 −24.693 1.00 7.93 | C C |
| ATOM | 9925 C THR I 408 | 30.192 −15.376 −22.966 1.00 8.55 | C C |
| ATOM | 9926 O THR I 408 | 31.419 −15.333 −23.065 1.00 9.07 | C O |
| ATOM | 9927 N SER I 409 | 29.503 −16.512 −22.970 1.00 8.70 | C N |
| ATOM | 9928 CA SER I 409 | 30.146 −17.813 −22.838 1.00 9.20 | C C |
| ATOM | 9929 CB SER I 409 | 29.126 −18.935 −23.044 1.00 9.72 | C C |
| ATOM | 9930 OG SER I 409 | 27.946 −18.700 −22.297 1.00 10.75 | C O |
| ATOM | 9931 C SER I 409 | 31.268 −17.958 −23.848 1.00 9.01 | C C |
| ATOM | 9932 O SER I 409 | 32.299 −18.571 −23.567 1.00 9.02 | C O |
| ATOM | 9933 N LEU I 410 | 31.027 −17.458 −25.053 1.00 8.91 | C N |
| ATOM | 9934 CA LEU I 410 | 31.814 −17.858 −26.204 1.00 9.29 | C C |
| ATOM | 9935 CB LEU I 410 | 31.024 −18.828 −27.081 1.00 9.61 | C C |
| ATOM | 9936 CG LEU I 410 | 31.702 −20.180 −27.323 1.00 9.70 | C C |
| ATOM | 9937 CD1 LEU I 410 | 31.975 −20.908 −26.014 1.00 11.11 | C C |
| ATOM | 9938 CD2 LEU I 410 | 30.895 −21.057 −28.274 1.00 9.16 | C C |
| ATOM | 9939 C LEU I 410 | 32.250 −16.644 −27.009 1.00 9.12 | C C |
| ATOM | 9940 O LEU I 410 | 32.844 −16.774 −28.077 1.00 9.08 | C O |
| ATOM | 9941 N GLY I 411 | 32.016 −15.462 −26.454 1.00 9.03 | C N |
| ATOM | 9942 CA GLY I 411 | 32.612 −14.247 −26.984 1.00 8.44 | C C |
| ATOM | 9943 C GLY I 411 | 32.234 −13.047 −26.146 1.00 7.91 | C C |
| ATOM | 9944 O GLY I 411 | 32.175 −13.131 −24.921 1.00 7.85 | C O |

APPENDIX-continued (APPENDIX discloses SEQ ID NOS 29-32, 29-32 and 29-32, respectively, in order of appearance)

| | | | |
|---|---|---|---|
| ATOM | 9945 N ALA I 412 | 31.868 −11.961 −26.816 1.00 7.30 | C N |
| ATOM | 9946 CA ALA I 412 | 31.416 −10.757 −26.130 1.00 6.92 | C C |
| ATOM | 9947 CB ALA I 412 | 32.609 −9.925 −25.672 1.00 6.90 | C C |
| ATOM | 9948 C ALA I 412 | 30.502 −9.934 −27.029 1.00 6.99 | C C |
| ATOM | 9949 O ALA I 412 | 30.597 −10.004 −28.255 1.00 6.94 | C O |
| ATOM | 9950 N ILE I 413 | 29.567 −9.216 −26.418 1.00 7.29 | C N |
| ATOM | 9951 CA ILE I 413 | 28.808 −8.200 −27.136 1.00 7.49 | C C |
| ATOM | 9952 CB ILE I 413 | 27.296 −8.285 −26.846 1.00 7.24 | C C |
| ATOM | 9953 CG1 ILE I 413 | 26.703 −9.550 −27.480 1.00 7.18 | C C |
| ATOM | 9954 CD1 ILE I 413 | 25.397 −9.315 −28.241 1.00 7.70 | C C |
| ATOM | 9955 CG2 ILE I 413 | 26.585 −7.051 −27.397 1.00 7.70 | C C |
| ATOM | 9956 C ILE I 413 | 29.304 −6.811 −26.776 1.00 7.94 | C C |
| ATOM | 9957 O ILE I 413 | 29.806 −6.591 −25.674 1.00 8.39 | C O |
| ATOM | 9958 N VAL I 414 | 29.155 −5.871 −27.703 1.00 8.22 | C N |
| ATOM | 9959 CA VAL I 414 | 29.498 −4.485 −27.420 1.00 8.77 | C C |
| ATOM | 9960 CB VAL I 414 | 30.965 −4.158 −27.782 1.00 8.57 | C C |
| ATOM | 9961 CG1 VAL I 414 | 31.293 −4.627 −29.197 1.00 9.12 | C C |
| ATOM | 9962 CG2 VAL I 414 | 31.245 −2.669 −27.607 1.00 8.90 | C C |
| ATOM | 9963 C VAL I 414 | 28.536 −3.470 −28.028 1.00 8.92 | C C |
| ATOM | 9964 O VAL I 414 | 28.246 −3.497 −29.227 1.00 9.00 | C O |
| ATOM | 9965 N SER I 415 | 27.947 −2.665 −27.152 1.00 8.97 | C N |
| ATOM | 9966 CA SER I 415 | 27.023 −1.623 −27.552 1.00 9.02 | C C |
| ATOM | 9967 CB SER I 415 | 25.805 −1.623 −26.629 1.00 8.98 | C C |
| ATOM | 9968 OG SER I 415 | 25.203 −2.903 −26.581 1.00 9.54 | C O |
| ATOM | 9969 C SER I 415 | 27.727 −0.277 −27.480 1.00 9.36 | C C |
| ATOM | 9970 O SER I 415 | 27.996 0.230 −26.392 1.00 9.61 | C O |
| ATOM | 9971 N CYS I 416 | 28.219 0.177 −28.626 1.00 9.57 | C N |
| ATOM | 9972 CA CYS I 416 | 28.920 1.447 −28.701 1.00 9.61 | C C |
| ATOM | 9973 CB CYS I 416 | 30.167 1.320 −29.572 1.00 9.62 | C C |
| ATOM | 9974 SG CYS I 416 | 31.508 2.403 −29.060 1.00 11.33 | C S |
| ATOM | 9975 C CYS I 416 | 28.011 2.519 −29.270 1.00 9.61 | C C |
| ATOM | 9976 O CYS I 416 | 27.619 2.458 −30.434 1.00 9.80 | C O |
| ATOM | 9977 N TYR I 417 | 27.662 3.493 −28.441 1.00 9.48 | C N |
| ATOM | 9978 CA TYR I 417 | 26.667 4.475 −28.829 1.00 9.28 | C C |
| ATOM | 9979 CB TYR I 417 | 25.305 4.117 −28.235 1.00 9.17 | C C |
| ATOM | 9980 CG TYR I 417 | 24.629 2.955 −28.924 1.00 8.71 | C C |
| ATOM | 9981 CD1 TYR I 417 | 23.902 2.024 −28.199 1.00 8.54 | C C |
| ATOM | 9982 CE1 TYR I 417 | 23.228 0.999 −28.830 1.00 9.56 | C C |
| ATOM | 9983 CZ TYR I 417 | 23.289 0.886 −30.201 1.00 9.83 | C C |
| ATOM | 9984 OH TYR I 417 | 22.658 −0.162 −30.829 1.00 10.51 | C O |
| ATOM | 9985 CE2 TYR I 417 | 24.025 1.783 −30.942 1.00 9.36 | C C |
| ATOM | 9986 CD2 TYR I 417 | 24.675 2.818 −30.305 1.00 8.95 | C C |
| ATOM | 9987 C TYR I 417 | 27.076 5.885 −28.422 1.00 9.35 | C C |
| ATOM | 9988 O TYR I 417 | 28.046 6.075 −27.687 1.00 9.11 | C O |
| ATOM | 9989 N GLY I 418 | 26.357 6.872 −28.946 1.00 9.71 | C N |
| ATOM | 9990 CA GLY I 418 | 26.662 8.270 −28.679 1.00 9.95 | C C |
| ATOM | 9991 C GLY I 418 | 28.094 8.602 −29.035 1.00 10.09 | C C |
| ATOM | 9992 O GLY I 418 | 28.623 8.112 −30.033 1.00 10.17 | C O |
| ATOM | 9993 N LYS I 419 | 28.768 9.307 −28.136 1.00 10.17 | C N |
| ATOM | 9994 CA LYS I 419 | 30.104 9.810 −28.415 1.00 10.50 | C C |
| ATOM | 9995 CB LYS I 419 | 30.381 11.077 −27.607 1.00 11.09 | C C |
| ATOM | 9996 CG LYS I 419 | 29.942 12.351 −28.300 1.00 12.94 | C C |
| ATOM | 9997 CD LYS I 419 | 30.697 13.553 −27.770 1.00 15.52 | C C |
| ATOM | 9998 CE LYS I 419 | 30.546 14.735 −28.708 1.00 17.07 | C C |
| ATOM | 9999 NZ LYS I 419 | 29.200 14.756 −29.349 1.00 19.30 | C N |
| ATOM | 10000 C LYS I 419 | 31.201 8.777 −28.168 1.00 10.23 | C C |
| ATOM | 10001 O LYS I 419 | 32.380 9.063 −28.374 1.00 10.58 | C O |
| ATOM | 10002 N THR I 420 | 30.823 7.592 −27.697 1.00 10.10 | C N |
| ATOM | 10003 CA THR I 420 | 31.789 6.687 −27.076 1.00 9.74 | C C |
| ATOM | 10004 CB THR I 420 | 31.106 5.656 −26.158 1.00 9.28 | C C |
| ATOM | 10005 OG1 THR I 420 | 29.766 6.076 −25.878 1.00 9.21 | C O |
| ATOM | 10006 CG2 THR I 420 | 31.870 5.521 −24.851 1.00 9.03 | C C |
| ATOM | 10007 C THR I 420 | 32.671 5.966 −28.096 1.00 9.95 | C C |
| ATOM | 10008 O THR I 420 | 32.289 5.800 −29.254 1.00 10.35 | C O |
| ATOM | 10009 N LYS I 421 | 33.880 5.608 −27.674 1.00 10.07 | C N |
| ATOM | 10010 CA LYS I 421 | 34.808 4.863 −28.521 1.00 10.21 | C C |
| ATOM | 10011 CB LYS I 421 | 36.194 5.513 −28.495 1.00 10.30 | C C |
| ATOM | 10012 CG LYS I 421 | 36.445 6.496 −29.626 1.00 12.43 | C C |
| ATOM | 10013 CD LYS I 421 | 37.766 7.225 −29.441 1.00 15.12 | C C |
| ATOM | 10014 CE LYS I 421 | 37.752 8.578 −30.134 1.00 15.21 | C C |
| ATOM | 10015 NZ LYS I 421 | 38.779 9.500 −29.575 1.00 15.98 | C N |
| ATOM | 10016 C LYS I 421 | 34.908 3.412 −28.063 1.00 10.09 | C C |
| ATOM | 10017 O LYS I 421 | 34.979 3.137 −26.866 1.00 10.36 | C O |
| ATOM | 10018 N CYS I 422 | 34.937 2.486 −29.017 1.00 9.81 | C N |
| ATOM | 10019 CA CYS I 422 | 35.063 1.075 −28.681 1.00 9.56 | C C |
| ATOM | 10020 CB CYS I 422 | 33.696 0.396 −28.633 1.00 9.72 | C C |
| ATOM | 10021 SG CYS I 422 | 32.479 1.300 −27.664 1.00 11.42 | C S |

APPENDIX-continued (APPENDIX discloses SEQ ID NOS 29-32, 29-32 and 29-32, respectively, in order of appearance)

| | | | | |
|---|---|---|---|---|
| ATOM | 10022 C CYS I 422 | 36.012 0.311 −29.590 1.00 9.18 | C C |
| ATOM | 10023 O CYS I 422 | 36.111 0.582 −30.787 1.00 9.27 | C O |
| ATOM | 10024 N THR I 423 | 36.636 −0.710 −29.016 1.00 8.93 | C N |
| ATOM | 10025 CA THR I 423 | 37.825 −1.322 −29.583 1.00 8.64 | C C |
| ATOM | 10026 CB THR I 423 | 39.104 −0.757 −28.940 1.00 8.32 | C C |
| ATOM | 10027 OG1 THR I 423 | 39.059 0.675 −28.954 1.00 7.97 | C O |
| ATOM | 10028 CG2 THR I 423 | 40.336 −1.230 −29.695 1.00 8.36 | C C |
| ATOM | 10029 C THR I 423 | 37.771 −2.810 −29.287 1.00 8.86 | C C |
| ATOM | 10030 O THR I 423 | 37.514 −3.214 −28.153 1.00 9.26 | C O |
| ATOM | 10031 N ALA I 424 | 37.993 −3.625 −30.310 1.00 8.74 | C N |
| ATOM | 10032 CA ALA I 424 | 38.356 −5.018 −30.097 1.00 8.79 | C C |
| ATOM | 10033 CB ALA I 424 | 37.512 −5.927 −30.977 1.00 8.94 | C C |
| ATOM | 10034 C ALA I 424 | 39.839 −5.233 −30.371 1.00 8.84 | C C |
| ATOM | 10035 O ALA I 424 | 40.316 −4.985 −31.477 1.00 9.24 | C O |
| ATOM | 10036 N SER I 425 | 40.570 −5.661 −29.347 1.00 8.81 | C N |
| ATOM | 10037 CA SER I 425 | 41.990 −5.958 −29.492 1.00 8.85 | C C |
| ATOM | 10038 CB SER I 425 | 42.803 −5.192 −28.446 1.00 8.94 | C C |
| ATOM | 10039 OG SER I 425 | 42.091 −4.060 −27.976 1.00 7.69 | C O |
| ATOM | 10040 C SER I 425 | 42.253 −7.456 −29.368 1.00 9.01 | C C |
| ATOM | 10041 O SER I 425 | 41.541 −8.163 −28.656 1.00 8.63 | C O |
| ATOM | 10042 N ASN I 426 | 43.246 −7.944 −30.102 1.00 9.54 | C N |
| ATOM | 10043 CA ASN I 426 | 43.519 −9.374 −30.153 1.00 10.19 | C C |
| ATOM | 10044 CB ASN I 426 | 44.105 −9.764 −31.511 1.00 9.77 | C C |
| ATOM | 10045 CG ASN I 426 | 45.597 −9.506 −31.599 1.00 9.43 | C C |
| ATOM | 10046 OD1 ASN I 426 | 46.249 −9.211 −30.597 1.00 9.01 | C O |
| ATOM | 10047 ND2 ASN I 426 | 46.146 −9.616 −32.803 1.00 9.01 | C N |
| ATOM | 10048 C ASN I 426 | 44.434 −9.853 −29.029 1.00 11.16 | C C |
| ATOM | 10049 O ASN I 426 | 44.674 −9.138 −28.056 1.00 11.06 | C O |
| ATOM | 10050 N LYS I 427 | 44.921 −11.083 −29.170 1.00 12.38 | C N |
| ATOM | 10051 CA LYS I 427 | 45.803 −11.703 −28.185 1.00 13.52 | C C |
| ATOM | 10052 CB LYS I 427 | 46.418 −12.978 −28.765 1.00 14.00 | C C |
| ATOM | 10053 CG LYS I 427 | 45.683 −14.255 −28.398 1.00 16.18 | C C |
| ATOM | 10054 CD LYS I 427 | 46.510 −15.478 −28.758 1.00 18.24 | C C |
| ATOM | 10055 CE LYS I 427 | 46.211 −16.641 −27.828 1.00 19.72 | C C |
| ATOM | 10056 NZ LYS I 427 | 46.794 −16.434 −26.474 1.00 21.43 | C N |
| ATOM | 10057 C LYS I 427 | 46.915 −10.758 −27.741 1.00 13.71 | C C |
| ATOM | 10058 O LYS I 427 | 47.180 −10.611 −26.547 1.00 13.63 | C O |
| ATOM | 10059 N ASN I 428 | 47.634 −10.210 −28.716 1.00 14.28 | C N |
| ATOM | 10060 CA ASN I 428 | 48.816 −9.400 −28.447 1.00 14.60 | C C |
| ATOM | 10061 CB ASN I 428 | 49.709 −9.331 −29.689 1.00 14.57 | C C |
| ATOM | 10062 CG ASN I 428 | 49.589 −10.565 −30.563 1.00 13.24 | C C |
| ATOM | 10063 OD1 ASN I 428 | 49.765 −11.690 −30.096 1.00 9.74 | C O |
| ATOM | 10064 ND2 ASN I 428 | 49.319 −10.358 −31.847 1.00 12.83 | C N |
| ATOM | 10065 C ASN I 428 | 48.466 −7.989 −27.982 1.00 14.83 | C C |
| ATOM | 10066 O ASN I 428 | 49.330 −7.255 −27.499 1.00 15.25 | C O |
| ATOM | 10067 N ARG I 429 | 47.225 −7.580 −28.226 1.00 14.78 | C N |
| ATOM | 10068 CA ARG I 429 | 46.775 −6.234 −27.885 1.00 14.74 | C C |
| ATOM | 10069 CB ARG I 429 | 47.695 −5.603 −26.837 1.00 14.93 | C C |
| ATOM | 10070 CG ARG I 429 | 47.475 −6.121 −25.424 1.00 16.26 | C C |
| ATOM | 10071 CD ARG I 429 | 46.452 −5.279 −24.677 1.00 19.79 | C C |
| ATOM | 10072 NE ARG I 429 | 45.979 −5.940 −23.464 1.00 22.68 | C N |
| ATOM | 10073 CZ ARG I 429 | 46.735 −6.172 −22.396 1.00 23.54 | C C |
| ATOM | 10074 NH1 ARG I 429 | 48.013 −5.817 −22.394 1.00 22.87 | C N |
| ATOM | 10075 NH2 ARG I 429 | 46.219 −6.777 −21.335 1.00 23.53 | C N |
| ATOM | 10076 C ARG I 429 | 46.689 −5.339 −29.117 1.00 14.35 | C C |
| ATOM | 10077 O ARG I 429 | 46.093 −4.262 −29.073 1.00 14.62 | C O |
| ATOM | 10078 N GLY I 430 | 47.270 −5.798 −30.221 1.00 13.67 | C N |
| ATOM | 10079 CA GLY I 430 | 46.898 −5.304 −31.540 1.00 12.80 | C C |
| ATOM | 10080 C GLY I 430 | 45.397 −5.149 −31.683 1.00 12.11 | C C |
| ATOM | 10081 O GLY I 430 | 44.634 −6.038 −31.306 1.00 12.18 | C O |
| ATOM | 10082 N ILE I 431 | 44.972 −4.001 −32.199 1.00 11.58 | C N |
| ATOM | 10083 CA ILE I 431 | 43.552 −3.678 −32.300 1.00 10.76 | C C |
| ATOM | 10084 CB ILE I 431 | 43.321 −2.162 −32.138 1.00 10.43 | C C |
| ATOM | 10085 CG1 ILE I 431 | 43.649 −1.718 −30.711 1.00 10.95 | C C |
| ATOM | 10086 CD1 ILE I 431 | 44.264 −0.337 −30.628 1.00 12.08 | C C |
| ATOM | 10087 CG2 ILE I 431 | 41.892 −1.796 −32.507 1.00 10.07 | C C |
| ATOM | 10088 C ILE I 431 | 43.011 −4.108 −33.660 1.00 10.68 | C C |
| ATOM | 10089 O ILE I 431 | 43.474 −3.623 −34.693 1.00 10.40 | C O |
| ATOM | 10090 N ILE I 432 | 42.063 −5.041 −33.669 1.00 10.90 | C N |
| ATOM | 10091 CA ILE I 432 | 41.497 −5.518 −34.931 1.00 11.42 | C C |
| ATOM | 10092 CB ILE I 432 | 41.106 −7.008 −34.884 1.00 11.63 | C C |
| ATOM | 10093 CG1 ILE I 432 | 41.784 −7.712 −33.709 1.00 12.68 | C C |
| ATOM | 10094 CD1 ILE I 432 | 41.172 −9.055 −33.369 1.00 13.89 | C C |
| ATOM | 10095 CG2 ILE I 432 | 41.453 −7.689 −36.201 1.00 12.24 | C C |
| ATOM | 10096 C ILE I 432 | 40.290 −4.703 −35.381 1.00 11.41 | C C |
| ATOM | 10097 O ILE I 432 | 40.172 −4.362 −36.558 1.00 11.63 | C O |
| ATOM | 10098 N LYS I 433 | 39.315 −4.555 −34.492 1.00 11.52 | C N |

APPENDIX-continued (APPENDIX discloses SEQ ID NOS 29-32, 29-32 and 29-32, respectively, in order of appearance)

| | | | |
|---|---|---|---|
| ATOM | 10099 CA LYS I 433 | 38.076 −3.878 −34.848 1.00 11.96 | C C |
| ATOM | 10100 CB LYS I 433 | 36.864 −4.767 −34.566 1.00 12.31 | C C |
| ATOM | 10101 CG LYS I 433 | 35.552 −4.201 −35.092 1.00 14.42 | C C |
| ATOM | 10102 CD LYS I 433 | 34.622 −5.301 −35.578 1.00 16.74 | C C |
| ATOM | 10103 CE LYS I 433 | 33.367 −4.723 −36.216 1.00 17.08 | C C |
| ATOM | 10104 NZ LYS I 433 | 33.135 −5.263 −37.585 1.00 17.30 | C N |
| ATOM | 10105 C LYS I 433 | 37.934 −2.543 −34.128 1.00 11.65 | C C |
| ATOM | 10106 O LYS I 433 | 38.620 −2.281 −33.140 1.00 11.48 | C O |
| ATOM | 10107 N THR I 434 | 37.059 −1.691 −34.651 1.00 11.28 | C N |
| ATOM | 10108 CA THR I 434 | 36.764 −0.407 −34.027 1.00 11.21 | C C |
| ATOM | 10109 CB THR I 434 | 37.809 0.653 −34.414 1.00 11.30 | C C |
| ATOM | 10110 OG1 THR I 434 | 37.324 1.955 −34.062 1.00 11.83 | C O |
| ATOM | 10111 CG2 THR I 434 | 38.088 0.608 −35.910 1.00 11.84 | C C |
| ATOM | 10112 C THR I 434 | 35.380 0.083 −34.446 1.00 10.94 | C C |
| ATOM | 10113 O THR I 434 | 34.982 −0.085 −35.597 1.00 10.93 | C O |
| ATOM | 10114 N PHE I 435 | 34.604 0.572 −33.484 1.00 11.10 | C N |
| ATOM | 10115 CA PHE I 435 | 33.176 0.281 −33.466 1.00 11.96 | C C |
| ATOM | 10116 CB PHE I 435 | 32.726 −0.248 −32.106 1.00 11.51 | C C |
| ATOM | 10117 CG PHE I 435 | 32.896 −1.732 −31.957 1.00 11.19 | C C |
| ATOM | 10118 CD1 PHE I 435 | 33.805 −2.246 −31.047 1.00 10.86 | C C |
| ATOM | 10119 CE1 PHE I 435 | 34.022 −3.608 −30.957 1.00 10.24 | C C |
| ATOM | 10120 CZ PHE I 435 | 33.375 −4.467 −31.823 1.00 9.89 | C C |
| ATOM | 10121 CE2 PHE I 435 | 32.512 −3.963 −32.774 1.00 10.78 | C C |
| ATOM | 10122 CD2 PHE I 435 | 32.300 −2.599 −32.858 1.00 11.14 | C C |
| ATOM | 10123 C PHE I 435 | 32.255 1.381 −33.984 1.00 13.00 | C C |
| ATOM | 10124 O PHE I 435 | 32.168 2.466 −33.407 1.00 13.03 | C O |
| ATOM | 10125 N SER I 436 | 31.429 1.001 −34.954 1.00 13.89 | C N |
| ATOM | 10126 CA SER I 436 | 30.556 1.929 −35.657 1.00 14.67 | C C |
| ATOM | 10127 CB SER I 436 | 30.282 1.417 −37.074 1.00 15.04 | C C |
| ATOM | 10128 OG SER I 436 | 30.877 2.256 −38.049 1.00 16.58 | C O |
| ATOM | 10129 C SER I 436 | 29.240 2.105 −34.903 1.00 14.75 | C C |
| ATOM | 10130 O SER I 436 | 28.192 1.626 −35.340 1.00 14.75 | C O |
| ATOM | 10131 N ASN I 437 | 29.302 2.785 −33.764 1.00 14.44 | C N |
| ATOM | 10132 CA ASN I 437 | 28.124 3.433 −33.203 1.00 14.35 | C C |
| ATOM | 10133 CB ASN I 437 | 27.891 4.781 −33.881 1.00 14.75 | C C |
| ATOM | 10134 CG ASN I 437 | 26.889 5.641 −33.139 1.00 15.51 | C C |
| ATOM | 10135 OD1 ASN I 437 | 27.054 5.920 −31.951 1.00 16.85 | C O |
| ATOM | 10136 ND2 ASN I 437 | 25.878 6.120 −33.856 1.00 16.10 | C N |
| ATOM | 10137 C ASN I 437 | 26.885 2.558 −33.345 1.00 13.69 | C C |
| ATOM | 10138 O ASN I 437 | 25.912 2.941 −33.995 1.00 13.40 | C O |
| ATOM | 10139 N GLY I 438 | 26.957 1.358 −32.782 1.00 13.39 | C N |
| ATOM | 10140 CA GLY I 438 | 25.931 0.345 −32.986 1.00 12.92 | C C |
| ATOM | 10141 C GLY I 438 | 26.000 −0.743 −31.934 1.00 12.72 | C C |
| ATOM | 10142 O GLY I 438 | 26.154 −0.459 −30.747 1.00 12.83 | C O |
| ATOM | 10143 N CYS I 439 | 25.949 −1.996 −32.375 1.00 12.17 | C N |
| ATOM | 10144 CA CYS I 439 | 26.014 −3.126 −31.456 1.00 11.52 | C C |
| ATOM | 10145 CB CYS I 439 | 24.672 −3.321 −30.750 1.00 11.68 | C C |
| ATOM | 10146 SG CYS I 439 | 24.046 −5.015 −30.795 1.00 12.89 | C S |
| ATOM | 10147 C CYS I 439 | 26.437 −4.411 −32.159 1.00 10.95 | C C |
| ATOM | 10148 O CYS I 439 | 25.714 −4.935 −33.007 1.00 10.77 | C O |
| ATOM | 10149 N ASP I 440 | 27.617 −4.909 −31.802 1.00 10.41 | C N |
| ATOM | 10150 CA ASP I 440 | 28.240 −6.017 −32.518 1.00 10.06 | C C |
| ATOM | 10151 CB ASP I 440 | 29.514 −5.548 −33.224 1.00 10.85 | C C |
| ATOM | 10152 CG ASP I 440 | 29.336 −5.417 −34.724 1.00 13.11 | C C |
| ATOM | 10153 OD1 ASP I 440 | 29.376 −6.453 −35.422 1.00 14.97 | C O |
| ATOM | 10154 OD2 ASP I 440 | 29.192 −4.275 −35.209 1.00 15.27 | C O |
| ATOM | 10155 C ASP I 440 | 28.566 −7.175 −31.578 1.00 9.01 | C C |
| ATOM | 10156 O ASP I 440 | 28.479 −7.040 −30.358 1.00 9.09 | C O |
| ATOM | 10157 N TYR I 441 | 29.027 −8.280 −32.159 1.00 7.92 | C N |
| ATOM | 10158 CA TYR I 441 | 29.448 −9.461 −31.403 1.00 7.24 | C C |
| ATOM | 10159 CB TYR I 441 | 28.448 −10.605 −31.610 1.00 7.04 | C C |
| ATOM | 10160 CG TYR I 441 | 28.862 −11.916 −30.979 1.00 6.77 | C C |
| ATOM | 10161 CD1 TYR I 441 | 28.439 −12.256 −29.701 1.00 7.41 | C C |
| ATOM | 10162 CE1 TYR I 441 | 28.805 −13.460 −29.122 1.00 6.79 | C C |
| ATOM | 10163 CZ TYR I 441 | 29.529 −14.381 −29.855 1.00 6.49 | C C |
| ATOM | 10164 OH TYR I 441 | 29.907 −15.573 −29.277 1.00 5.09 | C O |
| ATOM | 10165 CE2 TYR I 441 | 29.946 −14.076 −31.134 1.00 7.52 | C C |
| ATOM | 10166 CD2 TYR I 441 | 29.600 −12.853 −31.694 1.00 7.12 | C C |
| ATOM | 10167 C TYR I 441 | 30.833 −9.902 −31.872 1.00 6.89 | C C |
| ATOM | 10168 O TYR I 441 | 31.150 −9.809 −33.058 1.00 7.12 | C O |
| ATOM | 10169 N VAL I 442 | 31.664 −10.363 −30.944 1.00 6.73 | C N |
| ATOM | 10170 CA VAL I 442 | 32.959 −10.941 −31.301 1.00 6.78 | C C |
| ATOM | 10171 CB VAL I 442 | 34.133 −10.008 −30.925 1.00 6.51 | C C |
| ATOM | 10172 CG1 VAL I 442 | 34.206 −8.830 −31.879 1.00 7.38 | C C |
| ATOM | 10173 CG2 VAL I 442 | 34.007 −9.530 −29.488 1.00 6.00 | C C |
| ATOM | 10174 C VAL I 442 | 33.142 −12.285 −30.609 1.00 7.13 | C C |
| ATOM | 10175 O VAL I 442 | 32.307 −12.689 −29.800 1.00 7.77 | C O |

APPENDIX-continued (APPENDIX discloses SEQ ID NOS 29-32, 29-32 and 29-32, respectively, in order of appearance)

| | | | |
|---|---|---|---|
| ATOM | 10176 N SER I 443 | 34.241 −12.970 −30.908 1.00 7.12 | C N |
| ATOM | 10177 CA SER I 443 | 34.476 −14.283 −30.321 1.00 7.64 | C C |
| ATOM | 10178 CB SER I 443 | 33.940 −15.391 −31.233 1.00 7.83 | C C |
| ATOM | 10179 OG SER I 443 | 34.994 −16.091 −31.870 1.00 7.99 | C O |
| ATOM | 10180 C SER I 443 | 35.932 −14.541 −29.940 1.00 8.16 | C C |
| ATOM | 10181 O SER I 443 | 36.841 −13.847 −30.399 1.00 8.69 | C O |
| ATOM | 10182 N ASN I 444 | 36.135 −15.517 −29.058 1.00 8.73 | C N |
| ATOM | 10183 CA ASN I 444 | 37.473 −15.972 −28.692 1.00 9.50 | C C |
| ATOM | 10184 CB ASN I 444 | 37.408 −16.989 −27.546 1.00 9.65 | C C |
| ATOM | 10185 CG ASN I 444 | 36.105 −16.916 −26.772 1.00 10.64 | C C |
| ATOM | 10186 OD1 ASN I 444 | 35.530 −15.839 −26.602 1.00 12.28 | C O |
| ATOM | 10187 ND2 ASN I 444 | 35.617 −18.069 −26.325 1.00 11.75 | C N |
| ATOM | 10188 C ASN I 444 | 38.240 −16.558 −29.877 1.00 10.24 | C C |
| ATOM | 10189 O ASN I 444 | 37.657 −17.206 −30.748 1.00 9.89 | C O |
| ATOM | 10190 N LYS I 445 | 39.565 −16.467 −29.809 1.00 11.63 | C N |
| ATOM | 10191 CA LYS I 445 | 40.394 −16.179 −30.979 1.00 13.07 | C C |
| ATOM | 10192 CB LYS I 445 | 40.843 −17.470 −31.664 1.00 13.70 | C C |
| ATOM | 10193 CG LYS I 445 | 41.782 −17.255 −32.848 1.00 15.80 | C C |
| ATOM | 10194 CD LYS I 445 | 42.771 −16.114 −32.613 1.00 18.31 | C C |
| ATOM | 10195 CE LYS I 445 | 42.855 −15.717 −31.146 1.00 19.03 | C C |
| ATOM | 10196 NZ LYS I 445 | 43.703 −16.652 −30.355 1.00 20.02 | C N |
| ATOM | 10197 C LYS I 445 | 39.701 −15.268 −31.980 1.00 12.96 | C C |
| ATOM | 10198 O LYS I 445 | 38.486 −15.336 −32.159 1.00 13.24 | C O |
| ATOM | 10199 N GLY I 446 | 40.491 −14.448 −32.664 1.00 13.08 | C N |
| ATOM | 10200 CA GLY I 446 | 40.131 −13.057 −32.889 1.00 12.42 | C C |
| ATOM | 10201 C GLY I 446 | 40.305 −12.233 −31.631 1.00 11.83 | C C |
| ATOM | 10202 O GLY I 446 | 41.402 −11.756 −31.342 1.00 12.44 | C O |
| ATOM | 10203 N VAL I 447 | 39.264 −12.192 −30.808 1.00 10.63 | C N |
| ATOM | 10204 CA VAL I 447 | 39.157 −11.162 −29.785 1.00 10.01 | C C |
| ATOM | 10205 CB VAL I 447 | 37.758 −10.516 −29.764 1.00 9.97 | C C |
| ATOM | 10206 CG1 VAL I 447 | 37.778 −9.225 −28.957 1.00 10.51 | C C |
| ATOM | 10207 CG2 VAL I 447 | 37.287 −10.244 −31.180 1.00 10.50 | C C |
| ATOM | 10208 C VAL I 447 | 39.548 −11.648 −28.390 1.00 9.53 | C C |
| ATOM | 10209 O VAL I 447 | 39.184 −12.747 −27.967 1.00 9.61 | C O |
| ATOM | 10210 N ASP I 448 | 40.211 −10.766 −27.652 1.00 9.16 | C N |
| ATOM | 10211 CA ASP I 448 | 40.803 −11.093 −26.362 1.00 8.75 | C C |
| ATOM | 10212 CB ASP I 448 | 42.325 −11.159 −26.502 1.00 9.22 | C C |
| ATOM | 10213 CG ASP I 448 | 42.975 −12.024 −25.443 1.00 11.44 | C C |
| ATOM | 10214 OD1 ASP I 448 | 42.372 −12.204 −24.365 1.00 13.83 | C O |
| ATOM | 10215 OD2 ASP I 448 | 44.119 −12.472 −25.665 1.00 14.13 | C O |
| ATOM | 10216 C ASP I 448 | 40.427 −9.976 −25.398 1.00 8.18 | C C |
| ATOM | 10217 O ASP I 448 | 40.203 −10.209 −24.211 1.00 8.06 | C O |
| ATOM | 10218 N THR I 449 | 40.201 −8.794 −25.964 1.00 7.63 | C N |
| ATOM | 10219 CA THR I 449 | 39.894 −7.592 −25.197 1.00 6.80 | C C |
| ATOM | 10220 CB THR I 449 | 41.165 −6.750 −24.940 1.00 6.89 | C C |
| ATOM | 10221 OG1 THR I 449 | 41.805 −7.196 −23.738 1.00 6.16 | C O |
| ATOM | 10222 CG2 THR I 449 | 40.815 −5.275 −24.804 1.00 7.55 | C C |
| ATOM | 10223 C THR I 449 | 38.898 −6.751 −25.987 1.00 6.53 | C C |
| ATOM | 10224 O THR I 449 | 38.949 −6.708 −27.216 1.00 6.59 | C O |
| ATOM | 10225 N VAL I 450 | 37.947 −6.147 −25.288 1.00 6.07 | C N |
| ATOM | 10226 CA VAL I 450 | 37.318 −4.934 −25.781 1.00 6.02 | C C |
| ATOM | 10227 CB VAL I 450 | 35.839 −5.158 −26.121 1.00 5.61 | C C |
| ATOM | 10228 CG1 VAL I 450 | 35.697 −6.278 −27.136 1.00 5.32 | C C |
| ATOM | 10229 CG2 VAL I 450 | 35.047 −5.460 −24.860 1.00 5.55 | C C |
| ATOM | 10230 C VAL I 450 | 37.427 −3.837 −24.743 1.00 6.37 | C C |
| ATOM | 10231 O VAL I 450 | 37.359 −4.097 −23.542 1.00 6.54 | C O |
| ATOM | 10232 N SER I 451 | 37.704 −2.626 −25.207 1.00 6.41 | C N |
| ATOM | 10233 CA SER I 451 | 37.571 −1.451 −24.366 1.00 6.70 | C C |
| ATOM | 10234 CB SER I 451 | 38.845 −0.607 −24.422 1.00 7.13 | C C |
| ATOM | 10235 OG SER I 451 | 39.573 −0.864 −25.610 1.00 9.26 | C O |
| ATOM | 10236 C SER I 451 | 36.373 −0.626 −24.802 1.00 6.47 | C C |
| ATOM | 10237 O SER I 451 | 36.100 −0.493 −25.994 1.00 6.54 | C O |
| ATOM | 10238 N VAL I 452 | 35.577 −0.203 −23.830 1.00 6.56 | C N |
| ATOM | 10239 CA VAL I 452 | 34.627 0.872 −24.050 1.00 6.31 | C C |
| ATOM | 10240 CB VAL I 452 | 33.205 0.448 −23.647 1.00 5.74 | C C |
| ATOM | 10241 CG1 VAL I 452 | 32.189 1.471 −24.130 1.00 5.06 | C C |
| ATOM | 10242 CG2 VAL I 452 | 32.891 −0.929 −24.212 1.00 5.56 | C C |
| ATOM | 10243 C VAL I 452 | 35.056 2.087 −23.242 1.00 6.60 | C C |
| ATOM | 10244 O VAL I 452 | 35.499 1.950 −22.102 1.00 7.04 | C O |
| ATOM | 10245 N GLY I 453 | 35.141 3.234 −23.907 1.00 6.54 | C N |
| ATOM | 10246 CA GLY I 453 | 35.790 4.395 −23.314 1.00 6.43 | C C |
| ATOM | 10247 C GLY I 453 | 37.010 3.964 −22.525 1.00 6.09 | C C |
| ATOM | 10248 O GLY I 453 | 37.910 3.328 −23.071 1.00 5.90 | C O |
| ATOM | 10249 N ASN I 454 | 36.985 4.188 −21.216 1.00 6.02 | C N |
| ATOM | 10250 CA ASN I 454 | 38.156 3.904 −20.396 1.00 6.39 | C C |
| ATOM | 10251 CB ASN I 454 | 38.491 5.088 −19.491 1.00 6.81 | C C |
| ATOM | 10252 CG ASN I 454 | 39.518 6.009 −20.108 1.00 8.99 | C C |

APPENDIX-continued (APPENDIX discloses SEQ ID NOS 29-32, 29-32 and 29-32, respectively, in order of appearance)

| | | | | |
|---|---|---|---|---|
| ATOM | 10253 OD1 ASN I 454 | 40.718 5.817 −19.912 1.00 11.67 | C O |
| ATOM | 10254 ND2 ASN I 454 | 39.073 6.836 −21.048 1.00 10.25 | C N |
| ATOM | 10255 C ASN I 454 | 38.053 2.617 −19.588 1.00 6.15 | C C |
| ATOM | 10256 O ASN I 454 | 39.041 2.154 −19.016 1.00 6.47 | C O |
| ATOM | 10257 N THR I 455 | 36.888 1.983 −19.635 1.00 5.40 | C N |
| ATOM | 10258 CA THR I 455 | 36.730 0.659 −19.057 1.00 4.53 | C C |
| ATOM | 10259 CB THR I 455 | 35.251 0.352 −18.737 1.00 4.70 | C C |
| ATOM | 10260 OG1 THR I 455 | 34.662 1.471 −18.063 1.00 5.28 | C O |
| ATOM | 10261 CG2 THR I 455 | 35.141 −0.878 −17.845 1.00 5.57 | C C |
| ATOM | 10262 C THR I 455 | 37.296 −0.399 −19.999 1.00 4.01 | C C |
| ATOM | 10263 O THR I 455 | 37.333 −0.204 −21.216 1.00 3.78 | C O |
| ATOM | 10264 N LEU I 456 | 37.885 −1.438 −19.414 1.00 3.87 | C N |
| ATOM | 10265 CA LEU I 456 | 38.439 −2.542 −20.189 1.00 4.05 | C C |
| ATOM | 10266 CB LEU I 456 | 39.946 −2.660 −19.955 1.00 3.95 | C C |
| ATOM | 10267 CG LEU I 456 | 40.690 −3.636 −20.868 1.00 3.76 | C C |
| ATOM | 10268 CD1 LEU I 456 | 40.594 −3.192 −22.319 1.00 5.35 | C C |
| ATOM | 10269 CD2 LEU I 456 | 42.142 −3.770 −20.440 1.00 4.10 | C C |
| ATOM | 10270 C LEU I 456 | 37.755 −3.858 −19.845 1.00 4.47 | C C |
| ATOM | 10271 O LEU I 456 | 37.769 −4.293 −18.694 1.00 4.94 | C O |
| ATOM | 10272 N TYR I 457 | 37.248 −4.534 −20.869 1.00 4.59 | C N |
| ATOM | 10273 CA TYR I 457 | 36.626 −5.839 −20.695 1.00 4.60 | C C |
| ATOM | 10274 CB TYR I 457 | 35.248 −5.861 −21.363 1.00 4.71 | C C |
| ATOM | 10275 CG TYR I 457 | 34.244 −4.912 −20.739 1.00 5.62 | C C |
| ATOM | 10276 CD1 TYR I 457 | 34.230 −3.563 −21.074 1.00 7.09 | C C |
| ATOM | 10277 CE1 TYR I 457 | 33.316 −2.697 −20.510 1.00 8.22 | C C |
| ATOM | 10278 CZ TYR I 457 | 32.408 −3.173 −19.588 1.00 8.06 | C C |
| ATOM | 10279 OH TYR I 457 | 31.469 −2.318 −19.059 1.00 8.80 | C O |
| ATOM | 10280 CE2 TYR I 457 | 32.381 −4.513 −19.262 1.00 7.18 | C C |
| ATOM | 10281 CD2 TYR I 457 | 33.302 −5.371 −19.827 1.00 6.66 | C C |
| ATOM | 10282 C TYR I 457 | 37.513 −6.932 −21.285 1.00 4.46 | C C |
| ATOM | 10283 O TYR I 457 | 38.049 −6.780 −22.383 1.00 4.92 | C O |
| ATOM | 10284 N TYR I 458 | 37.706 −8.009 −20.529 1.00 3.90 | C N |
| ATOM | 10285 CA TYR I 458 | 38.520 −9.138 −20.980 1.00 3.26 | C C |
| ATOM | 10286 CB TYR I 458 | 39.407 −9.632 −19.832 1.00 3.16 | C C |
| ATOM | 10287 CG TYR I 458 | 40.399 −8.610 −19.320 1.00 3.29 | C C |
| ATOM | 10288 CD1 TYR I 458 | 40.076 −7.762 −18.269 1.00 3.93 | C C |
| ATOM | 10289 CE1 TYR I 458 | 40.993 −6.848 −17.782 1.00 4.90 | C C |
| ATOM | 10290 CZ TYR I 458 | 42.245 −6.766 −18.354 1.00 5.12 | C C |
| ATOM | 10291 OH TYR I 458 | 43.156 −5.850 −17.881 1.00 5.42 | C O |
| ATOM | 10292 CE2 TYR I 458 | 42.590 −7.599 −19.395 1.00 4.72 | C C |
| ATOM | 10293 CD2 TYR I 458 | 41.677 −8.528 −19.858 1.00 3.89 | C C |
| ATOM | 10294 C TYR I 458 | 37.638 −10.293 −21.464 1.00 3.04 | C C |
| ATOM | 10295 O TYR I 458 | 36.897 −10.869 −20.672 1.00 3.37 | C O |
| ATOM | 10296 N VAL I 459 | 37.857 −10.755 −22.696 1.00 2.71 | C N |
| ATOM | 10297 CA VAL I 459 | 36.818 −11.487 −23.441 1.00 2.61 | C C |
| ATOM | 10298 CB VAL I 459 | 36.856 −11.172 −24.940 1.00 2.22 | C C |
| ATOM | 10299 CG1 VAL I 459 | 35.936 −12.119 −25.698 1.00 2.62 | C C |
| ATOM | 10300 CG2 VAL I 459 | 36.459 −9.728 −25.187 1.00 2.61 | C C |
| ATOM | 10301 C VAL I 459 | 36.847 −13.006 −23.279 1.00 3.03 | C C |
| ATOM | 10302 O VAL I 459 | 37.324 −13.520 −22.267 1.00 3.21 | C O |
| ATOM | 10303 N ASN I 460 | 36.301 −13.724 −24.263 1.00 106.93 | C N |
| ATOM | 10304 CA ASN I 460 | 36.733 −15.100 −24.460 1.00 95.54 | C C |
| ATOM | 10305 CB ASN I 460 | 37.469 −15.533 −23.198 1.00 20.00 | C C |
| ATOM | 10306 CG ASN I 460 | 38.132 −16.862 −23.352 1.00 20.00 | C C |
| ATOM | 10307 OD1 ASN I 460 | 38.781 −17.118 −24.365 1.00 20.00 | C O |
| ATOM | 10308 ND2 ASN I 460 | 37.824 −17.783 −22.448 1.00 20.00 | C N |
| ATOM | 10309 C ASN I 460 | 35.684 −16.173 −24.797 1.00 99.41 | C C |
| ATOM | 10310 O ASN I 460 | 35.555 −17.141 −24.047 1.00108.91 | C O |
| ATOM | 10311 N LYS I 461 | 35.174 −16.182 −26.023 1.00 97.04 | C N |
| ATOM | 10312 CA LYS I 461 | 34.426 −17.350 −26.495 1.00105.93 | C C |
| ATOM | 10313 CB LYS I 461 | 33.128 −17.516 −25.700 1.00 20.00 | C C |
| ATOM | 10314 CG LYS I 461 | 33.324 −18.050 −24.284 1.00 20.00 | C C |
| ATOM | 10315 CD LYS I 461 | 32.012 −18.071 −23.510 1.00 20.00 | C C |
| ATOM | 10316 CE LYS I 461 | 32.154 −18.798 −22.179 1.00 20.00 | C C |
| ATOM | 10317 NZ LYS I 461 | 30.869 −19.408 −21.736 1.00 20.00 | C N |
| ATOM | 10318 C LYS I 461 | 34.141 −17.231 −27.987 1.00102.28 | C C |
| ATOM | 10319 O LYS I 461 | 34.601 −16.289 −28.627 1.00105.02 | C O |
| ATOM | 10320 N GLN I 462 | 33.377 −18.164 −28.545 1.00 96.68 | C N |
| ATOM | 10321 CA GLN I 462 | 32.944 −18.040 −29.939 1.00105.71 | C C |
| ATOM | 10322 CB GLN I 462 | 33.693 −19.032 −30.836 1.00 20.00 | C C |
| ATOM | 10323 CG GLN I 462 | 35.184 −18.748 −30.976 1.00 20.00 | C C |
| ATOM | 10324 CD GLN I 462 | 35.922 −19.829 −31.741 1.00 20.00 | C C |
| ATOM | 10325 OE1 GLN I 462 | 35.456 −20.965 −31.841 1.00 20.00 | C O |
| ATOM | 10326 NE2 GLN I 462 | 37.071 −19.475 −32.303 1.00 20.00 | C N |
| ATOM | 10327 C GLN I 462 | 31.440 −18.235 −30.082 1.00101.50 | C C |
| ATOM | 10328 O GLN I 462 | 30.881 −19.193 −29.553 1.00105.94 | C O |
| ATOM | 10329 N GLU I 463 | 30.787 −17.335 −30.809 1.00 98.92 | C N |

APPENDIX-continued (APPENDIX discloses SEQ ID NOS 29-32, 29-32 and 29-32, respectively, in order of appearance)

| | | | |
|---|---|---|---|
| ATOM | 10330 CA GLU I 463 | 29.339 −17.413 −30.975 1.00108.59 | C C |
| ATOM | 10331 CB GLU I 463 | 28.684 −16.055 −30.712 1.00 20.00 | C C |
| ATOM | 10332 CG GLU I 463 | 28.617 −15.668 −29.238 1.00 20.00 | C C |
| ATOM | 10333 CD GLU I 463 | 28.032 −14.283 −29.019 1.00 20.00 | C C |
| ATOM | 10334 OE1 GLU I 463 | 27.535 −13.682 −29.995 1.00 20.00 | C O |
| ATOM | 10335 OE2 GLU I 463 | 27.975 −13.842 −27.851 1.00 20.00 | C O |
| ATOM | 10336 C GLU I 463 | 28.950 −17.934 −32.353 1.00116.39 | C C |
| ATOM | 10337 O GLU I 463 | 29.396 −17.411 −33.375 1.00118.70 | C O |
| ATOM | 10338 N GLY I 464 | 28.103 −18.957 −32.372 1.00127.70 | C N |
| ATOM | 10339 CA GLY I 464 | 27.598 −19.512 −33.621 1.00143.17 | C C |
| ATOM | 10340 C GLY I 464 | 26.466 −18.687 −34.200 1.00149.77 | C C |
| ATOM | 10341 O GLY I 464 | 25.945 −17.784 −33.545 1.00155.06 | C O |
| ATOM | 10342 N LYS I 465 | 26.088 −18.997 −35.435 1.00153.73 | C N |
| ATOM | 10343 CA LYS I 465 | 25.034 −18.261 −36.124 1.00153.69 | C C |
| ATOM | 10344 CB LYS I 465 | 23.750 −18.259 −35.293 1.00 20.00 | C C |
| ATOM | 10345 CG LYS I 465 | 23.099 −19.626 −35.151 1.00 20.00 | C C |
| ATOM | 10346 CD LYS I 465 | 21.848 −19.555 −34.292 1.00 20.00 | C C |
| ATOM | 10347 CE LYS I 465 | 21.188 −20.919 −34.164 1.00 20.00 | C C |
| ATOM | 10348 NZ LYS I 465 | 19.972 −20.869 −33.307 1.00 20.00 | C N |
| ATOM | 10349 C LYS I 465 | 25.466 −16.831 −36.426 1.00155.37 | C C |
| ATOM | 10350 O LYS I 465 | 25.158 −16.292 −37.489 1.00155.20 | C O |
| ATOM | 10351 N GLU I 472 | 20.477 −14.304 −43.583 1.00145.47 | C N |
| ATOM | 10352 CA GLU I 472 | 19.435 −13.563 −44.284 1.00151.12 | C C |
| ATOM | 10353 CB GLU I 472 | 18.367 −14.521 −44.821 1.00 20.00 | C C |
| ATOM | 10354 CG GLU I 472 | 18.856 −15.453 −45.922 1.00 20.00 | C C |
| ATOM | 10355 CD GLU I 472 | 17.778 −16.409 −46.402 1.00 20.00 | C C |
| ATOM | 10356 OE1 GLU I 472 | 16.723 −16.504 −45.739 1.00 20.00 | C O |
| ATOM | 10357 OE2 GLU I 472 | 17.996 −17.083 −47.430 1.00 20.00 | C O |
| ATOM | 10358 C GLU I 472 | 18.796 −12.521 −43.369 1.00153.35 | C C |
| ATOM | 10359 O GLU I 472 | 18.205 −12.866 −42.345 1.00159.41 | C O |
| ATOM | 10360 N PRO I 473 | 18.943 −11.236 −43.722 1.00150.51 | C N |
| ATOM | 10361 CA PRO I 473 | 18.346 −10.158 −42.958 1.00141.97 | C C |
| ATOM | 10362 CB PRO I 473 | 19.542 −9.243 −42.691 1.00 20.00 | C C |
| ATOM | 10363 CG PRO I 473 | 20.496 −9.502 −43.863 1.00 20.00 | C C |
| ATOM | 10364 CD PRO I 473 | 20.007 −10.730 −44.602 1.00 20.00 | C C |
| ATOM | 10365 C PRO I 473 | 17.331 −9.429 −43.824 1.00 135.14 | C C |
| ATOM | 10366 O PRO I 473 | 17.408 −9.503 −45.051 1.00 144.93 | C O |
| ATOM | 10367 N ILE I 474 | 16.371 −8.757 −43.197 1.00 118.07 | C N |
| ATOM | 10368 CA ILE I 474 | 15.320 −8.071 −43.939 1.00105.14 | C C |
| ATOM | 10369 CB ILE I 474 | 14.440 −9.067 −44.737 1.00 20.00 | C C |
| ATOM | 10370 CG1 ILE I 474 | 15.255 −9.730 −45.856 1.00 20.00 | C C |
| ATOM | 10371 CD1 ILE I 474 | 14.525 −10.842 −46.588 1.00 20.00 | C C |
| ATOM | 10372 CG2 ILE I 474 | 13.224 −8.354 −45.317 1.00 20.00 | C C |
| ATOM | 10373 C ILE I 474 | 14.436 −7.226 −43.022 1.00 104.75 | C C |
| ATOM | 10374 O ILE I 474 | 13.471 −7.725 −42.443 1.00 111.83 | C O |
| ATOM | 10375 N ILE I 475 | 14.746 −5.934 −42.932 1.00 94.65 | C N |
| ATOM | 10376 CA ILE I 475 | 14.105 −5.051 −41.957 1.00 79.88 | C C |
| ATOM | 10377 CB ILE I 475 | 15.105 −4.568 −40.885 1.00 20.00 | C C |
| ATOM | 10378 CG1 ILE I 475 | 15.576 −5.737 −40.014 1.00 20.00 | C C |
| ATOM | 10379 CD1 ILE I 475 | 16.791 −5.417 −39.163 1.00 20.00 | C C |
| ATOM | 10380 CG2 ILE I 475 | 14.493 −3.458 −40.043 1.00 20.00 | C C |
| ATOM | 10381 C ILE I 475 | 13.459 −3.835 −42.617 1.00 79.52 | C C |
| ATOM | 10382 O ILE I 475 | 14.150 −2.913 −43.054 1.00 82.70 | C O |
| ATOM | 10383 N ASN I 476 | 12.133 −3.791 −42.590 1.00 69.64 | C N |
| ATOM | 10384 CA ASN I 476 | 11.404 −2.621 −43.048 1.00 68.88 | C C |
| ATOM | 10385 CB ASN I 476 | 9.979 −3.002 −43.442 1.00 20.00 | C C |
| ATOM | 10386 CG ASN I 476 | 9.939 −3.881 −44.672 1.00 20.00 | C C |
| ATOM | 10387 OD1 ASN I 476 | 10.854 −3.856 −45.496 1.00 20.00 | C O |
| ATOM | 10388 ND2 ASN I 476 | 8.918 −4.722 −44.762 1.00 20.00 | C N |
| ATOM | 10389 C ASN I 476 | 11.401 −1.512 −42.004 1.00 67.13 | C C |
| ATOM | 10390 O ASN I 476 | 11.491 −1.781 −40.806 1.00 73.10 | C O |
| ATOM | 10391 N PHE I 477 | 11.492 −0.273 −42.474 1.00 64.95 | C N |
| ATOM | 10392 CA PHE I 477 | 11.535 0.883 −41.585 1.00 68.13 | C C |
| ATOM | 10393 CB PHE I 477 | 12.064 2.118 −42.327 1.00 20.00 | C C |
| ATOM | 10394 CG PHE I 477 | 13.494 1.995 −42.778 1.00 20.00 | C C |
| ATOM | 10395 CD1 PHE I 477 | 14.532 2.409 −41.955 1.00 20.00 | C C |
| ATOM | 10396 CE1 PHE I 477 | 15.842 2.359 −42.391 1.00 20.00 | C C |
| ATOM | 10397 CZ PHE I 477 | 16.127 1.910 −43.665 1.00 20.00 | C C |
| ATOM | 10398 CE2 PHE I 477 | 15.100 1.529 −44.506 1.00 20.00 | C C |
| ATOM | 10399 CD2 PHE I 477 | 13.791 1.596 −44.070 1.00 20.00 | C C |
| ATOM | 10400 C PHE I 477 | 10.167 1.186 −40.968 1.00 65.57 | C C |
| ATOM | 10401 O PHE I 477 | 10.033 2.109 −40.165 1.00 49.83 | C O |
| ATOM | 10402 N TYR I 478 | 9.136 0.485 −41.432 1.00 51.97 | C N |
| ATOM | 10403 CA TYR I 478 | 7.811 0.580 −40.824 1.00 52.01 | C C |
| ATOM | 10404 CB TYR I 478 | 6.729 0.140 −41.815 1.00 20.00 | C C |
| ATOM | 10405 CG TYR I 478 | 6.638 1.012 −43.045 1.00 20.00 | C C |
| ATOM | 10406 CD1 TYR I 478 | 5.883 2.179 −43.040 1.00 20.00 | C C |

APPENDIX-continued (APPENDIX discloses SEQ ID NOS 29-32, 29-32 and 29-32, respectively, in order of appearance)

| | | | |
|---|---|---|---|
| ATOM | 10407 CE1 TYR I 478 | 5.824 2.997 −44.155 1.00 20.00 | C C |
| ATOM | 10408 CZ TYR I 478 | 6.512 2.642 −45.300 1.00 20.00 | C C |
| ATOM | 10409 OH TYR I 478 | 6.454 3.447 −46.414 1.00 20.00 | C O |
| ATOM | 10410 CE2 TYR I 478 | 7.260 1.484 −45.333 1.00 20.00 | C C |
| ATOM | 10411 CD2 TYR I 478 | 7.319 0.677 −44.210 1.00 20.00 | C C |
| ATOM | 10412 C TYR I 478 | 7.745 −0.269 −39.556 1.00 66.63 | C C |
| ATOM | 10413 O TYR I 478 | 6.674 −0.470 −38.983 1.00 63.45 | C O |
| ATOM | 10414 N ASP I 479 | 8.898 −0.790 −39.146 1.00 65.34 | C N |
| ATOM | 10415 CA ASP I 479 | 9.013 −1.509 −37.886 1.00 65.32 | C C |
| ATOM | 10416 CB ASP I 479 | 9.879 −2.758 −38.061 1.00 20.00 | C C |
| ATOM | 10417 CG ASP I 479 | 9.210 −3.815 −38.916 1.00 20.00 | C C |
| ATOM | 10418 OD1 ASP I 479 | 7.967 −3.791 −39.028 1.00 20.00 | C O |
| ATOM | 10419 OD2 ASP I 479 | 9.920 −4.701 −39.436 1.00 20.00 | C O |
| ATOM | 10420 C ASP I 479 | 9.590 −0.614 −36.796 1.00 64.83 | C C |
| ATOM | 10421 O ASP I 479 | 9.572 −0.976 −35.620 1.00 60.42 | C O |
| ATOM | 10422 N PRO I 480 | 10.076 0.579 −37.181 1.00 47.60 | C N |
| ATOM | 10423 CA PRO I 480 | 10.722 1.488 −36.253 1.00 46.52 | C C |
| ATOM | 10424 CB PRO I 480 | 11.789 2.143 −37.124 1.00 20.00 | C C |
| ATOM | 10425 CG PRO I 480 | 11.140 2.219 −38.487 1.00 20.00 | C C |
| ATOM | 10426 CD PRO I 480 | 10.043 1.155 −38.536 1.00 20.00 | C C |
| ATOM | 10427 C PRO I 480 | 9.736 2.550 −35.806 1.00 52.36 | C C |
| ATOM | 10428 O PRO I 480 | 9.629 3.601 −36.438 1.00 64.15 | C O |
| ATOM | 10429 N LEU I 481 | 8.945 2.229 −34.792 1.00 62.90 | C N |
| ATOM | 10430 CA LEU I 481 | 8.005 3.187 −34.233 1.00 54.24 | C C |
| ATOM | 10431 CB LEU I 481 | 6.576 2.656 −34.340 1.00 20.00 | C C |
| ATOM | 10432 CG LEU I 481 | 6.056 2.404 −35.756 1.00 20.00 | C C |
| ATOM | 10433 CD1 LEU I 481 | 4.735 1.662 −35.704 1.00 20.00 | C C |
| ATOM | 10434 CD2 LEU I 481 | 5.911 3.711 −36.524 1.00 20.00 | C C |
| ATOM | 10435 C LEU I 481 | 8.346 3.496 −32.783 1.00 59.81 | C C |
| ATOM | 10436 O LEU I 481 | 9.346 3.015 −32.250 1.00 64.98 | C O |
| ATOM | 10437 N VAL I 482 | 7.562 4.375 −32.176 1.00 59.66 | C N |
| ATOM | 10438 CA VAL I 482 | 7.706 4.645 −30.761 1.00 49.67 | C C |
| ATOM | 10439 CB VAL I 482 | 7.767 6.146 −30.484 1.00 20.00 | C C |
| ATOM | 10440 CG1 VAL I 482 | 8.060 6.388 −29.015 1.00 20.00 | C C |
| ATOM | 10441 CG2 VAL I 482 | 8.826 6.795 −31.358 1.00 20.00 | C C |
| ATOM | 10442 C VAL I 482 | 6.550 4.037 −29.987 1.00 53.03 | C C |
| ATOM | 10443 O VAL I 482 | 5.423 3.998 −30.476 1.00 46.27 | C O |
| ATOM | 10444 N PHE I 483 | 6.864 3.441 −28.842 1.00 61.61 | C N |
| ATOM | 10445 CA PHE I 483 | 5.847 2.831 −27.994 1.00 65.03 | C C |
| ATOM | 10446 CB PHE I 483 | 6.218 1.380 −27.662 1.00 20.00 | C C |
| ATOM | 10447 CG PHE I 483 | 6.212 0.463 −28.857 1.00 20.00 | C C |
| ATOM | 10448 CD1 PHE I 483 | 5.036 −0.124 −29.292 1.00 20.00 | C C |
| ATOM | 10449 CE1 PHE I 483 | 5.028 −0.963 −30.390 1.00 20.00 | C C |
| ATOM | 10450 CZ PHE I 483 | 6.201 −1.222 −31.068 1.00 20.00 | C C |
| ATOM | 10451 CE2 PHE I 483 | 7.379 −0.653 −30.639 1.00 20.00 | C C |
| ATOM | 10452 CD2 PHE I 483 | 7.382 0.185 −29.540 1.00 20.00 | C C |
| ATOM | 10453 C PHE I 483 | 5.627 3.653 −26.723 1.00 71.00 | C C |
| ATOM | 10454 O PHE I 483 | 5.934 3.199 −25.620 1.00 100.44 | C O |
| ATOM | 10455 N PRO I 484 | 5.255 4.928 −26.903 1.00 54.44 | C N |
| ATOM | 10456 CA PRO I 484 | 5.000 5.815 −25.781 1.00 47.46 | C C |
| ATOM | 10457 CB PRO I 484 | 6.136 6.828 −25.903 1.00 20.00 | C C |
| ATOM | 10458 CG PRO I 484 | 6.468 6.851 −27.406 1.00 20.00 | C C |
| ATOM | 10459 CD PRO I 484 | 5.760 5.686 −28.058 1.00 20.00 | C C |
| ATOM | 10460 C PRO I 484 | 3.661 6.533 −25.944 1.00 41.56 | C C |
| ATOM | 10461 O PRO I 484 | 3.430 7.190 −26.959 1.00 46.53 | C O |
| ATOM | 10462 N SER I 485 | 2.779 6.380 −24.964 1.00 46.30 | C N |
| ATOM | 10463 CA SER I 485 | 1.436 6.938 −25.048 1.00 49.30 | C C |
| ATOM | 10464 CB SER I 485 | 0.892 7.220 −23.649 1.00 20.00 | C C |
| ATOM | 10465 OG SER I 485 | 1.684 8.188 −22.983 1.00 20.00 | C O |
| ATOM | 10466 C SER I 485 | 1.380 8.204 −25.901 1.00 41.24 | C C |
| ATOM | 10467 O SER I 485 | 0.643 8.262 −26.883 1.00 46.93 | C O |
| ATOM | 10468 N ASP I 486 | 2.103 9.238 −25.482 1.00 49.48 | C N |
| ATOM | 10469 CA ASP I 486 | 2.085 10.518 −26.185 1.00 37.44 | C C |
| ATOM | 10470 CB ASP I 486 | 3.029 11.514 −25.511 1.00 20.00 | C C |
| ATOM | 10471 CG ASP I 486 | 2.509 11.993 −24.173 1.00 20.00 | C C |
| ATOM | 10472 OD1 ASP I 486 | 1.314 11.773 −23.887 1.00 20.00 | C O |
| ATOM | 10473 OD2 ASP I 486 | 3.299 12.566 −23.395 1.00 20.00 | C O |
| ATOM | 10474 C ASP I 486 | 2.456 10.359 −27.656 1.00 45.66 | C C |
| ATOM | 10475 O ASP I 486 | 1.752 10.848 −28.539 1.00 39.86 | C O |
| ATOM | 10476 N GLU I 487 | 3.559 9.665 −27.914 1.00 49.20 | C N |
| ATOM | 10477 CA GLU I 487 | 4.006 9.422 −29.280 1.00 45.70 | C C |
| ATOM | 10478 CB GLU I 487 | 5.346 8.684 −29.288 1.00 20.00 | C C |
| ATOM | 10479 CG GLU I 487 | 6.491 9.481 −28.685 1.00 20.00 | C C |
| ATOM | 10480 CD GLU I 487 | 7.766 8.669 −28.551 1.00 20.00 | C C |
| ATOM | 10481 OE1 GLU I 487 | 7.722 7.447 −28.804 1.00 20.00 | C O |
| ATOM | 10482 OE2 GLU I 487 | 8.794 9.238 −28.122 1.00 20.00 | C O |
| ATOM | 10483 C GLU I 487 | 2.966 8.648 −30.085 1.00 41.48 | C C |

APPENDIX-continued (APPENDIX discloses SEQ ID NOS 29-32, 29-32 and 29-32, respectively, in order of appearance)

| | | | |
|---|---|---|---|
| ATOM | 10484 O GLU I 487 | 2.656 9.011 −31.219 1.00 48.92 | C O |
| ATOM | 10485 N PHE I 488 | 2.402 7.606 −29.483 1.00 42.16 | C N |
| ATOM | 10486 CA PHE I 488 | 1.397 6.789 −30.155 1.00 39.33 | C C |
| ATOM | 10487 CB PHE I 488 | 0.968 5.623 −29.268 1.00 20.00 | C C |
| ATOM | 10488 CG PHE I 488 | 2.059 4.633 −29.005 1.00 20.00 | C C |
| ATOM | 10489 CD1 PHE I 488 | 2.403 3.694 −29.958 1.00 20.00 | C C |
| ATOM | 10490 CE1 PHE I 488 | 3.409 2.779 −29.715 1.00 20.00 | C C |
| ATOM | 10491 CZ PHE I 488 | 4.089 2.807 −28.517 1.00 20.00 | C C |
| ATOM | 10492 CE2 PHE I 488 | 3.752 3.737 −27.560 1.00 20.00 | C C |
| ATOM | 10493 CD2 PHE I 488 | 2.752 4.652 −27.810 1.00 20.00 | C C |
| ATOM | 10494 C PHE I 488 | 0.182 7.618 −30.540 1.00 43.06 | C C |
| ATOM | 10495 O PHE I 488 | −0.328 7.508 −31.654 1.00 61.71 | C O |
| ATOM | 10496 N ASP I 489 | −0.261 8.471 −29.624 1.00 41.95 | C N |
| ATOM | 10497 CA ASP I 489 | −1.454 9.273 −29.851 1.00 42.75 | C C |
| ATOM | 10498 CB ASP I 489 | −1.837 10.023 −28.581 1.00 20.00 | C C |
| ATOM | 10499 CG ASP I 489 | −2.352 9.102 −27.504 1.00 20.00 | C C |
| ATOM | 10500 OD1 ASP I 489 | −2.808 7.989 −27.848 1.00 20.00 | C O |
| ATOM | 10501 OD2 ASP I 489 | −2.184 9.435 −26.313 1.00 20.00 | C O |
| ATOM | 10502 C ASP I 489 | −1.255 10.256 −30.994 1.00 45.61 | C C |
| ATOM | 10503 O ASP I 489 | −2.206 10.617 −31.689 1.00 54.39 | C O |
| ATOM | 10504 N ALA I 490 | −0.020 10.714 −31.160 1.00 42.89 | C N |
| ATOM | 10505 CA ALA I 490 | 0.306 11.663 −32.215 1.00 38.40 | C C |
| ATOM | 10506 CB ALA I 490 | 1.684 12.262 −31.976 1.00 20.00 | C C |
| ATOM | 10507 C ALA I 490 | 0.240 10.994 −33.585 1.00 39.67 | C C |
| ATOM | 10508 O ALA I 490 | −0.356 11.529 −34.521 1.00 56.80 | C O |
| ATOM | 10509 N SER I 491 | 0.803 9.793 −33.676 1.00 40.38 | C N |
| ATOM | 10510 CA SER I 491 | 0.721 8.992 −34.893 1.00 41.77 | C C |
| ATOM | 10511 CB SER I 491 | 1.611 7.752 −34.784 1.00 20.00 | C C |
| ATOM | 10512 OG SER I 491 | 1.132 6.864 −33.788 1.00 20.00 | C O |
| ATOM | 10513 C SER I 491 | −0.717 8.580 −35.187 1.00 39.01 | C C |
| ATOM | 10514 O SER I 491 | −1.142 8.563 −36.342 1.00 36.91 | C O |
| ATOM | 10515 N ILE I 492 | −1.474 8.286 −34.135 1.00 38.11 | C N |
| ATOM | 10516 CA ILE I 492 | −2.896 8.000 −34.280 1.00 41.21 | C C |
| ATOM | 10517 CB ILE I 492 | −3.539 7.629 −32.938 1.00 20.00 | C C |
| ATOM | 10518 CG1 ILE I 492 | −2.964 6.311 −32.424 1.00 20.00 | C C |
| ATOM | 10519 CD1 ILE I 492 | −3.501 5.906 −31.076 1.00 20.00 | C C |
| ATOM | 10520 CG2 ILE I 492 | −5.050 7.533 −33.080 1.00 20.00 | C C |
| ATOM | 10521 C ILE I 492 | −3.646 9.182 −34.883 1.00 39.22 | C C |
| ATOM | 10522 O ILE I 492 | −4.494 9.008 −35.758 1.00 47.54 | C O |
| ATOM | 10523 N SER I 493 | −3.334 10.383 −34.408 1.00 41.64 | C N |
| ATOM | 10524 CA SER I 493 | −3.929 11.598 −34.952 1.00 35.15 | C C |
| ATOM | 10525 CB SER I 493 | −3.483 12.820 −34.146 1.00 20.00 | C C |
| ATOM | 10526 OG SER I 493 | −2.100 13.070 −34.322 1.00 20.00 | C O |
| ATOM | 10527 C SER I 493 | −3.547 11.773 −36.416 1.00 47.90 | C C |
| ATOM | 10528 O SER I 493 | −4.380 12.128 −37.250 1.00 50.94 | C O |
| ATOM | 10529 N GLN I 494 | −2.296 11.457 −36.727 1.00 42.51 | C N |
| ATOM | 10530 CA GLN I 494 | −1.784 11.587 −38.081 1.00 41.96 | C C |
| ATOM | 10531 CB GLN I 494 | −0.263 11.405 −38.085 1.00 20.00 | C C |
| ATOM | 10532 CG GLN I 494 | 0.495 12.482 −37.308 1.00 20.00 | C C |
| ATOM | 10533 CD GLN I 494 | 1.989 12.210 −37.223 1.00 20.00 | C C |
| ATOM | 10534 OE1 GLN I 494 | 2.410 11.104 −36.881 1.00 20.00 | C O |
| ATOM | 10535 NE2 GLN I 494 | 2.790 13.248 −37.433 1.00 20.00 | C N |
| ATOM | 10536 C GLN I 494 | −2.449 10.583 −39.023 1.00 33.86 | C C |
| ATOM | 10537 O GLN I 494 | −2.944 10.950 −40.090 1.00 54.89 | C O |
| ATOM | 10538 N VAL I 495 | −2.511 9.328 −38.594 1.00 34.99 | C N |
| ATOM | 10539 CA VAL I 495 | −3.226 8.300 −39.341 1.00 38.42 | C C |
| ATOM | 10540 CB VAL I 495 | −3.245 6.968 −38.576 1.00 20.00 | C C |
| ATOM | 10541 CG1 VAL I 495 | −4.032 5.922 −39.349 1.00 20.00 | C C |
| ATOM | 10542 CG2 VAL I 495 | −1.828 6.497 −38.309 1.00 20.00 | C C |
| ATOM | 10543 C VAL I 495 | −4.661 8.731 −39.618 1.00 42.74 | C C |
| ATOM | 10544 O VAL I 495 | −5.144 8.634 −40.747 1.00 44.00 | C O |
| ATOM | 10545 N ASN I 496 | −5.314 9.268 −38.592 1.00 42.45 | C N |
| ATOM | 10546 CA ASN I 496 | −6.705 9.685 −38.697 1.00 43.01 | C C |
| ATOM | 10547 CB ASN I 496 | −7.232 10.134 −37.333 1.00 20.00 | C C |
| ATOM | 10548 CG ASN I 496 | −7.416 8.977 −36.374 1.00 20.00 | C C |
| ATOM | 10549 OD1 ASN I 496 | −7.439 7.817 −36.784 1.00 20.00 | C O |
| ATOM | 10550 ND2 ASN I 496 | −7.495 9.283 −35.083 1.00 20.00 | C N |
| ATOM | 10551 C ASN I 496 | −6.906 10.790 −39.727 1.00 43.13 | C C |
| ATOM | 10552 O ASN I 496 | −7.893 10.793 −40.462 1.00 54.76 | C O |
| ATOM | 10553 N GLU I 497 | −5.990 11.752 −39.744 1.00 42.08 | C N |
| ATOM | 10554 CA GLU I 497 | −6.038 12.828 −40.726 1.00 43.13 | C C |
| ATOM | 10555 CB GLU I 497 | −4.947 13.863 −40.443 1.00 20.00 | C C |
| ATOM | 10556 CG GLU I 497 | −5.172 14.672 −39.175 1.00 20.00 | C C |
| ATOM | 10557 CD GLU I 497 | −4.045 15.647 −38.896 1.00 20.00 | C C |
| ATOM | 10558 OE1 GLU I 497 | −3.007 15.574 −39.587 1.00 20.00 | C O |
| ATOM | 10559 OE2 GLU I 497 | −4.192 16.480 −37.977 1.00 20.00 | C O |
| ATOM | 10560 C GLU I 497 | −5.884 12.275 −42.137 1.00 49.77 | C C |

APPENDIX-continued (APPENDIX discloses SEQ ID NOS 29-32, 29-32 and 29-32, respectively, in order of appearance)

| | | | |
|---|---|---|---|
| ATOM | 10561 O GLU I 497 | −6.542 12.736 −43.071 1.00 42.88 | C O |
| ATOM | 10562 N LYS I 498 | −5.051 11.249 −42.273 1.00 41.82 | C N |
| ATOM | 10563 CA LYS I 498 | −4.855 10.579 −43.552 1.00 53.60 | C C |
| ATOM | 10564 CB LYS I 498 | −3.676 9.609 −43.471 1.00 20.00 | C C |
| ATOM | 10565 CG LYS I 498 | −2.336 10.274 −43.228 1.00 20.00 | C C |
| ATOM | 10566 CD LYS I 498 | −1.193 9.356 −43.638 1.00 20.00 | C C |
| ATOM | 10567 CE LYS I 498 | 0.160 9.937 −43.247 1.00 20.00 | C C |
| ATOM | 10568 NZ LYS I 498 | 1.285 9.250 −43.942 1.00 20.00 | C N |
| ATOM | 10569 C LYS I 498 | −6.109 9.830 −43.994 1.00 55.29 | C C |
| ATOM | 10570 O LYS I 498 | −6.409 9.763 −45.186 1.00 61.06 | C O |
| ATOM | 10571 N ILE I 499 | −6.766 9.165 −43.047 1.00 52.22 | C N |
| ATOM | 10572 CA ILE I 499 | −8.038 8.500 −43.323 1.00 48.26 | C C |
| ATOM | 10573 CB ILE I 499 | −8.586 7.785 −42.076 1.00 20.00 | C C |
| ATOM | 10574 CG1 ILE I 499 | −7.657 6.642 −41.667 1.00 20.00 | C C |
| ATOM | 10575 CD1 ILE I 499 | −7.934 6.102 −40.286 1.00 20.00 | C C |
| ATOM | 10576 CG2 ILE I 499 | −9.994 7.267 −42.333 1.00 20.00 | C C |
| ATOM | 10577 C ILE I 499 | −9.067 9.516 −43.798 1.00 49.07 | C C |
| ATOM | 10578 O ILE I 499 | −9.858 9.244 −44.701 1.00 58.45 | C O |
| ATOM | 10579 N ASN I 500 | −8.961 10.726 −43.265 1.00 51.02 | C N |
| ATOM | 10580 CA ASN I 500 | −9.845 11.812 −43.644 1.00 52.06 | C C |
| ATOM | 10581 CB ASN I 500 | −9.741 12.940 −42.625 1.00 20.00 | C C |
| ATOM | 10582 CG ASN I 500 | −10.861 13.933 −42.753 1.00 20.00 | C C |
| ATOM | 10583 OD1 ASN I 500 | −11.927 13.622 −43.286 1.00 20.00 | C O |
| ATOM | 10584 ND2 ASN I 500 | −10.647 15.126 −42.232 1.00 20.00 | C N |
| ATOM | 10585 C ASN I 500 | −9.552 12.345 −45.041 1.00 48.31 | C C |
| ATOM | 10586 O ASN I 500 | −10.448 12.834 −45.729 1.00 56.89 | C O |
| ATOM | 10587 N GLN I 501 | −8.283 12.300 −45.434 1.00 55.87 | C N |
| ATOM | 10588 CA GLN I 501 | −7.900 12.610 −46.807 1.00 53.55 | C C |
| ATOM | 10589 CB GLN I 501 | −6.384 12.797 −46.917 1.00 20.00 | C C |
| ATOM | 10590 CG GLN I 501 | −5.851 13.987 −46.136 1.00 20.00 | C C |
| ATOM | 10591 CD GLN I 501 | −4.338 14.093 −46.191 1.00 20.00 | C C |
| ATOM | 10592 OE1 GLN I 501 | −3.648 13.146 −46.576 1.00 20.00 | C O |
| ATOM | 10593 NE2 GLN I 501 | −3.814 15.247 −45.793 1.00 20.00 | C N |
| ATOM | 10594 C GLN I 501 | −8.383 11.531 −47.777 1.00 45.67 | C C |
| ATOM | 10595 O GLN I 501 | −8.980 11.837 −48.810 1.00 58.31 | C O |
| ATOM | 10596 N SER I 502 | −8.234 10.273 −47.378 1.00 43.44 | C N |
| ATOM | 10597 CA SER I 502 | −8.704 9.157 −48.189 1.00 45.40 | C C |
| ATOM | 10598 CB SER I 502 | −8.367 7.830 −47.512 1.00 20.00 | C C |
| ATOM | 10599 OG SER I 502 | −9.001 7.735 −46.250 1.00 20.00 | C O |
| ATOM | 10600 C SER I 502 | −10.206 9.254 −48.413 1.00 55.15 | C C |
| ATOM | 10601 O SER I 502 | −10.708 8.934 −49.490 1.00 52.57 | C O |
| ATOM | 10602 N LEU I 503 | −10.920 9.673 −47.376 1.00 55.35 | C N |
| ATOM | 10603 CA LEU I 503 | −12.366 9.798 −47.447 1.00 52.12 | C C |
| ATOM | 10604 CB LEU I 503 | −12.950 10.025 −46.053 1.00 20.00 | C C |
| ATOM | 10605 CG LEU I 503 | −12.783 8.856 −45.082 1.00 20.00 | C C |
| ATOM | 10606 CD1 LEU I 503 | −13.061 9.290 −43.653 1.00 20.00 | C C |
| ATOM | 10607 CD2 LEU I 503 | −13.685 7.704 −45.481 1.00 20.00 | C C |
| ATOM | 10608 C LEU I 503 | −12.761 10.938 −48.371 1.00 55.74 | C C |
| ATOM | 10609 O LEU I 503 | −13.782 10.869 −49.052 1.00 57.75 | C O |
| ATOM | 10610 N ALA I 504 | −11.951 11.991 −48.382 1.00 57.22 | C N |
| ATOM | 10611 CA ALA I 504 | −12.187 13.129 −49.261 1.00 59.12 | C C |
| ATOM | 10612 CB ALA I 504 | −11.333 14.315 −48.831 1.00 20.00 | C C |
| ATOM | 10613 C ALA I 504 | −11.902 12.760 −50.713 1.00 58.10 | C C |
| ATOM | 10614 O ALA I 504 | −12.656 13.119 −51.618 1.00 63.64 | C O |
| ATOM | 10615 N PHE I 505 | −10.813 12.029 −50.922 1.00 58.17 | C N |
| ATOM | 10616 CA PHE I 505 | −10.485 11.505 −52.240 1.00 56.56 | C C |
| ATOM | 10617 CB PHE I 505 | −9.180 10.698 −52.186 1.00 20.00 | C C |
| ATOM | 10618 CG PHE I 505 | −7.971 11.517 −51.817 1.00 20.00 | C C |
| ATOM | 10619 CD1 PHE I 505 | −7.307 12.270 −52.773 1.00 20.00 | C C |
| ATOM | 10620 CE1 PHE I 505 | −6.230 13.063 −52.426 1.00 20.00 | C C |
| ATOM | 10621 CZ PHE I 505 | −5.768 13.067 −51.125 1.00 20.00 | C C |
| ATOM | 10622 CE2 PHE I 505 | −6.376 12.270 −50.176 1.00 20.00 | C C |
| ATOM | 10623 CD2 PHE I 505 | −7.471 11.499 −50.524 1.00 20.00 | C C |
| ATOM | 10624 C PHE I 505 | −11.625 10.637 −52.769 1.00 60.12 | C C |
| ATOM | 10625 O PHE I 505 | −12.014 10.746 −53.934 1.00 65.46 | C O |
| ATOM | 10626 N ILE I 506 | −12.214 9.844 −51.875 1.00 56.10 | C N |
| ATOM | 10627 CA ILE I 506 | −13.355 8.991 −52.213 1.00 57.32 | C C |
| ATOM | 10628 CB ILE I 506 | −13.782 8.109 −51.013 1.00 20.00 | C C |
| ATOM | 10629 CG1 ILE I 506 | −12.657 7.149 −50.619 1.00 20.00 | C C |
| ATOM | 10630 CD1 ILE I 506 | −12.804 6.591 −49.222 1.00 20.00 | C C |
| ATOM | 10631 CG2 ILE I 506 | −15.064 7.345 −51.330 1.00 20.00 | C C |
| ATOM | 10632 C ILE I 506 | −14.556 9.818 −52.669 1.00 67.33 | C C |
| ATOM | 10633 O ILE I 506 | −15.217 9.485 −53.652 1.00 76.99 | C O |
| ATOM | 10634 N ARG I 507 | −14.855 10.878 −51.925 1.00 67.87 | C N |
| ATOM | 10635 CA ARG I 507 | −15.936 11.788 −52.287 1.00 62.11 | C C |
| ATOM | 10636 CB ARG I 507 | −16.087 12.898 −51.240 1.00 20.00 | C C |
| ATOM | 10637 CG ARG I 507 | −16.795 12.450 −49.963 1.00 20.00 | C C |

APPENDIX-continued (APPENDIX discloses SEQ ID NOS 29-32, 29-32 and 29-32, respectively, in order of appearance)

| | | | |
|---|---|---|---|
| ATOM | 10638 CD ARG I 507 | −16.736 13.504 −48.861 1.00 20.00 | C C |
| ATOM | 10639 NE ARG I 507 | −17.140 12.957 −47.566 1.00 20.00 | C N |
| ATOM | 10640 CZ ARG I 507 | −17.292 13.683 −46.463 1.00 20.00 | C C |
| ATOM | 10641 NH1 ARG I 507 | −17.083 14.992 −46.499 1.00 20.00 | C N |
| ATOM | 10642 NH2 ARG I 507 | −17.687 13.106 −45.335 1.00 20.00 | C N |
| ATOM | 10643 C ARG I 507 | −15.685 12.391 −53.659 1.00 67.30 | C C |
| ATOM | 10644 O ARG I 507 | −16.488 12.224 −54.574 1.00 67.02 | C O |
| ATOM | 10645 N LYS I 508 | −14.518 13.001 −53.823 1.00 66.83 | C N |
| ATOM | 10646 CA LYS I 508 | −14.125 13.546 −55.112 1.00 68.12 | C C |
| ATOM | 10647 CB LYS I 508 | −12.693 14.086 −55.052 1.00 20.00 | C C |
| ATOM | 10648 CG LYS I 508 | −12.522 15.286 −54.117 1.00 20.00 | C C |
| ATOM | 10649 CD LYS I 508 | −11.072 15.750 −54.046 1.00 20.00 | C C |
| ATOM | 10650 CE LYS I 508 | −10.912 16.933 −53.098 1.00 20.00 | C C |
| ATOM | 10651 NZ LYS I 508 | −9.486 17.329 −52.912 1.00 20.00 | C N |
| ATOM | 10652 C LYS I 508 | −14.275 12.499 −56.215 1.00 65.22 | C C |
| ATOM | 10653 O LYS I 508 | −15.005 12.710 −57.183 1.00 72.34 | C O |
| ATOM | 10654 N SER I 509 | −13.727 11.312 −55.973 1.00 64.87 | C N |
| ATOM | 10655 CA SER I 509 | −13.783 10.230 −56.949 1.00 56.47 | C C |
| ATOM | 10656 CB SER I 509 | −13.014 9.008 −56.445 1.00 20.00 | C C |
| ATOM | 10657 OG SER I 509 | −13.561 8.528 −55.232 1.00 20.00 | C O |
| ATOM | 10658 C SER I 509 | −15.220 9.847 −57.299 1.00 56.96 | C C |
| ATOM | 10659 O SER I 509 | −15.537 9.599 −58.461 1.00 65.57 | C O |
| ATOM | 10660 N ASP I 510 | −16.077 9.760 −56.285 1.00 64.34 | C N |
| ATOM | 10661 CA ASP I 510 | −17.478 9.402 −56.500 1.00 64.83 | C C |
| ATOM | 10662 CB ASP I 510 | −18.217 9.244 −55.161 1.00 20.00 | C C |
| ATOM | 10663 CG ASP I 510 | −17.827 7.975 −54.416 1.00 20.00 | C C |
| ATOM | 10664 OD1 ASP I 510 | −17.292 7.044 −55.050 1.00 20.00 | C O |
| ATOM | 10665 OD2 ASP I 510 | −18.083 7.900 −53.197 1.00 20.00 | C O |
| ATOM | 10666 C ASP I 510 | −18.173 10.458 −57.356 1.00 62.11 | C C |
| ATOM | 10667 O ASP I 510 | −18.723 10.150 −58.412 1.00 67.61 | C O |
| ATOM | 10668 N GLU I 511 | −18.078 11.713 −56.928 1.00 64.95 | C N |
| ATOM | 10669 CA GLU I 511 | −18.673 12.822 −57.664 1.00 60.64 | C C |
| ATOM | 10670 CB GLU I 511 | −18.175 14.162 −57.117 1.00 20.00 | C C |
| ATOM | 10671 CG GLU I 511 | −18.700 14.509 −55.736 1.00 20.00 | C C |
| ATOM | 10672 CD GLU I 511 | −18.061 15.767 −55.172 1.00 20.00 | C C |
| ATOM | 10673 OE1 GLU I 511 | −17.166 16.329 −55.841 1.00 20.00 | C O |
| ATOM | 10674 OE2 GLU I 511 | −18.506 16.237 −54.102 1.00 20.00 | C O |
| ATOM | 10675 C GLU I 511 | −18.377 12.729 −59.159 1.00 59.91 | C C |
| ATOM | 10676 O GLU I 511 | −19.245 13.008 −59.983 1.00 55.45 | C O |
| ATOM | 10677 N LEU I 512 | −17.122 12.450 −59.503 1.00 44.35 | C N |
| ATOM | 10678 CA LEU I 512 | −16.712 12.392 −60.904 1.00 49.60 | C C |
| ATOM | 10679 CB LEU I 512 | −15.196 12.240 −61.021 1.00 20.00 | C C |
| ATOM | 10680 CG LEU I 512 | −14.353 13.460 −60.658 1.00 20.00 | C C |
| ATOM | 10681 CD1 LEU I 512 | −12.894 13.181 −60.963 1.00 20.00 | C C |
| ATOM | 10682 CD2 LEU I 512 | −14.831 14.678 −61.424 1.00 20.00 | C C |
| ATOM | 10683 C LEU I 512 | −17.396 11.239 −61.621 1.00 58.00 | C C |
| ATOM | 10684 O LEU I 512 | −17.946 11.411 −62.708 1.00 55.11 | C O |
| ATOM | 10685 N LEU I 513 | −17.306 10.051 −61.036 1.00 57.91 | C N |
| ATOM | 10686 CA LEU I 513 | −17.901 8.870 −61.636 1.00 57.49 | C C |
| ATOM | 10687 CB LEU I 513 | −17.632 7.629 −60.774 1.00 20.00 | C C |
| ATOM | 10688 CG LEU I 513 | −16.169 7.179 −60.678 1.00 20.00 | C C |
| ATOM | 10689 CD1 LEU I 513 | −15.992 6.055 −59.670 1.00 20.00 | C C |
| ATOM | 10690 CD2 LEU I 513 | −15.637 6.768 −62.042 1.00 20.00 | C C |
| ATOM | 10691 C LEU I 513 | −19.399 9.075 −61.852 1.00 58.78 | C C |
| ATOM | 10692 O LEU I 513 | −19.913 8.812 −62.940 1.00 59.88 | C O |
| ATOM | 10693 N HIS I 514 | −20.054 9.718 −60.888 1.00 60.07 | C N |
| ATOM | 10694 CA HIS I 514 | −21.494 9.975 −60.982 1.00 62.82 | C C |
| ATOM | 10695 CB HIS I 514 | −22.058 10.454 −59.635 1.00 20.00 | C C |
| ATOM | 10696 CG HIS I 514 | −21.878 9.472 −58.517 1.00 20.00 | C C |
| ATOM | 10697 ND1 HIS I 514 | −22.551 8.269 −58.465 1.00 20.00 | C N |
| ATOM | 10698 CE1 HIS I 514 | −22.192 7.612 −57.376 1.00 20.00 | C C |
| ATOM | 10699 NE2 HIS I 514 | −21.304 8.342 −56.723 1.00 20.00 | C N |
| ATOM | 10700 CD2 HIS I 514 | −21.104 9.517 −57.407 1.00 20.00 | C C |
| ATOM | 10701 C HIS I 514 | −21.799 10.989 −62.087 1.00 65.10 | C C |
| ATOM | 10702 O HIS I 514 | −22.898 11.002 −62.647 1.00 66.73 | C O |
| ATOM | 10703 N ASN I 515 | −20.795 11.787 −62.441 1.00 63.45 | C N |
| ATOM | 10704 CA ASN I 515 | −20.932 12.782 −63.499 1.00 56.53 | C C |
| ATOM | 10705 CB ASN I 515 | −19.903 13.909 −63.317 1.00 20.00 | C C |
| ATOM | 10706 CG ASN I 515 | −20.243 14.838 −62.159 1.00 20.00 | C C |
| ATOM | 10707 OD1 ASN I 515 | −21.400 14.948 −61.756 1.00 20.00 | C O |
| ATOM | 10708 ND2 ASN I 515 | −19.238 15.544 −61.652 1.00 20.00 | C N |
| ATOM | 10709 C ASN I 515 | −20.765 12.134 −64.868 1.00 60.06 | C C |
| ATOM | 10710 O ASN I 515 | −21.518 12.422 −65.799 1.00 66.48 | C O |
| ATOM | 10711 N VAL I 516 | −19.829 11.197 −64.959 1.00 54.29 | C N |
| ATOM | 10712 CA VAL I 516 | −19.617 10.460 −66.195 1.00 52.70 | C C |
| ATOM | 10713 CB VAL I 516 | −18.407 9.523 −66.097 1.00 20.00 | C C |
| ATOM | 10714 CG1 VAL I 516 | −18.398 8.554 −67.267 1.00 20.00 | C C |

APPENDIX-continued (APPENDIX discloses SEQ ID NOS 29-32, 29-32 and 29-32, respectively, in order of appearance)

| | | | |
|---|---|---|---|
| ATOM | 10715 CG2 VAL I 516 | −17.122 10.330 −66.063 1.00 20.00 | C C |
| ATOM | 10716 C VAL I 516 | −20.850 9.645 −66.551 1.00 60.10 | C C |
| ATOM | 10717 O VAL I 516 | −21.306 9.662 −67.693 1.00 61.55 | C O |
| ATOM | 10718 N ASN I 517 | −21.432 8.998 −65.549 1.00 69.10 | C N |
| ATOM | 10719 CA ASN I 517 | −22.648 8.224 −65.749 1.00 67.75 | C C |
| ATOM | 10720 CB ASN I 517 | −23.135 7.652 −64.421 1.00 20.00 | C C |
| ATOM | 10721 CG ASN I 517 | −22.254 6.530 −63.914 1.00 20.00 | C C |
| ATOM | 10722 OD1 ASN I 517 | −21.467 5.954 −64.667 1.00 20.00 | C O |
| ATOM | 10723 ND2 ASN I 517 | −22.368 6.226 −62.627 1.00 20.00 | C N |
| ATOM | 10724 C ASN I 517 | −23.751 9.051 −66.394 1.00 71.17 | C C |
| ATOM | 10725 O ASN I 517 | −24.535 8.544 −67.196 1.00 66.42 | C O |
| ATOM | 10726 N ALA I 518 | −23.811 10.326 −66.028 1.00 72.11 | C N |
| ATOM | 10727 CA ALA I 518 | −24.811 11.232 −66.571 1.00 74.82 | C C |
| ATOM | 10728 CB ALA I 518 | −24.936 12.464 −65.692 1.00 20.00 | C C |
| ATOM | 10729 C ALA I 518 | −24.471 11.628 −68.004 1.00 70.11 | C C |
| ATOM | 10730 O ALA I 518 | −25.328 11.590 −68.886 1.00 65.18 | C O |
| ATOM | 10731 N GLY I 519 | −23.212 11.989 −68.230 1.00 56.07 | C N |
| ATOM | 10732 CA GLY I 519 | −22.709 12.224 −69.577 1.00 53.01 | C C |
| ATOM | 10733 C GLY I 519 | −22.906 11.026 −70.483 1.00 63.58 | C C |
| ATOM | 10734 O GLY I 519 | −23.221 11.174 −71.663 1.00 69.35 | C O |
| ATOM | 10735 N LYS I 520 | −22.776 9.833 −69.912 1.00 58.33 | C N |
| ATOM | 10736 CA LYS I 520 | −22.996 8.592 −70.647 1.00 53.44 | C C |
| ATOM | 10737 CB LYS I 520 | −22.655 7.389 −69.767 1.00 20.00 | C C |
| ATOM | 10738 CG LYS I 520 | −21.194 7.319 −69.368 1.00 20.00 | C C |
| ATOM | 10739 CD LYS I 520 | −20.915 6.097 −68.525 1.00 20.00 | C C |
| ATOM | 10740 CE LYS I 520 | −19.428 5.920 −68.314 1.00 20.00 | C C |
| ATOM | 10741 NZ LYS I 520 | −19.148 4.767 −67.417 1.00 20.00 | C N |
| ATOM | 10742 C LYS I 520 | −24.437 8.485 −71.121 1.00 58.24 | C C |
| ATOM | 10743 O LYS I 520 | −24.714 7.920 −72.179 1.00 48.60 | C O |
| ATOM | 10744 N SER I 521 | −25.354 8.971 −70.293 1.00 67.19 | C N |
| ATOM | 10745 CA SER I 521 | −26.772 8.995 −70.632 1.00 60.42 | C C |
| ATOM | 10746 CB SER I 521 | −27.588 9.481 −69.436 1.00 20.00 | C C |
| ATOM | 10747 OG SER I 521 | −27.281 10.830 −69.130 1.00 20.00 | C O |
| ATOM | 10748 C SER I 521 | −27.047 9.892 −71.837 1.00 54.19 | C C |
| ATOM | 10749 O SER I 521 | −27.767 9.506 −72.758 1.00 65.36 | C O |
| ATOM | 10750 N THR I 522 | −26.556 11.124 −71.770 1.00 50.09 | C N |
| ATOM | 10751 CA THR I 522 | −26.650 12.048 −72.892 1.00 57.59 | C C |
| ATOM | 10752 CB THR I 522 | −25.950 13.377 −72.579 1.00 20.00 | C C |
| ATOM | 10753 OG1 THR I 522 | −24.538 13.159 −72.466 1.00 20.00 | C O |
| ATOM | 10754 CG2 THR I 522 | −26.478 13.957 −71.275 1.00 20.00 | C C |
| ATOM | 10755 C THR I 522 | −26.040 11.450 −74.153 1.00 59.16 | C C |
| ATOM | 10756 O THR I 522 | −26.682 11.416 −75.202 1.00 65.90 | C O |
| ATOM | 10757 N THR I 523 | −24.840 10.891 −74.020 1.00 52.59 | C N |
| ATOM | 10758 CA THR I 523 | −24.151 10.267 −75.148 1.00 42.19 | C C |
| ATOM | 10759 CB THR I 523 | −22.805 9.649 −74.725 1.00 20.00 | C C |
| ATOM | 10760 OG1 THR I 523 | −23.027 8.645 −73.726 1.00 20.00 | C O |
| ATOM | 10761 CG2 THR I 523 | −21.876 10.722 −74.172 1.00 20.00 | C C |
| ATOM | 10762 C THR I 523 | −25.002 9.194 −75.822 1.00 48.90 | C C |
| ATOM | 10763 O THR I 523 | −24.991 9.059 −77.047 1.00 63.19 | C O |
| ATOM | 10764 N ASN I 524 | −25.694 8.395 −75.018 1.00 52.51 | C N |
| ATOM | 10765 CA ASN I 524 | −26.597 7.386 −75.553 1.00 57.54 | C C |
| ATOM | 10766 CB ASN I 524 | −27.089 6.458 −74.444 1.00 20.00 | C C |
| ATOM | 10767 CG ASN I 524 | −26.002 5.533 −73.941 1.00 20.00 | C C |
| ATOM | 10768 OD1 ASN I 524 | −25.000 5.316 −74.620 1.00 20.00 | C O |
| ATOM | 10769 ND2 ASN I 524 | −26.153 5.050 −72.714 1.00 20.00 | C N |
| ATOM | 10770 C ASN I 524 | −27.776 7.996 −76.302 1.00 54.12 | C C |
| ATOM | 10771 O ASN I 524 | −28.076 7.601 −77.428 1.00 61.31 | C O |
| ATOM | 10772 N SER I 525 | −28.372 9.027 −75.714 1.00 48.97 | C N |
| ATOM | 10773 CA SER I 525 | −29.483 9.734 −76.336 1.00 64.81 | C C |
| ATOM | 10774 CB SER I 525 | −29.930 10.885 −75.441 1.00 61.22 | C C |
| ATOM | 10775 OG SER I 525 | −29.691 10.571 −74.078 1.00 85.90 | C O |
| ATOM | 10776 C SER I 525 | −29.114 10.265 −77.713 1.00 69.67 | C C |
| ATOM | 10777 O SER I 525 | −29.974 10.417 −78.580 1.00 72.60 | C O |
| ATOM | 10778 N LYS I 526 | −27.853 10.647 −77.872 1.00 66.06 | C N |
| ATOM | 10779 CA LYS I 526 | −27.365 11.130 −79.154 1.00 63.67 | C C |
| ATOM | 10780 CB LYS I 526 | −26.043 11.874 −78.980 1.00 70.55 | C C |
| ATOM | 10781 CG LYS I 526 | −26.196 13.332 −78.608 1.00 75.29 | C C |
| ATOM | 10782 CD LYS I 526 | −24.898 13.870 −78.032 1.00 85.03 | C C |
| ATOM | 10783 CE LYS I 526 | −25.144 15.017 −77.067 1.00 82.65 | C C |
| ATOM | 10784 NZ LYS I 526 | −24.040 15.141 −76.075 1.00 73.89 | C N |
| ATOM | 10785 C LYS I 526 | −27.182 9.975 −80.124 1.00 55.36 | C C |
| ATOM | 10786 O LYS I 526 | −27.591 10.050 −81.283 1.00 70.69 | C O |
| ATOM | 10787 N ILE I 527 | −26.593 8.892 −79.634 1.00 57.52 | C N |
| ATOM | 10788 CA ILE I 527 | −26.355 7.723 −80.461 1.00 58.48 | C C |
| ATOM | 10789 CB ILE I 527 | −25.712 6.589 −79.650 1.00 57.00 | C C |
| ATOM | 10790 CG1 ILE I 527 | −24.414 7.071 −78.993 1.00 49.07 | C C |
| ATOM | 10791 CD1 ILE I 527 | −23.516 7.882 −79.906 1.00 46.18 | C C |

APPENDIX-continued (APPENDIX discloses SEQ ID NOS 29-32, 29-32 and 29-32, respectively, in order of appearance)

| | | | |
|---|---|---|---|
| ATOM | 10792 CG2 ILE I 527 | −25.469 5.370 −80.530 1.00 52.63 | C C |
| ATOM | 10793 C ILE I 527 | −27.649 7.230 −81.097 1.00 65.20 | C C |
| ATOM | 10794 O ILE I 527 | −27.705 7.000 −82.304 1.00 66.48 | C O |
| ATOM | 10795 N TYR I 528 | −28.705 7.141 −80.293 1.00 69.78 | C N |
| ATOM | 10796 CA TYR I 528 | −30.027 6.783 −80.798 1.00 72.52 | C C |
| ATOM | 10797 CB TYR I 528 | −31.080 6.916 −79.695 1.00 73.16 | C C |
| ATOM | 10798 CG TYR I 528 | −30.768 6.138 −78.433 1.00 76.94 | C C |
| ATOM | 10799 CD1 TYR I 528 | −31.402 6.444 −77.233 1.00 70.95 | C C |
| ATOM | 10800 CE1 TYR I 528 | −31.123 5.739 −76.074 1.00 67.73 | C C |
| ATOM | 10801 CZ TYR I 528 | −30.200 4.712 −76.103 1.00 71.89 | C C |
| ATOM | 10802 OH TYR I 528 | −29.927 4.009 −74.954 1.00 75.44 | C O |
| ATOM | 10803 CE2 TYR I 528 | −29.534 4.407 −77.273 1.00 77.03 | C C |
| ATOM | 10804 CD2 TYR I 528 | −29.818 5.120 −78.431 1.00 77.84 | C C |
| ATOM | 10805 C TYR I 528 | −30.414 7.661 −81.985 1.00 71.63 | C C |
| ATOM | 10806 O TYR I 528 | −30.720 7.162 −83.069 1.00 84.20 | C O |
| ATOM | 10807 N HIS I 529 | −30.470 8.966 −81.748 1.00 67.69 | C N |
| ATOM | 10808 CA HIS I 529 | −30.934 9.902 −82.759 1.00 60.28 | C C |
| ATOM | 10809 CB HIS I 529 | −30.900 11.336 −82.218 1.00 67.84 | C C |
| ATOM | 10810 CG HIS I 529 | −31.927 11.615 −81.162 1.00 88.54 | C C |
| ATOM | 10811 ND1 HIS I 529 | −32.439 12.875 −80.934 1.00 93.34 | C N |
| ATOM | 10812 CE1 HIS I 529 | −33.289 12.828 −79.924 1.00 86.23 | C C |
| ATOM | 10813 NE2 HIS I 529 | −33.346 11.583 −79.486 1.00 91.95 | C N |
| ATOM | 10814 CD2 HIS I 529 | −32.495 10.807 −80.235 1.00 93.77 | C C |
| ATOM | 10815 C HIS I 529 | −30.094 9.785 −84.029 1.00 63.30 | C C |
| ATOM | 10816 O HIS I 529 | −30.632 9.642 −85.127 1.00 61.02 | C O |
| ATOM | 10817 N ILE I 530 | −28.775 9.752 −83.867 1.00 59.79 | C N |
| ATOM | 10818 CA ILE I 530 | −27.886 9.457 −84.984 1.00 45.70 | C C |
| ATOM | 10819 CB ILE I 530 | −26.413 9.365 −84.536 1.00 40.57 | C C |
| ATOM | 10820 CG1 ILE I 530 | −25.854 10.764 −84.270 1.00 42.86 | C C |
| ATOM | 10821 CD1 ILE I 530 | −24.376 10.902 −84.570 1.00 51.01 | C C |
| ATOM | 10822 CG2 ILE I 530 | −25.575 8.662 −85.596 1.00 35.31 | C C |
| ATOM | 10823 C ILE I 530 | −28.301 8.153 −85.660 1.00 57.52 | C C |
| ATOM | 10824 O ILE I 530 | −28.637 8.136 −86.845 1.00 71.18 | C O |
| ATOM | 10825 N GLU I 531 | −28.485 7.122 −84.841 1.00 67.55 | C N |
| ATOM | 10826 CA GLU I 531 | −28.876 5.801 −85.321 1.00 69.79 | C C |
| ATOM | 10827 CB GLU I 531 | −29.114 4.869 −84.134 1.00 84.02 | C C |
| ATOM | 10828 CG GLU I 531 | −28.794 3.415 −84.402 1.00104.22 | C C |
| ATOM | 10829 CD GLU I 531 | −28.980 2.551 −83.170 1.00116.08 | C C |
| ATOM | 10830 OE1 GLU I 531 | −28.474 2.927 −82.091 1.00118.71 | C O |
| ATOM | 10831 OE2 GLU I 531 | −29.736 1.564 −83.255 1.00119.69 | C O |
| ATOM | 10832 C GLU I 531 | −30.145 5.890 −86.151 1.00 64.87 | C C |
| ATOM | 10833 O GLU I 531 | −30.218 5.343 −87.250 1.00 55.58 | C O |
| ATOM | 10834 N ASN I 532 | −31.177 6.489 −85.566 1.00 65.70 | C N |
| ATOM | 10835 CA ASN I 532 | −32.459 6.657 −86.240 1.00 64.16 | C C |
| ATOM | 10836 CB ASN I 532 | −33.475 7.303 −85.296 1.00 60.58 | C C |
| ATOM | 10837 CG ASN I 532 | −34.859 7.396 −85.905 1.00 67.75 | C C |
| ATOM | 10838 OD1 ASN I 532 | −35.480 6.381 −86.221 1.00 53.59 | C O |
| ATOM | 10839 ND2 ASN I 532 | −35.352 8.618 −86.072 1.00 61.81 | C N |
| ATOM | 10840 C ASN I 532 | −32.330 7.486 −87.517 1.00 72.17 | C C |
| ATOM | 10841 O ASN I 532 | −32.999 7.220 −88.517 1.00 85.75 | C O |
| ATOM | 10842 N GLU I 533 | −31.469 8.495 −87.470 1.00 79.68 | C N |
| ATOM | 10843 CA GLU I 533 | −31.248 9.372 −88.611 1.00 71.96 | C C |
| ATOM | 10844 CB GLU I 533 | −30.422 10.590 −88.186 1.00 67.87 | C C |
| ATOM | 10845 CG GLU I 533 | −30.518 11.797 −89.125 1.00 81.94 | C C |
| ATOM | 10846 CD GLU I 533 | −31.932 12.348 −89.256 1.00 92.79 | C C |
| ATOM | 10847 OE1 GLU I 533 | −32.529 12.729 −88.227 1.00 95.90 | C O |
| ATOM | 10848 OE2 GLU I 533 | −32.399 12.511 −90.403 1.00 93.14 | C O |
| ATOM | 10849 C GLU I 533 | −30.546 8.622 −89.738 1.00 68.54 | C C |
| ATOM | 10850 O GLU I 533 | −30.737 8.928 −90.914 1.00 79.29 | C O |
| ATOM | 10851 N ILE I 534 | −29.742 7.631 −89.367 1.00 69.50 | C N |
| ATOM | 10852 CA ILE I 534 | −29.047 6.796 −90.342 1.00 72.55 | C C |
| ATOM | 10853 CB ILE I 534 | −27.786 6.137 −89.729 1.00 79.55 | C C |
| ATOM | 10854 CG1 ILE I 534 | −26.779 7.205 −89.298 1.00 80.41 | C C |
| ATOM | 10855 CD1 ILE I 534 | −26.687 8.374 −90.254 1.00 89.38 | C C |
| ATOM | 10856 CG2 ILE I 534 | −27.138 5.186 −90.724 1.00 78.63 | C C |
| ATOM | 10857 C ILE I 534 | −29.972 5.707 −90.883 1.00 74.92 | C C |
| ATOM | 10858 O ILE I 534 | −29.725 5.139 −91.948 1.00 81.01 | C O |
| ATOM | 10859 N ALA I 535 | −31.028 5.411 −90.130 1.00 79.52 | C N |
| ATOM | 10860 CA ALA I 535 | −32.056 4.474 −90.573 1.00 82.64 | C C |
| ATOM | 10861 CB ALA I 535 | −32.890 4.001 −89.386 1.00 75.39 | C C |
| ATOM | 10862 C ALA I 535 | −32.956 5.093 −91.645 1.00 81.39 | C C |
| ATOM | 10863 O ALA I 535 | −33.323 4.435 −92.622 1.00 85.54 | C O |
| ATOM | 10864 N ARG I 536 | −33.274 6.373 −91.474 1.00 78.41 | C N |
| ATOM | 10865 CA ARG I 536 | −34.100 7.098 −92.435 1.00 83.27 | C C |
| ATOM | 10866 CB ARG I 536 | −34.664 8.372 −91.804 1.00 84.58 | C C |
| ATOM | 10867 CG ARG I 536 | −35.623 8.123 −90.651 1.00103.24 | C C |
| ATOM | 10868 CD ARG I 536 | −36.750 9.145 −90.630 1.00114.72 | C C |

APPENDIX-continued (APPENDIX discloses SEQ ID NOS 29-32, 29-32 and 29-32, respectively, in order of appearance)

| | | | | |
|---|---|---|---|---|
| ATOM | 10869 NE ARG I 536 | −36.250 10.513 −90.521 1.00117.80 | C N | |
| ATOM | 10870 CZ ARG I 536 | −37.009 11.598 −90.638 1.00116.66 | C C | |
| ATOM | 10871 NH1 ARG I 536 | −38.311 11.478 −90.863 1.00114.57 | C N | |
| ATOM | 10872 NH2 ARG I 536 | −36.470 12.803 −90.520 1.00116.38 | C N | |
| ATOM | 10873 C ARG I 536 | −33.323 7.440 −93.703 1.00 82.20 | C C | |
| ATOM | 10874 O ARG I 536 | −33.838 7.298 −94.812 1.00 86.28 | C O | |
| ATOM | 10875 N ILE I 537 | −32.114 7.964 −93.532 1.00 77.08 | C N | |
| ATOM | 10876 CA ILE I 537 | −31.219 8.194 −94.659 1.00 66.79 | C C | |
| ATOM | 10877 CB ILE I 537 | −29.908 8.850 −94.204 1.00 64.76 | C C | |
| ATOM | 10878 CG1 ILE I 537 | −30.176 10.251 −93.649 1.00 66.92 | C C | |
| ATOM | 10879 CD1 ILE I 537 | −29.017 10.829 −92.869 1.00 70.83 | C C | |
| ATOM | 10880 CG2 ILE I 537 | −28.926 8.905 −95.354 1.00 51.02 | C C | |
| ATOM | 10881 C ILE I 537 | −30.900 6.892 −95.397 1.00 74.94 | C C | |
| ATOM | 10882 O ILE I 537 | −30.628 6.898 −96.599 1.00 97.16 | C O | |
| ATOM | 10883 N LYS I 538 | −30.959 5.777 −94.675 1.00 75.09 | C N | |
| ATOM | 10884 CA LYS I 538 | −30.769 4.462 −95.275 1.00 90.28 | C | C |
| ATOM | 10885 CB LYS I 538 | −30.228 3.472 −94.240 1.00 93.73 | C | C |
| ATOM | 10886 CG LYS I 538 | −29.538 2.255 −94.850 1.00 96.60 | C | C |
| ATOM | 10887 CD LYS I 538 | −29.040 1.288 −93.786 1.00 95.37 | C | C |
| ATOM | 10888 CE LYS I 538 | −28.132 0.235 −94.399 1.00 100.63 | C | C |
| ATOM | 10889 NZ LYS I 538 | −27.652 −0.753 −93.397 1.00 99.58 | C | N |
| ATOM | 10890 C LYS I 538 | −32.062 3.927 −95.884 1.00102.20 | C | C |
| ATOM | 10891 O LYS I 538 | −32.083 2.839 −96.461 1.00112.11 | C | O |
| ATOM | 10892 N LYS I 539 | −33.126 4.722 −95.795 1.00105.15 | C | N |
| ATOM | 10893 CA LYS I 539 | −34.422 4.355 −96.360 1.00105.65 | C | C |
| ATOM | 10894 CB LYS I 539 | −35.548 4.745 −95.398 1.00110.12 | C | C |
| ATOM | 10895 CG LYS I 539 | −36.926 4.269 −95.823 1.00113.31 | C | C |
| ATOM | 10896 CD LYS I 539 | −38.013 4.785 −94.889 1.00114.26 | C | C |
| ATOM | 10897 CE LYS I 539 | −39.395 4.373 −95.378 1.00118.39 | C | C |
| ATOM | 10898 NZ LYS I 539 | −40.449 4.593 −94.352 1.00121.77 | C | N |
| ATOM | 10899 C LYS I 539 | −34.646 5.008 −97.726 1.00108.88 | C | C |
| ATOM | 10900 O LYS I 539 | −35.717 4.876 −98.321 1.00110.77 | C | O |
| ATOM | 10901 N LEU I 540 | −33.612 5.675 −98.232 1.00111.50 | C | N |
| ATOM | 10902 CA LEU I 540 | −33.668 6.309 −99.544 1.00110.31 | C | C |
| ATOM | 10903 CB LEU I 540 | −33.272 7.777 −99.435 1.00101.19 | C | C |
| ATOM | 10904 CG LEU I 540 | −34.219 8.611 −98.581 1.00 94.26 | C | C |
| ATOM | 10905 CD1 LEU I 540 | −34.093 10.066 −98.978 1.00 86.40 | C | C |
| ATOM | 10906 CD2 LEU I 540 | −35.646 8.133 −98.783 1.00 84.54 | C | C |
| ATOM | 10907 C LEU I 540 | −32.738 5.601 −100.513 1.00118.37 | C | C |
| ATOM | 10908 O LEU I 540 | −32.526 6.059 −101.634 1.00116.71 | C | O |
| ATOM | 10909 N ILE I 541 | −32.163 4.493 −100.056 1.00130.80 | C | N |
| ATOM | 10910 CA ILE I 541 | −31.273 3.686 −100.882 1.00140.48 | C | C |
| ATOM | 10911 CB ILE I 541 | −29.821 4.210 −100.840 1.00138.99 | C | C |
| ATOM | 10912 CG1 ILE I 541 | −29.770 5.686 −101.240 1.00133.30 | C | C |
| ATOM | 10913 CD1 ILE I 541 | −30.650 6.027 −102.420 1.00136.26 | C | C |
| ATOM | 10914 CG2 ILE I 541 | −28.924 3.372 −101.744 1.00136.12 | C | C |
| ATOM | 10915 C ILE I 541 | −31.289 2.233 −100.426 1.00144.97 | C | C |
| ATOM | 10916 O ILE I 541 | −30.938 1.333 −101.188 1.00145.83 | C | O |
| ATOM | 10917 N GLY I 542 | −31.724 2.004 −99.191 1.00148.77 | C | N |
| ATOM | 10918 CA GLY I 542 | −31.789 0.655 −98.645 1.00153.58 | C | C |
| ATOM | 10919 C GLY I 542 | −33.208 0.136 −98.534 1.00160.45 | C | C |
| ATOM | 10920 O GLY I 542 | −34.109 0.602 −99.233 1.00163.41 | C | O |
| ATOM | 10921 N GLU I 543 | −33.412 −0.799 −97.611 1.00163.83 | C | N |
| ATOM | 10922 CA GLU I 543 | −34.718 −1.409 −97.392 1.00165.52 | C | C |
| ATOM | 10923 CB GLU I 543 | −34.576 −2.673 −96.538 1.00158.94 | C | C |
| ATOM | 10928 C GLU I 543 | −35.680 −0.430 −96.729 1.00168.27 | C | C |
| ATOM | 10929 O GLU I 543 | −35.373 0.753 −96.584 1.00167.37 | C | O |
| ATOM | 10930 C1 NAG J1535 | 24.849 −25.592 34.903 1.00 72.96 | C | |
| ATOM | 10931 C2 NAG J1535 | 24.818 −27.046 34.438 1.00 83.63 | C | |
| ATOM | 10932 N2 NAG J1535 | 23.774 −27.757 35.160 1.00 85.81 | N | |
| ATOM | 10933 C7 NAG J1535 | 23.087 −28.774 34.642 1.00 87.77 | C | |
| ATOM | 10934 O7 NAG J1535 | 23.376 −29.307 33.573 1.00 89.34 | O | |
| ATOM | 10935 C8 NAG J1535 | 21.991 −29.339 35.498 1.00 86.84 | C | |
| ATOM | 10936 C3 NAG J1535 | 26.183 −27.682 34.695 1.00 85.86 | C | |
| ATOM | 10937 O3 NAG J1535 | 27.009 −27.488 33.569 1.00 84.14 | O | |
| ATOM | 10938 C4 NAG J1535 | 26.823 −27.025 35.913 1.00 88.88 | C | |
| ATOM | 10939 O4 NAG J1535 | 27.730 −27.923 36.530 1.00 96.14 | O | |
| ATOM | 10940 C5 NAG J1535 | 25.692 −26.643 36.863 1.00 85.57 | C | |
| ATOM | 10941 C6 NAG J1535 | 26.185 −26.278 38.259 1.00 85.54 | C | |
| ATOM | 10942 O6 NAG J1535 | 27.307 −25.431 38.159 1.00 85.75 | O | |
| ATOM | 10943 O5 NAG J1535 | 24.941 −25.575 36.317 1.00 79.39 | O | |
| ATOM | 10944 C1 NAG J1536 | 29.076 −27.393 36.512 1.00101.26 | C | |
| ATOM | 10945 C2 NAG J1536 | 29.807 −27.737 37.810 1.00103.37 | C | |
| ATOM | 10946 N2 NAG J1536 | 30.222 −26.531 38.504 1.00104.36 | N | |
| ATOM | 10947 C7 NAG J1536 | 30.339 −26.483 39.830 1.00104.07 | C | |
| ATOM | 10948 O7 NAG J1536 | 30.062 −27.429 40.566 1.00103.82 | O | |
| ATOM | 10949 C8 NAG J1536 | 30.810 −25.183 40.413 1.00103.07 | C | |

APPENDIX-continued (APPENDIX discloses SEQ ID NOS 29-32, 29-32 and 29-32, respectively, in order of appearance)

| | | | | | | | | | | |
|---|---|---|---|---|---|---|---|---|---|---|
| ATOM | 10950 | C3 | NAG | J1536 | 31.013 | −28.638 | 37.568 | 1.00 | 104.12 | C |
| ATOM | 10951 | O3 | NAG | J1536 | 31.411 | −29.224 | 38.788 | 1.00 | 103.63 | O |
| ATOM | 10952 | C4 | NAG | J1536 | 30.689 | −29.737 | 36.565 | 1.00 | 104.68 | C |
| ATOM | 10953 | O4 | NAG | J1536 | 31.865 | −30.456 | 36.266 | 1.00 | 105.46 | O |
| ATOM | 10954 | C5 | NAG | J1536 | 30.104 | −29.166 | 35.277 | 1.00 | 104.39 | C |
| ATOM | 10955 | C6 | NAG | J1536 | 28.856 | −29.920 | 34.835 | 1.00 | 104.32 | C |
| ATOM | 10956 | O6 | NAG | J1536 | 28.929 | −30.178 | 33.450 | 1.00 | 104.22 | O |
| ATOM | 10957 | O5 | NAG | J1536 | 29.840 | −27.780 | 35.384 | 1.00 | 103.22 | O |
| ATOM | 10958 | C1 | NAG | J1545 | −15.969 | −4.075 | −43.033 | 1.00 | 56.85 | C |
| ATOM | 10959 | C2 | NAG | J1545 | −16.105 | −5.488 | −42.448 | 1.00 | 66.44 | C |
| ATOM | 10960 | N2 | NAG | J1545 | −14.794 | −6.111 | −42.415 | 1.00 | 69.47 | N |
| ATOM | 10961 | C7 | NAG | J1545 | −13.913 | −5.853 | −41.453 | 1.00 | 72.43 | C |
| ATOM | 10962 | O7 | NAG | J1545 | −14.178 | −5.152 | −40.481 | 1.00 | 73.31 | O |
| ATOM | 10963 | C8 | NAG | J1545 | −12.558 | −6.484 | −41.587 | 1.00 | 72.22 | C |
| ATOM | 10964 | C3 | NAG | J1545 | −17.084 | −6.379 | −43.216 | 1.00 | 68.81 | C |
| ATOM | 10965 | O3 | NAG | J1545 | −17.443 | −7.508 | −42.449 | 1.00 | 68.22 | O |
| ATOM | 10966 | C4 | NAG | J1545 | −18.314 | −5.557 | −43.561 | 1.00 | 71.19 | C |
| ATOM | 10967 | O4 | NAG | J1545 | −19.356 | −6.295 | −44.161 | 1.00 | 76.87 | O |
| ATOM | 10968 | C5 | NAG | J1545 | −17.827 | −4.416 | −44.429 | 1.00 | 67.79 | C |
| ATOM | 10969 | C6 | NAG | J1545 | −18.955 | −3.707 | −45.166 | 1.00 | 67.71 | C |
| ATOM | 10970 | O6 | NAG | J1545 | −19.545 | −2.754 | −44.311 | 1.00 | 67.33 | O |
| ATOM | 10971 | O5 | NAG | J1545 | −17.181 | −3.544 | −43.536 | 1.00 | 62.66 | O |
| ATOM | 10972 | C1 | NAG | J1546 | −20.251 | −6.690 | −43.101 | 1.00 | 83.18 | C |
| ATOM | 10973 | C2 | NAG | J1546 | −21.616 | −5.983 | −43.168 | 1.00 | 85.51 | C |
| ATOM | 10974 | N2 | NAG | J1546 | −21.766 | −5.147 | −41.990 | 1.00 | 84.12 | N |
| ATOM | 10975 | C7 | NAG | J1546 | −21.679 | −3.817 | −41.993 | 1.00 | 82.64 | C |
| ATOM | 10976 | O7 | NAG | J1546 | −21.413 | −3.148 | −42.990 | 1.00 | 81.92 | O |
| ATOM | 10977 | C8 | NAG | J1546 | −21.866 | −3.149 | −40.663 | 1.00 | 80.96 | C |
| ATOM | 10978 | C3 | NAG | J1546 | −22.846 | −6.884 | −43.261 | 1.00 | 87.47 | C |
| ATOM | 10979 | O3 | NAG | J1546 | −23.679 | −6.482 | −44.325 | 1.00 | 87.96 | O |
| ATOM | 10980 | C4 | NAG | J1546 | −22.495 | −8.356 | −43.377 | 1.00 | 87.61 | C |
| ATOM | 10981 | O4 | NAG | J1546 | −23.635 | −9.125 | −43.071 | 1.00 | 86.77 | O |
| ATOM | 10982 | C5 | NAG | J1546 | −21.399 | −8.665 | −42.371 | 1.00 | 87.12 | C |
| ATOM | 10983 | C6 | NAG | J1546 | −21.176 | −10.167 | −42.218 | 1.00 | 87.02 | C |
| ATOM | 10984 | O6 | NAG | J1546 | −20.698 | −10.439 | −40.920 | 1.00 | 86.44 | O |
| ATOM | 10985 | O5 | NAG | J1546 | −20.211 | −8.081 | −42.842 | 1.00 | 85.80 | O |
| ATOM | 10986 | C1 | NAG | J1525 | 19.621 | 34.609 | −15.280 | 1.00 | 72.96 | C |
| ATOM | 10987 | C2 | NAG | J1525 | 20.014 | 34.434 | −16.749 | 1.00 | 83.63 | C |
| ATOM | 10988 | N2 | NAG | J1525 | 21.459 | 34.306 | −16.817 | 1.00 | 85.81 | N |
| ATOM | 10989 | C7 | NAG | J1525 | 22.104 | 33.549 | −17.705 | 1.00 | 87.77 | C |
| ATOM | 10990 | O7 | NAG | J1525 | 21.559 | 33.036 | −18.682 | 1.00 | 89.34 | O |
| ATOM | 10991 | C8 | NAG | J1525 | 23.597 | 33.493 | −17.560 | 1.00 | 86.84 | C |
| ATOM | 10992 | C3 | NAG | J1525 | 19.546 | 35.624 | −17.590 | 1.00 | 85.86 | C |
| ATOM | 10993 | O3 | NAG | J1525 | 18.248 | 35.381 | −18.082 | 1.00 | 84.14 | O |
| ATOM | 10994 | C4 | NAG | J1525 | 19.548 | 36.890 | −16.742 | 1.00 | 88.88 | C |
| ATOM | 10995 | O4 | NAG | J1525 | 19.800 | 38.032 | −17.545 | 1.00 | 96.14 | O |
| ATOM | 10996 | C5 | NAG | J1525 | 20.649 | 36.717 | −15.706 | 1.00 | 85.57 | C |
| ATOM | 10997 | C6 | NAG | J1525 | 20.983 | 38.020 | −14.991 | 1.00 | 85.54 | C |
| ATOM | 10998 | O6 | NAG | J1525 | 19.792 | 38.678 | −14.623 | 1.00 | 85.75 | O |
| ATOM | 10999 | O5 | NAG | J1525 | 20.253 | 35.757 | −14.753 | 1.00 | 79.39 | O |
| ATOM | 11000 | C1 | NAG | J1526 | 18.686 | 38.953 | −17.492 | 1.00 | 101.26 | C |
| ATOM | 11001 | C2 | NAG | J1526 | 19.171 | 40.401 | −17.403 | 1.00 | 103.37 | C |
| ATOM | 11002 | N2 | NAG | J1526 | 18.643 | 41.051 | −16.216 | 1.00 | 104.36 | N |
| ATOM | 11003 | C7 | NAG | J1526 | 19.298 | 42.039 | −15.609 | 1.00 | 104.07 | C |
| ATOM | 11004 | O7 | NAG | J1526 | 20.406 | 42.432 | −15.972 | 1.00 | 103.82 | O |
| ATOM | 11005 | C8 | NAG | J1526 | 18.641 | 42.635 | −14.399 | 1.00 | 103.07 | C |
| ATOM | 11006 | C3 | NAG | J1526 | 18.781 | 41.209 | −18.636 | 1.00 | 104.12 | C |
| ATOM | 11007 | O3 | NAG | J1526 | 19.553 | 42.388 | −18.684 | 1.00 | 103.63 | O |
| ATOM | 11008 | C4 | NAG | J1526 | 19.007 | 40.409 | −19.911 | 1.00 | 104.68 | C |
| ATOM | 11009 | O4 | NAG | J1526 | 18.509 | 41.133 | −21.014 | 1.00 | 105.46 | O |
| ATOM | 11010 | C5 | NAG | J1526 | 18.320 | 39.050 | −19.846 | 1.00 | 104.39 | C |
| ATOM | 11011 | C6 | NAG | J1526 | 19.260 | 37.926 | −20.265 | 1.00 | 104.32 | C |
| ATOM | 11012 | O6 | NAG | J1526 | 18.612 | 37.103 | −21.209 | 1.00 | 104.22 | O |
| ATOM | 11013 | O5 | NAG | J1526 | 17.776 | 38.800 | −18.564 | 1.00 | 103.22 | O |
| ATOM | 11014 | C1 | NAG | K1535 | 41.248 | 18.154 | 31.115 | 1.00 | 72.96 | C |
| ATOM | 11015 | C2 | NAG | K1535 | 41.855 | 19.316 | 30.338 | 1.00 | 83.63 | C |
| ATOM | 11016 | N2 | NAG | K1535 | 43.088 | 18.851 | 29.728 | 1.00 | 85.81 | N |
| ATOM | 11017 | C7 | NAG | K1535 | 43.469 | 19.184 | 28.498 | 1.00 | 87.77 | C |
| ATOM | 11018 | O7 | NAG | K1535 | 42.908 | 20.051 | 27.830 | 1.00 | 89.34 | O |
| ATOM | 11019 | C8 | NAG | K1535 | 44.735 | 18.550 | 28.004 | 1.00 | 86.84 | C |
| ATOM | 11020 | C3 | NAG | K1535 | 42.118 | 20.499 | 31.270 | 1.00 | 85.86 | C |
| ATOM | 11021 | O3 | NAG | K1535 | 40.974 | 21.322 | 31.315 | 1.00 | 84.14 | O |
| ATOM | 11022 | C4 | NAG | K1535 | 42.448 | 20.012 | 32.677 | 1.00 | 88.88 | C |
| ATOM | 11023 | O4 | NAG | K1535 | 43.310 | 20.930 | 33.331 | 1.00 | 96.14 | O |
| ATOM | 11024 | C5 | NAG | K1535 | 43.123 | 18.655 | 32.535 | 1.00 | 85.57 | C |
| ATOM | 11025 | C6 | NAG | K1535 | 43.778 | 18.188 | 33.832 | 1.00 | 85.54 | C |
| ATOM | 11026 | O6 | NAG | K1535 | 43.027 | 18.627 | 34.942 | 1.00 | 85.75 | O |

APPENDIX-continued (APPENDIX discloses SEQ ID NOS 29-32, 29-32 and 29-32, respectively, in order of appearance)

| | | | | | | | | | | |
|---|---|---|---|---|---|---|---|---|---|---|
| ATOM | 11027 | O5 | NAG | K1535 | 42.190 | 17.694 | 32.074 | 1.00 | 79.39 | O |
| ATOM | 11028 | C1 | NAG | K1536 | 42.680 | 21.487 | 34.509 | 1.00 | 101.26 | C |
| ATOM | 11029 | C2 | NAG | K1536 | 43.698 | 21.677 | 35.636 | 1.00 | 103.37 | C |
| ATOM | 11030 | N2 | NAG | K1536 | 43.310 | 20.938 | 36.825 | 1.00 | 104.36 | N |
| ATOM | 11031 | C7 | NAG | K1536 | 44.214 | 20.505 | 37.702 | 1.00 | 104.07 | C |
| ATOM | 11032 | O7 | NAG | K1536 | 45.425 | 20.656 | 37.545 | 1.00 | 103.82 | O |
| ATOM | 11033 | C8 | NAG | K1536 | 43.689 | 19.781 | 38.906 | 1.00 | 103.07 | C |
| ATOM | 11034 | C3 | NAG | K1536 | 43.900 | 23.146 | 35.994 | 1.00 | 104.12 | C |
| ATOM | 11035 | O3 | NAG | K1536 | 45.102 | 23.286 | 36.719 | 1.00 | 103.63 | O |
| ATOM | 11036 | C4 | NAG | K1536 | 43.966 | 24.019 | 34.748 | 1.00 | 104.68 | C |
| ATOM | 11037 | O4 | NAG | K1536 | 43.988 | 25.378 | 35.126 | 1.00 | 105.46 | O |
| ATOM | 11038 | C5 | NAG | K1536 | 42.782 | 23.769 | 33.821 | 1.00 | 104.39 | C |
| ATOM | 11039 | C6 | NAG | K1536 | 43.229 | 23.554 | 32.380 | 1.00 | 104.32 | C |
| ATOM | 11040 | O6 | NAG | K1536 | 42.483 | 24.396 | 31.530 | 1.00 | 104.22 | O |
| ATOM | 11041 | O5 | NAG | K1536 | 41.980 | 22.692 | 34.267 | 1.00 | 103.22 | O |
| ATOM | 11042 | C1 | NAG | K1545 | 2.615 | 1.983 | −49.407 | 1.00 | 56.85 | C |
| ATOM | 11043 | C2 | NAG | K1545 | 2.918 | 2.869 | −50.621 | 1.00 | 66.44 | C |
| ATOM | 11044 | N2 | NAG | K1545 | 1.785 | 3.731 | −50.894 | 1.00 | 69.47 | N |
| ATOM | 11045 | C7 | NAG | K1545 | 1.517 | 4.812 | −50.168 | 1.00 | 72.43 | C |
| ATOM | 11046 | O7 | NAG | K1545 | 2.154 | 5.121 | −49.163 | 1.00 | 73.31 | O |
| ATOM | 11047 | C8 | NAG | K1545 | 0.302 | 5.589 | −50.579 | 1.00 | 72.22 | C |
| ATOM | 11048 | C3 | NAG | K1545 | 3.247 | 2.088 | −51.890 | 1.00 | 68.81 | C |
| ATOM | 11049 | O3 | NAG | K1545 | 3.890 | 2.929 | −52.817 | 1.00 | 68.22 | O |
| ATOM | 11050 | C4 | NAG | K1545 | 4.146 | 0.927 | −51.513 | 1.00 | 71.19 | C |
| ATOM | 11051 | O4 | NAG | K1545 | 4.688 | 0.219 | −52.606 | 1.00 | 76.87 | O |
| ATOM | 11052 | C5 | NAG | K1545 | 3.310 | 0.066 | −50.596 | 1.00 | 67.79 | C |
| ATOM | 11053 | C6 | NAG | K1545 | 3.861 | −1.348 | −50.446 | 1.00 | 67.71 | C |
| ATOM | 11054 | O6 | NAG | K1545 | 4.940 | −1.351 | −49.538 | 1.00 | 67.33 | O |
| ATOM | 11055 | O5 | NAG | K1545 | 3.330 | 0.760 | −49.372 | 1.00 | 62.66 | O |
| ATOM | 11056 | C1 | NAG | K1546 | 5.996 | 0.777 | −52.858 | 1.00 | 83.18 | C |
| ATOM | 11057 | C2 | NAG | K1546 | 7.149 | −0.188 | −52.527 | 1.00 | 85.51 | C |
| ATOM | 11058 | N2 | NAG | K1546 | 7.911 | 0.336 | −51.403 | 1.00 | 84.12 | N |
| ATOM | 11059 | C7 | NAG | K1546 | 8.044 | −0.298 | −50.234 | 1.00 | 82.64 | C |
| ATOM | 11060 | O7 | NAG | K1546 | 7.581 | −1.414 | −50.007 | 1.00 | 81.92 | O |
| ATOM | 11061 | C8 | NAG | K1546 | 8.880 | 0.392 | −49.197 | 1.00 | 80.96 | C |
| ATOM | 11062 | C3 | NAG | K1546 | 8.093 | −0.539 | −53.684 | 1.00 | 87.47 | C |
| ATOM | 11063 | O3 | NAG | K1546 | 8.280 | −1.934 | −53.775 | 1.00 | 87.96 | O |
| ATOM | 11064 | C4 | NAG | K1546 | 7.594 | 0.007 | −55.013 | 1.00 | 87.61 | C |
| ATOM | 11065 | O4 | NAG | K1546 | 8.586 | −0.124 | −56.008 | 1.00 | 86.77 | O |
| ATOM | 11066 | C5 | NAG | K1546 | 7.269 | 1.469 | −54.777 | 1.00 | 87.12 | C |
| ATOM | 11067 | C6 | NAG | K1546 | 7.145 | 2.266 | −56.074 | 1.00 | 87.02 | C |
| ATOM | 11068 | O6 | NAG | K1546 | 7.707 | 3.548 | −55.896 | 1.00 | 86.44 | O |
| ATOM | 11069 | O5 | NAG | K1546 | 6.050 | 1.508 | −54.073 | 1.00 | 85.80 | O |
| ATOM | 11070 | C1 | NAG | K1525 | −29.090 | 1.326 | 0.431 | 1.00 | 56.85 | C |
| ATOM | 11071 | C2 | NAG | K1525 | −30.509 | 1.450 | 1.026 | 1.00 | 66.44 | C |
| ATOM | 11072 | N2 | NAG | K1525 | −30.921 | 0.195 | 1.623 | 1.00 | 69.47 | N |
| ATOM | 11073 | C7 | NAG | K1525 | −30.381 | −0.257 | 2.752 | 1.00 | 72.43 | C |
| ATOM | 11074 | O7 | NAG | K1525 | −29.481 | 0.332 | 3.347 | 1.00 | 73.31 | O |
| ATOM | 11075 | C8 | NAG | K1525 | −30.965 | −1.518 | 3.317 | 1.00 | 72.22 | C |
| ATOM | 11076 | C3 | NAG | K1525 | −31.621 | 1.959 | 0.102 | 1.00 | 68.81 | C |
| ATOM | 11077 | O3 | NAG | K1525 | −32.692 | 2.482 | 0.855 | 1.00 | 68.22 | O |
| ATOM | 11078 | C4 | NAG | K1525 | −31.056 | 3.022 | −0.817 | 1.00 | 71.19 | C |
| ATOM | 11079 | O4 | NAG | K1525 | −32.040 | 3.689 | −1.591 | 1.00 | 76.87 | O |
| ATOM | 11080 | C5 | NAG | K1525 | −30.031 | 2.269 | −1.642 | 1.00 | 67.79 | C |
| ATOM | 11081 | C6 | NAG | K1525 | −29.635 | 3.028 | −2.906 | 1.00 | 67.71 | C |
| ATOM | 11082 | O6 | NAG | K1525 | −28.857 | 4.152 | −2.561 | 1.00 | 67.33 | O |
| ATOM | 11083 | O5 | NAG | K1525 | −28.906 | 2.013 | −0.814 | 1.00 | 62.66 | O |
| ATOM | 11084 | C1 | NAG | K1526 | −32.430 | 4.903 | −0.902 | 1.00 | 83.18 | C |
| ATOM | 11085 | C2 | NAG | K1526 | −31.984 | 6.181 | −1.635 | 1.00 | 85.51 | C |
| ATOM | 11086 | N2 | NAG | K1526 | −30.942 | 6.832 | −0.859 | 1.00 | 84.12 | N |
| ATOM | 11087 | C7 | NAG | K1526 | −29.678 | 6.943 | −1.267 | 1.00 | 82.64 | C |
| ATOM | 11088 | O7 | NAG | K1526 | −29.276 | 6.528 | −2.353 | 1.00 | 81.92 | O |
| ATOM | 11089 | C8 | NAG | K1526 | −28.739 | 7.632 | −0.321 | 1.00 | 80.96 | C |
| ATOM | 11090 | C3 | NAG | K1526 | −33.070 | 7.210 | −1.965 | 1.00 | 87.47 | C |
| ATOM | 11091 | O3 | NAG | K1526 | −32.990 | 7.586 | −3.320 | 1.00 | 87.96 | O |
| ATOM | 11092 | C4 | NAG | K1526 | −34.468 | 6.712 | −1.644 | 1.00 | 87.61 | C |
| ATOM | 11093 | O4 | NAG | K1526 | −35.385 | 7.783 | −1.653 | 1.00 | 86.77 | O |
| ATOM | 11094 | C5 | NAG | K1526 | −34.395 | 6.107 | −0.257 | 1.00 | 87.12 | C |
| ATOM | 11095 | C6 | NAG | K1526 | −35.779 | 5.918 | 0.354 | 1.00 | 87.02 | C |
| ATOM | 11096 | O6 | NAG | K1526 | −35.724 | 6.194 | 1.736 | 1.00 | 86.44 | O |
| ATOM | 11097 | O5 | NAG | K1526 | −33.754 | 4.862 | −0.395 | 1.00 | 85.80 | O |
| ATOM | 11098 | C1 | NAG | L1535 | −2.070 | 11.341 | 45.870 | 1.00 | 72.96 | C |
| ATOM | 11099 | C2 | NAG | L1535 | −3.565 | 11.622 | 45.740 | 1.00 | 83.63 | C |
| ATOM | 11100 | N2 | NAG | L1535 | −3.793 | 13.060 | 45.821 | 1.00 | 85.81 | N |
| ATOM | 11101 | C7 | NAG | L1535 | −4.706 | 13.721 | 45.104 | 1.00 | 87.77 | C |
| ATOM | 11102 | O7 | NAG | L1535 | −5.570 | 13.168 | 44.424 | 1.00 | 89.34 | O |
| ATOM | 11103 | C8 | NAG | L1535 | −4.727 | 15.213 | 45.270 | 1.00 | 86.84 | C |

APPENDIX-continued (APPENDIX discloses SEQ ID NOS 29-32, 29-32 and 29-32, respectively, in order of appearance)

| | | | |
|---|---|---|---|
| ATOM | 11104 C3 NAG L1535 | −4.303 10.883 46.855 1.00 85.86 | C |
| ATOM | 11105 O3 NAG L1535 | −4.575 9.563 46.441 1.00 84.14 | O |
| ATOM | 11106 C4 NAG L1535 | −3.441 10.862 48.115 1.00 88.88 | C |
| ATOM | 11107 O4 NAG L1535 | −4.260 10.849 49.273 1.00 96.14 | O |
| ATOM | 11108 C5 NAG L1535 | −2.549 12.100 48.077 1.00 85.57 | C |
| ATOM | 11109 C6 NAG L1535 | −1.872 12.404 49.410 1.00 85.54 | C |
| ATOM | 11110 O6 NAG L1535 | −1.282 11.235 49.931 1.00 85.75 | O |
| ATOM | 11111 O5 NAG L1535 | −1.585 11.956 47.052 1.00 79.39 | O |
| ATOM | 11112 C1 NAG L1536 | −4.061 9.626 50.020 1.00101.26 | C |
| ATOM | 11113 C2 NAG L1536 | −4.102 9.893 51.524 1.00103.37 | C |
| ATOM | 11114 N2 NAG L1536 | −2.863 9.461 52.140 1.00104.36 | N |
| ATOM | 11115 C7 NAG L1536 | −2.405 10.023 53.252 1.00104.07 | C |
| ATOM | 11116 O7 NAG L1536 | −2.958 10.972 53.807 1.00103.82 | O |
| ATOM | 11117 C8 NAG L1536 | −1.111 9.476 53.773 1.00103.07 | C |
| ATOM | 11118 C3 NAG L1536 | −5.265 9.179 52.199 1.00104.12 | C |
| ATOM | 11119 O3 NAG L1536 | −5.486 9.747 53.470 1.00103.63 | O |
| ATOM | 11120 C4 NAG L1536 | −6.532 9.306 51.370 1.00104.68 | C |
| ATOM | 11121 O4 NAG L1536 | −7.534 8.514 51.963 1.00105.46 | O |
| ATOM | 11122 C5 NAG L1536 | −6.309 8.841 49.937 1.00104.39 | C |
| ATOM | 11123 C6 NAG L1536 | −6.864 9.838 48.932 1.00104.32 | C |
| ATOM | 11124 O6 NAG L1536 | −7.576 9.132 47.943 1.00104.22 | O |
| ATOM | 11125 O5 NAG L1536 | −4.947 8.581 49.669 1.00103.22 | O |
| ATOM | 11126 C1 NAG L1545 | −11.652 16.132 −42.376 1.00 56.85 | C |
| ATOM | 11127 C2 NAG L1545 | −11.811 17.208 −43.449 1.00 66.44 | C |
| ATOM | 11128 N2 NAG L1545 | −10.485 17.531 −43.934 1.00 69.47 | N |
| ATOM | 11129 C7 NAG L1545 | −9.803 16.702 −44.718 1.00 72.43 | C |
| ATOM | 11130 O7 NAG L1545 | −10.291 15.689 −45.219 1.00 73.31 | O |
| ATOM | 11131 C8 NAG L1545 | −8.341 16.997 −44.865 1.00 72.22 | C |
| ATOM | 11132 C3 NAG L1545 | −12.475 18.463 −42.898 1.00 68.81 | C |
| ATOM | 11133 O3 NAG L1545 | −12.890 19.301 −43.953 1.00 68.22 | O |
| ATOM | 11134 C4 NAG L1545 | −13.667 18.017 −42.071 1.00 71.19 | C |
| ATOM | 11135 O4 NAG L1545 | −14.509 19.077 −41.672 1.00 76.87 | O |
| ATOM | 11136 C5 NAG L1545 | −13.113 17.218 −40.907 1.00 67.79 | C |
| ATOM | 11137 C6 NAG L1545 | −14.125 17.020 −39.786 1.00 67.71 | C |
| ATOM | 11138 O6 NAG L1545 | −15.086 16.069 −40.180 1.00 67.33 | O |
| ATOM | 11139 O5 NAG L1545 | −12.727 15.986 −41.467 1.00 62.66 | O |
| ATOM | 11140 C1 NAG L1546 | −15.574 19.184 −42.644 1.00 83.18 | C |
| ATOM | 11141 C2 NAG L1546 | −16.945 18.806 −42.055 1.00 85.51 | C |
| ATOM | 11142 N2 NAG L1546 | −17.436 17.613 −42.723 1.00 84.12 | N |
| ATOM | 11143 C7 NAG L1546 | −17.522 16.433 −42.114 1.00 82.64 | C |
| ATOM | 11144 O7 NAG L1546 | −17.214 16.256 −40.937 1.00 81.92 | O |
| ATOM | 11145 C8 NAG L1546 | −18.068 15.302 −42.933 1.00 80.96 | C |
| ATOM | 11146 C3 NAG L1546 | −18.033 19.883 −42.093 1.00 87.47 | C |
| ATOM | 11147 O3 NAG L1546 | −18.679 19.995 −40.846 1.00 87.96 | O |
| ATOM | 11148 C4 NAG L1546 | −17.484 21.228 −42.533 1.00 87.61 | C |
| ATOM | 11149 O4 NAG L1546 | −18.538 22.132 −42.784 1.00 86.77 | O |
| ATOM | 11150 C5 NAG L1546 | −16.723 20.935 −43.810 1.00 87.12 | C |
| ATOM | 11151 C6 NAG L1546 | −16.525 22.183 −44.663 1.00 87.02 | C |
| ATOM | 11152 O6 NAG L1546 | −17.041 21.939 −45.954 1.00 86.44 | O |
| ATOM | 11153 O5 NAG L1546 | −15.492 20.356 −43.444 1.00 85.80 | O |
| ATOM | 11154 C1 NAG L1525 | 21.793 −26.723 −18.244 1.00 56.85 | C |
| ATOM | 11155 C2 NAG L1525 | 22.365 −27.060 −19.634 1.00 66.44 | C |
| ATOM | 11156 N2 NAG L1525 | 22.402 −25.862 −20.460 1.00 69.47 | N |
| ATOM | 11157 C7 NAG L1525 | 23.351 −24.934 −20.342 1.00 72.43 | C |
| ATOM | 11158 O7 NAG L1525 | 24.279 −25.026 −19.540 1.00 73.31 | O |
| ATOM | 11159 C8 NAG L1525 | 23.280 −23.766 −21.282 1.00 72.22 | C |
| ATOM | 11160 C3 NAG L1525 | 21.624 −28.181 −20.369 1.00 68.81 | C |
| ATOM | 11161 O3 NAG L1525 | 22.407 −28.687 −21.427 1.00 68.22 | O |
| ATOM | 11162 C4 NAG L1525 | 21.308 −29.275 −19.364 1.00 71.19 | C |
| ATOM | 11163 O4 NAG L1525 | 20.761 −30.454 −19.918 1.00 76.87 | O |
| ATOM | 11164 C5 NAG L1525 | 20.389 −28.631 −18.348 1.00 67.79 | C |
| ATOM | 11165 C6 NAG L1525 | 19.627 −29.660 −17.520 1.00 67.71 | C |
| ATOM | 11166 O6 NAG L1525 | 20.442 −30.144 −16.478 1.00 67.33 | O |
| ATOM | 11167 O5 NAG L1525 | 21.225 −27.824 −17.551 1.00 62.66 | O |
| ATOM | 11168 C1 NAG L1526 | 21.846 −31.384 −20.124 1.00 83.18 | C |
| ATOM | 11169 C2 NAG L1526 | 21.792 −32.604 −19.182 1.00 85.51 | C |
| ATOM | 11170 N2 NAG L1526 | 22.928 −32.540 −18.274 1.00 84.12 | N |
| ATOM | 11171 C7 NAG L1526 | 22.851 −32.639 −16.945 1.00 82.64 | C |
| ATOM | 11172 O7 NAG L1526 | 21.797 −32.785 −16.328 1.00 81.92 | O |
| ATOM | 11173 C8 NAG L1526 | 24.156 −32.563 −16.207 1.00 80.96 | C |
| ATOM | 11174 C3 NAG L1526 | 21.773 −33.981 −19.854 1.00 87.47 | C |
| ATOM | 11175 O3 NAG L1526 | 20.751 −34.790 −19.316 1.00 87.96 | O |
| ATOM | 11176 C4 NAG L1526 | 21.648 −33.901 −21.365 1.00 87.61 | C |
| ATOM | 11177 O4 NAG L1526 | 21.965 −35.150 −21.938 1.00 86.77 | O |

APPENDIX-continued

| (APPENDIX discloses SEQ ID NOS 29-32, 29-32 and 29-32, respectively, in order of appearance) | | | | | | | | | | |
|---|---|---|---|---|---|---|---|---|---|---|
| ATOM | 11178 | C5 | NAG | L1526 | 22.647 | −32.860 | −21.827 | 1.00 | 87.12 | C |
| ATOM | 11179 | C6 | NAG | L1526 | 22.903 | −32.944 | −23.327 | 1.00 | 87.02 | C |
| ATOM | 11180 | O6 | NAG | L1526 | 24.294 | −32.969 | −23.563 | 1.00 | 86.44 | O |
| ATOM | 11181 | O5 | NAG | L1526 | 22.108 | −31.604 | −21.499 | 1.00 | 85.80 | O |
| END | | | | | | | | | | |

END

The invention claimed is:

1. A nucleic acid encoding a respiratory syncytial virus (RSV)-F polypeptide comprising a substitution of an amino acid residue in a helix α1 corresponding to amino acid residues 145 to 157 of SEQ ID NO: 1 or 2 for a first cysteine residue and a substitution of an amino acid residue in a heptad-repeat C (HRC) region corresponding to amino acid residues 50 to 109 of SEQ ID NO: 1 or 2 for a second cysteine residue.

2. The nucleic acid of claim 1, wherein the amino acid residue in the helix α1 corresponds to position 145, 146, 147, 148, 149, 150, 151, 152, 153, 154, 155, 156, or 157 of SEQ ID NO: 1 or 2.

3. The nucleic acid of claim 2, wherein the amino acid residue in the helix α1 corresponds to position 148 of SEQ ID NO: 1 or 2.

4. The nucleic acid of claim 1 further comprising a disulfide bond between the first cysteine residue and the second cysteine residue.

5. A nucleic acid encoding a respiratory syncytial virus (RSV)-F polypeptide comprising a substitution of an amino acid residue at position 148 of SEQ ID NO: 1 or 2 for a first cysteine residue and a substitution of an amino acid residue in a heptad-repeat C (HRC) region corresponding to amino acid residues 50 to 109 of SEQ ID NO: 1 or 2 for a second cysteine residue.

6. A vector comprising the nucleic acid of claim 1.

7. A host cell comprising the vector of claim 6.

8. A vector comprising the nucleic acid of claim 5.

9. A host cell comprising the vector of claim 8.

* * * * *

SEQUENCE LISTING

```
<160> NUMBER OF SEQ ID NOS: 41

<210> SEQ ID NO 1
<211> LENGTH: 574
<212> TYPE: PRT
<213> ORGANISM: Human respiratory syncytial virus
<220> FEATURE:
<223> OTHER INFORMATION: /note="Human respiratory syncytial virus A2"

<400> SEQUENCE: 1

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Pro Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
```

```
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Ile Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Met Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570


<210> SEQ ID NO 2
<211> LENGTH: 574
<212> TYPE: PRT
<213> ORGANISM: Human respiratory syncytial virus
<220> FEATURE:
<223> OTHER INFORMATION: /note="Human respiratory syncytial virus
      subgroup B/strain 18537"

<400> SEQUENCE: 2

Met Glu Leu Leu Ile His Arg Ser Ser Ala Ile Phe Leu Thr Leu Ala
1               5                   10                  15

Val Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60
```

```
Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Arg Leu Leu Pro Ile Val Asn
        195                 200                 205

Gln Gln Ser Cys Arg Ile Ser Asn Ile Glu Thr Val Ile Glu Phe Gln
    210                 215                 220

Gln Met Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
```

```
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Ile Met Ile Thr
        515                 520                 525

Thr Ile Ile Ile Val Ile Ile Val Val Leu Leu Ser Leu Ile Ala Ile
    530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565                 570


<210> SEQ ID NO 3
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Gly Gly Ser Ala Gly Ser Gly His His His His His His
1               5                   10


<210> SEQ ID NO 4
<211> LENGTH: 537
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Cys Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Cys Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190
```

-continued

```
Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Gly Gly Ser Ala
        515                 520                 525

Gly Ser Gly His His His His His His
    530                 535
```

<210> SEQ ID NO 5
<211> LENGTH: 537
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 5

-continued

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Cys Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Cys Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
```

```
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Gly Gly Ser Ala
        515                 520                 525

Gly Ser Gly His His His His His His
    530                 535


<210> SEQ ID NO 6
<211> LENGTH: 537
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Cys Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Cys Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240
```

```
Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Gly Gly Ser Ala
        515                 520                 525

Gly Ser Gly His His His His His His
    530                 535
```

<210> SEQ ID NO 7
<211> LENGTH: 537
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 7

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45
```

-continued

```
Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Cys Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Cys Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
```

465 470 475 480

Leu Val Phe Pro Ser Asp Glu Phe Asp Ala Ser Ile Ser Gln Val Asn
485 490 495

Glu Lys Ile Asn Gln Ser Leu Ala Phe Ile Arg Lys Ser Asp Glu Leu
500 505 510

Leu His Asn Val Asn Ala Gly Lys Ser Thr Thr Asn Gly Gly Ser Ala
515 520 525

Gly Ser Gly His His His His His His
530 535

<210> SEQ ID NO 8
<211> LENGTH: 537
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 8

Met Glu Leu Leu Ile Leu Lys Ala Asn Ala Ile Thr Thr Ile Leu Thr
1 5 10 15

Ala Val Thr Phe Cys Phe Ala Ser Gly Gln Asn Ile Thr Glu Glu Phe
20 25 30

Tyr Gln Ser Thr Cys Ser Ala Val Ser Lys Gly Tyr Leu Ser Ala Leu
35 40 45

Arg Thr Gly Trp Tyr Thr Ser Val Ile Thr Ile Glu Leu Ser Asn Ile
50 55 60

Lys Glu Asn Lys Cys Asn Gly Thr Asp Ala Lys Val Lys Leu Ile Lys
65 70 75 80

Gln Glu Leu Asp Lys Tyr Lys Asn Ala Val Thr Glu Leu Gln Leu Leu
85 90 95

Met Gln Ser Thr Pro Ala Thr Asn Asn Arg Ala Arg Arg Glu Leu Pro
100 105 110

Arg Phe Met Asn Tyr Thr Leu Asn Asn Ala Lys Lys Thr Asn Val Thr
115 120 125

Leu Ser Lys Lys Arg Lys Arg Arg Phe Leu Gly Phe Leu Leu Gly Val
130 135 140

Gly Ser Ala Ile Ala Ser Gly Val Ala Val Ser Lys Val Leu His Leu
145 150 155 160

Glu Gly Glu Val Asn Lys Ile Cys Ser Ala Leu Leu Ser Thr Asn Lys
165 170 175

Ala Val Val Ser Leu Ser Asn Gly Val Ser Val Leu Thr Ser Lys Val
180 185 190

Leu Asp Leu Lys Asn Tyr Ile Asp Lys Gln Leu Leu Pro Ile Val Asn
195 200 205

Lys Gln Ser Cys Ser Ile Ser Asn Ile Glu Thr Val Ile Glu Phe Gln
210 215 220

Gln Lys Asn Asn Arg Leu Leu Glu Ile Thr Arg Glu Phe Ser Val Asn
225 230 235 240

Ala Gly Val Thr Thr Pro Val Ser Thr Tyr Met Leu Thr Asn Ser Glu
245 250 255

Leu Leu Ser Leu Ile Asn Asp Met Pro Ile Thr Asn Asp Gln Lys Lys
260 265 270

Leu Met Ser Asn Asn Val Gln Ile Val Arg Gln Gln Ser Tyr Ser Ile
275 280 285

```
Met Ser Ile Ile Lys Glu Glu Cys Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Gly Gly Ser Ala
        515                 520                 525

Gly Ser Gly His His His His His His
    530                 535
```

<210> SEQ ID NO 9
<211> LENGTH: 537
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 9

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95
```

-continued

```
Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Cys Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Cys Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Gly Gly Ser Ala
```

```
        515                 520                 525

Gly Ser Gly His His His His His His
    530                 535


<210> SEQ ID NO 10
<211> LENGTH: 489
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Ser Ala Ile Ala Ser Gly Val Ala
    130                 135                 140

Val Ser Lys Val Leu His Leu Glu Gly Glu Val Asn Lys Ile Lys Ser
145                 150                 155                 160

Ala Leu Leu Ser Thr Asn Lys Ala Val Val Ser Leu Ser Asn Gly Val
                165                 170                 175

Ser Val Leu Thr Ser Lys Val Leu Asp Leu Lys Asn Tyr Ile Asp Lys
            180                 185                 190

Gln Leu Leu Pro Ile Val Asn Lys Gln Ser Cys Ser Ile Ser Asn Ile
        195                 200                 205

Glu Thr Val Ile Glu Phe Gln Gln Lys Asn Asn Arg Leu Leu Glu Ile
    210                 215                 220

Thr Arg Glu Phe Ser Val Asn Ala Gly Val Thr Thr Pro Val Ser Thr
225                 230                 235                 240

Tyr Met Leu Thr Asn Ser Glu Leu Leu Ser Leu Ile Asn Asp Met Pro
                245                 250                 255

Ile Thr Asn Asp Gln Lys Lys Leu Met Ser Asn Asn Val Gln Ile Val
            260                 265                 270

Arg Gln Gln Ser Tyr Ser Ile Met Ser Ile Ile Lys Glu Glu Val Leu
        275                 280                 285

Ala Tyr Val Val Gln Leu Pro Leu Tyr Gly Val Ile Asp Thr Pro Cys
    290                 295                 300

Trp Lys Leu His Thr Ser Pro Leu Cys Thr Thr Asn Thr Lys Glu Gly
305                 310                 315                 320

Ser Asn Ile Cys Leu Thr Arg Thr Asp Arg Gly Trp Tyr Cys Asp Asn
                325                 330                 335
```

```
Ala Gly Ser Val Ser Phe Phe Pro Gln Ala Glu Thr Cys Lys Val Gln
            340                 345                 350

Ser Asn Arg Val Phe Cys Asp Thr Met Asn Ser Leu Thr Leu Pro Ser
        355                 360                 365

Glu Val Asn Leu Cys Asn Val Asp Ile Phe Asn Pro Lys Tyr Asp Cys
    370                 375                 380

Lys Ile Met Thr Ser Lys Thr Asp Val Ser Ser Ser Val Ile Thr Ser
385                 390                 395                 400

Leu Gly Ala Ile Val Ser Cys Tyr Gly Lys Thr Lys Cys Thr Ala Ser
                405                 410                 415

Asn Lys Asn Arg Gly Ile Ile Lys Thr Phe Ser Asn Gly Cys Asp Tyr
            420                 425                 430

Val Ser Asn Lys Gly Val Asp Thr Val Ser Val Gly Asn Thr Leu Tyr
        435                 440                 445

Tyr Val Asn Lys Gln Glu Gly Lys Ser Leu Tyr Val Lys Gly Glu Pro
    450                 455                 460

Ile Ile Asn Phe Tyr Asp Pro Leu Val Phe Pro Ser Gly Gly Ser Ala
465                 470                 475                 480

Gly Ser Gly His His His His His His
                485
```

<210> SEQ ID NO 11
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (2)..(2)
<223> OTHER INFORMATION: Any amino acid
<220> FEATURE:
<221> NAME/KEY: VARIANT
<222> LOCATION: (3)..(3)
<223> OTHER INFORMATION: /replace="Thr"
<220> FEATURE:
<221> NAME/KEY: misc_feature
<222> LOCATION: (3)..(3)
<223> OTHER INFORMATION: /note="Residue given in the sequence has no preference with respect to the annotation for said position"

<400> SEQUENCE: 11

```
Ala Xaa Ser
1
```

<210> SEQ ID NO 12
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 6xHis tag"

<400> SEQUENCE: 12

```
His His His His His His
1               5
```

<210> SEQ ID NO 13
<211> LENGTH: 534
<212> TYPE: PRT
<213> ORGANISM: Artificial Sequence -continued
<220> FEATURE:
<221> NAME/KEY: source
<223> OTHER INFORMATION: /note="Description of Artificial Sequence:
Synthetic polypeptide"

<400> SEQUENCE: 13

```
Met Gly Ser Arg Ser Ser Thr Arg Ile Pro Val Pro Leu Met Leu Thr
1               5                   10                  15

Val Arg Val Met Leu Ala Leu Ser Cys Val Cys Pro Thr Ser Ala Leu
            20                  25                  30

Asp Gly Arg Pro Leu Ala Ala Ala Gly Ile Val Val Thr Gly Asp Lys
        35                  40                  45

Ala Val Asn Ile Tyr Thr Ser Ser Gln Thr Gly Ser Ile Ile Ile Lys
    50                  55                  60

Leu Leu Pro Asn Met Pro Lys Asp Lys Glu Ala Cys Ala Lys Ala Pro
65                  70                  75                  80

Leu Glu Ala Tyr Asn Arg Thr Leu Thr Thr Leu Leu Thr Pro Leu Gly
                85                  90                  95

Asp Ser Ile Arg Arg Ile Gln Glu Ser Val Thr Thr Ser Gly Gly Gly
            100                 105                 110

Lys Gln Gly Arg Leu Ile Gly Ala Ile Ile Gly Phe Leu Gly Phe Leu
        115                 120                 125

Leu Gly Val Gly Ser Ala Ile Ala Ser Gly Val Ala Val Ser Lys Val
    130                 135                 140

Leu His Leu Glu Gly Glu Val Asn Lys Ile Lys Ser Ala Leu Leu Ser
145                 150                 155                 160

Thr Asn Lys Ala Val Val Ser Leu Ser Asn Gly Val Ser Val Leu Thr
                165                 170                 175

Ser Lys Val Leu Asp Leu Lys Asn Tyr Ile Asp Lys Gln Leu Leu Pro
            180                 185                 190

Ile Val Asn Lys Gln Ser Cys Ile Lys Ile Thr Gln Gln Val Gly Val
        195                 200                 205

Glu Leu Asn Leu Tyr Leu Thr Glu Leu Thr Thr Val Phe Gly Pro Gln
    210                 215                 220

Ile Thr Ser Pro Ala Leu Thr Gln Leu Thr Ile Gln Ala Leu Tyr Asn
225                 230                 235                 240

Leu Ala Gly Gly Asn Met Asp Tyr Leu Leu Thr Lys Leu Gly Val Gly
                245                 250                 255

Asn Asn Gln Leu Ser Ser Leu Ile Ser Ser Gly Leu Ile Thr Gly Asn
            260                 265                 270

Pro Ile Leu Tyr Asp Ser Gln Thr Gln Leu Leu Gly Ile Gln Val Thr
        275                 280                 285

Leu Pro Ser Val Gly Asn Leu Asn Asn Met Arg Ala Thr Tyr Leu Glu
    290                 295                 300

Thr Leu Ser Val Ser Thr Thr Lys Gly Phe Ala Ser Ala Leu Val Pro
305                 310                 315                 320

Lys Val Val Thr Gln Val Gly Ser Val Ile Glu Glu Leu Asp Thr Ser
                325                 330                 335

Tyr Cys Ile Glu Thr Asp Leu Asp Leu Tyr Cys Thr Arg Ile Val Thr
            340                 345                 350

Phe Pro Met Ser Pro Gly Ile Tyr Ser Cys Leu Ser Gly Asn Thr Ser
        355                 360                 365

Ala Cys Met Tyr Ser Lys Thr Glu Gly Ala Leu Thr Thr Pro Tyr Met
    370                 375                 380
```

-continued

```
Thr Leu Lys Gly Ser Val Ile Ala Asn Cys Lys Met Thr Thr Cys Arg
385                 390                 395                 400

Cys Ala Asp Pro Pro Gly Ile Ile Ser Gln Asn Tyr Gly Glu Ala Val
                405                 410                 415

Ser Leu Ile Asp Arg Gln Ser Cys Asn Ile Leu Ser Leu Asp Gly Ile
            420                 425                 430

Thr Leu Arg Leu Ser Gly Glu Phe Asp Ala Thr Tyr Gln Lys Asn Ile
        435                 440                 445

Ser Ile Gln Asp Ser Gln Val Ile Val Thr Gly Asn Leu Asp Ile Ser
    450                 455                 460

Thr Glu Leu Gly Asn Val Asn Asn Ser Ile Ser Asn Ala Leu Asp Lys
465                 470                 475                 480

Leu Glu Glu Ser Asn Ser Lys Leu Asp Lys Val Glu Asp Lys Ile Glu
                485                 490                 495

Glu Ile Leu Ser Lys Ile Tyr His Ile Glu Asn Glu Ile Ala Arg Ile
            500                 505                 510

Lys Lys Leu Ile Gly Glu Ala Gly Gly Pro Leu Val Pro Arg Gly Ser
        515                 520                 525

His His His His His His
    530


<210> SEQ ID NO 14
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Arg Ala Arg Lys
1


<210> SEQ ID NO 15
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Arg Ala Arg Gln
1


<210> SEQ ID NO 16
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Gln Ala Gln Asn
1


<210> SEQ ID NO 17
<211> LENGTH: 4
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 17

Ile Glu Gly Arg
1

<210> SEQ ID NO 18
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 18

Arg Lys Lys Lys
1

<210> SEQ ID NO 19
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 19

Gln Asn Gln Asn
1

<210> SEQ ID NO 20
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 20

Gln Gln Gln Arg
1

<210> SEQ ID NO 21
<211> LENGTH: 64
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 21

```
Pro Leu Val Phe Pro Ser Asp Glu Phe Asp Ala Ser Ile Ser Gln Val
1               5                   10                  15

Asn Glu Lys Ile Asn Gln Ser Leu Ala Phe Ile Arg Lys Ser Asp Glu
            20                  25                  30

Leu Leu His Asn Val Asn Asp Lys Ile Glu Glu Ile Leu Ser Lys Ile
        35                  40                  45

Tyr His Ile Glu Asn Glu Ile Ala Arg Ile Lys Lys Leu Ile Gly Glu
    50                  55                  60
```

<210> SEQ ID NO 22
<211> LENGTH: 60
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 22

```
Pro Leu Val Phe Pro Ser Asp Glu Phe Asp Ala Ser Ile Ser Gln Val
1               5                   10                  15

Asn Glu Lys Ile Asn Gln Ser Leu Ala Phe Ile Arg Lys Ser Asp Glu
            20                  25                  30

Leu Leu His Asn Val Asn Glu Lys Phe His Gln Ile Glu Lys Glu Phe
        35                  40                  45

Ser Glu Val Glu Gly Arg Ile Gln Asp Leu Glu Lys
    50                  55                  60
```

<210> SEQ ID NO 23
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 23

```
Pro Leu Val Phe Pro Ser Asp Glu Phe Asp Ala Ser Ile Ser Gln Ile
1               5                   10                  15

Asn Glu Lys Ile Asn Gln Ile Leu Ala Phe Ile Arg Lys Ile Asp Glu
            20                  25                  30

Leu Leu His Asn Ile Asn
        35
```

<210> SEQ ID NO 24
<211> LENGTH: 67
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 24

```
Pro Leu Val Phe Pro Ser Asp Glu Phe Asp Ala Ser Ile Ser Gln Val
1               5                   10                  15

Asn Glu Lys Ile Asn Gln Ser Leu Ala Phe Ile Arg Lys Ser Asp Glu
            20                  25                  30

Leu Leu His Asn Val Asn Gly Ser Gly Tyr Ile Pro Glu Ala Pro Arg
        35                  40                  45

Asp Gly Gln Ala Tyr Val Arg Lys Asp Gly Glu Trp Val Leu Leu Ser
    50                  55                  60

Thr Phe Leu
65
```

<210> SEQ ID NO 25
<211> LENGTH: 73
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic polypeptide"

<400> SEQUENCE: 25

Pro Leu Val Phe Pro Ser Asp Glu Phe Asp Ala Ser Ile Ser Gln Val
1               5                   10                  15

Asn Glu Lys Ile Asn Gln Ser Leu Ala Phe Ile Arg Lys Ser Asp Glu
            20                  25                  30

Leu Leu His Asn Val Asn Asn Lys Asn Asp Asp Lys Gly Ser Gly Tyr
        35                  40                  45

Ile Pro Glu Ala Pro Arg Asp Gly Gln Ala Tyr Val Arg Lys Asp Gly
    50                  55                  60

Glu Trp Val Leu Leu Ser Thr Phe Leu
65                  70


<210> SEQ ID NO 26
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Leu Val Pro Arg
1


<210> SEQ ID NO 27
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Asp Asp Asp Asp Lys
1               5


<210> SEQ ID NO 28
<211> LENGTH: 498
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
```

-continued

```
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Gly Gly Ser Ala Gly Ser Gly His His His His
                485                 490                 495

His His
```

<210> SEQ ID NO 29
<211> LENGTH: 73
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 29

```
Gln Asn Ile Thr Glu Glu Phe Tyr Gln Ser Thr Cys Ser Ala Val Ser
1               5                   10                  15

Lys Gly Tyr Leu Ser Ala Leu Arg Thr Gly Trp Tyr Thr Ser Val Ile
            20                  25                  30

Thr Ile Glu Leu Ser Asn Ile Lys Glu Asn Lys Cys Asn Gly Thr Asp
        35                  40                  45

Ala Lys Val Lys Leu Ile Lys Gln Glu Leu Asp Lys Tyr Lys Asn Ala
    50                  55                  60

Val Thr Glu Leu Gln Leu Leu Met Gln
65                  70
```

<210> SEQ ID NO 30
<211> LENGTH: 189
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 30

```
Phe Leu Gly Phe Leu Leu Gly Val Gly Ser Ala Ile Ala Ser Gly Val
1               5                   10                  15

Ala Val Ser Lys Val Leu His Leu Glu Gly Glu Val Asn Lys Ile Lys
            20                  25                  30

Ser Ala Leu Leu Ser Thr Asn Lys Ala Val Val Ser Leu Ser Asn Gly
        35                  40                  45

Val Ser Val Leu Thr Ser Lys Val Leu Asp Leu Asn Asn Tyr Ile Asp
    50                  55                  60

Lys Gln Leu Leu Pro Ile Val Asn Lys Gln Ser Cys Ser Ile Ser Asn
65                  70                  75                  80

Ile Glu Thr Val Ile Glu Phe Gln Gln Lys Asn Asn Arg Leu Leu Glu
                85                  90                  95

Ile Thr Arg Glu Phe Ser Val Asn Ala Gly Val Thr Thr Pro Val Ser
            100                 105                 110

Thr Tyr Met Leu Thr Asn Ser Glu Leu Leu Ser Leu Ile Asn Asp Met
        115                 120                 125

Pro Ile Thr Asn Asp Gln Lys Lys Leu Met Ser Asn Asn Val Gln Ile
    130                 135                 140

Val Arg Gln Gln Ser Tyr Ser Ile Met Ser Ile Ile Lys Glu Glu Val
145                 150                 155                 160

Leu Ala Tyr Val Val Gln Leu Pro Ala Tyr Gly Val Ile Asp Thr Pro
                165                 170                 175

Cys Trp Lys Leu His Thr Ser Pro Leu Cys Thr Thr Asn
            180                 185
```

<210> SEQ ID NO 31
<211> LENGTH: 136
<212> TYPE: PRT

<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 31

Ser Asn Ile Cys Leu Thr Arg Thr Asp Arg Gly Trp Tyr Cys Asp Asn
1 5 10 15

Ala Gly Ser Val Ser Phe Phe Pro Gln Ala Glu Thr Cys Lys Val Gln
20 25 30

Ser Asn Arg Val Phe Cys Asp Thr Met Asn Ser Leu Thr Leu Pro Ser
35 40 45

Glu Val Asn Leu Cys Asn Val Asp Ile Phe Asn Pro Lys Tyr Asp Cys
50 55 60

Lys Ile Met Thr Ser Lys Thr Asp Val Ser Ser Ser Val Ile Thr Ser
65 70 75 80

Leu Gly Ala Ile Val Ser Cys Tyr Gly Lys Thr Lys Cys Thr Ala Ser
85 90 95

Asn Lys Asn Arg Gly Ile Ile Lys Thr Phe Ser Asn Gly Cys Asp Tyr
100 105 110

Val Ser Asn Lys Gly Val Asp Thr Val Ser Val Gly Asn Thr Leu Tyr
115 120 125

Tyr Val Asn Lys Gln Glu Gly Lys
130 135

<210> SEQ ID NO 32
<211> LENGTH: 72
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 32

Glu Pro Ile Ile Asn Phe Tyr Asp Pro Leu Val Phe Pro Ser Asp Glu
1 5 10 15

Phe Asp Ala Ser Ile Ser Gln Val Asn Glu Lys Ile Asn Gln Ser Leu
20 25 30

Ala Phe Ile Arg Lys Ser Asp Glu Leu Leu His Asn Val Asn Ala Gly
35 40 45

Lys Ser Thr Thr Asn Ser Lys Ile Tyr His Ile Glu Asn Glu Ile Ala
50 55 60

Arg Ile Lys Lys Leu Ile Gly Glu
65 70

<210> SEQ ID NO 33
<211> LENGTH: 499
<212> TYPE: PRT
<213> ORGANISM: Human respiratory syncytial virus

<400> SEQUENCE: 33

Gln Asn Ile Thr Glu Glu Phe Tyr Gln Ser Thr Cys Ser Ala Val Ser
1 5 10 15

Lys Gly Tyr Leu Ser Ala Leu Arg Thr Gly Trp Tyr Thr Ser Val Ile
20 25 30

Thr Ile Glu Leu Ser Asn Ile Lys Glu Asn Lys Cys Asn Gly Thr Asp
35 40 45

```
Ala Lys Val Lys Leu Ile Lys Gln Glu Leu Asp Lys Tyr Lys Asn Ala
    50                  55                  60

Val Thr Glu Leu Gln Leu Leu Met Gln Ser Thr Pro Ala Thr Asn Asn
65                  70                  75                  80

Arg Ala Arg Arg Glu Leu Pro Arg Phe Met Asn Tyr Thr Leu Asn Asn
                85                  90                  95

Ala Lys Lys Thr Asn Val Thr Leu Ser Lys Lys Arg Lys Arg Arg Phe
            100                 105                 110

Leu Gly Phe Leu Leu Gly Val Gly Ser Ala Ile Ala Ser Gly Val Ala
        115                 120                 125

Val Ser Lys Val Leu His Leu Glu Gly Glu Val Asn Lys Ile Lys Ser
    130                 135                 140

Ala Leu Leu Ser Thr Asn Lys Ala Val Val Ser Leu Ser Asn Gly Val
145                 150                 155                 160

Ser Val Leu Thr Ser Lys Val Leu Asp Leu Lys Asn Tyr Ile Asp Lys
                165                 170                 175

Gln Leu Leu Pro Ile Val Asn Lys Gln Ser Cys Ser Ile Ser Asn Ile
            180                 185                 190

Glu Thr Val Ile Glu Phe Gln Gln Lys Asn Asn Arg Leu Leu Glu Ile
        195                 200                 205

Thr Arg Glu Phe Ser Val Asn Ala Gly Val Thr Thr Pro Val Ser Thr
    210                 215                 220

Tyr Met Leu Thr Asn Ser Glu Leu Leu Ser Leu Ile Asn Asp Met Pro
225                 230                 235                 240

Ile Thr Asn Asp Gln Lys Lys Leu Met Ser Asn Asn Val Gln Ile Val
                245                 250                 255

Arg Gln Gln Ser Tyr Ser Ile Met Ser Ile Ile Lys Glu Glu Val Leu
            260                 265                 270

Ala Tyr Val Val Gln Leu Pro Leu Tyr Gly Val Ile Asp Thr Pro Cys
        275                 280                 285

Trp Lys Leu His Thr Ser Pro Leu Cys Thr Thr Asn Thr Lys Glu Gly
    290                 295                 300

Ser Asn Ile Cys Leu Thr Arg Thr Asp Arg Gly Trp Phe Cys Asp Asn
305                 310                 315                 320

Ala Gly Ser Val Ser Phe Phe Pro Gln Ala Glu Thr Cys Lys Val Gln
                325                 330                 335

Ser Asn Arg Val Phe Cys Asp Thr Met Asn Ser Leu Thr Leu Pro Ser
            340                 345                 350

Glu Val Asn Leu Cys Asn Val Asp Ile Phe Asn Pro Lys Tyr Asp Cys
        355                 360                 365

Lys Ile Met Thr Ser Lys Thr Asp Val Ser Ser Ser Val Ile Thr Ser
    370                 375                 380

Leu Gly Ala Ile Val Ser Cys Tyr Gly Lys Thr Lys Cys Thr Ala Ser
385                 390                 395                 400

Asn Lys Asn Arg Gly Ile Ile Lys Thr Phe Ser Asn Gly Cys Asp Tyr
                405                 410                 415

Val Ser Asn Lys Gly Val Asp Thr Val Ser Val Gly Asn Thr Leu Tyr
            420                 425                 430

Tyr Val Asn Lys Gln Glu Gly Lys Ser Leu Tyr Val Lys Gly Glu Pro
        435                 440                 445

Ile Ile Asn Phe Tyr Asp Pro Leu Val Phe Pro Ser Asp Glu Phe Asp
    450                 455                 460

Ala Ser Ile Ser Gln Val Asn Glu Lys Ile Asn Gln Ser Leu Ala Phe
```

```
465                 470                 475                 480

Ile Arg Lys Ser Asp Glu Leu Leu His Asn Val Asn Ala Gly Lys Ser
                485                 490                 495

Thr Thr Asn


<210> SEQ ID NO 34
<211> LENGTH: 466
<212> TYPE: PRT
<213> ORGANISM: Newcastle disease virus

<400> SEQUENCE: 34

Ser Ala Leu Asp Gly Arg Pro Leu Ala Ala Ala Gly Ile Val Val Thr
1               5                   10                  15

Gly Asp Lys Ala Val Asn Ile Tyr Thr Ser Ser Gln Thr Gly Ser Ile
            20                  25                  30

Ile Ile Lys Leu Leu Pro Asn Met Pro Lys Asp Lys Glu Ala Cys Ala
        35                  40                  45

Lys Ala Pro Leu Glu Ala Tyr Asn Arg Thr Leu Thr Thr Leu Leu Thr
    50                  55                  60

Pro Leu Gly Asp Ser Ile Arg Arg Ile Gln Glu Ser Val Thr Thr Ser
65                  70                  75                  80

Gly Gly Gly Lys Gln Gly Arg Leu Ile Gly Ala Ile Ile Gly Gly Val
                85                  90                  95

Ala Leu Gly Val Ala Thr Ala Ala Gln Ile Thr Ala Ala Ser Ala Leu
            100                 105                 110

Ile Gln Ala Asn Gln Asn Ala Ala Asn Ile Leu Arg Leu Lys Glu Ser
        115                 120                 125

Ile Ala Ala Thr Asn Glu Ala Val His Glu Val Thr Asn Gly Leu Ser
    130                 135                 140

Gln Leu Ala Val Ala Val Gly Lys Met Gln Gln Phe Val Asn Asp Gln
145                 150                 155                 160

Phe Asn Lys Thr Ala Gln Glu Leu Asp Cys Ile Lys Ile Thr Gln Gln
                165                 170                 175

Val Gly Val Glu Leu Asn Leu Tyr Leu Thr Glu Leu Thr Thr Val Phe
            180                 185                 190

Gly Pro Gln Ile Thr Ser Pro Ala Leu Thr Gln Leu Thr Ile Gln Ala
        195                 200                 205

Leu Tyr Asn Leu Ala Gly Gly Asn Met Asp Tyr Leu Leu Thr Lys Leu
    210                 215                 220

Gly Val Gly Asn Asn Gln Leu Ser Ser Leu Ile Ser Ser Gly Leu Ile
225                 230                 235                 240

Thr Gly Asn Pro Ile Leu Tyr Asp Ser Gln Thr Gln Leu Leu Gly Ile
                245                 250                 255

Gln Val Thr Leu Pro Ser Val Gly Asn Leu Asn Asn Met Arg Ala Thr
            260                 265                 270

Tyr Leu Glu Thr Leu Ser Val Ser Thr Thr Lys Gly Phe Ala Ser Ala
        275                 280                 285

Leu Val Pro Lys Val Val Thr Gln Val Gly Ser Val Ile Glu Glu Leu
    290                 295                 300

Asp Thr Ser Tyr Cys Ile Glu Thr Asp Leu Asp Leu Tyr Cys Thr Arg
305                 310                 315                 320

Ile Val Thr Phe Pro Met Ser Pro Gly Ile Tyr Ser Cys Leu Ser Gly
                325                 330                 335

Asn Thr Ser Ala Cys Met Tyr Ser Lys Thr Glu Gly Ala Leu Thr Thr
```

-continued

```
            340                 345                 350

Pro Tyr Met Thr Leu Lys Gly Ser Val Ile Ala Asn Cys Lys Met Thr
        355                 360                 365

Thr Cys Arg Cys Ala Asp Pro Pro Gly Ile Ile Ser Gln Asn Tyr Gly
    370                 375                 380

Glu Ala Val Ser Leu Ile Asp Arg Gln Ser Cys Asn Ile Leu Ser Leu
385                 390                 395                 400

Asp Gly Ile Thr Leu Arg Leu Ser Gly Glu Phe Asp Ala Thr Tyr Gln
                405                 410                 415

Lys Asn Ile Ser Ile Gln Asp Ser Gln Val Ile Val Thr Gly Asn Leu
            420                 425                 430

Asp Ile Ser Thr Glu Leu Gly Asn Val Asn Asn Ser Ile Ser Asn Ala
        435                 440                 445

Leu Asp Lys Leu Glu Glu Ser Asn Ser Lys Leu Asp Lys Val Asn Val
    450                 455                 460

Lys Leu
465


<210> SEQ ID NO 35
<211> LENGTH: 464
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Gly Ser Leu Asp Pro Ala Ala Leu Met Gln Ile Gly Val Ile Pro Thr
1               5                   10                  15

Asn Val Arg Gln Leu Met Tyr Tyr Thr Glu Ala Ser Ser Ala Phe Ile
            20                  25                  30

Val Val Lys Leu Met Pro Thr Ile Asp Ser Pro Ile Ser Gly Cys Asn
        35                  40                  45

Ile Thr Ser Ile Ser Ser Tyr Asn Ala Thr Val Thr Lys Leu Leu Gln
    50                  55                  60

Pro Ile Gly Glu Asn Leu Glu Thr Ile Arg Asn Gln Leu Ile Pro Thr
65                  70                  75                  80

Arg Arg Arg Arg Arg Phe Ala Gly Val Val Ile Gly Leu Ala Ala Leu
                85                  90                  95

Gly Val Ala Thr Ala Ala Gln Val Thr Ala Ala Val Ala Leu Val Lys
            100                 105                 110

Ala Asn Glu Asn Ala Ala Ala Ile Leu Asn Leu Lys Asn Ala Ile Gln
        115                 120                 125

Lys Thr Asn Ala Ala Val Ala Asp Val Val Gln Ala Thr Gln Ser Leu
    130                 135                 140

Gly Thr Ala Val Gln Ala Val Gln Asp His Ile Asn Ser Val Val Ser
145                 150                 155                 160

Pro Ala Ile Thr Ala Ala Asn Cys Lys Ala Gln Asp Ala Ile Ile Gly
                165                 170                 175

Ser Ile Leu Asn Leu Tyr Leu Thr Glu Leu Thr Thr Ile Phe His Asn
            180                 185                 190

Gln Ile Thr Asn Pro Ala Leu Ser Pro Ile Thr Ile Gln Ala Leu Arg
        195                 200                 205

Ile Leu Leu Gly Ser Thr Leu Pro Thr Val Val Glu Lys Ser Phe Asn
    210                 215                 220
```

```
Thr Gln Ile Ser Ala Ala Glu Leu Leu Ser Ser Gly Leu Leu Thr Gly
225                 230                 235                 240

Gln Ile Val Gly Leu Asp Leu Thr Tyr Met Gln Met Val Ile Lys Ile
                245                 250                 255

Glu Leu Pro Thr Leu Thr Val Gln Pro Ala Thr Gln Ile Ile Asp Leu
            260                 265                 270

Ala Thr Ile Ser Ala Phe Ile Asn Asn Gln Glu Val Met Ala Gln Leu
        275                 280                 285

Pro Thr Arg Val Met Val Thr Gly Ser Leu Ile Gln Ala Tyr Pro Ala
    290                 295                 300

Ser Gln Cys Thr Ile Thr Pro Asn Thr Val Tyr Cys Arg Tyr Asn Asp
305                 310                 315                 320

Ala Gln Val Leu Ser Asp Asp Thr Met Ala Cys Leu Gln Gly Asn Leu
                325                 330                 335

Thr Arg Cys Thr Phe Ser Pro Val Val Gly Ser Phe Leu Thr Arg Phe
            340                 345                 350

Val Leu Phe Asp Gly Ile Val Tyr Ala Asn Cys Arg Ser Met Leu Cys
        355                 360                 365

Lys Cys Met Gln Pro Ala Ala Val Ile Leu Gln Pro Ser Ser Ser Pro
    370                 375                 380

Val Thr Val Ile Asp Met Tyr Lys Cys Val Ser Leu Gln Leu Asp Asn
385                 390                 395                 400

Leu Arg Phe Thr Ile Thr Gln Leu Ala Asn Val Thr Tyr Asn Ser Thr
                405                 410                 415

Ile Lys Leu Glu Ser Ser Gln Ile Leu Ser Ile Asp Pro Leu Asp Ile
            420                 425                 430

Ser Gln Asn Leu Ala Ala Val Asn Lys Ser Leu Ser Asp Ala Leu Gln
        435                 440                 445

His Leu Ala Gln Ser Asp Thr Tyr Leu Ser Ala Ile Thr Ser Ala Thr
    450                 455                 460
```

<210> SEQ ID NO 36
<211> LENGTH: 471
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 36

```
Cys Gln Ile Asp Ile Thr Lys Leu Gln His Val Gly Val Leu Val Asn
1               5                   10                  15

Ser Pro Lys Gly Met Lys Ile Ser Gln Asn Phe Glu Thr Arg Tyr Leu
            20                  25                  30

Ile Leu Ser Leu Ile Pro Lys Ile Glu Asp Ser Asn Ser Cys Gly Asp
        35                  40                  45

Gln Gln Ile Lys Gln Tyr Lys Arg Leu Leu Asp Arg Leu Ile Ile Pro
    50                  55                  60

Leu Tyr Asp Gly Leu Arg Leu Gln Lys Asp Val Ile Val Ser Asn Gln
65                  70                  75                  80

Glu Ser Asn Glu Asn Thr Asp Pro Arg Thr Lys Arg Phe Phe Gly Gly
                85                  90                  95

Val Ile Gly Thr Ile Ala Leu Gly Val Ala Thr Ser Ala Gln Ile Thr
            100                 105                 110
```

-continued

```
Ala Ala Val Ala Leu Val Glu Ala Lys Gln Ala Arg Ser Asp Ile Glu
        115                 120                 125

Lys Leu Lys Glu Ala Ile Arg Asp Thr Asn Lys Ala Val Gln Ser Val
    130                 135                 140

Gln Ser Ser Ile Gly Asn Leu Ile Val Ala Ile Lys Ser Val Gln Asp
145                 150                 155                 160

Tyr Val Asn Lys Glu Ile Val Pro Ser Ile Ala Arg Leu Gly Cys Glu
                165                 170                 175

Ala Ala Gly Leu Gln Leu Gly Ile Ala Leu Thr Gln His Tyr Ser Glu
            180                 185                 190

Leu Thr Asn Ile Phe Gly Asp Asn Ile Gly Ser Leu Gln Glu Lys Gly
        195                 200                 205

Ile Lys Leu Gln Gly Ile Ala Ser Leu Tyr Arg Thr Asn Ile Thr Glu
    210                 215                 220

Ile Phe Thr Thr Ser Thr Val Asp Lys Tyr Asp Ile Tyr Asp Leu Leu
225                 230                 235                 240

Phe Thr Glu Ser Ile Lys Val Arg Val Ile Asp Val Asp Leu Asn Asp
                245                 250                 255

Tyr Ser Ile Thr Leu Gln Val Arg Leu Pro Leu Leu Thr Arg Leu Leu
            260                 265                 270

Asn Thr Gln Ile Tyr Arg Val Asp Ser Ile Ser Tyr Asn Ile Gln Asn
        275                 280                 285

Arg Glu Trp Tyr Ile Pro Leu Pro Ser His Ile Met Thr Lys Gly Ala
    290                 295                 300

Phe Leu Gly Gly Ala Asp Val Lys Glu Cys Ile Glu Ala Phe Ser Ser
305                 310                 315                 320

Tyr Ile Cys Pro Ser Asp Pro Gly Phe Val Leu Asn His Glu Met Glu
                325                 330                 335

Ser Cys Leu Ser Gly Asn Ile Ser Gln Cys Pro Arg Thr Val Val Lys
            340                 345                 350

Ser Asp Ile Val Pro Arg Tyr Ala Phe Val Asn Gly Gly Val Val Ala
        355                 360                 365

Asn Cys Ile Thr Thr Thr Cys Thr Cys Asn Gly Ile Gly Asn Arg Ile
    370                 375                 380

Asn Gln Pro Pro Asp Gln Gly Val Lys Ile Ile Thr His Lys Glu Cys
385                 390                 395                 400

Asn Thr Ile Gly Ile Asn Gly Met Leu Phe Asn Thr Asn Lys Glu Gly
                405                 410                 415

Thr Leu Ala Phe Tyr Thr Pro Asn Asp Ile Thr Leu Asn Asn Ser Val
            420                 425                 430

Ala Leu Asp Pro Ile Asp Ile Ser Ile Glu Leu Asn Lys Ala Lys Ser
        435                 440                 445

Asp Leu Glu Glu Ser Lys Glu Trp Ile Arg Arg Ser Asn Gln Lys Leu
    450                 455                 460

Asp Ser Ile Gly Asn Trp His
465                 470
```

<210> SEQ ID NO 37
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 37

Ile Ile Lys Thr Phe
1 5

<210> SEQ ID NO 38
<211> LENGTH: 468
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 38

Met Glu Leu Leu Ile Leu Lys Ala Asn Ala Ile Thr Thr Ile Leu Thr
1 5 10 15

Ala Val Thr Phe Cys Phe Ala Ser Gly Gln Asn Ile Thr Glu Glu Phe
20 25 30

Tyr Gln Ser Thr Cys Ser Ala Val Ser Lys Gly Tyr Leu Ser Ala Leu
35 40 45

Arg Thr Gly Trp Tyr Thr Ser Val Ile Thr Ile Glu Leu Ser Asn Ile
50 55 60

Lys Glu Asn Lys Cys Asn Gly Thr Asp Ala Lys Val Lys Leu Ile Lys
65 70 75 80

Gln Glu Leu Asp Lys Tyr Lys Asn Ala Val Thr Glu Leu Gln Leu Leu
85 90 95

Met Gln Ser Thr Pro Ala Thr Asn Asn Arg Ala Arg Arg Glu Leu Pro
100 105 110

Arg Phe Met Asn Tyr Thr Leu Asn Asn Ala Lys Lys Thr Asn Val Thr
115 120 125

Leu Ser Lys Lys Arg Lys Arg Arg Ser Ala Ile Ala Ser Gly Val Ala
130 135 140

Val Ser Lys Val Leu His Leu Glu Gly Glu Val Asn Lys Ile Lys Ser
145 150 155 160

Ala Leu Leu Ser Thr Asn Lys Ala Val Val Ser Leu Ser Asn Gly Val
165 170 175

Ser Val Leu Thr Ser Lys Val Leu Asp Leu Lys Asn Tyr Ile Asp Lys
180 185 190

Gln Leu Leu Pro Ile Val Asn Lys Gln Ser Cys Ser Ile Ser Asn Ile
195 200 205

Glu Thr Val Ile Glu Phe Gln Gln Lys Asn Asn Arg Leu Leu Glu Ile
210 215 220

Thr Arg Glu Phe Ser Val Asn Ala Gly Val Thr Thr Pro Val Ser Thr
225 230 235 240

Tyr Met Leu Thr Asn Ser Glu Leu Leu Ser Leu Ile Asn Asp Met Pro
245 250 255

Ile Thr Asn Asp Gln Lys Lys Leu Met Ser Asn Asn Val Gln Ile Val
260 265 270

Arg Gln Gln Ser Tyr Ser Ile Met Ser Ile Ile Lys Glu Glu Val Leu
275 280 285

Ala Tyr Val Val Gln Leu Pro Leu Tyr Gly Val Ile Asp Thr Pro Cys
290 295 300

Trp Lys Leu His Thr Ser Pro Leu Cys Thr Thr Asn Thr Lys Glu Gly
305 310 315 320

Ser Asn Ile Cys Leu Thr Arg Thr Asp Arg Gly Trp Tyr Cys Asp Asn
325 330 335

```
Ala Gly Ser Val Ser Phe Phe Pro Gln Ala Glu Thr Cys Lys Val Gln
            340                 345                 350

Ser Asn Arg Val Phe Cys Asp Thr Met Asn Ser Leu Thr Leu Pro Ser
        355                 360                 365

Glu Val Asn Leu Cys Asn Val Asp Ile Phe Asn Pro Lys Tyr Asp Cys
    370                 375                 380

Lys Ile Met Thr Ser Lys Thr Asp Val Ser Ser Ser Val Ile Thr Ser
385                 390                 395                 400

Leu Gly Ala Ile Val Ser Cys Tyr Gly Lys Thr Lys Cys Thr Ala Ser
                405                 410                 415

Asn Lys Asn Arg Gly Ile Ile Lys Thr Phe Ser Asn Gly Cys Asp Tyr
            420                 425                 430

Val Ser Asn Lys Gly Val Asp Thr Val Ser Val Gly Asn Thr Leu Tyr
        435                 440                 445

Tyr Val Asn Lys Gln Glu Gly Gly Gly Ser Ala Gly Ser Gly His His
    450                 455                 460

His His His His
465


<210> SEQ ID NO 39
<211> LENGTH: 528
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Ser Ala Ile Ala Ser Gly Val Ala
    130                 135                 140

Val Ser Lys Val Leu His Leu Glu Gly Glu Val Asn Lys Ile Lys Ser
145                 150                 155                 160

Ala Leu Leu Ser Thr Asn Lys Ala Val Val Ser Leu Ser Asn Gly Val
                165                 170                 175

Ser Val Leu Thr Ser Lys Val Leu Asp Leu Lys Asn Tyr Ile Asp Lys
            180                 185                 190

Gln Leu Leu Pro Ile Val Asn Lys Gln Ser Cys Ser Ile Ser Asn Ile
        195                 200                 205
```

-continued

```
Glu Thr Val Ile Glu Phe Gln Gln Lys Asn Asn Arg Leu Leu Glu Ile
    210                 215                 220

Thr Arg Glu Phe Ser Val Asn Ala Gly Val Thr Thr Pro Val Ser Thr
225                 230                 235                 240

Tyr Met Leu Thr Asn Ser Glu Leu Leu Ser Leu Ile Asn Asp Met Pro
                245                 250                 255

Ile Thr Asn Asp Gln Lys Lys Leu Met Ser Asn Asn Val Gln Ile Val
            260                 265                 270

Arg Gln Gln Ser Tyr Ser Ile Met Ser Ile Ile Lys Glu Glu Val Leu
        275                 280                 285

Ala Tyr Val Val Gln Leu Pro Leu Tyr Gly Val Ile Asp Thr Pro Cys
    290                 295                 300

Trp Lys Leu His Thr Ser Pro Leu Cys Thr Thr Asn Thr Lys Glu Gly
305                 310                 315                 320

Ser Asn Ile Cys Leu Thr Arg Thr Asp Arg Gly Trp Tyr Cys Asp Asn
                325                 330                 335

Ala Gly Ser Val Ser Phe Phe Pro Gln Ala Glu Thr Cys Lys Val Gln
            340                 345                 350

Ser Asn Arg Val Phe Cys Asp Thr Met Asn Ser Leu Thr Leu Pro Ser
        355                 360                 365

Glu Val Asn Leu Cys Asn Val Asp Ile Phe Asn Pro Lys Tyr Asp Cys
    370                 375                 380

Lys Ile Met Thr Ser Lys Thr Asp Val Ser Ser Ser Val Ile Thr Ser
385                 390                 395                 400

Leu Gly Ala Ile Val Ser Cys Tyr Gly Lys Thr Lys Cys Thr Ala Ser
                405                 410                 415

Asn Lys Asn Ser Gly Ile Thr Thr Thr Phe Phe Asn Gly Cys Asp Tyr
            420                 425                 430

Val Ser Asn Lys Gly Val Asp Thr Val Ser Val Gly Asn Thr Leu Tyr
        435                 440                 445

Tyr Val Asn Lys Gln Glu Gly Lys Ser Leu Tyr Val Lys Gly Glu Pro
    450                 455                 460

Ile Ile Asn Phe Tyr Asp Pro Leu Val Phe Pro Ser Asp Glu Phe Asp
465                 470                 475                 480

Ala Ser Ile Ser Gln Val Asn Glu Lys Ile Asn Gln Ser Leu Ala Phe
                485                 490                 495

Ile Arg Lys Ser Asp Glu Leu Leu His Asn Val Asn Ala Gly Lys Ser
            500                 505                 510

Thr Thr Asn Gly Gly Ser Ala Gly Ser Gly His His His His His His
        515                 520                 525
```

<210> SEQ ID NO 40
<211> LENGTH: 537
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 40

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
```

```
        35                  40                  45

Arg Thr Gly Trp Tyr Thr Ser Val Cys Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Cys Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460
```

Lys Ser Leu Tyr Val Lys Gly Glu Pro Ile Ile Asn Phe Tyr Asp Pro
465 470 475 480

Leu Val Phe Pro Ser Asp Glu Phe Asp Ala Ser Ile Ser Gln Val Asn
485 490 495

Glu Lys Ile Asn Gln Ser Leu Ala Phe Ile Arg Lys Ser Asp Glu Leu
500 505 510

Leu His Asn Val Asn Ala Gly Lys Ser Thr Thr Asn Gly Gly Ser Ala
515 520 525

Gly Ser Gly His His His His His His
530 535

<210> SEQ ID NO 41
<211> LENGTH: 528
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 41

Met Glu Leu Leu Ile Leu Lys Ala Asn Ala Ile Thr Thr Ile Leu Thr
1 5 10 15

Ala Val Thr Phe Cys Phe Ala Ser Gly Gln Asn Ile Thr Glu Glu Phe
20 25 30

Tyr Gln Ser Thr Cys Ser Ala Val Ser Lys Gly Tyr Leu Ser Ala Leu
35 40 45

Arg Thr Gly Trp Tyr Thr Ser Val Ile Thr Ile Glu Leu Ser Asn Ile
50 55 60

Lys Glu Asn Lys Cys Asn Gly Thr Asp Ala Lys Val Lys Leu Ile Lys
65 70 75 80

Gln Glu Leu Asp Lys Tyr Lys Asn Ala Val Thr Glu Leu Gln Leu Leu
85 90 95

Met Gln Ser Thr Pro Ala Thr Asn Asn Arg Ala Arg Arg Glu Leu Pro
100 105 110

Arg Phe Met Asn Tyr Thr Leu Asn Asn Ala Lys Lys Thr Asn Val Thr
115 120 125

Leu Ser Lys Lys Arg Lys Arg Arg Ser Ala Ile Ala Ser Gly Val Ala
130 135 140

Val Ser Lys Val Leu His Leu Glu Gly Glu Val Asn Lys Ile Lys Ser
145 150 155 160

Ala Leu Leu Ser Thr Asn Lys Ala Val Val Ser Leu Ser Asn Gly Val
165 170 175

Ser Val Leu Thr Ser Lys Val Leu Asp Leu Lys Asn Tyr Ile Asp Lys
180 185 190

Gln Leu Leu Pro Ile Val Asn Lys Gln Ser Cys Ser Ile Ser Asn Ile
195 200 205

Glu Thr Val Ile Glu Phe Gln Gln Lys Asn Asn Arg Leu Leu Glu Ile
210 215 220

Thr Arg Glu Phe Ser Val Asn Ala Gly Val Thr Thr Pro Val Ser Thr
225 230 235 240

Tyr Met Leu Thr Asn Ser Glu Leu Leu Ser Leu Ile Tyr Asp Met Pro
245 250 255

Ile Thr Ile Asp Gln Lys Met Leu Met Ser Asn Asn Val Gln Ile Val
260 265 270

-continued

```
Arg Gln Gln Ser Tyr Ser Ile Met Ser Ile Ile Lys Glu Glu Val Leu
        275                 280                 285

Ala Tyr Val Val Gln Leu Pro Leu Tyr Gly Val Ile Asp Thr Pro Cys
    290                 295                 300

Trp Lys Leu His Thr Ser Pro Leu Cys Thr Thr Asn Thr Lys Glu Gly
305                 310                 315                 320

Ser Asn Ile Cys Leu Thr Arg Thr Asp Arg Gly Trp Tyr Cys Asp Asn
                325                 330                 335

Ala Gly Ser Val Ser Phe Phe Pro Gln Ala Glu Thr Cys Lys Val Gln
            340                 345                 350

Ser Asn Arg Val Phe Cys Asp Thr Met Asn Ser Leu Thr Leu Pro Ser
        355                 360                 365

Glu Val Asn Leu Cys Asn Val Asp Ile Phe Asn Pro Lys Tyr Asp Cys
    370                 375                 380

Lys Ile Met Thr Ser Lys Thr Asp Val Ser Ser Ser Val Ile Thr Ser
385                 390                 395                 400

Leu Gly Ala Ile Val Ser Cys Tyr Gly Lys Thr Lys Cys Thr Ala Ser
                405                 410                 415

Asn Lys Asn Ser Gly Ile Thr Thr Thr Phe Phe Asn Gly Cys Asp Tyr
            420                 425                 430

Val Ser Asn Lys Gly Val Asp Thr Val Ser Val Gly Asn Thr Leu Tyr
        435                 440                 445

Tyr Val Asn Lys Gln Glu Gly Lys Ser Leu Tyr Val Lys Gly Glu Pro
    450                 455                 460

Ile Ile Asn Phe Tyr Asp Pro Leu Val Phe Pro Ser Asp Glu Phe Asp
465                 470                 475                 480

Ala Ser Ile Ser Gln Val Asn Glu Lys Ile Asn Gln Ser Leu Ala Phe
                485                 490                 495

Ile Arg Lys Ser Asp Glu Leu Leu His Asn Val Asn Ala Gly Lys Ser
            500                 505                 510

Thr Thr Asn Gly Gly Ser Ala Gly Ser Gly His His His His His His
        515                 520                 525
```